US010847252B2

(12) United States Patent
Yelensky et al.

(10) Patent No.: US 10,847,252 B2
(45) Date of Patent: *Nov. 24, 2020

(54) NEOANTIGEN IDENTIFICATION, MANUFACTURE, AND USE

(71) Applicant: Gritstone Oncology, Inc., Emeryville, CA (US)

(72) Inventors: Roman Yelensky, Newton, MA (US); Adnan Derti, Dedham, MA (US); Brendan Bulik-Sullivan, Cambridge, MA (US); Jennifer Busby, Burlington, MA (US)

(73) Assignee: Gritstone Oncology, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/001,569

(22) Filed: Jun. 6, 2018

(65) Prior Publication Data
US 2019/0065675 A1    Feb. 28, 2019

Related U.S. Application Data

(63) Continuation of application No. 15/466,729, filed on Mar. 22, 2017, now Pat. No. 10,055,540, which is a continuation of application No. 15/381,375, filed on Dec. 16, 2016.

(60) Provisional application No. 62/268,333, filed on Dec. 16, 2015, provisional application No. 62/317,823, filed on Apr. 4, 2016, provisional application No. 62/379,986, filed on Aug. 26, 2016, provisional application No. 62/394,074, filed on Sep. 13, 2016, provisional application No. 62/425,995, filed on Nov. 23, 2016.

(51) Int. Cl.
*G16B 30/00* (2019.01)
*A61K 39/00* (2006.01)
*A61K 35/15* (2015.01)

(52) U.S. Cl.
CPC .......... *G16B 30/00* (2019.02); *A61K 39/0011* (2013.01); *A61K 35/15* (2013.01)

(58) Field of Classification Search
None
See application file for complete search history.

(56) References Cited

U.S. PATENT DOCUMENTS

| | | | |
|---|---|---|---|
| 4,452,773 A | 6/1984 | Molday | |
| 4,795,698 A | 1/1989 | Owen et al. | |
| 5,130,538 A | 7/1992 | Fenn et al. | |
| 5,200,084 A | 4/1993 | Liberti et al. | |
| 5,204,244 A | 4/1993 | Fell et al. | |
| 5,504,329 A | 4/1996 | Mann et al. | |
| 5,514,578 A | 5/1996 | Hogness et al. | |
| 5,534,615 A | 7/1996 | Baker et al. | |
| 5,581,080 A | 12/1996 | Fenn et al. | |
| 5,608,217 A | 3/1997 | Franzen et al. | |
| 5,686,726 A | 11/1997 | Fenn et al. | |
| 6,040,177 A | 3/2000 | Riddell et al. | |
| 6,245,531 B1 | 6/2001 | Hogness et al. | |
| 6,405,917 B1 | 6/2002 | Mann | |
| 6,864,089 B2 | 3/2005 | Figeys et al. | |
| 7,091,038 B2 | 8/2006 | Palli et al. | |
| 7,695,725 B2 | 4/2010 | Dubensky, Jr. et al. | |
| 7,731,648 B2 | 6/2010 | Ivkov | |
| 7,833,775 B2 | 11/2010 | Dubensky, Jr. et al. | |
| 7,842,289 B2 | 11/2010 | Dubensky, Jr. et al. | |
| 7,935,804 B2 | 5/2011 | Dubensky, Jr. et al. | |
| 7,981,420 B2 | 7/2011 | Mueller et al. | |
| 8,053,552 B2 | 11/2011 | Von Knebel-Doeberitz et al. | |
| 8,121,797 B2 | 2/2012 | Heckerman | |
| 8,287,883 B2 | 10/2012 | Dubensky, Jr. et al. | |
| 8,583,380 B2 | 11/2013 | Stephan et al. | |
| 8,680,239 B2 | 3/2014 | Mueller et al. | |
| 8,741,556 B2 | 6/2014 | Mann et al. | |
| 8,768,629 B2 | 7/2014 | Von Hoff et al. | |
| 8,796,414 B2 | 8/2014 | Johnston | |
| 8,821,864 B2 | 9/2014 | Von Knebel-Doeberitz et al. | |
| 8,840,881 B2 | 9/2014 | Jooss et al. | |
| 8,926,993 B2 | 1/2015 | Dubensky, Jr. et al. | |
| 9,017,660 B2 | 4/2015 | Shahabi et al. | |
| 9,063,149 B2 | 6/2015 | Mann et al. | |
| 9,084,747 B2 | 7/2015 | Shahabi et al. | |
| 9,115,402 B2 | 8/2015 | Hacohen et al. | |
| 9,161,974 B2 | 10/2015 | Dubensky et al. | |
| 9,175,088 B2 | 11/2015 | Sahin et al. | |

(Continued)

FOREIGN PATENT DOCUMENTS

EP  0434792 A1  7/1991
EP   452342 A1  10/1991

(Continued)

OTHER PUBLICATIONS

Yadav et al Nature, 515:572-576, 2014.*
Bassani-Sternberg et al. Mol Cell Proteomics, 14:658-673, 2015.*
Zhang et al. J Immunol Methods, 374:53-61, 2011.*
Fritsch et al. Cancer Immunology Research, 2014, vol. 2, p. 522-529.*
Inza, I. et al., "Machine Learning: An Indispensable Tool in Bioinformatics," Bioinformatics Methods in Clinical Research, Methods in Molecular Biology 593, 2010, pp. 25-48.

(Continued)

*Primary Examiner* — Michael L Borin
(74) *Attorney, Agent, or Firm* — Goodwin Procter LLP

(57) ABSTRACT

Disclosed herein is a system and methods for determining the alleles, neoantigens, and vaccine composition as determined on the basis of an individual's tumor mutations. Also disclosed are systems and methods for obtaining high quality sequencing data from a tumor. Further, described herein are systems and methods for identifying somatic changes in polymorphic genome data. Finally, described herein are unique cancer vaccines.

31 Claims, 28 Drawing Sheets

Specification includes a Sequence Listing.

(56) References Cited

U.S. PATENT DOCUMENTS

| | | | |
|---|---|---|---|
| 9,194,004 B2 | 11/2015 | Sahin et al. | |
| 9,198,960 B2 | 12/2015 | Dubensky, Jr. et al. | |
| 9,267,177 B2 | 2/2016 | Tureci et al. | |
| 9,289,478 B2 | 3/2016 | Lewandrowski et al. | |
| 9,308,244 B2 | 4/2016 | Singh et al. | |
| 9,389,235 B2 | 7/2016 | Weinschenck et al. | |
| 9,463,227 B2 | 10/2016 | Rothman et al. | |
| 9,498,512 B2 | 11/2016 | Rammensee et al. | |
| 9,499,602 B2 | 11/2016 | Paterson et al. | |
| 9,511,128 B2 | 12/2016 | Singh et al. | |
| 9,527,916 B2 | 12/2016 | Van Eenennaam et al. | |
| 9,533,043 B2 | 1/2017 | Tureci et al. | |
| 9,549,973 B2 | 1/2017 | Paterson et al. | |
| 9,587,020 B2 | 3/2017 | Wu et al. | |
| 2002/0076817 A1 | 6/2002 | Figeys et al. | |
| 2002/0155447 A1* | 10/2002 | Zauderer | C07K 14/47 435/6.14 |
| 2002/0192708 A1 | 12/2002 | Steen et al. | |
| 2003/0171290 A1 | 9/2003 | Carr et al. | |
| 2003/0175722 A1 | 9/2003 | Mann et al. | |
| 2004/0002112 A1 | 1/2004 | Mann et al. | |
| 2004/0102376 A1 | 5/2004 | Mueller et al. | |
| 2005/0164326 A1 | 7/2005 | Figeys et al. | |
| 2006/0190226 A1 | 8/2006 | Jojic et al. | |
| 2009/0093050 A1 | 4/2009 | Wu et al. | |
| 2010/0127110 A1 | 5/2010 | Hagedorn et al. | |
| 2010/0286070 A1 | 11/2010 | Verheyden et al. | |
| 2011/0003380 A1 | 1/2011 | Miltenyi et al. | |
| 2011/0112280 A1 | 5/2011 | Mueller et al. | |
| 2011/0287055 A1 | 11/2011 | Lauer et al. | |
| 2011/0293637 A1 | 12/2011 | Hacohen et al. | |
| 2012/0077696 A1 | 3/2012 | Admon et al. | |
| 2012/0100173 A1 | 4/2012 | Leclair et al. | |
| 2012/0208706 A1 | 8/2012 | Downing et al. | |
| 2012/0264154 A1 | 10/2012 | Mann et al. | |
| 2013/0072667 A1 | 3/2013 | Mueller et al. | |
| 2013/0138414 A1 | 5/2013 | Bangera et al. | |
| 2013/0259883 A1 | 10/2013 | Hunt et al. | |
| 2013/0303594 A1 | 11/2013 | Kappei et al. | |
| 2013/0315950 A1 | 11/2013 | Dubensky et al. | |
| 2014/0037662 A1 | 2/2014 | Lauer et al. | |
| 2014/0072991 A1 | 3/2014 | Mann et al. | |
| 2014/0178438 A1 | 6/2014 | Sahin et al. | |
| 2014/0186387 A1 | 7/2014 | Lauer et al. | |
| 2014/0205653 A1 | 7/2014 | Dubensky et al. | |
| 2014/0234370 A1 | 8/2014 | Shahabi et al. | |
| 2014/0248304 A1 | 9/2014 | Paterson et al. | |
| 2014/0314708 A1 | 10/2014 | Maciag et al. | |
| 2014/0315314 A1 | 10/2014 | Dubensky et al. | |
| 2014/0335120 A1 | 11/2014 | Maciag et al. | |
| 2015/0044246 A1 | 2/2015 | Weinschenk et al. | |
| 2015/0056224 A1 | 2/2015 | Dubensky et al. | |
| 2015/0079119 A1 | 3/2015 | Johnston | |
| 2015/0098964 A1 | 4/2015 | Singh et al. | |
| 2015/0125465 A1 | 5/2015 | Binder et al. | |
| 2015/0125477 A1 | 5/2015 | Kuttruff-Coqui et al. | |
| 2015/0125485 A1 | 5/2015 | Dubensky et al. | |
| 2015/0140041 A1 | 5/2015 | Vitiello | |
| 2015/0238584 A1 | 8/2015 | Shahabi et al. | |
| 2015/0241420 A1 | 8/2015 | Johnston et al. | |
| 2015/0278441 A1* | 10/2015 | Min | G16B 20/00 706/12 |
| 2015/0297702 A1 | 10/2015 | Shahabi et al. | |
| 2015/0307567 A1 | 10/2015 | Leclair et al. | |
| 2015/0320848 A1 | 11/2015 | Rammensee | |
| 2015/0335721 A1 | 11/2015 | Paterson et al. | |
| 2015/0343047 A1 | 12/2015 | Paterson et al. | |
| 2015/0346068 A1 | 12/2015 | Kulak et al. | |
| 2015/0366955 A9 | 12/2015 | Shahabi et al. | |
| 2015/0368298 A1 | 12/2015 | Stickel | |
| 2015/0376718 A1 | 12/2015 | Tureci et al. | |
| 2016/0002738 A1 | 1/2016 | Sahin et al. | |
| 2016/0008447 A1 | 1/2016 | Hacohen et al. | |
| 2016/0022814 A1 | 1/2016 | Petit et al. | |
| 2016/0024173 A1 | 1/2016 | Paterson et al. | |
| 2016/0051654 A1 | 2/2016 | Singh et al. | |
| 2016/0058853 A1 | 3/2016 | Sahin et al. | |
| 2016/0069895 A1 | 3/2016 | Delamarre et al. | |
| 2016/0074491 A1 | 3/2016 | Lauer et al. | |
| 2016/0101170 A1* | 4/2016 | Hacohen | A61K 39/0011 424/277.1 |
| 2016/0115212 A1 | 4/2016 | Dengjel | |
| 2016/0117441 A1 | 4/2016 | Bremel | |
| 2016/0125129 A1 | 5/2016 | Sahin et al. | |
| 2016/0151472 A1 | 6/2016 | Jooss et al. | |
| 2016/0168200 A1 | 6/2016 | Weinschenk et al. | |
| 2016/0175357 A1 | 6/2016 | Weinschenk et al. | |
| 2016/0175414 A1 | 6/2016 | Sahin et al. | |
| 2016/0175415 A1 | 6/2016 | Dubensky, Jr. et al. | |
| 2016/0185870 A1 | 6/2016 | Van Eenennaam et al. | |
| 2016/0194402 A1 | 7/2016 | Van Eenennaam et al. | |
| 2016/0195539 A1 | 7/2016 | Tureci et al. | |
| 2016/0201137 A1 | 7/2016 | Wirtz et al. | |
| 2016/0202267 A1 | 7/2016 | Van Eenennaam et al. | |
| 2016/0215351 A1 | 7/2016 | Sahin et al. | |
| 2016/0220652 A1 | 8/2016 | Petit et al. | |
| 2016/0244825 A1 | 8/2016 | Vigneault et al. | |
| 2016/0250307 A1 | 9/2016 | Weinschenk et al. | |
| 2016/0250323 A1 | 9/2016 | Sahin et al. | |
| 2016/0264674 A1 | 9/2016 | Van Eenennaam et al. | |
| 2016/0265050 A1 | 9/2016 | Sahin et al. | |
| 2016/0272711 A1 | 9/2016 | Sahin et al. | |
| 2016/0279214 A1 | 9/2016 | Mahr et al. | |
| 2016/0279215 A1 | 9/2016 | Mahr et al. | |
| 2016/0279216 A1 | 9/2016 | Mahr et al. | |
| 2016/0279217 A1 | 9/2016 | Mahr et al. | |
| 2016/0279218 A1 | 9/2016 | Mahr et al. | |
| 2016/0280738 A1 | 9/2016 | Mahr et al. | |
| 2016/0280752 A1 | 9/2016 | Mahr et al. | |
| 2016/0280757 A1 | 9/2016 | Mahr et al. | |
| 2016/0280758 A1 | 9/2016 | Mahr et al. | |
| 2016/0280759 A1 | 9/2016 | Mahr et al. | |
| 2016/0280760 A1 | 9/2016 | Mahr et al. | |
| 2016/0287687 A1 | 10/2016 | Mahr et al. | |
| 2016/0289296 A1 | 10/2016 | Mahr et al. | |
| 2016/0298185 A1 | 10/2016 | Shukla et al. | |
| 2016/0324903 A1 | 11/2016 | Rothman et al. | |
| 2016/0331821 A1 | 11/2016 | Levey et al. | |
| 2016/0331822 A1 | 11/2016 | Hacohen et al. | |
| 2016/0339090 A1 | 11/2016 | Hacohen et al. | |
| 2016/0339092 A1 | 11/2016 | Schoor et al. | |
| 2016/0346369 A1 | 12/2016 | Lauer et al. | |
| 2016/0346371 A1 | 12/2016 | Schoor et al. | |
| 2016/0347798 A1* | 12/2016 | Poma | C07K 16/00 |
| 2016/0347808 A1 | 12/2016 | Schoor et al. | |
| 2016/0347815 A1 | 12/2016 | Sahin et al. | |
| 2016/0347847 A1 | 12/2016 | Van Dijk et al. | |
| 2016/0361401 A1 | 12/2016 | Shahabi et al. | |
| 2016/0368965 A1 | 12/2016 | Mahr et al. | |
| 2016/0368989 A1 | 12/2016 | Van Dijk et al. | |
| 2017/0002055 A1 | 1/2017 | Mahr et al. | |
| 2017/0022251 A1 | 1/2017 | Rammensee et al. | |
| 2017/0028044 A1 | 2/2017 | Soon-Shiong et al. | |
| 2017/0029486 A1 | 2/2017 | Mahr et al. | |
| 2017/0035807 A1 | 2/2017 | Schuster et al. | |
| 2017/0037089 A1 | 2/2017 | Mahr et al. | |
| 2017/0037092 A1 | 2/2017 | Mahr et al. | |
| 2017/0037093 A1 | 2/2017 | Mahr et al. | |
| 2017/0037094 A1 | 2/2017 | Mahr et al. | |
| 2017/0037095 A1 | 2/2017 | Mahr et al. | |
| 2017/0037096 A1 | 2/2017 | Mahr et al. | |
| 2017/0037097 A1 | 2/2017 | Mahr et al. | |
| 2017/0037098 A1 | 2/2017 | Mahr et al. | |
| 2017/0037107 A1 | 2/2017 | Mahr et al. | |
| 2017/0037110 A1 | 2/2017 | Mahr et al. | |
| 2017/0037111 A1 | 2/2017 | Mahr et al. | |
| 2017/0042996 A1 | 2/2017 | Wallecha et al. | |
| 2017/0052187 A1 | 2/2017 | Sahin et al. | |
| 2017/0056486 A1 | 3/2017 | Mahr et al. | |
| 2017/0056487 A1 | 3/2017 | Mahr et al. | |
| 2017/0056488 A1 | 3/2017 | Mahr et al. | |
| 2017/0116371 A1 | 4/2017 | Dimon et al. | |
| 2017/0166877 A1 | 6/2017 | Bayle et al. | |
| 2017/0199961 A1 | 7/2017 | Yelensky et al. | |

(56) References Cited

U.S. PATENT DOCUMENTS

| | | |
|---|---|---|
| 2017/0212984 A1 | 7/2017 | Yelensky et al. |
| 2017/0221176 A1 | 8/2017 | Munteanu et al. |
| 2018/0330055 A1 | 11/2018 | Yelensky et al. |
| 2020/0105377 A1 | 4/2020 | Bulik-Sullivan et al. |

FOREIGN PATENT DOCUMENTS

| | | |
|---|---|---|
| EP | 0434792 A1 | 5/1992 |
| EP | 0517805 A1 | 12/1992 |
| EP | 1021537 A1 | 7/2000 |
| EP | 1290450 A2 | 3/2003 |
| EP | 1355666 A2 | 10/2003 |
| EP | 1419518 A2 | 5/2004 |
| EP | 1608321 A2 | 12/2005 |
| EP | 2091046 A1 | 8/2009 |
| EP | 2134363 A2 | 12/2009 |
| EP | 2288379 A2 | 3/2011 |
| EP | 2309262 A1 | 4/2011 |
| EP | 2385062 A2 | 11/2011 |
| EP | 2413953 A2 | 2/2012 |
| EP | 1592441 B1 | 4/2012 |
| EP | 1603936 B1 | 4/2012 |
| EP | 1355666 B1 | 6/2012 |
| EP | 2498808 A2 | 9/2012 |
| EP | 2508537 A1 | 10/2012 |
| EP | 1575643 B1 | 4/2013 |
| EP | 2574346 A1 | 4/2013 |
| EP | 2576614 A2 | 4/2013 |
| EP | 2591001 A1 | 5/2013 |
| EP | 2616482 A1 | 7/2013 |
| EP | 2640842 A1 | 9/2013 |
| EP | 2643698 A1 | 10/2013 |
| EP | 2486405 B1 | 12/2013 |
| EP | 2694556 A1 | 2/2014 |
| EP | 2002263 B1 | 6/2014 |
| EP | 2744513 A1 | 6/2014 |
| EP | 2772262 A1 | 9/2014 |
| EP | 1991263 B1 | 12/2014 |
| EP | 2155243 B1 | 12/2014 |
| EP | 2825195 A1 | 1/2015 |
| EP | 2853269 A1 | 4/2015 |
| EP | 2859899 A1 | 4/2015 |
| EP | 2859901 A1 | 4/2015 |
| EP | 2860253 A2 | 4/2015 |
| EP | 2865387 A2 | 4/2015 |
| EP | 2931738 A1 | 10/2015 |
| EP | 2934749 A2 | 10/2015 |
| EP | 2267013 B1 | 11/2015 |
| EP | 2938627 A1 | 11/2015 |
| EP | 2959021 A1 | 12/2015 |
| EP | 2966082 A1 | 1/2016 |
| EP | 1708741 B1 | 3/2016 |
| EP | 2994159 A1 | 3/2016 |
| EP | 2996473 A1 | 3/2016 |
| EP | 2403528 B1 | 4/2016 |
| EP | 2266608 B1 | 5/2016 |
| EP | 2341927 B1 | 5/2016 |
| EP | 2547691 B1 | 6/2016 |
| EP | 2643698 B1 | 6/2016 |
| EP | 2767834 B1 | 6/2016 |
| EP | 3027203 A1 | 6/2016 |
| EP | 3027210 A1 | 6/2016 |
| EP | 3030255 A1 | 6/2016 |
| EP | 3041867 A1 | 7/2016 |
| EP | 3041868 A2 | 7/2016 |
| EP | 3042914 A1 | 7/2016 |
| EP | 2280082 B1 | 8/2016 |
| EP | 2694556 B1 | 8/2016 |
| EP | 3049065 A1 | 8/2016 |
| EP | 3058947 A2 | 8/2016 |
| EP | 3060679 A1 | 8/2016 |
| EP | 2311860 B1 | 9/2016 |
| EP | 3066115 A2 | 9/2016 |
| EP | 3069728 A1 | 9/2016 |
| EP | 2172212 B1 | 10/2016 |
| EP | 2283112 B1 | 10/2016 |
| EP | 2331118 B1 | 10/2016 |
| EP | 2567707 B1 | 10/2016 |
| EP | 2576791 B1 | 10/2016 |
| EP | 3095791 A1 | 11/2016 |
| EP | 2266613 B1 | 12/2016 |
| EP | 3099706 A1 | 12/2016 |
| EP | 3099708 A1 | 12/2016 |
| EP | 3103476 A2 | 12/2016 |
| EP | 3106175 A1 | 12/2016 |
| EP | 3107566 A1 | 12/2016 |
| EP | 3110942 A2 | 1/2017 |
| EP | 3111952 A1 | 1/2017 |
| EP | 3113794 A2 | 1/2017 |
| EP | 3120868 A1 | 1/2017 |
| EP | 3120869 A1 | 1/2017 |
| EP | 3120870 A1 | 1/2017 |
| EP | 3124043 A1 | 2/2017 |
| EP | 3132801 A1 | 2/2017 |
| EP | 2178557 B1 | 3/2017 |
| EP | 2619585 B1 | 3/2017 |
| EP | 2845604 B1 | 3/2017 |
| EP | 3134510 A1 | 3/2017 |
| WO | WO 2016/044530 A1 | 3/1916 |
| WO | WO 2016/100975 A1 | 6/1916 |
| WO | WO 2016/126876 A1 | 8/1916 |
| WO | WO 2016/146035 A1 | 9/1916 |
| WO | WO 2017/106638 A1 | 6/1917 |
| WO | WO 2017/184590 A1 | 10/1917 |
| WO | WO 2018/098362 A1 | 5/1918 |
| WO | WO 1990/014148 A1 | 11/1990 |
| WO | WO 1999/019484 A1 | 4/1999 |
| WO | WO 2001/025268 A1 | 4/2001 |
| WO | WO 2001/094935 A2 | 12/2001 |
| WO | WO 2002/037121 A2 | 5/2002 |
| WO | WO 2002/051438 A2 | 7/2002 |
| WO | WO 2002/080649 A2 | 10/2002 |
| WO | WO 2003/038055 A2 | 5/2003 |
| WO | WO 2003/087162 A2 | 10/2003 |
| WO | WO 2007/101227 A2 | 9/2007 |
| WO | WO 2008/109155 A2 | 9/2008 |
| WO | WO 2008/140812 A2 | 11/2008 |
| WO | 2009/072003 A2 | 6/2009 |
| WO | WO 2009/143167 A2 | 11/2009 |
| WO | WO 2010/028288 A2 | 3/2010 |
| WO | 2010/033140 A3 | 5/2010 |
| WO | WO 2011/042467 A1 | 4/2011 |
| WO | WO 2011/060260 A2 | 5/2011 |
| WO | WO 2011/100754 A1 | 8/2011 |
| WO | WO 2011/143656 A2 | 11/2011 |
| WO | WO 2011/149852 A1 | 12/2011 |
| WO | WO 2012/035066 A1 | 3/2012 |
| WO | WO 2012/068360 A1 | 5/2012 |
| WO | WO 2012/136737 A1 | 10/2012 |
| WO | WO 2012/138377 A2 | 10/2012 |
| WO | WO 2013/025925 A1 | 2/2013 |
| WO | WO 2013/138337 A1 | 9/2013 |
| WO | WO 2013/158611 A1 | 10/2013 |
| WO | WO 2014/082729 A1 | 6/2014 |
| WO | WO 2014/093936 A1 | 6/2014 |
| WO | WO 2014/106123 A1 | 7/2014 |
| WO | WO 2014/096136 A2 | 9/2014 |
| WO | WO 2015/095811 A2 | 6/2015 |
| WO | WO 2015/103037 A2 | 7/2015 |
| WO | WO 2015/126921 A1 | 8/2015 |
| WO | WO 2015/130810 A2 | 9/2015 |
| WO | WO 2015/134722 A2 | 9/2015 |
| WO | WO 2015030585 A2 | 9/2015 |
| WO | WO 2015/169945 A2 | 11/2015 |
| WO | WO 2015/172843 A1 | 11/2015 |
| WO | WO 2015/172960 A1 | 11/2015 |
| WO | WO 2015/173317 A1 | 11/2015 |
| WO | WO 2015/193359 A2 | 12/2015 |
| WO | WO 2016/011320 A1 | 1/2016 |
| WO | WO 2016/011357 A1 | 1/2016 |
| WO | WO 2016/011362 A1 | 1/2016 |
| WO | WO 2016/040900 A1 | 3/2016 |
| WO | WO 2016/054013 A1 | 4/2016 |
| WO | WO 2016/062323 A1 | 4/2016 |

(56) References Cited

FOREIGN PATENT DOCUMENTS

| | | |
|---|---|---|
| WO | WO 2016/062659 A1 | 4/2016 |
| WO | 2016/069283 A1 | 5/2016 |
| WO | WO 2016/074915 A1 | 5/2016 |
| WO | WO 2016/081947 A2 | 5/2016 |
| WO | WO 2016/100929 A1 | 6/2016 |
| WO | WO 2016/100977 A1 | 6/2016 |
| WO | WO 2016/102272 A1 | 6/2016 |
| WO | WO 2016/110584 A1 | 7/2016 |
| WO | WO 2016/110587 A1 | 7/2016 |
| WO | WO 2016/128060 A1 | 8/2016 |
| WO | WO 2016/128316 A1 | 8/2016 |
| WO | WO 2016/128376 A1 | 8/2016 |
| WO | WO 2016/131875 A1 | 8/2016 |
| WO | WO 2016126876 A2 | 8/2016 |
| WO | WO 2016/141121 A1 | 9/2016 |
| WO | WO 2016/144976 A1 | 9/2016 |
| WO | WO 2016/146751 A1 | 9/2016 |
| WO | WO 2016/154412 A2 | 9/2016 |
| WO | WO 2016/155809 A1 | 10/2016 |
| WO | WO 2016/156202 A1 | 10/2016 |
| WO | WO 2016/156230 A1 | 10/2016 |
| WO | WO 2016/156398 A1 | 10/2016 |
| WO | WO 2016/168198 A1 | 10/2016 |
| WO | WO 2016/168214 A2 | 10/2016 |
| WO | WO 2016/170139 A1 | 10/2016 |
| WO | WO 2016/172624 A1 | 10/2016 |
| WO | WO 2016/174085 A1 | 11/2016 |
| WO | WO 2016/177784 A1 | 11/2016 |
| WO | WO 2016/179517 A1 | 11/2016 |
| WO | WO 2016/180467 A1 | 11/2016 |
| WO | WO 2016/180778 A1 | 11/2016 |
| WO | WO 2016/183486 A1 | 11/2016 |
| WO | WO 2016/187508 A2 | 11/2016 |
| WO | WO 2016183361 A1 | 11/2016 |
| WO | WO 2016/191545 A1 | 12/2016 |
| WO | WO 2016/196237 A1 | 12/2016 |
| WO | WO 2016/202963 A2 | 12/2016 |
| WO | WO 2016/207164 A2 | 12/2016 |
| WO | WO 2016/207859 A1 | 12/2016 |
| WO | WO 2017/001491 A2 | 1/2017 |
| WO | WO 2017/005733 A2 | 1/2017 |
| WO | WO 2017/005898 A1 | 1/2017 |
| WO | WO 2017/009400 A1 | 1/2017 |
| WO | WO 2017/017232 A1 | 2/2017 |
| WO | WO 2017/021527 A2 | 2/2017 |
| WO | WO 2017/024006 A1 | 2/2017 |
| WO | WO 2017/030956 A1 | 2/2017 |
| WO | WO 2017/036936 A1 | 3/2017 |
| WO | WO 2017/040790 A1 | 3/2017 |
| WO | WO 2017/184590 A1 | 10/2017 |
| WO | 2018/195357 A1 | 10/2018 |
| WO | 2018/227030 A1 | 12/2018 |
| WO | 2019/050994 A1 | 3/2019 |
| WO | 2019/075112 A1 | 4/2019 |
| WO | 2019/104203 A1 | 5/2019 |

OTHER PUBLICATIONS

Larrañaga, P. et al., "Machine Learning in Bioinformatics," Briefings in Bioinformatics, vol. 7, No. 1, pp. 86-112.

Abelin, J.G. et al., "Mass Spectrometry Profiling of HLA-Associated Peptidomes in Mono-Allelic Cells Enables More Accurate Epitope Prediction," Immunity, Feb. 21, 2017, pp. 315-326, vol. 46.

Bassani-Sternberg, M. et al., "Unsupervised HLA Peptide Deconvolution Improves Ligand Prediciton Accuracy and Predicts Cooperative Effects in Peptide-HLA Interactions," The Journal of Immunology, 2016, pp. 2492-2499, vol. 197.

Chang, K.Y. et al., "Prediction of HLA-DQ8 β Cell Peptidome Using a Computational Program and Its Relationship to Autoreactive T Cells," International Immunology, Jun. 14, 2009, pp. 705-713, vol. 21.

Fritsch, E.F. et al., "HLA-Binding Properties of Tumor Neoepitopes in Humans," Cancer Immunology Research, Jun. 1, 2014, pp. 522-529, vol. 2, No. 6.

Lorente, E. et al., "Diversity of Natural Self-Derived Ligands Presented by Different HLA Class I Molecules in Transporter Antigen Processing-Deficient Cells," PLoS One, Mar. 26, 2013, pp. 1-10, vol. 8, e59118.

PCT International Search Report and Written Opinion, PCT Application No. PCT/US17/63133, dated Apr. 6, 2018, 20 pages.

Pearson, H. et al., "MHC Class I-Associated Peptides Derive from Selective Regions of the Human Genome," The Journal of Clinical Investigation, Dec. 2016, vol. 126, No. 12, pp. 4690-4701.

Pritchard, A.L. et al., "Exome Sequencing to Predict Neoantigens in Melanoma," Cancer Immunology Research, Sep. 2015, pp. 992-998, vol. 3, No. 9.

Schumacher, T. et al., "Neoantigens in Cancer Immunotherapy," Science, Apr. 3, 2015, 348(6230): 69-74.

Stranzl, T. et al., "NetCTLpan: Pan-Specific MHC Class I Pathway Epitope Predictions," Immunogenetics, Jun. 2010, 62(6): 357-368.

Suri, A. et al., "Specificity of Peptide Selection by Antigen-Presenting Cells Homozygous or Heterozygous for Expression of Class II MHC Molecules: The Lack of Competition," Proceedings of the National Academy of Sciences, Apr. 29, 2003, pp. 5330-5335, vol. 100, No. 9.

Yadav, M. et al., "Predicting Immunogenic Tumour Mutations by Combining Mass Spectrometry and Exome Sequencing," Nature, Nov. 27, 2014, pp. 572-573, vol. 515.

United States Office Action, U.S. Appl. No. 15/466,729, dated Jun. 20, 2017, 13 pages.

U.S. Appl. No. 62/268,333, filed Dec. 16, 2015, Inventors: Yelensky et al. [Copy Not Enclosed].

Andreatta et al., Accurate Pan-Specific Prediction of Peptide-MHC-Class II Binding Affinity with Improved Binding Core Identification, Immunogenetics, Nov. 2015, vol. 67, pp. 641-650.

Caron et al., "Analysis of Major Histocompatibility Complex (MHC) Immunopeptides Using Mass Spectrometry," Molecular Cellular Proteomics, Oct. 19, 2015, vol. 14, pp. 3105-3117.

Duan, et al, Genomic and Bioinformatic Profiling of Mutational Neopitopes Reveals New rules to Predict Anticancer Immunogenicity, The Journal of Experimental Medicine, Sep. 22, 2014, vol. 211, No. 11, pp. 2231-2248, p. 2240, col. 1, paragraph 3.

Fleri et al., The Immune Eitope Database and Analysis Resource in Epitope Discovery and Synthetic Vaccine Design, Frontiers in Immunology, Mar. 14 2017, vol. 8, No. 278; pp. 1-16; p. 4, col. 1, paragraph 3, p. 8, col. 1, paragraph 7, p. 8, col. 2, paragraph 3.

Johanns et al., "Targeting Neoantigens in Glioblastoma: An Overview of Cancer Immunogenomics and Translational Implications," Neurosurgery, Sep. 1, 2017, vol. 64, pp. 165-176.

Jurtz et al., "NetMHCpan-4.0: Improved Peptide-MHC Class I Interaction Predictions Integrating Eluted Ligand and Peptide binding Affinity Data," The Journal of Immunology, Nov. 1, 2017, vol. 199, No. 9, pp. 3360-3368.

Miller, et al., Correlation Between Somatic Mutation Burden, Neoantigen Load and Progression Free Survival in Multiple Myeloma; Analysis of MMRF CoMMpass Study, Blood, Dec. 2016, vol. 128, No. 22, pp. 193.

Office Action, U.S. Appl. No. 15/466,729, dated Jun. 20, 2017, 13 pages.

Office Action, U.S. Appl. No. 15/466,729, dated Oct. 19, 2017, 12 pages.

Office Action, U.S. Appl. No. 15/381,375, dated Apr. 11, 2019, 2019, 33 pages.

Office Action, U.S. Appl. No. 15/381,375, dated Sep. 5, 2019, 34 pages.

Office Action, U.S. Appl. No. 16/040,409, dated Dec. 27, 2018, 12 pages.

Office Action, U.S. Appl. No. 16/040,409, dated May 22, 2019, 12 pages.

Office Action, U.S. Appl. No. 16/128,421, dated Apr. 3, 2019, 29 pages.

Office Action, U.S. Appl. No. 16/128,421, dated Sep. 6, 2019, 31 pages.

PCT International Search Report and Written Opinion, PCT Application No. PCT/US2016/067159, dated Apr. 27, 2017, 14 pages.

(56) References Cited

OTHER PUBLICATIONS

PCT International Search Report and Written Opinion, PCT Application No. PCT/US2018/028438, dated Aug. 1, 2018, 7 pages.
PCT International Search Report and Written Opinion, PCT Application No. PCT/US18/036571, dated Jun. 8, 2018, 4 pages.
PCT International Search Report and Written Opinion, PCT Application No. PCT/US18/055283, Jan. 17, 1019, 5 pages.
PCT International Search Report and Written Opinion, PCT Application No. PCT/US18/049614, dated Jan. 4, 1019, 5 pages.
PCT International Search Report and Written Opinion, PCT Application No. PCT/US19/019836, dated Jun. 26, 1019, 5 pages.
Rajasaki, et al., Systematic Identification of Personal Tumor-Specific Neoantigens in Chronic Lumphocytic Leukemia. Blood. Jun. 2, 2014; vol. 124, No. 3, pp. 453-462, abstract, p. 454, col. 2, paragraph 4—p. 455, col. 1, paragraph 1, fig 2.
Zhang et al., "MULTIPRED2: A Computational Systems for Large-Scale Identification of Peptides to Bind to HLA Supertypes and Alleles," J Immunol Methods, 374:53-61, 2011.
Clarke, C. et al., "Immunomagnetic Cell Separation" Methods in Molecular Medicine, vol. 58 (2001): Metastasis Research Protocols, vol. 2: Cell Behavior In Vitro and In Vivo, p. 17-25 Edited by: S. A. Brooks and U. Schumacher Humana Press Inc., Totowa, N.J.
DTU Bioinformatics http://www.cbs.dtu.dk/services/NetMHCpan/, Oct. 27, 2019.
http://www.cbs.dtu.dk/services/NetMHCpan/ May 14, 2020.
Integrated DNA Technologies, Hybridization capture, https://www.idtdna.com/pages/products/next-generation-sequencing/hybridization-capture, Jan. 15, 2020.
Juliane Liepe, Fabio Marino, John Sidney, Anita Jeko, Daniel E. Bunting, Alessandro Sette, Peter M. Kloetzel, Michael P. H. Stumpf, Albert J. R. Heck, Michele Mishto. A large fraction of HLA class I ligands are proteasome-generated spliced peptides. Science, Oct. 21, 2016.
Käll, L., Storey, J. D., MacCoss, M. J. & Noble, W. S. Assigning significance to peptides identified by tandem mass spectrometry using decoy databases. J. Proteome Res. 7, 29-34 (2008).
Office Action, U.S. Appl. No. 16/040,409, dated Mar. 12, 2020, 28 pages.
PCT International Preliminary Report on Patentability, PCT Application No. PCT/US2018/055283, dated Apr. 23, 2020, 13 pages.
PCT International Search Report and Written Opinion, PCT Application No. PCT/US18/055283, dated Jan. 17, 2019, 15 pages.
PCT International Search Report and Written Opinion, PCT Application No. PCT/US18/62294, dated Nov. 21, 2018, 24 pages.
PCT International Search Report and Written Opinion, PCT Application No. PCT/US19/019836, dated Jun. 26, 2019, 5 pages.
Supplementary European Search Report, EP16876766, dated Nov. 29, 2019, 8 pages.
Target Capture for NextGen Sequencing—IDT. at <http://www.idtdna.com/pages/products/nextgen/target-capture>, May 19, 2020.
No Author, "The problem with neoantigen prediction," Nat. Biotechnol. 35, 97-97 (2017).
Ochi, Novel adoptive T-cell immunotherapy using a WT1-speci?c TCR vector encoding silencers for endogenous TCRs shows marked antileukemia reactivity and safety, Blood. Aug. 11, 2011;118(6):1495-503.
Office Action, U.S. Appl. No. 16/001,569, dated Feb. 4, 2019, 13 pages.
Office Action, U.S. Appl. No. 16/403,331, dated Oct. 25, 2019, 29 pages.
Okamoto, A promising vector for TCR gene therapy: differential effect of siRNA, 2A peptide, and disulfide bond on the introduced TCR expression, Mol Ther Nucleic Acids. Dec. 2012; 1(12): e63.
Ooi, J. D. et al. Dominant protection from HLA-linked autoimmunity by antigen-specific regulatory T-cells. Nature 545, 243-247 (2017).
Ott, P. A. et al., "An immunogenic personal neoantigen vaccine for patients with melanoma," Nature 547, 217-221 (2017).

O'Donnell, T. J. et al., "MHCflurry: Open-Source Class I MHC Binding Affinity Prediction," Cell Syst. (2018). doi:10.1016/j.cels. 2018.05.014.
Pasetto, A. et al. Tumor-and Neoantigen-Reactive T-cell Receptors Can Be Identified Based on Their Frequency in Fresh Tumor. Cancer Immunol. Res. 4, 734-743 (2016).
PCT International Search Report and Written Opinion, PCT Application No. PCT/US18/036571, dated Oct. 3, 2018, 9 pages.
PCT International Search Report and Written Opinion, PCT Application No. PCT/US18/049614, dated Jan. 4, 2019, 9 pages.
PCT International Search Report and Written Opinion, PCT Application No. PCT/US2017/63133, dated Apr. 6, 2018, pages.
Pertea, M. et al. StringTie enables improved reconstruction of a transcriptome from RNA-seq reads. Nat. Biotechnol. 33, 290-295 (2015).
Polyakova et al., "Proteogenomics meets cancer immunology; mass spectrometric discovery and analysis of neoantigens," Expert Review of Proteomics, vol. 12, No. 5, Jul. 15, 2015, pp. 533-541.
Purcell et al., "Immunoproteomics: Mass Spectrometry-Based Methods to Study the Targets of the Immune Response," Molecular & Cellular Proteomics, American Society for Biochemistry and Molecular Biology, US, vol. 3, No. 3, Mar. 1, 2004, pp. 193-208.
Quintarelli C, Vera JF, Savoldo B, Giordano Attianese GM, Pule M, Foster AE, Co-expression of cytokine and suicide genes to enhance the activity and safety of tumor-specific cytotoxic T lymphocytes. Blood. 2007;110:2793-802.
Rammensee et al., "HLA Ligandome Tumor Antigen Discovery for Personalized Vaccine Approach," Expert Review of Vaccines, vol. 12, No. 10, Oct. 1, 2013, pp. 1211-1127.
Rivas, M. A. et al. Human genomics. Effect of predicted protein-truncating genetic variants on the human transcriptome. Science 348, 666-669 (2015).
Rizvi, N. A. et al.,"Cancer immunology. Mutational landscape determines sensitivity to PD-1 blockade in non-small cell lung cancer," Science 348, 124-128 (2015).
Robbins, P. F. et al. A Pilot Trial Using Lymphocytes Genetically Engineered with an NY-ESO-1-Reactive T-cell Receptor: Long-term Follow-up and Correlates with Response. Clin. Cancer Res. 21, 1019-1027 (2015).
Roberts, A., et al., Identification of novel transcripts in annotated genomes using RNA-Seq. Bioinforma. Oxf. Engl. (2011). doi:10.1093/bioinformatics/btr355.
Roy, C. K., Olson, S., Graveley, B. R., Zamore, P. D. & Moore, M. J. Assessing long-distance RNA sequence connectivity via RNA-templated DNA-DNA ligation. eLife 4, (2015).
Rubinsteyn, A., O'Donnell, T., Damaraju, N. & Hammerbacher, J. Predicting Peptide-MHC Binding Affinities With Imputed Training Data. biorxiv (2016). doi:https://doi.org/10.1101/054775.
Sahin, U. et al., "Personalized RNA mutanome vaccines mobilize poly-specific therapeutic immunity against cancer," Nature 547, 222-226 (2017).
Saunders, C. T. et al., Strelka: accurate somatic small-variant calling from sequenced tumor-normal sample pairs. Bioinforma. Oxf. Engl. 28, 1811-1817 (2012).
Schneider, T. D. & Stephens, R. M. Sequence logos: a new way to display consensus sequences. Nucleic Acids Res. 18, 6097-6100 (1990).
Scholz, E. M. et al. Human Leukocyte Antigen (HLA)-DRB1*15:01 and HLA-DRB5*01:01 Present Complementary Peptide Repertoires. Front. Immunol. 8, 984 (2017).
Sette, A. et al., "The relationship between class I binding affinity and immunogenicity of potential cytotoxic T-cell epitopes," J. Immunol. Baltim. Md 1950 153, 5586-5592 (1994).
Shukla, S.A., Rooney, M.S., Rajasagi, M., Tiao, G., Dixon, P.M., Lawrence, M.S., Stevens, J., Lane, W.J., Dellagatta, J.L., Steelman, S., et al. (2015). Comprehensive analysis of cancer-associated somatic mutations in class I HLA genes. Nat. Biotechnol. 33, 1152-1158.
Skelly, D. A., Johansson, M., Madeoy, J., Wakefield, J. & Akey, J. M. A powerful and flexible statistical framework for testing hypotheses of allele-specific gene expression from RNA-seq data. Genome Res. 21, 1728-1737 (2011).

(56) References Cited

OTHER PUBLICATIONS

Snyder, A. et al. Genetic basis for clinical response to CTLA-4 blockade in melanoma. N. Engl. J. Med. 371, 2189-2199 (2014).
Song, L. & Florea, L. CLASS: constrained transcript assembly of RNA-seq reads. BMC Bioinformatics 14 Suppl 5, S14 (2013).
Stevanovic, S. et al. Landscape of immunogenic tumor antigens in successful immunotherapy of virally induced epithelial cancer. Science 356, 200-205 (2017).
Strønen et al., "Targeting of cancer neoantigens with donor-derived T-cell receptor repertoires," Science 352, 1337-1341 (2016).
Szolek, A. et al. OptiType: precision HLA typing from next-generation sequencing data. Bioinforma. Oxf. Engl. 30, 3310-3316 (2014).
Terakura et al., Generation of CD19-chimeric antigen receptor modified CD8+ T cells derived from virus-specific central memory T cells, (2012) Blood, 1:72-82.
Torikai, A foundation for universal T-cell based immunotherapy: T cells engineered to express a CD19-specific chimeric-antigen-receptor and eliminate expression of endogenous TCR, Blood. Jun. 14, 2012; 119(24): 5697-5705.
Torikai, Hiroki et al "HLA and TCR Knockout by Zinc Finger Nucleases: Toward "off-the-Shelf" Allogeneic T-Cell Therapy for CD19+ Malignancies," Blood 116.21 (2010): 3766.
Tran et al., "Cancer immunotherapy based on mutation-specific CD4+ T-cells in a patient with epithelial cancer," Science 344(6184) 641-645, May 2014.
Tran, E. et al., "Immunogenicity of somatic mutations in human gastrointestinal cancers," Science 350, 1387-1390 (2015).
Tran, E. et al.,"T-Cell Transfer Therapy Targeting Mutant KRAS in Cancer," N. Engl. J. Med. 375, 2255-2262 (2016).
Trolle, T. et al., "The Length Distribution of Class I-Restricted T-cell Epitopes Is Determined by Both Peptide Supply and MHC Allele-Specific Binding Preference," J. Immunol. Baltim. Md 1950 196, 1480-1487 (2016).
Turtle et al., "Artificial Antigen Presenting Cells for Use in Adoptive Immunotherapy," Cancer J. 2010; 16(4): 374-381.
Van Allen, E. M. et al., "Genomic correlates of response to CTLA-4 blockade in metastatic melanoma.," Science 350, 207-211 (2015).
Van Loo, P., Nordgard, S.H., Lingjærde, O.C., Russnes, H.G., Rye, I.H., Sun, W., Weigman, V.J., Marynen, P., Zetterberg, A., Naume, B., et al. (2010). Allele-specific copy number analysis of tumors. Proc. Natl. Acad. Sci. U. S. A. 107, 16910-16915.
Vita, R. et al., "The immune epitope database (IEDB) 3.0," Nucleic Acids Res. 43, D405-412 (2015).
Vitiello, A. & Zanetti, M., "Neoantigen prediction and the need for validation," Nat. Biotechnol. 35, 815-817 (2017).
Vitting-Seerup, K., Porse, B. T., Sandelin, A. & Waage, J. spliceR: an R package for classification of alternative splicing and prediction of coding potential from RNA-seq data. BMC Bioinformatics 15, 81 (2014).
Walter, M. J. et al. Clonal architecture of secondary acute myeloid leukemia. N. Engl. J. Med. 366, 1090-1098 (2012).
Wang et al., Phenotypic and functional attributes of Lentivirus-modified CD19-specific human CD8+ central memory T cells manufactured at clinical scale, (2012) J Immunother. 35(9):689-701.
Goldman JM, et al., HLA-DR monoclonal antibodies inhibit the proliferation of normal and chronic granulocytic leukaemia myeloid progenitor cells. Br J Haematol. Nov. 1982; 52(3):411-20.
Griffioen Retroviral transfer of human CD20 as a suicide gene for adoptive T-cell therapy, Haematologica. Sep. 2009; 94(9): 1316-1320.
Gros, A. et al., "Prospective identification of neoantigen-specific lymphocytes in the peripheral blood of melanoma patients," Nat. Med. 22, 433-438 (2016).
Gubin, et al. "Tumor neoantigens: building a framework for personalized cancer immunotherapy," J. Clin. Invest. 125, 3413-3421 (2015).
Hall M, Liu H, Malafa M, et al. Expansion of tumor-infiltrating lymphocytes (TIL) from human pancreatic tumors. Journal for Immunotherapy of Cancer. 2016;4:61. doi:10.1186/s40425-016-0164-7.
Han et al., Linking T-cell receptor sequence to functional phenotype at the single-cell level, Nat Biotech 2014 (PMID 24952902, doi 10.1038/nbt.2938).
Hegde et al., The surprising complexity of signal sequences, Trends Biochem Sci. Oct. 31, 2006(10):563-71. Epub Aug. 21, 2006.
Howie et al., High-throughput pairing of T cell receptor alpha and beta sequences, Science Translational Medicine 2015 (doi: 10.1126/scitranslmed.aac5624) vol. Issue 301, 301ra131.
Hsu C, Hughes MS, Zheng Z, Bray RB, Rosenberg SA, Morgan RA. Primary human T lymphocytes engineered with a codon-optimized IL-15 gene resist cytokine withdrawal-induced apoptosis and persist long-term in the absence of exogenous cytokine. J Immunol. 2005;175:7226-34.
Hsu C, Jones SA, Cohen CJ, Zheng Z, Kerstann K, Zhou J, Cytokine-independent growth and clonal expansion of a primary human CD8+ T-cell clone following retroviral transduction with the IL-15 gene. Blood. 2007;109:5168-77.
Hunt, D. F. et al. Pillars article: Characterization of peptides bound to the class I MHC molecule HLA-A2.1 by mass spectrometry. Science 1992. 255: 1261-1263, . J. Immunol. Baltim. Md 1950 179, 2669-2671 (2007).
Integrated DNA Technologies, Hybridization capture, https://www.idtdna.com/pages/products/next-generation-sequencing/hybridization-capture.
International Search Report and Written Opinion for PCT/US18/028438 dated Aug. 1, 2018.
International Search Report and Written Opinion for PCT/US18/036571 dated Oct. 3, 2018.
International Search Report and Written Opinion issued for PCT/US2018/055283, dated Jan. 17, 2019.
Janetzki, S. et al. Guidelines for the automated evaluation of Elispot assays. Nat. Protoc. 10, 1098-1115 (2015).
Janetzki, S., et al., Standardization and validation issues of the ELISPOT assay. Methods Mol. Biol. Clifton NJ 302, 51-86 (2005).
Jensen, Kamilla Kjaergaard, et al. "Improved Methods for Prediting Peptide Binding Affinity to MHC Class II Molecules." Immunology, 2018, doi:10.1111/imm.12889.
Johnson, D. B. et al. Melanoma-specific MHC-II expression represents a tumour-autonomous phenotype and predicts response to anti-PD-1/PD-L1 therapy. Nat. Commun. 7, 10582 (2016).
Jørgensen, K. W., Rasmussen, M., Buus, S. & Nielsen, M. NetMHCstab—predicting stability of peptide-MHC-I complexes; impacts for cytotoxic T lymphocyte epitope discovery. Immunology 141, 18-26 (2014).
Karosiene, E. et al. NetMHCIIpan-3.0, a common pan-specific MHC class II prediction method including all three human MHC class II isotypes, HLA-DR, HLA-DP and HLA-DQ. Immunogenetics 65, 711-724 (2013).
Kelderman, S. , Heemskerk, B. , Fanchi, L. , Philips, D. , Toebes, M. , Kvistborg, P., Buuren, M. M., Rooij, N., Michels, S., Germeroth, L., Haanen, J. B. and Schumacher, N. M. (2016), Antigen-specific TIL therapy for melanoma: A flexible platform for personalized cancer immunotherapy. Eur. J. Immunol., 46: 1351-1360. doi:10.1002/eji.201545849.
Kingma, D. & Ba, J. Adam: A method for stochastic optimization. ArXiv Prepr. ArXiv14126980 (2014).
Klebanoff et al., Sorting through subsets which T-Cell populations mediate highly effective adoptive immunotherapy, (2012) J Immunother. 35(9): 651-660.
Kosaloglu-Yalçin, Z. et al. Predicting T cell recognition of MHC class I restricted neoepitopes. J. OncoImmunology, 1-15 (2018).
Kreiter et al., "Mutant MHC class II epitopes drive therapeutic immune responses to cancer," Nature 520, 692-696, Apr. 2015.
Käll, L., et al., Semi-supervised learning for peptide identification from shotgun proteomics datasets. Nat. Methods 4, 923-925 (2007).
Käll, L., et al., Assigning significance to peptides identified by tandem mass spectrometry using decoy databases. J. Proteome Res. 7, 29-34 (2008).

(56) References Cited

OTHER PUBLICATIONS

Käll, L., et al., Non-parametric estimation of posterior error probabilities associated with peptides identified by tandem mass spectrometry. Bioinforma. Oxf. Engl. 24, i42-48 (2008).
Lam, H. Y. K. et al. Nucleotide-resolution analysis of structural variants using BreakSeq and a breakpoint library. Nat. Biotechnol. 28, 47-55 (2010).
Larsen, M. V. et al. An integrative approach to CTL epitope prediction: a combined algorithm integrating MHC class I binding, TAP transport efficiency, and proteasomal cleavage predictions. Eur. J. Immunol. 35, 2295-2303 (2005).
Legut, CRISPR-mediated TCR replacement generates superior anti-cancer transgenic T cells Blood. Jan. 18, 2018;131(3):311-322. doi: 10.1182/blood-2017-05-787598.
Li et al., Increasing the safety and efficacy of chimeric antigen receptor T cell therapy, Protein Cell. Aug. 2017; 8(8): 573-589.
Li, B. & Dewey, C. N. RSEM: accurate transcript quantification from RNA-Seq data with or without a reference genome. BMC Bioinformatics 12, 323 (2011).
Li, H. et al., Fast and accurate short read alignment with Burrows-Wheeler transform. Bioinforma. Oxf. Engl. 25, 1754-1760 (2009).
Liepe, et al., A large fraction of HLA class I ligands are proteasome-generated spliced peptides. Science, Oct. 21, 2016.
Lin Cereghino et al., New selectable marker/auxotrophic host strain combinations for molecular genetic manipulation of Pichia pastoris, Gene, Jan. 24, 2001;263(1-2)159-69.
Liu, C. et al. ATHLATES: accurate typing of human leukocyte antigen through exome sequencing. Nucleic Acids Res. 41, e142 (2013).
Liu, et al., Systematic comparison of 2A peptides for cloning multi-genes in a polycistronic vector, Scientific Reports vol. 7, Article No. 2193 (2017) doi:10.1038/s41598-017-02460-2.
Lundegaard, C., Hoof, I., Lund, O. & Nielsen, M. State of the art and challenges in sequence based T-cell epitope prediction. Immunome Res. 6 Suppl 2, S3 (2010).
Maguire, S. L. et al. SF3B1 mutations constitute a novel therapeutic target in breast cancer. J. Pathol. 235, 571-580 (2015).
Maretty, L., Sibbesen, J. A. & Krogh, A. Bayesian transcriptome assembly. Genome Biol. 15, 501 (2014).
Mayor, N. P. et al. HLA Typing for the Next Generation. PloS One 10, e0127153 (2015).
McGranahan, N., Rosenthal, R., Hiley, C.T., Rowan, A.J., Watkins, T.B.K., Wilson, G.A., Birkbak, N.J., Veeriah, S., Van Loo, P., Herrero, J., et al. (2017). Allele-Specific HLA Loss and Immune Escape in Lung Cancer Evolution. Cell 171, 1259-1271.e11.
Mommen et al., Sampling From the Proteome to the Human Leukocyte Antigen-DR (HLA-DR) Ligandome Proceeds Via High Specificity. Mol Cell Proteomics 15(4): 1412-1423, Apr. 2016.
Moon, EKCarpenito, CSun, JWang, LCKapoor, VPredina, J Expression of a functional CCR2 receptor enhances tumor localization and tumor eradication by retargeted human T-cells expressing a mesothelin-specific chimeric antibody receptor.Clin Cancer Res. 2011; 17: 4719-4730.
Mose, L. E., Wilkerson, M. D., Hayes, D. N., Perou, C. M. & Parker, J. S. ABRA: improved coding indel detection via assembly-based realignment. Bioinforma. Oxf. Engl. 30, 2813-2815 (2014).
Nielsen, et al., NN-align—An artificial neural network-based alignment algorithm for MHC class II peptide binding prediction. BMC Bioinformatics 10:296, Sep. 2009.
Nielsen, et al., "Prediction of MHC class II binding affinity using SMM-align, a novel stabilization matrix alignment method.," BMC Bioinformatics 8:238, Jul. 2007.
Nielsen, M., Lundegaard, C., Lund, O. & Kesmir, C. The role of the proteasome in generating cytotoxic T-cell epitopes: insights obtained from improved predictions of proteasomal cleavage. Immunogenetics 57, 33-41 (2005).
Weinmann, H. "Cancer Immunotherapy: Selected Targets and Small-Molecule Modulators" published Feb. 2, 2016, vol. 11, issue 5 450-466, ChemMedChem (DOI: 10.1002/cmdc.201500566), with Corrigendum ChemMedChem </journal/18607187>vol. 11, Issue 14 </toc/18607187/2016/11/14>, <https://doi.org/10.1002/cmdc.201600319>.
Wilkerson, M. D. et al. Integrated RNA and DNA sequencing improves mutation detection in low purity tumors. Nucleic Acids Res. 42, e107 (2014).
Wu et al., Remote control of therapeutic T cells through a small molecule-gated chimeric receptor, Science. Oct. 16, 2015; 350(6258): aab4077.
Xu, G. et al. RNA CoMPASS: a dual approach for pathogen and host transcriptome analysis of RNA-seq datasets. PloS One 9, e89445 (2014).
Ye, K., et al., Pindel: a pattern growth approach to detect break points of large deletions and medium sized insertions from paired-end short reads. Bioinforma. Oxf. Engl. 25, 2865-2871 (2009).
Yoshida, et al., Splicing factor mutations and cancer. Wiley Interdiscip. Rev. RNA 5, 445-459 (2014).
Zacharakis, N. et al., "Immune recognition of somatic mutations leading to complete durable regression in metastatic breast cancer," Nat. Med. 24, 724-730 (2018).
Zarling, A. L. et al. Identification of class I MHC-associated phosphopeptides as targets for cancer immunotherapy. Proc. Natl. Acad. Sci. U. S. A. 103, 14889-14894 (2006).
Zhang, J. et al. Intratumor heterogeneity in localized lung adenocarcinomas delineated by multiregion sequencing. Science 346, 256-259 (2014).
Zhang, J., et al. "PEAKS DB: de novo sequencing assisted database search for sensitive and accurate peptide identification. Molecular & Cellular Proteomics," 11(4):1-8. Jan. 2, 2012.
Zhou, Q. et al. A chemical genetics approach for the functional assessment of novel cancer genes. Cancer Res. (2015). doi:10.1158/0008-5472.CAN-14-2930.
Abelin, J. G. et al. Complementary IMAC enrichment methods for HLA-associated phosphopeptide identification by mass spectrometry. Nat. Protoc. 10, 1308-1318 (2015).
Altschul et al., Basic local alignment search tool, J. Mol. Biol. 215:403-410 (1990).
An, et al. "Construction of a New Anti-CD19 Chimeric Antigen Receptor and the Anti-Leukemia Function Study of the Transduced T-cells." Oncotarget 7.9 (2016): 10638-10649. PMC. Web. Aug. 16, 2018.
Anagnostou, V. et al. Evolution of Neoantigen Landscape during Immune Checkpoint Blockade in Non-Small Cell Lung Cancer. Cancer Discov. 7, 264-276 (2017).
Anders, S., Pyl, P. T. & Huber, W. HTSeq—a Python framework to work with high-throughput sequencing data. Bioinforma. Oxf. Engl. 31, 166-169 (2015).
Andreatta, M. & Nielsen, M, "Gapped sequence alignment using artificial neural networks: application to the MHC class I system," Bioinforma. Oxf. Engl. 32, 511-517 (2016).
Andreatta, M., Alvarez, B. & Nielsen, M., "GibbsCluster unsupervised clustering and alignment of peptide sequences," Nucleic Acids Res. (2017). doi:10.1093/nar/gkx248.
Andreatta, M., Lund, O. & Nielsen, M., "Simultaneous alignment and clustering of peptide data using a Gibbs sampling approach," Bioinforma. Oxf. Engl. 29, 8-14 (2013).
Barnstable, C. J. et al. Production of monoclonal antibodies to group A erythrocytes, HLA and other human cell surface antigens—new tools for genetic analysis. Cell 14, 9-20 (1978).
Bassani-Sternberg et al, Mass Spectrometry of Human Leukocyte Antigen Class I Peptidomes Reveals Strong Effects of Protein Abundance and Turnover on Antigen Presentation, Mol Cell Proteomics, 14:658-673, 2015.
Bassani-Sternberg, M. et al., "Deciphering HLA-I motifs across HLA peptidomes improves neo-antigen predictions and identifies allostery regulating HLA specificity," PLoS Comput. Biol. 13, e1005725 (2017).
Bassani-Sternberg, M. et al., "Direct identification of clinically relevant neoepitopes presented on native human melanoma tissue by mass spectrometry," Nat. Commun. 7, 13404 (2016).
Bentzen, A. K. et al., "Large-scale detection of antigen-specific T-cells using peptide-MHC-I multimers labeled with DNA barcodes," Nat. Biotechnol. 34, 1037-1045 (2016).

(56) References Cited

OTHER PUBLICATIONS

Bodini, M. et al. The hidden genomic landscape of acute myeloid leukemia: subclonal structure revealed by undetected mutations. Blood 125, 600-605 (2015).
Boegel, S. et al. HLA typing from RNA-Seq sequence reads. Genome Med. 4, 102 (2012).
Boegel, S., et al., A catalog of HLA type, HLA expression, and neo-epitope candidates in human cancer cell lines. Oncoimmunology 3, e954893 (2014).
Boisvert, F.-M. et al. A Quantitative Spatial Proteomics Analysis of Proteome Turnover in Human Cells. Mol. Cell. Proteomics 11, M111.011429-M111.011429 (2012).
Briggs A, Goldfless S, Timberlake S, et al. Tumor-infiltrating immune repertoires captured by single-cell barcoding in emulsion. bioRxiv. 2017. doi.org/10.1101/134841.
Calis, J. J. A. et al. Properties of MHC class I presented peptides that enhance immunogenicity. PLoS Comput. Biol. 9, e1003266 (2013).
Cancer Genome Atlas Research Network. Comprehensive molecular profiling of lung adenocarcinoma. Nature 511, 543-550 (2014).
Carithers, L. J. et al. A Novel Approach to High-Quality Postmortem Tissue Procurement: The GTEx Project. Biopreservation Biobanking 13, 311-319 (2015).
Carreno, B. M. et al. Cancer immunotherapy. A dendritic cell vaccine increases the breadth and diversity of melanoma neoantigen-specific T-cells. Science 348, 803-808 (2015).
Carter, S.L., Cibulskis, K., Helman, E., McKenna, A., Shen, H., Zack, T., Laird, P.W., Onofrio, R.C., Winckler, W., Weir, B.A., et al. (2012). Absolute quantification of somatic DNA alterations in human cancer. Nat. Biotechnol. 30, 413-421.
Cho et al. Human mammalian cell sorting using a highly integrated micro-fabricated fluorescence-activated cell sorter (mFACS), (2010) Lab Chip 10, 1567-1573.
Chollet, F. et al., Keras: The Python Deep Learning library (2015), <https://keras.io/>.
Chudley, L. et al., "Harmonisation of short-term in vitro culture for the expansion of antigen-specific CD8+ T-cells with detection by ELISPOT and HLA-multimer staining," Cancer Immunol. Immunother. 63, 1199-1211 (2014).
Cibulskis, K. et al. Sensitive detection of somatic point mutations in impure and heterogeneous cancer samples. Nat. Biotechnol. 31, 213-219 (2013).
Cieslik, M. et al. The use of exome capture RNA-seq for highly degraded RNA with application to clinical cancer sequencing. Genome Res. 25, 1372-1381 (2015).
Cingolani, P. et al. A program for annotating and predicting the effects of single nucleotide polymorphisms, SnpEff: SNPs in the genome of Drosophila melanogaster strain w1118; iso-2; iso-3. Fly (Austin) 6, 80-92 (2012).
Clarke, Immunomagnetic Cell Separation, From: Methods in Molecular Medicine, vol. 58: Metastasis Research Protocols, vol. 2: Cell Behavior In Vitro and In Vivo, p. 17-25 Edited by: S. A. Brooks and U. Schumacher Humana Press Inc., Totowa, N.J.
Cohen CJ, et al., Isolation of neoantigen-specific T cells from tumor and peripheral lymphocytes. The Journal of Clinical Investigation. 2015;125(10):3981-3991. doi:10.1172/JCI82416.
Craddock, JALu, ABear, APule, MBrenner, MKRooney, CM et al. Enhanced tumor trafficking of GD2 chimeric antigen receptor T-cells by expression of the chemokine receptor CCR2b., J Immunother. 2010; 33: 780-788.
Dash, P. et al. Quantifiable predictive features define epitope-specific T-cell receptor repertoires. Nature 547, 89-93 (2017).
Deniger et al. Molecular Therapy vol. 24, Supplement 1, May 2016, S155.
DePristo, M. A. et al. A framework for variation discovery and genotyping using next-generation DNA sequencing data. Nat Genet. 43, 491-498 (2011).
Desrichard, A., Snyder, A. & Chan, T. A. Cancer Neoantigens and Applications for Immunotherapy. Clin. Cancer Res. Off. J. Am. Assoc. Cancer Res. (2015). doi:10.1158/1078-0432.CCR-14-3175.
Di Marco, M. et al, "Unveiling the Peptide Motifs of HLA-C and HLA-G from Naturally Presented Peptides and Generation of Binding Prediction Matrices," J. Immunol. Baltim. Md 1950 199, 2639-2651 (2017).
DTU Bioinformatics http://www.cbs.dtu.dk/services/NetMHCpan/.
Dudley et al., Generation of Tumor-Infiltrating Lymphocyte Cultures for Use in Adoptive Transfer Therapy for Melanoma Patients. Journal of Immunotherapy 2003; 26(4):332-342.
Dudley ME, Gross CA, Langhan MM, et al. CD8+ enriched "young" tumor infiltrating lymphocytes can mediate regression of metastatic melanoma. Clinical cancer research?: an official journal of the American Association for Cancer Research. 2010;16(24):6122-6131. doi:10.1158/1078-0432.CCR-10-1297.
Eng, J. K. et al. A deeper look into Comet—implementation and features. J. Am. Soc. Mass Spectrom. 26, 1865-1874 (2015).
Eng, J. K., Jahan, T. A. & Hoopmann, M. R. Comet: an open-source MS/MS sequence database search tool. Proteomics 13, 22-24 (2013).
Fortier, M.-H. et al., "The MHC class I peptide repertoire is molded by the transcriptome," J. Exp. Med. 205, 595-610 (2008).
Frampton, G. M. et al. Development and validation of a clinical cancer genomic profiling test based on massively parallel DNA sequencing. Nat. Biotechnol. 31, 1023-1031 (2013).
Furney, S. J. et al. SF3B1 mutations are associated with alternative splicing in uveal melanoma. Cancer Discov. (2013). doi:10.1158/2159-8290.CD-13-0330.
Garrison, E. & Marth, G. Haplotype-based variant detection from short-read sequencing. arXiv (2012).
Gillette, M. A. & Carr, S. A. Quantitative analysis of peptides and proteins in biomedicine by targeted mass spectrometry. Nat. Methods 10, 28-34 (2013).
Glanville, J. et al. Identifying specificity groups in the T-cell receptor repertoire. Nature 547, 94-98 (2017).
Glorot, X. & Bengio, Y. Understanding the difficulty of training deep feedforward neural networks. in Proceedings of the Thirteenth International Conference on Artificial Intelligence and Statistics 249-256 (2010).
Godin et al., Microfluidics and photonics for Bio-System-on-a-Chip: A review of advancements in technology towards a microfluidic flow cytometry chip, (2008) J Biophoton. 1(5):355-376.

* cited by examiner

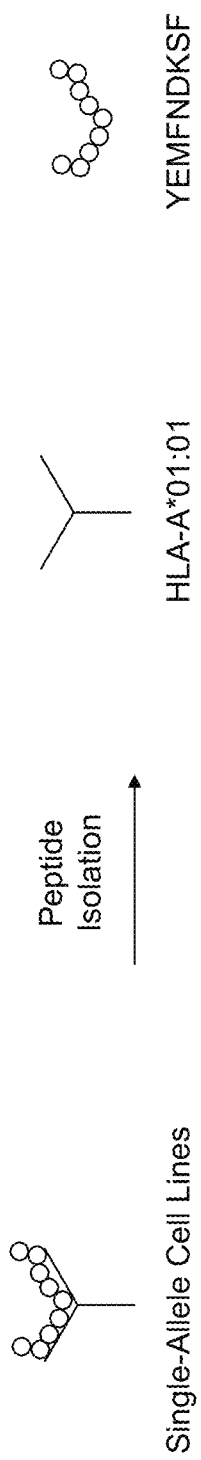
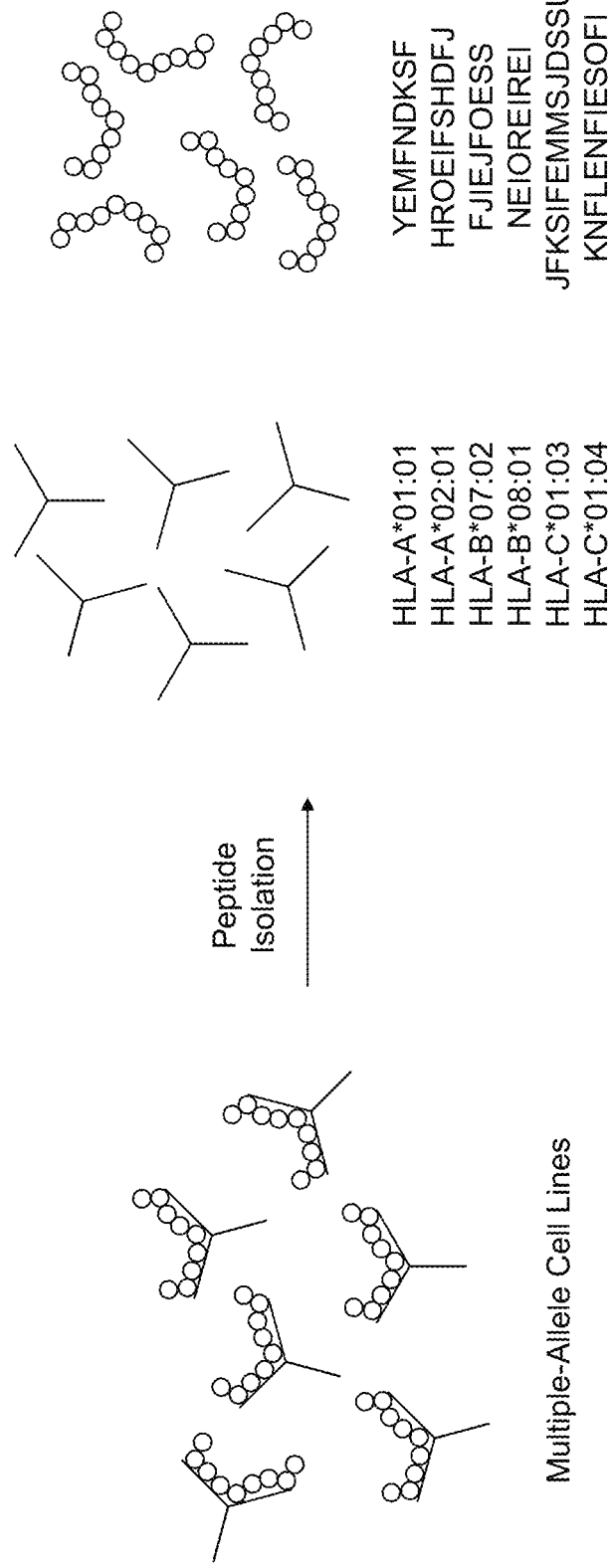
FIG. 2B
FIG. 2C

| Peptide Sequence ($p^i$) | Affinity ($b^i$-nM) | Stability ($s^i$-h) | Allele ($a^i$) | C-Flanking Sequence ($c^i$) | mRNA Q. ($m^i$-FPKM) | Label ($y^i$) |
|---|---|---|---|---|---|---|
| QCEIOWARE | 1000 | 1 | HLA-C*01:03 | FJELFISBOSJFIE | $10^2$ | Not Presented |
| FIEUHFWI | 1500 | 15 | HLA-C*01:03 | FEGRKUOOI | $10^{-3}$ | Presented |
| FEWRHRJTRUJR | 650 | 20 | HLA-C*01:03 | PJFIOEJOIJGEIO | $10^1$ | Presented |
| QIEJOEIJE | 500 | 1 | HLA-B*07:02 | PJFIOEJOIJGEIO | 1 | Presented |
| | 600 | 14 | HLA-C*01:03 | | | |
| | 1200 | 7 | HLA-A*01:01 | | | |

Allele-Dependent ($x^i$) — Allele-Independent ($w^i$)

Training Data 170A

FIG. 4

| Model | AUC | Log Loss | PPV at 10% Recall |
|---|---|---|---|
| Sigmoid-of-Sums | 0.9278 | $12.2 \cdot 10^{-4}$ | 0.114 |
| Sum-of-Sigmoids | 0.9723 | $5.78 \cdot 10^{-4}$ | 0.152 |
| Hyperbolic Tangent | 0.9734 | $5.72 \cdot 10^{-4}$ | 0.156 |
| Second Order | 0.9727 | $5.74 \cdot 10^{-4}$ | 0.160 |

FIG. 13C

| Model | AUC | Log Loss | PPV at 10% Recall |
|---|---|---|---|
| With A2/B7 Single-Allele Data | 0.9818 | $5.40 \cdot 10^{-4}$ | 0.215 |
| Without A2/B7 Single-Allele Data | 0.9803 | $5.31 \cdot 10^{-4}$ | 0.211 |

FIG. 13D

| Setup | Correlation |
|---|---|
| A2 model predicting B7 | 0.004 |
| A2 model predicting A2 | 0.294 |
| B7 model predicting B7 | 0.366 |
| B7 model predicting A2 | 0.002 |

FIG. 13E

| Allele | P2 | P9 |
|---|---|---|
| A2 | L 80% | V 58% |
|    | M 5%  | L 32% |
| B7 | P 98% | L 76% |
|    |       | V 8%  |

FIG. 13F

| Model | AUC | Log Loss | PPV at 10% Recall |
|---|---|---|---|
| Allele-interacting | 0.9723 | $5.78 \cdot 10^{-4}$ | 0.152 |
| Allele-noninteracting | 0.9732 | $5.53 \cdot 10^{-4}$ | 0.188 |

FIG. 13G

NEOANTIGEN IDENTIFICATION, MANUFACTURE, AND USE

CROSS REFERENCE TO RELATED APPLICATIONS

This application is a continuation of U.S. patent application Ser. No. 15/466,729, filed Mar. 22, 2017, which is a continuation of U.S. patent application Ser. No. 15/381,375, filed Dec. 16, 2016, which claims the benefit of and priority to U.S. Provisional Application 62/268,333, filed Dec. 16, 2015, U.S. Provisional Application 62/317,823, filed Apr. 4, 2016, U.S. Provisional Application 62/379,986, filed Aug. 26, 2016, U.S. Provisional Application 62/394,074, filed Sep. 13, 2016, and U.S. Provisional Application 62/425,995, filed Nov. 23, 2016, each of which is incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Mar. 8, 2017, is named 36842US_CRF-_sequencelisting.txt and is 7,588 bytes in size.

BACKGROUND

Therapeutic vaccines based on tumor-specific neoantigens hold great promise as a next-generation of personalized cancer immunotherapy.[1-3] Cancers with a high mutational burden, such as non-small cell lung cancer (NSCLC) and melanoma, are particularly attractive targets of such therapy given the relatively greater likelihood of neoantigen generation.[4,5] Early evidence shows that neoantigen-based vaccination can elicit T-cell responses[6] and that neoantigen targeted cell-therapy can cause tumor regression under certain circumstances in selected patients.[7]

One question for neoantigen vaccine design is which of the many coding mutations present in subject tumors can generate the "best" therapeutic neoantigens, e.g., antigens that can elicit anti-tumor immunity and cause tumor regression.

Initial methods have been proposed incorporating mutation-based analysis using next-generation sequencing, RNA gene expression, and prediction of MHC binding affinity of candidate neoantigen peptides[8]. However, these proposed methods can fail to model the entirety of the epitope generation process, which contains many steps (e.g., TAP transport, proteasomal cleavage, and/or TCR recognition) in addition to gene expression and MHC binding[9]. Consequently, existing methods are likely to suffer from reduced low positive predictive value (PPV). (FIG. 1A)

Indeed, analyses of peptides presented by tumor cells performed by multiple groups have shown that <5% of peptides that are predicted to be presented using gene expression and MHC binding affinity can be found on the tumor surface MHC[10,11] (FIG. 1B). This low correlation between binding prediction and MHC presentation was further reinforced by recent observations of the lack of predictive accuracy improvement of binding-restricted neoantigens for checkpoint inhibitor response over the number of mutations alone.[12]

This low positive predictive value (PPV) of existing methods for predicting presentation presents a problem for neoantigen-based vaccine design. If vaccines are designed using predictions with a low PPV, most patients are unlikely to receive a therapeutic neoantigen and fewer still are likely to receive more than one (even assuming all presented peptides are immunogenic). Thus, neoantigen vaccination with current methods is unlikely to succeed in a substantial number of subjects having tumors. (FIG. 1C)

Additionally, previous approaches generated candidate neoantigens using only cis-acting mutations, and largely neglected to consider additional sources of neo-ORFs, including mutations in splicing factors, which occur in multiple tumor types and lead to aberrant splicing of many genes[13], and mutations that create or remove protease cleavage sites.

Finally, standard approaches to tumor genome and transcriptome analysis can miss somatic mutations that give rise to candidate neoantigens due to suboptimal conditions in library construction, exome and transcriptome capture, sequencing, or data analysis. Likewise, standard tumor analysis approaches can inadvertently promote sequence artifacts or germline polymorphisms as neoantigens, leading to inefficient use of vaccine capacity or auto-immunity risk, respectively.

SUMMARY

Disclosed herein is an optimized approach for identifying and selecting neoantigens for personalized cancer vaccines. First, optimized tumor exome and transcriptome analysis approaches for neoantigen candidate identification using next-generation sequencing (NGS) are addressed. These methods build on standard approaches for NGS tumor analysis to ensure that the highest sensitivity and specificity neoantigen candidates are advanced, across all classes of genomic alteration. Second, novel approaches for high-PPV neoantigen selection are presented to overcome the specificity problem and ensure that neoantigens advanced for vaccine inclusion are more likely to elicit anti-tumor immunity. These approaches include, depending on the embodiment, trained statistic regression or nonlinear deep learning models that jointly model peptide-allele mappings as well as the per-allele motifs for peptide of multiple lengths, sharing statistical strength across peptides of different lengths. The nonlinear deep learning models particularly can be designed and trained to treat different MHC alleles in the same cell as independent, thereby addressing problems with linear models that would have them interfere with each other. Finally, additional considerations for personalized vaccine design and manufacturing based on neoantigens are addressed.

BRIEF DESCRIPTION OF THE SEVERAL VIEWS OF THE DRAWINGS

These and other features, aspects, and advantages of the present invention will become better understood with regard to the following description, and accompanying drawings, where:

FIGS. 2B and 2C illustrate a method of obtaining presentation information, in accordance with an embodiment. FIG. 2B discloses SEQ ID NO: 3. FIG. 2C discloses SEQ ID NOS 3-8, respectively, in order of appearance.

FIG. 4 illustrates an example set of training data, according to one embodiment. Figure discloses the "Peptide Sequences" as SEQ ID NOS 10-13 and the "C-Flanking Sequences" as SEQ ID NOS 14, 19-20, and 20, respectively, in order of appearance.

FIG. 13C compares performance results for an example function-of-sums model, an example sum-of-functions model, and an example second order model for predicting peptide presentation on multiple-allele mass spectrometry data.

FIG. 13D compares performance results for two example presentation models that are trained with and without single-allele mass spectrometry data on predicting peptide presentation for multiple-allele mass spectrometry data.

FIG. 13E shows performance for example models shown in FIG. 13D on single-allele mass spectrometry data that were held out in the analysis shown in FIG. 13D.

FIG. 13F shows the common anchor residues at positions 2 and 9 among nonamers predicted by the "without A2/B7 single-allele data" example model shown in FIG. 13D.

FIG. 13G compares performance results between an example presentation model that incorporated C- and N-terminal flanking sequences as allele-interacting variables, and an example presentation model that incorporated C- and N-terminal flanking sequences as allele-noninteracting variables.

DETAILED DESCRIPTION

I. Definitions

Figure 1A:
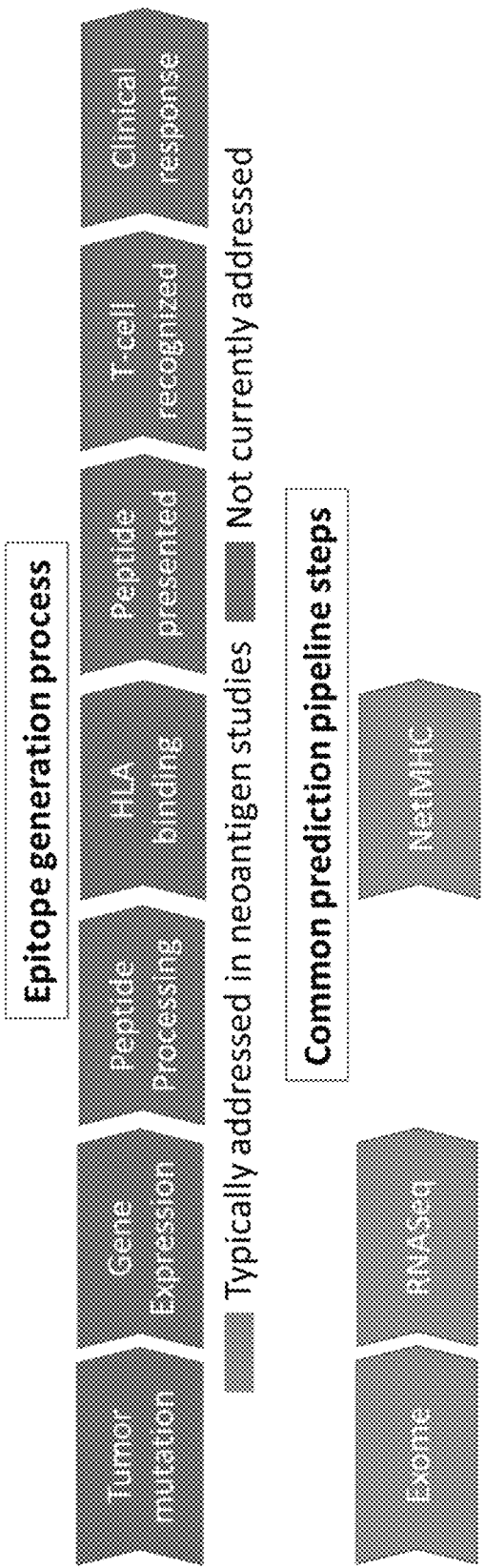
FIG. 1A shows current clinical approaches to neoantigen identification.
Figure 1B:
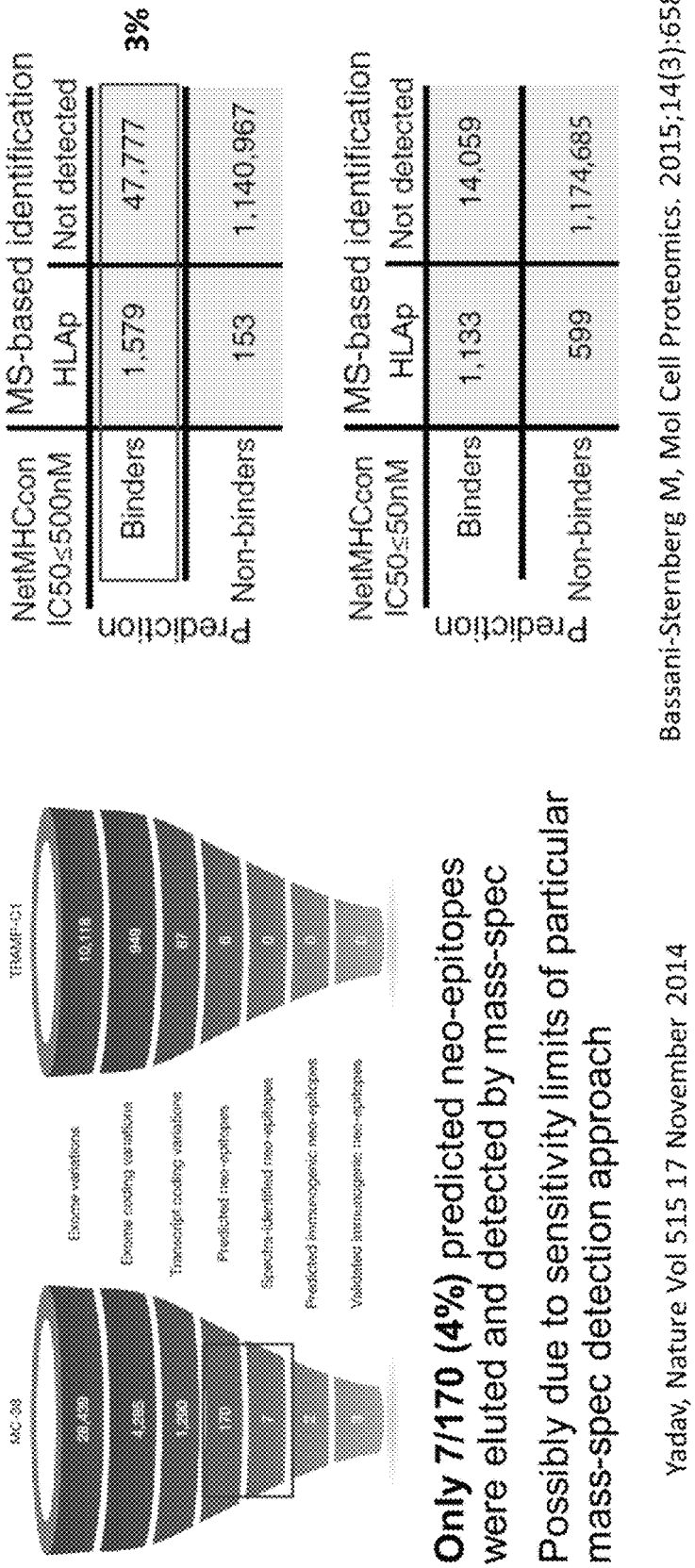
FIG. 1B shows that <5% of predicted bound peptides are presented on tumor cells.
Figure 1C:
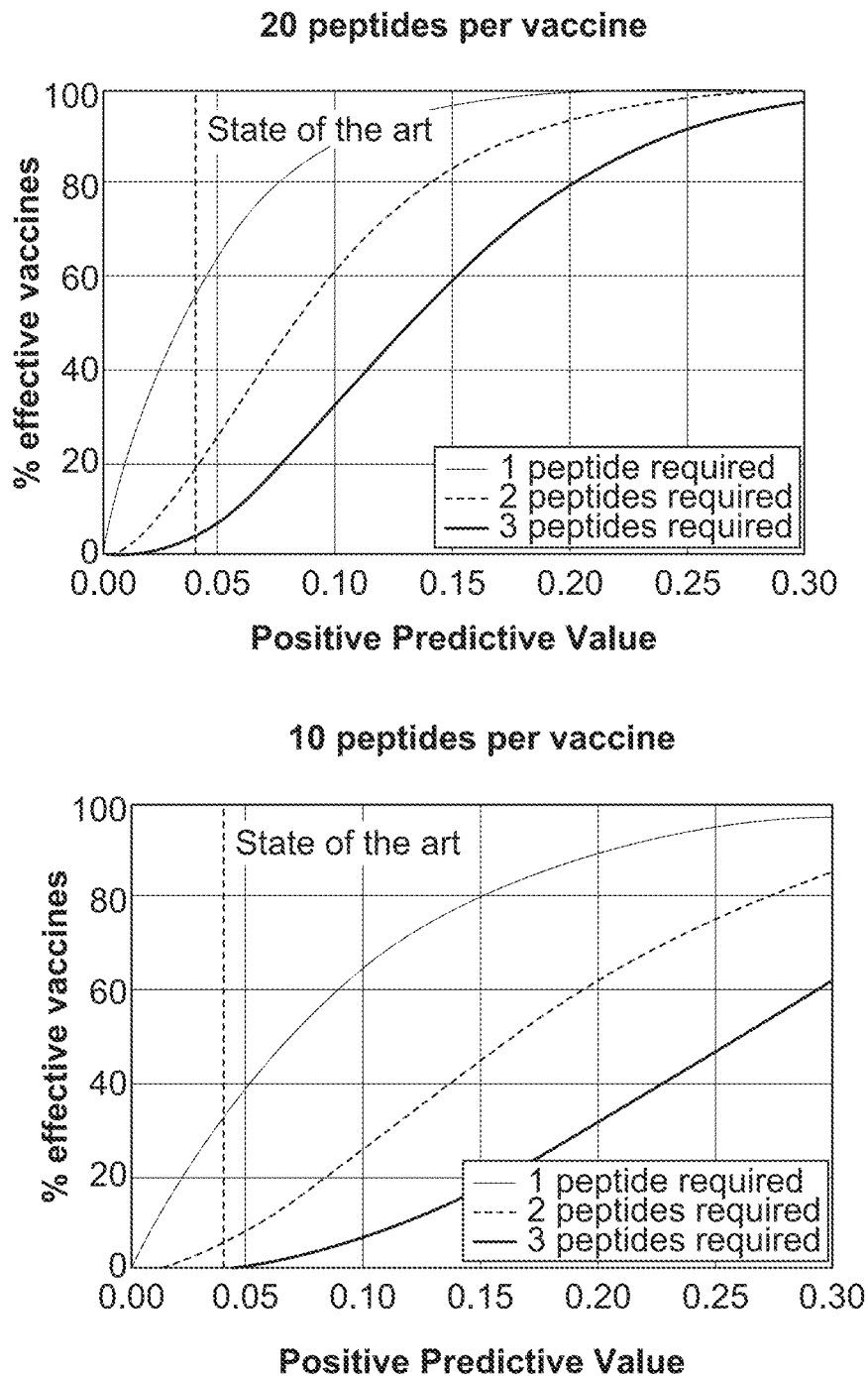
FIG. 1C shows the impact of the neoantigen prediction specificity problem.

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

As used herein the term "antigen" is a substance that induces an immune response.

As used herein the term "neoantigen" is an antigen that has at least one alteration that makes it distinct from the corresponding wild-type, parental antigen, e.g., via mutation in a tumor cell or post-translational modification specific to a tumor cell. A neoantigen can include a polypeptide sequence or a nucleotide sequence. A mutation can include a frameshift or nonframeshift indel, missense or nonsense substitution, splice site alteration, genomic rearrangement or gene fusion, or any genomic or expression alteration giving rise to a neoORF. A mutations can also include a splice variant. Post-translational modifications specific to a tumor cell can include aberrant phosphorylation. Post-translational modifications specific to a tumor cell can also include a proteasome-generated spliced antigen. See Liepe et al., A large fraction of HLA class I ligands are proteasome-generated spliced peptides; Science. 2016 Oct. 21; 354 (6310):354-358.

As used herein the term "tumor neoantigen" is a neoantigen present in a subject's tumor cell or tissue but not in the subject's corresponding normal cell or tissue.

As used herein the term "neoantigen-based vaccine" is a vaccine construct based on one or more neoantigens, e.g., a plurality of neoantigens.

As used herein the term "candidate neoantigen" is a mutation or other aberration giving rise to a new sequence that may represent a neoantigen.

As used herein the term "coding region" is the portion(s) of a gene that encode protein.

As used herein the term "coding mutation" is a mutation occurring in a coding region.

As used herein the term "ORF" means open reading frame.

As used herein the term "NEO-ORF" is a tumor-specific ORF arising from a mutation or other aberration such as splicing.

As used herein the term "missense mutation" is a mutation causing a substitution from one amino acid to another.

As used herein the term "nonsense mutation" is a mutation causing a substitution from an amino acid to a stop codon.

As used herein the term "frameshift mutation" is a mutation causing a change in the frame of the protein.

As used herein the term "indel" is an insertion or deletion of one or more nucleic acids.

As used herein, the term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Alternatively, sequence similarity or dissimilarity can be established by the combined presence or absence of particular nucleotides, or, for translated sequences, amino acids at selected sequence positions (e.g., sequence motifs).

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

As used herein the term "non-stop or read-through" is a mutation causing the removal of the natural stop codon.

As used herein the term "epitope" is the specific portion of an antigen typically bound by an antibody or T cell receptor.

As used herein the term "immunogenic" is the ability to elicit an immune response, e.g., via T cells, B cells, or both.

As used herein the term "HLA binding affinity" "MHC binding affinity" means affinity of binding between a specific antigen and a specific MHC allele.

As used herein the term "bait" is a nucleic acid probe used to enrich a specific sequence of DNA or RNA from a sample.

As used herein the term "variant" is a difference between a subject's nucleic acids and the reference human genome used as a control.

As used herein the term "variant call" is an algorithmic determination of the presence of a variant, typically from sequencing.

As used herein the term "polymorphism" is a germline variant, i.e., a variant found in all DNA-bearing cells of an individual.

As used herein the term "somatic variant" is a variant arising in non-germline cells of an individual.

As used herein the term "allele" is a version of a gene or a version of a genetic sequence or a version of a protein.

As used herein the term "HLA type" is the complement of HLA gene alleles.

As used herein the term "nonsense-mediated decay" or "NMD" is a degradation of an mRNA by a cell due to a premature stop codon.

As used herein the term "truncal mutation" is a mutation originating early in the development of a tumor and present in a substantial portion of the tumor's cells.

As used herein the term "subclonal mutation" is a mutation originating later in the development of a tumor and present in only a subset of the tumor's cells.

As used herein the term "exome" is a subset of the genome that codes for proteins. An exome can be the collective exons of a genome.

As used herein the term "logistic regression" is a regression model for binary data from statistics where the logit of the probability that the dependent variable is equal to one is modeled as a linear function of the dependent variables.

As used herein the term "neural network" is a machine learning model for classification or regression consisting of multiple layers of linear transformations followed by element-wise nonlinearities typically trained via stochastic gradient descent and back-propagation.

As used herein the term "proteome" is the set of all proteins expressed and/or translated by a cell, group of cells, or individual.

As used herein the term "peptidome" is the set of all peptides presented by MHC-I or MHC-II on the cell surface. The peptidome may refer to a property of a cell or a collection of cells (e.g., the tumor peptidome, meaning the union of the peptidomes of all cells that comprise the tumor).

As used herein the term "ELISPOT" means Enzyme-linked immunosorbent spot assay—which is a common method for monitoring immune responses in humans and animals.

As used herein the term "dextramers" is a dextran-based peptide-MHC multimers used for antigen-specific T-cell staining in flow cytometry.

As used herein the term "tolerance or immune tolerance" is a state of immune non-responsiveness to one or more antigens, e.g. self-antigens.

As used herein the term "central tolerance" is a tolerance affected in the thymus, either by deleting self-reactive T-cell clones or by promoting self-reactive T-cell clones to differentiate into immunosuppressive regulatory T-cells (Tregs).

As used herein the term "peripheral tolerance" is a tolerance affected in the periphery by downregulating or anergizing self-reactive T-cells that survive central tolerance or promoting these T cells to differentiate into Tregs.

The term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female. The term subject is inclusive of mammals including humans.

The term "mammal" encompasses both humans and non-humans and includes but is not limited to humans, non-human primates, canines, felines, murines, bovines, equines, and porcines.

The term "clinical factor" refers to a measure of a condition of a subject, e.g., disease activity or severity. "Clinical factor" encompasses all markers of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition. A clinical factor can also be predicted by markers and/or other parameters such as gene expression surrogates. Clinical factors can include tumor type, tumor sub-type, and smoking history.

Abbreviations

MHC: major histocompatibility complex; HLA: human leukocyte antigen, or the human MHC gene locus; NGS: next-generation sequencing; PPV: positive predictive value; TSNA: tumor-specific neoantigen; FFPE: formalin-fixed, paraffin-embedded; NMD: nonsense-mediated decay; NSCLC: non-small-cell lung cancer; DC: dendritic cell.

It should be noted that, as used in the specification and the appended claims, the singular forms "a," "an," and "the" include plural referents unless the context clearly dictates otherwise.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All references, issued patents and patent applications cited within the body of the specification are hereby incorporated by reference in their entirety, for all purposes.

II. Methods of Identifying Neoantigens

Disclosed herein is are methods for identifying neoantigens from a tumor of a subject that are likely to be presented on the cell surface of the tumor and/or are likely to be immunogenic. As an example, one such method may comprise the steps of: obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one alteration that makes it distinct from the corresponding wild-type, parental peptide sequence; inputting the peptide sequence of each neoantigen into one or more presentation models to generate a set of numerical likelihoods that each of the neoantigens is presented by one or more MHC alleles on the tumor cell surface of the tumor cell of the subject or cells present in the tumor, the set of numerical likelihoods having been identified at least based on received mass spectrometry data; and selecting a subset of the set of neoantigens based on the set of numerical likelihoods to generate a set of selected neoantigens.

The presentation model can comprise a statistical regression or a machine learning (e.g., deep learning) model trained on a set of reference data (also referred to as a training data set) comprising a set of corresponding labels, wherein the set of reference data is obtained from each of a plurality of distinct subjects where optionally some subjects can have a tumor, and wherein the set of reference data comprises at least one of: data representing exome nucleotide sequences from tumor tissue, data representing exome nucleotide sequences from normal tissue, data representing transcriptome nucleotide sequences from tumor tissue, data representing proteome sequences from tumor tissue, and data representing MHC peptidome sequences from tumor tissue, and data representing MHC peptidome sequences from normal tissue. The reference data can further comprise mass spectrometry data, sequencing data, RNA sequencing data, and proteomics data for single-allele cell lines engineered to express a predetermined MHC allele that are subsequently exposed to synthetic protein, normal and tumor human cell lines, and fresh and frozen primary samples, and T cell assays (e.g., ELISPOT). In certain aspects, the set of reference data includes each form of reference data.

The presentation model can comprise a set of features derived at least in part from the set of reference data, and wherein the set of features comprises at least one of allele dependent-features and allele-independent features. In certain aspects each feature is included.

Dendritic cell presentation to naïve T cell features can comprise at least one of: A feature described above. The dose and type of antigen in the vaccine. (e.g., peptide, mRNA, virus, etc.): (1) The route by which dendritic cells (DCs) take up the antigen type (e.g., endocytosis, micropinocytosis); and/or (2) The efficacy with which the antigen is taken up by DCs. The dose and type of adjuvant in the vaccine. The length of the vaccine antigen sequence. The number and sites of vaccine administration. Baseline patient immune functioning (e.g., as measured by history of recent infections, blood counts, etc). For RNA vaccines: (1) the turnover rate of the mRNA protein product in the dendritic cell; (2) the rate of translation of the mRNA after uptake by dendritic cells as measured in in vitro or in vivo experiments; and/or (3) the number or rounds of translation of the mRNA after uptake by dendritic cells as measured by in vivo or in vitro experiments. The presence of protease cleavage motifs in the peptide, optionally giving additional weight to proteases typically expressed in dendritic cells (as measured by RNA-seq or mass spectrometry). The level of expression of the proteasome and immunoproteasome in typical activated dendritic cells (which may be measured by RNA-seq, mass spectrometry, immunohistochemistry, or other standard techniques). The expression levels of the particular MHC allele in the individual in question (e.g., as measured by RNA-seq or mass spectrometry), optionally measured specifically in activated dendritic cells or other immune cells. The probability of peptide presentation by the particular MHC allele in other individuals who express the particular MHC allele, optionally measured specifically in activated dendritic cells or other immune cells. The probability of peptide presentation by MHC alleles in the same family of molecules (e.g., HLA-A, HLA-B, HLA-C, HLA-DQ, HLA-DR, HLA-DP) in other individuals, optionally measured specifically in activated dendritic cells or other immune cells.

Immune tolerance escape features can comprise at least one of: Direct measurement of the self-peptidome via protein mass spectrometry performed on one or several cell types. Estimation of the self-peptidome by taking the union of all k-mer (e.g. 5-25) substrings of self-proteins. Estimation of the self-peptidome using a model of presentation similar to the presentation model described above applied to all non-mutation self-proteins, optionally accounting for germline variants.

Ranking can be performed using the plurality of neoantigens provided by at least one model based at least in part on the numerical likelihoods. Following the ranking a selecting can be performed to select a subset of the ranked neoantigens according to a selection criteria. After selecting a subset of the ranked peptides can be provided as an output.

A number of the set of selected neoantigens may be 20.

The presentation model may represent dependence between presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

A method disclosed herein can also include applying the one or more presentation models to the peptide sequence of the corresponding neoantigen to generate a dependency score for each of the one or more MHC alleles indicating whether the MHC allele will present the corresponding neoantigen based on at least positions of amino acids of the peptide sequence of the corresponding neoantigen.

A method disclosed herein can also include transforming the dependency scores to generate a corresponding per-allele likelihood for each MHC allele indicating a likelihood that the corresponding MHC allele will present the corresponding neoantigen; and combining the per-allele likelihoods to generate the numerical likelihood.

The step of transforming the dependency scores can model the presentation of the peptide sequence of the corresponding neoantigen as mutually exclusive.

A method disclosed herein can also include transforming a combination of the dependency scores to generate the numerical likelihood.

The step of transforming the combination of the dependency scores can model the presentation of the peptide sequence of the corresponding neoantigen as interfering between MHC alleles.

The set of numerical likelihoods can be further identified by at least an allele noninteracting feature, and a method disclosed herein can also include applying an allele noninteracting one of the one or more presentation models to the allele noninteracting features to generate a dependency score for the allele noninteracting features indicating whether the peptide sequence of the corresponding neoantigen will be presented based on the allele noninteracting features.

A method disclosed herein can also include combining the dependency score for each MHC allele in the one or more MHC alleles with the dependency score for the allele noninteracting feature; transforming the combined dependency scores for each MHC allele to generate a corresponding per-allele likelihood for the MHC allele indicating a likelihood that the corresponding MHC allele will present the corresponding neoantigen; and combining the per-allele likelihoods to generate the numerical likelihood.

A method disclosed herein can also include transforming a combination of the dependency scores for each of the MHC alleles and the dependency score for the allele noninteracting features to generate the numerical likelihood.

A set of numerical parameters for the presentation model can be trained based on a training data set including at least a set of training peptide sequences identified as present in a plurality of samples and one or more MHC alleles associated with each training peptide sequence, wherein the training peptide sequences are identified through mass spectrometry on isolated peptides eluted from MHC alleles derived from the plurality of samples.

The samples can also include cell lines engineered to express a single MHC class I or class II allele.

The samples can also include cell lines engineered to express a plurality of MHC class I or class II alleles.

The samples can also include human cell lines obtained or derived from a plurality of patients.

The samples can also include fresh or frozen tumor samples obtained from a plurality of patients.

The samples can also include fresh or frozen tissue samples obtained from a plurality of patients.

The samples can also include peptides identified using T-cell assays.

The training data set can further include data associated with: peptide abundance of the set of training peptides present in the samples; peptide length of the set of training peptides in the samples.

The training data set may be generated by comparing the set of training peptide sequences via alignment to a database comprising a set of known protein sequences, wherein the set of training protein sequences are longer than and include the training peptide sequences.

The training data set may be generated based on performing or having performed nucleotide sequencing on a cell line to obtain at least one of exome, transcriptome, or whole genome sequencing data from the cell line, the sequencing data including at least one nucleotide sequence including an alteration.

The training data set may be generated based on obtaining at least one of exome, transcriptome, and whole genome normal nucleotide sequencing data from normal tissue samples.

The training data set may further include data associated with proteome sequences associated with the samples.

The training data set may further include data associated with MHC peptidome sequences associated with the samples.

The training data set may further include data associated with peptide-MHC binding affinity measurements for at least one of the isolated peptides.

The training data set may further include data associated with peptide-MHC binding stability measurements for at least one of the isolated peptides.

The training data set may further include data associated with transcriptomes associated with the samples.

The training data set may further include data associated with genomes associated with the samples.

The training peptide sequences may be of lengths within a range of k-mers where k is between 8-15, inclusive for MHC class I or 9-30 inclusive for MHC class II.

A method disclosed herein can also include encoding the peptide sequence using a one-hot encoding scheme.

A method disclosed herein can also include encoding the training peptide sequences using a left-padded one-hot encoding scheme.

A method of treating a subject having a tumor, comprising performing the steps of claim 1, and further comprising obtaining a tumor vaccine comprising the set of selected neoantigens, and administering the tumor vaccine to the subject.

Also disclosed herein is a methods for manufacturing a tumor vaccine, comprising the steps of: obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one mutation that makes it distinct from the corresponding wild-type, parental peptide sequence; inputting the peptide sequence of each neoantigen into one or more presentation models to generate a set of numerical likelihoods that each of the neoantigens is presented by one or more MHC alleles on the tumor cell surface of the tumor cell of the subject, the set of numerical likelihoods having been identified at least based on received mass spectrometry data; and selecting a subset of the set of neoantigens based on the set of numerical likelihoods to generate a set of selected neoantigens; and producing or having produced a tumor vaccine comprising the set of selected neoantigens.

Also disclosed herein is a tumor vaccine including a set of selected neoantigens selected by performing the method comprising the steps of: obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one mutation that makes it distinct from the corresponding wild-type, parental peptide sequence; inputting the peptide sequence of each neoantigen into one or more presentation models to generate a set of numerical likelihoods that each of the neoantigens is presented by one or more MHC alleles on the tumor cell surface of the tumor cell of the subject, the set of numerical likelihoods having been identified at least based on received mass spectrometry data; and selecting a subset of the set of neoantigens based on the set of numerical likelihoods to generate a set of selected neoantigens; and producing or having produced a tumor vaccine comprising the set of selected neoantigens.

The tumor vaccine may include one or more of a nucleotide sequence, a polypeptide sequence, RNA, DNA, a cell, a plasmid, or a vector.

The tumor vaccine may include one or more neoantigens presented on the tumor cell surface.

The tumor vaccine may include one or more neoantigens that is immunogenic in the subject.

The tumor vaccine may not include one or more neoantigens that induce an autoimmune response against normal tissue in the subject.

The tumor vaccine may include an adjuvant.

The tumor vaccine may include an excipient.

A method disclosed herein may also include selecting neoantigens that have an increased likelihood of being presented on the tumor cell surface relative to unselected neoantigens based on the presentation model.

A method disclosed herein may also include selecting neoantigens that have an increased likelihood of being capable of inducing a tumor-specific immune response in the subject relative to unselected neoantigens based on the presentation model.

A method disclosed herein may also include selecting neoantigens that have an increased likelihood of being capable of being presented to naïve T cells by professional antigen presenting cells (APCs) relative to unselected neoantigens based on the presentation model, optionally wherein the APC is a dendritic cell (DC).

A method disclosed herein may also include selecting neoantigens that have a decreased likelihood of being subject to inhibition via central or peripheral tolerance relative to unselected neoantigens based on the presentation model.

A method disclosed herein may also include selecting neoantigens that have a decreased likelihood of being capable of inducing an autoimmune response to normal tissue in the subject relative to unselected neoantigens based on the presentation model.

The exome or transcriptome nucleotide sequencing data may be obtained by performing sequencing on the tumor tissue.

The sequencing may be next generation sequencing (NGS) or any massively parallel sequencing approach.

The set of numerical likelihoods may be further identified by at least MHC-allele interacting features comprising at least one of: the predicted affinity with which the MHC allele and the neoantigen encoded peptide bind; the predicted stability of the neoantigen encoded peptide-MHC complex; the sequence and length of the neoantigen encoded peptide; the probability of presentation of neoantigen encoded peptides with similar sequence in cells from other individuals expressing the particular MHC allele as assessed by mass-spectrometry proteomics or other means; the expression levels of the particular MHC allele in the subject in question (e.g. as measured by RNA-seq or mass spectrometry); the overall neoantigen encoded peptide-sequence-independent probability of presentation by the particular MHC allele in other distinct subjects who express the particular MHC allele; the overall neoantigen encoded peptide-sequence-independent probability of presentation by MHC alleles in the same family of molecules (e.g., HLA-A, HLA-B, HLA-C, HLA-DQ, HLA-DR, HLA-DP) in other distinct subjects.

The set of numerical likelihoods are further identified by at least MHC-allele noninteracting features comprising at least one of: the C- and N-terminal sequences flanking the neoantigen encoded peptide within its source protein sequence; the presence of protease cleavage motifs in the neoantigen encoded peptide, optionally weighted according to the expression of corresponding proteases in the tumor cells (as measured by RNA-seq or mass spectrometry); the turnover rate of the source protein as measured in the appropriate cell type; the length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data; the level of expression of the proteasome, immunoproteasome, thymoproteasome, or other proteases in the tumor cells (which may be measured by RNA-seq, proteome mass spectrometry, or immunohistochemistry); the expression of the source gene of the neoantigen encoded peptide (e.g., as measured by RNA-seq or mass spectrometry); the typical tissue-specific expression of the source gene of the neoantigen encoded peptide during various stages of the cell cycle; a comprehensive catalog of features of the source protein and/or its domains as can be found in e.g. uniProt or PDB http://www.rcsb.org/pdb/home/home.do; features describing the properties of the domain of the source protein containing the peptide, for example: secondary or tertiary structure (e.g., alpha helix vs beta sheet); alternative splicing; the probability of presentation of peptides from the source protein of the neoantigen encoded peptide in question in other distinct subjects; the probability that the peptide will not be detected or over-represented by mass spectrometry due to technical biases; the expression of various gene modules/pathways as measured by RNASeq (which need not contain the source protein of the peptide) that are informative about the state of the tumor cells, stroma, or tumor-infiltrating lymphocytes (TILs); the copy number of the source gene of the neoantigen encoded peptide in the tumor cells; the probability that the peptide binds to the TAP or the measured or predicted binding affinity of the peptide to the TAP; the expression level of TAP in the tumor cells (which may be measured by RNA-seq, proteome mass spectrometry, immunohistochemistry); presence or absence of tumor mutations, including, but not limited to: driver mutations in known cancer driver genes such as EGFR, KRAS, ALK, RET, ROS1, TP53, CDKN2A, CDKN2B, NTRK1, NTRK2, NTRK3, and in genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOBHLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation; presence or absence of functional germline polymorphisms, including, but not limited to: in genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOBHLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome); tumor type (e.g., NSCLC, melanoma); clinical tumor subtype (e.g., squamous lung cancer vs. non-squamous); smoking history; the typical expression of the source gene of the peptide in the relevant tumor type or clinical subtype, optionally stratified by driver mutation.

The at least one mutation may be a frameshift or non-frameshift indel, missense or nonsense substitution, splice site alteration, genomic rearrangement or gene fusion, or any genomic or expression alteration giving rise to a neoORF.

The tumor cell may be selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

A method disclosed herein may also include obtaining a tumor vaccine comprising the set of selected neoantigens or a subset thereof, optionally further comprising administering the tumor vaccine to the subject.

At least one of neoantigens in the set of selected neoantigens, when in polypeptide form, may include at least one of: a binding affinity with MHC with an IC50 value of less than 1000 nM, for MHC Class 1 polypeptides a length of 8-15, 8, 9, 10, 11, 12, 13, 14, or 15 amino acids, presence of sequence motifs within or near the polypeptide in the parent protein sequence promoting proteasome cleavage, and presence of sequence motifs promoting TAP transport.

Also disclosed herein is a methods for generating a model for identifying one or more neoantigens that are likely to be presented on a tumor cell surface of a tumor cell, comprising the steps of: receiving mass spectrometry data comprising data associated with a plurality of isolated peptides eluted from major histocompatibility complex (MHC) derived from a plurality of samples; obtaining a training data set by at least identifying a set of training peptide sequences present in the samples and one or more MHCs associated with each training peptide sequence; training a set of numerical parameters of a presentation model using the training data set comprising the training peptide sequences, the presentation model providing a plurality of numerical likelihoods that peptide sequences from the tumor cell are presented by one or more MHC alleles on the tumor cell surface.

The presentation model may represent dependence between: presence of a particular amino acid at a particular position of a peptide sequence; and likelihood of presentation, by one of the MHC alleles on the tumor cell, of the peptide sequence containing the particular amino acid at the particular position.

The samples can also include cell lines engineered to express a single MHC class I or class II allele.

The samples can also include cell lines engineered to express a plurality of MHC class I or class II alleles.

The samples can also include human cell lines obtained or derived from a plurality of patients.

The samples can also include fresh or frozen tumor samples obtained from a plurality of patients.

The samples can also include peptides identified using T-cell assays.

The training data set may further include data associated with: peptide abundance of the set of training peptides present in the samples; peptide length of the set of training peptides in the samples.

A method disclosed herein can also include obtaining a set of training protein sequences based on the training peptide sequences by comparing the set of training peptide sequences via alignment to a database comprising a set of known protein sequences, wherein the set of training protein sequences are longer than and include the training peptide sequences.

A method disclosed herein can also include performing or having performed mass spectrometry on a cell line to obtain at least one of exome, transcriptome, or whole genome nucleotide sequencing data from the cell line, the nucleotide sequencing data including at least one protein sequence including a mutation.

A method disclosed herein can also include: encoding the training peptide sequences using a one-hot encoding scheme.

A method disclosed herein can also include obtaining at least one of exome, transcriptome, and whole genome normal nucleotide sequencing data from normal tissue samples; and training the set of parameters of the presentation model using the normal nucleotide sequencing data.

The training data set may further include data associated with proteome sequences associated with the samples.

The training data set may further include data associated with MHC peptidome sequences associated with the samples.

The training data set may further include data associated with peptide-MHC binding affinity measurements for at least one of the isolated peptides.

The training data set may further include data associated with peptide-MHC binding stability measurements for at least one of the isolated peptides.

The training data set may further include data associated with transcriptomes associated with the samples.

The training data set may further include data associated with genomes associated with the samples.

A method disclosed herein may also include logistically regressing the set of parameters.

The training peptide sequences may be lengths within a range of k-mers where k is between 8-15, inclusive for MHC class I or 9-30, inclusive for MHC class II.

A method disclosed herein may also include encoding the training peptide sequences using a left-padded one-hot encoding scheme.

A method disclosed herein may also include determining values for the set of parameters using a deep learning algorithm.

Disclosed herein is are methods for identifying one or more neoantigens that are likely to be presented on a tumor cell surface of a tumor cell, comprising executing the steps of: receiving mass spectrometry data comprising data associated with a plurality of isolated peptides eluted from major histocompatibility complex (MHC) derived from a plurality of fresh or frozen tumor samples; obtaining a training data set by at least identifying a set of training peptide sequences present in the tumor samples and presented on one or more MHC alleles associated with each training peptide sequence; obtaining a set of training protein sequences based on the training peptide sequences; and training a set of numerical parameters of a presentation model using the training protein sequences and the training peptide sequences, the presentation model providing a plurality of numerical likelihoods that peptide sequences from the tumor cell are presented by one or more MHC alleles on the tumor cell surface.

The presentation model may represent dependence between: presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

A method disclosed herein can also include selecting a subset of neoantigens, wherein the subset of neoantigens is selected because each has an increased likelihood that it is presented on the cell surface of the tumor relative to one or more distinct tumor neoantigens.

A method disclosed herein can also include selecting a subset of neoantigens, wherein the subset of neoantigens is selected because each has an increased likelihood that it is capable of inducing a tumor-specific immune response in the subject relative to one or more distinct tumor neoantigens.

A method disclosed herein can also include selecting a subset of neoantigens, wherein the subset of neoantigens is selected because each has an increased likelihood that it is capable of being presented to naïve T cells by professional antigen presenting cells (APCs) relative to one or more distinct tumor neoantigens, optionally wherein the APC is a dendritic cell (DC).

A method disclosed herein can also include selecting a subset of neoantigens, wherein the subset of neoantigens is selected because each has a decreased likelihood that it is subject to inhibition via central or peripheral tolerance relative to one or more distinct tumor neoantigens.

A method disclosed herein can also include selecting a subset of neoantigens, wherein the subset of neoantigens is selected because each has a decreased likelihood that it is capable of inducing an autoimmune response to normal tissue in the subject relative to one or more distinct tumor neoantigens.

A method disclosed herein can also include selecting a subset of neoantigens, wherein the subset of neoantigens is selected because each has a decreased likelihood that it will be differentially post-translationally modified in tumor cells versus APCs, optionally wherein the APC is a dendritic cell (DC).

The practice of the methods herein will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B(1992).

III. Identification of Tumor Specific Mutations in Neoantigens

Also disclosed herein are methods for the identification of certain mutations (e.g., the variants or alleles that are present in cancer cells). In particular, these mutations can be present in the genome, transcriptome, proteome, or exome of cancer cells of a subject having cancer but not in normal tissue from the subject.

Genetic mutations in tumors can be considered useful for the immunological targeting of tumors if they lead to changes in the amino acid sequence of a protein exclusively in the tumor. Useful mutations include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence. Mutations can also include one or more of nonframeshift indel, missense or nonsense substitution, splice site alteration, genomic rearrangement or gene fusion, or any genomic or expression alteration giving rise to a neoORF.

Peptides with mutations or mutated polypeptides arising from for example, splice-site, frameshift, readthrough, or gene fusion mutations in tumor cells can be identified by sequencing DNA, RNA or protein in tumor versus normal cells.

Also mutations can include previously identified tumor specific mutations. Known tumor mutations can be found at the Catalogue of Somatic Mutations in Cancer (COSMIC) database.

A variety of methods are available for detecting the presence of a particular mutation or allele in an individual's DNA or RNA. Advancements in this field have provided accurate, easy, and inexpensive large-scale SNP genotyping. For example, several techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods utilize amplification of a target genetic region, typically by PCR. Still other methods, based on the generation of small signal molecules by invasive cleavage followed by mass spectrometry or immobilized padlock probes and rolling-circle amplification. Several of the methods known in the art for detecting specific mutations are summarized below.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. For example, a single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide(s) present in the polymorphic site of the target molecule is complementary to that of the nucleotide derivative used in the reaction. This method has the advantage that it does not require the determination of large amounts of extraneous sequence data.

A solution-based method can be used for determining the identity of a nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. can be a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA in that they utilize incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

A number of initiatives obtain sequence information directly from millions of individual molecules of DNA or RNA in parallel. Real-time single molecule sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye. In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain. Other sequencing-by-synthesis technologies also exist.

Any suitable sequencing-by-synthesis platform can be used to identify mutations. As described above, four major sequencing-by-synthesis platforms are currently available: the Genome Sequencers from Roche/454 Life Sciences, the 1G Analyzer from Illumina/Solexa, the SOLiD system from Applied BioSystems, and the Heliscope system from Helicos Biosciences. Sequencing-by-synthesis platforms have also been described by Pacific BioSciences and VisiGen Biotechnologies. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids can be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ ligand, or the avidin-biotin pair as described in, e.g., US Patent Application No. 2006/0252077) can be linked to each fragment to be captured on a surface coated with a respective second member of that coupling pair.

Subsequent to the capture, the sequence can be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide can be incorporated and multiple lasers can be utilized for stimulation of incorporated nucleotides.

Sequencing can also include other massively parallel sequencing or next generation sequencing (NGS) techniques and platforms. Additional examples of massively parallel sequencing techniques and platforms are the Illumina HiSeq or MiSeq, Thermo PGM or Proton, the Pac Bio RS II or Sequel, Qiagen's Gene Reader, and the Oxford Nanopore MinION. Additional similar current massively parallel sequencing technologies can be used, as well as future generations of these technologies.

Any cell type or tissue can be utilized to obtain nucleic acid samples for use in methods described herein. For example, a DNA or RNA sample can be obtained from a tumor or a bodily fluid, e.g., blood, obtained by known techniques (e.g. venipuncture) or saliva. Alternatively, nucleic acid tests can be performed on dry samples (e.g. hair or skin). In addition, a sample can be obtained for sequencing from a tumor and another sample can be obtained from normal tissue for sequencing where the normal tissue is of the same tissue type as the tumor. A sample can be obtained for sequencing from a tumor and another sample can be obtained from normal tissue for sequencing where the normal tissue is of a distinct tissue type relative to the tumor.

Tumors can include one or more of lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

Alternatively, protein mass spectrometry can be used to identify or validate the presence of mutated peptides bound to MHC proteins on tumor cells. Peptides can be acid-eluted from tumor cells or from HLA molecules that are immunoprecipitated from tumor, and then identified using mass spectrometry.

IV. Neoantigens

Neoantigens can include nucleotides or polypeptides. For example, a neoantigen can be an RNA sequence that encodes for a polypeptide sequence. Neoantigens useful in vaccines can therefore include nucleotide sequences or polypeptide sequences.

Disclosed herein are isolated peptides that comprise tumor specific mutations identified by the methods disclosed herein, peptides that comprise known tumor specific mutations, and mutant polypeptides or fragments thereof identified by methods disclosed herein. Neoantigen peptides can be described in the context of their coding sequence where a neoantigen includes the nucleotide sequence (e.g., DNA or RNA) that codes for the related polypeptide sequence.

One or more polypeptides encoded by a neoantigen nucleotide sequence can comprise at least one of: a binding affinity with MHC with an IC50 value of less than 1000 nM, for MHC Class 1 peptides a length of 8-15, 8, 9, 10, 11, 12, 13, 14, or 15 amino acids, presence of sequence motifs within or near the peptide promoting proteasome cleavage, and presence or sequence motifs promoting TAP transport.

One or more neoantigens can be presented on the surface of a tumor.

One or more neoantigens can be is immunogenic in a subject having a tumor, e.g., capable of eliciting a T cell response or a B cell response in the subject.

One or more neoantigens that induce an autoimmune response in a subject can be excluded from consideration in the context of vaccine generation for a subject having a tumor.

The size of at least one neoantigenic peptide molecule can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the neoantigenic peptide molecules are equal to or less than 50 amino acids.

Neoantigenic peptides and polypeptides can be: for MHC Class I 15 residues or less in length and usually consist of between about 8 and about 11 residues, particularly 9 or 10 residues; for MHC Class II, 15-24 residues.

If desirable, a longer peptide can be designed in several ways. In one case, when presentation likelihoods of peptides on HLA alleles are predicted or known, a longer peptide could consist of either: (1) individual presented peptides with an extensions of 2-5 amino acids toward the N- and C-terminus of each corresponding gene product; (2) a concatenation of some or all of the presented peptides with extended sequences for each. In another case, when sequencing reveals a long (>10 residues) neoepitope sequence present in the tumor (e.g. due to a frameshift, read-through or intron inclusion that leads to a novel peptide sequence), a longer peptide would consist of: (3) the entire stretch of novel tumor-specific amino acids—thus bypassing the need for computational or in vitro test-based selection of the strongest HLA-presented shorter peptide. In both cases, use of a longer peptide allows endogenous processing by patient cells and may lead to more effective antigen presentation and induction of T cell responses.

Neoantigenic peptides and polypeptides can be presented on an HLA protein. In some aspects neoantigenic peptides and polypeptides are presented on an HLA protein with greater affinity than a wild-type peptide. In some aspects, a neoantigenic peptide or polypeptide can have an IC50 of at least less than 5000 nM, at least less than 1000 nM, at least less than 500 nM, at least less than 250 nM, at least less than 200 nM, at least less than 150 nM, at least less than 100 nM, at least less than 50 nM or less.

In some aspects, neoantigenic peptides and polypeptides do not induce an autoimmune response and/or invoke immunological tolerance when administered to a subject.

Also provided are compositions comprising at least two or more neoantigenic peptides. In some embodiments the composition contains at least two distinct peptides. At least two distinct peptides can be derived from the same polypeptide. By distinct polypeptides is meant that the peptide vary by length, amino acid sequence, or both. The peptides are derived from any polypeptide known to or have been found to contain a tumor specific mutation. Suitable polypeptides from which the neoantigenic peptides can be derived can be found for example in the COSMIC database. COSMIC curates comprehensive information on somatic mutations in human cancer. The peptide contains the tumor specific mutation. In some aspects the tumor specific mutation is a driver mutation for a particular cancer type.

Neoantigenic peptides and polypeptides having a desired activity or property can be modified to provide certain desired attributes, e.g., improved pharmacological characteristics, while increasing or at least retaining substantially all of the biological activity of the unmodified peptide to bind the desired MHC molecule and activate the appropriate T cell. For instance, neoantigenic peptide and polypeptides can be subject to various changes, such as substitutions, either conservative or non-conservative, where such changes might provide for certain advantages in their use, such as improved MHC binding, stability or presentation. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications can be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

Modifications of peptides and polypeptides with various amino acid mimetics or unnatural amino acids can be particularly useful in increasing the stability of the peptide and polypeptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half-life of the peptides can be conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4 degrees C.) for 15 minutes and then spun to pellet the precipitated serum proteins. The presence of the peptides is then determined by reversed-phase HPLC using stability-specific chromatography conditions.

The peptides and polypeptides can be modified to provide desired attributes other than improved serum half-life. For instance, the ability of the peptides to induce CTL activity can be enhanced by linkage to a sequence which contains at least one epitope that is capable of inducing a T helper cell response. Immunogenic peptides/T helper conjugates can be linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus can be a hetero- or homo-oligomer. When present, the spacer will usually be at least one or two residues, more usually three to six residues. Alternatively, the peptide can be linked to the T helper peptide without a spacer.

A neoantigenic peptide can be linked to the T helper peptide either directly or via a spacer either at the amino or carboxy terminus of the peptide. The amino terminus of either the neoantigenic peptide or the T helper peptide can be acylated. Exemplary T helper peptides include tetanus toxoid 830-843, influenza 307-319, malaria circumsporozoite 382-398 and 378-389.

Proteins or peptides can be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and can be found at computerized databases known to those of ordinary skill in the art. One such database is the National Center for Biotechnology Information's Genbank and GenPept databases located at the National Institutes of Health website. The coding regions for known genes can be amplified and/or expressed using the techniques disclosed herein or as would be known to those of ordinary skill in the art. Alternatively, various commercial preparations of proteins, polypeptides and peptides are known to those of skill in the art.

In a further aspect a neoantigen includes a nucleic acid (e.g. polynucleotide) that encodes a neoantigenic peptide or portion thereof. The polynucleotide can be, e.g., DNA, cDNA, PNA, CNA, RNA (e.g., mRNA), either single- and/or double-stranded, or native or stabilized forms of polynucleotides, such as, e.g., polynucleotides with a phosphorothiate backbone, or combinations thereof and it may or may not contain introns. A still further aspect provides an expression vector capable of expressing a polypeptide or portion thereof. Expression vectors for different cell types are well known in the art and can be selected without undue experimentation. Generally, DNA is inserted into an expression vector, such as a plasmid, in proper orientation and correct reading frame for expression. If necessary, DNA can be linked to the appropriate transcriptional and translational regulatory control nucleotide sequences recognized by the desired host, although such controls are generally available in the expression vector. The vector is then introduced into the host through standard techniques. Guidance can be found e.g. in Sambrook et al. (1989) Molecular Cloning, A Laboratory Manual, Cold Spring Harbor Laboratory, Cold Spring Harbor, N.Y.

IV. Vaccine Compositions

Also disclosed herein is an immunogenic composition, e.g., a vaccine composition, capable of raising a specific immune response, e.g., a tumor-specific immune response. Vaccine compositions typically comprise a plurality of neoantigens, e.g., selected using a method described herein. Vaccine compositions can also be referred to as vaccines.

A vaccine can contain between 1 and 30 peptides, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different peptides, 6, 7, 8, 9, 10 11, 12, 13, or 14 different peptides, or 12, 13 or 14 different peptides. Peptides can include post-translational modifications. A vaccine can contain between 1 and 100 or more nucleotide sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different nucleotide sequences, 6, 7, 8, 9, 10 11, 12, 13, or 14 different nucleotide sequences, or 12, 13 or 14 different nucleotide sequences. A vaccine can contain between 1 and 30 neoantigen sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different neoantigen sequences, 6, 7, 8, 9, 10 11, 12, 13, or 14 different neoantigen sequences, or 12, 13 or 14 different neoantigen sequences.

In one embodiment, different peptides and/or polypeptides or nucleotide sequences encoding them are selected so that the peptides and/or polypeptides capable of associating with different MHC molecules, such as different MHC class I molecule. In some aspects, one vaccine composition comprises coding sequence for peptides and/or polypeptides capable of associating with the most frequently occurring MHC class I molecules. Hence, vaccine compositions can comprise different fragments capable of associating with at least 2 preferred, at least 3 preferred, or at least 4 preferred MHC class I molecules.

The vaccine composition can be capable of raising a specific cytotoxic T-cells response and/or a specific helper T-cell response.

A vaccine composition can further comprise an adjuvant and/or a carrier. Examples of useful adjuvants and carriers are given herein below. A composition can be associated with a carrier such as e.g. a protein or an antigen-presenting cell such as e.g. a dendritic cell (DC) capable of presenting the peptide to a T-cell.

Adjuvants are any substance whose admixture into a vaccine composition increases or otherwise modifies the immune response to a neoantigen. Carriers can be scaffold structures, for example a polypeptide or a polysaccharide, to which a neoantigen, is capable of being associated. Optionally, adjuvants are conjugated covalently or non-covalently.

The ability of an adjuvant to increase an immune response to an antigen is typically manifested by a significant or substantial increase in an immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to 1018 ISS, alum, aluminium salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are useful. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines can be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives can readily be determined by the skilled artisan without undue experimentation. Additional adjuvants include colony-stimulating factors, such as Granulocyte Macrophage Colony Stimulating Factor (GM-CSF, sargramostim).

A vaccine composition can comprise more than one different adjuvant. Furthermore, a therapeutic composition can comprise any adjuvant substance including any of the above or combinations thereof. It is also contemplated that a vaccine and an adjuvant can be administered together or separately in any appropriate sequence.

A carrier (or excipient) can be present independently of an adjuvant. The function of a carrier can for example be to increase the molecular weight of in particular mutant to increase activity or immunogenicity, to confer stability, to increase the biological activity, or to increase serum half-life. Furthermore, a carrier can aid presenting peptides to T-cells. A carrier can be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier is generally a physiologically acceptable carrier acceptable to humans and safe. However, tetanus toxoid and/or diphtheria toxoid are suitable carriers. Alternatively, the carrier can be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments a vaccine composition additionally contains at least one antigen presenting cell.

Neoantigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J*. (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol*. (1998) 72 (12): 9873-9880). Dependent on the packaging capacity of the above mentioned viral vector-based vaccine platforms, this approach can deliver one or more nucleotide sequences that encode one or more neoantigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med*. (2016) 22 (4):433-8, Stronen et al., Targeting of cancer neoantigens with donor-derived T cell receptor repertoires, *Science*. (2016) 352 (6291):1337-41, Lu et al., Efficient identification of mutated cancer antigens recognized by T cells associated with durable tumor regressions, *Clin Cancer Res*. (2014) 20(13):3401-10). Upon introduction into a host, infected cells express the neoantigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (*Nature* 351:456-460 (1991)). A wide variety of other vaccine vectors useful for therapeutic administration or immunization of neoantigens, e.g., *Salmonella typhi* vectors, and the like will be apparent to those skilled in the art from the description herein.

IV.A. Additional Considerations for Vaccine Design and Manufacture

IV.A.1. Determination of a Set of Peptides that Cover all Tumor Subclones

Truncal peptides, meaning those presented by all or most tumor subclones, will be prioritized for inclusion into the vaccine.[53] Optionally, if there are no truncal peptides predicted to be presented and immunogenic with high probability, or if the number of truncal peptides predicted to be presented and immunogenic with high probability is small enough that additional non-truncal peptides can be included in the vaccine, then further peptides can be prioritized by estimating the number and identity of tumor subclones and choosing peptides so as to maximize the number of tumor subclones covered by the vaccine.[54]

IV.A.2. Neoantigen Prioritization

After all of the above neoantigen filters are applied, more candidate neoantigens may still be available for vaccine inclusion than the vaccine technology can support. Additionally, uncertainty about various aspects of the neoantigen analysis may remain and tradeoffs may exist between different properties of candidate vaccine neoantigens. Thus, in place of predetermined filters at each step of the selection process, an integrated multi-dimensional model can be considered that places candidate neoantigens in a space with at least the following axes and optimizes selection using an integrative approach.

1. Risk of auto-immunity or tolerance (risk of germline) (lower risk of auto-immunity is typically preferred)
2. Probability of sequencing artifact (lower probability of artifact is typically preferred)
3. Probability of immunogenicity (higher probability of immunogenicity is typically preferred)
4. Probability of presentation (higher probability of presentation is typically preferred)
5. Gene expression (higher expression is typically preferred)
6. Coverage of HLA genes (larger number of HLA molecules involved in the presentation of a set of neoantigens may lower the probability that a tumor will escape immune attack via downregulation or mutation of HLA molecules)

V. Therapeutic and Manufacturing Methods

Also provided is a method of inducing a tumor specific immune response in a subject, vaccinating against a tumor, treating and or alleviating a symptom of cancer in a subject by administering to the subject one or more neoantigens such as a plurality of neoantigens identified using methods disclosed herein.

In some aspects, a subject has been diagnosed with cancer or is at risk of developing cancer. A subject can be a human, dog, cat, horse or any animal in which a tumor specific immune response is desired. A tumor can be any solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas.

A neoantigen can be administered in an amount sufficient to induce a CTL response.

A neoantigen can be administered alone or in combination with other therapeutic agents. The therapeutic agent is for example, a chemotherapeutic agent, radiation, or immunotherapy. Any suitable therapeutic treatment for a particular cancer can be administered.

In addition, a subject can be further administered an anti-immunosuppressive/immunostimulatory agent such as a checkpoint inhibitor. For example, the subject can be further administered an anti-CTLA antibody or anti-PD-1 or anti-PD-L1. Blockade of CTLA-4 or PD-L1 by antibodies can enhance the immune response to cancerous cells in the patient. In particular, CTLA-4 blockade has been shown effective when following a vaccination protocol.

The optimum amount of each neoantigen to be included in a vaccine composition and the optimum dosing regimen can be determined. For example, a neoantigen or its variant can be prepared for intravenous (i.v.) injection, sub-cutaneous (s.c.) injection, intradermal (i.d.) injection, intraperitoneal (i.p.) injection, intramuscular (i.m.) injection. Methods of injection include s.c., i.d., i.p., i.m., and i.v. Methods of DNA or RNA injection include i.d., i.m., s.c., i.p. and i.v. Other methods of administration of the vaccine composition are known to those skilled in the art.

A vaccine can be compiled so that the selection, number and/or amount of neoantigens present in the composition is/are tissue, cancer, and/or patient-specific. For instance, the exact selection of peptides can be guided by expression patterns of the parent proteins in a given tissue. The selection can be dependent on the specific type of cancer, the status of the disease, earlier treatment regimens, the immune status of the patient, and, of course, the HLA-haplotype of the patient. Furthermore, a vaccine can contain individualized components, according to personal needs of the particular patient. Examples include varying the selection of neoantigens according to the expression of the neoantigen in the particular patient or adjustments for secondary treatments following a first round or scheme of treatment.

For a composition to be used as a vaccine for cancer, neoantigens with similar normal self-peptides that are expressed in high amounts in normal tissues can be avoided or be present in low amounts in a composition described herein. On the other hand, if it is known that the tumor of a patient expresses high amounts of a certain neoantigen, the respective pharmaceutical composition for treatment of this cancer can be present in high amounts and/or more than one neoantigen specific for this particularly neoantigen or pathway of this neoantigen can be included.

Compositions comprising a neoantigen can be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use will depend on, e.g., the composition, the manner of administration, the stage and severity of the disease being treated, the weight and general state of health of the patient, and the judgment of the prescribing physician. It should be kept in mind that compositions can generally be employed in serious disease states, that is, life-threatening or potentially life threatening situations, especially when the cancer has metastasized. In such cases, in view of the minimization of extraneous substances and the relative nontoxic nature of a neoantigen, it is possible and can be felt desirable by the treating physician to administer substantial excesses of these compositions.

For therapeutic use, administration can begin at the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. A pharmaceutical compositions can be administered parenterally, e.g., intravenously, subcutaneously, intradermally, or intramuscularly.

The compositions can be administered at the site of surgical exiscion to induce a local immune response to the tumor. Disclosed herein are compositions for parenteral administration which comprise a solution of the neoantigen and vaccine compositions are dissolved or suspended in an acceptable carrier, e.g., an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Neoantigens can also be administered via liposomes, which target them to a particular cells tissue, such as lymphoid tissue. Liposomes are also useful in increasing half-life. Liposomes include emulsions, foams, micelles, insoluble monolayers, liquid crystals, phospholipid dispersions, lamellar layers and the like. In these preparations the neoantigen to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired neoantigen can be directed to the site of lymphoid cells, where the liposomes then deliver the selected therapeutic/immunogenic compositions. Liposomes can be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension can be administered intravenously, locally, topically, etc. in a dose which varies according to, inter alia, the manner of administration, the peptide being delivered, and the stage of the disease being treated.

For therapeutic or immunization purposes, nucleic acids encoding a peptide and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Approaches for delivering nucleic acid sequences can include viral vectors, mRNA vectors, and DNA vectors with or without electroporation.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite, BioTechniques 6(7): 682-691 (1988); U.S. Pat. No. 5,279,833 Rose U.S. Pat. No. 5,279,833; 9106309WOAWO 91/06309; and Felgner et al., Proc. Natl. Acad. Sci. USA 84: 7413-7414 (1987).

Neoantigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleotide sequences that encode one or more neoantigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, *Science*. (2016) 352 (6291):1337-41, Lu et al., Efficient identification of mutated cancer antigens recognized by T cells associated with durable tumor regressions, *Clin Cancer Res.* (2014) 20(13):3401-10). Upon introduction into a host, infected cells express the neoantigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (*Nature* 351:456-460 (1991)). A wide variety of other vaccine vectors useful for therapeutic administration or immunization of neoantigens, e.g., *Salmonella typhi* vectors, and the like will be apparent to those skilled in the art from the description herein.

A means of administering nucleic acids uses minigene constructs encoding one or multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes can be improved by including synthetic (e.g. poly-alanine) or naturally-occurring flanking sequences adjacent to the CTL epitopes. The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Purified plasmid DNA can be prepared for injection using a variety of formulations. The simplest of these is reconstitution of lyophilized DNA in sterile phosphate-buffer saline (PBS). A variety of methods have been described, and new techniques can become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Also disclosed is a method of manufacturing a tumor vaccine, comprising performing the steps of a method disclosed herein; and producing a tumor vaccine comprising a plurality of neoantigens or a subset of the plurality of neoantigens.

Neoantigens disclosed herein can be manufactured using methods known in the art. For example, a method of producing a neoantigen or a vector (e.g., a vector including at least one sequence encoding one or more neoantigens) disclosed herein can include culturing a host cell under conditions suitable for expressing the neoantigen or vector wherein the host cell comprises at least one polynucleotide encoding the neoantigen or vector, and purifying the neoantigen or vector. Standard purification methods include chromatographic techniques, electrophoretic, immunological, precipitation, dialysis, filtration, concentration, and chromatofocusing techniques.

Host cells can include a Chinese Hamster Ovary (CHO) cell, NS0 cell, yeast, or a HEK293 cell. Host cells can be transformed with one or more polynucleotides comprising at least one nucleic acid sequence that encodes a neoantigen or vector disclosed herein, optionally wherein the isolated polynucleotide further comprises a promoter sequence operably linked to the at least one nucleic acid sequence that encodes the neoantigen or vector. In certain embodiments the isolated polynucleotide can be cDNA.

VI. Neoantigen Identification

VI.A. Neoantigen Candidate Identification

Research methods for NGS analysis of tumor and normal exome and transcriptomes have been described and applied in the neoantigen identification space.[6,14,15] The example below considers certain optimizations for greater sensitivity and specificity for neoantigen identification in the clinical setting. These optimizations can be grouped into two areas, those related to laboratory processes and those related to the NGS data analysis.

VI.A.1. Laboratory Process Optimizations

The process improvements presented here address challenges in high-accuracy neoantigen discovery from clinical specimens with low tumor content and small volumes by extending concepts developed for reliable cancer driver gene assessment in targeted cancer panels[16] to the whole-exome and -transcriptome setting necessary for neoantigen identification. Specifically, these improvements include:

1. Targeting deep (>500x) unique average coverage across the tumor exome to detect mutations present at low mutant allele frequency due to either low tumor content or subclonal state.
2. Targeting uniform coverage across the tumor exome, with <5% of bases covered at <100x, so that the fewest possible neoantigens are missed, by, for instance:
   a. Employing DNA-based capture probes with individual probe QC[17]
   b. Including additional baits for poorly covered regions
3. Targeting uniform coverage across the normal exome, where <5% of bases are covered at <20x so that the fewest neoantigens possible remain unclassified for somatic/germline status (and thus not usable as TSNAs)
4. To minimize the total amount of sequencing required, sequence capture probes will be designed for coding regions of genes only, as non-coding RNA cannot give rise to neoantigens. Additional optimizations include:
   a. supplementary probes for HLA genes, which are GC-rich and poorly captured by standard exome sequencing[18]
   b. exclusion of genes predicted to generate few or no candidate neoantigens, due to factors such as insufficient expression, suboptimal digestion by the proteasome, or unusual sequence features.
5. Tumor RNA will likewise be sequenced at high depth (>100M reads) in order to enable variant detection, quantification of gene and splice-variant ("isoform") expression, and fusion detection. RNA from FFPE samples will be extracted using probe-based enrichment[19], with the same or similar probes used to capture exomes in DNA.

VI.A.2. NGS Data Analysis Optimizations

Improvements in analysis methods address the suboptimal sensitivity and specificity of common research mutation calling approaches, and specifically consider customizations relevant for neoantigen identification in the clinical setting. These include:

1. Using the HG38 reference human genome or a later version for alignment, as it contains multiple MHC regions assemblies better reflective of population polymorphism, in contrast to previous genome releases.
2. Overcoming the limitations of single variant callers[20] by merging results from different programs.[5]
   a. Single-nucleotide variants and indels will be detected from tumor DNA, tumor RNA and normal DNA with a suite of tools including: programs based on comparisons of tumor and normal DNA, such as Strelka[21] and Mutect[22]; and programs that incorporate tumor DNA, tumor RNA and normal DNA, such as UNCeqR, which is particularly advantageous in low-purity samples[23].
   b. Indels will be determined with programs that perform local re-assembly, such as Strelka and ABRA[24].
   c. Structural rearrangements will be determined using dedicated tools such as Pindel[25] or Breakseq[26].
3. In order to detect and prevent sample swaps, variant calls from samples for the same patient will be compared at a chosen number of polymorphic sites.
4. Extensive filtering of artefactual calls will be performed, for instance, by:
   a. Removal of variants found in normal DNA, potentially with relaxed detection parameters in cases of low coverage, and with a permissive proximity criterion in case of indels
   b. Removal of variants due to low mapping quality or low base quality[27].
   c. Removal of variants stemming from recurrent sequencing artifacts, even if not observed in the corresponding normal[27]. Examples include variants primarily detected on one strand.
   d. Removal of variants detected in an unrelated set of controls[27]
5. Accurate HLA calling from normal exome using one of seq2HLA[28], ATHLATES[29] or Optitype and also combining exome and RNA sequencing data[28]. Additional potential optimizations include the adoption of a dedicated assay for HLA typing such as long-read DNA sequencing[30], or the adaptation of a method for joining RNA fragments to retain continuity[31].
6. Robust detection of neo-ORFs arising from tumor-specific splice variants will be performed by assembling transcripts from RNA-seq data using CLASS[32], Bayesembler[33], StringTie[34] or a similar program in its reference-guided mode (i.e., using known transcript structures rather than attempting to recreate transcripts in their entirety from each experiment). While Cufflinks[35] is commonly used for this purpose, it frequently produces implausibly large numbers of splice variants, many of them far shorter than the full-length gene, and can fail to recover simple positive controls. Coding sequences and nonsense-mediated decay potential will be determined with tools such as SpliceR[36] and MAMBA[37], with mutant sequences re-introduced. Gene expression will be determined with a tool such as Cufflinks[35] or Express (Roberts and Pachter, 2013). Wild-type and mutant-specific expression counts and/or relative levels will be determined with tools developed for these purposes, such as ASE[38] or HTSeq[39]. Potential filtering steps include:
   a. Removal of candidate neo-ORFs deemed to be insufficiently expressed.
   b. Removal of candidate neo-ORFs predicted to trigger non-sense mediated decay (NMD).
7. Candidate neoantigens observed only in RNA (e.g., neoORFs) that cannot directly be verified as tumor-specific will be categorized as likely tumor-specific according to additional parameters, for instance by considering:
   a. Presence of supporting tumor DNA-only cis-acting frameshift or splice-site mutations
   b. Presence of corroborating tumor DNA-only trans-acting mutation in a splicing factor. For instance, in three independently published experiments with R625-mutant SF3B1, the genes exhibiting the most differentially splicing were concordant even though one experiment examined uveal melanoma patients[40], the second a uveal melanoma cell line[41], and the third breast cancer patients[42].
   c. For novel splicing isoforms, presence of corroborating "novel" splice-junction reads in the RNASeq data.
   d. For novel re-arrangements, presence of corroborating juxta-exon reads in tumor DNA that are absent from normal DNA
   e. Absence from gene expression compendium such as GTEx[43] (i.e. making germline origin less likely)

8. Complementing the reference genome alignment-based analysis by comparing assembled DNA tumor and normal reads (or k-mers from such reads) directly to avoid alignment and annotation based errors and artifacts. (e.g. for somatic variants arising near germline variants or repeat-context indels)

In samples with poly-adenylated RNA, the presence of viral and microbial RNA in the RNA-seq data will be assessed using RNA COMPASS[44] or a similar method, toward the identification of additional factors that may predict patient response.

VI.B. Isolation and Detection of HLA Peptides

Isolation of HLA-peptide molecules was performed using classic immunoprecipitation (IP) methods after lysis and solubilization of the tissue sample (55-58). A clarified lysate was used for HLA specific IP.

Immunoprecipitation was performed using antibodies coupled to beads where the antibody is specific for HLA molecules. For a pan-Class I HLA immunoprecipitation, a pan-Class I CR antibody is used, for Class II HLA-DR, an HLA-DR antibody is used. Antibody is covalently attached to NHS-sepharose beads during overnight incubation. After covalent attachment, the beads were washed and aliquoted for IP. (59, 60)

The clarified tissue lysate is added to the antibody beads for the immunoprecipitation. After immunoprecipitation, the beads are removed from the lysate and the lysate stored for additional experiments, including additional IPs. The IP beads are washed to remove non-specific binding and the HLA/peptide complex is eluted from the beads using standard techniques. The protein components are removed from the peptides using a molecular weight spin column or C18 fractionation. The resultant peptides are taken to dryness by SpeedVac evaporation and in some instances are stored at −20 C prior to MS analysis.

Dried peptides are reconstituted in an HPLC buffer suitable for reverse phase chromatography and loaded onto a C-18 microcapillary HPLC column for gradient elution in a Fusion Lumos mass spectrometer (Thermo). MS1 spectra of peptide mass/charge (m/z) were collected in the Orbitrap detector at high resolution followed by MS2 low resolution scans collected in the ion trap detector after HCD fragmentation of the selected ion. Additionally, MS2 spectra can be obtained using either CID or ETD fragmentation methods or any combination of the three techniques to attain greater amino acid coverage of the peptide. MS2 spectra can also be measured with high resolution mass accuracy in the Orbitrap detector.

MS2 spectra from each analysis are searched against a protein database using Comet (61, 62) and the peptide identification are scored using Percolator (63-65).

Figure 1D:
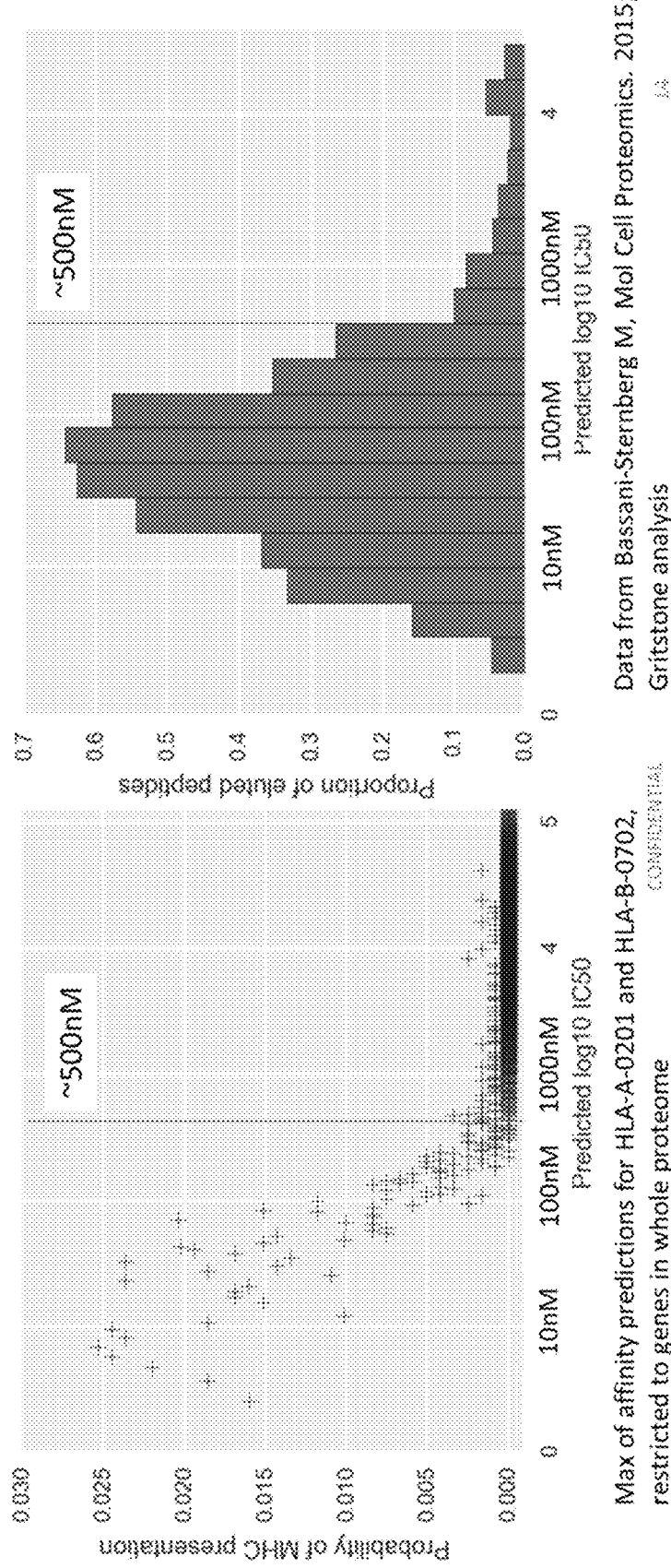
FIG. 1D shows that binding prediction is not sufficient for neoantigen identification.
Figure 1E:
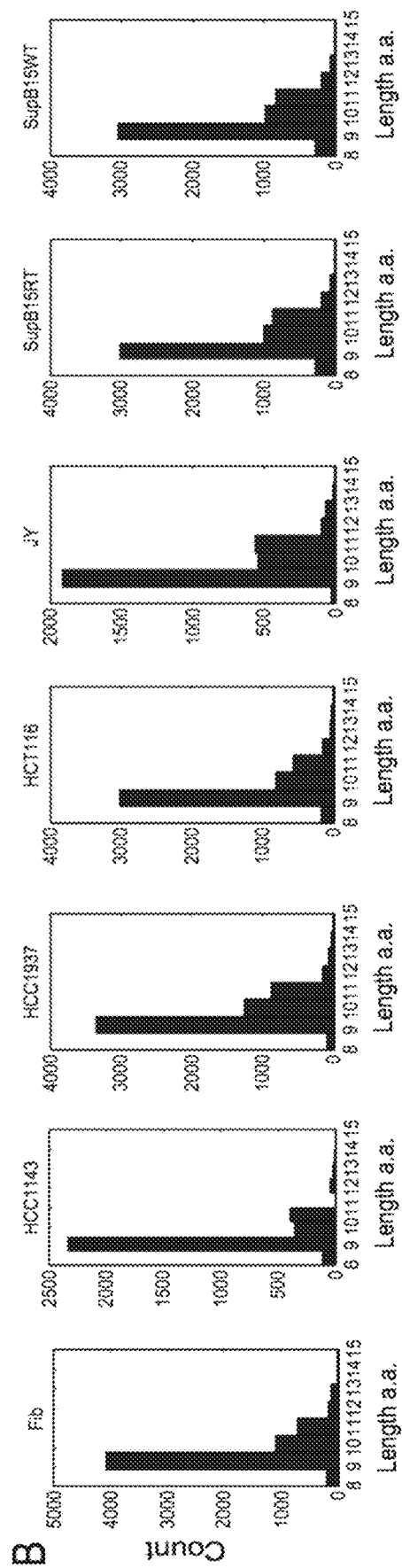
FIG. 1E shows probability of MHC-I presentation as a function of peptide length.
Figure 1F:
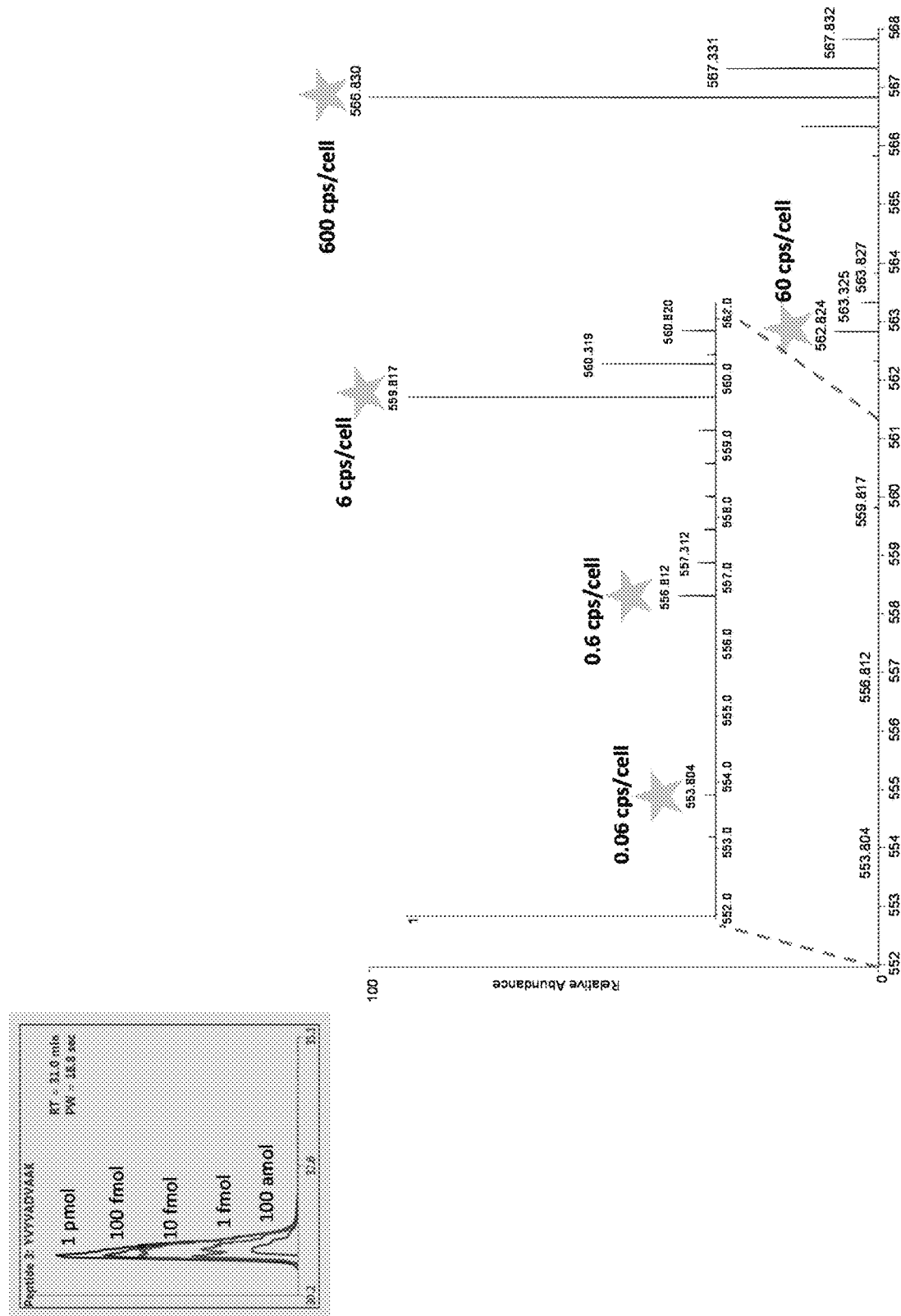
FIG. 1F shows an example peptide spectrum generated from Promega's dynamic range standard. Figure discloses SEQ ID NO: 1.
Figure 1G:
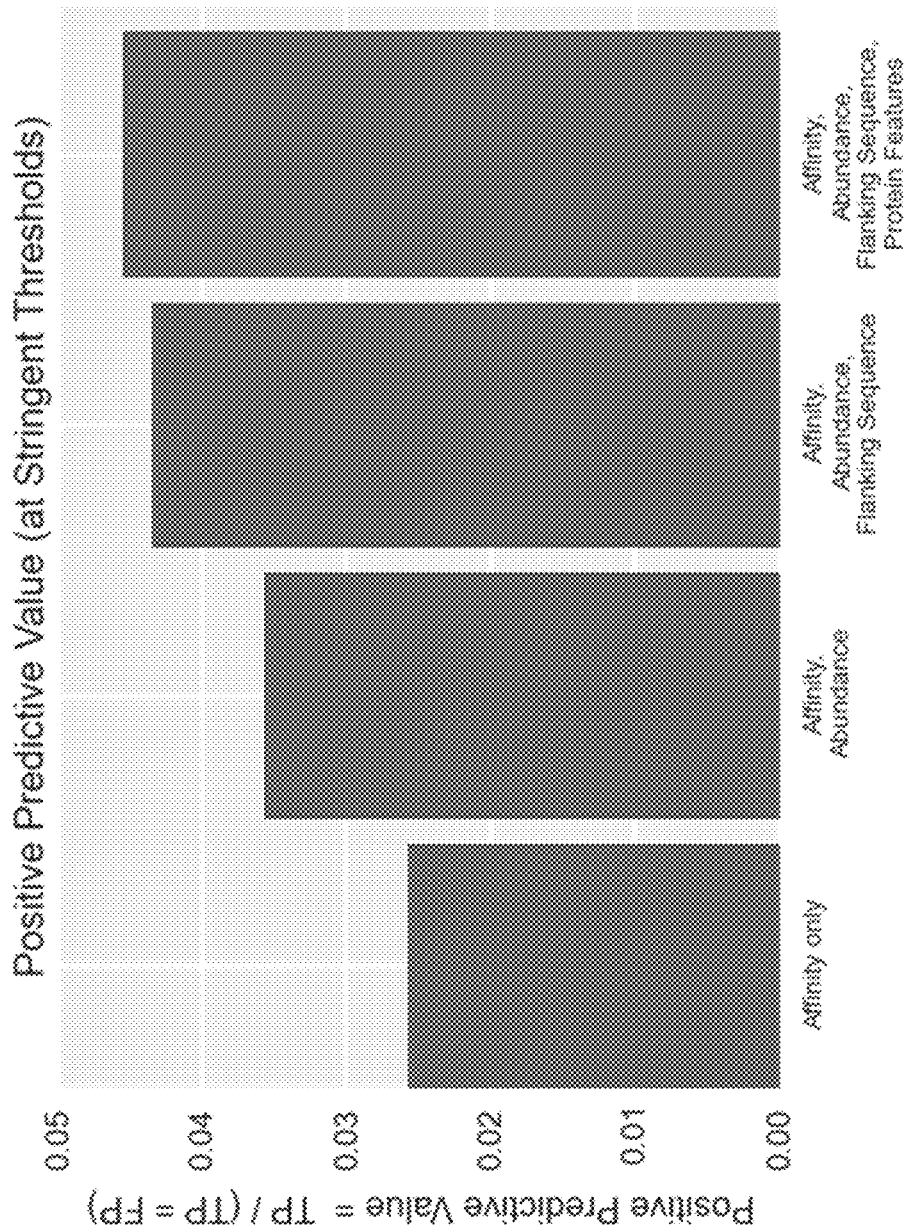
FIG. 1G shows how the addition of features increases the model positive predictive value.

VI.B.1. MS Limit of Detection Studies in Support of Comprehensive HLA Peptide Sequencing Using the peptide YVYVADVAAK (SEQ ID NO: 1) it was determined what the limits of detection are using different amounts of peptide loaded onto the LC column. The amounts of peptide tested were 1 pmol, 100 fmol, 10 fmol, 1 fmol, and 100 amol. (Table 1) The results are shown in FIG. 1F. These results indicate that the lowest limit of detection (LoD) is in the attomol range ($10^{-18}$), that the dynamic range spans five orders of magnitude, and that the signal to noise appears sufficient for sequencing at low femtomol ranges (10-15).

| Peptide m/z | Loaded on Column | Copies/Cell in 1e9cells |
|---|---|---|
| 566.830 | 1 pmol | 600 |
| 562.823 | 100 fmol | 60 |
| 559.816 | 10 fmol | 6 |
| 556.810 | 1 fmol | 0.6 |
| 553.802 | 100 amol | 0.06 |

VII. Presentation Model

VII.A. System Overview

Figure 2A:
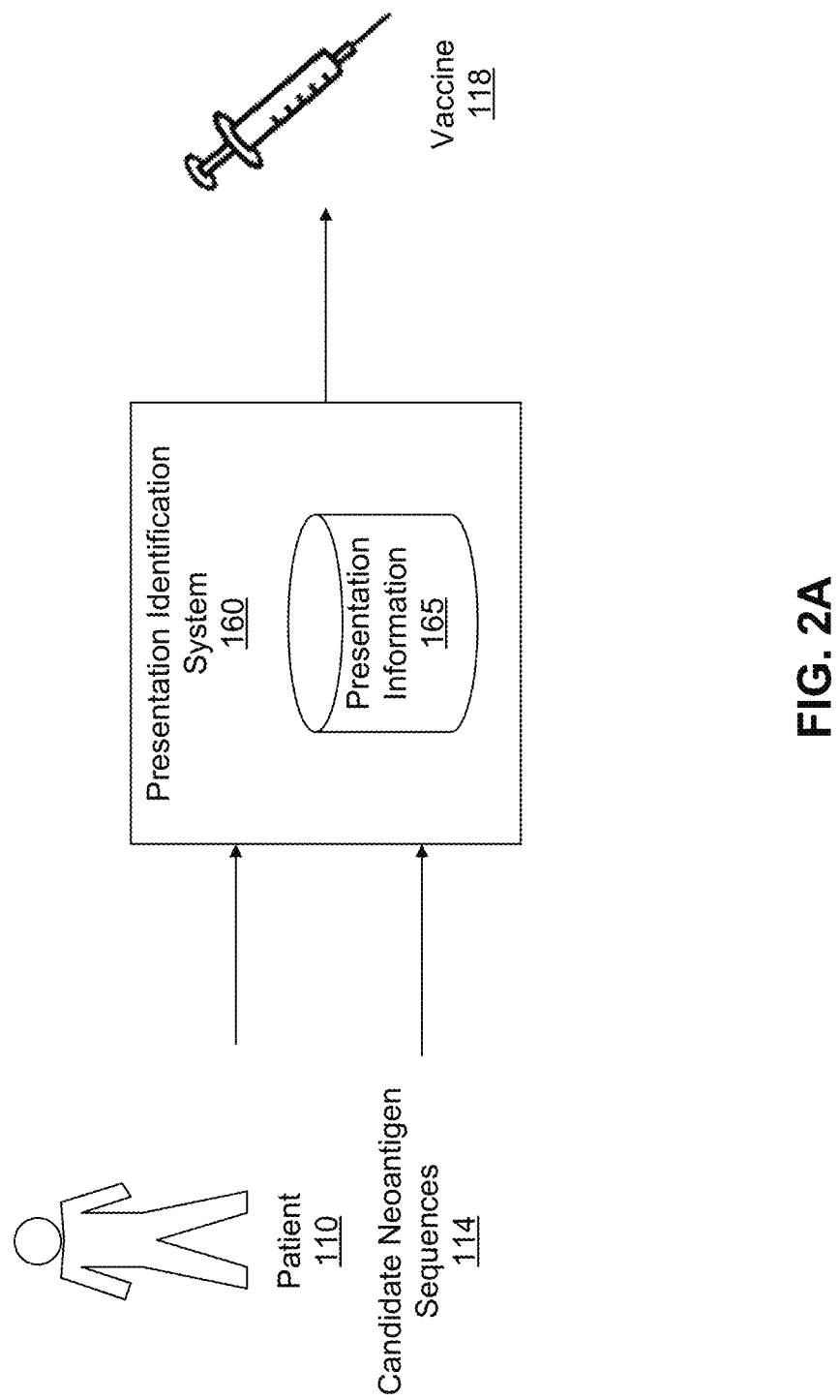
FIG. 2A is an overview of an environment for identifying likelihoods of peptide presentation in patients, in accordance with an embodiment.

FIG. 2A is an overview of an environment 100 for identifying likelihoods of peptide presentation in patients, in accordance with an embodiment. The environment 100 provides context in order to introduce a presentation identification system 160, itself including a presentation information store 165.

The presentation identification system 160 is one or computer models, embodied in a computing system as discussed below with respect to FIG. 14, that receives peptide sequences associated with a set of MHC alleles and determines likelihoods that the peptide sequences will be presented by one or more of the set of associated MHC alleles. This is useful in a variety of contexts. One specific use case for the presentation identification system 160 is that it is able to receive nucleotide sequences of candidate neoantigens associated with a set of MHC alleles from tumor cells of a patient 110 and determine likelihoods that the candidate neoantigens will be presented by one or more of the associated MHC alleles of the tumor and/or induce immunogenic responses in the immune system of the patient 110. Those candidate neoantigens with high likelihoods as determined by system 160 can be selected for inclusion in a vaccine 118, such an anti-tumor immune response can be elicited from the immune system of the patient 110 providing the tumor cells.

The presentation identification system 160 determines presentation likelihoods through one or more presentation models. Specifically, the presentation models generate likelihoods of whether given peptide sequences will be presented for a set of associated MHC alleles, and are generated based on presentation information stored in store 165. For example, the presentation models may generate likelihoods of whether a peptide sequence "YVYVADVAAK (SEQ ID NO: 1)" will be presented for the set of alleles HLA-A*02:01, HLA-B*07:02, HLA-B*08:03, HLA-C*01:04, HLA-A*06:03, HLA-B*01:04 on the cell surface of the sample. The presentation information 165 contains information on whether peptides bind to different types of MHC alleles such that those peptides are presented by MHC alleles, which in the models is determined depending on positions of amino acids in the peptide sequences. The presentation model can predict whether an unrecognized peptide sequence will be presented in association with an associated set of MHC alleles based on the presentation information 165.

VII.B. Presentation Information

FIG. 2 illustrates a method of obtaining presentation information, in accordance with an embodiment. The presentation information 165 includes two general categories of information: allele-interacting information and allele-noninteracting information. Allele-interacting information includes information that influence presentation of peptide sequences that are dependent on the type of MHC allele.

Allele-noninteracting information includes information that influence presentation of peptide sequences that are independent on the type of MHC allele.

VII.B.1. Allele-Interacting Information

Allele-interacting information primarily includes identified peptide sequences that are known to have been presented by one or more identified MHC molecules from humans, mice, etc. Notably, this may or may not include data obtained from tumor samples. The presented peptide sequences may be identified from cells that express a single MHC allele. In this case the presented peptide sequences are generally collected from single-allele cell lines that are engineered to express a predetermined MHC allele and that are subsequently exposed to synthetic protein. Peptides presented on the MHC allele are isolated by techniques such as acid-elution and identified through mass spectrometry. FIG. 2B shows an example of this, where the example peptide YEMFNDKS (SEQ ID NO: 2), presented on the predetermined MHC allele HLA-A*01:01, is isolated and identified through mass spectrometry. Since in this situation peptides are identified through cells engineered to express a single predetermined MHC protein, the direct association between a presented peptide and the MHC protein to which it was bound to is definitively known.

The presented peptide sequences may also be collected from cells that express multiple MHC alleles. Typically in humans, 6 different types of MHC molecules are expressed for a cell. Such presented peptide sequences may be identified from multiple-allele cell lines that are engineered to express multiple predetermined MHC alleles. Such presented peptide sequences may also be identified from tissue samples, either from normal tissue samples or tumor tissue samples. In this case particularly, the MHC molecules can be immunoprecipitated from normal or tumor tissue. Peptides presented on the multiple MHC alleles can similarly be isolated by techniques such as acid-elution and identified through mass spectrometry. FIG. 2C shows an example of this, where the six example peptides, YEMFNDKSF (SEQ ID NO: 3), HROEIFSHDFJ (SEQ ID NO: 4), FJIEJFOESS (SEQ ID NO: 5), NEIOREIREI (SEQ ID NO: 6), JFKSIFEMMSJDSSU (SEQ ID NO: 7), and KNFLENFIESOFI (SEQ ID NO: 8), are presented on identified MHC alleles HLA-A*01:01, HLA-A*02:01, HLA-B*07:02, HLA-B*08:01, HLA-C*01:03, and HLA-C*01:04 and are isolated and identified through mass spectrometry. In contrast to single-allele cell lines, the direct association between a presented peptide and the MHC protein to which it was bound to may be unknown since the bound peptides are isolated from the MHC molecules before being identified.

Allele-interacting information can also include mass spectrometry ion current which depends on both the concentration of peptide-MHC molecule complexes, and the ionization efficiency of peptides. The ionization efficiency varies from peptide to peptide in a sequence-dependent manner. Generally, ionization efficiency varies from peptide to peptide over approximately two orders of magnitude, while the concentration of peptide-MHC complexes varies over a larger range than that.

Allele-interacting information can also include measurements or predictions of binding affinity between a given MHC allele and a given peptide. One or more affinity models can generate such predictions. For example, going back to the example shown in FIG. 1D, presentation information 165 may include a binding affinity prediction of 1000 nM between the peptide YEMFNDKSF (SEQ ID NO: 3) and the allele HLA-A*01:01. Few peptides with IC50>1000 nm are presented by the MHC, and lower IC50 values increase the probability of presentation.

Allele-interacting information can also include measurements or predictions of stability of the MHC complex. One or more stability models that can generate such predictions. More stable peptide-MHC complexes (i.e., complexes with longer half-lives) are more likely to be presented at high copy number on tumor cells and on antigen-presenting cells that encounter vaccine antigen. For example, going back to the example shown in FIG. 2C, presentation information 165 may include a stability prediction of a half-life of 1 h for the molecule HLA-A*01:01.

Allele-interacting information can also include the measured or predicted rate of the formation reaction for the peptide-MHC complex. Complexes that form at a higher rate are more likely to be presented on the cell surface at high concentration.

Figure 5:
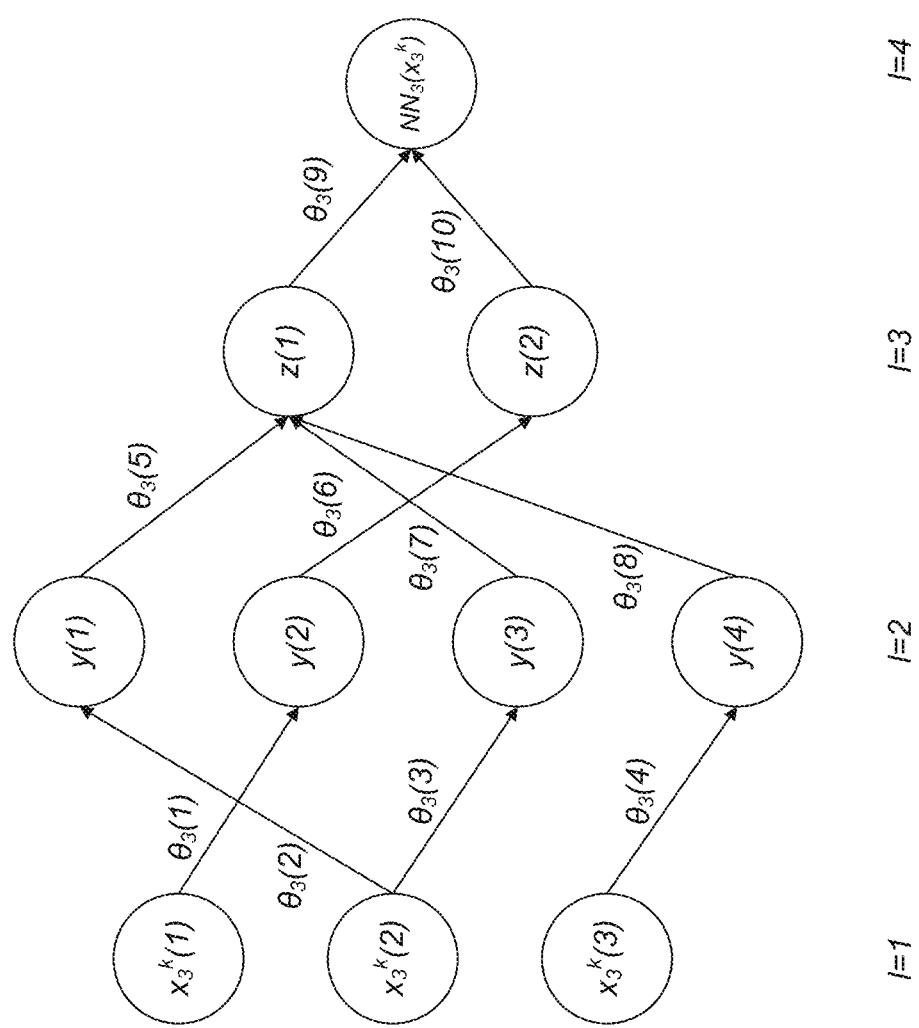
FIG. 5 illustrates an example network model in association with an MHC allele.

Allele-interacting information can also include the sequence and length of the peptide. MHC class I molecules typically prefer to present peptides with lengths between 8 and 15 peptides. 60-80% of presented peptides have length 9. Histograms of presented peptide lengths from several cell lines are shown in FIG. 5.

Allele-interacting information can also include the presence of kinase sequence motifs on the neoantigen encoded peptide, and the absence or presence of specific post-translational modifications on the neoantigen encoded peptide. The presence of kinase motifs affects the probability of post-translational modification, which may enhance or interfere with MHC binding.

Allele-interacting information can also include the expression or activity levels of proteins involved in the process of post-translational modification, e.g., kinases (as measured or predicted from RNA seq, mass spectrometry, or other methods).

Allele-interacting information can also include the probability of presentation of peptides with similar sequence in cells from other individuals expressing the particular MHC allele as assessed by mass-spectrometry proteomics or other means.

Allele-interacting information can also include the expression levels of the particular MHC allele in the individual in question (e.g. as measured by RNA-seq or mass spectrometry). Peptides that bind most strongly to an MHC allele that is expressed at high levels are more likely to be presented than peptides that bind most strongly to an MHC allele that is expressed at a low level.

Allele-interacting information can also include the overall neoantigen encoded peptide-sequence-independent probability of presentation by the particular MHC allele in other individuals who express the particular MHC allele.

Allele-interacting information can also include the overall peptide-sequence-independent probability of presentation by MHC alleles in the same family of molecules (e.g., HLA-A, HLA-B, HLA-C, HLA-DQ, HLA-DR, HLA-DP) in other individuals. For example, HLA-C molecules are typically expressed at lower levels than HLA-A or HLA-B molecules, and consequently, presentation of a peptide by HLA-C is a priori less probable than presentation by HLA-A or HLA-B 11.

Allele-interacting information can also include the protein sequence of the particular MHC allele.

Any MHC allele-noninteracting information listed in the below section can also be modeled as an MHC allele-interacting information.

VII.B.2. Allele-Noninteracting Information

Allele-noninteracting information can include C-terminal sequences flanking the neoantigen encoded peptide within its source protein sequence. C-terminal flanking sequences may impact proteasomal processing of peptides. However, the C-terminal flanking sequence is cleaved from the peptide by the proteasome before the peptide is transported to the endoplasmic reticulum and encounters MHC alleles on the surfaces of cells. Consequently, MHC molecules receive no information about the C-terminal flanking sequence, and thus, the effect of the C-terminal flanking sequence cannot vary depending on MHC allele type. For example, going back to the example shown in FIG. 2C, presentation information 165 may include the C-terminal flanking sequence FOEIFNDKSLDKFJI (SEQ ID NO: 9) of the presented peptide FJIEJFOESS (SEQ ID NO: 5) identified from the source protein of the peptide.

Allele-noninteracting information can also include mRNA quantification measurements. For example, mRNA quantification data can be obtained for the same samples that provide the mass spectrometry training data. As later described in reference to FIG. 13H, RNA expression was identified to be a strong predictor of peptide presentation. In one embodiment, the mRNA quantification measurements are identified from software tool RSEM. Detailed implementation of the RSEM software tool can be found at Bo Li and Colin N. Dewey. *RSEM: accurate transcript quantification from RNA-Seq data with or without a reference genome*. BMC Bioinformatics, 12:323, August 2011. In one embodiment, the mRNA quantification is measured in units of fragments per kilobase of transcript per Million mapped reads (FPKM).

Allele-noninteracting information can also include the N-terminal sequences flanking the peptide within its source protein sequence.

Allele-noninteracting information can also include the presence of protease cleavage motifs in the peptide, optionally weighted according to the expression of corresponding proteases in the tumor cells (as measured by RNA-seq or mass spectrometry). Peptides that contain protease cleavage motifs are less likely to be presented, because they will be more readily degraded by proteases, and will therefore be less stable within the cell.

Allele-noninteracting information can also include the turnover rate of the source protein as measured in the appropriate cell type. Faster turnover rate (i.e., lower half-life) increases the probability of presentation; however, the predictive power of this feature is low if measured in a dissimilar cell type.

Allele-noninteracting information can also include the length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data.

Allele-noninteracting information can also include the level of expression of the proteasome, immunoproteasome, thymoproteasome, or other proteases in the tumor cells (which may be measured by RNA-seq, proteome mass spectrometry, or immunohistochemistry). Different proteasomes have different cleavage site preferences. More weight will be given to the cleavage preferences of each type of proteasome in proportion to its expression level.

Allele-noninteracting information can also include the expression of the source gene of the peptide (e.g., as measured by RNA-seq or mass spectrometry). Possible optimizations include adjusting the measured expression to account for the presence of stromal cells and tumor-infiltrating lymphocytes within the tumor sample. Peptides from more highly expressed genes are more likely to be presented. Peptides from genes with undetectable levels of expression can be excluded from consideration.

Allele-noninteracting information can also include the probability that the source mRNA of the neoantigen encoded peptide will be subject to nonsense-mediated decay as predicted by a model of nonsense-mediated decay, for example, the model from Rivas et al, Science 2015.

Allele-noninteracting information can also include the typical tissue-specific expression of the source gene of the peptide during various stages of the cell cycle. Genes that are expressed at a low level overall (as measured by RNA-seq or mass spectrometry proteomics) but that are known to be expressed at a high level during specific stages of the cell cycle are likely to produce more presented peptides than genes that are stably expressed at very low levels.

Allele-noninteracting information can also include a comprehensive catalog of features of the source protein as given in e.g. uniProt or PDB http://www.rcsb.org/pdb/home/home.do. These features may include, among others: the secondary and tertiary structures of the protein, subcellular localization 11, Gene ontology (GO) terms. Specifically, this information may contain annotations that act at the level of the protein, e.g., 5' UTR length, and annotations that act at the level of specific residues, e.g., helix motif between residues 300 and 310. These features can also include turn motifs, sheet motifs, and disordered residues.

Allele-noninteracting information can also include features describing the properties of the domain of the source protein containing the peptide, for example: secondary or tertiary structure (e.g., alpha helix vs beta sheet); Alternative splicing.

Allele-noninteracting information can also include features describing the presence or absence of a presentation hotspot at the position of the peptide in the source protein of the peptide.

Allele-noninteracting information can also include the probability of presentation of peptides from the source protein of the peptide in question in other individuals (after adjusting for the expression level of the source protein in those individuals and the influence of the different HLA types of those individuals).

Allele-noninteracting information can also include the probability that the peptide will not be detected or over-represented by mass spectrometry due to technical biases.

The expression of various gene modules/pathways as measured by a gene expression assay such as RNASeq, microarray(s), targeted panel(s) such as Nanostring, or single/multi-gene representatives of gene modules measured by assays such as RT-PCR (which need not contain the source protein of the peptide) that are informative about the state of the tumor cells, stroma, or tumor-infiltrating lymphocytes (TILs).

Allele-noninteracting information can also include the copy number of the source gene of the peptide in the tumor cells. For example, peptides from genes that are subject to homozygous deletion in tumor cells can be assigned a probability of presentation of zero.

Allele-noninteracting information can also include the probability that the peptide binds to the TAP or the measured or predicted binding affinity of the peptide to the TAP.

Peptides that are more likely to bind to the TAP, or peptides that bind the TAP with higher affinity are more likely to be presented.

Allele-noninteracting information can also include the expression level of TAP in the tumor cells (which may be measured by RNA-seq, proteome mass spectrometry, immunohistochemistry). Higher TAP expression levels increase the probability of presentation of all peptides.

Allele-noninteracting information can also include the presence or absence of tumor mutations, including, but not limited to:

i. Driver mutations in known cancer driver genes such as EGFR, KRAS, ALK, RET, ROS1, TP53, CDKN2A, CDKN2B, NTRK1, NTRK2, NTRK3 ii. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOBHLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation.

Presence or absence of functional germline polymorphisms, including, but not limited to:

i. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOBHLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome)

Allele-noninteracting information can also include tumor type (e.g., NSCLC, melanoma).

Allele-noninteracting information can also include known functionality of HLA alleles, as reflected by, for instance HLA allele suffixes. For example, the N suffix in the allele name HLA-A*24:09N indicates a null allele that is not expressed and is therefore unlikely to present epitopes; the full HLA allele suffix nomenclature is described at https://www.ebi.ac.uk/ipd/imgt/hla/nomenclature/suffixes.html.

Allele-noninteracting information can also include clinical tumor subtype (e.g., squamous lung cancer vs. non-squamous).

Allele-noninteracting information can also include smoking history.

Allele-noninteracting information can also include history of sunburn, sun exposure, or exposure to other mutagens.

Allele-noninteracting information can also include the typical expression of the source gene of the peptide in the relevant tumor type or clinical subtype, optionally stratified by driver mutation. Genes that are typically expressed at high levels in the relevant tumor type are more likely to be presented.

Allele-noninteracting information can also include the frequency of the mutation in all tumors, or in tumors of the same type, or in tumors from individuals with at least one shared MHC allele, or in tumors of the same type in individuals with at least one shared MHC allele.

In the case of a mutated tumor-specific peptide, the list of features used to predict a probability of presentation may also include the annotation of the mutation (e.g., missense, read-through, frameshift, fusion, etc.) or whether the mutation is predicted to result in nonsense-mediated decay (NMD). For example, peptides from protein segments that are not translated in tumor cells due to homozygous early-stop mutations can be assigned a probability of presentation of zero. NMD results in decreased mRNA translation, which decreases the probability of presentation.

VII.C. Presentation Identification System

Figure 3:
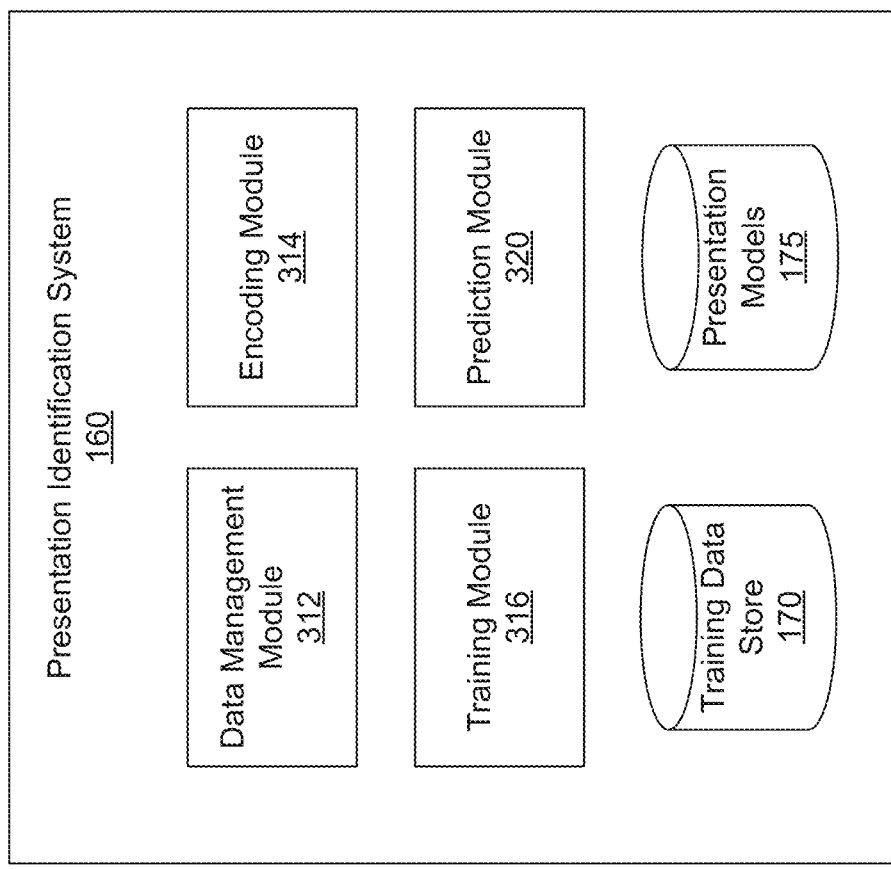
FIG. 3 is a high-level block diagram illustrating the computer logic components of the presentation identification system, according to one embodiment.

FIG. 3 is a high-level block diagram illustrating the computer logic components of the presentation identification system 160, according to one embodiment. In this example embodiment, the presentation identification system 160 includes a data management module 312, an encoding module 314, a training module 316, and a prediction module 320. The presentation identification system 160 is also comprised of a training data store 170 and a presentation models store 175. Some embodiments of the model management system 160 have different modules than those described here. Similarly, the functions can be distributed among the modules in a different manner than is described here.

VII.C.1. Data Management Module

The data management module 312 generates sets of training data 170 from the presentation information 165. Each set of training data contains a plurality of data instances, in which each data instance i contains a set of independent variables $z^i$ that include at least a presented or non-presented peptide sequence $p^i$, one or more associated MHC alleles $a^i$ associated with the peptide sequence $p^i$, and a dependent variable $y^i$ that represents information that the presentation identification system 160 is interested in predicting for new values of independent variables.

In one particular implementation referred throughout the remainder of the specification, the dependent variable $y^i$ is a binary label indicating whether peptide $p^i$ was presented by the one or more associated MHC alleles $a^i$. However, it is appreciated that in other implementations, the dependent variable $y^i$ can represent any other kind of information that the presentation identification system 160 is interested in predicting dependent on the independent variables $z^i$. For example, in another implementation, the dependent variable $y^i$ may also be a numerical value indicating the mass spectrometry ion current identified for the data instance.

The peptide sequence $p^i$ for data instance i is a sequence of $k_i$ amino acids, in which $k_i$ may vary between data instances i within a range. For example, that range may be 8-15 for MHC class I or 9-30 for MHC class II. In one specific implementation of system 160, all peptide sequences $p^i$ in a training data set may have the same length, e.g. 9. The number of amino acids in a peptide sequence may vary depending on the type of MHC alleles (e.g., MHC alleles in humans, etc.). The MHC alleles $a^i$ for data instance i indicate which MHC alleles were present in association with the corresponding peptide sequence $p^i$.

The data management module 312 may also include additional allele-interacting variables, such as binding affinity $b^i$ and stability $s^i$ predictions in conjunction with peptide sequences $p^i$ and associated MHC alleles $a^i$ contained in the training data 170. For example, the training data 170 may contain binding affinity predictions $b^i$ between a peptide $p^i$ and each of the associated MHC molecules indicated in $a^i$. As another example, the training data 170 may contain stability predictions $s^i$ for each of the MHC alleles indicated in $a^i$.

The data management module 312 may also include allele-noninteracting variables $w^i$, such as C-terminal flanking sequences and mRNA quantification measurements in conjunction with the peptide sequences $p^i$.

The data management module 312 also identifies peptide sequences that are not presented by MHC alleles to generate the training data 170. Generally, this involves identifying the "longer" sequences of source protein that include presented peptide sequences prior to presentation. When the presentation information contains engineered cell lines, the data management module 312 identifies a series of peptide sequences in the synthetic protein to which the cells were exposed to that were not presented on MHC alleles of the cells. When the presentation information contains tissue samples, the data management module 312 identifies source proteins from which presented peptide sequences originated from, and identifies a series of peptide sequences in the source protein that were not presented on MHC alleles of the tissue sample cells.

The data management module 312 may also artificially generate peptides with random sequences of amino acids and identify the generated sequences as peptides not presented on MHC alleles. This can be accomplished by randomly generating peptide sequences allows the data management module 312 to easily generate large amounts of synthetic data for peptides not presented on MHC alleles. Since in reality, a small percentage of peptide sequences are presented by MHC alleles, the synthetically generated peptide sequences are highly likely not to have been presented by MHC alleles even if they were included in proteins processed by cells.

FIG. 4 illustrates an example set of training data 170A, according to one embodiment. Specifically, the first 3 data instances in the training data 170A indicate peptide presentation information from a single-allele cell line involving the allele HLA-C*01:03 and 3 peptide sequences QCEIO-WARE (SEQ ID NO: 10), FIEUHFWI (SEQ ID NO: 11), and FEWRHRJTRUJR (SEQ ID NO: 12). The fourth data instance in the training data 170A indicates peptide information from a multiple-allele cell line involving the alleles HLA-B*07:02, HLA-C*01:03, HLA-A*01:01 and a peptide sequence QIEJOEIJE (SEQ ID NO: 13). The first data instance indicates that peptide sequence QCEIOWARE (SEQ ID NO: 10) was not presented by the allele HLA-C*01:03. As discussed in the prior two paragraphs, the peptide sequence may be randomly generated by the data management module 312 or identified from source protein of presented peptides. The training data 170A also includes a binding affinity prediction of 1000 nM and a stability prediction of a half-life of 1 h for the peptide sequence-allele pair. The training data 170A also includes allele-noninteracting variables, such as the C-terminal flanking sequence of the peptide FJELFISBOSJFIE (SEQ ID NO: 14), and a mRNA quantification measurement of $10^2$ FPKM. The fourth data instance indicates that peptide sequence QIE-JOEIJE (SEQ ID NO: 13) was presented by one of the alleles HLA-B*07:02, HLA-C*01:03, or HLA-A*01:01. The training data 170A also includes binding affinity predictions and stability predictions for each of the alleles, as well as the C-flanking sequence of the peptide and the mRNA quantification measurement for the peptide.

VII.C.2. Encoding Module

The encoding module 314 encodes information contained in the training data 170 into a numerical representation that can be used to generate the one or more presentation models. In one implementation, the encoding module 314 one-hot encodes sequences (e.g., peptide sequences or C-terminal flanking sequences) over a predetermined 20-letter amino acid alphabet. Specifically, a peptide sequence $p^i$ with $k_i$ amino acids is represented as a row vector of $20 \cdot k_i$ elements, where a single element among $p^i_{20 \cdot (j-1)+1}$, $p^i_{20 \cdot (j-1)+2}$, ... $p^i_{20 \cdot j}$ that corresponds to the alphabet of the amino acid at the j-th position of the peptide sequence has a value of 1. Otherwise, the remaining elements have a value of 0. As an example, for a given alphabet {A, C, D, E, F, G, H, I, K, L, M, N, P, Q, R, S, T, V, W, Y}, the peptide sequence EAF of 3 amino acids for data instance i may be represented by the row vector of 60 elements $p^i$=[0 0 0 1 0 0 0 0 0 0 0 0 0 0 0 0 0 0 0 0 0 0 0 0 0 1 0 0 0 0 0 0 0 0 0 0 0 0 0 0 0 0 0 0 0 0 0 0 0 0 1 0 0 0 0 0 0 0 0 0 0 0 0 0 0]. The C-terminal flanking sequence $c^j$ can be similarly encoded as described above, as well as the protein sequence $d_h$ for MHC alleles, and other sequence data in the presentation information.

When the training data 170 contains sequences of differing lengths of amino acids, the encoding module 314 may further encode the peptides into equal-length vectors by adding a PAD character to extend the predetermined alphabet. For example, this may be performed by left-padding the peptide sequences with the PAD character until the length of the peptide sequence reaches the peptide sequence with the greatest length in the training data 170. Thus, when the peptide sequence with the greatest length has $k_{max}$ amino acids, the encoding module 314 numerically represents each sequence as a row vector of $(20+1) \cdot k_{max}$ elements. As an example, for the extended alphabet {PAD, A, C, D, E, F, G, H, I, K, L, M, N, P, Q, R, S, T, V, W, Y} and a maximum amino acid length of $k_{max}$=5, the same example peptide sequence EAF of 3 amino acids may be represented by the row vector of 105 elements $p^i$=[1 0 0 0 0 0 0 0 0 0 0 0 0 0 0 0 0 0 0 0 0 1 0 0 0 0 0 0 0 0 0 0 0 0 0 0 0 0 0 0 0 0 0 0 1 0 0 0 0 0 0 0 0 0 0 0 0 0 0 0 0 0 0 0 1 0 0 0 0 0 0 0 0 0 0 0 0 0 0 0 0 0 0 0 0 0 0 0 0 0 1 0 0 0 0 0 0 0 0 0 0 0 0 0 0]. The C-terminal flanking sequence $c^j$ or other sequence data can be similarly encoded as described above. Thus, each independent variable or column in the peptide sequence $p^i$ or $c^j$ represents presence of a particular amino acid at a particular position of the sequence.

Although the above method of encoding sequence data was described in reference to sequences having amino acid sequences, the method can similarly be extended to other types of sequence data, such as DNA or RNA sequence data, and the like.

The encoding module 314 also encodes the one or more MHC alleles $a^i$ for data instance i as a row vector of m elements, in which each element h=1, 2, ..., m corresponds to a unique identified MHC allele. The elements corresponding to the MHC alleles identified for the data instance i have a value of 1. Otherwise, the remaining elements have a value of 0. As an example, the alleles HLA-B*07:02 and HLA-C*01:03 for a data instance i corresponding to a multiple-allele cell line among m=4 unique identified MHC allele types {HLA-A*01:01, HLA-C*01:08, HLA-B*07:02, HLA-C*01:03} may be represented by the row vector of 4 elements $a^i$=[0 0 1 1], in which $a_3^i$=1 and $a_4^i$=1. Although the example is described herein with 4 identified MHC allele types, the number of MHC allele types can be hundreds or thousands in practice. As previously discussed, each data instance i typically contains at most 6 different MHC allele types in association with the peptide sequence $p_i$.

The encoding module 314 also encodes the label $y_i$ for each data instance i as a binary variable having values from the set of {0, 1}, in which a value of 1 indicates that peptide $x^i$ was presented by one of the associated MHC alleles $a^i$, and a value of 0 indicates that peptide $x^i$ was not presented by any of the associated MHC alleles $a^i$. When the dependent variable $y_i$ represents the mass spectrometry ion current, the encoding module 314 may additionally scale the values using various functions, such as the log function having a range of $[-\infty, \infty]$ for ion current values between $[0, \infty]$.

The encoding module 314 may represent a pair of allele-interacting variables $x_h^i$ for peptide $p_i$ and an associated MHC allele h as a row vector in which numerical representations of allele-interacting variables are concatenated one after the other. For example, the encoding module 314 may represent $x_h^i$ as a row vector equal to $[p^i]$, $[p^i\ b_h^i]$, $[p^i\ s_h^i]$, or $[p^i\ b_h^i\ s_h^i]$, where $b_h^i$ is the binding affinity prediction for peptide $p_i$ and associated MHC allele h, and similarly for $s_h^i$ for stability. Alternatively, one or more combination of allele-interacting variables may be stored individually (e.g., as individual vectors or matrices).

In one instance, the encoding module 314 represents binding affinity information by incorporating measured or predicted values for binding affinity in the allele-interacting variables $x_h^i$.

In one instance, the encoding module 314 represents binding stability information by incorporating measured or predicted values for binding stability in the allele-interacting variables $x_h^i$, In one instance, the encoding module 314 represents binding on-rate information by incorporating measured or predicted values for binding on-rate in the allele-interacting variables $x_h^i$.

In one instance, the encoding module 314 represents peptide length as a vector $T_k = [\mathbb{1}(L_k=8)\ \mathbb{1}(L_k=9)\ \mathbb{1}(L_k=10)\ \mathbb{1}(L_k=11)\ \mathbb{1}(L_k=12)\ \mathbb{1}(L_k=13)\ \mathbb{1}(L_k=14)\ \mathbb{1}(L_k=15)]$ where $\mathbb{1}$ is the indicator function, and $L_k$ denotes the length of peptide $p_k$. The vector $T_k$ can be included in the allele-interacting variables $x_h^i$.

In one instance, the encoding module 314 represents RNA expression information of MHC alleles by incorporating RNA-seq based expression levels of MHC alleles in the allele-interacting variables $x_h^i$.

Similarly, the encoding module 314 may represent the allele-noninteracting variables $w^i$ as a row vector in which numerical representations of allele-noninteracting variables are concatenated one after the other. For example, $w^i$ may be a row vector equal to $[c^j]$ or $[c^j\ m^i\ w^i]$ in which $w^i$ is a row vector representing any other allele-noninteracting variables in addition to the C-terminal flanking sequence of peptide $p^i$ and the mRNA quantification measurement $m^i$ associated with the peptide. Alternatively, one or more combination of allele-noninteracting variables may be stored individually (e.g., as individual vectors or matrices).

In one instance, the encoding module 314 represents turnover rate of source protein for a peptide sequence by incorporating the turnover rate or half-life in the allele-noninteracting variables $w^i$.

In one instance, the encoding module 314 represents length of source protein or isoform by incorporating the protein length in the allele-noninteracting variables $w^i$.

In one instance, the encoding module 314 represents activation of immunoproteasome by incorporating the mean expression of the immunoproteasome-specific proteasome subunits including the $\beta 1_i$, $\beta 2_i$, $\beta 5_i$ subunits in the allele-noninteracting variables $w^i$.

In one instance, the encoding module 314 represents the RNA-seq abundance of the source protein of the peptide or gene or transcript of a peptide (quantified in units of FPKM, TPM by techniques such as RSEM) can be incorporating the abundance of the source protein in the allele-noninteracting variables $w^i$.

In one instance, the encoding module 314 represents the probability that the transcript of origin of a peptide will undergo nonsense-mediated decay (NMD) as estimated by the model in, for example, Rivas et. al. *Science*, 2015 by incorporating this probability in the allele-noninteracting variables $w^i$.

In one instance, the encoding module 314 represents the activation status of a gene module or pathway assessed via RNA-seq by, for example, quantifying expression of the genes in the pathway in units of TPM using e.g., RSEM for each of the genes in the pathway then computing a summary statistics, e.g., the mean, across genes in the pathway. The mean can be incorporated in the allele-noninteracting variables $w^i$.

In one instance, the encoding module 314 represents the copy number of the source gene by incorporating the copy number in the allele-noninteracting variables $w^i$.

In one instance, the encoding module 314 represents the TAP binding affinity by including the measured or predicted TAP binding affinity (e.g., in nanomolar units) in the allele-noninteracting variables $w^i$.

In one instance, the encoding module 314 represents TAP expression levels by including TAP expression levels measured by RNA-seq (and quantified in units of TPM by e.g., RSEM) in the allele-noninteracting variables $w^i$.

In one instance, the encoding module 314 represents tumor mutations as a vector of indicator variables (i.e., $d^k=1$ if peptide $p^k$ comes from a sample with a KRAS G12D mutation and 0 otherwise) in the allele-noninteracting variables $w^i$.

In one instance, the encoding module 314 represents germline polymorphisms in antigen presentation genes as a vector of indicator variables (i.e., $d^k=1$ if peptide $p^k$ comes from a sample with a specific germline polymorphism in the TAP). These indicator variables can be included in the allele-noninteracting variables $w^i$.

In one instance, the encoding module 314 represents tumor type as a length-one one-hot encoded vector over the alphabet of tumor types (e.g., NSCLC, melanoma, colorectal cancer, etc). These one-hot-encoded variables can be included in the allele-noninteracting variables $w^i$.

In one instance, the encoding module 314 represents MHC allele suffixes by treating 4-digit HLA alleles with different suffixes. For example, HLA-A*24:09N is considered a different allele from HLA-A*24:09 for the purpose of the model. Alternatively, the probability of presentation by an N-suffixed MHC allele can be set to zero for all peptides, because HLA alleles ending in the N suffix are not expressed.

In one instance, the encoding module 314 represents tumor subtype as a length-one one-hot encoded vector over the alphabet of tumor subtypes (e.g., lung adenocarcinoma, lung squamous cell carcinoma, etc). These onehot-encoded variables can be included in the allele-noninteracting variables $w^i$.

In one instance, the encoding module 314 represents smoking history as a binary indicator variable ($d^k=1$ if the patient has a smoking history, and 0 otherwise), that can be included in the allele-noninteracting variables $w^i$. Alternatively, smoking history can be encoded as a length-one one-hot-encoded variable over an alphabet of smoking severity. For example, smoking status can be rated on a 1-5 scale, where 1 indicates nonsmokers, and 5 indicates current heavy smokers. Because smoking history is primarily relevant to lung tumors, when training a model on multiple tumor types, this variable can also be defined to be equal to 1 if the patient has a history of smoking and the tumor type is lung tumors and zero otherwise.

In one instance, the encoding module 314 represents sunburn history as a binary indicator variable ($d^k=1$ if the patient has a history of severe sunburn, and 0 otherwise), which can be included in the allele-noninteracting variables $w^i$. Because severe sunburn is primarily relevant to melanomas, when training a model on multiple tumor types, this variable can also be defined to be equal to 1 if the patient has a history of severe sunburn and the tumor type is melanoma and zero otherwise.

In one instance, the encoding module 314 represents distribution of expression levels of a particular gene or transcript for each gene or transcript in the human genome as summary statistics (e.g., mean, median) of distribution of expression levels by using reference databases such as TCGA. Specifically, for a peptide $p^k$ in a sample with tumor type melanoma, we can include not only the measured gene or transcript expression level of the gene or transcript of origin of peptide $p^k$ in the allele-noninteracting variables $w^i$, but also the mean and/or median gene or transcript expression of the gene or transcript of origin of peptide $p^k$ in melanomas as measured by TCGA.

In one instance, the encoding module 314 represents mutation type as a length-one one-hot-encoded variable over the alphabet of mutation types (e.g., missense, frameshift, NMD-inducing, etc). These onehot-encoded variables can be included in the allele-noninteracting variables $w^i$.

In one instance, the encoding module 314 represents protein-level features of protein as the value of the annotation (e.g., 5' UTR length) of the source protein in the allele-noninteracting variables $w^i$. In another instance, the encoding module 314 represents residue-level annotations of the source protein for peptide $p^k$ by including an indicator variable, that is equal to 1 if peptide $p^k$ overlaps with a helix motif and 0 otherwise, or that is equal to 1 if peptide $p^k$ is completely contained with within a helix motif in the allele-noninteracting variables $w^i$. In another instance, a feature representing proportion of residues in peptide $p^k$ that are contained within a helix motif annotation can be included in the allele-noninteracting variables $w^i$.

In one instance, the encoding module 314 represents type of proteins or isoforms in the human proteome as an indicator vector $o^k$ that has a length equal to the number of proteins or isoforms in the human proteome, and the corresponding element $o^k_i$ is 1 if peptide $p^k$ comes from protein i and 0 otherwise.

The encoding module 314 may also represent the overall set of variables $z^i$ for peptide $p^i$ and an associated MHC allele h as a row vector in which numerical representations of the allele-interacting variables $x^i$ and the allele-noninteracting variables $w^i$ are concatenated one after the other. For example, the encoding module 314 may represent $z_h^i$ as a row vector equal to $[x_h^i \ w^i]$ or $[w_i \ x_h^i]$.

VIII. Training Module

The training module 316 constructs one or more presentation models that generate likelihoods of whether peptide sequences will be presented by MHC alleles associated with the peptide sequences. Specifically, given a peptide sequence $p^k$ and a set of MHC alleles $a^k$ associated with the peptide sequence $p^k$, each presentation model generates an estimate $u_k$ indicating a likelihood that the peptide sequence $p^k$ will be presented by one or more of the associated MHC alleles $a^k$.

VIII.A. Overview

The training module 316 constructs the one more presentation models based on the training data sets stored in store 170 generated from the presentation information stored in 165. Generally, regardless of the specific type of presentation model, all of the presentation models capture the dependence between independent variables and dependent variables in the training data 170 such that a loss function is minimized. Specifically, the loss function $\ell(y_{i \in S}, u_{i \in S}, \theta)$ represents discrepancies between values of dependent variables $y_{i \in S}$ for one or more data instances S in the training data 170 and the estimated likelihoods $u_{i \in S}$ for the data instances S generated by the presentation model. In one particular implementation referred throughout the remainder of the specification, the loss function $(y_{i \in S}, u_{i \in S}, \theta)$ is the negative log likelihood function given by equation (1a) as follows:

$$\ell(y_{i \in S}, u_{i \in S}; \theta) = \sum_{i \in S} (y_i \log u_i + (1 - y_i) \log(1 - u_i)). \quad (1a)$$

However, in practice, another loss function may be used. For example, when predictions are made for the mass spectrometry ion current, the loss function is the mean squared loss given by equation 1b as follows:

$$\ell(y_{i \in S}, u_{i \in S}; \theta) = \sum_{i \in S} (\|y_i - u_i\|_2^2). \quad (1b)$$

The presentation model may be a parametric model in which one or more parameters $\theta$ mathematically specify the dependence between the independent variables and dependent variables. Typically, various parameters of parametric-type presentation models that minimize the loss function $(y_{i \in S}, u_{i \in S}, \theta)$ are determined through gradient-based numerical optimization algorithms, such as batch gradient algorithms, stochastic gradient algorithms, and the like. Alternatively, the presentation model may be a non-parametric model in which the model structure is determined from the training data 170 and is not strictly based on a fixed set of parameters.

VIII.B. Per-Allele Models

The training module 316 may construct the presentation models to predict presentation likelihoods of peptides on a per-allele basis. In this case, the training module 316 may train the presentation models based on data instances S in the training data 170 generated from cells expressing single MHC alleles.

In one implementation, the training module 316 models the estimated presentation likelihood $u_k$ for peptide $p^k$ for a specific allele h by:

$$u_k^h = Pr(p^k \text{ presented; MHC allele } h) = f(g_h(x_h^k; \theta_h)), \quad (2)$$

where peptide sequence $x_h^k$ denotes the encoded allele-interacting variables for peptide $p^k$ and corresponding MHC allele h,$f(\cdot)$ is any function, and is herein throughout is referred to as a transformation function for convenience of description. Further, $g_h(\bullet)$ is any function, is herein throughout referred to as a dependency function for convenience of description, and generates dependency scores for the allele-interacting variables $x_h^k$ based on a set of parameters $\theta_h$ determined for MHC allele h. The values for the set of parameters $\theta_h$ for each MHC allele h can be determined by minimizing the loss function with respect to $\theta_h$, where i is each instance in the subset S of training data 170 generated from cells expressing the single MHC allele h.

The output of the dependency function $g_h(x_h^k; \theta_h)$ represents a dependency score for the MHC allele h indicating whether the MHC allele h will present the corresponding neoantigen based on at least the allele interacting features $x_h^k$, and in particular, based on positions of amino acids of the peptide sequence of peptide $p^k$. For example, the dependency score for the MHC allele h may have a high value if the MHC allele h is likely to present the peptide $p^k$, and may have a low value if presentation is not likely. The transformation function $f(\bullet)$ transforms the input, and more specifically, transforms the dependency score generated by $g_h(x_h^k; \theta_h)$ in this case, to an appropriate value to indicate the likelihood that the peptide $p^k$ will be presented by an MHC allele.

In one particular implementation referred throughout the remainder of the specification, $f(\bullet)$ is a function having the range within [0, 1] for an appropriate domain range. In one example, $f(\bullet)$ is the expit function given by:

$$f(z) = \frac{\exp(z)}{1 + \exp(z)}. \quad (4)$$

As another example, $f(\bullet)$ can also be the hyperbolic tangent function given by:

$$f(z) = \tan h(z) \quad (5)$$

when the values for the domain z is equal to or greater than 0. Alternatively, when predictions are made for the mass spectrometry ion current that have values outside the range [0, 1], $f(\bullet)$ can be any function such as the identity function, the exponential function, the log function, and the like.

Thus, the per-allele likelihood that a peptide sequence $p^k$ will be presented by a MHC allele h can be generated by applying the dependency function $g_h(\bullet)$ for the MHC allele h to the encoded version of the peptide sequence $p^k$ to generate the corresponding dependency score. The dependency score may be transformed by the transformation function $f(\bullet)$ to generate a per-allele likelihood that the peptide sequence $p^k$ will be presented by the MHC allele h.

VIII.B.1 Dependency Functions for Allele Interacting Variables

In one particular implementation referred throughout the specification, the dependency function $g_h(\bullet)$ is an affine function given by:

$$g_h(x_h; \theta_h) = x_h^i \cdot \theta_h. \quad (6)$$

that linearly combines each allele-interacting variable in $x_h^k$ with a corresponding parameter in the set of parameters $\theta_h$ determined for the associated MHC allele h.

In another particular implementation referred throughout the specification, the dependency function $g_h(\bullet)$ is a network function given by:

$$g_h(x_h^i; \theta_h) = NN_h(x_h^i; \theta_h). \quad (7)$$

represented by a network model $NN_h(\bullet)$ having a series of nodes arranged in one or more layers. A node may be connected to other nodes through connections each having an associated parameter in the set of parameters $\theta_h$. A value at one particular node may be represented as a sum of the values of nodes connected to the particular node weighted by the associated parameter mapped by an activation function associated with the particular node. In contrast to the affine function, network models are advantageous because the presentation model can incorporate non-linearity and process data having different lengths of amino acid sequences. Specifically, through non-linear modeling, network models can capture interaction between amino acids at different positions in a peptide sequence and how this interaction affects peptide presentation.

In general, network models $NN_h(\bullet)$ may be structured as feed-forward networks, such as artificial neural networks (ANN), convolutional neural networks (CNN), deep neural networks (DNN), and/or recurrent networks, such as long short-term memory networks (LSTM), bi-directional recurrent networks, deep bi-directional recurrent networks, and the like.

In one instance referred throughout the remainder of the specification, each MHC allele in h=1, 2, . . . , m is associated with a separate network model, and $NN_h(\bullet)$ denotes the output(s) from a network model associated with MHC allele h.

FIG. 5 illustrates an example network model $NN_3(\bullet)$ in association with an arbitrary MHC allele h=3. As shown in FIG. 5, the network model $NN_3(\bullet)$ for MHC allele h=3 includes three input nodes at layer l=1, four nodes at layer l=2, two nodes at layer l=3, and one output node at layer l=4. The network model $NN_3(\bullet)$ is associated with a set of ten parameters $\theta_3(1), \theta_3(2), \ldots, \theta_3(10)$. The network model $NN_3(\bullet)$ receives input values (individual data instances including encoded polypeptide sequence data and any other training data used) for three allele-interacting variables $x_3^k(1), x_3^k(2)$, and $x_3^k(3)$ for MHC allele h=3 and outputs the value $NN_3(x_3^k)$.

In another instance, the identified MHC alleles h=1, 2, . . . , m are associated with a single network model $NN_H(\bullet)$, and $NN_h(\bullet)$ denotes one or more outputs of the single network model associated with MHC allele h. In such an instance, the set of parameters $\theta_h$ may correspond to a set of parameters for the single network model, and thus, the set of parameters $\theta_h$ may be shared by all MHC alleles.

Figure 6A:
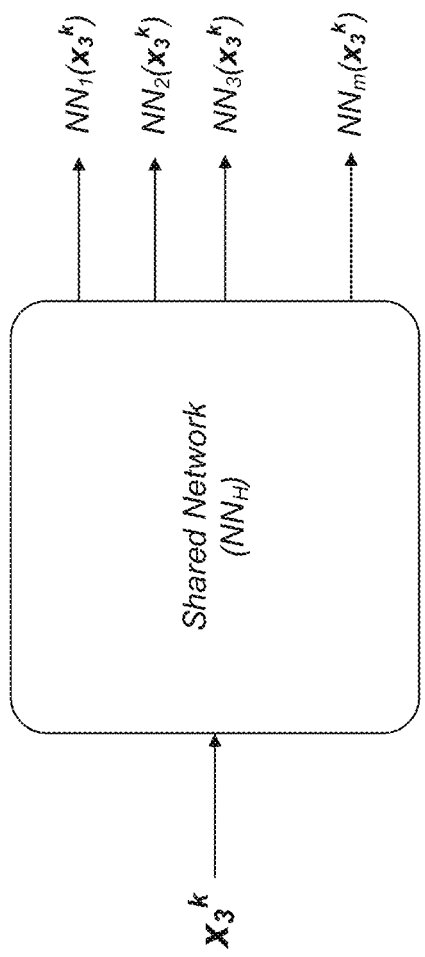
FIG. 6A illustrates an example network model $NN_H(\cdot)$ shared by MHC alleles, according to one embodiment.

FIG. 6A illustrates an example network model $NN_H(\bullet)$ shared by MHC alleles h=1, 2, . . . , m. As shown in FIG. 6A, the network model $NN_H(\bullet)$ includes m output nodes each corresponding to an MHC allele. The network model $NN_3(\bullet)$ receives the allele-interacting variables $x_3^k$ for MHC allele h=3 and outputs m values including the value $NN_3(x_3^k)$ corresponding to the MHC allele h=3.

In yet another instance, the single network model $NN_H(\bullet)$ may be a network model that outputs a dependency score given the allele interacting variables $x_h^k$ and the encoded protein sequence $d_h$ of an MHC allele h. In such an instance, the set of parameters $\theta_h$ may again correspond to a set of parameters for the single network model, and thus, the set of parameters $\theta_h$ may be shared by all MHC alleles. Thus, in such an instance, $NN_h(\bullet)$ may denote the output of the single network model $NN_H(\bullet)$ given inputs $[x_h^k\ d_h]$ to the single network model. Such a network model is advantageous because peptide presentation probabilities for MHC alleles that were unknown in the training data can be predicted just by identification of their protein sequence.

Figure 6B:
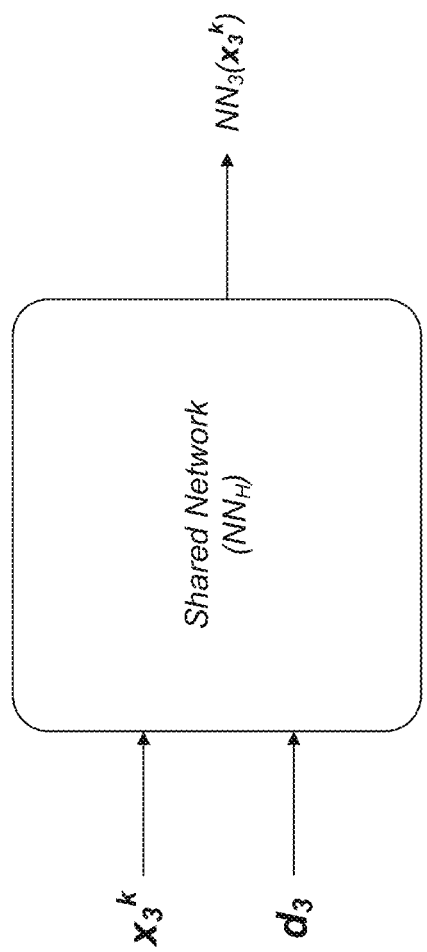
FIG. 6B illustrates an example network model $NN_H(\cdot)$ shared by MHC alleles, according to another embodiment.

FIG. 6B illustrates an example network model $NN_H(\cdot)$ shared by MHC alleles. As shown in FIG. 6B, the network model $NN_H(\cdot)$ receives the allele interacting variables and protein sequence of MHC allele h=3 as input, and outputs a dependency score $NN_3(x_3^k)$ corresponding to the MHC allele h=3.

In yet another instance, the dependency function $g_h(\cdot)$ can be expressed as:

$$g_h(x_h^k;\theta_h)=g'_h(x_h^k;\theta'_h)+\theta_h^0$$

where $g'_h(x_h^k;\theta'_h)$ is the affine function with a set of parameters $\theta'_h$, the network function, or the like, with a bias parameter $\theta_h^0$ in the set of parameters for allele interacting variables for the MHC allele that represents a baseline probability of presentation for the MHC allele h.

In another implementation, the bias parameter $\theta_h^0$ may be shared according to the gene family of the MHC allele h. That is, the bias parameter $\theta_h^0$ for MHC allele h may be equal to $\theta_{gene(h)}^0$, where gene(h) is the gene family of MHC allele h. For example, MHC alleles HLA-A*02:01, HLA-A*02:02, and HLA-A*02:03 may be assigned to the gene family of "HLA-A," and the bias parameter $\theta_h^0$ for each of these MHC alleles may be shared.

Returning to equation (2), as an example, the likelihood that peptide $p^k$ will be presented by MHC allele h=3, among m=4 different identified MHC alleles using the affine dependency function $g_h(\cdot)$, can be generated by:

$$u_k^3=f(x_3^k\cdot\theta_3),$$

where $x_3^k$ are the identified allele-interacting variables for MHC allele h=3, and $\theta_3$ are the set of parameters determined for MHC allele h=3 through loss function minimization.

As another example, the likelihood that peptide $p^k$ will be presented by MHC allele h=3, among m=4 different identified MHC alleles using separate network transformation functions $g_h(\cdot)$, can be generated by:

$$u_k^3=f(NN_3(x_3^k;\theta_3)),$$

where $x_3^k$ are the identified allele-interacting variables for MHC allele h=3, and $\theta_3$ are the set of parameters determined for the network model $NN_3(\cdot)$ associated with MHC allele h=3.

Figure 7:
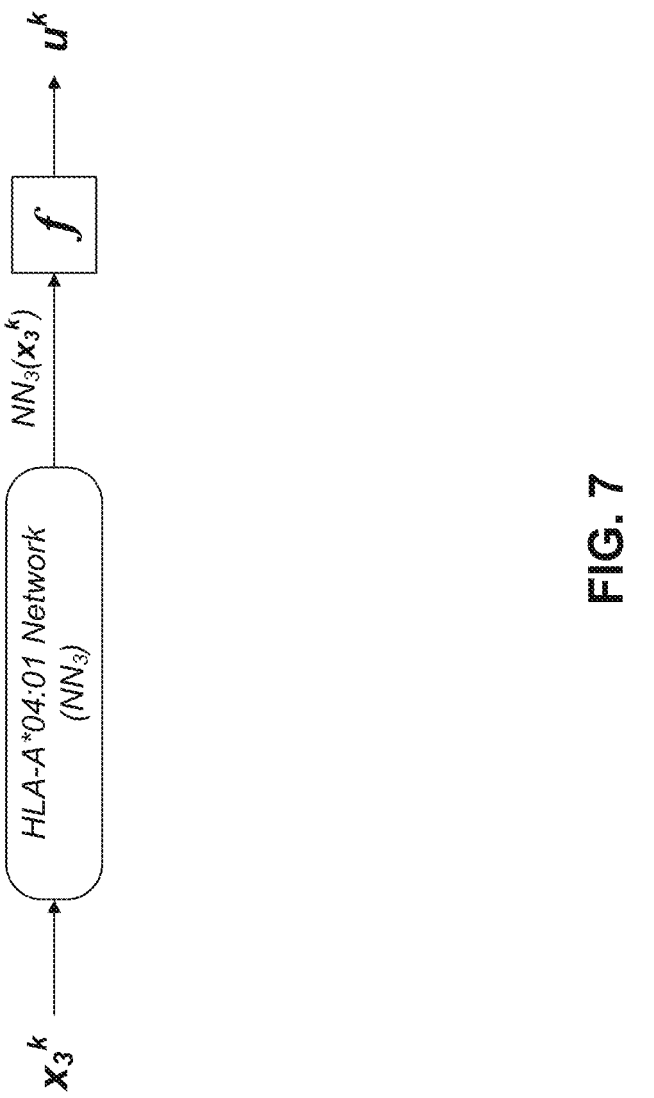
FIG. 7 illustrates generating a presentation likelihood for a peptide in association with an MHC allele using an example network model.

FIG. 7 illustrates generating a presentation likelihood for peptide $p^k$ in association with MHC allele h=3 using an example network model $NN_3(\cdot)$. As shown in FIG. 7, the network model $NN_3(\cdot)$ receives the allele-interacting variables $x_3^k$ for MHC allele h=3 and generates the output $NN_3(x_3^k)$. The output is mapped by function $f(\cdot)$ to generate the estimated presentation likelihood $u_k$.

VIII.B.2. Per-Allele with Allele-Noninteracting Variables

In one implementation, the training module 316 incorporates allele-noninteracting variables and models the estimated presentation likelihood $u_k$ for peptide $p^k$ by:

$$u_h^k=Pr(p^k \text{ presented})=f(g_w(w_k;\theta_w)+g_h(x_h^i;\theta_h)), \quad (8)$$

where $w^k$ denotes the encoded allele-noninteracting variables for peptide $p^k$, $g_w(\cdot)$ is a function for the allele-noninteracting variables $w^k$ based on a set of parameters $\theta_w$ determined for the allele-noninteracting variables. Specifically, the values for the set of parameters $\theta_h$ for each MHC allele h and the set of parameters $\theta_w$ for allele-noninteracting variables can be determined by minimizing the loss function with respect to $\theta_h$ and $\theta_w$, where i is each instance in the subset S of training data 170 generated from cells expressing single MHC alleles.

The output of the dependency function $g_w(w^k;\theta_w)$ represents a dependency score for the allele noninteracting variables indicating whether the peptide $p^k$ will be presented by one or more MHC alleles based on the impact of allele noninteracting variables. For example, the dependency score for the allele noninteracting variables may have a high value if the peptide $p^k$ is associated with a C-terminal flanking sequence that is known to positively impact presentation of the peptide $p^k$, and may have a low value if the peptide $p^k$ is associated with a C-terminal flanking sequence that is known to negatively impact presentation of the peptide $p^k$.

According to equation (8), the per-allele likelihood that a peptide sequence $p^k$ will be presented by a MHC allele h can be generated by applying the function $g_h(\cdot)$ for the MHC allele h to the encoded version of the peptide sequence $p^k$ to generate the corresponding dependency score for allele interacting variables. The function $g_w(\cdot)$ for the allele non-interacting variables are also applied to the encoded version of the allele noninteracting variables to generate the dependency score for the allele noninteracting variables. Both scores are combined, and the combined score is transformed by the transformation function $f(\cdot)$ to generate a per-allele likelihood that the peptide sequence $p^k$ will be presented by the MHC allele h.

Alternatively, the training module 316 may include allele-noninteracting variables $w^k$ in the prediction by adding the allele-noninteracting variables $w^k$ to the allele-interacting variables $x_h^k$ in equation (2). Thus, the presentation likelihood can be given by:

$$u_h^k=Pr(p^k \text{ presented; allele } h)=f(g_h([x_h^k w^k];\theta_h)). \quad (9)$$

VIII.B.3 Dependency Functions for Allele-Noninteracting Variables

Similarly to the dependency function $g_h(\cdot)$ for allele-interacting variables, the dependency function $g_w(\cdot)$ for allele noninteracting variables may be an affine function or a network function in which a separate network model is associated with allele-noninteracting variables $w^k$.

Specifically, the dependency function $g_w(\cdot)$ is an affine function given by:

$$g_w(w^k;\theta_w)=w^k\cdot\theta_w.$$

that linearly combines the allele-noninteracting variables in $w^k$ with a corresponding parameter in the set of parameters $\theta_w$.

The dependency function $g_w(\cdot)$ may also be a network function given by:

$$g_h(w^k;\theta_w)=NN_w(w^k;\theta_w).$$

represented by a network model $NN_w(\cdot)$ having an associated parameter in the set of parameters $\theta_w$.

In another instance, the dependency function $g_w(\cdot)$ for the allele-noninteracting variables can be given by:

$$g_w(w^k;\theta_w)=g'_w(w^k;\theta'_w)+h(m^k;\theta_w^m), \quad (10)$$

where $g'_w(w^k;\theta'_w)$ is the affine function, the network function with the set of allele noninteracting parameters $\theta'_w$, or the like, $m^k$ is the mRNA quantification measurement for peptide $p^k$, $h(\cdot)$ is a function transforming the quantification measurement, and $\theta_w^m$ is a parameter in the set of parameters for allele noninteracting variables that is combined with the mRNA quantification measurement to generate a dependency score for the mRNA quantification measurement. In one particular embodiment referred throughout the remainder of the specification, h(•) is the log function, however in practice h(•) may be any one of a variety of different functions.

In yet another instance, the dependency function the dependency function $g_w(•)$ for the allele-noninteracting variables can be given by:

$$g_w(w^k;\theta_w)=g'_w(w^k;\theta'_w)+\theta_w^o \cdot o^k, \quad (11)$$

where $g'_w(w^k; \theta'_w)$ is the affine function, the network function with the set of allele noninteracting parameters $\theta'_w$, or the like, $o^k$ is the indicator vector described above representing proteins and isoforms in the human proteome for peptide $p^k$, and $\theta_w^o$ is a set of parameters in the set of parameters for allele noninteracting variables that is combined with the indicator vector. In one variation, when the dimensionality of $o^k$ and the set of parameters $\theta_w^o$ are significantly high, a parameter regularization term, such as $\lambda \cdot \|\theta_w^o\|$, where $\|•\|$ represents L1 norm, L2 norm, a combination, or the like, can be added to the loss function when determining the value of the parameters. The optimal value of the hyperparameter $\lambda$ can be determined through appropriate methods.

Returning to equation (8), as an example, the likelihood that peptide $p^k$ will be presented by MHC allele h=3, among m=4 different identified MHC alleles using the affine transformation functions $g_h(•)$, $g_w(•)$, can be generated by:

$$u_k^3 = f(w^k \cdot \theta_w + x_k^3 \cdot \theta_3),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC allele h=3, among m=4 different identified MHC alleles using the network transformation functions $g_h(•)$, $g_w(•)$, can be generated by:

$$u_k^3 = f(NN_w(w^k;\theta_w)+NN_3(x_3^k;\theta_3))$$

where $w^k$ are the identified allele-interacting variables for peptide $p^k$, and $\theta_w$ are the set of parameters determined for allele-noninteracting variables.

Figure 8:
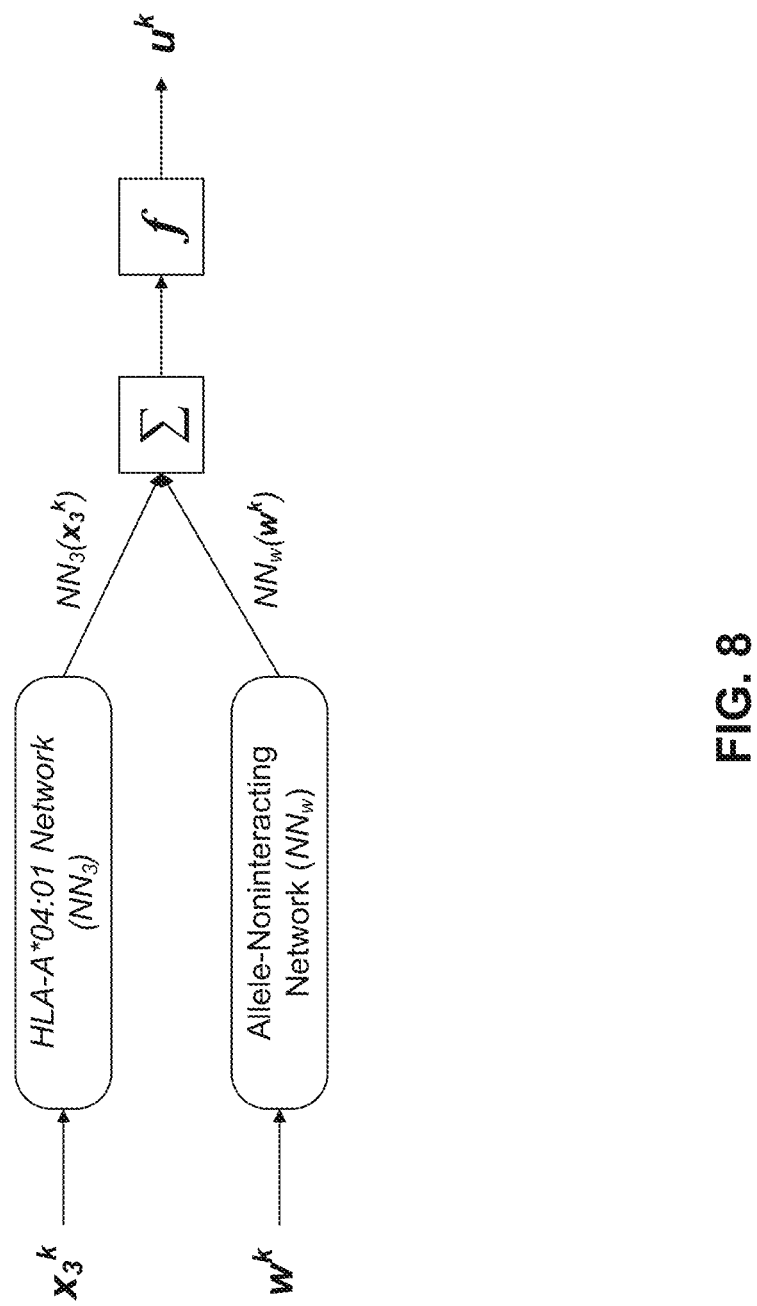
FIG. 8 illustrates generating a presentation likelihood for a peptide in association with a MHC allele using example network models.

FIG. 8 illustrates generating a presentation likelihood for peptide $p^k$ in association with MHC allele h=3 using example network models $NN_3(•)$ and $NN_w(•)$. As shown in FIG. 8, the network model $NN_3(•)$ receives the allele-interacting variables $x_3^k$ for MHC allele h=3 and generates the output $NN_3(x_3^k)$. The network model $NN_w(•)$ receives the allele-noninteracting variables $w^k$ for peptide $p^k$ and generates the output $NN_w(w^k)$. The outputs are combined and mapped by function $f(•)$ to generate the estimated presentation likelihood $u_k$.

VIII.C. Multiple-Allele Models

The training module 316 may also construct the presentation models to predict presentation likelihoods of peptides in a multiple-allele setting where two or more MHC alleles are present. In this case, the training module 316 may train the presentation models based on data instances S in the training data 170 generated from cells expressing single MHC alleles, cells expressing multiple MHC alleles, or a combination thereof.

VIII.C.1. Example 1: Maximum of Per-Allele Models

In one implementation, the training module 316 models the estimated presentation likelihood $u_k$ for peptide $p^k$ in association with a set of multiple MHC alleles H as a function of the presentation likelihoods $u_k^{h \in H}$ determined for each of the MHC alleles h in the set H determined based on cells expressing single-alleles, as described above in conjunction with equations (2)-(11). Specifically, the presentation likelihood $u_k$ can be any function of $u_k^{h \in H}$. In one implementation, as shown in equation (12), the function is the maximum function, and the presentation likelihood $u_k$ can be determined as the maximum of the presentation likelihoods for each MHC allele h in the set H.

$$u_k = Pr(p^k \text{ presented; alleles } H) = \max(u_k^{h \in H}). \quad (12)$$

VIII.C.2. Example 2.1: Function-of-Sums Models

In one implementation, the training module 316 models the estimated presentation likelihood $u_k$ for peptide $p^k$ by:

$$u_k = Pr(p^k \text{ presented}) = f\left(\sum_{h=1}^{m} a_h^k \cdot g_h(x_h^k; \theta_h)\right), \quad (13)$$

where elements $a_h^k$ are 1 for the multiple MHC alleles H associated with peptide sequence $p^k$ and $x_h^k$ denotes the encoded allele-interacting variables for peptide $p^k$ and the corresponding MHC alleles. The values for the set of parameters $\theta_h$ for each MHC allele h can be determined by minimizing the loss function with respect to $\theta_h$, where i is each instance in the subset S of training data 170 generated from cells expressing single MHC alleles and/or cells expressing multiple MHC alleles. The dependency function $g_h$ may be in the form of any of the dependency functions $g_h$ introduced above in sections VIII.B. 1.

According to equation (13), the presentation likelihood that a peptide sequence $p^k$ will be presented by one or more MHC alleles h can be generated by applying the dependency function $g_h(•)$ to the encoded version of the peptide sequence $p^k$ for each of the MHC alleles H to generate the corresponding score for the allele interacting variables. The scores for each MHC allele h are combined, and transformed by the transformation function $f(•)$ to generate the presentation likelihood that peptide sequence $p^k$ will be presented by the set of MHC alleles H.

The presentation model of equation (13) is different from the per-allele model of equation (2), in that the number of associated alleles for each peptide $p^k$ can be greater than 1. In other words, more than one element in $a_h^k$ can have values of 1 for the multiple MHC alleles H associated with peptide sequence $p^k$.

As an example, the likelihood that peptide $p^k$ will be presented by MHC alleles h=2, h=3, among m=4 different identified MHC alleles using the affine transformation functions $g_h(•)$, can be generated by:

$$u_k = f(x_2^k \cdot \theta_2 + x_3^k \cdot \theta_3),$$

where $x_2^k$, $x_3^k$ are the identified allele-interacting variables for MHC alleles h=2, h=3, and $\theta_2$, $\theta_3$ are the set of parameters determined for MHC alleles h=2, h=3.

As another example, the likelihood that peptide $p^k$ will be presented by MHC alleles h=2, h=3, among m=4 different identified MHC alleles using the network transformation functions $g_h(•)$, $g_w(•)$, can be generated by:

$$u_k = f(NN_2(x_2^k;\theta_2)+NN_3(x_3^k;\theta_3)),$$

where $NN_2(•)$, $NN_3(•)$ are the identified network models for MHC alleles h=2, h=3, and $\theta_2$, $\theta_3$ are the set of parameters determined for MHC alleles h=2, h=3.

Figure 9:
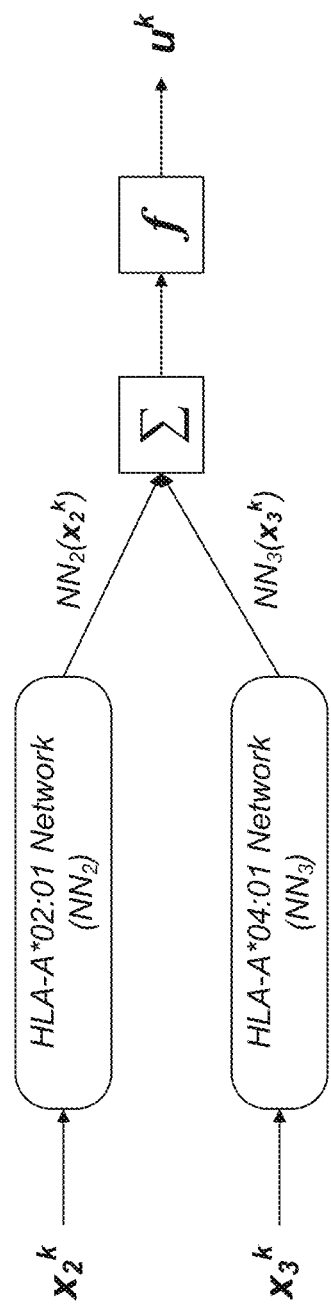
FIG. 9 illustrates generating a presentation likelihood for a peptide in association with MHC alleles using example network models.

FIG. 9 illustrates generating a presentation likelihood for peptide $p^k$ in association with MHC alleles h=2, h=3 using example network models $NN_2(\cdot)$ and $NN_3(\cdot)$. As shown in FIG. 9, the network model $NN_2(\cdot)$ receives the allele-interacting variables $x_2^k$ for MHC allele h=2 and generates the output $NN_2(x_2^k)$ and the network model $NN_3(\cdot)$ receives the allele-interacting variables $x_3^k$ for MHC allele h=3 and generates the output $NN_3(x_3^k)$. The outputs are combined and mapped by function $f(\cdot)$ to generate the estimated presentation likelihood $u_k$.

VIII.C.3. Example 2.2: Function-of-Sums Models with Allele-Noninteracting Variables In one implementation, the training module 316 incorporates allele-noninteracting variables and models the estimated presentation likelihood $u_k$ for peptide $p^k$ by:

$$u_k = Pr(p^k \text{ presented}) = f\left(g_w(w^k;\theta_w) + \sum_{h=1}^{m} a_h^k \cdot g_h(x_h^k;\theta_h)\right), \quad (14)$$

where $w^k$ denotes the encoded allele-noninteracting variables for peptide $p^k$. Specifically, the values for the set of parameters $\theta_h$ for each MHC allele h and the set of parameters $\theta_w$ for allele-noninteracting variables can be determined by minimizing the loss function with respect to $\theta_h$ and $\theta_w$, where i is each instance in the subset S of training data 170 generated from cells expressing single MHC alleles and/or cells expressing multiple MHC alleles. The dependency function $g_w$ may be in the form of any of the dependency functions $g_w$ introduced above in sections VIII.B.3.

Thus, according to equation (14), the presentation likelihood that a peptide sequence $p^k$ will be presented by one or more MHC alleles H can be generated by applying the function $g_h(\cdot)$ to the encoded version of the peptide sequence $p^k$ for each of the MHC alleles H to generate the corresponding dependency score for allele interacting variables for each MHC allele h. The function $g_w(\cdot)$ for the allele noninteracting variables is also applied to the encoded version of the allele noninteracting variables to generate the dependency score for the allele noninteracting variables. The scores are combined, and the combined score is transformed by the transformation function $f(\cdot)$ to generate the presentation likelihood that peptide sequence $p^k$ will be presented by the MHC alleles H.

In the presentation model of equation (14), the number of associated alleles for each peptide $p^k$ can be greater than 1. In other words, more than one element in $a_h^k$ can have values of 1 for the multiple MHC alleles H associated with peptide sequence $p^k$.

As an example, the likelihood that peptide $p^k$ will be presented by MHC alleles h=2, h=3, among m=4 different identified MHC alleles using the affine transformation functions $g_h(\cdot)$, $g_w(\cdot)$, can be generated by:

$$u_k f(w^k \cdot \theta_w + x_2^k \cdot \theta_2 + x_3^k \cdot \theta_3),$$

where $w^k$ are the identified allele-noninteracting variables for peptide $p^k$, and $\theta_w$, are the set of parameters determined for the allele-noninteracting variables.

As another example, the likelihood that peptide $p^k$ will be presented by MHC alleles h=2, h=3, among m=4 different identified MHC alleles using the network transformation functions $g_h(\cdot)$, $g_w(\cdot)$, can be generated by:

$$u_k = f(NN_w(w^k;\theta_w) + NN_2(x_2^k;\theta_2) + NN_3(x_3^k;\theta_3))$$

where $w^k$ are the identified allele-interacting variables for peptide $p^k$, and $\theta_w$ are the set of parameters determined for allele-noninteracting variables.

Figure 10:
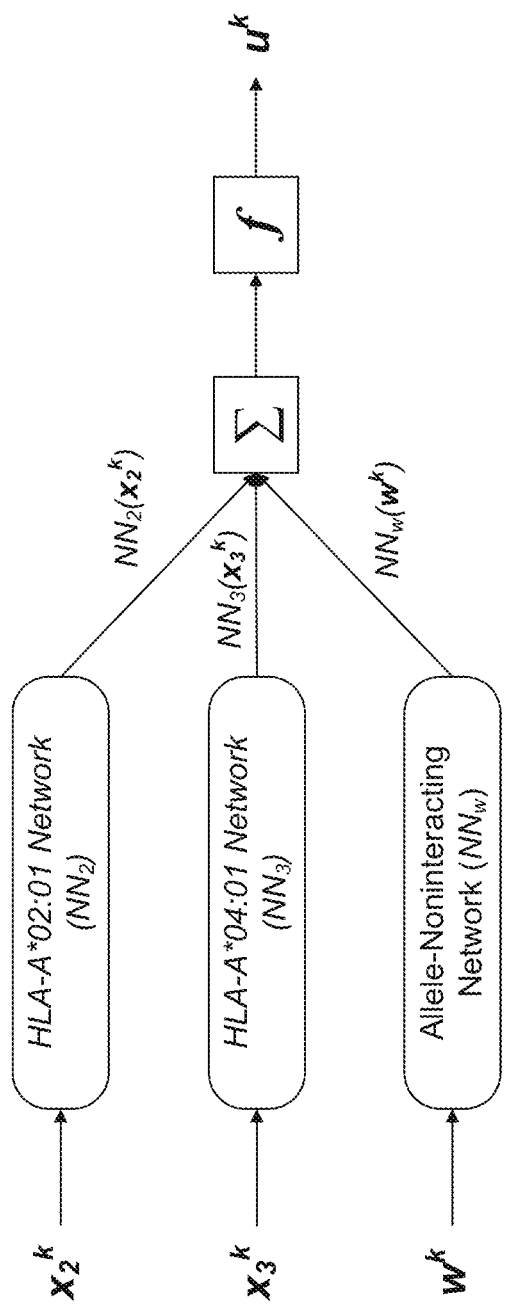
FIG. 10 illustrates generating a presentation likelihood for a peptide in association with MHC alleles using example network models.

FIG. 10 illustrates generating a presentation likelihood for peptide $p^k$ in association with MHC alleles h=2, h=3 using example network models $NN_2(\cdot)$, $NN_3(\cdot)$, and $NN_w(\cdot)$. As shown in FIG. 10, the network model $NN_2(\cdot)$ receives the allele-interacting variables $x_2^k$ for MHC allele h=2 and generates the output $NN_2(x_2^k)$. The network model $NN_3(\cdot)$ receives the allele-interacting variables $x_3^k$ for MHC allele h=3 and generates the output $NN_3(x_3^k)$. The network model $NN_w(\cdot)$ receives the allele-noninteracting variables $w^k$ for peptide $p^k$ and generates the output $NN_w(w^k)$. The outputs are combined and mapped by function $f(\cdot)$ to generate the estimated presentation likelihood $u_k$.

Alternatively, the training module 316 may include allele-noninteracting variables $w^k$ in the prediction by adding the allele-noninteracting variables $w^k$ to the allele-interacting variables $x_h^k$ in equation (15). Thus, the presentation likelihood can be given by:

$$u_k = Pr(p^k \text{ presented}) = f\left(\sum_{h=1}^{m} a_h^k \cdot g_h([x_h^k w^k]; \theta_h)\right). \quad (15)$$

VIII.C.4. Example 3.1: Models Using Implicit Per-Allele Likelihoods

In another implementation, the training module 316 models the estimated presentation likelihood $u_k$ for peptide $p^k$ by:

$$u_k = Pr(p^k \text{ presented}) = r(s(v = [a_1^k \cdot u'_k{}^1(\theta) \ldots a_m^k \cdot u'_k{}^m (\theta)])), \quad (16)$$

where elements $a_h^k$ are 1 for the multiple MHC alleles h∈H associated with peptide sequence $p^k$, $u'_k{}^h$ is an implicit per-allele presentation likelihood for MHC allele h, vector v is a vector in which element $v_h$ corresponds to $a_h^k \cdot u'_k{}^h$, $s(\cdot)$ is a function mapping the elements of v, and $r(\cdot)$ is a clipping function that clips the value of the input into a given range. As described below in more detail, $s(\cdot)$ may be the summation function or the second-order function, but it is appreciated that in other embodiments, $s(\cdot)$ can be any function such as the maximum function. The values for the set of parameters $\theta$ for the implicit per-allele likelihoods can be determined by minimizing the loss function with respect to $\theta$, where i is each instance in the subset S of training data 170 generated from cells expressing single MHC alleles and/or cells expressing multiple MHC alleles.

The presentation likelihood in the presentation model of equation (17) is modeled as a function of implicit per-allele presentation likelihoods $u'_k{}^h$ that each correspond to the likelihood peptide $p^k$ will be presented by an individual MHC allele h. The implicit per-allele likelihood is distinct from the per-allele presentation likelihood of section VIII.B in that the parameters for implicit per-allele likelihoods can be learned from multiple allele settings, in which direct association between a presented peptide and the corresponding MHC allele is unknown, in addition to single-allele settings. Thus, in a multiple-allele setting, the presentation model can estimate not only whether peptide $p^k$ will be presented by a set of MHC alleles H as a whole, but can also provide individual likelihoods $u'_k{}^{h \in H}$ that indicate which MHC allele h most likely presented peptide $p^k$. An advantage of this is that the presentation model can generate the implicit likelihoods without training data for cells expressing single MHC alleles.

In one particular implementation referred throughout the remainder of the specification, $r(\cdot)$ is a function having the range [0, 1]. For example, $r(\cdot)$ may be the clip function:

$$r(z)=\min(\max(z,0),1),$$

where the minimum value between z and 1 is chosen as the presentation likelihood $u_k$. In another implementation, $r(\cdot)$ is the hyperbolic tangent function given by:

$$r(z)=\tan h(z)$$

when the values for the domain z is equal to or greater than 0.

VIII.C.5. Example 3.2: Sum-of-Functions Model

In one particular implementation, $s(\cdot)$ is a summation function, and the presentation likelihood is given by summing the implicit per-allele presentation likelihoods:

$$u_k = Pr(p^k \text{ presented}) = r\left(\sum_{h=1}^{m} a_h^k \cdot u'^h_k(\theta)\right). \quad (17)$$

In one implementation, the implicit per-allele presentation likelihood for MHC allele h is generated by:

$$u'^h_k = f(g_h(x_h^k; \theta_h)), \quad (18)$$

such that the presentation likelihood is estimated by:

$$u_k = Pr(p^k \text{ presented}) = r\left(\sum_{h=1}^{m} a_h^k \cdot f(g_h(x_h^k; \theta_h))\right). \quad (19)$$

According to equation (19), the presentation likelihood that a peptide sequence $p^k$ will be presented by one or more MHC alleles H can be generated by applying the function $g_h(\cdot)$ to the encoded version of the peptide sequence $p^k$ for each of the MHC alleles H to generate the corresponding dependency score for allele interacting variables. Each dependency score is first transformed by the function $f(\cdot)$ to generate implicit per-allele presentation likelihoods $u'^h_k$. The per-allele likelihoods $u'^h_k$ are combined, and the clipping function may be applied to the combined likelihoods to clip the values into a range [0, 1] to generate the presentation likelihood that peptide sequence $p^k$ will be presented by the set of MHC alleles H. The dependency function $g_h$ may be in the form of any of the dependency functions $g_h$ introduced above in sections VIII.B.1.

As an example, the likelihood that peptide $p^k$ will be presented by MHC alleles h=2, h=3, among m=4 different identified MHC alleles using the affine transformation functions $g_h(\cdot)$, can be generated by:

$$u_k = r(f(x_2^k \cdot \theta_2) + f(x_3^k \cdot \theta_3)).$$

where $x_2^k$, $x_3^k$ are the identified allele-interacting variables for MHC alleles h=2, h=3, and $\theta_2$, $\theta_3$ are the set of parameters determined for MHC alleles h=2, h=3.

As another example, the likelihood that peptide $p^k$ will be presented by MHC alleles h=2, h=3, among m=4 different identified MHC alleles using the network transformation functions $g_h(\cdot)$, $g_w(\cdot)$, can be generated by:

$$u_k = r(f(NN_2(x_2^k; \theta_2)) + f(NN_3(x_3^k; \theta_3))),$$

where $NN_2(\cdot)$, $NN_3(\cdot)$ are the identified network models for MHC alleles h=2, h=3, and $\theta_2$, $\theta_3$ are the set of parameters determined for MHC alleles h=2, h=3.

Figure 11:
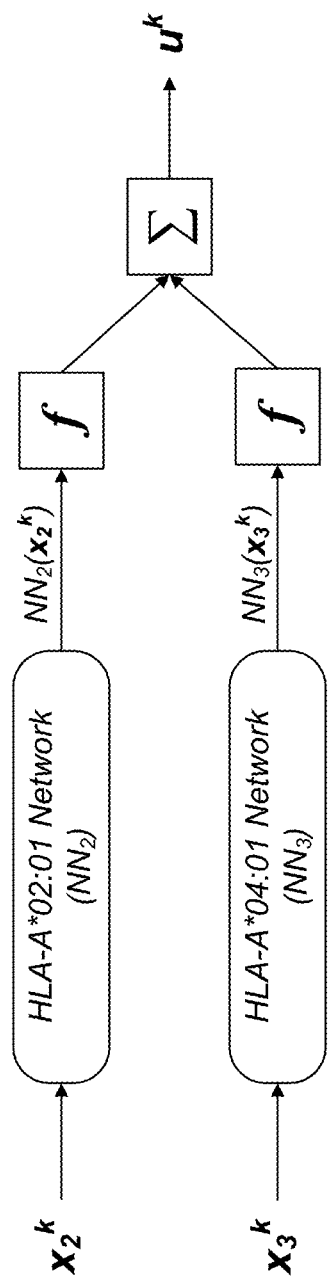
FIG. 11 illustrates generating a presentation likelihood for a peptide in association with MHC alleles using example network models.

FIG. 11 illustrates generating a presentation likelihood for peptide $p^k$ in association with MHC alleles h=2, h=3 using example network models $NN_2(\cdot)$ and $NN_3(\cdot)$. As shown in FIG. 9, the network model $NN_2(\cdot)$ receives the allele-interacting variables $x_2^k$ for MHC allele h=2 and generates the output $NN_2(x_2^k)$ and the network model $NN_3(\cdot)$ receives the allele-interacting variables $x_3^k$ for MHC allele h=3 and generates the output $NN_3(x_3^k)$. Each output is mapped by function $f(\cdot)$ and combined to generate the estimated presentation likelihood $u_k$.

In another implementation, when the predictions are made for the log of mass spectrometry ion currents, $r(\cdot)$ is the log function and $f(\cdot)$ is the exponential function.

VIII.C.6. Example 3.3: Sum-of-Functions Models with Allele-Noninteracting Variables In one implementation, the implicit per-allele presentation likelihood for MHC allele h is generated by:

$$u'^h_k = f(g_h(x_h^k; \theta_h) + g_w(w^k; \theta_w)), \quad (20)$$

such that the presentation likelihood is generated by:

$$u_k = Pr(p^k \text{ presented}) = r\left(\sum_{h=1}^{m} a_h^k \cdot f(g_w(w^k; \theta_w) + g_h(x_h^k; \theta_h))\right), \quad (21)$$

to incorporate the impact of allele noninteracting variables on peptide presentation.

According to equation (21), the presentation likelihood that a peptide sequence $p^k$ will be presented by one or more MHC alleles H can be generated by applying the function $g_h(\cdot)$ to the encoded version of the peptide sequence $p^k$ for each of the MHC alleles H to generate the corresponding dependency score for allele interacting variables for each MHC allele h. The function $g_w(\cdot)$ for the allele noninteracting variables is also applied to the encoded version of the allele noninteracting variables to generate the dependency score for the allele noninteracting variables. The score for the allele noninteracting variables are combined to each of the dependency scores for the allele interacting variables. Each of the combined scores are transformed by the function $f(\cdot)$ to generate the implicit per-allele presentation likelihoods. The implicit likelihoods are combined, and the clipping function may be applied to the combined outputs to clip the values into a range [0,1] to generate the presentation likelihood that peptide sequence $p^k$ will be presented by the MHC alleles H. The dependency function $g_w$ may be in the form of any of the dependency functions $g_w$ introduced above in sections VIII.B.3.

As an example, the likelihood that peptide $p^k$ will be presented by MHC alleles h=2, h=3, among m=4 different identified MHC alleles using the affine transformation functions $g_h(\cdot)$, $g_w(\cdot)$, can be generated by:

$$u_k = r(f(w^k \cdot \theta_w + x_2^k \cdot \theta_2) + f(w^k \cdot \theta_w + x_3^k \cdot \theta_3)),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC alleles h=2, h=3, among m=4 different identified MHC alleles using the network transformation functions $g_h(\cdot)$, $g_w(\cdot)$, can be generated by:

$$u_k = r(f(NN_w(w^k; \theta_w) + NN_2(x_2^k; \theta_2)) + f(NN_w(w^k; \theta_w) + NN_3(x_3^k; \theta_3)))$$

where $w^k$ are the identified allele-interacting variables for peptide $p^k$, and $\theta_w$ are the set of parameters determined for allele-noninteracting variables.

Figure 12:
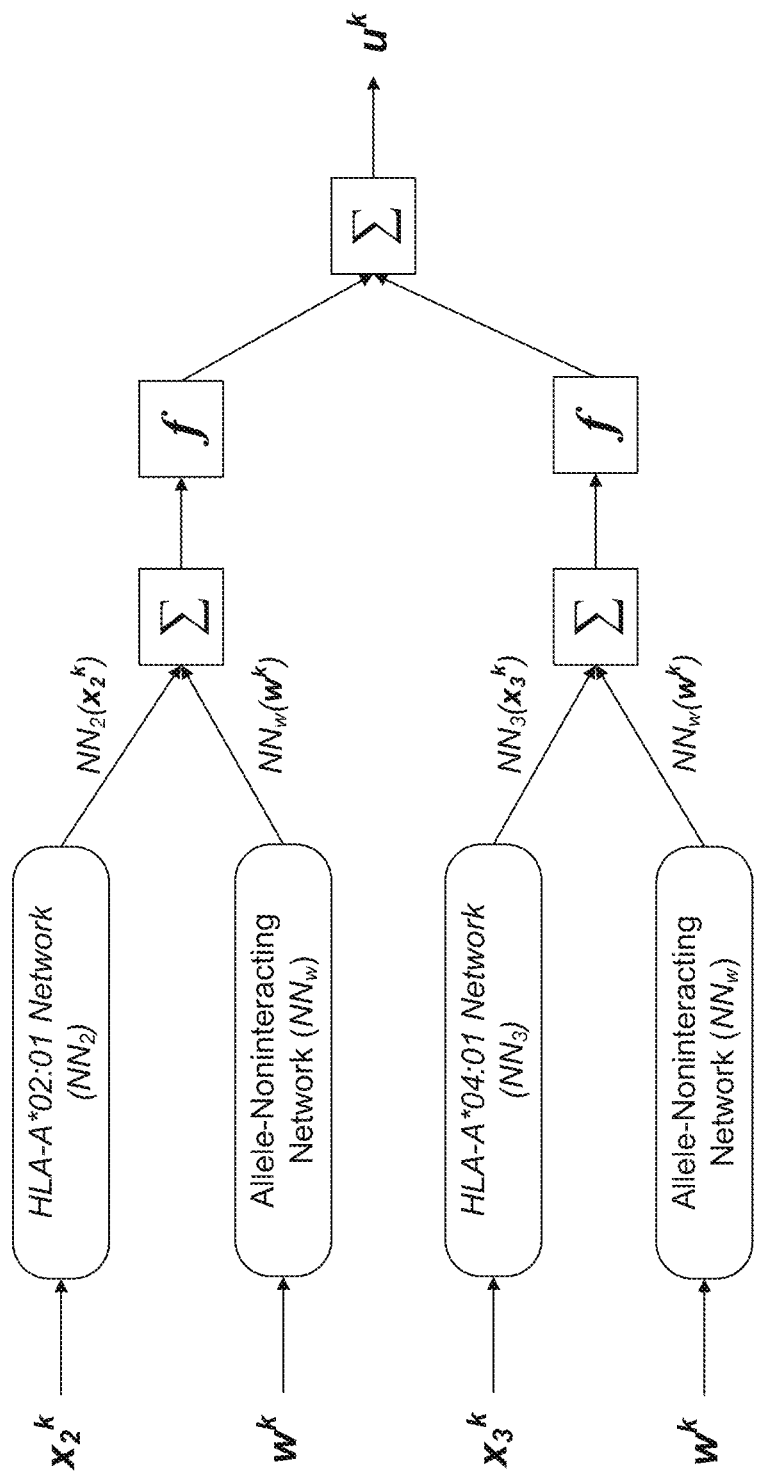
FIG. 12 illustrates generating a presentation likelihood for a peptide in association with MHC alleles using example network models.

FIG. 12 illustrates generating a presentation likelihood for peptide $p^k$ in association with MHC alleles h=2, h=3 using example network models $NN_2(\cdot)$, $NN_3(\cdot)$, and $NN_w(\cdot)$. As shown in FIG. 12, the network model $NN_2(\cdot)$ receives the allele-interacting variables $x_2^k$ for MHC allele h=2 and generates the output $NN_2(x_2^k)$. The network model $NN_w(\cdot)$ receives the allele-noninteracting variables $w^k$ for peptide $p^k$ and generates the output $NN_w(w^k)$. The outputs are combined and mapped by function $f(\cdot)$. The network model $NN_3(\cdot)$ receives the allele-interacting variables $x_3^k$ for MHC allele h=3 and generates the output $NN_3(x_3^k)$, which is again combined with the output $NN_w(w^k)$ of the same network model $NN_w(\cdot)$ and mapped by function $f(\cdot)$. Both outputs are combined to generate the estimated presentation likelihood $u_k$.

In another implementation, the implicit per-allele presentation likelihood for MHC allele h is generated by:

$$u'^h_k = f(g_h([x_h^k w^k]; \theta_h)). \quad (22)$$

such that the presentation likelihood is generated by:

$$u_k = Pr(p^k \text{ presented}) = r\left(\sum_{h=1}^{m} a_h^k \cdot f(g_h([x_h^k w^k]; \theta_h))\right).$$

VIII.C.7. Example 4: Second Order Models

In one implementation, $s(\cdot)$ is a second-order function, and the estimated presentation likelihood $u_k$ for peptide $p^k$ is given by:

$$u_k = Pr(p^k \text{ presented}) = \sum_{h=1}^{m} a_h^k \cdot u'^h_k(\theta) - \sum_{h=1}^{m} \sum_{j<h} a_h^k \cdot a_j^k \cdot u'^h_k(\theta) \cdot u'^j_k(\theta) \quad (23)$$

where elements $u'^h_k$ are the implicit per-allele presentation likelihood for MHC allele h. The values for the set of parameters $\theta$ for the implicit per-allele likelihoods can be determined by minimizing the loss function with respect to $\theta$, where i is each instance in the subset S of training data 170 generated from cells expressing single MHC alleles and/or cells expressing multiple MHC alleles. The implicit per-allele presentation likelihoods may be in any form shown in equations (18), (20), and (22) described above.

In one aspect, the model of equation (23) may imply that there exists a possibility peptide $p^k$ will be presented by two MHC alleles simultaneously, in which the presentation by two HLA alleles is statistically independent.

According to equation (23), the presentation likelihood that a peptide sequence $p^k$ will be presented by one or more MHC alleles H can be generated by combining the implicit per-allele presentation likelihoods and subtracting the likelihood that each pair of MHC alleles will simultaneously present the peptide $p^k$ from the summation to generate the presentation likelihood that peptide sequence $p^k$ will be presented by the MHC alleles H.

As an example, the likelihood that peptide $p^k$ will be presented by HLA alleles h=2, h=3, among m=4 different identified HLA alleles using the affine transformation functions $g_h(\cdot)$, can be generated by:

$$u_k = \theta(x_2^k \cdot \theta_2) + f(x_3^k \cdot \theta_3) - f(x_2^k \cdot \theta_2) \cdot f(x_3^k \cdot \theta_3),$$

where $x_2^k$, $x_3^k$ are the identified allele-interacting variables for HLA alleles h=2, h=3, and $\theta_2$, $\theta_3$ are the set of parameters determined for HLA alleles h=2, h=3.

As another example, the likelihood that peptide $p^k$ will be presented by HLA alleles h=2, h=3, among m=4 different identified HLA alleles using the network transformation functions $g_h(\cdot)$, $g_w(\cdot)$, can be generated by:

$$u_k = f(NN_2(x_2^k; \theta_2)) + f(NN_3(x_3^k; \theta_3)) - f(NN_2(x_2^k; \theta_2)) \cdot f(NN_3(x_3^k; \theta_3)),$$

where $NN_2(\cdot)$, $NN_3(\cdot)$ are the identified network models for HLA alleles h=2, h=3, and $\theta_2$, $\theta_3$ are the set of parameters determined for HLA alleles h=2, h=3.

IX. Example 5: Prediction Module

The prediction module 320 receives sequence data and selects candidate neoantigens in the sequence data using the presentation models. Specifically, the sequence data may be DNA sequences, RNA sequences, and/or protein sequences extracted from tumor tissue cells of patients. The prediction module 320 processes the sequence data into a plurality of peptide sequences $p^k$ having 8-15 amino acids. For example, the prediction module 320 may process the given sequence "IEFROEIFJEF (SEQ ID NO: 15) into three peptide sequences having 9 amino acids "IEFROEIFJ (SEQ ID NO: 16)," "EFROEIFJE (SEQ ID NO: 17)," and "FROEIFJEF (SEQ ID NO: 18)." In one embodiment, the prediction module 320 may identify candidate neoantigens that are mutated peptide sequences by comparing sequence data extracted from normal tissue cells of a patient with the sequence data extracted from tumor tissue cells of the patient to identify portions containing one or more mutations.

The presentation module 320 applies one or more of the presentation models to the processed peptide sequences to estimate presentation likelihoods of the peptide sequences. Specifically, the prediction module 320 may select one or more candidate neoantigen peptide sequences that are likely to be presented on tumor HLA molecules by applying the presentation models to the candidate neoantigens. In one implementation, the prediction module 320 selects candidate neoantigen sequences that have estimated presentation likelihoods above a predetermined threshold. In another implementation, the presentation model selects the N candidate neoantigen sequences that have the highest estimated presentation likelihoods (where N is generally the maximum number of epitopes that can be delivered in a vaccine). A vaccine including the selected candidate neoantigens for a given patient can be injected into the patient to induce immune responses.

X. Example 6: Experimentation Results Showing Example Presentation Model Performance The validity of the various presentation models described above were tested on test data T that were subsets of training data 170 that were not used to train the presentation models or a separate dataset from the training data 170 that have similar variables and data structures as the training data 170.

A relevant metric indicative of the performance of a presentation models is:

Positive Predictive Value (PPV) =

$$P(y_{i \in T} = 1 \mid u_{i \in T} \geq t) = \frac{\Sigma_{i \in T} \mathbb{1}(y_i = 1, u_i \geq t)}{\Sigma_{i \in T} \mathbb{1}(u_i \geq t)}$$

that indicates the ratio of the number of peptide instances that were correctly predicted to be presented on associated HLA alleles to the number of peptide instances that were predicted to be presented on the HLA alleles. In one implementation, a peptide $p^i$ in the test data T was predicted to be presented on one or more associated HLA alleles if the corresponding likelihood estimate $u_i$ is greater or equal to a given threshold value t. Another relevant metric indicative of the performance of presentation models is:

$$\text{Recall} = P(u_{i \in T} \geq t \mid y_{i \in T} = 1) = \frac{\Sigma_{i \in T} \mathbb{1}(y_i = 1, u_i \geq t)}{\Sigma_{i \in T} \mathbb{1}(y_i = 1)}$$

that indicates the ratio of the number of peptide instances that were correctly predicted to be presented on associated HLA alleles to the number of peptide instances that were known to be presented on the HLA alleles. Another relevant metric indicative of the performance of presentation models is the area-under-curve (AUC) of the receiver operating characteristic (ROC). The ROC plots the recall against the false positive rate (FPR), which is given by:

$$FPR = P(u_{i \in T} \geq t \mid y_{i \in T} = 0) = \frac{\Sigma_{i \in T} \mathbb{1}(y_i = 0, u_i \geq t)}{\Sigma_{i \in T} \mathbb{1}(y_i = 0)}.$$

Figure 13A:
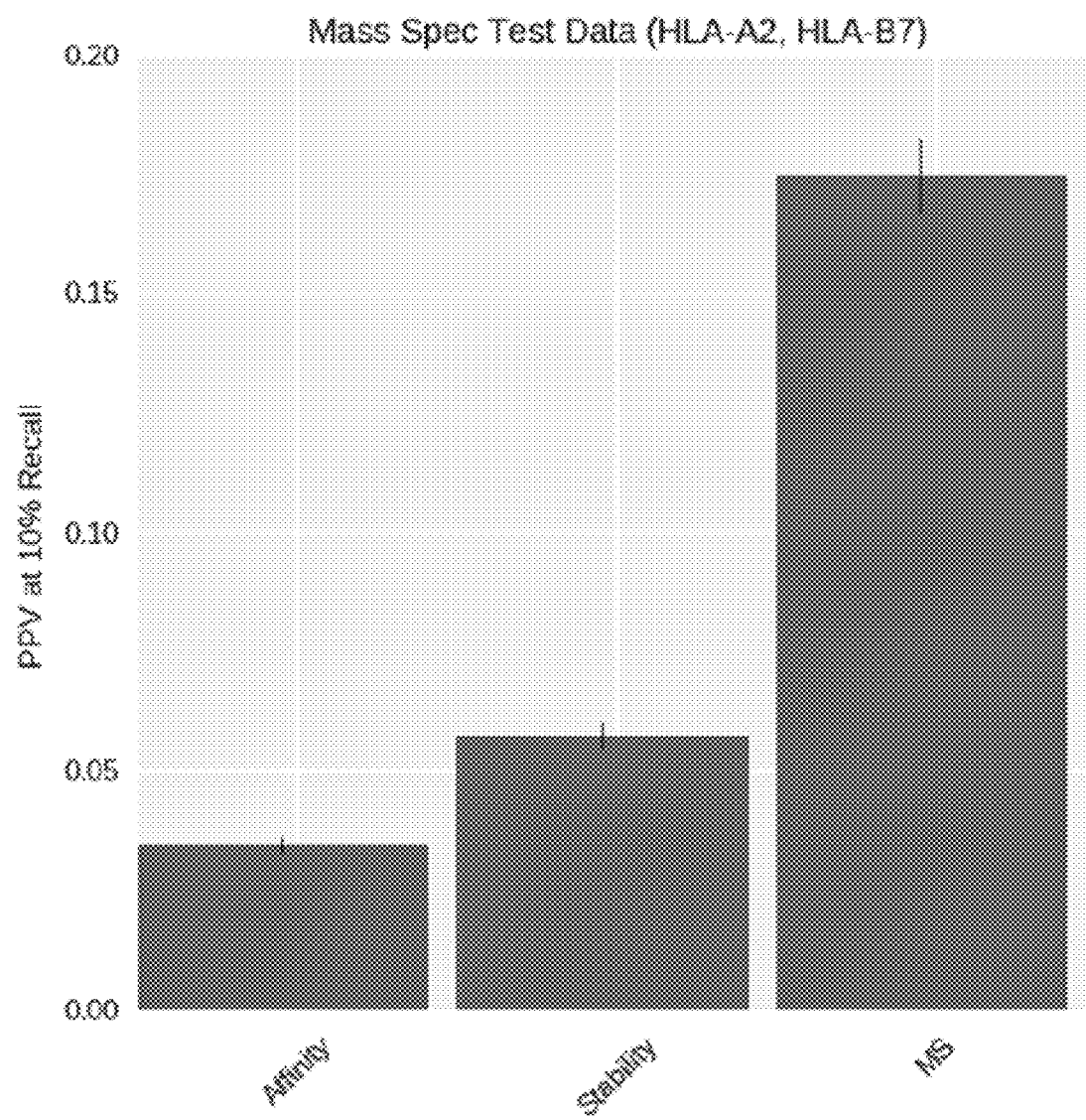
FIG. 13A compares performance results of an example presentation model and state-of-the-art models for predicting peptide presentation on multiple-allele mass spectrometry data.

X.A. Comparison of Presentation Model Performance on Mass Spectrometry Data Against State-of-the-Art Model FIG. 13A compares performance results of an example presentation model, as presented herein, and state-of-the-art models for predicting peptide presentation on multiple-allele mass spectrometry data. Results showed that the example presentation model performed significantly better at predicting peptide presentation than state-of-the-art models based on affinity and stability predictions.

Specifically, the example presentation model shown in FIG. 13A as "MS" was the maximum of per-alleles presentation model shown in equation (12), using the affine dependency function $g_h(\bullet)$ and the expit function $f(\bullet)$. The example presentation model was trained based on a subset of the single-allele HLA-A*02:01 mass spectrometry data from the IEDB data set (data set "D1") (data can be found at http://www.iedb.org/doc/mhc_ligand_full.zip) and a subset of the single-allele HLA-B*07:02 mass spectrometry from the IEDB data set (data set "D2") (data can be found at http://www.iedb.org/doc/mhc_ligand_full.zip). All peptides from source protein that contain presented peptides in the test set were eliminated from the training data such that the example presentation model could not simply memorize the sequences of presented antigens.

The model shown in FIG. 13A as "Affinity" was a model similar to the current state-of-the-art model that predicts peptide presentation based on affinity predictions NETMHCpan. Implementation of NETMHCpan is provided in detail at http://www.cbs.dtu.dk/services/NetMHCpan/. The model shown in FIG. 13A as "Stability" was a model similar to the current state-of-the-art model that predicts peptide presentation based on stability predictions NETMHCstab. Implementation of NETMHCstab is provided in detail at http://www.cbs.dtu.dk/services/NetMHCstab-1.0/. The test data that is a subset of the multiple-allele JY cell line HLA-A*02:01 and HLA-B*07:02 mass spectrometry data from the Bassani-Stemberg data set (data set "D3") (data can be found at www.ebi.ac.uk/pride/archive/projects/PXD000394). The error bars (as indicated in solid lines) show 95% confidence intervals.

As shown in the results of FIG. 13A, the example presentation model trained on mass spectrometry data had a significantly higher PPV value at 10% recall rate relative to the state-of-the-art models that predict peptide presentation based on MHC binding affinity predictions or MHC binding stability predictions. Specifically, the example presentation model had approximately 14% higher PPV than the model based on affinity predictions, and had approximately 12% higher PPV than the model based on stability predictions.

These results demonstrate that the example presentation model had significantly better performance than the state-of-the-art models that predict peptide presentation based on MHC binding affinity or MHC binding stability predictions even though the example presentation model was not trained based on protein sequences that contained presented peptides.

Figure 13B:
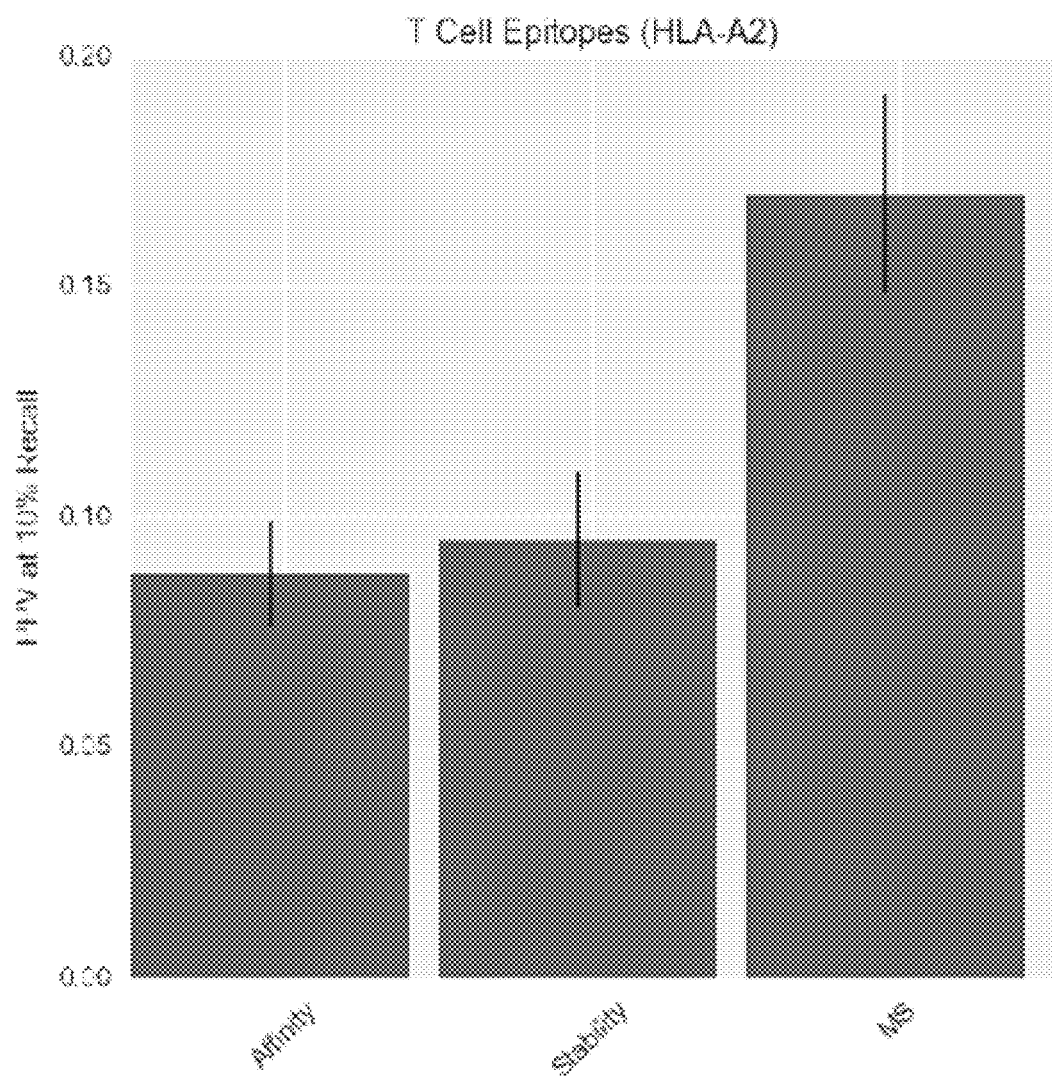
FIG. 13B compares performance results of another example presentation model, and state-of-the-art models for predicting peptide presentation on T-cell epitope data.

X.B. Comparison of Presentation Model Performance on T-Cell Epitope Data Against State-of-the-Art Models FIG. 13B compares performance results of another example presentation model, as presented herein, and state-of-the-art models for predicting peptide presentation on T-cell epitope data. T-cell epitope data contains peptide sequences that were presented by MHC alleles on the cell surface, and recognized by T-cells. Results showed that even though the example presentation model is trained based on mass spectrometry data, the example presentation model performed significantly better at predicting T-cell epitopes than state-of-the-art models based on affinity and stability predictions. In other words, the results of FIG. 13B indicated that not only did the example presentation model perform better than state-of-the-art models at predicting peptide presentation on mass spectrometry test data, but the example presentation model also performed significantly better than state-of-the-art models at predicting epitopes that were actually recognized by T-cells. This is an indication that the variety of presentation models as presented herein can provide improved identification of antigens that are likely to induce immunogenic responses in the immune system.

Specifically, the example presentation model shown in FIG. 13B as "MS" was the per-allele presentation model shown in equation (2), using the affine transformation function $g_h(\bullet)$ and the expit function $f(\bullet)$ that was trained based on a subset of data set D1. All peptides from source protein that contain presented peptides in the test set were eliminated from the training data such that the presentation model could not simply memorize the sequences of presented antigens.

Each of the models were applied to the test data that is a subset of mass spectrometry data on HLA-A*02:01 T-cell epitope data (data set "D4") (data can be found at www.iedb.org/doc/tcell full v3.zip). The model shown in FIG. 13B as "Affiinity" was a model similar to the current state-of-the-art model that predicts peptide presentation based on affinity predictions NETMHCpan, and the model shown in FIG. 13B as "Stability" was a model similar to the current state-of-the-art model that predicts peptide presentation based on stability predictions NETMHCstab. The error bars (as indicated in solid lines) show 95% confidence intervals.

As shown in the results of FIG. 13A, the per-allele presentation model trained on mass spectrometry data had a significantly higher PPV value at 10% recall rate than the state-of-the-art models that predict peptide presentation based on MHC binding affinity or MHC binding stability predictions even though the presentation model was not trained based on protein sequences that contained presented peptides. Specifically, the per-allele presentation model had approximately 9% higher PPV than the model based on affinity predictions, and had approximately 8% higher PPV than the model based on stability predictions.

These results demonstrated that the example presentation model trained on mass spectrometry data performed significantly better than state-of-the-art models on predicting epitopes that were recognized by T-cells.

X.C. Comparison of Different Presentation Model Performances on Mass Spectrometry Data FIG. 13C compares performance results for an example function-of-sums model (equation (13)), an example sum-of-functions model (equation (19)), and an example second order model (equation (23)) for predicting peptide presentation on multiple-allele mass spectrometry data. Results showed that the sum-of-functions model and second order model performed better than the function-of-sums model. This is because the function-of-sums model implies that alleles in a multiple-allele setting can interfere with each other for peptide presentation, when in reality, the presentation of peptides are effectively independent.

Specifically, the example presentation model labeled as "sigmoid-of-sums" in FIG. 13C was the function-of-sums model using a network dependency function $g_h(\cdot)$, the identity function $f(\cdot)$, and the expit function $r(\cdot)$. The example model labeled as "sum-of-sigmoids" was the sum-of-functions model in equation (19) with a network dependency function $g_h(\cdot)$, the expit function $f(\cdot)$, and the identity function $r(\cdot)$. The example model labeled as "hyperbolic tangent" was the sum-of-functions model in equation (19) with a network dependency function $g_h(\cdot)$, the expit function $f(\cdot)$, and the hyperbolic tangent function $r(\cdot)$. The example model labeled as "second order" was the second order model in equation (23) using an implicit per-allele presentation likelihood form shown in equation (18) with a network dependency function $g_h(\cdot)$ and the expit function $f(\cdot)$. Each model was trained based on a subset of data set D1, D2, and D3. The example presentation models were applied to a test data that is a random subset of data set D3 that did not overlap with the training data.

As shown in FIG. 13C, the first column refers to the AUC of the ROC when each presentation model was applied to the test set, the second column refers to the value of the negative log likelihood loss, and the third column refers to the PPV at 10% recall rate. As shown in FIG. 13C, the performance of presentation models "sum-of-sigmoids," "hyperbolic tangent," and "second order" were approximately tied at approximately 15-16% PPV at 10% recall, while the performance of the model "sigmoid-of-sums" was slightly lower at approximately 11%.

As discussed previously in section VIII.C.4., the results showed that the presentation models "sum-of-sigmoids," "hyperbolic tangent," and "second order" have high values of PPV compared to the "sigmoid-of-sums" model because the models correctly account for how peptides are presented independently by each MHC allele in a multiple-allele setting.

X.D. Comparison of Presentation Model Performance with and without Training on Single-Allele Mass Spectrometry Data FIG. 13D compares performance results for two example presentation models that are trained with and without single-allele mass spectrometry data on predicting peptide presentation for multiple-allele mass spectrometry data. The results indicated that example presentation models that are trained without single-allele data achieve comparable performance to that of example presentation models trained with single-allele data.

The example model "with A2/B7 single-allele data" was the "sum-of-sigmoids" presentation model in equation (19) with a network dependency function $g_h(\cdot)$, the expit function $f(\cdot)$, and the identity function $r(\cdot)$. The model was trained based on a subset of data set D3 and single-allele mass spectrometry data for a variety of MHC alleles from the IEDB database (data can be found at: http://www.iedb.org/doc/mhc_ligand_full.zip). The example model "without A2/B7 single-allele data" was the same model, but trained based on a subset of the multiple-allele D3 data set without single-allele mass spectrometry data for alleles HLA-A*02:01 and HLA-B*07:02, but with single-allele mass spectrometry data for other alleles. Within the multiple-allele training data, cell line HCC1937 expressed HLA-B*07:02 but not HLA-A*02:01, and cell line HCT116 expressed HLA-A*02:01 but not HLA-B*07:02. The example presentation models were applied to a test data that was a random subset of data set D3 and did not overlap with the training data.

The column "Correlation" refers to the correlation between the actual labels that indicate whether the peptide was presented on the corresponding allele in the test data, and the label for prediction. As shown in FIG. 13D, the predictions based on the implicit per-allele presentation likelihoods for MHC allele HLA-A*02:01 performed significantly better on single-allele test data for MHC allele HLA-A*02:01 rather than for MHC allele HLA-B*07:02. Similar results are shown for MHC allele HLA-B*07:02.

These results indicate that the implicit per-allele presentation likelihoods of the presentation model can correctly predict and distinguish binding motifs to individual MHC alleles, even though direct association between the peptides and each individual MHC allele was not known in the training data.

X.E. Comparison of Per-Allele Prediction Performance without Training on Single-Allele Mass Spectrometry Data FIG. 13E shows performance for the "without A2/B7 single-allele data" and "with A2/B7 single-allele data" example models shown in FIG. 13D on single-allele mass spectrometry data for alleles HLA-A*02:01 and HLA-B*07:02 that were held out in the analysis shown in FIG. 13D. Results indicate that even through the example presentation model is trained without single-allele mass spectrometry data for these two alleles, the model is able to learn binding motifs for each MHC allele.

As shown in FIG. 13E, "A2 model predicting B7" indicates the performance of the model when peptide presentation is predicted for single-allele HLA-B*07:02 data based on the implicit per-allele presentation likelihood estimate for MHC allele HLA-A*02:01. Similarly, "A2 model predicting A2" indicates the performance of the model when peptide presentation is predicted for single-allele HLA-A*02:01 based on the implicit per-allele presentation likelihood estimate for MHC allele HLA-A*02:01. "B7 model predicting B7" indicates the performance of the model when peptide presentation is predicted for single-allele HLA-B*07:02 data based on the implicit per-allele presentation likelihood estimate for MHC allele HLA-B*07:02. "B7 model predicting A2" indicates the performance of the model when peptide presentation is predicted for single-allele HLA-A*02:01 based on the implicit per-allele presentation likelihood estimate for MHC allele HLA-B*07:02.

As shown in FIG. 13E, the predictive capacity of implicit per-allele likelihoods for an HLA allele is significantly higher for the intended allele, and significantly lower for the other HLA allele. Similarly to the results shown in FIG. 13D, the example presentation models correctly learned to differentiate peptide presentation of individual alleles HLA-A*02:01 and HLA-B*07:02, even though direct association between peptide presentation and these alleles were not present in the multiple-allele training data.

X.F. Frequently Occurring Anchor Residues in Per-Allele Predictions Match Known Canonical Anchor Motifs FIG. 13F shows the common anchor residues at positions 2 and 9 among nonamers predicted by the "without A2/B7 single-allele data" example model shown in FIG. 13D. The peptides were predicted to be presented if the estimated likelihood was above 5%. Results show that most common anchor residues in the peptides identified for presentation on the MHC alleles HLA-A*02:01 and HLA-B*07:02 matched previously known anchor motifs for these MHC alleles. This indicates that the example presentation models correctly learned peptide binding based on particular positions of amino acids of the peptide sequences, as expected.

As shown in FIG. 13F, amino acids L/M at position 2 and amino acids V/L at position 9 were known to be canonical anchor residue motifs (as shown in Table 4 of https://link.springer.com/article/10.1186/1745-7580-4-2) for HLA-A*02:01, and amino acid P at position 2 and amino acids L/V at position 9 were known to be canonical anchor residue motifs for HLA-B*07:02. The most common anchor residue motifs at positions 2 and 9 for peptides identified the model matched the known canonical anchor residue motifs for both HLA alleles.

X.G. Comparison of Presentation Model Performances with and Without Allele Noninteracting Variables FIG. 13G compares performance results between an example presentation model that incorporated C- and N-terminal flanking sequences as allele-interacting variables, and an example presentation model that incorporated C- and N-terminal flanking sequences as allele-noninteracting variables. Results showed that incorporating C- and N-terminal flanking sequences as allele noninteracting variables significantly improved model performance. More specifically, it is valuable to identify appropriate features for peptide presentation that are common across different MHC alleles, and model them such that statistical strength for these allele-noninteracting variables are shared across MHC alleles to improve presentation model performance.

The example "allele-interacting" model was the sum-of-functions model using the form of implicit per-allele presentation likelihoods in equation (22) that incorporated C- and N-terminal flanking sequences as allele-interacting variables, with a network dependency function $g_h(\cdot)$ and the expit function $f(\cdot)$. The example "allele-noninteracting" model was the sum-of-functions model shown in equation (21) that incorporated C- and N-terminal flanking sequences as allele-noninteracting variables, with a network dependency function $g_h(\cdot)$ and the expit function $f(\cdot)$. The allele-noninteracting variables were modeled through a separate network dependency function $g_w(\cdot)$. Both models were trained on a subset of data set D3 and single-allele mass spectrometry data for a variety of MHC alleles from the IEDB database (data can be found at: http://www.iedb.org/doc/mhc_ligand_full.zip). Each of the presentation models was applied to a test data set that is a random subset of data set D3 that did not overlap with the training data.

As shown in FIG. 13G, incorporating C- and N-terminal flanking sequences in the example presentation model as allele-noninteracting variables achieved an approximately 3% improvement in PPV value relative to modeling them as allele-interacting variables. This is because, in general, the "allele-noninteracting" example presentation model was able to share statistical strength of allele-noninteracting variables across MHC alleles by modeling the effect with a separate network dependency function with very little addition in computing power.

X.H. Dependency Between Presented Peptides and mRNA Quantification

Figure 13H:
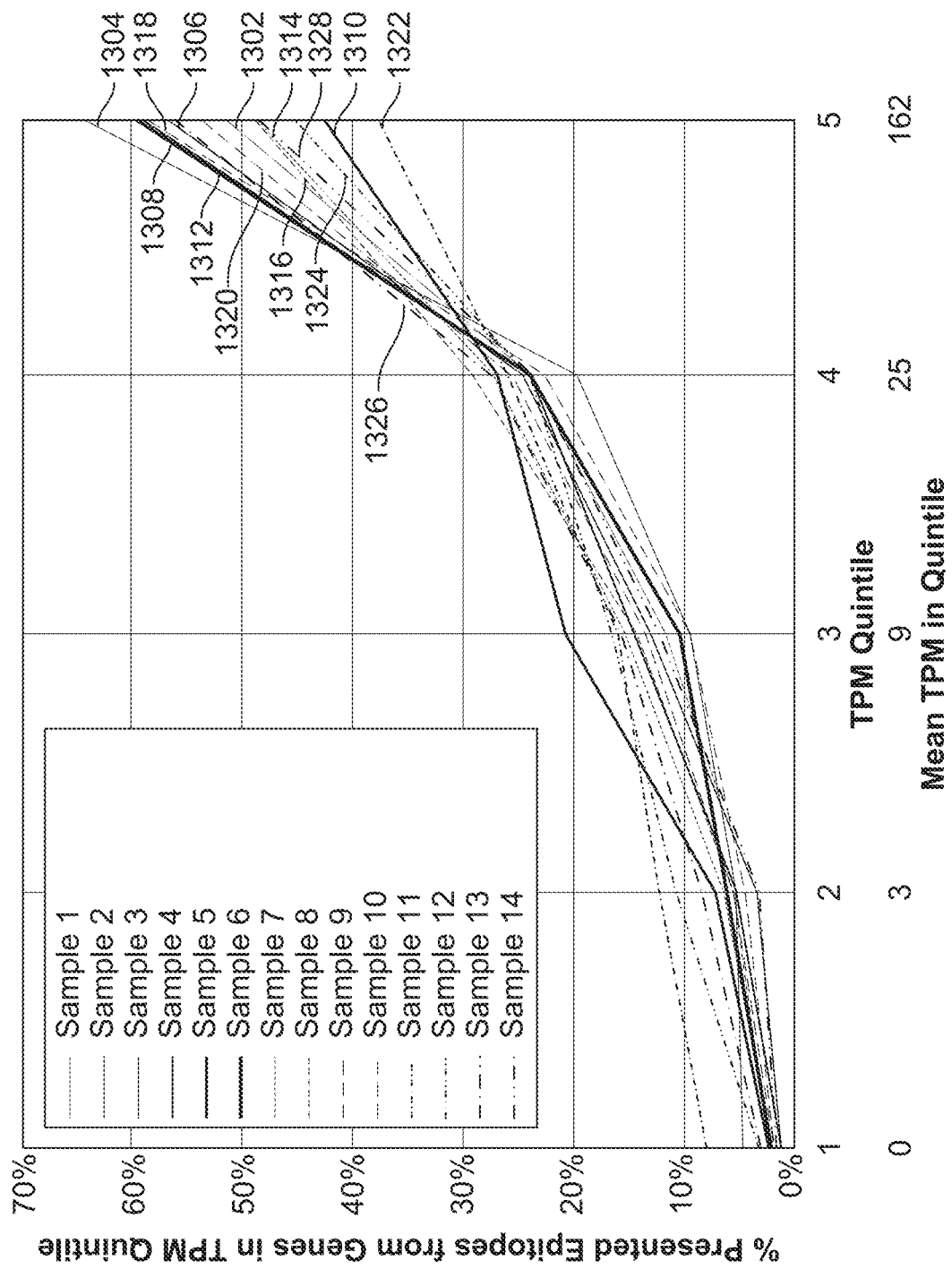
FIG. 13H illustrates the dependency between fraction of presented peptides for genes based on mRNA quantification for mass spectrometry data on tumor cells.

FIG. 13H illustrates the dependency between fraction of presented peptides for genes based on mRNA quantification for mass spectrometry data on tumor cells. Results show that there is a strong dependency between mRNA expression and peptide presentation.

Specifically, the horizontal axis in FIG. 13G indicates mRNA expression in terms of transcripts per million (TPM) quartiles. The vertical axis in FIG. 13G indicates fraction of presented epitopes from genes in corresponding mRNA expression quartiles. Each solid line is a plot relating the two measurements from a tumor sample that is associated with corresponding mass spectrometry data and mRNA expression measurements. As shown in FIG. 13G, there is a strong positive correlation between mRNA expression, and the fraction of peptides in the corresponding gene. Specifically, peptides from genes in the top quartile of RNA expression are more than 20 times likely to be presented than the bottom quartile. Moreover, essentially 0 peptides are presented from genes that are not detected through RNA.

The results indicate that the performance of the presentation model can be greatly improved by incorporating mRNA quantification measurements, as these measurements are strongly predictive of peptide presentation.

Figure 13I:
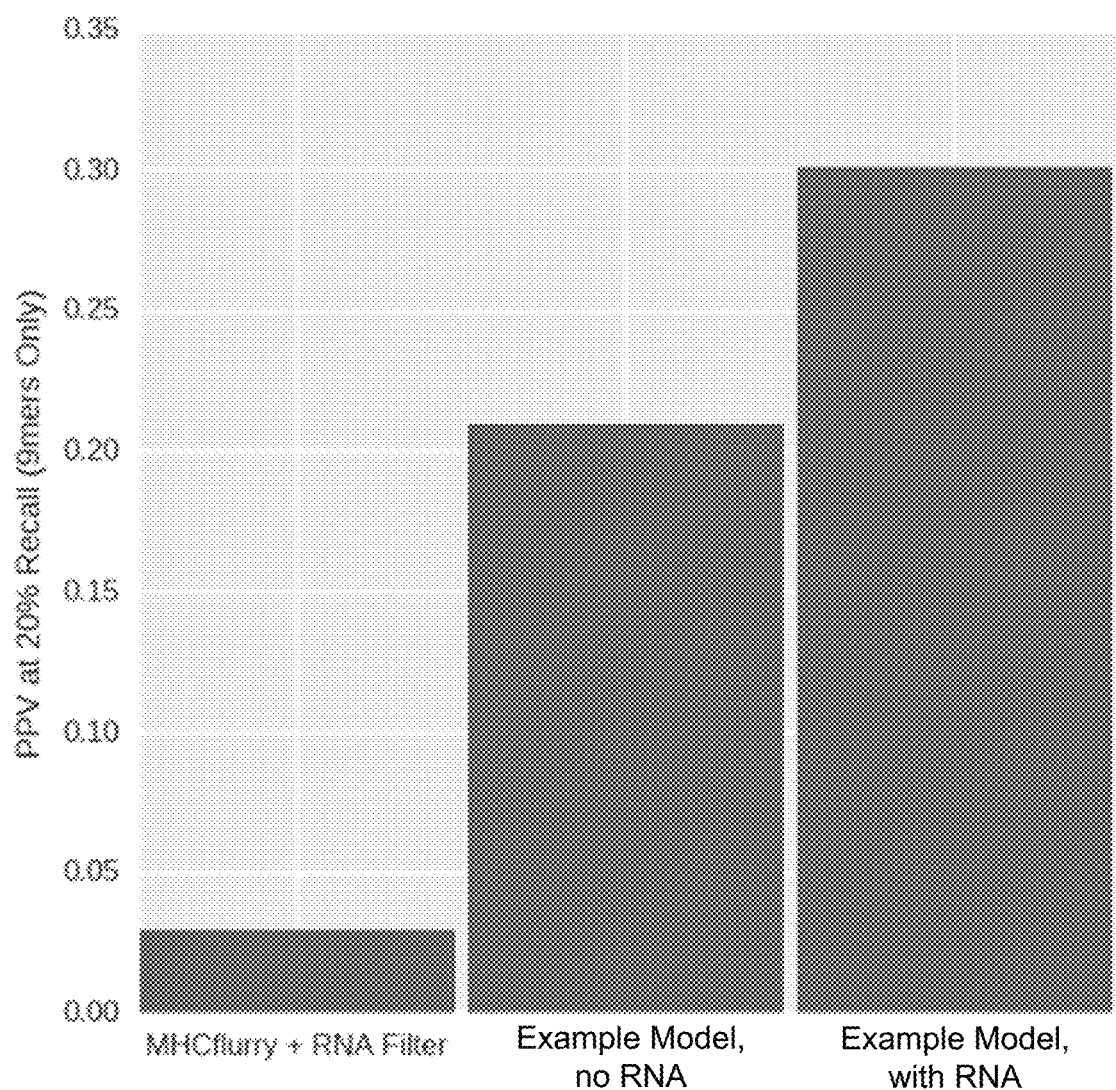
FIG. 13I shows performance of two example presentation models, one of which is trained based on mass spectrometry tumor cell data, another of which incorporates mRNA quantification data and mass spectrometry tumor cell data.

X.I. Comparison of Presentation Model Performance with Incorporation of RNA Quantification Data FIG. 13I shows performance of two example presentation models, one of which is trained based on mass spectrometry tumor cell data, another of which incorporates mRNA quantification data and mass spectrometry tumor cell data. As expected from FIG. 13H, results indicated that there is a significant improvement in performance by incorporating mRNA quantification measurements in the example presentation model, since the mRNA expression is a strong indicator of peptide presentation.

"MHCflurry+RNA filter" was a model similar to the current state-of-the-art model that predicts peptide presentation based on affinity predictions. It was implemented using MHCflurry along with a standard gene expression filter that removed all peptides from proteins with mRNA quantification measurements that were less than 3.2 FPKM. Implementation of MHCflurry is provided in detail at https://github.com/hammerlab/mhcflurry/, and at http://biorxiv.org/content/early/2016/05/22/054775. The "Example Model, no RNA" model was the "sum-of-sigmoids" example presentation model shown in equation (21) with the network dependency function $g_h(\cdot)$, the network dependency function $g_w(\cdot)$, and the expit function $f(\cdot)$. The "Example Model, no RNA" model incorporated C-terminal flanking sequences as allele-noninteracting variables through a network dependency function $g_w(\cdot)$.

The "Example Model, with RNA" model was the "sum-of-sigmoids" presentation model shown in equation (19) with network dependency function $g_h(\cdot)$, the network dependency function $g_w(\cdot)$ in equation (10) incorporating mRNA quantification data through a log function, and the expit function $f(\cdot)$. The "Example Model, with RNA" model incorporated C-terminal flanking sequences as allele-noninteracting variables through the network dependency functions $g_w(\cdot)$ and incorporated mRNA quantification measurements through the log function.

Each model was trained on a combination of the single-allele mass spectrometry data from the IEDB data set, 7 cell lines from the multiple-allele mass spectrometry data from the Bassani-Sternberg data set, and 20 mass spectrometry tumor samples. Each model was applied to a test set including 5,000 held-out proteins from 7 tumor samples that constituted 9,830 presented peptides from a total of 52,156, 840 peptides.

As shown in the first two bar graphs of FIG. 13I, the "Example Model, no RNA" model has a PPV value at 20% Recall of 21%, while that of the state-of-the-art model is approximately 3%, This indicates an initial performance improvement of 18% in PPV value, even without the incorporation of mRNA quantification measurements. As shown in the third bar graph of FIG. 13I, the "Example Model, with RNA" model that incorporates mRNA quantification data into the presentation model shows a PPV value of approximately 30%, which is almost a 10% increase in performance compared to the example presentation model without mRNA quantification measurements.

Thus, results indicate that as expected from the findings in FIG. 13H, mRNA expression is indeed a strong predictor of peptide prediction, that allows significant improvement in the performance of a presentation model with very little addition of computational complexity.

X.J. Example of Parameters Determined for MHC Allele HLA-C*16:04

Figure 13J:
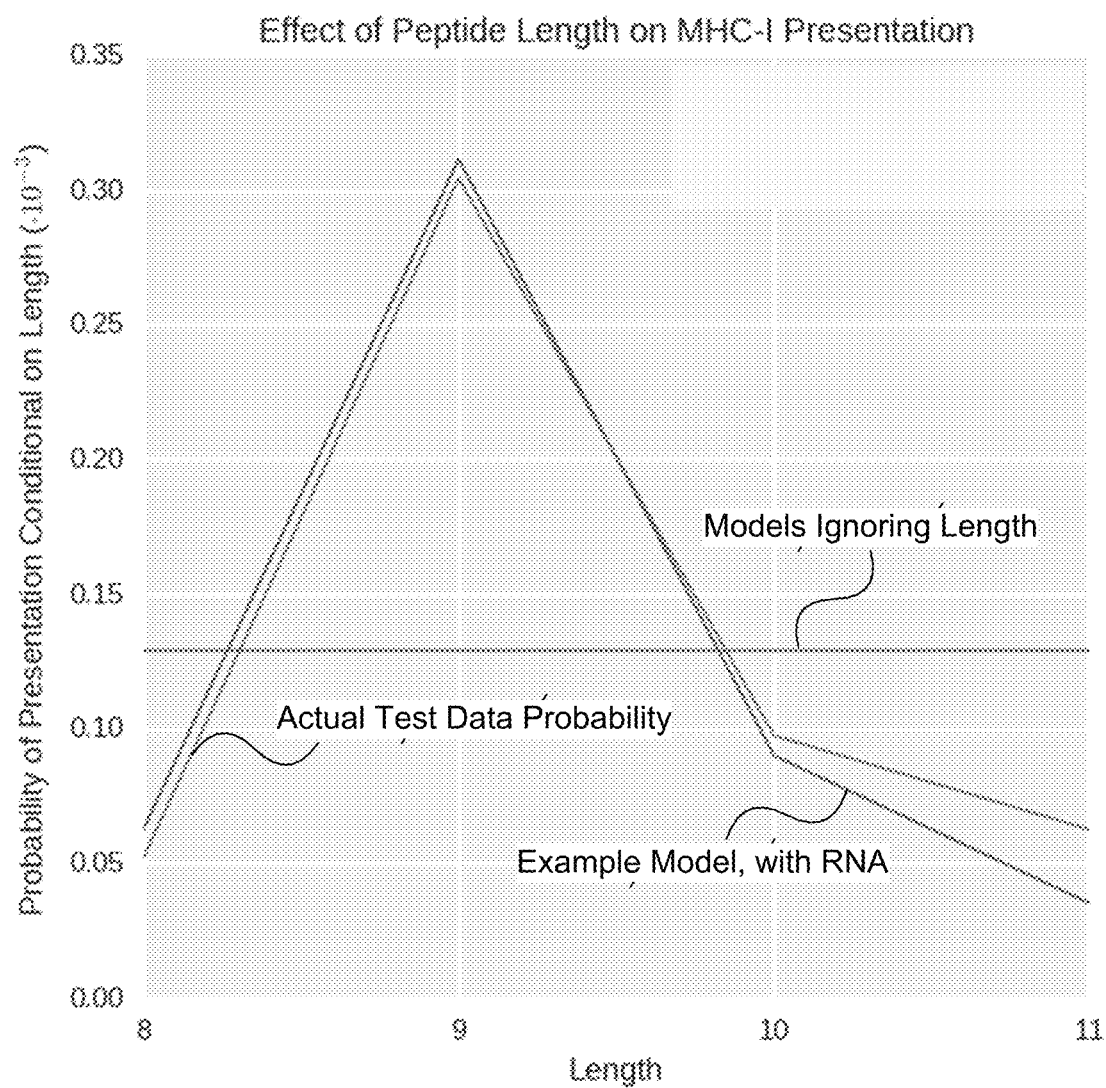
FIG. 13J compares probability of peptide presentation for different peptide lengths between results generated by presentation models described in FIG. 13I, and predicted results by state-of-the-art models that do not account for peptide length when predicting peptide presentation.

FIG. 13J compares probability of peptide presentation for different peptide lengths between results generated by the "Example Model, with RNA" presentation model described in reference to FIG. 13I, and predicted results by state-of-the-art models that do not account for peptide length when predicting peptide presentation. Results indicated that the "Example Model, with RNA" example presentation model from FIG. 13I captured variation in likelihoods across peptides of differing lengths.

The horizontal axis denoted samples of peptides with lengths 8, 9, 10, and 11. The vertical axis denoted the probability of peptide presentation conditioned on the lengths of the peptide. The plot "Actual Test Data Probability" showed the proportion of presented peptides according to the length of the peptide in a sample test data set. The presentation likelihood varied with the length of the peptide. For example, as shown in FIG. 13J, a 10mer peptide with canonical HLA-A2 L/V anchor motifs was approximately 3 times less likely to be presented than a 9mer with the same anchor residues. The plot "Models Ignoring Length" indicated predicted measurements if state-of-the-art models that ignore peptide length were to be applied to the same test data set for presentation prediction. These models may be NetMHC versions before version 4.0, NetMHCpan versions before version 3.0, and MHCflurry, that do not take into account variation in peptide presentation according to peptide length. As shown in FIG. 13J, the proportion of presented peptides would be constant across different values of peptide length, indicating that these models would fail to capture variation in peptide presentation according to length. The plot "Gritstone, with RNA" indicated measurements generated from the "Gritstone, with RNA" presentation model. As shown in FIG. 13J, the measurements generated by the "Gritstone, with RNA" model closely followed those shown in "Actual Test Data Probability" and correctly accounted for different degrees of peptide presentation for lengths 8, 9, 10, and 11.

Thus, the results showed that the example presentation models as presented herein generated improved predictions not only for 9mer peptides, but also for peptides of other lengths between 8-15, which account for up to 40% of the presented peptides in HLA class I alleles.

X.K. Example of Parameters Determined for MHC Allele HLA-C*16:04

The following shows a set of parameters determined for a variation of the per-allele presentation model (equation (2)) for MHC allele HLA-C*16:04 denoted by h:

$$u_k = \text{expit}(\text{relu}(x_h^k \cdot W_h^1 + b_h^1) \cdot W_h^2 + b_h^2),$$

where relu(•) is the rectified linear unit (RELU) function, and $W_h^1$, $b_h^1$, $W_h^2$, and $b_h^2$ are the set of parameters θ determined for the model. The allele interacting variables $x_h^k$ consist of peptide sequences. The dimensions of $W_h^1$ are (231×256), the dimensions of $b_h^1$ (1×256), the dimensions of $W_h^2$ are (256×1), and $b_h^2$ is a scalar. For demonstration purposes, values for $b_h^1$, $b_h^2$, $W_h^1$, and $W_h^2$ are listed below.

$b_h^1$:

[−1.25887644   −0.84448904   −1.71391594   −1.38860381
−1.15529644   −2.42168117   −1.98687959   −0.8488462
−1.6607399    −1.12956274   −2.08983159   −0.53710765
−0.49313864   −1.15045631   −0.48757577   −0.55577797
−0.31031775   −0.70026076   −1.04614675   −1.3850919
−1.82895124   −1.15633833   −1.2794342    −2.40924239
−1.38725305   −1.98276925   −1.45160246   −0.81624526
−0.59441668   −1.86188185   −0.83900708   −1.33677316
−1.68388879   −1.1717515    −1.27319682   −1.05872869
−1.34773123   −1.61631954   −0.82552254   −1.64032412
−1.26584375   −0.56390315   −1.00684011   −1.16896808
−2.27648878   −0.66619354   −2.08268309   −0.90704113
−1.17440355   −1.06266129   −1.14868402   −0.98686731
−1.1801722    −1.41404176   −0.92722374   −0.61310995
−1.69453728   −1.26077592   −1.80019915   −0.55121636
−1.42537642   −2.1196804    −1.32291269   −1.30997157
−0.8173914    −1.23448598   −0.92230183   −1.04590237

[−0.68719882 −0.99965096 −1.85294855 −0.67477435
−1.31483507 −1.21778536 −1.18890083 −0.80372357
−1.90210617 −1.85402811 −1.05570829 −1.345541
−0.68872309 −1.91153145 −1.15126705 −0.9407478
−1.01246905 −1.36009204 −1.15897787 −1.38631177
−0.87737125 −0.81053489 −0.5077101 −0.36021063
−1.06372654 −1.03310466 −1.15494275 −2.19268966
−0.80285913 −0.79190463 −0.93620723 −1.30614185
−1.85568225 −2.38452196 −1.67495275 −0.70025575
−0.98393178 −1.83200908 −1.07078218 −0.98362595
−0.71674275 −2.04092884 −0.81029147 −0.92036235
−1.75404763 −1.45618188 −0.87118417 −0.54004192
−1.65154266 −1.28891158 −1.98474801 −1.20875657
−1.51076365 −1.44827867 −1.60024345 −1.5518645
−1.22961164 −1.33044851 −1.78681803 −1.60184741
−1.70247972 −1.48592603 −1.19963896 −2.06061363
−1.59096014 −1.18787074 −1.19529891 −0.61437321
−0.92168951 −0.91861475 −1.55775297 −1.57438934
−1.76918828 −2.1351223 −1.28325438 −1.17691207
−0.9070273 −0.92114311 −1.37144518 −1.05090868
−1.00942171 −1.12824321 −0.94788575 −1.27639067
−1.39774501 −1.06832922 −1.03379047 −1.49880815
−1.23712206 −1.15053117 −1.34290957 −1.66009867
−0.92846054 −0.97625399 −0.77744013 −1.93288314
−1.11750412 −0.97511715 −0.74683744 −1.13343358
−1.20803583 −1.436432 −1.50354922 −1.00136673
−2.01420403 −1.2733649 −0.92629886 −1.29439116
−1.64390576 −1.23867738 −0.88478297 −0.85971212
−1.85386622 −1.53856933 −2.06025767 −1.88411045
−1.49906313 −1.32475007 −1.117347 −1.68465662
−0.69363773 −1.5894047 −1.97358358 −2.59916759
−1.35396743 −2.30461049 −0.99292755 −1.27674675
−0.86507457 −0.94777668 −1.35009873 −1.47957981
−0.66513908 −1.06404948 −1.06712294 −1.72618425
−1.63874471 −1.46202075 −0.89948207 −1.20573676
−1.24084079 −1.19317305 −0.93100727 −1.02617919
−0.76241934 −1.87542462 −1.03179228 −1.45539415
−1.36384034 −0.96758604 −0.86005205 −0.80283695
−1.1137774 −1.53601909 −1.13732922 −1.12731791
−1.23490679 −1.33152759 −1.02586186 −1.44582832
−1.92057085 −1.30637109 −2.32667851 −1.57416546
−1.30796921 −0.70605123 −2.00818539 −1.46872818
−0.92903972 −1.57068658 −1.23099935 −1.05193675
−1.35168147 −0.52318192 −0.8894254 −1.69644272
−1.18933356 −1.11279356 −1.06844199 −1.36696768
−1.31789732 −1.63881576 −0.56565195 −0.52174371
−0.93638539 −2.07027268 −1.60358965 −1.22863901]

$b_h^2$:
−2.88706302643

$W_h^2$:
[−1.35359335 −0.578529 −0.13680433 0.17503858
−0.20488028 −0.54827738 −0.2597248 −1.73813021
−1.02167261 0.09387285 −0.63083726 −0.40662372
−0.47041351 −0.32108155 0.11540248 −0.10392507
−0.27698821 0.03336413 −0.72273839 −0.53308272
−0.25452602 −0.68693435 −0.11388378 −1.02962244
−1.22807848 −0.56124699 −0.56379735 −0.18465492
0.14469336 −0.41948733 −1.01185989 −1.1557889
−0.70585167 −0.54171222 −0.14044708 −0.4110463
−0.90434784 −0.61688143 −0.99438584 −1.55196273
−0.94430661 −0.39086425 −0.99821037 0.33283517
−0.69542056 0.14739829 −0.47792649 0.27000278
−0.64110023 −1.90988696 −0.37607646 0.11039938
−0.7492047 −0.17413628 −1.15171742 −0.68284678
−0.06158932 −1.04064727 −0.7101987 −0.86431879
−0.67057228 −0.68295568 0.08244683 −0.86153275
−0.31266105 −0.21919173 −0.79513979 0.17517358
−0.29372135 −1.68132675 −0.6964252 −0.47992685
0.00768639 −0.3944906 −0.99549603 −1.29167581
−0.82665157 −0.66138375 0.14107071 −0.89010292
−0.49536058 −0.90695 −0.84300721 −0.85446638
−0.99457145 −0.84283727 −1.26285946 −0.7482127
−1.32341206 −0.14178833 −0.47957143 0.22300801
0.22044657 −0.07665028 0.19888243 −0.68686688
0.09093325 0.20991775 −0.47505447 −1.29607451
−0.79738855 −0.6163758 −0.25245398 −0.24964713
−0.70785236 −0.14511365 0.23526534 −1.37460887
−0.42035979 −0.76954895 0.01340491 −0.23353948
−1.45486987 −2.10253382 0.31412357 0.05441735
−1.16719246 −0.53678679 −1.21121192 0.36880198
−1.7501055 −1.08759594 −1.03163946 −0.87725466
−1.04990077 −0.23935798 −0.70022678 −0.30579087
−1.51719499 −0.05505106 −0.30621436 −0.37509263
−0.35138479 0.08471824 −0.30281609 −0.40951991
−0.88454992 0.04506355 0.12505099 −0.79208314
−0.98382056 −0.73998731 −0.68265402 −0.30925721
−0.30487028 −0.18522757 −0.51589108 −0.14071934
−0.58638161 −0.37126878 −0.36587363 −1.98553813
−0.52241606 −0.33231446 −1.05311215 −1.1445843
0.1126269 −0.18052928 −0.87758267 −1.06622291
−1.76154435 −0.16173303 −1.38007092 −0.67007738
−0.95604581 −0.71263856 0.04040499 −0.84706324
0.3145974 −0.89040732 −0.75084466 −2.24529719
−0.90706474 0.08718969 −2.26292086 −0.43557408
−0.16575792 −1.28786123 −0.76409894 −1.2387414
−1.00480986 −1.59728515 −1.76675069 −0.45098865
0.37770402 −2.14156651 0.17127 −1.07672346
−0.63889885 −1.85108674 0.09201332 −0.64665085
−1.47701621 −0.27428123 0.11656716 −0.71997839
0.25774828 −0.65556616 −0.12599011 −1.19412673
0.05263189 −0.25015593 0.15155405 −0.71724749
−1.8973484 −0.01961765 −0.85265714 −0.54098094
−1.15418613 −0.55546618 −0.95463139 −1.48755825
−1.03432381 −0.82399344 −0.91085857 0.0421642
−0.55967122 −0.70061207 0.24029407 −0.97962326
−0.75661993 −0.6151405 −1.64357328 −1.16723275
−0.04848668 −0.62112832 −0.91200793 −0.5882951
−0.50034207 0.01658128 −0.58651829 −0.12295453
−0.13033544 0.07790214 −0.678482 −0.62363708
0.08507859 −0.94984204 0.00797078 −1.03968978
0.01618595 −0.11407378 0.2762318 −0.7622599
−1.18186867 −0.71437931 0.25219718 −1.02577722
−0.3844451 −0.210338 −0.34110329 −1.00708425
−0.23432316 −0.29608929 0.1013524 −0.40958044]

XI. Example Computer

Figure 14:
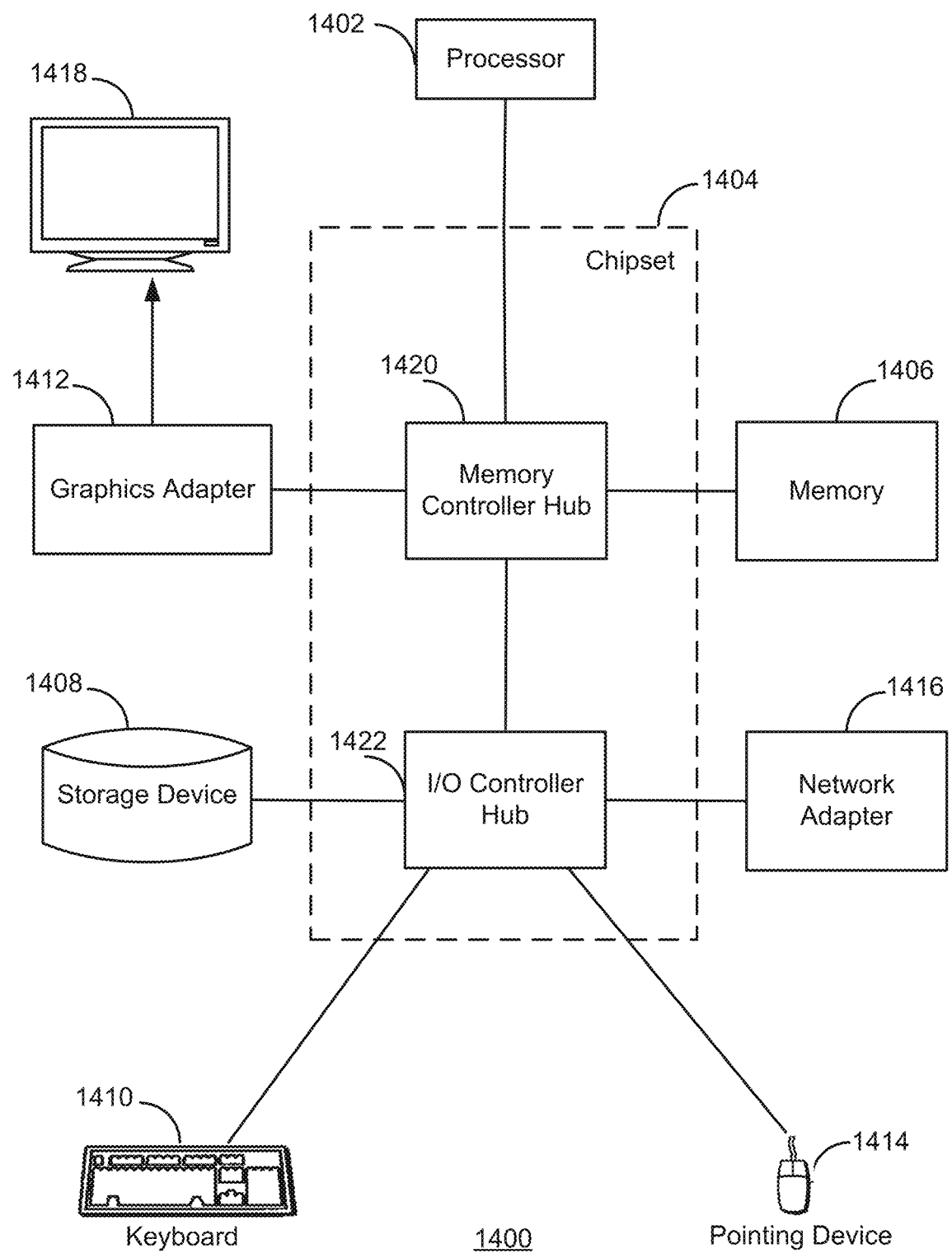
FIG. 14 illustrates an example computer for implementing the entities shown in FIGS. 1 and 3.

FIG. 14 illustrates an example computer 1400 for implementing the entities shown in FIGS. 1 and 3. The computer 1400 includes at least one processor 1402 coupled to a chipset 1404. The chipset 1404 includes a memory controller hub 1420 and an input/output (I/O) controller hub 1422. A memory 1406 and a graphics adapter 1412 are coupled to the memory controller hub 1420, and a display 1418 is coupled to the graphics adapter 1412. A storage device 1408, an input device 1414, and network adapter 1416 are coupled to the I/O controller hub 1422. Other embodiments of the computer 1400 have different architectures.

The storage device 1408 is a non-transitory computer-readable storage medium such as a hard drive, compact disk read-only memory (CD-ROM), DVD, or a solid-state memory device. The memory 1406 holds instructions and data used by the processor 1402. The input interface 1414 is a touch-screen interface, a mouse, track ball, or other type of pointing device, a keyboard, or some combination thereof, and is used to input data into the computer 1400. In some embodiments, the computer 1400 may be configured to receive input (e.g., commands) from the input interface 1414 via gestures from the user. The graphics adapter 1412 displays images and other information on the display 1418. The network adapter 1416 couples the computer 1400 to one or more computer networks.

The computer 1400 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 1408, loaded into the memory 1406, and executed by the processor 1402.

The types of computers 1400 used by the entities of FIG. 1 can vary depending upon the embodiment and the processing power required by the entity. For example, the presentation identification system 160 can run in a single computer 1400 or multiple computers 1400 communicating with each other through a network such as in a server farm. The computers 1400 can lack some of the components described above, such as graphics adapters 1412, and displays 1418.

REFERENCES

1. Desrichard, A., Snyder, A. & Chan, T. A. Cancer Neoantigens and Applications for Immunotherapy. *Clin. Cancer Res*. Off *J Am. Assoc. Cancer Res*. (2015). doi: 10.1158/1078-0432.CCR-14-3175
2. Schumacher, T. N. & Schreiber, R. D. Neoantigens in cancer immunotherapy. *Science* 348, 69-74 (2015).
3. Gubin, M. M., Artyomov, M. N., Mardis, E. R. & Schreiber, R. D. Tumor neoantigens: building a framework for personalized cancer immunotherapy. *J. Clin. Invest*. 125, 3413-3421 (2015).
4. Rizvi, N. A. et al. Cancer immunology. Mutational landscape determines sensitivity to PD-1 blockade in non-small cell lung cancer. *Science* 348, 124-128 (2015).
5. Snyder, A. et al. Genetic basis for clinical response to CTLA-4 blockade in melanoma. *N Engl. J. Med*. 371, 2189-2199 (2014).
6. Carreno, B. M. et al. Cancer immunotherapy. A dendritic cell vaccine increases the breadth and diversity of melanoma neoantigen-specific T cells. *Science* 348, 803-808 (2015).
7. Tran, E. et al. Cancer immunotherapy based on mutation-specific CD4+ T cells in a patient with epithelial cancer. *Science* 344, 641-645 (2014).
8. Hacohen, N. & Wu, C. J.-Y. United States Patent Application: 0110293637—COMPOSITIONS AND METHODS OF IDENTIFYING TUMOR SPECIFIC NEOANTIGENS. (A1). at <http://appft1.uspto.gov/netacgi/nph-Parser?Sect1=PTO1&Sect2=HITOFF&d=PG01&p=1&u=/netahtml/PTO/srchnum.html&r=1& f=G&1=50&s1=20110293637.PGNR.>
9. Lundegaard, C., Hoof, I., Lund, O. & Nielsen, M. State of the art and challenges in sequence based T-cell epitope prediction. *Immunome Res*. 6 Suppl 2, S3 (2010).
10. Yadav, M. et al. Predicting immunogenic tumour mutations by combining mass spectrometry and exome sequencing. *Nature* 515, 572-576 (2014).
11. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. *Mol. Cell. Proteomics MCP* 14, 658-673 (2015).
12. Van Allen, E. M. et al. Genomic correlates of response to CTLA-4 blockade in metastatic melanoma. *Science* 350, 207-211 (2015).
13. Yoshida, K. & Ogawa, S. Splicing factor mutations and cancer. *Wiley Interdiscip. Rev. RNA* 5, 445-459 (2014).
14. Cancer Genome Atlas Research Network. Comprehensive molecular profiling of lung adenocarcinoma. *Nature* 511, 543-550 (2014).
15. Rajasagi, M. et al. Systematic identification of personal tumor-specific neoantigens in chronic lymphocytic leukemia. *Blood* 124, 453-462 (2014).
16. Downing, S. R. et al. United States Patent Application: 0120208706—OPTIMIZATION OF MULTIGENE ANALYSIS OF TUMOR SAMPLES. (A1). at <http://appft1.uspto.gov/netacgi/nph-Parser?Sect1=PTO1&Sect2=HITOFF&d=PG01&p=1&u=/netahtml/PTO/srchnum.html&r=1& f=G&1=50&s1=20120208706.PGNR.>
17. Target Capture for NextGen Sequencing—IDT. at <http://www.idtdna.com/pages/products/nextgen/target-capture>
18. Shukla, S. A. et al. Comprehensive analysis of cancer-associated somatic mutations in class I HLA genes. *Nat. Biotechnol*. 33, 1152-1158 (2015).
19. Cieslik, M. et al. The use of exome capture RNA-seq for highly degraded RNA with application to clinical cancer sequencing. *Genome Res*. 25, 1372-1381 (2015).
20. Bodini, M. et al. The hidden genomic landscape of acute myeloid leukemia: subclonal structure revealed by undetected mutations. *Blood* 125, 600-605 (2015).
21. Saunders, C. T. et al. Strelka: accurate somatic small-variant calling from sequenced tumor-normal sample pairs. *Bioinforma. Oxf Engl*. 28, 1811-1817 (2012).
22. Cibulskis, K. et al. Sensitive detection of somatic point mutations in impure and heterogeneous cancer samples. *Nat. Biotechnol*. 31, 213-219 (2013).
23. Wilkerson, M. D. et al. Integrated RNA and DNA sequencing improves mutation detection in low purity tumors. *Nucleic Acids Res*. 42, e107 (2014).
24. Mose, L. E., Wilkerson, M. D., Hayes, D. N., Perou, C. M. & Parker, J. S. ABRA: improved coding indel detection via assembly-based realignment. *Bioinforma. Oxf Engl*. 30, 2813-2815 (2014).
25. Ye, K., Schulz, M. H., Long, Q., Apweiler, R. & Ning, Z. Pindel: a pattern growth approach to detect break points of large deletions and medium sized insertions from paired-end short reads. *Bioinforma. Oxf Engl*. 25, 2865-2871 (2009).
26. Lam, H. Y. K. et al. Nucleotide-resolution analysis of structural variants using BreakSeq and a breakpoint library. *Nat. Biotechnol*. 28, 47-55 (2010).
27. Frampton, G. M. et al. Development and validation of a clinical cancer genomic profiling test based on massively parallel DNA sequencing. *Nat. Biotechnol*. 31, 1023-1031 (2013).
28. Boegel, S. et al. HLA typing from RNA-Seq sequence reads. *Genome Med*. 4, 102 (2012).
29. Liu, C. et al. ATHLATES: accurate typing of human leukocyte antigen through exome sequencing. *Nucleic Acids Res*. 41, e142 (2013).
30. Mayor, N. P. et al. HLA Typing for the Next Generation. *PloS One* 10, e0127153 (2015).
31. Roy, C. K., Olson, S., Graveley, B. R., Zamore, P. D. & Moore, M. J. Assessing long-distance RNA sequence connectivity via RNA-templated DNA-DNA ligation. *eLife* 4, (2015).

32. Song, L. & Florea, L. CLASS: constrained transcript assembly of RNA-seq reads. *BMC Bioinformatics* 14 Suppl 5, S14 (2013).
33. Maretty, L., Sibbesen, J. A. & Krogh, A. Bayesian transcriptome assembly. *Genome Biol.* 15, 501 (2014).
34. Pertea, M. et al. StringTie enables improved reconstruction of a transcriptome from RNA-seq reads. *Nat. Biotechnol.* 33, 290-295 (2015).
35. Roberts, A., Pimentel, H., Trapnell, C. & Pachter, L. Identification of novel transcripts in annotated genomes using RNA-Seq. *Bioinforma. Oxf Engl.* (2011). doi: 10.1093/bioinformatics/btr355
36. Vitting-Seerup, K., Porse, B. T., Sandelin, A. & Waage, J. spliceR: an R package for classification of alternative splicing and prediction of coding potential from RNA-seq data. *BMC Bioinformatics* 15, 81 (2014).
37. Rivas, M. A. et al. Human genomics. Effect of predicted protein-truncating genetic variants on the human transcriptome. *Science* 348, 666-669 (2015).
38. Skelly, D. A., Johansson, M., Madeoy, J., Wakefield, J. & Akey, J. M. A powerful and flexible statistical framework for testing hypotheses of allele-specific gene expression from RNA-seq data. *Genome Res.* 21, 1728-1737 (2011).
39. Anders, S., Pyl, P. T. & Huber, W. HTSeq—a Python framework to work with high-throughput sequencing data. *Bioinforma. Oxf Engl.* 31, 166-169 (2015).
40. Furney, S. J. et al. SF3B1 mutations are associated with alternative splicing in uveal melanoma. *Cancer Discov.* (2013). doi:10.1158/2159-8290.CD-13-0330
41. Zhou, Q. et al. A chemical genetics approach for the functional assessment of novel cancer genes. *Cancer Res.* (2015). doi: 10.1158/0008-5472.CAN-14-2930
42. Maguire, S. L. et al. SF3B1 mutations constitute a novel therapeutic target in breast cancer. *J. Pathol.* 235, 571-580 (2015).
43. Carithers, L. J. et al. A Novel Approach to High-Quality Postmortem Tissue Procurement: The GTEx Project. *Biopreservation Biobanking* 13, 311-319 (2015).
44. Xu, G. et al. RNA COMPASS: a dual approach for pathogen and host transcriptome analysis of RNA-seq datasets. *PloS One* 9, e89445 (2014).
45. Andreatta, M. & Nielsen, M. Gapped sequence alignment using artificial neural networks: application to the MHC class I system. *Bioinforma. Oxf Engl.* (2015). doi:10.1093/bioinformatics/btv639
46. Jorgensen, K. W., Rasmussen, M., Buus, S. & Nielsen, M. NetMHCstab-predicting stability of peptide-MHC-I complexes; impacts for cytotoxic T lymphocyte epitope discovery. *Immunology* 141, 18-26 (2014).
47. Larsen, M. V. et al. An integrative approach to CTL epitope prediction: a combined algorithm integrating MHC class I binding, TAP transport efficiency, and proteasomal cleavage predictions. *Eur. J. Immunol.* 35, 2295-2303 (2005).
48. Nielsen, M., Lundegaard, C., Lund, O. & Keşmir, C. The role of the proteasome in generating cytotoxic T-cell epitopes: insights obtained from improved predictions of proteasomal cleavage. *Immunogenetics* 57, 33-41 (2005).
49. Boisvert, F.-M. et al. A Quantitative Spatial Proteomics Analysis of Proteome Turnover in Human Cells. *Mol. Cell. Proteomics* 11, M111.011429-M111.011429 (2012).
50. Duan, F. et al. Genomic and bioinformatic profiling of mutational neoepitopes reveals new rules to predict anticancer immunogenicity. *J. Exp. Med.* 211, 2231-2248 (2014).
51. Janeway's Immunobiology: 9780815345312: Medicine & Health Science Books @ Amazon.com. at <http://www.amazon.com/Janeways-Immunobiology-Kenneth-Murphy/dp/0815345313>
52. Calis, J. J. A. et al. Properties of MHC Class I Presented Peptides That Enhance Immunogenicity. *PLoS Comput. Biol.* 9, e1003266 (2013).
53. Zhang, J. et al. Intratumor heterogeneity in localized lung adenocarcinomas delineated by multiregion sequencing. *Science* 346, 256-259 (2014)
54. Walter, M. J. et al. Clonal architecture of secondary acute myeloid leukemia. *N. Engl. J. Med.* 366, 1090-1098 (2012).
55. Hunt D F, Henderson R A, Shabanowitz J, Sakaguchi K, Michel H, Sevilir N, Cox A L, Appella E, Engelhard V H. Characterization of peptides bound to the class I MHC molecule HLA-A2.1 by mass spectrometry. Science 1992. 255: 1261-1263.
56. Zarling A L, Polefrone J M, Evans A M, Mikesh L M, Shabanowitz J, Lewis S T, Engelhard V H, Hunt D F. Identification of class I MHC-associated phosphopeptides as targets for cancer immunotherapy. Proc Natl Acad Sci USA. 2006 Oct. 3; 103(40):14889-94.
57. Bassani-Sternberg M, Pletscher-Frankild S, Jensen L J, Mann M. Mass spectrometry of human leukocyte antigen class I peptidomes reveals strong effects of protein abundance and turnover on antigen presentation. Mol Cell Proteomics. 2015 March; 14(3):658-73. doi: 10.1074/mcp.M114.042812.
58. Abelin J G, Trantham P D, Penny S A, Patterson A M, Ward S T, Hildebrand W H, Cobbold M, Bai D L, Shabanowitz J, Hunt D F. Complementary IMAC enrichment methods for HLA-associated phosphopeptide identification by mass spectrometry. Nat Protoc. 2015 September; 10(9):1308-18. doi: 10.1038/nprot.2015.086. Epub 2015 Aug. 6
59. Barnstable C J, Bodmer W F, Brown G, Galfre G, Milstein C, Williams A F, Ziegler A. Production of monoclonal antibodies to group A erythrocytes, HLA and other human cell surface antigens-new tools for genetic analysis. Cell. 1978 May; 14(1):9-20.
60. Goldman J M, Hibbin J, Keamey L, Orchard K, Th'ng K H. HLA-DR monoclonal antibodies inhibit the proliferation of normal and chronic granulocytic leukaemia myeloid progenitor cells. Br J Haematol. 1982 November; 52(3):411-20.
61. Eng J K, Jahan T A, Hoopmann M R. Comet: an open-source MS/MS sequence database search tool. Proteomics. 2013 January; 13(1):22-4. doi: 10.1002/pmic.201200439. Epub 2012 Dec. 4.
62. Eng J K, Hoopmann M R, Jahan T A, Egertson J D, Noble W S, MacCoss M J. A deeper look into Comet—implementation and features. J Am Soc Mass Spectrom. 2015 November; 26(11):1865-74. doi: 10.1007/s13361-015-1179-x. Epub 2015 Jun. 27.
63. Lukas Käll, Jesse Canterbury, Jason Weston, William Stafford Noble and Michael J. MacCoss. Semi-supervised learning for peptide identification from shotgun proteomics datasets. Nature Methods 4:923-925, November 2007
64. Lukas Käll, John D. Storey, Michael J. MacCoss and William Stafford Noble. Assigning confidence measures to peptides identified by tandem mass spectrometry. Journal of Proteome Research, 7(1):29-34, January 2008
65. Lukas Käll, John D. Storey and William Stafford Noble. Nonparametric estimation of posterior error probabilities associated with peptides identified by tandem mass spectrometry. Bioinformatics, 24(16):i42-i48, August 2008

66. Bo Li and Colin N. Dewey. RSEM: accurate transcript quantification from RNA-Seq data with or without a referenfe genome. BMC Bioinformatics, 12:323, August 2011
67. Hillary Pearson, Tariq Daouda, Diana Paola Granados, Chantal Durette, Eric Bonneil, Mathieu Courcelles, Anja Rodenbrock, Jean-Philippe Laverdure, Caroline Côté, Sylvie Mader, Sébastien Lemieux, Pierre Thibault, and Claude Perreault. MHC class I-associated peptides derive from selective regions of the human genome. The Journal of Clinical Investigation, 2016,
68. Juliane Liepe, Fabio Marino, John Sidney, Anita Jeko, Daniel E. Bunting, Alessandro Sette, Peter M. Kloetzel, Michael P. H. Stumpf, Albert J. R. Heck, Michele Mishto. A large fraction of HLA class I ligands are proteasome-generated spliced peptides. Science, 21, Oct. 2016.

TABLE $W_h^1$

| | | | |
|---|---|---|---|
| [[−9.58197042e−02 | 7.56232589e−02 | 6.49665967e−02 | 2.01870017e−02 |
| −1.57726035e−02 | 6.70053959e−02 | 6.31582811e−02 | 2.71013658e−02 |
| −1.85769901e−03 | 9.28699002e−02 | −2.05408484e−02 | −6.78262189e−02 |
| 5.95255755e−02 | −4.69360314e−02 | 4.15655412e−02 | 4.62860949e−02 |
| 4.31108475e−02 | 5.52384816e−02 | −8.56619626e−02 | −9.53818634e−02 |
| −8.01674724e−02 | −8.76654610e−02 | −5.73782623e−03 | −7.28556514e−02 |
| −4.19468060e−02 | −7.96996281e−02 | 2.62921620e−02 | −8.37965086e−02 |
| −6.93939254e−02 | 1.04108684e−01 | 1.35314343e−02 | 5.19381128e−02 |
| −9.24314409e−02 | 3.07035930e−02 | −7.40122721e−02 | 7.62409344e−02 |
| −5.20897955e−02 | 8.87199268e−02 | 6.86418936e−02 | −1.01768389e−01 |
| −1.10887200e−01 | 3.67772467e−02 | −9.33126267e−03 | −1.05012909e−01 |
| −9.48817581e−02 | −6.68237358e−03 | −5.00904433e−02 | −9.41782296e−02 |
| −4.29538600e−02 | −4.04749848e−02 | −5.24228364e−02 | 4.22890037e−02 |
| −1.2681615e−03 | 3.54878753e−02 | −7.43927434e−02 | 1.00494884e−01 |
| −2.46253833e−02 | 2.50501046e−03 | −8.82150009e−02 | −4.08044867e−02 |
| 7.85917640e−02 | 9.10436586e−02 | 2.39423104e−02 | 7.92752802e−02 |
| 1.07104070e−01 | 1.88544188e−02 | −5.51663525e−02 | 1.78724546e−02 |
| 8.94777328e−02 | −1.90386847e−02 | 8.09452981e−02 | 7.85440058e−02 |
| 1.67981833e−02 | 6.90974817e−02 | −3.54140028e−02 | 2.22839825e−02 |
| −3.06125898e−02 | 8.95451289e−03 | −6.40854612e−02 | −5.22008613e−02 |
| −8.89242887e−02 | −6.72021061e−02 | −3.53715606e−02 | 5.38809225e−02 |
| 9.26230103e−02 | 5.67429978e−03 | −4.75810753e−04 | −6.89378604e−02 |
| 6.88603669e−02 | 1.31481998e−02 | 2.27763504e−02 | 9.34335366e−02 |
| 9.14454535e−02 | −1.01448841e−01 | −5.32976761e−02 | 6.13460578e−02 |
| −6.90631429e−03 | −1.01597376e−01 | 9.70802456e−02 | −7.15771094e−02 |
| −2.69618444e−02 | −2.24708822e−02 | −1.09046891e−01 | 3.34660779e−03 |
| −7.26794004e−02 | −3.64635745e−03 | −4.81818244e−02 | 2.13046949e−02 |
| 7.96534121e−03 | 4.53755036e−02 | 9.28816721e−02 | 4.49454077e−02 |
| −3.34177278e−02 | −3.75583284e−02 | 8.87972023e−03 | −8.55135173e−02 |
| 9.30208117e−02 | −6.74017891e−02 | 7.14414343e−02 | 5.99252209e−02 |
| −1.02022178e−01 | −5.96355423e−02 | −7.51459748e−02 | −3.47332247e−02 |
| −3.64217870e−02 | 1.72556390e−03 | −8.12090337e−02 | 6.69583008e−02 |
| −4.85072844e−02 | 9.42988172e−02 | 9.61549580e−02 | 2.20732987e−02 |
| −6.05181418e−02 | 7.90210813e−02 | −2.36348491e−02 | −4.81229573e−02 |
| 6.17466159e−02 | −3.03851068e−02 | −1.07663326e−01 | 1.09333992e−01 |
| 5.11612073e−02 | 1.58940759e−02 | 7.23326728e−02 | 5.45808300e−03 |
| 1.08254239e−01 | −1.41248479e−02 | 5.32003604e−02 | 3.14737037e−02 |
| −9.80302170e−02 | −1.11003714e−02 | 1.06234349e−01 | −3.52378041e−02 |
| 4.35375944e−02 | 4.28303406e−02 | 4.77622375e−02 | 6.46792799e−02 |
| 4.02734317e−02 | −6.78237155e−02 | 6.60944581e−02 | −2.50118617e−02 |
| 2.83700470e−02 | 8.15215558e−02 | 3.84903885e−03 | 1.08146459e−01 |
| 2.66368091e−02 | −5.40494844e−02 | 8.71888846e−02 | −9.84378755e−02 |
| −3.63388844e−02 | −7.11599663e−02 | −3.83533575e−02 | 2.62812544e−02 |
| −2.31098793e−02 | −6.34376034e−02 | −1.06968284e−01 | −1.10898346e−01 |
| 8.53130186e−04 | 2.25414578e−02 | −6.46606088e−02 | −5.70152998e−02 |
| 1.01264544e−01 | −7.71749020e−02 | −5.57538532e−02 | 7.01399595e−02 |
| 4.70534600e−02 | −1.02531545e−01 | 9.10027474e−02 | 4.35170047e−02 |
| −8.04423466e−02 | −3.64360921e−02 | 7.31077883e−03 | −7.45170712e−02 |
| 9.19470042e−02 | 9.04803053e−02 | 1.08166806e−01 | 3.23268995e−02 |
| 2.73287352e−02 | 3.47150955e−04 | −8.95141363e−02 | −8.10640976e−02 |
| −2.16244515e−02 | 8.75734240e−02 | 9.06624049e−02 | −9.56058055e−02 |
| 1.10849515e−01 | −1.03079341e−01 | 5.95886000e−02 | 9.47969109e−02 |
| 2.27052439e−02 | 5.26850857e−03 | 3.14926878e−02 | 1.07392803e−01 |
| 4.64981683e−02 | −1.03517212e−01 | 1.54533787e−02 | −2.86811441e−02 |
| −9.08850804e−02 | 2.39420887e−02 | 7.07382113e−02 | 5.67317568e−02 |
| −5.26179411e−02 | −5.20538948e−02 | 9.50870886e−02 | 8.35265964e−02 |
| −2.31429078e−02 | −7.13810548e−02 | 1.22702401e−02 | −3.51645146e−03 |
| 9.81885865e−02 | 1.77868339e−03 | 8.59211981e−02 | 3.63484435e−02 |
| 2.39258893e−02 | −5.97248264e−02 | 6.53061792e−02 | 8.78992602e−02 |
| 9.11217034e−02 | 7.82457218e−02 | 5.10050803e−02 | 1.04491845e−01 |
| 1.10578209e−01 | −8.54283124e−02 | −7.92483147e−03 | 6.72285110e−02 |
| 7.36182854e−02 | 6.96587786e−02 | 5.74156754e−02 | 2.66469605e−02 |
| 2.91525703e−02 | −3.96789350e−02 | −1.68352146e−02 | 9.19131190e−02 |
| −1.01197441e−03 | −8.44446048e−02 | 4.93224636e−02 | −6.84068725e−02] |
| [9.53666791e−02 | 2.14357406e−01 | −2.10078299e−01 | 2.07034543e−01 |
| −3.35836522e−02 | −1.58688277e−01 | 1.24542251e−01 | 1.84451699e−01 |
| 2.88550317e−01 | 9.67212245e−02 | 3.90703887e−01 | 1.32693285e−02 |
| −7.58918673e−02 | 1.48696899e−01 | −2.75522292e−01 | −1.61144689e−01 |
| −1.67630702e−01 | 2.29855567e−01 | 4.19466347e−01 | −1.84869468e−01 |

TABLE $W_h^1$-continued

| | | | |
|---|---|---|---|
| 3.70466076e−02 | −1.51625946e−01 | 2.99367189e−01 | −6.27778172e−02 |
| −4.12421465e−01 | −3.89454961e−02 | −1.12054152e−02 | 2.30770558e−01 |
| −1.83909312e−01 | −6.57103777e−01 | −6.72084808e−01 | 1.06058607e−04 |
| 1.48590013e−01 | −4.29323375e−01 | −2.81680167e−01 | −1.62513137e−01 |
| 4.26407337e−01 | 3.23676504e−02 | −4.96260613e−01 | −3.95452619e−01 |
| −1.17338255e−01 | −1.08496547e−01 | 3.81219059e−01 | −1.56909004e−01 |
| 1.86422065e−01 | 4.11044091e−01 | 3.43924373e−01 | 1.76993489e−01 |
| 1.44174919e−01 | −6.43986613e−02 | −3.36453587e−01 | −6.52214587e−02 |
| −1.91006616e−01 | 1.49241939e−01 | −2.45621949e−01 | 3.26014578e−01 |
| 2.31840372e−01 | −1.99004151e−02 | −7.63505548e−02 | 2.16796890e−01 |
| −1.17375024e−01 | 4.10133228e−02 | 3.44824530e−02 | 2.82385319e−01 |
| 4.18511689e−01 | 9.19384584e−02 | 3.07013392e−01 | 8.36220622e−01 |
| −2.48115107e−01 | 1.25812218e−01 | 1.25646457e−01 | −9.53571219e−03 |
| −5.66991570e−04 | −6.06277026e−02 | −2.66027927e−01 | 1.29066765e−01 |
| 1.48669839e−01 | 4.22279760e−02 | −1.11163810e−01 | 3.02686193e−03 |
| −5.07124245e−01 | −1.06916837e−01 | 6.50652051e−02 | −3.12266797e−01 |
| 5.31901896e−01 | −4.02476400e−01 | 1.71787411e−01 | 2.22139686e−01 |
| −7.83186965e−03 | 2.39493117e−01 | 1.93411149e−02 | 3.79074425e−01 |
| 5.18679678e−01 | 1.66447144e−02 | −4.54198159e−02 | −8.58265683e−02 |
| −3.59301157e−02 | 3.20713818e−01 | 5.96632123e−01 | −4.77748066e−02 |
| 1.30229488e−01 | 3.28714967e−01 | −1.28599852e−01 | −1.52906403e−01 |
| −1.15303561e−01 | 4.38593999e−02 | 6.09287880e−02 | 1.44524217e−01 |
| −4.06937152e−02 | −2.49650568e−01 | −1.12289498e−02 | −3.70559692e−02 |
| 3.58256936e−01 | 4.03834209e−02 | 3.16804349e−02 | 2.64547784e−02 |
| 2.69557148e−01 | 9.70447585e−02 | −1.39938444e−01 | 1.77781999e−01 |
| 4.91077989e−01 | 1.42553717e−01 | 1.79266125e−01 | 1.75232857e−01 |
| 1.74145564e−01 | 7.60381445e−02 | 1.36554882e−01 | 2.23177910e−01 |
| 2.27316752e−01 | 2.34653413e−01 | −6.09202273e−02 | −2.44906992e−01 |
| 2.87948102e−01 | 4.86297488e−02 | 4.98013571e−04 | 4.20814604e−01 |
| 1.17470600e−01 | 1.77569047e−01 | 4.96056825e−01 | 2.87835687e−01 |
| −2.32694689e−02 | −9.03505553e−03 | 1.47552639e−01 | 6.09157234e−02 |
| 1.46991998e−01 | 5.51038325e−01 | 8.77546072e−02 | 8.47725347e−02 |
| 3.85186613e−01 | 2.09822059e−01 | 2.13800728e−01 | 2.02686284e−01 |
| −4.02820557e−01 | 7.41484225e−01 | 2.13410836e−02 | −5.94995730e−02 |
| 6.93776533e−02 | 2.09194198e−01 | 5.50036371e−01 | 1.83337688e−01 |
| −5.07102907e−01 | 7.04911232e−01 | −9.93238166e−02 | −2.03203112e−01 |
| 3.66285652e−01 | 2.73433983e−01 | 5.82989363e−04 | 5.14323115e−02 |
| 5.15649021e−01 | 1.73331220e−02 | −5.77610210e−02 | −5.52357435e−02 |
| 2.71363766e−03 | 2.28661135e−01 | 1.81674004e−01 | 1.55327842e−01 |
| −6.06040470e−02 | −2.60483861e−01 | 1.60333022e−01 | 1.22551665e−01 |
| −1.49570808e−01 | 2.58748710e−01 | −2.73482241e−02 | −9.24080089e−02 |
| −1.91770252e−02 | 3.73763144e−01 | 4.23310459e−01 | −8.60571712e−02 |
| −5.20343101e−03 | −1.33692473e−01 | −2.47785039e−02 | −2.58431762e−01 |
| 9.66768898e−03 | −2.37032741e−01 | 4.20124263e−01 | −3.52241024e−02 |
| −4.91204709e−02 | 1.08868264e−01 | −2.22106189e−01 | 1.42905191e−02 |
| 1.72619820e−01 | −2.17177533e−02 | −8.51963535e−02 | −4.21556860e−01 |
| 1.62384808e−01 | 3.05634111e−01 | −2.12750584e−01 | 2.51117378e−01 |
| −2.73797382e−03 | 7.12627769e−02 | −2.25315392e−01 | −2.19607756e−01 |
| −2.01131165e−01 | 4.00942147e−01 | −1.63521469e−01 | −3.60163003e−02 |
| 1.71943843e−01 | 2.13147458e−02 | 1.41159013e−01 | 1.48509100e−01 |
| −4.41105887e−02 | −1.98368981e−01 | −5.03787577e−01 | 8.71597207e−04 |
| −5.93928657e−02 | −1.98545977e−01 | −1.78798556e−01 | −2.99428571e−02 |
| 3.40895988e−02 | 7.86127057e−03 | 4.44962122e−02 | 1.63171012e−02 |
| −2.76241809e−01 | 2.86432117e−01 | 2.87341058e−01 | −1.11780060e−03 |
| 3.21589023e−01 | 3.35151970e−01 | −1.35162055e−01 | 4.26442057e−01 |
| 7.36489445e−02 | 2.01280252e−03 | 4.73382063e−02 | 3.82604659e−01 |
| 2.11715445e−01 | −2.62247890e−01 | 2.86650099e−02 | 1.76085941e−02 |
| −2.27241740e−02 | 1.02433577e−01 | −3.41867357e−01 | −2.71186624e−02 |
| 1.01638891e−01 | −1.90898180e−02 | −2.55970776e−01 | 1.18024699e−01] |
| [9.15727913e−02 | 9.61944938e−01 | 1.17508125e−00 | 6.65987194e−01 |
| 1.42283142e−00 | 5.07135868e−01 | 6.88862383e−01 | 1.29201758e−00 |
| 6.86946511e−01 | 1.48623013e−00 | 3.02037925e−01 | 2.06433678e−00 |
| 1.51899588e−00 | 5.89009345e−01 | 9.10730362e−01 | 1.68339860e−00 |
| 1.68489623e−00 | 1.88797771e−04 | −1.55404344e−01 | 2.40668476e−01 |
| 5.41015446e−01 | 4.22919422e−01 | 1.14955771e−00 | 3.60492654e−02 |
| 1.33174300e−00 | 3.31684589e−01 | 1.40722349e−01 | 8.65442306e−02 |
| 1.12794757e−00 | 4.08566684e−01 | 3.00249368e−01 | 5.04167080e−01 |
| 2.41379037e−01 | 7.66830027e−01 | 1.11514878e−00 | −1.92141667e−01 |
| −2.64646620e−01 | 3.87975812e−01 | 5.12425562e−01 | 9.19657707e−01 |
| 9.78871286e−01 | 1.18475425e−00 | 1.31078446e−00 | 5.91042519e−01 |
| 1.53285757e−00 | 1.35341609e−00 | 4.38825071e−01 | 9.41051424e−01 |
| 9.37549293e−01 | 4.36640412e−01 | 5.10609150e−01 | 6.89545691e−01 |
| 3.19397211e−01 | 1.08583200e−00 | 7.31935322e−01 | 5.96237957e−01 |
| 7.67621636e−01 | 3.83449078e−01 | 2.48716712e−01 | 4.37910587e−01 |
| 4.18314427e−01 | 3.10618281e−01 | 7.99585700e−01 | 7.64953792e−01 |
| 6.22827053e−01 | 1.01851499e−00 | 1.05604208e−00 | 7.20882654e−01 |
| 1.01113284e−00 | −5.82943738e−01 | 2.43137062e−01 | −9.12802741e−02 |
| 5.71727753e−01 | 2.73379087e−01 | 5.16359746e−01 | 2.74244547e−01 |
| 5.67032814e−01 | 4.03017074e−01 | 8.24207723e−01 | 7.27704465e−02 |
| 1.05442381e−00 | 3.28098476e−01 | 5.05999029e−01 | 1.05825591e−00 |

TABLE $W_h^1$-continued

| | | | |
|---|---|---|---|
| 1.29423213e−00 | 3.94708216e−01 | 4.87959087e−01 | 7.74836719e−01 |
| 1.03608513e−00 | −3.57363462e−01 | 1.06973970e−00 | 6.72274351e−01 |
| 1.09326792e−00 | 1.28396082e−00 | 1.20403290e−00 | 5.12960315e−01 |
| 1.04955459e−00 | 3.90356600e−01 | 4.49606329e−01 | 1.35091174e−00 |
| 7.33664095e−01 | 4.68058437e−01 | 2.17450619e−01 | 4.43146490e−02 |
| 7.22386956e−01 | 2.03466967e−01 | 5.90778887e−01 | 1.75333548e−00 |
| 1.22674191e−00 | 3.58571202e−01 | 7.12451518e−01 | 1.24361897e−00 |
| 1.04833722e−00 | 9.29950893e−01 | 1.65685928e−00 | 3.42439473e−01 |
| 9.57376182e−01 | 2.45604843e−01 | 6.98677123e−01 | 5.63246347e−02 |
| 1.92545801e−01 | 6.00870430e−01 | 2.32278958e−01 | 5.90453625e−01 |
| 6.08646572e−01 | 9.59588349e−01 | 4.69905913e−01 | 8.98672462e−01 |
| 3.51658076e−01 | 4.73248541e−01 | 1.89359739e−01 | 4.13397044e−01 |
| 5.15953183e−01 | 6.84655309e−01 | 1.06031001e−00 | 1.06844282e−00 |
| 1.13116527e−00 | 1.15497434e−00 | 1.13041997e−00 | 1.16377914e−00 |
| 6.55401707e−01 | 2.48636499e−01 | 5.46791911e−01 | 6.62730515e−01 |
| 1.40359604e−00 | 7.59152412e−01 | 2.65330106e−01 | 7.29131341e−01 |
| 9.76068497e−01 | 8.18979621e−01 | 7.43434668e−01 | 6.44338608e−01 |
| 6.46554470e−01 | 4.45527464e−01 | 1.25314748e−00 | 4.18563217e−01 |
| 1.50817677e−01 | −5.23273759e−02 | 5.56973457e−01 | 6.94330096e−01 |
| 1.48839974e−00 | 1.39106774e−00 | 1.22843099e−00 | 6.85023844e−01 |
| 2.67875075e−01 | 5.07414877e−01 | 1.14300370e−00 | 3.99291992e−01 |
| 8.02654386e−01 | 3.12820256e−01 | −1.33582249e−01 | 6.35647833e−01 |
| 5.40086210e−01 | 1.27960718e−00 | 1.22219982e−00 | 2.60745063e−02 |
| 7.84427762e−01 | 2.86077738e−01 | 5.34774125e−01 | 2.43067130e−01 |
| 4.21470940e−01 | 8.37719262e−01 | 4.48532939e−01 | 5.11203229e−01 |
| 7.02982724e−01 | 3.59911978e−01 | 6.34011030e−01 | 6.18056417e−01 |
| 5.91568470e−01 | 2.55797178e−01 | 7.15207815e−01 | 3.30699623e−01 |
| 4.35641766e−01 | 1.47226945e−01 | 9.03157473e−01 | 5.82193434e−01 |
| 1.22448826e−00 | 1.30536079e−00 | 9.48542356e−01 | 3.88406575e−01 |
| 1.31921959e−00 | −2.60626581e−02 | 8.19493651e−01 | 8.03836063e−02 |
| −3.82899977e−02 | 6.80132329e−01 | 6.12996995e−01 | 3.32319617e−01 |
| 1.18576217e−00 | 7.29485333e−01 | 9.15373385e−01 | 8.78847122e−01 |
| 9.72742677e−01 | 1.37699321e−00 | 2.24308282e−01 | 8.69728506e−01 |
| 1.79280981e−01 | 5.74839830e−01 | 2.04965615e−00 | −2.36275375e−01 |
| 9.44302440e−01 | 1.90410107e−01 | 4.60213095e−01 | 1.23309307e−01 |
| 1.05679393e−00 | 4.03901786e−02 | 4.67618644e−01 | 1.19975495e−00 |
| 5.61596692e−01 | 7.57421970e−01 | 4.21356350e−01 | 9.76076841e−01 |
| 6.00874364e−01 | 1.66656468e−02 | 7.52632260e−01 | 1.23231339e−00 |
| 1.22919405e−00 | 2.00755930e−00 | 2.68390834e−01 | 9.14578557e−01 |
| 6.86902285e−01 | 1.68872774e−00 | 7.63035119e−01 | 4.16670471e−01 |
| 1.23675537e−00 | 1.28878999e−00 | −1.19021675e−02 | 9.84509736e−02 |
| 1.15303922e−00 | 3.90712440e−01 | 7.06244528e−01 | 1.22395849e−00 |
| 1.70630775e−02 | 4.62798059e−01 | 9.66367960e−01 | 6.78866744e−01] |
| [7.57340640e−02 | 1.00417696e−01 | 2.81253695e−01 | 2.74199814e−01 |
| 4.62136209e−01 | −7.26636313e−03 | 7.89297894e−02 | 1.00634050e−00 |
| 9.71579477e−02 | 1.14250563e−01 | 5.32950275e−03 | 5.27222931e−01 |
| 6.98612928e−01 | 5.42843081e−02 | 7.97841787e−01 | 2.51057655e−01 |
| 1.16445243e−01 | −2.65864767e−02 | −2.45333806e−01 | −8.11915770e−02 |
| 2.06442431e−01 | 4.96104628e−01 | 5.05606353e−01 | 3.62226591e−02 |
| 2.94297427e−01 | −3.42348397e−01 | 6.83907449e−01 | 3.05818677e−01 |
| 6.31109774e−01 | 3.06040257e−01 | 1.05375342e−01 | 1.31469786e−01 |
| 3.00069213e−01 | −4.48802978e−01 | 2.05164760e−01 | 1.20080329e−01 |
| −1.16298482e−01 | 1.54190004e−01 | −5.79788070e−03 | 1.75570458e−01 |
| 7.89289474e−02 | 5.66586971e−01 | 2.20049545e−01 | 6.52869880e−01 |
| 3.38790953e−01 | −5.32961249e−01 | 3.49760383e−01 | 2.79675245e−01 |
| −7.28846490e−02 | −2.65332937e−01 | −3.24437991e−02 | 7.48379469e−01 |
| −1.13067396e−01 | −1.47155866e−01 | 7.19041765e−01 | 4.45201516e−01 |
| 3.25276554e−01 | 3.49964589e−01 | 1.31168365e−01 | −1.80067047e−01 |
| −2.25881368e−01 | 5.62377155e−01 | −6.62059635e−02 | 1.39365003e−01 |
| 2.38164738e−01 | 8.46547723e−01 | −1.70588922e−02 | −4.75566089e−01 |
| −9.14443359e−02 | 1.27267420e−01 | 3.37331593e−01 | 1.21241726e−01 |
| 5.79418361e−01 | 5.46303809e−01 | −1.68895155e−01 | −1.63720131e−01 |
| 4.44202647e−02 | 1.94140613e−01 | −2.29610622e−01 | 2.12136462e−01 |
| 6.81408942e−01 | −8.27276483e−02 | 4.44127023e−01 | −1.21573970e−01 |
| 5.48345685e−01 | 3.07541918e−02 | 7.67728150e−01 | −1.98392659e−01 |
| 2.78701633e−01 | 2.88206413e−02 | 7.54262030e−01 | −1.71496108e−01 |
| 2.96349853e−01 | 6.86720848e−02 | 6.17905080e−01 | 3.22012395e−01 |
| 1.99436888e−01 | −4.19240981e−01 | −2.51350850e−01 | 8.23035777e−01 |
| 4.38638061e−01 | 3.14594150e−01 | 4.76209726e−03 | −1.23962127e−01 |
| 2.02119097e−01 | 3.35830450e−01 | 4.00430441e−01 | −2.47337177e−01 |
| 1.58519164e−01 | 9.74370480e−01 | 4.43591446e−01 | −2.42588922e−01 |
| 3.19061875e−01 | 1.71483550e−02 | 3.15775007e−01 | 2.37264261e−01 |
| 6.95333123e−01 | −4.89875898e−02 | 2.30262354e−01 | 3.60532910e−01 |
| −2.50993282e−01 | 2.28247672e−01 | 2.55946219e−01 | 4.05897200e−01 |
| 1.57565296e−01 | 7.22751990e−01 | −2.23856587e−02 | 3.77946913e−01 |
| 6.16804302e−01 | 1.84550732e−01 | 1.30693585e−01 | 3.09580773e−01 |
| −1.96713760e−01 | −2.21598372e−01 | −2.98059076e−01 | 4.23459083e−01 |
| 5.73567376e−02 | 1.87850773e−01 | −1.94392711e−01 | −1.43364862e−01 |
| 3.05267513e−01 | 2.42535278e−01 | 1.49680912e−01 | −2.83584863e−01 |
| −4.84546199e−02 | 3.17592211e−02 | 2.22276539e−01 | 1.38190854e−02 |

TABLE $W_h^1$-continued

| | | | |
|---|---|---|---|
| 4.66412544e-01 | 5.12860775e-01 | 3.43709201e-01 | -1.77636638e-01 |
| -1.02544583e-01 | -3.99097562e-01 | 2.29537070e-01 | -3.11557949e-01 |
| 1.88843951e-01 | -1.76257461e-01 | 4.44550782e-01 | 3.74947518e-01 |
| 1.48051798e-00 | -3.96580219e-01 | -3.98361593e-01 | 5.84568322e-01 |
| -3.10134679e-01 | -1.25386909e-01 | 1.16749716e-00 | 6.18198216e-01 |
| 1.07133366e-01 | 4.09459054e-01 | 5.49347878e-01 | 2.44902462e-01 |
| 2.60084182e-01 | -7.19761014e-01 | -2.46561170e-01 | -1.39314041e-01 |
| -1.65641814e-01 | -1.19461313e-01 | 2.38059431e-01 | 4.75583002e-02 |
| 2.96780884e-01 | -2.93885916e-01 | 5.80180949e-03 | 3.34313661e-01 |
| 4.22710210e-01 | 2.09339604e-01 | 1.79575369e-01 | 1.05304889e-01 |
| -2.41408378e-01 | 2.36776277e-01 | 1.90145776e-01 | 5.81004918e-01 |
| -1.51001498e-01 | 6.59389079e-01 | 1.50808692e-01 | 2.34348550e-01 |
| 4.37698394e-01 | 4.63062972e-02 | -1.42889738e-01 | -4.16885652e-01 |
| 6.91093385e-01 | -2.13597670e-01 | 1.21279550e-00 | 4.35403734e-01 |
| 4.74667549e-02 | -2.67199337e-01 | 3.13056499e-01 | 2.35620603e-01 |
| 6.22328520e-01 | 5.40551484e-01 | 1.17488325e-00 | 4.50076401e-01 |
| 5.62531650e-01 | 1.76571056e-01 | 5.68237960e-01 | 8.75641108e-02 |
| 3.35845739e-01 | -3.44931304e-01 | 7.98876584e-01 | -3.20641786e-01 |
| 4.99281958e-02 | 3.67973715e-01 | 1.03791666e-00 | 2.37950772e-01 |
| 1.27015524e-02 | 4.14055809e-02 | -2.85356373e-01 | 3.70310545e-01 |
| 6.31989956e-01 | -4.51907188e-01 | 1.79410651e-01 | 5.72332144e-01 |
| 2.97444742e-02 | 1.57257617e-01 | -4.11774337e-01 | -1.72638074e-01 |
| -4.61038619e-01 | 5.32568634e-01 | -1.39234243e-02 | -7.61111200e-01 |
| 2.92509347e-01 | 1.06120043e-01 | -4.30320948e-01 | -1.47446930e-01 |
| -1.59795001e-01 | -4.73222196e-01 | 2.33451039e-01 | 2.65773326e-01 |
| -2.46364906e-01 | 5.70678711e-01 | 6.21164382e-01 | 3.65058780e-01 |
| 4.40323085e-01 | 1.23749539e-01 | 1.02173162e-00 | -3.38886157e-02] |
| [4.90310192e-01 | 1.24714755e-01 | 8.94120410e-02 | 3.70235354e-01 |
| 5.20714998e-01 | 6.00576699e-02 | 2.53099382e-01 | 2.52006948e-01 |
| -1.18230812e-01 | -1.48633465e-01 | 5.86914644e-02 | 6.53172076e-01 |
| 3.08773696e-01 | -2.74905582e-01 | 4.47179079e-01 | 1.06959909e-01 |
| 8.57716501e-01 | -5.48863597e-02 | 2.39216294e-02 | -1.15030207e-01 |
| 1.74544439e-01 | 7.72935674e-02 | 2.48688087e-01 | 1.55387729e-01 |
| 1.99479982e-01 | -4.05286282e-01 | 3.10289532e-01 | -1.34296328e-01 |
| 3.89965266e-01 | 2.66224712e-01 | 8.36755455e-01 | 1.49262518e-01 |
| -8.49651769e-02 | -3.00422907e-01 | 2.62326866e-01 | -3.07812452e-01 |
| 6.08555675e-02 | 4.64430869e-01 | -5.02167404e-01 | 1.69182047e-01 |
| 4.87886518e-01 | 4.88448739e-01 | 1.57244131e-01 | 3.11892718e-01 |
| 1.31363925e-02 | -5.33765078e-01 | 1.55127108e-01 | 2.56102324e-01 |
| 2.09493861e-01 | -4.71634358e-01 | 3.69972527e-01 | 3.61080617e-01 |
| -9.70385149e-02 | -8.33615959e-02 | 2.34465394e-02 | 8.21837783e-02 |
| 1.31773800e-01 | 2.76587427e-01 | 2.79506087e-01 | -3.12144101e-01 |
| 2.99833149e-01 | 5.62581792e-02 | -5.21156192e-02 | -1.35139376e-01 |
| 5.26172757e-01 | 8.36945847e-02 | 8.92653912e-02 | 9.27996188e-02 |
| -3.75565678e-01 | -4.99247983e-02 | 6.58577502e-01 | 8.94338265e-02 |
| 3.10531437e-01 | -3.86395305e-02 | 2.93073803e-01 | 2.71508992e-01 |
| 3.88256498e-02 | 2.70781934e-01 | -1.43839374e-01 | 4.26278293e-01 |
| -7.98870996e-02 | 4.10286993e-01 | 8.97658393e-02 | -4.02146094e-02 |
| 2.77241766e-01 | -3.80324833e-02 | 1.85403153e-01 | 1.81492902e-02 |
| 1.30640268e-01 | 4.59974557e-01 | 3.06175530e-01 | 1.80384424e-01 |
| 4.51464355e-01 | 7.87598193e-01 | 7.84212112e-01 | 4.26049568e-02 |
| 5.29556274e-01 | -3.46596897e-01 | 9.57139488e-03 | 6.94420695e-01 |
| 6.04787111e-01 | -2.19500110e-01 | -5.56302294e-02 | -6.26128078e-01 |
| 1.87633708e-01 | 1.58473775e-02 | 5.15548587e-01 | 6.91860795e-01 |
| 6.07557707e-02 | 3.02075595e-01 | -4.12084401e-01 | -1.30150244e-01 |
| 6.50710523e-01 | -8.94109719e-03 | 3.76323670e-01 | 1.45194679e-01 |
| 7.64847100e-02 | -3.21965396e-01 | 1.60647705e-01 | 5.46663105e-01 |
| -1.04948387e-01 | -2.71735787e-01 | -1.58806536e-02 | 2.70856351e-01 |
| -3.43448818e-02 | 1.82654470e-01 | -1.60259157e-01 | 2.11935773e-01 |
| 4.94741857e-01 | -5.69439411e-01 | 1.06478646e-01 | 6.34513721e-02 |
| -3.88724118e-01 | 9.79085192e-02 | -5.06212153e-02 | 9.99381989e-02 |
| 5.73632956e-01 | 6.51815593e-01 | 6.33971617e-02 | 2.27266625e-01 |
| 3.57017182e-02 | 1.75720021e-01 | -2.67875910e-01 | 5.61534194e-03 |
| -3.74332041e-01 | -3.07498991e-01 | -3.32862705e-01 | 4.60421264e-01 |
| 2.17105702e-01 | 7.80015647e-01 | 3.65163982e-01 | -3.91874984e-02 |
| 1.14951953e-01 | -2.19886303e-01 | 8.09762254e-03 | -9.96533558e-02 |
| -8.82087871e-02 | -1.16672270e-01 | 1.73736289e-01 | 1.55844703e-01 |
| 1.27170026e-00 | -2.92294979e-01 | 4.08143222e-01 | 5.11399627e-01 |
| -3.00743371e-01 | 3.55735451e-01 | 8.59110951e-01 | 4.19549108e-01 |
| -2.71614134e-01 | 2.62845725e-01 | 1.75456434e-01 | 5.64706504e-01 |
| 1.57969683e-01 | -1.30594239e-01 | 1.33634925e-01 | -6.25280440e-01 |
| -2.03475699e-01 | -2.52930522e-01 | 2.20110156e-02 | -3.01879585e-01 |
| 9.42591429e-02 | -5.03917038e-01 | 3.01428795e-01 | 3.43113065e-01 |
| 1.93408877e-01 | -1.12607740e-01 | -1.44158781e-01 | 1.12934127e-01 |
| 4.04722840e-01 | 7.46552289e-01 | -4.67603505e-01 | -1.62442364e-02 |
| -2.13310197e-02 | 2.44985551e-01 | 2.87311733e-01 | -2.19731465e-01 |
| 5.92185318e-01 | 5.64451635e-01 | -3.54860872e-02 | 6.07913872e-03 |
| 3.94733578e-01 | -4.99700040e-01 | 7.90329099e-01 | 3.99260260e-02 |
| 1.36160687e-01 | -6.42879605e-02 | -1.02001011e-01 | 8.49740565e-01 |
| 3.91686082e-01 | -1.33521780e-01 | 7.51921356e-01 | -1.02607772e-01 |

TABLE $W_h^1$-continued

| | | | |
|---|---|---|---|
| −1.32223323e−01 | 3.68520357e−02 | 5.76244175e−01 | −2.41328523e−01 |
| 6.32566884e−02 | −1.17744692e−01 | 4.05215055e−01 | −4.35327441e−01 |
| 4.76747938e−02 | −5.38700595e−02 | 5.10803938e−01 | 1.16647132e−01 |
| 2.23991826e−01 | −1.22258566e−01 | −1.65259317e−01 | 9.14559439e−02 |
| 1.08067364e−01 | −4.07320172e−01 | 9.24708843e−02 | 3.14973235e−01 |
| 4.29636985e−02 | 4.07840610e−01 | 6.76170960e−02 | −7.45529458e−02 |
| 3.26812193e−02 | 4.04978752e−01 | −1.73718520e−02 | −4.84860927e−01 |
| 6.37003258e−02 | 6.88581765e−02 | −7.41562724e−01 | 6.95328489e−01 |
| 5.95287144e−01 | −2.43050372e−03 | 5.65033376e−01 | −2.93610513e−01 |
| −3.33984345e−01 | 1.94924980e−01 | 8.52663040e−01 | 5.19821569e−02 |
| 6.35693371e−02 | 1.33736372e−01 | −1.22714728e−01 | 2.68601924e−01] |
| [1.67209446e−02 | −2.44850695e−01 | 2.30588779e−01 | −9.47125480e−02 |
| 8.04930106e−02 | 4.02397543e−01 | 2.29272276e−01 | −4.66775261e−02 |
| 6.68233037e−01 | −6.85842335e−01 | 2.64167070e−01 | 1.80635884e−01 |
| 5.96650660e−01 | −1.04860686e−01 | −3.64273846e−01 | 4.89683837e−01 |
| 1.92185249e−02 | −3.19218069e−01 | 1.05659656e−01 | 5.23662306e−02 |
| 1.26091659e−02 | 3.45010430e−01 | 6.05875731e−01 | 9.18669224e−01 |
| −5.23518883e−02 | 1.07316172e−00 | −1.91636413e−01 | 1.23296089e−01 |
| −3.30536246e−01 | 2.60012299e−01 | −2.60844566e−02 | −2.15358570e−01 |
| 1.75700918e−01 | −1.54208317e−01 | −1.69062875e−02 | 2.85385728e−01 |
| 2.36871153e−01 | −2.97433555e−01 | 4.41498488e−01 | 3.59789193e−01 |
| 1.86478812e−02 | −7.12428465e−02 | 1.89437494e−01 | −1.35413960e−01 |
| 8.87740612e−01 | 2.43663758e−01 | 4.93419141e−01 | 1.32597864e−01 |
| 2.63692796e−01 | 2.06278712e−01 | −6.46708347e−03 | 2.71301717e−01 |
| 4.85277951e−01 | 9.78213400e−02 | 3.78584594e−01 | −5.58445215e−01 |
| 4.85792190e−01 | −4.38447416e−01 | 1.93663985e−01 | 3.89746577e−01 |
| 5.27265131e−01 | −9.60208662e−03 | −1.92574665e−01 | −4.53990027e−02 |
| −2.49336913e−01 | −1.72422945e−01 | −2.31664851e−01 | −1.86427042e−01 |
| 7.12963223e−01 | 6.56575486e−02 | 4.28575099e−01 | −1.31743224e−01 |
| 5.20790398e−01 | 2.39174709e−01 | 1.75802022e−01 | −3.23165320e−02 |
| 2.97348201e−01 | 5.91455936e−01 | 4.12376761e−01 | 3.16817880e−01 |
| −9.61049050e−02 | 3.69226158e−01 | 3.43652427e−01 | 2.53601670e−01 |
| −1.18095770e−01 | 4.35799956e−01 | −2.31147557e−03 | 2.04639480e−01 |
| −5.60258003e−03 | −2.98906088e−01 | 3.73741984e−01 | −1.41470015e−01 |
| −3.57113302e−01 | −3.96239012e−01 | 1.30617749e−02 | 7.66287893e−02 |
| −2.79138088e−01 | 1.82979956e−01 | −3.57069880e−01 | −1.16163097e−01 |
| 1.09225838e−02 | 4.42251503e−01 | −1.51889324e−01 | 1.29920676e−01 |
| −1.25885949e−01 | −5.69637120e−02 | 2.18269870e−01 | −2.21054424e−01 |
| −2.27806076e−01 | 3.56288046e−01 | −2.36545309e−01 | 5.93382232e−02 |
| 1.08213134e−01 | −2.43441120e−01 | −3.16878885e−01 | 6.22779310e−01 |
| −1.76157877e−01 | −2.72913605e−01 | 5.28528750e−01 | −3.11152220e−01 |
| 5.31538963e−01 | 3.94599199e−01 | −1.38440788e−01 | 2.96629846e−01 |
| −1.77028403e−02 | 1.27785087e−01 | −5.31683803e−01 | 8.68189037e−01 |
| 4.59713459e−01 | −5.86539730e−02 | 3.63377810e−01 | 3.47922206e−01 |
| 4.01621908e−01 | 7.53837898e−02 | 3.51522416e−01 | −1.16891451e−01 |
| 7.63900459e−01 | −4.99825627e−02 | 4.32581484e−01 | 2.19957618e−01 |
| 2.71017432e−01 | 1.84820876e−01 | −2.99247116e−01 | 3.85616720e−02 |
| −7.87999406e−02 | −1.04849644e−01 | −2.95407623e−01 | 7.45901614e−02 |
| −1.45196304e−01 | −6.85868740e−01 | −4.32614744e−01 | −3.59948248e−01 |
| 7.47733951e−01 | 1.08890980e−01 | 3.56020063e−01 | −3.43526155e−02 |
| −1.03091687e−01 | −4.74300422e−02 | −1.14985682e−01 | 2.80679017e−01 |
| −2.30858982e−01 | −2.97477007e−01 | 5.57059407e−01 | 3.95879716e−01 |
| 1.73349068e−01 | −1.53545916e−01 | −8.94336849e−02 | 3.44715148e−01 |
| 1.02113761e−01 | 5.00819266e−01 | 3.36348295e−01 | 1.64918512e−01 |
| 5.63115954e−01 | 3.01304776e−02 | −2.16974154e−01 | −2.94280469e−01 |
| 5.63294053e−01 | 1.82513535e−01 | 2.26063114e−02 | 2.61965767e−02 |
| −5.12074590e−01 | 1.23579100e−01 | 2.00505644e−01 | 2.09972989e−02 |
| 6.82637244e−01 | 2.53889233e−01 | 3.46433967e−01 | 2.46920764e−01 |
| 7.34904349e−01 | 5.54249883e−01 | 2.52907783e−01 | 4.34586734e−01 |
| −3.35689560e−02 | 5.60987461e−03 | 1.86543599e−01 | −2.71206230e−01 |
| −3.95982623e−01 | −4.28851455e−01 | 3.87572832e−02 | −1.26481920e−01 |
| −1.04576662e−01 | 3.96878421e−01 | 1.92825526e−01 | −1.12392731e−01 |
| 1.94073871e−01 | −1.55217484e−01 | 7.79146075e−01 | −7.74037465e−02 |
| 6.53210819e−01 | 7.66862407e−02 | 8.14163327e−01 | −1.90370515e−01 |
| 1.40930086e−01 | −1.85462356e−01 | 4.94277775e−02 | −2.13369373e−02 |
| 4.11366578e−03 | 2.51608998e−01 | −3.32781300e−03 | 2.27573723e−01 |
| 2.96410508e−02 | 2.99230158e−01 | 2.96149462e−01 | −7.44722545e−01 |
| 2.08657026e−01 | 3.37586105e−01 | −1.09207571e−01 | 1.35837972e−01 |
| 1.22116230e−01 | 5.10608673e−01 | 5.96996784e−01 | 2.47980088e−01 |
| 3.64855647e−01 | −5.56589738e−02 | 1.14440240e−01 | 7.10227787e−01 |
| 4.66122836e−01 | 2.87551850e−01 | 4.98663709e−02 | 2.38479659e−01 |
| −2.65819252e−01 | 1.30016103e−01 | 4.80178654e−01 | 1.64778352e−01 |
| −2.08973140e−01 | 8.49389672e−01 | −3.97880554e−01 | 9.67234932e−03 |
| 5.38081050e−01 | 5.31238854e−01 | 1.05729952e−01 | 5.26967235e−02 |
| −6.46394864e−01 | 5.01864076e−01 | 6.08751029e−01 | −1.37770742e−01] |
| [3.78173769e−01 | 3.63725513e−01 | 2.80882418e−02 | −2.60618836e−01 |
| 2.22789403e−02 | 1.42089888e−01 | 1.46754482e−03 | −3.36668998e−01 |
| 1.15605533e−01 | 2.91383564e−01 | 3.27669799e−01 | 2.07511842e−01 |
| −2.35077776e−02 | 3.17710161e−01 | 1.92318000e−02 | 1.10123545e−01 |
| 5.44414017e−03 | 4.91029263e−01 | 2.38407522e−01 | 4.17107582e−01 |

TABLE $W_h^1$-continued

| | | | |
|---|---|---|---|
| 1.92736045e-01 | -3.63358140e-01 | -1.21984132e-01 | 1.78979523e-02 |
| -4.93796431e-02 | -2.56439783e-02 | 1.76584631e-01 | 4.29589152e-02 |
| 1.95341319e-01 | 4.96026039e-01 | -2.54657567e-01 | 2.18641441e-02 |
| -1.35738552e-01 | 8.10500514e-03 | 2.80244827e-01 | 1.05584085e-01 |
| -1.28236905e-01 | 8.55238214e-02 | 1.13591298e-01 | -1.40881807e-01 |
| 3.63211753e-03 | -1.55133843e-01 | -2.98489481e-01 | 2.12945446e-01 |
| 1.17225554e-02 | 5.97988605e-01 | 9.77294967e-02 | 1.58116102e-01 |
| -4.20697302e-02 | -1.29475579e-01 | -3.63629520e-01 | -2.49886841e-01 |
| 4.93101448e-01 | 2.08982885e-01 | 1.12762310e-01 | 3.03648233e-01 |
| 2.02563092e-01 | -1.91834673e-01 | 1.48780540e-01 | 8.18756640e-01 |
| -9.37505066e-02 | -6.18347116e-02 | 4.31532294e-01 | 4.97958153e-01 |
| 3.03331375e-01 | 6.50227964e-02 | 2.36691341e-01 | 2.10016981e-01 |
| 3.94401044e-01 | 3.93660098e-01 | 2.92628288e-01 | 2.34194398e-01 |
| -1.77332804e-01 | 1.03920568e-02 | -3.81357558e-02 | 1.66357875e-01 |
| -1.26654640e-01 | 6.05001040e-02 | -3.08329146e-02 | 1.44037604e-01 |
| 2.45751143e-01 | -4.48956117e-02 | -1.23780102e-01 | -3.52162272e-01 |
| 5.21501064e-01 | -7.23235542e-03 | 1.03638910e-01 | 2.83201873e-01 |
| -2.84854233e-01 | 4.34029490e-01 | -5.72290421e-02 | 9.12540197e-01 |
| 1.26816660e-01 | 9.42552835e-02 | -4.71465699e-02 | 1.59297377e-01 |
| 1.52797908e-01 | 7.00691462e-01 | -5.71913384e-02 | 9.44315642e-03 |
| -3.28491896e-01 | 4.71200109e-01 | 2.62578517e-01 | 1.28034800e-01 |
| 4.61674750e-01 | 3.87200087e-01 | 2.03702971e-02 | 3.17942202e-02 |
| 4.75962222e-01 | 2.41236195e-01 | -2.84422129e-01 | 1.61647096e-01 |
| 9.45112556e-02 | -2.78534908e-02 | 5.68255723e-01 | 4.02648211e-01 |
| 1.73274931e-02 | 2.38628060e-01 | 1.00562409e-01 | -1.34951556e-02 |
| 4.28490311e-01 | 9.86034572e-02 | 1.81767002e-01 | 3.10190022e-01 |
| -1.48927063e-01 | 3.41419607e-01 | 1.38051271e-01 | 2.67790794e-01 |
| -5.76959876e-03 | 5.49781919e-01 | 3.11031759e-01 | 1.53881654e-01 |
| -2.87218869e-01 | 3.30338240e-01 | -2.05733851e-02 | -5.44922203e-02 |
| -2.97627621e-03 | 5.51750243e-01 | -9.28060636e-02 | 9.67758745e-02 |
| 1.22756965e-01 | 4.22094017e-01 | 2.06769124e-01 | 3.93602282e-01 |
| 3.66054058e-01 | 9.05824840e-01 | 1.38708174e-01 | 2.73038507e-01 |
| 3.59446891e-02 | 8.97859558e-02 | 1.98232457e-02 | 2.41321158e-02 |
| 2.93492854e-01 | 5.20107210e-01 | -1.92475706e-01 | 1.27187252e-01 |
| -6.14588195e-03 | 3.44355926e-02 | -4.74944152e-02 | 2.44394332e-01 |
| -2.29041606e-01 | 8.06888640e-01 | 1.25594884e-01 | 2.75313497e-01 |
| 1.36442214e-01 | 1.89942941e-01 | -1.23315072e-02 | -1.45621046e-01 |
| 6.59865797e-02 | -4.54624332e-02 | 6.70367479e-02 | -1.97466999e-01 |
| -8.21407810e-02 | 1.55208692e-01 | 1.98092654e-01 | 3.15136194e-01 |
| -1.08453035e-01 | -1.02117606e-01 | 1.64792866e-01 | 4.95413601e-01 |
| 2.87311137e-01 | 1.24296047e-01 | 3.40485811e-01 | 7.36116767e-02 |
| 1.18947327e-01 | -9.64976624e-02 | 1.68216258e-01 | 3.61406617e-02 |
| 6.68024942e-02 | -1.78162009e-01 | 1.91889852e-01 | 3.17158401e-01 |
| -1.81394503e-01 | 8.46027285e-02 | 4.46081519e-01 | 2.81553507e-01 |
| 2.16903821e-01 | 2.17287809e-01 | 7.71342635e-01 | 2.23370045e-01 |
| 1.17297977e-01 | -3.14214826e-01 | -2.75033921e-01 | 1.89296842e-01 |
| -2.62123942e-01 | 5.65438688e-01 | -1.60052866e-01 | 4.58708107e-01 |
| 2.12292627e-01 | -8.55080113e-02 | 1.94638774e-01 | 1.61696866e-01 |
| -3.60790789e-02 | 4.10464048e-01 | -1.93032280e-01 | 5.85464060e-01 |
| 2.74220835e-01 | 2.47609571e-01 | -2.10328400e-01 | 8.15250203e-02 |
| 3.65281463e-01 | 1.66598499e-01 | -9.63449329e-02 | 2.17436813e-02 |
| 6.77033812e-02 | -8.82504955e-02 | 9.76276025e-02 | 6.00467473e-02 |
| 3.13335896e-01 | -8.40989128e-02 | -9.33009724e-04 | 7.56498426e-02 |
| -1.01458669e-01 | 2.52405554e-01 | -6.77393600e-02 | 1.23025380e-01 |
| 1.89092994e-01 | -3.63620520e-02 | 2.54204780e-01 | 8.32604289e-01 |
| 7.68356621e-01 | 3.48849535e-01 | 4.10870202e-02 | 3.05002630e-01 |
| 4.20299500e-01 | 1.47562712e-01 | 1.37780905e-01 | 2.04736471e-01 |
| 3.11402865e-02 | -1.83904767e-01 | -5.33251226e-01 | 2.23578930e-01 |
| -8.80944803e-02 | 1.70566738e-01 | 1.85129091e-01 | 5.17327309e-01] |
| [3.96425724e-01 | 1.22911341e-01 | 3.49920481e-01 | -5.65419421e-02 |
| 2.99809370e-02 | 1.55672595e-01 | 5.05207837e-01 | 4.45575207e-01 |
| 2.42117897e-01 | 6.69273660e-02 | 1.34481430e-01 | 2.25825220e-01 |
| -4.46259119e-02 | 3.59173000e-01 | -4.89981845e-02 | -1.87081054e-01 |
| 7.65073299e-02 | 1.64357387e-02 | -3.08433324e-02 | 4.08717990e-01 |
| -5.68024516e-02 | -6.00727536e-02 | 2.63390452e-01 | -2.49258354e-02 |
| 1.95358805e-02 | 4.55701873e-02 | 1.03693359e-01 | 4.33562368e-01 |
| 2.75194138e-01 | 6.13605566e-02 | 3.27470392e-01 | 2.12404221e-01 |
| 2.89540708e-01 | 3.27144027e-01 | 1.67872205e-01 | 1.37147948e-01 |
| -3.17399114e-01 | 9.05109346e-02 | 4.12255228e-02 | 4.73663747e-01 |
| -7.39811808e-02 | 3.18587452e-01 | -4.46696989e-02 | 3.72974038e-01 |
| 1.70831814e-01 | 2.19394997e-01 | 1.81958839e-01 | 2.67562121e-01 |
| 4.53004241e-02 | -9.86437127e-02 | 1.74344987e-01 | -4.37869728e-01 |
| 6.19742870e-01 | -4.30398285e-02 | 4.17884529e-01 | 2.32757628e-01 |
| 1.25871584e-01 | 2.73970723e-01 | 6.39863849e-01 | 3.87325823e-01 |
| 3.35950106e-01 | 3.40690881e-01 | -1.16676830e-01 | 1.84699595e-01 |
| 1.51341394e-01 | 9.37772617e-02 | 5.22549033e-01 | -1.16991058e-01 |
| -2.38981396e-02 | 1.51531652e-01 | 1.14962399e-01 | 3.00836086e-01 |
| 3.02521646e-01 | -1.70557350e-02 | 5.75188935e-01 | 4.80716795e-01 |
| 2.80501127e-01 | 4.77082402e-01 | 1.63920730e-01 | 3.61017406e-01 |
| 3.27851862e-01 | 4.29153532e-01 | 2.81966776e-02 | 4.41234022e-01 |

TABLE $W_h^1$-continued

| | | | |
|---|---|---|---|
| −3.16302061e−01 | −5.51988602e−01 | 1.76053509e−01 | 3.85373265e−01 |
| 2.86649883e−01 | 7.85417855e−02 | 1.23916872e−01 | 1.70804605e−01 |
| −1.75750971e−01 | 4.20118600e−01 | −2.29921222e−01 | 2.35023826e−01 |
| 2.81406373e−01 | −9.89416167e−02 | −4.04439420e−01 | −6.06207410e−03 |
| 1.33002847e−01 | 3.83041292e−01 | 3.76337171e−01 | 3.63592654e−01 |
| −7.53351524e−02 | 3.88376445e−01 | 6.27034009e−01 | 9.67005342e−02 |
| 4.28402036e−01 | 2.50429332e−01 | 7.62472749e−02 | −3.36857617e−01 |
| −1.86342761e−01 | −7.06615299e−02 | 8.43787193e−02 | 1.06285378e−01 |
| 1.02765337e−01 | 5.28765261e−01 | 4.91841078e−01 | 4.59748119e−01 |
| 3.15453380e−01 | −1.45135000e−01 | 6.64812684e−01 | 6.94104671e−01 |
| 2.97025442e−01 | 1.28770098e−01 | 5.08182287e−01 | 3.56022656e−01 |
| 3.91201168e−01 | 1.41027093e−01 | 1.63377717e−01 | 1.54425919e−01 |
| 4.38465923e−01 | 5.68061322e−02 | −1.26994923e−01 | 1.73072517e−01 |
| −2.71810770e−01 | 3.34061444e−01 | 2.27060601e−01 | 2.41143808e−01 |
| 1.94726735e−02 | 2.42832214e−01 | 4.54367278e−03 | 5.06656766e−01 |
| 2.32741401e−01 | −3.13663781e−01 | 1.28012523e−01 | 7.43701100e−01 |
| −7.21269548e−02 | −3.44605654e−01 | −1.26942337e−01 | 4.46823955e−01 |
| 9.40070078e−02 | 1.45602897e−02 | 3.45352203e−01 | 2.59710222e−01 |
| 3.92802775e−01 | 1.38739198e−01 | 1.83658451e−01 | 3.70990306e−01 |
| 1.71097293e−01 | 5.73124066e−02 | 3.14559102e−01 | 2.06219316e−01 |
| −4.41565752e−02 | 3.34408402e−01 | 1.49574608e−01 | 2.51585811e−01 |
| 3.23340923e−01 | −9.14784148e−02 | −2.23709896e−01 | 8.30220059e−02 |
| 2.87485540e−01 | 1.29425392e−01 | 2.72780081e−01 | 3.30743492e−01 |
| 3.78189892e−01 | 2.38568678e−01 | 1.22834735e−01 | 1.89450249e−01 |
| −1.22337257e−02 | −6.07206859e−02 | 1.35784209e−01 | 3.15303236e−01 |
| 3.18185747e−01 | −4.22311604e−01 | −7.16615617e−02 | 2.86125839e−01 |
| −4.48552817e−02 | 1.00120120e−01 | 3.50135952e−01 | 4.41463798e−01 |
| 4.00890350e−01 | 4.86209810e−01 | 8.28796327e−02 | 9.57469791e−02 |
| −1.44557618e−02 | 1.15585618e−01 | 1.62323371e−01 | 1.81435958e−01 |
| −4.98125181e−02 | −2.21967816e−01 | 1.06265239e−01 | 6.68775856e−01 |
| −3.68996143e−01 | 2.32544348e−01 | 1.21787861e−01 | −1.20233126e−01 |
| 3.72844845e−01 | 1.33010477e−01 | 1.20111275e−02 | 1.92873910e−01 |
| −3.03327531e−01 | 8.78137499e−02 | 1.98167339e−01 | 3.16422135e−01 |
| 1.20260036e−02 | 3.15645397e−01 | −4.58183587e−02 | 1.33576930e−01 |
| −7.85778090e−02 | 3.52927864e−01 | −9.65515748e−02 | 1.54410809e−01 |
| −1.79170102e−01 | 2.19995618e−01 | −3.86431664e−02 | −1.01054952e−01 |
| 1.72132701e−01 | 2.92280644e−01 | 3.85088891e−01 | 1.65724769e−01 |
| 1.25885019e−02 | −5.01617134e−01 | 3.14883709e−01 | 4.77650642e−01 |
| −7.68288001e−02 | 3.10914040e−01 | 2.23618582e−01 | −9.03037470e−03 |
| 3.38402122e−01 | 1.50503591e−01 | 1.30802721e−01 | 7.91889504e−02 |
| 2.92725593e−01 | 1.07565746e−01 | 5.10855198e−01 | 2.32344091e−01 |
| 2.50914395e−01 | 4.03553188e−01 | 3.19811404e−01 | 6.17147684e−01 |
| −3.87703836e−01 | 3.95573258e−01 | 4.43935931e−01 | −2.55008340e−01] |
| [2.47208789e−01 | 1.89097133e−02 | 4.09410894e−01 | 2.07880318e−01 |
| −2.16177672e−01 | 3.83813322e−01 | 2.81322658e−01 | 1.37683317e−01 |
| 3.97839755e−01 | 3.18257898e−01 | 3.57822448e−01 | 3.44153959e−04 |
| 4.81237382e−01 | 2.86156386e−01 | 4.60529439e−02 | 6.54604957e−01 |
| 2.42640749e−01 | −2.58847717e−02 | 4.10941660e−01 | 2.73454711e−02 |
| 1.56445831e−01 | 8.63464475e−02 | 4.79130186e−02 | 1.96993455e−01 |
| 1.65641993e−01 | 5.46268880e−02 | 8.00699517e−02 | −1.15143182e−03 |
| 8.17586184e−02 | 8.05453286e−02 | 2.13487834e−01 | −1.39341846e−01 |
| 2.06293538e−01 | −2.69409269e−01 | 6.08746968e−02 | 3.55152339e−01 |
| 1.55042425e−01 | 8.86951759e−02 | 5.02836287e−01 | 2.62929410e−01 |
| −1.01987511e−01 | 2.54410058e−01 | −6.64452672e−01 | 1.85108781e−01 |
| 4.75153297e−01 | 2.23072976e−01 | 2.29469538e−01 | 6.85378090e−02 |
| 7.85860717e−02 | 2.45252743e−01 | 3.24214578e−01 | 1.78420842e−01 |
| −3.07747304e−01 | 4.69642401e−01 | −1.02659315e−01 | 2.87840843e−01 |
| −4.88545820e−02 | −6.78502843e−02 | 4.33961540e−01 | −4.68886383e−02 |
| 1.76022992e−01 | 1.45886213e−01 | −1.06201276e−01 | −5.97269572e−02 |
| −3.63170981e−01 | −3.40764876e−03 | −6.07218519e−02 | 4.45159853e−01 |
| 1.90428212e−01 | 5.43656722e−02 | 4.05901335e−02 | 2.63475388e−01 |
| 2.60021299e−01 | 6.97708905e−01 | −2.53451262e−02 | −8.81246198e−03 |
| 2.94311911e−01 | 7.99028724e−02 | 4.99257743e−01 | −3.39868009e−01 |
| −7.90215433e−02 | 4.33963895e−01 | −2.98349947e−01 | 3.16292465e−01 |
| −3.14570934e−01 | 1.60315216e−01 | −3.04804265e−01 | 1.82597023e−02 |
| 2.93344986e−02 | 2.02204019e−01 | 5.12449890e−02 | 8.52026641e−02 |
| −3.71837139e−01 | 1.11961357e−01 | 2.75321573e−01 | −4.00462151e−02 |
| −1.62334498e−02 | 2.80197620e−01 | 1.66628778e−01 | −3.36707592e−01 |
| 4.59537536e−01 | 3.74881268e−01 | 5.67257643e−01 | 2.90126681e−01 |
| 1.52256757e−01 | 2.94130683e−01 | −5.08547090e−02 | 2.30414212e−01 |
| 1.45115959e−03 | 1.38496667e−01 | 4.97208416e−01 | 6.45312667e−01 |
| 1.22678995e−01 | 4.38369781e−01 | −1.46704242e−01 | −8.91284551e−03 |
| 9.04837176e−02 | 1.68858185e−01 | −3.37846130e−02 | −3.68105918e−02 |
| −9.52479523e−03 | 2.06114680e−01 | 1.52361915e−02 | 2.96829611e−01 |
| 1.78452089e−01 | 5.21421134e−01 | −1.21265903e−01 | 9.51881334e−02 |
| 1.95370167e−01 | 4.28356349e−01 | −1.62378177e−02 | 4.20488298e−01 |
| 5.27258635e−01 | −3.05528268e−02 | 2.84211308e−01 | 2.78623343e−01 |
| 2.20767576e−02 | −1.40271988e−02 | −6.46510273e−02 | −9.31657292e−03 |
| 2.63669372e−01 | 7.23650157e−01 | 2.27337509e−01 | 2.52162367e−01 |
| −1.90732852e−01 | 1.10826366e−01 | −7.88696706e−02 | 2.58595228e−01 |

TABLE W$_h^1$-continued

| | | | |
|---|---|---|---|
| 5.42894565e−02 | −6.75722733e−02 | −2.09731832e−02 | 4.11976814e−01 |
| 2.78946996e−01 | 5.65935671e−02 | 2.89758414e−01 | 2.95643091e−01 |
| 2.15002060e−01 | 3.74456584e−01 | 2.32879162e−01 | −7.70094693e−02 |
| −2.05309108e−01 | 1.37772590e−01 | −5.55325067e−04 | 3.69598687e−01 |
| 2.86320239e−01 | −1.14993766e−01 | 3.83963361e−02 | −2.62944132e−01 |
| 3.14202309e−01 | 2.89836615e−01 | 1.63977128e−03 | 1.36203514e−02 |
| 1.79577067e−01 | 3.92328799e−01 | 1.40496954e−01 | 1.12632580e−01 |
| 5.55862248e−01 | 2.12268367e−01 | −9.87882614e−02 | 1.73244283e−01 |
| 1.95624549e−02 | 1.11084737e−01 | 1.91741064e−01 | 6.22449256e−02 |
| −9.75239873e−02 | −4.99718189e−01 | 2.59296864e−01 | 2.11202562e−01 |
| −2.34233111e−01 | −4.67932870e−04 | 9.25613567e−02 | 5.53936422e−01 |
| 6.07707143e−01 | 1.34499505e−01 | 3.85140270e−01 | 2.92412966e−01 |
| 3.15245748e−01 | −2.47473851e−01 | 5.79936266e−01 | 1.88770652e−01 |
| 1.02988286e−02 | 1.60253420e−01 | 5.58343679e−02 | 6.82051256e−02 |
| −5.14447466e−02 | 1.18549608e−01 | 2.11601436e−01 | −3.57330471e−01 |
| 8.64711031e−02 | −3.96752924e−01 | 6.91544935e−02 | 9.35511738e−02 |
| 1.59008294e−01 | 1.49404760e−02 | 2.75040239e−01 | 3.99516851e−01 |
| 9.16870609e−02 | −1.63004369e−01 | 3.35365117e−01 | −3.99900675e−02 |
| 2.14654595e−01 | 3.52748781e−01 | 3.73365849e−01 | 2.29857951e−01 |
| 2.61469871e−01 | 1.65179297e−01 | 3.88430208e−01 | 5.20090938e−01 |
| −6.13031201e−02 | 2.96984911e−01 | −3.90070793e−03 | 4.18161720e−01 |
| −5.06325476e−02 | −6.29813597e−02 | 5.00726342e−01 | 1.06375150e−01 |
| 2.72352576e−01 | −2.06165195e−01 | 2.63125545e−01 | −3.93097326e−02 |
| 3.95684838e−01 | 2.62523979e−01 | 1.26659334e−01 | 6.07744932e−01 |
| 1.66647628e−01 | 5.59760690e−01 | 2.57373154e−01 | 1.91636398e−01 |
| 6.47988677e−01 | 3.83548856e−01 | 2.07592070e−01 | 1.28206179e−01 |
| 3.75946224e−01 | 5.15222475e−02 | 5.26878297e−01 | 8.56218413e−02] |
| [1.80950854e−02 | 4.27797884e−02 | 1.19649865e−01 | 1.81752503e−01 |
| 1.76844209e−01 | 1.30011022e−01 | 3.55428696e−01 | 5.82382195e−02 |
| −1.65643811e−01 | −2.72847831e−01 | −4.53205347e−01 | −2.05219179e−01 |
| −1.51333168e−01 | −8.15110747e−03 | −2.41808891e−01 | 1.73844114e−01 |
| 1.44949004e−01 | −3.48919004e−01 | 4.17457461e−01 | 1.20365791e−01 |
| −1.46288916e−01 | −2.92901725e−01 | −3.29244226e−01 | −1.42127097e−01 |
| −9.87015441e−02 | 4.03806530e−02 | −9.75651890e−02 | 1.69285268e−01 |
| −3.18107992e−01 | −3.36214676e−02 | 2.35925004e−01 | −6.84256330e−02 |
| 6.90464750e−02 | 4.71195847e−01 | −2.06740186e−01 | 1.80861980e−01 |
| 1.06299333e−01 | 1.48856744e−01 | 3.71193439e−01 | −1.82837352e−01 |
| 5.46519339e−01 | −6.14151768e−02 | −5.77279925e−02 | −3.74045931e−02 |
| 4.90672141e−02 | 6.91899419e−01 | 1.38729587e−01 | −2.13909090e−01 |
| −3.12205732e−01 | −6.54302165e−02 | −4.87590507e−02 | −2.81354487e−01 |
| 9.08859968e−02 | 4.25840616e−01 | 2.55712047e−02 | 3.04698437e−01 |
| −2.23424435e−01 | 2.05065072e−01 | 5.62380031e−01 | 1.48410186e−01 |
| −2.54256010e−01 | −5.04452959e−02 | 8.75581801e−01 | 1.51073143e−01 |
| 2.42981553e−01 | 1.87578529e−01 | −6.22754125e−03 | 6.13734603e−01 |
| −2.28605032e−01 | −1.41832829e−01 | −9.90402605e−03 | −4.06183861e−02 |
| −4.44659621e−01 | −1.67000815e−01 | 3.35632861e−02 | 2.29433417e−01 |
| −1.88158557e−01 | −7.93217346e−02 | 4.58944887e−01 | 2.60086685e−01 |
| −7.93920830e−02 | 1.11687347e−01 | −4.89314497e−02 | 7.99777284e−02 |
| −1.56839252e−01 | 3.03376883e−01 | −4.51572705e−03 | 6.19729161e−01 |
| −5.41712008e−02 | −4.62473594e−02 | −2.99802065e−01 | 1.37454018e−01 |
| 3.90794203e−02 | 2.68519014e−01 | −1.02116279e−01 | 1.23847034e−02 |
| −4.05738503e−01 | 3.47049117e−01 | 2.89967090e−01 | 1.67648733e−01 |
| −8.98481086e−02 | 2.03805953e−01 | 4.45486745e−03 | 5.98132730e−01 |
| 6.14735544e−01 | 4.80036080e−01 | −2.11922230e−01 | −2.01449811e−01 |
| 1.58619657e−01 | −1.71078995e−01 | −2.11559579e−01 | 1.86978683e−01 |
| 1.25333846e−01 | 1.64775312e−01 | 3.62409279e−02 | −2.36393809e−01 |
| −2.15402991e−02 | −4.67584990e−02 | −1.17065892e−01 | −2.30122089e−01 |
| 6.18871935e−01 | 5.21516204e−01 | 1.97826087e−01 | 6.84940070e−02 |
| 5.05441010e−01 | −1.73407182e−01 | −1.61438912e−01 | 1.70905143e−01 |
| −1.78682968e−01 | 3.88933361e−01 | 3.18326235e−01 | −4.15791720e−02 |
| 2.22019300e−01 | 2.71770388e−01 | −1.11543149e−01 | −3.37788105e−01 |
| −1.66360945e−01 | −1.20033905e−01 | −6.19432889e−02 | 1.08500920e−01 |
| 2.48790368e−01 | 2.20309254e−02 | 6.26964793e−01 | 2.09007058e−01 |
| −2.04415500e−01 | 2.86455303e−01 | 9.59887132e−02 | 1.93176687e−01 |
| 2.54756570e−01 | −2.51669493e−02 | 7.27772176e−01 | 6.54164404e−02 |
| 9.74864811e−02 | 3.46177280e−01 | −2.58883715e−01 | 7.72999883e−01 |
| −1.58803195e−01 | 2.12951034e−01 | 1.55007513e−01 | 2.71474034e−01 |
| −3.46370041e−01 | 8.01159501e−01 | 2.53088679e−02 | 2.20592141e−01 |
| −1.93995401e−01 | −3.14303674e−02 | 3.53597365e−02 | −4.86461014e−01 |
| 1.06582969e−01 | −7.17301592e−02 | −1.87885389e−01 | −3.27432871e−01 |
| −6.72582388e−02 | 2.94058025e−01 | 2.72157013e−01 | 1.02264211e−01 |
| 5.54690182e−01 | −1.57394543e−01 | 2.54049748e−01 | 2.69047230e−01 |
| −2.76017547e−01 | 3.17252874e−01 | −1.43895641e−01 | −1.69476435e−01 |
| −3.27089876e−02 | 1.85882896e−01 | 3.19394708e−01 | 6.94492981e−02 |
| 1.07272819e−01 | −1.54497743e−01 | 1.89441070e−01 | 3.72841805e−01 |
| 2.57125378e−01 | −4.28787768e−02 | 4.02214855e−01 | 3.70224178e−01 |
| 5.24002761e−02 | −1.51367202e−01 | 3.91881704e−01 | 2.68976897e−01 |
| 4.55925107e−01 | 6.91103518e−01 | 2.80441254e−01 | −1.58108070e−01 |
| −1.16327718e−01 | 2.45225430e−01 | −1.20213620e−01 | −2.88882643e−01 |
| −2.34204248e−01 | −9.14040133e−02 | −4.72270966e−01 | −4.74334449e−01 |

TABLE $W_h^1$-continued

| | | | |
|---|---|---|---|
| −3.42100173e−01 | 7.31954873e−02 | 3.24377529e−02 | 6.04534745e−01 |
| 1.63607776e−01 | 6.29926443e−01 | −2.47992143e−01 | 8.02149922e−02 |
| −3.14977169e−02 | 1.54207006e−01 | −6.52718961e−01 | 1.56429723e−01 |
| 1.31367758e−01 | 9.90094543e−02 | 5.57091460e−02 | −4.94105220e−02 |
| 1.00483157e−01 | 3.28888655e−01 | 1.73266649e−01 | −1.14158548e−01 |
| 6.27948165e−01 | −3.67196411e−01 | −5.69064021e−02 | 2.43254185e−01 |
| 1.44329667e−01 | −4.23501760e−01 | −2.36189604e−01 | 4.97261733e−01 |
| 2.24259138e−01 | −1.06400855e−01 | 1.30273476e−01 | 5.96157193e−01 |
| −2.31801614e−01 | −2.59695858e−01 | −1.41888201e−01 | −7.53294379e−02 |
| 4.24239933e−01 | −4.18341517e−01 | −4.21429992e−01 | 7.35428482e−02 |
| 4.52519596e−01 | 2.05311030e−01 | −1.99330643e−01 | −6.28161207e−02] |
| [4.76429433e−01 | −3.95832181e−01 | 5.21583676e−01 | 1.54290289e−01 |
| 3.73188078e−01 | 1.26710132e−01 | 3.87729943e−01 | 4.11582202e−01 |
| 3.74434829e−01 | 1.79425776e−01 | 1.80805773e−01 | −1.10487983e−01 |
| 2.17757717e−01 | 4.71239030e−01 | 1.77098215e−01 | 3.59403431e−01 |
| 2.57732142e−02 | 2.43001774e−01 | 3.95115882e−01 | 3.73278588e−01 |
| 1.60312578e−01 | −6.73271194e−02 | 4.37483072e−01 | 1.80735469e−01 |
| 5.31675160e−01 | 9.54286158e−01 | 1.95313349e−01 | 5.64550832e−02 |
| 1.74065888e−01 | 1.71184421e−01 | 1.46779463e−01 | −4.91558947e−03 |
| 3.98509830e−01 | −1.65126711e−01 | −1.88471340e−02 | 1.33589268e−01 |
| 1.69631317e−01 | 5.95040359e−02 | 4.16808516e−01 | 2.26607129e−01 |
| 3.20952088e−01 | 3.99326712e−01 | 2.62888044e−01 | 1.89503297e−01 |
| 1.22714916e−03 | 3.35227787e−01 | 3.56239080e−01 | 1.47536444e−02 |
| 1.42109975e−01 | 6.86705232e−01 | 4.27840620e−01 | 1.32935971e−01 |
| 2.64921784e−01 | 1.56533495e−01 | 4.33136523e−01 | −2.56322086e−01 |
| 1.92901090e−01 | 5.91412961e−01 | 2.72037357e−01 | 1.66239664e−01 |
| 2.04171166e−01 | 3.29233617e−01 | −4.41485569e−02 | 1.56555936e−01 |
| −3.11166853e−01 | 2.33616099e−01 | −9.88964513e−02 | 5.29660404e−01 |
| 4.59134579e−01 | 7.09123239e−02 | −1.74274351e−01 | −6.54286370e−02 |
| 6.32125199e−01 | 3.41713697e−01 | 1.95798486e−01 | 1.25750795e−01 |
| 3.94560307e−01 | 1.59243777e−01 | 8.45881999e−02 | −2.30183937e−02 |
| 1.92449540e−01 | 4.55644578e−01 | 6.36642635e−01 | 1.52030647e−01 |
| −2.08767653e−01 | −3.05380046e−01 | 2.54686140e−01 | −3.82032812e−01 |
| 5.20764709e−01 | −3.47470462e−01 | 3.58864576e−01 | 3.18299502e−01 |
| −1.83555707e−01 | 9.02488977e−02 | 5.97568631e−01 | 8.78489316e−02 |
| −7.18397200e−01 | 2.18403682e−01 | 6.85690120e−02 | −3.46912116e−01 |
| −1.65602922e−01 | 1.67938009e−01 | 2.99579650e−01 | 1.27191111e−01 |
| −7.77890831e−02 | 6.31308675e−01 | −1.52588531e−01 | 2.22719863e−01 |
| 2.06637204e−01 | 2.09005103e−01 | 3.17120194e−01 | −9.40296724e−02 |
| 4.64212179e−01 | −1.20819025e−01 | −1.77609082e−02 | 6.64574876e−02 |
| 5.43331578e−02 | −4.87524271e−02 | 4.93548959e−01 | 3.15909982e−01 |
| 5.04112579e−02 | 9.54358950e−02 | 1.31333172e−01 | −8.69551152e−02 |
| 7.86887184e−02 | 9.37997922e−02 | 8.57828975e−01 | 9.23396721e−02 |
| 2.57436365e−01 | −7.51112923e−02 | 3.91854286e−01 | 3.06816876e−01 |
| 3.15153837e−01 | 4.84350622e−01 | 3.99292171e−01 | 4.90313411e−01 |
| 3.54750454e−01 | −1.08788334e−01 | 4.09053326e−01 | 1.78038359e−01 |
| 2.60353118e−01 | 3.67106348e−01 | 3.29070538e−01 | 2.37758234e−01 |
| 3.22802722e−01 | 2.91669637e−01 | −3.90321046e−01 | 1.53593436e−01 |
| 5.43452837e−02 | −2.51006812e−01 | 2.06702933e−01 | 1.55486465e−01 |
| 7.77098536e−01 | 6.11185059e−02 | 1.68433964e−01 | 6.55287951e−02 |
| 3.06437105e−01 | 3.17365438e−01 | 4.07221407e−01 | 3.12881947e−01 |
| 5.23270309e−01 | 7.13300347e−01 | 1.76004991e−01 | 3.01952422e−01 |
| 5.47661960e−01 | −4.76752259e−02 | 4.19437200e−01 | 4.60223466e−01 |
| 1.61539048e−01 | −1.41728101e−01 | 3.53916049e−01 | 2.80955553e−01 |
| 2.65184343e−01 | 4.97157335e−01 | −1.76597625e−01 | 1.35639057e−01 |
| 2.77866960e−01 | 3.67572308e−01 | −6.24797791e−02 | 3.10291141e−01 |
| 2.08296150e−01 | 1.06775999e−00 | 2.22479314e−01 | 4.75460328e−02 |
| 4.09570873e−01 | −2.01304480e−01 | −1.89814786e−03 | 7.27368146e−03 |
| 1.83219194e−01 | 3.65639597e−01 | 3.69461656e−01 | 5.59832573e−01 |
| 5.14650226e−01 | 4.24707718e−02 | 7.44462162e−02 | 2.07347080e−01 |
| 2.54032135e−01 | 3.42801899e−01 | −7.63180330e−02 | 6.59233212e−01 |
| 1.98013246e−01 | 7.86048114e−01 | −4.20190781e−01 | 2.99561262e−02 |
| 7.86376834e−01 | −3.71607058e−02 | −1.62398666e−01 | 7.41728842e−01 |
| 6.11030459e−01 | 5.66173792e−01 | 4.06375051e−01 | 2.07597971e−01 |
| 3.66324246e−01 | 4.12059993e−01 | 6.10136271e−01 | 2.45409712e−01 |
| 6.81653261e−01 | 1.93951353e−01 | 3.85258138e−01 | 3.65778238e−01 |
| 1.62432730e−01 | 1.16382413e−01 | −1.35664627e−01 | −6.29880279e−02 |
| 3.84999037e−01 | 3.15219045e−01 | 6.74990475e−01 | 1.99981540e−01 |
| 3.27968717e−01 | 3.18154037e−01 | 3.63407314e−01 | 2.30964735e−01 |
| 1.37870535e−01 | −3.01228277e−02 | 5.03383219e−01 | 4.35096651e−01 |
| 4.43161845e−01 | 6.32284284e−01 | 5.52869916e−01 | 1.78098843e−01 |
| 5.86836815e−01 | 3.41961145e−01 | 2.59519309e−01 | 6.37174726e−01 |
| 2.13404283e−01 | 5.43342710e−01 | 1.89441457e−01 | 8.58584940e−02 |
| 1.99655116e−01 | 5.55377185e−01 | 4.08801496e−01 | 3.39483351e−01 |
| −2.13485092e−01 | 7.07992911e−01 | 6.32608235e−01 | 3.62800807e−01] |
| [−1.05800614e−01 | −5.12699932e−02 | 3.68551701e−01 | 4.17658120e−01 |
| 3.07246953e−01 | 6.91565454e−01 | 6.66492954e−02 | 2.38484472e−01 |
| 8.18987191e−01 | −2.51280695e−01 | 8.69792104e−01 | 1.17457978e−01 |
| 6.05288595e−02 | 8.37885216e−02 | 2.38922164e−01 | −9.88901779e−02 |
| 2.95835555e−01 | −4.27816629e−01 | 2.12089479e−01 | −1.68072172e−02 |

TABLE $W_h^1$-continued

| | | | |
|---|---|---|---|
| −3.85507606e−02 | 6.97626383e−04 | 4.12280470e−01 | 6.39069319e−01 |
| 2.16235131e−01 | 7.15860963e−01 | 2.20304474e−01 | −2.35722251e−02 |
| −1.33338124e−01 | 3.52690458e−01 | 7.99934268e−01 | −2.12953359e−01 |
| 3.56542096e−01 | 4.59509678e−01 | 4.75710958e−01 | 1.17901891e−01 |
| −1.23246975e−01 | −5.50309531e−02 | 1.83635101e−01 | 2.23031476e−01 |
| 8.35758969e−02 | 1.46342203e−01 | −6.16189539e−01 | 3.15247983e−01 |
| 8.57776701e−01 | 1.50246546e−01 | 4.29724097e−01 | 3.79846990e−01 |
| 3.72695446e−01 | 8.87185410e−02 | 3.47693324e−01 | 3.45518500e−01 |
| −7.80168548e−02 | −1.47644252e−01 | 1.95850670e−01 | −2.71508723e−01 |
| 3.15835416e−01 | 5.60399890e−01 | −8.32841471e−02 | 2.92214632e−01 |
| 6.80371702e−01 | 7.77272806e−02 | 2.88240314e−01 | 1.33853287e−01 |
| −3.09387296e−01 | 1.75443083e−01 | −2.31558103e−02 | 5.85506022e−01 |
| 5.20374954e−01 | 4.28814441e−02 | 2.92924233e−03 | 1.78684726e−01 |
| 4.53517914e−01 | −7.36407861e−02 | 4.03179020e−01 | 2.25916162e−01 |
| 3.01563531e−01 | −1.52780026e−01 | −1.50172794e−02 | −2.12862775e−01 |
| 5.18820822e−01 | 4.33243692e−01 | 1.11495167e−01 | 2.62036234e−01 |
| 1.10466309e−01 | 1.10764556e−01 | −9.09415931e−02 | 3.80815208e−01 |
| 7.40182400e−01 | 2.58867919e−01 | 5.86050928e−01 | 1.77268401e−01 |
| −4.90354784e−02 | −1.48485109e−01 | 3.76238614e−01 | −6.69119656e−02 |
| 2.71964133e−01 | −5.25333546e−03 | 1.34770185e−01 | −2.25216486e−02 |
| 7.24115074e−02 | 4.10136193e−01 | 3.24437439e−01 | 1.53013706e−01 |
| −5.55450916e−02 | 5.44454120e−02 | 5.65661907e−01 | 2.91370958e−01 |
| 4.85349894e−02 | 2.20040400e−02 | 7.17220604e−02 | −1.17505245e−01 |
| 1.98326390e−02 | −9.87789631e−02 | −1.00627519e−01 | 4.26580250e−01 |
| 1.00970231e−01 | 6.79639757e−02 | 6.23054087e−01 | 3.23107019e−02 |
| 5.55690408e−01 | −1.52371034e−01 | −1.44114271e−01 | 2.45630100e−01 |
| 1.97407112e−01 | −1.27560869e−01 | −3.58738378e−02 | −1.54414833e−01 |
| 3.07690829e−01 | −7.56403357e−02 | 2.53295571e−01 | 4.01307493e−01 |
| 4.90037829e−01 | 7.33490586e−02 | −9.33942795e−02 | 3.91381294e−01 |
| 4.40098643e−01 | 1.82684138e−01 | 2.52296571e−02 | −2.03939348e−01 |
| 3.11753899e−01 | −5.38656004e−02 | 7.39361227e−01 | 1.55432113e−02 |
| 2.82709748e−01 | 3.55865844e−02 | −1.71725914e−01 | −1.60159290e−01 |
| −1.39971599e−01 | −1.25426188e−01 | −8.71313587e−02 | 2.08098456e−01 |
| 6.90690279e−01 | −4.36040806e−03 | 9.35334712e−02 | −2.72770319e−02 |
| 1.36323020e−01 | 2.71919310e−01 | 1.62566841e−01 | 1.93876430e−01 |
| 4.92277622e−01 | 3.34014326e−01 | −3.58296521e−02 | 5.63910127e−01 |
| 3.80170047e−01 | 1.58957109e−01 | −6.95235059e−02 | 2.74637759e−01 |
| 2.15851113e−01 | 3.62958044e−01 | 2.66754299e−01 | 4.72413450e−01 |
| −1.16250604e−01 | 4.18873608e−01 | −2.72658080e−01 | 2.71334499e−01 |
| −1.85828805e−02 | 5.78471124e−01 | 4.35024768e−01 | 7.18076229e−02 |
| 2.29171604e−01 | 2.00454086e−01 | 5.13971448e−01 | −1.00712188e−01 |
| 4.39083755e−01 | 2.44608298e−02 | −1.18351437e−01 | 2.89941996e−01 |
| 1.71033442e−01 | −8.60843807e−03 | 4.62498933e−01 | 1.88573018e−01 |
| 2.19389826e−01 | 1.06797427e−01 | 1.55940980e−01 | 3.46738070e−01 |
| −8.41813460e−02 | −6.13635145e−02 | −2.88109422e−01 | 1.37214616e−01 |
| 3.79781872e−01 | 3.59297007e−01 | 1.71864063e−01 | −2.13395268e−01 |
| −1.95239276e−01 | 2.78043985e−01 | −6.00055046e−02 | −6.07073195e−02 |
| 3.68602812e−01 | 2.17025518e−01 | 6.81584001e−01 | 1.05399959e−01 |
| 1.38173014e−01 | 3.47300470e−01 | 5.79077899e−02 | 1.42334066e−02 |
| 3.80082071e−01 | −7.09252656e−02 | 8.46003667e−02 | 1.82237789e−01 |
| 5.72542995e−02 | 5.28836608e−01 | −2.60120243e−01 | 1.08353995e−01 |
| 7.73272887e−02 | 1.64425552e−01 | 3.94618250e−02 | 8.07075575e−02 |
| −6.56576678e−02 | −1.00593075e−01 | 1.45386219e−01 | 3.20566744e−01 |
| 3.63105118e−01 | −5.17522633e−02 | 2.29231119e−01 | 3.38258177e−01 |
| 1.18869595e−01 | 7.57427737e−02 | 8.12984765e−01 | 1.69791013e−01 |
| 5.53274214e−01 | 4.32539247e−02 | 3.65162879e−01 | 4.97525632e−01 |
| −5.22900335e−02 | 5.24321258e−01 | 1.17169037e−01 | 1.56774834e−01 |
| 8.05292502e−02 | 4.12524492e−01 | 3.77256572e−02 | 3.01311225e−01 |
| 8.36694911e−02 | 4.37430799e−01 | 3.57834429e−01 | 1.83807984e−01] |
| [1.19492471e−01 | 1.26642555e−01 | 5.09520173e−01 | 5.79546727e−02 |
| 6.27978325e−01 | 4.88259226e−01 | 1.31015897e−01 | 2.22080097e−01 |
| 8.80644917e−02 | 2.63455778e−01 | 1.36922121e−01 | 3.48609596e−01 |
| 1.30275816e−01 | 1.14418522e−01 | −3.36981565e−01 | −2.24465132e−01 |
| 3.39572966e−01 | −1.75022513e−01 | −2.10827947e−01 | 1.52283132e−01 |
| 4.53469455e−01 | 1.64757490e−01 | 4.98277247e−01 | 3.73867035e−01 |
| 1.75606430e−01 | 2.43547484e−01 | 4.74289834e−01 | 2.24286720e−01 |
| 3.00585866e−01 | 1.06243217e−00 | 5.05018294e−01 | 2.64610171e−01 |
| 9.23341453e−01 | 4.22469884e−01 | −6.21095151e−02 | 2.45367423e−01 |
| 2.39419162e−01 | 3.50826919e−01 | 7.12764338e−02 | 3.97279799e−01 |
| −9.92426798e−02 | 8.94663110e−02 | 4.42213178e−01 | 1.81723163e−01 |
| 4.72917050e−01 | −1.76112920e−01 | 4.46918815e−01 | 1.09506048e−01 |
| 2.92596638e−01 | −5.88503014e−03 | 5.14240503e−01 | 3.90125304e−01 |
| −2.03537360e−01 | −1.73394736e−02 | 2.42169976e−01 | 5.42088389e−01 |
| −9.50733498e−02 | −2.30798364e−01 | 7.70296872e−01 | −2.63711642e−02 |
| 6.54941350e−01 | 8.89542878e−01 | −2.67449349e−01 | 1.32650822e−01 |
| 3.01278442e−01 | 7.95119226e−01 | 1.77408412e−01 | −4.67427447e−02 |
| 1.28929406e−01 | 4.15967219e−02 | 3.72264504e−01 | 2.36447603e−01 |
| 5.24938047e−01 | 3.02093387e−01 | 4.27618802e−01 | 2.94437438e−01 |
| 4.85939533e−01 | 4.85539585e−01 | 1.57941431e−01 | 3.98304254e−01 |
| 7.32325912e−01 | 4.35857117e−01 | 4.63735223e−01 | 2.29834393e−01 |

TABLE $W_h^1$-continued

| | | | |
|---|---|---|---|
| 3.24360728e−01 | 2.42893592e−01 | 5.00744581e−01 | −6.45000339e−02 |
| 2.11429924e−01 | 1.78347945e−01 | 4.14691716e−01 | −2.08352357e−01 |
| 3.93929899e−01 | 3.58949788e−02 | 4.57399786e−01 | 1.69362783e−01 |
| 4.50081259e−01 | −3.99815023e−01 | −2.60547072e−01 | 3.61547559e−01 |
| 6.33824527e−01 | 6.40875220e−01 | 5.24716973e−01 | −4.48302925e−02 |
| 4.48541343e−01 | −4.28213887e−02 | 8.90404359e−03 | 2.34009922e−01 |
| 3.72783631e−01 | 9.91074920e−01 | 7.41398573e−01 | 2.76090354e−02 |
| 3.05897564e−01 | 2.33917505e−01 | 2.24781737e−01 | 3.46545637e−01 |
| 2.88341716e−02 | 4.82331693e−01 | 1.64424136e−01 | 1.07682139e−01 |
| 3.62471253e−01 | 4.46586758e−01 | 7.01198101e−01 | 5.71615696e−01 |
| 4.07655120e−01 | 1.81528971e−01 | 6.73984647e−01 | 2.54143119e−01 |
| 5.15764058e−01 | 9.60974321e−02 | 9.10181925e−02 | 2.80456394e−01 |
| 1.39431700e−01 | 2.41785143e−02 | 2.10759357e−01 | 4.08042192e−01 |
| 3.59064311e−01 | 1.94881320e−01 | 6.23769462e−01 | 4.88343477e−01 |
| 8.14642489e−01 | 5.59322417e−01 | 3.35653186e−01 | 1.93115935e−01 |
| 7.10520446e−02 | −1.04908332e−01 | 1.26759544e−01 | 1.19517289e−01 |
| 1.25598967e−01 | 3.29034269e−01 | 1.30617931e−01 | 2.41849616e−01 |
| 5.24160504e−01 | 1.43545240e−01 | 1.76385760e−01 | 6.16871238e−01 |
| 1.84000254e−01 | −1.36258841e−01 | −1.66009218e−02 | 1.05378322e−01 |
| 1.86229154e−01 | −1.83153540e−01 | 1.48550481e−01 | 5.00746131e−01 |
| 1.56894550e−01 | −2.66144853e−02 | 2.82471359e−01 | 4.84082609e−01 |
| 2.88380891e−01 | 4.00164187e−01 | 2.49122381e−01 | −3.16526353e−01 |
| 2.49805093e−01 | 2.14149384e−03 | −1.50874496e−01 | −1.45653054e−01 |
| 1.07134558e−01 | 2.38306150e−01 | 3.44485253e−01 | −1.16761871e−01 |
| 1.01051293e−01 | 2.12820515e−01 | 3.99798900e−01 | 2.17758447e−01 |
| 1.97799504e−01 | −1.79794744e−01 | 2.07693323e−01 | −1.11422829e−01 |
| 1.98078305e−01 | 1.50889546e−01 | 6.42333984e−01 | 3.72306138e−01 |
| 3.97747040e−01 | 3.55727941e−01 | 1.57934099e−01 | 1.96019635e−01 |
| 1.61611795e−01 | 4.46617037e−01 | 3.30393642e−01 | −3.04114431e−01 |
| −2.31118158e−01 | −2.17449039e−01 | 5.04729748e−02 | 6.72065854e−01 |
| −3.07015419e−01 | 3.78286183e−01 | 2.92690545e−01 | −7.78220668e−02 |
| −3.17564495e−02 | −3.97802651e−01 | 7.00721085e−01 | 5.59759438e−01 |
| 5.66448927e−01 | −2.11075872e−01 | −3.12814116e−01 | 4.62353826e−01 |
| 4.57556814e−01 | 2.70099640e−01 | 4.56544161e−01 | −1.01834454e−01 |
| 4.06110920e−02 | 2.77473748e−01 | 4.83037055e−01 | 2.95749724e−01 |
| 9.61958319e−02 | 1.85456574e−01 | 5.85026443e−01 | 1.29845589e−01 |
| 5.22792041e−01 | 2.75150299e−01 | 3.49143893e−01 | 3.08562726e−01 |
| 2.47105747e−01 | −3.05424780e−01 | 5.77768683e−01 | 3.29901546e−01 |
| −4.12550792e−02 | 2.35001490e−01 | 2.82633275e−01 | −1.99574288e−02 |
| 2.80238807e−01 | 6.41199127e−02 | 3.15995840e−03 | 1.52553722e−01 |
| 6.12351477e−01 | 4.52025495e−02 | 2.98135102e−01 | 3.60080183e−01 |
| 2.63632685e−01 | 8.22029769e−01 | 5.90005159e−01 | 5.41432381e−01 |
| 6.10141307e−02 | 5.12749135e−01 | 3.89392704e−01 | 4.41791087e−01] |
| [−1.60831228e−01 | 3.40402693e−01 | 8.36377561e−01 | 1.77365586e−01 |
| 1.25399160e−00 | 4.66218472e−01 | 9.72428262e−01 | 7.85368204e−01 |
| 9.82173562e−01 | 2.14364752e−01 | 7.64999986e−01 | 3.78893316e−01 |
| 8.17763090e−01 | 5.67479432e−01 | 3.32215101e−01 | 5.11956930e−01 |
| 1.23269939e−00 | −1.47899359e−01 | 4.53247279e−02 | 5.01362026e−01 |
| 9.70108390e−01 | 4.06267464e−01 | 4.52269882e−01 | 4.62924510e−01 |
| 1.21576536e−00 | 5.88098288e−01 | 2.50607133e−01 | 6.30994201e−01 |
| 2.17840791e−01 | 7.96884477e−01 | 8.01072299e−01 | 2.33074233e−01 |
| −1.87289909e−01 | 4.25330967e−01 | 6.76719666e−01 | 5.21005750e−01 |
| 3.99003655e−01 | 3.79798174e−01 | −7.55879357e−02 | 9.20373499e−01 |
| 6.46916449e−01 | 9.19919729e−01 | 4.76091832e−01 | 5.46566308e−01 |
| 6.35463774e−01 | 1.50442183e−01 | 2.30491281e−01 | 1.26050627e−00 |
| −1.96899995e−01 | 3.48250955e−01 | 7.84026325e−01 | 7.03649342e−01 |
| 2.74593771e−01 | 8.27984691e−01 | 1.50591210e−01 | 2.51518190e−01 |
| 2.72462130e−01 | 2.49056622e−01 | 8.25671792e−01 | 8.74279737e−02 |
| 1.47380650e−01 | 6.51037276e−01 | 7.80430287e−02 | 8.90000165e−01 |
| 1.70992166e−01 | 5.41459024e−01 | 8.21833193e−01 | 6.39159203e−01 |
| 2.00089484e−01 | −9.22345221e−02 | 7.68648684e−01 | 7.06415176e−02 |
| 6.96836174e−01 | 9.12428141e−01 | 2.13590786e−01 | −2.02291682e−01 |
| 8.97742331e−01 | 9.01010931e−01 | 7.11884022e−01 | 2.67847657e−01 |
| 5.26010633e−01 | 4.89042401e−01 | −2.87428409e−01 | 4.45860893e−01 |
| −2.52738297e−01 | −1.48348873e−02 | −3.14378858e−01 | 7.45753646e−01 |
| 4.18668807e−01 | −1.30445325e−00 | 2.15867087e−01 | −5.36373779e−02 |
| 1.24875510e−01 | 8.40279341e−01 | 7.19594777e−01 | 1.11665094e−00 |
| 5.34169734e−01 | 2.09486276e−01 | 2.76566714e−01 | 6.42672062e−01 |
| 1.13911545e−00 | 8.10473442e−01 | 6.10495687e−01 | 7.64503926e−02 |
| 4.22081769e−01 | 6.64626539e−01 | 3.38736661e−02 | 1.32950377e−00 |
| 6.08516991e−01 | 1.14862669e−00 | 6.03848159e−01 | 9.83452201e−01 |
| 1.29487705e−00 | 7.04851925e−01 | 1.44875824e−00 | 1.48673728e−01 |
| 7.72207677e−01 | 3.12727720e−01 | 1.03774166e−00 | 2.99054772e−01 |
| 4.69678432e−01 | 4.64325875e−01 | −2.69266784e−01 | 6.70448363e−01 |
| 2.59454340e−01 | 1.04007828e−00 | 6.33548677e−01 | 5.93711436e−01 |
| 6.54977798e−01 | 9.24297646e−02 | −1.16703309e−01 | 1.21607494e−00 |
| 5.89820087e−01 | 6.43366456e−01 | 8.69632542e−01 | −1.66509211e−01 |
| 3.84838015e−01 | 2.32159093e−01 | 7.39551127e−01 | 4.85028535e−01 |
| 3.44900712e−02 | 7.65138626e−01 | 3.80074531e−02 | 5.31912625e−01 |
| 1.58282375e−00 | 2.32511356e−01 | 6.93346485e−02 | 8.37694168e−01 |

TABLE $W_h^1$-continued

| | | | |
|---|---|---|---|
| 9.68226731e−01 | 5.19716918e−01 | 8.59677434e−01 | 2.08456904e−01 |
| 3.80433649e−01 | 1.02356887e−00 | 3.31869721e−01 | 8.05859685e−01 |
| −3.25552404e−01 | −2.40830667e−02 | 1.94723174e−01 | 7.66784132e−01 |
| 3.26601446e−01 | 8.53629589e−01 | 5.28594315e−01 | 8.36415648e−01 |
| −1.13345850e−02 | 4.25782263e−01 | 2.72732109e−01 | 6.98983788e−01 |
| 3.22911918e−01 | −7.56267667e−01 | −7.07429290e−01 | 1.10468364e−00 |
| 8.22338223e−01 | 5.27554929e−01 | 2.89363652e−01 | −1.40524134e−02 |
| 3.40180784e−01 | 3.90929192e−01 | 2.76025087e−01 | 3.21512520e−01 |
| 6.72172010e−02 | 3.01165372e−01 | 3.70217830e−01 | 3.72316420e−01 |
| 1.23248255e−00 | 1.62934855e−01 | −1.07374942e−00 | 7.32405961e−01 |
| 5.49328744e−01 | 1.62012339e−00 | 1.81964755e−01 | 2.86750376e−01 |
| 6.61348045e−01 | 1.25934803e−00 | 2.77412206e−01 | 9.09673989e−01 |
| 8.50673378e−01 | 6.02396786e−01 | 9.30462897e−01 | 3.58400851e−01 |
| 9.30060506e−01 | 4.33194488e−01 | 5.98293245e−01 | −1.39379084e−01 |
| 2.33774871e−01 | 1.08396840e−00 | 8.22475135e−01 | 1.35565907e−01 |
| 6.53783023e−01 | −4.31248695e−02 | 3.77837658e−01 | 6.24572635e−01 |
| 8.41141820e−01 | 7.84764588e−01 | 4.78020102e−01 | 1.34508252e−00 |
| 8.63735825e−02 | 8.23972285e−01 | 4.68614578e−01 | 2.34056503e−01 |
| 2.40609691e−01 | 6.80350363e−01 | 5.29160619e−01 | 5.89349210e−01 |
| 6.07507348e−01 | 1.09929955e−00 | 3.43811139e−02 | 5.02911270e−01 |
| 1.40515912e−00 | 8.51095855e−01 | 4.04589504e−01 | 8.61537397e−01 |
| 9.33532476e−01 | 3.63192827e−01 | 3.72614622e−01 | 8.48466635e−01 |
| 7.98842371e−01 | 5.45101881e−01 | 1.03073478e−01 | 6.16967082e−01 |
| 4.47914958e−01 | 7.73019433e−01 | 3.55805397e−01 | 5.36096878e−02 |
| 7.08307445e−01 | 1.02322376e−00 | 6.85979784e−01 | 7.00571299e−01 |
| 8.83260250e−01 | 2.33350709e−01 | 5.88247836e−01 | 2.50767708e−01 |
| 6.33471429e−01 | 1.31038833e−00 | 4.50755864e−01 | 7.86127090e−01] |
| [3.79554361e−01 | 3.94126952e−01 | 2.20847279e−01 | 4.50402163e−02 |
| 3.40761364e−01 | 1.36417180e−01 | 4.69046295e−01 | −1.70241430e−01 |
| 3.91601741e−01 | −9.11697522e−02 | 1.76231787e−01 | 4.85503584e−01 |
| 2.18921632e−01 | 2.00481892e−01 | 3.52144122e−01 | 2.27165937e−01 |
| 3.47950161e−01 | 2.73906469e−01 | 1.17883973e−01 | 2.16190666e−01 |
| 3.09652865e−01 | 5.30160293e−02 | 4.04274128e−02 | 1.60896316e−01 |
| 1.37246149e−02 | 9.09615010e−02 | 2.85842866e−01 | 2.86133975e−01 |
| 2.81062663e−01 | 5.21398425e−01 | 2.10020185e−01 | 2.47443467e−01 |
| 1.86148182e−01 | 1.28486410e−01 | 1.88952580e−01 | 1.47938803e−01 |
| 2.21960589e−01 | 5.02582192e−02 | 4.75604013e−02 | 3.97354603e−01 |
| 2.03643054e−01 | 3.45523298e−01 | −2.37190817e−02 | 2.59701759e−01 |
| 3.05549890e−01 | 5.83234847e−01 | 3.45938563e−01 | 4.98394281e−01 |
| 1.78279564e−01 | 9.85238999e−02 | 2.56325603e−01 | 4.74899054e−01 |
| 1.32949129e−01 | 3.04188341e−01 | 9.43754762e−02 | −3.93243320e−02 |
| 6.55145347e−01 | 1.11448161e−01 | 1.23229155e−01 | 2.59132266e−01 |
| −3.61380398e−01 | 1.04365788e−01 | 3.43843609e−01 | 5.53855300e−01 |
| 2.84393370e−01 | −3.30758929e−01 | 4.22239840e−01 | 5.33014834e−01 |
| 1.58202931e−01 | 3.74028087e−01 | 4.57528204e−01 | 2.87133157e−01 |
| 8.96079093e−02 | −1.21639967e−01 | −9.84440520e−02 | 6.83762059e−02 |
| 1.77785590e−01 | −3.32969264e−03 | 2.07223251e−01 | 4.04580384e−01 |
| 9.94927622e−03 | 3.89279038e−01 | 9.96294618e−02 | 1.33235797e−01 |
| 4.69054542e−02 | 4.07228135e−02 | 9.16565061e−02 | 4.31656688e−02 |
| 1.86162189e−01 | 1.54585063e−01 | 3.00855517e−01 | 1.19433977e−01 |
| 7.55500674e−01 | 8.72858167e−02 | −3.31329294e−02 | 5.91803730e−01 |
| 3.05227011e−01 | 2.70483136e−01 | 1.00137115e−01 | 1.61761835e−01 |
| 6.19173795e−02 | 2.90265858e−01 | 1.30360886e−01 | 5.85702136e−02 |
| 2.28337318e−01 | 3.43107671e−01 | 1.95546687e−01 | 8.73829424e−03 |
| 5.20739734e−01 | 3.98628384e−01 | 2.73608923e−01 | 1.96582854e−01 |
| 1.89685270e−01 | 4.00754035e−01 | 5.01042783e−01 | 1.99485466e−01 |
| 5.03211319e−01 | −3.47661078e−01 | 4.42580041e−03 | 4.95173305e−01 |
| −2.46481244e−02 | 1.29403502e−01 | 3.92194748e−01 | 3.11436474e−01 |
| 2.32085615e−01 | 1.56696275e−01 | 2.71593988e−01 | 4.04281944e−01 |
| 2.27485791e−01 | 1.08353741e−01 | −8.82542692e−03 | 2.35022694e−01 |
| 2.93368667e−01 | 3.34826149e−02 | 6.19075187e−02 | 9.56283137e−02 |
| 2.64081478e−01 | 1.61325559e−01 | 1.66802227e−01 | 2.78182566e−01 |
| 2.56876320e−01 | 1.10798560e−01 | 1.87383220e−01 | −2.20536619e−01 |
| 1.96771666e−01 | 3.10372710e−01 | 3.26269865e−01 | −1.44242331e−01 |
| 1.00133181e−01 | 6.50042653e−01 | 2.31175989e−01 | −1.35074675e−01 |
| −6.08582050e−02 | 2.18767077e−01 | −1.06288068e−01 | −3.02323818e−01 |
| 8.94752517e−01 | 2.78390616e−01 | −1.31444320e−01 | 7.26253748e−01 |
| 3.60642850e−01 | 3.19946468e−01 | 2.53223896e−01 | −1.30036861e−01 |
| −2.36609414e−01 | 1.70825064e−01 | 2.02618584e−01 | 2.12159961e−01 |
| 3.31344664e−01 | 1.86207637e−01 | 3.11323971e−01 | 3.22633207e−01 |
| 6.02849424e−01 | 6.45415708e−02 | 2.94636309e−01 | 2.69894928e−01 |
| 1.61507398e−01 | −1.34016082e−01 | 2.30556294e−01 | 2.46768743e−01 |
| −2.65757322e−01 | 3.01468605e−03 | 3.52840610e−02 | 1.94132790e−01 |
| 3.75026256e−01 | −5.05988523e−02 | 1.86207592e−01 | −1.77603632e−01 |
| −1.05554081e−01 | 3.00081670e−01 | 3.67149085e−01 | 1.42247349e−01 |
| 1.07214130e−01 | 3.87753159e−01 | 3.70167673e−01 | 1.37999594e−01 |
| 5.34552395e−01 | 1.29482061e−01 | 4.83737171e−01 | 3.85392100e−01 |
| 2.18496144e−01 | −1.90906510e−01 | 1.30560637e−01 | 4.41307396e−01 |
| 4.11928505e−01 | 7.91050613e−01 | −1.91331804e−02 | 1.68978915e−01 |
| 2.10878268e−01 | −1.79527774e−01 | 3.74185205e−01 | −6.45132270e−03 |

TABLE $W_h^1$-continued

| | | | |
|---|---|---|---|
| 3.10708642e−01 | 1.25598505e−01 | 9.88661498e−02 | 3.32885683e−01 |
| 9.22605675e−03 | 6.08727038e−02 | 7.36670792e−02 | 1.09556004e−01 |
| 4.71493781e−01 | −1.56667568e−02 | 2.07024217e−01 | 1.77354723e−01 |
| 2.62018144e−01 | 1.02795959e−01 | −4.53154072e−02 | 1.52111128e−01 |
| 1.19493701e−01 | 1.17932066e−01 | 4.79405046e−01 | 2.66890049e−01 |
| 2.17729777e−01 | −3.77305120e−01 | 3.90044659e−01 | −7.09612900e−03 |
| −1.23685829e−01 | −2.75137778e−02 | 1.03493340e−01 | 3.04736286e−01 |
| 2.90135324e−01 | 2.53372848e−01 | 5.16340248e−01 | 1.81652382e−01 |
| 1.63460910e−01 | −2.28207394e−01 | 8.43513757e−02 | −2.19167635e−01 |
| 3.06268096e−01 | 2.09191054e−01 | −2.00746849e−01 | 3.08822453e−01 |
| 1.00421913e−01 | 1.45239159e−01 | 6.16993234e−02 | 5.62457561e−01] |
| [−1.10178538e−01 | 4.25363988e−02 | −6.75490648e−02 | −1.25883922e−01 |
| 6.90560192e−02 | 1.26548586e−02 | 4.92494814e−02 | 2.19556224e−02 |
| 2.33284101e−01 | −1.96520627e−01 | −1.69607118e−01 | −1.06033355e−01 |
| −1.03843912e−01 | 9.63789672e−02 | −4.68334965e−02 | 1.90428376e−01 |
| 1.92293093e−01 | 2.51321942e−01 | 9.80741694e−04 | 2.39938095e−01 |
| −4.78827178e−01 | −2.69791543e−01 | −3.23940843e−01 | −5.35122938e−02 |
| 1.54196173e−01 | 6.73918128e−02 | −1.43302500e−01 | 5.63067436e−01 |
| −2.20060691e−01 | −2.02458724e−01 | −3.56149554e−01 | −1.23943999e−01 |
| −1.89707175e−01 | 4.17305350e−01 | 1.78051010e−01 | 1.39418766e−01 |
| 4.53183830e−01 | −2.17371121e−01 | 2.06989288e−01 | 1.51999041e−01 |
| 2.45674938e−01 | 1.71192005e−01 | 5.24023622e−02 | 7.71423504e−02 |
| −1.35960337e−02 | 5.64717948e−01 | −7.59704474e−02 | 8.10984448e−02 |
| 3.31849128e−01 | 1.44979268e−01 | 1.15372464e−01 | −2.89011687e−01 |
| 1.11888133e−01 | 5.63178360e−01 | 1.47486059e−02 | −6.91970587e−02 |
| 5.24872988e−02 | 3.32748324e−01 | 5.33409826e−02 | −1.36606455e−01 |
| −2.23227148e−03 | 2.21872792e−01 | 7.84154892e−01 | 1.12874262e−01 |
| 2.87073702e−01 | −2.39388645e−01 | −5.84809333e−02 | 3.60221744e−01 |
| −1.29812628e−01 | 7.72423670e−02 | 1.12419851e−01 | −1.27347156e−01 |
| −5.45193017e−01 | −2.26692066e−01 | 2.63516068e−01 | −1.38611779e−01 |
| 3.73065233e−01 | −1.32719815e−01 | 3.95408213e−01 | 6.55321479e−02 |
| −2.30212167e−01 | 2.58735120e−01 | −1.69347003e−01 | −1.21203169e−01 |
| −2.87198201e−02 | 1.31799251e−01 | −2.43223310e−01 | 6.21670127e−01 |
| 3.42001736e−01 | −6.08743690e−02 | −2.35429645e−01 | 2.84773469e−01 |
| 2.06592098e−01 | 4.11128312e−01 | −9.91733819e−02 | 1.84404224e−01 |
| −5.96125782e−01 | 3.12623143e−01 | 1.23782307e−01 | 1.99947953e−01 |
| 7.46881813e−02 | −9.43387747e−02 | −1.57470182e−01 | 7.64518738e−01 |
| 6.27721623e−02 | −3.45584303e−02 | 8.63737911e−02 | −4.76999134e−02 |
| −7.29845315e−02 | 9.02562961e−02 | 2.10930407e−01 | 1.81604415e−01 |
| 2.70570040e−01 | 2.94624239e−01 | 1.95424575e−02 | −1.52839929e−01 |
| 1.17368117e−01 | 7.94525743e−02 | 3.11732620e−01 | −2.35094309e−01 |
| 1.53628096e−01 | 4.46496636e−01 | 1.88676417e−01 | −2.41479710e−01 |
| 3.09892744e−01 | 2.06013739e−01 | −4.41261008e−02 | −4.83215228e−02 |
| −1.68381874e−02 | 2.92313874e−01 | 1.33549467e−01 | 3.28027278e−01 |
| −1.26765728e−01 | 5.07004499e−01 | −1.72806606e−01 | −4.77667414e−02 |
| −4.39256638e−01 | 2.48245463e−01 | −1.73439234e−01 | 1.58763170e−01 |
| 5.33642694e−02 | 2.25626469e−01 | 2.69725382e−01 | −1.30429909e−01 |
| −7.03138337e−02 | 1.19388409e−01 | −1.12329513e−01 | −1.38728216e−01 |
| 1.05451502e−01 | −1.07879169e−01 | 9.85464156e−01 | −4.72423658e−02 |
| −1.32224962e−01 | 9.52682853e−01 | 2.05001190e−01 | 1.03805184e−00 |
| 2.96681345e−01 | 4.30970222e−01 | 2.80543000e−01 | −1.64004378e−01 |
| −2.92878225e−02 | 8.47582102e−01 | 2.49083005e−02 | −2.26252954e−02 |
| 1.28042534e−01 | −9.02463794e−02 | 3.86280846e−03 | −2.87847996e−01 |
| −4.41003829e−01 | 2.24610642e−01 | −3.25388573e−02 | −1.02338731e−01 |
| 1.70825422e−01 | 3.07792015e−02 | 5.48011541e−01 | 1.52578667e−01 |
| 4.35806096e−01 | −3.54287148e−01 | 5.72055221e−01 | 2.00959772e−01 |
| −3.25647146e−01 | 2.62341917e−01 | 2.01014668e−01 | 5.35588386e−03 |
| −1.84478596e−01 | −1.47094615e−01 | 3.50975901e−01 | 1.91370040e−01 |
| 1.51316494e−01 | −6.74433336e−02 | 1.98346123e−01 | −1.02071255e−01 |
| −1.10089161e−01 | 2.48146839e−02 | 8.82590637e−02 | 3.84982377e−01 |
| −3.05914432e−01 | 4.26038280e−02 | −1.95157118e−02 | 5.03717661e−02 |
| 2.89726824e−01 | 5.53918004e−01 | 3.53730321e−02 | −4.71051671e−02 |
| −9.18760449e−02 | 5.05575359e−01 | −2.59565502e−01 | −2.30341852e−01 |
| 6.76245764e−02 | −4.67400879e−01 | −5.46513021e−01 | −3.19368601e−01 |
| 3.27427350e−02 | 1.67748996e−03 | 3.01135212e−01 | 9.84259918e−02 |
| 5.39897740e−01 | 9.73584473e−01 | −4.98502523e−01 | 4.11091119e−01 |
| −5.53586986e−03 | 1.87699243e−01 | −2.45930955e−01 | 1.76937133e−01 |
| 2.40073025e−01 | −3.46291950e−03 | 1.42208338e−01 | 2.73262948e−01 |
| 1.24605499e−01 | 5.73626310e−02 | 8.18298608e−02 | −3.35214138e−02 |
| 1.85303614e−01 | −6.11705333e−02 | 5.28540790e−01 | 2.98748195e−01 |
| −1.79145873e−01 | 1.57232299e−01 | 1.00976810e−01 | 6.52189016e−01 |
| 1.67058453e−01 | −2.10405681e−02 | 3.43291998e−01 | 6.36828318e−02 |
| −4.22250658e−01 | −3.59133631e−01 | 1.05930611e−01 | −5.24148904e−02 |
| 1.08149096e−01 | −1.07657388e−01 | −3.19524765e−01 | 7.57098421e−02 |
| −6.56773597e−02 | 1.12575412e−01 | −2.40658090e−01 | −4.45829295e−02] |
| [−2.66600311e−01 | 2.31535017e−01 | 3.06910556e−02 | 1.76708668e−01 |
| 5.01942873e−01 | 3.60278279e−01 | −3.00499171e−01 | −7.36610293e−02 |
| −2.76962847e−01 | 1.65967166e−01 | 1.26717716e−01 | −9.12594274e−02 |
| −2.09135324e−01 | 8.08286369e−02 | −1.15735576e−01 | 3.42889279e−02 |
| −1.59944415e−01 | 8.03992003e−02 | −1.96464077e−01 | 7.30275502e−03 |

TABLE $W_h^1$-continued

| | | | |
|---|---|---|---|
| 4.46624637e-01 | 8.51421282e-02 | 3.26493025e-01 | 3.94859537e-02 |
| 1.68068334e-02 | 1.93151347e-02 | 2.22844377e-01 | 1.98529437e-01 |
| 3.14719319e-01 | -1.63732767e-01 | -1.27839655e-01 | 4.28672403e-01 |
| -5.26396669e-02 | 4.02805693e-02 | 2.09727213e-01 | -2.57916540e-01 |
| 1.09150745e-01 | 2.22856686e-01 | -7.22867623e-02 | 1.95266142e-01 |
| -2.88561266e-03 | -1.30826250e-01 | 8.54224414e-02 | 1.37060046e-01 |
| -1.04469366e-01 | 1.81958646e-01 | 7.77500421e-02 | -7.60880252e-03 |
| 7.66518936e-02 | 2.70765632e-01 | -9.22202766e-02 | 1.40651353e-02 |
| 1.92864835e-02 | -3.92760821e-02 | -1.31039694e-02 | 1.62227675e-01 |
| 3.80016178e-01 | 2.22006440e-01 | 3.54090966e-02 | 5.01124710e-02 |
| -1.03237033e-01 | -5.74389845e-03 | 1.76913753e-01 | -2.24071309e-01 |
| 4.74499255e-01 | 1.79285318e-01 | 6.08700573e-01 | 3.89044225e-01 |
| 1.62835106e-02 | 2.87498862e-01 | 2.76037157e-01 | 2.26379946e-01 |
| 2.16775626e-01 | 1.73867345e-01 | -8.51545781e-02 | 3.16774219e-01 |
| -3.47813852e-02 | 1.48069824e-03 | 2.25016817e-01 | 2.29215883e-02 |
| 1.89400554e-01 | 8.47751647e-02 | 9.92775187e-02 | 4.06057462e-02 |
| 2.52396166e-02 | -2.28816137e-01 | -5.57362512e-02 | 2.40579173e-01 |
| -1.99939162e-01 | 2.69152433e-01 | 1.11002132e-01 | 3.83963406e-01 |
| 1.50837556e-01 | 1.23272412e-01 | -9.99539644e-02 | 1.44666463e-01 |
| 3.70691389e-01 | 3.65216643e-01 | 5.07067554e-02 | 1.94153339e-01 |
| 1.44792438e-01 | 2.05596481e-02 | 4.57694709e-01 | 1.03415288e-01 |
| 8.39289799e-02 | 3.90422046e-01 | -4.62669373e-01 | -1.68714731e-03 |
| 1.19380943e-01 | -1.59387723e-01 | -1.19708054e-01 | -1.05252350e-02 |
| 4.81952168e-03 | 2.82953471e-01 | 1.62312746e-01 | 7.08834529e-02 |
| 7.33103901e-02 | -1.34088129e-01 | -1.66950002e-01 | 2.68470317e-01 |
| 1.87124368e-02 | 2.04111695e-01 | -2.09371537e-01 | -2.06146881e-01 |
| -1.26622677e-01 | 3.48165363e-01 | 3.64856988e-01 | 4.79239114e-02 |
| 8.11247081e-02 | 3.28211308e-01 | 1.45770967e-01 | -1.11037372e-02 |
| 8.17032829e-02 | 2.31501013e-01 | 4.91838716e-02 | 3.87560241e-02 |
| 6.34152591e-02 | 2.02748150e-01 | 2.84683198e-01 | 3.18682455e-02 |
| 2.42518365e-01 | 1.08044147e-01 | 1.60843991e-02 | -1.17889990e-03 |
| 3.86017323e-01 | -3.87045555e-02 | -3.51425335e-02 | 1.93563208e-01 |
| 2.27144390e-01 | 1.19633839e-01 | 3.27980340e-01 | 2.46296171e-02 |
| -5.82512915e-01 | 8.92416164e-02 | -4.83983159e-02 | -3.48413467e-01 |
| 1.26607373e-01 | 4.22769673e-02 | -2.11722571e-02 | -2.93656811e-02 |
| -2.03864604e-01 | 8.01638588e-02 | -2.20679983e-01 | -2.09517732e-01 |
| 2.32907444e-01 | 1.25529945e-01 | 2.51607358e-01 | 3.23669195e-01 |
| 5.26029229e-01 | -1.88125875e-01 | -2.25864902e-01 | 1.86911523e-01 |
| -1.16827693e-02 | -1.31665602e-01 | 1.45027980e-01 | 2.23649979e-01 |
| 7.63980672e-02 | -1.82400253e-02 | 1.20947137e-01 | 1.81422278e-01 |
| -3.13677117e-02 | 4.69348997e-01 | 1.69875578e-03 | 7.83837959e-02 |
| 4.10614721e-03 | 3.22420448e-01 | 1.48568213e-01 | 1.93399176e-01 |
| 7.14588612e-02 | -3.67334373e-02 | -1.19961739e-01 | 1.16362888e-02 |
| 1.44856989e-01 | 8.33054334e-02 | 1.40999153e-01 | -4.32399996e-02 |
| 1.37746900e-01 | 5.26113212e-01 | 1.50794059e-01 | -4.77527231e-01 |
| 1.50295189e-02 | -7.86687955e-02 | -2.85331644e-02 | -7.08918348e-02 |
| 3.82878512e-01 | 4.65780705e-01 | -2.64097720e-01 | 2.67516375e-01 |
| -1.48010105e-01 | -9.52192098e-02 | -2.90979624e-01 | -2.42501110e-01 |
| -2.95368761e-01 | 2.14763284e-01 | -6.15353063e-02 | 1.28509164e-01 |
| -6.58743968e-03 | 1.34824906e-02 | 1.53775007e-01 | 1.42746031e-01 |
| 2.05218986e-02 | -2.57530600e-01 | -2.88038462e-01 | 2.20177695e-01 |
| -2.46471912e-01 | 1.21814162e-01 | -6.66250437e-02 | 1.46354154e-01 |
| 1.51145145e-01 | -2.65026450e-01 | 1.22988839e-02 | -4.22306925e-01 |
| 1.72026336e-01 | 2.13807538e-01 | 1.07309525e-03 | 2.50130985e-01 |
| 2.36379251e-01 | 4.53470886e-01 | 2.53445238e-01 | 1.98926404e-01 |
| 2.18723103e-01 | 1.65912569e-01 | 1.20555133e-01 | 3.65267298e-03 |
| 5.47306314e-02 | 1.96664348e-01 | 3.27392876e-01 | -2.13949203e-01 |
| -5.15288003e-02 | 6.28340244e-02 | -3.54819782e-02 | 1.57483369e-02 |
| -6.17559589e-02 | -1.40092224e-01 | -1.57142103e-01 | 2.97259897e-01] |
| [-6.47429982e-03 | 2.68108577e-01 | 3.64975661e-01 | 5.70509136e-02 |
| 2.90376276e-01 | 2.27810591e-01 | 4.11302745e-01 | 2.81191558e-01 |
| 3.00830215e-01 | 5.51124215e-01 | 1.42492622e-01 | 2.79137880e-01 |
| 1.22505846e-01 | 2.85257697e-01 | -4.66104269e-01 | 2.37907358e-01 |
| 2.69869000e-01 | -1.77444264e-01 | 1.81335092e-01 | -8.70687589e-02 |
| 2.54019380e-01 | 6.87434196e-01 | -1.49436355e-01 | -1.18260086e-01 |
| 2.48064950e-01 | 1.58481389e-01 | -2.04891428e-01 | 9.96840522e-02 |
| 1.79869518e-01 | 9.20804441e-02 | 4.73450631e-01 | 1.00270994e-01 |
| 7.79197067e-02 | -1.00494456e-02 | 2.72010803e-01 | 4.05460835e-01 |
| 3.60431790e-01 | 4.24527854e-01 | 1.57472730e-01 | 1.91104397e-01 |
| 1.46308646e-01 | 1.34992152e-01 | 2.40075782e-01 | 6.29140913e-02 |
| 2.18068257e-01 | 5.79876304e-02 | 1.45409241e-01 | 1.49827271e-01 |
| 8.76842663e-02 | 1.83286250e-01 | -4.89329964e-01 | 2.71864355e-01 |
| 2.28601247e-01 | 1.66801348e-01 | 2.19194502e-01 | 1.36952356e-01 |
| 1.37154460e-01 | 2.36275107e-01 | 2.49978304e-01 | -4.06387560e-02 |
| 3.71288285e-02 | 6.19217217e-01 | 1.82033926e-01 | -8.36172998e-02 |
| 3.57834190e-01 | 1.36590585e-01 | 2.90216625e-01 | -4.70527820e-02 |
| 7.37700462e-02 | 3.70897114e-01 | 8.71351212e-02 | 2.66243398e-01 |
| 2.40142807e-01 | 2.22331211e-02 | 2.01218262e-01 | 2.62744576e-01 |
| 1.96801156e-01 | 2.79960871e-01 | 3.70645583e-01 | 5.05326912e-02 |
| 4.41396177e-01 | 2.48289838e-01 | 3.24749172e-01 | 4.75040823e-01 |

TABLE $W_h^1$-continued

| | | | |
|---|---|---|---|
| 9.78434980e−02 | 4.19207931e−01 | 1.98790789e−01 | −3.07824537e−02 |
| 1.29420966e−01 | 8.87456313e−02 | 2.21243173e−01 | −2.62409151e−01 |
| 2.78454661e−01 | 3.78146857e−01 | 3.89775872e−01 | 2.00345680e−01 |
| 5.84825911e−02 | −1.12482212e−01 | 1.20804518e−01 | 1.96331069e−01 |
| 7.91901723e−02 | −1.89638466e−01 | 9.96737182e−03 | −1.02442116e−01 |
| 4.94521618e−01 | 1.29774094e−01 | 2.71792412e−01 | 1.07016169e−01 |
| 3.64918202e−01 | 1.74134791e−01 | 5.86964607e−01 | −2.60358509e−02 |
| 4.80536580e−01 | 3.69862825e−01 | 1.22584626e−01 | 3.36326897e−01 |
| 8.33923370e−02 | 5.27961329e−02 | 3.01189184e−01 | −2.18075439e−02 |
| −5.65050207e−02 | −5.20973355e−02 | 2.45395467e−01 | 1.04368933e−01 |
| 2.05761909e−01 | 3.08542773e−02 | 2.07675947e−03 | 3.11252743e−01 |
| −1.49208024e−01 | −1.71120152e−01 | −1.60398126e−01 | 2.25251272e−01 |
| 3.97598535e−01 | −5.00879735e−02 | 1.28155863e−02 | 7.71428198e−02 |
| −1.18717067e−02 | 2.67691642e−01 | 1.87990531e−01 | 2.57562250e−01 |
| 5.16678654e−02 | 1.10525876e−01 | −5.90911061e−02 | 4.60891604e−01 |
| 3.28665137e−01 | 1.44372657e−01 | −2.48912588e−01 | 3.98682237e−01 |
| 2.89220184e−01 | 3.64572406e−01 | 3.21424723e−01 | −5.03916502e−01 |
| −7.91044086e−02 | 2.06742913e−01 | 3.49996313e−02 | 2.09219053e−01 |
| 3.13337713e−01 | −4.36280668e−02 | −9.73233506e−02 | 1.16475806e−01 |
| 3.76314260e−02 | −2.29593769e−01 | −6.79723918e−03 | 2.33830109e−01 |
| 4.79251407e−02 | 7.10114464e−02 | 1.79338783e−01 | 3.28323156e−01 |
| 3.05553406e−01 | 2.42414743e−01 | 1.43409505e−01 | 1.23171009e−01 |
| 4.72908586e−01 | −5.57190478e−02 | 3.91896702e−02 | 1.88140050e−01 |
| −4.05729339e−02 | 2.06731766e−01 | 5.62996268e−02 | 2.23726496e−01 |
| 1.47891656e−01 | −9.08304844e−03 | −5.33915125e−02 | 4.10225123e−01 |
| 3.37155849e−01 | 6.91505000e−02 | 1.62715673e−01 | −9.50331613e−02 |
| −1.15094364e−01 | −4.03389558e−02 | 8.04712772e−02 | 3.20574313e−01 |
| 1.92954943e−01 | −7.15776682e−02 | −3.26277092e−02 | 3.22185829e−02 |
| 2.49562263e−01 | 2.25750715e−01 | 1.28170058e−01 | −5.86864278e−02 |
| 1.32578701e−01 | −4.30155657e−02 | 1.57817632e−01 | 3.03152651e−01 |
| 2.03739151e−01 | −4.28667255e−02 | 4.14085686e−01 | 3.08584034e−01 |
| −7.51527473e−02 | 3.05602793e−02 | −1.17410913e−01 | 1.26391336e−01 |
| 4.29043978e−01 | 3.76857609e−02 | −2.79406339e−01 | 1.99193493e−01 |
| −2.29383618e−01 | 2.05543712e−02 | 3.31760168e−01 | 1.12705417e−01 |
| −1.02491202e−02 | 1.13526983e−02 | 5.12473658e−02 | 1.68085545e−01 |
| −6.34846538e−02 | 4.27516937e−01 | 5.55409752e−02 | −8.78512114e−02 |
| 1.16669253e−01 | 2.48911813e−01 | 1.79458514e−01 | 2.24654928e−01 |
| 3.08485366e−02 | 5.51843122e−02 | 3.55478734e−01 | −4.52970147e−01 |
| −1.52178006e−02 | 1.27113596e−01 | 7.97416717e−02 | 2.49470994e−01 |
| 1.18758194e−01 | 2.52105594e−01 | 3.17172229e−01 | 1.80762455e−01 |
| −1.03913732e−01 | −5.79422526e−03 | 1.35130778e−01 | 1.37915820e−01 |
| 7.48724770e−03 | 1.90386534e−01 | 2.22957700e−01 | 2.16653913e−01 |
| 1.67027593e−01 | 2.45954007e−01 | 2.55168408e−01 | 4.43201184e−01] |
| [−5.22811115e−02 | −3.99651751e−02 | 5.95142663e−01 | −4.21660960e−01 |
| −2.00785041e−01 | 2.07021479e−02 | 2.77512103e−01 | 4.90046255e−02 |
| 3.49219710e−01 | 2.75841415e−01 | 1.67030782e−01 | 1.59737617e−01 |
| 5.15694976e−01 | 3.31833005e−01 | −1.37398392e−01 | 3.39789480e−01 |
| −1.08406739e−02 | 2.78017908e−01 | 2.76187509e−01 | 1.51682958e−01 |
| 5.43974280e−01 | 2.93994159e−01 | 2.95467317e−01 | 2.23538965e−01 |
| 2.97054559e−01 | 3.73875827e−01 | 6.65574506e−03 | −1.89791113e−01 |
| −2.97873706e−01 | 2.46685192e−01 | −1.52302906e−01 | 4.01457585e−02 |
| 9.52770486e−02 | 4.89351332e−01 | 3.34512591e−01 | 3.44361424e−01 |
| 1.03663146e−01 | 5.57145774e−01 | 4.48806643e−01 | 4.00425605e−02 |
| 5.07460721e−02 | 2.34578222e−01 | −1.24229230e−01 | −5.07829804e−03 |
| 2.83578448e−02 | −1.15129031e−01 | 4.60592479e−01 | 1.98126018e−01 |
| 1.66570887e−01 | 1.80546880e−01 | 3.27737659e−01 | 1.80452570e−01 |
| 3.59441370e−01 | 2.28183299e−01 | −3.75154972e−01 | −1.38830125e−01 |
| 3.27505380e−01 | 2.69879371e−01 | 1.23584857e−02 | 1.08144298e−01 |
| −2.50335578e−02 | 2.26547837e−01 | 2.14647904e−01 | 6.49488419e−02 |
| −4.04529780e−01 | 2.34975055e−01 | 1.02504037e−01 | 1.73692182e−01 |
| −9.12930295e−02 | 5.80553152e−02 | 1.05825007e−01 | 2.69373745e−01 |
| 4.15377915e−01 | 1.96331590e−02 | 1.30604848e−01 | 8.59244075e−03 |
| 1.96826950e−01 | −1.18115626e−01 | 2.63552755e−01 | −1.45727038e−01 |
| −4.35984254e−01 | 1.69271991e−01 | 2.55716503e−01 | −1.03456520e−01 |
| −2.18300559e−02 | 4.79325891e−01 | 1.52047426e−01 | 3.00547220e−02 |
| 1.12324305e−01 | −6.81340471e−02 | −1.77468270e−01 | 4.50286716e−01 |
| 6.61085099e−02 | −1.44737614e−01 | −9.55804437e−03 | 2.70992279e−01 |
| 1.35062801e−04 | 7.15463907e−02 | 6.22679651e−02 | −2.43155226e−01 |
| 1.61756650e−01 | 1.83905482e−01 | 4.07725424e−01 | −7.75671154e−02 |
| 2.68320758e−02 | 1.13567449e−01 | −8.28552768e−02 | 1.71786025e−01 |
| −3.74244004e−02 | 1.44646302e−01 | 3.01117808e−01 | 1.83846667e−01 |
| −1.15119107e−01 | 1.52347311e−01 | 5.21362245e−01 | 6.91572502e−02 |
| 6.22044690e−02 | 2.63076216e−01 | −2.26822682e−03 | −1.31603017e−01 |
| 8.12299401e−02 | −3.52270663e−01 | 1.95045881e−02 | −3.75737607e−01 |
| −1.63820401e−01 | 1.90707445e−01 | −5.55392765e−01 | −3.59139621e−01 |
| 1.32330939e−01 | 1.53191432e−01 | 3.69325101e−01 | 1.99962348e−01 |
| −3.26079578e−04 | 2.64692456e−01 | 4.71786886e−01 | 8.30979645e−02 |
| 1.22995250e−01 | −1.16760008e−01 | 4.57101017e−01 | 2.89016187e−01 |
| 2.46390387e−01 | 7.12285563e−02 | 7.55094945e−01 | 6.67251647e−02 |
| 3.86519194e−01 | 3.34439307e−01 | 5.79585098e−02 | 4.36913744e−02 |

TABLE $W_h^1$-continued

| | | | |
|---|---|---|---|
| 1.28484694e−02 | 1.88096926e−01 | 9.59844664e−02 | 3.68349582e−01 |
| 1.40366629e−01 | 1.81105658e−01 | −6.61102968e−05 | 3.40325654e−01 |
| 7.41975904e−02 | 2.47043028e−01 | 1.72899947e−01 | 1.91331401e−01 |
| −1.01109691e−01 | 2.08771318e−01 | 6.41731918e−02 | 2.14721650e−01 |
| 4.45785195e−01 | −3.74185899e−03 | −1.19491788e−02 | 9.14733931e−02 |
| 5.70600666e−02 | 1.83019206e−01 | −6.09773174e−02 | 1.31963387e−01 |
| 3.87290239e−01 | 3.38826746e−01 | 2.77726632e−03 | 3.05575311e−01 |
| 4.63578045e−01 | 4.88721341e−01 | −9.41082835e−02 | −2.16772392e−01 |
| 1.96867242e−01 | 1.50089890e−01 | 2.36904100e−01 | −1.44836977e−01 |
| 4.46260333e−01 | 9.17900652e−02 | 3.47972155e−01 | 5.62563911e−02 |
| 2.10077614e−01 | 3.60630900e−01 | 1.74232230e−01 | −9.93064046e−02 |
| 3.61930341e−01 | 3.09809834e−01 | 4.54162546e−02 | 8.18568245e−02 |
| 1.95850402e−01 | −2.10226923e−01 | 2.51617692e−02 | −5.84602952e−02 |
| 1.14057675e−01 | 2.56107837e−01 | 8.77315700e−02 | 5.29562294e−01 |
| 2.81034261e−01 | −1.29561678e−01 | 8.54712259e−03 | −4.09162432e−01 |
| 1.08804651e−01 | 9.67672616e−02 | −7.06035644e−02 | 1.26635656e−01 |
| −3.39189693e−02 | 2.34792247e−01 | −3.87785695e−02 | 3.57872367e−01 |
| 3.53945553e−01 | −1.78187937e−02 | 3.47341388e−01 | 2.14751229e−01 |
| 2.66902536e−01 | 7.57777393e−01 | 3.55561763e−01 | 9.53333154e−02 |
| 3.48896682e−01 | 2.55176336e−01 | 9.45550799e−02 | 4.63517606e−01 |
| −1.05890948e−02 | 7.53521442e−01 | 3.71078253e−01 | 3.97104830e−01 |
| 2.26605609e−01 | 9.63694900e−02 | 1.27922684e−01 | −9.44019258e−02 |
| 2.33514383e−01 | −1.86816797e−01 | 3.00703645e−01 | 1.50962040e−01 |
| 3.89231473e−01 | 1.43564925e−01 | 1.62665680e−01 | 3.58266205e−01 |
| 3.03764641e−01 | 4.08228427e−01 | 3.48672301e−01 | 1.99907236e−02 |
| 1.62825748e−01 | −2.77100056e−01 | 2.31093943e−01 | −1.36638418e−01 |
| 2.00683758e−01 | 2.32362106e−01 | 4.42389071e−01 | 1.54134095e−01] |
| [−5.75742126e−02 | 5.82889438e−01 | 3.64213675e−01 | 4.94016677e−01 |
| 3.48267823e−01 | 1.10442376e−00 | 5.69395304e−01 | 5.64715683e−01 |
| 7.41590083e−01 | 4.10875708e−01 | 8.73537302e−01 | 7.94389248e−01 |
| 6.20584130e−01 | 5.34663200e−01 | −4.54715006e−02 | 2.37443611e−01 |
| 9.92109597e−01 | 4.83497590e−01 | 2.80808598e−01 | 1.59785852e−01 |
| 5.65970123e−01 | −1.68261826e−01 | 9.85321403e−01 | 1.26325786e−00 |
| 2.29464605e−01 | 5.58495700e−01 | 9.37848315e−02 | 3.76432478e−01 |
| 3.29434484e−01 | 3.99896026e−01 | 3.73319685e−02 | 2.62999594e−01 |
| 7.76803017e−01 | 2.76586741e−01 | 4.24912959e−01 | 1.91833675e−01 |
| 5.91594130e−02 | 4.34954345e−01 | 4.19954062e−01 | 2.35376984e−01 |
| 3.15763235e−01 | 4.73344117e−01 | −4.63452861e−02 | 1.08724046e−00 |
| 9.32280123e−01 | 4.76584166e−01 | 3.34870338e−01 | 8.77468050e−01 |
| 4.22471054e−02 | 4.79373932e−01 | 5.18389642e−01 | 3.46903414e−01 |
| 5.48679233e−01 | 3.63305718e−01 | 3.40171695e−01 | 4.48778957e−01 |
| 7.16597378e−01 | 4.28556144e−01 | 4.45109785e−01 | 3.34314376e−01 |
| 4.33829755e−01 | 8.21829498e−01 | 2.06825733e−01 | 3.02979857e−01 |
| 1.31759569e−01 | 3.54548573e−01 | 2.67363638e−01 | 1.80935450e−02 |
| 9.16638374e−01 | 2.87041843e−01 | 5.95957935e−01 | −6.93830729e−01 |
| 4.26795542e−01 | 1.94013074e−01 | 9.02097404e−01 | 2.51086831e−01 |
| 7.15481639e−01 | 5.86902440e−01 | 5.83870709e−01 | 7.42678165e−01 |
| 3.63627434e−01 | 1.60905570e−01 | −8.09496641e−03 | 7.87427664e−01 |
| 5.88668287e−01 | 1.55442640e−01 | 2.38237679e−01 | 1.49899527e−01 |
| 2.90033996e−01 | −4.98067617e−01 | −4.28519882e−01 | 6.52035952e−01 |
| −8.32471475e−02 | 5.43877542e−01 | 3.15348327e−01 | 4.12509948e−01 |
| 5.44408262e−01 | 4.31780487e−01 | 9.01265368e−02 | 6.73413754e−01 |
| 3.38351816e−01 | 5.59560418e−01 | 1.31984606e−01 | 2.91723937e−01 |
| 1.71616822e−01 | 5.96219115e−02 | 3.40641290e−01 | 6.76182806e−01 |
| 4.28732455e−01 | 4.09142584e−01 | 5.92364334e−02 | 3.30847472e−01 |
| 1.84021860e−01 | 6.17327332e−01 | 3.04313809e−01 | 6.04324162e−01 |
| 3.60456973e−01 | 5.52011669e−01 | 6.51759386e−01 | 4.32648510e−01 |
| 6.36400878e−01 | 2.43782163e−01 | 5.62763631e−01 | 3.49660873e−01 |
| 6.78558767e−01 | 9.59025323e−01 | 5.47256947e−01 | 5.94000816e−01 |
| 7.46328712e−01 | 6.00254655e−01 | 1.91829547e−01 | 9.95957732e−01 |
| 4.47792083e−01 | 3.03245813e−01 | 5.11791825e−01 | −6.23255000e−02 |
| 4.46354836e−01 | 1.20268717e−01 | 7.53315091e−01 | 1.03289947e−01 |
| 9.81522918e−01 | −3.23866792e−02 | 1.85809806e−01 | 2.92716563e−01 |
| 5.44896305e−01 | 1.83548659e−01 | 4.42924768e−01 | 4.11596358e−01 |
| 3.21364522e−01 | 4.74890471e−01 | 3.19944113e−01 | 5.42109869e−02 |
| 7.52687752e−01 | 3.75153542e−01 | 4.82947677e−01 | 4.07587200e−01 |
| 3.59667689e−01 | 1.46097720e−01 | 4.94837135e−01 | 5.08312166e−01 |
| 2.58944303e−01 | 4.84489292e−01 | 1.99214190e−01 | 6.49095833e−01 |
| 2.89740086e−01 | 1.73092961e−01 | 1.61535233e−01 | 1.37877211e−01 |
| 7.54787505e−01 | 2.52072185e−01 | −7.30205849e−02 | 6.23090684e−01 |
| 7.79640019e−01 | 6.15893543e−01 | 4.63686824e−01 | 2.76885301e−01 |
| 3.78848314e−01 | 8.94681990e−01 | −9.34692547e−02 | 6.27835631e−01 |
| 9.78176832e−01 | 5.69974661e−01 | 4.99083668e−01 | 3.10835481e−01 |
| 3.26004416e−01 | −2.61082411e−01 | 3.76732260e−01 | 5.66661000e−01 |
| 2.92115390e−01 | 4.44781899e−01 | 1.02073836e−00 | 9.79415119e−01 |
| 3.54367793e−01 | 5.77585578e−01 | 1.15468219e−01 | 2.15700522e−01 |
| 1.88891068e−01 | 6.57817543e−01 | 6.17924631e−01 | 7.11990118e−01 |
| 3.56998593e−02 | 3.88149053e−01 | 3.79964352e−01 | −2.97896504e−01 |
| −1.02705322e−01 | 1.90223396e−01 | 5.46169162e−01 | 7.26066232e−01 |
| 8.91675293e−01 | 1.44194767e−01 | 4.16839749e−01 | 8.00511241e−01 |

TABLE $W_h^1$-continued

| | | | |
|---|---|---|---|
| 5.59817076e-01 | 4.04937953e-01 | 1.49808545e-02 | 3.80833954e-01 |
| 2.30012476e-01 | 9.20950830e-01 | 2.23509282e-01 | -1.52986785e-02 |
| 5.75773418e-01 | 9.26429749e-01 | 1.63718611e-01 | 3.81726921e-01 |
| 5.16628444e-01 | 3.50477457e-01 | 3.13084394e-01 | 4.05258745e-01 |
| 4.22502458e-01 | 5.71573615e-01 | 7.25745797e-01 | 3.57023835e-01 |
| 4.99566346e-02 | 1.03135146e-02 | 4.47163790e-01 | 6.40850604e-01 |
| 4.90105093e-01 | 3.44948143e-01 | 4.28585671e-02 | 7.18711257e-01 |
| 6.82585239e-01 | 5.73365748e-01 | 4.19241667e-01 | 6.20823324e-01 |
| 3.22042465e-01 | 6.56723201e-01 | -1.15233719e-01 | 5.23514211e-01 |
| 1.10522556e-00 | 3.41650516e-01 | 5.89997292e-01 | 9.14923489e-01 |
| -2.14014843e-01 | 1.08844507e-00 | 5.71454942e-01 | 1.36300698e-01] |
| [-3.63289341e-02 | -3.75404030e-01 | 2.63598084e-01 | 1.36850536e-01 |
| -1.70521095e-01 | 2.04468176e-01 | -6.60637915e-02 | -1.02139093e-01 |
| 5.33989191e-01 | 7.04433843e-02 | 1.57485485e-01 | -2.86450237e-02 |
| 3.57990945e-03 | 2.31814563e-01 | -5.86073041e-01 | 2.41742730e-01 |
| -3.79570909e-02 | 2.83179134e-01 | 5.00717945e-02 | 4.72201198e-01 |
| 3.08572292e-01 | 2.21820176e-01 | 1.28446743e-01 | 2.62224197e-01 |
| 1.66603833e-01 | 2.94663042e-01 | -1.24430563e-02 | 3.17300595e-02 |
| -4.81746197e-01 | 7.27877319e-01 | 3.77668172e-01 | 3.10786217e-01 |
| 1.48961514e-01 | 1.94917887e-01 | -7.66680390e-02 | 6.37776434e-01 |
| -8.83712545e-02 | 1.91236943e-01 | 2.44394720e-01 | 4.59122181e-01 |
| -1.66444167e-01 | 1.09071717e-01 | -2.46692151e-01 | -8.56556371e-03 |
| 3.29973340e-01 | -8.13775137e-02 | 3.65065098e-01 | 2.17855245e-01 |
| -7.31957629e-02 | 6.00962281e-01 | 4.19249654e-01 | -1.19042099e-01 |
| 1.11964211e-01 | -1.35702372e-01 | 9.98098478e-02 | -2.12430015e-01 |
| 5.14273465e-01 | 3.12228948e-01 | 1.93770871e-01 | 2.06877932e-01 |
| 2.51861364e-01 | 1.04441948e-01 | 5.31992167e-02 | 4.68981177e-01 |
| 1.16775732e-03 | 6.15741201e-02 | -5.20105064e-01 | 1.54925704e-01 |
| 6.50899410e-01 | 2.12457746e-01 | -5.11260852e-01 | 1.50153518e-03 |
| 4.77077067e-01 | -5.02914637e-02 | 2.68382818e-01 | -1.69454736e-03 |
| 1.63081199e-01 | 2.20548227e-01 | 1.46915421e-01 | 1.10297382e-01 |
| -2.69505829e-01 | 2.18240023e-01 | 3.91447902e-01 | 2.79739231e-01 |
| -1.46381751e-01 | 6.27421439e-01 | 1.74272045e-01 | -5.30838892e-02 |
| 1.50199786e-01 | 3.10833395e-01 | -1.01688258e-01 | -1.15760796e-01 |
| -2.91153461e-01 | -1.81616411e-01 | -1.38193145e-01 | 2.46486828e-01 |
| -4.27890539e-01 | 3.35425250e-02 | -6.64797425e-02 | -4.50320065e-01 |
| 2.34691173e-01 | 5.00918388e-01 | 6.51027203e-01 | 1.94722429e-01 |
| -3.38782698e-01 | 3.68062049e-01 | 3.65263313e-01 | 6.65450022e-02 |
| -1.86418042e-01 | 5.08628011e-01 | 1.37566984e-01 | -1.58474967e-01 |
| -2.60487407e-01 | -5.15851617e-01 | -8.10077116e-02 | 1.59125432e-01 |
| -4.01819218e-03 | 1.15442045e-01 | 1.07606351e-01 | 6.65407255e-02 |
| 2.22000182e-01 | -2.71097094e-01 | 1.02182202e-01 | -3.27882051e-01 |
| -1.76199049e-01 | 4.52901393e-01 | 8.70236903e-02 | 1.73949733e-01 |
| 5.11286438e-01 | 2.04791605e-01 | 2.87117541e-01 | 5.94464615e-02 |
| 4.91935641e-01 | 3.86603564e-01 | 2.36928761e-01 | -6.61043748e-02 |
| 2.55610913e-01 | 1.39106363e-01 | 7.14269996e-01 | 2.96776503e-01 |
| 1.33595794e-01 | 1.25033170e-01 | 1.06350303e-01 | -6.59436807e-02 |
| 2.08891168e-01 | 2.36737564e-01 | -3.60447258e-01 | -1.52770253e-02 |
| -1.44214749e-01 | -1.92336813e-01 | -2.10407991e-02 | 4.09980118e-01 |
| 4.78274614e-01 | 6.28602281e-02 | 5.67231178e-01 | 1.90834209e-01 |
| -7.94751048e-02 | 4.87552464e-01 | -4.09472100e-02 | 5.32904804e-01 |
| 2.04910770e-01 | 1.58417657e-01 | -2.33506374e-02 | 5.01984239e-01 |
| -1.15125351e-01 | -4.42286320e-02 | -1.62462607e-01 | 2.29111448e-01 |
| -7.70729706e-02 | 3.13009880e-01 | 6.11113369e-01 | 2.80617356e-01 |
| 9.81168598e-02 | 5.40050626e-01 | -2.55729765e-01 | 3.10020834e-01 |
| 1.16368227e-01 | 4.55511719e-01 | -2.21532851e-01 | 1.53317288e-01 |
| 2.48869672e-01 | 3.43394935e-01 | 2.46125311e-01 | 3.77611905e-01 |
| -9.76670459e-02 | -2.33922936e-01 | -5.49384236e-01 | -2.13320464e-01 |
| 2.55509555e-01 | 5.17462850e-01 | 2.74542153e-01 | 1.69190735e-01 |
| 3.38671692e-02 | 7.44269118e-02 | -1.81426093e-01 | 1.68069780e-01 |
| -6.51673734e-01 | 2.17256725e-01 | -1.08002834e-01 | 3.24281603e-01 |
| -1.44168377e-01 | 4.91245955e-01 | 9.61910412e-02 | 2.29570508e-01 |
| 3.09351087e-01 | 2.96161979e-01 | 6.29284918e-01 | 2.08605260e-01 |
| -5.33406250e-02 | 1.10678814e-01 | 3.05315316e-01 | 6.43485904e-01 |
| 2.09442854e-01 | -3.41407880e-02 | 2.47203675e-03 | 6.41010925e-02 |
| 2.90577054e-01 | 1.74181715e-01 | 4.14070822e-02 | 2.88965017e-01 |
| 1.40987366e-01 | -1.84849590e-01 | 2.00808346e-01 | -3.59494716e-02 |
| 2.17418626e-01 | 2.47026846e-01 | 3.27570736e-01 | -2.72151858e-01 |
| 3.38924751e-02 | 1.90618277e-01 | 1.85836896e-01 | 3.53445888e-01 |
| 4.53947306e-01 | -1.54215144e-02 | 3.81587744e-01 | 5.71539998e-01 |
| 5.12103975e-01 | 4.07482505e-01 | 2.43591532e-01 | -1.73802987e-01 |
| 6.06520362e-02 | -4.63861646e-03 | -2.36411896e-02 | -3.90394479e-02 |
| 9.00954232e-02 | 4.85394388e-01 | -3.01006198e-01 | 4.27237540e-01 |
| 6.59974575e-01 | 3.25813442e-01 | 1.47631913e-01 | 3.80401909e-02 |
| 3.99525426e-02 | 6.26525541e-01 | 1.36130720e-01 | 2.03729421e-01] |
| [-9.03109983e-02 | 8.82413164e-02 | -1.32967476e-02 | 9.63456184e-02 |
| 5.60786389e-02 | -8.25692620e-03 | 5.63275209e-03 | -9.31885391e-02 |
| -7.98900798e-02 | 3.23248245e-02 | 8.43988173e-03 | -7.52946958e-02 |
| 9.27009135e-02 | 9.09098461e-02 | -3.58464941e-02 | -8.61182343e-03 |
| -9.99379605e-02 | 4.44478467e-02 | -1.03507444e-01 | 5.91321811e-02 |

TABLE $W_h^1$-continued

| | | | |
|---|---|---|---|
| −1.38298776e−02 | 8.24353285e−03 | −4.36839275e−02 | 1.02944061e−01 |
| −6.86918795e−02 | 8.15521553e−02 | 7.19776005e−02 | −5.66352438e−03 |
| 6.08051270e−02 | −5.75411431e−02 | −1.03136510e−01 | 2.92501766e−02 |
| 4.46804687e−02 | 1.03781544e−01 | 3.88921686e−02 | 1.04196459e−01 |
| −1.01355933e−01 | 4.62970585e−02 | −1.08494200e−01 | −1.91799793e−02 |
| −6.42163306e−02 | 5.54081239e−02 | −1.99943874e−02 | 6.20534383e−02 |
| 1.06988750e−01 | −2.42856350e−02 | 1.94083806e−02 | 1.00924931e−01 |
| −6.10687360e−02 | −7.07525983e−02 | 7.40026906e−02 | −1.31016318e−02 |
| 2.20691320e−02 | −6.87990934e−02 | 8.35180506e−02 | 7.98041523e−02 |
| −9.38367844e−02 | 4.53806184e−02 | 3.29195075e−02 | 1.10255301e−01 |
| 8.57854262e−02 | −8.17674994e−02 | 1.80318803e−02 | −9.39199105e−02 |
| 4.43230756e−02 | −3.46171856e−02 | −7.50819594e−02 | −2.07192618e−02 |
| 4.54219505e−02 | −8.51242468e−02 | −1.44026279e−02 | −1.02210782e−01 |
| 2.46490655e−03 | 8.76448080e−02 | −2.15975046e−02 | 3.36256474e−02 |
| 5.46076931e−02 | 8.45682025e−02 | −3.15555036e−02 | −7.62568489e−02 |
| 1.51756564e−02 | −6.68186545e−02 | −9.35041681e−02 | −4.73966785e−02 |
| −1.09389402e−01 | −7.72732645e−02 | 3.47732902e−02 | 5.64851202e−02 |
| −1.46999285e−02 | −9.64399278e−02 | 7.91210383e−02 | 1.06799208e−01 |
| −6.71751350e−02 | −4.16733418e−03 | 8.81759003e−02 | 8.73125717e−02 |
| 9.40782577e−02 | −1.93529744e−02 | 1.04387686e−01 | −5.08077629e−03 |
| −2.92739850e−02 | −1.17733330e−02 | −9.16404128e−02 | −4.44655777e−02 |
| 4.72131036e−02 | −9.18584391e−02 | −3.05064768e−02 | 9.24991891e−02 |
| 2.58504525e−02 | −6.42889664e−02 | 6.23947494e−02 | −1.51132783e−02 |
| 6.79885745e−02 | 9.82391238e−02 | −5.04119620e−02 | 4.72253114e−02 |
| −9.96715873e−02 | 7.47062126e−03 | −1.30354576e−02 | 4.58725132e−02 |
| −1.09494559e−01 | 2.54183188e−02 | −1.60732027e−02 | −1.39193954e−02 |
| 7.48508098e−03 | 3.67206158e−05 | −3.68687212e−02 | 9.86271501e−02 |
| 3.66496667e−02 | 8.51303115e−02 | 5.90433702e−02 | −6.26143813e−02 |
| −3.06184944e−02 | 7.34689981e−02 | −1.63055286e−02 | 8.87688994e−02 |
| 3.99536043e−02 | 2.17103329e−03 | 6.69522658e−02 | −5.54628521e−02 |
| 5.33382185e−02 | 1.06916018e−01 | 9.04025044e−03 | 4.59647812e−02 |
| 3.79616246e−02 | −4.60861698e−02 | −1.18570412e−02 | −8.99703503e−02 |
| −1.06179520e−01 | 4.70475666e−02 | 7.75649175e−02 | 5.54758385e−02 |
| −2.05206275e−02 | −1.53012928e−02 | −5.79457618e−02 | −4.86655422e−02 |
| −8.52143671e−03 | −4.54008929e−04 | 1.52121233e−02 | 1.56276766e−02 |
| 9.93247479e−02 | −4.39539030e−02 | 7.26399645e−02 | −1.05017513e−01 |
| 5.78038730e−02 | 7.70876184e−02 | 6.78827912e−02 | 8.75806957e−02 |
| −3.50694656e−02 | −9.55357328e−02 | 1.52279539e−02 | −8.15035701e−02 |
| −3.54796425e−02 | 1.89874675e−02 | 7.15017272e−03 | 9.17477608e−02 |
| −2.46892720e−02 | 1.10048711e−01 | 3.36604193e−02 | −8.29231292e−02 |
| −2.47397237e−02 | −1.33214174e−02 | −3.30058001e−02 | 4.53423373e−02 |
| 1.01128280e−01 | 9.19729471e−02 | 9.68303978e−02 | −6.02778234e−02 |
| −3.03285792e−02 | −5.48100956e−02 | 5.18399067e−02 | 7.28561059e−02 |
| 2.99587399e−02 | 6.78855851e−02 | −6.49139881e−02 | −8.05988312e−02 |
| 2.38256902e−03 | −3.70660685e−02 | 5.62797636e−02 | 9.24766343e−03 |
| −9.88447815e−02 | −9.43479165e−02 | −2.86961105e−02 | 1.00358352e−01 |
| −5.95888831e−02 | −1.04823597e−01 | 4.42460924e−03 | −7.99584538e−02 |
| 2.19271500e−02 | −1.09094717e−01 | −3.01371254e−02 | −4.44178432e−02 |
| −2.28080191e−02 | 9.68044177e−02 | −8.71378556e−02 | −6.88598678e−02 |
| 4.54004109e−02 | 7.58306831e−02 | −8.66472721e−02 | −6.80044442e−02 |
| 9.40134078e−02 | 1.04802750e−01 | −5.70301376e−02 | 9.70235392e−02 |
| 8.74358341e−02 | −4.51306663e−02 | 5.19731380e−02 | −3.41140628e−02 |
| −6.09258339e−02 | 6.22549802e−02 | 5.50769968e−03 | 2.76563000e−02 |
| −2.01777015e−02 | −4.52322401e−02 | 2.85943877e−02 | −3.52810457e−04 |
| −2.17382610e−03 | −1.04646094e−01 | 1.03066461e−02 | −8.43154714e−02 |
| 4.40074317e−02 | 3.72465849e−02 | 7.26886243e−02 | 9.23798457e−02 |
| 2.51173582e−02 | −7.11997598e−02 | −5.77743389e−02 | 1.06661506e−01 |
| −4.55684774e−02 | 8.58038440e−02 | −2.38036327e−02 | 2.68821623e−02 |
| −9.48315486e−03 | 7.10818842e−02 | 2.52035297e−02 | −6.48104995e−02] |
| [−2.21618384e−01 | −2.19221398e−01 | 1.28183872e−01 | 2.62898862e−01 |
| 7.48660937e−02 | 2.44594485e−01 | 2.59935707e−01 | 4.95725542e−01 |
| 2.23403797e−01 | −2.39912868e−01 | 6.51353359e−01 | −3.58828872e−01 |
| 3.44788402e−01 | 1.17330603e−01 | −8.34217891e−02 | 1.82403162e−01 |
| −1.77756250e−01 | −4.39364351e−02 | 2.51260340e−01 | −2.64690429e−01 |
| 4.86956596e−01 | −7.71167427e−02 | −2.43139878e−01 | 1.66635007e−01 |
| −1.52811199e−01 | 3.70188355e−01 | 2.11873904e−01 | −3.86754781e−01 |
| −2.47964114e−01 | 1.98566988e−01 | 2.38823757e−01 | 6.02453249e−03 |
| 2.68441170e−01 | −8.16046372e−02 | 2.83766657e−01 | 8.62589926e−02 |
| 3.83518487e−01 | 2.83873975e−01 | 1.84854463e−01 | −7.77918026e−02 |
| 3.46033067e−01 | −1.39805973e−01 | 1.96832921e−02 | −2.33874664e−01 |
| 2.88346916e−01 | 1.85366526e−01 | 2.77620554e−01 | −9.40600410e−02 |
| −3.87588620e−01 | 3.23767722e−01 | 8.26180726e−02 | −2.37048656e−01 |
| −2.02422574e−01 | 2.80367464e−01 | −3.86276692e−01 | −9.98757124e−01 |
| 4.16188985e−01 | −1.41260326e−01 | −1.06482515e−02 | −7.46992305e−02 |
| 2.28143595e−01 | −1.39603049e−01 | 4.41069424e−01 | −1.00811593e−01 |
| 4.65310700e−02 | 2.85191135e−03 | 3.02223593e−01 | 4.67490047e−01 |
| 7.82947719e−01 | −4.89990979e−01 | 6.23241782e−01 | 4.28529456e−02 |
| 3.35659862e−01 | −2.84798741e−01 | 1.59929603e−01 | −9.09382701e−02 |
| 5.00244856e−01 | 6.68073371e−02 | −2.55285084e−01 | −3.24995369e−02 |
| −2.23648608e−01 | 5.94621524e−02 | −2.20089555e−01 | 4.45320636e−01 |

TABLE $W_h^1$-continued

| | | | |
|---|---|---|---|
| 1.10632911e-01 | 5.69737982e-03 | -3.15825969e-01 | -1.23035878e-01 |
| -1.15729079e-01 | -6.10021770e-01 | 3.83498937e-01 | 2.45782301e-01 |
| -5.96998632e-02 | 6.60616830e-02 | 1.00639639e-02 | -1.01855926e-01 |
| -9.84972343e-02 | 2.15460639e-02 | 7.10797071e-01 | -5.26559353e-01 |
| -1.17038496e-01 | 2.31536612e-01 | -8.56231228e-02 | -2.26396183e-03 |
| -2.93601036e-01 | 4.16477233e-01 | -2.22558854e-03 | -1.17770284e-01 |
| -1.19138829e-01 | 1.13671571e-01 | 9.93726432e-01 | 1.39758721e-01 |
| 1.25106126e-01 | 1.07978016e-01 | 2.35231429e-01 | 5.32461345e-01 |
| -3.36723059e-01 | -1.91390365e-01 | -3.41466926e-02 | 2.04272419e-01 |
| 3.99794936e-01 | -3.68103296e-01 | 3.41424704e-01 | 3.49625945e-02 |
| -1.11670852e-01 | 2.27559637e-02 | 2.34480172e-01 | -2.32365802e-01 |
| 7.58685827e-01 | 2.32798681e-01 | 3.38021666e-01 | 3.87294561e-01 |
| 3.44876170e-01 | -1.35005284e-02 | 1.31308585e-01 | 4.38787222e-01 |
| 2.80471355e-01 | 9.53633562e-02 | 4.31812137e-01 | 4.93529513e-02 |
| 1.81254774e-01 | 4.84399140e-01 | 3.12279254e-01 | 3.22619766e-01 |
| -3.78820211e-01 | 3.57520673e-03 | 2.24363536e-01 | -2.36703023e-01 |
| -3.15017700e-02 | 1.25339348e-02 | -2.08557606e-01 | 1.35648355e-01 |
| 2.87893504e-01 | 3.10213286e-02 | -1.44922763e-01 | 1.20818876e-01 |
| -3.20584685e-01 | 2.25151509e-01 | -3.21569853e-02 | 2.96437204e-01 |
| 4.17483568e-01 | 3.73350322e-01 | 2.09398106e-01 | -3.01356763e-01 |
| 2.78937221e-01 | -1.71682253e-01 | 1.87927410e-01 | -1.46769211e-01 |
| -9.54513177e-02 | -1.13339603e-01 | 4.01611030e-01 | -4.56782043e-01 |
| 1.58187225e-01 | 5.79131067e-01 | 1.26948982e-01 | 3.95509511e-01 |
| 1.94521204e-01 | -8.74290764e-02 | 2.36399487e-01 | -2.04948694e-01 |
| 2.26071551e-01 | 3.23313326e-01 | 3.57218206e-01 | -9.69795436e-02 |
| 1.61064252e-01 | 1.14995196e-01 | 1.29180662e-02 | -1.34645462e-01 |
| -9.23883095e-02 | 9.10715312e-02 | 4.70689446e-01 | 4.99337137e-01 |
| 5.79181425e-02 | 2.86877841e-01 | 3.39548856e-01 | 2.92197824e-01 |
| 1.55621916e-01 | -3.91971972e-03 | 2.20234036e-01 | 1.75316278e-02 |
| 2.91753411e-01 | 2.37604037e-01 | -5.52873254e-01 | -1.10086471e-01 |
| -2.86798298e-01 | 2.01074362e-01 | -4.49621938e-02 | 9.05299932e-02 |
| 4.32908326e-01 | 1.73638463e-01 | 4.51677710e-01 | 8.07022750e-02 |
| 4.68049556e-01 | 5.35006821e-01 | 4.65715855e-01 | -4.00190413e-01 |
| 1.50149941e-01 | 2.06193879e-01 | -3.44261438e-01 | -1.14299208e-01 |
| 1.94918841e-01 | 4.69300836e-01 | 2.35723168e-01 | -2.95271575e-01 |
| -1.39309734e-01 | -2.75069326e-02 | -3.07062715e-02 | 3.05191781e-02 |
| -1.08360894e-01 | 3.68736722e-02 | 5.25271714e-01 | 1.23089299e-01 |
| 5.17777085e-01 | 4.19701226e-02 | 4.38239068e-01 | 2.33220875e-01 |
| -1.35740787e-01 | -1.28017187e-01 | 3.35970163e-01 | 3.20071697e-01 |
| 3.74287158e-01 | -2.13398814e-01 | 5.84878325e-01 | 5.75030267e-01 |
| -4.24305677e-01 | 2.82891065e-01 | 2.24056497e-01 | 8.82427841e-02 |
| 7.85899907e-02 | -4.15049531e-02 | 3.17936987e-01 | -1.65984035e-02 |
| -3.98845404e-01 | -2.44400263e-01 | -4.35962260e-01 | -2.16005921e-01] |
| [6.29256964e-01 | 8.69122982e-01 | 6.26099169e-01 | 7.29844868e-01 |
| 9.38836098e-01 | 3.86660874e-01 | 1.50953561e-01 | 6.24971509e-01 |
| 2.68268764e-01 | 1.32068086e-00 | 7.16712832e-01 | 1.69400430e-01 |
| 1.27090693e-00 | 6.21859968e-01 | 7.29668617e-01 | 1.09572554e-00 |
| 1.57797098e-00 | 1.28137385e-02 | 2.52728224e-01 | -7.10064769e-02 |
| 4.70115781e-01 | 2.75339812e-01 | 1.00118005e-00 | 7.72788703e-01 |
| 7.72685528e-01 | 7.07936466e-01 | -3.12487334e-02 | 1.31623030e-01 |
| 3.53191078e-01 | 7.34749317e-01 | -1.07719205e-01 | 4.32242334e-01 |
| 4.09153640e-01 | 3.62863056e-02 | 8.69854629e-01 | 3.78474556e-02 |
| 1.08034208e-01 | 7.25081205e-01 | 6.58174455e-01 | 3.79202008e-01 |
| 1.08729422e-00 | 7.11855173e-01 | 1.82702196e-00 | 1.32244253e-01 |
| 4.42164212e-01 | 8.82805884e-01 | 1.01708162e-00 | 4.11267102e-01 |
| 1.33765376e-00 | 8.09563279e-01 | 1.88087255e-01 | 4.65755701e-01 |
| 4.63963985e-01 | 6.33813262e-01 | 6.24162853e-01 | 6.28001511e-01 |
| 2.58363008e-01 | 6.41754210e-01 | -9.78560001e-03 | 7.15173900e-01 |
| 5.50309479e-01 | 2.77657121e-01 | 2.94407874e-01 | 4.97253776e-01 |
| 9.25017715e-01 | 7.94409096e-01 | 9.60001588e-01 | 1.19297504e-00 |
| 6.37466967e-01 | 5.82836747e-01 | 5.25941193e-01 | -6.13092482e-01 |
| 7.96230793e-01 | 6.43102527e-01 | 3.23359102e-01 | 4.24042553e-01 |
| 8.43556583e-01 | 2.16499880e-01 | 3.68021369e-01 | 2.92142630e-01 |
| 8.59621942e-01 | 8.08218002e-01 | 3.76532614e-01 | 4.81609851e-01 |
| 1.80167627e-00 | 3.51648450e-01 | 2.36754596e-01 | 5.88980913e-01 |
| 8.34663272e-01 | -2.52252668e-01 | 1.03433120e-00 | -2.31774077e-02 |
| 6.05782628e-01 | 1.20448971e-01 | 5.53407431e-01 | 8.18883955e-01 |
| 5.03771603e-01 | 1.01181972e-00 | 2.97039956e-01 | 1.32249033e-00 |
| 3.23018461e-01 | 5.55837512e-01 | -5.38309962e-02 | 7.04688728e-01 |
| 6.44483268e-01 | 4.27038163e-01 | 6.91263497e-01 | 1.40774679e-00 |
| 5.05819857e-01 | 9.71441269e-01 | 9.26360786e-01 | 1.25265455e-00 |
| 1.09532917e-00 | 8.74210536e-01 | 1.03268933e-00 | 1.73037559e-00 |
| 3.72999161e-01 | -4.53161336e-02 | 5.57882488e-01 | 2.45530292e-01 |
| 5.77441990e-01 | 6.61034167e-01 | -3.39653157e-02 | 1.79213762e-01 |
| 4.73937094e-01 | 5.49713850e-01 | 9.13817406e-01 | 1.52247238e-00 |
| 2.41994470e-01 | 4.26037252e-01 | 1.38055727e-01 | 1.60798520e-01 |
| 2.82267213e-01 | 8.54195833e-01 | 1.02671647e-00 | 9.85363066e-01 |
| 6.50847018e-01 | 1.27052104e-00 | 3.91415477e-01 | 1.20768929e-00 |
| 2.83813179e-01 | 5.06057680e-01 | 4.85995293e-01 | 3.91306281e-01 |
| 7.73144782e-01 | 6.80195391e-01 | 1.29831538e-01 | 5.82260132e-01 |

TABLE $W_h^1$-continued

| | | | |
|---|---|---|---|
| 7.94662535e−01 | 1.24587715e−00 | 4.94321316e−01 | 6.94266140e−01 |
| 6.96010232e−01 | 4.56971496e−01 | 1.22448158e−00 | 2.82310337e−01 |
| 6.17907904e−02 | 2.30766147e−01 | 9.22429144e−01 | 2.59005904e−01 |
| 6.15109324e−01 | 8.60729873e−01 | 8.49460244e−01 | 8.36933970e−01 |
| 9.11110491e−02 | 7.49668360e−01 | 1.01714337e−00 | 4.50844094e−02 |
| 7.03958511e−01 | 3.59776646e−01 | −2.92175382e−01 | 8.76781225e−01 |
| 4.80658174e−01 | 7.27399051e−01 | 1.41801763e−00 | 8.20054859e−02 |
| 6.59858048e−01 | 2.57468015e−01 | 4.67681646e−01 | 5.17696917e−01 |
| 2.09855333e−01 | 5.27750492e−01 | 2.62766927e−01 | 1.23414719e−00 |
| 5.46940744e−01 | 2.64015526e−01 | 4.65465754e−01 | 4.92387682e−01 |
| 3.29138577e−01 | 3.46055776e−01 | 3.82521600e−01 | 7.84738004e−01 |
| 1.71213374e−01 | 5.34278512e−01 | 8.45456243e−01 | 2.17439830e−01 |
| 7.25462496e−01 | 1.22492635e−00 | 2.81238735e−01 | 2.86588877e−01 |
| 1.13282728e−00 | 2.28473723e−01 | 5.29257715e−01 | 2.61476054e−03 |
| 3.27750176e−01 | 7.82356024e−01 | −9.54013169e−02 | 8.04186702e−01 |
| 5.93156636e−01 | 7.10783005e−01 | 9.80319381e−01 | 7.23633826e−01 |
| 2.77573496e−01 | 9.76809740e−01 | 6.48452461e−01 | 9.02854145e−01 |
| 4.32131141e−01 | 5.35358965e−01 | 4.40571010e−01 | 4.78176564e−01 |
| 6.60012066e−01 | 6.50240660e−01 | 1.12072968e−00 | 3.72822315e−01 |
| 5.59990346e−01 | 4.63407159e−01 | 3.15751225e−01 | 1.19571662e−00 |
| 5.59635341e−01 | 5.19850671e−01 | 6.52427435e−01 | 5.34650207e−01 |
| 9.94009852e−01 | 2.21984789e−01 | 8.27995598e−01 | 9.83289957e−01 |
| 4.17920500e−01 | 7.71579504e−01 | 2.88166076e−01 | 1.68618071e−00 |
| 7.42983043e−01 | 1.66423023e−00 | 7.00147033e−01 | 2.02913865e−01 |
| 6.84448063e−01 | 2.65414774e−01 | 5.86843491e−01 | 2.56265551e−01 |
| 8.38941336e−01 | 6.03821933e−01 | 5.00650942e−01 | 1.26891601e−00 |
| 5.58459222e−01 | 9.85815525e−01 | 5.08266270e−01 | 6.02855146e−01] |
| [7.62718558e−01 | −2.85993248e−01 | −8.35890397e−02 | 2.13035360e−01 |
| 8.87574330e−02 | 1.40469801e−00 | 1.03528690e−00 | −3.77466202e−01 |
| 9.25161719e−01 | 5.96989214e−01 | 1.21649396e−00 | −9.87663493e−02 |
| −1.37975767e−01 | 6.14416182e−01 | −2.43484527e−01 | −3.21247935e−01 |
| 1.87485471e−01 | 1.93207741e−01 | 6.66597128e−01 | −4.74019557e−01 |
| 9.80552852e−01 | 6.97120070e−01 | 6.27300799e−01 | 5.20186245e−01 |
| 6.04034901e−01 | 3.47040236e−01 | 9.05195415e−01 | 4.44450900e−02 |
| −5.55797964e−02 | 9.85491276e−01 | 7.89098203e−01 | 8.13632235e−02 |
| 9.43355739e−01 | −1.68852374e−01 | −3.03357840e−01 | 4.42672968e−01 |
| 4.56780851e−01 | 6.72850966e−01 | 7.35805035e−01 | 9.09024119e−01 |
| 5.30339181e−01 | 6.46072745e−01 | 9.06041205e−01 | 9.13503230e−01 |
| 6.58160686e−01 | −4.71518129e−01 | 9.20151889e−01 | −3.18050057e−01 |
| 8.22283566e−01 | 1.28732800e−01 | 9.44289446e−01 | 3.03584218e−01 |
| 3.28548104e−01 | 4.79497582e−01 | −2.26510927e−01 | −1.07831769e−01 |
| 4.49587762e−01 | 5.01665115e−01 | 2.40854874e−01 | 3.74287665e−01 |
| 7.56834984e−01 | 8.76413882e−01 | −1.78617418e−01 | 8.67256463e−01 |
| 3.71688515e−01 | 9.27654356e−02 | 2.27444574e−01 | 1.32104397e−00 |
| −4.87631381e−01 | 6.76111460e−01 | 3.46199125e−01 | −1.59729898e−01 |
| 2.56115794e−01 | 6.59757197e−01 | 8.87768567e−01 | −1.86595768e−01 |
| 1.09426439e−00 | 1.40244317e−00 | −9.70558822e−02 | 3.50904524e−01 |
| 1.00917828e−00 | 3.59565139e−01 | −3.55750248e−02 | 5.80092132e−01 |
| 7.89687157e−01 | 2.77584821e−01 | 4.19611394e−01 | 5.56098044e−01 |
| −1.49514943e−01 | 3.96631688e−01 | −3.53500038e−01 | −5.01311958e−01 |
| 1.96425050e−01 | −1.22486569e−01 | 3.15801725e−02 | 4.48182076e−01 |
| 9.01099861e−01 | −3.41175765e−01 | 1.69436410e−01 | 1.25249937e−01 |
| 3.24985027e−01 | 8.80813658e−01 | 1.06407034e−00 | 3.18540275e−01 |
| −3.77013683e−01 | 8.79113734e−01 | 9.35029462e−02 | 5.47977209e−01 |
| 1.34828496e−00 | 1.17714977e−00 | −7.71263093e−02 | 5.25240600e−01 |
| 6.40280724e−01 | 1.67367235e−01 | −2.40982547e−01 | 5.04406929e−01 |
| 6.76222563e−01 | 1.35106623e−00 | 1.26267327e−02 | 1.81054935e−01 |
| −4.39309366e−02 | 6.85910061e−02 | 1.65476650e−01 | 1.29471183e−00 |
| 5.12612343e−01 | 1.18366981e−00 | 1.41165721e−00 | 5.17007351e−01 |
| 4.51250970e−01 | 6.66195512e−01 | 1.05082944e−01 | 8.68473172e−01 |
| 2.66277343e−01 | −9.19052679e−03 | −3.54842037e−01 | 3.99223149e−01 |
| −3.90400109e−03 | −1.40163496e−01 | 3.53885621e−01 | 1.08009838e−00 |
| 6.51010692e−01 | 9.23445344e−01 | 4.23455507e−01 | 1.12606061e−00 |
| 2.18300551e−01 | 3.66884768e−01 | 4.06357467e−01 | 7.53808841e−02 |
| −2.37006381e−01 | 2.20785245e−01 | 1.62344217e−01 | 6.51738048e−01 |
| 4.30328429e−01 | 4.27911162e−01 | 2.13868231e−01 | 5.09213984e−01 |
| 2.75709480e−01 | 2.03130767e−01 | 8.48217785e−01 | 7.15824246e−01 |
| −5.44518888e−01 | 2.90873647e−01 | −6.95376754e−01 | 7.30938554e−01 |
| 1.37544596e−00 | 1.91558838e−01 | 5.08567333e−01 | 1.05990994e−00 |
| 3.49079460e−01 | 7.07772195e−01 | −4.66210634e−01 | 6.35306120e−01 |
| 1.26136327e−01 | −3.49475175e−01 | 9.74806607e−01 | 4.70802844e−01 |
| 1.23783231e−00 | 2.34904006e−01 | 2.69894898e−01 | 5.44931769e−01 |
| −3.53190720e−01 | 1.97820738e−01 | 5.92534602e−01 | 9.68396306e−01 |
| 4.58469987e−01 | −2.06060365e−01 | 1.59422189e−01 | 6.02990426e−02 |
| −8.02627802e−01 | 4.32570547e−01 | 7.37498164e−01 | 6.82180822e−01 |
| −1.69299424e−01 | 7.97582194e−02 | −3.77822906e−01 | 1.60172895e−01 |
| 1.38079047e−01 | 1.30588663e−00 | −5.32870321e−03 | 2.94082284e−01 |
| 9.66834068e−01 | 1.40474588e−01 | 4.16175187e−01 | 2.75434889e−02 |
| 8.12092781e−01 | 5.62277853e−01 | 7.62126625e−01 | 2.83385217e−01 |
| 9.99401510e−02 | 1.27343214e−00 | 6.44147336e−01 | −1.81591709e−03 |

TABLE $W_h^1$-continued

| | | | |
|---|---|---|---|
| 1.26089931e−01 | 4.21434373e−01 | 1.84732571e−01 | 4.35671210e−01 |
| 7.06712842e−01 | 5.43734848e−01 | 7.18270659e−01 | 6.40309691e−01 |
| 6.25470102e−01 | 1.39018133e−01 | 5.04673600e−01 | −1.04757994e−01 |
| 7.85873175e−01 | 8.61517310e−01 | 4.17003542e−01 | 7.34598815e−01 |
| 3.33579928e−01 | 6.96644932e−02 | 7.16480017e−01 | 4.31235760e−01 |
| 1.46806017e−01 | 7.58129358e−01 | 9.37449932e−01 | 7.64230788e−02 |
| −5.61824143e−02 | 8.09839010e−01 | 7.44611561e−01 | 1.43576249e−01 |
| 1.21767008e−00 | 8.01265121e−01 | −4.47866350e−01 | 2.97907263e−01 |
| −2.00950906e−01 | 7.96024799e−01 | 1.39214054e−01 | −2.26887271e−01 |
| −4.40543257e−02 | 4.55320895e−01 | −7.35944584e−02 | 1.26878762e−00 |
| 6.55185699e−01 | 3.78956199e−01 | 4.85393912e−01 | 2.48972811e−02] |
| [6.20283842e−01 | −7.03603089e−01 | −5.27839065e−01 | −4.65642750e−01 |
| −3.33319217e−01 | −4.02364939e−01 | −1.13778859e−01 | −8.16464961e−01 |
| 1.45440012e−01 | −7.20245600e−01 | 3.02129716e−01 | 4.54149172e−02 |
| −4.71205562e−02 | −5.95747769e−01 | −4.81958352e−02 | 2.54509956e−01 |
| 1.89132676e−01 | −1.01153076e−00 | −1.24646115e−00 | −5.07983387e−01 |
| −3.84357087e−02 | −5.85669637e−01 | 2.28424326e−01 | 5.36138639e−02 |
| 3.99049670e−01 | −2.96938926e−01 | 4.11421716e−01 | −7.64408559e−02 |
| 1.90241322e−01 | 7.21080080e−02 | −5.18967867e−01 | −5.14693201e−01 |
| −3.23951006e−01 | −6.13126159e−01 | −1.84448004e−01 | −4.33310866e−02 |
| 2.45815560e−01 | −8.78774941e−01 | −3.03194135e−01 | 7.90106580e−02 |
| −2.41215035e−01 | −2.97246516e−01 | 1.39479887e−00 | −5.29036224e−01 |
| −4.80768055e−01 | −6.41705871e−01 | −4.12240289e−02 | −5.54108560e−01 |
| 4.23806071e−01 | −5.09695821e−02 | −1.83853865e−01 | 1.03082418e−00 |
| −2.63323244e−02 | 8.76703411e−02 | 2.16406778e−01 | 9.11318958e−01 |
| −6.85733974e−01 | 2.50359744e−01 | −3.99793029e−01 | 4.77000087e−01 |
| 5.23662940e−02 | −6.03819668e−01 | −9.22925696e−02 | −7.05550388e−02 |
| 1.23710823e−00 | −6.39856815e−01 | 2.87395120e−01 | 4.96128857e−01 |
| −9.40393865e−02 | 1.23790550e−00 | −1.34358004e−01 | −6.96497440e−01 |
| −5.95059633e−01 | −1.71296269e−01 | −3.12312990e−01 | 6.53079450e−01 |
| −5.80116332e−01 | −8.49615857e−02 | −5.38036704e−01 | −1.84648111e−01 |
| −1.45025834e−01 | −2.42575258e−01 | −7.95843124e−01 | −3.22658062e−01 |
| 1.22265840e−01 | −3.70828450e−01 | −2.63417453e−01 | 4.63279523e−02 |
| −5.99481106e−01 | 6.08332008e−02 | 1.54887334e−01 | 8.47524330e−02 |
| −1.89382747e−01 | −1.56539418e−02 | −1.43062115e−01 | 3.30512151e−02 |
| −2.64083833e−01 | 3.73268872e−01 | 1.83303043e−01 | −1.55891404e−01 |
| −5.57694554e−01 | −3.62207621e−01 | −1.08736001e−01 | −4.03042138e−01 |
| −5.27345240e−01 | −6.74294651e−01 | −1.87823191e−01 | −6.96657419e−01 |
| 1.19106483e−00 | −5.56735992e−01 | −5.94069541e−01 | −1.61857337e−01 |
| 2.79147029e−02 | 2.82812536e−01 | −7.46450007e−01 | −7.86187530e−01 |
| −5.95375359e−01 | 2.36249477e−01 | −2.67476141e−01 | 5.07831097e−01 |
| −6.60143197e−01 | −4.95299757e−01 | −1.88834444e−01 | −4.53693092e−01 |
| −3.28621894e−01 | −7.88096040e−02 | 2.76762862e−02 | −3.06123763e−01 |
| −3.28883171e−01 | −5.71794689e−01 | −3.03891033e−01 | −3.27134132e−01 |
| −5.18044889e−01 | 2.24831194e−01 | −9.39309657e−01 | −2.14976147e−01 |
| −6.26485050e−02 | −5.01358747e−01 | −2.95589149e−01 | −2.29984030e−01 |
| −1.16088353e−01 | −1.57833155e−02 | 1.09676731e−00 | 1.70642838e−01 |
| −3.99862379e−01 | −2.76814699e−01 | −1.84236631e−01 | −3.95556539e−02 |
| −1.41951114e−01 | −2.39002891e−02 | −2.08247632e−01 | 6.03399038e−01 |
| 2.87258495e−02 | 2.88098872e−01 | 4.18203682e−01 | 5.97364120e−02 |
| −5.55242002e−01 | −3.58669370e−01 | −2.08250806e−01 | −3.38625669e−01 |
| −2.98008859e−01 | 2.87162483e−01 | −5.36048830e−01 | −1.57653913e−01 |
| 1.31452426e−01 | 5.13508558e−01 | −6.69196010e−01 | −1.69232294e−01 |
| −4.27470714e−01 | −3.28347534e−01 | −3.04807574e−01 | −8.01217794e−01 |
| −4.57270443e−01 | −3.64712059e−01 | 1.08880687e−00 | 1.12444973e−00 |
| −1.69643030e−01 | −3.69971931e−01 | −3.45518768e−01 | 5.88837683e−01 |
| −4.29356128e−01 | 4.60683890e−02 | −2.84155488e−01 | −2.16223225e−01 |
| 2.91315198e−01 | 1.64933309e−01 | −3.58046055e−01 | −2.87155747e−01 |
| −5.85429728e−01 | 2.69442238e−03 | −1.74330428e−01 | −1.38846874e−01 |
| −2.77521104e−01 | −2.31183439e−01 | −6.67519987e−01 | −9.66598511e−01 |
| −5.07679403e−01 | 9.49541450e−01 | −4.21300113e−01 | 2.00102311e−02 |
| 5.88142693e−01 | −2.33123764e−01 | −3.88602197e−01 | −3.91536832e−01 |
| −4.85532582e−02 | −4.43226937e−03 | −4.34768081e−01 | −2.26935253e−01 |
| −1.57544032e−01 | −5.69563270e−01 | 1.80615500e−01 | −5.15471637e−01 |
| −8.50558937e−01 | −1.71722531e−01 | −3.66887063e−01 | −5.37340105e−01 |
| −1.19005948e−01 | −1.03571371e−03 | −1.02914050e−01 | 4.71388455e−03 |
| −8.05398151e−01 | −6.75615549e−01 | 3.11843544e−01 | 5.53993396e−02 |
| 6.41321242e−01 | 5.94120800e−01 | 2.16725599e−02 | 4.20765221e−01 |
| −4.26823199e−01 | 1.35322481e−01 | −3.40084523e−01 | −3.69597197e−01 |
| −7.39305556e−01 | −4.39340696e−02 | −6.08897842e−02 | −4.83287007e−01 |
| −2.98280537e−01 | −7.83744991e−01 | −2.06950203e−01 | 4.39369082e−01 |
| −1.70810997e−01 | 4.06387933e−02 | −8.94095600e−01 | −3.61643344e−01 |
| 5.37081137e−02 | −1.70563668e−01 | −2.03440249e−01 | −2.38194913e−01 |
| −5.68029098e−02 | −1.92222357e−01 | −1.00231320e−01 | 1.35445964e−00 |
| −4.09239799e−01 | −2.58366078e−01 | 1.03804134e−01 | −5.73826730e−01] |
| [1.01154536e−01 | 2.77917206e−01 | −1.08720679e−02 | −2.57795900e−01 |
| 1.97125986e−01 | 2.02137679e−01 | 6.60700619e−01 | 1.08531885e−01 |
| 3.56300473e−01 | 6.03782572e−02 | 1.76938638e−01 | 4.68344152e−01 |
| 6.68191969e−01 | −1.51826143e−01 | −2.94846296e−01 | −1.03878409e−01 |
| 1.30537951e−00 | 3.66123676e−01 | 3.14623535e−01 | 6.63838685e−01 |

TABLE $W_h^1$-continued

| | | | |
|---|---|---|---|
| 4.01368171e-01 | 1.53731316e-01 | 8.48792791e-01 | 1.25322104e-01 |
| 3.59387189e-01 | -5.87781928e-02 | 1.17057241e-01 | 4.15882841e-02 |
| 1.27117246e-01 | 5.61778963e-01 | -1.58311367e-01 | 4.91382629e-01 |
| 7.92691588e-01 | 3.70909303e-01 | 7.81408727e-01 | 7.21606538e-02 |
| 6.61664426e-01 | 3.81925046e-01 | 4.00117725e-01 | 1.04104333e-01 |
| 2.28565857e-01 | 3.18266988e-01 | 6.62741780e-01 | 3.84545445e-01 |
| 7.03241348e-01 | -9.63959172e-02 | 3.07079703e-01 | 3.96047235e-01 |
| 1.23510420e-00 | 3.33433777e-01 | 6.66200578e-01 | -1.23217642e-01 |
| 3.94448906e-01 | 4.07798775e-03 | 5.41806281e-01 | 6.22717083e-01 |
| 6.28194511e-01 | 3.87774229e-01 | 5.04191160e-01 | -2.03404620e-01 |
| 7.39804685e-01 | 5.70994020e-01 | 1.34723172e-01 | 3.26464742e-01 |
| 1.47194415e-01 | -3.08631547e-02 | -1.61420498e-02 | -5.11552513e-01 |
| -1.29455596e-01 | -2.05243886e-01 | 4.29647774e-01 | -2.32601184e-01 |
| -3.20299007e-02 | 3.61410618e-01 | 5.19795895e-01 | 5.66817867e-03 |
| 2.32867643e-01 | 4.77673382e-01 | 3.06243867e-01 | 7.44150504e-02 |
| 4.60999869e-02 | 6.06003761e-01 | 5.34407079e-01 | -1.13566630e-01 |
| 3.02200322e-03 | 3.78487527e-01 | 4.73782897e-01 | 2.82573223e-01 |
| 3.63323987e-01 | 1.50258794e-01 | 4.40141737e-01 | 3.39325845e-01 |
| 1.90133482e-01 | 3.85763794e-01 | 4.79711175e-01 | 3.27582926e-01 |
| 1.86149120e-01 | 1.04278289e-01 | 6.37136877e-01 | 3.26242626e-01 |
| 1.69822678e-01 | 2.73824811e-01 | 4.14525598e-01 | -8.91708657e-02 |
| 1.38522834e-01 | 7.82671750e-01 | 2.05315530e-01 | 4.47805226e-01 |
| 2.51531780e-01 | 1.00107402e-01 | 2.45954946e-01 | 6.06231689e-01 |
| 3.00897479e-01 | 5.19905575e-02 | 3.37986112e-01 | -4.30471539e-01 |
| 1.97101012e-01 | 1.63109958e-01 | 4.84082729e-01 | 5.61694205e-01 |
| 1.12837248e-01 | 8.32695246e-01 | -7.08963394e-01 | 3.46041210e-02 |
| 1.58316284e-01 | -2.45442092e-02 | 8.19586933e-01 | 2.01293677e-01 |
| 3.59792769e-01 | 1.68362305e-01 | 1.69217184e-01 | 2.45529581e-02 |
| 2.41188347e-01 | -2.67178155e-02 | 1.14000320e-00 | 3.16820949e-01 |
| -1.16317548e-01 | 1.06103972e-01 | 4.41673040e-01 | 2.98209846e-01 |
| 1.59747601e-01 | 8.80365491e-01 | 5.94002247e-01 | 4.14572917e-02 |
| 3.31539243e-01 | -2.83197254e-01 | 3.13025624e-01 | 2.34815657e-01 |
| 1.34963199e-01 | 2.95547634e-01 | 2.16961265e-01 | 7.46864855e-01 |
| 1.37981132e-01 | 5.79924285e-01 | 9.97282788e-02 | 2.79057026e-01 |
| 1.06873429e-00 | 4.06922579e-01 | 5.94365001e-01 | 3.65198612e-01 |
| 2.55910575e-01 | 5.59036970e-01 | 6.89558744e-01 | 3.50010216e-01 |
| 5.15298247e-01 | 2.33276919e-01 | -1.97047159e-01 | 6.53516173e-01 |
| 4.71911579e-01 | 5.84289014e-01 | 5.70558906e-01 | 5.28028429e-01 |
| 1.28692955e-01 | -1.32693440e-01 | 6.64767444e-01 | 9.62265313e-01 |
| 7.99730599e-01 | 9.97392774e-01 | 1.87740579e-01 | 4.04737622e-01 |
| 3.48107874e-01 | -1.09304346e-01 | 4.04832125e-01 | 4.05616671e-01 |
| 2.06827283e-01 | 4.91220117e-01 | 4.37086046e-01 | 4.50683922e-01 |
| 4.70056921e-01 | -1.17781892e-01 | 3.58685911e-01 | 4.10874426e-01 |
| 3.26220781e-01 | 5.66401303e-01 | 4.42711025e-01 | 1.54595897e-01 |
| -3.13556530e-02 | 6.55465946e-02 | 4.06359673e-01 | 2.52238121e-02 |
| -3.61764252e-01 | 8.19586143e-02 | 1.51761845e-01 | 2.94549137e-01 |
| 6.95955634e-01 | 5.50669253e-01 | 4.12465304e-01 | 3.22586656e-01 |
| 2.93197155e-01 | 6.18189536e-02 | -2.15485282e-02 | 5.95902979e-01 |
| 6.50545955e-01 | 3.76719654e-01 | 1.30795956e-01 | 4.58257310e-02 |
| -1.08399935e-01 | 3.93663794e-01 | 2.06728756e-01 | -1.79608017e-02 |
| 2.50333250e-01 | 5.88119030e-01 | 1.19024873e-01 | 9.59534664e-03 |
| -3.02911967e-01 | 7.78298080e-01 | 8.77325594e-01 | 2.02983871e-01 |
| 8.31903443e-02 | 4.42849964e-01 | 5.15081584e-01 | 3.96966666e-01 |
| -1.77299529e-01 | 7.04331398e-01 | -1.15709290e-01 | 3.92913789e-01 |
| 4.58266079e-01 | 3.33271235e-01 | -5.93235232e-02 | 3.11506480e-01 |
| 6.27116501e-01 | 1.06018990e-01 | 4.30058092e-01 | 5.02733290e-01 |
| 1.14966440e-00 | 3.31150562e-01 | 3.50871570e-02 | 3.46941769e-01 |
| -2.49467865e-01 | 7.60982335e-01 | 9.22192037e-02 | -3.18208665e-01 |
| 2.14522406e-02 | 3.19608837e-01 | 6.66638017e-01 | 2.93815434e-01] |
| [4.49114492e-01 | -1.95372969e-01 | 1.38061389e-01 | 1.90588772e-01 |
| 7.87321210e-01 | 1.21098733e-00 | 6.79323962e-03 | 7.88581610e-01 |
| 9.05288458e-01 | 4.63872850e-01 | 4.91413862e-01 | -2.80715823e-01 |
| 9.00635302e-01 | 2.88011823e-02 | 1.47035286e-01 | 2.25763559e-01 |
| -1.91008821e-02 | 1.21521354e-02 | 4.43814695e-01 | 2.76879370e-01 |
| 7.73897827e-01 | -5.20377494e-02 | 4.02149260e-01 | 9.38157082e-01 |
| 2.55153291e-02 | 7.23608077e-01 | 5.42669654e-01 | -2.54812866e-01 |
| -2.69059896e-01 | 8.32886755e-01 | 1.97142705e-01 | 7.66323656e-01 |
| 6.75960660e-01 | 3.63471285e-02 | 3.20093423e-01 | 3.22106481e-01 |
| 8.80065560e-01 | 6.66655719e-01 | -1.13993660e-01 | 6.32900417e-01 |
| 2.96166241e-01 | 4.96274978e-01 | 9.74756598e-01 | 3.46828759e-01 |
| 6.14474192e-02 | 1.19297616e-01 | 7.53376484e-01 | 1.21534131e-01 |
| 7.26694584e-01 | 1.04771577e-01 | 4.52006310e-01 | 3.36841881e-01 |
| 1.98734909e-01 | 2.95154065e-01 | -8.76128525e-02 | -1.10270068e-01 |
| 6.84108257e-01 | 8.75689268e-01 | 3.50867063e-01 | 7.45495111e-02 |
| 7.45618224e-01 | 1.08974361e-00 | 2.57949144e-01 | 5.45037873e-02 |
| 3.79504383e-01 | 6.17734075e-01 | 7.10972488e-01 | 5.21715760e-01 |
| 6.12965345e-01 | 1.30042881e-01 | 1.35802054e-00 | -1.91335574e-01 |
| 2.15512604e-01 | 3.56466144e-01 | 2.35636085e-01 | 1.74694061e-01 |
| 3.25124413e-01 | 4.45151538e-01 | 5.11717379e-01 | 6.21401906e-01 |
| 3.52532983e-01 | 5.66837549e-01 | -6.68631196e-02 | 2.49898404e-01 |

TABLE $W_h^1$-continued

| | | | |
|---|---|---|---|
| 3.81720304e−01 | 2.72765756e−01 | 1.48675099e−01 | −1.97985042e−02 |
| −7.19581395e−02 | 1.02410555e−01 | 6.46810591e−01 | 2.67017871e−01 |
| 2.19767004e−01 | −1.89473499e−02 | 3.83148521e−01 | 2.18471870e−01 |
| 2.76807398e−01 | −1.68567955e−01 | 7.14154124e−01 | 2.30026711e−02 |
| 2.60927141e−01 | 6.67493820e−01 | 4.00934607e−01 | 4.41344470e−01 |
| −1.60033271e−01 | 3.11650425e−01 | 5.93348861e−01 | 4.46214378e−01 |
| 1.03976868e−01 | 3.65127623e−02 | 6.08915746e−01 | 1.84088141e−01 |
| 6.55293882e−01 | 7.19791412e−01 | 3.63386452e−01 | 4.08490524e−02 |
| 5.71421504e−01 | 2.54599512e−01 | 7.54213274e−01 | 4.32753533e−01 |
| 3.86291355e−01 | 9.54538137e−02 | 5.26438832e−01 | 5.79725444e−01 |
| 5.13447225e−01 | 2.11173743e−01 | 1.09123647e−00 | 5.81979752e−01 |
| 1.02554846e−00 | 7.36328781e−01 | −2.14690760e−01 | 3.46697599e−01 |
| 2.90273964e−01 | 1.81750461e−01 | 6.65395781e−02 | 7.20505714e−01 |
| −1.14615284e−01 | 3.63284536e−02 | 6.20939553e−01 | 7.47605503e−01 |
| 6.22240245e−01 | 4.52422291e−01 | 7.70839751e−01 | 3.19990188e−01 |
| 2.79015992e−02 | 9.67976227e−02 | 4.33075190e−01 | 9.96040031e−02 |
| 2.25614101e−01 | 7.98104852e−02 | 4.49344069e−01 | 2.71856278e−01 |
| 1.89469844e−01 | 1.05781808e−01 | 1.21874120e−02 | 3.67267132e−01 |
| 1.94418132e−01 | 2.28641137e−01 | 5.62932193e−01 | 2.82008827e−01 |
| 4.56098855e−01 | 4.22775537e−01 | 5.20720065e−01 | 7.26791382e−01 |
| −1.09141067e−01 | 1.87345013e−01 | 1.00397241e−00 | 5.92485785e−01 |
| 4.26517099e−01 | 4.29344267e−01 | 7.41126835e−01 | 2.20927373e−01 |
| 4.22788441e−01 | 3.31983358e−01 | 3.58648598e−01 | 8.46790731e−01 |
| 3.31019014e−01 | 9.48350728e−02 | 4.07304138e−01 | 7.09034428e−02 |
| −1.26424909e−01 | 1.50760725e−01 | 5.38778543e−01 | 1.15496135e−00 |
| 1.19399585e−01 | 3.17517281e−01 | 1.49779767e−01 | 2.29092211e−01 |
| 1.19226284e−01 | 3.12765747e−01 | 3.90583605e−01 | 4.69338030e−01 |
| 4.77595419e−01 | 3.37524533e−01 | 4.36324805e−01 | 5.45465708e−01 |
| 2.83340394e−01 | 2.96926677e−01 | 2.70363241e−01 | 1.55975506e−01 |
| 4.59511012e−01 | 5.69660604e−01 | −8.43491554e−02 | 3.93049568e−01 |
| 2.92746365e−01 | 5.69582045e−01 | 4.04037088e−01 | −5.22312708e−02 |
| 2.53777981e−01 | 4.05403048e−01 | 3.26077104e−01 | 3.78218234e−01 |
| 5.89298844e−01 | 2.62008488e−01 | 3.62884402e−01 | 4.82523769e−01 |
| 7.13749886e−01 | 6.46445274e−01 | −3.19606900e−01 | 4.41100389e−01 |
| 2.00131193e−01 | 1.01847923e−00 | 3.07666361e−01 | 3.01051617e−01 |
| 5.10415196e−01 | 5.53505778e−01 | 7.35539198e−02 | 2.79595584e−01 |
| 3.96092862e−01 | 3.52316946e−01 | 6.62356615e−01 | 5.22656739e−02 |
| 2.69113481e−01 | 9.67214406e−02 | 1.18078828e−00 | 4.43153977e−01 |
| 2.38705739e−01 | 7.96139657e−01 | 3.46414745e−01 | −1.00399077e−01 |
| 3.24095279e−01 | 2.95392632e−01 | −1.66425124e−01 | 1.00196183e−00 |
| 3.25395495e−01 | 4.05922323e−01 | 2.67640024e−01 | −6.98218584e−01 |
| 2.01785833e−01 | 4.06816244e−01 | 5.99922359e−01 | 5.57625592e−01 |
| 2.18957648e−01 | 8.48554730e−01 | −3.64033550e−01 | 4.13584232e−01] |
| [4.56605330e−02 | 6.96277201e−01 | 8.98990214e−01 | 5.84734976e−01 |
| 5.32233603e−02 | 8.33230078e−01 | 7.02062368e−01 | 9.10592794e−01 |
| 8.32866788e−01 | 4.41109419e−01 | 6.93723261e−01 | 2.24395886e−01 |
| −4.35293972e−01 | −1.77631855e−01 | −2.77627613e−02 | 2.80645359e−02 |
| 1.89730868e−01 | −3.55666757e−01 | −2.50467658e−01 | −3.15733522e−01 |
| 6.60614252e−01 | 6.80939078e−01 | 2.63931483e−01 | 1.47762597e−00 |
| −2.47965604e−01 | 1.05350590e−00 | 1.02779925e−00 | 8.01303685e−01 |
| 7.95616508e−01 | 4.00096297e−01 | −4.87486959e−01 | −2.19802827e−01 |
| −8.18219543e−01 | −8.96697164e−01 | 4.78184611e−01 | 9.23941806e−02 |
| 7.47101068e−01 | 3.31616625e−02 | 1.43919438e−02 | 9.98425961e−01 |
| 5.23626566e−01 | 5.19892275e−01 | 2.47965634e−01 | −3.66185233e−02 |
| 1.23966002e−00 | −3.27953696e−01 | 1.02491999e−00 | 1.37208894e−01 |
| 3.72578800e−01 | 1.23654520e−02 | −6.90748036e−01 | 4.22321036e−02 |
| 6.05449736e−01 | 4.72799480e−01 | 1.75551981e−01 | −9.93251335e−03 |
| 4.28338259e−01 | 3.40246439e−01 | −3.11651289e−01 | 3.11510533e−01 |
| 1.09332395e−00 | 6.48530602e−01 | −4.84469160e−02 | 1.93306997e−01 |
| −6.62479177e−02 | 1.21959579e−00 | 6.25264227e−01 | 5.14325142e−01 |
| −8.09799969e−01 | −2.47726277e−01 | 1.02791882e−00 | 2.92567730e−01 |
| 3.59392762e−01 | −2.11814284e−01 | 4.95239109e−01 | 1.10051572e−00 |
| 6.47740185e−01 | 4.49600041e−01 | 4.84132588e−01 | 5.73661804e−01 |
| −4.93208915e−01 | 3.70947510e−01 | −1.58892706e−01 | 1.06954984e−01 |
| −3.56272571e−02 | −6.00776136e−01 | −1.04681924e−02 | 7.54505277e−01 |
| −9.94047001e−02 | −5.03293633e−01 | 3.08690876e−01 | −7.32697010e−01 |
| −4.44196388e−02 | −2.26134911e−01 | −1.76994890e−01 | 8.67099345e−01 |
| 1.06604624e−00 | 1.12024158e−01 | −9.64352548e−01 | −4.79157627e−01 |
| 1.00000143e−00 | 1.36933374e−00 | 9.48860049e−01 | −1.73244346e−02 |
| −4.23692197e−01 | 3.60115498e−01 | 2.94273645e−01 | 1.12371516e−00 |
| −6.09014928e−01 | 7.81075716e−01 | 2.28100598e−01 | 1.04159970e−01 |
| 2.38957271e−01 | 3.92664403e−01 | −4.18196097e−02 | −8.12517762e−01 |
| 6.60028338e−01 | 4.16116059e−01 | 4.27550614e−01 | 6.14665568e−01 |
| 6.84309483e−01 | 4.36050564e−01 | 5.42103648e−01 | 4.37452421e−02 |
| 1.11703582e−01 | 8.19241256e−02 | 8.36680949e−01 | 1.08156061e−01 |
| 1.22042252e−02 | 8.00270498e−01 | 1.02524889e−00 | 1.87168658e−01 |
| 4.72127706e−01 | 4.47642863e−01 | 5.73915839e−01 | −6.29996955e−01 |
| −1.09864533e−01 | 1.37888598e−00 | 6.38014555e−01 | 2.61030674e−01 |
| 1.34057426e−00 | 1.13291144e−00 | 8.26491773e−01 | 6.71196878e−02 |
| 8.48842084e−01 | −1.03718191e−02 | 6.01001978e−01 | 1.16783118e−00 |

TABLE $W_h^1$-continued

| | | | |
|---|---|---|---|
| 4.32332158e−01 | −2.85807699e−01 | 7.96372890e−01 | 1.22178006e−00 |
| 5.01231492e−01 | −7.52944686e−03 | 3.96580175e−02 | 7.62960672e−01 |
| −2.82581598e−01 | 7.82358885e−01 | 8.93189728e−01 | 5.52624941e−01 |
| −1.79985583e−01 | 6.44818664e−01 | 1.42960215e−00 | 9.24088240e−01 |
| −4.77341153e−02 | 3.73005569e−01 | 5.53180635e−01 | 7.13631809e−01 |
| 1.19914405e−01 | −3.20428312e−01 | 2.80565202e−01 | 1.56330717e−00 |
| 6.58436418e−01 | 6.60670698e−01 | 5.58828712e−01 | 7.02645123e−01 |
| 6.28961802e−01 | 4.91026849e−01 | −7.98049122e−02 | 6.55949771e−01 |
| 1.09792829e−00 | 6.62983358e−01 | 8.01499963e−01 | 8.74724925e−01 |
| 1.72480986e−01 | 5.08354306e−01 | 4.58408706e−02 | 4.97625709e−01 |
| 2.93617934e−01 | 3.33075821e−01 | 4.11854267e−01 | 1.10503459e−00 |
| 4.57820684e−01 | 1.24619150e−00 | 3.54629941e−03 | 1.97055638e−01 |
| 8.42335165e−01 | 3.93794417e−01 | 7.58461416e−01 | 2.48798370e−01 |
| −4.20205235e−01 | 5.32762051e−01 | 4.81971174e−01 | −5.30621931e−02 |
| −3.60399038e−01 | 4.29067612e−01 | 8.34058166e−01 | −3.46645974e−02 |
| 8.73475850e−01 | 1.72387749e−01 | 7.87987113e−02 | 1.77058995e−01 |
| 1.20278621e−00 | 4.47273254e−01 | −2.85595536e−01 | −8.06888640e−01 |
| −1.86986297e−01 | 2.60603726e−01 | −4.47515175e−02 | 2.21341684e−01 |
| 3.02536339e−01 | −5.31028032e−01 | 2.03933597e−01 | −1.47054181e−01 |
| 5.76786101e−01 | 3.06227565e−01 | 4.61574316e−01 | 3.16496819e−01 |
| 9.11190063e−02 | 6.92594826e−01 | 7.48708665e−01 | 1.75573602e−01 |
| 4.28938806e−01 | 9.29875433e−01 | 6.75368130e−01 | 9.30396974e−01 |
| −3.19552086e−02 | 9.34434831e−01 | 5.94151497e−01 | 8.99594486e−01 |
| 5.35106003e−01 | −3.87382239e−01 | −3.38086963e−01 | 7.67893791e−01 |
| 9.49026942e−01 | 9.38248217e−01 | 1.12738833e−01 | 2.39518825e−02 |
| 5.31620145e−01 | 4.16608095e−01 | −1.63087144e−01 | 5.05373836e−01 |
| −3.48339714e−02 | 1.22187042e−00 | 2.39631742e−01 | 3.46881539e−01] |
| [6.08408153e−01 | 5.76918125e−01 | 6.95715994e−02 | 5.73342502e−01 |
| 1.30668819e−01 | 3.46524835e−01 | 1.15144260e−01 | 7.44899921e−03 |
| 3.03622276e−01 | 2.88581461e−01 | 4.74897295e−01 | 1.11645214e−01 |
| 1.01238526e−01 | 6.36263132e−01 | 2.33851910e−01 | −1.62149239e−02 |
| 1.86105017e−02 | 3.29582632e−01 | 5.43313265e−01 | 3.36165577e−01 |
| −1.58330411e−01 | 4.21464503e−01 | 1.59068048e−01 | 2.15599790e−01 |
| −9.40814465e−02 | 2.89715618e−01 | 3.65125120e−01 | 3.40177387e−01 |
| 6.68930769e−01 | 4.42400485e−01 | −1.67184789e−03 | −3.70589346e−02 |
| 3.46720785e−01 | 5.56304216e−01 | 2.03775335e−02 | 4.75173831e−01 |
| 5.33053041e−01 | 3.43562484e−01 | −3.52561474e−02 | 4.96286750e−01 |
| −1.49469763e−01 | 1.66992798e−01 | 5.61470509e−01 | 5.85321724e−01 |
| 6.88929200e−01 | 6.21817410e−01 | 3.29439908e−01 | 2.85555124e−01 |
| 1.97311938e−01 | −2.37347722e−01 | 1.21432163e−01 | −2.98363566e−01 |
| 1.72189295e−01 | 1.95872992e−01 | 4.72017489e−02 | 2.77096629e−01 |
| 8.64804983e−01 | −1.45837422e−02 | 3.14897031e−01 | 1.87644958e−01 |
| 4.39656436e−01 | 4.33445752e−01 | −6.90342933e−02 | 3.57863009e−01 |
| 2.00615644e−01 | 1.86221614e−01 | −1.70500427e−01 | 1.68766499e−01 |
| 1.64493293e−01 | 3.22123796e−01 | 5.42141497e−01 | 3.03742290e−01 |
| 7.36967176e−01 | 3.93402457e−01 | −3.33345272e−01 | −9.50735807e−02 |
| 9.53709111e−02 | −1.21805213e−01 | 5.20203769e−01 | 2.74471313e−01 |
| −1.43018186e−01 | −7.63695985e−02 | 3.65492493e−01 | 2.33478457e−01 |
| 4.99062806e−01 | 4.93196547e−01 | −5.11273369e−02 | 1.07007986e−02 |
| 8.86252001e−01 | 2.19713613e−01 | −1.71399802e−01 | 4.58021075e−01 |
| −4.12041433e−02 | 2.96135902e−01 | 4.55561131e−01 | 7.22561479e−01 |
| −2.18172930e−02 | 2.61152953e−01 | −3.099932362e−02 | 1.81635931e−01 |
| 9.09750238e−02 | 7.76210546e−01 | 5.31465054e−01 | 4.65767264e−01 |
| 5.85215926e−01 | 5.27997494e−01 | −1.72441781e−01 | 2.04948053e−01 |
| 1.94496661e−01 | 1.25395775e−01 | 4.27422613e−01 | −2.74308890e−01 |
| −1.36826500e−01 | 3.28525692e−01 | 1.50930345e−01 | 2.39323184e−01 |
| 2.35539183e−01 | −3.37428674e−02 | −1.38097703e−02 | 6.15660846e−01 |
| 7.82438457e−01 | 3.92417789e−01 | 2.05701381e−01 | 6.35297775e−01 |
| 2.15442106e−01 | 2.60824323e−01 | 6.47102416e−01 | 9.51329097e−02 |
| 2.33630031e−01 | 5.14541626e−01 | 3.11100811e−01 | 1.24379344e−01 |
| 5.15853226e−01 | 1.09653987e−01 | 2.44657919e−01 | −1.36802360e−01 |
| 5.49101651e−01 | 9.45903882e−02 | 7.13301837e−01 | 2.86939256e−02 |
| 3.84221137e−01 | 7.58484364e−01 | 7.57046282e−01 | 6.41883835e−01 |
| 3.58577102e−01 | 2.04438314e−01 | −6.18671142e−02 | 2.01208457e−01 |
| 2.61985362e−01 | 1.82863176e−01 | −4.99645397e−02 | 3.07709903e−01 |
| 2.18207955e−01 | 1.34185269e−01 | −1.12457722e−01 | 3.46118718e−01 |
| 5.41913211e−01 | 4.05988157e−01 | 1.41961753e−01 | 3.07511926e−01 |
| 1.43647417e−01 | 8.27684924e−02 | 2.60170698e−02 | −2.65864879e−01 |
| −6.28968328e−02 | 2.50782669e−01 | 4.95942533e−01 | 1.50362909e−01 |
| 5.92184305e−01 | 4.87800956e−01 | −8.26898962e−02 | 1.58858776e−01 |
| 4.40794766e−01 | 5.10368049e−01 | −4.42378193e−01 | 4.78017986e−01 |
| 8.46628919e−02 | 2.94014335e−01 | −7.45297223e−02 | −6.48041368e−02 |
| 4.39196914e−01 | 7.16682792e−01 | 3.46862793e−01 | 3.96147847e−01 |
| −6.14329092e−02 | 5.44178843e−01 | 4.61822599e−01 | 2.46619105e−01 |
| 3.25137615e−01 | 1.90689728e−01 | 3.46744239e−01 | 1.42435610e−01 |
| 2.96830237e−01 | 6.89239353e−02 | −2.20089197e−01 | 3.00872087e−01 |
| 5.29897928e−01 | −3.14042978e−02 | 4.47826087e−02 | 3.58563453e−01 |
| −8.29270631e−02 | 8.95898789e−02 | 2.35408887e−01 | 1.15402624e−01 |
| 3.59269202e−01 | −3.94342057e−02 | 3.33797514e−01 | −6.11527152e−02 |
| −1.12814672e−01 | 3.86009276e−01 | 2.18319565e−01 | 1.38143361e−01 |

TABLE $W_h^1$-continued

| | | | |
|---|---|---|---|
| 3.22853178e−01 | 4.02619153e−01 | 2.65836090e−01 | −2.11316738e−02 |
| 1.27389893e−01 | 3.53562199e−02 | 3.71018320e−01 | −2.05751066e−03 |
| 1.58754945e−01 | 2.39291355e−01 | 3.04246992e−01 | 3.57229114e−01 |
| 2.39078552e−01 | −8.38449132e−03 | −1.58619180e−01 | −2.37935498e−01 |
| 1.26078814e−01 | 3.91640402e−02 | 2.64807701e−01 | 2.02153828e−02 |
| 6.43695831e−01 | −1.08922049e−01 | 2.05999389e−01 | −1.95570230e−01 |
| 2.52653271e−01 | 4.24700171e−01 | 3.21250379e−01 | −7.36766383e−02 |
| 5.66338122e−01 | −3.09090950e−02 | 2.97262996e−01 | 2.11192593e−01 |
| 3.11242968e−01 | 2.67090619e−01 | 2.31230870e−01 | 5.19737741e−03 |
| −2.36856844e−02 | 1.11712359e−01 | −1.14910625e−01 | −2.45454669e−01 |
| 4.24651623e−01 | 3.19519758e−01 | 5.11181116e−01 | 9.83780026e−02] |
| [1.18756855e−00 | 9.07238841e−01 | 8.39930415e−01 | 5.54284930e−01 |
| 9.33741271e−01 | 3.48465174e−01 | 1.65152058e−01 | 2.78556049e−01 |
| 2.74815053e−01 | 5.95407546e−01 | 1.34942317e−00 | 9.25674856e−01 |
| 6.73881888e−01 | 3.36881369e−01 | 9.24307108e−01 | 5.53764582e−01 |
| 1.32493973e−00 | −8.28613415e−02 | 2.12256983e−01 | 7.65806139e−01 |
| 1.03551686e−00 | −4.97211158e−01 | 1.30944324e−00 | 2.15465561e−01 |
| 7.41693199e−01 | 7.62200415e−01 | 1.10876225e−01 | 4.61211838e−02 |
| 6.75123513e−01 | 4.03187037e−01 | −1.00746661e−01 | 1.81559101e−01 |
| 3.66488457e−01 | −2.89906859e−01 | 8.20200026e−01 | 4.37403023e−01 |
| 9.21422362e−01 | 1.67432833e−00 | 3.37413222e−01 | 1.12427187e−00 |
| 1.97768211e−00 | 1.23351526e−00 | 1.15256667e−00 | 8.06495845e−01 |
| 1.07167053e−00 | 2.73215562e−01 | 1.94056556e−01 | 3.51082981e−01 |
| 9.78854179e−01 | 6.60371482e−01 | 1.02220786e−00 | 3.72575045e−01 |
| −7.66376257e−02 | 1.50967538e−00 | 9.37320352e−01 | 2.04284251e−01 |
| −5.11027351e−02 | 7.35069275e−01 | −1.25888437e−01 | 4.47497100e−01 |
| 3.38691264e−01 | 6.65277898e−01 | 2.13340893e−01 | 5.47995448e−01 |
| 8.91208291e−01 | 5.84527791e−01 | 1.33751726e−00 | 8.25503647e−01 |
| 2.28158519e−01 | 8.60805511e−01 | 3.16963136e−01 | −5.43902040e−01 |
| 1.04295444e−00 | 4.30425286e−01 | 2.62815833e−01 | 5.19418538e−01 |
| 1.31320763e−00 | 1.18242919e−01 | 4.98244822e−01 | 1.28585771e−01 |
| 1.19357860e−00 | 6.47250235e−01 | 1.83457613e−01 | 4.63755399e−01 |
| 1.18168664e−00 | −5.53311668e−02 | 6.91733599e−01 | 9.36368942e−01 |
| 8.47927034e−01 | −4.50621367e−01 | 5.52514732e−01 | −2.99964190e−01 |
| 8.31327021e−01 | 1.21514630e−00 | 8.03863704e−01 | 1.38298082e−00 |
| 5.41461706e−01 | 8.47383738e−01 | 5.77688873e−01 | 1.55861080e−00 |
| 4.54596698e−01 | 9.56522822e−01 | 2.13469654e−01 | 6.33796930e−01 |
| 7.24850595e−01 | 3.89596909e−01 | 2.28553951e−01 | 1.11667526e−00 |
| 2.83929437e−01 | 9.79861856e−01 | 4.44213539e−01 | 1.17290950e−00 |
| 1.11661613e−00 | 5.58342993e−01 | 9.71275568e−01 | 2.74975032e−01 |
| 5.13770580e−01 | 2.33437270e−01 | 1.42155394e−01 | 3.48672271e−01 |
| 1.23674560e−00 | 4.86252755e−01 | −1.02800786e−01 | 1.15250088e−01 |
| 5.35109520e−01 | 1.12530494e−00 | 1.84019053e−00 | 6.16590023e−01 |
| 5.30038059e−01 | 1.24031615e−00 | −2.01049328e−01 | 1.65945876e−00 |
| 3.91371697e−01 | 7.06774235e−01 | 2.50834972e−01 | 8.86740208e−01 |
| 7.84991503e−01 | 1.67081690e−00 | 2.31845662e−01 | 2.11198401e−00 |
| 3.05974960e−01 | 3.98883551e−01 | 6.09643877e−01 | 1.04621458e−00 |
| 8.40012133e−01 | 7.16667891e−01 | 4.32346761e−01 | 2.81569123e−01 |
| 6.53145313e−01 | 7.39015043e−01 | 8.86575699e−01 | 1.23909211e−00 |
| 3.24204862e−01 | 3.18682969e−01 | 5.70516706e−01 | 6.28118753e−01 |
| 7.63944089e−01 | 1.48679182e−01 | 1.23799324e−00 | 6.57713413e−01 |
| 8.34538400e−01 | 8.33532691e−01 | 7.52327740e−01 | 6.04759932e−01 |
| 7.87340760e−01 | 1.26854086e−00 | 9.16235685e−01 | 2.95403451e−01 |
| 2.41178185e−01 | 6.37075901e−02 | −5.17548099e−02 | 9.51779366e−01 |
| 7.20992386e−01 | 8.64132226e−01 | 1.22256160e−00 | −7.64744505e−02 |
| 4.34158146e−01 | 3.51999342e−01 | 8.11719239e−01 | 6.28732860e−01 |
| 4.65478957e−01 | 1.20020330e−00 | 6.46356285e−01 | 1.84719050e−00 |
| 6.45584524e−01 | 3.21909964e−01 | 1.10177171e−00 | 3.15303385e−01 |
| 1.91542819e−01 | 1.34713367e−01 | 6.05294406e−01 | 8.41079175e−01 |
| 1.48451030e−01 | 9.50219870e−01 | −6.44578561e−02 | −1.95279449e−01 |
| 3.27376246e−01 | 1.49257922e−00 | 1.91529751e−01 | 1.78643525e−01 |
| 1.18790078e−00 | 1.87732220e−01 | 4.43478703e−01 | −2.64224172e−01 |
| −5.45742810e−02 | 1.32351637e−00 | −1.69321552e−01 | 9.46916759e−01 |
| 9.54839587e−01 | 8.08954895e−01 | 9.15158451e−01 | 3.87508869e−01 |
| 2.26674363e−01 | 3.84609282e−01 | 4.31876659e−01 | 8.83444905e−01 |
| 1.23336300e−01 | 9.62854147e−01 | 2.06676051e−01 | 9.71019506e−01 |
| 1.12016296e−00 | 1.61452627e−00 | 1.42155218e−00 | 1.22987352e−01 |
| 4.03785914e−01 | 1.17871785e−00 | 4.06528950e−01 | 8.88520718e−01 |
| 5.64593613e−01 | 8.83477926e−01 | 1.18785596e−00 | 4.17038679e−01 |
| −1.96975935e−02 | 8.83581221e−01 | 7.29120731e−01 | 1.32732344e−00 |
| 3.65620926e−01 | 8.70632648e−01 | 1.13376513e−00 | 1.39173830e−00 |
| 1.64869413e−01 | 1.23849249e−00 | 3.40006232e−01 | 4.49160665e−01 |
| 1.40587294e−00 | −1.23918550e−02 | 2.55828232e−01 | −2.33877137e−01 |
| 6.91853344e−01 | 3.98793906e−01 | 5.50001442e−01 | 7.22150981e−01 |
| 3.35548401e−01 | 6.75624251e−01 | 1.02388692e−00 | 8.23205471e−01] |
| [1.57579944e−01 | 5.60822189e−01 | 9.46712643e−02 | 5.25197908e−01 |
| −2.76167303e−01 | 1.90480545e−01 | 6.27849251e−02 | −3.91569644e−01 |
| −5.04931688e−01 | 1.67909637e−01 | 1.65499300e−01 | 1.10523164e−01 |
| 2.06204861e−01 | 2.39224836e−01 | −9.43510011e−02 | 2.94421837e−02 |
| 7.94006959e−02 | 2.19414920e−01 | 1.12564790e−00 | −6.17305115e−02 |

TABLE $W_h^1$-continued

| | | | |
|---|---|---|---|
| 4.47794229e-01 | 5.45512438e-01 | 2.72325724e-01 | 1.93004012e-01 |
| 2.14359015e-01 | 1.95267439e-01 | 6.55554421e-03 | 5.44786990e-01 |
| 5.44853806e-01 | 5.44866741e-01 | -9.98267755e-02 | 3.50471556e-01 |
| 6.65179670e-01 | 3.52034181e-01 | -4.17198628e-01 | 2.35199928e-01 |
| 4.06538963e-01 | -5.87631837e-02 | -2.97577623e-02 | 6.86303675e-01 |
| 2.59866834e-01 | -1.71047300e-02 | 4.13831979e-01 | 5.17934263e-01 |
| 6.62856281e-01 | 3.94655555e-01 | -7.04765022e-02 | 5.04101992e-01 |
| -5.58663726e-01 | 6.80020079e-02 | -7.83456340e-01 | 1.97686732e-01 |
| -1.10287048e-01 | 6.67065307e-02 | 2.83400774e-01 | 9.03466418e-02 |
| 6.80010617e-01 | -5.56822941e-02 | 2.85520643e-01 | 8.95931572e-02 |
| -2.04599649e-01 | -1.11491032e-01 | -2.53845215e-01 | 4.69683647e-01 |
| -2.99713731e-01 | 1.33165061e-01 | -2.99038947e-01 | -1.76334679e-01 |
| 5.97273052e-01 | 4.00035739e-01 | 4.44141418e-01 | -3.53230210e-03 |
| -6.86321855e-02 | 3.59987676e-01 | 9.62092131e-02 | -1.11511517e-02 |
| -3.83334160e-01 | 1.14817046e-01 | 9.27500352e-02 | -2.55983710e-01 |
| 2.34203324e-01 | 1.33289427e-01 | 4.59009111e-01 | 1.00946754e-01 |
| 2.62805015e-01 | 6.16163552e-01 | 1.48286059e-01 | 3.11881393e-01 |
| 1.53741196e-01 | 1.97626844e-01 | -1.58101380e-01 | -6.31412268e-02 |
| -1.73314929e-01 | 9.05882642e-02 | 5.85342884e-01 | 1.69390470e-01 |
| 1.39505684e-01 | 6.32823467e-01 | -5.76094687e-01 | -3.24900933e-02 |
| -4.82300594e-02 | 3.26762229e-01 | 1.68793723e-01 | 3.99145544e-01 |
| 7.23857641e-01 | 7.25411996e-02 | -2.18987972e-01 | 3.48219462e-02 |
| -1.72875032e-01 | 2.77165114e-03 | -4.14345920e-01 | -1.25993937e-01 |
| -6.68579936e-01 | 1.97871640e-01 | 1.68327224e-02 | -3.71177425e-03 |
| 1.80076599e-01 | 8.44034627e-02 | 6.20913446e-01 | -1.62108958e-01 |
| 9.76118922e-01 | 1.89283088e-01 | -9.85151082e-02 | 1.03286259e-01 |
| 1.91175252e-01 | 4.90169466e-01 | 5.04898310e-01 | -2.44743809e-01 |
| -8.76615644e-02 | 6.22253306e-02 | -3.39126021e-01 | -3.88632901e-02 |
| 3.61531973e-01 | 8.56630564e-01 | -1.17360897e-01 | -4.41787511e-01 |
| 3.54023606e-01 | 3.16469848e-01 | 3.54249567e-01 | -1.18618153e-01 |
| 1.49377406e-01 | 1.95401728e-01 | -1.90428063e-01 | -2.20962048e-01 |
| 5.00781476e-01 | 2.86257386e-01 | 3.33418429e-01 | -4.30383440e-03 |
| 4.22262222e-01 | -7.17227012e-02 | 2.31390774e-01 | 1.66549116e-01 |
| 3.40830058e-01 | -3.20406199e-01 | -2.49969391e-01 | 5.59423268e-01 |
| 3.25376064e-01 | 1.63600028e-01 | 8.77197146e-01 | 2.31436342e-01 |
| -2.64664441e-01 | -2.53602386e-01 | -2.53463238e-01 | 3.00540328e-01 |
| 3.62724550e-02 | 6.31672144e-01 | 5.84971905e-01 | 2.12280273e-01 |
| -9.81071889e-02 | 1.46519735e-01 | 3.31598252e-01 | 1.54042961e-01 |
| 1.86403804e-02 | 2.88963258e-01 | -5.57728291e-01 | -1.61413714e-01 |
| 2.28683859e-01 | -1.13956362e-01 | -1.43723518e-01 | 1.91970855e-01 |
| 1.33833677e-01 | 4.78169769e-01 | -6.07844703e-02 | -1.46427259e-01 |
| -3.94026697e-01 | -1.24287151e-01 | 5.43856204e-01 | 6.47590458e-02 |
| 1.42977282e-01 | 1.66315854e-01 | -2.19987378e-01 | 3.86395901e-02 |
| 4.43552643e-01 | 2.43589193e-01 | -4.42607999e-02 | 2.49687552e-01 |
| 4.72567946e-01 | 2.05300823e-01 | 1.92726608e-02 | 5.18716931e-01 |
| -2.28226095e-01 | 7.18899727e-01 | 6.89414442e-01 | 9.52339172e-02 |
| 2.44993940e-01 | 3.94812793e-01 | 2.62923032e-01 | 1.99015941e-02 |
| -1.89313069e-02 | 3.43692213e-01 | 1.51515767e-01 | 8.62196237e-02 |
| 2.41103303e-02 | 3.05708140e-01 | 5.70389703e-02 | 3.03470343e-01 |
| -2.02552602e-01 | 3.45569611e-01 | -5.89402579e-02 | 3.07910204e-01 |
| -2.16712490e-01 | -2.50198364e-01 | 1.00020878e-01 | 3.87349278e-02 |
| 5.67758560e-01 | -7.28878826e-02 | -2.32455224e-01 | -4.00059134e-01 |
| -4.78893556e-02 | 4.05590087e-01 | -6.57382188e-03 | -1.07003413e-01 |
| 4.29310799e-01 | -6.37174249e-01 | -3.41889381e-01 | -9.28188115e-02 |
| 4.25840944e-01 | 5.12246847e-01 | 1.88934699e-01 | 2.86745280e-01 |
| 3.98854107e-01 | -3.14304233e-01 | 7.45688751e-02 | 7.53662288e-01 |
| -1.15717370e-02 | 4.03225690e-01 | 1.72233011e-03 | 8.83954093e-02 |
| -1.67710781e-01 | 3.86488855e-01 | -4.92970675e-01 | -1.81688324e-01 |
| 6.21220648e-01 | 1.71144903e-01 | 3.50421906e-01 | 2.19967976e-01] |
| [5.08241579e-02 | 3.48696470e-01 | 6.17039613e-02 | -4.21646163e-02 |
| 2.42802143e-01 | 2.78251991e-02 | 7.25540444e-02 | -2.47132462e-02 |
| -1.38998598e-01 | -5.03016651e-01 | 1.26025140e-01 | -1.85925215e-01 |
| 4.17951763e-01 | 2.89474738e-05 | 1.73042521e-01 | -1.65809467e-01 |
| -2.00467795e-01 | 1.25409722e-01 | 1.01640689e-00 | 1.90718368e-01 |
| -1.78542495e-01 | 6.07653260e-01 | 6.82734847e-01 | 3.88054073e-01 |
| 4.80327666e-01 | 6.21765256e-01 | 4.05664861e-01 | 4.02666330e-01 |
| -5.25076874e-01 | 6.99415922e-01 | 1.16002738e-01 | 8.93373787e-01 |
| 3.28356892e-01 | 1.00645292e-00 | -1.96619853e-01 | 8.55338797e-02 |
| 5.10351844e-02 | 1.86567232e-01 | 2.70753592e-01 | 3.09834033e-01 |
| -2.54116617e-02 | 1.51744485e-02 | 1.00455451e-00 | 5.02828360e-01 |
| 5.01578569e-01 | 6.49807692e-01 | -2.60183334e-01 | 2.91934848e-01 |
| 2.83232093e-01 | 1.20347977e-01 | 2.36510873e-01 | 3.11688483e-01 |
| 3.66568774e-01 | 2.18386784e-01 | 2.58854538e-01 | 1.03558756e-01 |
| 6.36783719e-01 | 1.69853091e-01 | 2.72731185e-01 | 4.60772395e-01 |
| 8.65764141e-01 | 4.39567119e-01 | 2.46194914e-01 | 4.50204074e-01 |
| -5.35796583e-01 | -3.41382861e-01 | -2.03658715e-01 | -2.45914876e-01 |
| 7.45841444e-01 | 7.14925110e-01 | 4.96623248e-01 | 2.49432221e-01 |
| 8.28763470e-03 | 2.82069355e-01 | 5.00999987e-01 | -1.43261120e-01 |
| 3.24997187e-01 | 1.19618639e-01 | -1.60297155e-02 | 2.29437694e-01 |
| -1.64461206e-03 | 5.69303393e-01 | 2.80348808e-01 | -4.43409324e-01 |

TABLE $W_h^1$-continued

| | | | |
|---|---|---|---|
| 2.19925329e−01 | 5.46490252e−01 | 3.73898953e−01 | 7.03641996e−02 |
| −1.75203666e−01 | −5.21175414e−02 | −2.14106828e−01 | 5.70561402e−02 |
| 1.64287403e−01 | −2.89691180e−01 | 2.31593311e−01 | −6.36936650e−02 |
| −6.33958494e−03 | 1.98927671e−01 | 7.31572285e−02 | 1.25195578e−01 |
| 1.66196376e−01 | 4.82657075e−01 | 4.11647975e−01 | 4.78885353e−01 |
| 3.55908215e−01 | 6.35039330e−01 | 6.52225539e−02 | 2.01451570e−01 |
| 1.18002780e−01 | 6.42107427e−01 | −3.47531252e−02 | 1.38768423e−02 |
| 3.87036294e−01 | 8.90707672e−02 | 1.89943969e−01 | 2.49315634e−01 |
| 5.41799068e−01 | −1.15826294e−01 | 2.61833042e−01 | 5.03860891e−01 |
| 3.19582611e−01 | 1.76401943e−01 | 2.78108686e−01 | 2.52925009e−01 |
| 4.31804895e−01 | 3.16259176e−01 | 3.09221536e−01 | 5.69985174e−02 |
| 5.21011613e−02 | 7.49565214e−02 | −2.20971853e−01 | 2.76639849e−01 |
| 1.69826642e−01 | 4.79399145e−01 | 2.95741230e−01 | −3.04393411e−01 |
| −8.30118805e−02 | 3.95387501e−01 | 1.95086852e−01 | −2.96465695e−01 |
| 4.24030036e−01 | 4.25860882e−01 | 7.09076822e−01 | 3.57296199e−01 |
| −1.60004459e−02 | 6.77493885e−02 | 1.24031596e−01 | 6.69468269e−02 |
| 3.10119111e−02 | 3.77886333e−01 | 3.46184433e−01 | 3.19086611e−01 |
| 2.51883388e−01 | −4.47797656e−01 | 1.59269676e−01 | 3.66542429e−01 |
| 1.08341686e−01 | 2.97475696e−01 | 1.06067407e−00 | 2.82439470e−01 |
| 1.17573395e−01 | 1.22264186e−02 | −2.27994964e−01 | 3.01208943e−01 |
| 3.88213582e−02 | 4.54200238e−01 | 2.78974563e−01 | 2.35062316e−01 |
| 2.66745538e−01 | 2.97323346e−01 | 1.45453081e−01 | 1.33481845e−01 |
| 3.13464612e−01 | 4.37374115e−02 | −2.99073398e−01 | 5.01786530e−01 |
| 1.51658088e−01 | 2.24225163e−01 | −1.05909288e−01 | 1.36307880e−01 |
| 6.06844962e−02 | −5.10179885e−02 | 1.01773247e−01 | −9.89686102e−02 |
| 1.93424627e−01 | 6.37968034e−02 | 6.26394391e−01 | 9.64206010e−02 |
| 1.16327524e−01 | −1.91752508e−01 | 4.01827693e−01 | 2.29481503e−01 |
| 3.75052124e−01 | 1.45191267e−01 | 1.11182645e−01 | 2.17752352e−01 |
| 4.50747639e−01 | 2.49079764e−01 | 3.82249326e−01 | 4.39193666e−01 |
| −3.06786656e−01 | 4.10288751e−01 | 2.07416102e−01 | 1.59205079e−01 |
| 8.92404169e−02 | 5.40602863e−01 | 1.35332257e−01 | −2.26560682e−02 |
| −2.45219208e−02 | 3.88452858e−01 | 2.05247596e−01 | 2.51377046e−01 |
| 2.19858035e−01 | 2.29501203e−01 | 8.26559588e−02 | 5.25142729e−01 |
| 3.46089631e−01 | 1.83159515e−01 | 2.90480882e−01 | 6.26342237e−01 |
| −2.06764564e−01 | 5.58510065e−01 | 1.53621137e−01 | −2.87072212e−01 |
| −3.98060307e−02 | 2.45644376e−01 | 1.38786271e−01 | 1.24141581e−01 |
| 6.70642495e−01 | 5.08613646e−01 | 3.03439289e−01 | 2.58608341e−01 |
| −6.67533576e−02 | −4.88351613e−01 | −6.41463399e−02 | −4.48738962e−01 |
| 6.01818323e−01 | 2.58985043e−01 | 3.19749042e−02 | 2.17127539e−02 |
| 1.70564383e−01 | −1.21253863e−01 | 3.32803726e−01 | 4.53625880e−02 |
| 4.51829731e−01 | 2.07183942e−01 | −2.67539740e−01 | −1.02749048e−02 |
| −6.37780905e−02 | 1.51631832e−01 | −2.32256368e−01 | −1.07283130e−01 |
| 1.49280161e−01 | 1.07045360e−01 | 1.38669863e−01 | 2.41717830e−01] |
| [8.31156790e−01 | −2.23659426e−01 | 1.10405910e−00 | 2.76028454e−01 |
| 7.37585902e−01 | 1.05371678e−00 | 7.30166197e−01 | 7.35018432e−01 |
| 5.91448963e−01 | 4.67375278e−01 | 1.21580982e−00 | 5.93607366e−01 |
| 6.68383837e−02 | 5.94982743e−01 | 5.06167293e−01 | −4.43050601e−02 |
| 7.00216234e−01 | 6.96443141e−01 | 7.48473525e−01 | 4.71243858e−01 |
| 6.79656506e−01 | 1.48971468e−01 | 3.39861363e−01 | 6.10579789e−01 |
| 4.57333297e−01 | 4.77117449e−01 | 1.17778158e−00 | 1.00060046e−01 |
| 4.47284371e−01 | 5.47937691e−01 | −5.43257654e−01 | 5.54320700e−02 |
| 5.27409792e−01 | −7.43371528e−03 | 5.89543402e−01 | 2.31941000e−01 |
| 1.31787932e−00 | 5.87254941e−01 | −1.44985497e−01 | 1.30737215e−01 |
| 7.36781538e−01 | 3.43942553e−01 | 1.37905705e−00 | 8.17380667e−01 |
| 1.13733232e−00 | −1.42764241e−01 | 1.52722144e−00 | 6.96630299e−01 |
| 4.15433347e−01 | 2.31936008e−01 | 7.98261762e−01 | 2.98076510e−01 |
| 1.30927131e−01 | 2.24841386e−01 | 2.95132041e−01 | 3.47923428e−01 |
| 7.04960823e−01 | 6.33902192e−01 | 4.59474236e−01 | 2.03324974e−01 |
| 9.70526993e−01 | 8.23491395e−01 | 3.42830420e−01 | 3.54881398e−03 |
| 8.42057705e−01 | 7.88775504e−01 | 5.84822953e−01 | 2.19109118e−01 |
| 4.21368957e−01 | 5.39094865e−01 | 1.47382498e−00 | −2.00066075e−01 |
| 1.00264347e−00 | 4.97544885e−01 | 4.42277372e−01 | 1.69855326e−01 |
| 1.00832915e−00 | 3.58212471e−01 | 2.78576076e−01 | 4.83982146e−01 |
| 5.64143777e−01 | 6.21958673e−01 | 3.79328400e−01 | 9.45961654e−01 |
| 6.38345301e−01 | 8.95178970e−03 | −2.52635567e−03 | 9.09630060e−02 |
| 1.03907359e−00 | −4.33330685e−01 | 4.85069811e−01 | 5.25440514e−01 |
| 4.66900349e−01 | 1.75433531e−01 | 6.43061876e−01 | 3.19255203e−01 |
| 8.45940173e−01 | 3.51665884e−01 | 6.94398165e−01 | 1.97334260e−01 |
| 7.97372639e−01 | 9.52195644e−01 | 3.39834452e−01 | 4.05474722e−01 |
| 1.82026744e−01 | 6.28376901e−01 | 4.86288190e−01 | 1.48522928e−01 |
| 6.91898465e−01 | 1.21347082e−00 | 7.12146342e−01 | 1.62874311e−01 |
| 1.05602252e−00 | 7.03793526e−01 | 4.16600347e−01 | 6.16971672e−01 |
| 5.07929683e−01 | 3.99273872e−01 | 3.96470428e−01 | 7.26470530e−01 |
| 3.89380664e−01 | 3.48561406e−01 | 7.60834992e−01 | 7.07184732e−01 |
| 1.65603012e−01 | 1.24220997e−01 | 7.16000676e−01 | 9.71146107e−01 |
| 5.32514513e−01 | 4.35232818e−01 | 9.54764858e−02 | 9.90643263e−01 |
| 4.44519460e−01 | 3.34981680e−01 | 5.20268738e−01 | 6.64403174e−01 |
| 4.91685033e−01 | 3.52200449e−01 | 1.37176466e−00 | 2.78590232e−01 |
| 5.71140826e−01 | 3.51869971e−01 | 1.02337050e−00 | 1.10383141e−00 |
| 9.71453264e−02 | 4.88148659e−01 | −8.98678079e−02 | 1.16151676e−01 |

TABLE $W_h^1$-continued

| | | | |
|---|---|---|---|
| 6.71229437e−02 | 6.32395208e−01 | 1.87705040e−01 | 2.93811888e−01 |
| 5.43903232e−01 | 8.18149894e−02 | 1.96800753e−01 | 2.55369782e−01 |
| −1.09102987e−01 | 6.83731735e−01 | 9.29504991e−01 | 8.03142071e−01 |
| 7.03974545e−01 | 1.43526703e−01 | 7.72695303e−01 | 1.13617468e−00 |
| −1.75070196e−01 | 3.80718291e−01 | 5.36406219e−01 | 1.06763616e−01 |
| 3.26613039e−01 | 2.04305083e−01 | 7.24821389e−01 | 6.42693937e−01 |
| 3.73278767e−01 | 3.81743789e−01 | 4.62741077e−01 | 4.89915103e−01 |
| 2.54831791e−01 | 4.04832065e−01 | 5.27667403e−01 | 1.90872103e−01 |
| 3.53590518e−01 | 7.60326862e−01 | 4.53950614e−01 | 1.11177814e−00 |
| 2.20070183e−01 | 6.42115295e−01 | 4.99914169e−01 | −1.67689486e−05 |
| 3.05085242e−01 | 6.10562205e−01 | 1.18268621e−00 | 1.17642558e−00 |
| 2.38557890e−01 | 1.11094296e−00 | 2.87356079e−01 | 6.77272797e−01 |
| 7.58072495e−01 | 3.86084914e−01 | 2.90519267e−01 | 8.00727129e−01 |
| 1.41293854e−01 | 3.51323038e−01 | 8.40396821e−01 | −6.51426166e−02 |
| 1.36999702e−00 | 3.28988194e−01 | 6.39291763e−01 | 7.58503616e−01 |
| 3.64870012e−01 | 6.81057811e−01 | 4.52386215e−02 | 3.43410939e−01 |
| 6.73547864e−01 | 9.42581534e−01 | 6.42286777e−01 | 6.33110344e−01 |
| 7.76438653e−01 | 5.58808506e−01 | 7.59760976e−01 | 5.31769037e−01 |
| 2.40837112e−01 | 1.02134657e−00 | −2.56636798e−01 | 1.43971398e−01 |
| 3.67872059e−01 | 6.52742982e−01 | 5.08779347e−01 | 6.85377955e−01 |
| 4.52682853e−01 | 1.16985135e−01 | 9.26071882e−01 | 3.93829644e−01 |
| 6.38998628e−01 | 2.75323898e−01 | 1.19819188e−00 | 2.24031568e−01 |
| 2.77870566e−01 | 6.61692023e−01 | 4.66516733e−01 | 2.79750675e−02 |
| 7.00766027e−01 | 9.33788903e−03 | 5.07692456e−01 | 5.37908614e−01 |
| 5.93442261e−01 | 1.05270967e−01 | 2.94172794e−01 | −2.12890491e−01 |
| 1.92585483e−01 | 5.87193131e−01 | 8.32258403e−01 | 2.52440184e−01 |
| 2.50569224e−01 | 8.03864598e−01 | 4.81353521e−01 | 6.93131089e−01] |
| [−2.04924658e−01 | 3.33031341e−02 | 2.59858906e−01 | −1.55603513e−01 |
| 3.71582448e−01 | −3.40652645e−01 | 2.55834237e−01 | −5.11806726e−01 |
| −5.65627754e−01 | −2.11250946e−01 | −5.56638896e−01 | 1.47735819e−01 |
| −3.20273697e−01 | −3.08631156e−02 | 2.13906387e−04 | −1.37317151e−01 |
| −2.23391280e−01 | −6.33285105e−01 | −7.85171032e−01 | −1.51510701e−01 |
| 2.99631119e−01 | −3.94737065e−01 | −3.93653184e−01 | −4.33796376e−01 |
| −2.28893787e−01 | −8.21766376e−01 | −3.38989012e−02 | 3.45290303e−02 |
| −7.26407409e−01 | −1.71313912e−01 | 7.92895555e−01 | 2.82633513e−01 |
| −3.37745130e−01 | −1.41257972e−01 | 3.33819315e−02 | 2.57749587e−01 |
| −4.31728400e−02 | 4.57580417e−02 | −1.16320327e−01 | −2.26794317e−01 |
| −3.21467251e−01 | 9.11320895e−02 | −6.24871254e−02 | −1.40336007e−01 |
| −2.95741588e−01 | 1.89092413e−01 | 1.79626778e−01 | −2.30446965e−01 |
| −2.29582459e−01 | −8.52490008e−01 | −1.83322892e−01 | 3.02599296e−02 |
| −3.26300412e−01 | 1.10294610e−01 | −4.73659605e−01 | −9.51114984e−04 |
| −6.08407140e−01 | 4.96420890e−01 | −4.37100083e−01 | −4.74605531e−01 |
| 5.71926832e−01 | −6.36673812e−03 | 3.68851349e−02 | −1.09725580e−01 |
| 6.64253116e−01 | 5.96106052e−01 | 8.50553036e−01 | −9.47011292e−01 |
| 7.69848585e−01 | −1.11465597e−00 | −1.89588770e−01 | 6.51616812e−01 |
| 6.63046360e−01 | −2.86684871e−01 | 1.52744621e−01 | −2.50366628e−01 |
| −5.74846193e−02 | 3.21619719e−01 | −2.21639678e−01 | 2.49113753e−01 |
| 8.05507481e−01 | −3.57446559e−02 | −1.62068874e−01 | 4.87679124e−01 |
| −4.08755541e−01 | −5.18076234e−02 | 3.51071686e−01 | 5.09274974e−02 |
| 1.40177011e−00 | −1.75936967e−01 | 7.96170473e−01 | −3.42741668e−01 |
| 2.17379496e−01 | 4.77838874e−01 | 3.27701598e−01 | −1.62073731e−01 |
| 9.07445103e−02 | −1.18399955e−01 | 5.08050323e−01 | 2.60185093e−01 |
| 3.08572322e−01 | −2.98118014e−02 | 3.45639944e−01 | 2.61969548e−02 |
| 3.03804010e−01 | 9.21813995e−02 | −4.93761301e−01 | −4.02068883e−01 |
| −7.09075332e−02 | 2.35648930e−01 | 5.10709405e−01 | 3.69280607e−01 |
| 7.32993186e−01 | 3.10268193e−01 | −1.44271255e−01 | 3.02497864e−01 |
| 2.74224669e−01 | 2.66136795e−01 | −2.82637119e−01 | −2.52812475e−01 |
| −1.57965258e−01 | 4.49098974e−01 | 8.17075372e−02 | 2.68754270e−02 |
| 6.99619949e−02 | −7.80052692e−02 | −3.80952954e−01 | 5.76974928e−01 |
| 5.36537766e−02 | 1.37832373e−01 | −2.68082827e−01 | −4.36372250e−01 |
| 5.54611683e−01 | −2.68735170e−01 | 2.43905500e−01 | 1.05315197e−00 |
| −6.19760752e−02 | 4.86216284e−02 | −2.58118391e−01 | 2.75779784e−01 |
| 5.49179077e−01 | −2.86638260e−01 | −7.52377152e−01 | −5.07821262e−01 |
| −1.57695606e−01 | −1.84571773e−01 | 5.78264073e−02 | −1.38215691e−01 |
| 8.13690573e−02 | 3.27828854e−01 | −4.04026844e−02 | −3.69514346e−01 |
| 2.82045305e−01 | 2.90826648e−01 | −5.58583215e−02 | −1.12290084e−01 |
| 6.89784512e−01 | −3.68766397e−01 | −6.25379980e−01 | −2.25047842e−01 |
| 2.06043005e−01 | −8.24252248e−01 | −3.69346768e−01 | −8.79822299e−02 |
| −5.59812844e−01 | 9.41415727e−01 | −3.63936722e−01 | −2.09026009e−01 |
| 7.32012242e−02 | −1.66634098e−01 | 2.54374951e−01 | −8.99227679e−01 |
| 2.48114288e−01 | −5.95194519e−01 | 4.99499500e−01 | −7.87258267e−01 |
| −1.75443456e−01 | −4.74728197e−01 | 3.44591290e−01 | −5.39232254e−01 |
| −1.19562335e−02 | −6.36991918e−01 | −2.92673320e−01 | 4.31051731e−01 |
| 5.53118549e−02 | −8.36374238e−02 | 7.48698950e−01 | 2.45721862e−01 |
| −3.75891238e−01 | −1.23173699e−01 | −4.52680051e−01 | −3.34077835e−01 |
| −1.87614635e−01 | −2.13202000e−01 | 6.42091453e−01 | −4.81651425e−01 |
| −1.17133372e−01 | −2.02458426e−01 | 9.77344513e−02 | 2.50547022e−01 |
| 3.44978601e−01 | −7.68988967e−01 | −2.96256542e−01 | −3.51196647e−01 |
| 4.84820679e−02 | 3.49170834e−01 | −2.14634333e−02 | 8.35801587e−02 |
| 1.09769113e−01 | 7.80247092e−01 | 6.37883723e−01 | 7.98863709e−01 |

TABLE $W_h^1$-continued

| | | | |
|---|---|---|---|
| 1.75569355e−01 | 6.76466152e−02 | −2.64459610e−01 | −4.15881485e−01 |
| −4.99093056e−01 | −1.25080049e−01 | 1.76601842e−01 | 6.54357910e−01 |
| −4.18653280e−01 | 1.69940665e−01 | −2.02904493e−01 | −2.70879745e−01 |
| −6.38051152e−01 | −6.28705084e−01 | −3.39642644e−01 | 7.14348376e−01 |
| 2.20770352e−02 | 3.87243219e−02 | −3.20162296e−01 | 6.60541713e−01 |
| 7.43880346e−02 | −3.62843156e−01 | −4.23225701e−01 | −1.43449232e−01 |
| −3.91773582e−01 | −3.65923941e−01 | −6.20579541e−01 | 1.41560435e−01 |
| −5.37579417e−01 | 6.04574569e−02 | 3.91516387e−02 | −3.63897473e−01 |
| −4.76357669e−01 | −8.71609807e−02 | −1.97640955e−01 | −3.19429308e−01 |
| 4.22660589e−01 | −3.01551670e−01 | 7.86569566e−02 | 1.15693021e−00 |
| −3.33345950e−01 | 1.35463789e−01 | −2.82972783e−01 | −1.49031281e−01] |
| [6.47952080e−01 | 6.32142007e−01 | −2.88648069e−01 | −4.82543819e−02 |
| −5.86530603e−02 | 2.84588844e−01 | −9.94824544e−02 | 2.67892033e−01 |
| 3.37796241e−01 | 4.06773202e−02 | 3.07410240e−01 | −2.58216113e−01 |
| 6.36595845e−01 | 5.86468764e−02 | −5.60965955e−01 | −5.32119945e−02 |
| 8.67990479e−02 | −2.21751466e−01 | 1.54805332e−01 | 3.65787774e−01 |
| 1.52626768e−01 | 5.45814872e−01 | 5.71783110e−02 | 6.33357346e−01 |
| −1.33972028e−02 | 1.12191051e−01 | −3.50842655e−01 | −2.32481658e−01 |
| 1.03228521e−00 | 1.04065299e−01 | 1.94076836e−01 | 2.59703696e−01 |
| 7.28515625e−01 | −8.25929269e−02 | 2.41136268e−01 | −3.08171093e−01 |
| 4.65613961e−01 | 3.11297983e−01 | 1.58135042e−01 | 2.29927003e−01 |
| −2.21082624e−02 | 2.06936374e−01 | 1.81411088e−01 | 7.55007863e−01 |
| 1.95441470e−01 | 3.58880013e−01 | 2.76259601e−01 | −1.38336629e−01 |
| 6.97079480e−01 | 1.55783355e−01 | 2.34770194e−01 | −8.41579363e−02 |
| 1.08992875e−00 | 3.81559134e−01 | 4.35883969e−01 | 1.59517094e−01 |
| −1.29329324e−01 | 3.65247875e−01 | 1.54826254e−01 | 1.17841315e−00 |
| 3.14776659e−01 | 5.67473769e−01 | 2.92786658e−01 | −2.12238058e−01 |
| −1.96355417e−01 | −9.18406695e−02 | −5.00502706e−01 | 2.72679090e−01 |
| 1.20721489e−01 | 5.99108338e−01 | 1.98048875e−01 | 4.42487895e−01 |
| 3.19488466e−01 | 4.78669852e−01 | 1.89250946e−01 | −3.10518146e−01 |
| 1.37726143e−01 | 9.23535079e−02 | 3.82644713e−01 | −4.96394932e−02 |
| 5.00225015e−02 | 2.00271130e−01 | 1.07646659e−01 | −8.35876167e−02 |
| 4.49670911e−01 | 1.85299322e−01 | 1.09142847e−02 | −6.63848743e−02 |
| 7.45445564e−02 | −1.52467564e−01 | 3.41387764e−02 | −1.40732050e−01 |
| 2.29693353e−01 | 2.06176877e−01 | 6.56793788e−02 | 3.06756109e−01 |
| −4.04737182e−02 | −5.05270422e−01 | 3.41177016e−01 | 1.18984058e−01 |
| 2.49483511e−01 | 3.52373928e−01 | −1.35951385e−02 | −3.16936076e−01 |
| −2.60454535e−01 | 3.61633658e−01 | 2.16272585e−01 | 4.56443548e−01 |
| 2.39949271e−01 | 2.97254235e−01 | 6.01701774e−02 | 4.64450568e−01 |
| −6.42147809e−02 | −6.78885952e−02 | 5.69748819e−01 | 2.74551064e−01 |
| 4.21926767e−01 | 5.44818875e−04 | 2.22469270e−01 | 2.42542848e−01 |
| −2.51881957e−01 | −2.22439736e−01 | 9.59707499e−02 | 1.15547471e−01 |
| 2.13517800e−01 | −2.74613887e−01 | −1.13711311e−02 | −7.13945599e−03 |
| 1.09832443e−01 | 1.27542028e−02 | 1.78911820e−01 | 3.82567316e−01 |
| −1.23218529e−01 | 2.61282474e−01 | −8.27408507e−02 | 3.30705345e−01 |
| 1.12637274e−01 | −3.91188294e−01 | 6.27285196e−03 | 4.63626891e−01 |
| 3.42929631e−01 | 8.70881319e−01 | −6.62435368e−02 | 8.24327946e−01 |
| 2.51092792e−01 | 5.27190030e−01 | 4.04582709e−01 | −6.49440885e−01 |
| 1.11104198e−01 | 5.73803544e−01 | 1.89641421e−03 | −2.03732755e−02 |
| 3.06627810e−01 | −9.41915989e−01 | 3.69787626e−01 | 7.48409927e−01 |
| −2.42043585e−01 | −3.99157964e−02 | 2.01523811e−01 | 5.90193748e−01 |
| 1.82380334e−01 | 1.77562505e−01 | −3.94298047e−01 | 4.69432414e−01 |
| 7.25003242e−01 | 2.62997359e−01 | 7.48174787e−01 | −3.29435796e−01 |
| −3.92320871e−01 | 2.70922277e−01 | 1.38319507e−01 | 8.47247541e−01 |
| 4.34410870e−01 | −3.46585125e−01 | 5.80824986e−02 | 1.83514319e−02 |
| 2.75975496e−01 | −6.73437268e−02 | 4.09649074e−01 | 8.69701523e−03 |
| 5.16867399e−01 | 3.57583821e−01 | 8.21461603e−02 | 4.75263625e−01 |
| 5.56689762e−02 | 1.27081648e−01 | 9.93083790e−02 | 4.87756312e−01 |
| −3.57199758e−01 | −2.31925726e−01 | −3.01879570e−02 | 6.67769969e−01 |
| −2.55693123e−03 | 2.12015346e−01 | −2.78186500e−01 | −1.85744595e−02 |
| −1.03781462e−01 | −1.83194745e−02 | 2.99398601e−01 | 5.38026810e−01 |
| −7.92099722e−03 | −7.82402307e−02 | 1.98250890e−01 | 1.34718895e−01 |
| 8.67177844e−02 | −9.95540693e−02 | 2.12200060e−01 | −1.58272117e−01 |
| 1.42327502e−01 | 1.29237399e−01 | −3.35403115e−01 | 1.97326392e−01 |
| −4.43651378e−01 | 1.19592524e−00 | 3.02116483e−01 | 1.58823729e−01 |
| 3.79624695e−01 | 3.18586975e−01 | 1.08813666e−01 | 8.54913443e−02 |
| 7.63242245e−01 | −7.29096457e−02 | 2.08111539e−01 | 2.25902304e−01 |
| 2.12719753e−01 | −5.70638366e−02 | −7.42081031e−02 | 3.59658003e−01 |
| 3.08877915e−01 | 1.26269475e−01 | 2.11446658e−01 | −2.05594182e−01 |
| 1.03291363e−01 | −4.57848124e−02 | 2.05296591e−01 | 1.96629092e−01 |
| 1.13962106e−01 | 6.25315130e−01 | 4.61228676e−01 | −4.17776853e−01 |
| 3.61340910e−01 | −3.08580399e−01 | 6.89340086e−05 | 6.60525620e−01 |
| −1.56881824e−01 | 2.79543936e−01 | 1.91843227e−01 | −4.98500615e−01 |
| −3.23104829e−01 | 7.04524100e−01 | −1.72918066e−01 | −2.57247835e−01 |
| 4.16322112e−01 | 3.64552647e−01 | −1.00227505e−01 | 5.29001176e−01] |
| [−4.09176677e−01 | 9.51360315e−02 | −5.29352367e−01 | −2.43873179e−01 |
| −5.30956507e−01 | −5.78848183e−01 | −4.21770424e−01 | 4.41838324e−01 |
| −2.11680576e−01 | 8.59875143e−01 | −1.46206722e−01 | 1.10916495e−00 |
| −3.56466293e−01 | −2.59051263e−01 | 2.88980752e−01 | 3.97296436e−02 |
| 7.41046607e−01 | −3.54082704e−01 | 4.61919755e−01 | 3.32471281e−01 |

TABLE $W_h^1$-continued

| | | | |
|---|---|---|---|
| −1.53487295e−01 | −4.58147705e−01 | −2.33419448e−01 | −3.75427514e−01 |
| −4.79040653e−01 | −4.48618054e−01 | −4.63421673e−01 | −1.61465690e−01 |
| −6.51738584e−01 | −3.66261214e−01 | −4.52512443e−01 | −2.29570776e−01 |
| −3.54893833e−01 | −5.99490881e−01 | 8.89146104e−02 | −3.60747069e−01 |
| 3.36301625e−01 | −5.33562005e−01 | −1.75461635e−01 | −2.09763199e−01 |
| 8.98126781e−01 | −2.54722565e−01 | −4.54228371e−02 | −8.81868243e−01 |
| −4.65649635e−01 | −4.79964823e−01 | −4.32874322e−01 | 2.71804184e−01 |
| −5.60746789e−01 | −2.71750629e−01 | −3.36780578e−01 | −7.63417602e−01 |
| −1.42655730e−01 | −4.48291898e−01 | −2.33626664e−01 | 4.72060561e−01 |
| −4.81119156e−01 | −4.08825696e−01 | −6.90359592e−01 | 8.63372147e−01 |
| −1.53667375e−01 | −9.63203087e−02 | −7.19660401e−01 | −6.81312740e−01 |
| −2.15722010e−01 | −4.67873186e−01 | 3.63281399e−01 | 6.55369818e−01 |
| 4.85940054e−02 | −5.23721986e−02 | 1.34095418e−00 | −5.28516293e−01 |
| −1.55813918e−01 | −6.50293469e−01 | −6.54147267e−02 | 5.75970292e−01 |
| −5.41290104e−01 | −4.29919332e−01 | −8.22874665e−01 | −2.62184858e−01 |
| −6.42969847e−01 | −2.61462092e−01 | −5.26406884e−01 | −6.78058445e−01 |
| −6.79251552e−01 | −2.99588889e−01 | 3.30968082e−01 | −2.50085562e−01 |
| 1.01138091e−00 | −6.32336080e−01 | −1.40242159e−01 | −9.18978333e−01 |
| −5.26888967e−01 | −2.71346480e−01 | −7.09177434e−01 | −2.99556464e−01 |
| 3.96494195e−02 | 8.74082327e−01 | −6.59772515e−01 | 1.82320863e−01 |
| −3.62486303e−01 | −3.51285219e−01 | −2.27989018e−01 | −2.00139001e−01 |
| −7.61547983e−01 | −5.11244059e−01 | 6.69143200e−01 | −3.81323576e−01 |
| −7.10209250e−01 | 6.70341134e−01 | −8.51585329e−01 | −3.53300311e−02 |
| −2.17330530e−01 | −5.34447692e−02 | −3.64829391e−01 | −6.19577825e−01 |
| 2.42940575e−01 | −4.64732081e−01 | −1.53450966e−01 | −3.01068664e−01 |
| 1.11766183e−00 | −4.05357301e−01 | −1.93224370e−01 | 5.16505361e−01 |
| 2.91856170e−01 | 2.65619993e−01 | −9.36486498e−02 | −3.89100164e−01 |
| −6.95532620e−01 | 8.64404321e−01 | −5.22867262e−01 | −5.19829094e−01 |
| −7.08120167e−01 | −3.13350886e−01 | −3.38595867e−01 | −5.43542922e−01 |
| −4.62874055e−01 | 1.50452840e−00 | −4.68921065e−01 | −3.00945491e−02 |
| −2.57052690e−01 | −2.47399881e−01 | 4.57123339e−01 | −6.00637645e−02 |
| −4.03986603e−01 | 7.22859979e−01 | −4.20509726e−01 | −7.61553347e−01 |
| −3.97011101e−01 | 3.70771140e−01 | −5.98142803e−01 | 9.52148736e−01 |
| −3.27613652e−01 | −5.47319889e−01 | 3.62849087e−01 | 7.06079543e−01 |
| −2.73447603e−01 | −2.77095705e−01 | 4.43765402e−01 | −2.41682958e−02 |
| −1.98724046e−01 | 9.82679605e−01 | −3.88475060e−01 | 1.88899845e−01 |
| −4.80414689e−01 | −6.27715230e−01 | −8.67838025e−01 | −3.91197383e−01 |
| −4.70467359e−01 | −3.55407363e−03 | −4.40751702e−01 | 9.71176028e−01 |
| −2.22536281e−01 | −5.04887164e−01 | −2.60401607e−01 | −9.08474147e−01 |
| −6.70014024e−01 | −2.75101930e−01 | 7.40046442e−01 | 3.47749859e−01 |
| −5.57853281e−01 | −9.46488157e−02 | −1.47629693e−01 | 1.21630704e−00 |
| −7.13574111e−01 | −2.98165804e−04 | −2.98429459e−01 | −3.57679278e−01 |
| −3.28311235e−01 | −4.24750805e−01 | −1.77944675e−02 | −3.30825001e−01 |
| −4.40348655e−01 | −2.14081332e−01 | −4.13146287e−01 | −5.10917783e−01 |
| −4.15568471e−01 | −6.77204847e−01 | −8.68858874e−01 | −4.50362116e−01 |
| −2.48635516e−01 | −6.40481889e−01 | −7.32525229e−01 | −5.78106046e−01 |
| −3.09530407e−01 | −2.19464824e−01 | −9.16509449e−01 | 4.42310363e−01 |
| 9.74238932e−01 | −5.50633788e−01 | −5.10957479e−01 | −7.02942133e−01 |
| −6.49917543e−01 | −4.94505882e−01 | −1.71866771e−02 | −2.07767710e−02 |
| 1.01678297e−01 | 3.17719281e−01 | −5.03441036e−01 | 5.94408751e−01 |
| 9.65242982e−02 | −4.44189191e−01 | −2.35366806e−01 | −9.70558047e−01 |
| −3.48252535e−01 | −4.08598870e−01 | −7.13946164e−01 | 5.95811069e−01 |
| −2.89813489e−01 | −5.76103747e−01 | −3.35805953e−01 | −2.57505536e−01 |
| −3.70657682e−01 | −1.17046647e−01 | −1.48052141e−01 | 1.46647587e−01 |
| −8.23716760e−01 | −4.30764049e−01 | −4.27679807e−01 | 9.41153705e−01 |
| −4.91264671e−01 | 1.56808507e−00 | −4.89670187e−01 | −4.82085258e−01 |
| 1.06289200e−01 | −8.60254049e−01 | −4.97449011e−01 | −6.55561611e−02 |
| 9.70290124e−01 | 1.03068598e−01 | −6.76099360e−01 | 1.62920427e−00 |
| −2.31886938e−01 | −3.69674355e−01 | −5.40835798e−01 | 8.58261108e−01] |
| [3.50630403e−01 | −2.23802462e−01 | 1.84005275e−02 | 2.64293402e−01 |
| 3.25179070e−01 | 5.60665607e−01 | 3.92945111e−02 | 6.40013397e−01 |
| 1.12102099e−01 | 4.06656384e−01 | 5.31182349e−01 | −1.35353208e−02 |
| 9.57018435e−02 | 1.08145468e−01 | 1.79652959e−01 | 5.85737228e−01 |
| −1.25880450e−01 | 5.86683333e−01 | 4.12463337e−01 | −1.73038021e−01 |
| 6.29661530e−02 | −3.76617140e−03 | 1.14119481e−02 | 2.95717448e−01 |
| 1.55695990e−01 | 3.93232375e−01 | 4.14953083e−01 | −7.64592215e−02 |
| 2.63250507e−01 | 3.22974235e−01 | 3.53478968e−01 | 1.43534750e−01 |
| 6.58815727e−02 | 3.47650975e−01 | −6.47035167e−02 | 3.08537215e−01 |
| 2.23620415e−01 | 3.66491467e−01 | 1.88640915e−02 | −2.64307469e−01 |
| 1.33207992e−01 | 1.82015393e−02 | 4.05079633e−01 | 2.25909147e−02 |
| 2.01482296e−01 | 6.00161493e−01 | 7.28442892e−01 | 5.60192108e−01 |
| 8.18644613e−02 | 4.18225378e−01 | −5.60035110e−02 | 5.11627138e−01 |
| 3.15741688e−01 | 1.44049907e−02 | 2.18520358e−01 | −4.95738894e−01 |
| 4.22133744e−01 | 2.66491938e−02 | −5.00571467e−02 | 1.32498547e−01 |
| 3.43539447e−01 | 5.90993941e−01 | 4.95436400e−01 | 2.60752261e−01 |
| 2.14749485e−01 | −1.72443792e−01 | 7.01137483e−02 | 5.76551914e−01 |
| −1.28456354e−01 | 2.50868797e−01 | 2.94453949e−01 | 3.69975537e−01 |
| 4.39879745e−01 | 3.52028370e−01 | −3.98811221e−01 | −9.11936760e−02 |
| 8.64352524e−01 | −1.08845398e−01 | −7.73939164e−03 | 4.50639725e−01 |
| −4.22016174e−01 | 6.18374765e−01 | 4.59990084e−01 | 1.61207899e−01 |

TABLE $W_h^1$-continued

| | | | |
|---|---|---|---|
| 5.04796982e−01 | 2.72871524e−01 | −1.78339049e−01 | −1.35443052e−02 |
| −1.93028644e−01 | 1.01240262e−01 | −1.48806348e−02 | 6.23053849e−01 |
| 7.02247679e−01 | −3.83465320e−01 | −1.90353036e−01 | 1.44506231e−01 |
| 4.01204348e−01 | 4.95029204e−02 | 7.62692541e−02 | −4.89162430e−02 |
| 2.45818064e−01 | 3.71765316e−01 | −4.98051057e−04 | 2.60108024e−01 |
| −5.20121772e−03 | 5.43769589e−03 | 4.81817752e−01 | 1.53823078e−01 |
| 2.67312229e−01 | 7.72688270e−01 | 7.82919943e−01 | −2.11630791e−01 |
| 2.45729104e−01 | 7.37623647e−02 | 5.67741871e−01 | 4.25464958e−01 |
| 7.73436725e−02 | 3.77789065e−02 | 4.58637744e−01 | −2.94308245e−01 |
| 8.35344270e−02 | −8.29379335e−02 | −4.46320735e−02 | −6.79352926e−03 |
| −1.48123518e−01 | −5.16118668e−03 | 4.56285566e−01 | −5.57020493e−02 |
| 1.35188065e−02 | 4.08467472e−01 | 6.68744147e−01 | −2.05888990e−02 |
| −2.03629322e−02 | −7.81617686e−02 | 6.58352748e−02 | −1.66120172e−01 |
| 3.26301754e−01 | 6.25352487e−02 | 3.77949148e−01 | 1.29592255e−01 |
| 9.49102938e−02 | 4.23732221e−01 | 9.34650183e−01 | 3.99720185e−02 |
| −2.67510563e−01 | 3.73909712e−01 | 2.74422079e−01 | 2.87863851e−01 |
| −9.33925658e−02 | 1.71151478e−02 | 3.93327445e−01 | 1.97689325e−01 |
| 1.43866941e−01 | 2.13445187e−01 | −7.34469220e−02 | 1.59793064e−01 |
| −4.74502593e−02 | 4.33446050e−01 | −2.83077406e−03 | 2.76903994e−02 |
| −1.31786376e−01 | 7.10509717e−01 | 2.95507640e−01 | 1.46046713e−01 |
| 9.33988810e−01 | −3.03603411e−01 | 5.73990047e−01 | 3.31367642e−01 |
| 7.49387816e−02 | −3.50771993e−02 | 2.59543896e−01 | 1.24227792e−01 |
| 5.02462208e−01 | 2.32452869e−01 | −2.07419842e−01 | 3.62945259e−01 |
| 2.65115499e−01 | 9.57517028e−02 | 2.47952640e−01 | 1.41655266e−01 |
| 1.05719954e−01 | 4.17400688e−01 | −3.48318405e−02 | 2.58989692e−01 |
| 1.88399062e−01 | 1.81712508e−01 | 2.33220041e−01 | −3.86096165e−02 |
| 4.37738866e−01 | 2.25356922e−01 | −8.49172175e−02 | 1.29768178e−01 |
| 1.56757429e−01 | −2.05994677e−02 | 4.02447104e−01 | 3.21472615e−01 |
| 1.65292740e−01 | 3.93853962e−01 | −2.51948714e−01 | −1.44104436e−01 |
| 6.47425592e−01 | 5.39685249e−01 | −1.24012269e−02 | 2.02559292e−01 |
| 1.10502906e−01 | 4.15621340e−01 | −9.22956690e−02 | 2.87533194e−01 |
| 2.20887691e−01 | 3.83810729e−01 | 2.07056671e−01 | 2.72254676e−01 |
| −2.05978885e−02 | 3.07710648e−01 | 4.91000921e−01 | 2.01537758e−01 |
| −1.39714088e−02 | −9.90834087e−02 | 4.59302336e−01 | 1.18590035e−01 |
| 1.59061626e−01 | 5.82505167e−01 | 6.97326541e−01 | 6.10893667e−01 |
| 2.42425635e−01 | 3.20074320e−01 | 8.46567154e−02 | −5.11063747e−02 |
| 3.44751656e−01 | 4.32243720e−02 | −4.71132901e−03 | −1.36583015e−01 |
| 9.01080668e−02 | 5.97241163e−01 | 6.79855227e−01 | −1.09930215e−02 |
| 4.06690419e−01 | 4.31844056e−01 | 6.53587103e−01 | −9.58705097e−02 |
| 1.17934763e−01 | 4.86891210e−01 | 2.79637873e−01 | 4.34763342e−01 |
| −3.06234539e−01 | 2.44583532e−01 | 8.02691579e−01 | 1.79861948e−01 |
| 2.29488492e−01 | −2.00136289e−01 | 2.25984052e−01 | 8.07113424e−02 |
| 3.89628053e−01 | 4.16315228e−01 | 1.82000577e−01 | −9.13488418e−02] |
| [−6.47633672e−02 | 4.70991060e−02 | −2.76143532e−02 | 8.58192742e−01 |
| 1.05605803e−01 | −1.51150525e−01 | 2.61992216e−01 | 3.01536888e−01 |
| 2.83858359e−01 | 3.77671897e−01 | 1.23161368e−01 | −1.43391728e−01 |
| −1.33169249e−01 | 1.39780819e−01 | −2.25624204e−01 | 2.22186849e−01 |
| −1.27185732e−01 | 7.79052138e−01 | 5.09362102e−01 | −1.98089436e−01 |
| −3.13767977e−02 | 1.37078270e−01 | 1.00050634e−02 | −1.65481538e−01 |
| −8.67681354e−02 | 6.41683638e−02 | 4.12069529e−01 | 2.51758963e−01 |
| −1.15742132e−01 | 2.66363263e−01 | 5.41949332e−01 | 2.85298247e−02 |
| 1.51701614e−01 | 1.60551876e−01 | −3.26179415e−01 | 5.97425699e−01 |
| 2.67477691e−01 | −2.06075281e−01 | −7.96601102e−02 | 1.56887442e−01 |
| −1.19333461e−01 | −2.64820278e−01 | 2.16711447e−01 | −2.63377011e−01 |
| 1.14255629e−01 | 3.93839270e−01 | 2.83751190e−01 | 4.50437367e−01 |
| −3.53306144e−01 | 4.78626549e−01 | −3.84042919e−01 | 1.95787504e−01 |
| −2.10880622e−01 | 1.81291044e−01 | −1.24708019e−01 | −4.74220246e−01 |
| 1.40881762e−01 | −2.44943351e−01 | 2.57362813e−01 | −9.98210609e−02 |
| −4.29081321e−02 | 3.74169856e−01 | 6.56617165e−01 | 1.94251642e−01 |
| −2.56418847e−02 | 3.18212807e−01 | −5.46749294e−01 | 5.07013619e−01 |
| −2.12946564e−01 | 3.95557970e−01 | 2.74263144e−01 | 2.21986979e−01 |
| −2.47902106e−02 | 3.97990882e−01 | −2.84849018e−01 | −4.82710917e−03 |
| −3.51750314e−01 | 1.78669225e−01 | −2.46267691e−01 | −4.63688374e−01 |
| −5.27647495e−01 | 2.05631927e−01 | 3.69159758e−01 | 2.97607213e−01 |
| 6.29787594e−02 | 2.21880674e−01 | −5.09696722e−01 | −3.55713367e−01 |
| −1.52052447e−01 | 3.91658485e−01 | −4.43356931e−02 | 7.34565079e−01 |
| 8.28918278e−01 | 3.20312440e−01 | 5.80390021e−02 | 5.28889447e−01 |
| 4.07901555e−01 | −7.50663951e−02 | −2.66441107e−01 | 1.20607831e−01 |
| −2.32277513e−01 | −1.38307974e−01 | 2.43023947e−01 | 1.56989172e−01 |
| 2.45797932e−01 | −9.13736224e−02 | 9.35077444e−02 | 1.73342973e−01 |
| 2.91767657e−01 | 2.28259433e−01 | 4.30804104e−01 | −4.71817583e−01 |
| −1.19902506e−01 | 1.39225647e−01 | 1.57032162e−01 | 5.10319591e−01 |
| 3.55435982e−02 | 1.03874011e−02 | 1.56719759e−01 | 2.80192643e−02 |
| −2.99715549e−01 | 3.92225176e−01 | −4.81293872e−02 | −8.03183243e−02 |
| −1.63208082e−01 | −1.80904970e−01 | 2.54581600e−01 | 2.44546339e−01 |
| 2.28422597e−01 | −2.71653086e−01 | 6.16427660e−01 | 2.38399237e−01 |
| 2.59615928e−01 | −1.15267567e−01 | 3.36971283e−01 | −2.29977787e−01 |
| 6.68574214e−01 | −2.70889694e−04 | 5.42688109e−02 | 1.63461044e−01 |
| −1.20880455e−01 | 1.77270442e−01 | 4.68694925e−01 | 2.56166250e−01 |
| −6.75532222e−02 | 4.18527335e−01 | −1.79610159e−02 | 4.85790133e−01 |

TABLE $W_h^1$-continued

| | | | |
|---|---|---|---|
| 1.83890030e−01 | 2.48105928e−01 | 2.35178694e−01 | 9.46226940e−02 |
| 8.40872675e−02 | 2.64805228e−01 | −1.10520467e−01 | −1.20511884e−02 |
| 6.81879148e−02 | 3.77094924e−01 | 1.86665624e−01 | 5.64531207e−01 |
| 2.68223315e−01 | 8.30761939e−02 | 1.00766726e−01 | −1.90274850e−01 |
| 4.81536448e−01 | −4.69932318e−01 | 5.31729817e−01 | 2.58711725e−01 |
| 4.22825307e−01 | −3.28171998e−02 | −1.99958578e−01 | 2.17207208e−01 |
| 1.59927756e−02 | 2.95393497e−01 | −3.24355960e−01 | 4.05541033e−01 |
| 1.59765296e−02 | 6.28336221e−02 | −5.50177574e−01 | −8.26524794e−02 |
| 2.35537753e−01 | 4.38045889e−01 | 1.56416252e−01 | 2.01562360e−01 |
| −2.61026978e−01 | 1.61347628e−01 | 2.54184216e−01 | 4.34255786e−02 |
| 6.76820576e−01 | 2.45008662e−01 | −2.49979451e−01 | 2.81578675e−02 |
| 2.56887764e−01 | 1.01190656e−01 | 2.21761670e−02 | 5.97282410e−01 |
| 2.92355984e−01 | 1.55427516e−01 | −2.49653295e−01 | −1.21810399e−01 |
| 4.19028968e−01 | 7.15958774e−01 | −2.15573221e−01 | 1.80698305e−01 |
| 8.15838650e−02 | −8.87143090e−02 | −1.44798860e−01 | −2.65582353e−02 |
| −1.14423573e−01 | 5.59314489e−01 | −2.23074317e−01 | 4.41738330e−02 |
| −3.30044955e−03 | −1.22026466e−01 | 2.13261411e−01 | 4.06736702e−01 |
| −3.62773612e−02 | −4.14684832e−01 | 6.40048862e−01 | 1.18587419e−01 |
| 9.44932476e−02 | 3.27629685e−01 | 2.57584870e−01 | 6.37353837e−01 |
| 4.38968211e−01 | −1.54669404e−01 | 4.53761160e−01 | −2.68947810e−02 |
| 3.82475462e−03 | −2.40517616e−01 | 2.83028148e−01 | 9.72506776e−02 |
| 6.25063002e−01 | 3.91129583e−01 | 3.31115216e−01 | 8.32858831e−02 |
| 3.09812695e−01 | −4.17351753e−01 | 7.28295684e−01 | −2.37669423e−01 |
| 2.40306765e−01 | 6.10288084e−01 | 2.79412180e−01 | 2.63545752e−01 |
| −4.46975231e−01 | 1.21518830e−01 | 8.21979165e−01 | 3.63335796e−02 |
| −3.28403294e−01 | 3.12775597e−02 | 4.67099518e−01 | −5.06800056e−01 |
| 7.33815372e−01 | 1.84945256e−01 | −4.63711470e−02 | −7.72289485e−02] |
| [1.20715171e−01 | 3.31858307e−01 | 1.11031593e−04 | −2.57121213e−02 |
| −1.13024069e−02 | −2.22042575e−01 | −3.58225182e−02 | −5.40309064e−02 |
| 1.99305490e−01 | 1.49445727e−01 | −8.11325610e−02 | −2.40178421e−01 |
| −1.30939633e−01 | 2.44802564e−01 | −2.10638389e−01 | 4.39819656e−02 |
| −6.71456754e−02 | 3.82072031e−01 | −6.86521307e−02 | 3.51936460e−01 |
| −2.51217425e−01 | −1.65909529e−01 | 3.41609061e−01 | 1.29786497e−02 |
| −6.09405488e−02 | 1.13277406e−01 | 5.91845810e−01 | −9.30048376e−02 |
| 3.01105946e−01 | −3.85677367e−01 | 2.67104119e−01 | −3.75620229e−03 |
| −4.78956461e−01 | 1.88666712e−02 | −2.88064986e−01 | 2.62069732e−01 |
| 1.54884800e−01 | 3.22346538e−02 | 6.65420294e−02 | −2.58216530e−01 |
| 4.99563925e−02 | 3.83808054e−02 | −9.97013524e−02 | 3.27843487e−01 |
| 1.12222902e−01 | 3.82286191e−01 | −2.05582082e−02 | −2.05505207e−01 |
| −3.21190417e−01 | −3.68966302e−03 | −2.23321483e−01 | −4.18144941e−01 |
| −1.02248929e−01 | 1.97518736e−01 | −7.22045600e−02 | 2.13292614e−01 |
| 8.03751051e−02 | −2.06000075e−01 | −1.09692225e−01 | −2.68053412e−01 |
| 1.86132267e−01 | 5.68233430e−01 | 9.94142517e−02 | 3.44397724e−01 |
| 1.16605852e−02 | 1.26603976e−01 | −2.61257976e−01 | 1.24428391e−01 |
| 1.83149055e−01 | −4.03137244e−02 | 2.32774571e−01 | 5.59345111e−02 |
| 1.50193393e−01 | −1.76515192e−01 | −3.37987453e−01 | −8.74068141e−02 |
| −5.54632768e−03 | −2.43129134e−01 | 3.81635576e−02 | −2.60112494e−01 |
| −1.03075109e−01 | 3.13682944e−01 | 3.18315744e−01 | 2.78645784e−01 |
| 2.54428774e−01 | 1.12367079e−01 | −2.01574922e−01 | 1.79053858e−01 |
| −9.10050236e−03 | 7.13948190e−01 | −2.15502635e−01 | 7.88930893e−01 |
| 1.46957099e−01 | 5.96573293e−01 | 2.93869287e−01 | 9.62710902e−02 |
| 4.31229286e−02 | 2.94555485e−01 | −8.85665491e−02 | −3.99066538e−01 |
| −5.12025237e−01 | 9.94225889e−02 | 1.33824453e−01 | 6.41214475e−02 |
| 4.10890579e−01 | 9.10329819e−02 | −4.87925857e−02 | 1.08715013e−01 |
| −3.03782877e−02 | −3.45400125e−01 | 3.45829099e−01 | −5.26730537e−01 |
| −1.04944244e−01 | 1.26616254e−01 | −1.11321047e−01 | 7.28757143e−01 |
| 3.82361449e−02 | 2.07524940e−01 | −1.40997926e−02 | −1.96299508e−01 |
| 1.96793437e−01 | 4.43113059e−01 | −2.80817777e−01 | 2.07454246e−02 |
| 2.76160300e−01 | 3.60265840e−03 | −1.27727464e−01 | 2.85379708e−01 |
| −4.99057956e−02 | 2.67956465e−01 | 2.34507039e−01 | 1.23139247e−02 |
| 2.52010167e−01 | 9.90069360e−02 | 2.26042703e−01 | −1.63009614e−01 |
| 2.74247438e−01 | 5.92514239e−02 | 2.15583354e−01 | −1.29609495e−01 |
| 1.63066819e−01 | 1.50750265e−01 | 2.92367011e−01 | 1.13232203e−01 |
| 1.77318990e−01 | 2.34367512e−02 | −3.83686215e−01 | −1.25539884e−01 |
| 5.04783154e−01 | −8.82196724e−02 | 1.30913004e−01 | 1.69493973e−01 |
| 8.13610554e−02 | 1.85676038e−01 | 6.26747264e−03 | −1.68221474e−01 |
| 2.37915710e−01 | 4.76634890e−01 | −1.89096592e−02 | −2.47096851e−01 |
| 3.57856490e−02 | −4.16245073e−01 | 2.19752163e−01 | −3.15900028e−01 |
| −4.81614843e−02 | −1.36284947e−01 | 5.03686488e−01 | 1.95408523e−01 |
| 4.68149811e−01 | −2.70806909e−01 | 9.92579609e−02 | 3.89314085e−01 |
| −2.98867803e−02 | 3.50097358e−01 | −4.56537813e−01 | −1.15741625e−01 |
| −2.30369885e−02 | −1.11260740e−02 | 2.75907278e−01 | −7.15982392e−02 |
| −8.04281086e−02 | 2.95130700e−01 | −1.22945085e−02 | −5.94602451e−02 |
| −1.23985540e−02 | −1.42145485e−01 | 1.67213246e−01 | −1.32721722e−01 |
| 2.94126153e−01 | 1.38187826e−01 | −2.75047660e−01 | −1.35778770e−01 |
| 8.97918120e−02 | −2.39367619e−01 | −3.53956640e−01 | 3.07654351e−01 |
| 2.48659208e−01 | 2.26540178e−01 | 1.60769790e−01 | 3.76325846e−01 |
| −8.45293701e−02 | 3.28283340e−01 | 2.80924320e−01 | −1.91410050e−01 |
| −1.33888219e−02 | −2.38897335e−02 | −2.44713619e−01 | −4.26838100e−02 |
| 1.21854879e−02 | 2.58128215e−02 | −4.50786613e−02 | 1.91417694e−01 |

TABLE $W_h^1$-continued

| | | | |
|---|---|---|---|
| 2.95402378e−01 | −1.73354030e−01 | −1.42477959e−01 | 3.21679741e−01 |
| 1.65043995e−02 | −3.26550484e−01 | 4.81624663e−01 | −1.55584261e−01 |
| −1.70079544e−01 | 8.12894180e−02 | 6.63906708e−02 | −5.86517006e−02 |
| 4.98135746e−01 | −8.02076459e−02 | 5.50919883e−02 | −3.29634607e−01 |
| 6.37644669e−03 | −1.00292727e−01 | −4.74235900e−02 | −1.83671758e−01 |
| 4.22405392e−01 | 2.74133056e−01 | 7.43223727e−02 | 1.31766438e−01 |
| 2.23311827e−01 | −2.20602229e−01 | 6.19303167e−01 | 1.84747446e−02 |
| 3.74645919e−01 | −1.49027422e−01 | 2.78334290e−01 | −2.86487132e−01 |
| −9.62609276e−02 | −8.99230167e−02 | 2.22628921e−01 | 1.48930579e−01 |
| −8.13691318e−02 | 9.34498161e−02 | 1.00308515e−01 | −2.69988537e−01 |
| 9.15129259e−02 | −1.70806497e−01 | 7.86971226e−02 | 5.19193053e−01] |
| [7.18201637e−01 | 2.72539228e−01 | 2.49127060e−01 | 2.73543924e−01 |
| 1.72934785e−01 | 3.91859621e−01 | 7.00983882e−01 | 2.36362636e−01 |
| −4.93099131e−02 | 6.16854243e−02 | 6.77539408e−02 | 3.76171410e−01 |
| 9.14215624e−01 | 1.72478646e−01 | 1.96949393e−01 | −1.49114043e−01 |
| 1.73336303e−00 | −8.85113254e−02 | 5.29106855e−01 | 6.22094035e−01 |
| 3.30333292e−01 | 3.75721157e−01 | 6.40943170e−01 | 5.45083880e−01 |
| 8.41308057e−01 | 2.30609894e−01 | 1.02182019e−00 | 1.11793898e−01 |
| −1.59663369e−03 | 1.70484111e−01 | 1.41797125e−01 | 2.09239811e−01 |
| 2.66912431e−01 | 2.50782669e−01 | 9.36396956e−01 | 4.72253531e−01 |
| 6.59331262e−01 | 8.70415747e−01 | 6.42698288e−01 | 1.03010798e−00 |
| 1.18847883e−00 | −1.33748621e−01 | 4.96258587e−01 | 4.77532089e−01 |
| 1.00681424e−00 | −1.18682504e−01 | 2.66121030e−01 | 1.02717972e−00 |
| 4.04182106e−01 | 6.11703634e−01 | 8.41964543e−01 | 1.13620900e−01 |
| 4.21913207e−01 | 4.34702367e−01 | 4.70014066e−01 | 9.54481602e−01 |
| 9.11522150e−01 | 5.25261283e−01 | 9.26130190e−02 | 4.22389477e−01 |
| 5.82188606e−01 | −1.35834053e−01 | 5.33535890e−02 | 6.07328773e−01 |
| 3.93829167e−01 | 1.48247421e−01 | 5.35317183e−01 | −1.84143245e−01 |
| 1.77443266e−01 | 6.13306426e−02 | 3.13682646e−01 | 3.51534218e−01 |
| 4.40950412e−03 | 7.79410839e−01 | 9.57656503e−01 | 5.51632762e−01 |
| 9.55004454e−01 | 1.78023167e−02 | 2.87369341e−01 | −7.38771865e−03 |
| 3.76925468e−01 | 6.82112396e−01 | 1.89741164e−01 | 4.57530171e−01 |
| 1.04647481e−00 | 4.89391297e−01 | 5.42592883e−01 | 5.49979687e−01 |
| 1.04165591e−01 | −2.49576736e−02 | 5.51636294e−02 | 1.05338641e−01 |
| 1.33141851e−00 | 1.80165470e−01 | 9.44585800e−01 | 2.74753660e−01 |
| 3.85412097e−01 | −3.19164321e−02 | 5.06639957e−01 | 6.76718652e−01 |
| 1.99598297e−01 | 3.55698884e−01 | 2.70850778e−01 | −3.31985533e−01 |
| 3.51203054e−01 | 8.69766533e−01 | 1.84653997e−01 | 7.57496297e−01 |
| 3.01242154e−02 | 4.94196385e−01 | 4.84391093e−01 | 6.49210393e−01 |
| 7.36153603e−01 | 3.12148184e−01 | 6.67192996e−01 | −1.07485585e−01 |
| 7.77368844e−01 | 1.92032859e−01 | 5.58294952e−01 | 2.69144297e−01 |
| 7.89732039e−01 | 1.15250731e−00 | −2.55177915e−01 | 8.52482557e−01 |
| 2.42616817e−01 | 3.61387789e−01 | 2.57813424e−01 | 1.82185662e−00 |
| 1.11256766e−00 | 1.01104528e−01 | −4.18762773e−01 | 2.26237684e−01 |
| −1.24852598e−01 | 5.34266293e−01 | 1.11785996e−00 | 3.61558169e−01 |
| 1.50972353e−02 | 3.49406570e−01 | 7.13876486e−01 | 5.38872600e−01 |
| 2.12478459e−01 | 7.27085948e−01 | 7.88591862e−01 | 7.63717532e−01 |
| 7.55913615e−01 | 7.67876953e−02 | 3.04704964e−01 | 6.16679013e−01 |
| 3.35057005e−02 | 2.65504837e−01 | 5.96138716e−01 | 1.18710923e−00 |
| 5.44643819e−01 | 8.82211745e−01 | 4.69371617e−01 | 2.59198278e−01 |
| 1.01203069e−01 | 4.48030144e−01 | 6.85937047e−01 | 1.01513410e−00 |
| 3.99920434e−01 | 9.09061372e−01 | 4.33318496e−01 | 4.33963686e−01 |
| 7.03680217e−01 | 5.21746576e−01 | −2.04774871e−01 | 2.33542114e−01 |
| 2.46433347e−01 | 2.86773294e−01 | 3.61903191e−01 | 5.63719511e−01 |
| 4.75307226e−01 | 2.56039381e−01 | 9.45529163e−01 | 1.05715382e−00 |
| 1.92084894e−01 | 5.69515467e−01 | 2.12327376e−01 | 8.81739736e−01 |
| 5.40057063e−01 | 4.95122850e−01 | 4.38915044e−01 | 4.83638406e−01 |
| 7.69609749e−01 | 2.79917687e−01 | 4.36467797e−01 | 6.66476846e−01 |
| 3.53175402e−01 | 4.09755826e−01 | 2.92415321e−01 | 6.86218500e−01 |
| 4.15428340e−01 | 3.56582820e−01 | 2.75403410e−01 | 5.33293366e−01 |
| 5.07013619e−01 | 5.20015776e−01 | 3.28103364e−01 | 1.43598706e−01 |
| −5.68773746e−02 | 5.83023392e−02 | 5.81284881e−01 | −4.47916389e−01 |
| −8.31117690e−01 | 9.70643163e−01 | 1.20020151e−01 | 1.54035330e−01 |
| 5.49919426e−01 | 2.74637252e−01 | 4.90051001e−01 | 2.57307947e−01 |
| 6.93926871e−01 | 4.16917592e−01 | −2.29257904e−02 | 4.84798104e−01 |
| 3.80421400e−01 | 8.16197097e−01 | 1.98524296e−01 | 7.52471566e−01 |
| 4.30080920e−01 | 4.95577119e−02 | 3.14490080e−01 | −2.62603819e−01 |
| 6.02734804e−01 | 4.36801821e−01 | 1.40850857e−01 | 8.18387032e−01 |
| 5.12695909e−01 | 2.31322408e−01 | 5.35823405e−01 | 4.68608290e−01 |
| 8.28370929e−01 | 6.41990542e−01 | 6.78463995e−01 | 5.82592368e−01 |
| 5.73177516e−01 | 5.58692813e−01 | 4.78478819e−01 | 3.43661487e−01 |
| 2.29791597e−01 | −6.03095815e−02 | 3.48690361e−01 | 6.38095856e−01 |
| 4.17253286e−01 | 7.68694162e−01 | 6.36954904e−02 | −1.13430001e−01 |
| 7.03642666e−01 | 2.80069649e−01 | 1.20390922e−01 | 8.47209990e−02 |
| 2.22179785e−01 | 3.83191645e−01 | 7.12651432e−01 | 6.32434130e−01] |
| [1.56703845e−01 | −2.49664560e−01 | −2.34808221e−01 | 1.66442052e−01 |
| 2.89917618e−01 | 1.95080742e−01 | 8.54359210e−01 | −5.04376113e−01 |
| 5.87803423e−01 | −2.80314595e−01 | 4.13906336e−01 | −4.96391766e−03 |
| −1.39032573e−01 | 3.87053698e−01 | −1.47061273e−01 | −1.63649321e−01 |
| 1.24978447e−00 | −2.80657053e−01 | −3.25099915e−01 | 6.77142382e−01 |

TABLE $W_h^1$-continued

| | | | |
|---|---|---|---|
| 1.97735541e−02 | 1.18067935e−01 | 1.43481836e−01 | 1.80931926e−01 |
| 6.27306640e−01 | 7.90471435e−01 | 1.92019731e−01 | 3.89504939e−01 |
| −2.88701773e−01 | 1.80268884e−02 | −4.61292565e−01 | −3.50265950e−01 |
| −4.78448004e−01 | 8.92468542e−01 | 6.82184041e−01 | −2.84653246e−01 |
| 1.59215078e−01 | −2.05391318e−01 | −8.74503180e−02 | 1.27537921e−01 |
| 3.78807664e−01 | 2.58361734e−02 | 2.04764962e−01 | 4.45322633e−01 |
| 3.42227370e−01 | −3.29816192e−01 | −3.91163975e−02 | −3.63295786e−02 |
| 1.02869952e−00 | 4.09494996e−01 | 6.86116517e−01 | −2.04834398e−02 |
| 1.58978209e−01 | −3.58088493e−01 | 4.42068651e−02 | 6.17919207e−01 |
| 5.86434662e−01 | 3.14224660e−01 | 1.94808751e−01 | −2.04436809e−01 |
| −1.81173205e−01 | −1.35676339e−01 | 8.88332203e−02 | −2.58657873e−01 |
| 5.43034934e−02 | −3.75641882e−01 | −1.63557068e−01 | −5.50291955e−01 |
| −3.71526033e−01 | −5.81106067e−01 | 3.54752034e−01 | −1.64429113e−01 |
| 3.28314632e−01 | −5.25891483e−01 | 6.96317196e−01 | 6.05528044e−01 |
| 7.26246417e−01 | 2.36746728e−01 | 2.01585054e−01 | 6.70632482e−01 |
| 2.31579825e−01 | −4.70412299e−02 | 4.37805593e−01 | −2.01246724e−01 |
| −4.00687128e−01 | −2.20315764e−03 | 5.46540320e−01 | 2.17859760e−01 |
| −9.61587280e−02 | 1.34501562e−01 | 5.03920019e−02 | −4.18276995e−01 |
| 5.68178833e−01 | −7.54573345e−02 | 1.48862332e−01 | −2.25091264e−01 |
| 4.80987191e−01 | −3.25779498e−01 | 7.11249888e−01 | 2.33367145e−01 |
| 3.02067511e−01 | 3.09376508e−01 | 3.60569447e−01 | 2.89567947e−01 |
| 3.99612755e−01 | 4.66420390e−02 | 4.82378989e−01 | 6.59051955e−01 |
| −1.75880745e−01 | 2.60345131e−01 | −6.64893508e−01 | 5.70074618e−01 |
| 1.35602236e−01 | −1.61191300e−01 | 4.44626629e−01 | −3.68284702e−01 |
| 1.24907777e−01 | 3.61421049e−01 | 4.68894154e−01 | −8.36616009e−02 |
| −2.40354002e−01 | 7.50330836e−02 | −3.94182742e−01 | 3.49924684e−01 |
| 8.46179202e−03 | 1.37012094e−01 | 5.74067056e−01 | 5.60321569e−01 |
| −1.12396769e−01 | 1.18595757e−01 | −2.28878617e−01 | 1.60365954e−01 |
| 5.18056657e−03 | −2.85897166e−01 | 1.32727265e−00 | −8.97879303e−02 |
| −2.46120885e−01 | 2.81563222e−01 | 1.00521430e−01 | −3.07145510e−01 |
| −1.36794388e−01 | −2.68528312e−02 | 2.02244632e−02 | −2.64399588e−01 |
| 1.41107246e−01 | −2.83505797e−01 | −6.24245293e−02 | 2.66080797e−01 |
| 1.53911218e−01 | 5.29249124e−02 | 8.03958118e−01 | 5.80795228e−01 |
| −6.55695423e−02 | 6.52806044e−01 | 2.75250852e−01 | −4.10528451e−01 |
| 5.72103381e−01 | 7.17368126e−02 | 3.45455378e−01 | 1.96158692e−01 |
| −1.60148799e−01 | 3.15028131e−01 | 1.61377504e−01 | 2.58362442e−01 |
| −5.96733272e−01 | −6.71866357e−01 | −4.20823382e−01 | 3.43864918e−01 |
| 1.37295917e−01 | 1.16654277e−00 | 1.87271200e−02 | 6.96380854e−01 |
| 1.99484043e−02 | 1.38309225e−02 | 2.45007575e−01 | −9.60223228e−02 |
| 4.40135971e−02 | 7.94267297e−01 | −2.65886515e−01 | 4.38619405e−01 |
| 1.52214140e−01 | −1.64852694e−01 | 3.62125754e−01 | 3.79678071e−01 |
| −2.08143413e−01 | 2.40866810e−01 | 2.24424023e−01 | 1.65312275e−01 |
| 1.73888147e−01 | 3.33037585e−01 | 2.65640318e−01 | 3.65179807e−01 |
| 1.78411737e−01 | 4.50235695e−01 | 2.65776783e−01 | 3.73807132e−01 |
| −1.14731282e−01 | −5.33282384e−02 | −2.11800799e−01 | 1.72632977e−01 |
| −4.70782816e−02 | −2.57856827e−01 | 4.09795880e−01 | −1.12624928e−01 |
| 7.08925664e−01 | −8.11139494e−02 | 3.46997865e−02 | 1.92696080e−01 |
| −3.43590826e−02 | −1.40691802e−01 | −3.50993067e−01 | 2.92058200e−01 |
| 6.25590563e−01 | 2.03171983e−01 | 5.02497017e−01 | 4.97455448e−01 |
| −2.11439371e−01 | 8.69636714e−01 | 4.32290472e−01 | −2.17080399e−01 |
| 3.04246712e−02 | 8.11234355e−01 | 1.24451637e−01 | −1.70464918e−01 |
| −5.31019308e−02 | 6.10450685e−01 | 5.89609027e−01 | 3.20645154e−01 |
| 4.76990789e−01 | 1.41106114e−01 | 4.70234007e−01 | 1.33178934e−01 |
| 2.47120708e−01 | 4.96588320e−01 | −1.10730432e−01 | 5.25736749e−01 |
| −5.19609042e−02 | 1.65066198e−01 | 2.02886105e−01 | −2.70751864e−01 |
| 6.34292737e−02 | 1.17300257e−01 | 3.51374030e−01 | 3.58302772e−01 |
| 7.95156240e−01 | −4.59689617e−01 | −1.05546322e−02 | 4.61149931e−01 |
| 1.05072312e−01 | −9.90348756e−02 | 7.49007523e−01 | −4.33571339e−01 |
| 1.38640285e−01 | 1.31139308e−01 | 2.91657597e−01 | 3.95733446e−01] |
| [−2.32628379e−02 | 1.00441091e−01 | −1.24987634e−02 | 1.37352236e−02 |
| 6.67930692e−02 | −6.65659085e−02 | −8.86937752e−02 | −6.28482224e−03 |
| −9.49767083e−02 | 7.11680427e−02 | −4.12237607e−02 | −2.62977090e−02 |
| 9.36934352e−02 | 9.00819898e−02 | 7.53892437e−02 | 6.72758510e−03 |
| −8.70801434e−02 | 2.10653823e−02 | −1.40937977e−03 | 9.85732675e−03 |
| 4.37651388e−02 | 3.36881317e−02 | −3.83061394e−02 | 2.83077303e−02 |
| 9.01711956e−02 | −4.97946963e−02 | 2.91642770e−02 | −1.00842506e−01 |
| −1.14169829e−01 | −3.98067534e−02 | −9.14870203e−02 | 1.10424802e−01 |
| 5.50854951e−02 | 1.10185165e−02 | 4.92302328e−02 | −9.33992937e−02 |
| −2.02160664e−02 | 2.18786299e−02 | 1.07970595e−01 | −7.35805184e−02 |
| 1.48590682e−02 | 8.62787515e−02 | −6.52998239e−02 | −2.41543259e−03 |
| 5.22552803e−02 | 6.44154847e−02 | −7.05622658e−02 | 6.42691255e−02 |
| 6.55321172e−03 | 1.06452577e−01 | 7.76731819e−02 | 3.20576392e−02 |
| −5.32111898e−02 | −4.54161502e−02 | −4.92257886e−02 | 1.11707887e−02 |
| 3.37729696e−03 | −9.68225375e−02 | 9.27743688e−02 | −6.47410378e−02 |
| −2.56476831e−02 | −1.01074673e−01 | 4.69389930e−02 | 1.98311266e−02 |
| 1.00622818e−01 | −1.74260326e−02 | −6.34956062e−02 | 1.07198209e−01 |
| −1.42839532e−02 | 9.92120281e−02 | −1.18544009e−02 | 4.37521450e−02 |
| 7.79165253e−02 | −9.91405472e−02 | −9.90522280e−02 | −2.85227597e−02 |
| 1.01147830e−01 | −6.45641163e−02 | −5.39036561e−03 | 1.25432741e−02 |
| −4.81318831e−02 | 4.56275605e−02 | −4.65392619e−02 | −3.58070508e−02 |

TABLE $W_h^1$-continued

| | | | |
|---|---|---|---|
| −7.40657449e−02 | 5.15714549e−02 | −1.03456765e−01 | −1.77977569e−02 |
| −2.13360619e−02 | 6.36073470e−04 | −4.84661087e−02 | 8.40911418e−02 |
| −6.26763478e−02 | −8.99102762e−02 | 9.28108394e−02 | −8.06123391e−02 |
| −9.94438455e−02 | −7.83783421e−02 | −1.12278461e−02 | 4.06587385e−02 |
| −4.76619229e−02 | −2.87145711e−02 | 6.10124469e−02 | −1.07041225e−02 |
| −2.04929672e−02 | −4.65822965e−02 | 1.13624334e−02 | −7.07423836e−02 |
| −1.05231013e−02 | 5.00716567e−02 | 9.36767533e−02 | 1.08855344e−01 |
| 2.93931868e−02 | 1.01037540e−01 | −9.42792967e−02 | −4.96254526e−02 |
| 1.01239279e−01 | 1.02955431e−01 | 6.15913905e−02 | 2.11562384e−01 |
| 8.26092064e−02 | −9.95447263e−02 | −7.35062435e−02 | −3.28087322e−02 |
| 8.90703797e−02 | −4.14426177e−04 | 8.67896378e−02 | −8.85861218e−02 |
| 6.94129020e−02 | 2.06841342e−02 | 4.00665700e−02 | 1.94797330e−02 |
| 6.37749210e−02 | 5.46393357e−02 | −8.60737264e−02 | −6.43747821e−02 |
| −8.66781026e−02 | −8.26598480e−02 | 1.06871910e−01 | −1.37039533e−04 |
| 1.08193949e−01 | −6.55757487e−02 | −2.17900798e−02 | −6.96296841e−02 |
| −9.18777883e−02 | 7.31516033e−02 | 1.02053121e−01 | 1.06604084e−01 |
| 4.95135114e−02 | −1.04764059e−01 | 9.46646631e−02 | 4.68210392e−02 |
| 6.13602400e−02 | −1.86460335e−02 | 2.99927276e−02 | −5.92454001e−02 |
| −8.25610012e−02 | 4.96329106e−02 | −3.08874473e−02 | 6.45416006e−02 |
| −4.13072295e−02 | −2.51813047e−02 | 3.98072153e−02 | −5.53210340e−03 |
| 3.51222605e−02 | 6.47681812e−03 | 9.12201032e−02 | 5.39527647e−03 |
| 2.43597571e−02 | 4.88485582e−02 | −4.81698923e−02 | −4.12965603e−02 |
| 1.73875801e−02 | 1.04723580e−01 | −3.44403312e−02 | 9.05521065e−02 |
| 5.45582436e−02 | 8.56090263e−02 | −2.89319232e−02 | 3.27256992e−02 |
| 7.30188936e−02 | 9.65016112e−02 | 1.49715459e−02 | −4.72346954e−02 |
| −2.97077596e−02 | −3.60609815e−02 | −7.91240260e−02 | −1.26052869e−03 |
| −1.53080914e−02 | 2.94599701e−02 | −3.45857777e−02 | −1.08873993e−01 |
| 1.55240940e−02 | 9.51889381e−02 | −1.05351582e−01 | 9.09859389e−02 |
| −4.56163734e−02 | 3.56896943e−03 | −4.24581505e−02 | −6.06899001e−02 |
| 3.04655731e−02 | −8.31302404e−02 | −3.79588045e−02 | −8.60401168e−02 |
| −1.31908059e−02 | −5.72404750e−02 | −3.38801146e−02 | 1.06855914e−01 |
| 7.09778517e−02 | 8.72239470e−02 | 7.26637915e−02 | −4.36290354e−02 |
| 2.99101300e−03 | 8.42762366e−02 | −8.08830280e−03 | −9.73681211e−02 |
| 9.47125182e−02 | −1.51018919e−02 | −6.87822178e−02 | 7.94910789e−02 |
| −1.84313133e−02 | −1.51578858e−02 | 9.46580097e−02 | −6.93273023e−02 |
| −1.95841882e−02 | 1.00544401e−01 | −3.09797153e−02 | 8.66465271e−02 |
| −2.81298868e−02 | −9.85550657e−02 | −1.05859056e−01 | 1.85667910e−02 |
| 1.04988948e−01 | −4.46928628e−02 | 8.53113681e−02 | 1.15757133e−03 |
| 6.42767968e−03 | 9.29054320e−02 | 7.80874491e−02 | −6.23315088e−02 |
| −5.88839501e−03 | −2.14929413e−02 | 5.10966778e−02 | 8.87458548e−02 |
| 7.10175261e−02 | −2.27631666e−02 | 5.23159020e−02 | 1.99247468e−02 |
| 2.36778967e−02 | −4.06450070e−02 | 9.81896445e−02 | 2.14461777e−02 |
| 5.18415831e−02 | −4.40347791e−02 | 8.62575099e−02 | −9.34339911e−02] |
| [−2.33316757e−02 | 1.32287189e−01 | 1.43264189e−01 | 3.58170390e−01 |
| 2.01926976e−01 | 1.28897876e−01 | 8.28476176e−02 | −1.72678635e−01 |
| 3.19853336e−01 | −2.79610902e−01 | 4.35060263e−01 | 1.30099803e−01 |
| 1.23773128e−01 | 6.22164384e−02 | −1.92278668e−01 | 5.89711312e−03 |
| −9.01489705e−02 | −1.99346766e−02 | 9.03027654e−02 | 7.43903294e−02 |
| −2.15826422e−01 | 2.83647627e−01 | −3.11496574e−02 | 7.34077320e−02 |
| 4.41326857e−02 | 8.15843642e−02 | 2.87394365e−03 | −3.88575159e−02 |
| 7.95489550e−02 | 1.90675944e−01 | 4.40185100e−01 | 2.31103674e−01 |
| 5.72626553e−02 | 1.51331857e−01 | 1.80493042e−01 | 3.50087553e−01 |
| −7.00570196e−02 | 4.39307481e−01 | 6.90795854e−02 | −1.41968764e−02 |
| −9.47334617e−02 | 1.18627578e−01 | 1.68201789e−01 | 5.02739727e−01 |
| −7.50250891e−02 | 1.69095639e−02 | 8.63882974e−02 | 1.29610285e−01 |
| −2.65951455e−01 | 1.26061320e−01 | −2.78804339e−02 | 2.76735634e−01 |
| −1.41695872e−01 | 2.10595593e−01 | 2.11172864e−01 | 1.19409174e−01 |
| 1.89336896e−01 | 1.85258925e−01 | 1.50934145e−01 | −2.12362200e−01 |
| −1.59559920e−02 | 1.03288956e−01 | 5.70278540e−02 | 2.62608528e−01 |
| −4.56153564e−02 | −3.40666883e−02 | 1.45419061e−01 | 3.73847216e−01 |
| 2.26634428e−01 | 1.77530184e−01 | 1.46197081e−02 | 1.98298931e−01 |
| 4.27662373e−01 | 2.84199476e−01 | 5.90767935e−02 | −2.00711697e−01 |
| 3.47611457e−01 | 1.52596846e−01 | 1.42309159e−01 | 8.62292573e−03 |
| 9.49044898e−02 | −1.58928037e−01 | 1.40779644e−01 | 8.91468152e−02 |
| 5.62960744e−01 | 5.92365935e−02 | −7.37189800e−02 | 1.51640505e−01 |
| −1.02948938e−02 | 2.06313238e−01 | 1.11563124e−01 | 4.52367127e−01 |
| 4.41937745e−01 | 4.69780982e−02 | 2.13298947e−01 | 8.23843032e−02 |
| 1.43806085e−01 | 8.04148465e−02 | −2.95856625e−01 | −1.13318488e−01 |
| −8.16751048e−02 | 7.99908862e−02 | −2.21699879e−01 | 1.18646301e−01 |
| 1.38827547e−01 | −3.51680338e−01 | −1.12066366e−01 | 2.17210203e−01 |
| 2.56122082e−01 | 2.51111418e−01 | 1.95901990e−01 | 1.98291004e−01 |
| 1.64878279e−01 | 3.69502276e−01 | 3.34501863e−01 | 9.70379561e−02 |
| 1.86075881e−01 | −9.70701724e−02 | −2.80131370e−01 | −4.53568757e−01 |
| 1.56992063e−01 | −2.01246172e−01 | 1.54429078e−01 | 7.12446272e−02 |
| 3.79033267e−01 | 3.22677076e−01 | −4.99288999e−02 | 5.40449396e−02 |
| −9.33664441e−02 | −3.51609707e−01 | 3.86613637e−01 | 9.03502926e−02 |
| −2.89209802e−02 | 2.26269081e−01 | −2.83309937e−01 | 1.41098469e−01 |
| 2.87734658e−01 | 9.60831195e−02 | 1.15774743e−01 | 5.03318422e−02 |
| −1.06517635e−01 | 2.57491440e−01 | 3.78375679e−01 | 9.00671352e−03 |
| 1.48857087e−01 | 4.45752889e−01 | −6.08779639e−02 | 1.41514823e−01 |

TABLE $W_h^1$-continued

| | | | |
|---|---|---|---|
| 1.25309199e−01 | 5.35124063e−01 | 3.23606521e−01 | 1.99325308e−01 |
| 8.45194235e−03 | 3.31823438e−01 | 6.31074095e−03 | 1.50354922e−01 |
| −3.67409512e−02 | 1.06839977e−01 | 1.17526092e−02 | −1.34367019e−01 |
| 3.86401981e−02 | 2.12479755e−01 | 8.64100903e−02 | 1.13147967e−01 |
| −3.91268469e−02 | 3.91941667e−01 | 4.99610975e−02 | 3.90253961e−01 |
| 2.58071925e−02 | 1.72867707e−03 | −2.59314150e−01 | 1.97772935e−01 |
| 5.91679573e−01 | 1.64624415e−02 | 1.66823983e−01 | −5.17950021e−02 |
| −1.74022451e−01 | −1.46355852e−01 | 9.49611962e−02 | 1.66813165e−01 |
| −1.02076381e−02 | 2.52499551e−01 | −1.07465692e−01 | −6.64946362e−02 |
| 2.13479429e−01 | 2.87963301e−01 | −1.52554035e−01 | −1.46300167e−01 |
| 3.46849263e−01 | 2.66408324e−01 | −2.63563484e−01 | 1.52848884e−01 |
| −1.37492418e−01 | 1.92080557e−01 | 1.66880667e−01 | −1.47336945e−01 |
| 1.97466895e−01 | −7.51521960e−02 | 1.77084491e−01 | 3.35676879e−01 |
| 1.67652741e−01 | 2.15050012e−01 | 2.32402921e−01 | −1.45335138e−01 |
| 4.13164608e−02 | −1.51143625e−01 | −2.29800656e−01 | −1.24370508e−01 |
| −1.25527397e−01 | −1.10908709e−01 | 2.82932669e−01 | −3.21769357e−01 |
| 2.93502122e−01 | 2.78280079e−01 | 2.02793956e−01 | 8.01295415e−02 |
| −1.13794729e−01 | −6.83109984e−02 | −1.04146361e−01 | 5.59965447e−02 |
| 3.74396145e−01 | 1.75909340e−01 | 2.62933761e−01 | −2.13353276e−01 |
| 1.43942162e−01 | −4.72631492e−02 | 1.57577455e−01 | 6.93079084e−02 |
| 3.78803492e−01 | 1.40255436e−01 | 1.07621983e−01 | 1.25442475e−01 |
| 1.60552099e−01 | −3.53563607e−01 | 1.90254554e−01 | 2.59303719e−01 |
| −6.33208603e−02 | 3.89288843e−01 | −2.61068139e−02 | 1.55502960e−01 |
| 1.04714401e−01 | 5.00368839e−03 | −4.70968112e−02 | 6.16670214e−02 |
| 6.05347514e−02 | 2.55261719e−01 | 3.18776548e−01 | 9.34475064e−02 |
| −7.88858533e−02 | −1.80776954e−01 | 2.19753444e−01 | 5.72157465e−02 |
| 3.42890799e−01 | 4.45094019e−01 | −1.45289555e−01 | 2.12999046e−01] |
| [3.70433539e−01 | 5.14830828e−01 | 4.60661501e−01 | 5.37165225e−01 |
| 5.77546000e−01 | 2.58976191e−01 | 5.44807911e−01 | 7.99961209e−01 |
| 5.63446999e−01 | 6.26509309e−01 | 3.14241678e−01 | 1.34035265e−00 |
| 1.00518107e−00 | 4.15421873e−01 | 4.91653681e−01 | 7.29914844e−01 |
| 1.03950584e−00 | 1.92825451e−01 | −3.09935749e−01 | −7.54418448e−02 |
| 6.46149099e−01 | −5.21134973e−01 | 8.01852465e−01 | 1.93977594e−00 |
| 8.01181436e−01 | 7.03847945e−01 | −1.93168491e−01 | 4.42890704e−01 |
| 1.42878056e−01 | 5.07312775e−01 | 5.25544435e−02 | 3.72607470e−01 |
| 1.42753154e−01 | 1.12005973e−00 | 1.27318263e−00 | 2.60584533e−01 |
| 1.52662903e−01 | 7.48438299e−01 | 5.72690129e−01 | 1.07240379e−00 |
| 8.65273356e−01 | 5.68603218e−01 | 3.35906386e−01 | 7.45696664e−01 |
| 1.00186646e−00 | 1.04454681e−00 | 9.30149913e−01 | 9.14107502e−01 |
| −2.28927478e−01 | 5.14464200e−01 | 4.44934994e−01 | 7.86425471e−01 |
| 2.84154177e−01 | 5.50231278e−01 | 6.60185635e−01 | 1.94369465e−01 |
| 6.18627012e−01 | −2.59199813e−02 | 5.27537942e−01 | 3.15406233e−01 |
| 1.00470209e−00 | 6.77108824e−01 | 2.63197958e−01 | 6.31982327e−01 |
| 5.63027084e−01 | 2.58051306e−01 | 3.11633646e−01 | 8.96832108e−01 |
| 8.47425640e−01 | −1.44689292e−01 | 3.20667803e−01 | 7.80592740e−01 |
| 4.94336098e−01 | 3.77080709e−01 | 5.03194630e−01 | 3.64179790e−01 |
| 1.38935530e−00 | 9.93455410e−01 | 6.33744717e−01 | 1.11958849e−00 |
| 6.52176559e−01 | 5.72186649e−01 | 5.70520759e−01 | 7.92978525e−01 |
| 5.12051702e−01 | 2.07543328e−01 | 4.03114587e−01 | 4.60185438e−01 |
| 9.93783355e−01 | −6.26470089e−01 | 3.76047760e−01 | 1.55096993e−01 |
| 3.17753136e−01 | 6.54509306e−01 | 7.78424799e−01 | 5.77605426e−01 |
| 6.51011586e−01 | 7.73546159e−01 | 1.27872095e−01 | 6.28469288e−01 |
| 3.67680818e−01 | 9.51425374e−01 | 5.67927480e−01 | 2.91135699e−01 |
| 7.15757191e−01 | 7.84772217e−01 | 2.01918870e−01 | 7.76681840e−01 |
| 5.04574358e−01 | 9.72841978e−01 | 1.92318633e−01 | 6.63032293e−01 |
| 7.03308702e−01 | 9.68075216e−01 | 6.53678596e−01 | 5.19282520e−01 |
| 7.97649860e−01 | 6.71017766e−01 | 6.08244419e−01 | −2.71597713e−01 |
| 9.61652584e−03 | 1.34429061e−00 | 7.03485548e−01 | 3.44862640e−01 |
| 1.13264406e−00 | 7.49437690e−01 | 6.15065873e−01 | 7.00766921e−01 |
| 6.88403070e−01 | 4.31823552e−01 | −1.41273960e−01 | 3.50158125e−01 |
| 4.53589082e−01 | 3.26723993e−01 | 6.41969144e−01 | 6.81335688e−01 |
| 3.81364852e−01 | 1.05725670e−00 | 9.01394188e−01 | 7.31854260e−01 |
| 3.65513504e−01 | −2.21423253e−01 | −7.18514547e−02 | 1.41989455e−01 |
| 6.97134018e−01 | 6.65009022e−01 | 3.64190906e−01 | 2.90063411e−01 |
| 7.46249259e−01 | 7.38820255e−01 | 4.66036201e−01 | 3.99700969e−01 |
| 1.31528065e−01 | 5.33921123e−02 | 1.00277913e−00 | 7.39213467e−01 |
| 3.15431386e−01 | 4.73918319e−01 | 3.81575346e−01 | 5.68545103e−01 |
| 6.60822153e−01 | 7.37447143e−01 | 6.85970902e−01 | 6.65328205e−01 |
| 6.81992471e−01 | 6.77817106e−01 | 5.10144055e−01 | 6.31938875e−01 |
| 8.27419817e−01 | 7.09965050e−01 | 5.32249451e−01 | 1.32900745e−00 |
| 3.69804949e−01 | 1.07614541e−00 | 4.56753612e−01 | −5.27079068e−02 |
| 7.60262668e−01 | 3.43268216e−01 | 5.07459641e−01 | 5.80657005e−01 |
| 9.15852070e−01 | 5.29288173e−01 | 3.52548391e−01 | 3.96745265e−01 |
| 4.46162790e−01 | 6.52154803e−01 | −8.09308231e−01 | 2.77886689e−01 |
| 5.05384445e−01 | 5.64083576e−01 | 5.76753736e−01 | 9.62639868e−01 |
| 7.08302021e−01 | 5.23455322e−01 | 1.56120256e−01 | 4.41900522e−01 |
| 3.75085741e−01 | 5.21105468e−01 | 4.98628169e−01 | 4.82873917e−01 |
| 3.07104826e−01 | 7.98504591e−01 | 7.44932115e−01 | −9.95599627e−02 |
| −6.63099647e−01 | 7.34581530e−01 | 3.05285871e−01 | 9.77706790e−01 |
| 7.14630425e−01 | 1.43465564e−01 | 3.92993987e−01 | 3.01327705e−01 |

TABLE $W_h^1$-continued

| | | | |
|---|---|---|---|
| 1.02284360e−00 | 8.10332119e−01 | 2.59908676e−01 | 5.91496050e−01 |
| 7.14296252e−02 | 3.51214051e−01 | 8.06378543e−01 | −1.34169355e−01 |
| 8.91941726e−01 | 2.05109105e−01 | −3.57158924e−03 | 5.17701507e−01 |
| 1.21619487e−00 | 6.76293224e−01 | 1.89694077e−01 | 5.76334596e−01 |
| 9.56405163e−01 | 6.35932863e−01 | 1.20557857e−00 | 6.19378388e−01 |
| 6.27113879e−01 | −5.40527165e−01 | 1.11151767e−00 | 1.54011607e−00 |
| 6.47592485e−01 | 9.04567182e−01 | 4.11982238e−01 | 5.02118707e−01 |
| 5.93221784e−01 | 9.08567905e−01 | 5.88496983e−01 | 1.06229937e−00 |
| 8.96126807e−01 | 4.77277219e−01 | 5.26588798e−01 | 8.25070590e−02 |
| 8.59032333e−01 | 1.95422038e−01 | 8.37989926e−01 | 1.25868428e−00 |
| 2.85754472e−01 | 9.86715376e−01 | 7.71016836e−01 | 8.52191687e−01] |
| [−2.87362993e−01 | −6.18863285e−01 | −2.45903343e−01 | −1.36669680e−01 |
| −1.65640980e−01 | 3.68103176e−01 | 2.12390244e−01 | −6.83708116e−02 |
| 5.24474740e−01 | −5.03773868e−01 | 1.73012819e−02 | 6.03327513e−01 |
| −4.29670453e−01 | −2.59615004e−01 | −5.68523288e−01 | 4.44264859e−01 |
| −3.30444872e−01 | 5.12715578e−01 | 4.17353660e−02 | −2.90627837e−01 |
| −3.69613767e−01 | 1.15466738e−01 | 3.40071380e−01 | 1.87594205e−01 |
| −1.87608972e−01 | 1.75491139e−01 | 2.18175706e−02 | 4.37233984e−01 |
| −4.71576810e−01 | −3.34189743e−01 | 1.09459169e−01 | −3.54897887e−01 |
| −2.39130616e−01 | −4.72118348e−01 | 2.91191250e−01 | 7.10550845e−01 |
| 1.72735795e−01 | −3.13441604e−01 | 6.50614917e−01 | −2.70421088e−01 |
| −1.65799081e−01 | −4.95534480e−01 | −7.20610261e−01 | −1.42611608e−01 |
| 1.59471966e−02 | −6.11699700e−01 | 1.55342827e−02 | 5.04058659e−01 |
| 4.43467617e−01 | −1.58585146e−01 | 3.95324826e−01 | 3.89773816e−01 |
| 2.95088161e−01 | −1.90779492e−01 | 1.58547148e−01 | −4.63206440e−01 |
| −2.46610194e−01 | 4.35652509e−02 | −9.39162970e−02 | −1.54513553e−01 |
| 1.57029647e−02 | −3.59970868e−01 | 3.94496210e−02 | −4.50841010e−01 |
| −1.86269358e−01 | 1.74914569e−01 | 2.14630485e−01 | 4.88781631e−01 |
| −8.94510329e−01 | 1.65930226e−01 | 3.88850212e−01 | 1.03640072e−01 |
| 2.16727167e−01 | −1.12383929e−03 | 5.53559978e−03 | −3.20602208e−02 |
| 6.75371408e−01 | 3.17801200e−02 | −4.68593031e−01 | −2.86103994e−01 |
| 2.23484188e−01 | −3.02034438e−01 | −5.81627190e−01 | −3.17229152e−01 |
| 2.13246178e−02 | 2.62197107e−01 | −3.90061468e−01 | 5.20705760e−01 |
| −9.91665293e−03 | 1.32183447e−01 | 1.81948990e−01 | −1.05017614e−01 |
| 3.13820273e−01 | 2.04852477e−01 | −1.79247760e−01 | 1.17412880e−01 |
| 1.39638651e−02 | 1.60520539e−01 | 2.20473319e−01 | 3.12833756e−01 |
| 2.65527189e−01 | −1.42156973e−01 | −1.99778050e−01 | −1.52662709e−01 |
| −1.97118595e−01 | −1.80981934e−01 | −7.56824249e−03 | −1.73746660e−01 |
| 1.31778911e−01 | 5.11874147e−02 | 2.37887204e−01 | 6.26964688e−01 |
| 4.06841248e−01 | −3.40355664e−01 | −6.78221226e−01 | 2.51602143e−01 |
| 5.75329661e−01 | 4.26041514e−01 | −8.93778354e−03 | 2.54198369e−02 |
| 7.22722173e−01 | −3.17276478e−01 | −1.05870560e−01 | 1.42291725e−01 |
| 6.61597490e−01 | 3.10835719e−01 | 1.09920003e−01 | −6.39901161e−02 |
| 6.91965893e−02 | 2.29534835e−01 | 9.78765562e−02 | −6.78368136e−02 |
| −3.49608660e−01 | 1.90799654e−01 | −6.33446932e−01 | 2.64994085e−01 |
| 8.58738244e−01 | 1.13658600e−01 | −1.19330019e−01 | −4.58456457e−01 |
| 3.61731738e−01 | −4.70024198e−02 | −7.74576291e−02 | −9.06868577e−02 |
| 7.43675172e−01 | 9.55947459e−01 | 2.61903256e−01 | −6.26316488e−01 |
| −6.50494769e−02 | 1.51192874e−01 | −4.87524755e−02 | −1.09953053e−01 |
| 1.62098333e−01 | −1.10803545e−02 | −6.95099880e−04 | −4.10085171e−02 |
| −2.41911963e−01 | −9.64189917e−02 | −3.22284073e−01 | 4.22342777e−01 |
| −8.42796117e−02 | −2.01596782e−01 | −4.00532186e−01 | 9.17736068e−02 |
| 6.99305058e−01 | −6.28676862e−02 | −7.47249722e−02 | −1.48790210e−01 |
| −2.16366112e−01 | 2.29425561e−01 | 6.01444185e−01 | −2.90955544e−01 |
| 4.43670481e−01 | −4.58644599e−01 | 4.42671090e−01 | 2.58500725e−01 |
| −4.36583519e−01 | 2.35692903e−01 | 3.88784468e−01 | 1.63483843e−01 |
| −3.44243109e−01 | −1.74559459e−01 | 1.48380697e−01 | 3.87407541e−01 |
| 6.49504960e−01 | −1.23326704e−01 | 3.52954417e−01 | 1.13876462e−01 |
| 7.45764315e−01 | −3.58361565e−02 | 1.69558659e−01 | 1.56578898e−01 |
| −5.19410253e−01 | −1.23848341e−01 | 5.15826225e−01 | 6.55997992e−01 |
| 6.71289861e−01 | −5.03208578e−01 | −1.49817050e−01 | −2.34537095e−01 |
| −1.96672142e−01 | 2.70626545e−01 | −5.05617797e−01 | −6.53066067e−03 |
| 4.99129146e−01 | 2.48402655e−01 | 1.32687062e−01 | 9.05801535e−01 |
| 3.48174088e−02 | 1.06152818e−01 | 2.60997236e−01 | −5.62279880e−01 |
| −4.29879785e−01 | 7.31398940e−01 | −4.25417691e−01 | −5.93238175e−01 |
| −1.05020024e−01 | 1.57772824e−01 | 2.78371930e−01 | 7.89756328e−02 |
| 9.96595323e−01 | −2.20440924e−01 | −1.07661583e−01 | 4.62082505e−01 |
| 1.55580014e−01 | 2.67045498e−01 | 3.58479798e−01 | 5.95680714e−01 |
| −9.30576548e−02 | −1.21849619e−01 | 2.94699222e−01 | 3.77808630e−01 |
| 1.10927060e−01 | 1.56342685e−01 | 7.92167187e−02 | −2.04381943e−01 |
| 3.27438384e−01 | 8.49590376e−02 | 2.48481765e−01 | 3.27074416e−02 |
| −1.72153220e−01 | 2.52522856e−01 | −9.11314368e−01 | −4.23087832e−03 |
| 1.50278613e−01 | 9.98179615e−01 | 1.17805636e−01 | 6.97213054e−01 |
| −1.79157645e−01 | 1.27142578e−01 | −2.95980126e−01 | 7.27541745e−02 |
| 2.78764784e−01 | −3.55792671e−01 | 5.95519304e−01 | 1.79754600e−01] |
| [6.40312433e−01 | 1.41642645e−01 | −7.90941343e−02 | 5.49186468e−01 |
| 5.60745060e−01 | 5.07882118e−01 | 4.75309998e−01 | −1.29214272e−01 |
| 3.26286674e−01 | 2.74347723e−01 | −5.33197336e−02 | 8.66890073e−01 |
| 2.40218863e−02 | −1.73841957e−02 | −5.50998636e−02 | 5.43694019e−01 |
| 3.00171316e−01 | 2.82191694e−01 | 5.76061197e−02 | 2.60832459e−01 |

TABLE $W_h^1$-continued

| | | | |
|---|---|---|---|
| 3.60607505e−01 | 2.32469782e−01 | 4.95158643e−01 | 4.93879579e−02 |
| 3.66340488e−01 | 6.31492510e−02 | 3.00630987e−01 | 4.45808679e−01 |
| 6.69145659e−02 | 1.54652268e−01 | 6.44804418e−01 | −1.79411814e−01 |
| 2.49366641e−01 | 5.29621877e−02 | 6.42036021e−01 | 4.52637300e−02 |
| −7.00956434e−02 | 2.58410841e−01 | 2.63163000e−01 | 1.47320762e−01 |
| −3.67077947e−01 | 1.57598883e−01 | −2.91033536e−01 | 3.30993414e−01 |
| 2.49009393e−02 | −4.45402354e−01 | −1.52847081e−01 | 4.60455656e−01 |
| 6.72349334e−02 | 3.43539044e−02 | 3.67944926e−01 | 3.87778610e−01 |
| 2.20296949e−01 | 9.84298903e−03 | 4.69266027e−01 | −2.00050510e−02 |
| −2.83686161e−01 | −1.06711714e−02 | 4.44608063e−01 | −3.10037434e−01 |
| 5.79151154e−01 | 5.79424739e−01 | 3.27189237e−01 | −4.14352268e−01 |
| 2.29451075e−01 | 4.82718527e−01 | 6.21614158e−01 | 3.92399967e−01 |
| −4.52568054e−01 | 4.41259712e−01 | 2.21677884e−01 | 3.78401726e−01 |
| −4.13992368e−02 | 1.50728494e−01 | 3.97057123e−02 | −9.88293290e−02 |
| −4.79984358e−02 | 4.20039594e−01 | −1.69734925e−01 | 5.22981957e−02 |
| 3.22627336e−01 | 1.96633250e−01 | −2.49453261e−01 | −1.07345000e−02 |
| 3.89532268e−01 | 2.29961082e−01 | 2.50697166e−01 | 3.31121296e−01 |
| −3.84476595e−02 | −1.98137403e−01 | 5.96469223e−01 | −4.00535256e−01 |
| 8.95546675e−01 | 4.50746089e−01 | 8.63005891e−02 | −3.93487252e−02 |
| 5.63982606e−01 | −7.31060207e−02 | 5.86245298e−01 | 4.59191501e−01 |
| 4.08354312e−01 | 4.28530097e−01 | −2.56616086e−01 | −8.96738693e−02 |
| 2.36305654e−01 | −4.87436019e−02 | 3.42925608e−01 | 4.66750652e−01 |
| 7.91566253e−01 | 3.26203972e−01 | −1.13425869e−02 | 3.03824067e−01 |
| 4.01023299e−01 | −1.12795860e−01 | 8.97408873e−02 | 6.34231031e−01 |
| 3.49916697e−01 | 1.70699760e−01 | 3.20019335e−01 | −8.23582038e−02 |
| 1.33743733e−01 | 3.32287222e−01 | 2.77199715e−01 | 4.94142354e−01 |
| 4.59907562e−01 | −1.89253330e−01 | 1.01710327e−01 | 5.39427511e−02 |
| −2.15749800e−01 | −1.05201438e−01 | 2.37877548e−01 | 2.64296293e−01 |
| 3.54314238e−01 | 5.33031940e−01 | −3.04684967e−01 | 3.98416251e−01 |
| 7.13114262e−01 | 5.83601654e−01 | −2.49946073e−01 | −4.72717993e−02 |
| 1.95035785e−01 | 2.79903024e−01 | −2.11753935e−01 | 4.10235107e−01 |
| 7.46738553e−01 | 4.15764540e−01 | 1.09825902e−01 | 1.03011274e−00 |
| 3.24389458e−01 | 1.59100085e−01 | 5.70167780e−01 | −8.42646807e−02 |
| −5.29437959e−02 | −1.34003267e−01 | 3.08422863e−01 | 3.13869834e−01 |
| −3.92228886e−02 | 1.88891321e−01 | 4.95340645e−01 | 4.60976511e−01 |
| −3.23889673e−01 | −8.02966207e−02 | −2.93182969e−01 | 1.82386070e−01 |
| 9.74985540e−01 | 4.97093946e−01 | 1.85336068e−01 | −3.34255517e−01 |
| 8.68006349e−02 | −4.59205329e−01 | 5.28741181e−01 | −1.22442596e−01 |
| 1.43938139e−01 | −2.91159958e−01 | 3.85091603e−01 | 5.54612577e−01 |
| −1.30927339e−01 | 7.06182599e−01 | 5.57454586e−01 | 3.93498003e−01 |
| −2.79381305e−01 | 2.49150828e−01 | 1.12692855e−01 | 4.36265737e−01 |
| 6.73970819e−01 | 5.58716714e−01 | −2.03936830e−01 | 2.83522695e−01 |
| 7.07618892e−01 | 8.69958624e−02 | 1.66530833e−01 | 1.07298687e−01 |
| −1.26763657e−01 | 3.56599391e−01 | 7.42456973e−01 | 9.98792946e−01 |
| 3.29155475e−01 | 1.25531241e−01 | −1.34102315e−01 | 3.71298969e−01 |
| 6.85043156e−02 | 1.37888640e−01 | −8.23804438e−02 | 1.93047062e−01 |
| 1.87728047e−01 | 4.38179404e−01 | 3.40736777e−01 | 5.57701528e−01 |
| −1.28791898e−01 | 2.58646935e−01 | 6.23941481e−01 | −3.28597389e−02 |
| 2.09626719e−01 | 5.76357603e−01 | 7.65391812e−02 | 2.22394526e−01 |
| 2.21531466e−01 | 3.55165541e−01 | 5.61660528e−01 | 1.65031403e−01 |
| 2.80123234e−01 | 5.46598770e−02 | 1.66267663e−01 | 2.63336122e−01 |
| 7.92437255e−01 | 1.15717433e−01 | 3.14621121e−01 | 3.07453722e−01 |
| 2.68307567e−01 | 1.17348678e−01 | 2.64707744e−01 | 1.21281125e−01 |
| −3.10303620e−03 | 3.15680951e−01 | −3.20162505e−01 | −2.62907539e−02 |
| 7.49509111e−02 | 3.73989016e−01 | 1.42283633e−01 | 1.13920614e−01 |
| 2.96457708e−01 | 6.47250533e−01 | −4.27317649e−01 | 5.34378529e−01 |
| 2.55506545e−01 | 5.41359365e−01 | 9.73088741e−01 | 4.83482391e−01 |
| −2.35595435e−01 | 1.43826157e−01 | −1.08393736e−01 | 7.00061142e−01 |
| 2.83571869e−01 | −3.01145852e−01 | 4.59743142e−01 | 5.74162483e−01] |
| [9.69862789e−02 | 4.30031866e−01 | 2.09726751e−01 | −5.32269441e−01 |
| −3.38767231e−01 | 2.58671671e−01 | −1.43065944e−01 | 5.74450910e−01 |
| 2.48455629e−01 | 6.07311428e−01 | 3.15377772e−01 | 2.96660466e−03 |
| −2.05890108e−01 | 1.00765571e−01 | −2.62364924e−01 | −2.90512294e−01 |
| −9.48226675e−02 | 3.50559473e−01 | 2.88909465e−01 | 2.41391957e−01 |
| 2.85790861e−01 | −7.12511539e−02 | 4.99040782e−01 | −2.99835671e−02 |
| 1.02611087e−01 | 1.52097836e−01 | 3.77830446e−01 | 5.72585650e−02 |
| 9.22084153e−02 | 2.14387849e−01 | −3.16902459e−01 | −8.55312496e−02 |
| −4.63728793e−02 | −3.32615823e−02 | −3.74619327e−02 | 1.05960608e−01 |
| 3.79525781e−01 | −5.16504934e−03 | 1.30060151e−01 | −1.04180723e−01 |
| 5.59450649e−02 | −1.17632508e−01 | −2.17658728e−01 | 3.44706506e−01 |
| 5.06019592e−02 | 4.55862463e−01 | 2.41354808e−01 | 1.11734197e−02 |
| −4.36949134e−01 | 2.71361560e−01 | −4.34138745e−01 | 1.59864649e−01 |
| −7.42801353e−02 | 9.86778811e−02 | −2.45604277e−01 | 3.88128757e−01 |
| 5.07071316e−01 | 6.55020922e−02 | −5.30739725e−02 | 8.94590855e−01 |
| 2.19599724e−01 | 5.85286133e−02 | −1.19428709e−01 | 2.65968651e−01 |
| −1.97904810e−01 | −3.21391448e−02 | −1.72213078e−01 | −2.01362111e−02 |
| −4.95329639e−03 | 4.38621283e−01 | 3.21489349e−02 | −1.59370955e−02 |
| 1.09492745e−02 | 2.14801729e−02 | −1.20196834e−01 | 4.26917881e−01 |
| −5.14929473e−01 | 2.30242242e−03 | 8.10045823e−02 | −2.50913948e−02 |
| 1.20619461e−01 | 3.77280354e−01 | −4.28478718e−02 | −2.13504314e−01 |

TABLE $W_h^1$-continued

| | | | |
|---|---|---|---|
| −3.69371802e−01 | 3.36623013e−01 | −3.35231572e−01 | 3.78186665e−02 |
| 2.09285803e−02 | 2.34299764e−01 | −7.29031786e−02 | 3.67288977e−01 |
| −1.27889156e−01 | −5.52956283e−01 | 2.35866189e−01 | 2.77132392e−01 |
| 1.83118761e−01 | 6.37536347e−01 | 1.09662019e−01 | −1.92614615e−01 |
| 1.26774861e−02 | 4.74505246e−01 | 7.64556276e−03 | 1.74705833e−01 |
| 1.82624221e−01 | −1.91804506e−02 | 1.97412595e−01 | −1.65441036e−01 |
| −2.53568172e−01 | −7.24921823e−02 | −2.09251165e−01 | −2.20157728e−01 |
| −1.34284303e−01 | −1.90968737e−01 | −7.48396888e−02 | 3.90462667e−01 |
| 8.93108025e−02 | 1.25544131e−01 | 1.47606343e−01 | −3.29685844e−02 |
| 3.10316324e−01 | −1.95221245e−01 | 3.88689637e−02 | 2.88731515e−01 |
| −5.99552430e−02 | 2.91039437e−01 | 1.04013145e−01 | −1.50525972e−01 |
| 2.28979394e−01 | 1.18821897e−01 | −2.63853967e−01 | −3.18713337e−01 |
| 2.62491196e−01 | −3.79649401e−01 | 5.45563340e−01 | 1.97473004e−01 |
| −2.61637211e−01 | 1.52421087e−01 | 6.27410859e−02 | 1.13638761e−02 |
| −2.53200740e−01 | 2.28186965e−01 | 3.30214143e−01 | 7.24819005e−02 |
| −3.99425805e−01 | −2.31613800e−01 | 2.02594578e−01 | −1.59729674e−01 |
| −1.65115416e−01 | −6.98703647e−01 | −1.07091084e−01 | 3.97240937e−01 |
| 7.37411082e−02 | 2.91724801e−01 | 3.68689954e−01 | 2.68468350e−01 |
| −2.39180431e−01 | 5.88675618e−01 | 4.46910381e−01 | 4.71015483e−01 |
| 3.01496953e−01 | 2.90950060e−01 | −3.47023308e−02 | 1.09137334e−01 |
| 1.32592738e−01 | −1.37277693e−01 | 1.92761153e−01 | −3.23027730e−01 |
| 1.75159782e−01 | 2.00672314e−01 | −3.03366989e−01 | 3.12008351e−01 |
| −1.44705012e−01 | 3.98304582e−01 | −6.13724291e−01 | 2.32083201e−01 |
| 2.53890455e−01 | 1.75220400e−01 | −3.84928733e−02 | 1.31116033e−01 |
| 4.00223583e−01 | −5.88956363e−01 | 2.41107985e−01 | 4.70004454e−01 |
| −5.24812303e−02 | 1.79929398e−02 | 4.33321744e−01 | −6.47643134e−02 |
| −2.49073893e−01 | 1.69306602e−02 | 2.15206489e−01 | 1.83652624e−01 |
| −1.26958147e−01 | 1.84751395e−02 | −4.93929952e−01 | −2.98267931e−01 |
| −4.23246361e−01 | −1.67342916e−01 | 3.64868939e−01 | 2.04590589e−01 |
| −4.20277536e−01 | 1.73721373e−01 | −1.13108978e−01 | 1.25375330e−01 |
| −1.77382708e−01 | 3.44734192e−01 | −1.57614559e−01 | 1.31436929e−01 |
| 7.17783749e−01 | 2.06764583e−02 | −2.42679909e−01 | 1.76103320e−02 |
| −1.67146742e−01 | −2.80098051e−01 | −3.21746878e−02 | 2.05384582e−01 |
| 2.65017837e−01 | 1.52338997e−01 | 4.14592445e−01 | 9.72638205e−02 |
| −3.88602883e−01 | 3.70101780e−02 | 1.09606653e−01 | 5.98046510e−03 |
| 2.50257760e−01 | 8.71038511e−02 | 1.46804959e−01 | 5.02416305e−02 |
| −3.31463516e−01 | 4.00658101e−01 | 1.24529622e−01 | 2.66065776e−01 |
| 3.42619061e−01 | −4.42559153e−01 | 2.85424113e−01 | 3.56710404e−01 |
| 2.99793959e−01 | 3.33839685e−01 | 3.30633849e−01 | 2.74820954e−01 |
| 1.95673943e−01 | 4.50091243e−01 | −8.50720406e−02 | 2.01573476e−01 |
| −2.08340166e−03 | −6.69908077e−02 | −3.98476541e−01 | 2.66436845e−01 |
| 7.07908034e−01 | 2.43873015e−01 | 3.73381138e−01 | 4.74404454e−01 |
| 1.35126948e−01 | −2.22146243e−01 | 1.88930348e−01 | 1.36033535e−01] |
| [3.81371200e−01 | −1.40506789e−01 | 7.05093145e−01 | −2.70970762e−01 |
| 4.36512083e−01 | 4.28902715e−01 | 1.21294647e−01 | −1.15393996e−01 |
| 5.25612473e−01 | 2.45386690e−01 | 6.10675290e−01 | 4.43018943e−01 |
| 3.10657471e−01 | 3.66885900e−01 | −2.18975291e−01 | 2.78809965e−01 |
| 2.15422601e−01 | −3.75181317e−01 | −2.30508074e−01 | −4.35338020e−02 |
| 5.99801362e−01 | 6.79536641e−01 | 5.01023471e−01 | 3.57976556e−01 |
| 7.18431056e−01 | 3.89158338e−01 | −2.86713988e−01 | 2.40675822e−01 |
| −9.79355499e−02 | 4.73354906e−01 | 5.16905963e−01 | 2.92612731e−01 |
| 3.60462546e−01 | 9.20526981e−02 | 1.31177887e−01 | 9.89426970e−02 |
| 1.77834213e−01 | 2.66775876e−01 | 4.55905765e−01 | 2.43938893e−01 |
| 3.99855196e−01 | 4.45852757e−01 | −5.48151545e−02 | 7.60754406e−01 |
| 2.87534952e−01 | 7.44388923e−02 | 2.14751810e−01 | 2.37895787e−01 |
| 5.10595143e−01 | 1.31900966e−01 | 3.79331440e−01 | 2.15475217e−01 |
| 7.26337135e−01 | 3.52058351e−01 | 1.15515500e−01 | 3.83364558e−01 |
| 1.73615322e−01 | −1.43277779e−01 | 7.54209280e−01 | −1.98521018e−01 |
| 5.01148663e−02 | 5.51127076e−01 | 5.23176491e−01 | 5.11957288e−01 |
| 1.11887120e−01 | 6.16758525e−01 | 4.90999967e−01 | 6.24709249e−01 |
| −9.01957676e−02 | 6.43352047e−02 | 1.93564072e−01 | 1.66883230e−01 |
| 6.97818696e−01 | 3.18367779e−01 | 1.52932424e−02 | 6.64197862e−01 |
| 4.85040843e−01 | 3.49353880e−01 | 4.26008403e−01 | 2.37898782e−01 |
| 5.30508876e−01 | 7.56942511e−01 | 2.44226098e−01 | −1.14130452e−01 |
| 1.02970801e−01 | 5.80420315e−01 | 1.79341167e−01 | 6.34350121e−01 |
| 2.67656129e−02 | −1.95970610e−02 | 1.84687674e−01 | 2.16729492e−01 |
| 8.71070683e−01 | 7.08038628e−01 | −1.75094679e−01 | 4.60921794e−01 |
| 6.31329790e−02 | 3.09880912e−01 | 4.57091749e−01 | 4.97155368e−01 |
| 5.10664403e−01 | 2.07698688e−01 | 5.17930150e−01 | 5.94818853e−02 |
| 3.24254751e−01 | 1.77663133e−01 | −3.18787336e−01 | 3.84061158e−01 |
| 6.11619055e−01 | 1.18219411e−00 | −3.21234673e−01 | 4.93946252e−03 |
| 6.53187156e−01 | 2.19140455e−01 | 5.69954813e−01 | 3.45211625e−01 |
| 6.95710063e−01 | 5.70861638e−01 | 7.84320414e−01 | 3.24123740e−01 |
| −4.35454920e−02 | 1.52673334e−01 | 3.85439634e−01 | 2.55522251e−01 |
| 6.93980634e−01 | 8.08928013e−01 | 2.20342413e−01 | −3.63514051e−01 |
| 1.65559307e−01 | 9.06220675e−02 | −2.57045239e−01 | 4.17055577e−01 |
| −3.24261785e−02 | 6.20980203e−01 | 1.80493817e−01 | −5.86112635e−03 |
| 4.60772187e−01 | 1.34488121e−01 | 3.46567482e−01 | 5.81802726e−01 |
| −1.52983323e−01 | 8.86608005e−01 | −7.78240487e−02 | −4.02792513e−01 |
| 2.26543322e−01 | 5.73629200e−01 | 4.28489670e−02 | 3.70165378e−01 |

TABLE $W_h^1$-continued

| | | | |
|---|---|---|---|
| 7.91473687e−02 | 7.27260888e−01 | 3.83899838e−01 | 2.28266686e−01 |
| 2.38373294e−01 | 7.95030951e−01 | −6.48947060e−02 | −2.53282934e−02 |
| 1.24562882e−01 | −5.27014099e−02 | −9.25049260e−02 | 1.13965571e−00 |
| 2.79345363e−01 | 3.53769481e−01 | 2.68078651e−01 | 6.37710154e−01 |
| 2.65495658e−01 | 4.62494373e−01 | 1.37689292e−01 | 3.10552120e−01 |
| 5.11553168e−01 | 2.82528639e−01 | 4.85055923e−01 | 3.38516653e−01 |
| 9.27021623e−01 | 7.40698397e−01 | 6.99404955e−01 | −1.09629594e−01 |
| 5.62651157e−01 | 4.07276988e−01 | 1.75626948e−01 | 6.41957372e−02 |
| −2.00503320e−01 | 3.81660879e−01 | 3.88178438e−01 | 4.72911030e−01 |
| 3.61735702e−01 | 4.45156574e−01 | 2.06229985e−01 | 7.61054575e−01 |
| −2.97355860e−01 | 8.21236789e−01 | −1.77508712e−01 | 4.53578889e−01 |
| 8.64243135e−03 | 2.68498808e−01 | 2.56975681e−01 | 3.35538179e−01 |
| 6.19371831e−01 | 3.89465421e−01 | 4.44477290e−01 | 6.93061650e−01 |
| 5.41958153e−01 | 2.57487118e−01 | −9.56287682e−02 | 7.07249403e−01 |
| 7.51155078e−01 | 2.35108346e−01 | 1.06528425e−00 | 1.33597955e−01 |
| −5.38966209e−02 | −3.08896154e−02 | 4.14090216e−01 | −1.26903400e−01 |
| 3.89552861e−01 | 1.35377154e−01 | −1.18308095e−02 | 3.80954951e−01 |
| 5.71714759e−01 | 2.63782293e−01 | 1.52250111e−01 | −5.32502294e−01 |
| 5.58782876e−01 | 4.57946360e−01 | −1.00437745e−01 | 6.10500038e−01 |
| 5.42473137e−01 | 1.45348176e−01 | 9.35351372e−01 | 5.19617021e−01 |
| 1.02440345e−00 | 3.26786190e−01 | 2.15788007e−01 | 9.21543986e−02 |
| 3.58668249e−03 | −3.72598380e−01 | 5.28590798e−01 | −2.39087269e−01 |
| 4.84532386e−01 | 6.35202229e−01 | 2.33829677e−01 | −5.03787883e−02 |
| 6.14040256e−01 | 2.16169864e−01 | 2.86054075e−01 | 2.84981936e−01 |
| 9.40221071e−01 | 4.70414996e−01 | 4.58601654e−01 | 7.04917192e−01 |
| 8.99153128e−02 | 3.73162180e−01 | 5.62592328e−01 | −2.16117010e−01 |
| 1.74587667e−02 | 4.91957098e−01 | 2.06258625e−01 | 1.73207298e−01] |
| [2.13005215e−01 | 3.14417809e−01 | 4.97628629e−01 | 3.76835734e−01 |
| 3.51329774e−01 | 6.32433236e−01 | 5.94726145e−01 | 3.84024024e−01 |
| −1.04060564e−02 | −7.79061243e−02 | 3.84063929e−01 | −1.51830003e−01 |
| 3.99441272e−01 | 8.24894547e−01 | −2.18478292e−01 | −2.17982814e−01 |
| 2.06298288e−02 | 2.15708196e−01 | 1.62097692e−01 | 4.13705736e−01 |
| 4.19118911e−01 | 2.02676475e−01 | 1.18513465e−01 | 4.09009039e−01 |
| 9.42714214e−02 | 1.41220391e−01 | 2.82395750e−01 | 4.97169882e−01 |
| 2.16306642e−01 | 2.88005710e−01 | 1.85036018e−01 | 6.44137025e−01 |
| 2.76083231e−01 | 5.75637996e−01 | 1.18334271e−01 | −7.47941285e−02 |
| 5.38782299e−01 | 1.79923683e−01 | 7.01298639e−02 | 6.01239800e−01 |
| 4.39867109e−01 | 6.13384008e−01 | 6.27011538e−01 | 3.33678633e−01 |
| −2.05278378e−02 | 6.90030605e−02 | 2.66769052e−01 | 6.40212670e−02 |
| 4.46683139e−01 | 3.29781741e−01 | 2.39189297e−01 | 2.92354971e−01 |
| 4.77620840e−01 | 2.88278908e−01 | 1.26014203e−01 | −9.49671194e−02 |
| 3.47201109e−01 | −2.81518120e−01 | 5.66771090e−01 | 3.82877082e−01 |
| 1.25489682e−01 | 6.72829270e−01 | 3.45536739e−01 | 8.23095068e−02 |
| 3.63286555e−01 | 1.02019764e−01 | 4.00098354e−01 | 3.89518857e−01 |
| 7.41098896e−02 | 3.73420894e−01 | 6.12965107e−01 | 3.37102592e−01 |
| 5.41897535e−01 | −3.66402604e−02 | 3.13997358e−01 | −8.57034400e−02 |
| 4.84083951e−01 | 4.38308448e−01 | −5.42278171e−01 | 5.22418320e−01 |
| 1.35845095e−01 | 5.26023090e−01 | 5.43429196e−01 | 5.19843936e−01 |
| 6.35378003e−01 | −7.60308430e−02 | 2.10637040e−02 | 5.30518055e−01 |
| 3.52555543e−01 | 7.23203495e−01 | 9.23421830e−01 | 7.48341680e−01 |
| 1.55412972e−01 | 1.26668409e−01 | 2.79470623e−01 | 8.09985220e−01 |
| −3.15745622e−02 | 2.81046927e−02 | −2.43529561e−03 | 2.60460407e−01 |
| 5.60575247e−01 | 6.43604577e−01 | 4.84846205e−01 | 2.32644334e−01 |
| 4.24484819e−01 | 2.92456865e−01 | 3.25563222e−01 | 6.34747073e−02 |
| 3.40934962e−01 | 6.12507761e−01 | −1.86961129e−01 | 3.32953304e−01 |
| −5.83898015e−02 | 4.28201526e−01 | 1.79787874e−01 | −3.15215774e−02 |
| 2.20228419e−01 | 6.51021957e−01 | 3.64693373e−01 | 2.21076101e−01 |
| −1.78268522e−01 | 3.39851260e−01 | 8.03808153e−01 | 4.96915728e−01 |
| 2.88462996e−01 | 1.07784018e−01 | 2.18541265e−01 | 2.86535203e−01 |
| 1.92420855e−01 | 1.87928274e−01 | 2.23907933e−01 | 5.45825183e−01 |
| 1.69801936e−01 | 3.30427289e−01 | 1.70500100e−01 | −2.36749858e−01 |
| −2.15204597e−01 | 2.89174706e−01 | 3.25394690e−01 | 5.80369890e−01 |
| 1.59864612e−02 | 3.73136997e−01 | 4.27276671e−01 | 3.16892505e−01 |
| −6.13147736e−01 | 2.05069125e−01 | 1.45466983e−01 | 1.92390263e−01 |
| 4.57387120e−01 | −1.64192870e−01 | 5.60411453e−01 | 2.35653326e−01 |
| −1.06923580e−01 | 1.98987976e−01 | −3.85416746e−02 | 5.30414164e−01 |
| −1.74006850e−01 | −1.46978438e−01 | 1.11883752e−01 | 5.40231943e−01 |
| 2.25245714e−01 | 4.10907626e−01 | 4.28199470e−01 | 2.45049641e−01 |
| −5.37474789e−02 | 4.18834716e−01 | 1.60142675e−01 | −5.40520698e−02 |
| 3.93953055e−01 | 1.40968949e−01 | 2.52458811e−01 | −2.68149287e−01 |
| 3.66521254e−01 | −1.06416814e−01 | 4.20603424e−01 | 2.72869051e−01 |
| −3.03535862e−03 | 9.70414802e−02 | 2.59237468e−01 | 4.18723077e−01 |
| 3.71452004e−01 | −1.21818081e−01 | 4.32975590e−01 | 3.16558897e−01 |
| 4.09871131e−01 | 2.35817228e−02 | 2.10225713e−02 | 8.32827017e−02 |
| −4.93727587e−02 | 1.93627432e−01 | 4.00221020e−01 | 4.35701996e−01 |
| 6.96547270e−01 | 4.73736376e−01 | 5.54891288e−01 | 2.23819330e−01 |
| 5.01677431e−02 | 2.98959851e−01 | 7.00912297e−01 | 1.01010486e−01 |
| 4.29204851e−01 | 2.89541811e−01 | −1.28539160e−01 | 5.21435678e−01 |
| 1.71379566e−01 | 3.22510600e−01 | 5.20672917e−01 | 1.83584556e−01 |
| 1.23265669e−01 | 6.15027100e−02 | 3.07352394e−01 | 2.24612042e−01 |

TABLE $W_h^1$-continued

| | | | |
|---|---|---|---|
| 1.11324310e−01 | 1.50770709e−01 | −1.39217734e−01 | 5.79469278e−02 |
| 3.17455083e−01 | 4.18973327e−01 | −1.07997589e−01 | 1.61620408e−01 |
| 3.46340358e−01 | 3.27842921e−01 | −1.97751611e−01 | 6.31684512e−02 |
| −1.49881775e−02 | 1.06076770e−01 | −4.46287729e−02 | 2.23817989e−01 |
| 5.47285318e−01 | 4.32703607e−02 | 4.89049822e−01 | 2.22651541e−01 |
| 1.18825257e−01 | −2.92173177e−01 | 3.83064240e−01 | 2.25384384e−01 |
| 2.81555615e−02 | 5.11447370e−01 | 4.95709687e−01 | 1.09397881e−01 |
| 4.17468309e−01 | 1.28615260e−01 | 2.38029286e−01 | 3.19280088e−01 |
| 5.52817546e−02 | 3.81932110e−02 | 1.24177299e−01 | 5.11932671e−01 |
| 3.64539295e−01 | 2.50918269e−01 | 5.63798100e−02 | 4.24200088e−01 |
| 2.27013499e−01 | 5.85559011e−01 | 2.84247786e−01 | −9.94324908e−02] |
| [2.78289258e−01 | 1.53482646e−01 | 7.44638294e−02 | −1.69353858e−01 |
| −3.91402766e−01 | 2.96173580e−02 | −2.93109059e−01 | 1.56504408e−01 |
| 1.21603787e−01 | −2.15616778e−01 | −1.94154996e−02 | −1.12642169e−01 |
| 3.55271757e−01 | −3.80541176e−01 | −1.64021164e−01 | −1.35120451e−01 |
| 1.04328915e−01 | −3.62725973e−01 | 2.52205759e−01 | −3.89915891e−02 |
| 2.10044190e−01 | 1.96463287e−01 | −7.37124756e−02 | −1.15718774e−01 |
| 5.77170253e−02 | 1.10358596e−01 | −3.26959975e−02 | 7.59512857e−02 |
| 2.91904688e−01 | −7.58360922e−02 | 1.39336899e−01 | −1.10563431e−02 |
| 1.01694584e−01 | −9.70801190e−02 | −1.37221277e−01 | −7.88577348e−02 |
| 2.96928473e−01 | −2.22209126e−01 | 4.18489128e−02 | 1.92872450e−01 |
| −1.75909206e−01 | −1.18301138e−01 | 5.38539980e−03 | −3.14698845e−01 |
| −4.35883738e−02 | 1.64086409e−02 | −1.89075723e−01 | 3.27544928e−01 |
| −1.76274404e−02 | 5.38526297e−01 | −1.46705210e−01 | 5.53790145e−02 |
| 1.92826211e−01 | 8.96718428e−02 | −1.68062240e−01 | 1.95166796e−01 |
| 3.71818095e−01 | 3.44340950e−01 | −1.47488147e−01 | 2.61448085e−01 |
| 1.08266369e−01 | −8.05879533e−02 | −1.98164999e−01 | 2.50789803e−02 |
| 5.87958060e−02 | −3.01008254e−01 | −1.43099457e−01 | 5.39271355e−01 |
| 4.17798191e−01 | 2.60656446e−01 | 2.48403400e−01 | −3.06520373e−01 |
| 3.56589854e−02 | 3.00793260e−01 | 5.23050129e−01 | −6.24387115e−02 |
| −1.56725064e−01 | −5.36286756e−02 | 2.38547608e−01 | −2.45300457e−01 |
| 8.11149701e−02 | 1.96217343e−01 | −9.05906931e−02 | 6.91687703e−01 |
| 1.02105647e−01 | 6.21863544e−01 | 3.81498337e−01 | −1.65081859e−01 |
| −2.42648140e−01 | −1.58158511e−01 | −4.46768943e−04 | 3.03549796e−01 |
| −5.36667883e−01 | −1.30820215e−01 | 1.36928186e−01 | −1.23439364e−01 |
| 3.95774752e−01 | 2.41249099e−01 | 2.37320706e−01 | −5.08651614e−01 |
| −3.65633130e−01 | 1.91133797e−01 | 2.94819102e−02 | 4.09524590e−02 |
| 2.15160802e−01 | 7.38208368e−02 | 1.17358461e−01 | −1.15288213e−01 |
| −1.90000132e−01 | −2.67256528e−01 | 1.37641057e−01 | 3.30652863e−01 |
| −2.80432284e−01 | −1.62256062e−01 | 1.30997524e−01 | 5.15394747e−01 |
| −5.98060071e−01 | −1.49211735e−01 | −1.21697053e−01 | 3.07396561e−01 |
| 4.68370587e−01 | 2.00831518e−01 | −1.71475075e−01 | 1.07455760e−01 |
| −7.90495947e−02 | 1.39045298e−01 | 1.99216262e−01 | −2.08595902e−01 |
| −1.83927834e−01 | 3.61134440e−01 | 3.16359222e−01 | −3.51749957e−02 |
| 1.70973748e−01 | −1.66250281e−02 | −2.71735480e−03 | −1.44559816e−01 |
| 9.54681113e−02 | −1.18467808e−01 | 1.03550501e−01 | −6.20627888e−02 |
| −1.48051515e−01 | −1.56275883e−01 | 1.67060271e−01 | 2.21095532e−01 |
| −6.03317507e−02 | −1.67039916e−01 | −8.57684687e−02 | 2.27388024e−01 |
| 1.32021189e−01 | −3.75104696e−01 | −4.66684252e−03 | −1.10154830e−01 |
| −8.19694921e−02 | 1.48782693e−02 | 2.34488919e−01 | 6.24114200e−02 |
| −6.21630214e−02 | −7.91426152e−02 | 5.29383831e−02 | 2.73125470e−01 |
| −7.18908831e−02 | 3.67494859e−02 | 4.35649723e−01 | −1.28651649e−01 |
| −2.32751712e−01 | 1.44004419e−01 | 1.92114100e−01 | −2.02193856e−01 |
| 1.57182217e−01 | 4.10466939e−01 | −1.19021676e−01 | 4.34029281e−01 |
| −2.53398627e−01 | 5.78717105e−02 | −1.08044818e−01 | 5.78736305e−01 |
| −1.88711300e−01 | 1.76546967e−03 | −1.11897670e−01 | 4.91628274e−02 |
| −1.86858609e−01 | 1.15228355e−01 | 5.14106527e−02 | −2.97110170e−01 |
| −4.58759040e−02 | −3.35875839e−01 | −2.59139806e−01 | −2.38301426e−01 |
| −5.76451309e−02 | 2.12116748e−01 | 7.62095302e−02 | −1.41191304e−01 |
| 1.16522424e−01 | −1.54692307e−01 | −9.54504982e−02 | 1.29163759e−02 |
| −3.78043473e−01 | 1.94079265e−01 | 4.27019671e−02 | 5.79963066e−02 |
| −4.98034209e−02 | 8.58650059e−02 | 3.29034358e−01 | −1.54771969e−01 |
| 7.20365122e−02 | −1.68130904e−01 | −6.15977459e−02 | −2.99309969e−01 |
| 3.88349771e−01 | 6.15528189e−02 | −5.26216477e−02 | −3.54560488e−03 |
| 3.67230654e−01 | −5.36716077e−03 | 1.41641825e−01 | 3.84634882e−01 |
| 3.97760198e−02 | 2.74865448e−01 | 2.10317180e−01 | −3.09445187e−02 |
| −2.66018987e−01 | 4.08202484e−01 | 3.96461815e−01 | 1.25237098e−02 |
| 1.38290197e−01 | 4.99995261e−01 | −2.20654547e−01 | 9.84096006e−02 |
| −1.32858425e−01 | 3.52373779e−01 | −3.22977871e−01 | 2.79790044e−01 |
| −1.39319763e−01 | −2.64008701e−01 | −1.16266161e−01 | 1.79281965e−01 |
| −1.83129534e−01 | 1.70375109e−01 | 4.28512245e−01 | 3.88799608e−01 |
| 2.66521722e−01 | 3.52331661e−02 | 4.68477041e−01 | 3.79794999e−03 |
| −2.89015353e−01 | 2.43414402e−01 | −2.46707991e−01 | 1.11292824e−01 |
| 4.43075120e−01 | −2.65356392e−01 | −7.09054172e−02 | 8.43776837e−02 |
| 8.34996477e−02 | −9.41132605e−02 | −3.08968902e−01 | 3.37488949e−01] |
| [−1.84158936e−01 | −1.17230423e−01 | 2.06296682e−01 | −4.02505428e−01 |
| 3.36696565e−01 | 3.95554751e−01 | 1.90514579e−01 | 6.26753509e−01 |
| −1.96611717e−01 | −4.99157190e−01 | 5.63287735e−01 | −2.76079684e−01 |
| 4.14887480e−02 | 1.83011696e−01 | −9.04374272e−02 | 1.47718847e−01 |
| 4.59299207e−01 | 4.06139702e−01 | 3.80695283e−01 | 4.06066000e−01 |

TABLE $W_h^1$-continued

| | | | |
|---|---|---|---|
| 1.44810945e-01 | 2.86721557e-01 | -3.45645577e-01 | 2.48845473e-01 |
| 2.94102039e-02 | 2.25576967e-01 | -1.95631117e-01 | 7.79920891e-02 |
| 2.38237619e-01 | 4.10932541e-01 | 4.10630077e-01 | 2.78388768e-01 |
| 3.99079174e-01 | 4.46709245e-01 | 1.37018319e-02 | 2.53206253e-01 |
| 1.68821096e-01 | -4.30536196e-02 | 7.74651021e-02 | 1.01951256e-01 |
| 4.14308757e-01 | 1.24480844e-00 | 6.30952656e-01 | 9.91059840e-02 |
| 6.23255670e-02 | 7.92907059e-01 | 3.13112348e-01 | -3.57028991e-02 |
| 2.37148255e-01 | 3.18545938e-01 | -3.55381757e-01 | 3.05814799e-02 |
| 6.27951801e-01 | 3.66984159e-01 | 2.95153379e-01 | 4.92631122e-02 |
| 1.53772235e-01 | 4.51910824e-01 | 6.06505036e-01 | 2.01227337e-01 |
| -5.74986815e-01 | 2.46400326e-01 | -6.34195879e-02 | 3.96881849e-01 |
| 4.74643052e-01 | 3.23717266e-01 | -2.33394235e-01 | 4.29204881e-01 |
| 2.91959792e-01 | -2.72596210e-01 | 5.84615111e-01 | 1.83780313e-01 |
| 4.85992223e-01 | -1.72858518e-02 | -3.70156258e-01 | -1.16156526e-01 |
| 2.78573036e-01 | -7.30531067e-02 | 7.84625292e-01 | 4.63478863e-01 |
| -3.78122807e-01 | 7.52704442e-01 | 6.30504370e-01 | 1.42452329e-01 |
| 2.12076679e-01 | 5.17875999e-02 | 5.59507251e-01 | 5.12799919e-01 |
| 9.00224507e-01 | -4.75878239e-01 | -1.28128335e-01 | 1.72597930e-01 |
| 4.60982978e-01 | 5.02068818e-01 | -1.50602639e-01 | 1.66102171e-01 |
| 3.14558417e-01 | -4.49989110e-01 | 3.71853620e-01 | 2.66536176e-01 |
| 1.19084895e-01 | 4.29199189e-01 | 4.28582311e-01 | -4.98845838e-02 |
| 5.30317128e-01 | 4.81067717e-01 | 3.28160852e-01 | 6.66273832e-01 |
| 5.97269535e-01 | 5.55304587e-01 | -2.08101004e-01 | -6.14651799e-01 |
| 2.16846630e-01 | 3.60936731e-01 | 3.01713556e-01 | -2.52943002e-02 |
| -2.81712553e-03 | 2.16056705e-01 | 1.20959450e-02 | 1.57591090e-01 |
| 2.22555071e-01 | 5.76006711e-01 | 1.06341861e-01 | -3.62596035e-01 |
| -3.26411098e-01 | 3.12637657e-01 | 6.64494395e-01 | -3.78909223e-02 |
| 1.27002609e-00 | -4.45356555e-02 | 2.73896784e-01 | 4.30251092e-01 |
| 8.35307240e-01 | 4.40268338e-01 | 1.81079239e-01 | 2.24758804e-01 |
| -8.19350183e-02 | 7.02829957e-02 | 1.75512090e-01 | 9.00685966e-01 |
| 1.63431093e-01 | 3.94278504e-02 | 4.00327891e-02 | 4.70340610e-01 |
| -3.27000111e-01 | -5.65467961e-02 | -5.04462561e-03 | 1.73220932e-01 |
| 7.42582619e-01 | 1.71522528e-01 | 4.88511562e-01 | 1.37831196e-01 |
| 3.34290355e-01 | 6.15582645e-01 | 3.68911326e-01 | 2.35069290e-01 |
| 3.08708757e-01 | 2.30020434e-01 | 1.80991098e-01 | 3.73803556e-01 |
| 1.62259534e-01 | -2.18245134e-01 | 2.92743534e-01 | 3.80064458e-01 |
| 9.99332294e-02 | -5.21836460e-01 | 7.46067405e-01 | -8.57793614e-02 |
| -4.80929613e-01 | 7.48186588e-01 | 2.37328619e-01 | 1.05458230e-01 |
| 2.59368420e-01 | 2.34996900e-01 | 3.20705414e-01 | 2.84080863e-01 |
| 4.07120913e-01 | -4.64608610e-01 | 2.13184118e-01 | -2.42873892e-01 |
| -2.24979773e-01 | -4.99965809e-02 | 1.20468438e-01 | 1.68180898e-01 |
| -3.88945609e-01 | 4.45683300e-01 | 3.49993765e-01 | 3.38839591e-01 |
| 5.03967762e-01 | -3.22299451e-02 | 9.50630069e-01 | 1.95624977e-01 |
| 3.83539677e-01 | 3.33449990e-01 | 7.67551601e-01 | 1.07903272e-01 |
| 6.33284030e-03 | 3.15980017e-01 | 6.06062710e-01 | -1.98381051e-01 |
| 6.85884058e-01 | 6.10600770e-01 | 4.83152390e-01 | 3.51445943e-01 |
| -6.83061853e-02 | 4.68499571e-01 | 4.76855010e-01 | 2.30736852e-01 |
| 2.33120680e-01 | -2.36792862e-01 | -2.69816145e-02 | 1.10061836e-00 |
| -2.63920635e-01 | -7.07732514e-02 | 2.61293352e-01 | -1.99437067e-02 |
| 1.37306646e-01 | 3.91603142e-01 | 1.06961392e-01 | -1.56835601e-01 |
| 4.26235460e-02 | 5.93149424e-01 | 9.73195732e-02 | 3.26763719e-01 |
| 1.15029611e-01 | 2.33816847e-01 | 2.15673205e-02 | 1.04077710e-02 |
| 6.09007597e-01 | 5.26547618e-02 | 9.33667362e-01 | 3.33769947e-01 |
| 4.12219346e-01 | 4.87739682e-01 | 3.10042232e-01 | 3.33978266e-01 |
| -1.58873890e-02 | 3.91765118e-01 | -2.27056414e-01 | 2.85286866e-02 |
| -2.09994927e-01 | -2.59344876e-01 | 5.90852797e-01 | 4.28194463e-01 |
| 4.49514508e-01 | 4.57469895e-02 | -2.09503055e-01 | -2.76425034e-01 |
| 2.47908875e-01 | 1.03401907e-01 | -4.23262734e-03 | 1.71930984e-01 |
| 2.99962938e-01 | 5.71183801e-01 | 2.42864937e-01 | -2.99655646e-01] |
| [1.71096027e-01 | 3.87901872e-01 | 3.55024368e-01 | 1.60855889e-01 |
| 1.91566154e-01 | -1.13592474e-02 | 6.43904731e-02 | 2.63387501e-01 |
| 2.18052343e-01 | 6.06658936e-01 | 5.86782619e-02 | 3.06310683e-01 |
| 2.66196281e-01 | 1.11205734e-01 | -1.85908452e-02 | 3.20544243e-01 |
| 3.91929209e-01 | 1.19472407e-01 | 4.68327433e-01 | 1.68899298e-01 |
| 2.13653401e-01 | 3.22157919e-01 | 2.91815162e-01 | 3.26293588e-01 |
| 4.28957909e-01 | 4.96751100e-01 | 2.01014243e-03 | 5.52206933e-02 |
| 3.38112041e-01 | 1.88665390e-01 | 7.19863735e-03 | -2.08260235e-03 |
| -6.49758950e-02 | 3.82911325e-01 | 4.12886173e-01 | -3.25739197e-02 |
| -3.57087821e-01 | -2.82494634e-01 | 1.21895581e-01 | 3.61856133e-01 |
| 2.64317691e-01 | 2.28542611e-01 | -2.35038966e-01 | 1.61914912e-03 |
| 1.68017000e-01 | 3.68179351e-01 | 1.75165087e-01 | 2.00052142e-01 |
| -6.84030473e-01 | 2.11108670e-01 | 5.18784672e-02 | 4.48622584e-01 |
| -3.87309939e-01 | 4.10609655e-02 | 4.41738069e-02 | 4.94509608e-01 |
| 5.49104989e-01 | 7.69168809e-02 | 1.87509507e-01 | 4.84724045e-01 |
| 9.11154822e-02 | 2.23308846e-01 | 1.73247587e-01 | -1.02604374e-01 |
| -3.42034876e-01 | 8.95829499e-03 | 3.04217562e-02 | 2.66105473e-01 |
| 2.91771889e-01 | -1.92109868e-02 | -3.66096832e-02 | 1.26144290e-01 |
| 3.38856250e-01 | -1.86737895e-01 | 4.56864417e-01 | 1.15269862e-01 |
| 4.01881933e-02 | -1.01175673e-01 | 1.33883819e-01 | 8.27148929e-02 |
| -5.16467504e-02 | 7.33021796e-02 | 1.40419886e-01 | 4.04590219e-02 |

TABLE $W_h^1$-continued

| | | | |
|---|---|---|---|
| −1.90358832e−01 | −1.01737633e−01 | −8.60280916e−02 | −2.83645447e−02 |
| 6.44514561e−01 | 7.76654705e−02 | 2.30343044e−01 | 2.20973000e−01 |
| −1.21911533e−01 | −2.47996133e−02 | 2.44416431e−01 | −1.92724690e−01 |
| 5.12457378e−02 | 3.89238149e−01 | −2.47671247e−01 | 2.26740502e−02 |
| 2.37855703e−01 | 8.79213661e−02 | 2.59207696e−01 | 5.07942587e−02 |
| −4.75381054e−02 | 3.92261483e−02 | 2.60616809e−01 | 5.77244498e−02 |
| −2.09033743e−01 | −2.45555282e−01 | −1.88545093e−01 | 2.93542445e−01 |
| 2.60402948e−01 | −2.66741306e−02 | 3.68537277e−01 | 3.29959899e−01 |
| −3.39292258e−01 | −2.60195017e−01 | 2.79034108e−01 | 2.22664431e−01 |
| 2.94158220e−01 | −1.84576556e−01 | 2.54495203e−01 | −9.80926454e−02 |
| −2.32436776e−01 | 3.35389823e−01 | −4.79226887e−01 | 1.82736263e−01 |
| −2.05307633e−01 | 2.19532043e−01 | −3.03200275e−01 | 8.04684162e−02 |
| 4.91633207e−01 | 2.12396160e−01 | 5.21967411e−01 | 1.71506271e−01 |
| 1.80218413e−01 | 1.66699812e−01 | 3.03651839e−01 | 8.85347128e−02 |
| −2.04226106e−01 | 1.12738818e−01 | −6.43089563e−02 | 1.38452187e−01 |
| 2.44965672e−01 | 1.39235467e−01 | 4.62302007e−03 | 7.97455013e−02 |
| −1.25151828e−01 | 1.63588271e−01 | −1.76670030e−01 | −1.58880815e−01 |
| 3.03107738e−01 | 2.17211515e−01 | 4.85700704e−02 | 1.32086217e−01 |
| 2.08730534e−01 | 4.27783608e−01 | 1.13032721e−01 | 2.32646793e−01 |
| 4.23573136e−01 | 4.96726364e−01 | −8.11557323e−02 | 2.80758232e−01 |
| 2.79977620e−01 | −1.19188353e−01 | 3.63652438e−01 | −1.44223422e−01 |
| 3.80639017e−01 | −5.13339713e−02 | 3.69914249e−02 | −1.09911282e−02 |
| −3.24890107e−01 | 3.51370305e−01 | 4.94819768e−02 | 2.85735935e−01 |
| 1.92981452e−01 | 5.09482957e−02 | 4.42787111e−01 | 2.42600337e−01 |
| 8.56555998e−02 | 5.11661053e−01 | −1.60935298e−01 | 1.07451491e−01 |
| 1.16221070e−01 | 7.22766072e−02 | 3.45547125e−02 | 5.29977493e−02 |
| −6.72908127e−02 | 5.58066592e−02 | 3.00858647e−01 | 4.56595868e−01 |
| 3.72963130e−01 | 1.14601567e−01 | 2.58270681e−01 | −1.11701883e−01 |
| −6.69816218e−04 | 4.47445184e−01 | 1.79375261e−01 | −4.62025344e−01 |
| 9.88053009e−02 | 3.56077969e−01 | −1.39004618e−01 | −5.90075366e−03 |
| 3.61259907e−01 | 3.90918195e−01 | 6.10036263e−03 | 2.32962649e−02 |
| 3.53193015e−01 | −4.66898456e−02 | 1.84681490e−01 | 4.25578982e−01 |
| 3.41416031e−01 | 7.04531521e−02 | 2.52318293e−01 | 6.09223545e−01 |
| 2.79609591e−01 | −2.14579493e−01 | 2.46780962e−01 | 9.33979675e−02 |
| −2.62954384e−01 | 3.00268233e−01 | 1.67582378e−01 | −6.73224628e−02 |
| 3.89114529e−01 | −7.50195980e−02 | −1.40932545e−01 | 7.79413879e−02 |
| 3.05314451e−01 | 1.63943261e−01 | 3.49899650e−01 | −1.30417660e−01 |
| 2.83991665e−01 | 3.22026372e−01 | 3.05739880e−01 | 4.58950490e−01 |
| 1.98942795e−01 | 4.58642900e−01 | 1.27589539e−01 | 4.85341400e−01 |
| 2.79998183e−01 | 1.33723512e−01 | 4.78405029e−01 | 2.71675974e−01 |
| 5.10936379e−01 | 6.90071359e−02 | −4.83997650e−02 | 3.97418253e−03 |
| 3.88107836e−01 | 7.30558097e−01 | 4.18598831e−01 | 4.71322179e−01 |
| −1.63229331e−01 | −1.89582124e−01 | 9.25823525e−02 | 2.72351712e−01] |
| [−1.09660797e−01 | 1.92196071e−01 | 1.57638397e−02 | 3.52034383e−01 |
| 1.39087752e−01 | −2.19871104e−01 | 3.68984342e−01 | 1.98433608e−01 |
| 2.46731088e−01 | 1.29739672e−01 | 3.09122950e−01 | 5.70080802e−02 |
| −2.60876060e−01 | 1.78876445e−01 | 2.28769496e−01 | 2.82152533e−03 |
| 5.21563999e−02 | 1.88673884e−01 | 1.74726129e−01 | 2.44685054e−01 |
| 5.59522569e−01 | 4.80880849e−02 | 2.07046434e−01 | 5.77051401e−01 |
| 7.11954013e−02 | 1.57970384e−01 | 1.50075778e−01 | −9.77909863e−02 |
| 4.82940748e−02 | 2.79451609e−01 | −5.39587975e−01 | 1.03691667e−01 |
| 2.86609352e−01 | −8.06347206e−02 | 3.41939777e−01 | 6.69915378e−02 |
| 1.12491712e−01 | 1.63624540e−01 | −1.77265137e−01 | 1.52453348e−01 |
| 3.49467108e−03 | 1.39248464e−01 | −7.37754881e−01 | 2.54864722e−01 |
| 3.12076777e−01 | 3.26919705e−01 | −6.08465411e−02 | 7.11385310e−02 |
| −2.67210454e−01 | −1.64677113e−01 | −6.53748810e−02 | 1.51300758e−01 |
| −4.76425253e−02 | −2.37382904e−01 | 1.09175950e−01 | 3.97217900e−01 |
| 5.88643670e−01 | −2.55475819e−01 | 2.87459567e−01 | −1.57436996e−03 |
| 1.84556067e−01 | 4.85952914e−01 | 8.23593065e−02 | 2.56388068e−01 |
| 3.53261381e−01 | −1.14325017e−01 | 2.49668464e−01 | −1.17982104e−01 |
| 7.48139083e−01 | −4.07169499e−02 | 4.65797126e−01 | 7.92591646e−02 |
| −5.12538813e−02 | 2.47513726e−01 | 1.73569560e−01 | −6.54650480e−02 |
| 1.37120828e−01 | 9.50770602e−02 | 4.68547791e−01 | 1.78082556e−01 |
| −2.99520642e−01 | 1.12177625e−01 | −4.40993868e−02 | −7.19269179e−03 |
| 7.57906288e−02 | −1.73071727e−01 | 1.14778109e−01 | 1.58066034e−01 |
| 2.34681576e−01 | 2.36164048e−01 | 1.52384918e−02 | −4.30677831e−02 |
| −1.66020498e−01 | −2.40249529e−01 | 1.24946266e−01 | 1.15484998e−01 |
| 1.61165986e−02 | 9.64243561e−02 | −5.04307747e−02 | −1.07543200e−01 |
| −1.83565095e−02 | 3.16862762e−01 | 2.06190497e−02 | −1.73280034e−02 |
| 2.94525534e−01 | 2.02429652e−01 | 4.52843189e−01 | 1.66385069e−01 |
| −3.52904409e−01 | 3.30756783e−01 | 6.92221671e−02 | −1.60030182e−01 |
| 2.07908139e−01 | 1.71783060e−01 | 1.58109948e−01 | 1.12612046e−01 |
| −4.66446504e−02 | 7.83833936e−02 | −2.40272745e−01 | 1.01781711e−01 |
| 4.59739178e−01 | 6.64072096e−01 | 3.88379306e−01 | −1.08513739e−02 |
| 7.72794709e−02 | 1.50364079e−01 | 5.78738574e−04 | 5.81585646e−01 |
| 3.08368132e−02 | 2.99343556e−01 | 2.26247922e−01 | 2.25823998e−01 |
| 1.83140531e−01 | −1.20555109e−03 | 3.33416700e−01 | −5.47684841e−02 |
| 1.16820566e−01 | 3.57993186e−01 | 2.22631782e−01 | 2.76537985e−01 |
| 1.24743089e−01 | 1.41147941e−01 | 4.81362939e−01 | 4.63282615e−01 |
| 8.79903138e−02 | 3.75954449e−01 | 9.46413353e−02 | 1.03830546e−01 |

TABLE $W_h^1$-continued

| | | | |
|---|---|---|---|
| 8.58908221e−02 | 8.41622576e−02 | 6.39697686e−02 | 5.34159660e−01 |
| 2.83214360e−01 | 2.17935577e−01 | 5.36498148e−03 | 4.06179996e−03 |
| 5.98339438e−01 | 3.33181381e−01 | 3.30733418e−01 | 7.01643899e−02 |
| 8.14908296e−02 | 2.86149561e−01 | −4.79210308e−03 | −1.79848850e−01 |
| −2.77164727e−02 | 2.76284575e−01 | −4.67482992e−02 | 3.59831125e−01 |
| 5.99565923e−01 | −1.07965186e−01 | 1.89193394e−02 | 2.86962926e−01 |
| 1.27682701e−01 | 1.22603424e−01 | −2.00330913e−01 | 3.18289608e−01 |
| −2.08129380e−02 | 5.04162669e−02 | −6.10322282e−02 | 2.87497759e−01 |
| 1.37579694e−02 | 2.37092357e−02 | 1.17985688e−01 | 2.52855808e−01 |
| 1.01144992e−01 | 1.24804027e−01 | 8.22769701e−02 | 4.93492149e−02 |
| −4.86308672e−02 | −6.93400949e−02 | 2.22312748e−01 | 9.12306458e−02 |
| 1.02379061e−01 | −2.04880774e−01 | 3.39056015e−01 | 6.15309030e−02 |
| −4.18285374e−03 | −4.16078530e−02 | 1.39768317e−01 | 9.47608575e−02 |
| −8.18410590e−02 | −5.44607919e−03 | −1.44692451e−01 | 2.78056800e−01 |
| 2.33706653e−01 | 1.20798014e−01 | 2.50242412e−01 | 6.16804808e−02 |
| 1.78477779e−01 | 1.57362428e−02 | −6.31692484e−02 | 1.70107439e−01 |
| −3.48715067e−02 | 1.88440546e−02 | 4.08172935e−01 | 5.44051588e−01 |
| 2.68242747e−01 | −1.54886678e−01 | 1.51066378e−01 | 5.65138936e−01 |
| −8.23541638e−03 | 3.93250585e−01 | −1.29636914e−01 | −3.55209596e−02 |
| 6.03762329e−01 | −9.87820849e−02 | 2.48456106e−01 | 2.81403493e−02 |
| 2.89784092e−01 | −1.35079697e−01 | 2.80207872e−01 | 3.88558842e−01 |
| 4.35290068e−01 | 3.89947176e−01 | −2.34248772e−01 | 2.71237165e−01 |
| 3.03133011e−01 | 4.38975513e−01 | 5.63013375e−01 | 1.97017357e−01 |
| 5.36824286e−01 | 4.91800159e−02 | 8.95403773e−02 | −1.24622464e−01 |
| 3.16105962e−01 | −1.95852116e−01 | 1.89880151e−01 | 4.47967686e−02 |
| 3.38170193e−02 | −1.16392054e−01 | −1.25391185e−01 | −2.41158232e−01 |
| 1.69897437e−01 | 1.26300678e−01 | 5.22807360e−01 | 3.49517375e−01] |
| [3.77569258e−01 | −6.83980659e−02 | 5.05440593e−01 | −2.47139141e−01 |
| 2.50887215e−01 | −6.63181245e−02 | 2.55800277e−01 | −3.10174257e−01 |
| 3.72989744e−01 | −2.02778429e−01 | 1.55258235e−02 | 3.33943397e−01 |
| −1.41695753e−01 | 4.91771430e−01 | −1.10916309e−01 | −6.18386492e−02 |
| 2.76029259e−01 | 3.34413685e−02 | 1.18482985e−01 | 3.01411182e−01 |
| 4.14050549e−02 | −1.33880287e−01 | 4.50871475e−02 | 2.63603419e−01 |
| 1.02904879e−01 | 1.23512052e−01 | −2.53709584e−01 | 3.75968546e−01 |
| 8.88826251e−02 | 4.10595298e−01 | 9.03465748e−02 | 5.10749340e−01 |
| 3.04615676e−01 | 1.70754045e−01 | 2.99274802e−01 | −4.12325971e−02 |
| 3.84528071e−01 | 2.26530254e−01 | −9.25659314e−02 | −1.07909247e−01 |
| 6.57877564e−01 | 1.49743825e−01 | 3.06365848e−01 | 2.69759625e−01 |
| 1.47436813e−01 | −4.62556072e−02 | 3.87298435e−01 | 2.67526269e−01 |
| 8.52600951e−03 | 2.02563092e−01 | 2.69134697e−02 | 3.07054937e−01 |
| −1.40153199e−01 | 4.51165676e−01 | −7.17947111e−02 | 2.79700160e−01 |
| 3.87065560e−01 | 1.96694409e−01 | 5.34752190e−01 | −3.56522463e−02 |
| 9.31788459e−02 | 5.96413128e−02 | 2.12211266e−01 | 1.47581592e−01 |
| 1.59664556e−01 | 5.48878551e−01 | 2.48190135e−01 | 1.56154066e−01 |
| 3.44634116e−01 | −1.70500189e−01 | 3.49857628e−01 | 1.13977611e−01 |
| 1.43278196e−01 | 1.51653573e−01 | 1.38553409e−02 | 1.20492280e−01 |
| 1.15178809e−01 | 4.75084156e−01 | −1.12767536e−02 | 1.00851461e−01 |
| −1.41606420e−01 | 1.69322435e−02 | 2.73713320e−01 | −2.22530544e−01 |
| 9.70935374e−02 | 1.74303919e−01 | −2.00611860e−01 | 3.76620799e−01 |
| 9.23954695e−02 | 1.96424603e−01 | 1.53763816e−01 | 4.21831518e−01 |
| 5.36765099e−01 | 1.66190773e−01 | 3.84617686e−01 | 5.32882035e−01 |
| −3.23759615e−01 | −1.52172968e−01 | 1.82834983e−01 | 2.26745740e−01 |
| 3.83739173e−01 | 6.92175925e−01 | 1.46962360e−01 | 7.37622827e−02 |
| 1.42626688e−01 | 5.54715157e−01 | −9.75018274e−03 | −7.90887475e−02 |
| 4.29037698e−02 | 4.50762659e−01 | 3.51668745e−01 | −8.15007985e−02 |
| 4.86028641e−01 | −8.08102638e−02 | 2.36744657e−01 | 1.61996797e−01 |
| 8.77812058e−02 | 1.15721330e−01 | 4.48213220e−01 | −1.83230355e−01 |
| 2.08729450e−02 | 2.77788956e−02 | 7.33808875e−02 | 2.76650608e−01 |
| −1.01827279e−01 | 1.81333065e−01 | 8.88169780e−02 | 1.09879747e−01 |
| 1.93516552e−01 | 1.36476621e−01 | −2.81234652e−01 | 3.60197395e−01 |
| 2.40217134e−01 | 3.72191340e−01 | 3.23860288e−01 | 1.52412593e−01 |
| −1.38500869e−01 | 5.43607593e−01 | 4.57365423e−01 | 2.38517612e−01 |
| 4.62489039e−01 | 2.67946720e−01 | 3.17528665e−01 | −1.92967296e−01 |
| −2.13737398e−01 | 1.74529970e−01 | 2.76811093e−01 | −1.55233145e−01 |
| 9.85153690e−02 | 3.27942431e−01 | 3.40163112e−01 | 1.33881820e−02 |
| 2.25532100e−01 | 2.61000055e−03 | −2.11223349e−01 | 5.14038324e−01 |
| −3.75621468e−02 | 1.28140777e−01 | 4.06368017e−01 | 7.12779760e−02 |
| −2.51870245e−01 | 5.23840010e−01 | −1.51889771e−01 | 1.87430993e−01 |
| 4.16818649e−01 | 7.35381618e−02 | 1.82543665e−01 | 1.87943473e−01 |
| −1.37345847e−02 | −2.21930947e−02 | 3.68371427e−01 | 1.07643224e−01 |
| 4.38720703e−01 | 4.07189071e−01 | 1.67171415e−01 | 2.48783737e−01 |
| 5.42733014e−01 | −1.37949828e−02 | −1.03150457e−01 | 7.99380392e−02 |
| 5.74128255e−02 | 1.58219546e−01 | 3.61745298e−01 | 6.12723708e−01 |
| 4.84732151e−01 | 1.50431648e−01 | 3.21798734e−02 | 1.69106081e−01 |
| −4.35567982e−02 | −1.14180550e−01 | 9.99820977e−02 | 4.81051564e−01 |
| 2.43037596e−01 | 2.79801130e−01 | 9.20344740e−02 | 4.66375113e−01 |
| 2.44648457e−01 | 3.50160956e−01 | 3.08272541e−01 | −1.58892021e−01 |
| 1.05624452e−01 | −6.87757283e−02 | 1.04405388e−01 | 6.40344381e−01 |
| 2.27923676e−01 | 3.32711458e−01 | −1.68824866e−01 | 6.06968105e−01 |
| −8.65706503e−02 | 1.03307277e−01 | 2.18249530e−01 | −9.54897478e−02 |

TABLE $W_h^1$-continued

| | | | |
|---|---|---|---|
| 4.66290146e−01 | 1.13571480e−01 | 3.56196165e−02 | 1.12375908e−01 |
| 3.98812085e−01 | 1.18231289e−01 | 1.61085799e−01 | 9.72025990e−02 |
| 2.19283223e−01 | 2.92522699e−01 | 2.36088131e−02 | 4.56268847e−01 |
| −2.60109622e−02 | 2.65204281e−01 | 4.78226602e−01 | −1.82751432e−01 |
| 6.45738482e−01 | −2.13602692e−01 | 5.45628548e−01 | 1.57965645e−01 |
| 3.89630944e−01 | 2.14632943e−01 | 7.24174857e−01 | −6.55950457e−02 |
| 1.16923943e−01 | 3.90945703e−01 | −2.72731520e−02 | 1.55255243e−01 |
| −1.99610353e−01 | 1.50523901e−01 | 4.74949032e−02 | 1.95489004e−01 |
| −5.59930280e−02 | −1.40197109e−02 | 4.11851972e−01 | 1.37363493e−01 |
| −1.90266833e−01 | 6.22357249e−01 | 3.26290518e−01 | 1.76640391e−01 |
| 1.44932270e−01 | 6.22896016e−01 | 4.70385313e−01 | 3.61833870e−01] |
| [4.69471395e−01 | 3.94926928e−02 | 6.95271492e−01 | 1.16862498e−01 |
| 1.16604125e−00 | 1.25592902e−01 | −1.18763782e−02 | 1.96901917e−01 |
| 4.21454310e−01 | 1.55256048e−01 | 6.89954937e−01 | 8.29625875e−02 |
| 1.01972187e−00 | −2.68637806e−01 | 8.96198153e−02 | 6.27778351e−01 |
| 4.02719855e−01 | −1.25756860e−01 | 2.31123239e−01 | 6.90146759e−02 |
| 7.60030448e−01 | 1.18706048e−01 | 3.77722085e−01 | 6.22614264e−01 |
| 2.68298894e−01 | 2.12947473e−01 | 5.40402293e−01 | 3.68019611e−01 |
| −8.43520463e−02 | 6.39865935e−01 | −1.11402228e−01 | 5.16788661e−01 |
| 3.78895760e−01 | 6.89914078e−02 | −1.23195551e−01 | −2.59347767e−01 |
| 3.65582347e−01 | 3.21121603e−01 | 4.43702519e−01 | −1.49058640e−01 |
| −1.96333990e−01 | 4.01625127e−01 | −1.09437920e−01 | 5.43528020e−01 |
| 1.46097705e−01 | 3.24414283e−01 | 1.63342655e−01 | 7.18095526e−02 |
| 4.75180626e−01 | −4.12943661e−01 | 1.40545130e−01 | 1.96680784e−01 |
| −1.46373689e−01 | 1.99396938e−01 | 3.96170795e−01 | 2.70493366e−02 |
| −2.14586496e−01 | 3.65261286e−01 | 8.25793073e−02 | −1.74667671e−01 |
| −2.70544082e−01 | 3.07626814e−01 | 8.21632922e−01 | 1.41114427e−03 |
| 1.23131730e−01 | 1.01253283e−00 | 1.10967480e−01 | −1.72414482e−01 |
| −1.21288955e−00 | −2.08330691e−01 | 1.41086802e−01 | 3.17391187e−01 |
| 1.30756274e−01 | −3.59857231e−01 | 4.73354161e−01 | −3.19228470e−01 |
| 7.51153409e−01 | 3.08888525e−01 | 6.18898392e−01 | 5.57407737e−02 |
| 9.33787301e−02 | 2.02372536e−01 | 6.59918264e−02 | −2.98081916e−02 |
| 4.72660989e−01 | 2.80816048e−01 | −1.62561368e−02 | 2.54698038e−01 |
| −3.20220321e−01 | 3.30306053e−01 | 6.30579174e−01 | −7.60038346e−02 |
| 3.48686099e−01 | 5.33704937e−01 | 3.65442634e−01 | 1.84759930e−01 |
| −1.12683512e−02 | −2.19608441e−01 | 9.36478823e−02 | 1.26763642e−01 |
| 5.47298491e−01 | 6.62356615e−01 | 4.69197601e−01 | 2.10493788e−01 |
| 1.73881173e−01 | −2.56709546e−01 | 2.67900638e−02 | 1.28463626e−00 |
| 6.18909478e−01 | 1.31000996e−01 | 4.00576830e−01 | −3.04189384e−01 |
| 5.76319277e−01 | 3.26173455e−01 | 9.06375885e−01 | 2.63874922e−02 |
| 7.70382583e−01 | −4.42883559e−03 | 2.51039833e−01 | 8.51308763e−01 |
| −4.29822236e−01 | −3.00611500e−02 | 4.32237208e−01 | −1.52359098e−01 |
| −2.40191951e−01 | −1.28026813e−01 | 6.14545941e−01 | 5.81932008e−01 |
| −4.03445102e−02 | −5.49835145e−01 | 6.56763732e−01 | 3.17734599e−01 |
| 8.13950300e−02 | −3.11893135e−01 | 6.67479217e−01 | 6.26232207e−01 |
| 4.24917012e−01 | 1.25488818e−01 | 5.97092807e−01 | 1.47150069e−01 |
| 2.88744628e−01 | 7.33060002e−01 | 1.94037631e−01 | −6.21052027e−01 |
| 9.87926185e−01 | 1.61611214e−01 | −1.50987178e−01 | 1.13103354e−00 |
| −1.22438602e−01 | 1.72604993e−01 | 5.10535717e−01 | −9.74059850e−02 |
| 2.29587909e−01 | 2.37272412e−01 | −2.84676496e−02 | −3.50490779e−01 |
| 3.07857186e−01 | −2.04659939e−01 | 2.35688865e−01 | 2.82927454e−01 |
| 4.99895215e−02 | 8.01806748e−01 | 7.70021081e−01 | 2.13364229e−01 |
| −3.54628265e−01 | 7.43812993e−02 | 2.41041303e−01 | 5.27811646e−01 |
| 2.17756778e−01 | −1.06881350e−01 | 2.11007357e−01 | 5.61725318e−01 |
| 1.59081101e−01 | −4.03437801e−02 | 5.34819365e−01 | 1.73159435e−01 |
| −3.65729630e−02 | −1.74054995e−01 | 9.24782827e−02 | 1.09670095e−01 |
| 6.76707625e−01 | 2.22089589e−01 | 4.26180273e−01 | 8.08065891e−01 |
| −2.69442014e−01 | 1.31274208e−01 | −2.08987528e−03 | 2.26341516e−01 |
| 4.12523776e−01 | 3.40543598e−01 | 3.41633916e−01 | 2.47232258e−01 |
| 9.32226554e−02 | 8.04232955e−01 | −5.99765405e−02 | −3.14518183e−01 |
| 3.00292015e−01 | −2.09563375e−01 | 2.20876813e−01 | −2.46952832e−01 |
| 7.60696471e−01 | −2.28237823e−01 | 1.63191289e−01 | 3.74863833e−01 |
| 3.27754319e−01 | 2.86343992e−01 | 3.00338924e−01 | 3.49632233e−01 |
| −3.26218694e−01 | 1.55260086e−01 | 2.63978660e−01 | 2.10234433e−01 |
| 6.35685563e−01 | 5.87502182e−01 | 2.59079009e−01 | −1.01954103e−01 |
| 2.71257043e−01 | 4.06377137e−01 | −2.93411165e−01 | −3.58475059e−01 |
| 6.62380934e−01 | 5.32889009e−01 | 4.29256797e−01 | 5.29099464e−01 |
| 2.34769374e−01 | 1.66887105e−01 | −1.07454836e−01 | 3.79254997e−01 |
| 3.78066182e−01 | 5.77271700e−01 | 2.28385046e−01 | 1.87520310e−01 |
| −6.81036934e−02 | −4.56510395e−01 | 3.94053996e−01 | −2.17735320e−01 |
| 5.33585429e−01 | 5.66504776e−01 | 6.26197278e−01 | −1.64361402e−01 |
| 2.25596920e−01 | 3.34233880e−01 | 1.76565662e−01 | 1.01405859e−01 |
| −3.03990513e−01 | 9.26904400e−02 | −2.56835241e−02 | 3.18571389e−01 |
| −3.94617826e−01 | 2.09455669e−01 | 1.60729408e−01 | −2.45056197e−01 |
| 2.28470668e−01 | 7.26114273e−01 | −4.59820658e−01 | 1.44483641e−01] |
| [−1.66797206e−01 | 2.12075114e−01 | 1.09670937e−01 | 1.58430308e−01 |
| 7.42391467e−01 | 4.72881764e−01 | 4.22074378e−01 | 1.16147034e−01 |
| 1.35650277e−01 | 3.75078470e−01 | 2.57772356e−01 | 3.66845250e−01 |
| −8.74353275e−02 | −1.02766879e−01 | 3.59955907e−01 | 8.77641025e−04 |
| 3.49542439e−01 | −1.20485485e−01 | 1.24918990e−01 | 3.19065154e−01 |

TABLE $W_h^1$-continued

| | | | |
|---|---|---|---|
| −1.86130404e−02 | 1.72679245e−01 | 9.27519575e−02 | 2.03594103e−01 |
| 2.90017109e−02 | 2.04471454e−01 | 2.53589362e−01 | 1.68589056e−01 |
| 2.38415614e−01 | 3.44436824e−01 | 2.56331533e−01 | 8.04609507e−02 |
| 1.32230237e−01 | −4.46531102e−02 | 4.91044700e−01 | 6.57834113e−01 |
| 1.28469735e−01 | 1.64585665e−01 | −2.62839533e−03 | 7.91796669e−02 |
| 9.75961760e−02 | 2.75885165e−01 | 2.68494278e−01 | 4.01333213e−01 |
| 1.61620393e−01 | −2.21044466e−01 | 7.33963490e−01 | −1.70246109e−01 |
| 4.51534092e−01 | 4.08543020e−01 | 3.54136586e−01 | −6.71941638e−02 |
| 1.53584450e−01 | 3.16012621e−01 | 3.50296311e−02 | 8.55687633e−01 |
| 3.79979789e−01 | 2.49271169e−01 | 2.99443871e−01 | −2.60233223e−01 |
| −1.60997823e−01 | 4.87888783e−01 | 1.52151108e−01 | 3.19167495e−01 |
| −2.79584993e−02 | 3.50476205e−02 | 5.93524873e−01 | 3.71224642e−01 |
| 1.79193690e−01 | 3.75031531e−01 | 1.32077888e−01 | 4.10305411e−01 |
| 8.55646878e−02 | 2.28150293e−01 | 9.23575163e−02 | −7.99906924e−02 |
| 1.13869555e−01 | 1.37319997e−01 | 4.60691780e−01 | −5.11590719e−01 |
| 1.33179486e−01 | 4.04370487e−01 | 1.07591160e−01 | −5.22210896e−01 |
| 1.52997240e−01 | 2.97174364e−01 | 3.05887669e−01 | 2.50806548e−02 |
| −2.25455627e−01 | 1.08974822e−01 | 2.12041140e−01 | 3.46458763e−01 |
| 3.27283174e−01 | −6.42545298e−02 | 5.35740912e−01 | 2.76672035e−01 |
| 5.18738568e−01 | 1.20898820e−01 | 5.72855175e−01 | 2.50405610e−01 |
| 2.85670608e−01 | 4.75898355e−01 | 4.21978772e−01 | −4.16628877e−03 |
| 1.28787309e−01 | 3.77810389e−01 | 5.41859157e−02 | 4.60535020e−01 |
| 1.23937301e−01 | 1.20913111e−01 | 1.21532269e−01 | 5.23690820e−01 |
| 1.35537937e−01 | 2.99838185e−01 | 5.62145650e−01 | 1.56324461e−01 |
| −6.26500547e−02 | 8.61089900e−02 | −1.15362279e−01 | 3.51239532e−01 |
| 1.36658162e−01 | 2.90597111e−01 | 4.39177245e−01 | 1.17460124e−01 |
| −1.42238721e−01 | 4.12866734e−02 | 4.30023313e−01 | 3.61645855e−02 |
| 3.17029417e−01 | 3.42263877e−01 | 1.47400573e−01 | 4.39043850e−01 |
| 1.21240936e−01 | −3.33997165e−03 | 4.79531914e−01 | 3.20818484e−01 |
| −8.36906657e−02 | 5.43112516e−01 | 2.84513146e−01 | −6.55821040e−02 |
| −1.82467476e−01 | 4.42715406e−01 | 3.41486245e−01 | 2.66009182e−01 |
| 2.14773402e−01 | 4.19197202e−01 | −5.84900565e−03 | −2.35982109e−02 |
| 3.27306956e−01 | 5.17022133e−01 | 4.05036241e−01 | 3.90047692e−02 |
| 2.78520554e−01 | 4.85327207e−02 | 9.61412024e−03 | −2.40055144e−01 |
| 1.98869631e−01 | −3.97985950e−02 | 5.61678112e−01 | 5.39322913e−01 |
| 5.54187875e−03 | 8.48996639e−02 | 3.39487106e−01 | 3.23942989e−01 |
| 5.04423082e−01 | 3.56251806e−01 | 1.87702209e−01 | 2.85009742e−01 |
| 4.14962769e−01 | 5.31408906e−01 | 2.24385545e−01 | −4.03996468e−01 |
| 2.71454513e−01 | −3.59192699e−01 | 4.73010570e−01 | −5.08309416e−02 |
| −2.39373837e−02 | 7.32816979e−02 | 1.27834588e−01 | 9.07359719e−02 |
| 1.16784938e−01 | 3.52141261e−01 | 6.59967422e−01 | −2.83247773e−02 |
| 5.51321387e−01 | 4.44113255e−01 | 8.41715261e−01 | −4.27997392e−03 |
| 3.13779563e−01 | 1.63338259e−01 | 3.75094503e−01 | 1.63805425e−01 |
| 5.62886477e−01 | 1.80378273e−01 | 5.29451191e−01 | 6.37835562e−01 |
| 2.41468534e−01 | 6.35179818e−01 | 1.14251748e−01 | −1.50630131e−01 |
| 3.96334827e−01 | −1.28013700e−01 | 2.11799830e−01 | −5.89655042e−01 |
| 3.11854184e−01 | 6.64666653e−01 | −8.55435524e−03 | −1.10813841e−01 |
| 1.21218987e−01 | 2.44139031e−01 | 4.74809289e−01 | −4.11245525e−01 |
| −2.53997535e−01 | 1.81182921e−01 | 3.04230392e−01 | 3.48216891e−01 |
| 2.18433753e−01 | −5.44141494e−02 | 3.93930107e−01 | 2.17824131e−01 |
| 2.00131744e−01 | 5.00828624e−01 | −3.81824113e−02 | −1.52198732e−01 |
| 1.96277753e−01 | 1.27809465e−01 | 4.68716845e−02 | −3.38858664e−01 |
| 3.93789023e−01 | 1.29098222e−01 | 4.43563938e−01 | 3.02818954e−01 |
| 1.96272239e−01 | 6.49207830e−01 | 1.17468974e−01 | −7.88045153e−02 |
| 1.44604877e−01 | 4.85031903e−01 | 4.42112476e−01 | −1.25599831e−01 |
| 5.05258262e−01 | 1.68480903e−01 | 4.39388722e−01 | 2.20330134e−01 |
| 2.05213293e−01 | 1.62441041e−02 | 1.92195892e−01 | 2.44117901e−01 |
| 1.96586162e−01 | −4.83953170e−02 | 1.46855548e−01 | 2.32080162e−01 |
| −4.85299714e−02 | 1.01936355e−01 | 3.36111993e−01 | 4.80524540e−01] |
| [−4.70728166e−02 | 4.23605591e−01 | 5.38993657e−01 | −5.56648374e−01 |
| 3.38102281e−01 | 3.78493100e−01 | 4.84187633e−01 | 1.45341396e−01 |
| 1.28859073e−02 | −4.32769656e−01 | 1.97586358e−01 | −3.37854803e−01 |
| −1.92500595e−01 | 5.23426458e−02 | 9.49664712e−02 | 1.52211055e−01 |
| 2.44460851e−01 | −3.66434492e−02 | 2.79082775e−01 | 6.89993918e−01 |
| 5.76887012e−01 | −1.22593746e−01 | −1.43061996e−01 | 2.38440022e−01 |
| 1.45278797e−01 | 4.52879488e−01 | 3.07721019e−01 | 4.90866512e−01 |
| 2.26518229e−01 | 6.37270868e−01 | 4.53940034e−01 | 1.81761011e−01 |
| 4.79953051e−01 | 4.07775849e−01 | 1.96188204e−02 | 1.42726928e−01 |
| 2.85221219e−01 | 4.40686464e−01 | −1.85361966e−01 | 7.39226997e−01 |
| 3.73560995e−01 | 1.44231963e−00 | −9.16910172e−02 | −2.21702978e−01 |
| 8.72344017e−02 | 8.98264945e−01 | 3.41354907e−01 | −2.65462399e−01 |
| 2.54369617e−01 | 2.37169877e−01 | 4.59088415e−01 | 5.75919859e−02 |
| 7.11857557e−01 | 2.17755675e−01 | 5.32907009e−01 | 9.53228548e−02 |
| 1.94715440e−01 | 4.49333698e−01 | 7.29911146e−04 | −3.14257026e−01 |
| −1.66495629e−02 | 9.72625971e−01 | 7.87588000e−01 | 6.03829980e−01 |
| 3.69234562e−01 | 1.04491092e−01 | 1.83838233e−02 | 6.96935356e−02 |
| 6.08748436e−01 | −2.24512890e−01 | 7.13623911e−02 | 1.49777651e−01 |
| 6.23713732e−01 | −4.85195458e−01 | −1.13402694e−01 | 1.90928981e−01 |
| 2.62599796e−01 | 3.23245943e−01 | 8.12269575e−01 | 3.80518705e−01 |
| 2.03053981e−01 | 5.28877795e−01 | 6.05846465e−01 | 1.55984446e−01 |

TABLE $W_h^1$-continued

| | | | |
|---|---|---|---|
| −3.29579681e−01 | 2.38037810e−01 | 4.35654312e−01 | −1.50927275e−01 |
| 9.48301375e−01 | −1.80689782e−01 | 1.97289750e−01 | −7.15081394e−02 |
| 6.15626812e−01 | 7.70196795e−01 | −4.94069085e−02 | 3.31966020e−02 |
| 3.01461946e−02 | 4.07767706e−02 | 1.48048237e−01 | 5.28165340e−01 |
| 3.67287964e−01 | 5.68290412e−01 | 6.55687988e−01 | 2.53194988e−01 |
| 4.41506177e−01 | 1.39473811e−01 | 4.16460246e−01 | 2.38664731e−01 |
| 5.65687895e−01 | 4.91617501e−01 | 5.44475436e−01 | −3.16626966e−01 |
| 3.76851320e−01 | 6.04157448e−01 | −1.49850845e−01 | −9.75779057e−01 |
| −2.47473985e−01 | 4.03016478e−01 | 1.63225383e−01 | 2.59409904e−01 |
| 3.62214386e−01 | 2.55146861e−01 | 2.95192868e−01 | −9.97212306e−02 |
| −3.95940617e−02 | 4.93558019e−01 | 8.30843598e−02 | 6.49317026e−01 |
| 8.14311445e−01 | 3.20557863e−01 | 4.66040313e−01 | 3.42988700e−01 |
| 4.35726255e−01 | 1.54177070e−01 | 2.66963929e−01 | 1.53279468e−01 |
| −6.11657053e−02 | 1.27882376e−01 | −1.93601966e−01 | 3.31349730e−01 |
| 3.52465779e−01 | 1.69113800e−01 | 4.91059989e−01 | 5.54852784e−01 |
| −3.27916563e−01 | −2.18736708e−01 | 3.52031589e−01 | −4.30549085e−01 |
| 8.29046488e−01 | 1.28673568e−01 | 4.64056641e−01 | 2.65621424e−01 |
| 7.28124678e−01 | 6.83962107e−01 | 3.84090692e−01 | 4.59343284e−01 |
| 2.16337487e−01 | 4.11271960e−01 | 2.38202885e−02 | 2.33522773e−01 |
| 5.05718052e−01 | 2.49502480e−01 | 1.32881030e−01 | 3.01895410e−01 |
| −1.58276156e−01 | 1.67993102e−02 | 3.24110612e−02 | 2.41236854e−01 |
| 1.19269460e−01 | 5.29403269e−01 | 5.16635180e−01 | −3.73104326e−02 |
| 2.96146631e−01 | 3.52451444e−01 | 2.64940172e−01 | 1.00929767e−01 |
| 9.21066880e−01 | 2.91231573e−01 | 4.08340812e−01 | −1.38218358e−01 |
| −4.20205258e−02 | 1.96723625e−01 | 4.20618743e−01 | 3.37318033e−01 |
| −1.60796463e−01 | 5.07808030e−01 | 6.34754479e−01 | 5.35100818e−01 |
| 6.16971970e−01 | 3.83528084e−01 | 4.35705245e−01 | 9.23236236e−02 |
| 3.11712205e−01 | 2.28914812e−01 | 8.48309278e−01 | 1.89864933e−01 |
| −5.34698665e−01 | 4.88324404e−01 | 7.32203603e−01 | 3.27946156e−01 |
| 7.49509215e−01 | 5.72673142e−01 | 4.50635374e−01 | 3.73589009e−01 |
| −2.55858809e−01 | 6.93930924e−01 | −1.31409153e−01 | −2.03051955e−01 |
| 4.89850879e−01 | 8.29626694e−02 | 1.18427195e−01 | 2.69286990e−01 |
| −3.33179116e−01 | 1.84545964e−01 | 1.25581503e−01 | −2.89171606e−01 |
| 3.71380776e−01 | 1.56656519e−01 | −4.19114828e−01 | −8.17991436e−01 |
| 5.42415380e−02 | 5.78530431e−01 | 2.76561528e−01 | 4.48163599e−01 |
| −2.17114151e−01 | −2.16746125e−02 | 2.98708379e−01 | 4.22506481e−02 |
| 5.06126285e−01 | 4.10845011e−01 | 5.87838173e−01 | 2.67148614e−01 |
| 5.89640379e−01 | 6.83612287e−01 | 5.89857042e−01 | 7.55405664e−01 |
| −7.94512257e−02 | 4.27272469e−01 | −8.89849197e−03 | 5.09248137e−01 |
| −5.72847500e−02 | −3.01369399e−01 | 4.98274058e−01 | 2.75261223e−01 |
| −7.82005638e−02 | −1.45442069e−01 | −1.24457344e−01 | −1.26089789e−02 |
| 8.70496869e−01 | 6.11624837e−01 | −1.43724769e−01 | 5.27619302e−01 |
| −8.19982663e−02 | 5.42663097e−01 | 2.30581522e−01 | −1.87314406e−01] |
| [−1.36114106e−01 | 3.53333168e−02 | 4.40351188e−01 | −1.76925689e−01 |
| 6.02701545e−01 | 2.11099863e−01 | 5.24471819e−01 | −3.13661546e−01 |
| 4.71745819e−01 | 8.07725787e−02 | −1.42454848e−01 | 3.65567207e−01 |
| −5.04840072e−03 | 3.32561284e−01 | −1.23682670e−01 | 4.86321375e−02 |
| 2.82219779e−02 | 7.34830350e−02 | 5.53659797e−02 | 4.52908427e−01 |
| −2.38791127e−02 | 1.49094120e−01 | 2.46767327e−01 | 1.76336646e−01 |
| 5.01204170e−01 | −1.21092550e−01 | −1.93053246e−01 | 2.22937092e−01 |
| −7.09053874e−02 | 2.24721376e−02 | 4.50272202e−01 | 1.12244368e−01 |
| 4.41519916e−01 | −2.94198692e−01 | 7.53403753e−02 | 6.83876052e−02 |
| 2.60730505e−01 | 4.75819558e−01 | −2.24525388e−02 | −8.65406841e−02 |
| 2.31542885e−01 | −3.02643999e−02 | −1.86470911e−01 | 3.96712661e−01 |
| −4.43534330e−02 | −2.01342218e−02 | 1.51554078e−01 | 5.06571710e−01 |
| −1.55866161e−01 | 2.47335762e−01 | 2.26629928e−01 | −7.10647032e−02 |
| −1.84030384e−01 | −8.53692666e−02 | 1.16352744e−01 | 3.55134726e−01 |
| −4.57969308e−02 | 1.86833218e−01 | 7.73024797e−01 | 1.26799837e−01 |
| 3.54380280e−01 | 2.03955710e−01 | 1.83522955e−01 | 2.53521442e−01 |
| 2.39445269e−01 | 5.68984449e−01 | 4.05905619e−02 | 4.31586802e−01 |
| −5.36634773e−02 | 2.34023258e−01 | 2.45904729e−01 | 2.29530111e−01 |
| 3.85216087e−01 | 1.37806118e−01 | 1.75177172e−01 | 1.99043199e−01 |
| 2.97104597e−01 | 2.87760526e−01 | −1.01917475e−01 | 1.05843574e−01 |
| 3.99791390e−01 | 4.88712162e−01 | 3.20992798e−01 | 2.11020127e−01 |
| 1.68563668e−02 | 4.38577123e−03 | 1.25138178e−01 | 3.89964461e−01 |
| 6.17954880e−03 | 4.42165166e−01 | 8.71277824e−02 | 2.60686368e−01 |
| 6.97415054e−01 | 5.34012377e−01 | 1.60161823e−01 | 4.02225018e−01 |
| 1.44757196e−01 | 1.27052620e−01 | 8.91025290e−02 | 7.77455628e−01 |
| 2.07836285e−01 | 3.45176369e−01 | 4.98396844e−01 | 2.49597073e−01 |
| 2.84060597e−01 | 3.85210514e−01 | −4.38585788e−01 | −2.56237924e−01 |
| 3.53106767e−01 | 5.51818013e−01 | 3.76811981e−01 | 3.92299145e−01 |
| 4.01011854e−01 | 4.66569215e−01 | 4.84326303e−01 | 2.74655193e−01 |
| 4.97316360e−01 | −8.16278681e−02 | 3.57157774e−02 | −4.36127409e−02 |
| −1.59946140e−02 | 5.61898470e−01 | 3.33740741e−01 | 2.49922603e−01 |
| 5.85943401e−01 | 2.00785622e−01 | 2.56228238e−01 | −2.29422331e−01 |
| −2.13116109e−01 | 6.36525899e−02 | −1.23042315e−01 | 3.98164243e−03 |
| 2.59607553e−01 | 1.56009331e−01 | 2.56250292e−01 | −1.83547348e−01 |
| 2.68924892e−01 | 3.54007363e−01 | 4.06600088e−02 | 4.54351515e−01 |
| 1.80083752e−01 | 2.19337940e−01 | 2.36117929e−01 | −5.60068414e−02 |
| 3.95324469e−01 | 2.56665885e−01 | −1.07203394e−01 | 3.68363142e−01 |

TABLE $W_h^1$-continued

| | | | |
|---|---|---|---|
| 4.69675362e-01 | 6.02608740e-01 | 2.88621396e-01 | -2.85715647e-02 |
| 3.33273977e-01 | -2.92769987e-02 | -2.08680689e-01 | 1.05321266e-01 |
| 5.03815413e-01 | 1.45122573e-01 | 2.04598159e-01 | 2.35461563e-01 |
| 2.27521703e-01 | 3.23059589e-01 | 1.98616400e-01 | 1.92888886e-01 |
| 1.86348036e-01 | 1.89937681e-01 | 2.14614701e-02 | 3.10158879e-01 |
| 3.54879141e-01 | -1.47606567e-01 | 4.40551460e-01 | -6.60571232e-02 |
| -1.49178430e-02 | -2.80603603e-03 | 2.93549776e-01 | -1.98356032e-01 |
| 1.71520114e-01 | 3.67266864e-01 | -1.30480826e-01 | 2.65656233e-01 |
| -1.00845709e-01 | 4.57965344e-01 | 2.09269702e-01 | 2.05246165e-01 |
| 3.61702383e-01 | 3.90040666e-01 | 1.92491800e-01 | 2.93369219e-02 |
| 2.21775547e-01 | -1.59325168e-01 | 8.59554559e-02 | 3.97549123e-01 |
| 1.50887027e-01 | 5.06043613e-01 | 2.00889155e-01 | -5.66663891e-02 |
| 1.47308126e-01 | 1.80415243e-01 | -4.10919264e-02 | 4.64716524e-01 |
| 1.56308636e-01 | -1.49016008e-01 | -4.18607816e-02 | 1.51322469e-01 |
| 2.79788345e-01 | -6.51465058e-02 | 1.38382956e-01 | 3.67327034e-01 |
| 3.55842672e-02 | -2.79080600e-01 | 2.67372102e-01 | -5.61032057e-02 |
| 6.33974075e-02 | 1.27521425e-01 | 4.16861564e-01 | 2.95114636e-01 |
| 3.23671013e-01 | -2.51680464e-01 | 2.08384618e-01 | 2.09240153e-01 |
| 4.30846632e-01 | -7.44243637e-02 | 7.71209449e-02 | -5.56463748e-03 |
| -1.67435616e-01 | 1.21357627e-01 | 1.33050710e-01 | -3.29188146e-02 |
| -1.14140920e-02 | -1.17998064e-01 | -1.26889274e-01 | 1.18383527e-01 |
| 8.51105154e-02 | -9.32924271e-01 | 6.73457682e-02 | -1.71870783e-01 |
| 1.86687529e-01 | 4.56262499e-01 | 5.85658550e-02 | 1.49700597e-01 |
| 4.44914430e-01 | 1.43062457e-01 | 3.39869410e-01 | -1.81909725e-01 |
| 2.53991842e-01 | 1.87552899e-01 | 3.96974951e-01 | 3.90057355e-01 |
| -4.77078073e-02 | 1.52498752e-01 | 8.77393857e-02 | 2.92527722e-03 |
| 1.60705566e-01 | 5.21306872e-01 | 2.94103056e-01 | 3.07416379e-01] |
| [7.37073347e-02 | -2.34904692e-01 | 2.80501902e-01 | -3.45699638e-01 |
| 4.12358254e-01 | 3.39977503e-01 | 9.72796738e-01 | 2.43481457e-01 |
| -1.28876865e-01 | -5.49755134e-02 | -9.14402190e-04 | 3.24109197e-01 |
| 5.81958652e-01 | 4.16271061e-01 | -2.28391558e-01 | -9.78376437e-03 |
| 1.46139026e-01 | 1.49809733e-01 | -4.60697012e-03 | 4.49301690e-01 |
| 2.71608770e-01 | 3.80643427e-01 | 1.99043915e-01 | 3.27265084e-01 |
| 2.69073129e-01 | 3.14941525e-01 | 7.49313891e-01 | 1.37035802e-01 |
| -1.61908731e-01 | 1.86905533e-01 | 4.51533109e-01 | 2.05203533e-01 |
| 6.85515821e-01 | -5.54606542e-02 | -9.29956809e-02 | 8.64640921e-02 |
| 2.16745287e-02 | 7.31930733e-01 | 6.83737770e-02 | 3.91171694e-01 |
| 7.49935567e-01 | 5.13997674e-03 | 2.97707506e-02 | 6.98312700e-01 |
| 2.76609451e-01 | 2.85476148e-01 | 5.58782041e-01 | 2.30795383e-01 |
| -2.24054400e-02 | -2.09846660e-01 | 2.33925819e-01 | -4.54466529e-02 |
| 9.01894495e-02 | 5.01099646e-01 | 6.11191541e-02 | 1.46179572e-01 |
| 3.73455614e-01 | -2.73698363e-01 | 7.27124929e-01 | 4.97362241e-02 |
| 5.71160018e-01 | 7.10362434e-01 | -2.00634629e-01 | 2.38526955e-01 |
| 6.53022110e-01 | 4.82797533e-01 | 7.26221681e-01 | 3.98280025e-01 |
| 3.57075363e-01 | 4.95605081e-01 | 4.68549788e-01 | 1.61620528e-02 |
| 9.33529735e-02 | 2.17528909e-01 | 4.39002037e-01 | 3.69266927e-01 |
| 5.77485085e-01 | 7.29535937e-01 | 1.64487615e-01 | 2.83127189e-01 |
| 4.29137886e-01 | 3.35818022e-01 | 1.07156709e-01 | 5.09727478e-01 |
| 2.24550799e-01 | -9.03234072e-03 | 5.25074005e-01 | 1.45480828e-02 |
| -1.38868541e-01 | -3.31129543e-02 | 1.74692646e-01 | 2.12126240e-01 |
| 3.50073844e-01 | 4.52018052e-01 | 6.83485389e-01 | 7.19566166e-01 |
| -2.17208996e-01 | 5.79750612e-02 | 2.01844797e-01 | 3.80530030e-01 |
| 6.76324069e-01 | 5.69382012e-01 | 8.19595456e-02 | -1.60851508e-01 |
| 1.55875519e-01 | 4.86976653e-01 | 5.63809574e-01 | 2.20061108e-01 |
| 1.73700213e-01 | 5.77761173e-01 | 1.82963148e-01 | 5.88161469e-01 |
| 3.55021179e-01 | 2.88181931e-01 | 2.00688526e-01 | 2.65746474e-01 |
| 2.01871142e-01 | 4.87147689e-01 | 8.68538469e-02 | 5.32164156e-01 |
| 1.15266927e-02 | 3.25549513e-01 | 1.07938647e-00 | -9.11266450e-03 |
| 3.06574732e-01 | 3.08353920e-03 | 6.27965212e-01 | 6.23649061e-01 |
| 6.41458869e-01 | 5.08313954e-01 | 8.73167336e-01 | 4.28750128e-01 |
| 4.88865882e-01 | 2.12919891e-01 | 2.28477135e-01 | -2.55488157e-01 |
| 2.02360988e-01 | -1.15324380e-02 | 3.11733812e-01 | 3.76572341e-01 |
| 6.19919956e-01 | 2.19372824e-01 | 2.16538668e-01 | 4.62625362e-01 |
| 5.06808102e-01 | 3.91820222e-02 | 3.99312466e-01 | 4.42561150e-01 |
| 6.22733593e-01 | 6.42841399e-01 | -6.00167736e-02 | 1.43441498e-01 |
| -3.14179003e-01 | 6.71902969e-02 | 1.38680011e-01 | -4.02977079e-01 |
| 4.20121878e-01 | 1.17252484e-01 | 6.00612581e-01 | 4.16837960e-01 |
| -2.15554714e-01 | 5.78171134e-01 | 3.33609432e-01 | 6.37274384e-01 |
| 1.48370236e-01 | 2.53990084e-01 | 1.76656604e-01 | 5.12966096e-01 |
| 3.03855479e-01 | 2.74753720e-01 | 3.61048698e-01 | 1.36363015e-01 |
| 4.61805642e-01 | -4.31734800e-01 | 2.98968166e-01 | 5.13353646e-01 |
| 4.43335265e-01 | -5.28573766e-02 | 1.78572580e-01 | 5.67211099e-02 |
| 3.81900787e-01 | 4.55641776e-01 | 4.16412145e-01 | 3.62700552e-01 |
| -8.38606283e-02 | -2.01751500e-01 | -1.49044991e-01 | 4.60129112e-01 |
| -3.51426929e-01 | 4.15893435e-01 | 2.25035965e-01 | 2.91346669e-01 |
| 3.72732610e-01 | 6.41049087e-01 | 2.90551007e-01 | 5.82169473e-01 |
| 4.51326996e-01 | 3.68615746e-01 | 1.37793243e-01 | 7.79327810e-01 |
| 2.34924167e-01 | 2.51752228e-01 | 3.05925101e-01 | 4.81238008e-01 |
| 1.43085375e-01 | 3.39783013e-01 | 3.66521001e-01 | 2.66759038e-01 |
| -1.68071195e-01 | -3.55514944e-01 | 5.34616470e-01 | 1.76623985e-01 |

TABLE W$_h^1$-continued

| | | | |
|---|---|---|---|
| 4.69184965e−01 | 3.52436513e−01 | 2.70357758e−01 | 5.33646524e−01 |
| −1.22463875e−01 | −1.24371193e−01 | 2.64061064e−01 | 8.30437914e−02 |
| 1.29438609e−01 | 1.59287110e−01 | 1.72336414e−01 | 2.21935526e−01 |
| 1.72562003e−02 | 1.22856554e−02 | 4.41182673e−01 | 7.72178099e−02 |
| 4.79940563e−01 | −1.43485948e−01 | 5.14199734e−01 | 2.14393914e−01 |
| −1.86286792e−01 | −4.09151495e−01 | 3.16743374e−01 | 3.14229690e−02 |
| −3.55825499e−02 | 5.10481775e−01 | −5.09335399e−01 | 1.84693918e−01 |
| 3.57722253e−01 | 3.10915947e−01 | 6.94962069e−02 | 2.21118033e−01 |
| 1.71139285e−01 | 4.45920348e−01 | 4.78854030e−01 | 9.18881297e−02 |
| 4.78630438e−02 | 1.99166745e−01 | 2.12464362e−01 | 1.12493970e−01 |
| 7.68920779e−02 | 3.25689554e−01 | 5.27619123e−01 | 5.93219697e−01] |
| [1.08478121e−01 | −8.58757086e−03 | −6.87011778e−02 | 3.49260747e−01 |
| 6.80381432e−02 | 2.47198567e−01 | −4.85956557e−02 | 1.37965837e−02 |
| 9.33191404e−02 | 2.71611840e−01 | 8.70446935e−02 | 2.37109333e−01 |
| 4.82452512e−01 | −9.28675085e−02 | 2.84855440e−02 | 3.65336746e−01 |
| 7.09192395e−01 | −2.84547389e−01 | −1.07336558e−01 | 7.10785165e−02 |
| −4.35201190e−02 | −2.93017291e−01 | −2.47051418e−01 | 1.68976575e−01 |
| 1.84905842e−01 | 1.71101138e−01 | −1.67931229e−01 | −9.94461924e−02 |
| 5.63334189e−02 | 2.11911738e−01 | 2.45908245e−01 | −9.16325152e−02 |
| 3.37488115e−01 | −1.82771742e−01 | 8.13858658e−02 | 2.23244682e−01 |
| −2.00977504e−01 | −8.85584671e−03 | 2.27949053e−01 | 1.84656680e−01 |
| 1.84328899e−01 | 1.97814126e−02 | 8.88160169e−02 | 1.15759119e−01 |
| 2.60450274e−01 | 2.66811669e−01 | −1.38737801e−02 | 1.79169863e−01 |
| −4.53696340e−01 | 1.17179811e−01 | 3.02292585e−01 | −2.41186097e−01 |
| 7.97351971e−02 | −1.01206817e−01 | 3.00886780e−01 | 1.25578220e−01 |
| 2.48971328e−01 | −7.49340355e−02 | 1.26010358e−01 | 1.69006452e−01 |
| 1.01403669e−01 | 2.65742183e−01 | −1.64306730e−01 | 3.93246524e−02 |
| 3.45161140e−01 | 2.53762901e−01 | 4.97152150e−01 | 1.60107106e−01 |
| 1.01279452e−01 | 3.34592730e−01 | −6.08911291e−02 | −1.14572562e−01 |
| 1.40979558e−01 | 1.98071554e−01 | −1.64800137e−01 | 4.33012247e−01 |
| 3.53858083e−01 | 2.51240939e−01 | 5.01515031e−01 | −2.67186582e−01 |
| 1.45515263e−01 | 4.28092748e−01 | 1.93818972e−01 | 3.98946881e−01 |
| 1.43539682e−01 | −3.43327999e−01 | 4.38925177e−01 | −1.26917347e−01 |
| −1.64136648e−01 | 1.56768829e−01 | 3.02873313e−01 | 4.99009311e−01 |
| −6.01401106e−02 | 3.28095734e−01 | 2.15132698e−01 | 1.72163546e−01 |
| 3.07514649e−02 | 3.22948039e−01 | 4.44108061e−02 | −1.45345420e−01 |
| −8.92910808e−02 | −1.20462857e−01 | −6.63643107e−02 | 4.73445579e−02 |
| 5.32724373e−02 | −8.22597146e−02 | 2.70634115e−01 | 3.33862692e−01 |
| −4.22223061e−02 | 3.18310231e−01 | 1.44529760e−01 | −1.86806209e−02 |
| 6.82853386e−02 | 9.45857912e−03 | −3.11322689e−01 | 5.06118298e−01 |
| 2.55279243e−01 | −1.88139811e−01 | 1.10908501e−01 | −1.52677715e−01 |
| 2.32734859e−01 | 1.80977046e−01 | 2.67365396e−01 | 1.35657161e−01 |
| 8.50517750e−02 | −5.44793308e−02 | 3.39938253e−01 | 7.60664046e−02 |
| 1.85702816e−01 | 2.37509012e−01 | 3.09515864e−01 | 2.23551169e−01 |
| 3.26875657e−01 | 1.66479602e−01 | 1.34145364e−01 | −3.23502440e−03 |
| 3.53370726e−01 | −2.27827415e−01 | 2.94467248e−02 | 3.32919776e−01 |
| 9.13112462e−02 | 1.02397583e−01 | 2.95928955e−01 | 1.24226995e−01 |
| 2.11937964e−01 | 8.51321220e−02 | −1.36187421e−02 | 4.49746251e−01 |
| 2.81500816e−01 | 1.58019200e−01 | 3.15295547e−01 | 3.41617875e−02 |
| 2.43872717e−01 | 4.30968441e−02 | 2.50103716e−02 | 1.56295411e−02 |
| 5.35976216e−02 | 3.42348248e−01 | −1.00247107e−01 | 2.87027657e−01 |
| 3.30831856e−01 | 2.88612604e−01 | 3.68532062e−01 | 3.06347549e−01 |
| −1.67441908e−02 | −1.82726189e−01 | 4.78252500e−01 | 5.64322114e−01 |
| 2.44655430e−01 | −4.27459814e−02 | −1.10670619e−01 | 3.13284069e−01 |
| 3.11847508e−01 | 3.42732519e−01 | −2.44042277e−01 | 2.64038563e−01 |
| 2.69646972e−01 | 1.67422548e−01 | 1.17355801e−01 | 8.54849070e−02 |
| 6.83912858e−02 | 4.31965083e−01 | 1.78861424e−01 | −4.46479581e−02 |
| −4.62832600e−02 | −1.94973484e−01 | 8.92384797e−02 | −1.91033408e−02 |
| 6.42890949e−03 | 1.23943366e−01 | 2.23399580e−01 | −2.34323218e−02 |
| 4.08287160e−02 | 4.74007010e−01 | 3.43382269e−01 | 1.29112780e−01 |
| −1.77302033e−01 | 1.63504303e−01 | −3.63271743e−01 | 2.10939825e−01 |
| 1.29947394e−01 | 2.11832717e−01 | 3.80003542e−01 | 3.12545784e−02 |
| 3.41177911e−01 | −8.60811397e−02 | −1.02143986e−01 | −1.17684379e−01 |
| 1.21156961e−01 | 4.81138267e−02 | 5.36426544e−01 | −2.82520384e−01 |
| 4.48274612e−01 | −4.30806354e−02 | 2.28160292e−01 | 6.05287433e−01 |
| −3.46383825e−02 | −2.25205332e−01 | 1.50673285e−01 | −9.37607232e−03 |
| 1.05951503e−01 | 1.42225504e−01 | 2.77009279e−01 | −1.43670559e−01 |
| 2.79639140e−02 | 2.75153816e−01 | 1.98560014e−01 | 1.14119269e−01 |
| 9.58046541e−02 | 1.44132540e−01 | 1.08981408e−01 | −1.52531952e−01 |
| −1.83348224e−01 | −5.53233743e−01 | 1.88636228e−01 | 5.46835780e−01 |
| 2.42151245e−01 | 4.78731930e−01 | 2.50268370e−01 | 1.75263733e−01 |
| 2.78238535e−01 | 3.99140149e−01 | 4.02756959e−01 | 3.33949417e−01 |
| 2.26686001e−01 | 2.94142246e−01 | −4.20572795e−02 | 2.14968637e−01 |
| 5.18256605e−01 | 2.52806425e−01 | 6.46720409e−01 | 2.76287585e−01 |
| 9.36180428e−02 | 2.81387687e−01 | 2.66214609e−01 | 2.33597726e−01] |
| [1.69416353e−01 | 6.37662113e−01 | 2.26684868e−01 | 2.87311673e−01 |
| −3.17133039e−01 | 4.43693995e−01 | −3.57191102e−03 | 7.22743809e−01 |
| 3.74748915e−01 | 4.98168856e−01 | 7.90794075e−01 | 2.25356847e−01 |
| −8.04327875e−02 | 3.33508253e−01 | 5.99535465e−01 | −3.35108131e−01 |
| 1.43521503e−01 | 1.44230789e−02 | 6.55511558e−01 | 5.74970067e−01 |

TABLE $W_h^1$-continued

| | | | |
|---|---|---|---|
| 5.49073279e−01 | 2.45058805e−01 | 2.51467407e−01 | 3.68301362e−01 |
| 2.76960582e−01 | 3.04020137e−01 | 7.10239708e−01 | 1.50245935e−01 |
| −5.36871552e−02 | 9.91105199e−01 | −3.87378782e−01 | 2.77325749e−01 |
| 3.47456306e−01 | 2.25252211e−01 | 3.12178612e−01 | −2.00333551e−01 |
| 8.51990581e−02 | 1.49607211e−01 | 5.40313542e−01 | 6.46755576e−01 |
| 5.78961559e−02 | 2.65202969e−01 | −4.50147957e−01 | 7.17375502e−02 |
| 1.07759655e−00 | 3.50714177e−01 | 5.29031992e−01 | −4.75816503e−02 |
| 4.20182832e−02 | 3.25175226e−01 | 4.12058264e−01 | 5.10899484e−01 |
| 5.41216254e−01 | 7.41043091e−02 | 4.57095765e−02 | −1.23971533e−02 |
| 5.65677822e−01 | 2.15190619e−01 | 5.43890893e−01 | 7.11000443e−01 |
| 3.07317317e−01 | 5.98972201e−01 | 5.62631264e−02 | 2.45433018e−01 |
| −2.17626944e−01 | 6.18529953e−02 | −4.74353023e−02 | 1.20705299e−01 |
| 6.14353836e−01 | 8.75618994e−01 | 4.33527291e−01 | 4.99424815e−01 |
| 7.14527890e−02 | 1.50288284e−01 | 1.02194101e−01 | 3.72118145e−01 |
| 5.51623166e−01 | 9.39922482e−02 | −1.53293848e−01 | 5.27727306e−01 |
| −1.02549963e−01 | 3.90068859e−01 | 7.94122145e−02 | 1.00871541e−01 |
| −2.07989812e−01 | 2.54501969e−01 | 1.81039572e−02 | 2.27914721e−01 |
| 5.10139585e−01 | −1.70476198e−01 | −1.66545033e−01 | 1.90459624e−01 |
| 3.49577248e−01 | −5.14816642e−01 | 1.75048694e−01 | 3.61888468e−01 |
| −4.95512486e−02 | 7.89064288e−01 | −5.46085499e−02 | 1.10881738e−02 |
| 4.08006072e−01 | 8.11393261e−01 | 3.26726496e−01 | 9.25560296e−01 |
| 9.13247913e−02 | −4.11470532e−02 | 3.98447901e−01 | 8.91607925e−02 |
| −3.73337828e−02 | 7.78359056e−01 | −3.15439731e−01 | −4.32894766e−01 |
| 4.43790644e−01 | −2.59784490e−01 | 8.71063098e−02 | 3.22897017e−01 |
| 1.38808805e−02 | 5.36723435e−01 | 4.13681775e−01 | 1.68958887e−01 |
| 5.68984807e−01 | 2.80924737e−01 | 6.39804840e−01 | 4.58870709e−01 |
| 4.79802340e−01 | 3.71199995e−01 | 4.74633753e−01 | 8.85025620e−01 |
| 3.41765106e−01 | 8.34974527e−01 | 3.13766189e−02 | 8.43321681e−02 |
| 5.55583239e−01 | 3.47747058e−01 | 1.47068158e−01 | 2.34985724e−01 |
| −9.30622444e−02 | 4.87537801e−01 | −1.77434936e−01 | 6.24114648e−02 |
| 4.62088659e−02 | −3.70170265e−01 | 6.53196156e−01 | 4.94409382e−01 |
| 9.37677268e−03 | 2.85965264e−01 | 5.03671803e−02 | 4.82186861e−02 |
| −1.4084393e−01 | −4.66836780e−01 | −8.34353641e−01 | 7.28543878e−01 |
| 4.01266456e−01 | 2.06480533e−01 | 8.14424872e−01 | 7.14695334e−01 |
| −5.67035675e−02 | 1.59454942e−01 | 8.28582704e−01 | 2.08623797e−01 |
| 1.47487149e−01 | 8.03760141e−02 | 3.68138671e−01 | 1.23944022e−01 |
| 3.94696295e−02 | 2.74306595e−01 | 4.85102713e−01 | −9.57846567e−02 |
| 8.54013622e−01 | 2.26510748e−01 | −7.90971667e−02 | 3.80035013e−01 |
| 3.63802582e−01 | 2.32969552e−01 | −1.83923453e−01 | 5.09801321e−03 |
| 2.73097336e−01 | −4.61502336e−02 | −8.41621682e−02 | 4.55634207e−01 |
| 4.28139083e−02 | 5.83974481e−01 | 4.14344877e−01 | 7.89599359e−01 |
| 3.39850932e−01 | 2.20361844e−01 | 4.42113876e−01 | 5.18252194e−01 |
| −8.07239860e−02 | −5.41572575e−04 | 5.35725713e−01 | 1.49265155e−01 |
| 3.93589199e−01 | 5.45424700e−01 | −2.56728698e−02 | −3.72118175e−01 |
| −1.75918207e−01 | 3.08891386e−01 | 2.33066186e−01 | 2.36732632e−01 |
| −3.60160232e−01 | 6.47471726e−01 | 1.73727795e−01 | 3.34439307e−01 |
| 3.25393379e−01 | 7.02787578e−01 | 4.01991218e−01 | 3.90486628e−01 |
| 1.05882311e−00 | 5.58912568e−03 | 2.76040435e−02 | 3.55255127e−01 |
| 3.28175336e−01 | 4.43263501e−02 | 4.50754315e−01 | 1.61764175e−01 |
| 2.27177113e−01 | 3.17544013e−01 | 3.06013167e−01 | 1.92739204e−01 |
| −1.71803936e−01 | 2.90591300e−01 | 2.88877040e−01 | 4.86321263e−02 |
| 3.77244145e−01 | 6.70535043e−02 | −1.22241089e−02 | 6.07663691e−01 |
| 2.98273504e−01 | 3.07455540e−01 | 3.86297315e−01 | 1.04694307e−00 |
| 1.69597283e−01 | −8.84699523e−02 | 3.46026659e−01 | 4.70801979e−01 |
| 4.14710850e−01 | −9.13838204e−03 | −1.80134222e−01 | 4.60066080e−01 |
| 1.32740393e−01 | 2.96694189e−01 | −2.41964519e−01 | 9.60790515e−01 |
| 3.24292451e−01 | 2.85665870e−01 | −3.39914970e−02 | 4.74277020e−01 |
| 5.82040250e−01 | 1.54619306e−01 | 3.89579058e−01 | 7.85436511e−01 |
| 2.74799615e−01 | 2.71275997e−01 | 3.13141435e−01 | 2.50728607e−01] |
| [2.47881517e−01 | 4.13669318e−01 | −6.20563477e−02 | 1.52497143e−01 |
| −4.12190825e−01 | −9.05245692e−02 | 1.06485665e−01 | 3.92783403e−01 |
| −4.50364687e−03 | 1.20082438e−01 | 2.62203306e−01 | −5.83491743e−01 |
| 1.88971490e−01 | 1.92423403e−01 | −3.37981693e−02 | −2.36969888e−01 |
| −3.20180714e−01 | 3.01385462e−01 | −1.20285839e−01 | 4.38415885e−01 |
| 2.58335680e−01 | 1.38102248e−01 | 1.17888197e−01 | −1.12417072e−01 |
| −1.84487998e−01 | 4.43493307e−01 | −1.32775947e−01 | 1.99748382e−01 |
| 1.19641975e−01 | −1.14666177e−02 | −2.95735538e−01 | 3.07651430e−01 |
| −3.29950154e−02 | −1.40022814e−01 | 2.38168880e−01 | 1.32122815e−01 |
| 7.64065981e−02 | −3.73458385e−01 | 2.53537327e−01 | 2.37749696e−01 |
| 6.39440864e−02 | 1.20873109e−01 | 1.92473903e−01 | 2.28395209e−01 |
| 3.32162410e−01 | 1.48458332e−01 | 4.69457172e−01 | 3.01084965e−01 |
| −5.59720173e−02 | −9.35013667e−02 | 1.10536799e−04 | 4.20558929e−01 |
| −1.56028390e−01 | 1.35869965e−01 | −3.01009655e−01 | −2.52121270e−01 |
| 4.00798209e−02 | −4.46694493e−02 | 3.76917660e−01 | 4.95468706e−01 |
| 4.17664379e−01 | 1.65795445e−01 | 6.73638284e−01 | −1.27465650e−01 |
| −3.15634280e−01 | −4.50076699e−01 | −4.12309945e−01 | −3.02715123e−01 |
| 4.15634722e−01 | −1.12955878e−03 | −8.48422721e−02 | 2.02396005e−01 |
| −2.07675770e−01 | 2.22304717e−01 | 4.89205420e−01 | 3.45122606e−01 |
| −2.82289982e−01 | 1.24565251e−01 | −1.59187526e−01 | 2.34422237e−02 |
| −8.54154676e−02 | 1.88381359e−01 | 1.05899356e−01 | −3.42416614e−01 |

TABLE $W_h^1$-continued

| | | | |
|---|---|---|---|
| −3.05845410e−01 | −1.81821778e−01 | −1.55360505e−01 | 1.50826961e−01 |
| 4.13702667e−01 | 2.12992549e−01 | −1.04316972e−01 | 2.21091196e−01 |
| −1.10284545e−01 | −4.34225231e−01 | 2.04542905e−01 | −4.44626838e−01 |
| −2.49337003e−01 | 5.64056337e−01 | −5.17799377e−01 | −1.24896660e−01 |
| −8.33937526e−03 | −8.46106187e−02 | 3.49067390e−01 | 7.71620264e−03 |
| −2.39493459e−01 | −1.43231004e−01 | 1.02558151e−01 | −4.34083045e−01 |
| −3.19249451e−01 | −5.07433534e−01 | 2.22050115e−01 | −7.32787848e−01 |
| −3.78863782e−01 | 1.62226066e−01 | −2.34472781e−01 | 1.47062778e−01 |
| −4.33000803e−01 | 1.67985722e−01 | 3.68295610e−01 | −2.13903472e−01 |
| 2.89356619e−01 | 1.20088361e−01 | −2.97210723e−01 | −4.05901931e−02 |
| 5.01533628e−01 | 1.92140922e−01 | −1.96729079e−01 | −4.22906242e−02 |
| 8.23434256e−03 | −5.75915426e−02 | 1.87431909e−02 | 9.70917791e−02 |
| 2.93033957e−01 | −9.94982794e−02 | 3.05103380e−02 | −6.02426715e−02 |
| −5.11314094e−01 | −3.82299200e−02 | 1.40461549e−01 | −1.20548561e−01 |
| −4.46716733e−02 | 3.64117622e−01 | 1.94408059e−01 | 3.21578056e−01 |
| −9.16426897e−01 | −1.28461709e−02 | 3.76803130e−01 | −1.41025707e−01 |
| −4.24280345e−01 | −5.68322718e−01 | −5.13707817e−01 | 2.08250850e−01 |
| 1.47468239e−01 | 1.42503425e−01 | 4.86046463e−01 | −8.39323923e−02 |
| 8.57277662e−02 | 4.18586522e−01 | 1.94969848e−01 | 2.21441358e−01 |
| 1.02083184e−01 | 1.39915571e−01 | −7.46724457e−02 | −1.14524797e−01 |
| 1.02248512e−01 | −1.00887664e−01 | 1.26174301e−01 | −2.90485322e−01 |
| 3.02631371e−02 | −1.85721219e−01 | 3.73049378e−01 | 1.82303041e−01 |
| 1.36387587e−01 | 2.77602315e−01 | −5.02898335e−01 | 1.16817243e−01 |
| 2.04612538e−01 | 4.36569154e−01 | −2.84203112e−01 | −2.49524459e−01 |
| 3.93361300e−01 | −4.92530942e−01 | 2.73099691e−01 | 1.80254444e−01 |
| 2.86732614e−01 | −9.93551984e−02 | 2.10863337e−01 | −1.85773838e−02 |
| −2.42450252e−01 | 4.17630486e−02 | 2.43898973e−01 | −3.99343716e−03 |
| −6.34785295e−02 | 1.14552192e−01 | −4.39743102e−01 | −5.89109242e−01 |
| 1.54505104e−01 | −6.22388959e−01 | 1.28484294e−01 | 2.41125628e−01 |
| −4.06595200e−01 | 3.42010230e−01 | 1.84222698e−01 | 2.15567857e−01 |
| 4.56841141e−02 | −1.16446935e−01 | −1.04981940e−02 | −7.93989673e−02 |
| 4.37497288e−01 | 3.37849021e−01 | −4.87978816e−01 | 2.35882685e−01 |
| −1.67265803e−01 | 3.22651304e−01 | −3.60051870e−01 | 1.64381728e−01 |
| 4.43691820e−01 | −3.11785936e−01 | 2.46201560e−01 | 1.96192220e−01 |
| −2.56708264e−01 | 3.56581509e−01 | 4.06469852e−02 | 3.45486752e−03 |
| 2.16899246e−01 | −6.02223165e−02 | −1.15477383e−01 | 1.01661831e−01 |
| 7.61052966e−02 | 4.50814366e−01 | 4.94441800e−01 | 8.94335583e−02 |
| 2.27814272e−01 | −2.77183563e−01 | 4.72998898e−03 | 5.38862467e−01 |
| 2.16815054e−01 | 2.26946041e−01 | 4.19918954e−01 | 7.40083084e−02 |
| −1.88910320e−01 | −6.19798116e−02 | 2.81171408e−02 | −1.81322888e−01 |
| −6.94457769e−01 | −2.57123172e−01 | 6.46363869e−02 | 9.49534029e−03 |
| 2.70018190e−01 | 3.05366874e−01 | −2.52798647e−01 | 2.67449528e−01 |
| 9.52155367e−02 | 3.19994502e−02 | 1.70371830e−01 | −8.19084942e−02] |
| [−1.00229666e−01 | −2.98776347e−02 | 5.03572747e−02 | 3.72694135e−01 |
| 1.01132922e−01 | −7.11412579e−02 | −7.07741678e−02 | −1.07791021e−01 |
| −3.13745998e−02 | −7.78523684e−02 | 5.59531003e−02 | 3.72148044e−02 |
| −6.28743842e−02 | −2.01071631e−02 | −5.56782745e−02 | 5.13832271e−03 |
| 5.07176965e−02 | 9.55580920e−02 | −8.15277267e−03 | 1.06385671e−01 |
| −7.30637312e−02 | −5.34940884e−02 | −1.59330200e−02 | 6.36813715e−02 |
| −4.23618481e−02 | 1.12749273e−01 | 1.10427558e−01 | 1.40558183e−03 |
| 2.15104930e−02 | −5.60213737e−02 | −1.02417536e−01 | 4.38066982e−02 |
| 9.61592644e−02 | −5.00241667e−02 | 7.49675557e−02 | 8.83785561e−02 |
| 7.62272179e−02 | 5.95414788e−02 | −4.84930240e−02 | 8.10408220e−03 |
| 6.01211842e−03 | −7.05197081e−02 | 7.96359554e−02 | −5.99661581e−02 |
| −9.02647153e−02 | −7.92417452e−02 | −7.69064762e−03 | 5.68202771e−02 |
| 1.40449554e−02 | 2.36277450e−02 | 8.46119598e−02 | 9.35463682e−02 |
| −6.96625113e−02 | 9.86901205e−03 | 5.30094355e−02 | −2.32620053e−02 |
| 8.03253520e−03 | 2.35821754e−02 | 6.03143685e−02 | 1.03784628e−01 |
| −4.56919633e−02 | −4.57943790e−02 | −3.31224613e−02 | 5.66034131e−02 |
| −6.38524219e−02 | 4.44083847e−02 | 7.05840811e−02 | −8.51929188e−02 |
| −3.69541533e−02 | 9.22822431e−02 | 9.44843590e−02 | −4.08904217e−02 |
| −2.50435043e−02 | 2.02877913e−03 | 7.51245692e−02 | −6.31650314e−02 |
| 8.04564357e−02 | −6.23011999e−02 | 9.83520970e−02 | −5.81054427e−02 |
| 6.64616451e−02 | 1.09575130e−01 | 9.43628773e−02 | 7.51023591e−02 |
| 3.41576152e−02 | −5.14946580e−02 | −6.71889335e−02 | 8.95964280e−02 |
| −9.80346873e−02 | 4.70938273e−02 | 8.94335210e−02 | −5.59377111e−03 |
| −9.60712805e−02 | −8.57297778e−02 | −2.85877474e−02 | 1.08797930e−01 |
| 7.57836699e−02 | −5.81425093e−02 | 1.02601983e−01 | 1.03316352e−01 |
| −1.05343916e−01 | −7.12740198e−02 | −1.74947706e−02 | −1.03293099e−02 |
| −5.25881201e−02 | −5.02343848e−02 | −9.81568247e−02 | 7.95774385e−02 |
| 1.02388643e−01 | −1.19815655e−01 | 7.41878971e−02 | −5.30164056e−02 |
| 4.73288372e−02 | −8.60049725e−02 | 9.13973060e−03 | −9.64845717e−02 |
| 1.67359207e−02 | −1.05495073e−01 | 1.02964096e−01 | 1.66283585e−02 |
| 1.04912937e−01 | 4.59013395e−02 | 2.08596289e−02 | 7.10290670e−02 |
| 1.10302411e−01 | 8.34540501e−02 | −4.80832569e−02 | 5.37692085e−02 |
| 5.36063462e−02 | −1.05386399e−01 | −2.48728041e−02 | 6.99574649e−02 |
| −3.32497470e−02 | −5.73511906e−02 | 4.11955118e−02 | −8.71521086e−02 |
| −9.42716449e−02 | −1.85862333e−02 | −6.02194900e−03 | −3.25041302e−02 |
| −4.33523059e−02 | −8.65584761e−02 | −1.34267136e−02 | −2.80945171e−02 |
| −4.06036265e−02 | 6.45181686e−02 | 1.38865570e−02 | 2.75131017e−02 |

TABLE $W_h^1$-continued

| | | | |
|---|---|---|---|
| −8.90368521e−02 | 4.49254699e−02 | −7.97148570e−02 | −1.09648250e−01 |
| −1.34794787e−02 | 1.59819098e−03 | −2.70373630e−03 | 8.99767354e−02 |
| 4.75746840e−02 | −8.98077637e−02 | 7.25987107e−02 | 2.90701352e−02 |
| −2.87823100e−02 | −1.63267776e−02 | −6.64914176e−02 | −5.36970608e−02 |
| 1.46717820e−02 | −7.32108057e−02 | −4.77346256e−02 | 5.35309277e−02 |
| 1.01403028e−01 | 5.53280823e−02 | 2.58712675e−02 | 3.78721394e−02 |
| −2.48837215e−03 | 7.25915432e−02 | 5.24923988e−02 | −7.48659819e−02 |
| −9.20101777e−02 | −3.71210054e−02 | −4.61314805e−02 | −2.72433776e−02 |
| 5.27954586e−02 | 3.76780406e−02 | 1.60561595e−02 | 1.04717091e−01 |
| −6.34250268e−02 | −8.52692276e−02 | 2.41909549e−02 | 9.23288241e−02 |
| −3.57545428e−02 | −1.69682689e−02 | −3.76720470e−03 | −1.08408444e−01 |
| −7.32821748e−02 | −4.24779244e−02 | 5.80067858e−02 | 6.88871294e−02 |
| 7.46498480e−02 | −1.40744438e−02 | −1.47072691e−03 | 7.68365785e−02 |
| −4.57776003e−02 | −5.65257370e−02 | −9.64634418e−02 | −3.27511393e−02 |
| 3.18154581e−02 | −4.16067690e−02 | −8.16478208e−02 | 1.98145788e−02 |
| 9.11007077e−02 | −1.05944976e−01 | −8.71466752e−03 | −9.28241834e−02 |
| −2.92776562e−02 | 4.87257121e−03 | 2.04197504e−02 | 4.12364639e−02 |
| 9.12615880e−02 | −4.15295921e−02 | −5.57773747e−02 | −7.04881325e−02 |
| −6.52840659e−02 | −4.42323126e−02 | −6.10983465e−03 | −1.06835976e−01 |
| −6.58759400e−02 | −9.29389298e−02 | −2.98228692e−02 | 3.30829099e−02 |
| 9.07765515e−03 | 6.65348470e−02 | 5.92934061e−03 | 8.69208500e−02 |
| 3.92726958e−02 | −9.36317518e−02 | −2.78358907e−02 | −8.59299600e−02 |
| −3.71195562e−02 | 5.04290424e−02 | 1.02928951e−01 | −1.05276577e−01 |
| −4.01229821e−02 | 4.21245359e−02 | −2.35327147e−02 | 3.77033278e−02 |
| −9.09047201e−02 | 5.81619255e−02 | 9.95997638e−02 | −3.29032168e−02 |
| 3.21683288e−02 | 2.93595716e−02 | 5.31154089e−02 | −7.30695873e−02 |
| −8.39696527e−02 | 8.53705183e−02 | 3.17655802e−02 | −1.33085586e−02] |
| [2.51169056e−01 | 1.44914344e−01 | −3.92662026e−02 | 2.20533516e−02 |
| −3.51149067e−02 | 9.33700874e−02 | 4.89786327e−01 | −1.01321951e−01 |
| 2.73955882e−01 | 1.68543801e−01 | 4.71141160e−01 | 1.81764945e−01 |
| 2.42331818e−01 | 3.44490647e−01 | −5.27544953e−02 | 1.65042982e−01 |
| 3.25983971e−01 | 4.09481339e−02 | 4.32677120e−02 | 2.90425420e−01 |
| 1.17261007e−01 | 2.81472728e−02 | −1.09773293e−01 | 3.23055208e−01 |
| 1.49925977e−01 | −2.23853752e−01 | 2.19190851e−01 | 3.04135174e−01 |
| 1.00895189e−01 | 2.41764233e−01 | 2.21364051e−02 | 1.55540481e−01 |
| 9.99487787e−02 | 1.95400342e−01 | 8.79012421e−02 | 1.15447424e−01 |
| 3.78486067e−01 | 3.03485811e−01 | 2.95895755e−01 | 1.11916006e−01 |
| 2.16357544e−01 | 1.14937052e−01 | −4.63055745e−02 | 2.19004974e−01 |
| 3.15475017e−01 | 2.44872168e−01 | 1.96748748e−02 | 2.94863880e−01 |
| 3.93770933e−01 | 2.60443151e−01 | 2.40140944e−04 | 8.74262750e−02 |
| −3.65773328e−02 | −2.52527833e−01 | 6.24303818e−02 | 1.52568594e−01 |
| 4.09024268e−01 | 2.29299679e−01 | 7.48678446e−02 | −2.06216499e−01 |
| −1.16489502e−02 | 2.69285977e−01 | 4.71612886e−02 | 2.17533465e−02 |
| 4.55211513e−02 | 5.76550663e−02 | 1.24445751e−01 | 3.95040005e−01 |
| 1.31113589e−01 | −1.95992395e−01 | 2.02950925e−01 | 4.30506021e−01 |
| 5.09353280e−01 | 1.00650355e−01 | −1.01020828e−01 | 8.68260264e−01 |
| 4.52501774e−01 | −2.11044252e−01 | 1.33538604e−01 | 7.03129321e−02 |
| −1.15997724e−01 | 3.50938598e−03 | 6.44481331e−02 | 1.37921855e−01 |
| 1.21766984e−01 | 1.13034524e−01 | −4.29870784e−02 | −2.84613930e−02 |
| 1.34119540e−01 | −1.12373099e−01 | 4.36384887e−01 | 2.23840371e−01 |
| 3.60309184e−01 | −7.38218576e−02 | 3.07163209e−01 | 2.05791101e−01 |
| 2.03101397e−01 | 6.82489350e−02 | −4.70197722e−02 | 3.70170712e−01 |
| 9.78175849e−02 | 4.94031250e−01 | 9.89066586e−02 | −4.93387252e−01 |
| 2.17239648e−01 | 1.18080325e−01 | 1.77680880e−01 | 2.71256298e−01 |
| 2.74756104e−02 | 6.44120157e−01 | 2.83609301e−01 | 2.24085793e−01 |
| 4.04705971e−01 | −1.35068083e−02 | 2.74986867e−02 | 3.99667859e−01 |
| 1.45573542e−01 | 2.14358419e−01 | 2.52524048e−01 | 3.72979611e−01 |
| 2.74853468e−01 | 1.30804209e−01 | −1.43844448e−03 | 2.84046143e−01 |
| 1.75390542e−01 | 2.57004023e−01 | −2.38566175e−02 | 2.67163157e−01 |
| 4.38241422e−01 | 1.95541814e−01 | 1.75160561e−02 | −2.02205062e−01 |
| 2.60031283e−01 | 1.34018973e−01 | 1.40434295e−01 | 2.76376516e−01 |
| 6.76910430e−02 | 3.46873701e−01 | 3.46419401e−02 | 4.49122608e−01 |
| 3.31582099e−01 | −1.14910662e−01 | −2.04842955e−02 | 2.74293065e−01 |
| 3.75342220e−01 | 3.37196022e−01 | 2.11385414e−01 | 2.40587667e−01 |
| −1.52176823e−02 | −4.09993939e−02 | 3.89237553e−01 | 9.88513231e−02 |
| 2.01940536e−01 | −2.15281054e−01 | −8.31177738e−03 | 2.81484008e−01 |
| −8.61835703e−02 | 2.41705272e−01 | −5.98558709e−02 | 3.63614410e−01 |
| 5.92488050e−02 | 1.37241647e−01 | 6.54159812e−03 | −4.12539616e−02 |
| 9.80469286e−02 | 2.57459432e−01 | 1.75413549e−01 | 3.76997381e−01 |
| 2.75352567e−01 | −1.72660202e−01 | 3.05715557e−02 | −3.46224084e−02 |
| 3.06546450e−01 | 1.85486808e−01 | 2.26724342e−01 | 9.94594917e−02 |
| 3.55405539e−01 | 4.49712843e−01 | 1.40399143e−01 | 5.44955721e−03 |
| −1.32484525e−01 | 1.70579612e−01 | 4.34324831e−01 | 1.53555527e−01 |
| 6.93785250e−01 | −9.70336571e−02 | 7.87856355e−02 | 2.12281421e−01 |
| 2.08074287e−01 | 4.81645107e−01 | 2.07619473e−01 | 3.33979070e−01 |
| 8.60332996e−02 | 3.10428113e−01 | 1.41614256e−02 | −1.88877627e−01 |
| 1.51384354e−01 | 1.16839238e−01 | 3.23480517e−02 | 3.85516584e−01 |
| 1.27328917e−01 | 2.92385459e−01 | 3.63412589e−01 | −4.95812632e−02 |
| −1.85151786e−01 | 1.73460424e−01 | 5.08625470e−02 | 2.32998252e−01 |
| 8.72124806e−02 | 9.74388942e−02 | 2.16674417e−01 | −1.82698637e−01 |

TABLE $W_h^1$-continued

| | | | |
|---|---|---|---|
| 2.06535921e−01 | 4.04411644e−01 | 6.69364855e−02 | 4.37857032e−01 |
| 3.70902389e−01 | 7.40699396e−02 | 5.16434759e−02 | 1.54717520e−01 |
| 2.50680804e−01 | −2.12550536e−02 | 1.74617678e−01 | 2.49713585e−01 |
| 3.01364064e−01 | 3.39281112e−01 | 5.77907264e−02 | 6.25878498e−02 |
| 2.48633936e−01 | 1.05066806e−01 | 8.23254287e−02 | 2.84075230e−01 |
| −1.05591767e−01 | 4.55332160e−01 | 7.19862878e−02 | −1.19173445e−01 |
| 2.68589377e−01 | 2.60573864e−01 | 1.50721699e−01 | 2.93337256e−01 |
| 2.23762229e−01 | 9.17985886e−02 | 8.36017877e−02 | 3.84765774e−01 |
| 3.60911697e−01 | 2.55095989e−01 | 2.19233483e−01 | 2.55029708e−01 |
| 3.00074637e−01 | 2.23822072e−01 | 1.33758575e−01 | 1.68077156e−01 |
| 1.80968702e−01 | 2.78000325e−01 | 5.31844318e−01 | 1.92052051e−01] |
| [−1.12626411e−01 | 1.07956553e−00 | 1.00082469e−00 | 5.71794927e−01 |
| 1.71215928e−01 | 5.48826218e−01 | 3.41214597e−01 | 9.10762370e−01 |
| 5.27917206e−01 | 9.93373513e−01 | 6.83710873e−01 | 1.51124227e−00 |
| 9.72317457e−01 | 5.67308784e−01 | 9.41403568e−01 | 1.42231691e−00 |
| 1.43334305e−00 | 1.41719833e−01 | 9.30866413e−03 | 2.57118404e−01 |
| 9.67110753e−01 | 2.54098624e−01 | 1.65140581e−01 | 1.54787481e−01 |
| 8.65905821e−01 | 1.55579543e−00 | −2.29254767e−01 | 8.72418523e−01 |
| 4.93214250e−01 | 1.87366456e−01 | 1.82091177e−01 | 6.02540135e−01 |
| 3.04399580e−01 | 3.77028376e−01 | 9.60637152e−01 | −2.38546506e−02 |
| −2.18893170e−01 | 3.06984127e−01 | 4.20625627e−01 | 7.14854479e−01 |
| 1.66760898e−01 | 1.36078882e−00 | 2.67791867e−01 | 9.93034542e−01 |
| 1.42382908e−00 | 3.66995305e−01 | 1.66789517e−01 | 1.04150558e−00 |
| 2.37449139e−01 | 6.29903972e−01 | 9.08127844e−01 | 7.67332733e−01 |
| 3.63924980e−01 | 1.01412284e−00 | 1.08082926e−00 | 4.51765031e−01 |
| 7.55749404e−01 | 1.86566055e−00 | 2.58031636e−01 | −1.05384059e−01 |
| 4.64208305e−01 | 5.81293583e−01 | 5.46631634e−01 | 3.95797789e−01 |
| 6.41269565e−01 | 9.55319822e−01 | 8.39152396e−01 | 8.44918668e−01 |
| 5.73809505e−01 | −5.36846697e−01 | 9.63882878e−02 | −1.92072257e−01 |
| 8.05351973e−01 | 3.43831718e−01 | 2.78154641e−01 | −3.51462960e−01 |
| 1.23473859e−00 | 3.86728913e−01 | 1.10820627e−00 | 1.40771326e−02 |
| 1.00755894e−00 | 3.49660814e−01 | 8.88496995e−01 | 1.03067255e−00 |
| 1.38992143e−00 | 2.00285137e−01 | 7.98915684e−01 | 6.24762952e−01 |
| 1.50097311e−00 | −5.73430717e−01 | 1.08825731e−00 | 2.85559356e−01 |
| 1.02897835e−00 | 1.47425210e−00 | 1.08342397e−00 | 3.31800789e−01 |
| 8.36280048e−01 | 3.79065156e−01 | −1.85206354e−01 | 1.13822460e−00 |
| 6.45911574e−01 | 8.28592062e−01 | 1.39876559e−01 | 4.66709703e−01 |
| −5.69024161e−01 | 4.19699997e−01 | 2.90287912e−01 | 1.27886474e−00 |
| 7.60420084e−01 | 1.28541434e−00 | 1.32964313e−01 | 7.49036610e−01 |
| 1.30273771e−00 | 1.21020186e−00 | 1.59023476e−00 | 4.16725785e−01 |
| 1.00220084e−00 | 4.66254801e−02 | 8.72136772e−01 | 5.65978810e−02 |
| 1.28768229e−00 | 9.11865473e−01 | −6.33308440e−02 | 5.43937087e−01 |
| 9.26433861e−01 | 4.17638004e−01 | 4.29677606e−01 | 1.19354939e−00 |
| 6.15272105e−01 | 6.68864548e−01 | 2.14314461e−01 | 3.97888809e−01 |
| 4.52434033e−01 | 7.43614495e−01 | 1.41531396e−00 | 8.30277860e−01 |
| 4.22863543e−01 | 9.34147894e−01 | 1.05197358e−00 | 1.26759076e−00 |
| 5.78297138e−01 | 4.16240618e−02 | 7.14323461e−01 | 7.29017138e−01 |
| 7.70552099e−01 | 7.33485699e−01 | −2.47078780e−02 | 7.24994242e−01 |
| 1.43605363e−00 | 1.05487669e−00 | 9.82844114e−01 | 6.85893297e−01 |
| 7.94114530e−01 | 4.54092324e−01 | 1.18260908e−00 | 8.14526618e−01 |
| 6.30581602e−02 | 3.52495641e−01 | 5.76413512e−01 | 6.76532269e−01 |
| 1.41489804e−00 | 1.03686678e−00 | 1.09626615e−00 | 8.08658302e−01 |
| 2.26143003e−01 | 3.41023147e−01 | 1.47640216e−00 | 2.48346105e−01 |
| 7.81956911e−01 | 1.14963567e−00 | −2.87771612e−00 | 1.59166586e−00 |
| 6.27382874e−01 | 1.52118731e−00 | 7.70335674e−01 | 3.26347888e−01 |
| 8.52991581e−01 | 5.56037903e−01 | 6.72730803e−01 | 5.18086016e−01 |
| 2.46318355e−01 | 1.10310304e−00 | 5.45692742e−01 | 3.54692161e−01 |
| 6.24409497e−01 | 2.88647771e−01 | −2.62000442e−01 | 7.26556718e−01 |
| 6.84232831e−01 | 4.17024970e−01 | 6.15497530e−01 | 1.11309254e−00 |
| 8.63065422e−01 | 3.43480676e−01 | 7.77894914e−01 | 1.26179516e−00 |
| 1.06680036e−00 | 1.22809136e−00 | 7.66867161e−01 | 3.41251075e−01 |
| 1.22419822e−00 | 5.49935639e−01 | 6.02155507e−01 | 1.26336962e−01 |
| 4.86136563e−02 | 7.50226259e−01 | 2.78443813e−01 | 8.73889863e−01 |
| 8.42499495e−01 | 6.73031390e−01 | 7.36829281e−01 | 9.83019114e−01 |
| 9.05483782e−01 | 4.94924963e−01 | 2.53934801e−01 | 1.42872870e−00 |
| 3.05926979e−01 | 7.96724498e−01 | 6.66386962e−01 | 6.99806884e−02 |
| 1.03139508e−00 | 2.88525969e−01 | 4.34567407e−02 | 4.20268714e−01 |
| 6.46028459e−01 | 3.39224517e−01 | 1.93745613e−01 | 1.05636632e−00 |
| 9.85225081e−01 | 6.29835367e−01 | 7.23137036e−02 | 8.47735703e−01 |
| 6.86614275e−01 | 1.69638291e−01 | 1.65439928e−00 | 1.55864012e−00 |
| 1.06038392e−00 | 8.85429621e−01 | 1.87563315e−00 | 6.83137655e−01 |
| 3.09387684e−01 | 1.43288600e−00 | 7.33327866e−01 | 4.66869622e−01 |
| 1.18537986e−00 | 1.31836092e−00 | 3.62724245e−01 | 2.63216466e−01 |
| 1.22661173e−00 | 1.68782815e−01 | 6.29855275e−01 | 8.95699084e−01 |
| 8.28314722e−01 | 7.75375783e−01 | 7.36645520e−01 | 6.64819539e−01] |
| [−1.22343831e−01 | 2.70842612e−01 | 2.22213008e−02 | −8.29295442e−01 |
| 1.66164026e−01 | −2.63156384e−01 | −2.17330649e−01 | −1.32933289e−01 |
| 4.82995287e−02 | 1.13994673e−01 | −3.34124714e−01 | 1.08216755e−01 |
| −1.27191514e−01 | −2.61652589e−01 | −4.64314640e−01 | 4.85027842e−02 |
| 4.97698747e−02 | −1.18662924e−01 | 5.25337234e−02 | −6.51145801e−02 |

TABLE $W_h^1$-continued

| | | | |
|---|---|---|---|
| −1.77806526e−01 | 1.96164802e−01 | 9.30351466e−02 | −3.01985174e−01 |
| 8.11472759e−02 | −2.39947751e−01 | −5.21146990e−02 | 3.11994366e−02 |
| −1.78277865e−01 | 8.06396008e−02 | −2.38364264e−01 | 7.59419873e−02 |
| −1.98353156e−01 | −4.62784052e−01 | 5.21476626e−01 | −7.12351575e−02 |
| 2.83014119e−01 | 1.25841185e−01 | 9.95567888e−02 | −2.80973613e−01 |
| −6.01760268e−01 | −4.71800119e−01 | −1.92259729e−01 | 4.08578396e−01 |
| −1.54629588e−01 | −3.09119016e−01 | −1.95380747e−01 | −2.32672751e−01 |
| −4.62588295e−03 | −3.95141810e−01 | 1.11480169e−01 | 1.95967760e−02 |
| −1.84303761e−01 | 1.10782817e−01 | 8.47811550e−02 | −8.72510523e−01 |
| −2.52816290e−01 | 2.64670372e−01 | −1.91457823e−01 | 1.30419835e−01 |
| −3.92151326e−02 | −1.57057449e−01 | −1.36557072e−01 | 1.63902521e−01 |
| −2.48039037e−01 | 2.44268104e−01 | 9.97040197e−02 | −1.51294589e−01 |
| −4.17811602e−01 | 1.63260773e−01 | 5.80973877e−03 | 2.66813815e−01 |
| −2.06302181e−01 | −4.90589499e−01 | −5.21659777e−02 | −1.66472793e−01 |
| −1.30965978e−01 | −5.59696183e−02 | −2.07964331e−02 | −4.89123948e−02 |
| −1.16816282e−01 | −3.33692878e−01 | 4.74732637e−01 | −1.01467758e−01 |
| 7.83202946e−02 | 2.44862303e−01 | 1.53551489e−01 | −4.03043330e−01 |
| −3.84351403e−01 | 7.56057277e−02 | −7.97882974e−02 | 1.93862990e−01 |
| 4.45121586e−01 | 3.63106579e−01 | −2.48565689e−01 | −1.67754367e−01 |
| 7.14155985e−03 | 2.23459989e−01 | 2.33597204e−01 | 3.69185627e−01 |
| 4.19897474e−01 | −2.56278783e−01 | 2.00375095e−01 | 1.61218300e−01 |
| 2.17658967e−01 | −1.17181219e−01 | −1.43041477e−01 | 1.26328334e−01 |
| −1.91252336e−01 | −6.71523362e−02 | −2.11573631e−01 | −5.89796789e−02 |
| 2.07022652e−01 | −2.59214938e−01 | −2.25884974e−01 | 6.11014187e−01 |
| 3.58009219e−01 | −3.96060832e−02 | −2.74135679e−01 | 1.16840415e−01 |
| −2.46644899e−01 | −3.38525385e−01 | −3.23566049e−02 | 9.03550908e−02 |
| 1.49841279e−01 | −3.68549526e−01 | −1.65912181e−01 | 6.39511347e−02 |
| −3.11064065e−01 | −3.88194501e−01 | 2.92870760e−01 | −2.94140399e−01 |
| −2.07173526e−01 | 1.09266721e−01 | 3.10509264e−01 | 1.66221365e−01 |
| 3.81971389e−01 | 4.36224014e−01 | −3.16098750e−01 | −5.23650110e−01 |
| −1.27985835e−01 | 3.50799114e−02 | 2.84528099e−02 | 6.77228048e−02 |
| 1.20249107e−01 | 3.13277721e−01 | −2.00053945e−01 | −1.12050384e−01 |
| 3.81045282e−01 | 1.30397409e−01 | 2.24351957e−01 | −1.22996554e−01 |
| 1.98348835e−01 | −4.71708626e−01 | −1.83831900e−01 | −3.58589999e−02 |
| −1.16583526e−01 | −3.11643422e−01 | −3.25292572e−02 | −1.02812663e−01 |
| 1.96286470e−01 | −4.41140570e−02 | 3.53941973e−03 | 2.46948332e−01 |
| 4.43661623e−02 | 6.34780675e−02 | 4.46546748e−02 | 2.41722569e−01 |
| −3.25239807e−01 | −2.05968574e−01 | 1.26446053e−01 | 1.16713360e−01 |
| 2.54477020e−02 | −1.60366476e−01 | 1.14052489e−01 | 9.75800082e−02 |
| −5.92523336e−01 | 9.86788124e−02 | −4.14885134e−01 | 4.07253385e−01 |
| −2.07237527e−01 | −2.12268546e−01 | −2.23911062e−01 | 6.07734807e−02 |
| −4.32513654e−02 | −4.02262807e−01 | −6.98495805e−02 | −3.98843676e−01 |
| 1.68978348e−02 | −4.82099414e−01 | −4.64063436e−01 | −2.14431062e−01 |
| −3.26153278e−01 | −5.34409545e−02 | −3.49211544e−01 | 1.13061599e−01 |
| 1.12030841e−01 | −1.33591881e−02 | 2.89344817e−01 | −1.84045047e−01 |
| 3.78540941e−02 | −4.03549112e−02 | −2.40577355e−01 | 2.01654196e−01 |
| −2.11577892e−01 | 2.00947091e−01 | −1.67721957e−01 | 4.15466040e−01 |
| 7.43554533e−02 | −2.69444346e−01 | 1.34161264e−02 | −8.24128687e−02 |
| 1.88509136e−01 | 2.69276291e−01 | −2.18639344e−01 | −1.50696278e−01 |
| 2.32576355e−01 | 5.72797097e−02 | −1.25742421e−01 | −8.16799551e−02 |
| 3.66530418e−01 | 3.16267014e−02 | −3.05635273e−01 | −6.37498051e−02 |
| −5.06272256e−01 | 5.84792383e−02 | −1.50359496e−01 | 2.52935410e−01 |
| −2.60168612e−01 | 2.04773769e−01 | −2.65436441e−01 | −2.39323750e−01 |
| 1.47588030e−01 | −1.81692392e−01 | 1.80380587e−01 | 4.23272923e−02 |
| 1.53426662e−01 | 1.37949154e−01 | −5.24950624e−02 | −1.75586969e−01 |
| −8.88204947e−02 | −9.95008722e−02 | −4.84583646e−01 | 1.10435598e−01 |
| −3.50596547e−01 | 2.68107712e−01 | 3.38505745e−01 | 2.56082136e−03 |
| −4.92902040e−01 | 5.28510883e−02 | 1.59316465e−01 | −1.49805486e−01 |
| −1.29125699e−01 | −2.44222566e−01 | 2.52211175e−04 | 1.34892851e−01] |
| [2.91690361e−02 | 1.90033957e−01 | −1.22436047e−01 | −7.06864148e−03 |
| 1.49768502e−01 | 7.11202919e−02 | −1.93383276e−01 | 1.48966551e−01 |
| 5.46238432e−03 | 3.99637222e−02 | −8.52554105e−03 | −2.35295013e−01 |
| 7.77817294e−02 | 2.59071887e−01 | −2.25495607e−01 | −8.98491889e−02 |
| −3.93311121e−02 | −2.74802059e−01 | 2.75588185e−01 | −4.60756868e−02 |
| 2.13409603e−01 | 3.28381062e−02 | 5.33348501e−01 | −4.26868230e−01 |
| 1.13451205e−01 | −1.76863506e−01 | 6.99211136e−02 | 4.88675497e−02 |
| 6.41925335e−02 | 7.47099444e−02 | −1.26010984e−01 | −1.97224580e−01 |
| 1.31013513e−01 | −1.56947225e−01 | 3.84578794e−01 | −8.48912448e−02 |
| −2.16032326e−01 | −3.23993862e−01 | −3.15708727e−01 | −1.32138997e−01 |
| −1.76646393e−02 | −2.05106005e−01 | 1.55189615e−02 | 3.39502275e−01 |
| −3.07333022e−01 | −9.59608182e−02 | −1.30017221e−01 | 6.42572939e−02 |
| −1.56538591e−01 | 3.28405738e−01 | −7.38254040e−02 | 2.92267948e−01 |
| 1.25045419e−01 | 9.94597971e−02 | −1.31092131e−01 | −9.68275517e−02 |
| −1.59537673e−01 | 2.78199881e−01 | 5.55882044e−02 | 2.41921529e−01 |
| −5.38816229e−02 | 9.95760411e−02 | −1.48514763e−01 | 4.03033476e−03 |
| 1.91563696e−01 | 1.76380917e−01 | 2.20445499e−01 | 1.87838320e−01 |
| −3.92906703e−02 | 3.26226175e−01 | 1.47817448e−01 | 9.88392532e−02 |
| 3.05653036e−01 | −3.72403413e−01 | −2.25081369e−01 | −2.24742025e−01 |
| 1.33779095e−02 | 2.15137191e−02 | −6.30426034e−02 | −9.72699448e−02 |
| −2.33870521e−01 | −5.98602579e−04 | 3.79304081e−01 | −3.47122401e−02 |

TABLE $W_h^1$-continued

| | | | |
|---|---|---|---|
| 3.28624062e−02 | 2.05374975e−02 | −2.25006677e−02 | −9.89477634e−02 |
| −1.56412542e−01 | 7.08431005e−02 | −7.60603026e−02 | 8.85371789e−02 |
| 3.23710382e−01 | 5.40479347e−02 | 4.23248447e−02 | −1.54124483e−01 |
| −3.34376067e−01 | −7.19710290e−02 | 8.66363347e−02 | 9.41111818e−02 |
| 1.60054356e−01 | −1.14443980e−01 | 2.76652157e−01 | 3.25165153e−01 |
| 5.23939021e−02 | 1.80439651e−01 | 1.32718444e−01 | 2.29725942e−01 |
| −2.05319881e−01 | 2.90014297e−01 | −1.56730544e−02 | 5.10493703e−02 |
| 2.18745485e−01 | −1.69600010e−01 | 6.19673356e−02 | 4.06786442e−01 |
| 1.79717183e−01 | 1.56883113e−02 | −2.75811642e−01 | −1.17943786e−01 |
| −5.50316535e−02 | −3.15933019e−01 | −2.21597329e−02 | −1.06831186e−01 |
| −7.67908320e−02 | −1.80702522e−01 | 1.01698101e−01 | −8.56315866e−02 |
| −9.96760949e−02 | −2.15045542e−01 | 2.44856939e−01 | 8.27473123e−03 |
| 9.72533897e−02 | 1.71886310e−02 | −2.72306260e−01 | 1.48723736e−01 |
| −1.51759442e−02 | 2.84756035e−01 | 6.69693947e−02 | 8.08445141e−02 |
| −2.43071243e−01 | 1.12391703e−01 | 1.48854926e−01 | −1.29539847e−01 |
| 1.48490295e−01 | 3.11105847e−01 | −1.30899608e−01 | −4.49712306e−01 |
| −2.76124608e−02 | 7.86761940e−02 | 3.03735882e−01 | −6.04090057e−02 |
| 1.36565089e−01 | −9.29275081e−02 | 4.99361083e−02 | 2.91777104e−01 |
| −1.98649019e−01 | −1.49971411e−01 | 2.36314833e−01 | 4.27720845e−02 |
| 3.52242798e−01 | 2.06057221e−01 | 1.67026475e−01 | 3.56054664e−01 |
| 3.52969259e−01 | 1.53528064e−01 | 1.38700843e−01 | 1.10154457e−01 |
| 6.78737015e−02 | 3.28080952e−02 | 4.74442318e−02 | 6.02034619e−03 |
| −7.47550875e−02 | −5.56570925e−02 | 3.86863798e−01 | −1.55282333e−01 |
| −4.20190662e−01 | −3.97068597e−02 | 3.07842493e−01 | 4.66032773e−01 |
| −7.57951513e−02 | 9.57830809e−04 | −3.22093144e−02 | 1.95958853e−01 |
| 2.32419670e−01 | −1.11335739e−01 | −2.26017952e−01 | −1.68921083e−01 |
| 2.00149611e−01 | −3.77491504e−01 | 5.04659750e−02 | 7.67277703e−02 |
| −1.18641317e−01 | 1.42565668e−01 | −2.06311539e−01 | 4.26987447e−02 |
| 2.80272812e−01 | 7.67924413e−02 | 2.44974345e−01 | −1.47073671e−01 |
| −7.34438598e−02 | −9.93954018e−02 | −3.79520088e−01 | 8.72773454e−02 |
| −1.06556959e−01 | 3.51903766e−01 | −4.24714945e−02 | 4.61274296e−01 |
| 1.98356137e−01 | −1.28533775e−02 | −2.88410988e−02 | −1.44085884e−01 |
| 1.95169970e−01 | 1.79120138e−01 | −8.35601520e−03 | −2.13184163e−01 |
| 1.12712175e−01 | −4.68750633e−02 | −6.62500188e−02 | 2.04652250e−01 |
| 2.48797923e−01 | 1.92757010e−01 | −2.92929681e−03 | 5.76690473e−02 |
| −2.30375946e−01 | 5.86177781e−03 | 1.25177637e−01 | −9.52387676e−02 |
| −6.95787519e−02 | −1.69620477e−02 | 4.17864919e−02 | 7.54497945e−02 |
| −7.62524754e−02 | 3.60057093e−02 | 1.78083688e−01 | −3.62808198e−01 |
| 2.03212440e−01 | −2.54832685e−01 | −1.22921541e−01 | −1.40554205e−01 |
| 2.18676552e−01 | −7.31238723e−02 | −4.21951324e−01 | −3.95347774e−02 |
| −1.07953861e−01 | 3.79849821e−01 | 3.56247723e−01 | −1.08117171e−01 |
| −2.22819835e−01 | 8.19380358e−02 | 2.99203098e−01 | 5.51683046e−02 |
| −1.58516511e−01 | −1.01558134e−01 | 2.73892134e−01 | −2.33823098e−02] |
| [2.59423524e−01 | −6.36175647e−03 | 4.35690403e−01 | 5.07866144e−01 |
| 2.63448078e−02 | 7.00941205e−01 | 5.06376088e−01 | 2.14282081e−01 |
| 8.28402579e−02 | 3.52992982e−01 | 5.94339013e−01 | 5.58021665e−01 |
| 1.47151381e−01 | 3.73902529e−01 | 2.09258035e−01 | 2.85729617e−01 |
| 4.19058263e−01 | 2.20320791e−01 | 2.48706684e−01 | 2.48658746e−01 |
| 6.03589058e−01 | 4.40651208e−01 | 4.60949302e−01 | 2.93979377e−01 |
| 5.80674291e−01 | 7.86255181e−01 | 1.92630351e−01 | 8.12084451e−01 |
| −9.94642451e−02 | 4.50677872e−01 | 5.25184348e−02 | 4.33745444e−01 |
| 1.31042421e−01 | −7.70370662e−02 | 1.16506308e−01 | 2.10543185e−01 |
| 1.18210927e−01 | 1.72906533e−01 | 2.47767344e−01 | 6.51824117e−01 |
| 8.44021663e−02 | 3.18200618e−01 | 2.18442410e−01 | 4.32328396e−01 |
| 5.58694541e−01 | 1.17705248e−01 | 2.24872410e−01 | 3.69564086e−01 |
| −7.68946018e−03 | 1.48303464e−01 | 1.07826918e−01 | 2.63208836e−01 |
| −6.91815913e−02 | 2.27232724e−01 | 1.83337599e−01 | 2.99506396e−01 |
| 2.70817220e−01 | 3.35976452e−01 | 3.35626841e−01 | 9.50467363e−02 |
| 1.03088766e−01 | 4.51947242e−01 | 2.38798141e−01 | 8.48178342e−02 |
| 2.56513178e−01 | 3.83338273e−01 | −8.47543702e−02 | 3.83731961e−01 |
| 3.37651640e−01 | 1.04596019e−01 | 4.87473994e−01 | 9.61343721e−02 |
| 4.17918921e−01 | 4.65569019e−01 | 2.95458972e−01 | 4.19988436e−01 |
| 5.88707626e−01 | 2.74771988e−01 | 3.69739860e−01 | 1.89686760e−01 |
| −4.99461219e−02 | 4.01868314e−01 | −5.17244376e−02 | 4.10347641e−01 |
| 1.02984242e−01 | −4.05939996e−01 | 5.33188060e−02 | −9.80819296e−03 |
| 3.31848949e−01 | −1.27487153e−01 | 1.05203547e−01 | 3.26613396e−01 |
| −3.90052944e−01 | −2.16352463e−01 | 1.30692884e−01 | 2.92774737e−01 |
| 1.24015041e−01 | 1.82005718e−01 | 3.67962301e−01 | 5.46473190e−02 |
| 3.27475756e−01 | 5.22890747e−01 | 2.26016954e−01 | −2.00638235e−01 |
| 8.60708281e−02 | −2.88138449e−01 | 4.67113078e−01 | 3.47426206e−01 |
| 2.74201363e−01 | 9.53209922e−02 | 1.82916373e−01 | 2.18410701e−01 |
| 4.65510190e−01 | −2.25613102e−01 | 7.05327034e−01 | −7.40930289e−02 |
| 2.38640949e−01 | 1.15499482e−01 | 4.57284987e−01 | 6.09387159e−01 |
| 4.66794640e−01 | 2.69056380e−01 | 6.43490791e−01 | 6.68641776e−02 |
| 5.85907400e−01 | 7.43060172e−01 | 1.56970426e−01 | 2.61357818e−01 |
| 2.03824550e−01 | −1.59808192e−02 | 4.33520436e−01 | 3.05973500e−01 |
| 5.68083167e−01 | 1.81941807e−01 | 4.14317250e−01 | 7.95300156e−02 |
| 4.16851431e−01 | 2.91415602e−01 | 1.73933506e−01 | 3.53159904e−01 |
| 6.89656809e−02 | 4.87345457e−01 | 2.71271914e−01 | 1.77423269e−01 |
| 4.10212636e−01 | 2.35105857e−01 | 2.95027822e−01 | 6.08419664e−02 |

TABLE $W_h^1$-continued

| | | | |
|---|---|---|---|
| 3.62997472e−01 | 6.89362884e−01 | 1.28850326e−01 | 4.81244057e−01 |
| 2.48919025e−01 | 3.33049238e−01 | 2.69374609e−01 | 2.46049970e−01 |
| 1.65320292e−01 | 5.47640681e−01 | 4.63019550e−01 | 2.75780439e−01 |
| −6.52187541e−02 | 3.90921712e−01 | −4.34750579e−02 | 2.97973990e−01 |
| 3.51508528e−01 | 1.03915848e−01 | −1.09315552e−01 | 2.68000454e−01 |
| 4.45868313e−01 | −1.50105149e−01 | 2.48326659e−01 | 6.47578299e−01 |
| 4.31598216e−01 | 1.36423409e−01 | −1.46929502e−01 | 4.92073804e−01 |
| 7.38516524e−01 | 3.86292666e−01 | −7.29478821e−01 | −6.00098334e−02 |
| 6.92558941e−03 | 5.94775081e−01 | 8.69353190e−02 | −2.56650478e−01 |
| 1.72838777e−01 | 1.29187047e−01 | 2.93838710e−01 | 2.22595349e−01 |
| 2.07528457e−01 | 3.32105011e−01 | 4.27799463e−01 | 3.94485116e−01 |
| 2.73258656e−01 | 3.57395083e−01 | 2.30346367e−01 | 2.47957915e−01 |
| 7.30027109e−02 | 2.18270555e−01 | 4.76381451e−01 | 2.21120313e−01 |
| 1.29948229e−01 | −5.00590354e−02 | 3.06044996e−01 | −1.55476714e−02 |
| 2.48623863e−01 | 3.53499591e−01 | 4.11676094e−02 | 4.76023585e−01 |
| 3.76568884e−01 | 1.50164306e−01 | 4.32226926e−01 | 8.80548265e−03 |
| −1.63467322e−01 | 7.14866161e−01 | 1.33881405e−01 | 4.48293358e−01 |
| 6.33991539e−01 | 3.30930203e−01 | 7.75330484e−01 | 4.79179084e−01 |
| 6.42259195e−02 | −6.92504048e−02 | −2.92896211e−01 | 1.23680659e−01 |
| 6.47642434e−01 | 5.12417853e−01 | 4.83018577e−01 | 3.77787739e−01 |
| 1.17852800e−01 | 4.24965173e−01 | 4.08710450e−01 | 3.96228969e−01 |
| 5.18903792e−01 | −4.32408124e−01 | 3.13747913e−01 | 6.96969867e−01 |
| 7.58260489e−02 | 1.15970179e−01 | 5.08308589e−01 | 4.22123671e−01 |
| 3.71212274e−01 | 8.03660631e−01 | 2.24030584e−01 | 8.01793098e−01 |
| 5.18539786e−01 | 3.48171413e−01 | 2.07917944e−01 | 1.19357444e−01 |
| 9.98811126e−01 | 5.06760895e−01 | 1.46094769e−01 | 5.30288875e−01 |
| 2.60268390e−01 | 7.40050972e−01 | 1.43772274e−01 | 5.39296985e−01] |
| [1.20581537e−01 | 6.20315298e−02 | 5.35709202e−01 | −1.65839970e−01 |
| 1.90036938e−01 | −1.14322975e−01 | −1.79097176e−01 | −2.71107614e−01 |
| 1.05043977e−01 | 7.60851055e−02 | −3.80915478e−02 | 3.08197588e−01 |
| 2.69394964e−01 | 4.25906330e−02 | 8.17754865e−02 | 1.21325925e−01 |
| 1.58922642e−01 | 1.73181057e−01 | 3.65862772e−02 | 4.41746674e−02 |
| 1.02448985e−01 | −3.04583222e−01 | 2.47158900e−01 | −1.03057779e−01 |
| 2.62214318e−02 | −2.65460163e−01 | 2.99419343e−01 | 4.72376496e−01 |
| −2.04160362e−02 | 2.38413617e−01 | 6.76559284e−02 | −3.54434162e−01 |
| −6.37537464e−02 | 2.54742831e−01 | 7.24664032e−02 | 1.03142902e−01 |
| −2.15691626e−01 | 2.92430431e−01 | 1.43527403e−01 | 2.30719537e−01 |
| −7.38597065e−02 | −1.03281930e−01 | 3.22429426e−01 | −1.26153603e−01 |
| −1.75828904e−01 | 6.89849555e−02 | 9.35070366e−02 | −1.92359880e−01 |
| −5.19143068e−04 | 4.72794883e−02 | 8.42377394e−02 | −2.70250529e−01 |
| 4.93895650e−01 | −1.49618823e−03 | 1.13817066e−01 | 2.36527845e−01 |
| −2.19006941e−01 | 2.23532781e−01 | −3.17710161e−01 | 2.23344818e−01 |
| −9.59337801e−02 | 3.47509116e−01 | 2.01291293e−01 | 2.62470961e−01 |
| 1.25248596e−01 | 3.44324589e−01 | 1.35899797e−01 | 3.16299170e−01 |
| 1.95935413e−01 | 2.64882833e−01 | −7.01582525e−03 | 9.02441293e−02 |
| 8.29808488e−02 | −9.20906477e−03 | −3.80525917e−01 | −5.36051169e−02 |
| 8.49809274e−02 | −4.64903377e−02 | 1.73730077e−03 | 3.12831136e−04 |
| −1.46676034e−01 | 1.59416974e−01 | −3.71406227e−02 | −1.78911835e−01 |
| 3.19268405e−01 | −1.91163540e−01 | 1.76414549e−01 | 3.17528307e−01 |
| −3.93223129e−02 | 2.95006543e−01 | 8.68277624e−02 | 3.88326555e−01 |
| 2.07812220e−01 | 5.14785409e−01 | 1.00159854e−01 | 5.46425134e−02 |
| −1.98628053e−01 | −4.65506986e−02 | −3.43447998e−02 | 2.30942518e−01 |
| 3.59525025e−01 | 1.98765725e−01 | −9.76077765e−02 | 2.80393839e−01 |
| 3.98494363e−01 | 9.83233843e−01 | −9.12277475e−02 | 1.97999969e−01 |
| 1.40982687e−01 | −1.58273149e−02 | 7.76961446e−02 | 1.03927061e−01 |
| 7.25637376e−02 | −3.25982660e−01 | 3.82809401e−01 | 7.96811134e−02 |
| 4.86071557e−02 | −4.91925552e−02 | −1.68662369e−01 | 1.96828812e−01 |
| −2.54882835e−02 | −3.93691994e−02 | −5.83029427e−02 | 1.47400692e−01 |
| −1.27396137e−01 | −1.14039071e−01 | −1.27170002e−02 | 9.24870074e−02 |
| −1.33210048e−01 | 3.08653563e−01 | 2.32269466e−01 | −1.02178432e−01 |
| −2.44483110e−02 | 3.61623198e−01 | 1.16959617e−01 | 9.43331886e−03 |
| 5.63105702e−01 | 4.14365053e−01 | −4.81033549e−02 | −8.82137343e−02 |
| −3.15077193e−02 | 2.60439366e−01 | 9.80390310e−02 | −1.67385504e−01 |
| 2.22007319e−01 | 2.64190227e−01 | −1.64892405e−01 | 5.41784823e−01 |
| 4.67134088e−01 | 2.03116566e−01 | 4.06746119e−01 | 4.84132990e−02 |
| −4.61185575e−02 | 1.40043721e−01 | 1.84241682e−01 | 2.06628725e−01 |
| 1.78537983e−01 | −3.07420522e−01 | 1.61542624e−01 | 3.65715809e−01 |
| 5.22361621e−02 | 2.71985773e−02 | −1.57394838e−02 | −1.56808674e−01 |
| −1.37308329e−01 | 1.72109649e−01 | −2.42693108e−02 | 6.31245524e−02 |
| 1.63469821e−01 | −9.82047021e−02 | 6.06917636e−03 | 2.08505332e−01 |
| −1.08227693e−02 | 2.56210953e−01 | 1.98261455e−01 | −1.21300310e−01 |
| −3.44146565e−02 | −1.81517512e−01 | 1.13841414e−01 | 2.38914490e−01 |
| −1.21282987e−01 | 1.60285845e−01 | 2.92377949e−01 | 1.22091636e−01 |
| 6.87834248e−02 | −2.83789694e−01 | 2.67864078e−01 | −1.07214386e−02 |
| 3.49333584e−01 | 2.11749956e−01 | 1.37860224e−01 | 1.68934047e−01 |
| −4.30013202e−02 | −1.02305703e−01 | −1.71728030e−01 | −2.84505486e−01 |
| 8.88043270e−02 | −2.38435082e−02 | 1.76609322e−01 | −3.43474954e−01 |
| 3.46953943e−02 | −8.16991832e−03 | −5.32881208e−02 | −3.45683843e−02 |
| −1.13631606e−01 | 1.25333413e−01 | 1.52891189e−01 | 2.20090136e−01 |
| −2.10878775e−01 | 1.98152155e−01 | −2.60847830e−03 | −2.17591181e−01 |

TABLE $W_h^1$-continued

| | | | |
|---|---|---|---|
| 9.06250179e-02 | 3.24357837e-01 | 1.21815927e-01 | -1.75635144e-01 |
| 1.66539326e-01 | 3.89549464e-01 | -4.03461546e-01 | 7.82945827e-02 |
| 1.40620336e-01 | 3.58087495e-02 | -2.86106598e-02 | -9.31188315e-02 |
| 7.36268312e-02 | -5.67817800e-02 | 2.05981806e-01 | -3.74600105e-02 |
| 4.92987573e-01 | 2.87792295e-01 | 4.91226204e-02 | 2.03891635e-01 |
| -1.09175771e-01 | -1.84688762e-01 | -4.86124046e-02 | -1.98167145e-01 |
| -6.76619029e-03 | -2.53624022e-01 | 8.85850936e-02 | 2.69762754e-01 |
| 1.81643069e-01 | 1.80407062e-01 | 2.37733468e-01 | -1.76076382e-01 |
| -1.25904337e-01 | -1.88198977e-03 | -1.81675002e-01 | -1.62619710e-01 |
| -4.63275574e-02 | 6.70531243e-02 | 8.96927621e-03 | -1.19331583e-01 |
| -1.08083159e-01 | -2.91738771e-02 | -2.12110393e-02 | 1.09798752e-01] |
| [1.10060722e-01 | 1.52397156e-02 | 7.81173408e-01 | 1.10050403e-01 |
| 1.29890725e-01 | 4.74078029e-01 | -6.44227415e-01 | 2.63712436e-01 |
| 1.12568982e-01 | -1.06865302e-01 | 1.56660348e-01 | 4.02189404e-01 |
| 1.38317347e-02 | 9.21421275e-02 | -3.64059448e-01 | 8.46040845e-02 |
| -5.53131364e-02 | 1.81985527e-01 | -4.40661877e-01 | 7.56534159e-01 |
| 2.03093126e-01 | 5.87915182e-01 | 1.61995478e-01 | 8.61131847e-01 |
| 2.10547984e-01 | 5.11720598e-01 | 3.23430359e-01 | 5.05170643e-01 |
| 5.33008836e-02 | -7.07776546e-02 | 1.27634019e-01 | 7.93445557e-02 |
| 4.63130563e-01 | 7.65296280e-01 | 2.36470222e-01 | 1.82717666e-01 |
| 7.00779557e-01 | 2.51525998e-01 | 5.87079465e-01 | 2.87717104e-01 |
| 1.67374372e-01 | 3.89523864e-01 | 3.89657021e-01 | 5.16896248e-01 |
| 4.65290993e-01 | 4.89985108e-01 | 4.51720893e-01 | 1.74371526e-01 |
| 1.75165355e-01 | 1.84950471e-01 | 1.24003902e-01 | 4.45305437e-01 |
| -1.68875954e-03 | 9.66997445e-02 | 2.10343659e-01 | 2.48407334e-01 |
| 3.06682259e-01 | -4.34963517e-02 | 6.51780486e-01 | -6.45996770e-03 |
| 4.96176407e-02 | 6.92631662e-01 | 7.10948408e-01 | 5.28041162e-02 |
| 3.02232504e-01 | 5.43330014e-01 | 3.09978217e-01 | -3.22813727e-02 |
| 2.11747184e-01 | 1.51150927e-01 | 5.49410820e-01 | 6.77301064e-02 |
| 9.80690047e-02 | 8.27288702e-02 | 4.30203438e-01 | -2.41146579e-01 |
| 5.13971567e-01 | 2.97673523e-01 | 7.48236001e-01 | -1.12699941e-01 |
| 4.36921299e-01 | 3.49147826e-01 | 3.02453279e-01 | 3.85469168e-01 |
| 2.04202637e-01 | 6.12732649e-01 | -1.10572293e-01 | 6.53336406e-01 |
| 3.71797115e-01 | 3.01278383e-01 | 2.76593149e-01 | 2.69416690e-01 |
| 6.36680067e-01 | 3.60833615e-01 | -1.63337275e-01 | 6.41720891e-01 |
| 1.40698701e-01 | 6.53627664e-02 | 3.71247977e-01 | 9.93576199e-02 |
| 4.18334246e-01 | 5.63594162e-01 | 1.51733324e-01 | 2.56982595e-01 |
| 2.81767100e-01 | 5.46858668e-01 | 1.56481669e-03 | 2.67111242e-01 |
| 5.42231381e-01 | 4.88406658e-01 | 5.50174117e-01 | 2.05638140e-01 |
| 7.04182506e-01 | 5.25528908e-01 | 2.45506406e-01 | 2.23171362e-03 |
| 6.18771017e-01 | -2.59410199e-02 | 4.24529403e-01 | 2.67161041e-01 |
| 2.81008989e-01 | 3.34884822e-01 | 2.39116073e-01 | 1.87688798e-01 |
| 1.96732283e-02 | 1.46550462e-02 | 7.58775771e-01 | 4.89607781e-01 |
| 4.07423228e-01 | 4.21057343e-01 | 5.67772938e-03 | 5.68966269e-01 |
| 8.93101618e-02 | 2.95989364e-01 | 4.44167852e-01 | -1.67078361e-01 |
| 2.24205986e-01 | 2.00839445e-01 | 4.50542420e-01 | 4.53862518e-01 |
| 6.69284537e-02 | 2.69767851e-01 | 1.02017097e-01 | 8.10678601e-02 |
| -2.93210186e-02 | 1.69818655e-01 | 3.11050892e-01 | 4.63826716e-01 |
| 2.16650471e-01 | 4.92777348e-01 | 6.37986243e-01 | -1.92037299e-01 |
| 5.33961535e-01 | 6.65333927e-01 | 1.90205872e-01 | 2.26495862e-01 |
| -7.97483549e-02 | 2.49245614e-01 | -1.86886191e-02 | -2.54896849e-01 |
| 5.06580584e-02 | 7.45539188e-01 | 1.81894466e-01 | 2.20507085e-01 |
| 3.68487298e-01 | 3.69796246e-01 | 5.24716675e-01 | 1.28466278e-01 |
| -3.73222046e-01 | 4.15477186e-01 | 1.42935142e-01 | 6.64883554e-01 |
| 6.99240088e-01 | 3.61531824e-01 | 1.70270026e-01 | -7.53126070e-02 |
| 4.42410260e-01 | 5.54229498e-01 | 3.10710281e-01 | 3.00000787e-01 |
| 2.34753937e-01 | 2.27948412e-01 | 5.99815428e-01 | 7.04211175e-01 |
| 2.85472661e-01 | 4.49339509e-01 | 3.70169252e-01 | 2.03417242e-01 |
| -1.97173655e-02 | -5.93514182e-02 | 2.63394684e-01 | 7.83840656e-01 |
| 3.31851155e-01 | 4.51216221e-01 | 2.62874007e-01 | 5.25662661e-01 |
| 2.94784069e-01 | 4.88034189e-01 | 5.88207245e-01 | 3.46564382e-01 |
| 3.96572977e-01 | 1.93633810e-01 | 4.34675187e-01 | 2.85890698e-01 |
| -1.13466367e-01 | 3.40732872e-01 | 6.48730695e-01 | 6.34903684e-02 |
| 2.06047863e-01 | -1.16750352e-01 | 4.86622840e-01 | 1.88965857e-01 |
| 5.29825807e-01 | 5.91559470e-01 | -8.08036793e-03 | -4.04588296e-04 |
| -4.36201319e-02 | 1.96995810e-01 | 2.09972337e-02 | 5.55818975e-02 |
| 2.57809877e-01 | 7.83280015e-01 | 3.00053269e-01 | 1.36445299e-01 |
| -5.21372072e-02 | 3.73342335e-01 | 4.74065900e-01 | 5.72276950e-01 |
| 3.78912449e-01 | 7.12346613e-01 | 4.52219367e-01 | 3.39116335e-01 |
| 3.07491392e-01 | 3.43810320e-01 | 6.01896942e-01 | 9.24762264e-02 |
| 3.64574522e-01 | 3.77394170e-01 | -1.76078409e-01 | 3.36982399e-01 |
| -7.33389705e-02 | 3.25700492e-02 | 2.97392547e-01 | 5.76107740e-01 |
| 4.85411435e-01 | 3.90384078e-01 | 5.02141416e-01 | -9.71271917e-02 |
| 2.12766364e-01 | 6.87255383e-01 | 2.22265020e-01 | 2.42232934e-01 |
| -2.06431419e-01 | 8.38174045e-01 | 1.96050644e-01 | 5.58571052e-03] |
| [-3.81850630e-01 | -1.56358385e-03 | 8.82875826e-03 | -2.57505804e-01 |
| 3.66292000e-01 | 5.39036155e-01 | 3.42091948e-01 | 4.68452603e-01 |
| 4.17626381e-01 | 2.81114310e-01 | 8.40371609e-01 | 1.41237289e-01 |
| 1.40114024e-01 | 3.30954075e-01 | 2.24249050e-01 | 1.87394619e-01 |
| 3.40809852e-01 | -4.11541983e-02 | 3.22407514e-01 | -2.95236617e-01 |

TABLE $W_h^1$-continued

| | | | |
|---|---|---|---|
| 5.13208747e-01 | 7.76333988e-01 | 5.18425591e-02 | 3.50231677e-01 |
| 4.49957311e-01 | 7.53257453e-01 | -9.20075029e-02 | -1.03134282e-01 |
| 4.31374609e-01 | 1.55356005e-01 | 2.76716501e-01 | 2.76572794e-01 |
| 1.53524175e-01 | -2.57358840e-03 | 1.57235846e-01 | 1.84374541e-01 |
| -5.98835461e-02 | 2.52447724e-01 | 2.27096185e-01 | 5.42157292e-01 |
| 4.28045094e-02 | 5.11489034e-01 | 3.97179693e-01 | 5.84906042e-02 |
| 9.07841325e-01 | 4.35514115e-02 | 4.23657686e-01 | 6.75349236e-01 |
| -2.98591197e-01 | 3.65627557e-01 | 1.45583034e-01 | 1.51710093e-01 |
| 2.76572138e-01 | 6.23509176e-02 | 2.57528424e-01 | 1.72952250e-01 |
| 9.03114200e-01 | 1.21238872e-01 | 4.41465944e-01 | 1.75540537e-01 |
| 5.61325401e-02 | 1.37235880e-01 | 2.45005712e-01 | 3.91452983e-02 |
| 3.50251496e-01 | -1.68074340e-01 | 3.53458710e-02 | 4.23485488e-01 |
| 8.03930610e-02 | 3.83234739e-01 | 6.91881061e-01 | 7.09499493e-02 |
| 6.87804163e-01 | 4.46389705e-01 | 4.69658136e-01 | 6.39290094e-01 |
| 1.66826352e-01 | 3.42847615e-01 | 3.30848157e-01 | 3.86266083e-01 |
| -4.69633415e-02 | 6.04036391e-01 | 2.62680370e-02 | -1.43092811e-01 |
| 7.01291785e-02 | 1.41195759e-01 | 2.14363515e-01 | 1.49701061e-01 |
| 2.26673827e-01 | 1.14084139e-01 | 9.92214680e-02 | -2.00518996e-01 |
| -1.36769973e-02 | -1.62429735e-01 | 4.27145630e-01 | 2.89982438e-01 |
| -1.68900862e-01 | 2.10357010e-01 | -1.94912627e-02 | -1.05071545e-01 |
| 1.15178041e-01 | 4.46513504e-01 | 3.32530290e-01 | 2.63960510e-01 |
| 1.11927770e-01 | 4.94516492e-01 | 4.33520198e-01 | 2.77360439e-01 |
| 9.78331491e-02 | 6.91989884e-02 | 4.86894462e-01 | 3.16607296e-01 |
| 2.91724503e-01 | 1.11041836e-01 | 3.69151264e-01 | -1.70904443e-01 |
| 3.20802294e-02 | 5.70576847e-02 | 5.33782244e-01 | -1.46414116e-01 |
| 5.26367664e-01 | 9.55885053e-02 | 2.16848448e-01 | 1.32641524e-01 |
| 3.51684928e-01 | 4.99319851e-01 | -7.44854361e-02 | 2.95027733e-01 |
| 3.90681028e-01 | 6.72402501e-01 | -2.26076946e-01 | 1.50614455e-01 |
| 3.13385040e-01 | 3.39895397e-01 | 1.06057942e-01 | 1.21579453e-01 |
| -2.76347380e-02 | -9.00001228e-02 | 2.72439241e-01 | 2.69308150e-01 |
| 8.24623346e-01 | -1.91860069e-02 | 1.71181917e-01 | 8.80242229e-01 |
| 2.19921514e-01 | 6.71279654e-02 | 3.78425509e-01 | 2.34111428e-01 |
| -3.78638208e-01 | 6.48787543e-02 | -1.01340622e-01 | 4.96739268e-01 |
| 2.29307175e-01 | 3.06257427e-01 | 2.87153989e-01 | 3.05385798e-01 |
| 3.67719024e-01 | 4.58078563e-01 | 1.36617967e-03 | 3.96706015e-01 |
| 2.67215520e-01 | 1.40643865e-01 | -1.54257298e-01 | 5.43894649e-01 |
| 4.01946992e-01 | -5.87872192e-02 | -1.08677917e-03 | 1.39738256e-02 |
| 4.86829579e-01 | 6.68055415e-01 | 1.18996464e-01 | 5.41637838e-01 |
| 2.42360130e-01 | 5.13157010e-01 | -3.63062732e-02 | 2.09775060e-01 |
| 4.51031029e-01 | 4.34887819e-02 | -2.14082286e-01 | -5.16379833e-01 |
| 8.43144134e-02 | 1.45336047e-01 | -7.01258779e-02 | 2.36347795e-01 |
| 1.67659819e-01 | 3.55308473e-01 | 2.60887295e-01 | 1.45006418e-01 |
| 2.88576987e-02 | 2.92139024e-01 | 8.85188520e-01 | 5.83555341e-01 |
| 3.43499243e-01 | 4.76632208e-01 | 6.03496313e-01 | 4.83265100e-03 |
| -2.01531768e-01 | 2.48474941e-01 | -1.18387811e-01 | 5.48540205e-02 |
| 3.68899316e-01 | 2.97240525e-01 | 4.60522354e-01 | 2.66500950e-01 |
| 2.09664717e-01 | 1.56395853e-01 | 3.55813295e-01 | 7.83994794e-02 |
| 5.10071337e-01 | -2.61765033e-01 | 2.75072783e-01 | 2.83520482e-02 |
| 2.41214558e-01 | -1.05647981e-01 | -3.87129217e-01 | 3.57251853e-01 |
| 1.46926448e-01 | -2.68278599e-01 | 2.52429634e-01 | 5.00282608e-02 |
| 1.16280727e-01 | 2.27359563e-01 | 3.20439130e-01 | 3.33529204e-01 |
| 3.98192734e-01 | 1.79986164e-01 | -2.34988824e-01 | 5.84515370e-02 |
| 2.28851721e-01 | 2.06144571e-01 | 2.31705800e-01 | 1.35280684e-01 |
| -1.57084465e-02 | -1.46241277e-01 | -4.17086631e-02 | 7.82082856e-02 |
| -1.66246608e-01 | 2.59528041e-01 | 3.87451530e-01 | 5.05331159e-02 |
| 3.08162898e-01 | 1.77184254e-01 | 2.52654642e-01 | 4.20306087e-01 |
| 1.17206112e-01 | 2.40870863e-01 | 3.22313935e-01 | 6.94116950e-01 |
| 1.64894879e-01 | 5.58673553e-02 | 3.77366930e-01 | 7.17434347e-01 |
| 4.23610657e-01 | 4.03212845e-01 | 8.74928385e-02 | 5.07320881e-01] |
| [2.77239949e-01 | 1.95338726e-01 | 5.24705529e-01 | -3.19448173e-01 |
| 9.54462513e-02 | 4.41437155e-01 | 4.18298095e-01 | 2.80439019e-01 |
| 3.05833101e-01 | 7.92142078e-02 | 6.80244029e-01 | -3.91083211e-02 |
| 3.28600854e-01 | 1.20101400e-01 | -1.67950511e-01 | 1.27824601e-02 |
| -6.30859658e-02 | 3.21946591e-02 | 1.51294142e-01 | 6.59322858e-01 |
| 2.18116611e-01 | 2.21468315e-01 | -2.40034293e-02 | 2.68449485e-01 |
| 8.28540847e-02 | 1.99339002e-01 | 4.47294801e-01 | 4.29748654e-01 |
| 1.12239540e-01 | -3.42513137e-02 | 4.12889957e-01 | 6.45188630e-01 |
| 5.23777902e-01 | 4.64552253e-01 | 1.43774137e-01 | 9.02444590e-03 |
| 7.56139979e-02 | 3.19797665e-01 | 4.99031842e-01 | 5.68893790e-01 |
| 6.79312646e-01 | 4.33658659e-01 | -4.10228670e-02 | -2.14900061e-01 |
| 1.91628113e-01 | 4.16076452e-01 | 3.61850172e-01 | -8.78727660e-02 |
| 3.88969839e-01 | 1.98679462e-01 | 4.01812613e-01 | 6.89569488e-02 |
| 6.85113490e-01 | 3.59297544e-01 | 2.10878164e-01 | 7.36469552e-02 |
| -8.93744528e-02 | 2.54366159e-01 | 8.35222602e-01 | 1.84416175e-01 |
| -2.26331949e-01 | 7.79848695e-01 | 5.60888290e-01 | -8.39251056e-02 |
| 2.52594560e-01 | 4.14262637e-02 | 3.29395741e-01 | 1.56772375e-01 |
| 3.16919565e-01 | 2.39288807e-02 | 1.85752451e-01 | 3.50564092e-01 |
| -7.30812401e-02 | 5.54868840e-02 | 1.49919346e-01 | 5.81675649e-01 |
| 3.44604969e-01 | -1.13585100e-01 | 6.65488780e-01 | 5.11579394e-01 |
| 3.15934062e-01 | 6.25311971e-01 | 2.24061787e-01 | 1.85845718e-01 |

TABLE $W_h^1$-continued

| | | | |
|---|---|---|---|
| −2.20619023e−01 | 4.04275179e−01 | 3.59271169e−01 | 4.80786502e−01 |
| 7.43128419e−01 | 1.59010410e−01 | −3.23694378e−01 | −2.47433335e−02 |
| 2.48646855e−01 | 1.08908266e−01 | 2.05000743e−01 | 3.96807224e−01 |
| 1.05532713e−01 | 2.39843935e−01 | 3.16109359e−01 | 1.63151443e−01 |
| 7.94836730e−02 | 4.93949592e−01 | −1.34355808e−02 | 1.60642862e−01 |
| 2.28800863e−01 | 2.20765039e−01 | 1.71468720e−01 | −7.29383156e−02 |
| 2.35820740e−01 | 3.78385514e−01 | −2.81593800e−02 | 9.51036215e−02 |
| 1.22379050e−01 | 3.10047977e−01 | 1.23224072e−01 | 5.31222187e−02 |
| 2.54861414e−01 | 4.41261411e−01 | 3.19073945e−01 | 1.49825171e−01 |
| 4.60153759e−01 | 9.06054154e−02 | 6.49035633e−01 | −7.72100762e−02 |
| 3.40074271e−01 | 6.43523559e−02 | 3.66683096e−01 | 5.15004545e−02 |
| 6.47698224e−01 | 3.52016002e−01 | 1.13328196e−01 | 3.54133993e−01 |
| 2.86646541e−02 | 9.50913597e−03 | −3.50643724e−01 | −2.50733256e−01 |
| 7.07433000e−02 | −1.21236809e−01 | 4.83780295e−01 | 3.33002061e−01 |
| −1.31422952e−01 | 6.57104403e−02 | 1.61931932e−01 | −5.33351898e−02 |
| 6.54525682e−02 | 1.43760309e−01 | 1.27538377e−02 | 3.30032736e−01 |
| 1.35044396e−01 | 3.31489742e−01 | 4.91690755e−01 | −3.24122101e−01 |
| 1.52107343e−01 | 5.53245604e−01 | 4.64362986e−02 | 2.86567032e−01 |
| 1.07218243e−01 | 2.71587878e−01 | 3.38220119e−01 | −2.53508762e−02 |
| 2.09479630e−01 | 4.23337698e−01 | 5.68530411e−02 | 1.75834388e−01 |
| 1.92284226e−01 | 9.81206000e−02 | 4.98131961e−01 | −7.66146928e−02 |
| 1.43173099e−01 | 3.20884913e−01 | −5.40983640e−02 | −8.51355642e−02 |
| 1.58488512e−01 | −6.82538599e−02 | 6.95770979e−02 | 3.51186126e−01 |
| 4.17599767e−01 | 1.42510280e−01 | 2.66357392e−01 | 9.64950472e−02 |
| 1.20426670e−01 | 7.65527487e−01 | 1.66095048e−01 | 9.77642536e−02 |
| −2.17543721e−01 | 2.03677312e−01 | 7.46279135e−02 | 6.79376841e−01 |
| −5.79436347e−02 | −3.16842459e−02 | 2.60111570e−01 | 1.74041539e−01 |
| 5.88306189e−01 | 4.09565449e−01 | 1.89473316e−01 | 1.06965512e−01 |
| 3.11396360e−01 | 1.25291094e−01 | −1.77213982e−01 | 3.34486604e−01 |
| 3.57898951e−01 | 4.16131943e−01 | 2.11593047e−01 | 5.04865527e−01 |
| 4.56658185e−01 | 8.29021260e−02 | 5.93252003e−01 | −4.55012023e−01 |
| −1.78244412e−01 | 1.18314870e−01 | 1.69018526e−02 | −8.31069052e−03 |
| 1.18634075e−01 | 1.90192312e−01 | 3.80623847e−01 | 2.86561906e−01 |
| 1.87267154e−01 | 1.79659918e−01 | 7.97438994e−02 | 1.61999926e−01 |
| −2.23739311e−01 | 5.61704457e−01 | 4.67562586e−01 | −4.16731089e−02 |
| −1.68090299e−01 | −3.92674208e−02 | −6.48628101e−02 | 1.03185833e−01 |
| 8.84463787e−02 | 3.09546798e−01 | 4.74698931e−01 | 1.84049811e−02 |
| 1.91718996e−01 | −2.85361171e−01 | 4.99766111e−01 | 1.59493804e−01 |
| 9.18977633e−02 | 2.14073449e−01 | −4.54768017e−02 | 5.71115166e−02 |
| 2.50968128e−01 | 2.93877810e−01 | 1.35344535e−01 | 3.50003660e−01 |
| 3.08905154e−01 | −4.46460731e−02 | 1.97232336e−01 | −6.04475401e−02 |
| 3.07100177e−01 | 1.34575278e−01 | −2.24963248e−01 | 2.09961191e−01 |
| 3.09728831e−01 | 1.92909777e−01 | 9.78728905e−02 | 1.21300712e−01] |
| [2.26581488e−02 | 1.01800159e−01 | 3.91955078e−01 | −1.74360976e−01 |
| 3.65591615e−01 | 5.64704180e−01 | 2.13218257e−01 | 1.00183219e−01 |
| 3.62561405e−01 | −4.63797152e−02 | 1.46531612e−01 | 1.23333484e−01 |
| 3.24195653e−01 | 1.65313929e−01 | 2.16512233e−01 | 2.53253728e−01 |
| 4.76685822e−01 | 1.09376654e−01 | 1.64545581e−01 | 1.93604723e−01 |
| 3.66833776e−01 | 2.21855193e−01 | 1.66563794e−01 | 1.11869849e−01 |
| 4.18549448e−01 | 6.01658285e−01 | 2.42578387e−01 | 1.85609236e−01 |
| −2.35445686e−02 | 2.21456409e−01 | 3.18107843e−01 | 2.37374499e−01 |
| 1.76380575e−01 | 1.79783374e−01 | 2.35472292e−01 | 2.72355765e−01 |
| 2.90011317e−01 | 4.95304048e−01 | 2.91427881e−01 | 3.23474467e−01 |
| 1.40852794e−01 | 3.19706827e−01 | 6.12206042e−01 | 1.61614701e−01 |
| 2.39166155e−01 | 5.23079157e−01 | 2.36514002e−01 | 5.22722125e−01 |
| 2.59635299e−02 | 1.68074872e−02 | 3.75272632e−01 | 1.28041908e−01 |
| 1.95022091e−01 | 3.81110191e−01 | 1.48006350e−01 | 1.00848660e−01 |
| 2.61401415e−01 | 2.40451038e−01 | 6.43059850e−01 | 2.59877920e−01 |
| 1.95206881e−01 | 1.97564438e−01 | −1.35165304e−02 | 3.89578640e−01 |
| −4.96831117e−03 | 1.67723075e−02 | −6.84730187e−02 | 3.43636602e−01 |
| 4.40326810e−01 | −8.65673348e−02 | 2.46432111e−01 | −1.24058381e−01 |
| 3.42033684e−01 | 1.11446708e−01 | 2.81989574e−01 | 5.36870956e−01 |
| 4.18822706e−01 | 3.64991367e−01 | 3.74922186e−01 | 5.27838245e−03 |
| 4.51453775e−02 | 5.52232981e−01 | 1.38381064e−01 | −5.51233478e−02 |
| 6.94096312e−02 | 4.03201189e−01 | 2.53067881e−01 | 2.01314971e−01 |
| 1.61611781e−01 | −3.09791595e−01 | 2.03934968e−01 | 1.27115905e−01 |
| 1.86356455e−01 | −9.59176943e−02 | 2.53952712e−01 | 5.85328043e−01 |
| 1.06283277e−01 | 4.98228073e−01 | −2.62033194e−02 | −1.69341058e−01 |
| −2.95047015e−02 | 4.97868419e−01 | −7.00360686e−02 | 1.50863796e−01 |
| 1.65398702e−01 | 8.72026309e−02 | −2.83886373e−01 | −8.73771012e−02 |
| 3.12143415e−01 | 4.34733182e−01 | 6.55960143e−01 | 5.82024790e−02 |
| 3.45471740e−01 | 1.67226464e−01 | 6.94281161e−01 | 2.77673572e−01 |
| −1.20097034e−01 | 9.49887410e−02 | 4.11641568e−01 | 2.24459633e−01 |
| 2.41062805e−01 | 2.37256721e−01 | −2.32441798e−01 | 7.90940374e−02 |
| 4.86835361e−01 | 3.85335356e−01 | −3.94260027e−01 | −1.61469549e−01 |
| 3.31513137e−01 | 2.24336132e−01 | −2.78372760e−03 | 1.91040501e−01 |
| 1.86047032e−01 | −7.18655512e−02 | 1.60694972e−01 | 1.88781396e−01 |
| 2.37310857e−01 | 4.00372269e−03 | 4.04355407e−01 | 4.26310629e−01 |
| 2.49262869e−01 | 4.30579603e−01 | 3.74778599e−01 | 1.42931908e−01 |
| 7.08169714e−02 | −2.53275852e−03 | 1.12879820e−01 | −7.83462003e−02 |

TABLE $W_h^1$-continued

| | | | |
|---|---|---|---|
| −3.01249027e−01 | 2.37924278e−01 | −5.74182808e−01 | 4.49219972e−01 |
| 6.59034133e−01 | −1.67680271e−02 | 2.93465197e−01 | −1.28872514e−01 |
| 3.64749551e−01 | 5.91773808e−01 | −1.08807698e−01 | 3.82199496e−01 |
| 1.94194749e−01 | 2.93125100e−01 | 6.65370449e−01 | 2.77807325e−01 |
| 5.09513795e−01 | 7.14914799e−02 | 4.94529381e−02 | −1.87430575e−01 |
| 3.37115437e−01 | 4.80341703e−01 | 3.71427774e−01 | 1.86597377e−01 |
| 3.00435305e−01 | 2.84004658e−01 | 4.89138216e−02 | 2.86650807e−01 |
| 4.07709390e−01 | 1.69513270e−01 | −1.83610037e−01 | −5.15297353e−01 |
| 2.97526598e−01 | 3.86440724e−01 | 4.61758226e−01 | 1.74391106e−01 |
| 3.05764914e−01 | 4.12326902e−01 | 3.29095155e−01 | −1.11988120e−01 |
| −4.29252535e−02 | 5.40501297e−01 | 1.82170197e−01 | 3.31462771e−01 |
| 2.71686856e−01 | 6.29664660e−01 | 2.71448076e−01 | 3.47510397e−01 |
| −2.61505358e−02 | 3.93294215e−01 | 2.72011638e−01 | 3.69760364e−01 |
| 3.35168660e−01 | −1.24468751e−01 | −4.47549164e−01 | 1.63804963e−01 |
| 4.33659405e−01 | 1.92342233e−02 | 2.26150006e−01 | −6.90496899e−03 |
| 1.59048170e−01 | −1.93620414e−01 | 1.96217358e−01 | 2.27279797e−01 |
| −3.06333899e−01 | 2.08954141e−01 | 3.65045965e−01 | 7.89069712e−01 |
| 1.56505257e−01 | 2.12009907e−01 | 4.27696794e−01 | 3.70969921e−01 |
| −4.57196832e−02 | 2.80360729e−01 | 5.08243144e−01 | 3.38789165e−01 |
| 4.74000424e−01 | −1.64973382e−02 | −1.08533487e−01 | 2.70691961e−01 |
| 2.02155411e−01 | −6.99773282e−02 | 2.80057937e−01 | 3.06137890e−01 |
| 2.89795816e−01 | −3.38418067e−01 | 5.49256504e−02 | 3.77484202e−01 |
| 1.25945002e−01 | 3.99024278e−01 | −3.07938874e−01 | 1.52092025e−01 |
| 4.12930660e−02 | 6.16806209e−01 | 3.38380085e−03 | −3.82417031e−02 |
| 4.47722971e−01 | −4.45296988e−02 | 3.40592802e−01 | 4.05087054e−01 |
| 4.98603523e−01 | 3.34299833e−01 | 1.95689291e−01 | 9.17901933e−01 |
| 1.74676776e−01 | 5.61920702e−01 | 3.25898051e−01 | 6.44941807e−01] |
| [1.75712928e−01 | 2.79652566e−01 | 6.93738282e−01 | 4.89962041e−01 |
| 3.56812656e−01 | 5.93786418e−01 | 5.16847491e−01 | 4.51818794e−01 |
| 2.74968594e−01 | 2.95233041e−01 | 2.73809701e−01 | 6.13837004e−01 |
| 6.59389570e−02 | 3.40363383e−01 | 1.18814021e−01 | 2.62796491e−01 |
| 2.84083486e−01 | 2.57350653e−01 | −1.97488889e−01 | −3.19938153e−01 |
| 9.60828424e−01 | 1.41279653e−01 | 6.99499488e−01 | 7.73096740e−01 |
| 3.67588282e−01 | 9.78451014e−01 | −1.00401230e−01 | 3.33639830e−01 |
| 1.89278364e−01 | 7.06036508e−01 | −1.89400166e−01 | 2.42417946e−01 |
| −2.47435411e−03 | 5.10979235e−01 | 1.71163708e−01 | 2.59146154e−01 |
| 2.95478459e−02 | 1.82930857e−01 | 2.19553992e−01 | 6.17803574e−01 |
| 5.92277110e−02 | 2.64174372e−01 | −6.40818328e−02 | 5.04868388e−01 |
| 1.16087162e−00 | 2.10141107e−01 | 7.61627331e−02 | 6.40824735e−01 |
| 3.09020132e−02 | 2.34710515e−01 | 2.54723847e−01 | 3.49579960e−01 |
| 4.09132913e−02 | 1.37442112e−01 | 7.41882920e−01 | 2.62002707e−01 |
| 1.68578625e−01 | 1.14415102e−01 | 3.15737695e−01 | 2.34877095e−01 |
| 1.24381825e−01 | 5.82925200e−01 | 2.91128576e−01 | 7.99783021e−02 |
| −1.52296349e−01 | 5.23016870e−01 | 2.79906727e−02 | 4.13978666e−01 |
| 1.98703438e−01 | 7.76922107e−02 | 6.05901778e−01 | 1.30275115e−01 |
| 3.26014757e−01 | 3.69837195e−01 | 3.05711508e−01 | 3.45119536e−02 |
| 3.33162546e−01 | 3.54330689e−01 | 2.74922282e−01 | 1.95345178e−01 |
| 1.28009126e−01 | 3.66587549e−01 | 1.65859777e−02 | −9.99066755e−02 |
| 5.84771447e−02 | 4.85218614e−01 | 1.93717480e−01 | 3.48754108e−01 |
| 7.71010160e−01 | −1.52446970e−01 | 3.34426820e−01 | −9.73591134e−02 |
| 1.59785241e−01 | −9.47568938e−02 | 5.20811737e−01 | 8.86551499e−01 |
| 2.70997554e−01 | 4.14595604e−01 | 9.70504731e−02 | 2.23900184e−01 |
| 6.07110918e−01 | 8.36839139e−01 | 9.27519426e−02 | 2.96329647e−01 |
| 2.78892308e−01 | 6.95631027e−01 | 6.80147469e−01 | 3.05025250e−01 |
| 2.62707531e−01 | 4.15592790e−01 | 2.65149921e−01 | 4.35878694e−01 |
| 3.65570873e−01 | 1.61666304e−01 | 3.40436623e−02 | 2.62083232e−01 |
| 3.56179208e−01 | 2.32165083e−02 | 6.84311211e−01 | 8.37069452e−02 |
| 8.31957996e−01 | 2.57292509e−01 | 2.20264032e−01 | −1.19383372e−01 |
| −2.00918764e−02 | 7.65217066e−01 | 4.37563598e−01 | 4.67008442e−01 |
| 3.07293594e−01 | 3.81596655e−01 | 2.83287823e−01 | 3.22581381e−01 |
| 2.32309952e−01 | 4.62540895e−01 | 3.68111193e−01 | 3.95272493e−01 |
| −8.92346948e−02 | 2.75551140e−01 | 5.26936427e−02 | 5.47481000e−01 |
| 6.29179001e−01 | 5.65660596e−01 | 1.64909437e−01 | 3.89925212e−01 |
| 8.44950974e−02 | 3.87218952e−01 | −2.89568841e−01 | 2.01231420e−01 |
| 3.51663291e−01 | −1.53781399e−01 | 1.86533242e−01 | 1.65000111e−01 |
| 1.33278221e−01 | 4.41490859e−01 | 3.02069187e−01 | 3.69691789e−01 |
| 2.11018860e−01 | 3.81840497e−01 | 4.43063438e−01 | 1.40281335e−01 |
| 3.16249132e−01 | 2.93213636e−01 | 3.37807298e−01 | 4.64719713e−01 |
| −1.49742011e−02 | 2.05562800e−01 | 4.60803628e−01 | −3.43159363e−02 |
| 4.72951353e−01 | 8.16898197e−02 | 1.98489234e−01 | 2.01993749e−01 |
| 8.06509435e−01 | 3.98970991e−01 | 2.94415541e−01 | 3.90414953e−01 |
| 9.89604950e−01 | 1.18108071e−01 | 1.23031296e−01 | 1.20063461e−01 |
| 6.44835234e−01 | 2.31718302e−01 | 2.23440796e−01 | 4.67667103e−01 |
| 3.93351406e−01 | −1.44884154e−01 | 3.24400961e−02 | 6.20325029e−01 |
| 2.59462565e−01 | 2.31500790e−01 | 5.12203336e−01 | 4.98402715e−01 |
| 5.11874080e−01 | 1.91457063e−01 | 1.56042695e−01 | 9.23312921e−03 |
| 6.42792761e−01 | 1.10162996e−01 | 1.95829928e−01 | −1.80085301e−01 |
| 1.33101299e−01 | 3.02179575e−01 | 6.49008989e−01 | 2.54138529e−01 |
| 4.11240339e−01 | 3.93639624e−01 | 3.01112682e−01 | 4.81843889e−01 |
| 3.29760522e−01 | −1.25698587e−02 | 7.09231675e−01 | −1.73645705e−01 |

TABLE $W_h^1$-continued

| | | | |
|---|---|---|---|
| −2.41851181e−01 | 5.94333291e−01 | 6.10953309e−02 | 1.74807101e−01 |
| 2.72999585e−01 | 8.92499387e−02 | 2.97686514e−02 | −3.30307901e−01 |
| 2.51973838e−01 | −7.06522688e−02 | 4.17602152e−01 | 1.96227521e−01 |
| −4.12765257e−02 | 2.64635801e−01 | −1.23666391e−01 | 1.83736324e−01 |
| 2.55052932e−02 | 1.99419513e−01 | 4.14287895e−01 | 3.54489237e−01 |
| 6.77542016e−02 | −2.08688546e−02 | 1.44198343e−01 | 9.88775134e−01 |
| 6.25308454e−01 | 6.95367336e−01 | −1.78463668e−01 | 3.47241044e−01 |
| 3.70217800e−01 | 5.36108434e−01 | 2.60084629e−01 | 2.05585271e−01 |
| 5.02932549e−01 | 3.74427021e−01 | −1.29288718e−01 | 3.52636762e−02 |
| 7.92356193e−01 | 6.49051428e−01 | −2.59791523e−01 | 8.83728802e−01 |
| 6.76261634e−02 | 6.37610197e−01 | 4.62480277e−01 | 1.95832342e−01] |
| [1.31369889e−04 | −1.05402082e−01 | −3.47959340e−01 | 4.00287798e−03 |
| 3.97242934e−01 | 2.49256060e−01 | 1.22565821e−01 | −2.16670670e−02 |
| 7.30105769e−03 | −1.30125612e−01 | −9.66240242e−02 | 1.64912716e−01 |
| 1.20414644e−01 | 1.53467491e−01 | −4.85091954e−02 | 1.30173683e−01 |
| 1.82119623e−01 | −3.48488577e−02 | −1.58673555e−01 | 4.27504331e−01 |
| 7.79065192e−02 | −9.19729918e−02 | −5.92558682e−02 | 4.51025248e−01 |
| 2.11357698e−01 | 1.24194987e−01 | 1.82283685e−01 | 3.74846160e−02 |
| −9.39136893e−02 | 3.95629734e−01 | 3.04377764e−01 | −5.45432307e−02 |
| 9.23170447e−02 | 8.46513584e−02 | 2.63402194e−01 | −1.39291123e−01 |
| 1.21755160e−01 | 6.11308441e−02 | 1.50798976e−01 | 2.10557550e−01 |
| 1.15627542e−01 | 5.24125807e−02 | 1.55680120e−01 | 3.75416726e−02 |
| −7.21830549e−03 | −7.69052655e−03 | 1.94956258e−01 | 1.27551362e−01 |
| 3.31266463e−01 | 1.21293321e−01 | 1.31226614e−01 | 1.04680143e−01 |
| 3.51368755e−01 | 4.28570628e−01 | 1.13363869e−01 | 1.81397945e−01 |
| 2.16958046e−01 | 3.76966745e−01 | 1.46966368e−01 | −1.41326368e−01 |
| −1.02371797e−02 | 4.29978430e−01 | 8.23924094e−02 | 4.30634648e−01 |
| 1.54067636e−01 | 4.68231529e−01 | 9.24625695e−02 | 2.95637310e−01 |
| 1.23853885e−01 | 2.85810709e−01 | 3.66022289e−01 | 4.27580178e−02 |
| 1.01617657e−01 | 2.35332996e−01 | −2.18344182e−01 | 5.90258017e−02 |
| 8.04209858e−02 | 4.46715415e−01 | 1.88667819e−01 | 3.97244990e−02 |
| 2.85691857e−01 | −4.40257750e−02 | 2.43082911e−01 | 1.73913732e−01 |
| 2.43216425e−01 | −2.17409432e−02 | 8.40103030e−02 | 2.57701129e−01 |
| 2.25527674e−01 | 2.45951757e−01 | 6.34444728e−02 | 3.97077233e−01 |
| 1.08280554e−01 | 2.53069997e−01 | 7.82002807e−02 | −1.20003253e−01 |
| 4.25334662e−01 | 2.61552900e−01 | 3.71836454e−01 | 2.27225691e−01 |
| −2.94493288e−02 | 2.75490165e−01 | 1.30885705e−01 | 2.26402134e−01 |
| 1.40753582e−01 | 4.69884835e−02 | 1.45753488e−01 | 8.30736458e−02 |
| −1.09688580e−01 | 5.51179051e−01 | 5.49155995e−02 | 4.13264722e−01 |
| 2.93995500e−01 | 9.60551575e−02 | −1.01933986e−01 | 3.38996090e−02 |
| 2.77530700e−01 | 7.29588419e−02 | 1.15064122e−01 | 2.15882748e−01 |
| 1.07310407e−01 | 1.82509333e−01 | 3.06920409e−01 | −2.06653789e−01 |
| −3.53757082e−03 | 1.54715776e−01 | 2.95851976e−01 | 1.89522967e−01 |
| 1.65624335e−01 | −1.40397370e−01 | 4.49171871e−01 | 1.70917213e−01 |
| −1.73834413e−02 | 4.90541846e−01 | 1.82264209e−01 | 3.34007084e−01 |
| 2.06015229e−01 | 2.41121456e−01 | 8.01974162e−02 | 2.91619357e−02 |
| 1.70638978e−01 | 6.18279636e−01 | 1.80445388e−01 | 3.73633564e−01 |
| 1.08386546e−01 | 1.76084936e−01 | −1.52089432e−01 | 3.36906493e−01 |
| 1.84982419e−01 | 3.85266066e−01 | 2.60163873e−01 | −2.43359715e−01 |
| 3.46810520e−01 | −6.29463652e−03 | 9.78904143e−02 | 4.30553019e−01 |
| 1.25840036e−02 | 4.72496331e−01 | −8.51718560e−02 | 1.60911351e−01 |
| −1.07762657e−01 | 3.22400570e−01 | 4.10218358e−01 | 3.32159609e−01 |
| 2.42611021e−01 | 3.44955683e−01 | 2.60478795e−01 | 8.36789981e−02 |
| −1.70355350e−01 | 1.36284754e−01 | 2.27097005e−01 | 1.88899368e−01 |
| 1.48695230e−01 | 2.75630385e−01 | 1.94426373e−01 | −1.12609401e−01 |
| −4.29054610e−02 | 1.82219774e−01 | 8.41512159e−02 | 3.78508151e−01 |
| 1.97732791e−01 | 4.27400112e−01 | 8.03199857e−02 | 3.01944375e−01 |
| 3.29114467e−01 | 2.96077549e−01 | 3.00853364e−01 | −2.83283561e−01 |
| −2.29809299e−01 | −3.37997917e−03 | 1.83816254e−01 | −1.07710533e−01 |
| 7.62077421e−02 | 3.89564246e−01 | −9.29480791e−02 | 1.83163807e−01 |
| 5.88268459e−01 | 3.44267845e−01 | 5.09548821e−02 | 2.09719628e−01 |
| 2.36794919e−01 | 3.45732808e−01 | 2.58243144e−01 | 2.34858632e−01 |
| 1.73225906e−01 | 4.84113038e−01 | 3.34347069e−01 | 5.95142469e−02 |
| 2.39455342e−01 | 8.67447853e−02 | 8.56506638e−03 | −4.39207144e−02 |
| 1.62541643e−01 | 4.62446719e−01 | 8.36945325e−02 | −2.23547611e−02 |
| 3.34259391e−01 | 3.61195616e−02 | 1.84522763e−01 | 4.60827202e−01 |
| 3.66138041e−01 | 2.30786428e−01 | 7.79895782e−02 | 5.11482842e−01 |
| 8.57727602e−02 | 1.20935746e−01 | −9.80819464e−02 | 4.12823677e−01 |
| 8.68824124e−02 | 2.24203601e−01 | 2.67227411e−01 | 2.27080584e−01 |
| 4.63886380e−01 | 1.92606717e−01 | 4.92549211e−01 | 2.13135988e−01 |
| 4.38422322e−01 | 2.22496793e−01 | 4.51645494e−01 | 3.70016783e−01 |
| 8.52853134e−02 | −1.40668422e−01 | 3.84140253e−01 | 1.55249298e−01 |
| −4.73558716e−02 | 2.47864068e−01 | −1.11201130e−01 | 1.28525212e−01 |
| 1.70161799e−01 | −1.64444029e−01 | 1.04252763e−01 | 9.93754715e−02 |
| 2.43629426e−01 | 3.24817419e−01 | 5.91551848e−02 | −7.10823536e−02] |
| [−6.77766025e−01 | 2.72434294e−01 | −5.80888987e−02 | 1.37287229e−01 |
| 5.28611600e−01 | 4.62341696e−01 | −2.97389597e−01 | 7.08149746e−02 |
| −2.79803544e−01 | −4.78588939e−02 | −2.00246513e−01 | 7.20098568e−03 |
| −4.86726733e−03 | −5.75258791e−01 | 1.59002572e−01 | −1.74599633e−01 |
| −9.77475569e−02 | 5.20501398e−02 | 1.29410103e−01 | −3.90080847e−02 |

TABLE $W_h^1$-continued

| | | | |
|---|---|---|---|
| 1.60031065e−01 | −1.46803036e−01 | −1.69120446e−01 | −2.57030070e−01 |
| −4.26548481e−01 | 9.79737341e−02 | −4.43145148e−02 | 4.05807823e−01 |
| −1.70573175e−01 | 1.12052768e−01 | 9.35859885e−03 | −1.79500878e−01 |
| 3.67292434e−01 | −1.40797779e−01 | −3.00963253e−01 | 2.64641374e−01 |
| −2.44971633e−01 | −9.47832987e−02 | −1.31648406e−01 | −1.83275744e−01 |
| −6.39921874e−02 | −1.56631231e−01 | 4.04207557e−02 | −9.57081541e−02 |
| −9.92109701e−02 | 2.23031387e−01 | 1.04667105e−01 | 8.79889578e−02 |
| 9.60644186e−02 | 1.42704800e−01 | −2.57261097e−01 | −1.29181713e−01 |
| 1.08636804e−02 | 1.98150262e−01 | −1.94752645e−02 | −2.29006168e−03 |
| −4.05939281e−01 | −7.82851055e−02 | −1.70067921e−01 | 1.74927339e−01 |
| −3.68227750e−01 | 1.73801720e−01 | 6.36676848e−02 | −5.69888465e−02 |
| 3.42730463e−01 | 2.06296787e−01 | 2.99822569e−01 | −4.58021052e−02 |
| 3.47930379e−01 | 5.00967018e−02 | −1.00127451e−01 | −1.05923340e−01 |
| −1.75934672e−01 | 1.54396132e−01 | 6.07353985e−01 | 3.06118056e−02 |
| −2.42334753e−01 | −1.01254582e−01 | 2.30725452e−01 | 4.95139398e−02 |
| 1.68060511e−01 | −2.36829668e−01 | −9.78860334e−02 | −1.28226250e−01 |
| 1.24749489e−01 | 8.23416635e−02 | 2.23357260e−01 | 1.92210108e−01 |
| −2.04210356e−01 | −3.16489674e−02 | −9.37547386e−02 | −1.43072799e−01 |
| −1.26304030e−01 | 1.93899632e−01 | 1.43681422e−01 | −3.74512412e−02 |
| −1.54683758e−02 | −1.08151399e−01 | 3.34908068e−02 | −1.74250737e−01 |
| 1.54255614e−01 | −5.81738949e−02 | −5.35236411e−02 | 5.53333089e−02 |
| 1.42732278e−01 | 1.26331955e−01 | −1.55795708e−01 | −1.17463823e−02 |
| −1.06553659e−02 | −6.07598186e−01 | 3.24909166e−02 | −8.34421366e−02 |
| −3.99484098e−01 | −5.48510738e−02 | 8.14131200e−02 | 1.55319989e−01 |
| 2.45848730e−01 | 9.42167565e−02 | 1.55337512e−01 | −2.55927950e−01 |
| −6.79419413e−02 | 1.76259756e−01 | 2.27098718e−01 | 1.00616608e−02 |
| 3.47841978e−02 | −3.44018459e−01 | 2.04801172e−01 | 3.65511328e−02 |
| −6.09081164e−02 | 1.96378633e−01 | −4.12936173e−02 | 2.66451657e−01 |
| 9.43992808e−02 | −1.63460478e−01 | 1.59228832e−01 | −2.15363234e−01 |
| 2.72552460e−01 | 2.89278716e−01 | −1.32290497e−01 | −3.16402805e−03 |
| −3.37658793e−01 | 2.02307358e−01 | 1.03076242e−01 | −1.92489222e−01 |
| 6.62413120e−01 | −2.88247899e−03 | 5.87395467e−02 | 6.00565672e−01 |
| 5.64225018e−01 | −1.15400769e−01 | −2.90705264e−01 | −2.89968282e−01 |
| −3.02367806e−01 | −1.35801449e−01 | 2.45404229e−01 | −7.93496296e−02 |
| −1.08289691e−02 | −3.32336664e−01 | 2.07680330e−01 | 2.26948902e−01 |
| −2.19908535e−01 | 2.19231099e−01 | −1.37184009e−01 | −3.32259536e−02 |
| −2.53566485e−02 | −1.39768533e−02 | −1.67844310e−01 | −1.95654526e−01 |
| 1.60872459e−01 | 5.15871644e−01 | 3.33157293e−02 | 3.90028395e−03 |
| 1.50843173e−01 | −4.82511938e−01 | −2.43112985e−02 | 5.79062223e−01 |
| −3.87161136e−01 | −1.48406938e−01 | 2.95360953e−01 | 2.51054466e−01 |
| 3.93382050e−02 | −1.16733216e−01 | −5.19439615e−02 | −2.07207546e−01 |
| −1.38217688e−01 | −6.96814060e−02 | 1.31335380e−01 | 1.90619864e−01 |
| 4.20568101e−02 | −1.11238189e−01 | −1.96257100e−01 | −5.35302721e−02 |
| 2.54536092e−01 | 2.98318535e−01 | 3.02647829e−01 | 2.96370506e−01 |
| 3.06986403e−02 | 1.61476448e−01 | 1.60613552e−01 | 1.98535055e−01 |
| 2.92795263e−02 | 6.36827111e−01 | 5.88263161e−02 | −1.63576245e−01 |
| 2.71973647e−02 | 3.17159370e−02 | −5.07608056e−01 | −2.39081740e−01 |
| −1.13325112e−01 | −1.95592474e−02 | 5.85550442e−02 | 1.20234713e−01 |
| 2.97069162e−01 | −1.19007364e−01 | 3.46363753e−01 | −1.99292839e−01 |
| −2.46739145e−02 | −1.73090547e−01 | 8.27262625e−02 | −2.30601400e−01 |
| 1.85002938e−01 | 1.99904636e−01 | −2.19493657e−01 | 1.65047407e−01 |
| −2.37969771e−01 | −3.29807065e−02 | 3.76622230e−02 | −1.45827224e−02 |
| 6.26661703e−02 | −1.51800349e−01 | 3.79757822e−01 | −1.75881788e−01 |
| 2.77998764e−02 | 3.83479595e−02 | −3.51340592e−01 | −4.50764120e−01 |
| 1.75610110e−01 | 4.50451970e−01 | 1.72941208e−01 | 3.36209983e−01 |
| 1.48888469e−01 | 9.19787586e−02 | 1.27272666e−01 | −5.99070340e−02 |
| −2.69248754e−01 | −1.45356774e−01 | 9.56947431e−02 | −4.50013608e−01 |
| −4.42661755e−02 | −8.00326169e−02 | −2.49896556e−01 | 1.02407187e−01 |
| 2.09176213e−01 | −2.91337699e−01 | −2.76986696e−02 | −1.79028567e−02] |
| [−1.84342965e−01 | 2.36670058e−02 | 1.76816940e−01 | −1.08685277e−01 |
| 1.98360682e−02 | 9.22055990e−02 | 4.26459014e−01 | 1.20191410e−01 |
| 3.56411561e−02 | −3.20282131e−02 | −1.61197141e−01 | 1.20807178e−01 |
| 7.01375604e−02 | 2.60587662e−01 | −2.86208421e−01 | −5.23812026e−02 |
| 6.40305132e−02 | 2.85444528e−01 | 6.55713305e−02 | −1.64073095e−01 |
| 2.35320598e−01 | −8.71215295e−03 | 2.35356271e−01 | 1.75393224e−01 |
| 4.19833092e−03 | 4.26882416e−01 | 2.62434870e−01 | 1.94909066e−01 |
| 3.51654589e−01 | 6.04461193e−01 | 2.60328859e−01 | 1.65855214e−01 |
| 2.73619056e−01 | 1.00493193e−01 | 6.13040701e−02 | 1.61889523e−01 |
| 9.46807340e−02 | 3.43166649e−01 | 1.62235811e−01 | 1.73900649e−01 |
| −8.53088200e−02 | 2.00060412e−01 | 9.33230016e−03 | 4.60891575e−01 |
| 2.50836194e−01 | 2.93702453e−01 | −8.57026428e−02 | 9.35772806e−02 |
| 5.91611937e−02 | 1.47528335e−01 | 2.05409124e−01 | 2.54287332e−01 |
| −1.59292445e−01 | −3.32270227e−02 | 1.28626868e−01 | −6.94197863e−02 |
| 4.92292672e−01 | 3.45618188e−01 | 2.07289428e−01 | 1.87817597e−04 |
| 4.81133163e−01 | 9.36530437e−03 | 1.70113802e−01 | 1.02124669e−01 |
| 4.85257711e−03 | −1.78517669e−01 | 8.53771064e−03 | 5.11859059e−01 |
| 1.06637999e−01 | −7.48727769e−02 | 1.05062649e−01 | 3.07923496e−01 |
| −2.22021684e−01 | 1.44211754e−01 | −2.82737643e−01 | 1.28989339e−01 |
| 4.61412668e−01 | 3.54540527e−01 | 6.51703998e−02 | 1.81319356e−01 |
| 2.56234825e−01 | −2.78879017e−01 | 9.23202094e−03 | 1.24908000e−01 |

TABLE $W_h^1$-continued

| | | | |
|---|---|---|---|
| 4.43179280e−01 | −3.08147259e−02 | 8.12596902e−02 | 9.80122238e−02 |
| 1.84588075e−01 | 3.30424070e−01 | −1.23579860e−01 | 1.40038937e−01 |
| 9.37369838e−02 | 1.41358465e−01 | 3.52362543e−01 | 4.65172201e−01 |
| 7.14067323e−03 | 1.41028836e−01 | 2.17266917e−01 | −8.55357870e−02 |
| 1.67142347e−01 | 1.30105481e−01 | 1.62479430e−01 | 1.73160315e−01 |
| 2.91155219e−01 | 3.86788934e−01 | 4.19710398e−01 | 1.51437446e−01 |
| 3.20647247e−02 | 1.83963180e−01 | 2.65409648e−01 | 4.36832875e−01 |
| 4.07615662e−01 | 7.49878883e−02 | −3.75560559e−02 | 1.60223588e−01 |
| 6.03786148e−02 | 2.38364249e−01 | 1.58404484e−01 | −4.84052300e−02 |
| −2.68724233e−01 | 1.54809088e−01 | 2.64050871e−01 | 9.48113278e−02 |
| 2.48600185e−01 | 7.27144675e−03 | 4.21865553e−01 | 2.41817787e−01 |
| −1.41970605e−01 | 1.85333341e−01 | 1.70442104e−01 | 2.08378896e−01 |
| 4.39096183e−01 | 3.26784372e−01 | 6.70460612e−02 | 6.37493208e−02 |
| 1.05900720e−01 | 1.32553503e−01 | 2.50277758e−01 | −3.54731120e−02 |
| 5.73451370e−02 | 4.48113143e−01 | 1.72363356e−01 | 6.88720644e−02 |
| −1.09369189e−01 | 2.98117280e−01 | 1.55148342e−01 | 1.71604916e−01 |
| 2.30891347e−01 | 4.57792729e−01 | 4.90908563e−01 | 3.24653298e−01 |
| 1.53183788e−01 | 2.46988803e−01 | 1.30229697e−01 | 1.82732075e−01 |
| 5.41750371e−01 | 2.62159675e−01 | 1.19288571e−01 | 1.00768574e−01 |
| 3.33734632e−01 | 2.94714153e−01 | 1.74246430e−01 | 9.54322983e−03 |
| 6.47990480e−02 | 5.85095026e−02 | 3.04488987e−01 | −6.99747056e−02 |
| 4.00828689e−01 | 1.64758965e−01 | −7.40937144e−02 | 2.83736438e−01 |
| 7.69026717e−03 | 1.52263284e−01 | 1.95811853e−01 | 2.76567757e−01 |
| 1.13217115e−01 | −9.69473273e−02 | 1.13886647e−01 | 4.06061172e−01 |
| 2.32219025e−02 | 5.19318394e−02 | −1.03218414e−01 | −1.22883387e−01 |
| 5.21255374e−01 | 1.31683186e−01 | 1.80849001e−01 | −1.07873328e−01 |
| 1.23835839e−02 | 2.55707558e−02 | 3.13646525e−01 | 5.24549007e−01 |
| 2.09472656e−01 | 3.48217189e−01 | 4.56254333e−01 | 3.58081579e−01 |
| 2.56727040e−01 | −1.49906904e−01 | 3.61457884e−01 | 5.69162220e−02 |
| 3.63776684e−01 | 1.63758621e−01 | 1.33593827e−01 | 1.03604473e−01 |
| 1.63474232e−01 | 1.45943403e−01 | 7.64197037e−02 | 2.39306405e−01 |
| 2.62168974e−01 | −2.47632004e−02 | 3.15490097e−01 | 1.18716754e−01 |
| 7.75394887e−02 | 2.92699903e−01 | 5.24047539e−02 | 3.63138974e−01 |
| 4.89318483e−02 | −3.57014924e−01 | −2.78190635e−02 | 7.21452087e−02 |
| 1.75390482e−01 | 3.50961745e−01 | −6.85556754e−02 | 2.85021126e−01 |
| 1.67398065e−01 | −5.84963970e−02 | 1.84507638e−01 | −2.11353868e−01 |
| −3.81476097e−02 | 2.36433104e−01 | 3.02140504e−01 | 2.42768019e−01 |
| 1.66948006e−01 | 5.82736842e−02 | 2.12228596e−01 | −2.54901703e−02 |
| 6.18567728e−02 | 1.60526142e−01 | 3.85224551e−01 | 4.02675062e−01 |
| 3.03748757e−01 | 7.08907843e−02 | 5.95622733e−02 | 2.34495893e−01 |
| 4.17193115e−01 | 2.18540043e−01 | 7.74558485e−02 | 2.42475085e−02 |
| 3.97848301e−01 | 4.37030852e−01 | 6.37682825e−02 | 7.40449652e−02 |
| 2.32992664e−01 | 4.74056631e−01 | 2.09410086e−01 | 1.56324640e−01] |
| [1.69887081e−01 | 1.84517607e−01 | 5.45845568e−01 | 3.75896037e−01 |
| 5.06277800e−01 | 5.98722279e−01 | 5.19553125e−01 | 7.38818169e−01 |
| 3.63393188e−01 | −8.56140926e−02 | 2.93150842e−01 | 1.56105891e−01 |
| 3.11179996e−01 | 2.48540998e−01 | −3.83862495e−01 | 3.51809353e−01 |
| 5.55600286e−01 | 2.45174170e−01 | 1.58019662e−01 | 4.64963466e−01 |
| 5.87375760e−01 | 2.26094663e−01 | −1.94406763e−01 | 3.15216422e−01 |
| 1.15290940e−01 | 2.92454720e−01 | −1.57825291e−01 | 3.85152727e−01 |
| 3.02405268e−01 | 4.64905620e−01 | 3.60809535e−01 | 5.20785689e−01 |
| 6.31657720e−01 | 2.39542663e−01 | 1.09384231e−01 | 2.55643800e−02 |
| −3.52502555e−01 | −1.50695816e−01 | 4.01394397e−01 | 7.29157269e−01 |
| 2.81369567e−01 | 3.02642256e−01 | −3.66440177e−01 | 2.19878823e−01 |
| 7.09968030e−01 | 5.89680195e−01 | 7.16795504e−01 | 1.13437869e−01 |
| 5.21304011e−01 | 3.38771224e−01 | 1.63448289e−01 | 1.09719142e−01 |
| 7.15111315e−01 | 4.69346970e−01 | 5.78400314e−01 | −1.95636544e−02 |
| 3.34908932e−01 | −3.74655500e−02 | 7.46945918e−01 | 9.00500789e−02 |
| 4.30903912e−01 | 3.31407428e−01 | 8.47399235e−01 | 6.39135659e−01 |
| 1.03505827e−01 | 2.35526398e−01 | 4.32770193e−01 | 1.39217094e−01 |
| 4.46764112e−01 | 2.02814758e−01 | 3.62004995e−01 | 1.25995040e−01 |
| 1.59194633e−01 | −1.58025756e−01 | 5.05469441e−01 | 6.63991094e−01 |
| 4.67348516e−01 | 3.60868067e−01 | 2.62930840e−01 | 2.14016959e−01 |
| 2.96459824e−01 | 8.34842741e−01 | 4.09258842e−01 | 5.18149376e−01 |
| −4.85380441e−02 | −1.41821159e−02 | 4.10686523e−01 | 5.26166558e−01 |
| 2.98567683e−01 | 3.12829137e−01 | 6.70027494e−01 | 3.47797245e−01 |
| 4.97237533e−01 | 6.44052982e−01 | −2.86751031e−03 | 3.18227708e−01 |
| 2.97906250e−01 | 4.34820592e−01 | 2.91999400e−01 | 3.98177087e−01 |
| 1.88699648e−01 | 4.62544739e−01 | 7.04526544e−01 | −1.48909852e−01 |
| −1.06017962e−01 | 5.93182147e−01 | 1.74351826e−01 | −6.50990754e−02 |
| 5.98905444e−01 | 6.58911228e−01 | 3.81019086e−01 | 2.98856362e−03 |
| 6.06042325e−01 | 4.47247624e−01 | −2.09647134e−01 | −8.95816013e−02 |
| 4.58710790e−01 | 2.93984026e−01 | 2.87857056e−01 | −3.39926444e−02 |
| 7.50103235e−01 | 1.58216432e−01 | 2.76417863e−02 | −2.10909531e−01 |
| 4.71198469e−01 | 1.19298480e−01 | 5.26373208e−01 | 1.05020607e−00 |
| 1.01001132e−00 | 1.31324038e−01 | 1.44060344e−01 | 7.73245037e−01 |
| 1.07823938e−01 | 6.47144020e−01 | 1.19074717e−01 | −2.33323187e−01 |
| −1.26366867e−02 | 1.05251357e−01 | 2.58267283e−01 | 6.10875607e−01 |
| 5.02124250e−01 | 4.69775856e−01 | 7.15280920e−02 | 2.33064413e−01 |
| 1.01096712e−01 | 2.65686870e−01 | −3.79485898e−02 | 2.51846343e−01 |

TABLE W$_h^1$-continued

| | | | |
|---|---|---|---|
| 4.06671524e−01 | 3.27191234e−01 | 1.98923379e−01 | 1.13670677e−01 |
| 7.74478972e−01 | 6.51979625e−01 | 2.08008647e−01 | 1.11568019e−01 |
| 4.02952850e−01 | 1.81811318e−01 | 7.28520155e−01 | 5.90589583e−01 |
| 4.51619774e−01 | 8.90699804e−01 | 3.27914417e−01 | 4.00195777e−01 |
| 1.01617515e−01 | 4.25049216e−01 | 4.62927967e−01 | 3.29068899e−02 |
| 1.17335200e−01 | 5.54356456e−01 | −2.15220019e−01 | −1.17364272e−01 |
| 7.29215622e−01 | 5.79747677e−01 | 4.64200079e−01 | 8.82318318e−02 |
| 1.33042908e−00 | −1.77876756e−01 | −2.57238507e−01 | 2.01775819e−01 |
| 2.77037412e−01 | 5.34634829e−01 | 4.69821334e−01 | 3.06613505e−01 |
| −4.51646239e−01 | 4.24330115e−01 | 4.70146209e−01 | 4.04608220e−01 |
| 3.48753214e−01 | 2.22368017e−01 | 4.60782379e−01 | 4.35886234e−01 |
| 8.50005507e−01 | 5.77408254e−01 | 4.35318291e−01 | 2.32505575e−01 |
| 2.17760161e−01 | 1.83010355e−01 | 3.14520895e−01 | −1.05957292e−01 |
| 1.71488076e−01 | 5.76884210e−01 | 6.67727068e−02 | 4.51758415e−01 |
| −9.88407582e−02 | 5.30979693e−01 | 3.32045704e−01 | 1.13584548e−01 |
| 2.46288553e−02 | 1.00764528e−01 | 4.32153434e−01 | 6.11739755e−02 |
| 4.32940781e−02 | 2.36939132e−01 | 9.29092824e−01 | 4.23481971e−01 |
| 3.55018288e−01 | −1.18628442e−01 | −3.29977691e−01 | −4.42241400e−01 |
| 2.88069427e−01 | 1.04199022e−01 | 5.41850269e−01 | 1.19572349e−01 |
| 9.42029655e−02 | 2.33523697e−01 | −3.76130566e−02 | 4.98500429e−02 |
| 3.58337671e−01 | 4.16555628e−02 | 5.41943967e−01 | 3.40584815e−01 |
| 4.85804528e−01 | 1.14821747e−01 | 3.16249907e−01 | 6.63616657e−01 |
| 6.05212510e−01 | 4.66198772e−01 | 3.67005728e−02 | 5.73902547e−01 |
| 1.72893122e−01 | −6.40971065e−02 | 6.10608697e−01 | 5.03246665e−01 |
| 5.29715598e−01 | 2.85479248e−01 | 1.34430900e−01 | 3.20525885e−01 |
| 8.13885510e−01 | 1.02963291e−01 | 3.59639645e−01 | 2.62938887e−01 |
| −3.09189688e−02 | 5.46395540e−01 | 1.22258931e−01 | 1.31393299e−01] |
| [−1.89535692e−02 | 6.00858368e−02 | −4.83813323e−02 | −1.03104487e−01 |
| 2.16205344e−01 | 1.66540682e−01 | 2.75200576e−01 | −8.18353295e−02 |
| −7.18805268e−02 | −8.33735168e−02 | −2.83890098e−01 | 1.68097392e−01 |
| 2.48796120e−01 | −6.72422536e−03 | −1.75638154e−01 | 2.86621034e−01 |
| 2.92807251e−01 | 1.09347351e−01 | 4.49531488e−02 | 4.95557040e−02 |
| −4.76184767e−03 | −1.99132916e−01 | 4.93362635e−01 | −1.07241131e−01 |
| 3.53730619e−01 | −1.78479984e−01 | −1.72959212e−02 | −1.31318597e−01 |
| 1.86175853e−02 | 1.90148689e−02 | 2.39728346e−01 | −1.60516620e−01 |
| −2.16778040e−01 | −2.67555565e−01 | 3.60903025e−01 | 1.73900500e−01 |
| 1.30931318e−01 | 1.18875124e−01 | 4.20791358e−02 | 1.41137734e−01 |
| −8.76462981e−02 | −6.81860419e−03 | −5.36076605e−01 | 3.56692851e−01 |
| 1.99873522e−02 | 2.88076252e−01 | −1.01618029e−01 | 3.33371937e−01 |
| −4.19353098e−02 | −3.42323661e−01 | −3.84096831e−01 | 2.10391525e−02 |
| −1.74462825e−01 | 5.96938282e−02 | −7.64127374e−02 | 3.45310390e−01 |
| 1.46774739e−01 | 9.66434777e−02 | −1.71309680e−01 | −2.39306793e−01 |
| 2.93847710e−01 | 2.18294248e−01 | 1.69864923e−01 | 1.91707015e−01 |
| 4.93626297e−02 | 2.61183619e−01 | 2.37462625e−01 | 3.70487362e−01 |
| 1.05400987e−01 | 1.05654463e−01 | 5.54412641e−02 | 2.37929091e−01 |
| 8.89648423e−02 | 2.97114253e−01 | 7.13460520e−02 | 2.67835725e−02 |
| 2.50936061e−01 | 7.62389135e−03 | 1.74757630e−01 | 2.40618810e−01 |
| −8.24742094e−02 | 1.26323879e−01 | 5.47943376e−02 | 3.21867883e−01 |
| 3.11238080e−01 | 4.10596728e−01 | −4.76578483e−03 | 2.50816822e−01 |
| −1.06145897e−04 | 6.53972477e−02 | 1.22316495e−01 | 2.99190134e−01 |
| 1.79923256e−03 | 2.22705901e−01 | 2.80195892e−01 | −1.07040480e−01 |
| −1.27847776e−01 | −1.42028451e−01 | 2.24957913e−02 | 3.09358597e−01 |
| 4.91343200e−01 | 1.61642637e−02 | 8.92766472e−03 | 3.29315849e−02 |
| 4.36631739e−01 | 2.75531232e−01 | 1.63562261e−02 | −9.62877572e−02 |
| 4.13977401e−03 | 3.07003319e−01 | 3.65940571e−01 | 1.62311271e−01 |
| 3.42735142e−01 | 3.34003001e−01 | 4.17398036e−01 | 3.24904054e−01 |
| 3.88525099e−01 | 3.26350480e−01 | 1.30190715e−01 | −2.82447577e−01 |
| 9.73718613e−02 | 2.55936116e−01 | −6.25153421e−04 | −8.11229274e−02 |
| 2.64519632e−01 | −2.19185814e−01 | 1.62588164e−01 | 7.01274946e−02 |
| −3.65406990e−01 | 1.52787447e−01 | 3.29330891e−01 | −1.47645101e−01 |
| −2.74083316e−01 | 4.16364491e−01 | 3.21879297e−01 | −5.96941740e−04 |
| 3.07458192e−01 | 3.65361154e−01 | 1.91236928e−01 | −9.02309641e−02 |
| 5.66221066e−02 | 1.38449907e−01 | 1.54699966e−01 | −4.51790690e−02 |
| 9.78475437e−02 | 1.61458775e−01 | −3.34412634e−01 | 1.94952339e−01 |
| 2.26000443e−01 | 1.13074057e−01 | 3.35758090e−01 | −6.96543604e−02 |
| −1.82886094e−01 | 1.09243132e−02 | 1.74174741e−01 | 2.59114057e−01 |
| 1.90684721e−02 | 2.22452823e−01 | 4.92337376e−02 | −2.34427750e−01 |
| 1.65351793e−01 | 5.66159904e−01 | 1.18174963e−01 | −9.44992676e−02 |
| −1.67800784e−02 | 9.53841582e−02 | 3.48523200e−01 | −2.87439555e−01 |
| 2.32314810e−01 | −1.66125596e−01 | 2.38438606e−01 | −1.26137823e−01 |
| 2.17886969e−01 | 5.59813902e−02 | 5.45964092e−02 | 3.86599422e−01 |
| 6.82176501e−02 | 3.10143232e−01 | 4.65871572e−01 | 2.92381253e−02 |
| 2.59910300e−02 | 2.56629199e−01 | 1.24269791e−01 | −3.22875008e−02 |
| −8.91516134e−02 | −1.58500940e−01 | −3.40093742e−03 | −1.10236540e−01 |
| 9.37009677e−02 | 1.99585482e−01 | 1.33683294e−01 | 1.61244944e−01 |
| −4.51335795e−02 | 5.79193570e−02 | 1.52502805e−01 | 1.29180327e−01 |
| 1.28601447e−01 | 8.82003084e−02 | 1.04227670e−01 | −8.78746435e−02 |
| 1.73406377e−01 | 9.50331092e−02 | 2.04496652e−01 | 4.31264341e−02 |
| 2.55093783e−01 | 1.06622480e−01 | 2.19122339e−02 | 5.87950908e−02 |
| 1.32584721e−01 | 1.36551008e−01 | −1.03379758e−02 | −1.05060577e−01 |

TABLE $W_h^1$-continued

| | | | |
|---|---|---|---|
| 7.23570734e-02 | 1.96890175e-01 | -7.12908059e-02 | -8.19430798e-02 |
| 4.18814600e-01 | -5.07537834e-02 | 1.51721582e-01 | 1.11428134e-01 |
| 3.96784022e-02 | 8.31378996e-02 | -3.78039628e-02 | -1.45611927e-01 |
| 3.19886267e-01 | -1.55050596e-02 | 2.67048627e-01 | 3.96714568e-01 |
| 1.96773887e-01 | -1.15384683e-01 | -1.94972202e-01 | -9.86741763e-03 |
| 2.41526321e-01 | 4.18944955e-01 | 3.71635169e-01 | -5.63664827e-03 |
| 4.39367563e-01 | 2.80275792e-01 | 4.24244583e-01 | 2.65526325e-01 |
| 4.71548051e-01 | 1.20113276e-01 | 3.38153511e-01 | -2.58134063e-02 |
| 7.16430619e-02 | 8.68799984e-02 | 2.51284063e-01 | -2.99203452e-02 |
| 7.52134323e-02 | 2.62034833e-02 | -5.77420630e-02 | 6.04508854e-02 |
| 3.41878712e-01 | 7.80835375e-02 | 2.72067450e-02 | -4.54334430e-02] |
| [3.16768706e-01 | -1.36205792e-01 | 2.68170238e-01 | 5.34613505e-02 |
| 2.55265892e-01 | 9.14761648e-02 | 1.18099310e-01 | 4.13285106e-01 |
| 5.11648536e-01 | -1.19621322e-01 | 2.44708836e-01 | 3.49476561e-02 |
| 1.65520579e-01 | 3.67818266e-01 | 2.84927394e-02 | 3.22179794e-01 |
| 4.44784127e-02 | 6.76533043e-01 | 1.65689901e-01 | 2.43844897e-01 |
| 3.76018882e-01 | 4.78521645e-01 | 1.35952473e-01 | 2.29345396e-01 |
| 1.37186036e-01 | 1.77544698e-01 | 1.62459090e-01 | -1.71155892e-02 |
| -6.53340295e-02 | -1.27331270e-02 | -6.43202215e-02 | 3.09115857e-01 |
| -1.23446636e-01 | -1.41590908e-01 | 2.53998786e-01 | 4.27271575e-01 |
| -7.27656111e-02 | 2.04264432e-01 | 2.10669078e-02 | 1.52808726e-01 |
| 5.41894436e-01 | 2.69380897e-01 | -1.72327131e-01 | 3.49995077e-01 |
| -6.65843813e-03 | 2.35042334e-01 | 2.91460723e-01 | 2.56284446e-01 |
| 2.73472965e-01 | 2.63286650e-01 | 2.30033293e-01 | -3.06777507e-02 |
| -7.18626156e-02 | 2.58460462e-01 | 2.02145070e-01 | 1.89380273e-01 |
| 9.45930481e-02 | 1.56233320e-03 | 1.86848596e-01 | 1.10056572e-01 |
| 2.67068654e-01 | 3.14638644e-01 | 4.60311085e-01 | 1.11536287e-01 |
| 1.41287595e-02 | 3.46962005e-01 | 1.47553235e-01 | 2.67581195e-01 |
| 2.69582510e-01 | 3.77973944e-01 | 5.09285368e-01 | 1.91577096e-02 |
| 4.40260857e-01 | -2.95066498e-02 | 9.74306017e-02 | 2.87991673e-01 |
| 5.65916777e-01 | 1.10276498e-01 | 1.94163136e-02 | 4.52316999e-02 |
| 3.54111522e-01 | 5.04443169e-01 | 3.01352531e-01 | 1.31058306e-01 |
| -1.72793850e-01 | 1.02521695e-01 | 1.55449152e-01 | 3.09248716e-01 |
| 1.68429732e-01 | -1.11227691e-01 | 1.22820802e-01 | 2.98373222e-01 |
| 2.86962092e-01 | -4.75638062e-02 | 2.70198613e-01 | 2.64517874e-01 |
| 1.69743190e-03 | 2.89049894e-02 | 5.62863231e-01 | 3.34963799e-01 |
| 1.37473300e-01 | 3.47832263e-01 | -3.28474715e-02 | -2.65808944e-02 |
| -8.96234065e-03 | 2.77343422e-01 | -6.90395683e-02 | 6.75876290e-02 |
| 5.40566482e-02 | 2.99081653e-01 | 3.06077123e-01 | 1.48693711e-01 |
| 1.33653179e-01 | 1.31368488e-01 | 4.22153205e-01 | 3.21892291e-01 |
| -1.41217515e-01 | -1.75994396e-01 | 1.79685146e-01 | -1.17519267e-01 |
| 4.25098658e-01 | 1.52031714e-01 | 1.23865925e-01 | 1.86118156e-01 |
| 2.19066545e-01 | 5.26135027e-01 | -1.12887345e-01 | 5.35723507e-01 |
| 3.31526548e-01 | 2.47134134e-01 | 2.56391019e-01 | 5.09282164e-02 |
| 2.63550393e-02 | -1.58311471e-01 | 1.54049203e-01 | 7.98462480e-02 |
| -4.33352813e-01 | -4.67822291e-01 | 1.31207123e-01 | 3.39452922e-01 |
| -2.93624699e-01 | -1.37995362e-01 | 2.46959627e-01 | 2.65901446e-01 |
| 3.66281345e-02 | 7.33460113e-02 | 4.76743728e-02 | -5.04880771e-02 |
| 1.38589647e-02 | 9.36853513e-02 | 3.61449271e-01 | -2.87066563e-03 |
| 1.43268168e-01 | 4.24087077e-01 | -1.89998802e-02 | -8.77138153e-02 |
| 1.52344510e-01 | 1.22935340e-01 | -1.02613926e-01 | 7.47108981e-02 |
| 1.71008259e-01 | 3.21870834e-01 | 4.33729440e-01 | 1.21141411e-01 |
| 1.60624295e-01 | 1.82821572e-01 | 5.28746128e-01 | -4.84694242e-02 |
| 3.60596478e-02 | 2.93147326e-01 | 1.62889183e-01 | 3.23694289e-01 |
| -3.66769552e-01 | 5.09570301e-01 | 1.55164719e-01 | -2.19834018e-02 |
| 1.10350129e-06 | 2.01062694e-01 | 3.17359686e-01 | 1.01275377e-01 |
| 2.00317934e-01 | 2.85914004e-01 | 1.15479372e-01 | -5.03376126e-01 |
| 4.07878876e-01 | 4.77121696e-01 | 1.15722880e-01 | -1.88679993e-01 |
| 2.92028189e-01 | -9.35031623e-02 | 6.58938810e-02 | 3.17845196e-01 |
| -7.93424994e-02 | -1.32437170e-01 | 3.28575224e-01 | -2.31656849e-01 |
| 2.06720397e-01 | -1.11570828e-01 | -1.42549202e-01 | 2.11781800e-01 |
| -3.71361338e-02 | -6.67990670e-02 | 8.85794406e-02 | -2.46416166e-01 |
| -1.39990270e-01 | 9.19508412e-02 | 2.03846231e-01 | 1.84154645e-01 |
| 3.35011512e-01 | -7.54632130e-02 | 2.83712715e-01 | 3.39313120e-01 |
| 3.09934599e-01 | -6.85770884e-02 | 6.52895272e-01 | 1.21056959e-01 |
| -3.05559605e-01 | 2.10169703e-01 | 6.56926692e-01 | -2.35668272e-01 |
| -3.16773430e-01 | 5.04195355e-01 | 1.63121834e-01 | 6.45712903e-03 |
| 4.48943853e-01 | 4.39675003e-01 | 2.53282756e-01 | 2.49121025e-01 |
| 2.09804326e-01 | 4.32060093e-01 | -1.81523070e-01 | 1.00568444e-01 |
| 4.42516237e-01 | 9.13668796e-02 | 1.08924024e-01 | 1.14732273e-01 |
| 1.58393160e-01 | 3.44061941e-01 | 2.11327255e-01 | 2.68940061e-01 |
| 2.82948345e-01 | 2.29109749e-01 | 3.91655862e-01 | 4.20983285e-01 |
| 1.47144184e-01 | -4.25928980e-02 | 4.70052540e-01 | 2.71560282e-01 |
| 4.78519127e-02 | 1.90888792e-01 | 2.74415851e-01 | 1.56361029e-01 |
| 1.33667275e-01 | 3.44992250e-01 | 4.66056019e-02 | -4.74329107e-02] |
| [-1.66822419e-01 | -2.69617867e-02 | 4.88676101e-01 | 4.73645449e-01 |
| -1.63211018e-01 | 1.49708122e-01 | 4.92214461e-01 | 2.09439367e-01 |
| 1.81913003e-01 | 7.63967261e-02 | 1.29091173e-01 | 2.87956800e-02 |
| 5.44891238e-01 | 1.57369524e-01 | 1.64905339e-01 | 1.31650075e-01 |
| 3.65598440e-01 | 3.69849533e-01 | 2.80226707e-01 | 1.59462392e-01 |

TABLE $W_h^1$-continued

| | | | |
|---|---|---|---|
| 4.07110721e−01 | 3.96720350e−01 | 2.64415115e−01 | 5.19379795e−01 |
| 2.03460872e−01 | 2.37856328e−01 | 4.77889538e−01 | 9.23681259e−03 |
| 1.74978435e−01 | 1.88345596e−01 | 4.19354230e−01 | 1.40860647e−01 |
| 4.27080035e−01 | 8.35025534e−02 | −3.90760630e−01 | 3.38545591e−01 |
| 2.45784193e−01 | 7.00336823e−05 | 2.21868277e−01 | 4.20996875e−01 |
| 5.86274207e−01 | 5.17401338e−01 | 2.22798854e−01 | 3.29226069e−02 |
| 3.58889431e−01 | 3.64698112e−01 | 2.09212437e−01 | 2.76735336e−01 |
| −1.67909056e−01 | 4.97793376e−01 | 9.24167484e−02 | 1.19157918e−01 |
| 1.49772704e−01 | −2.40155887e−02 | −1.28795609e−01 | 1.92424521e−01 |
| 6.23187602e−01 | −2.09799424e−01 | 5.72455466e−01 | 3.52814913e−01 |
| −2.23236252e−02 | 3.45064551e−01 | 3.44250381e−01 | 1.60561040e−01 |
| 1.84068829e−01 | 1.51727274e−01 | 8.69098026e−03 | 3.05956453e−01 |
| 6.94531668e−03 | 2.80074805e−01 | 1.55874550e−01 | 2.14177333e−02 |
| 5.87758064e−01 | 2.63238758e−01 | 3.25956047e−01 | 3.22558045e−01 |
| 2.44898677e−01 | 3.10130090e−01 | 3.79098773e−01 | 4.16347794e−02 |
| 3.61529738e−01 | 3.62090379e−01 | 1.62465706e−01 | −1.81863874e−01 |
| −9.19931829e−02 | −5.08637764e−02 | −1.16603496e−02 | −7.24872276e−02 |
| 2.00404570e−01 | 3.08498621e−01 | 2.22775057e−01 | 2.99298279e−02 |
| 4.03754674e−02 | 1.91617534e−01 | 4.26336735e−01 | 2.90516943e−01 |
| −1.78028047e−01 | 2.32820556e−01 | −1.17482074e−01 | −9.51608941e−02 |
| 1.97475031e−01 | 4.67792481e−01 | 5.03351390e−01 | −1.16313651e−01 |
| 1.78297609e−01 | 4.22498554e−01 | 1.47029385e−02 | 8.99626613e−02 |
| 3.60464543e−01 | 3.93318594e−01 | 1.42279640e−01 | 1.52245983e−01 |
| 2.27744102e−01 | 2.04311371e−01 | 6.56274974e−01 | 1.05897799e−01 |
| 1.79400876e−01 | 1.36563674e−01 | 3.64252120e−01 | 1.32112294e−01 |
| 3.73627961e−01 | 6.42437518e−01 | 7.17692226e−02 | 4.51383382e−01 |
| 4.31291610e−01 | 6.01188183e−01 | 3.05425197e−01 | 2.31940150e−01 |
| 1.24676205e−01 | 1.26205266e−01 | −3.09461087e−01 | 7.26396918e−01 |
| 3.95622194e−01 | 3.95809591e−01 | 1.72034085e−01 | 5.28378367e−01 |
| −1.53232291e−01 | −3.40808071e−02 | 3.39504689e−01 | 3.77943158e−01 |
| 1.55193031e−01 | 6.14802897e−01 | 2.48970538e−02 | 4.96924631e−02 |
| 6.20995648e−04 | −1.03913888e−01 | 2.34619826e−01 | 1.54777104e−03 |
| −2.37813964e−01 | −1.06775284e−01 | −1.94932401e−01 | 1.63323224e−01 |
| 3.09061021e−01 | 5.56442440e−01 | −3.75058427e−02 | 2.01983169e−01 |
| 7.60151073e−02 | 2.29028583e−01 | −4.27651495e−01 | 5.39192855e−01 |
| −5.04550971e−02 | 1.44059584e−01 | 5.54620102e−02 | 3.78885001e−01 |
| 1.33572504e−01 | 2.41815448e−01 | 3.24807465e−01 | −1.03423566e−01 |
| 5.90690821e−02 | 3.33089054e−01 | 3.31589282e−01 | 5.02753966e−02 |
| 4.66886729e−01 | 2.80908197e−01 | −5.74338529e−03 | 2.81073719e−01 |
| 2.06209958e−01 | −4.85384986e−02 | 1.11207500e−01 | −3.39384049e−01 |
| 3.35614592e−01 | 2.34852910e−01 | 3.87403995e−01 | 3.11288655e−01 |
| 2.18764573e−01 | 1.53487355e−01 | 5.36670722e−02 | 5.12787580e−01 |
| 4.38995719e−01 | 1.75744921e−01 | 3.12061131e−01 | 4.90652442e−01 |
| 1.05743386e−01 | 3.83098155e−01 | 4.13846582e−01 | 1.38609976e−01 |
| 1.33116702e−02 | −1.37688117e−02 | 3.76094580e−02 | −1.81295667e−02 |
| 3.87360245e−01 | −4.05818447e−02 | 3.07141870e−01 | 4.20500040e−01 |
| 7.51812637e−01 | 5.50172329e−01 | 8.60803723e−02 | 2.15191171e−01 |
| 6.69914261e−02 | 1.63620174e−01 | 4.21116889e−01 | 3.34001064e−01 |
| −2.43747026e−01 | 5.49968071e−02 | 1.81376487e−01 | 6.17615759e−01 |
| 1.71009496e−01 | 9.15868133e−02 | 5.99450350e−01 | −1.56041577e−01 |
| 3.25937569e−01 | −2.52298340e−02 | 1.62005112e−01 | 2.83757020e−02 |
| 1.41024545e−01 | 1.10787213e−01 | 7.73635805e−02 | −4.28174995e−02 |
| 2.53701836e−01 | 3.14354658e−01 | 8.61879706e−01 | 9.23914686e−02 |
| 2.07610890e−01 | −2.24718243e−01 | 4.17318910e−01 | 8.09882104e−01 |
| −2.44555548e−01 | 5.51402271e−01 | −5.51326722e−02 | 2.02104211e−01 |
| 4.58792895e−01 | −2.55318061e−02 | 4.57063884e−01 | 4.08726096e−01 |
| 4.91888911e−01 | 1.57373801e−01 | 2.55089730e−01 | 2.08774626e−01 |
| 1.51062638e−01 | 1.00636177e−01 | 1.23605162e−01 | 4.54345010e−02 |
| 1.91806778e−02 | 7.08824635e−01 | 5.73986173e−01 | 3.29953641e−01] |
| [3.51825774e−01 | 5.65416157e−01 | 3.33813608e−01 | 7.97905743e−01 |
| 2.13408038e−01 | 1.16005373e−00 | 5.61864913e−01 | 1.05726115e−01 |
| 8.50547671e−01 | 6.56173766e−01 | 2.95616329e−01 | 7.61783779e−01 |
| 3.72856975e−01 | 4.34215039e−01 | 5.15632331e−01 | 2.79117942e−01 |
| 6.19731188e−01 | 9.25790668e−02 | 1.82673931e−01 | 6.49082601e−01 |
| 7.12014556e−01 | −1.81337178e−01 | 5.68048060e−01 | 7.79027939e−01 |
| 6.39213383e−01 | 8.08394670e−01 | −2.51732975e−01 | 2.27249891e−01 |
| 7.48495630e−04 | 6.52301729e−01 | 2.72269577e−01 | 2.45539010e−01 |
| 2.65228152e−01 | −2.37787440e−01 | 5.03046155e−01 | 2.21222237e−01 |
| 4.59395200e−01 | 6.95086956e−01 | 5.26600301e−01 | 4.53703463e−01 |
| 3.37934047e−01 | 2.91670203e−01 | −1.33588940e−01 | 4.50052887e−01 |
| 7.61029303e−01 | 3.97966623e−01 | 6.63055718e−01 | 7.07364380e−01 |
| 4.28525686e−01 | 4.85015929e−01 | 2.74243593e−01 | 7.42021441e−01 |
| 2.62351841e−01 | 4.98572707e−01 | 4.40810412e−01 | 5.41205585e−01 |
| 6.17159843e−01 | 1.86858550e−02 | 5.41391969e−01 | 1.58229560e−01 |
| 1.76744565e−01 | 2.67446220e−01 | 7.00500607e−01 | 2.46163920e−01 |
| −2.22060293e−01 | 1.20102480e−01 | 1.18665285e−01 | 4.73584324e−01 |
| 7.69358933e−01 | 3.48739445e−01 | 6.61641955e−01 | −3.27282175e−02 |
| 6.11574173e−01 | 6.17611587e−01 | 9.31411445e−01 | 5.16028225e−01 |
| 3.95402014e−01 | 5.68046033e−01 | 3.93863946e−01 | 3.05453390e−01 |
| 4.01799642e−02 | 9.46979344e−01 | 3.52407455e−01 | 2.28982717e−01 |

TABLE $W_h^1$-continued

| | | | |
|---|---|---|---|
| −8.80056396e−02 | 1.51447952e−01 | 4.20466572e−01 | 4.91594613e−01 |
| 7.11412072e−01 | −4.32548910e−01 | 1.34082334e−02 | 2.80249864e−01 |
| 2.69252449e−01 | 1.92687184e−01 | 5.77563882e−01 | 5.89067221e−01 |
| 6.45973146e−01 | 6.17869258e−01 | 3.50585341e−01 | 3.80368710e−01 |
| 4.16556597e−01 | 7.64380693e−01 | 5.93311250e−01 | 3.09358507e−01 |
| 5.34034371e−01 | 6.63654566e−01 | 2.11708739e−01 | 5.18540084e−01 |
| 2.30109960e−01 | 6.22481108e−01 | 6.08644009e−01 | 2.69603163e−01 |
| 2.44719908e−01 | 1.70390815e−01 | 5.55605888e−01 | 4.99176592e−01 |
| 4.94637877e−01 | −5.27265728e−01 | 2.96195239e−01 | 1.55002013e−01 |
| 5.79913139e−01 | 1.10302307e−01 | −1.27809003e−01 | 6.01007283e−01 |
| 7.34507859e−01 | 9.31489825e−01 | 2.65278608e−01 | 8.72813940e−01 |
| 5.65380991e−01 | 1.84634253e−01 | 2.37426132e−01 | 7.08020091e−01 |
| 6.22084558e−01 | 5.83602667e−01 | 5.54099344e−02 | 4.74701561e−02 |
| 3.06452941e−02 | 6.43056870e−01 | 5.21164954e−01 | 5.50274849e−01 |
| 3.97410810e−01 | 5.04035711e−01 | 1.32744431e−01 | 1.04297541e−01 |
| 3.25251430e−01 | 8.22505891e−01 | −5.89237809e−02 | 5.61679363e−01 |
| 3.22901100e−01 | 6.66847169e−01 | −8.25991929e−02 | 2.47139245e−01 |
| 1.14467591e−01 | 2.75743186e−01 | 4.84958500e−01 | 5.85167289e−01 |
| 1.78364456e−01 | 3.19022238e−01 | 5.24279475e−01 | 5.01844466e−01 |
| 5.00764191e−01 | 5.53181708e−01 | 2.19434798e−01 | 2.68851697e−01 |
| 1.99211597e−01 | 3.69833857e−01 | 1.23155624e−01 | 1.80765793e−01 |
| 6.48229241e−01 | 5.90970159e−01 | 9.47238922e−01 | 5.36119401e−01 |
| 3.80137980e−01 | 2.64027834e−01 | −2.28092015e−01 | 1.64600581e−01 |
| 3.49782854e−01 | −9.41745043e−02 | 2.28050306e−01 | 2.52601415e−01 |
| 4.79692131e−01 | 7.15927303e−01 | 7.26137877e−01 | 2.19174266e−01 |
| 6.65726662e−01 | 6.39214456e−01 | 4.67939556e−01 | 3.06415498e−01 |
| 9.23443586e−02 | 4.98829663e−01 | 6.89800560e−01 | 7.46982753e−01 |
| 5.26013136e−01 | 1.30584598e−00 | 2.52129167e−01 | 1.65448591e−01 |
| 5.71919560e−01 | 2.36014575e−01 | 5.13339639e−01 | 3.54815871e−01 |
| 6.16621897e−02 | −1.19923607e−01 | 7.82891512e−01 | 1.30173549e−01 |
| 1.91714078e−01 | 5.07309377e−01 | 2.45499551e−01 | 5.19133508e−01 |
| 8.27710092e−01 | 3.82307529e−01 | 4.49341744e−01 | 5.84087789e−01 |
| 9.26737845e−01 | 5.70651591e−01 | −1.19362019e−01 | 4.55588877e−01 |
| −2.71828145e−01 | 5.13538897e−01 | 3.79910320e−01 | 1.01932464e−02 |
| 4.08753991e−01 | −4.35259759e−01 | 6.00814819e−01 | 2.35920504e−01 |
| 5.92804253e−01 | 3.85064811e−01 | −7.68530369e−02 | 6.80332720e−01 |
| 5.02035201e−01 | 6.49332404e−01 | 6.74276292e−01 | 5.32449186e−01 |
| 3.68390590e−01 | −3.30789447e−01 | 9.01304126e−01 | 7.21634567e−01 |
| 3.92434388e−01 | 1.07590094e−01 | 1.54837921e−01 | 6.97656333e−01 |
| 4.78582948e−01 | 6.01441085e−01 | 6.17806494e−01 | 4.72146630e−01 |
| 4.20830786e−01 | 2.67916173e−01 | 5.21794260e−01 | 1.71176031e−01 |
| 7.66772211e−01 | 1.79226920e−01 | 3.33407938e−01 | 7.46340394e−01 |
| 1.77087426e−01 | 5.45297146e−01 | 5.81776798e−01 | 2.58292168e−01] |
| [2.73017406e−01 | 7.26514310e−02 | 2.68709540e−01 | 2.03562304e−02 |
| 1.79650053e−01 | 6.23755574e−01 | 2.52305537e−01 | 3.17820907e−01 |
| 4.58619118e−01 | 2.62125432e−01 | 8.43551397e−01 | 2.21133903e−01 |
| 6.95064738e−02 | 1.22487985e−01 | 3.64295505e−02 | 6.48794770e−02 |
| 2.33658850e−01 | 3.35187376e−01 | −5.32074757e−02 | 3.12924325e−01 |
| 6.09042466e−01 | −1.11811116e−01 | 2.67214447e−01 | −3.78534980e−02 |
| 5.19200563e−01 | 5.51648736e−01 | 3.64803374e−01 | −1.48181483e−01 |
| 3.74766707e−01 | 4.03489202e−01 | 2.84872174e−01 | 1.06555432e−01 |
| 1.90437958e−01 | 2.33291904e−03 | 4.28276986e−01 | 4.13721055e−01 |
| 5.56410909e−01 | −4.57908995e−02 | 2.77496457e−01 | 7.04069793e−01 |
| 8.20876807e−01 | 3.92777264e−01 | −2.43421569e−01 | 5.22906840e−01 |
| 7.10214436e−01 | 2.89041758e−01 | 4.00314212e−01 | 4.43031728e−01 |
| 1.90968454e−01 | 4.16994721e−01 | 3.05879444e−01 | 5.03615677e−01 |
| −6.22090772e−02 | −1.08506437e−02 | 2.69231617e−01 | 1.23304233e−01 |
| 6.97296679e−01 | −7.12751299e−02 | 5.87322831e−01 | 3.07495087e−01 |
| 2.62469292e−01 | 9.04968441e−01 | −3.38729657e−02 | 1.44922003e−01 |
| −8.47522840e−02 | 4.30329889e−01 | 1.86268017e−02 | 3.20174485e−01 |
| 4.09518927e−01 | −1.06864691e−01 | 5.22873044e−01 | 1.76529959e−01 |
| 5.81855893e−01 | 1.40980333e−01 | −6.99968991e−02 | 1.13751106e−01 |
| 2.13871047e−01 | 5.99500060e−01 | 4.12994087e−01 | 2.10634768e−01 |
| 2.81427681e−01 | 3.17641288e−01 | 3.96742761e−01 | −5.08976355e−02 |
| 4.43457291e−02 | −1.64666563e−01 | 1.32311732e−01 | 2.54391164e−01 |
| 3.99251372e−01 | 2.19300404e−01 | 2.10476637e−01 | 2.05936134e−01 |
| 2.25734144e−01 | −1.42294437e−01 | 3.00778419e−01 | 3.77492905e−01 |
| 2.37378016e−01 | 2.12933734e−01 | 1.67814195e−01 | −2.26949930e−01 |
| 9.38635170e−02 | 3.06442589e−01 | 3.74194473e−01 | −1.23450570e−01 |
| 3.63325894e−01 | 4.91061509e−01 | 2.40329474e−01 | 4.51897323e−01 |
| 1.92593500e−01 | 5.04869521e−01 | 2.65026987e−01 | 2.87744641e−01 |
| 3.24247599e−01 | −1.97160304e−01 | 3.69333893e−01 | −1.25002176e−01 |
| 2.56057948e−01 | 2.97231913e−01 | 3.49552184e−01 | 5.72722912e−01 |
| 5.22249520e−01 | 1.84744909e−01 | 2.74985194e−01 | 3.71808231e−01 |
| 1.86672300e−01 | 5.25555432e−01 | 7.06718862e−01 | 4.65953536e−02 |
| −7.96929188e−03 | 4.73959118e−01 | −1.76494032e−01 | 4.58395034e−01 |
| 1.82141010e−02 | 4.24237609e−01 | 1.33612975e−01 | 4.42070812e−01 |
| 1.05939463e−01 | 2.39262685e−01 | 4.94993538e−01 | 6.46531045e−01 |
| 1.12091586e−01 | 5.32572687e−01 | 3.24965537e−01 | 3.31593812e−01 |
| −1.35334313e−01 | 5.13893247e−01 | 2.24557251e−01 | 5.24013281e−01 |

TABLE $W_h^1$-continued

| | | | |
|---|---|---|---|
| −2.15420146e−02 | 2.71596527e−03 | 6.30630106e−02 | 3.30121100e−01 |
| 4.16281044e−01 | 4.29018557e−01 | 1.60066649e−01 | 5.88408768e−01 |
| 5.84548652e−01 | 1.00583506e−00 | 3.61978859e−01 | 1.63473397e−01 |
| 3.69314849e−01 | 5.26511788e−01 | 2.29329884e−01 | 2.99902707e−01 |
| 1.80534527e−01 | 5.71209610e−01 | 4.54733431e−01 | −1.13808937e−01 |
| −3.83886024e−02 | 9.95272771e−02 | −1.58073939e−02 | 5.46314776e−01 |
| 5.39347470e−01 | 4.46505278e−01 | −2.41448492e−01 | 3.29803586e−01 |
| −1.65102974e−01 | 7.29912519e−02 | 2.55789161e−01 | −1.34432688e−01 |
| 4.39401150e−01 | 3.84364456e−01 | 6.05433524e−01 | 9.70645770e−02 |
| 5.00344217e−01 | 4.83276635e−01 | 4.11765128e−01 | 5.25102675e−01 |
| 2.48662103e−02 | 1.76554814e−01 | 7.34059989e−01 | 5.92460930e−01 |
| 2.93144405e−01 | 4.36592877e−01 | 5.91157556e−01 | −2.16852546e−01 |
| 1.49590269e−01 | 1.44929039e−01 | 1.83929995e−01 | −4.26409431e−02 |
| 8.18812549e−02 | 2.80068275e−02 | −3.64368945e−01 | 5.68992257e−01 |
| 4.09532666e−01 | 4.82630193e−01 | 3.10899854e−01 | 1.59937546e−01 |
| 3.53126615e−01 | 1.49280876e−01 | 2.29702517e−01 | 2.90617377e−01 |
| 7.51114935e−02 | 7.13140309e−01 | 4.72740024e−01 | 6.30380690e−01 |
| 1.81861036e−02 | −1.30562829e−02 | 4.28355545e−01 | 2.75535017e−01 |
| 2.22777814e−01 | 1.68970034e−01 | 4.39002454e−01 | −5.94680756e−02 |
| 5.07661760e−01 | 2.93896705e−01 | −2.57136971e−01 | 5.56499287e−02 |
| 1.42399609e−01 | 1.43769279e−01 | 7.41256773e−02 | 5.61555326e−01 |
| 4.27456826e−01 | 2.97387898e−01 | 4.73562509e−01 | 7.17747808e−01 |
| 1.19896382e−01 | 3.60188454e−01 | 1.16468377e−01 | 3.63713264e−01 |
| 2.76764452e−01 | 3.37084532e−01 | −9.06639770e−02 | 3.92661512e−01 |
| 4.66701925e−01 | −7.36481473e−02 | 4.81714457e−02 | 3.98701251e−01 |
| 6.13238096e−01 | 2.96771735e−01 | 1.25149101e−01 | 4.15581495e−01 |
| 1.62108794e−01 | 4.28210318e−01 | 1.49964228e−01 | 2.59990990e−01] |
| [−3.22704464e−01 | 8.35291073e−02 | −5.46004951e−01 | −6.66002393e−01 |
| 5.77315986e−01 | −2.32651785e−01 | −3.85905683e−01 | 3.32072318e−01 |
| −2.58755833e−01 | −3.59870702e−01 | −4.99768913e−01 | −1.82121724e−01 |
| 1.13184899e−01 | 5.32766953e−02 | −8.83512199e−01 | 1.00548640e−01 |
| −1.44518331e−01 | −1.07363954e−01 | −1.28449276e−01 | −8.42200369e−02 |
| −5.66831708e−01 | −2.34995052e−01 | −5.49960583e−02 | −6.05520248e−01 |
| 4.48820777e−02 | −6.51096880e−01 | −4.32820082e−01 | 2.48642519e−01 |
| 2.08698288e−02 | −4.42792922e−01 | −3.65692168e−01 | −2.49147370e−01 |
| −6.22524559e−01 | −2.78045595e−01 | 3.22454959e−01 | 5.60394749e−02 |
| −5.34222960e−01 | −1.94430321e−01 | 2.72225648e−01 | −2.70659924e−02 |
| −3.06607038e−01 | 3.56452577e−02 | −4.06062156e−01 | 4.31142338e−02 |
| −5.71833551e−01 | −7.42560253e−03 | −7.14369893e−01 | −2.52750367e−01 |
| −2.20837027e−01 | −1.87945113e−01 | −2.30931222e−01 | −1.15709007e−01 |
| −1.50994852e−01 | −2.74105996e−01 | 4.92237568e−01 | −7.70058930e−02 |
| −3.28312576e−01 | −2.98431545e−01 | −5.53396404e−01 | −4.83647629e−04 |
| −1.46372229e−01 | −2.48479068e−01 | −1.08748443e−01 | 7.56001547e−01 |
| −2.20653817e−01 | −2.11344868e−01 | −8.94953012e−02 | −3.88693690e−01 |
| 4.00147848e−02 | 1.95745863e−02 | −3.86962146e−01 | 8.69889557e−02 |
| −1.26828897e−00 | −4.49572980e−01 | −1.39653059e−02 | −3.13609093e−01 |
| −4.74620402e−01 | −5.11699200e−01 | −9.55850407e−02 | −7.27000907e−02 |
| 1.07290000e−01 | −2.67503858e−01 | −8.63381720e−04 | −2.52979994e−03 |
| −1.27526391e−02 | −1.96755528e−01 | −1.66554242e−01 | −1.11584933e−02 |
| 9.77943167e−02 | −3.03419642e−01 | 2.48369370e−01 | −1.33079708e−01 |
| −2.87803948e−01 | −1.85160354e−01 | −1.29495263e−01 | −4.07044768e−01 |
| −2.13284746e−01 | −5.53272329e−02 | −3.01018767e−02 | 2.81501740e−01 |
| −3.67663354e−01 | −7.38819361e−01 | −4.39008594e−01 | −2.54867047e−01 |
| −4.15835641e−02 | −2.50583291e−01 | −1.74568400e−01 | −1.44678652e−01 |
| −1.12473048e−01 | −5.92325389e−01 | −3.27062607e−01 | 1.45147875e−01 |
| −4.04599488e−01 | −1.87289968e−01 | −1.83445483e−01 | −3.59596405e−03 |
| 6.19877689e−02 | −2.46664166e−01 | −4.28202152e−01 | −6.89251721e−01 |
| −5.02362847e−01 | 1.74547024e−01 | −4.49031800e−01 | −3.46967876e−01 |
| −3.99718583e−02 | −4.49151695e−01 | −3.90788645e−01 | −1.88572839e−01 |
| −2.23867923e−01 | −7.68897593e−01 | −3.18997622e−01 | −8.51304173e−01 |
| −6.97510302e−01 | −4.08595093e−02 | −1.03495000e−02 | 3.69376540e−01 |
| −7.41044134e−02 | 1.63450390e−01 | −6.22249901e−01 | −6.45502925e−01 |
| −4.39747781e−01 | −4.73231763e−01 | −5.32078147e−01 | 2.27681156e−02 |
| −9.31231398e−03 | −1.35897711e−01 | −4.10145015e−01 | −2.67832965e−01 |
| 3.73572074e−02 | 6.74637705e−02 | −1.83498666e−01 | −1.34162784e−01 |
| −3.10861111e−01 | −1.64768159e−01 | −2.90754378e−01 | −2.46235073e−01 |
| −3.38214010e−01 | −1.38570979e−01 | −4.90782820e−01 | −4.87226039e−01 |
| 4.48375225e−01 | −2.83734173e−01 | 4.04962540e−01 | −5.01587808e−01 |
| 2.03776106e−01 | 1.23768924e−02 | 1.15152210e−01 | −4.66533989e−01 |
| −4.02060688e−01 | 2.12417915e−02 | −3.07687342e−01 | −1.13219574e−01 |
| −5.08241236e−01 | −1.02025576e−01 | 6.96302205e−02 | −3.47056240e−01 |
| −2.43059322e−01 | −5.08495979e−02 | −1.68542042e−01 | 2.95696229e−01 |
| −1.61291644e−01 | −1.23715833e−01 | −4.53567028e−01 | −5.51784158e−01 |
| −2.32747272e−01 | −4.22936350e−01 | −3.21420074e−01 | −1.92615435e−01 |
| 4.26749408e−01 | −5.18420100e−01 | −5.45495570e−01 | −1.64231807e−01 |
| 6.23489246e−02 | −5.47029674e−01 | −3.10557038e−01 | −2.36383408e−01 |
| −1.35522988e−02 | −1.70642719e−01 | −1.30112708e−01 | −4.29971009e−01 |
| 1.48697808e−01 | −3.72572601e−01 | −2.92475939e−01 | −3.26257437e−01 |
| −4.02394265e−01 | −9.77819562e−02 | −1.72994584e−01 | −2.24948063e−01 |
| 1.83329582e−02 | −2.48259053e−01 | −1.59793869e−01 | 1.64269432e−01 |

TABLE $W_h^1$-continued

| | | | |
|---|---|---|---|
| −1.64061874e−01 | −8.01719427e−02 | −1.57998800e−01 | −5.00756562e−01 |
| −3.18691969e−01 | −1.46785736e−01 | −4.60560411e−01 | 1.31755903e−01 |
| 1.53230783e−02 | −7.00491443e−02 | −2.19922662e−01 | 1.91355795e−02 |
| −4.33069497e−01 | −6.02687061e−01 | −2.68249601e−01 | −3.08073074e−01 |
| −4.86316085e−01 | −2.36752629e−01 | −5.47923207e−01 | −2.35534832e−01 |
| −2.33125582e−01 | −3.08881313e−01 | −4.28750992e−01 | −4.04536664e−01 |
| 2.57411569e−01 | −4.15899992e−01 | −5.18723845e−01 | −9.31714624e−02 |
| −3.80438030e−01 | 1.04793020e−01 | −8.44550803e−02 | −2.98672348e−01 |
| −2.92697430e−01 | −1.96243703e−01 | −2.97691196e−01 | −2.40642935e−01 |
| 4.29785810e−02 | −4.10705388e−01 | 1.79124713e−01 | 6.85455501e−02 |
| −3.67960453e−01 | −7.03709900e−01 | −3.16477031e−01 | −2.50007242e−01] |
| [−1.70714214e−01 | −9.87701043e−02 | 3.61915082e−01 | 1.50531158e−01 |
| 1.66224286e−01 | 3.24011981e−01 | −5.21573387e−02 | 2.99714208e−02 |
| −4.36582416e−02 | 4.91679944e−02 | −1.42996490e−01 | 3.10511291e−01 |
| 2.75761396e−01 | −8.29074159e−02 | −1.47242233e−01 | 2.79670328e−01 |
| 5.46837933e−02 | 7.95657560e−03 | −3.24126258e−02 | 3.21443796e−01 |
| −1.43464416e−01 | 3.71986091e−01 | 1.87475160e−01 | 4.46088940e−01 |
| 2.63865203e−01 | 1.29815772e−01 | 5.69940358e−02 | −2.31816828e−01 |
| −6.11542817e−03 | 1.36630297e−01 | 5.41308165e−01 | −3.20622548e−02 |
| 3.72181028e−01 | 2.02569097e−01 | 1.50282264e−01 | −1.10939257e−01 |
| −1.33250222e−01 | 8.88347924e−02 | 1.12800077e−01 | 1.39098898e−01 |
| −1.00981444e−01 | 3.28046769e−01 | 4.88320999e−02 | 1.91403050e−02 |
| 2.67404556e−01 | 3.95812020e−02 | −1.65032417e−01 | 3.19014132e−01 |
| 1.13622323e−01 | 3.80797014e−02 | −2.57081864e−03 | 2.50789374e−01 |
| 2.69420505e−01 | 1.79716960e−01 | −9.61446986e−02 | 6.25394210e−02 |
| 3.13088834e−01 | 2.48467103e−01 | 2.21966326e−01 | 9.65732187e−02 |
| 3.02694112e−01 | 4.90868330e−01 | 1.67457595e−01 | 2.16395222e−03 |
| 8.39280412e−02 | 3.07158858e−01 | −5.45615549e−05 | 2.36680314e−01 |
| −3.05572376e−01 | −3.84265482e−02 | 1.51151508e−01 | 1.77617624e−01 |
| 6.38585627e−01 | 2.52896845e−01 | 2.55055755e−01 | 1.65205017e−01 |
| 1.74090862e−01 | 7.51077682e−02 | 3.40727448e−01 | −2.44903639e−01 |
| 2.60842264e−01 | 1.08592376e−01 | 1.55465841e−01 | 5.89524284e−02 |
| −4.31580216e−01 | −1.88631862e−02 | −1.11995332e−01 | 7.75950998e−02 |
| 1.82091579e−01 | −1.61702052e−01 | 4.87179905e−01 | 9.05189589e−02 |
| 3.50315459e−02 | 1.15737960e−01 | 6.71143591e−01 | 3.02816749e−01 |
| 1.68919027e−01 | −1.96331695e−01 | 2.56897986e−01 | 2.69723445e−01 |
| 2.91839063e−01 | 6.04519367e−01 | 6.96258396e−02 | −1.90463454e−01 |
| −3.05183232e−01 | −1.37017025e−02 | 2.24319324e−01 | 3.94601554e−01 |
| −1.22735955e−01 | 2.79131085e−01 | 2.53255963e−01 | 1.31794751e−01 |
| 5.86095989e−01 | −1.35957897e−01 | 2.42942125e−01 | 3.38655561e−01 |
| −1.94475263e−01 | 8.92461389e−02 | 4.32018727e−01 | −1.69883147e−01 |
| −1.50560483e−01 | −1.48584053e−01 | −5.45311607e−02 | −5.85083067e−02 |
| −6.18697926e−02 | 3.39535236e−01 | 2.37143472e−01 | 7.37010613e−02 |
| 3.35402489e−01 | 5.13909698e−01 | 4.81897593e−01 | 8.34879458e−01 |
| 1.19180977e−01 | −5.64078271e−01 | 4.92872983e−01 | 1.22097008e−01 |
| 1.86741631e−02 | −1.84212372e−01 | 4.89082962e−01 | 5.86636126e−01 |
| −2.94933617e−01 | 1.97744548e−01 | −1.72871351e−01 | 3.82315405e−02 |
| 2.28036314e−01 | 9.46947373e−03 | 4.76919961e−01 | 4.96790782e−02 |
| −2.95010824e−02 | 9.85280946e−02 | 3.92739736e−02 | −6.61892116e−01 |
| 5.47782719e−02 | 1.11117795e−01 | 5.31136274e−01 | −3.52311701e−01 |
| 1.64534196e−01 | −4.46172357e−02 | −3.48903351e−02 | −1.89284593e−01 |
| −1.05035506e−01 | 1.89281255e−01 | 1.58521175e−01 | 9.25122872e−02 |
| −3.18876296e−01 | 2.53549337e−01 | 1.72991320e−01 | 2.00545922e−01 |
| 3.75118822e−01 | 6.53156638e−02 | 9.18654725e−02 | 4.76543866e−02 |
| 3.29297155e−01 | 1.76999211e−01 | −1.27560198e−01 | 2.22633854e−02 |
| 4.34492856e−01 | −1.24724619e−01 | 5.15253767e−02 | −1.51800171e−01 |
| 4.50845063e−01 | −1.42221645e−01 | 3.66079569e−01 | −5.65887243e−02 |
| 8.42071138e−03 | 2.47043192e−01 | −7.86922127e−02 | 1.96433634e−01 |
| −1.56085968e−01 | 1.62332192e−01 | 1.62723139e−01 | 4.02175516e−01 |
| 1.49787784e−01 | 5.74760795e−01 | 1.97018862e−01 | 1.03308149e−01 |
| −1.24250010e−01 | 3.03777218e−01 | 2.01147422e−01 | 3.48563910e−01 |
| 4.40808803e−01 | 2.25449324e−01 | 2.38775462e−01 | 9.77436379e−02 |
| 6.87895641e−02 | 1.61043666e−02 | 4.46736723e−01 | 1.75744370e−01 |
| 3.00763637e−01 | 5.19881189e−01 | 3.52058738e−01 | 7.74709880e−02 |
| 4.95247655e−02 | −3.61293368e−03 | 2.55622745e−01 | 2.04875305e−01 |
| 3.64192992e−01 | −3.34517330e−01 | 2.84336030e−01 | 1.03498235e−01 |
| −7.54320845e−02 | 1.38691189e−02 | −3.01848233e−01 | 5.40121123e−02 |
| 3.90942752e−01 | 8.30001384e−02 | −1.62851810e−02 | 3.86646241e−01 |
| 5.44723235e−02 | 3.37616295e−01 | 1.75189063e−01 | 2.89356738e−01 |
| −5.01548946e−02 | −2.02253480e−02 | 4.71727937e−01 | 6.93295121e−01 |
| −1.25191361e−01 | −6.67585209e−02 | 2.21066833e−01 | −2.87360668e−01 |
| 8.77611637e−02 | 7.43534276e−03 | 1.06478520e−01 | 2.50251383e−01 |
| 2.30751425e−01 | 9.84039381e−02 | −4.75816205e−02 | 2.31370524e−01 |
| 3.58798146e−01 | −5.44047296e−01 | 4.66939881e−02 | 3.93326730e−01 |
| 2.79213965e−01 | 3.81510168e−01 | −1.77390128e−01 | 4.58193034e−01] |
| [5.55926800e−01 | 7.10408270e−01 | 9.71809626e−01 | 5.86169124e−01 |
| 1.30854774e−00 | 1.65980831e−01 | 3.39506030e−01 | 7.06156015e−01 |
| 1.75008968e−01 | 7.27686703e−01 | 5.12395859e−01 | 1.96398771e−00 |
| 1.19390261e−00 | 7.69575953e−01 | 6.18452370e−01 | 1.15345895e−00 |
| 1.13412595e−00 | −1.34345457e−01 | −2.27961764e−01 | 2.16454923e−01 |

TABLE W$_h^1$-continued

| | | | |
|---|---|---|---|
| 5.94427645e−01 | 3.42358835e−02 | 1.05038238e−00 | 1.67178974e−01 |
| 9.01451051e−01 | 9.38240349e−01 | 2.15010017e−01 | 6.32235467e−01 |
| 7.54284203e−01 | 4.59131420e−01 | 1.02852091e−01 | 5.79404533e−01 |
| 1.30709434e−00 | 7.63193965e−01 | 9.87069130e−01 | −1.04301274e−01 |
| 2.38966686e−03 | 6.50415182e−01 | 3.84274393e−01 | 8.36809635e−01 |
| 1.11817598e−00 | 9.66839314e−01 | 1.68103516e−00 | 8.10037374e−01 |
| 2.54713118e−01 | 5.74950814e−01 | 5.37991166e−01 | 5.16924381e−01 |
| 1.25703180e−00 | 5.55855393e−01 | 3.41725767e−01 | 1.06311452e−00 |
| 2.95751780e−01 | 6.52379453e−01 | 9.77014661e−01 | 4.06702876e−01 |
| 7.58187532e−01 | 1.31206393e−01 | 2.68543541e−01 | −1.08107723e−01 |
| 3.32015753e−01 | 7.89147139e−01 | 7.38987386e−01 | 8.88905048e−01 |
| 8.02899182e−01 | 1.07069123e−00 | 5.11734903e−01 | 2.49221951e−01 |
| 7.91458130e−01 | −2.75010824e−01 | 1.56206101e−01 | 1.39900632e−02 |
| 8.39258611e−01 | 4.47810888e−01 | 2.40689367e−01 | 6.34854555e−01 |
| 7.56438792e−01 | 2.30954569e−02 | 6.66657627e−01 | −3.43271494e−02 |
| 9.28971648e−01 | 3.74056697e−01 | 4.57699075e−02 | 7.33603597e−01 |
| 3.56511548e−02 | 9.58790332e−02 | 4.00647134e−01 | 1.23942658e−01 |
| 7.55247772e−01 | −7.64864087e−01 | 9.89519477e−01 | −7.70262599e−01 |
| 8.86656106e−01 | 1.27200055e−00 | 7.18974769e−01 | 9.87935439e−02 |
| 5.09523869e−01 | −2.11297810e−01 | −4.22147483e−01 | 1.74688303e−00 |
| 6.09784484e−01 | 6.16265476e−01 | 1.87773839e−01 | 1.41310200e−01 |
| 2.60475218e−01 | 5.22311449e−01 | 5.82591355e−01 | 1.23791778e−00 |
| 8.64701033e−01 | 8.37193906e−01 | 6.06065512e−01 | 1.07271039e−00 |
| 7.07682252e−01 | 8.82187188e−01 | 1.05726278e−00 | 3.28790784e−01 |
| 1.00846159e−00 | 3.79329264e−01 | 1.01255134e−01 | 2.32189819e−01 |
| 2.86583841e−01 | 1.33627737e−00 | 2.53704488e−01 | 5.28100252e−01 |
| 7.08630800e−01 | 6.26618445e−01 | 3.87233347e−01 | 7.49975741e−01 |
| 1.73769072e−01 | 4.25803781e−01 | 1.12109400e−01 | 4.71347451e−01 |
| 3.50916862e−01 | 5.90048373e−01 | 1.00842643e−00 | 6.80015206e−01 |
| 7.40964055e−01 | 9.20715153e−01 | 4.81566548e−01 | 8.84187520e−01 |
| 5.82701445e−01 | 1.49069965e−01 | 3.50356191e−01 | 5.86975634e−01 |
| 5.06031930e−01 | 4.18766588e−01 | 3.22194695e−01 | 8.08743894e−01 |
| 9.77711916e−01 | 4.34164286e−01 | 6.07189178e−01 | 3.41571003e−01 |
| 4.93421972e−01 | 1.54122368e−01 | 1.27600610e−00 | 5.69579005e−01 |
| −2.24701911e−01 | 1.45064726e−01 | 8.03588390e−01 | 2.17424959e−01 |
| 8.19449008e−01 | 9.75712657e−01 | 8.53157043e−01 | 4.79071945e−01 |
| 5.31492531e−01 | 3.70496541e−01 | 9.21649218e−01 | 4.71361578e−01 |
| 4.86183375e−01 | 9.31380332e−01 | 4.94809300e−01 | 6.75674677e−01 |
| 1.94480687e−01 | 1.13950241e−00 | 6.37964666e−01 | 5.33041120e−01 |
| 6.58874035e−01 | 1.62317321e−01 | 2.76329666e−01 | 4.92350012e−01 |
| 8.45565856e−01 | 2.03981295e−01 | 4.07304049e−01 | 5.45536280e−01 |
| 6.00697160e−01 | −7.74334222e−01 | −3.61179858e−01 | 1.14410973e−00 |
| 1.10093206e−01 | 1.00802910e−00 | 2.73541063e−01 | 1.15711951e−00 |
| 6.67957246e−01 | 6.34203315e−01 | 3.38138551e−01 | 4.20847327e−01 |
| 4.36262608e−01 | 1.26466286e−00 | 1.35379449e−01 | 5.83288550e−01 |
| 1.08195543e−00 | 5.88646650e−01 | 5.96655011e−01 | 2.06101298e−01 |
| −1.75815836e−01 | 7.33092725e−01 | 2.17150629e−01 | 7.90174484e−01 |
| 1.00082326e−00 | 9.91007328e−01 | 1.13249540e−00 | 1.37536657e−00 |
| 8.59190762e−01 | 5.94972610e−01 | 1.52252123e−01 | 6.36616409e−01 |
| 2.49562263e−01 | 7.26815939e−01 | 1.02124023e−00 | −2.55091399e−01 |
| 9.01963234e−01 | 5.15284836e−02 | 4.83129650e−01 | −5.36317900e−02 |
| 6.59132540e−01 | 5.89284122e−01 | 3.66299301e−01 | 1.16646898e−00 |
| 6.24013305e−01 | 8.54428947e−01 | 8.60185623e−01 | 7.10146248e−01 |
| 3.81726325e−01 | 1.30590069e−00 | 9.34213758e−01 | 8.26345536e−01 |
| 4.33210373e−01 | 9.68938351e−01 | 2.72600502e−01 | 8.50208521e−01 |
| 3.65704030e−01 | 1.17105651e−00 | 5.53252697e−01 | 8.26823533e−01 |
| 1.20749557e−00 | 6.20359957e−01 | 3.21099877e−01 | −5.94338812e−02 |
| 9.44640934e−01 | 8.67396116e−01 | 6.93732202e−01 | 1.20342517e−00 |
| 2.90236324e−01 | 5.05105853e−01 | 4.37403023e−01 | 5.34034312e−01] |
| [2.99855441e−01 | 3.95853817e−02 | 3.12436998e−01 | 3.00064921e−01 |
| −5.70401363e−02 | 2.81252742e−01 | 3.41940284e−01 | −3.39468986e−01 |
| 2.56263036e−02 | 5.15568376e−01 | −1.72301203e−01 | 2.93368042e−01 |
| 2.19395876e−01 | 1.87071696e−01 | 1.38464436e−01 | 1.95352167e−01 |
| 1.66314051e−01 | −1.29350901e−01 | 5.74350059e−02 | −3.03618848e−01 |
| −4.30425853e−02 | −2.41017304e−02 | 2.26352550e−02 | −2.92124855e−03 |
| 3.07389051e−02 | −9.23023224e−02 | 4.00948375e−02 | −3.01568806e−01 |
| 4.00106274e−02 | −2.27391973e−01 | 2.92022169e−01 | −6.95076436e−02 |
| 6.04239583e−01 | −1.44786119e−01 | −3.77687439e−02 | −1.54203594e−01 |
| 1.76561594e−01 | −6.82313442e−02 | 8.29019919e−02 | 1.56778473e−01 |
| −1.56269073e−01 | −2.94494117e−03 | 2.21836716e−01 | 1.36436224e−01 |
| 3.82204466e−02 | −4.22942564e−01 | 5.86486533e−02 | −9.62991565e−02 |
| 2.63594270e−01 | 3.69255513e−01 | 3.24057519e−01 | 4.06167768e−02 |
| 5.10852277e−01 | −4.01374549e−02 | 2.19090432e−01 | −6.95517287e−02 |
| −3.34659338e−01 | 2.80601662e−02 | 3.12349409e−01 | 4.78792675e−02 |
| −1.46695673e−01 | 5.39997071e−01 | −8.30093846e−02 | 1.46772154e−01 |
| −4.17279415e−02 | 3.77661318e−01 | 3.51624310e−01 | −5.10605685e−02 |
| 2.11641833e−01 | 2.42261291e−01 | 1.88846543e−01 | −1.31048560e−01 |
| 5.52147031e−01 | −2.57489793e−02 | −2.45783091e−01 | 2.31788471e−01 |
| 6.73027709e−02 | 1.62293181e−01 | −8.45224634e−02 | 3.04962732e−02 |
| 1.99627191e−01 | 1.82625115e−01 | 1.50694400e−01 | 2.30005667e−01 |

TABLE $W_h^1$-continued

| | | | |
|---|---|---|---|
| 1.85318559e−01 | −3.60252112e−01 | −2.11763501e−01 | −1.46012202e−01 |
| −1.88243210e−01 | −3.48228961e−01 | 3.12462747e−01 | 1.06793001e−01 |
| 2.67905444e−01 | 1.74404919e−01 | 1.81793571e−01 | 9.00443792e−01 |
| 2.71325588e−01 | 9.18981284e−02 | 4.99617308e−02 | 7.98120070e−03 |
| 6.32161438e−01 | −1.40834600e−01 | −1.72538459e−02 | 1.90200955e−01 |
| −4.76969600e−01 | 2.09265575e−01 | −3.11159603e−02 | 6.72842935e−02 |
| 7.04878211e−01 | 1.81106962e−02 | 2.50887394e−01 | 3.39239538e−01 |
| 4.75657463e−01 | 1.11403421e−01 | 6.85542673e−02 | 2.69024283e−01 |
| 4.02039677e−01 | 3.82770687e−01 | 2.23935813e−01 | 4.70054507e−01 |
| −1.43377006e−01 | −1.74513943e−02 | −3.40018794e−02 | 2.89140671e−01 |
| 2.54364491e−01 | −1.13548338e−01 | 3.85137312e−02 | 4.06004429e−01 |
| 7.57485256e−02 | 1.30088121e−01 | 2.21645251e−01 | 2.44622603e−01 |
| −1.10653877e−01 | 1.18211024e−01 | −1.40098259e−01 | 2.12643310e−01 |
| −8.97744447e−02 | 8.92514959e−02 | 1.99726477e−01 | 3.96618843e−01 |
| −8.49973857e−02 | 1.34019241e−01 | −8.98236334e−02 | 2.29936112e−02 |
| 4.65017974e−01 | 3.27042758e−01 | 2.15512887e−01 | 7.67437220e−01 |
| −2.11552233e−02 | 2.45925322e−01 | 2.77178526e−01 | −5.44891246e−02 |
| −1.80115066e−02 | −2.39170328e−01 | 3.31127137e−01 | −3.10748387e−02 |
| −1.35894557e−02 | 5.84067442e−02 | −1.01849169e−01 | −1.15027383e−01 |
| 2.28004411e−01 | 2.37699330e−01 | 1.76435575e−01 | 1.84659258e−01 |
| −1.03098504e−01 | 7.33650476e−02 | 3.68766785e−01 | 2.43214130e−01 |
| 2.35283285e−01 | −2.21291929e−01 | 2.71679282e−01 | 6.78900704e−02 |
| 1.70510367e−01 | 3.21421623e−01 | 2.41439894e−01 | 2.86891788e−01 |
| −4.58356515e−02 | 2.05641448e−01 | 3.83706987e−01 | 3.08350712e−01 |
| 5.08734547e−02 | 7.71319643e−02 | 5.27685471e−02 | 3.21719736e−01 |
| 4.62092698e−01 | −4.06534262e−02 | −1.46038935e−01 | 1.44441873e−01 |
| 2.19854772e−01 | 1.47625342e−01 | 2.70437568e−01 | −1.43091723e−01 |
| −1.65827349e−01 | 2.39089817e−01 | 1.80397093e−01 | 3.82816702e−01 |
| 2.65797824e−01 | −9.44972932e−02 | −8.10556114e−02 | 2.54620850e−01 |
| 2.22666398e−01 | 1.10552087e−01 | −3.48838279e−03 | 2.68732160e−01 |
| 2.31140479e−01 | 4.43496138e−01 | 2.20217660e−01 | 4.23380256e−01 |
| −1.31134428e−02 | 4.82126832e−01 | 3.11729133e−01 | 7.71178529e−02 |
| 8.38767529e−02 | 1.96131513e−01 | 1.97797969e−01 | 6.50465310e−01 |
| 2.00348303e−01 | 2.84834176e−01 | 1.79966718e−01 | −6.75111040e−02 |
| 4.84888524e−01 | −1.18460916e−01 | 9.35860723e−02 | 1.90850735e−01 |
| 1.85912117e−01 | 3.25411856e−01 | 6.58650398e−01 | −1.26509234e−01 |
| 1.94408000e−01 | 1.16804317e−01 | −1.95291609e−01 | 1.31419793e−01 |
| 4.03648257e−01 | −2.73154322e−02 | 2.76024938e−01 | 3.06599289e−01 |
| −1.83056504e−01 | −2.44640216e−01 | 7.51423240e−02 | −4.04286325e−01 |
| 1.16668232e−01 | 2.11464018e−01 | −6.12840578e−02 | 2.01993957e−01 |
| 2.88208663e−01 | 5.92038572e−01 | 4.86113250e−01 | 9.34537277e−02 |
| −5.99368811e−01 | 2.95422614e−01 | 8.17118511e−02 | 2.45532215e−01 |
| 6.44312128e−02 | 2.38164604e−01 | −9.41680372e−03 | 1.12150647e−01] |
| [1.79853812e−01 | 2.08635673e−01 | 8.85526538e−02 | −2.95874216e−02 |
| 1.07174471e−01 | 5.09822927e−02 | 3.45782703e−03 | 1.45664677e−01 |
| 9.58634913e−02 | 1.19545765e−01 | −3.67512852e−02 | 2.26738676e−01 |
| 2.41913155e−01 | 4.05740403e−02 | 1.36242986e−01 | 3.20741385e−01 |
| 4.77466673e−01 | −1.33476838e−01 | 2.43550222e−02 | 2.12436486e−02 |
| 4.01553303e−01 | 3.10479850e−01 | 4.17471677e−01 | 1.53832555e−01 |
| 1.18737276e−04 | 4.41338688e−01 | −4.24486026e−01 | −1.35587364e−01 |
| 1.73145086e−01 | 4.28143650e−01 | 2.93544054e−01 | 1.07167035e−01 |
| −2.54925322e−02 | −5.05727082e−02 | 1.13991506e−01 | 9.30813178e−02 |
| 2.57820576e−01 | −3.90252173e−01 | 9.52228606e−02 | −9.63599980e−03 |
| −1.34884790e−01 | −2.26019938e−02 | 4.90742952e−01 | 4.28663284e−01 |
| −2.52997149e−02 | −5.88312820e−02 | 2.41523072e−01 | −1.34313861e−02 |
| −1.44017637e−01 | 3.57466787e−01 | 1.30370691e−01 | −2.87079103e−02 |
| 3.50346774e−01 | 1.97977170e−01 | 2.17084914e−01 | −1.97110429e−01 |
| −3.39825541e−01 | −1.18568270e−01 | 2.14291647e−01 | 3.24265301e−01 |
| 4.31815200e−02 | 1.21927068e−01 | 2.19907463e−01 | −1.52705923e−01 |
| −2.63524264e−01 | 3.59407306e−01 | 5.50603926e−01 | 3.80494893e−01 |
| 4.40415233e−01 | 1.76631391e−01 | 3.62652354e−02 | −3.72778416e−01 |
| 2.33070031e−01 | −5.21657206e−02 | 1.27182171e−01 | 5.34034073e−02 |
| 3.84662896e−02 | 3.30269068e−01 | −1.71913475e−01 | 1.61107369e−01 |
| 6.14467204e−01 | 9.13624763e−02 | 2.08049472e−02 | 2.67382786e−02 |
| 8.55529401e−03 | −5.83928704e−01 | −4.53169756e−02 | 4.57529016e−02 |
| −3.79669756e−01 | −1.79532990e−01 | 3.00663739e−01 | 2.09782541e−01 |
| 2.72649705e−01 | 1.11487940e−01 | −8.43687356e−02 | 2.89018840e−01 |
| 1.17236093e−01 | 1.16538122e−01 | −1.61217242e−01 | 6.92994073e−02 |
| 3.23556542e−01 | −6.95274398e−02 | 5.12445420e−02 | 5.29107690e−01 |
| 1.70699671e−01 | 3.13738137e−01 | −3.57601233e−02 | 3.02736402e−01 |
| 4.98068780e−01 | −8.94922838e−02 | 7.88437128e−02 | 2.68209487e−01 |
| 6.32290393e−02 | −9.66319293e−02 | 3.08671802e−01 | 4.70839173e−01 |
| 2.88454592e−01 | −8.90046284e−02 | 2.06374079e−02 | 1.23683222e−01 |
| −3.16439837e−01 | −7.88210854e−02 | 1.34066239e−01 | −2.39255205e−02 |
| 2.25188881e−01 | −5.49044646e−02 | −5.27545035e−02 | −4.28338943e−04 |
| 2.70548552e−01 | −2.01479662e−02 | 2.54125684e−01 | 6.29986286e−01 |
| 5.22652268e−02 | 5.34963667e−01 | 4.08805050e−02 | 7.48899460e−01 |
| 1.39736250e−01 | 2.55474150e−01 | −2.30554957e−02 | 4.61392313e−01 |
| 1.18302718e−01 | 2.12835163e−01 | −1.74847573e−01 | 2.62580931e−01 |
| 2.60210723e−01 | 1.90384984e−02 | 1.74314901e−01 | 4.68917102e−01 |

TABLE $W_h^1$-continued

| | | | |
|---|---|---|---|
| 4.68184829e−01 | 1.80612579e−02 | 7.19076157e−01 | −6.25751466e−02 |
| 9.43518132e−02 | −2.24062875e−01 | 1.61687672e−01 | −1.56995922e−01 |
| −1.91840753e−01 | −2.24823490e−01 | 3.15907776e−01 | −3.66671719e−02 |
| −1.50926366e−01 | 2.91612834e−01 | 2.49526426e−01 | 1.56111673e−01 |
| 4.62855190e−01 | 2.37009019e−01 | −3.10412273e−02 | 1.19636431e−01 |
| 2.58406550e−01 | −2.97258377e−01 | 2.95849115e−01 | 5.70794865e−02 |
| 3.48952413e−01 | −9.36064348e−02 | 5.70892274e−01 | 4.70736213e−02 |
| −2.09545851e−01 | 2.41266981e−01 | 1.57217309e−01 | 2.32891798e−01 |
| 1.90147385e−03 | −1.39535144e−01 | 3.84465493e−02 | 4.32417363e−01 |
| 1.97644413e−01 | 3.83435525e−02 | 2.30292529e−01 | 4.44851458e−01 |
| −2.48415917e−02 | −7.94876739e−02 | 2.45961025e−01 | 2.61737466e−01 |
| −1.52138188e−01 | 6.70805812e−02 | −9.98587161e−02 | 4.77919169e−02 |
| 6.08004257e−02 | −8.29326063e−02 | −1.44056045e−02 | 2.35403895e−01 |
| 1.98925838e−01 | −1.97835453e−03 | −3.11812460e−01 | 3.40614140e−01 |
| 3.22890550e−01 | −2.54753530e−01 | 2.18316659e−01 | 6.02064967e−01 |
| −3.98721471e−02 | 9.38840955e−02 | 1.75162464e−01 | 7.00639039e−02 |
| 3.65533084e−01 | 2.34195650e−01 | 6.95254430e−01 | 2.42225647e−01 |
| 4.21293408e−01 | 5.63404299e−02 | 4.58020777e−01 | −1.29111677e−01 |
| 5.53098321e−02 | 7.02598393e−02 | −1.62268847e−01 | −4.77493275e−03 |
| 1.96523778e−02 | 4.68753099e−01 | −1.73809260e−01 | 3.04008186e−01 |
| 3.89243513e−01 | −3.74647416e−02 | 2.03984946e−01 | 2.85099089e−01 |
| −8.63796473e−02 | −5.34394383e−01 | 2.93238848e−01 | 3.81226629e−01 |
| −2.13728920e−01 | 1.21616468e−01 | −2.54579902e−01 | −1.89447239e−01 |
| −2.49401793e−01 | 9.27020982e−02 | −1.27907321e−01 | −5.66312075e−02 |
| 2.04751074e−01 | 1.85157433e−01 | 4.18183804e−01 | −3.67265999e−01 |
| −3.42180580e−02 | 1.30477771e−01 | 3.30147535e−01 | 4.33149636e−01 |
| −1.26599535e−01 | 7.68320337e−02 | 3.71754356e−02 | 7.03018382e−02] |
| [1.52863070e−01 | 3.27577144e−01 | −1.01545617e−01 | 6.73466682e−01 |
| 1.17923230e−01 | 3.00105125e−01 | 6.53172016e−01 | 6.47839606e−01 |
| 2.38739923e−01 | 3.37842964e−02 | 4.83000726e−01 | 1.27092870e−02 |
| 3.09435517e−01 | −2.62350962e−02 | 5.68403490e−02 | −2.58502215e−01 |
| 4.60679740e−01 | −4.72350605e−02 | 1.91965606e−02 | 3.35811257e−01 |
| 3.78616005e−01 | 4.53600407e−01 | 3.10797185e−01 | 4.74186748e−01 |
| 4.03508484e−01 | 5.87940276e−01 | 4.66251969e−02 | −1.91447690e−01 |
| 4.70612019e−01 | 2.74111480e−01 | 2.46355101e−03 | 8.74758303e−01 |
| 1.52230889e−01 | 4.31745380e−01 | 4.81620282e−01 | 2.51591861e−01 |
| 3.40962201e−01 | 4.51719493e−01 | 2.73590505e−01 | 5.61002791e−01 |
| 9.73628536e−02 | 3.16109896e−01 | 3.87419552e−01 | −5.09397388e−02 |
| 9.86084938e−01 | −1.03691621e−02 | 3.70653272e−01 | 3.91774744e−01 |
| 1.46223187e−01 | 4.53088582e−01 | 2.19526947e−01 | 1.83686763e−01 |
| 4.07813191e−01 | 8.94553661e−02 | −2.01065749e−01 | 3.25324774e−01 |
| 3.60979050e−01 | 2.54644245e−01 | 5.58509827e−01 | 1.08887725e−01 |
| 4.06678677e−01 | 2.89247662e−01 | 3.49331260e−01 | 1.38588712e−01 |
| 4.02564913e−01 | 2.62705481e−01 | 3.25277627e−01 | 9.02122632e−02 |
| 4.43595082e−01 | 2.57358938e−01 | 4.13144052e−01 | −1.57771796e−01 |
| 4.77860212e−01 | 2.42358968e−01 | 4.31894094e−01 | 2.13266879e−01 |
| 2.95474976e−01 | 4.63915437e−01 | 4.92682338e−01 | 4.53666449e−01 |
| 3.03561590e−03 | 6.69764578e−01 | 1.60765484e−01 | 2.67393533e−02 |
| 2.23910391e−01 | 4.28184748e−01 | 1.89249992e−01 | 9.25083365e−03 |
| 1.86938688e−01 | −1.44420773e−01 | 1.53204322e−01 | 9.82094705e−02 |
| 3.93053621e−01 | −7.89661929e−02 | 3.81484449e−01 | 5.56469560e−01 |
| 8.29063579e−02 | 2.55026102e−01 | −1.39660140e−01 | 1.54895648e−01 |
| 3.45180452e−01 | 6.38534904e−01 | 2.66245365e−01 | 2.58342177e−01 |
| 2.25936383e−01 | 1.25506461e−01 | 2.42839143e−01 | 5.46981156e−01 |
| −1.37283325e−01 | 6.34750068e−01 | −7.57528096e−03 | 6.76941574e−02 |
| 7.89504409e−01 | 2.36401424e−01 | 9.40335616e−02 | −4.26163167e−01 |
| −1.59983158e−01 | 4.95224595e−01 | 5.90148628e−01 | 3.40746433e−01 |
| 7.92242646e−01 | 2.70829380e−01 | −1.86108664e−01 | 2.09797427e−01 |
| 5.05200982e−01 | 8.77450228e−01 | 7.34810904e−02 | 3.51008773e−01 |
| 2.84055144e−01 | 5.69608748e−01 | −2.21876219e−01 | 2.97544926e−01 |
| 6.70696139e−01 | 1.87361181e−01 | 6.73408136e−02 | 1.79095343e−01 |
| 3.16470176e−01 | 2.10345566e−01 | 3.56141418e−01 | 4.64809418e−01 |
| 8.04053724e−01 | 5.46072185e−01 | 2.91773140e−01 | 7.68099487e−01 |
| 6.45211861e−02 | −5.27765043e−02 | 6.57212794e−01 | 1.91927776e−01 |
| 1.42449155e−01 | 4.72162329e−02 | 3.00993353e−01 | 6.30330920e−01 |
| 2.11441949e−01 | 6.37932643e−02 | 5.47507823e−01 | 2.30432481e−01 |
| 1.73716292e−01 | 3.70874852e−01 | 2.61739008e−02 | 4.56000298e−01 |
| 4.62797135e−01 | 2.02996567e−01 | −8.33295435e−02 | 8.71356010e−01 |
| 5.19815087e−01 | −1.22108966e−01 | 6.06518447e−01 | 2.06870493e−02 |
| 1.53089629e−03 | 1.82432726e−01 | 2.73171693e−01 | 3.78621340e−01 |
| 7.64959753e−02 | 3.23780745e−01 | −3.66542190e−02 | −2.45729238e−02 |
| 1.14793405e−01 | −1.02897938e−02 | 5.80131859e−02 | −2.46447861e−01 |
| 1.14049748e−01 | 1.65703759e−01 | 2.34745607e−01 | 1.11578450e−01 |
| 5.91388159e−02 | 3.01075786e−01 | 2.92656541e−01 | 4.15409803e−01 |
| −1.75163522e−02 | 5.86637855e−01 | 4.87198710e−01 | 3.17746550e−01 |
| 2.03671217e−01 | 4.30828810e−01 | −3.68643731e−01 | 2.02456906e−01 |
| 6.33976877e−01 | 5.03911316e−01 | 7.54399523e−02 | 1.31477579e−01 |
| −3.30438912e−01 | −1.34275958e−01 | 1.32667154e−01 | 1.40859440e−01 |
| 2.66811937e−01 | 2.06358254e−01 | −2.61551328e−02 | 4.61831033e−01 |
| 7.49718189e−01 | 7.82231867e−01 | 2.83495575e−01 | 9.38416898e−01 |

TABLE $W_h^1$-continued

| | | | |
|---|---|---|---|
| 5.47313690e−01 | 3.32375377e−01 | −2.12231070e−01 | 6.01326585e−01 |
| 2.80744344e−01 | 6.62491798e−01 | 3.13717932e−01 | −5.11458278e−01 |
| −2.74670689e−04 | 2.63943851e−01 | 4.93918598e−01 | 1.56156436e−01 |
| 1.52295157e−01 | 2.98146576e−01 | 3.90400559e−01 | 2.86955118e−01 |
| 4.37780112e−01 | 4.00890559e−01 | 3.31439167e−01 | 4.97690707e−01 |
| 4.15191203e−01 | −3.02825421e−01 | 2.85844475e−01 | 6.53396904e−01 |
| −4.28123735e−02 | 2.96965003e−01 | 3.48363757e−01 | −1.21499099e−01 |
| −2.82868654e−01 | −1.02189146e−01 | 1.52987778e−01 | 2.97225416e−01 |
| 1.41849428e−01 | 1.12175774e−02 | 2.51549259e−02 | 2.73012668e−01 |
| 4.24885571e−01 | 7.51697421e−02 | 1.51353581e−02 | 4.94215578e−01 |
| −2.15971190e−02 | 3.06491107e−01 | 2.47661501e−01 | 2.06529349e−01] |
| [−1.40490264e−01 | 3.83529328e−02 | 4.79135722e−01 | 3.50259632e−01 |
| 1.09249800e−01 | 2.22724050e−01 | 3.59881490e−01 | 2.19574213e−01 |
| 5.30133769e−02 | −1.73573419e−01 | 1.92520174e−03 | 3.74384522e−01 |
| 3.14760953e−01 | −1.08141579e−01 | −8.17822441e−02 | −3.94171244e−03 |
| −1.76286176e−01 | 6.23771101e−02 | 4.74756062e−02 | −9.19522718e−02 |
| −2.60956675e−01 | 1.03860535e−01 | 1.92364305e−01 | 2.79325545e−01 |
| 3.11567694e−01 | 1.53493816e−02 | −1.06321424e−01 | −1.24736696e−01 |
| −1.04911923e−01 | 2.57059395e−01 | 4.66476887e−01 | 1.51314870e−01 |
| 1.16692826e−01 | −3.71538661e−02 | −4.22019571e−01 | 4.31683868e−01 |
| 4.37224567e−01 | 3.00972581e−01 | 2.04073079e−02 | 1.55493543e−01 |
| 3.91512334e−01 | 2.14489982e−01 | −1.24954745e−01 | −1.16022490e−01 |
| −1.23069771e−01 | 3.41507047e−01 | 1.59237772e−01 | −2.47773286e−02 |
| 5.74747175e−02 | 4.34892513e−02 | 6.45274743e−02 | −7.58988783e−02 |
| 2.35660493e−01 | −1.48573428e−01 | −5.76718114e−02 | −2.95477211e−01 |
| −1.22667842e−01 | 5.05479276e−01 | 5.51042974e−01 | 2.13284716e−01 |
| 2.58007646e−01 | −6.19352236e−02 | 3.05428892e−01 | 9.89017487e−02 |
| 6.85673356e−02 | 3.69868547e−01 | 2.00842798e−01 | 1.37418374e−01 |
| 7.48307407e−02 | 3.45830709e−01 | 3.70419532e−01 | −1.89532548e−01 |
| 5.01523614e−01 | 3.34918410e−01 | −6.43090531e−02 | −1.01397984e−01 |
| 9.50804502e−02 | 2.07352638e−01 | 5.22609770e−01 | −2.60739803e−01 |
| 2.49103382e−01 | 2.04703495e−01 | 9.68108699e−02 | 1.57085061e−01 |
| 1.80445075e−01 | 2.11924359e−01 | 3.03307265e−01 | 4.87636238e−01 |
| 5.03422916e−02 | 1.50219262e−01 | 2.45647177e−01 | −3.77904475e−02 |
| 1.62475571e−01 | 4.84411091e−01 | 1.28521085e−01 | 2.56670624e−01 |
| −3.92920636e−02 | 2.38954723e−01 | 3.11445117e−01 | 3.28550041e−01 |
| 2.28911377e−02 | 2.46559545e−01 | 7.80329108e−02 | −1.61515363e−02 |
| −3.20829004e−01 | 2.17098445e−01 | 6.93363324e−02 | 1.45333350e−01 |
| −2.48877844e−03 | 4.16456372e−01 | 4.80067313e−01 | 2.01342613e−01 |
| 4.41229224e−01 | −1.36390217e−02 | 1.15819678e−01 | 5.04696906e−01 |
| −3.92040238e−02 | 3.14583294e−02 | 2.63487399e−01 | 3.74795258e−01 |
| 1.40306642e−02 | 2.36737654e−01 | 2.94835180e−01 | 3.38698030e−01 |
| 2.69008994e−01 | −2.38109097e−01 | −5.90482317e−02 | −2.27203906e−01 |
| 4.73183662e−01 | 4.91805226e−01 | −1.63705200e−01 | 3.97731990e−01 |
| 1.31767705e−01 | 3.69367629e−01 | −2.36379996e−01 | −2.05282167e−01 |
| 4.72152263e−01 | −2.84639120e−01 | 5.82744367e−01 | 5.50043762e−01 |
| 2.01024503e−01 | −1.85515024e−02 | −4.20859680e−02 | −6.83519095e−02 |
| 1.70109302e−01 | −1.15224391e−01 | 1.25979437e−02 | −1.91633612e−01 |
| 6.59633130e−02 | 4.36803222e−01 | −1.71791539e−02 | 1.82127789e−01 |
| 5.59216365e−02 | 1.74320005e−01 | 8.93834531e−02 | −6.02706373e−02 |
| −3.14672440e−01 | 2.52240986e−01 | 2.33302623e−01 | 1.75184663e−02 |
| −1.75886244e−01 | 1.50766209e−01 | −1.72653601e−01 | 2.55411863e−01 |
| −1.73714414e−01 | −2.77343392e−01 | 2.88289897e−02 | 2.96936482e−01 |
| 6.88085780e−02 | 1.97947081e−01 | 8.72054249e−02 | 3.16379815e−01 |
| 4.81969297e−01 | −1.01975583e−01 | 2.99172580e−01 | −1.96399633e−03 |
| 3.95914257e−01 | −2.82768726e−01 | 4.42472130e−01 | −4.66524661e−02 |
| −3.72217029e−01 | 1.85530916e−01 | 1.08082794e−01 | 2.96672508e−02 |
| 2.11282045e−01 | 2.67733544e−01 | −1.88760504e−01 | 4.54149917e−02 |
| −3.16529311e−02 | 3.09965909e−01 | 1.19368754e−01 | −7.59941787e−02 |
| 4.01398480e−01 | 5.20948172e−01 | 1.79742321e−01 | 4.76611912e−01 |
| −2.82661729e−02 | 2.33745649e−01 | 7.08091957e−03 | 4.23657387e−01 |
| 8.26665014e−02 | 2.11267263e−01 | 3.01054388e−01 | 5.64054132e−01 |
| 2.39967793e−01 | −2.66332030e−01 | 6.86435401e−02 | 9.70508382e−02 |
| 1.54931054e−01 | 4.52933073e−01 | 1.64810762e−01 | 2.58698374e−01 |
| 2.14096069e−01 | −2.16195080e−02 | −5.98211475e−02 | 1.28021419e−01 |
| −6.79896921e−02 | −2.41486747e−02 | −9.11333635e−02 | −2.35395059e−01 |
| 3.08941066e−02 | −5.11474386e−02 | 2.09816396e−01 | −1.36471331e−01 |
| −7.97722787e−02 | 2.96884567e−01 | 2.60791063e−01 | 6.02372885e−01 |
| 3.85021240e−01 | −1.71836138e−01 | 4.39731807e−01 | 2.21347749e−01 |
| −2.51832515e−01 | −7.69963086e−01 | 3.71889442e−01 | −8.33551735e−02 |
| −1.95138067e−01 | 2.32685447e−01 | −1.51389286e−01 | −1.44706173e−01 |
| 1.89667165e−01 | 3.17585096e−02 | 3.21220487e−01 | 1.12701416e−01 |
| 3.04186165e−01 | 1.90360874e−01 | −3.82274017e−02 | 1.59461483e−01 |
| 3.18378925e−01 | 1.54477283e−01 | −3.61208171e−01 | −4.88885045e−02 |
| 4.78682034e−01 | 2.53665984e−01 | 4.11172122e−01 | 6.09045401e−02] |
| [1.08336687e−01 | 4.87142831e−01 | 1.26036957e−01 | −8.74289125e−02 |
| 2.98438281e−01 | 2.69696593e−01 | 4.16415371e−02 | 5.30960679e−01 |
| −1.24108456e−01 | 2.39257336e−01 | 4.84182388e−01 | −1.08090281e−01 |
| 3.84922586e−02 | 1.06751941e−01 | −8.14471245e−02 | −2.32800797e−01 |
| 1.72041550e−01 | 1.77200124e−01 | 3.96608353e−01 | 5.30121148e−01 |

TABLE $W_h^1$-continued

| | | | |
|---|---|---|---|
| 3.09008241e−01 | 5.19556701e−01 | 5.58813214e−01 | 4.02075440e−01 |
| 7.65037164e−02 | 6.53067768e−01 | 7.36698031e−01 | 4.53732237e−02 |
| 3.15980405e−01 | 2.73910593e−02 | 6.56753600e−01 | 4.58294451e−01 |
| 3.24797481e−01 | 3.40442419e−01 | 2.41839588e−01 | 1.53856173e−01 |
| 9.25213769e−02 | 5.87794445e−02 | 3.55502784e−01 | 5.32818735e−01 |
| 5.09051383e−01 | 4.75703180e−01 | 2.48406619e−01 | 1.26427025e−01 |
| 7.58715332e−01 | −1.17018439e−01 | 4.07658786e−01 | 3.45150918e−01 |
| 3.51824939e−01 | 3.75448823e−01 | 4.18653578e−01 | 2.20872924e−01 |
| 3.42701346e−01 | 5.04695885e−02 | 1.50149196e−01 | 1.19842902e−01 |
| −1.30628750e−01 | 6.09120307e−03 | 7.99937248e−01 | −1.16613418e−01 |
| −6.26242012e−02 | 3.82077575e−01 | 2.20547169e−01 | 7.54653364e−02 |
| 3.01872492e−01 | 2.23245129e−01 | −1.90663397e−01 | 1.01776347e−02 |
| 1.02371819e−01 | −5.27121484e−01 | 3.09147626e−01 | −6.41899168e−01 |
| 4.15079594e−01 | 6.54820576e−02 | −1.19624667e−01 | 6.03505969e−01 |
| 4.61980730e−01 | 2.96001676e−02 | 6.30422473e−01 | 7.47660995e−01 |
| 4.48933244e−01 | 3.96545380e−01 | 5.17153442e−01 | 6.10239916e−02 |
| 1.78398758e−01 | −9.19191241e−02 | −2.44878270e−02 | 3.88053387e−01 |
| 2.06181437e−01 | 1.60391375e−01 | 1.46857426e−01 | 3.19517285e−01 |
| 1.02162354e−01 | 6.21134758e−01 | 4.60811824e−01 | 3.66418004e−01 |
| −6.04206361e−02 | −2.27901768e−02 | 2.27442309e−01 | 5.99255800e−01 |
| 4.05191392e−01 | 5.61373293e−01 | 2.46679068e−01 | 1.36735095e−02 |
| 1.92883730e−01 | 5.97520053e−01 | 6.55487359e−01 | 4.55196947e−02 |
| 2.84285784e−01 | 3.29761744e−01 | 4.39575732e−01 | 2.35595509e−01 |
| 4.68226403e−01 | 1.39004439e−01 | 1.60878137e−01 | 3.31570596e−01 |
| 3.80646259e−01 | 8.97146016e−02 | 4.28203076e−01 | −1.74155980e−02 |
| 3.88427794e−01 | 5.29191554e−01 | 2.57717162e−01 | 4.92200941e−01 |
| 5.56359708e−01 | 1.57519802e−01 | 5.22305548e−01 | 2.11768046e−01 |
| 3.31265688e−01 | 3.59422714e−01 | 1.16483867e−01 | 6.98672473e−01 |
| 3.89975846e−01 | 2.72805154e−01 | 9.51397866e−02 | 3.75302136e−01 |
| 1.51632026e−01 | 1.92487419e−01 | 5.41425109e−01 | 3.32489789e−01 |
| 2.99304992e−01 | 5.40850580e−01 | 1.24169476e−01 | 3.60713542e−01 |
| 1.42329171e−01 | 9.36084762e−02 | 9.43052649e−01 | 2.27192864e−01 |
| 3.48245978e−01 | 1.38565943e−01 | 5.48377991e−01 | 3.91948253e−01 |
| 4.54113670e−02 | 4.22338933e−01 | 2.35574439e−01 | 1.02764301e−01 |
| −1.79836340e−02 | 2.41513222e−01 | 2.52857953e−01 | 8.03670362e−02 |
| 2.82413632e−01 | −8.04907605e−02 | 5.93864620e−01 | 3.64263624e−01 |
| 1.56238213e−01 | 5.51942512e−02 | 6.33849919e−01 | 2.94235110e−01 |
| 5.07438600e−01 | 6.86139405e−01 | 9.32595283e−02 | 3.11348826e−01 |
| 6.53333962e−01 | 1.44653603e−01 | 6.51975721e−02 | −6.05001487e−02 |
| 6.94270968e−01 | 5.19878626e−01 | 7.07912073e−02 | 1.08366832e−01 |
| 4.08659667e−01 | 4.16695923e−02 | 3.64171237e−01 | −2.66131829e−03 |
| 2.68729389e−01 | 1.37551963e−01 | 2.71722853e−01 | 7.83501267e−01 |
| 7.62637854e−02 | −2.03476753e−02 | 7.82018676e−02 | 4.10195827e−01 |
| 4.79927689e−01 | 1.82530992e−02 | 3.01024050e−01 | 3.11070114e−01 |
| 4.38228726e−01 | 1.20809093e−01 | 2.80199163e−02 | 2.04633355e−01 |
| 4.94422913e−01 | 1.92002416e−01 | 3.44702840e−01 | 4.07283604e−02 |
| 2.05559403e−01 | −1.65292799e−01 | 5.05118430e−01 | 1.53954625e−01 |
| 3.33100915e−01 | 6.82829022e−02 | 2.64415890e−01 | 5.48572958e−01 |
| 8.31313133e−02 | 3.08233321e−01 | 1.02852233e−01 | 1.51988730e−01 |
| 4.91789490e−01 | 3.93706083e−01 | 2.39220075e−02 | −6.59743607e−01 |
| 1.95028305e−01 | 4.92036611e−01 | 5.39111018e−01 | 4.53080177e−01 |
| −7.16533279e−04 | 4.02555138e−01 | 5.33120394e−01 | 3.53537112e−01 |
| 3.25530082e−01 | 1.99433208e−01 | 6.06560826e−01 | 1.64696917e−01 |
| −2.55676121e−01 | 1.62502617e−01 | 8.26691389e−01 | 3.21008921e−01 |
| 2.31793806e−01 | −1.01243407e−01 | 9.76561010e−02 | 3.23023014e−02 |
| 3.61701369e−01 | 1.33023903e−01 | 1.76175937e−01 | 2.41777182e−01 |
| 5.36270022e−01 | 1.00375384e−01 | 9.21536312e−02 | 7.37961233e−02 |
| 2.71986052e−01 | 7.59911239e−02 | 2.78305382e−01 | 2.19710559e−01 |
| 1.72570080e−01 | 1.08687472e−00 | −3.87440920e−02 | 6.26556128e−02] |
| [−1.53339997e−01 | 1.05865136e−01 | 1.98318824e−01 | −7.66291320e−02 |
| 2.01348469e−01 | 1.18178897e−01 | 3.76911342e−01 | 4.11000401e−01 |
| −1.66510791e−02 | 1.94161877e−01 | 4.70697246e−02 | 4.63122249e−01 |
| 2.63873100e−01 | −9.21056345e−02 | −1.51014160e−01 | 6.52564839e−02 |
| 5.00345647e−01 | 6.31653331e−03 | 1.88595548e−01 | −8.80623981e−02 |
| 3.96091819e−01 | 5.28465398e−02 | 2.74567276e−01 | 6.82955921e−01 |
| −7.05722198e−02 | 5.30493975e−01 | 1.87297821e−01 | −1.67305350e−01 |
| 1.40756473e−01 | 2.46539205e−01 | −2.16842499e−01 | 1.85800880e−01 |
| 3.37682754e−01 | −9.00175795e−02 | 1.50748178e−01 | 3.01439583e−01 |
| −3.56631950e−02 | 2.47046258e−02 | 3.62822354e−01 | 1.53011918e−01 |
| 2.06789866e−01 | 1.83538958e−01 | 9.18082818e−02 | −9.23639461e−02 |
| 5.57742894e−01 | 4.27895010e−01 | 3.92793268e−01 | 2.18267322e−01 |
| −1.41591907e−01 | 4.74761218e−01 | −1.26848385e−01 | 4.30520087e−01 |
| 1.86457992e−01 | −2.00700536e−01 | −1.44729912e−01 | 3.01150411e−01 |
| −4.43410389e−02 | −3.13250840e−01 | 5.13511777e−01 | 3.14739048e−01 |
| 1.10633902e−01 | 5.21344729e−01 | 1.79277182e−01 | −2.57816732e−01 |
| 3.83876473e−01 | −1.38250003e−02 | −9.93492361e−03 | 4.13720384e−02 |
| −4.84406017e−02 | 1.48495153e−01 | 1.20995797e−01 | −6.93341494e−02 |
| 4.55578417e−01 | 6.74662888e−01 | 3.66346240e−01 | 6.06382310e−01 |
| 3.78128618e−01 | 2.77336895e−01 | 2.03880727e−01 | 4.46799219e−01 |
| −1.24317683e−01 | 3.22372735e−01 | 4.10675220e−02 | 3.25652659e−02 |

TABLE $W_h^1$-continued

| | | | |
|---|---|---|---|
| 3.26545268e−01 | −1.55603617e−01 | −8.92735496e−02 | 2.78863728e−01 |
| 2.71801418e−03 | −3.96862894e−01 | 2.30059132e−01 | −7.77320415e−02 |
| 6.42185062e−02 | −4.06108834e−02 | 6.14445388e−01 | 4.39223766e−01 |
| 1.87563047e−01 | 3.37913573e−01 | −1.24684207e−01 | −1.67466059e−01 |
| −7.25248978e−02 | 3.06145459e−01 | 1.80045411e−01 | 1.32591516e−01 |
| 2.31819928e−01 | −3.07431724e−02 | 2.48759300e−01 | 9.40459371e−02 |
| 8.37974250e−02 | 5.48973203e−01 | −1.70735195e−01 | −8.94232318e−02 |
| 1.54222980e−01 | −2.97145456e−01 | 6.10980764e−02 | 4.92612273e−01 |
| 2.27186263e−01 | 6.84596784e−03 | 3.62535119e−01 | 1.74467653e−01 |
| 4.82436925e−01 | 1.35387808e−01 | 3.49840760e−01 | 9.39504802e−02 |
| 4.46838945e−01 | 1.86554953e−01 | 4.88245457e−01 | 2.34351292e−01 |
| 2.41299734e−01 | 5.73559105e−01 | −4.15095657e−01 | 6.47384882e−01 |
| 4.23082829e−01 | −8.56870636e−02 | 2.72499502e−01 | −2.99982522e−02 |
| 1.05101056e−01 | 3.87781024e−01 | 2.88682371e−01 | 1.89075530e−01 |
| −8.83421162e−04 | −1.00651361e−01 | −1.77035865e−03 | 5.86987555e−01 |
| −2.11783111e−01 | −2.14738697e−01 | 5.96108973e−01 | 4.26603824e−01 |
| 2.58669615e−01 | −3.86972904e−01 | −1.59662887e−01 | 2.03984708e−01 |
| 7.38505244e−01 | 3.03673707e−02 | 3.00723761e−01 | −1.51929231e−02 |
| 5.74148834e−01 | 1.30815983e−01 | −2.02105641e−02 | −1.15475459e−02 |
| 3.56211782e−01 | −3.25000048e−01 | −2.19823822e−01 | 3.55331391e−01 |
| 2.61030555e−01 | 9.23292339e−02 | 2.93881506e−01 | 3.82225454e−01 |
| −8.58581588e−02 | 6.14946783e−01 | 4.51768368e−01 | −4.08647768e−02 |
| 6.22183621e−01 | 3.03039640e−01 | −3.51552516e−01 | −1.10024288e−01 |
| 2.76062312e−03 | 1.31468214e−02 | 2.88080752e−01 | −4.47589830e−02 |
| 3.75294060e−01 | −1.14903092e−01 | 2.86749959e−01 | 3.82855833e−01 |
| 3.03193852e−02 | 6.01186715e−02 | 4.41858321e−01 | 4.63533044e−01 |
| −2.25173265e−01 | 5.08516371e−01 | 7.44783401e−01 | 4.80048746e−01 |
| −5.67165352e−02 | 4.02339727e−01 | 7.77648911e−02 | 1.22636013e−01 |
| 1.97394744e−01 | 3.22682410e−01 | 9.19927135e−01 | 5.52124202e−01 |
| −2.06176057e−01 | 1.93339840e−01 | 7.87243322e−02 | 3.91160965e−01 |
| −1.85455129e−01 | 1.37303233e−01 | 2.93778598e−01 | 2.21779823e−01 |
| 2.16314957e−01 | 4.36740011e−01 | 7.99109757e−01 | 6.17449164e−01 |
| 3.38660479e−01 | −1.09247595e−01 | 1.32494261e−02 | 2.72938490e−01 |
| 6.72262162e−02 | −3.31343189e−02 | 7.00150728e−02 | 3.17996830e−01 |
| −2.26365149e−01 | 2.40963578e−01 | 5.90269625e−01 | 3.37198496e−01 |
| 3.49508971e−01 | 1.82745740e−01 | 3.06184739e−01 | 3.46174031e−01 |
| 6.94457665e−02 | 4.00242001e−01 | 7.24251509e−01 | 5.06596863e−01 |
| 2.33457401e−01 | −5.97299159e−01 | 2.90209670e−02 | 5.68534553e−01 |
| 4.63411063e−01 | −1.03485435e−01 | 2.17312068e−01 | 6.80844765e−03 |
| 8.64813328e−02 | 5.18073738e−01 | 5.77195957e−02 | 2.63905168e−01 |
| 1.39445409e−01 | 6.50485978e−02 | 3.29551220e−01 | 1.06254593e−01 |
| 5.24098694e−01 | 1.28235519e−01 | 4.58322793e−01 | 4.46949929e−01 |
| −1.10127263e−01 | −1.39600173e−01 | 2.41122931e−01 | 1.12064570e−01] |
| [3.14246565e−02 | 5.74316047e−02 | 2.80602396e−01 | −3.77734713e−02 |
| 7.10859597e−01 | 3.80533785e−01 | 7.17871606e−01 | 2.25440994e−01 |
| 2.62277007e−01 | 2.76184052e−01 | 2.44666710e−01 | 1.97655156e−01 |
| 3.62930596e−01 | 6.67065024e−01 | 1.83175668e−01 | 3.46766025e−01 |
| 1.47250965e−01 | 1.15146928e−01 | −1.50121927e−01 | 2.67737687e−01 |
| −1.23154514e−01 | 1.32041901e−01 | 2.16007009e−01 | −3.41187753e−02 |
| 2.08971575e−01 | 1.77209020e−01 | 7.99749643e−01 | 5.69438159e−01 |
| 3.86420369e−01 | 2.61812747e−01 | 4.72009838e−01 | 4.08524036e−01 |
| 8.80111337e−01 | 1.70951858e−01 | −2.21946090e−01 | 1.43014282e−01 |
| −4.74416837e−02 | 7.76563048e−01 | 2.86036402e−01 | 4.08927232e−01 |
| 5.35847545e−01 | 6.65705681e−01 | −1.44046117e−02 | 1.88739244e−01 |
| 3.86130035e−01 | 6.71110451e−02 | 3.47783029e−01 | 7.45134428e−02 |
| 1.03721265e−02 | 2.31730208e−01 | −1.44305304e−01 | 3.05573438e−01 |
| 2.96470761e−01 | 5.83959639e−01 | 7.65061378e−01 | 9.16319340e−02 |
| −1.27528995e−01 | 8.96397457e−02 | 7.68709540e−01 | 5.59311770e−02 |
| 1.44884571e−01 | 1.30298063e−01 | 3.61512959e−01 | 4.34247218e−01 |
| 1.21096671e−01 | 4.64332640e−01 | 4.39792067e−01 | 4.06265765e−01 |
| 4.75105166e−01 | −3.11121672e−01 | −5.11408336e−02 | −4.35413152e−01 |
| 5.55540204e−01 | 1.39360636e−01 | −9.45796743e−02 | 3.43470722e−02 |
| 2.56728917e−01 | 1.01017058e−01 | 6.56147718e−01 | 1.56565979e−01 |
| 2.70511240e−01 | 4.88607496e−01 | 4.07319814e−01 | 6.70186341e−01 |
| −1.19076833e−01 | 3.24989706e−01 | 4.82962996e−01 | 6.80524945e−01 |
| 6.99817598e−01 | −1.04749352e−01 | 9.76869836e−02 | 1.56050716e−02 |
| 9.84230340e−02 | 8.12665343e−01 | −1.49560601e−01 | 4.96015251e−01 |
| −3.74999344e−01 | 2.24733874e−01 | −6.71931356e−02 | 8.03862810e−01 |
| 3.36579174e−01 | 4.12369043e−01 | 2.72868335e−01 | 2.03593642e−01 |
| 4.51030195e−01 | 4.49693143e−01 | 2.39505321e−01 | 4.03565675e−01 |
| 1.18869200e−01 | 1.95726171e−01 | 7.65586734e−01 | 3.20178777e−01 |
| 1.27641365e−01 | 6.10912926e−02 | 1.04281342e−00 | −1.10189632e−01 |
| 3.70944500e−01 | 5.52302420e−01 | 2.70274282e−01 | −1.40469717e−02 |
| 1.84572130e−01 | 1.35491803e−01 | 1.54268980e−01 | 2.15763927e−01 |
| −1.32192716e−01 | 3.00538063e−01 | −4.57563139e−02 | 3.85087938e−03 |
| 4.53280091e−01 | −2.82926947e−01 | −4.91551787e−01 | 2.60987371e−01 |
| 6.17308199e−01 | 4.97303367e−01 | 7.52986893e−02 | −3.53922925e−01 |
| 2.73066044e−01 | 1.11906104e−01 | 6.59496427e−01 | 8.89579058e−01 |
| 3.17295343e−01 | 1.94173604e−01 | 1.17130391e−02 | 1.61284328e−01 |
| −1.46937087e−01 | 2.62365609e−01 | 1.82050169e−01 | 2.26051271e−01 |

TABLE $W_h^1$-continued

| | | | |
|---|---|---|---|
| 4.52362478e-01 | 6.75129950e-01 | 6.50647104e-01 | 2.33639497e-02 |
| -1.48149639e-01 | 4.20313805e-01 | 2.18590751e-01 | 3.97029109e-02 |
| 2.35551879e-01 | -5.81915416e-02 | 9.19788480e-02 | 9.64541808e-02 |
| -2.79673729e-02 | 3.70963246e-01 | 6.23765290e-01 | 5.88199258e-01 |
| 3.51645887e-01 | 2.37763941e-01 | 6.04952514e-01 | 5.50977960e-02 |
| 2.44600952e-01 | 3.87167573e-01 | 5.61836839e-01 | 1.49456114e-01 |
| 5.53474128e-01 | 1.77912086e-01 | 5.98279357e-01 | -2.42455930e-01 |
| 7.88786590e-01 | 1.43016130e-01 | 1.90196350e-01 | 4.03325558e-01 |
| 9.11279023e-01 | 5.57585120e-01 | 1.61386043e-01 | 1.45589679e-01 |
| 5.73231541e-02 | 4.75794345e-01 | 9.58479941e-03 | 6.88923061e-01 |
| -2.01463178e-02 | 2.04863176e-01 | 2.48822123e-01 | 8.94181952e-02 |
| 7.74858892e-01 | 6.99600637e-01 | 1.43636972e-01 | 2.49687344e-01 |
| 3.83515239e-01 | 3.32653373e-01 | 2.47069806e-01 | 6.70811087e-02 |
| 6.70297623e-01 | -2.62513250e-01 | 6.46426857e-01 | 3.53984535e-01 |
| 4.31797624e-01 | -1.60687223e-01 | 8.86114955e-01 | -1.46966264e-01 |
| -1.37879014e-01 | 2.09658854e-02 | 4.56906902e-03 | 6.62996113e-01 |
| 5.44602752e-01 | 1.79770693e-01 | 4.29100901e-01 | 6.95551395e-01 |
| 2.84833848e-01 | -2.45963171e-01 | 2.61642307e-01 | -7.49336481e-02 |
| 1.31243989e-01 | 3.64728868e-01 | 3.06780219e-01 | 3.58806551e-01 |
| 1.30907446e-01 | 2.13473171e-01 | 5.09336293e-01 | 3.59568566e-01 |
| 6.88927054e-01 | 1.26503304e-01 | 6.92631066e-01 | -4.59788851e-02 |
| 1.16330862e-01 | 1.14212766e-01 | 1.35262296e-01 | 5.51134109e-01 |
| 8.45920891e-02 | 2.96518177e-01 | -1.38594866e-01 | 1.29185691e-01 |
| -4.98396158e-02 | 4.19252515e-01 | 4.10004467e-01 | 3.83656591e-01 |
| 5.56715190e-01 | 4.09850210e-01 | 3.61267120e-01 | 2.09975988e-01 |
| 5.19625358e-02 | 2.58589000e-01 | 6.98653841e-03 | 4.34617102e-01 |
| 4.90190871e-02 | 1.12961650e-00 | -7.34917149e-02 | 2.90499240e-01] |
| [-2.97164973e-02 | -2.40641177e-01 | 4.35683429e-01 | -1.76917523e-01 |
| 2.21492182e-01 | 5.97688675e-01 | 5.58643416e-01 | 4.05082047e-01 |
| -2.44782329e-01 | 1.59640044e-01 | -9.74248126e-02 | 6.43965900e-01 |
| 5.65026879e-01 | -4.99336272e-02 | 3.48298222e-01 | 4.67257649e-01 |
| 3.85083526e-01 | 1.12005882e-01 | -7.45314956e-02 | 1.53103575e-01 |
| 4.78684843e-01 | -1.12426858e-02 | 2.06225410e-01 | 4.98531312e-01 |
| 5.19539297e-01 | 2.14371935e-01 | 4.50249463e-01 | 3.25726122e-01 |
| -6.22941330e-02 | 4.43434089e-01 | 4.32293396e-03 | 1.16407327e-01 |
| 3.86934161e-01 | 1.55687230e-02 | 5.96568473e-02 | -4.62387949e-02 |
| 2.57354975e-01 | 1.01711743e-01 | 4.82128084e-01 | 4.23027873e-02 |
| 4.51359123e-01 | 2.59439856e-01 | 6.03999972e-01 | 5.16723357e-02 |
| 5.06922364e-01 | 1.20406814e-01 | 7.18708575e-01 | 2.05036998e-01 |
| -1.63955227e-01 | 5.82913935e-01 | 3.80496323e-01 | 1.38525724e-01 |
| 2.36836508e-01 | 2.55317003e-01 | -1.78398415e-02 | 1.33380398e-01 |
| -1.30813211e-01 | -1.71872646e-01 | 5.93820691e-01 | -2.66321246e-02 |
| 2.09929183e-01 | 3.16453457e-01 | 1.66350737e-01 | 1.24975942e-01 |
| 1.88554004e-01 | 3.71081293e-01 | 1.75038442e-01 | 4.96060401e-01 |
| 6.68014705e-01 | -5.57954051e-02 | 1.27963170e-01 | -8.36547136e-01 |
| 3.82195950e-01 | 3.60208184e-01 | 2.53102034e-01 | 5.18521309e-01 |
| -2.39731789e-01 | 5.61953723e-01 | -9.95973274e-02 | 2.20979750e-01 |
| -1.12812981e-01 | 1.72803953e-01 | -6.59375936e-02 | 2.13545918e-01 |
| -1.45163327e-01 | -5.18653765e-02 | 6.82968438e-01 | 1.09626941e-01 |
| 1.62943631e-01 | -2.50740051e-01 | 9.80445743e-03 | 4.56216894e-02 |
| -1.06439233e-01 | -2.71093667e-01 | 7.27192638e-03 | 3.92507046e-01 |
| 3.53458315e-01 | 1.08373761e-01 | 8.67948085e-02 | -3.60847294e-01 |
| 6.61745369e-01 | 4.21810359e-01 | 6.20360315e-01 | 3.29230875e-01 |
| -4.50977385e-02 | 8.03920031e-02 | 2.83768624e-01 | 4.21666771e-01 |
| 7.16967061e-02 | 2.80852895e-02 | 1.09999806e-01 | 1.06462613e-01 |
| 2.59753019e-01 | 3.39402467e-01 | 6.21626735e-01 | 4.65517581e-01 |
| 4.81042452e-02 | 4.05868143e-01 | 3.80467400e-02 | 3.94980669e-01 |
| -1.01271681e-01 | 4.53889996e-01 | -1.56997532e-01 | 1.35264024e-01 |
| 3.10050339e-01 | 6.22118890e-01 | 3.06073517e-01 | 5.29516876e-01 |
| 1.79477200e-01 | 5.71575284e-01 | -1.55624226e-01 | 2.68395662e-01 |
| 7.95423925e-01 | -5.76674268e-02 | 5.80882251e-01 | 5.39784789e-01 |
| 5.70303202e-01 | 6.18998349e-01 | 2.33962357e-01 | 1.50002733e-01 |
| 2.94617146e-01 | 2.26845279e-01 | 7.49060437e-02 | 4.79789078e-01 |
| -1.44702658e-01 | -1.88067287e-01 | 4.70372349e-01 | 2.83028692e-01 |
| -4.93952585e-03 | -3.37255150e-01 | 2.07303977e-03 | 7.19436765e-01 |
| -2.10271850e-01 | 1.87014699e-01 | 4.34773624e-01 | 2.10216835e-01 |
| -1.33668363e-01 | 7.92745873e-02 | -3.43999192e-02 | 1.45121207e-01 |
| 2.58991152e-01 | -9.76011828e-02 | -1.83010787e-01 | -4.92281951e-02 |
| 9.54147428e-02 | 2.35199407e-01 | 6.20248258e-01 | 3.95947210e-02 |
| 2.54157096e-01 | -3.76223400e-02 | 3.73164654e-01 | 3.62986289e-02 |
| 4.73148674e-01 | 2.64357984e-01 | 1.04984697e-01 | 6.44922629e-02 |
| 7.48712301e-01 | -1.47738650e-01 | 4.07108098e-01 | 1.75311696e-02 |
| 3.33039850e-01 | 3.20593715e-01 | 3.90515953e-01 | 2.66685575e-01 |
| 2.80547559e-01 | -1.04231276e-01 | 5.63877702e-01 | 5.06250143e-01 |
| 1.85368702e-01 | 4.43300962e-01 | 1.93933323e-01 | 3.57784688e-01 |
| 2.83845812e-01 | 3.13466609e-01 | 1.43649474e-01 | 1.02266714e-01 |
| 4.81843740e-01 | 1.81417614e-01 | -6.31583631e-02 | 1.36421099e-01 |
| 4.32294123e-02 | 1.14430904e-01 | 1.96849748e-01 | -3.97435315e-02 |
| 1.48390960e-02 | -2.52569914e-01 | 4.96836752e-01 | 7.45371953e-02 |
| 5.81739604e-01 | 3.40051174e-01 | 5.37768781e-01 | 3.04346174e-01 |

TABLE $W_h^1$-continued

| | | | |
|---|---|---|---|
| 8.63428786e−02 | 1.74183384e−01 | 2.45637119e−01 | 5.28089583e−01 |
| 3.65259238e−02 | 3.24603111e−01 | 5.55799901e−01 | −3.62357795e−01 |
| 3.95831391e−02 | 1.26781181e−01 | 1.84885666e−01 | 1.54282777e−02 |
| 1.59515813e−01 | 1.70038268e−01 | 3.17622066e−01 | 4.09001291e−01 |
| 6.03121102e−01 | 3.84715676e−01 | 5.12180090e−01 | 2.90692359e−01 |
| 3.65613699e−01 | 4.05624330e−01 | 1.57393992e−01 | 3.18632185e−01 |
| 4.54038680e−01 | 2.77329534e−01 | −3.62922698e−01 | −9.47006941e−02 |
| 2.98744261e−01 | 3.36537927e−01 | 5.72740078e−01 | 1.87050357e−01 |
| 4.21754956e−01 | −1.37327403e−01 | 1.01038292e−01 | 3.02609652e−01 |
| 2.99193174e−01 | 2.29596749e−01 | 1.24980703e−01 | 3.28583926e−01 |
| −1.03364572e−01 | −6.54420331e−02 | −2.88024135e−02 | 7.29897916e−02] |
| [2.45144874e−01 | 3.72480452e−01 | 6.57757342e−01 | 3.77605796e−01 |
| 4.68147606e−01 | 7.32969224e−01 | 5.68058014e−01 | 2.25895584e−01 |
| 2.36093953e−01 | 1.93717062e−01 | 7.12025762e−01 | 4.94464755e−01 |
| 1.98728487e−01 | 4.30007488e−01 | 3.46777946e−01 | 2.18068540e−01 |
| 5.76490521e−01 | −2.08505362e−01 | −4.67571914e−01 | 3.10243279e−01 |
| 4.76644129e−01 | 5.88867247e−01 | 1.06265262e−01 | 6.14617825e−01 |
| 3.15300375e−01 | 4.24341917e−01 | −2.35555768e−01 | 8.37344676e−02 |
| 1.79167744e−02 | 6.37763679e−01 | 4.47223037e−01 | 3.11956674e−01 |
| 5.27037829e−02 | −5.52302562e−02 | 4.35733497e−01 | 2.87002057e−01 |
| 4.95063215e−01 | 4.93358970e−01 | 3.80989909e−01 | 3.38261485e−01 |
| 4.47638303e−01 | 4.24980581e−01 | 8.52986038e−01 | −3.96294743e−02 |
| 3.77252728e−01 | −4.43187058e−02 | 1.50013924e−01 | 6.59779770e−01 |
| 2.93505460e−01 | 3.96877587e−01 | 3.18473667e−01 | 1.96057677e−01 |
| 3.50451171e−01 | −2.67863959e−01 | 2.04921022e−01 | 2.41506487e−01 |
| 7.61904299e−01 | 1.35096774e−01 | 3.15445930e−01 | −1.04250327e−01 |
| 3.84838432e−01 | 7.65292525e−01 | 5.57997346e−01 | 2.76796550e−01 |
| 4.83191282e−01 | 2.83579141e−01 | 4.60495710e−01 | 2.09203586e−01 |
| 2.48300985e−01 | 3.23871881e−01 | 5.54058552e−01 | −2.50374287e−01 |
| 4.83801752e−01 | 5.89652508e−02 | 6.75035298e−01 | 7.62711823e−01 |
| 7.55987287e−01 | 8.06899071e−01 | 6.61700666e−01 | 4.60003316e−01 |
| 5.88325202e−01 | 9.58660394e−02 | −6.88751936e−02 | 1.14936888e−01 |
| 3.02792042e−01 | 1.35166705e−01 | 4.06572342e−01 | 3.97081494e−01 |
| 2.82057613e−01 | −2.94888113e−03 | 2.59401381e−01 | 1.57115132e−01 |
| 2.43601814e−01 | 3.50568026e−01 | 1.27728254e−01 | 6.30755723e−01 |
| 3.11954319e−01 | 2.16106549e−01 | 2.47676238e−01 | 1.56838641e−01 |
| 3.54860991e−01 | 6.13909483e−01 | 6.07446909e−01 | 6.26136363e−02 |
| 1.79525882e−01 | 3.61927271e−01 | 4.97194111e−01 | 4.13865566e−01 |
| 6.03956655e−02 | 8.92210126e−01 | 5.82662821e−01 | 1.77451000e−01 |
| 2.93489873e−01 | 1.80908605e−01 | 6.20676279e−01 | 1.57267928e−01 |
| 2.77973443e−01 | 3.22017729e−01 | 5.62937737e−01 | 6.10478044e−01 |
| 4.04434025e−01 | 2.66590089e−01 | 1.18314279e−01 | 2.44482022 5e−01 |
| 3.54231030e−01 | 1.73980922e−01 | −1.26895560e−02 | 4.35866535e−01 |
| 6.84567750e−01 | 3.67018610e−01 | 2.81965494e−01 | 5.83093882e−01 |
| 3.38706821e−01 | 1.22789465e−01 | 2.90286124e−01 | 4.07036513e−01 |
| 3.84196006e−02 | −1.69998720e−01 | −1.51639760e−01 | 8.69116724e−01 |
| 5.05831897e−01 | 1.36259273e−02 | 2.72972077e−01 | 5.14053762e−01 |
| 5.99125504e−01 | −1.14862248e−01 | 2.74067521e−01 | 8.33761752e−01 |
| 4.62499350e−01 | 2.14496478e−02 | 5.22317708e−01 | 2.31297806e−01 |
| 4.56059128e−01 | 5.10290265e−01 | 5.84125280e−01 | 5.73819280e−01 |
| −2.67164614e−02 | 2.29811087e−01 | 1.73215512e−02 | 3.93369108e−01 |
| 3.90506774e−01 | 1.27885222e−01 | 6.75631702e−01 | 3.02001327e−01 |
| 5.45300484e−01 | −1.21612661e−01 | 2.38124207e−01 | 4.38783616e−01 |
| 3.42674702e−01 | −2.36811228e−02 | 3.43343556e−01 | 8.54032859e−02 |
| 7.27320492e−01 | 5.08999407e−01 | 2.82943547e−01 | 2.39039987e−01 |
| 5.13297260e−01 | −1.37067929e−01 | 5.83827078e−01 | 1.19323581e−01 |
| 4.77975994e−01 | 4.16434139e−01 | 4.36963260e−01 | 9.03862596e−01 |
| 4.72581238e−01 | 1.23938829e−01 | 1.63660362e−01 | 2.91832477e−01 |
| 1.21929184e−01 | 7.62342572e−01 | 7.13499188e−01 | 6.64296865e−01 |
| 9.57910046e−02 | 5.12052238e−01 | 2.06254553e−02 | 5.23985207e−01 |
| 3.44825000e−01 | 2.24781722e−01 | 2.71281272e−01 | 6.81550741e−01 |
| 5.69712460e−01 | 1.03562482e−01 | 3.93388778e−01 | 3.80960226e−01 |
| −7.76270032e−02 | 2.01868653e−01 | 5.25182426e−01 | 5.46328604e−01 |
| 3.98891121e−01 | 3.82667273e−01 | 2.18894795e−01 | 5.21156549e−01 |
| 2.96514481e−01 | −8.61436203e−02 | 1.71153978e−01 | 7.60548532e−01 |
| 4.37667191e−01 | 7.14966238e−01 | 4.83633786e−01 | −6.90010071e−01 |
| 3.80935878e−01 | 1.78809240e−01 | 3.81810963e−01 | 3.27021718e−01 |
| 7.23411679e−01 | −3.51733295e−03 | 2.61651963e−01 | 7.08173871e−01 |
| 4.42704767e−01 | 7.63493001e−01 | 3.06056798e−01 | 6.57373607e−01 |
| 1.60594419e−01 | −4.68408048e−01 | 2.86170810e−01 | 4.97970641e−01 |
| 5.96686363e−01 | 4.12170351e−01 | −3.04244280e−01 | 1.01828821e−01 |
| 1.89535156e−01 | 5.18002659e−02 | 4.35038060e−01 | 3.57918680e−01 |
| 4.48147655e−01 | 3.20005655e−01 | 1.58446044e−01 | 2.55025119e−01 |
| 3.64698470e−01 | 5.37370980e−01 | 3.83641005e−01 | 9.40700650e−01 |
| −2.08777994e−01 | 4.14111078e−01 | 6.74746454e−01 | 2.60901511e−01] |
| [1.60501152e−01 | 2.45297641e−01 | 1.71949983e−01 | −4.30990994e−01 |
| 4.27593619e−01 | 3.06990623e−01 | 4.28057641e−01 | 1.68443434e−02 |
| 1.82620898e−01 | 1.43853202e−01 | 3.00300300e−01 | 4.18822557e−01 |
| 6.75223321e−02 | 1.57383844e−01 | 3.21276218e−01 | 1.63968474e−01 |
| 4.54719543e−01 | 2.11045250e−01 | 1.57629445e−01 | 2.97708988e−01 |

TABLE $W_h^1$-continued

| | | | |
|---|---|---|---|
| 5.21842599e−01 | 1.08989673e−02 | −1.05001494e−01 | 1.98445082e−01 |
| 2.37388045e−01 | 6.17577314e−01 | −8.31551943e−03 | −2.74406403e−01 |
| 1.58714414e−01 | 4.60950911e−01 | 5.55152774e−01 | 3.96216094e−01 |
| 1.44588351e−01 | 7.51395663e−03 | 6.64393455e−02 | 1.11213706e−01 |
| 2.40504876e−01 | 4.18245971e−01 | 3.38706315e−01 | −2.54919622e−02 |
| 4.42584008e−02 | 1.75187096e−01 | 5.28767824e−01 | 4.11473870e−01 |
| 7.44445145e−01 | −1.94134533e−01 | 8.70869398e−01 | 1.72260061e−01 |
| 2.36502737e−02 | −4.07904051e−02 | 1.48772627e−01 | 3.32033068e−01 |
| 1.91444874e−01 | −1.88011020e−01 | 3.05511624e−01 | 2.47383147e−01 |
| 1.00302361e−01 | 1.50290489e−01 | 5.27414382e−01 | 7.48563139e−03 |
| 3.55329871e−01 | 3.52610230e−01 | 4.64543551e−01 | −1.53834745e−01 |
| 4.96515751e−01 | 1.89709172e−01 | 2.23317072e−01 | 1.14442766e−01 |
| 2.24611565e−01 | 3.58063310e−01 | 2.88844287e−01 | 1.01430193e−01 |
| 9.17353630e−01 | 1.52935669e−01 | 4.51785028e−01 | 3.48927498e−01 |
| 5.36230743e−01 | 3.77871305e−01 | 3.16166818e−01 | 1.92827091e−01 |
| −1.66334430e−04 | 2.68609911e−01 | 1.26460373e−01 | 2.03575641e−01 |
| 3.08251176e−02 | 4.55764562e−01 | 2.37277240e−01 | 6.34149611e−02 |
| 8.90021324e−02 | −2.91566759e−01 | 1.94643408e−01 | 1.02539249e−01 |
| 3.39846462e−01 | 2.79400557e−01 | 2.33161092e−01 | 5.61382055e−01 |
| 4.78832424e−01 | 3.64907421e−02 | 1.40471652e−01 | 2.82937914e−01 |
| 1.02575548e−01 | 5.09717524e−01 | 6.45044208e−01 | 3.22673857e−01 |
| 2.61855572e−01 | 3.12905759e−02 | 1.90873072e−01 | 4.65471506e−01 |
| 2.59053856e−01 | 7.90621996e−01 | 1.69203162e−01 | 3.24681163e−01 |
| 1.91574588e−01 | 3.42797399e−01 | 6.00492477e−01 | 1.24512449e−01 |
| 4.00321931e−01 | 1.90967232e−01 | 3.93738180e−01 | 3.85983586e−01 |
| 8.98914561e−02 | 7.33708367e−02 | 3.45674753e−01 | 7.85080194e−02 |
| 3.64734411e−01 | 6.19776472e−02 | 3.27000290e−01 | 2.22370610e−01 |
| −9.68905911e−02 | 3.98486108e−01 | −2.23182663e−01 | 2.24017978e−01 |
| 3.57397467e−01 | 2.11613983e−01 | 6.60478622e−02 | −1.23843469e−01 |
| 1.47363633e−01 | 2.35933706e−01 | 1.30694032e−01 | 9.58267033e−01 |
| 6.49764776e−01 | 3.12109083e−01 | −1.70253634e−01 | 1.44831032e−01 |
| 2.91485667e−01 | 1.00001119e−01 | 4.34340268e−01 | 9.39787507e−01 |
| 1.87844977e−01 | 2.91292578e−01 | 1.64456412e−01 | 3.96365523e−01 |
| 4.19492275e−01 | 3.88302922e−01 | 2.41778672e−01 | 1.14597762e−02 |
| 2.17928678e−01 | 2.90323406e−01 | −1.62590984e−02 | 4.01463181e−01 |
| 5.43860674e−01 | −7.61059374e−02 | 6.04110420e−01 | 2.17659585e−03 |
| −6.04663454e−02 | 4.62405151e−03 | 4.86293823e−01 | 4.53130573e−01 |
| 1.58212334e−01 | 3.32719475e−01 | 6.99927151e−01 | −1.26246586e−01 |
| 3.93638551e−01 | −2.44042531e−01 | 4.23292726e−01 | 1.35348380e−01 |
| 2.42179707e−01 | −3.65480214e−01 | 8.13573152e−02 | 2.16216817e−01 |
| 1.91186383e−01 | 4.68437433e−01 | 4.09884810e−01 | 3.84840846e−01 |
| −6.74291840e−03 | 5.38653672e−01 | 4.95368063e−01 | 2.33933151e−01 |
| −1.95233107e−01 | 2.83417076e−01 | 3.22896451e−01 | 4.74830836e−01 |
| −3.66544211e−03 | 1.95161149e−01 | 3.16992670e−01 | 4.15236831e−01 |
| 5.16494393e−01 | 1.05465949e−03 | 3.42925787e−01 | 3.29312593e−01 |
| 1.64463714e−01 | 8.61899182e−02 | 2.01038837e−01 | 5.86671591e−01 |
| 5.99836648e−01 | 3.68899740e−02 | 4.30117041e−01 | 9.56440791e−02 |
| 1.10553615e−01 | 4.01723057e−01 | 6.87124908e−01 | 8.73910040e−02 |
| 5.76108634e−01 | 2.04200804e−01 | 2.86336571e−01 | 3.84276569e−01 |
| 2.64482617e−01 | −3.20068985e−01 | 2.58114368e−01 | 2.08285730e−02 |
| −1.14042632e−01 | −2.50107467e−01 | 1.54935241e−01 | 3.16606015e−01 |
| 2.49216575e−02 | 3.54437232e−01 | 2.60495692e−01 | 2.41029650e−01 |
| 3.96648914e−01 | 2.30343387e−01 | 4.15771037e−01 | 6.42960489e−01 |
| −2.81877965e−01 | −3.47452849e−01 | 1.08545572e−01 | 7.08302334e−02 |
| −1.52037457e−01 | −9.62185413e−02 | −1.10345155e−01 | 8.06037895e−03 |
| 8.89369488e−01 | 7.81537294e−02 | 5.42982399e−01 | 2.50505418e−01 |
| 4.43603575e−01 | 3.75366569e−01 | −4.17465456e−02 | −2.23394379e−01 |
| 1.25831187e−01 | 1.25260696e−01 | 2.45741859e−01 | 3.90044123e−01 |
| 2.02470258e−01 | 3.74983698e−01 | 3.49139333e−01 | −1.11280516e−01] |
| [2.59029269e−01 | 5.77083565e−02 | −1.66295618e−01 | −1.73601717e−01 |
| 2.11039975e−01 | 1.03536218e−01 | 3.24730098e−01 | 8.75092205e−03 |
| 1.69207051e−01 | −3.05251271e−01 | −1.21011823e−01 | 2.19090477e−01 |
| 2.19125852e−01 | 1.53744206e−01 | 1.96877077e−01 | 2.49473155e−01 |
| 3.38089973e−01 | −1.48641169e−01 | −1.47130296e−01 | 2.00478658e−01 |
| 9.50085223e−02 | 2.83361524e−01 | 1.10802442e−01 | 1.20188892e−01 |
| −1.79796189e−01 | −6.73926920e−02 | 5.77244043e−01 | 4.25507545e−01 |
| 8.98802206e−02 | −4.70730364e−02 | −8.42698589e−02 | −2.58750826e−01 |
| 1.87938198e−01 | −8.76005143e−02 | −1.45233467e−01 | −1.58294126e−01 |
| −1.02192536e−01 | 3.31980407e−01 | 4.00429731e−03 | −1.01494364e−01 |
| 1.04131743e−01 | 3.80695105e−01 | −1.71554521e−01 | −1.24382451e−01 |
| −2.51220018e−01 | 1.40051870e−01 | 2.11716369e−01 | 1.08541645e−01 |
| 1.24015003e−01 | −4.14756313e−02 | −8.13662075e−03 | −1.48243248e−01 |
| 2.50201821e−01 | 1.38206318e−01 | −2.22071841e−01 | −1.73954926e−02 |
| −1.34645879e−01 | −3.41326624e−01 | 1.90735310e−01 | 1.79135054e−01 |
| −7.96205997e−02 | −2.05106679e−01 | 8.55891630e−02 | 2.12489478e−01 |
| −1.32292762e−01 | −2.81682312e−01 | −1.89080551e−01 | 6.11671880e−02 |
| 3.50899696e−02 | 5.14051728e−02 | 2.51243357e−02 | 2.62378544e−01 |
| 2.82076746e−01 | −3.19618881e−01 | 1.38397872e−01 | 2.54789323e−01 |
| 1.64556235e−01 | 4.91855264e−01 | 4.34783757e−01 | 4.56989631e−02 |
| 2.35640228e−01 | −2.23410487e−01 | −1.12600192e−01 | 2.19653244e−03 |

TABLE $W_h^1$-continued

| | | | |
|---|---|---|---|
| 2.90504783e−01 | −2.48665795e−01 | 1.06403470e−01 | 3.82000297e−01 |
| −1.67326540e−01 | −1.01202112e−02 | 3.44961137e−01 | −1.48312151e−01 |
| 1.11554168e−01 | 5.78328669e−02 | −5.77735454e−02 | 2.88364828e−01 |
| 4.36591730e−02 | 2.85634547e−02 | −2.17682958e−01 | −8.55879933e−02 |
| −1.76485166e−01 | −1.68763429e−01 | 1.58116385e−01 | 7.35319257e−02 |
| −3.68735462e−01 | 5.72624020e−02 | −1.09294496e−01 | −4.88449819e−02 |
| 5.93793988e−01 | 3.32069427e−01 | 4.10402983e−01 | 1.64120585e−01 |
| 1.83464382e−02 | −3.05592239e−01 | 5.34799635e−01 | 6.48482069e−02 |
| 1.33267134e−01 | −1.00893036e−01 | 2.22929955e−01 | −1.18052237e−01 |
| −4.16279882e−01 | −5.53722262e−01 | 5.53537868e−02 | 2.75393426e−02 |
| 2.95983791e−01 | 7.17347264e−02 | −2.97381338e−02 | 2.00415850e−01 |
| −1.22337617e−01 | 3.95369291e−01 | −2.92436987e−01 | 2.42448207e−02 |
| 2.97999308e−02 | −1.94829404e−01 | −2.72543222e−01 | −4.58103448e−01 |
| 7.53963143e−02 | 3.72849740e−02 | 1.67626694e−01 | 3.16937231e−02 |
| 2.66782880e−01 | −2.11479180e−02 | 5.29969335e−02 | −3.31108391e−01 |
| 6.29226506e−01 | −1.48120150e−01 | 2.08499312e−01 | 8.02969635e−02 |
| 8.04927126e−01 | 3.62634152e−01 | −1.17538564e−01 | −1.39809757e−01 |
| 1.07695803e−01 | 1.55754119e−01 | 1.84025273e−01 | 1.86922140e−02 |
| 2.71589518e−01 | −1.65563554e−01 | −1.78257637e−02 | −2.25741901e−02 |
| −4.65169877e−01 | 4.48313296e−01 | 2.38414675e−01 | 3.25700611e−01 |
| −4.93246466e−01 | −2.30026409e−01 | −2.24531412e−01 | −3.50129098e−01 |
| 4.85827416e−01 | −9.39611048e−02 | 4.91596758e−01 | 1.20780930e−01 |
| −2.50568017e−02 | −3.53106052e−01 | 3.02452624e−01 | 9.03103948e−02 |
| −3.92167777e−01 | −7.65149519e−02 | −2.73804009e−01 | 5.68977278e−03 |
| 2.46046931e−01 | 6.49935380e−02 | −1.05109088e−01 | 4.74337488e−02 |
| 1.08889647e−01 | 2.09853247e−01 | 2.37818122e−01 | 2.77797341e−01 |
| −1.38642147e−01 | 3.50658834e−01 | 4.63232771e−02 | 9.88654122e−02 |
| 1.08107306e−01 | 2.14746341e−01 | −4.93743449e−01 | −2.67127931e−01 |
| −1.95900463e−02 | 1.70606777e−01 | −2.71729939e−02 | 1.24326698e−01 |
| 5.04889786e−01 | 1.26212358e−01 | 1.57632932e−01 | 2.16762245e−01 |
| 8.98465887e−02 | −5.21637559e−01 | −2.02640831e−01 | 3.44063073e−01 |
| −1.29330382e−01 | −4.46556687e−01 | 4.38532501e−01 | 1.42156467e−01 |
| 3.05013984e−01 | 1.95676591e−01 | −1.22359574e−01 | 9.43695456e−02 |
| 4.07131672e−01 | 4.69991326e−01 | −1.47631362e−01 | −2.51182407e−01 |
| −1.15609922e−01 | 4.77565527e−02 | −2.04632893e−01 | −7.66123235e−02 |
| 1.24003127e−01 | 8.34802911e−02 | 5.63274205e−01 | 9.22884718e−02 |
| 3.43192250e−01 | −3.24287236e−01 | −2.46449616e−02 | −1.91182401e−02 |
| −8.17869678e−02 | −2.71389365e−01 | −2.49515042e−01 | −1.39677182e−01 |
| −3.69405746e−01 | −7.44215176e−02 | −4.59831506e−02 | −5.57555296e−02 |
| −1.38068035e−01 | 3.50384444e−01 | 4.76604611e−01 | 2.30627522e−01 |
| 5.44592559e−01 | 2.13694707e−01 | 2.26031095e−01 | 3.72266024e−01 |
| −1.86962709e−01 | −6.47509173e−02 | −3.69598806e−01 | 2.27036521e−01 |
| −1.26050711e−01 | 4.03724641e−01 | −1.28938928e−01 | −3.93297300e−02] |
| [3.72955799e−01 | 4.84712906e−02 | 4.12941903e−01 | −1.35820165e−01 |
| 4.42271084e−01 | 4.55231398e−01 | 3.57861146e−02 | 1.37613922e−01 |
| 2.08457619e−01 | 2.03211725e−01 | 2.98742533e−01 | 1.91396177e−01 |
| 3.93612295e−01 | 3.87981057e−01 | 2.07063835e−02 | −2.84238532e−02 |
| 2.33010590e−01 | 4.01888907e−01 | 5.85233532e−02 | 3.53739470e−01 |
| 2.46598780e−01 | −1.71682730e−01 | 9.16721448e−02 | 5.98238111e−01 |
| 2.59717852e−01 | −8.33429489e−03 | 1.04941055e−01 | −1.44936711e−01 |
| 2.50534594e−01 | 1.71524480e−01 | 1.71179339e−01 | 5.60425036e−02 |
| 5.02375424e−01 | 4.11376894e−01 | 2.76700944e−01 | −4.70279045e−02 |
| 5.66917598e−01 | 2.66102403e−01 | 2.80612499e−01 | 4.03430820e−01 |
| 4.50946718e−01 | −3.82751636e−02 | 4.06563997e−01 | 1.46575183e−01 |
| −1.10430099e−01 | 2.37129763e−01 | 2.98048496e−01 | 2.80029297e−01 |
| 2.70462155e−01 | 4.96900499e−01 | 4.73750710e−01 | 1.64684542e−02 |
| 4.29029137e−01 | 2.35541359e−01 | 2.58678019e−01 | 1.66974217e−01 |
| 2.02033997e−01 | 7.61061981e−02 | 4.61162090e−01 | 1.12272367e−01 |
| 4.53733504e−01 | 1.40641809e−01 | −1.43417448e−01 | −9.14162248e−02 |
| 5.44422984e−01 | 9.79169980e−02 | 2.48208791e−01 | −5.08169942e−02 |
| 4.56010133e−01 | 2.22861439e−01 | 2.45000005e−01 | 3.97584699e−02 |
| 4.46316242e−01 | 6.39449209e−02 | 1.12403870e−01 | 2.90951997e−01 |
| 3.83534044e−01 | 1.82180867e−01 | 3.67250502e−01 | −1.02096386e−01 |
| 2.67050743e−01 | 2.87286133e−01 | 3.60798597e−01 | 2.65053511e−01 |
| −5.80959059e−02 | 1.72897726e−01 | 1.26532972e−01 | 4.45671737e−01 |
| 1.48365587e−01 | −7.72240674e−05 | −6.91878647e−02 | 3.23363990e−01 |
| 2.99247026e−01 | 6.05086207e−02 | 2.69210935e−01 | 9.25280675e−02 |
| 4.37933385e−01 | 5.64179309e−02 | 4.56416994e−01 | 1.78726777e−01 |
| 5.70924044e−01 | 1.36882275e−01 | 5.72576940e−01 | 1.94560900e−01 |
| 1.79594271e−02 | 2.69156456e−01 | 2.35245511e−01 | 3.75778228e−01 |
| 3.30787003e−01 | 1.80086289e−01 | 4.00686771e−01 | 2.86861897e−01 |
| −3.41013931e−02 | −3.30702156e−01 | 3.08804233e−02 | 3.18938434e−01 |
| 2.21214816e−01 | 5.28658509e−01 | 2.57276207e−01 | 1.31472930e−01 |
| 8.19108263e−02 | 3.52961779e−01 | 2.82447547e−01 | 5.87129518e−02 |
| 1.47686392e−01 | 4.25532728e−01 | 2.25005805e−01 | 1.92601025e−01 |
| 2.45807320e−01 | 4.24423516e−01 | 5.52489996e−01 | 5.22469342e−01 |
| 2.66161233e−01 | −3.65027875e−01 | 2.69029826e−01 | 8.95913020e−02 |
| 2.34781265e−01 | 1.48028240e−01 | 1.74172089e−01 | 5.18179893e−01 |
| 3.46810132e−01 | 4.24001992e−01 | 5.38551845e−02 | 8.73480141e−02 |
| 2.14117467e−01 | −8.86471048e−02 | 4.26645160e−01 | 1.51833251e−01 |

TABLE $W_h^1$-continued

| | | | |
|---|---|---|---|
| 3.17207038e−01 | 1.55933991e−01 | 4.23053533e−01 | 1.50884002e−01 |
| 6.34012818e−02 | 2.07201019e−02 | 2.55022496e−01 | −6.66413456e−02 |
| −5.40595781e−03 | 3.20429504e−01 | −6.81017200e−03 | 1.33980121e−02 |
| 1.18819810e−03 | 5.10595858e−01 | −7.79205859e−02 | 9.04754102e−02 |
| 1.25274956e−01 | 3.36717695e−01 | 4.23667222e−01 | 3.40947062e−01 |
| 2.55361825e−01 | 3.17085795e−02 | 5.97649872e−01 | 1.33617684e−01 |
| 6.36605620e−01 | 1.87454149e−01 | 6.11490548e−01 | −6.57062903e−02 |
| 2.65639901e−01 | 1.22957133e−01 | 8.25549662e−02 | 2.21205488e−01 |
| 3.45986694e−01 | 2.96452999e−01 | 2.97300130e−01 | −1.44669205e−01 |
| 1.82991236e−01 | −1.45643681e−01 | 1.05927728e−01 | 5.84435582e−01 |
| 5.07476293e−02 | 3.80807638e−01 | 1.17102778e−02 | 8.14967379e−02 |
| 7.34380245e−01 | 3.98391098e−01 | −9.94719043e−02 | 5.33630610e−01 |
| 3.82158726e−01 | 3.37340325e−01 | 3.65626186e−01 | 4.49341446e−01 |
| 3.54786307e−01 | 3.72835025e−02 | 2.08952039e−01 | 3.13913554e−01 |
| 2.28690311e−01 | 2.43272394e−01 | 4.39908504e−01 | 1.47009984e−01 |
| 6.63250219e−03 | 2.91713357e−01 | 1.21568821e−01 | 6.59388959e−01 |
| 5.43070495e−01 | 1.93189040e−01 | −9.84581071e−04 | 6.07668936e−01 |
| −2.78315637e−02 | −5.29619940e−02 | 4.64671522e−01 | −2.07486153e−01 |
| 2.20929626e−02 | 7.48390481e−02 | 1.09901689e−01 | 2.66349494e−01 |
| 1.28778070e−01 | 2.87559450e−01 | 9.67471749e−02 | 5.68073988e−01 |
| −7.75315985e−02 | 4.56950545e−01 | 4.40986305e−01 | 2.63471901e−01 |
| −2.14300811e−01 | 1.70824036e−01 | −3.20465527e−02 | 2.34333694e−01 |
| 2.41645038e−01 | −4.66282338e−01 | −1.71157479e−01 | 3.87387931e−01 |
| 1.83191523e−01 | 4.71824706e−01 | 5.05578041e−01 | 1.29202545e−01 |
| 3.02200783e−02 | −6.29536435e−03 | 4.15011585e−01 | −3.01583737e−01 |
| 2.44382024e−01 | 3.34926546e−02 | 9.76480469e−02 | −7.76225701e−02 |
| −8.31835568e−02 | 5.89543819e−01 | 2.18326807e−01 | 1.65703550e−01] |
| [−1.88706309e−01 | 2.63813943e−01 | 1.22019768e−00 | 4.17958707e−01 |
| 4.87023056e−01 | 9.84302938e−01 | 6.13772571e−01 | 6.37831986e−01 |
| 2.69828737e−01 | −1.74825042e−01 | 4.68582690e−01 | 5.03208101e−01 |
| 2.35875681e−01 | −6.09912910e−02 | 1.47886306e−01 | 3.19973256e−01 |
| 5.71260333e−01 | −6.14739992e−02 | 2.27882922e−01 | 8.01658273e−01 |
| 5.98729730e−01 | 2.53434002e−01 | 4.42341596e−01 | 5.36172807e−01 |
| 1.47033960e−01 | 7.27661729e−01 | 3.57298672e−01 | 3.22711706e−01 |
| 8.87282729e−01 | 5.69056988e−01 | 8.02667201e−01 | 4.60102975e−01 |
| 1.03416705e−00 | 1.07131284e−02 | 8.73005018e−02 | 7.42217958e−01 |
| 3.29315625e−02 | 7.76053727e−01 | 1.22327656e−01 | 7.37706900e−01 |
| 5.07532299e−01 | 6.04154050e−01 | 2.29001001e−01 | −1.54507384e−01 |
| 9.26206172e−01 | 4.51666087e−01 | 5.01193404e−01 | 1.01982325e−03 |
| 5.52195370e−01 | 4.87685740e−01 | 3.51348460e−01 | −8.19816906e−03 |
| 2.30278984e−01 | 3.60007256e−01 | 1.37370542e−01 | 2.31300235e−01 |
| 5.07360622e−02 | 1.13446265e−01 | 7.41524994e−01 | −3.30069512e−01 |
| 1.76587492e−01 | 8.33286762e−01 | 1.26886979e−01 | 1.24797076e−01 |
| 4.91679341e−01 | 6.23649538e−01 | 4.01469499e−01 | 4.70409185e−01 |
| 5.87683201e−01 | −2.91497350e−01 | 7.48819113e−01 | −7.40358755e−02 |
| 8.39802384e−01 | 3.45594108e−01 | 5.29452384e−01 | 2.12713897e−01 |
| 3.35732847e−01 | 3.84837061e−01 | 8.94313991e−01 | 5.90662181e−01 |
| −4.99820597e−02 | 9.13475573e−01 | 5.11698544e−01 | −3.60771157e−02 |
| 3.00711989e−01 | −4.54085357e−02 | 5.51909447e−01 | 7.11847782e−01 |
| 8.13860059e−01 | −2.42295891e−01 | 4.78364855e−01 | 3.25153172e−01 |
| 2.39762098e−01 | 1.00822365e−00 | 2.93463290e−01 | 7.02004790e−01 |
| 2.91278902e−02 | −2.91345231e−02 | 5.73949469e−03 | 5.22978604e−01 |
| 9.16827679e−01 | 8.91585290e−01 | 2.45106637e−01 | 3.00459981e−01 |
| 2.38666371e−01 | 5.04630744e−01 | 4.33063239e−01 | 8.68965089e−01 |
| 4.49221313e−01 | 1.05302572e−00 | 1.07380736e−00 | 1.63244918e−01 |
| 1.53379932e−01 | 2.67100900e−01 | 8.54950964e−01 | 4.48629297e−02 |
| 2.27828518e−01 | 4.13663715e−01 | 3.53768736e−01 | 1.78750992e−01 |
| 5.45370221e−01 | 1.76252991e−01 | −2.86911074e−02 | 2.76176631e−01 |
| 1.01976961e−01 | 5.35211980e−01 | 4.21439677e−01 | 5.10097504e−01 |
| 1.30490029e−00 | 6.01098716e−01 | 3.53149265e−01 | 6.10646963e−01 |
| 1.01392651e−00 | −3.28692019e−01 | 1.07441604e−00 | −1.16256617e−01 |
| 7.57756531e−01 | 1.65272966e−01 | −9.78806335e−03 | 1.09951067e−00 |
| 3.26667428e−01 | 5.65734088e−01 | −3.23144019e−01 | 2.90335208e−01 |
| 4.04277593e−01 | −4.72789481e−02 | 6.18969202e−01 | 1.25968754e−00 |
| 1.40049130e−01 | 1.82264611e−01 | 6.28146231e−01 | 1.27116024e−01 |
| 3.09427083e−01 | 5.32198787e−01 | 1.62978083e−01 | 7.24981131e−04 |
| −3.98360714e−02 | −3.21481004e−02 | −1.62802592e−01 | 6.38488114e−01 |
| 6.56464517e−01 | 8.00670907e−02 | 5.42479873e−01 | 8.34599972e−01 |
| 4.23984230e−01 | −1.77353427e−01 | 8.00051272e−01 | 6.55204803e−02 |
| −6.70473874e−02 | 8.52003872e−01 | 3.10557544e−01 | 2.13563114e−01 |
| 5.31862676e−01 | 3.42819363e−01 | 3.56058031e−01 | 2.44970679e−01 |
| 1.04368758e−00 | −9.93564501e−02 | 1.73338786e−01 | −1.41836599e−01 |
| 7.71088123e−01 | 9.89054561e−01 | 7.21327066e−01 | 4.87108856e−01 |
| 3.16187054e−01 | 2.39820927e−01 | 4.24235433e−01 | 7.13716865e−01 |
| −1.07459389e−01 | 5.57203412e−01 | 4.99007046e−01 | 1.06345427e−00 |
| 6.89796746e−01 | 6.40418172e−01 | 6.13316059e−01 | 3.69624227e−01 |
| 4.45992768e−01 | 8.50471914e−01 | 3.43958139e−01 | 4.89101440e−01 |
| 5.19771278e−01 | −4.83344011e−02 | 5.80849409e−01 | 2.67495990e−01 |
| 3.48908991e−01 | 4.53011036e−01 | 9.80162323e−01 | −1.04443870e−01 |
| 4.86182511e−01 | 6.24625623e−01 | 7.94413626e−01 | 7.57624805e−01 |

TABLE $W_h^1$-continued

| | | | |
|---|---|---|---|
| 2.56539613e-01 | 5.39213002e-01 | 4.65779692e-01 | 5.81389628e-02 |
| 4.72217232e-01 | -7.59285130e-03 | 8.71273801e-02 | -2.48886719e-02 |
| 3.36031094e-02 | 1.30386844e-01 | 5.73874056e-01 | 7.26261199e-01 |
| 1.13218039e-01 | -1.44018114e-01 | 3.69427770e-01 | 5.80120906e-02 |
| 5.90099871e-01 | 5.02847493e-01 | 9.01401937e-01 | 6.67036623e-02 |
| -5.21245562e-02 | 1.81291535e-01 | 4.31837767e-01 | 5.64505994e-01 |
| 1.15961023e-01 | 6.44435287e-01 | 3.71907115e-01 | 5.16877174e-01 |
| 5.33026755e-02 | -8.61862376e-02 | 5.28457880e-01 | 1.09895468e-00 |
| 5.66521406e-01 | 2.47969717e-01 | 4.22383249e-01 | -3.86393480e-02 |
| 5.22628725e-01 | -3.17885309e-01 | 3.92110884e-01 | 4.95727122e-01 |
| 5.57980359e-01 | 5.76282680e-01 | 1.98971614e-01 | -1.49994388e-01] |
| [-4.45458815e-02 | -5.07004522e-02 | 5.90731323e-01 | 4.48348224e-01 |
| 2.32218221e-01 | 3.54771614e-01 | 2.29357034e-01 | 8.63313675e-02 |
| -4.66968939e-02 | 1.93506107e-01 | 2.11877480e-01 | 5.19971192e-01 |
| 2.29521945e-01 | -1.53434291e-01 | -5.95127121e-02 | 7.58131519e-02 |
| 2.94238001e-01 | 3.27247441e-01 | 7.69883692e-02 | -1.12161622e-03 |
| 2.96834230e-01 | 2.08273679e-01 | 4.16923761e-01 | 3.32659066e-01 |
| 1.47811219e-01 | 2.54832596e-01 | -5.94095252e-02 | -3.92960668e-01 |
| 3.59166086e-01 | 6.39797673e-02 | 3.36051106e-01 | 3.65314782e-01 |
| 3.96720320e-01 | -1.54667392e-01 | -1.21180020e-01 | -7.72227645e-02 |
| 3.15185368e-01 | 3.94032300e-01 | -1.21108823e-01 | 2.20805109e-01 |
| 4.98685181e-01 | 2.42878616e-01 | -9.30697937e-03 | 2.83866376e-03 |
| 1.07291363e-01 | 1.61519185e-01 | 4.79002774e-01 | 1.42484412e-01 |
| 1.81384712e-01 | 3.07408899e-01 | 2.10568607e-01 | 1.71263397e-01 |
| 1.60855621e-01 | 5.80243394e-02 | -4.83158156e-02 | 1.17162958e-01 |
| -5.19209653e-02 | 1.26661360e-01 | 5.33708215e-01 | -1.62163123e-01 |
| 3.60345036e-01 | 3.32471341e-01 | 2.40925024e-03 | 1.96190357e-01 |
| 3.06386173e-01 | 2.23320425e-01 | 1.42833799e-01 | 2.65017420e-01 |
| 3.95528495e-01 | -8.74584764e-02 | -1.85786307e-01 | 2.31659606e-01 |
| 5.37071347e-01 | 8.69423524e-02 | -1.95604283e-02 | 4.94893752e-02 |
| 1.04003571e-01 | 1.27316743e-01 | 5.43099679e-02 | 2.57937133e-01 |
| 2.68131495e-01 | 3.50162387e-01 | 2.47654185e-01 | 3.01362723e-01 |
| -1.90107182e-01 | -6.13807142e-02 | 1.59575567e-01 | 1.04872346e-01 |
| 2.95577884e-01 | -1.44025549e-01 | 1.27534553e-01 | 1.58159226e-01 |
| 2.17011258e-01 | 2.99399137e-01 | -1.19789824e-01 | 5.18563509e-01 |
| -8.68188590e-02 | 1.30468160e-01 | -1.95209403e-02 | -2.68562678e-02 |
| 2.41106227e-01 | 2.62315303e-01 | 1.77564800e-01 | 1.41612202e-01 |
| -1.53134957e-01 | 2.75106192e-01 | 3.91604334e-01 | 2.16278031e-01 |
| 2.98569560e-01 | 4.14514035e-01 | 4.85942990e-01 | 3.78558755e-01 |
| 1.01865470e-01 | 5.48516177e-02 | 1.91909865e-01 | 9.84983593e-02 |
| 3.54900509e-01 | 3.38695467e-01 | -6.57858476e-02 | -6.48966581e-02 |
| -1.27157578e-01 | 4.52001274e-01 | 3.45507354e-01 | -3.76094431e-02 |
| 2.82600075e-01 | -6.81881011e-02 | 3.06061000e-01 | 3.60933602e-01 |
| 1.80519551e-01 | 1.91725671e-01 | 9.75280628e-02 | 4.24728513e-01 |
| 5.33973575e-01 | -9.19206515e-02 | 2.89605707e-01 | 3.80284756e-01 |
| 3.56765836e-01 | -2.78624266e-01 | 4.71967399e-01 | 8.05226326e-01 |
| -1.62859321e-01 | 3.14371467e-01 | 2.95284986e-01 | 1.05405919e-01 |
| 2.23572671e-01 | 6.15383573e-02 | 5.58424056e-01 | 2.18090773e-01 |
| 9.74560827e-02 | 3.69712323e-01 | 1.51863530e-01 | -1.29199058e-01 |
| 1.64974377e-01 | -4.06605564e-02 | 5.15485764e-01 | -8.90785158e-02 |
| -7.84317032e-02 | 8.18653777e-02 | -1.35630772e-01 | 2.33124182e-01 |
| 1.55627280e-01 | 1.31612137e-01 | 3.61464918e-01 | 1.30352899e-01 |
| -5.85942529e-02 | 4.11847711e-01 | 3.19742918e-01 | 1.42922387e-01 |
| 2.98277736e-01 | -1.43318325e-01 | 6.24758936e-02 | 3.42850655e-01 |
| -6.16225377e-02 | 2.13354468e-01 | 2.85683513e-01 | -8.78941193e-02 |
| 1.65787548e-01 | -2.24514648e-01 | 2.45159548e-02 | -2.02018023e-01 |
| 2.17244834e-01 | 3.15233827e-01 | 1.00816615e-01 | 2.84091413e-01 |
| 2.68886983e-01 | -5.08753210e-02 | 1.03625143e-02 | -1.24973379e-01 |
| 1.61683589e-01 | -3.99778001e-02 | 5.08171320e-01 | 7.35204816e-01 |
| 1.15279101e-01 | 2.34698262e-02 | 2.34407321e-01 | 2.33320564e-01 |
| 2.62424187e-03 | 2.09089026e-01 | 1.64310802e-02 | 4.32680249e-01 |
| 3.81147385e-01 | 6.53776750e-02 | 3.02967757e-01 | 1.98786288e-01 |
| 2.56013483e-01 | -1.69612244e-01 | 1.60532549e-01 | 3.06757808e-01 |
| -3.97532880e-02 | 4.79786366e-01 | 4.03318137e-01 | -1.35764197e-01 |
| 3.55544269e-01 | 2.13344231e-01 | -2.69595355e-01 | 3.14173251e-01 |
| 4.70883340e-01 | -1.43773198e-01 | 4.32356656e-01 | -5.97680826e-03 |
| 1.40224427e-01 | -9.27116871e-02 | 1.90542430e-01 | 3.69532228e-01 |
| 1.42133579e-01 | 3.26226540e-02 | 3.08715194e-01 | -6.34028837e-02 |
| 3.46746564e-01 | 7.23804608e-02 | 8.17813799e-02 | 1.75285622e-01 |
| 3.16119462e-01 | 1.84871376e-01 | 2.31532045e-02 | -2.79616594e-01 |
| -1.89441517e-01 | 1.14147097e-01 | 1.54554043e-01 | -3.66329590e-01 |
| 3.24310660e-01 | 5.61642766e-01 | 3.57867360e-01 | 1.00181878e-01 |
| 4.89301652e-01 | 2.77377188e-01 | 4.48383123e-01 | -6.04427714e-02 |
| 9.17747244e-02 | -1.22498266e-01 | 2.24836960e-01 | 1.11633033e-01 |
| 3.14198405e-01 | 5.83208025e-01 | 1.99946806e-01 | -2.93181324e-03] |
| [1.35928005e-01 | 1.16541423e-01 | 5.66671789e-02 | 1.85355201e-01 |
| 5.01213849e-01 | 1.95527345e-01 | 2.31507719e-01 | 1.85695767e-01 |
| 2.29411677e-01 | -6.03034236e-02 | 2.65098065e-01 | 2.21779138e-01 |
| 2.94238031e-01 | 4.18868899e-01 | -1.55357510e-01 | -6.93554729e-02 |
| 5.41613102e-01 | 2.00143635e-01 | 6.11918211e-01 | -1.54337585e-01 |

TABLE $W_h^1$-continued

| | | | |
|---|---|---|---|
| 5.70573509e−01 | 2.66919106e−01 | 4.78516400e−01 | 4.54949498e−01 |
| −1.70162562e−02 | 3.22007328e−01 | 4.87597167e−01 | −1.07086394e−02 |
| 4.81870711e−01 | 3.38792622e−01 | 3.90040785e−01 | 3.65276545e−01 |
| 3.17837633e−01 | −4.67385091e−02 | −9.34561640e−01 | −3.99278760e−01 |
| 1.53874785e−01 | 3.23854387e−01 | 2.33383581e−01 | 2.63071150e−01 |
| 5.77991270e−02 | 8.19302648e−02 | 2.10461706e−01 | 1.69614419e−01 |
| 2.56544948e−01 | 3.69893372e−01 | 7.01436043e−01 | 3.21884215e−01 |
| 2.64746547e−01 | 2.25561708e−01 | 1.00973181e−01 | −8.69678855e−02 |
| 4.26134735e−01 | −2.08561331e−01 | −1.56321689e−01 | 1.75596237e−01 |
| −5.44261374e−02 | 2.05876783e−01 | 3.43852639e−01 | −5.44346683e−02 |
| 2.13510469e−01 | 1.74258396e−01 | 1.24170169e−01 | 2.73802847e−01 |
| 3.84966165e−01 | 3.65081996e−01 | −3.13774757e−02 | 2.96465337e−01 |
| 1.47028729e−01 | −4.21378389e−03 | −1.17419757e−01 | −1.36894166e−01 |
| 1.03655410e−00 | 3.98345441e−01 | −1.09821714e−01 | 2.00168446e−01 |
| 6.12781167e−01 | 2.24962030e−02 | 6.05610013e−01 | 5.58676273e−02 |
| 5.29511094e−01 | 2.29117155e−01 | −2.89302289e−01 | 2.74402499e−01 |
| 1.09252542e−01 | 1.58189505e−01 | −8.14595520e−02 | 1.44359916e−01 |
| 4.12380517e−01 | −6.83516860e−02 | 5.24994850e−01 | 5.42671643e−02 |
| −6.87778965e−02 | 6.03675365e−01 | 2.63141841e−01 | 3.43989402e−01 |
| −1.74345672e−01 | 7.63995200e−02 | 2.29804680e−01 | 1.97361365e−01 |
| 1.39199615e−01 | 4.76978242e−01 | 2.92362601e−01 | 2.92292535e−01 |
| 7.29234368e−02 | −6.06376082e−02 | 1.64497048e−02 | 5.65454327e−02 |
| −2.30783019e−02 | 4.11046483e−02 | 3.01355809e−01 | 4.82827276e−01 |
| 2.04923794e−01 | 1.17181204e−01 | 1.79258846e−02 | 5.47913790e−01 |
| −1.21554352e−01 | 3.93577963e−01 | 3.95908773e−01 | 4.16842014e−01 |
| 5.06544299e−02 | 3.87246370e−01 | −3.09240043e−01 | −4.93259616e−02 |
| 3.72500837e−01 | 7.04650730e−02 | 2.50305608e−03 | 1.71184286e−01 |
| 5.13882935e−01 | 2.78085530e−01 | −1.09933004e−01 | 2.83657968e−01 |
| 3.15537572e−01 | 9.20400843e−02 | 1.83105230e−01 | 3.61157179e−01 |
| 4.43164378e−01 | 1.19508199e−01 | 4.17889446e−01 | 3.26256573e−01 |
| 2.62484401e−01 | 2.45130081e−02 | 2.65741855e−01 | 3.75079326e−02 |
| 1.95932493e−01 | −1.76159009e−01 | 3.99980545e−01 | 3.27184081e−01 |
| 2.37648427e−01 | 4.00319934e−01 | 3.24448228e−01 | 2.68142581e−01 |
| 1.89410701e−01 | −1.02894619e−01 | 6.51901066e−01 | 1.38141429e−02 |
| 8.73505771e−02 | −1.86154082e−01 | −1.09752407e−02 | 1.34444401e−01 |
| 5.34483254e−01 | 4.41875249e−01 | 3.66463900e−01 | 3.22706193e−01 |
| −4.91577201e−02 | 6.82054907e−02 | 6.50062084e−01 | 1.36134386e−01 |
| 1.82507560e−01 | 1.90970913e−01 | 5.11824787e−01 | 2.33050600e−01 |
| 3.05763811e−01 | 2.51956046e−01 | −6.24791421e−02 | 5.20430923e−01 |
| 2.39451021e−01 | 2.45185476e−02 | −1.93803720e−02 | −1.90067291e−01 |
| 3.30706686e−01 | 1.84598953e−01 | 2.22077876e−01 | −1.32293971e−02 |
| 5.89577675e−01 | 2.17682198e−01 | 4.15285498e−01 | 3.27477664e−01 |
| −2.70772427e−02 | 5.50818205e−01 | 3.57049495e−01 | 6.11133277e−01 |
| 1.51822910e−01 | 5.00261903e−01 | −1.26331095e−02 | 8.36519003e−02 |
| −8.35216641e−02 | 1.02593489e−01 | −2.50365645e−01 | 3.68714370e−02 |
| 1.58747941e−01 | −4.11295712e−01 | 3.33536506e−01 | 3.09606850e−01 |
| 1.39760196e−01 | 1.28444005e−02 | 5.03221035e−01 | 1.83668077e−01 |
| −1.95413120e−02 | 2.17684656e−01 | 6.33030474e−01 | −1.28191337e−01 |
| 5.71893930e−01 | −1.39674127e−01 | 3.55147451e−01 | 3.43775332e−01 |
| 9.44269747e−02 | −1.12748705e−01 | 2.79054016e−01 | −1.27531517e−00 |
| 2.07239240e−01 | 2.29493961e−01 | 3.44565868e−01 | 2.53164202e−01 |
| 1.35153234e−01 | 5.09319901e−01 | 1.32336557e−01 | 6.53659463e−01 |
| 1.61306977e−01 | 2.85651162e−02 | 1.76751956e−01 | 8.12889412e−02 |
| 2.74071723e−01 | −8.88177902e−02 | 4.54090685e−01 | 3.56929392e−01 |
| 3.89841408e−01 | −1.07391350e−01 | 4.37890291e−02 | −2.05616996e−01 |
| 9.04880688e−02 | 1.71490833e−01 | 3.90917152e−01 | −2.08115727e−01 |
| 1.66285634e−01 | 4.43759382e−01 | 1.65086910e−01 | −6.36938885e−02 |
| −2.40119293e−01 | −7.98458830e−02 | 6.30400240e−01 | 1.49062067e−01 |
| −2.64565319e−01 | 8.10267091e−01 | 5.58723748e−01 | 3.77293043e−02] |
| [4.36284721e−01 | 1.74557105e−01 | 1.50979117e−01 | −2.10092992e−01 |
| 2.21522544e−02 | 1.89514011e−01 | −2.04108864e−01 | 6.78161263e−01 |
| 2.93792963e−01 | −2.29628291e−02 | 4.10546929e−01 | 1.52277693e−01 |
| 1.20253868e−01 | −1.36577350e−03 | −9.24854875e−02 | −1.33939892e−01 |
| 7.24036753e−01 | 7.79327229e−01 | 4.39417094e−01 | 4.10613179e−01 |
| 5.66295743e−01 | 2.66065836e−01 | 2.51683801e−01 | 4.90490228e−01 |
| 2.64552325e−01 | 4.60942298e−01 | 4.22699988e−01 | −4.03492272e−01 |
| 1.50733680e−01 | 4.92950708e−01 | 3.08105201e−01 | 3.37039113e−01 |
| 3.37863088e−01 | 1.38740391e−01 | 1.27842911e−02 | −2.05140054e−01 |
| −1.47340700e−01 | −4.45846505e−02 | 5.97855123e−03 | 3.61469388e−01 |
| 3.16930205e−01 | 3.56844872e−01 | −5.45141518e−01 | −6.31479919e−02 |
| 3.22522372e−01 | 2.37764642e−01 | 7.87263811e−02 | 3.35702226e−01 |
| 9.81340632e−02 | 4.34136957e−01 | 3.19355786e−01 | 7.35675097e−02 |
| 2.27430075e−01 | 1.41987158e−02 | 6.99590519e−02 | 1.80436015e−01 |
| 3.79360259e−01 | −1.66312397e−01 | 3.85126442e−01 | 7.65640736e−02 |
| 1.23722017e−01 | 2.26926774e−01 | 2.13847443e−01 | 1.08180046e−01 |
| −2.00800478e−01 | 1.11907236e−01 | 1.61755025e−01 | 1.08367182e−01 |
| 8.77816752e−02 | 1.88414797e−01 | −2.30284899e−01 | −1.30919829e−01 |
| 6.19620562e−01 | 5.99255800e−01 | 2.41245795e−02 | 5.69265306e−01 |
| 2.49263719e−01 | 7.83587713e−03 | 1.80914462e−01 | −1.03255965e−01 |
| 3.13023627e−01 | 2.63931483e−01 | −1.24741293e−01 | 2.04494625e−01 |

TABLE $W_h^1$-continued

| | | | |
|---|---|---|---|
| 1.54585019e-02 | 2.06823736e-01 | 1.22969337e-01 | -1.87711164e-01 |
| 4.06608045e-01 | -1.60098627e-01 | 4.79825854e-01 | -1.02705948e-01 |
| 2.89658099e-01 | 8.27198476e-02 | 1.80034950e-01 | 8.80962908e-02 |
| 2.31034636e-01 | 1.78445309e-01 | 2.17144907e-01 | 1.28861994e-01 |
| 1.28267020e-01 | 6.08810782e-01 | -7.87099265e-03 | 4.43876177e-01 |
| 2.26792693e-01 | 2.96528935e-01 | 1.74162492e-01 | -1.67330652e-02 |
| -7.52011314e-02 | 1.28051504e-01 | 4.17677790e-01 | 3.66203412e-02 |
| 3.90532821e-01 | -3.52671683e-01 | 1.64090887e-01 | 3.96178156e-01 |
| 3.81109059e-01 | 1.99540854e-01 | 4.93146060e-03 | 1.51900604e-01 |
| 2.85705626e-01 | 6.57724440e-02 | 8.82232189e-02 | 1.55187905e-01 |
| 2.56710440e-01 | 4.01713103e-01 | 3.43823507e-02 | -1.51000902e-01 |
| -3.52108851e-02 | 5.61591089e-01 | 8.36657435e-02 | 3.17332745e-01 |
| 3.86279285e-01 | 8.77848566e-02 | 2.40967691e-01 | -6.42808080e-02 |
| 1.70255929e-01 | -1.65660605e-01 | 4.62471604e-01 | 6.16120808e-02 |
| 2.40340576e-01 | 2.36235008e-01 | 3.08925092e-01 | 2.73782462e-01 |
| 3.69439900e-01 | -1.16356023e-01 | 3.95174652e-01 | 7.62843993e-03 |
| -1.61729753e-01 | -1.05132610e-01 | -1.13568105e-01 | -3.03360075e-01 |
| -1.96383782e-02 | 2.91631728e-01 | 3.18316817e-01 | 3.19987118e-01 |
| 1.03498608e-01 | 1.94784731e-01 | -8.33914429e-02 | 1.47953376e-01 |
| 1.00704238e-01 | 1.72933385e-01 | -1.60774842e-01 | 4.80966596e-03 |
| 1.98038891e-01 | 3.32834750e-01 | 2.74549156e-01 | -5.35213389e-02 |
| 4.18401301e-01 | 2.30675459e-01 | 3.36586595e-01 | -1.07689537e-01 |
| 4.09884602e-02 | 3.09094816e-01 | 1.12276236e-02 | 3.89919549e-01 |
| 3.74740452e-01 | 2.57942796e-01 | 5.14150858e-01 | 7.76438266e-02 |
| 3.01056594e-01 | 4.22241181e-01 | 4.10089105e-01 | 6.08159602e-01 |
| 5.57297878e-02 | 9.50043201e-02 | 3.34914982e-01 | 1.08309679e-01 |
| 9.30803120e-02 | 4.94387984e-01 | 2.94659287e-01 | 6.44555986e-01 |
| -2.37908348e-01 | 2.87097711e-02 | 7.07994282e-01 | 2.50245869e-01 |
| 1.91762447e-01 | -6.22784123e-02 | -1.07048422e-01 | 1.82977825e-01 |
| 2.65393436e-01 | 8.40615854e-02 | -2.11370122e-02 | -7.29568361e-04 |
| 7.52104372e-02 | 8.16969946e-02 | 7.62419701e-02 | 9.28623080e-02 |
| 1.51518539e-01 | 4.28930759e-01 | 4.22716767e-01 | 3.12962264e-01 |
| 2.84682691e-01 | 3.40585589e-01 | -2.14997903e-01 | 2.36595437e-01 |
| 5.58029115e-01 | 2.73839027e-01 | 7.78747320e-01 | 4.31957170e-02 |
| 9.59033743e-02 | 2.68296421e-01 | 5.68839967e-01 | 9.84800905e-02 |
| 4.00723636e-01 | 2.50642359e-01 | 4.12045240e-01 | 4.75505918e-01 |
| 3.94276947e-01 | 1.78659111e-01 | 4.82251830e-02 | 5.08745730e-01 |
| 3.58607918e-01 | -2.40041912e-01 | 1.52230144e-01 | 3.24495822e-01 |
| -3.22773755e-02 | 1.29493684e-01 | -1.70381248e-01 | 6.72888756e-02 |
| 2.99559981e-01 | 7.65572302e-04 | 2.52566695e-01 | 1.93373695e-01 |
| 3.86061281e-01 | 3.41287017e-01 | 2.68154927e-02 | 5.32973349e-01 |
| 2.17842430e-01 | -4.71711308e-01 | 2.30368957e-01 | 4.42903042e-01 |
| 2.86604226e-01 | 1.79808717e-02 | 7.71348536e-01 | -1.79230437e-01] |
| [-1.48520619e-02 | 7.14633942e-01 | 4.56010640e-01 | 3.74152660e-01 |
| 5.54109216e-01 | 4.28159177e-01 | 9.27283645e-01 | -1.40400389e-02 |
| 4.34199989e-01 | 8.35843623e-01 | 7.10798919e-01 | 4.99941528e-01 |
| 5.40248096e-01 | 6.11260414e-01 | 3.08651656e-01 | -3.12937461e-02 |
| 5.07433236e-01 | -6.51086643e-02 | 4.76586789e-01 | 1.16817676e-01 |
| 3.84844393e-01 | 4.44002032e-01 | 2.88291305e-01 | 1.07208610e-00 |
| 5.18084884e-01 | 7.25152135e-01 | 1.51847884e-01 | 1.75755173e-02 |
| 3.50744277e-01 | 3.28102738e-01 | -2.83396873e-03 | 3.09993654e-01 |
| 3.50849271e-01 | 1.93207674e-02 | 5.66513658e-01 | 1.18085893e-03 |
| 3.62980627e-02 | 6.41934276e-01 | 2.34916389e-01 | 6.35185778e-01 |
| 2.06024438e-01 | 4.10069913e-01 | 1.72832124e-02 | 1.02775626e-01 |
| 7.73233473e-01 | 2.45500758e-01 | 9.20030832e-01 | 3.79784852e-01 |
| 2.49057040e-01 | 5.44847786e-01 | 4.32621449e-01 | 2.32728511e-01 |
| 6.54611707e-01 | 1.90780222e-01 | 4.59728539e-01 | 5.85940301e-01 |
| 6.25421524e-01 | 5.36189258e-01 | 6.63243592e-01 | 3.05268794e-01 |
| 2.11592317e-01 | 3.60549003e-01 | 4.77120608e-01 | 8.57602000e-01 |
| 1.91613346e-01 | 2.74901420e-01 | 2.74702907e-01 | 3.16382676e-01 |
| 4.26533848e-01 | 2.82296121e-01 | 3.45047802e-01 | -3.74955446e-01 |
| 6.04741037e-01 | 6.71744525e-01 | 5.89986563e-01 | 9.46691155e-01 |
| 7.64797449e-01 | 4.83872682e-01 | 3.19375962e-01 | 1.33671820e-01 |
| 4.46022242e-01 | 6.56426251e-01 | 1.80692434e-01 | 2.48262599e-01 |
| 9.17818025e-02 | 2.27666944e-01 | 1.82961598e-01 | 5.77630997e-01 |
| 1.37077972e-01 | -4.28236306e-01 | 2.39081606e-01 | -3.48738059e-02 |
| 7.21400321e-01 | 3.06263685e-01 | 8.36996317e-01 | 1.10600960e-00 |
| 1.79480106e-01 | 5.40448785e-01 | 2.18336850e-01 | 5.36250114e-01 |
| 4.66430008e-01 | 6.52158558e-01 | 6.58434212e-01 | 9.66446996e-02 |
| -9.54834148e-02 | 8.89842033e-01 | 5.22739053e-01 | 3.66562247e-01 |
| 1.82315350e-01 | 5.38835943e-01 | 3.96292567e-01 | 4.98525828e-01 |
| 4.23232108e-01 | 5.13649821e-01 | 7.67807245e-01 | 2.39317998e-01 |
| 2.41559878e-01 | 2.23120183e-01 | 3.17195326e-01 | 1.85318753e-01 |
| 1.25379590e-02 | 7.80256450e-01 | 2.60296255e-01 | 7.69864738e-01 |
| 4.82545853e-01 | 4.97515738e-01 | 5.86689040e-01 | 3.34713370e-01 |
| 8.28860641e-01 | 5.03665686e-01 | -4.44655977e-02 | 5.14180601e-01 |
| 3.69573355e-01 | 1.09468438e-01 | 6.07372761e-01 | 5.47022402e-01 |
| 3.15948963e-01 | 1.05147350e-00 | 4.56152499e-01 | 5.23232043e-01 |
| 2.15871185e-01 | 3.27178568e-01 | 2.94660747e-01 | 5.64496994e-01 |
| 3.20908874e-01 | 3.22634846e-01 | 3.93196762e-01 | 1.19263731e-01 |

TABLE $W_h^1$-continued

| | | | |
|---|---|---|---|
| 4.36604291e−01 | 4.49601442e−01 | 1.82134956e−01 | 7.48335063e−01 |
| 8.08795989e−02 | 2.33869940e−01 | 4.98400152e−01 | 3.71858209e−01 |
| 3.83037664e−02 | 3.01156133e−01 | 5.80238283e−01 | 1.14753388e−01 |
| 3.65908235e−01 | 4.50147659e−01 | 4.23878908e−01 | 1.74182907e−01 |
| 1.84375823e−01 | 2.67977715e−01 | 6.31052494e−01 | 4.47584629e−01 |
| 2.18400791e−01 | 6.42607033e−01 | 3.60727072e−01 | 3.87369514e−01 |
| 3.07556897e−01 | 4.55652058e−01 | 1.98069550e−02 | 6.05957322e−02 |
| 5.25514126e−01 | 5.92907816e−02 | 2.60344446e−01 | 1.85381517e−01 |
| 1.13494611e−00 | 1.53368637e−01 | 6.27436161e−01 | 3.26917320e−01 |
| 5.59848666e−01 | 4.51506317e−01 | 1.84047297e−01 | 1.18780363e−00 |
| −5.97523898e−02 | 5.32535315e−01 | 4.27245289e−01 | 5.30846000e−01 |
| 4.34059530e−01 | 9.94210124e−01 | 3.06331575e−01 | 1.18014328e−01 |
| 6.17685497e−01 | 3.25651854e−01 | 2.36010239e−01 | 2.83637017e−01 |
| 2.12499008e−01 | 3.71534494e−03 | 8.14399838e−01 | 3.59026551e−01 |
| −1.88776001e−01 | 4.30554241e−01 | −8.94053727e−02 | 6.05486691e−01 |
| 6.71536028e−01 | 3.76787543e−01 | 1.33554846e−01 | 1.02064359e−00 |
| 1.91912740e−01 | 9.20845151e−01 | −3.19549181e−02 | 3.90209615e−01 |
| 3.00410300e−01 | 6.13002062e−01 | 4.75768119e−01 | −2.17218339e−01 |
| 4.89935040e−01 | 4.91147339e−01 | 3.86476129e−01 | 4.35952693e−01 |
| 2.55851388e−01 | 4.59820293e−02 | 2.01629087e−01 | 4.34896767e−01 |
| 7.00000763e−01 | 4.94495422e−01 | 1.33364165e−00 | 7.82856464e−01 |
| 3.41533095e−01 | −6.26467705e−01 | 7.99544752e−01 | 5.78976452e−01 |
| 6.17694795e−01 | 3.09486181e−01 | 3.25384408e−01 | 3.98241788e−01 |
| 7.61795091e−03 | 5.16477823e−01 | 6.38091862e−01 | 1.36362016e−01 |
| 2.15336502e−01 | 4.69351739e−01 | 3.82846184e−02 | 2.55727172e−01 |
| 3.21140796e−01 | 5.86845100e−01 | 4.11094606e−01 | 5.46695530e−01 |
| 2.08171010e−01 | 5.36827326e−01 | 5.89286864e−01 | 6.69407547e−01] |
| [3.93316984e−01 | 3.41844141e−01 | 5.75783193e−01 | 2.21032053e−01 |
| 1.59895811e−02 | 5.00869393e−01 | 4.89634007e−01 | 1.22217312e−01 |
| −2.07132339e−01 | 3.76797587e−01 | −2.26288587e−02 | 5.57139397e−01 |
| 3.44301254e−01 | 1.03245929e−01 | 6.88293517e−01 | −1.59512326e−01 |
| 7.60003984e−01 | 4.25054729e−02 | 4.11232561e−01 | 2.63912588e−01 |
| 3.51336151e−01 | −1.76322594e−01 | 6.77737296e−01 | 2.46709049e−01 |
| 9.48473588e−02 | 3.64544868e−01 | −1.12803578e−01 | −9.27280486e−02 |
| 6.74728274e−01 | 2.98894018e−01 | 5.99198878e−01 | 3.43978286e−01 |
| 2.98488140e−01 | 3.06406528e−01 | −4.23175842e−02 | 2.25094929e−01 |
| 3.27517718e−01 | 1.52134866e−01 | −2.32186839e−01 | 3.67639065e−01 |
| 3.08806539e−01 | 3.55548233e−01 | 2.91153967e−01 | 4.75958198e−01 |
| 4.16457385e−01 | 3.73397321e−02 | 6.19766355e−01 | 4.38104808e−01 |
| 3.03308368e−01 | 4.93055046e−01 | 5.88009953e−01 | 6.57213867e−01 |
| 2.27115542e−01 | 1.39073404e−02 | 1.09672122e−01 | 4.18990940e−01 |
| 6.54883265e−01 | 5.70190609e−01 | 2.63007671e−01 | 2.71270454e−01 |
| 1.63612306e−01 | 5.68926334e−01 | −9.86792892e−02 | 2.20406100e−01 |
| 4.81263995e−02 | 1.72763839e−01 | 2.68707518e−02 | −2.85290599e−01 |
| 2.56644726e−01 | 5.02777934e−01 | 5.82240283e−01 | −4.27615821e−01 |
| 3.06858659e−01 | 5.68386838e−02 | 6.46395609e−02 | 2.51960665e−01 |
| 2.46620029e−01 | 5.55369593e−02 | 2.60008723e−01 | 5.59061587e−01 |
| 5.51647842e−01 | 4.13917571e−01 | 1.90859940e−02 | 2.30002478e−01 |
| 1.69404745e−01 | 4.07908410e−02 | 1.89602494e−01 | 4.50108409e−01 |
| 5.12555361e−01 | −2.76629031e−01 | 8.64984989e−02 | 2.76773721e−01 |
| 2.45507598e−01 | 1.23054750e−01 | 2.22008333e−01 | 2.06010953e−01 |
| −1.17969245e−01 | 4.61977243e−01 | −7.22301230e−02 | 4.19709474e−01 |
| 1.70572191e−01 | 3.45941603e−01 | 7.98201084e−01 | 3.78369391e−01 |
| 2.60515690e−01 | 3.62533212e−01 | 5.92732847e−01 | 4.74116534e−01 |
| 1.55150399e−01 | 5.44758320e−01 | 3.86346102e−01 | 3.18304859e−02 |
| −1.24470800e−01 | 3.05419207e−01 | 1.75507786e−01 | 2.51686186e−01 |
| 1.12316608e−02 | 6.42438650e−01 | 7.63808668e−01 | 7.51634717e−01 |
| 2.59630919e−01 | 2.41116062e−01 | 3.23839217e−01 | 4.55207855e−01 |
| 5.25160670e−01 | 6.76830411e−01 | −1.78323999e−01 | 1.12656385e−01 |
| 5.20950913e−01 | 5.04287720e−01 | −1.26525849e−01 | 3.63303453e−01 |
| 2.83136755e−01 | 3.83883983e−01 | 1.27728954e−01 | 5.63754797e−01 |
| 2.39269167e−01 | 2.30399400e−01 | 2.70861447e−01 | 4.37042534e−01 |
| 1.16388097e−01 | 3.67588669e−01 | 2.16199905e−01 | 3.00208330e−01 |
| 3.82148251e−02 | 3.17408502e−01 | 1.21933922e−01 | 5.84146678e−02 |
| 2.10542947e−01 | 1.55386880e−01 | −2.28696704e−01 | 7.50777006e−01 |
| 3.68139684e−01 | 2.69139200e−01 | 7.11986363e−01 | 9.05259311e−01 |
| −6.78026583e−03 | 4.62778091e−01 | 4.29904521e−01 | −9.68437493e−02 |
| 6.24839902e−01 | 3.75030309e−01 | 2.79287845e−01 | 4.23656762e−01 |
| 2.45421335e−01 | −1.90050915e−01 | 6.68566227e−01 | 3.14231098e−01 |
| 2.31516957e−01 | 3.98028284e−01 | 6.32783622e−02 | 5.26025057e−01 |
| 3.11376244e−01 | 1.17808014e−01 | 1.86990499e−01 | −1.16893783e−01 |
| 5.51965833e−01 | 2.76473731e−01 | 3.46081883e−01 | −2.80430049e−01 |
| 3.00815940e−01 | 4.04764665e−03 | 5.14113605e−01 | 1.95483997e−01 |
| 2.35607415e−01 | 5.04122972e−01 | 3.28475505e−01 | 2.54325211e−01 |
| 2.80592948e−01 | 2.07044527e−01 | 4.49340075e−01 | 6.58730745e−01 |
| 1.86248645e−01 | 1.05667546e−01 | 3.09352219e−01 | 2.46499345e−01 |
| −1.32347897e−01 | 1.15644410e−01 | 3.85122955e−01 | 1.25687003e−01 |
| 2.98382103e−01 | 1.92902610e−01 | 7.98600614e−01 | 2.90314704e−01 |
| 6.83335662e−01 | −1.54029399e−01 | 7.79213369e−01 | 2.21815020e−01 |
| 3.46609265e−01 | 2.61782795e−01 | 1.73156023e−01 | 1.33858770e−01 |

TABLE $W_h^1$-continued

| | | | |
|---|---|---|---|
| 5.39440930e−01 | 5.14609814e−01 | 4.14943725e−01 | 5.19701421e−01 |
| 7.08577752e−01 | 3.34649116e−01 | 5.00109017e−01 | 2.79759616e−01 |
| −2.65721045e−02 | 4.68496174e−01 | 5.11710882e−01 | 4.19951797e−01 |
| 1.61311388e−01 | −5.76792695e−02 | 1.92916796e−01 | 6.85246885e−01 |
| 1.56023636e−01 | 5.93171477e−01 | 5.39828181e−01 | 5.08335710e−01 |
| 3.27708930e−01 | −1.98518671e−03 | 3.51804823e−01 | 5.42607307e−01 |
| 3.18316787e−01 | 2.68438667e−01 | 1.08497545e−01 | 2.96887875e−01 |
| −1.50119638e−04 | 1.54034317e−01 | 3.96992326e−01 | 2.66970903e−01 |
| 4.40174490e−01 | −1.64493650e−01 | 2.63427258e−01 | −1.89354226e−01 |
| −1.96995184e−01 | 2.84440964e−01 | 2.83420235e−01 | 5.66228509e−01 |
| 1.35356247e−01 | 4.87462670e−01 | 4.50493932e−01 | 3.03570479e−01] |
| [−6.20525420e−01 | −5.61452359e−02 | −5.03387034e−01 | −5.71426332e−01 |
| −2.80127048e−01 | −1.14665341e−00 | −6.34289563e−01 | 3.29278670e−02 |
| −7.13849485e−01 | −5.95857501e−01 | −8.84690225e−01 | 1.94608137e−01 |
| 5.77129900e−01 | −2.39365295e−01 | −7.03465998e−01 | 4.67997640e−01 |
| 3.24260503e−01 | −5.96738219e−01 | −3.75608474e−01 | −3.95126134e−01 |
| −7.46729195e−01 | −4.78302181e−01 | −1.80958956e−01 | −9.77432251e−01 |
| −2.10155234e−01 | −6.13679528e−01 | −6.08188331e−01 | −2.38812834e−01 |
| −4.46778834e−01 | −6.49607241e−01 | −1.12649813e−01 | −3.52805316e−01 |
| −3.50984931e−01 | −5.01962841e−01 | −3.54320347e−01 | −3.84908736e−01 |
| −4.83769685e−01 | −5.41939378e−01 | −4.44628596e−02 | −1.58691928e−01 |
| −4.34356332e−01 | 5.34174860e−01 | −3.97493333e−01 | −6.66390836e−01 |
| −8.88670623e−01 | 7.47611523e−02 | −5.18080413e−01 | −3.06480736e−01 |
| −6.17163002e−01 | −2.48477057e−01 | −2.56864697e−01 | −9.79648232e−02 |
| −3.46217006e−01 | −5.14315307e−01 | 5.05020991e−02 | −1.88583340e−02 |
| −8.31255853e−01 | −4.64400828e−01 | −3.89153868e−01 | −1.53443456e−01 |
| −6.41322672e−01 | −7.07873583e−01 | −3.35444301e−01 | −5.12035131e−01 |
| −1.83775976e−01 | −2.14296848e−01 | −1.31954893e−01 | −2.75416851e−01 |
| 1.73199102e−01 | −3.65123272e−01 | −7.64541984e−01 | −3.38442653e−01 |
| 2.13805467e−01 | −4.45336193e−01 | −4.56939578e−01 | −3.07678878e−01 |
| −7.06196308e−01 | −7.18038797e−01 | −1.99441567e−01 | −6.12418354e−01 |
| 1.36528254e−01 | −6.81983709e−01 | −2.77577013e−01 | −1.75507575e−01 |
| −4.50594008e−01 | −4.29522514e−01 | −2.27593958e−01 | −3.72702301e−01 |
| −8.04307759e−02 | −5.28842747e−01 | 4.86537009e−01 | −1.86264858e−01 |
| −4.18065965e−01 | −1.69171304e−01 | −2.26983950e−01 | −7.12345302e−01 |
| −7.01270878e−01 | −8.26558098e−02 | −2.75799274e−01 | −2.15034351e−01 |
| −5.64869702e−01 | −7.90382981e−01 | −6.31578147e−01 | −6.18668258e−01 |
| −3.64573598e−01 | −6.45477414e−01 | −5.18868983e−01 | −8.23328346e−02 |
| −1.63413899e−03 | −8.13145638e−01 | −1.64751068e−01 | 1.29142851e−01 |
| −6.19118810e−01 | −6.84760988e−01 | −6.76845312e−02 | −2.82909572e−01 |
| −4.52463537e−01 | −4.53882456e−01 | −7.36573637e−01 | −4.81003791e−01 |
| −4.43151653e−01 | −3.20481360e−01 | −6.95321083e−01 | −5.58075190e−01 |
| −2.17778042e−01 | −1.77263796e−01 | −6.54259086e−01 | −7.95173585e−01 |
| −2.79950440e−01 | −1.69166133e−01 | −4.66042548e−01 | −4.37641054e−01 |
| −4.46918458e−01 | −2.41590098e−01 | −3.60540003e−02 | 5.31974472e−02 |
| 5.71071133e−02 | −2.97181696e−01 | −4.87063169e−01 | −1.40262917e−01 |
| −5.13646483e−01 | −7.47951567e−01 | −7.12303102e−01 | −3.03577930e−01 |
| −5.60539514e−02 | −4.00399804e−01 | −3.03483158e−01 | −2.64965087e−01 |
| −2.33375758e−01 | −1.77086905e−01 | −2.85546631e−01 | −6.24490917e−01 |
| −3.36170405e−01 | −2.82306731e−01 | 3.02812278e−01 | −5.84081292e−01 |
| −7.80298352e−01 | −2.58067906e−01 | −3.70871902e−01 | −7.90630460e−01 |
| 6.23316579e−02 | −2.22831815e−01 | 3.14409448e−01 | −7.59383619e−01 |
| −3.03667247e−01 | −1.98867500e−01 | 4.39083613e−02 | −4.31524336e−01 |
| −3.27242583e−01 | −5.27364135e−01 | −3.46251160e−01 | −2.48194888e−01 |
| −4.91109908e−01 | −2.16192976e−01 | 9.22777876e−02 | −6.27439797e−01 |
| −5.67204773e−01 | −3.36333096e−01 | −2.82082379e−01 | −1.80737957e−01 |
| −5.61740339e−01 | −3.41797709e−01 | −7.32569933e−01 | −7.49865472e−01 |
| −4.11303014e−01 | −5.48344672e−01 | −1.92526281e−01 | −4.39304978e−01 |
| 1.49607077e−01 | −3.61618727e−01 | −8.48076582e−01 | −6.50464535e−01 |
| −2.44833544e−01 | −9.07756090e−01 | −6.32189333e−01 | −2.71652788e−01 |
| −1.70365065e−01 | −1.86812773e−01 | −5.34628630e−01 | −5.75027049e−01 |
| 3.69472235e−01 | −3.21320176e−01 | −6.06845081e−01 | −5.83472252e−01 |
| −5.12397528e−01 | −6.20525837e−01 | −1.97837681e−01 | −3.35321993e−01 |
| −3.53531659e−01 | −5.00895977e−01 | 1.29395008e−01 | −1.98517546e−01 |
| −1.43262371e−01 | −5.80566108e−01 | −6.90191031e−01 | −4.81651455e−01 |
| −3.36549252e−01 | −4.65096653e−01 | −4.50749174e−02 | −3.95646036e−01 |
| −2.83041149e−01 | −5.39079785e−01 | −2.77114391e−01 | −1.62325084e−01 |
| −4.00379539e−01 | −2.08373591e−01 | −4.08308804e−01 | −3.47884327e−01 |
| −5.23345113e−01 | −2.23832875e−01 | −8.76062572e−01 | −4.57268447e−01 |
| −5.85919082e−01 | −8.03410530e−01 | −7.81780362e−01 | −2.85886407e−01 |
| −2.77396083e−01 | −6.80852950e−01 | −6.89279258e−01 | −3.27312708e−01 |
| −4.14382249e−01 | 3.49908322e−01 | −1.31704286e−01 | −7.08147287e−01 |
| −2.04205364e−01 | −2.36079857e−01 | −1.91304222e−01 | −6.57904506e−01 |
| −3.91939044e−01 | −8.00098419e−01 | −1.39256373e−01 | 3.43372673e−01 |
| −3.07235897e−01 | −4.59312290e−01 | −4.16511834e−01 | −4.69136387e−01] |
| [3.59364748e−01 | −1.31759606e−02 | −7.86488131e−03 | −6.33784711e−01 |
| −6.99515492e−02 | 8.98548514e−02 | 1.69499084e−01 | −6.64307596e−03 |
| 2.15890244e−01 | 2.88710613e−02 | 2.12219849e−01 | −1.46347225e−01 |
| −6.42551184e−02 | 5.04880659e−02 | 1.23339750e−01 | −3.40317816e−01 |
| 6.00389540e−01 | 6.72171116e−02 | −1.67323425e−02 | −5.20875026e−03 |

TABLE $W_h^1$-continued

| | | | |
|---|---|---|---|
| 2.63440222e−01 | 2.79529154e−01 | −7.74604157e−02 | 7.18384266e−01 |
| 3.66489261e−01 | 2.72719353e−01 | −5.71450859e−04 | 1.55796766e−01 |
| 5.46715856e−02 | 3.69739123e−02 | 4.62584883e−01 | 2.43758395e−01 |
| 8.92253444e−02 | 4.20132160e−01 | −1.46496013e−01 | 1.21522285e−01 |
| −3.66648100e−02 | 2.46763498e−01 | 3.27178925e−01 | −2.14535177e−01 |
| 4.26607043e−01 | −2.97942162e−01 | 8.49187732e−01 | −3.16441804e−01 |
| 8.76627788e−02 | 2.27434620e−01 | 1.56940788e−01 | −3.80112119e−02 |
| 2.93521345e−01 | 1.86085492e−01 | 3.78712088e−01 | 1.20823912e−03 |
| 3.99130195e−01 | −2.21473277e−01 | 5.26495390e−02 | −1.68465942e−01 |
| 3.80400926e−01 | 2.76061565e−01 | 2.90975451e−01 | 2.20920127e−02 |
| 1.25581056e−01 | −1.43297315e−01 | 9.65438224e−03 | 2.39449292e−01 |
| 5.07778525e−02 | −1.13668084e−01 | 8.26649964e−02 | 7.73042068e−02 |
| 1.30978063e−01 | −9.46515426e−02 | 2.98828721e−01 | −5.61156750e−01 |
| 1.88413560e−01 | 6.03941130e−03 | 1.60035625e−01 | 1.38184279e−01 |
| 2.98802435e−01 | 3.71567518e−01 | 3.34189951e−01 | 2.58329362e−01 |
| 8.54665413e−02 | 4.74049926e−01 | 1.30030379e−01 | 2.12679580e−01 |
| −1.22549541e−01 | 8.24017897e−02 | −1.49386674e−01 | 5.92061169e−02 |
| 2.04468295e−01 | −3.86689425e−01 | 3.08780909e−01 | −2.04640970e−01 |
| −5.46931207e−01 | −1.21872678e−01 | −2.33626254e−02 | 3.64771008e−01 |
| 4.02340561e−01 | −4.16582674e−01 | 6.61751404e−02 | 2.88556755e−01 |
| −8.32844526e−02 | 5.36203921e−01 | 3.48773420e−01 | 3.10873240e−01 |
| 1.00029461e−01 | 3.15292239e−01 | 1.47265092e−01 | 1.07589349e−01 |
| −1.57553405e−01 | 3.67852971e−02 | 4.29603755e−01 | −8.01660866e−02 |
| 1.09246686e−01 | −1.98585346e−01 | 1.37034282e−01 | 3.68616551e−01 |
| 7.57853538e−02 | 4.47497129e−01 | 7.71030709e−02 | −4.23192717e−02 |
| −2.49270175e−04 | 1.77408174e−01 | −8.96258652e−02 | −2.95862138e−01 |
| 1.18195705e−01 | 8.60626921e−02 | −5.77009246e−02 | 7.54001290e−02 |
| 3.91755432e−01 | 2.38431126e−01 | −2.81228960e−01 | 7.02698410e−01 |
| 3.87892723e−01 | −3.44060153e−01 | −3.49501610e−01 | 1.15520142e−01 |
| 6.15973584e−02 | 2.08406880e−01 | −1.04973711e−01 | 3.53782505e−01 |
| −1.44780427e−01 | −1.46380350e−01 | 4.13520157e−01 | 2.02412069e−01 |
| −1.87075049e−01 | −4.58485097e−01 | 3.29058409e−01 | 1.36469126e−01 |
| −2.19368309e−01 | 2.43186988e−02 | −6.54899552e−02 | 5.22036850e−01 |
| 1.71911940e−01 | −6.04722679e−02 | 2.81698495e−01 | −3.57386976e−01 |
| −3.20798531e−02 | 2.39881501e−01 | 2.06431169e−02 | 1.94287926e−01 |
| 1.62719563e−01 | −6.22526407e−02 | −4.01506536e−02 | 9.61326342e−03 |
| 2.75165308e−03 | 7.29086176e−02 | −9.39508229e−02 | 1.59722880e−01 |
| −5.98124824e−01 | 3.03398103e−01 | 3.25776786e−01 | 1.50417507e−01 |
| 3.31390470e−01 | 2.39465833e−01 | 9.52397585e−02 | 1.58457294e−01 |
| 1.90245077e−01 | −1.35747902e−02 | −1.06470063e−01 | −1.67197973e−01 |
| 3.43919009e−01 | −5.22895575e−01 | 3.39003235e−01 | 2.49292165e−01 |
| −5.17968357e−01 | −4.42824559e−03 | 4.54635285e−01 | 2.74604559e−01 |
| −3.23310316e−01 | 3.35356563e−01 | 4.18909937e−01 | 1.94895655e−01 |
| 1.93906292e−01 | 7.59953782e−02 | −4.59716544e−02 | 2.64931530e−01 |
| −1.97182581e−01 | −1.72142372e−01 | −1.02977782e−01 | 4.19278890e−01 |
| −3.85133475e−01 | −2.17359126e−01 | 3.05512547e−01 | 3.61012340e−01 |
| 3.90640825e−01 | −2.42356602e−02 | 4.09495771e−01 | −1.25081047e−01 |
| −1.10627756e−01 | 6.65302217e−01 | 1.32255644e−01 | 4.85243559e−01 |
| 1.69255380e−02 | 1.21325709e−01 | 4.62818474e−01 | 1.31409988e−01 |
| 5.36424220e−01 | 1.65163115e−01 | −1.43782541e−01 | 2.54285578e−02 |
| 2.90286876e−02 | 5.08606374e−01 | 1.58349887e−01 | 3.39270353e−01 |
| −2.86613256e−01 | 3.68730098e−01 | 1.62457928e−01 | 4.54882473e−01 |
| −2.08362080e−02 | −1.56174630e−01 | 5.58078706e−01 | 1.53737336e−01 |
| 2.55301654e−01 | 3.71219784e−01 | 3.18623841e−01 | 1.11364536e−01 |
| 9.26098228e−02 | 2.13248596e−01 | −4.62834626e−01 | −2.11135626e−01 |
| −9.22897607e−02 | −6.32287562e−02 | −5.59253246e−02 | −9.70431790e−02 |
| 1.37476400e−01 | 2.07238376e−01 | −1.73072651e−01 | −4.43695694e−01 |
| 2.68123507e−01 | 2.28912890e−01 | 2.94234186e−01 | 1.92279622e−01 |
| 6.66779429e−02 | 8.38092193e−02 | 1.15741372e−01 | 1.03016995e−01] |
| [1.90294281e−01 | 3.47618490e−01 | 7.10604456e−01 | 8.53783965e−01 |
| 9.91113901e−01 | 1.91660166e−01 | 4.38736707e−01 | 3.69230419e−01 |
| 1.14343770e−01 | 7.40250111e−01 | 3.08284163e−01 | 1.00188947e−00 |
| 9.91321623e−01 | 5.67948103e−01 | 7.48020649e−01 | 1.04405916e−01 |
| 1.21951950e−00 | −5.95262200e−02 | 1.73044905e−01 | 5.66034019e−02 |
| 1.55980121e−02 | 2.67129004e−01 | 7.26265371e−01 | 1.07068443e−00 |
| 3.71368825e−01 | 4.67371821e−01 | −4.97420318e−02 | 3.12186658e−01 |
| 7.94749558e−01 | 2.10403353e−01 | 3.40873718e−01 | 8.96476090e−01 |
| 2.70129442e−01 | 5.07821918e−01 | 3.24463427e−01 | 5.84795214e−02 |
| −3.94292548e−03 | 3.26013684e−01 | 2.74185896e−01 | 2.55112290e−01 |
| 6.38176322e−01 | 9.11350429e−01 | 1.26504993e−00 | 5.77519178e−01 |
| 2.46781662e−01 | 4.48576272e−01 | 2.57009178e−01 | 4.31729019e−01 |
| 5.45786023e−01 | 2.19819337e−01 | 1.92444950e−01 | 7.12944925e−01 |
| 2.18713462e−01 | 4.07051653e−01 | 7.75247746e−01 | 5.06778896e−01 |
| 3.87769431e−01 | −4.76368777e−02 | 1.79945722e−01 | −2.64067918e−01 |
| 1.96450844e−01 | 9.09423828e−02 | 4.62883323e−01 | 3.82153451e−01 |
| 2.45947570e−01 | 5.62999547e−01 | 5.20468950e−01 | 2.00768597e−02 |
| 4.45396602e−01 | −2.47672617e−01 | 4.08660574e−03 | −2.40261421e−01 |
| 9.15661454e−01 | 5.37677050e−01 | 1.79310843e−01 | 1.92562893e−01 |
| 5.25637507e−01 | 2.65411943e−01 | 5.14029801e−01 | 2.50846982e−01 |
| 9.63796020e−01 | 3.86864990e−01 | 1.98090509e−01 | 5.10173023e−01 |

TABLE $W_h^1$-continued

| | | | |
|---|---|---|---|
| 2.72326559e-01 | 4.28837031e-01 | 2.28429779e-01 | 4.13160592e-01 |
| 1.19441080e-00 | -3.73882681e-01 | 1.08381128e-00 | 2.31569320e-01 |
| 6.15587056e-01 | 7.37502277e-01 | 6.76073313e-01 | 1.32501632e-01 |
| 7.60165751e-01 | 5.94812743e-02 | 2.73417145e-01 | 9.33844149e-01 |
| 2.14498505e-01 | 4.99593675e-01 | 8.92580822e-02 | 4.16765302e-01 |
| 4.07855988e-01 | 5.06248951e-01 | 5.01335204e-01 | 2.11011696e-00 |
| 3.66516322e-01 | 2.83927500e-01 | 4.90184367e-01 | 7.75429845e-01 |
| 7.25258946e-01 | 3.40344131e-01 | 1.13005650e-00 | 4.43282634e-01 |
| 6.61880374e-01 | 1.88032895e-01 | 7.08774567e-01 | 1.41950103e-03 |
| -2.25280523e-02 | 2.48507306e-01 | 1.54611140e-01 | 1.93239510e-01 |
| 3.75401407e-01 | 3.98792595e-01 | 6.05720878e-01 | 6.41583145e-01 |
| 5.34350097e-01 | 8.04780006e-01 | -8.70076418e-02 | 5.42010903e-01 |
| 5.17798781e-01 | 4.26279277e-01 | 1.29851556e-00 | 3.60545099e-01 |
| 3.08892667e-01 | 8.61160517e-01 | 6.93715990e-00 | 1.40613365e-00 |
| 2.77251124e-01 | 1.39826640e-01 | 2.11900890e-01 | 4.10046011e-01 |
| 6.39959574e-01 | 3.67662668e-01 | 1.74809515e-01 | 7.46295929e-01 |
| 5.62911868e-01 | 5.53089619e-01 | 4.16556805e-01 | 9.83215153e-01 |
| 3.56965840e-01 | 5.46942651e-01 | 1.36268938e-00 | 1.49882123e-01 |
| -1.27070427e-01 | 1.66946262e-01 | -6.15957826e-02 | 5.75322568e-01 |
| 9.85235631e-01 | 5.62876284e-01 | 1.32449484e-00 | 4.24168468e-01 |
| 3.14489380e-02 | 7.51265168e-01 | 1.16640830e-00 | 1.45740941e-01 |
| 2.92455107e-01 | 5.22041202e-01 | 1.72256321e-01 | 3.47656846e-01 |
| 1.30933976e-00 | 1.00747335e-00 | 3.19855988e-01 | -9.78459194e-02 |
| 5.81475973e-01 | 3.61576825e-01 | 4.23093468e-01 | 1.79730609e-01 |
| 1.18895340e-01 | 3.41719657e-01 | 8.39607269e-02 | 9.60137188e-01 |
| 5.15409529e-01 | 4.13926989e-01 | 1.69302374e-01 | 6.27193093e-01 |
| 4.74389225e-01 | 3.72567892e-01 | 5.16542494e-01 | 2.32999966e-01 |
| 5.20766973e-01 | 2.59487003e-01 | 2.71700442e-01 | 4.06935751e-01 |
| 5.02929688e-01 | 1.18230784e-00 | 3.37526917e-01 | 6.09281361e-01 |
| 1.09342360e-00 | 3.87434185e-01 | 3.42037737e-01 | -1.10105788e-02 |
| -8.60223174e-02 | 6.28187776e-01 | 1.23058386e-01 | 4.69426453e-01 |
| 6.76313758e-01 | 1.65632629e-00 | 7.07527280e-01 | 6.23079538e-01 |
| 5.76702297e-01 | 2.01402485e-01 | -9.71246958e-02 | 5.57339907e-01 |
| 2.73096412e-01 | 4.08412576e-01 | 5.62895298e-01 | 7.46275708e-02 |
| 4.90411907e-01 | 1.25106305e-01 | 2.53007412e-01 | 5.20979837e-02 |
| 2.61910379e-01 | -7.50472024e-02 | 4.87120479e-01 | 1.13105416e-00 |
| 9.93895411e-01 | 6.60402477e-01 | 7.85431027e-01 | 3.66234362e-01 |
| 3.66946578e-01 | 8.55333805e-01 | 6.46837473e-01 | 1.04376233e-00 |
| 4.16387200e-01 | 6.41429484e-01 | 3.31144370e-02 | 1.51836157e-01 |
| 6.70143783e-01 | 1.26980257e-00 | 6.71547890e-01 | 3.16110790e-01 |
| 7.50372708e-01 | 4.21146154e-01 | 8.04734409e-01 | 1.44375101e-01 |
| 4.96261239e-01 | 1.62455216e-01 | 1.07447278e-00 | 1.30586731e-00 |
| 9.49808583e-02 | 2.69255072e-01 | 2.10614830e-01 | 2.57735968e-01] |
| [2.56724238e-01 | 3.78711164e-01 | -7.06595788e-03 | -1.47722393e-01 |
| 2.46550098e-01 | 3.59097391e-01 | 1.27801418e-01 | 6.73858151e-02 |
| -2.36183912e-01 | -1.89706713e-01 | -9.33458731e-02 | -1.43553734e-01 |
| -2.13755637e-01 | -1.95894077e-01 | -4.64478046e-01 | -1.99148357e-01 |
| -1.68144792e-01 | 6.33432567e-01 | -2.38484796e-02 | -1.92977246e-02 |
| 1.74127638e-01 | -2.24875838e-01 | 2.56412067e-02 | 1.32150322e-01 |
| 7.03118043e-03 | -2.80527025e-01 | 2.04687074e-01 | -7.52251685e-01 |
| 2.91492313e-01 | 9.16333050e-02 | 2.44436502e-01 | 2.91421711e-02 |
| 1.30227536e-01 | -3.66639256e-01 | -5.10783009e-02 | 2.24086672e-01 |
| 2.97756582e-01 | 6.73205778e-02 | 7.70437717e-02 | 3.31166126e-02 |
| 6.05917722e-01 | -3.64396572e-01 | 2.90310025e-01 | 7.72110224e-01 |
| -5.64450212e-03 | -5.25210500e-01 | 1.90043971e-01 | 3.33751649e-01 |
| -3.97614576e-02 | 1.60701111e-01 | 1.74923092e-01 | -1.16856605e-01 |
| 4.35114056e-02 | -3.66637975e-01 | 1.57191187e-01 | -4.17024583e-01 |
| 2.10343048e-01 | 2.07625329e-01 | 1.81141004e-01 | 1.61996767e-01 |
| 5.06412685e-01 | 9.18488726e-02 | -2.85528839e-01 | -2.25830495e-01 |
| 4.80439998e-02 | 4.97228885e-03 | -7.30929524e-02 | 1.92006797e-01 |
| -1.44719139e-01 | 1.64178804e-01 | 2.92883962e-01 | -3.66102308e-01 |
| -8.91646445e-02 | 3.19734812e-01 | -1.57150894e-01 | 5.24136543e-01 |
| 3.47613931e-01 | 3.20422173e-01 | 3.23429704e-02 | 2.20912069e-01 |
| 3.40324998e-01 | 1.78914983e-02 | -1.67381495e-01 | -1.18649356e-01 |
| 8.71050805e-02 | -1.32567197e-01 | -3.46390724e-01 | 1.51200835e-02 |
| 3.35638672e-02 | -1.41129106e-01 | 4.06894796e-02 | -2.86968444e-02 |
| 1.97300240e-01 | -1.11928895e-01 | 1.20213412e-01 | 3.01332935e-03 |
| 3.30708057e-01 | 6.92878757e-03 | -1.05257876e-01 | -1.21366024e-01 |
| -9.49829221e-02 | 1.81572601e-01 | 2.30875775e-01 | 5.08977734e-02 |
| -1.93316743e-01 | 8.55451673e-02 | 6.13421202e-02 | -5.32516688e-02 |
| -6.56115115e-02 | 2.84753948e-01 | 2.73649603e-01 | 6.45773187e-02 |
| -5.81272952e-02 | -1.23218305e-01 | -8.91626030e-02 | 6.42597556e-01 |
| 1.57361522e-01 | 2.63920754e-01 | 1.23852685e-01 | 2.22018510e-01 |
| 1.48846626e-01 | -2.75251120e-02 | 3.41734678e-01 | 3.20102870e-02 |
| 4.83390242e-01 | -5.40205874e-01 | 1.62656307e-01 | -1.22404262e-01 |
| 2.50183493e-01 | 3.69074881e-01 | 8.16009566e-02 | 9.88367274e-02 |
| -1.06196374e-01 | -1.80722162e-01 | -2.41632864e-01 | 4.53084528e-01 |
| 2.31725097e-01 | 6.68553188e-02 | -6.55519664e-01 | 1.16585761e-01 |
| 7.03762472e-02 | 7.07532167e-02 | 2.09084764e-01 | 5.56343198e-01 |
| -7.44615868e-02 | 2.00033456e-01 | 1.94313571e-01 | 3.13497424e-01 |

TABLE $W_h^1$-continued

| | | | |
|---|---|---|---|
| 2.86371391e−02 | 3.27892482e−01 | 1.79660305e−01 | 1.46523982e−01 |
| 4.21255454e−02 | −6.34534001e−01 | −1.47314966e−01 | 4.18861695e−02 |
| −1.73541252e−03 | −1.08939625e−01 | 4.09747027e−02 | 1.43305749e−01 |
| 4.32088971e−02 | −6.66495562e−02 | −1.66998357e−01 | 1.88680917e−01 |
| 5.02373874e−02 | −1.39656678e−01 | −2.33334675e−01 | 3.92992586e−01 |
| −1.65763587e−01 | 2.88063765e−01 | −1.20365314e−01 | 1.28813133e−01 |
| −9.74842459e−02 | −3.71659219e−01 | 4.14946586e−01 | 6.33067638e−03 |
| −1.76584929e−01 | −1.25382856e−01 | 3.10873896e−01 | 2.43163869e−01 |
| −1.66520372e−01 | −1.25329763e−01 | −1.31337136e−01 | −2.39667781e−02 |
| −1.11944377e−01 | −1.49213240e−01 | −1.48160979e−01 | 1.57065764e−01 |
| −1.58128068e−01 | 1.87233433e−01 | −1.64602935e−01 | 5.19505262e−01 |
| −2.53182292e−01 | −3.38005535e−02 | 1.04869738e−01 | 8.61136839e−02 |
| −2.76378095e−01 | −7.84901753e−02 | −4.19637561e−01 | 7.93611631e−02 |
| −5.02921402e−01 | −3.61104459e−01 | 9.27829221e−02 | 2.00432077e−01 |
| −3.52431051e−02 | −1.68000869e−02 | 3.18706155e−01 | 2.21544936e−01 |
| 8.34575072e−02 | 2.98357308e−01 | 4.28743482e−01 | 1.86012536e−01 |
| 3.81127119e−01 | 8.07846617e−03 | 4.79841642e−02 | 3.32209229e−01 |
| 9.08564627e−02 | 1.09790862e−01 | 1.76403806e−01 | 1.05974786e−01 |
| 3.82049046e−02 | 8.43477994e−03 | 2.89115012e−01 | 1.43180966e−01 |
| 5.59028517e−03 | 2.94246793e−01 | 2.25399449e−01 | 3.31489682e−01 |
| 1.58938438e−01 | −1.36274606e−01 | 2.30601475e−01 | 1.20517323e−02 |
| −7.60007575e−02 | 8.03104788e−02 | 3.53766263e−01 | −1.02368899e−01 |
| −2.32483730e−01 | −1.27813473e−01 | −2.16018528e−01 | −2.17424244e−01 |
| −3.01593065e−01 | 1.52218089e−01 | −8.94823000e−02 | −2.29473919e−01 |
| −2.20033303e−01 | 3.10968935e−01 | 5.59707638e−03 | −7.85798654e−02 |
| −1.19854845e−02 | 1.30483778e−02 | 8.14575031e−02 | 5.69019355e−02 |
| −2.05922842e−01 | −9.07532573e−02 | 4.81905997e−01 | 1.01230638e−02] |
| [1.10622570e−01 | 2.83694595e−01 | −2.02047184e−01 | −2.49364853e−01 |
| −3.09212506e−02 | 2.48103410e−01 | 2.84634113e−01 | −3.01639289e−01 |
| −7.49429464e−02 | −9.40590352e−03 | 6.39888048e−02 | −1.43706307e−01 |
| −4.88584936e−02 | 2.56681945e−02 | 3.13461483e−01 | −4.05792326e−01 |
| 2.90228933e−01 | 4.13583487e−01 | 1.00819752e−01 | −2.47603625e−01 |
| −1.11992642e−01 | 1.50367126e−01 | 1.83138445e−01 | 2.13195428e−01 |
| 7.90769085e−02 | −1.49301626e−02 | −7.91576505e−02 | −2.57195026e−01 |
| 5.41857839e−01 | 2.00592075e−02 | 7.08566383e−02 | 4.86191452e−01 |
| −6.60222992e−02 | −7.40391761e−02 | 1.21546321e−01 | 1.94678649e−01 |
| −4.93990704e−02 | 1.70196563e−01 | −2.11095042e−03 | −6.56109378e−02 |
| 1.55408621e−01 | 1.50851412e−01 | 2.06509069e−01 | 4.16674048e−01 |
| 2.00882088e−02 | −1.38932168e−01 | −2.09833309e−01 | 4.13541682e−02 |
| 4.00999933e−01 | 3.96684259e−01 | −1.84698865e−01 | −1.10239305e−01 |
| −1.20408100e−03 | −5.67696430e−02 | 3.30386668e−01 | −5.65765724e−02 |
| 7.26670846e−02 | −1.08907878e−01 | 2.40391135e−01 | −3.53531055e−02 |
| 2.93885142e−01 | 2.45479569e−01 | 1.57105312e−01 | 7.94693232e−02 |
| −6.83689415e−02 | −7.73019865e−02 | 8.47808421e−02 | −6.68819621e−02 |
| −8.53834823e−02 | 1.13510869e−01 | 7.10695907e−02 | −1.16070545e−00 |
| 3.66063803e−01 | 2.41487667e−01 | 3.44826639e−01 | 2.09318668e−01 |
| 3.97375524e−01 | 3.58541578e−01 | 1.05060510e−01 | 1.46368966e−01 |
| 1.18509121e−01 | 6.05959296e−02 | 1.41665727e−01 | 1.05791122e−01 |
| 4.69957292e−01 | −2.27478489e−01 | −3.76161575e−01 | −7.05629289e−02 |
| 5.71214370e−01 | −1.56157985e−01 | −2.63113081e−02 | 2.29266137e−01 |
| 9.73588973e−03 | 2.29054809e−01 | 1.90586209e−01 | 5.76708198e−01 |
| 1.64119720e−01 | 2.26035655e−01 | 3.97983268e−02 | 7.30173364e−02 |
| 2.74995029e−01 | 1.15614422e−01 | 3.17051947e−01 | 4.80933130e−01 |
| 1.44010618e−01 | 3.18413347e−01 | 1.56442255e−01 | 1.64008096e−01 |
| −7.73902610e−02 | 2.62187928e−01 | 4.55883443e−02 | 3.67698111e−02 |
| 4.05566901e−01 | 1.27336755e−01 | −1.06812038e−01 | 2.81266451e−01 |
| 3.93915534e−01 | 3.09509188e−01 | −2.08350942e−02 | −6.78036273e−01 |
| 7.72041678e−02 | −8.90671089e−02 | −3.45463566e−02 | 6.16650641e−01 |
| 1.79968148e−01 | −2.00595334e−01 | −2.18534946e−01 | 3.62245500e−01 |
| 1.21513754e−02 | 2.66147673e−01 | 1.02741532e−02 | 1.32141858e−01 |
| 4.52053726e−01 | 3.31676900e−02 | −3.40163022e−01 | 6.92484796e−01 |
| 6.01478778e−02 | 5.67865431e−01 | −3.48247796e−01 | 7.18671978e−02 |
| 2.16436654e−01 | 2.34068096e−01 | 5.27164936e−01 | −1.16236940e−01 |
| −4.19423431e−02 | 3.55442941e−01 | 2.54574805e−01 | 4.40567672e−01 |
| 4.45140377e−02 | −2.61919443e−02 | 3.80011231e−01 | 1.69971421e−01 |
| 1.59381181e−01 | −2.12269425e−01 | −8.50893110e−02 | 2.88610548e−01 |
| 3.21236551e−01 | 3.14086787e−02 | 4.53862280e−01 | 2.98427939e−01 |
| 5.95923364e−02 | 4.83573042e−02 | −3.13357562e−01 | 3.35732028e−02 |
| 2.81291962e−01 | −1.01608500e−01 | 1.41767412e−01 | 5.12246609e−01 |
| −1.88509494e−01 | 4.55006987e−01 | 2.64353216e−01 | 1.00831807e−01 |
| 2.72595882e−01 | −2.10180998e−01 | 6.42504217e−03 | −2.45402940e−01 |
| −2.34214187e−01 | 1.27871737e−01 | 2.32348979e−01 | 1.40831172e−01 |
| 2.76040792e−01 | −1.38689905e−01 | 1.03256211e−01 | 2.19501540e−01 |
| −3.32349464e−02 | 8.94992277e−02 | −5.21682501e−02 | 7.36208260e−02 |
| 8.18505883e−02 | 1.21741854e−01 | 1.42666012e−01 | 4.30921376e−01 |
| −3.73640023e−02 | 2.18268931e−01 | −1.06277943e−01 | 3.64431292e−02 |
| 1.97311357e−01 | −1.64438829e−01 | 1.20196581e−01 | 2.81766146e−01 |
| −2.77843624e−01 | −2.19558671e−01 | −5.17232008e−02 | 3.59388441e−01 |
| −1.60503551e−01 | 4.41662036e−04 | 2.95546353e−01 | −5.69097511e−02 |
| −9.25556943e−03 | 9.87966731e−02 | −1.16329655e−01 | 2.31187597e−01 |

TABLE $W_h^1$-continued

| | | | |
|---|---|---|---|
| 5.58102965e−01 | 5.91601789e−01 | 3.14686924e−01 | −1.80578768e−01 |
| −5.47900870e−02 | 2.75663286e−01 | 1.49866685e−01 | 7.07154861e−03 |
| 2.57357061e−01 | −1.35634765e−01 | −6.36272132e−02 | 3.93243283e−02 |
| −7.72211328e−02 | 1.32079646e−01 | 3.72983128e−01 | 7.21718520e−01 |
| −1.05328411e−02 | −2.99658030e−01 | 2.28492334e−01 | 2.12783143e−01 |
| 5.77576309e−02 | 2.60394722e−01 | 5.49243927e−01 | −2.71994054e−01 |
| 5.21597415e−02 | −1.43857196e−01 | −2.78409600e−01 | −2.22651348e−01 |
| −5.75486898e−02 | −9.72836390e−02 | 2.71059990e−01 | 6.12288900e−02 |
| 2.26083934e−01 | 3.28451455e−01 | 1.69912785e−01 | 3.15230608e−01 |
| −7.57357553e−02 | −8.95830467e−02 | 1.28104135e−01 | −1.75918847e−01 |
| 1.84378937e−01 | −4.22811173e−02 | −3.23127657e−02 | 1.63123414e−01] |
| [1.68667972e−01 | 2.78001100e−01 | 7.90335119e−01 | 5.40852904e−01 |
| 2.71649510e−01 | 6.01196170e−01 | 1.86099127e−01 | 2.99630482e−02 |
| −9.48692486e−03 | 1.11456104e−01 | 3.86024892e−01 | 1.88657671e−01 |
| 1.38806090e−01 | 5.65779544e−02 | 5.17411411e−01 | −1.24182455e−01 |
| 1.58720464e−01 | 2.53725171e−01 | −6.27581298e−01 | 2.60843694e−01 |
| 1.14553824e−01 | 6.30168855e−01 | 5.32945991e−01 | 8.61704648e−01 |
| 5.68095505e−01 | 2.76454091e−01 | 2.25396544e−01 | 2.36032277e−01 |
| 5.67509055e−01 | 4.95154649e−01 | 5.02907574e−01 | 6.28533736e−02 |
| 6.02236271e−01 | 5.62824570e−02 | 5.14863312e−01 | 1.19878657e−01 |
| 5.57523131e−01 | 8.59626472e−01 | 1.45320565e−01 | 6.13016002e−02 |
| 6.97452962e−01 | 4.68576789e−01 | 1.22336127e−01 | 4.02820826e−01 |
| 4.02572751e−01 | 3.75717342e−01 | 2.92078972e−01 | 1.22697584e−01 |
| 3.92134190e−01 | 1.79453060e−01 | 1.90165937e−01 | 8.44853446e−02 |
| 4.21073675e−01 | 1.72364071e−01 | 2.46038899e−01 | 3.28982651e−01 |
| 5.40678978e−01 | −7.72287101e−02 | 4.62197691e−01 | −1.53804660e−01 |
| 5.42272031e−01 | 2.90003508e−01 | 4.69712496e−01 | 1.14425138e−01 |
| 4.31427956e−01 | 4.37992215e−01 | 1.78931192e−01 | 4.48208451e−01 |
| 1.77232817e−01 | −5.52735329e−02 | 3.73659760e−01 | −2.01832741e−01 |
| 7.60707796e−01 | 2.20917404e−01 | 2.40139723e−01 | 4.55208361e−01 |
| 3.61903548e−01 | 4.07502681e−01 | 3.47406924e−01 | 4.29063857e−01 |
| 5.06618500e−01 | 2.44984627e−01 | 1.91401213e−01 | 3.60887647e−01 |
| 9.65771139e−01 | 6.03853106e−01 | 7.94312507e−02 | 4.73523527e−01 |
| 3.31550211e−01 | −2.22306818e−01 | −8.56827796e−02 | −2.72830307e−01 |
| 2.98187673e−01 | 3.56788874e−01 | 5.24383366e−01 | 3.01890641e−01 |
| −8.10471401e−02 | −1.98997539e−02 | 6.99814081e−01 | 4.69907701e−01 |
| 3.96736205e−01 | 2.75138646e−01 | 8.39607477e−01 | 1.90110609e−01 |
| 2.87840843e−01 | 5.74903190e−01 | 3.50029498e−01 | 4.32803631e−01 |
| 3.92078489e−01 | 1.98714629e−01 | 2.52711594e−01 | 3.41769069e−01 |
| 7.80220866e−01 | 2.41555303e−01 | 3.74094695e−01 | 2.15975598e−01 |
| 1.86733752e−01 | 7.64808178e−01 | 3.28406155e−01 | 4.79917042e−02 |
| 8.36627781e−01 | 5.62248409e−01 | 3.02806318e−01 | 2.29029566e−01 |
| 2.82198370e−01 | 5.31399012e−01 | 4.66273665e−01 | 2.60643721e−01 |
| 2.18334690e−01 | 5.32755017e−01 | −1.89275518e−01 | 7.16690302e−01 |
| 1.00791097e−00 | 1.66051179e−01 | 2.08831504e−01 | 4.26190019e−01 |
| 6.56456649e−02 | 5.71280420e−01 | 5.60628474e−01 | 6.16057038e−01 |
| 1.88327506e−01 | 1.69651404e−01 | 1.73235506e−01 | 5.97142577e−01 |
| 1.18424512e−01 | 1.60706565e−01 | 8.07433128e−01 | 3.47978234e−01 |
| 4.19518888e−01 | 4.44987983e−01 | 1.33505329e−01 | 3.83411318e−01 |
| 1.56847298e−01 | 3.16578239e−01 | 5.80396175e−01 | −1.44830719e−01 |
| −1.87960491e−02 | 3.94564182e−01 | 4.06731933e−01 | 1.08188353e−01 |
| 1.97622240e−01 | 3.60884637e−01 | 4.57637548e−01 | −3.10981609e−02 |
| 3.81496027e−02 | −3.95724177e−01 | 4.28140283e−01 | 3.64255577e−01 |
| 2.54995823e−01 | 3.72452915e−01 | 3.79372001e−01 | 7.97883034e−01 |
| 2.81746805e−01 | 4.44554269e−01 | 5.14129817e−01 | 1.56680390e−01 |
| 1.71712339e−01 | 8.03852379e−02 | 1.65480450e−01 | 1.81583926e−01 |
| 4.61747348e−01 | 3.26658010e−01 | 2.44384378e−01 | 1.68309569e−01 |
| 3.80437076e−01 | 1.85878128e−01 | 2.12031946e−01 | 8.89227927e−01 |
| −1.00107282e−01 | 3.07169825e−01 | 5.80066979e−01 | 5.30690134e−01 |
| 3.01477969e−01 | 6.41897023e−01 | 4.24587205e−02 | 7.23445296e−01 |
| 4.66222577e−02 | 1.16448544e−01 | 1.59271464e−01 | 8.44282448e−01 |
| 6.53563321e−01 | 1.43270016e−01 | 2.14281622e−02 | 2.28971615e−01 |
| 2.21517324e−01 | −2.48789974e−03 | 1.80841878e−01 | 2.61483900e−01 |
| 3.70232433e−01 | 5.37882626e−01 | 2.27372482e−01 | 6.96009159e−01 |
| 4.18569446e−01 | 2.86546886e−01 | 5.03619134e−01 | 5.39972663e−01 |
| 3.77946138e−01 | 8.87583047e−02 | 3.31322253e−01 | 1.91574678e−01 |
| 2.50843912e−01 | −6.01424798e−02 | 2.86042511e−01 | 2.28156075e−01 |
| 4.01445001e−01 | 7.31079876e−02 | 2.91599333e−01 | 5.44489503e−01 |
| 4.60701048e−01 | 3.03223163e−01 | 4.81565177e−01 | 3.95079494e−01 |
| 5.94270527e−02 | −4.01769131e−02 | 3.25453937e−01 | 4.75168705e−01 |
| 3.03348482e−01 | 3.79209906e−01 | −2.12231100e−01 | 1.50328368e−01 |
| 3.41304779e−01 | −7.40814209e−02 | 6.00333750e−01 | 2.65231550e−01 |
| 7.49681711e−01 | −1.26192542e−02 | −1.50762433e−02 | −7.56152123e−02 |
| 7.36005247e−01 | 1.58328876e−01 | 1.14429437e−01 | 5.06740749e−01 |
| 2.45631397e−01 | 4.20694023e−01 | 3.05406928e−01 | 5.58599591e−01] |
| [2.42920771e−01 | −2.13787630e−01 | 3.82752828e−02 | 2.74857759e−01 |
| −2.35309154e−01 | 2.64188766e−01 | 4.96618509e−01 | 1.87520653e−01 |
| −1.85854957e−01 | −2.40120129e−03 | −1.01529464e−01 | −7.74934664e−02 |
| −1.50641888e−01 | −1.43136486e−01 | 1.31017089e−01 | −2.21988708e−01 |
| −4.87693772e−02 | 1.41057923e−01 | −1.60631735e−03 | −1.93105504e−01 |

TABLE $W_h^1$-continued

| | | | |
|---|---|---|---|
| −2.58428007e−01 | 3.50045651e−01 | −7.81904384e−02 | 1.66319847e−01 |
| 3.18901956e−01 | 1.97146997e−01 | 1.16093554e−01 | 2.18143970e−01 |
| 3.12879652e−01 | −6.51625991e−01 | 2.24310488e−01 | 2.19090194e−01 |
| −2.54420906e−01 | 1.85938105e−01 | 1.77123621e−01 | 2.15753436e−01 |
| 9.04678851e−02 | 1.58253938e−01 | −5.23397699e−02 | −3.35582465e−01 |
| 2.60685384e−01 | −4.41509128e−01 | −3.94673906e−02 | −3.71830985e−02 |
| −5.81219140e−03 | −1.51587442e−01 | 1.46090426e−02 | −2.89472401e−01 |
| 1.61134735e−01 | −1.65093929e−01 | −3.21586937e−01 | −1.43881544e−01 |
| 2.19068646e−01 | −1.69787616e−01 | 3.35556656e−01 | −1.86695427e−01 |
| −1.17202913e−02 | −3.68437707e−01 | 1.71320871e−01 | 2.59092778e−01 |
| 3.12392831e−01 | −1.43094599e−01 | 1.16667688e−01 | −7.49781579e−02 |
| −1.45954013e−01 | 2.74900533e−02 | −2.39101365e−01 | −9.11090448e−02 |
| 1.38580859e−01 | 2.51694590e−01 | 1.81840315e−01 | −1.00601174e−01 |
| −3.40167023e−02 | 1.26871258e−01 | −2.27772400e−01 | 1.98751971e−01 |
| 2.55746752e−01 | 1.81630492e−01 | −5.26928939e−02 | 1.76321313e−01 |
| 2.16718122e−01 | 1.56552419e−01 | −3.41513783e−01 | 9.10107344e−02 |
| −2.54149940e−01 | −1.03621200e−01 | 1.32546341e−03 | −2.37966016e−01 |
| 1.62494019e−01 | −6.72944248e−01 | 3.06034833e−01 | −4.59148698e−02 |
| −2.46292308e−01 | −8.73934850e−02 | 1.61915854e−01 | 1.71322301e−01 |
| −2.50554131e−03 | −1.81433260e−01 | 4.56463061e−02 | 1.57524884e−01 |
| 3.67503166e−02 | 1.15497887e−01 | 7.86127076e−02 | 1.28243014e−01 |
| −1.17953449e−01 | −1.88617259e−02 | 3.06195408e−01 | 3.29616815e−02 |
| 2.97633886e−01 | −1.80416666e−02 | −7.48699829e−02 | −6.81869015e−02 |
| 1.68728754e−01 | 2.14592770e−01 | −5.92751279e−02 | 8.83128569e−02 |
| 3.95166129e−02 | −1.28774077e−01 | −1.21761654e−02 | −2.14864939e−01 |
| 7.13797063e−02 | −1.26539841e−01 | 1.16448484e−01 | 3.24378937e−01 |
| 3.88012975e−02 | −4.45544440e−03 | −2.09432393e−01 | −9.73881111e−02 |
| 5.21897823e−02 | 1.72110379e−01 | 8.77227262e−02 | −2.73889210e−02 |
| 5.91893494e−02 | −2.00386137e−01 | −1.04397878e−01 | 2.03125551e−01 |
| −1.29481599e−01 | −1.12530842e−01 | 1.02018309e−03 | −2.53092468e−01 |
| −1.01082280e−01 | 8.82471800e−02 | 4.59010415e−02 | −2.84370333e−01 |
| −3.77517641e−01 | −9.74058583e−02 | 2.20264256e−01 | 2.06179321e−01 |
| 9.77177322e−02 | −1.47456571e−01 | 1.29217595e−01 | 1.31978065e−01 |
| −4.14205156e−02 | −1.01970285e−01 | −2.02630498e−02 | 1.34384796e−01 |
| −1.75451159e−01 | −1.25761002e−01 | −1.46491215e−01 | −6.91602901e−02 |
| 5.42604029e−02 | −1.94292918e−01 | −6.60779178e−02 | 7.32620955e−02 |
| −1.17594332e−01 | 1.04101389e−04 | −4.26344424e−02 | 3.57211679e−01 |
| 3.77760492e−02 | 2.64615901e−02 | 1.16097406e−01 | 2.02744499e−01 |
| −2.50025451e−01 | −4.62460071e−01 | 1.51372433e−01 | −4.23796140e−02 |
| 1.49569005e−01 | −3.65778029e−01 | 8.44931155e−02 | −1.19472444e−01 |
| −4.36510667e−02 | −2.28504136e−01 | 4.50104661e−02 | 8.18689018e−02 |
| −3.04115742e−01 | −5.54132983e−02 | −1.64751783e−01 | 1.80297017e−01 |
| −2.32129097e−01 | −1.32864654e−01 | −3.52876037e−01 | 2.86975741e−01 |
| 1.82655424e−01 | −2.46606499e−01 | 3.96876901e−01 | −9.55488533e−02 |
| −4.71857190e−02 | −2.59208858e−01 | 4.62131714e−03 | −2.45865673e−01 |
| −8.85085464e−02 | −3.60042542e−01 | 2.43587449e−01 | 4.24696207e−01 |
| 1.48308396e−01 | −2.69870818e−01 | 2.02928647e−01 | 1.53047904e−01 |
| 1.37207523e−01 | 2.69749016e−01 | 1.07499421e−01 | 5.99663518e−02 |
| 1.60785869e−01 | −7.24160150e−02 | 3.64475727e−01 | 7.07243681e−02 |
| 2.82961011e−01 | 3.17277736e−03 | −4.11372423e−01 | −4.95515913e−01 |
| −8.69913250e−02 | −2.98318624e−01 | 1.47451237e−01 | 2.86976218e−01 |
| −1.78406537e−01 | −1.17593542e−01 | 3.67710680e−01 | 1.48895830e−01 |
| −7.36898277e−03 | −2.37091556e−01 | 4.44849096e−02 | −9.82970223e−02 |
| 7.25057675e−04 | 7.05119520e−02 | 1.70994475e−01 | −9.52227488e−02 |
| −2.23377764e−01 | 2.68099993e−01 | −9.40567479e−02 | −3.76714230e−01 |
| 4.57013249e−02 | −6.97695389e−02 | 3.16726923e−01 | −1.33735284e−01 |
| 9.46402550e−02 | −1.84028670e−01 | −8.68166685e−02 | 3.50117922e−01 |
| −2.22349361e−01 | 2.33474374e−01 | 1.75840735e−01 | −9.31799337e−02 |
| −2.81008035e−01 | −1.46701708e−01 | −3.29612523e−01 | −1.43879801e−01] |
| [2.17454806e−01 | 3.77147466e−01 | 4.03999805e−01 | 1.40401259e−01 |
| 1.95384264e−01 | 6.30300939e−01 | 3.63411814e−01 | 3.94516498e−01 |
| 3.50619346e−01 | −3.30681235e−01 | 3.95202726e−01 | −1.95849121e−01 |
| 1.92344487e−01 | 5.08672118e−01 | 3.02086532e−01 | 1.40927836e−01 |
| 3.35560620e−01 | 5.49073398e−01 | 1.59113228e−01 | 2.24005848e−01 |
| 1.01119243e−01 | −5.40283099e−02 | 4.94975984e−01 | 5.63468575e−01 |
| 4.03529525e−01 | 1.73627481e−01 | 2.92015746e−02 | 2.93979108e−01 |
| 4.16225940e−01 | 9.21752676e−02 | 2.05426142e−01 | 1.03690065e−01 |
| 2.84489334e−01 | 2.76725322e−01 | 3.33080351e−01 | 1.63991272e−01 |
| 6.07620031e−02 | 1.87364355e−01 | 6.04451180e−01 | 4.02422011e−01 |
| 4.77904409e−01 | 2.91486353e−01 | 1.36205658e−01 | −1.45473406e−01 |
| 8.63802060e−01 | 2.83243835e−01 | 1.94587111e−01 | 6.03520423e−02 |
| 1.18744880e−01 | 4.34730768e−01 | 2.45855115e−02 | −4.57184948e−03 |
| 5.95277429e−01 | 2.59526789e−01 | 1.34426743e−01 | −2.19500381e−02 |
| 4.53733057e−01 | 2.83171058e−01 | 2.26963665e−02 | −2.99349517e−01 |
| 2.38407686e−01 | 5.26830614e−01 | 4.85541493e−01 | 6.72704518e−01 |
| 1.64259285e−01 | 7.21363902e−01 | −4.95574586e−02 | 2.66090155e−01 |
| 1.33625612e−01 | 1.62129939e−01 | 3.77371579e−01 | −7.34161496e−01 |
| 5.56298435e−01 | 1.48066014e−01 | 7.64256045e−02 | 5.74420810e−01 |
| 8.09443414e−01 | 3.32427770e−02 | 2.84019947e−01 | 6.44586459e−02 |
| 6.26736641e−01 | 3.00427020e−01 | −2.13676363e−01 | 2.25454733e−01 |

TABLE $W_h^1$-continued

| | | | |
|---|---|---|---|
| 1.43133178e−01 | 9.24348533e−02 | −9.99843329e−02 | 5.46701670e−01 |
| 1.83211580e−01 | −4.39544052e−01 | 2.62401730e−01 | −1.05051450e−01 |
| 2.12352797e−01 | 3.94448072e−01 | −1.90493539e−02 | 6.77797377e−01 |
| −8.96818191e−02 | −1.37454167e−01 | 3.57372761e−01 | 2.43659168e−01 |
| 3.48212034e−01 | 6.20409250e−01 | 9.47923213e−02 | 6.22766793e−01 |
| −1.91641245e−02 | 5.55602372e−01 | 1.28549442e−01 | 3.23084533e−01 |
| 3.49481374e−01 | 2.76601464e−01 | 7.14688301e−01 | 7.34712720e−01 |
| 2.74105757e−01 | 2.75230199e−01 | −7.77990520e−02 | −2.10676581e−01 |
| −5.51522002e−02 | 5.15994072e−01 | 3.45482379e−01 | 1.24291003e−01 |
| 1.12197369e−01 | 3.54742438e−01 | 4.72672544e−02 | 2.51642596e−02 |
| 5.56400836e−01 | 7.22936005e−04 | 2.24854171e−01 | 3.55511487e−01 |
| 4.15741175e−01 | −6.33693561e−02 | 1.37801573e−01 | 2.16506004e−01 |
| 7.24887073e−01 | 4.10726368e−02 | 3.68076563e−01 | 3.43067527e−01 |
| 2.41314426e−01 | 2.17163280e−01 | 2.73356616e−01 | 2.92658806e−01 |
| 7.59070873e−01 | 6.71467602e−01 | 1.85946062e−01 | 2.73672938e−01 |
| 3.77342962e−02 | 2.28682701e−02 | 1.38620883e−01 | 6.92584276e−01 |
| 2.73168862e−01 | 1.41102731e−01 | 5.82892239e−01 | 2.38986388e−01 |
| 2.36876935e−01 | 2.73104310e−01 | 4.72296059e−01 | 5.09241641e−01 |
| 1.87823195e−02 | 3.90147626e−01 | 6.02684379e−01 | 9.64709967e−02 |
| 1.86671972e−01 | −4.47762012e−02 | 3.86538923e−01 | 4.03598517e−01 |
| 3.02871168e−01 | 1.59966528e−01 | 2.20090240e−01 | 1.32397532e−01 |
| −4.28248674e−01 | 6.29199743e−01 | 6.23879969e−01 | 3.64806086e−01 |
| 3.18420440e−01 | 4.06029761e−01 | 2.37419114e−01 | 2.01338470e−01 |
| 1.18638568e−01 | −3.56745899e−01 | 6.74360469e−02 | −1.49934357e−02 |
| 1.00384869e−01 | 2.45776683e−01 | −9.75336730e−02 | 1.59728333e−01 |
| 3.44264299e−01 | 4.48857509e−02 | 4.38328147e−01 | 5.59674144e−01 |
| 8.35889354e−02 | 1.76461652e−01 | 4.49541599e−01 | 2.70597845e−01 |
| 3.04966509e−01 | 4.15513396e−01 | 2.84586906e−01 | 1.53037593e−01 |
| −4.30541366e−01 | 2.61038423e−01 | 7.48393834e−01 | −1.16981126e−01 |
| 4.55765337e−01 | 2.70635962e−01 | 5.53624988e−01 | 1.72953829e−01 |
| 2.80739553e−02 | 3.17907304e−01 | 4.46954876e−01 | 1.18303366e−01 |
| 2.23431364e−01 | 1.92796156e−01 | 2.80757785e−01 | 1.70826614e−01 |
| 5.25193512e−01 | 4.04161483e−01 | 4.28901494e−01 | 8.66961628e−02 |
| 2.69003272e−01 | 4.07142192e−01 | −1.06136993e−01 | −4.26060185e−01 |
| 3.10115337e−01 | −4.34135571e−02 | 2.88123041e−01 | 2.81724215e−01 |
| −7.72857741e−02 | −1.34867027e−01 | 6.39239848e−01 | 3.35904926e−01 |
| 5.84583640e−01 | 3.04177515e−02 | 5.39530456e−01 | 6.28113925e−01 |
| 3.06622535e−01 | −3.31850231e−01 | 6.95260465e−01 | 2.15380922e−01 |
| 5.18770039e−01 | 2.51978666e−01 | 1.85669199e−01 | 1.00600190e−01 |
| 1.19685039e−01 | −1.75048709e−01 | 5.52768350e−01 | 2.18513444e−01 |
| 2.92102069e−01 | 3.00376624e−01 | 3.14246655e−01 | −2.60527402e−01 |
| 2.34176189e−01 | 4.22518551e−01 | 1.91014215e−01 | 1.80898830e−01 |
| −1.12052582e−01 | 2.92868435e−01 | 3.85040492e−01 | −3.46307047e−02] |
| [−1.27704620e−01 | 3.24459784e−02 | −1.90029815e−01 | 3.40554774e−01 |
| 3.45205329e−03 | 1.18552156e−01 | 2.78530437e−02 | 2.62223244e−01 |
| 4.73875552e−01 | 7.31728256e−01 | 3.27730268e−01 | 3.07663903e−02 |
| −7.94025287e−02 | −3.40403914e−02 | 3.99996608e−01 | −5.03930151e−01 |
| 2.27327466e−01 | 1.87887698e−01 | 1.46261305e−01 | −8.94372165e−02 |
| 3.73413831e−01 | 3.44401985e−01 | 9.97816846e−02 | 6.74963295e−01 |
| 3.69839907e−01 | 2.56960452e−01 | 6.83136404e−01 | −6.39425635e−01 |
| 2.98219442e−01 | 3.66273820e−01 | 1.51089102e−01 | 4.88739491e−01 |
| 3.47460389e−01 | 1.01315916e−01 | 4.91571091e−02 | 3.76375914e−02 |
| 2.52600938e−01 | −7.90252388e−02 | −1.90356895e−01 | −7.12098852e−02 |
| 2.01691315e−01 | −5.83767593e−01 | 2.18376085e−01 | 9.19006690e−01 |
| 6.07373476e−01 | −4.85003471e−01 | 2.67569214e−01 | 6.26975298e−01 |
| 5.88303387e−01 | 1.17667682e−01 | 4.61536825e−01 | 6.77659512e−02 |
| −9.19485688e−02 | −1.25401735e−01 | −2.28351995e−01 | 8.30875337e−02 |
| 8.12971666e−02 | −1.21950641e−01 | 1.02170661e−01 | −4.30639744e−01 |
| 1.18874244e−01 | 9.14245769e−02 | −2.37996235e−01 | −4.01906699e−01 |
| 2.93797720e−02 | 5.34872949e−01 | 2.60670304e−01 | −7.48807043e−02 |
| 3.07113588e−01 | 6.25096977e−01 | 4.39994246e−01 | −2.83664465e−01 |
| 1.52963594e−01 | 3.28237921e−01 | −4.31492589e−02 | 7.29877412e−01 |
| 9.66413692e−02 | 7.66722336e−02 | −2.67436597e−02 | 4.12269771e−01 |
| 3.92333448e−01 | 3.09176892e−01 | −3.41559649e−01 | 1.15151346e−01 |
| 4.61814016e−01 | −6.33666292e−02 | 2.43257672e−01 | −4.78800684e−01 |
| −7.21710324e−02 | −3.65526713e−02 | −1.26484171e−01 | 6.98015690e−02 |
| −1.53690845e−01 | −1.78468198e−01 | 1.40447393e−01 | 4.32658166e−01 |
| 1.48261264e−01 | 3.69725287e−01 | 2.34989136e−01 | −1.90358430e−01 |
| −8.46591070e−02 | 7.05164373e−01 | 4.05118406e−01 | 3.96834224e−01 |
| 7.19589740e−02 | 2.92736351e−01 | 2.66809404e−01 | 2.56981611e−01 |
| −3.71012866e−01 | 5.72985351e−01 | 3.29585254e−01 | −3.14773321e−01 |
| 4.78545338e−01 | 2.85683945e−03 | 2.27371633e−01 | 6.30159497e−01 |
| 1.35203555e−01 | 2.10513592e−01 | 4.70447630e−01 | 4.48114276e−01 |
| −1.96005795e−02 | −7.96764567e−02 | 1.33990645e−01 | 6.57491207e−01 |
| 2.37786904e−01 | 6.90411404e−02 | 5.87233268e−02 | 5.71375012e−01 |
| 3.06905955e−01 | 4.26016748e−01 | 9.90424752e−02 | 4.35529798e−01 |
| 2.00938761e−01 | −2.08245352e−01 | 2.54202038e−01 | 3.08446079e−01 |
| −8.72064829e−02 | 3.86561006e−01 | 7.06765577e−02 | 7.04794824e−02 |
| 5.38253523e−02 | 4.88357902e−01 | 5.07371962e−01 | −1.23770550e−01 |
| 3.16301808e−02 | −1.57159299e−01 | 2.52852719e−02 | 4.78729814e−01 |

TABLE $W_h^1$-continued

| | | | |
|---|---|---|---|
| −1.12828158e−01 | −2.09192187e−01 | −1.03697397e−01 | 3.09366196e−01 |
| 1.07024938e−01 | −4.09123480e−01 | 1.89555675e−01 | 2.52461046e−01 |
| 4.08527672e−01 | −2.97129415e−02 | 4.05740291e−01 | −1.84420452e−01 |
| 3.36518288e−01 | 2.15223193e−01 | −9.91979912e−01 | −7.69653022e−02 |
| 4.59828712e−02 | −6.49697557e−02 | 2.37334356e−01 | 1.86725155e−01 |
| 3.04305166e−01 | 5.31963348e−01 | 2.01310173e−01 | 5.91093481e−01 |
| 3.25373501e−01 | −1.38095453e−01 | −4.07801837e−01 | 1.04373544e−01 |
| −4.96759713e−02 | 4.67080772e−01 | 2.57213354e−01 | −6.30094707e−02 |
| 7.08872199e−02 | −1.96235050e−02 | 3.62462029e−02 | −3.32810022e−02 |
| −8.63832235e−02 | −2.19379306e−01 | −4.33875740e−01 | 3.10116529e−01 |
| −3.33685398e−01 | 4.21147287e−01 | 2.01341107e−01 | 2.64541239e−01 |
| 3.38608593e−01 | 1.98910356e−01 | 1.72554657e−01 | −8.76890272e−02 |
| −2.42461428e−01 | 2.04996914e−01 | −9.08607617e−02 | 9.35352296e−02 |
| −3.23113561e−01 | −3.32754076e−01 | 4.12266582e−01 | 2.77678281e−01 |
| −2.31931508e−02 | 7.15832114e−02 | 2.26503208e−01 | 1.42629042e−01 |
| 4.37460005e−01 | 2.49806046e−01 | 5.37173569e−01 | 2.46271148e−01 |
| 5.65793395e−01 | 1.83124170e−01 | 1.30113319e−01 | 3.68431300e−01 |
| 4.66334641e−01 | 3.84824835e−02 | 3.13737802e−02 | 1.30006775e−01 |
| −1.57913670e−01 | 3.65162157e−02 | 1.45987365e−02 | 2.56713629e−01 |
| −2.28396535e−01 | 9.62279662e−02 | 4.06609297e−01 | 3.93719137e−01 |
| 1.29622161e−01 | −1.01550467e−01 | 4.42462653e−01 | 3.11322566e−02 |
| 7.97972009e−02 | 8.93238485e−02 | 9.65485945e−02 | 5.28900146e−01 |
| 4.54015583e−02 | 3.32867920e−01 | −1.85681775e−01 | −1.72336087e−01 |
| 2.24799052e−01 | 8.40877742e−02 | 1.87161475e−01 | 4.46971416e−01 |
| 5.42531610e−02 | 5.08305756e−03 | −1.98816985e−01 | −1.09349497e−01 |
| 5.67820296e−02 | −1.49135321e−01 | 2.52025396e−01 | 1.94036186e−01 |
| −3.32229257e−01 | 1.76939845e−01 | 4.18577850e−01 | −4.31638770e−02] |
| [−1.69577777e−01 | −6.74057081e−02 | 4.99608248e−01 | −1.88211471e−01 |
| 2.57459462e−01 | 8.64420116e−01 | 2.36604363e−01 | 4.28278208e−01 |
| −4.95398268e−02 | 5.93893006e−02 | 8.39025974e−02 | −3.26851709e−03 |
| −3.65747988e−01 | 2.15034828e−01 | 5.52852042e−02 | −1.70160949e−01 |
| 1.17540639e−02 | 3.80991817e−01 | 2.89068203e−02 | 2.79376328e−01 |
| 3.01199585e−01 | −2.26281241e−01 | 4.70095016e−02 | 5.08135498e−01 |
| −8.77268389e−02 | 8.39788243e−02 | 3.68335575e−01 | 1.88379154e−01 |
| 3.00106287e−01 | 5.56361899e−02 | 2.90662348e−01 | 4.22540039e−01 |
| 1.73453227e−01 | 6.09797299e−01 | −2.09397957e−01 | 3.36981565e−01 |
| 1.04946047e−02 | 6.05599523e−01 | 1.54813990e−01 | 3.72773975e−01 |
| 6.79324389e−01 | 2.89224625e−01 | 2.74778605e−01 | −6.24470785e−02 |
| 3.79163116e−01 | 2.16872022e−01 | −2.11001307e−01 | 2.82157630e−01 |
| 4.83251095e−01 | 6.93275392e−01 | 4.24938016e−02 | −3.93215641e−02 |
| 2.57942408e−01 | 1.66447029e−01 | 3.16886514e−01 | 1.47740301e−02 |
| 8.94102827e−03 | −8.51003546e−03 | 4.02237207e−01 | 1.39608487e−01 |
| 2.66362667e−01 | 6.96805045e−02 | 1.53271675e−01 | 1.55720249e−01 |
| 1.18550912e−01 | 3.49037588e−01 | 7.24289268e−02 | 1.72240943e−01 |
| 1.76254898e−01 | 1.22967944e−01 | 3.38436127e−01 | 1.35946676e−01 |
| 3.17976028e−01 | −6.82433695e−02 | 5.48637629e−01 | 4.66163754e−01 |
| 2.52842993e−01 | 1.68970883e−01 | 4.95559424e−01 | 1.24831371e−01 |
| 4.51120585e−01 | −6.91038743e−02 | 3.94704677e−02 | 2.49192730e−01 |
| −1.17837675e−01 | −7.52974600e−02 | −2.58963674e−01 | 6.35583937e−01 |
| 2.71789819e−01 | −1.63817748e−01 | −1.20922394e−01 | −9.33257043e−02 |
| 1.90762714e−01 | 2.52597600e−01 | −1.07326277e−01 | 1.24179125e−00 |
| 1.10748030e−01 | −3.49289238e−01 | 4.90146637e−01 | 2.81418234e−01 |
| 5.43842196e−01 | 2.44480729e−01 | 4.98615950e−02 | 4.42111939e−01 |
| 3.26599091e−01 | 6.36796430e−01 | 1.79746881e−01 | 2.22964182e−01 |
| 3.59338611e−01 | 4.67003584e−01 | 6.83875918e−01 | 4.53175418e−02 |
| 8.37275088e−02 | 5.60370982e−01 | 1.28795698e−01 | −1.20803736e−01 |
| 2.19577048e−02 | 3.51407558e−01 | 3.92914683e−01 | −7.11916268e−01 |
| 5.55764399e−02 | 3.29738677e−01 | 2.42884345e−02 | 2.81881869e−01 |
| 9.32249427e−02 | −2.49582350e−01 | −1.21446282e−01 | 5.11892378e−01 |
| 4.24381614e−01 | 3.61134082e−01 | 3.36557925e−01 | 3.51130992e−01 |
| 3.55470151e−01 | −1.72378957e−01 | −2.64918566e−01 | 8.10398981e−02 |
| 2.00458094e−01 | 2.10050806e−01 | 1.28947213e−01 | 4.07037377e−01 |
| 6.23302639e−01 | 3.96180093e−01 | −1.23550929e−01 | 2.70227998e−01 |
| 5.76959103e−02 | 1.74695194e−01 | 4.31625843e−01 | 1.71923012e−01 |
| 1.36340171e−01 | 2.86727756e−01 | 3.18766057e−01 | 1.13941781e−01 |
| −1.25259385e−01 | 2.98261702e−01 | −2.05568030e−01 | 2.10373566e−01 |
| 3.95759851e−01 | −2.26434782e−01 | −2.97855679e−02 | −2.33469494e−01 |
| −4.49817404e−02 | 3.60355079e−01 | 1.69134393e−01 | 3.90559107e−01 |
| 4.44657169e−02 | 6.51498958e−02 | 6.24615289e−02 | 8.58146176e−02 |
| −1.83829755e−01 | 3.92229021e−01 | 2.37135857e−01 | −1.27924979e−01 |
| 2.02149570e−01 | 1.73444524e−01 | 1.65303156e−01 | 7.56466463e−02 |
| 2.08868161e−01 | −1.39193758e−01 | 8.74776915e−02 | −6.39811680e−02 |
| 7.70248353e−01 | −2.84410473e−02 | 2.12803155e−01 | 1.36413217e−01 |
| −2.89852411e−01 | 4.18655872e−01 | 2.51234233e−01 | 3.06654215e−01 |
| −1.41444057e−01 | 3.09224725e−01 | 1.96245447e−01 | 6.01768315e−01 |
| 5.96506953e−01 | 7.08574831e−01 | 6.80842474e−02 | 5.56844711e−01 |
| −1.43965900e−01 | 3.79955262e−01 | 1.20561101e−01 | 7.75420487e−01 |
| −1.14521734e−01 | −5.64343370e−02 | 7.48438716e−01 | 4.78003561e−01 |
| −2.17251405e−01 | 2.03460574e−01 | 6.40424266e−02 | −1.68491021e−01 |
| 6.61622062e−02 | 6.62383080e−01 | 8.29868775e−04 | 2.52988696e−01 |

TABLE $W_h^1$-continued

| | | | |
|---|---|---|---|
| −4.06465046e−02 | 1.06605202e−01 | 6.49502933e−01 | −3.28697525e−02 |
| 6.03128374e−02 | 2.65246570e−01 | 4.55141328e−02 | −1.33558050e−01 |
| 1.77850410e−01 | 1.90127462e−01 | 1.40432164e−01 | 6.30887330e−01 |
| −2.49337807e−01 | −2.37151742e−01 | 8.37028623e−01 | 2.89493471e−01 |
| 3.12716126e−01 | 2.61177775e−02 | 4.16045427e−01 | −3.15694511e−02 |
| 2.78668851e−01 | 2.52151452e−02 | 1.48587123e−01 | 3.03034753e−01 |
| 3.52031551e−02 | 2.95414329e−01 | 2.02487588e−01 | 2.15047076e−01 |
| −5.44403493e−02 | −1.25787735e−01 | 5.14533184e−02 | 1.18987694e−01 |
| 7.18528569e−01 | −5.51828444e−02 | 3.15361351e−01 | −2.36410633e−01 |
| 7.19293728e−02 | −1.58836722e−01 | −1.74693242e−02 | 9.08361748e−03 |
| −1.06753588e−01 | 2.57756799e−01 | −1.57701850e−01 | 7.01610446e−02] |
| [4.04692799e−01 | −4.53907847e−02 | 4.02356029e−01 | 1.98617294e−01 |
| 3.28105152e−01 | 3.60489994e−01 | 2.92529881e−01 | 1.85267199e−02 |
| 1.43737599e−01 | 5.25903404e−01 | 5.20751297e−01 | −4.56434131e−01 |
| 5.17728627e−02 | −8.96310508e−02 | 1.98777586e−01 | −4.27975416e−01 |
| 1.24925792e−01 | 1.36735037e−01 | −1.51749626e−01 | 3.17027420e−01 |
| 5.87025225e−01 | 2.22780243e−01 | 3.39703023e−01 | 6.60685360e−01 |
| 1.85887784e−01 | 3.48858356e−01 | 2.41632029e−01 | −4.23121005e−01 |
| 4.51744050e−01 | 2.41018340e−01 | 1.33743808e−01 | −3.37114185e−02 |
| 1.96779966e−01 | 9.31791887e−02 | 3.01118761e−01 | 2.10917085e−01 |
| 3.22471470e−01 | 1.99679583e−01 | −8.91501158e−02 | 2.70370156e−01 |
| 2.74167955e−01 | −1.93578556e−01 | 2.37259537e−01 | 1.05924577e−01 |
| 2.89728492e−01 | 2.17413992e−01 | 1.44432321e−01 | 4.53595102e−01 |
| 3.85541707e−01 | 5.36627412e−01 | 1.95750162e−01 | 6.43493980e−02 |
| 4.56947625e−01 | 1.67704031e−01 | 2.84811646e−01 | −6.46046549e−02 |
| 9.30130556e−02 | 6.30768612e−02 | 2.06115589e−01 | 2.58767307e−01 |
| 5.57797909e−01 | −2.01562084e−02 | 8.01368356e−02 | 2.83672810e−01 |
| −9.00961086e−02 | −9.16972160e−02 | 1.53592542e−01 | 1.69517085e−01 |
| 3.92130613e−01 | 3.79006386e−01 | 3.65918547e−01 | −7.29709208e−01 |
| 2.46175721e−01 | 2.53441364e−01 | −9.35049504e−02 | 5.66526055e−01 |
| 2.01261103e−01 | 6.62753701e−01 | 2.90154576e−01 | 1.37068987e−01 |
| 4.52584952e−01 | 4.41281885e−01 | 3.66880983e−01 | 4.13028300e−01 |
| −5.30229360e−02 | 2.72619098e−01 | 2.77183741e−01 | 2.37504616e−02 |
| −1.22177219e−02 | −6.09798908e−01 | 9.36162695e−02 | 1.94699079e−01 |
| 5.34316078e−02 | −1.26185752e−02 | 3.30940247e−01 | 4.78339136e−01 |
| 2.56455272e−01 | 1.25761509e−01 | 3.25997472e−01 | 5.14598526e−02 |
| 4.79766279e−02 | 5.74012458e−01 | 3.04971457e−01 | 3.77283275e−01 |
| 2.55722195e−01 | 6.53668284e−01 | 2.70522177e−01 | 3.90642315e−01 |
| 6.34980481e−03 | 3.97314459e−01 | 4.75607276e−01 | 3.79623860e−01 |
| 4.20499265e−01 | −2.79677361e−01 | 2.03537539e−01 | 3.18512768e−01 |
| 2.89167047e−01 | 4.43624556e−01 | 4.56859171e−01 | 7.85670578e−02 |
| 1.12043574e−01 | 3.04438740e−01 | −1.81278393e−01 | 2.54876260e−01 |
| 2.24900931e−01 | 2.98261553e−01 | 1.05737686e−01 | 2.58313507e−01 |
| 2.06545472e−01 | 5.02064109e−01 | 2.22267643e−01 | 3.68290246e−01 |
| 7.99950778e−01 | −2.16618165e−01 | 3.17100435e−01 | 3.01020984e−02 |
| 2.02405289e−01 | 1.45494029e−01 | 3.62015247e−01 | 1.78605109e−01 |
| 4.61917371e−01 | 1.96923122e−01 | 3.31329077e−01 | 5.19653380e−01 |
| 1.22433700e−01 | 3.23366672e−01 | 3.01714092e−01 | 1.35488123e−01 |
| 5.64868189e−02 | 6.28975108e−02 | −1.33719796e−03 | 4.89361852e−01 |
| 3.55149597e−01 | −1.96092296e−03 | −2.37323478e−01 | −5.88986389e−01 |
| 5.84709346e−01 | −1.65718928e−01 | −2.28038996e−01 | 2.40909517e−01 |
| 1.02749847e−01 | −1.84267089e−01 | 2.95275092e−01 | 5.75797409e−02 |
| 4.18062419e−01 | −1.08901761e−01 | 3.59767765e−01 | 3.90123487e−01 |
| 2.33356312e−01 | 4.24517572e−01 | 4.67613578e−01 | 4.51010495e−01 |
| 5.98671615e−01 | 2.19775185e−01 | 1.30056977e−01 | 4.21750903e−01 |
| 3.50526243e−01 | 2.83542275e−01 | 1.86396524e−01 | 6.36669919e−02 |
| 6.85988963e−01 | 5.19434959e−02 | 2.98710525e−01 | 4.45428729e−01 |
| 3.32560912e−01 | 1.07538797e−01 | 1.96420208e−01 | 1.14650361e−01 |
| −3.45507920e−01 | 4.91775572e−01 | 4.50358808e−01 | 3.17738086e−01 |
| 1.67025551e−02 | 6.80324495e−01 | 4.69744466e−02 | 1.08840711e−01 |
| −1.54392138e−01 | 5.68953156e−02 | 1.01308234e−01 | 7.27866828e−01 |
| −2.42298260e−01 | −3.94283652e−01 | 3.62354934e−01 | 1.49660455e−02 |
| 1.44442871e−01 | 6.95465729e−02 | 4.13584113e−01 | −8.29335898e−02 |
| 2.53180474e−01 | 4.08889472e−01 | 3.48371565e−01 | 5.79943478e−01 |
| 1.72427818e−01 | 3.13431740e−01 | 4.83900428e−01 | 4.94418412e−01 |
| 1.13790080e−01 | 2.20100924e−01 | 4.58451241e−01 | −2.24737450e−01 |
| 3.34622264e−01 | 8.51106942e−01 | 2.13157758e−01 | 5.80658972e−01 |
| 3.24834436e−01 | 7.67737329e−02 | 2.05869034e−01 | −5.47794215e−02 |
| 1.21738099e−01 | −2.20635325e−01 | 6.27180040e−01 | 3.55236351e−01 |
| 2.38111883e−01 | 1.93390429e−01 | 8.12172294e−02 | 4.60882038e−01 |
| −6.68621138e−02 | −6.39876500e−02 | −4.73928638e−02 | 8.47662538e−02 |
| 5.11262357e−01 | 2.25948039e−02 | 3.14958453e−01 | 5.37884295e−01 |
| 3.09558570e−01 | 3.74476761e−01 | −2.09592551e−01 | 8.66296142e−02 |
| 8.15184265e−02 | 7.97358751e−02 | 3.21476430e−01 | 4.49196517e−01 |
| −7.81863406e−02 | 6.97664261e−01 | 3.46706420e−01 | 1.49744451e−01] |
| [−6.50601694e−03 | 3.71127844e−01 | 7.29161948e−02 | 2.99851298e−01 |
| 5.03475726e−01 | 2.55587965e−01 | 3.33733372e−02 | 1.01762831e−01 |
| 3.18993211e−01 | 5.49443245e−01 | 1.03149094e−01 | 1.56329885e−01 |
| 3.37123156e−01 | 4.31305528e−01 | 2.05956817e−01 | −1.57784492e−01 |
| 8.30882728e−01 | 2.58971691e−01 | −1.16779104e−01 | 2.71264195e−01 |

TABLE $W_h^1$-continued

| | | | |
|---|---|---|---|
| 2.67125964e-01 | 1.54211193e-01 | 4.03812766e-01 | 6.11343801e-01 |
| 5.53082168e-01 | -7.34931603e-02 | 2.89595604e-01 | -2.29696813e-03 |
| 5.33114552e-01 | 4.14038509e-01 | 2.29061827e-01 | 3.94365758e-01 |
| 2.20592603e-01 | 1.83733389e-01 | 5.11568367e-01 | -2.18820810e-01 |
| 2.60439903e-01 | 2.20127165e-01 | 2.97167879e-02 | 3.83523017e-01 |
| 6.66760564e-01 | 3.94619763e-01 | 8.00213218e-01 | 3.91341567e-01 |
| 1.85326129e-01 | -6.35213032e-02 | 4.08818483e-01 | 4.08304423e-01 |
| 3.30572516e-01 | 3.05695653e-01 | 3.29987168e-01 | -1.00659328e-02 |
| 5.57814717e-01 | 5.87160923e-02 | 3.03471476e-01 | 6.51888192e-01 |
| 2.78607070e-01 | 3.64111185e-01 | 5.98722041e-01 | -6.20698035e-01 |
| 6.05078265e-02 | 4.38756019e-01 | 3.76277580e-03 | -9.37349629e-03 |
| 3.43910307e-01 | 5.20240366e-02 | 2.50617385e-01 | 5.15760332e-02 |
| 2.84219712e-01 | 1.07740097e-01 | 4.18743938e-01 | -2.80066997e-01 |
| 7.61884153e-02 | 3.60199541e-01 | 1.56105787e-01 | 4.69512641e-01 |
| 3.38699490e-01 | 2.11104527e-01 | 2.38513544e-01 | 3.31717342e-01 |
| 2.98121542e-01 | 2.04359412e-01 | 1.65143818e-01 | 3.80117178e-01 |
| 1.37734979e-01 | -2.64796585e-02 | -8.46040144e-04 | 4.00036991e-01 |
| 3.42053354e-01 | -2.02653706e-01 | 7.47374594e-02 | 2.71837488e-02 |
| 4.83457856e-02 | -6.74872324e-02 | 4.75320101e-01 | 4.68872815e-01 |
| 2.87342936e-01 | 2.44312838e-01 | 2.64764249e-01 | 3.29561770e-01 |
| 5.03840506e-02 | 3.56504411e-01 | 1.82575583e-01 | -2.20433921e-01 |
| 5.07830799e-01 | 7.12293029e-01 | 3.25844914e-01 | 2.41521031e-01 |
| 1.72077760e-01 | 5.26874959e-01 | 5.00622869e-01 | 3.41099501e-02 |
| 2.29614928e-01 | -2.07033083e-02 | 5.28027534e-01 | 3.51464123e-01 |
| -9.67064034e-03 | -3.55107971e-01 | 6.24680519e-01 | 2.46357322e-01 |
| 1.49474040e-01 | 4.42125082e-01 | 1.47463545e-01 | 4.47199702e-01 |
| 1.41302317e-01 | 3.69186044e-01 | 1.33904815e-01 | 3.07811260e-01 |
| 8.18882644e-01 | 1.29967973e-01 | 2.08835900e-01 | 3.03607553e-01 |
| 3.65671992e-01 | 2.07001925e-01 | 1.76157579e-01 | 4.88644004e-01 |
| 1.92582786e-01 | 4.49671984e-01 | 7.06516132e-02 | 5.01939058e-01 |
| -1.63324729e-01 | 2.06527025e-01 | 4.11791384e-01 | 7.08755031e-02 |
| 3.30483854e-01 | -5.94855696e-02 | 3.04113925e-01 | 2.98419803e-01 |
| 2.58683473e-01 | 2.44916007e-01 | 1.21073961e-01 | 3.31311703e-01 |
| 1.70914959e-02 | 3.48641306e-01 | 3.41076374e-01 | 1.89541101e-01 |
| -3.78657728e-01 | 9.85705778e-02 | 2.23598301e-01 | 3.23274195e-01 |
| 5.51720619e-01 | 3.75029385e-01 | 4.33440059e-01 | 1.81918517e-01 |
| 2.92694151e-01 | 1.36138767e-01 | 5.79855621e-01 | 4.04085636e-01 |
| 1.10660791e-01 | 2.37864614e-01 | 2.73933560e-01 | 6.83560014e-01 |
| 1.15677258e-02 | 4.49996114e-01 | -3.14463452e-02 | 1.62333176e-01 |
| 2.91883409e-01 | 8.32648799e-02 | 3.86980176e-01 | 4.90228415e-01 |
| 5.63136160e-01 | 1.76364213e-01 | 1.29700437e-01 | 2.40324959e-01 |
| 5.66978455e-01 | -9.34186503e-02 | 2.30100285e-01 | 5.76733708e-01 |
| 1.91194713e-01 | 5.70549786e-01 | 2.75194228e-01 | 6.24534130e-01 |
| 6.23209998e-02 | 3.15882236e-01 | -3.14539939e-01 | 3.24883550e-01 |
| 4.72814739e-01 | 2.29548886e-01 | 7.09884539e-02 | 4.05992977e-02 |
| -9.37273204e-02 | 5.42357899e-02 | 4.80548859e-01 | 1.75540268e-01 |
| 4.83700335e-02 | 9.05092712e-03 | 3.45081896e-01 | 2.20557213e-01 |
| 7.55279601e-01 | 1.03895023e-01 | 6.41766071e-01 | 8.81950974e-01 |
| 5.07207930e-01 | 2.64591366e-01 | 3.74107301e-01 | 1.80565953e-01 |
| 9.20167491e-01 | 2.15012936e-01 | 3.24801147e-01 | 1.13683924e-01 |
| 3.30941111e-01 | 4.55834419e-01 | 2.91087598e-01 | -1.25879809e-01 |
| -1.56195581e-01 | 2.45427921e-01 | 4.44881797e-01 | 3.38326782e-01 |
| -6.26683757e-02 | -8.18358213e-02 | 3.60011965e-01 | 2.66013920e-01 |
| 2.64306627e-02 | 3.38141412e-01 | 2.98890740e-01 | 7.91028738e-01 |
| 3.49982262e-01 | 4.88631487e-01 | 3.48829418e-01 | 3.42263073e-01 |
| 4.29831743e-01 | 1.41065419e-01 | 4.73047853e-01 | 5.55025399e-01 |
| 6.57557011e-01 | -2.12666258e-01 | 3.28339934e-01 | 2.86924876e-02 |
| 3.00395917e-01 | 3.32280099e-01 | 1.99127853e-01 | 1.36730060e-01 |
| -2.76661247e-01 | 4.11653191e-01 | 4.47306752e-01 | 3.37213457e-01] |
| [1.40261546e-01 | 5.32246113e-01 | -6.66026250e-02 | 2.53702611e-01 |
| 1.48892358e-01 | 9.97882187e-02 | 1.46362469e-01 | 1.11141302e-01 |
| -2.03152820e-01 | 1.99748188e-01 | 2.14726999e-01 | 1.11043535e-01 |
| -1.30099505e-01 | 3.02058518e-01 | -1.30118299e-02 | -3.06487888e-01 |
| -5.32527752e-02 | 4.58333790e-02 | -1.57096878e-01 | 9.66844484e-02 |
| 2.24680766e-01 | 1.42131150e-01 | -1.78342406e-02 | 2.22023115e-01 |
| 7.27435425e-02 | -3.03730607e-01 | 4.77818489e-01 | 3.11674535e-01 |
| 6.88093722e-02 | -2.07991362e-01 | 2.88761020e-01 | 4.78240252e-01 |
| 2.06903562e-01 | 7.20909685e-02 | 7.87732154e-02 | 3.12892407e-01 |
| 1.68279529e-01 | 5.07257342e-01 | 1.20820768e-01 | -1.71567023e-01 |
| 3.33111048e-01 | -1.31495103e-01 | -4.76271659e-03 | 4.93947923e-01 |
| -8.71951878e-02 | 2.89164841e-01 | 4.60996568e-01 | 4.40199584e-01 |
| 2.58367330e-01 | 4.33914393e-01 | 6.53667673e-02 | -9.32014883e-02 |
| 6.71768725e-01 | -2.55382955e-02 | 2.85574198e-01 | 7.18396753e-02 |
| 5.95040098e-02 | 2.08824605e-01 | 2.61583388e-01 | 3.03478301e-01 |
| 6.36709154e-01 | 1.32295698e-01 | 6.11332022e-01 | -2.18848899e-01 |
| -1.84439316e-01 | 2.28391424e-01 | -6.97385296e-02 | 7.59430528e-02 |
| -3.09415208e-03 | 3.19425374e-01 | 1.83678791e-01 | -6.37312680e-02 |
| 3.15719306e-01 | 5.86056784e-02 | 2.23273877e-02 | 2.36887276e-01 |
| 1.28870770e-01 | -9.79530532e-03 | 5.58640897e-01 | 5.09301201e-02 |
| 3.28219444e-01 | 1.55888945e-01 | 1.77845508e-01 | 2.59319335e-01 |

TABLE $W_h^1$-continued

| | | | |
|---|---|---|---|
| −1.12821482e−01 | 5.85718900e−02 | 5.28614111e−02 | 2.55603436e−02 |
| 5.13942003e−01 | −2.24532515e−01 | 2.21689269e−01 | 1.75808653e−01 |
| −1.03729658e−01 | 4.69189346e−01 | 4.25330520e−01 | 2.04127848e−01 |
| 1.74299210e−01 | 2.27747425e−01 | 1.39603332e−01 | 2.56871819e−01 |
| 2.20511198e−01 | 3.14535826e−01 | 2.31146351e−01 | 3.41118276e−01 |
| −2.96846516e−02 | 6.01292312e−01 | 3.96701634e−01 | 2.90676691e−02 |
| −2.18731686e−01 | 9.36200619e−02 | 4.64205265e−01 | 6.95755184e−02 |
| 2.84558266e−01 | 2.29832917e−01 | 1.41233191e−01 | 2.71743029e−01 |
| −4.70277257e−02 | 6.63025677e−01 | 6.36700094e−02 | 2.84848101e−02 |
| −3.94046716e−02 | 1.92533016e−01 | 3.80674452e−02 | 6.07169330e−01 |
| 1.93778332e−02 | 3.94068956e−02 | 1.54639468e−01 | −2.25747615e−01 |
| 1.62801325e−01 | 3.20374846e−01 | 1.79648295e−01 | 3.52878451e−01 |
| 1.84240207e−01 | −7.93547332e−02 | 8.01484734e−02 | 3.72627914e−01 |
| −5.12758382e−02 | 5.11496186e−01 | 4.13461663e−02 | −1.05023487e−02 |
| 3.37795913e−01 | 4.17394787e−01 | 1.16827093e−01 | 2.81747609e−01 |
| −3.35705578e−02 | 9.33580026e−02 | 6.85166478e−01 | −1.65937901e−01 |
| 3.96184683e−01 | 2.47807518e−01 | −2.16454677e−02 | 2.12198481e−01 |
| −2.38328949e−01 | 2.15292480e−02 | 5.62688299e−02 | 3.28020334e−01 |
| −1.20660737e−01 | 2.12047532e−01 | 2.54471719e−01 | 2.75054723e−01 |
| −1.74329504e−01 | 5.86034209e−02 | 1.12015240e−01 | 3.98104452e−03 |
| 7.52414763e−01 | 2.95828313e−01 | 4.95930649e−02 | 5.40333509e−01 |
| 3.23958248e−02 | −1.30638108e−02 | 4.21955466e−01 | 2.45128855e−01 |
| 2.60557458e−02 | −3.96804452e−01 | 3.99742633e−01 | 1.99985765e−02 |
| 3.37063938e−01 | 1.62786275e−01 | 2.28842989e−01 | 1.73134878e−01 |
| 4.52821285e−01 | 2.71627367e−01 | 1.93673924e−01 | 2.17225090e−01 |
| 5.78780293e−01 | 2.20089689e−01 | 7.06581697e−02 | 9.92560163e−02 |
| 1.08093135e−01 | 1.03867717e−01 | 1.24048553e−01 | 3.27668279e−01 |
| 3.66789490e−01 | 7.65055180e−01 | 1.03326738e−01 | 3.22533995e−01 |
| 2.77858734e−01 | 3.47119644e−02 | 1.01389065e−01 | 2.06813723e−01 |
| −1.05599696e−02 | 1.02870695e−01 | 3.01076472e−01 | 1.97476551e−01 |
| 3.89349699e−01 | 2.63012230e−01 | 3.71380210e−01 | 1.51644453e−01 |
| 2.28394479e−01 | 7.27960169e−01 | 1.63802087e−01 | 4.96517032e−01 |
| 2.54575819e−01 | 4.83834654e−01 | 3.11012477e−01 | −1.40151396e−01 |
| 1.84638008e−01 | 9.39422697e−02 | 7.61524662e−02 | −3.94438356e−01 |
| 4.38658834e−01 | 3.72777879e−01 | 3.41749668e−01 | 5.07633269e−01 |
| −2.45216236e−01 | 5.84267527e−02 | 1.83630154e−01 | 3.50506008e−01 |
| 3.68046373e−01 | −1.42601088e−02 | 6.54674411e−01 | 5.38320206e−02 |
| 3.02171726e−02 | 8.55632871e−02 | 7.51870990e−02 | −1.52279377e−01 |
| 1.07885487e−01 | 1.37169793e−01 | −2.80829847e−01 | 2.86289514e−03 |
| −2.87636876e−01 | −2.53948182e−01 | 1.89178914e−01 | 3.61382701e−02 |
| 1.49782807e−01 | 1.38633847e−01 | 4.08266395e−01 | 1.27625450e−01 |
| 1.18444212e−01 | −3.94437136e−03 | 1.56980544e−01 | 3.09792548e−01 |
| −2.77434468e−01 | 1.20717794e−01 | −3.82863469e−02 | −2.57633869e−02] |
| [1.81248188e−01 | 2.06266999e−01 | −8.54932442e−02 | −1.03707528e−01 |
| 1.07954368e−01 | −4.08684686e−02 | 1.44757301e−01 | −1.24281794e−01 |
| 1.30226284e−01 | 2.51795501e−01 | 1.51560366e−01 | 2.85193145e−01 |
| 1.39021933e−01 | 1.78203717e−01 | −1.25727624e−01 | −3.89186889e−01 |
| 2.51135111e−01 | 1.56962872e−01 | 3.66989464e−01 | 6.17216006e−02 |
| −7.31326081e−03 | 5.77695947e−03 | 3.22829425e−01 | 7.06170797e−01 |
| 8.73927996e−02 | 1.50966436e−01 | 2.14437693e−01 | −9.05573964e−02 |
| 3.74847770e−01 | 6.40852675e−02 | −1.99061975e−01 | 3.69041383e−01 |
| 4.33761254e−02 | −6.38426691e−02 | 3.38542849e−01 | 1.92249492e−01 |
| 1.88101386e−03 | 1.62440136e−01 | 3.50658357e−01 | 1.93923675e−02 |
| 4.03914601e−01 | −2.16396719e−01 | 2.44223624e−01 | 1.09167166e−01 |
| −3.14950496e−01 | 3.88359874e−02 | 5.73652744e−01 | 4.46731001e−01 |
| 5.75961232e−01 | 3.61662596e−01 | 3.12974304e−01 | −3.24921101e−01 |
| 2.83913091e−02 | −2.27515921e−02 | −1.06086724e−01 | 1.24417834e−01 |
| 3.83383930e−02 | 7.65364021e−02 | 5.21700904e−02 | 1.44120842e−01 |
| 1.80079892e−01 | −1.73520893e−02 | −1.24473847e−01 | −1.32375091e−01 |
| −7.83946812e−02 | 3.23781550e−01 | 1.87157959e−01 | −1.09522246e−01 |
| 3.09654176e−01 | 4.51365352e−01 | 5.74042261e−01 | −3.84635255e−02 |
| 2.46486560e−01 | −6.86298460e−02 | 3.60205650e−01 | 1.70344010e−01 |
| 2.61155158e−01 | 3.92613001e−02 | 2.41140157e−01 | 4.02722746e−01 |
| 6.57688230e−02 | −9.17666331e−02 | −3.12344193e−01 | 2.07319289e−01 |
| 2.78855979e−01 | −4.51627970e−02 | −4.49232385e−02 | 1.53088361e−01 |
| 1.28100932e−01 | −3.56701314e−01 | −1.05203856e−02 | 2.48867273e−01 |
| −2.23249555e−01 | 1.45100772e−01 | 3.16929340e−01 | 3.44790667e−01 |
| −3.72873724e−01 | −1.03996187e−01 | −1.37567714e−01 | −1.21516980e−01 |
| 2.14875326e−01 | 1.93956897e−01 | 3.80208045e−01 | 3.54149938e−01 |
| −2.15753794e−01 | 1.53710604e−01 | 2.44827718e−01 | 1.30054355e−01 |
| 1.71915889e−01 | 2.94245780e−01 | −3.74268293e−02 | −7.94283524e−02 |
| 8.68833959e−02 | −2.01212559e−02 | 5.39124250e−01 | 6.32258177e−01 |
| −8.85859728e−02 | −1.56483389e−02 | 7.06527010e−02 | 2.63249930e−02 |
| −6.06723540e−02 | −1.56514376e−01 | −1.48584932e−01 | 3.14068228e−01 |
| 3.31663132e−01 | −2.97572047e−01 | 1.32647306e−01 | 9.33689103e−01 |
| 2.40030080e−01 | 4.01317537e−01 | 1.82877600e−01 | 4.25838858e−01 |
| −2.61769205e−01 | −2.71558076e−01 | 1.92700848e−01 | 5.57701252e−02 |
| 4.10251878e−03 | 9.50556770e−02 | −1.36180311e−01 | 5.84553741e−02 |
| 5.85302152e−02 | −2.25447580e−01 | 7.43554085e−02 | 3.92480046e−02 |
| 1.62843227e−01 | −1.71591360e−02 | 3.39167625e−01 | 1.76882416e−01 |

TABLE $W_h^1$-continued

| | | | |
|---|---|---|---|
| −1.70857124e−02 | 2.38480106e−01 | 1.80690829e−02 | 2.41157725e−01 |
| 1.50207028e−01 | −2.21906856e−01 | −1.03683598e−01 | −2.62766242e−01 |
| −1.81251749e−01 | 5.58840483e−02 | 5.93740754e−02 | −1.74112603e−01 |
| 1.33261204e−01 | 9.28163975e−02 | −6.02870584e−02 | 1.55871734e−01 |
| 1.00576855e−01 | 7.14245737e−02 | 9.56927543e−05 | 1.77502930e−01 |
| 3.47558439e−01 | 5.00112057e−01 | 2.82355487e−01 | 9.46895033e−03 |
| −1.66892081e−01 | −8.25034603e−02 | 2.98421919e−01 | −4.00809087e−02 |
| −6.21600486e−02 | 1.03887411e−04 | 4.17916954e−01 | 6.53080940e−01 |
| 5.08935690e−01 | −2.31722578e−01 | 2.15372622e−01 | 2.63060242e−01 |
| 1.25940263e−01 | 3.23233545e−01 | −1.33763283e−01 | 1.39085978e−01 |
| −1.05421327e−01 | −9.86831561e−02 | 1.61176994e−01 | 3.54117274e−01 |
| −1.17983751e−01 | 2.44427726e−01 | −3.35038304e−02 | 2.50296861e−01 |
| −1.88489273e−01 | 3.97384137e−01 | −1.15739457e−01 | 2.11410120e−01 |
| −3.47978085e−01 | −1.76300146e−02 | 3.76344472e−01 | −8.60906243e−02 |
| 1.85920209e−01 | −2.69675881e−01 | 8.40600431e−01 | 3.14979643e−01 |
| 2.97742598e−02 | 4.81269360e−01 | 1.39556691e−01 | 1.39840208e−02 |
| 6.08293295e−01 | 4.87141274e−01 | −5.65995611e−02 | 1.69641137e−01 |
| 2.10703522e−01 | −6.46270290e−02 | −2.28752971e−01 | −1.87584579e−01 |
| 3.38176936e−02 | −4.23645979e−04 | −4.06022891e−02 | 4.12927896e−01 |
| 1.85009569e−01 | 3.09271395e−01 | 2.03722686e−01 | 8.92434083e−03 |
| 2.53185004e−01 | −3.47364455e−01 | 3.45712006e−01 | −1.52976783e−02 |
| −5.52105419e−02 | −1.42124474e−01 | −1.11832283e−01 | 1.55161053e−01 |
| −3.38211805e−02 | 2.59749983e−02 | −2.23257542e−01 | −9.54344720e−02 |
| −6.29885793e−02 | −2.74389118e−01 | 2.98811525e−01 | 2.70453751e−01 |
| 8.77632618e−01 | 1.41649187e−01 | 7.33625293e−02 | 2.16484256e−01 |
| −3.57295126e−01 | −4.25979346e−02 | 4.45471436e−01 | −2.50064075e−01 |
| −3.03669542e−01 | 2.51362622e−01 | −7.79270753e−02 | 1.47590458e−01] |
| [2.53011048e−01 | 3.14271122e−01 | 2.78361231e−01 | −1.95085909e−02 |
| 2.29478940e−01 | 5.19807875e−01 | 2.25250423e−01 | 2.55564481e−01 |
| 1.74132183e−01 | 2.42548048e−01 | 2.67933995e−01 | −1.28389016e−01 |
| −2.01526329e−01 | −2.50887522e−03 | 2.17575014e−01 | −2.13153124e−01 |
| 2.62998268e−02 | 2.96141237e−01 | −9.82000455e−02 | 3.53081934e−02 |
| −1.47955894e−01 | 4.69516784e−01 | 8.58059973e−02 | 3.74653578e−01 |
| 3.20583850e−01 | −5.61560392e−02 | 4.00141269e−01 | 1.31410033e−01 |
| 5.45486748e−01 | 8.28060880e−03 | 5.10156900e−02 | 2.81504601e−01 |
| 3.14967901e−01 | −1.61193147e−01 | −3.37114781e−01 | 6.01559579e−02 |
| 2.58897334e−01 | 4.72112447e−01 | −6.49222499e−03 | 8.49827677e−02 |
| 2.04783157e−01 | 3.87348756e−02 | 1.48728207e−01 | 4.35497999e−01 |
| 3.08835119e−01 | 1.33513987e−01 | 2.08795245e−04 | 2.34535962e−01 |
| −1.61204010e−01 | 2.18871400e−01 | 2.63852268e−01 | −1.45277232e−01 |
| 2.38376617e−01 | −7.85076469e−02 | 4.17353511e−01 | 1.85865715e−01 |
| 3.14502239e−01 | 1.25349164e−01 | 2.63135791e−01 | 4.62606192e−01 |
| 3.82907182e−01 | 3.27125877e−01 | −1.40841767e−01 | 1.01650156e−01 |
| 2.98470229e−01 | −9.25863627e−04 | −8.45596939e−02 | 4.35444772e−01 |
| 3.01183581e−01 | 3.18981051e−01 | 4.35609072e−01 | −5.34399271e−01 |
| 8.07041228e−02 | 3.66460890e−01 | 7.70685002e−02 | 3.99167448e−01 |
| 5.64751685e−01 | 5.19060850e−01 | 4.59182501e−01 | 5.58255374e−01 |
| 3.88408005e−01 | 2.12866664e−01 | 2.39798546e−01 | −1.60547003e−01 |
| 5.23875654e−01 | −3.96443546e−01 | −3.60440426e−02 | 9.81187075e−02 |
| 1.37615934e−01 | −1.27599552e−01 | −3.63308042e−01 | 4.13813919e−01 |
| −7.85213485e−02 | 1.59528956e−01 | 3.24767590e−01 | 4.36806411e−01 |
| 1.45791963e−01 | −3.69575396e−02 | 1.39136046e−01 | 2.65386939e−01 |
| 6.17272258e−02 | 3.57757688e−01 | 2.95188934e−01 | 1.70290604e−01 |
| −4.34125252e−02 | 1.56409100e−01 | 3.08000118e−01 | 1.29010510e−02 |
| 1.15887165e−01 | 4.66675997e−01 | 3.31586530e−03 | −3.30013596e−02 |
| 1.54024184e−01 | 1.09489448e−01 | 5.40761113e−01 | 3.93051147e−01 |
| 3.45070183e−01 | 5.58717310e−01 | 7.62690961e−01 | 1.98578492e−01 |
| 5.46678454e−01 | −3.58194136e−03 | 2.21960649e−01 | 1.17312156e−01 |
| 9.65892971e−02 | 1.16977558e−01 | −6.98076701e−03 | 2.97247153e−02 |
| 3.84981215e−01 | 3.99014592e−01 | 4.02459472e−01 | 7.51905799e−01 |
| 3.15730155e−01 | −9.55080763e−02 | 3.64193559e−01 | 4.28186744e−01 |
| −4.38431166e−02 | 4.46561456e−02 | 3.07804197e−01 | 1.74762487e−01 |
| 1.89956382e−01 | 1.03382058e−02 | 2.54791945e−01 | 4.03954446e−01 |
| 4.17381495e−01 | 1.21174075e−01 | 6.85033381e−01 | 5.67841828e−01 |
| 1.74740836e−01 | −2.27408111e−02 | 2.53785580e−01 | 3.04216295e−01 |
| 1.42117962e−01 | −4.97241318e−01 | −2.11980283e−01 | −6.66386411e−02 |
| 9.20879468e−02 | 7.50585422e−02 | −1.97960883e−01 | 3.40915889e−01 |
| 3.11597526e−01 | 1.38863415e−01 | 1.06722437e−01 | −1.63428709e−02 |
| 4.54387702e−02 | −2.00038269e−01 | 3.31249505e−01 | 7.35454783e−02 |
| 3.25413123e−02 | 1.70373321e−01 | 4.36769128e−02 | 1.90726817e−01 |
| 2.95894027e−01 | 6.99579641e−02 | 2.21022353e−01 | 1.71391621e−01 |
| 3.40186149e−01 | 1.27049565e−01 | 2.00097427e−01 | 2.07194969e−01 |
| 3.19213927e−01 | −8.70005265e−02 | 4.01369989e−01 | 5.72922885e−01 |
| −1.62366331e−01 | −1.27815511e−02 | −2.91401535e−01 | 2.57640570e−01 |
| −3.87444580e−03 | 1.02000512e−01 | 2.05227166e−01 | 4.75230813e−01 |
| 3.91662896e−01 | 3.09733987e−01 | 2.84938551e−02 | 4.03892726e−01 |
| 2.91267782e−01 | 1.68514520e−01 | 1.23896003e−01 | 2.15355664e−01 |
| −1.18310623e−01 | 1.50381522e−02 | 5.39256930e−01 | 3.03768396e−01 |
| −1.69582278e−01 | 1.44272536e−01 | 3.51796597e−01 | 2.41298512e−01 |
| 3.31901431e−01 | 1.78974509e−01 | −5.78349270e−02 | 4.92438495e−01 |

TABLE $W_h^1$-continued

| | | | |
|---|---|---|---|
| 1.42852202e−01 | 2.16024294e−01 | 1.12461552e−01 | 1.74248993e−01 |
| −1.24071337e−01 | 6.26576021e−02 | 3.05620819e−01 | −6.61521778e−02 |
| 1.04441099e−01 | 2.78184861e−01 | 1.30278006e−01 | 3.23865056e−01 |
| 5.22511423e−01 | 1.44578263e−01 | 1.94329694e−01 | 2.79449016e−01 |
| 2.65602738e−01 | 2.15669889e−02 | 3.39078039e−01 | 9.87645909e−02 |
| 9.30947810e−02 | 4.53528315e−02 | 3.94349337e−01 | 7.22654343e−01 |
| 1.21768557e−01 | 1.71253964e−01 | 1.62734866e−01 | 1.09108146e−02 |
| −5.44325821e−02 | −2.57084846e−01 | 2.42030114e−01 | 2.38305196e−01 |
| 1.33069694e−01 | 1.42563060e−01 | 1.55653894e−01 | 1.93244457e−01 |
| 1.44970685e−01 | 4.14785087e−01 | 1.89751416e−01 | −6.60994798e−02 |
| 3.39593977e−01 | −8.76635462e−02 | 7.35516995e−02 | 9.90247130e−02] |
| [1.88926756e−01 | −3.14404704e−02 | 3.63503456e−01 | 2.72553116e−01 |
| 2.31759176e−01 | 4.96347457e−01 | 4.00330335e−01 | 3.38584781e−01 |
| −2.19591320e−01 | −8.06516781e−02 | 4.19976115e−01 | −1.84125915e−01 |
| −1.24157809e−01 | 2.75854468e−01 | 2.45857924e−01 | −1.59438029e−01 |
| −2.40861893e−01 | −1.42668679e−01 | 8.34641382e−02 | 5.50510406e−01 |
| 2.23393545e−01 | 2.40912392e−01 | −6.79421574e−02 | 5.84813237e−01 |
| −3.31863791e−01 | 2.98761219e−01 | 6.19216383e−01 | 3.51679116e−01 |
| 4.07357275e−01 | 3.99581194e−01 | 4.84846383e−01 | 5.10632217e−01 |
| 4.01790947e−01 | 6.94529116e−01 | −8.18039775e−02 | 1.92689151e−01 |
| −2.47681707e−01 | 6.43703640e−01 | 2.13610992e−01 | 4.93230790e−01 |
| 5.21177948e−01 | 3.65957588e−01 | 3.13025475e−01 | −4.71458107e−01 |
| 6.59015059e−01 | 1.25929981e−01 | 2.00076938e−01 | −2.36099735e−01 |
| 2.05709741e−01 | −3.94773960e−01 | 1.48280844e−01 | 4.16834235e−01 |
| 2.49358907e−01 | −1.32768676e−01 | 2.28580803e−01 | 2.34667256e−01 |
| −1.20690331e−01 | 1.18901044e−01 | 4.73476052e−02 | −1.62990034e−01 |
| 3.35601240e−01 | 8.56355548e−01 | 3.34601641e−01 | 5.04511118e−01 |
| 6.73298240e−01 | 2.53645658e−01 | 5.20186014e−02 | −5.11213660e−01 |
| 6.95281997e−02 | 1.59678131e−01 | 1.35669336e−01 | 1.10998318e−01 |
| 7.20585227e−01 | 9.75502208e−02 | 2.48210609e−01 | 5.00768900e−01 |
| 5.90742707e−01 | 3.99334729e−01 | 2.74965912e−01 | 4.93886113e−01 |
| 1.56116903e−01 | 7.01796174e−01 | −3.95052359e−02 | 4.34400380e−01 |
| 2.03034014e−01 | 4.59771752e−01 | −4.86875065e−02 | 5.95644712e−01 |
| 5.27397931e−01 | −1.69725232e−02 | −1.57349795e−01 | −2.33515620e−01 |
| −3.64733040e−02 | 3.67326587e−01 | −2.90303111e−01 | 5.40756702e−01 |
| −1.14280675e−02 | −3.56325686e−01 | 7.54893944e−02 | 4.81727451e−01 |
| 5.05459666e−01 | 5.52960157e−01 | 1.68640569e−01 | 3.09625715e−02 |
| −8.35176483e−02 | 3.39781344e−01 | 7.01114461e−02 | 2.29416132e−01 |
| 9.13189292e−01 | 3.38141382e−01 | 6.44470692e−01 | 4.69976008e−01 |
| 3.77886385e−01 | 7.17728436e−01 | −9.80949849e−02 | −3.95296007e−01 |
| 8.20760280e−02 | 3.10747147e−01 | −1.02846801e−01 | 2.83212036e−01 |
| 4.30060983e−01 | 1.90687001e−01 | 4.65413272e−01 | −1.83033615e−01 |
| 2.80382335e−02 | 3.15448403e−01 | −3.27659398e−02 | 1.08105218e−00 |
| 5.89300990e−01 | 3.20495546e−01 | 5.49258515e−02 | 1.03104904e−01 |
| 1.03618193e−00 | −1.69628989e−02 | 2.68167593e−02 | 1.88775674e−01 |
| 2.21585631e−01 | −3.87865126e−01 | 4.79656570e−02 | 5.77791572e−01 |
| 6.45017147e−01 | 2.43153647e−01 | 2.60386676e−01 | 4.33765918e−01 |
| 1.34570315e−01 | −3.50047380e−01 | 5.61828911e−01 | −3.22727207e−03 |
| 3.20399068e−02 | 6.23054087e−01 | −2.88574189e−01 | 2.90367812e−01 |
| 4.56327409e−01 | 1.76820397e−01 | −1.53281465e−01 | 8.03277493e−02 |
| 4.55374420e−01 | −1.74950007e−02 | 1.73809201e−01 | 2.72034615e−01 |
| −1.10751875e−01 | −1.81645870e−01 | 5.92159808e−01 | 3.52428406e−01 |
| 9.72136036e−02 | −1.26741409e−01 | −8.75897110e−02 | −2.57894527e−02 |
| 2.61260986e−01 | 2.20090225e−01 | 2.82077700e−01 | −5.94386607e−02 |
| 1.33918449e−01 | 1.39016956e−01 | 3.60364735e−01 | −1.60643607e−01 |
| 4.75979000e−01 | 1.33492023e−01 | 1.55555457e−01 | −4.67251182e−01 |
| 9.90979910e−01 | 8.60367045e−02 | 4.16886359e−01 | 3.53872061e−01 |
| −2.25348383e−01 | 3.07380110e−01 | 2.99167126e−01 | 4.64541256e−01 |
| 7.17906877e−02 | 5.34922183e−01 | 1.49774179e−01 | 7.06010222e−01 |
| 6.41076267e−01 | 6.29505455e−01 | 4.99634892e−01 | 1.72247708e−01 |
| −9.64719895e−03 | 4.77553159e−01 | 1.30918846e−01 | 6.29353642e−01 |
| −1.05903605e−02 | 1.58895567e−01 | 1.56889215e−01 | 1.55964643e−01 |
| −2.94565529e−01 | 3.36906642e−01 | 2.03438342e−01 | −3.36201817e−01 |
| 9.74396691e−02 | 4.08538193e−01 | 6.68708861e−01 | 4.56384003e−01 |
| −2.85006732e−01 | 2.28173345e−01 | 2.32083023e−01 | 3.61063937e−03 |
| 1.11989528e−01 | −4.54685651e−02 | −2.78893739e−01 | 3.95843461e−02 |
| −1.23182356e−01 | 4.19500887e−01 | 8.15670609e−01 | 2.29621172e−01 |
| −1.10100664e−01 | −3.21060210e−01 | 6.43116534e−01 | 3.44195604e−01 |
| 5.46142519e−01 | 2.13058040e−01 | 7.45602667e−01 | 7.45975152e−02 |
| 3.37923348e−01 | −2.10910626e−02 | 7.80508518e−01 | 2.68319398e−01 |
| 5.87207898e−02 | 2.13702559e−01 | −2.19893336e−01 | 8.39995742e−02 |
| −1.03442825e−01 | −1.43956915e−01 | 2.51392156e−01 | 2.00222388e−01 |
| −1.99732751e−01 | −1.73253283e−01 | −1.41237661e−01 | −8.11779723e−02 |
| 4.46534574e−01 | 1.12739317e−01 | 3.10060024e−01 | 5.25158525e−01 |
| 1.69363528e−01 | 3.58463428e−03 | 1.03952929e−01 | −2.65282422e−01] |
| [2.21175343e−01 | −2.82094449e−01 | 1.33397624e−01 | 2.75700659e−01 |
| −1.58701092e−01 | −8.01391676e−02 | −7.62490556e−02 | −1.57973140e−01 |
| −1.09277822e−01 | 5.42659014e−02 | −3.30987349e−02 | −4.23061140e−02 |
| −1.12214722e−01 | −2.01958910e−01 | −1.10421829e−01 | −3.41087192e−01 |
| 7.23209381e−02 | 1.25756249e−01 | −4.54652729e−03 | 2.88952589e−01 |

TABLE $W_h^1$-continued

| | | | |
|---|---|---|---|
| −1.31409720e−01 | −3.64091769e−02 | −2.23935202e−01 | 6.68529347e−02 |
| 7.02223331e−02 | 1.28329799e−01 | −2.68437833e−01 | −1.66771665e−01 |
| 3.52742374e−01 | −5.95059507e−02 | 6.10948773e−03 | 1.35423345e−02 |
| 1.09497204e−01 | −4.91756275e−02 | −9.36455056e−02 | −1.27940461e−01 |
| 2.66179562e−01 | 3.23910177e−01 | 1.63966075e−01 | −1.61277637e−01 |
| 1.72048524e−01 | −1.75843254e−01 | 1.44825533e−01 | 3.00369989e−02 |
| 2.78858066e−01 | −5.36385886e−02 | −3.68791372e−02 | 2.37570964e−02 |
| 2.43084803e−01 | 1.37955248e−01 | 2.06440791e−01 | −3.91077213e−02 |
| −9.19078067e−02 | −5.65070331e−01 | −2.78768331e−01 | −3.33642036e−01 |
| −1.39317691e−01 | 1.16877273e−01 | 3.08697671e−01 | −7.85620585e−02 |
| 4.21081483e−01 | −2.73282323e−02 | −1.22035228e−01 | 4.14319813e−01 |
| −3.12762633e−02 | 1.47633033e−03 | 1.15153491e−01 | −1.78984031e−01 |
| 6.67578131e−02 | 1.05372153e−01 | −5.08594094e−03 | 1.39296085e−01 |
| 4.78585988e−01 | 9.75859687e−02 | 1.49749815e−01 | 4.85703088e−02 |
| −2.64394760e−01 | 4.51048017e−02 | 1.41336605e−01 | 3.38131845e−01 |
| 2.43419230e−01 | 1.87470540e−01 | −3.60871106e−01 | 2.00025156e−01 |
| 2.21650228e−01 | −6.60711974e−02 | −1.95359468e−01 | 1.92055240e−01 |
| 2.43739877e−02 | −3.24588001e−01 | −9.64980274e−02 | 1.25831887e−02 |
| 8.59388337e−02 | −1.35323077e−01 | 1.38835544e−02 | 2.74085850e−01 |
| 3.88012342e−02 | 1.21523611e−01 | 2.69878745e−01 | 1.28709793e−01 |
| −1.30595013e−01 | 1.26807421e−01 | 6.85776994e−02 | 8.56653228e−02 |
| −5.00759840e−01 | 2.96744019e−01 | 1.39727145e−01 | −6.66024089e−02 |
| −3.58476251e−01 | 1.78539068e−01 | 1.83251679e−01 | 4.69994321e−02 |
| 1.87135667e−01 | −1.35083441e−02 | 4.95349437e−01 | 2.80377239e−01 |
| −8.50258768e−02 | −1.02492698e−01 | 1.69355676e−01 | −4.22512367e−02 |
| −3.17065306e−02 | 2.78960496e−01 | 9.36679989e−02 | 3.74191016e−01 |
| −1.11623950e−01 | 1.17675990e−01 | 4.72088419e−02 | 1.78118721e−01 |
| 1.22754753e−01 | 1.96788520e−01 | −4.09242898e−01 | 4.15414959e−01 |
| −1.25943646e−01 | −1.42700940e−01 | −5.53486086e−02 | 2.18385637e−01 |
| −5.89391738e−02 | 5.69829606e−02 | −2.52507836e−01 | 3.30142945e−01 |
| −7.92537704e−02 | 2.79318988e−01 | 2.84696172e−04 | 2.60902733e−01 |
| −1.26543075e−01 | −2.00803299e−02 | 7.96681121e−02 | −1.89180955e−01 |
| 7.07256496e−02 | 1.76590189e−01 | 2.34411284e−01 | 1.55297101e−01 |
| 7.87643492e−02 | −2.00740263e−01 | 3.30923833e−02 | 4.67393100e−02 |
| −1.43397242e−01 | −2.40066916e−01 | −1.62627488e−01 | −2.39704400e−01 |
| −1.06858984e−01 | −1.86037257e−01 | 9.88996401e−02 | 2.30246231e−01 |
| 3.29693183e−02 | −8.89323503e−02 | −1.02052197e−03 | 2.01104134e−01 |
| −5.03970623e−02 | 3.28250021e−01 | 3.39976102e−01 | 7.69128427e−02 |
| 1.98269516e−01 | −2.52802938e−01 | −1.68215437e−03 | −2.45923325e−01 |
| −1.22515284e−01 | 1.40643746e−01 | 3.51710886e−01 | 1.83660001e−01 |
| 1.52175352e−01 | −1.22948729e−01 | −8.85744467e−02 | −4.79916148e−02 |
| 1.41184432e−01 | 2.02273980e−01 | −5.63663617e−02 | 2.76289552e−01 |
| −5.03167391e−01 | −2.37190500e−01 | 1.79774523e−01 | 3.17918509e−01 |
| 2.47924447e−01 | −3.87853011e−02 | −1.26119256e−01 | 7.45875239e−02 |
| −3.46305281e−01 | 3.57310772e−02 | 5.63044064e−02 | 6.02440119e−01 |
| −1.91320181e−01 | −1.88709125e−01 | 4.05475914e−01 | 2.80828774e−01 |
| −1.53800547e−01 | −1.47715047e−01 | 2.05772266e−01 | −9.61163081e−03 |
| 1.49117514e−01 | 4.25306201e−01 | −1.15867838e−01 | 1.62970662e−01 |
| 1.12739773e−02 | −1.78939953e−01 | −3.51210237e−02 | 2.18183771e−01 |
| 3.13882351e−01 | 4.72751185e−02 | −1.03554748e−01 | −1.60250708e−01 |
| −8.90705809e−02 | −1.06687009e−01 | −6.39236793e−02 | 1.37327556e−02 |
| −2.63864726e−01 | −1.52146682e−01 | 3.37443769e−01 | 3.59248579e−01 |
| 2.14752108e−01 | −1.26990393e−01 | 5.46391189e−01 | 1.66059226e−01 |
| −1.80703402e−01 | 1.35997191e−01 | 9.36414897e−02 | −7.62742087e−01 |
| −2.63957798e−01 | −1.35078013e−03 | −1.75492764e−01 | −2.16404602e−01 |
| −2.46595770e−01 | −2.17301756e−01 | 5.18960059e−01 | 1.24811575e−01 |
| 1.01252705e−01 | 1.18730165e−01 | 2.55154431e−01 | −1.92815930e−01 |
| −2.36870232e−03 | −1.87207073e−01 | 3.33834112e−01 | −4.10556309e−02 |
| −2.55247861e−01 | 2.13242903e−01 | −6.13794103e−02 | −4.18431964e−03] |
| [−2.18386695e−01 | 4.04705586e−02 | −2.54217029e−01 | 6.28455505e−02 |
| 9.75243226e−02 | 1.28131524e−01 | 5.12941420e−01 | 1.46667540e−01 |
| −1.60397992e−01 | 8.30945596e−02 | 3.29515785e−02 | 2.91163892e−01 |
| −1.58902973e−01 | −2.61527538e−01 | 5.88176847e−02 | −5.52927911e−01 |
| 3.10653567e−01 | 4.64810103e−01 | −1.08824380e−01 | 8.15915838e−02 |
| −1.19946674e−01 | 1.97053283e−01 | −1.21795774e−01 | 4.34538454e−01 |
| 9.96052101e−02 | 2.30690345e−01 | −1.10721402e−01 | −4.21665221e−01 |
| 2.81384028e−02 | −3.40795368e−02 | 5.53883798e−03 | 4.69292626e−02 |
| 2.28407964e−01 | 1.62047461e−01 | 1.09401479e−01 | 1.58859327e−01 |
| 1.09281629e−01 | −2.02663898e−01 | −1.00765072e−01 | 1.46836052e−02 |
| 5.25443554e−01 | −3.95636290e−01 | 1.39532387e−01 | 3.01029831e−01 |
| −3.89645323e−01 | −1.56475138e−01 | −1.83612779e−01 | 3.94309491e−01 |
| −3.60830091e−02 | 2.22229153e−01 | 2.75690019e−01 | −2.99129009e−01 |
| 6.85335845e−02 | −4.17866588e−01 | −2.26888791e−01 | 1.33981988e−01 |
| 2.71098822e−01 | 3.47343057e−01 | 1.92335218e−01 | 7.54925832e−02 |
| −5.96881434e−02 | 1.09258890e−01 | −7.78760985e−02 | −1.45803258e−01 |
| −1.09040113e−02 | 2.74627209e−01 | −4.10849713e−02 | 8.52899812e−03 |
| 2.29052976e−01 | 1.44610867e−01 | 2.06983447e−01 | −3.36358279e−01 |
| 1.43692464e−01 | 1.22476004e−01 | 2.87218899e−01 | 3.52411032e−01 |
| 2.15336666e−01 | 2.52489179e−01 | 3.02600384e−01 | 3.59424770e−01 |
| 1.22665063e−01 | −1.90032661e−01 | −1.69347361e−01 | −1.77180603e−01 |

TABLE $W_h^1$-continued

| | | | |
|---|---|---|---|
| 1.07755162e-01 | 4.85620588e-01 | -2.39546686e-01 | 2.80905180e-02 |
| 6.98855072e-02 | -3.66943270e-01 | -1.69453159e-01 | 1.61525995e-01 |
| -9.28075425e-03 | 8.89756531e-02 | 7.52077103e-02 | 4.98506069e-01 |
| 5.11015989e-02 | 2.07760409e-01 | 3.24229240e-01 | -6.44645318e-02 |
| 4.45863120e-02 | 4.21365589e-01 | 2.93786585e-01 | 2.93869436e-01 |
| -8.34085569e-02 | 7.84682408e-02 | 3.87900800e-01 | 1.30675644e-01 |
| -2.55537659e-01 | 1.87796667e-01 | 5.53021610e-01 | 2.20437959e-01 |
| 2.17184067e-01 | 2.47458011e-01 | 1.91968247e-01 | 4.72219497e-01 |
| 5.21646887e-02 | 5.41082501e-01 | 5.01734205e-02 | 5.98483905e-02 |
| 7.01613426e-02 | 7.79893696e-02 | -3.35776716e-01 | 7.53409714e-02 |
| -1.67989701e-01 | -1.60549968e-01 | -2.11606957e-02 | 1.53184772e-01 |
| 6.74161455e-03 | 9.39528793e-02 | 1.04056589e-01 | 2.19988123e-01 |
| 1.64430365e-01 | 1.04412295e-01 | 1.07630752e-01 | 3.74955624e-01 |
| -3.08249965e-02 | -2.21242919e-03 | 3.95395607e-02 | 2.06221312e-01 |
| 3.74362081e-01 | 2.85774231e-01 | 7.85841420e-03 | 2.90571272e-01 |
| -1.43203199e-01 | -3.90421152e-02 | 6.88671097e-02 | 3.15790147e-01 |
| -3.20854366e-02 | -1.51450545e-01 | -3.19213480e-01 | 1.09534107e-01 |
| 1.05255440e-01 | -1.49695918e-01 | -1.58749059e-01 | -5.90667017e-02 |
| 2.17223793e-01 | -6.15466833e-02 | 2.76888847e-01 | 1.83289990e-01 |
| 2.04049096e-01 | -7.73117468e-02 | 4.06613499e-02 | -1.36006087e-01 |
| 3.05021286e-01 | -1.35116324e-01 | 3.57963651e-01 | 3.83134335e-01 |
| 1.36923697e-02 | 5.02081752e-01 | 2.28833035e-01 | -1.04595805e-02 |
| 4.44376409e-01 | -2.82415599e-01 | -2.75853455e-01 | -1.83696702e-01 |
| 2.27956086e-01 | -6.73436970e-02 | 2.78251141e-01 | 1.57499075e-01 |
| 3.31287459e-02 | -2.07281366e-01 | 9.12361741e-01 | 2.14288443e-01 |
| -4.06868290e-03 | -3.60036008e-02 | -5.52186416e-03 | 4.42063212e-01 |
| -2.43478552e-01 | 8.82440731e-02 | 8.88869464e-02 | 5.70752397e-02 |
| 2.28877649e-01 | 1.47217691e-01 | 2.41773859e-01 | 2.76240170e-01 |
| 5.59480637e-02 | -6.81802770e-03 | -4.43967171e-01 | 1.98728412e-01 |
| -1.88231006e-01 | -1.51877046e-01 | 3.46014857e-01 | 3.07214677e-01 |
| 3.53493989e-01 | -5.27282767e-02 | 5.97174525e-01 | 1.32439196e-01 |
| 1.71822473e-01 | 5.55618882e-01 | 6.53835526e-03 | 6.26028955e-01 |
| 5.41870713e-01 | 1.21108815e-01 | 3.56191874e-01 | 1.45257652e-01 |
| -1.12925179e-01 | -2.12590888e-01 | -6.32951083e-03 | -5.15349686e-01 |
| 3.64152342e-02 | 8.32387432e-02 | 3.17646414e-01 | 6.84561506e-02 |
| 9.34304744e-02 | 2.02301234e-01 | 3.42334509e-01 | 3.68858665e-01 |
| 1.46572843e-01 | -1.16352089e-01 | 4.10490066e-01 | 3.19231778e-01 |
| 1.98003575e-01 | 2.73637980e-01 | 3.25838745e-01 | 1.10368527e-01 |
| -1.09989196e-01 | -1.54389918e-01 | 3.00774164e-02 | -4.47662830e-01 |
| 7.65769407e-02 | -1.28242046e-01 | 6.44254148e-01 | 2.35570014e-01 |
| 2.03256503e-01 | 3.82490337e-01 | 5.60326390e-02 | 4.20844890e-02 |
| -1.71859905e-01 | 2.14376569e-01 | 2.99412489e-01 | -1.32580906e-01 |
| -1.54790476e-01 | -1.71777576e-01 | 5.49395010e-02 | -9.61450953e-03] |
| [-1.48455933e-01 | 2.03280002e-01 | 1.69268344e-02 | 4.39927280e-01 |
| 1.37966320e-01 | 4.25647199e-01 | 2.14036539e-01 | 1.07297152e-02 |
| -9.02399272e-02 | 2.94498414e-01 | -2.51753211e-01 | 1.62282705e-01 |
| -3.41478378e-01 | 2.68647283e-01 | 1.96728796e-01 | -2.97893733e-01 |
| 3.92063744e-02 | 2.02813029e-01 | 1.93072006e-01 | 1.30270422e-01 |
| 1.83786854e-01 | 2.54608572e-01 | 2.52677709e-01 | 5.12904584e-01 |
| -5.09006381e-02 | 9.26161781e-02 | 2.25380838e-01 | 1.69671267e-01 |
| 6.34449303e-01 | -7.95208942e-03 | 2.36008111e-02 | 7.68497884e-02 |
| 3.00345600e-01 | 3.97082753e-02 | 3.63999717e-02 | 4.77068186e-01 |
| -5.44215977e-01 | 5.33379018e-01 | -1.63177118e-01 | 1.18606418e-01 |
| 1.92022964e-01 | 2.03660782e-01 | 5.43685675e-01 | 4.58172441e-01 |
| 2.75418401e-01 | 1.80506557e-01 | 2.56090224e-01 | 2.05486134e-01 |
| 3.11383009e-01 | 1.42920211e-01 | 2.51246393e-01 | -2.70701975e-01 |
| 4.23415154e-01 | -3.50833297e-01 | -2.66942173e-01 | 6.29919469e-02 |
| 1.37284786e-01 | 7.78905272e-01 | 1.15000807e-01 | 5.81446514e-01 |
| 1.98973924e-01 | 3.46276850e-01 | 6.12246506e-02 | -4.44054836e-03 |
| 4.91277277e-02 | 7.04834163e-02 | 1.74338683e-01 | 2.03263834e-01 |
| 2.99957126e-01 | 6.48706615e-01 | 3.21395814e-01 | -4.34617698e-01 |
| 1.10701069e-01 | 3.59102666e-01 | -2.62228489e-01 | 5.46627700e-01 |
| -9.52761248e-02 | 2.18532279e-01 | 3.02262962e-01 | 4.24128890e-01 |
| 6.23579510e-02 | 1.22828886e-01 | 4.74542268e-02 | 4.58219856e-01 |
| 1.42758980e-01 | -5.27017534e-01 | 1.83184057e-01 | 4.11436975e-01 |
| 5.49336553e-01 | 1.16569415e-01 | -1.46690950e-01 | 4.66899484e-01 |
| -1.06804535e-01 | 1.32696465e-01 | -1.91396996e-01 | 7.78256357e-01 |
| 9.20442641e-02 | 3.83384973e-01 | 2.29409620e-01 | 8.26011673e-02 |
| 1.51637718e-01 | 7.14703500e-01 | 5.43270946e-01 | 7.55363032e-02 |
| 1.98950291e-01 | 3.21007818e-01 | 1.98712438e-01 | 3.75035346e-01 |
| 2.30751887e-02 | 1.44214854e-01 | 2.29848847e-01 | -3.03203613e-01 |
| 3.42566431e-01 | 1.13166422e-01 | 1.06504485e-01 | 6.75870240e-01 |
| 9.15653929e-02 | 8.61029774e-02 | 3.65131408e-01 | -1.59909114e-01 |
| 2.78209835e-01 | 2.19008937e-01 | 3.25001627e-01 | 1.82192057e-01 |
| -1.58206746e-02 | 2.27983236e-01 | 2.46546656e-01 | 2.62821466e-01 |
| 1.76975071e-01 | 3.03514242e-01 | -5.42035848e-02 | 1.18894234e-01 |
| 3.83338988e-01 | 7.54413940e-03 | 3.93029749e-01 | 1.90044239e-01 |
| 4.23887037e-02 | 8.43584761e-02 | 2.19057396e-01 | 3.58030766e-01 |
| 8.08811653e-03 | 1.14671640e-01 | 1.39889896e-01 | -7.24985525e-02 |
| 3.10556144e-01 | -1.58170834e-01 | 3.08784723e-01 | 3.66758168e-01 |

TABLE $W_h^1$-continued

| | | | |
|---|---|---|---|
| 3.02708596e-01 | 4.63063084e-02 | -3.02896827e-01 | 5.87310314e-01 |
| -8.56007561e-02 | -1.36057697e-02 | -3.51716548e-01 | 4.40505855e-02 |
| 6.44570440e-02 | -2.05272228e-01 | -2.60018613e-02 | 1.62577569e-01 |
| -5.35213351e-02 | 1.49491668e-01 | 1.11096971e-01 | 4.77618963e-01 |
| -2.13046968e-01 | 2.44788781e-01 | 1.14879929e-01 | 2.02530399e-01 |
| 4.08969492e-01 | 2.29953483e-01 | 3.67318928e-01 | 3.96937966e-01 |
| 5.09187579e-01 | 1.78303480e-01 | 3.63457650e-01 | 7.09792692e-03 |
| 2.28120267e-01 | -5.83561063e-01 | 6.59476399e-01 | 8.97801518e-02 |
| 2.05580480e-02 | -5.89923501e-01 | 6.03959858e-01 | 1.89699486e-01 |
| -2.32219566e-02 | 2.13021427e-01 | 1.68026447e-01 | 1.76737428e-01 |
| -4.19912726e-01 | -3.45407546e-01 | 3.00178260e-01 | 8.84025216e-01 |
| 8.23127404e-02 | 5.12379706e-01 | -4.38404828e-02 | 3.10776144e-01 |
| 4.32790130e-01 | -8.46135318e-02 | -7.23456359e-03 | 6.85282111e-01 |
| -1.30646840e-01 | -2.10343674e-01 | 3.13217342e-01 | 4.14003402e-01 |
| -2.21078426e-01 | 1.50593277e-02 | 4.41617608e-01 | -2.52786670e-02 |
| 3.72292638e-01 | 7.80205011e-01 | 3.48883301e-01 | 4.60020334e-01 |
| 3.22231978e-01 | 6.60109580e-01 | 1.84101984e-01 | -7.92987365e-03 |
| 2.94100996e-02 | 1.14545830e-01 | 3.11238170e-01 | 8.38978514e-02 |
| 9.82460007e-02 | 3.55495989e-01 | 2.16939449e-01 | 8.70640874e-02 |
| -3.95362265e-02 | -1.10242791e-01 | -1.93599805e-01 | -7.45699331e-02 |
| 8.58439729e-02 | -2.92366952e-01 | 6.31264329e-01 | 2.74282008e-01 |
| 2.06328377e-01 | 1.56887382e-01 | 5.05406439e-01 | -2.16964539e-02 |
| 7.61502907e-02 | 2.71371692e-01 | 9.82696563e-02 | -1.45117387e-01 |
| 2.38359272e-01 | -2.75442719e-01 | 4.27853465e-01 | 2.61570960e-01 |
| 2.61673570e-01 | 1.95864841e-01 | 1.78006306e-01 | -1.69549227e-01 |
| 2.43437454e-01 | 2.43550628e-01 | 1.82308480e-01 | 2.32004404e-01 |
| -2.70295650e-01 | 1.90045491e-01 | 3.10501307e-01 | 8.29515457e-02] |
| [6.02103531e-01 | 4.13641006e-01 | 2.98397481e-01 | 5.40968657e-01 |
| 7.07757235e-01 | 3.96988511e-01 | 3.56061384e-02 | 3.76088470e-01 |
| 2.70103574e-01 | 2.95089245e-01 | 3.35874170e-01 | 7.05548584e-01 |
| 5.49454451e-01 | 4.72720325e-01 | 3.60500067e-01 | 5.23631930e-01 |
| 5.21549284e-01 | -1.83336824e-01 | 8.36879387e-02 | 3.59474681e-02 |
| 2.62842625e-01 | -5.55507354e-02 | 1.02298546e-00 | 5.47752082e-01 |
| 8.09969425e-01 | 1.13443315e-00 | 2.32127625e-02 | 4.68346685e-01 |
| 3.15485179e-01 | 2.83094317e-01 | 3.76030594e-01 | 3.24832410e-01 |
| 3.59441042e-01 | -1.09031878e-03 | 4.92532253e-01 | -1.23566903e-01 |
| -1.72547489e-01 | 2.33307898e-01 | 3.04455776e-02 | 3.17545235e-01 |
| 4.40950871e-01 | 6.36615276e-01 | 2.93376893e-01 | 5.37373245e-01 |
| 5.70142746e-01 | 4.64958936e-01 | 3.27961504e-01 | 2.29879797e-01 |
| 5.86804032e-01 | 7.35473156e-01 | 7.21146762e-01 | 7.04641879e-01 |
| 6.52018428e-01 | 3.43014956e-01 | 4.61315215e-01 | 2.46503025e-01 |
| 5.81774473e-01 | -8.20680347e-04 | 2.91425198e-01 | 2.82274425e-01 |
| 1.59178823e-01 | 1.37016445e-01 | 3.59928071e-01 | 3.55770558e-01 |
| 4.44669038e-01 | 1.34864494e-01 | 6.94164097e-01 | 5.00987530e-01 |
| 3.74736845e-01 | -1.22590037e-02 | 6.44281833e-03 | -3.90083253e-01 |
| 3.74226362e-01 | 2.38864943e-01 | 2.47095913e-01 | 1.91941410e-01 |
| 2.76813895e-01 | 1.57529749e-02 | 2.71743804e-01 | 6.49242043e-01 |
| 1.08862019e-00 | 2.79558510e-01 | -5.48494002e-03 | 6.72795892e-01 |
| 2.76182950e-01 | 2.80700862e-01 | 1.78172141e-01 | 1.36800706e-01 |
| 6.18586361e-01 | -1.55800432e-01 | 7.84778953e-01 | 2.29797810e-01 |
| 1.12581976e-01 | 5.42021990e-01 | 4.10241485e-01 | 1.01352906e-00 |
| 1.09286137e-01 | 1.45703316e-01 | 1.87141761e-01 | 5.16288936e-01 |
| 2.92071283e-01 | 4.76673841e-02 | 1.63926795e-01 | 3.59647602e-01 |
| 3.09092309e-02 | 3.79414946e-01 | 4.36146557e-01 | 1.06477928e-00 |
| 2.93324143e-01 | 3.84651393e-01 | 2.47674048e-01 | 5.47222733e-01 |
| 3.48200947e-01 | 3.56044412e-01 | 4.92892981e-01 | 3.65487576e-01 |
| 8.12171102e-01 | 3.97429615e-01 | 6.05715334e-01 | 1.24078296e-01 |
| 3.60556096e-01 | 7.55339026e-02 | 6.69362172e-02 | 1.39597699e-01 |
| 4.79754090e-01 | 3.98813307e-01 | 2.34797686e-01 | 1.04503357e-00 |
| 7.03328252e-02 | 3.98916602e-01 | -1.76154703e-01 | 3.45797509e-01 |
| 2.54900545e-01 | 3.89359534e-01 | 1.04027689e-00 | 5.25367260e-01 |
| 3.49348783e-01 | 9.70373273e-01 | 2.75299728e-01 | 3.58764142e-01 |
| 3.05848420e-01 | 2.96970904e-01 | 4.95137781e-01 | 6.05747223e-01 |
| 1.69203773e-01 | 1.84727892e-01 | 2.18353182e-01 | 6.00969195e-01 |
| 9.56316769e-01 | 4.22220707e-01 | 6.21254683e-01 | 1.62249804e-01 |
| 1.01151653e-01 | 1.22630551e-01 | 1.14678037e-00 | 2.11375758e-01 |
| 2.64985591e-01 | 6.36837125e-01 | 2.38082796e-01 | 8.36575329e-01 |
| 6.78728342e-01 | 3.58239889e-01 | 7.50486851e-01 | 4.00079787e-01 |
| 4.94612455e-01 | 2.35534608e-01 | 6.65366292e-01 | 4.62125093e-01 |
| 4.86475557e-01 | 2.74170756e-01 | 2.90903777e-01 | 2.48760819e-01 |
| 8.26492429e-01 | 4.56789225e-01 | 5.68431497e-01 | 2.29862824e-01 |
| 6.25070512e-01 | -1.13708250e-01 | 4.34094638e-01 | 2.81912744e-01 |
| 5.20526290e-01 | 6.10434830e-01 | 1.99921399e-01 | 2.45032087e-01 |
| 2.33324215e-01 | -3.49578559e-02 | -8.26695710e-02 | 3.64218086e-01 |
| 5.63006341e-01 | 3.28854561e-01 | 1.46280304e-01 | 2.19120637e-01 |
| 2.43028715e-01 | 2.05831528e-01 | 3.35221589e-01 | 2.87225157e-01 |
| 3.02834809e-01 | 5.24079382e-01 | 4.21876729e-01 | 2.53259242e-01 |
| 1.14065695e-00 | 4.05453332e-02 | 5.06398439e-01 | -6.77842945e-02 |
| 6.69968575e-02 | 2.91712373e-01 | 4.60193425e-01 | 3.13593894e-01 |
| 4.64514345e-01 | 9.04256523e-01 | 6.09186649e-01 | 5.94448268e-01 |

TABLE $W_h^1$-continued

| | | | |
|---|---|---|---|
| 8.74031365e-01 | 6.11279070e-01 | 3.62352520e-01 | 4.24569696e-01 |
| 5.38036674e-02 | 7.18041956e-01 | 5.29341877e-01 | -1.92630276e-01 |
| 4.31013346e-01 | 5.89073181e-01 | 2.50361890e-01 | -7.13897776e-03 |
| 1.91760793e-01 | 3.62851918e-01 | 4.54681963e-01 | 8.96503389e-01 |
| 4.44502860e-01 | 4.01681393e-01 | 7.75485277e-01 | 3.28865469e-01 |
| 6.85152858e-02 | 2.20017582e-01 | 8.00515294e-01 | 7.38743424e-01 |
| 7.00274825e-01 | 5.40827930e-01 | 1.94905788e-01 | 3.26840699e-01 |
| 3.24208319e-01 | 8.82760048e-01 | 3.98211569e-01 | 1.84720859e-01 |
| 7.76339531e-01 | 8.69001389e-01 | -3.89265008e-02 | 1.46295235e-01 |
| 6.21346593e-01 | -3.26057039e-02 | 6.05224907e-01 | 8.18302155e-01 |
| -2.80748568e-02 | 8.79179910e-02 | 4.24658239e-01 | 6.42481446e-01] |
| [1.87749609e-01 | -6.08759224e-02 | 3.69898289e-01 | 4.41004425e-01 |
| 1.11837737e-01 | 9.02250350e-01 | 2.33142167e-01 | 4.45726186e-01 |
| 2.45323077e-01 | 4.05327290e-01 | 3.82791698e-01 | 1.28215432e-01 |
| 6.08391725e-02 | 3.50656241e-01 | -2.38216016e-02 | 2.16197029e-01 |
| 1.68638185e-01 | 4.75805908e-01 | -2.31681570e-01 | 5.10982759e-02 |
| 9.24571455e-02 | -2.97248550e-01 | 3.63288045e-01 | 1.03200853e-00 |
| 3.69098842e-01 | 6.55704737e-01 | 3.91122967e-01 | -8.81860778e-02 |
| 2.43289337e-01 | 1.66302085e-01 | 2.23931894e-01 | 2.55303025e-01 |
| 4.98964727e-01 | 5.21269977e-01 | 3.53261054e-01 | 1.92832381e-01 |
| 1.23536006e-01 | 3.10173780e-01 | 1.12680018e-01 | 8.01823735e-01 |
| 5.02920151e-01 | 8.20592344e-01 | 4.02775556e-01 | 3.64604235e-01 |
| 2.99879342e-01 | 2.79865801e-01 | 1.22373432e-01 | 3.54181200e-01 |
| 4.41371500e-01 | 3.80982697e-01 | 4.28416401e-01 | 2.83663154e-01 |
| 3.28088552e-01 | 4.17017303e-02 | 5.27049422e-01 | 4.27362323e-01 |
| 5.11628747e-01 | 4.89693582e-01 | 4.27865326e-01 | 1.74067631e-01 |
| 5.83663702e-01 | 7.16995478e-01 | 3.25490534e-01 | -1.31884310e-02 |
| 2.07559615e-02 | 9.43102166e-02 | -8.81827474e-02 | 4.73700836e-02 |
| 1.01031877e-01 | 1.07612293e-02 | 5.34279831e-01 | -5.67762554e-01 |
| 3.14166158e-01 | 4.55133498e-01 | 4.07493591e-01 | 4.11782146e-01 |
| 4.02757049e-01 | 7.29988217e-01 | 3.26445609e-01 | 7.78154194e-01 |
| 3.17469418e-01 | 4.60424833e-02 | -2.46370789e-02 | 3.35985541e-01 |
| 3.97625208e-01 | 1.65119410e-01 | 1.28502443e-01 | 5.53963900e-01 |
| 8.52718115e-01 | -4.93533820e-01 | -5.84468208e-02 | 4.48744185e-02 |
| 7.55597472e-01 | 6.71923220e-01 | 4.69973505e-01 | 5.43996155e-01 |
| 3.55069786e-01 | -1.02165371e-01 | 1.70745537e-01 | 4.28411961e-01 |
| 3.54488522e-01 | 8.42608333e-01 | 3.22691023e-01 | 6.05066530e-02 |
| 4.35681343e-01 | 3.38936687e-01 | 3.12269807e-01 | 2.60181069e-01 |
| 5.08956552e-01 | 3.36929560e-01 | 5.92513859e-01 | 1.72318667e-01 |
| 6.08527184e-01 | 2.36269951e-01 | 3.83701354e-01 | 4.80425328e-01 |
| 2.47260526e-01 | 1.05039883e-00 | 2.58700818e-01 | 2.68665016e-01 |
| 3.82229984e-01 | 6.03381336e-01 | 2.10509837e-01 | 9.07065645e-02 |
| -2.37343851e-02 | 2.54032761e-01 | 8.17428753e-02 | 8.20410192e-01 |
| 9.68289793e-01 | 3.19841802e-01 | 1.69996217e-01 | 6.83278561e-01 |
| 8.49728882e-01 | 2.42443368e-01 | 3.05017740e-01 | -9.42963287e-02 |
| 6.11100018e-01 | -1.16652818e-01 | 1.93435431e-01 | 5.60934961e-01 |
| 6.81254268e-01 | 2.70424634e-01 | 2.61631280e-01 | 1.77039638e-01 |
| 1.03131860e-01 | 2.99966395e-01 | 5.55834234e-01 | 3.70351762e-01 |
| 1.22060962e-01 | 5.21384001e-01 | 1.50897428e-01 | 6.34552240e-01 |
| 3.47526282e-01 | 4.27771717e-01 | 5.14945030e-01 | 4.31236982e-01 |
| 2.01993942e-01 | -8.96399245e-02 | -5.22496514e-02 | 2.34760880e-01 |
| 2.10328385e-01 | 1.12207688e-01 | 3.39285493e-01 | 1.95095718e-01 |
| 2.90556431e-01 | 1.18977621e-01 | 2.43695319e-01 | 3.51831496e-01 |
| -2.15253476e-02 | 6.33309066e-01 | 4.66783613e-01 | 3.62227231e-01 |
| 8.04767251e-01 | 5.95530808e-01 | 3.89117032e-01 | 4.73905921e-01 |
| 2.07190394e-01 | -2.55967110e-01 | -8.17623734e-03 | 7.85362720e-02 |
| 6.48657799e-01 | 4.60339248e-01 | 4.28468406e-01 | 4.57061470e-01 |
| 4.22850877e-01 | 2.55660802e-01 | 8.56190175e-02 | 4.44224983e-01 |
| 6.51241839e-02 | 2.46535942e-01 | 6.44846559e-01 | 8.03230882e-01 |
| 3.40127200e-01 | 3.82923990e-01 | 4.21450227e-01 | 5.08597255e-01 |
| 1.15782045e-01 | 2.90472925e-01 | 2.08160058e-01 | 5.29565692e-01 |
| 1.88138522e-02 | 1.05315797e-01 | 4.14362997e-01 | 3.72699529e-01 |
| 7.60616437e-01 | -6.45114928e-02 | 2.59501249e-01 | 4.96538132e-01 |
| 4.61480677e-01 | 3.78252268e-01 | 2.80072957e-01 | 7.17529356e-01 |
| 2.71797270e-01 | 4.96514201e-01 | -6.04180992e-03 | 1.65864050e-01 |
| -1.88640535e-01 | 1.99255139e-01 | 5.20302832e-01 | -1.32257015e-01 |
| 9.63008627e-01 | 4.90757614e-01 | 1.98515467e-01 | 1.26835942e-01 |
| -6.99839145e-02 | 1.77365437e-01 | 9.94491935e-01 | 4.03387308e-01 |
| 1.83008328e-01 | 6.02209210e-01 | 5.13027430e-01 | 3.79325449e-01 |
| 3.15912634e-01 | -1.14080403e-02 | 5.64842463e-01 | 8.62710834e-01 |
| 7.21071780e-01 | 2.34790385e-01 | 1.23491026e-01 | 2.58886814e-01 |
| 1.72533467e-01 | 3.30691159e-01 | 4.44591820e-01 | 1.96644232e-01 |
| 3.89446974e-01 | -2.41982061e-02 | 4.91194189e-01 | -2.03084876e-03 |
| 6.96799815e-01 | 6.06368124e-01 | 2.39784941e-01 | 1.45160034e-01 |
| -2.61959076e-02 | 6.75799668e-01 | 4.26315516e-01 | 1.54556438e-01] |
| [-5.59473753e-01 | 3.81591171e-01 | 6.85201168e-01 | 3.06670606e-01 |
| 6.40326083e-01 | 7.49772668e-01 | 2.67496765e-01 | 4.68168557e-01 |
| 4.00171280e-02 | -5.43674469e-01 | 4.36478823e-01 | 4.82989877e-01 |
| 8.34557176e-01 | -4.52312261e-01 | 2.85978019e-01 | 1.04362559e-00 |
| 8.04096103e-01 | -3.32636029e-01 | -3.51161897e-01 | 4.27780569e-01 |

TABLE $W_h^1$-continued

| | | | |
|---|---|---|---|
| 2.25508377e−01 | −1.05997242e−01 | 2.99389333e−01 | 4.40547109e−01 |
| −4.36051697e−01 | 1.00132629e−01 | 2.23066285e−01 | 4.75757927e−01 |
| 3.24585915e−01 | 1.68733463e−01 | −7.09729195e−01 | 3.33402783e−01 |
| −1.76164731e−01 | 2.51271427e−01 | 6.54326618e−01 | 5.00809610e−01 |
| 4.67663765e−01 | −2.48486593e−01 | −8.61216784e−02 | −2.20392048e−01 |
| −1.54428594e−02 | 1.14445508e−00 | 3.06058913e−01 | −9.94123742e−02 |
| 3.57014716e−01 | 1.41108915e−01 | 5.43170154e−01 | −1.23094872e−01 |
| −6.56898990e−02 | 2.75632143e−01 | −2.51506060e−01 | 1.77079722e−01 |
| 2.58428365e−01 | 1.62303641e−01 | 9.18432951e−01 | −3.55757087e−01 |
| 3.25335979e−01 | 2.17248887e−01 | −1.72258392e−01 | −3.85501981e−01 |
| −2.59176552e−01 | −6.66282922e−02 | 2.34798044e−01 | −2.60143310e−01 |
| 1.56569272e−01 | −2.36753464e−01 | 6.11076020e−02 | −4.52378988e−01 |
| −3.91434617e−02 | −5.92372000e−02 | 8.27429533e−01 | 1.28955081e−01 |
| −1.63570851e−01 | 9.94864553e−02 | 8.65857303e−02 | −9.67126012e−01 |
| 4.99715954e−02 | 3.66840601e−01 | 1.94763078e−03 | 1.04952447e−01 |
| 7.82214940e−01 | −2.61635125e−01 | 1.07419670e−01 | 7.79165551e−02 |
| 3.52592021e−01 | 3.90608758e−01 | −3.53904903e−01 | 7.06529081e−01 |
| −2.67332375e−01 | −1.74343571e−01 | 6.36982799e−01 | 1.43779382e−01 |
| −1.81324512e−01 | 1.68881938e−01 | 6.69979930e−01 | 1.15927912e−01 |
| 1.73438460e−01 | 3.63967597e−01 | −3.85125428e−01 | 3.95516485e−01 |
| 1.83684364e−01 | 1.04871839e−01 | 7.19977200e−01 | −6.21940851e−01 |
| 4.93908256e−01 | 3.49332124e−01 | 9.10052285e−02 | 1.00265682e−00 |
| −2.12542087e−01 | 6.08147355e−03 | −5.59856035e−02 | 2.97475070e−01 |
| −2.89332792e−02 | 1.47807017e−01 | 3.84862542e−01 | 9.32786018e−02 |
| −1.44201010e−01 | 5.24475336e−01 | 2.85252512e−01 | 2.34591156e−01 |
| 1.01361245e−01 | 3.47771972e−01 | 2.65840709e−01 | −2.87237763e−01 |
| −3.66516382e−01 | −1.86415553e−01 | 2.30017841e−01 | 5.92612088e−01 |
| −2.41317227e−01 | 3.94386470e−01 | 1.42750472e−01 | −2.60363966e−01 |
| 1.94445372e−01 | 1.01482637e−01 | 3.71369481e−01 | 4.61187869e−01 |
| 5.85224330e−01 | 1.01364112e−00 | −1.33715734e−01 | −9.86830071e−02 |
| 1.73086040e−02 | 2.31682703e−01 | 4.41824257e−01 | 7.75768876e−01 |
| 5.63837826e−01 | 3.39331239e−01 | 2.86161423e−01 | 2.87743807e−01 |
| 6.79068744e−01 | 4.83245440e−01 | 3.75199407e−01 | −1.72727063e−01 |
| 2.67436773e−01 | 9.01229456e−02 | 6.70475781e−01 | 3.63332093e−01 |
| −7.74396807e−02 | −1.45018687e−02 | 4.16746642e−03 | 4.02991772e−01 |
| 4.64228183e−01 | −1.31838918e−01 | 7.35917568e−01 | 5.12324274e−01 |
| 5.68831384e−01 | −4.54989880e−01 | 1.26822615e−00 | 1.15887724e−01 |
| −2.39734650e−02 | −1.92642152e−01 | −3.18502933e−01 | −7.73285627e−01 |
| 5.04603446e−01 | 3.73860002e−01 | −3.75251561e−01 | 1.12467907e−01 |
| 3.43013525e−01 | 1.34758666e−01 | 3.38934720e−01 | 1.17284812e−01 |
| 3.36235374e−01 | −5.11443056e−02 | 4.12721425e−01 | 2.07611695e−01 |
| 1.14084229e−01 | 4.52380627e−01 | −1.02597056e−02 | 1.83468208e−01 |
| 8.75124156e−01 | 1.37603870e−02 | 3.80751878e−01 | 4.14708793e−01 |
| 4.86183465e−02 | 6.72793090e−01 | −5.80335706e−02 | 1.78255185e−01 |
| 1.46458885e−02 | 7.05904484e−01 | 4.58441317e−01 | −2.90323436e−01 |
| 1.49627650e−00 | 5.34290038e−02 | −6.70973659e−02 | 4.16603297e−01 |
| 1.55326575e−01 | 2.99888253e−01 | 5.12486935e−01 | 4.65494663e−01 |
| −2.44223271e−02 | −5.48467517e−01 | 4.02133822e−01 | 4.58499879e−01 |
| −5.41622937e−01 | 9.22542453e−01 | −1.53329372e−01 | −5.35299540e−01 |
| 3.16646993e−01 | 3.28384757e−01 | −5.02281666e−01 | −6.12424970e−01 |
| −5.97067550e−02 | −2.49560967e−01 | −1.48481220e−01 | −7.14690378e−03 |
| −3.71201605e−01 | −3.67345661e−01 | 1.66527256e−01 | 4.43347842e−01 |
| 1.62466452e−01 | 6.58775151e−01 | 4.22746241e−01 | 1.16735145e−01 |
| 1.94762677e−01 | 3.59925888e−02 | 3.97685915e−01 | 4.00772095e−01 |
| 4.23214763e−01 | 5.43789327e−01 | 4.90405232e−01 | 7.03383029e−01 |
| 6.65973127e−02 | 8.18199217e−01 | −1.16086509e−02 | 5.34851909e−01 |
| −3.69490266e−01 | −1.02483295e−01 | −9.73433256e−02 | −1.71440601e−01 |
| −2.94216901e−01 | 3.45393091e−01 | −6.93264976e−02 | 1.31531334e−00 |
| −2.79750787e−02 | 2.11713940e−01 | 5.28380275e−01 | 5.94018996e−01] |
| [1.29305527e−01 | 1.96200967e−01 | −1.98864639e−01 | −7.48397261e−02 |
| 1.91891957e−02 | 1.15940988e−01 | 9.42213610e−02 | 1.79669946e−01 |
| 7.77633265e−02 | 2.99954806e−02 | 2.06567813e−03 | 2.99799442e−01 |
| 3.10047299e−01 | 3.40996504e−01 | −3.10046189e−02 | 2.89905250e−01 |
| 3.00535768e−01 | −6.73683137e−02 | 1.72398090e−01 | 1.92453578e−01 |
| −7.37421289e−02 | 8.66372809e−02 | −2.75520593e−01 | −3.69953807e−03 |
| 1.52008131e−01 | 2.35198468e−01 | 1.36152646e−02 | 2.23761126e−01 |
| −5.32006957e−02 | −2.65393347e−01 | 1.12403199e−01 | 1.25024736e−01 |
| −7.84685314e−02 | −7.38652423e−02 | 2.12475374e−01 | −6.49282187e−02 |
| −6.33060187e−02 | 2.61842739e−02 | 5.04956007e−01 | −2.05862939e−01 |
| 6.79376945e−02 | 2.05055356e−01 | −2.51271762e−03 | 6.38919175e−02 |
| −1.01514431e−02 | 6.95421398e−02 | 1.95500523e−01 | 1.53116912e−01 |
| −8.16928130e−03 | −4.90070470e−02 | 1.31100327e−01 | −6.37427568e−02 |
| 8.82300735e−02 | 5.15766535e−03 | −1.16972566e−01 | 2.20644712e−01 |
| 3.67964596e−01 | 3.73645663e−01 | −1.12495892e−01 | −5.23027107e−02 |
| −1.72203049e−01 | 9.55955908e−02 | 2.52100646e−01 | −1.41174525e−01 |
| −4.19735350e−02 | −2.17788607e−01 | −5.06551471e−03 | 2.94129968e−01 |
| 2.58983433e−01 | 1.37736052e−01 | −1.54538631e−01 | 2.19347641e−01 |
| 1.26731098e−01 | −8.31771940e−02 | 4.45423245e−01 | 2.09940419e−01 |
| −7.51302764e−02 | 2.23432295e−02 | 2.31124327e−01 | 2.28290349e−01 |
| −4.00281232e−03 | 2.54891545e−01 | 1.66548133e−01 | 3.97013873e−01 |

TABLE $W_h^1$-continued

| | | | |
|---|---|---|---|
| −1.05086029e−01 | −7.78298080e−02 | 2.46089339e−01 | 2.30390534e−01 |
| 1.00112624e−01 | 1.63861901e−01 | 1.52812615e−01 | 1.85538888e−01 |
| −1.18602261e−01 | 2.10594565e−01 | −5.62255532e−02 | −1.01843894e−01 |
| −1.48998499e−01 | 3.21335852e−01 | 3.30837518e−01 | 4.23653036e−01 |
| −2.36483123e−02 | 1.89623237e−02 | −4.29325253e−02 | 1.51755154e−01 |
| 1.42547637e−01 | 3.23092937e−02 | 1.27371162e−01 | 3.66132706e−02 |
| 5.28610125e−02 | 5.37141114e−02 | 2.62401104e−01 | −3.12336665e−02 |
| 4.20603365e−01 | −2.15781331e−01 | 1.50482342e−01 | 3.17674249e−01 |
| 1.74737945e−01 | 8.56397822e−02 | 1.62282363e−02 | −1.93694830e−01 |
| −9.01997276e−03 | −5.26894182e−02 | −1.96489364e−01 | −6.28211945e−02 |
| 1.28860727e−01 | 1.35492861e−01 | −6.28112853e−02 | 2.73379628e−02 |
| −3.92365968e−03 | 1.09947488e−01 | 7.74030238e−02 | −9.33093578e−02 |
| 1.94310114e−01 | 1.16231039e−01 | 5.03912508e−02 | 9.39576030e−02 |
| 2.45836914e−01 | 8.85751173e−02 | 4.53567393e−02 | −1.33133546e−01 |
| 2.83739273e−03 | 1.33820936e−01 | 3.46711697e−03 | 1.17539704e−01 |
| 9.70216021e−02 | 1.84310853e−01 | −1.09402649e−02 | 1.94974780e−01 |
| 1.80237174e−00 | 9.69070271e−02 | −6.85084537e−02 | 2.30660722e−01 |
| 3.34301707e−03 | 2.20946431e−01 | 1.47575244e−01 | −1.59131810e−01 |
| 6.18173033e−02 | −1.58453748e−01 | 2.20290750e−01 | −7.01430291e−02 |
| 1.56309903e−01 | 2.70752721e−02 | 2.10878253e−01 | −6.45098910e−02 |
| 2.43545458e−01 | 3.84581953e−01 | 1.80004328e−01 | −1.51732815e−02 |
| 4.42516245e−02 | −2.25738034e−01 | 9.06782746e−02 | 4.16090578e−01 |
| −1.36177734e−01 | 2.13616610e−01 | 2.61383325e−01 | 5.66691279e−01 |
| 4.10725653e−01 | 8.62549692e−02 | 2.28910178e−01 | 1.44202653e−02 |
| 7.17181191e−02 | 9.69426520e−03 | 1.60294339e−01 | 6.65722706e−02 |
| 2.01743335e−01 | −4.84107435e−02 | −3.63900095e−01 | 2.06150055e−01 |
| 3.79045308e−01 | 7.35813603e−02 | 3.98561843e−02 | 2.26380125e−01 |
| 1.66724011e−01 | −3.01231116e−01 | 3.25418830e−01 | 6.30726293e−02 |
| 1.48400351e−01 | −2.83694088e−01 | 3.54629546e−01 | 3.62919509e−01 |
| 3.11729401e−01 | 2.56544918e−01 | 5.56031615e−02 | 2.81754881e−01 |
| −3.90333161e−02 | −1.08981751e−01 | −1.18991762e−01 | −1.00309081e−01 |
| −3.42288874e−02 | −2.64294118e−01 | 4.95974123e−02 | 7.64782652e−02 |
| 1.89725667e−01 | 4.11387160e−02 | 1.62077546e−01 | 5.50097525e−01 |
| −3.85689318e−01 | −9.73273218e−02 | 3.92251879e−01 | 2.61298001e−01 |
| −6.21827058e−02 | 1.53275013e−01 | −7.86547456e−03 | 4.27631885e−01 |
| 3.19507807e−01 | 1.43678859e−01 | 2.98217144e−02 | 1.27860785e−01 |
| 2.49618873e−01 | 1.98883843e−02 | −2.11946309e−01 | 3.08268350e−02 |
| 9.33320671e−02 | 1.76952407e−02 | −1.25745684e−02 | 1.37482658e−01 |
| 3.40571105e−01 | 2.30545059e−01 | 3.19224894e−01 | −1.20194755e−01 |
| 3.38045657e−02 | 1.84466138e−01 | 4.83567774e−01 | 2.67462552e−01 |
| −4.74143267e−01 | 3.39038558e−02 | −3.15265693e−02 | 2.08263338e−01 |
| 3.04736316e−01 | −4.44300383e−01 | −6.01506941e−01 | 1.17797397e−01 |
| 5.16978323e−01 | −2.85217613e−01 | 2.63815999e−01 | −5.19809201e−02] |
| [3.54502082e−01 | 6.35857761e−01 | 9.00381684e−01 | 4.50723797e−01 |
| 1.11031771e−00 | 1.29189983e−01 | 5.23140907e−01 | 1.04985261e−00 |
| 8.07261884e−01 | 9.69958842e−01 | 1.25167310e−01 | 1.60515869e−00 |
| 7.72700071e−01 | 6.77351236e−01 | 8.21291983e−01 | 8.17542613e−01 |
| 1.84940350e−00 | −8.37582171e−01 | −2.78195560e−01 | 4.26360756e−01 |
| 1.70481786e−01 | 2.67933607e−01 | 6.50883853e−01 | 1.10087836e−00 |
| 1.17312539e−00 | 1.05234134e−00 | 5.72980382e−01 | 2.68022692e−01 |
| 4.50543135e−01 | 5.47657728e−01 | 1.45477682e−01 | 4.11831260e−01 |
| 2.21903518e−01 | 2.42770270e−01 | 1.13086772e−00 | 2.35168889e−01 |
| 1.35443091e−01 | 5.78337252e−01 | 6.30191326e−01 | 1.32819009e−00 |
| 8.50764215e−01 | 6.91832662e−01 | 1.29105911e−01 | 1.70122205e−00 |
| 1.76802206e−00 | 5.31118095e−01 | 1.31800473e−00 | 1.10333526e−00 |
| 3.76778334e−01 | 6.21342003e−01 | 3.68222386e−01 | 8.97246182e−01 |
| 7.57186636e−02 | 5.66188574e−01 | 4.18710351e−01 | 6.38025880e−01 |
| 1.04609501e−00 | −9.41643938e−02 | 8.54438543e−02 | 6.99636340e−02 |
| 1.22052938e−01 | 4.08146352e−01 | 9.66669858e−01 | 6.35323524e−01 |
| −2.58074731e−01 | 3.50650162e−01 | 6.44704700e−01 | 8.41369212e−01 |
| 7.06843674e−01 | −4.06588376e−01 | 4.92753297e−01 | −5.04597366e−01 |
| 9.97203112e−01 | 2.11451486e−01 | 5.34530044e−01 | 6.46970719e−02 |
| 6.37560546e−01 | 3.82416934e−01 | 7.57227302e−01 | 6.15357161e−01 |
| 1.04411709e−00 | 6.00867927e−01 | 2.87649810e−01 | 8.13331962e−01 |
| 6.96239173e−01 | −1.95616633e−01 | 5.83489716e−01 | 8.41723263e−01 |
| 8.17040861e−01 | −3.57327849e−01 | 6.99027479e−01 | 2.49496564e−01 |
| 7.24953353e−01 | 9.61029768e−01 | 6.83063328e−01 | 3.75540555e−01 |
| 5.92620254e−01 | 3.96965206e−01 | −1.14049636e−01 | 9.60170031e−01 |
| 6.26444280e−01 | 2.77871221e−01 | 2.36199573e−01 | 3.07962775e−01 |
| 2.37482831e−01 | 3.66770387e−01 | 4.04857516e−01 | 9.42891598e−01 |
| 5.96805990e−01 | 6.98785663e−01 | 4.50601697e−01 | 1.03610957e−00 |
| 4.87097055e−01 | 6.58132792e−01 | 8.51849794e−01 | 2.23724574e−01 |
| 1.41887844e−00 | 1.37917891e−01 | 4.51695770e−01 | −2.93669611e−01 |
| 3.41765821e−01 | 7.63583243e−01 | 1.41707152e−01 | −2.11498868e−02 |
| 4.76139396e−01 | 8.03326249e−01 | 4.66930211e−01 | 6.48397028e−01 |
| 4.25956339e−01 | 2.74500281e−01 | −5.56935012e−01 | 5.24716258e−01 |
| 6.99987292e−01 | 9.63948965e−01 | 7.59450793e−01 | 4.42780912e−01 |
| 8.24580371e−01 | 7.50103772e−01 | 1.39223969e−00 | 5.47915161e−01 |
| −3.20825130e−02 | 2.61442214e−01 | 1.67784154e−01 | 8.65234971e−01 |
| 7.78712571e−01 | 6.76005721e−01 | 9.59999785e−02 | 5.96010268e−01 |

TABLE $W_h^1$-continued

| | | | |
|---|---|---|---|
| 8.18942964e−01 | 8.16779613e−01 | 8.88283610e−01 | 4.73726690e−01 |
| 5.14382422e−01 | 3.34565014e−01 | 1.34952319e−00 | 2.09841028e−01 |
| −1.04289047e−01 | 2.35512808e−01 | 2.33870849e−01 | 5.34333527e−01 |
| 1.46663404e−00 | 7.43052661e−01 | 6.92415118e−01 | 6.16797984e−01 |
| 6.70465708e−01 | 8.89452636e−01 | 8.88520420e−01 | −9.43001825e−03 |
| 4.07681584e−01 | 5.36569655e−01 | −3.02658468e−01 | 9.18062270e−01 |
| 2.97458947e−01 | 7.59348273e−01 | 1.11403680e−00 | −2.47729465e−01 |
| 1.15382814e−00 | −2.27457449e−01 | 5.74937284e−01 | 4.84680563e−01 |
| 1.08848788e−01 | 6.24844730e−01 | 1.97321564e−01 | 8.34682822e−01 |
| 1.12841058e−00 | 1.27987310e−01 | −5.82275689e−01 | 7.40391910e−01 |
| 4.85222578e−01 | 7.95852184e−01 | 6.32871866e−01 | 2.99630821e−01 |
| 6.17539763e−01 | 1.82741582e−01 | 2.88112581e−01 | −4.08667624e−01 |
| 2.97948450e−01 | 7.51134038e−01 | 5.91941714e−01 | −4.46122997e−02 |
| 8.67316961e−01 | 7.02049136e−01 | 7.85961211e−01 | −1.35097265e−01 |
| −4.75533754e−02 | 7.50354469e−01 | 3.38044852e−01 | 3.28738838e−01 |
| 6.35809064e−01 | −5.98474257e−02 | 9.47518766e−01 | 6.81364775e−01 |
| 5.99278510e−01 | 1.01983094e−00 | 1.10019557e−01 | 4.79343563e−01 |
| 8.24977815e−01 | 3.44773561e−01 | 9.60333645e−01 | −6.76809698e−02 |
| 9.00286257e−01 | 1.00715142e−02 | 4.89881068e−01 | 4.84179169e−01 |
| 3.21985573e−01 | 8.62696886e−01 | 3.02993476e−01 | 1.67736316e−00 |
| 5.91813743e−01 | 1.03619754e−00 | 5.95287621e−01 | 3.63098234e−01 |
| 8.12637508e−01 | 1.68158576e−01 | 1.37124634e−00 | 9.73116398e−01 |
| 6.01027429e−01 | 1.17340517e−00 | 1.40780464e−01 | 8.05826306e−01 |
| 6.22691512e−01 | 1.05505741e−00 | 6.09269679e−01 | 1.25143540e−00 |
| 8.57696056e−01 | 2.38667220e−01 | 7.13650584e−01 | 8.55882049e−01 |
| 1.16315186e−00 | 3.36592644e−01 | 6.71233833e−01 | 1.08054900e−00 |
| 5.03805518e−01 | 7.09931731e−01 | 8.95413518e−01 | 5.10396957e−01] |
| [−7.48629346e−02 | 4.88081247e−01 | −5.54831177e−02 | 2.96455830e−01 |
| 4.54946876e−01 | 1.63693681e−01 | 2.87378132e−01 | −7.84686357e−02 |
| −2.20257506e−01 | 2.23135188e−01 | −2.13462651e−01 | 3.65545690e−01 |
| 7.75738135e−02 | 2.69620437e−02 | −1.65222079e−01 | 2.66064346e−01 |
| 4.23629023e−02 | 9.39970240e−02 | 5.17997742e−01 | 1.52276382e−01 |
| 3.33895177e−01 | 1.12716839e−01 | 4.86035228e−01 | 1.32111177e−01 |
| 4.60516393e−01 | −1.28236860e−01 | 1.68870226e−01 | 4.41960320e−01 |
| 3.38740736e−01 | −1.69426610e−03 | 3.66646558e−01 | 1.58838913e−01 |
| 3.89371812e−02 | −1.32210450e−02 | 4.81819659e−01 | 6.99038386e−01 |
| 3.17751348e−01 | −3.45883123e−03 | 9.81432348e−02 | 1.13930106e−01 |
| −2.35765949e−01 | −6.79850280e−02 | −3.44967306e−01 | 1.10936928e−00 |
| −1.50902078e−01 | −1.12488694e−01 | 3.38673025e−01 | 2.78351694e−01 |
| −2.21191198e−01 | 1.40360132e−01 | 9.34012048e−03 | −1.78588763e−01 |
| −3.19121540e−01 | 3.42829108e−01 | 2.88043380e−01 | 1.06425568e−01 |
| −1.82053924e−01 | 2.74643242e−01 | 4.47939366e−01 | 2.90698707e−01 |
| 1.16569549e−01 | 1.59706905e−01 | 3.67258132e−01 | 1.94295228e−01 |
| 9.82041508e−02 | 2.33960915e−02 | 2.18748063e−01 | 4.79768872e−01 |
| 1.83894947e−01 | 7.25845546e−02 | 3.27936202e−01 | −3.28102186e−02 |
| −1.86531708e−01 | 2.58057296e−01 | 5.54261655e−02 | 1.43204063e−01 |
| 1.69158340e−01 | 1.98752046e−01 | 5.55096194e−02 | 2.36788169e−01 |
| 6.39410138e−01 | 3.21021497e−01 | −2.05331326e−01 | 3.48594606e−01 |
| 3.23325157e−01 | −2.95820296e−01 | 1.04647890e−01 | 3.10019739e−02 |
| −2.64565378e−01 | 3.10809743e−01 | 1.87987745e−01 | −2.17458662e−01 |
| 6.00184441e−01 | 3.82811069e−01 | 3.32447141e−01 | 1.48156047e−01 |
| 4.18880701e−01 | 5.39437383e−02 | 1.41231371e−02 | 6.76599145e−01 |
| 3.15280527e−01 | −2.24053472e−01 | 2.82655805e−01 | −1.11176014e−01 |
| −3.57814319e−02 | 4.50762242e−01 | 4.04428005e−01 | −3.82150970e−02 |
| 4.64827925e−01 | 1.73678502e−01 | −5.14310179e−03 | 4.54352915e−01 |
| 3.13836902e−01 | 2.60880560e−01 | 2.36594722e−01 | 5.96251786e−01 |
| 5.44232666e−01 | −1.27105296e−01 | 3.03272545e−01 | 1.69632081e−02 |
| −2.44406343e−01 | 3.22220862e−01 | −1.69402748e−01 | 3.70223224e−01 |
| 5.61198950e−01 | 2.54549176e−01 | 2.00930491e−01 | 1.53834492e−01 |
| 9.19089913e−02 | 4.60782379e−01 | 8.26681480e−02 | 1.89077884e−01 |
| 1.55896604e−01 | 5.06324232e−01 | 1.89662144e−01 | 6.77794218e−01 |
| 2.31239364e−01 | 2.51507640e−01 | 8.97628069e−02 | 1.41554356e−01 |
| −1.09232940e−01 | 1.78249944e−02 | 6.91489205e−01 | 8.49247873e−01 |
| 2.21978724e−01 | 6.56910300e−01 | −1.53737634e−01 | 4.95844364e−01 |
| 1.85645014e−01 | 6.00144982e−01 | 5.14754355e−01 | −1.09777324e−01 |
| 3.29923272e−01 | 1.56567559e−01 | −1.23612825e−02 | 2.63013422e−01 |
| 1.98762208e−01 | −6.92674965e−02 | 5.50985932e−01 | 3.83026212e−01 |
| 3.45803171e−01 | 3.70308638e−01 | 7.72105604e−02 | −1.94315851e−01 |
| 6.36337996e−01 | 3.38633776e−01 | 2.51342617e−02 | 2.68426001e−01 |
| −3.32708657e−02 | −1.66314393e−02 | 5.20722903e−02 | 3.21532995e−01 |
| 3.13744992e−01 | −1.03347450e−01 | 6.69361472e−01 | 3.35842371e−01 |
| −2.63078511e−01 | 2.12743998e−01 | 8.59323516e−02 | 4.62960362e−01 |
| 3.09980720e−01 | 3.51579189e−01 | −1.57211348e−01 | 2.13273391e−02 |
| 4.63319242e−01 | 3.16798121e−01 | −4.58159328e−01 | 1.86057284e−01 |
| 2.73289621e−01 | 5.04878163e−01 | 2.24808022e−01 | 4.21946645e−01 |
| −9.73925069e−02 | 1.64863974e−01 | 2.80442387e−02 | 4.62647676e−02 |
| 2.30880350e−01 | −1.34667799e−01 | −9.19184065e−04 | 7.49414861e−02 |
| 2.58560240e−01 | −3.52717703e−03 | −2.48555511e−01 | 6.81319311e−02 |
| 3.04436505e−01 | 3.51541370e−01 | 2.13296637e−01 | 3.19209218e−01 |
| −8.48392323e−02 | −1.35173544e−01 | 4.54765320e−01 | −5.19421399e−01 |

TABLE $W_h^1$-continued

| | | | |
|---|---|---|---|
| 5.04731596e−01 | 2.73878992e−01 | 5.34461856e−01 | 2.05770776e−01 |
| 1.98356196e−01 | 4.36107852e−02 | 1.96999803e−01 | −2.39172410e−02 |
| 5.74399829e−01 | −8.64471048e−02 | 4.21508960e−02 | −1.27741054e−01 |
| 1.57965068e−02 | 5.82344048e−01 | 2.63668984e−01 | −6.58410043e−02 |
| 2.01757416e−01 | −5.85145913e−02 | −1.91011325e−01 | 1.75631776e−01 |
| 2.92178810e−01 | −1.06997125e−01 | −2.08682637e−03 | −1.27476662e−01 |
| 2.66812205e−01 | −1.51357979e−01 | 1.56638011e−01 | −2.33617518e−02 |
| 1.19943544e−01 | 3.47637862e−01 | 1.75120756e−02 | −1.93648547e−01 |
| −1.13726042e−01 | 4.00460660e−01 | 7.38966882e−01 | 1.80346981e−01 |
| −4.71987352e−02 | 5.76219242e−03 | 3.25732082e−01 | 2.51886304e−02 |
| 1.85204428e−02 | 1.83784276e−01 | 5.24926841e−01 | 4.30240840e−01] |
| [−2.89082557e−01 | 2.32246131e−01 | −1.51323631e−01 | −2.13389233e−01 |
| 8.26189891e−02 | 2.98022807e−01 | 2.00617447e−01 | −4.54424322e−02 |
| 2.91912764e−01 | −8.19091126e−02 | 1.78314462e−01 | 4.04036045e−01 |
| 2.59741813e−01 | 2.06386708e−02 | −7.96110034e−02 | 3.34471650e−02 |
| 2.49602273e−01 | 7.16412142e−02 | 3.62360924e−01 | −1.55276164e−01 |
| 1.65021613e−01 | 8.94332975e−02 | 2.84864217e−01 | −4.09144983e−02 |
| 3.22124004e−01 | −3.38322550e−01 | −3.21346164e−01 | 1.93270996e−01 |
| −1.64738614e−02 | 7.31688514e−02 | 2.76666969e−01 | 2.31589794e−01 |
| −1.24540955e−01 | −1.39764264e−01 | 5.66059910e−02 | −8.05162117e−02 |
| 5.42512536e−02 | 1.85396120e−01 | 3.82133394e−01 | −4.52003807e−01 |
| −1.65500998e−01 | 1.01612359e−02 | −4.03671384e−01 | 8.44918847e−01 |
| −2.97467649e−01 | −1.40849456e−01 | 1.90034121e−01 | 2.21401259e−01 |
| −3.88973355e−01 | −1.13320738e−01 | −1.19223222e−01 | 1.89526398e−02 |
| −1.58241585e−01 | 4.35696393e−02 | 3.35944146e−01 | 5.19334106e−03 |
| −1.32163808e−01 | 1.60815999e−01 | 2.88892835e−01 | 3.93200815e−01 |
| 2.19701767e−01 | 1.49981722e−01 | −2.52234302e−02 | 5.27265012e−01 |
| 1.19808257e−01 | 2.59252399e−01 | 4.47412729e−01 | 6.43975258e−01 |
| −7.15539083e−02 | 3.08053475e−01 | 1.53848201e−01 | 2.88449347e−01 |
| −8.99561569e−02 | −2.97974255e−02 | 4.89025742e−01 | 4.86011989e−02 |
| 1.65624335e−01 | 1.03533931e−01 | −5.82238846e−02 | 4.19874303e−02 |
| 2.35200226e−01 | 2.59041607e−01 | 5.60725987e−01 | −5.70431165e−03 |
| 4.09211308e−01 | −2.86599219e−01 | 2.62303166e−02 | −1.99223105e−02 |
| −1.32373765e−01 | 1.31205976e−01 | 1.71714753e−01 | −2.34802544e−01 |
| 4.08085823e−01 | 4.93533909e−01 | −6.99582472e−02 | 2.06895560e−01 |
| −5.22895977e−02 | 3.01471442e−01 | 2.34923869e−01 | −2.40534935e−02 |
| 2.93788970e−01 | −1.84746593e−01 | 9.70031321e−03 | 4.91657376e−01 |
| 2.53049701e−01 | −1.44926399e−01 | 8.90391618e−02 | 2.93481529e−01 |
| 3.84471267e−01 | 3.02241564e−01 | 1.37524396e−01 | 6.49879098e−01 |
| 2.68664241e−01 | 2.43481994e−02 | 3.62736359e−02 | 4.47401732e−01 |
| 2.53157109e−01 | 4.70828682e−01 | 1.82187840e−01 | 2.56415665e−01 |
| −1.32953629e−01 | 7.72615001e−02 | −3.84686515e−02 | 1.06046744e−01 |
| 2.20270589e−01 | 1.83576003e−01 | −2.04481669e−02 | 9.58678052e−02 |
| −1.83668658e−01 | −2.37359568e−01 | 6.81036189e−02 | −1.03433589e−02 |
| 8.91902857e−03 | 3.68525356e−01 | 3.82674113e−02 | 6.21905208e−01 |
| 3.92097026e−01 | 3.34758312e−01 | 6.80949166e−02 | 2.93919981e−01 |
| 2.21038237e−01 | 1.53117672e−01 | −2.02946112e−01 | −3.57512049e−02 |
| 1.06728151e−01 | 2.97404379e−01 | 2.50165444e−02 | 1.44017383e−01 |
| 4.54831719e−01 | 4.86352831e−01 | 3.14593345e−01 | 2.59173900e−01 |
| 1.69729516e−01 | −2.24451963e−02 | 5.81378303e−02 | 2.85656840e−01 |
| 3.98460031e−02 | −1.09544925e−01 | 3.29511881e−01 | 2.46481150e−01 |
| 4.54220176e−01 | 4.01843280e−01 | −2.52125412e−01 | 8.70637819e−02 |
| 3.74738693e−01 | 5.14171183e−01 | 7.32224956e−02 | 1.68270946e−01 |
| 2.53515542e−01 | −5.15603907e−02 | 1.05719134e−01 | 9.41415578e−02 |
| 3.36027861e−01 | −1.50023818e−01 | 5.87542355e−01 | 4.97418642e−01 |
| 3.12545337e−02 | −2.13220716e−02 | 2.59222537e−02 | 3.78480583e−01 |
| 1.04819238e−01 | 4.12270933e−01 | −5.12401387e−02 | 4.40506577e−01 |
| 3.40143234e−01 | −4.10999581e−02 | 1.91005424e−01 | 3.80143613e−01 |
| 4.21698064e−01 | −2.07635880e−01 | 1.04360558e−01 | 9.25638452e−02 |
| 1.35794774e−01 | −3.84899415e−02 | 4.70901951e−02 | −2.18342505e−02 |
| 2.57481337e−01 | −4.67600644e−01 | 3.24672669e−01 | −1.26414448e−01 |
| 1.43782124e−01 | −2.37439219e−02 | 5.69998808e−02 | −9.60743874e−02 |
| 1.94559380e−01 | 5.21288097e−01 | 1.45216495e−01 | 2.72535831e−01 |
| 1.81100667e−02 | −5.36506213e−02 | 6.18565440e−01 | −7.82939494e−02 |
| 3.33373815e−01 | 1.60938680e−01 | 3.44845146e−01 | 1.18288044e−02 |
| 4.47667748e−01 | 7.41445422e−01 | 2.43819773e−01 | 2.13905182e−02 |
| 2.00959831e−01 | −1.60097405e−02 | 7.72693660e−03 | 4.53286618e−01 |
| 1.78099826e−01 | 2.80883759e−01 | 1.19573474e−01 | 7.93511719e−02 |
| 2.09463105e−01 | −2.16425374e−01 | 1.50337636e−01 | 1.22246027e−01 |
| −1.24495581e−01 | 5.04878946e−02 | −4.10166681e−02 | −2.56660134e−01 |
| 1.34513034e−02 | −4.25172478e−01 | 2.88870901e−01 | 3.10963273e−01 |
| 2.01733075e−02 | 4.12024289e−01 | −3.11586391e−02 | −2.09545717e−01 |
| 2.25978434e−01 | 1.65074334e−01 | 7.21852779e−01 | 1.74362883e−01 |
| 1.65928286e−02 | 4.21450257e−01 | 1.95554614e−01 | 1.39359221e−01 |
| 2.58514225e−01 | 2.95701861e−01 | 4.32283878e−02 | 1.32952899e−01] |
| [6.07648417e−02 | 1.27562154e−02 | 4.87488389e−01 | 4.22825694e−01 |
| −2.18385998e−02 | 2.90512234e−01 | 2.82549381e−01 | 4.54771399e−01 |
| 2.62893796e−01 | 4.20493960e−01 | 3.72234464e−01 | 1.62220120e−01 |
| 1.96622878e−01 | 3.36838335e−01 | 6.63277367e−03 | −4.28518020e−02 |
| 9.75657478e−02 | 1.96759216e−02 | 4.83002186e−01 | 1.43223211e−01 |

TABLE $W_h^1$-continued

| | | | |
|---|---|---|---|
| 4.48267460e−01 | 3.01718771e−01 | 4.86853868e−01 | 4.77665395e−01 |
| 3.19308609e−01 | 7.98218250e−01 | 6.49072766e−01 | 2.87247509e−01 |
| 3.46090615e−01 | 8.14466119e−01 | 3.46115232e−01 | 2.15663791e−01 |
| 4.35581625e−01 | −3.36094573e−02 | 1.13325760e−01 | 2.47636028e−02 |
| 4.44794267e−01 | 1.77323863e−01 | 6.33561835e−02 | 6.61359549e−01 |
| −1.04202420e−01 | 1.00522466e−01 | 3.34277153e−01 | −2.74898887e−01 |
| 8.42642367e−01 | 3.90873969e−01 | 6.06361151e−01 | 4.21222478e−01 |
| 5.01477897e−01 | 5.75620495e−02 | 1.48438290e−01 | 2.64215827e−01 |
| 3.71435493e−01 | −1.58497930e−01 | −2.82627612e−01 | 4.18338150e−01 |
| 4.34170753e−01 | 4.27192748e−01 | 7.07382202e−01 | 3.05597126e−01 |
| 5.72850525e−01 | 3.36307704e−01 | −1.65149316e−01 | −1.22204095e−01 |
| 4.38722342e−01 | 4.11131710e−01 | −1.82645038e−01 | 3.04203033e−01 |
| 3.48755896e−01 | 3.07486981e−01 | −1.58584967e−01 | 1.92797005e−01 |
| 6.62438571e−01 | 3.83901745e−01 | 2.86854029e−01 | 5.09034395e−01 |
| −6.41345158e−02 | 5.78509212e−01 | 1.96933746e−01 | 1.48955092e−01 |
| −3.63974273e−02 | 1.14734851e−01 | 4.13411170e−01 | 4.10207331e−01 |
| 1.51823029e−01 | −2.98961520e−01 | 3.75908554e−01 | 2.30865166e−01 |
| −5.58607094e−02 | 4.00210172e−01 | 4.69027832e−02 | −2.96695270e−02 |
| 1.27692074e−01 | 6.71436042e−02 | 7.46988475e−01 | 8.63167107e−01 |
| 1.89406965e−02 | 4.30907786e−01 | 7.16905817e−02 | −1.34440750e−01 |
| 1.13620713e−01 | 7.42229104e−01 | 2.18495399e−01 | −2.38290578e−01 |
| −7.49570131e−02 | −8.17245468e−02 | 3.38803649e−01 | 2.46024551e−03 |
| −2.44300768e−01 | 2.68057138e−01 | −2.28945520e−02 | −1.51590616e−01 |
| 7.73786485e−01 | 4.28435728e−02 | 1.31022111e−01 | 9.62990895e−02 |
| 7.84604773e−01 | 4.55123901e−01 | 9.44740027e−02 | 7.32752264e−01 |
| 3.34472835e−01 | 2.58563846e−01 | 4.74941730e−01 | 3.05792809e−01 |
| 4.41313207e−01 | 5.80564201e−01 | 4.30660218e−01 | 1.82686046e−01 |
| 8.65173340e−01 | 8.33122671e−01 | 3.14795338e−02 | 3.21828395e−01 |
| 8.30062747e−01 | 6.37388378e−01 | 5.21040559e−01 | −1.05092280e−01 |
| 7.36139417e−02 | 1.75801381e−01 | 5.98085642e−01 | 3.35502505e−01 |
| 4.19035524e−01 | 3.29345793e−01 | 2.73973197e−02 | 5.19519329e−01 |
| −6.24389295e−03 | 1.48347259e−01 | 4.18370098e−01 | 2.28795588e−01 |
| 2.90694069e−02 | −2.35350579e−01 | 7.77143314e−02 | 6.49519980e−01 |
| −7.80738592e−02 | 5.37038922e−01 | 5.18540144e−01 | 4.07953024e−01 |
| 2.01568589e−01 | 5.33952594e−01 | 4.52322125e−01 | 1.50575131e−01 |
| 2.52648927e−02 | 2.55539298e−01 | −3.56908664e−02 | 2.42117587e−02 |
| 2.10297227e−01 | −1.53316990e−01 | 4.11826223e−01 | 4.33864266e−01 |
| 6.23839617e−01 | 2.31454253e−01 | 1.45133838e−01 | 2.28719592e−01 |
| 2.07575515e−01 | 1.89513505e−01 | −2.97323346e−01 | 2.06953406e−01 |
| 3.54203820e−01 | 4.45151180e−01 | −2.01456681e−01 | 1.92875341e−02 |
| 2.03671038e−01 | 5.58229685e−01 | 1.31113440e−01 | −9.85530540e−02 |
| 3.15763384e−01 | 3.95229012e−01 | 4.19792116e−01 | −1.15479156e−01 |
| −3.06701928e−01 | 5.43534756e−01 | 5.65925121e−01 | 6.61553860e−01 |
| 2.24058494e−01 | 2.36078754e−01 | 1.34350270e−01 | 2.86222368e−01 |
| 6.63603097e−02 | 1.94549620e−01 | 1.33343190e−01 | 4.91291195e−01 |
| −2.13425547e−01 | 3.04745346e−01 | 3.24350417e−01 | 2.61038542e−01 |
| 6.75890028e−01 | 2.03950644e−01 | 2.89544642e−01 | 1.53944284e−01 |
| 7.33024538e−01 | 3.73282999e−01 | 3.66547614e−01 | 3.40465963e−01 |
| 9.24354121e−02 | 3.14668268e−01 | −8.83662626e−02 | −8.63071457e−02 |
| 1.15995526e−01 | 6.19940534e−01 | 3.40149909e−01 | 2.48136684e−01 |
| −3.02957207e−01 | 5.37740029e−02 | −4.60638590e−02 | −1.70912575e−02 |
| 9.86613631e−02 | 6.07118905e−01 | −2.48917900e−02 | 4.50857133e−01 |
| 2.86919653e−01 | 2.69774258e−01 | 6.96093678e−01 | 5.16777575e−01 |
| 6.17309988e−01 | 2.88259566e−01 | 4.64779437e−01 | 4.66162920e−01 |
| −3.76452506e−01 | 2.45404303e−01 | 1.28212884e−01 | 3.97660613e−01 |
| 1.65238515e−01 | 2.09378719e−01 | 2.23914936e−01 | 2.54531085e−01 |
| 3.20846945e−01 | 2.29619175e−01 | 2.58733213e−01 | 5.94561659e−02 |
| 6.88048422e−01 | 7.74279982e−02 | 2.30017066e−01 | 3.26823205e−01 |
| −1.16256289e−01 | 4.06018853e−01 | 5.36110938e−01 | 2.64493555e−01] |
| [−2.39609070e−02 | 1.21493839e−01 | 4.04894084e−01 | 2.34330967e−02 |
| 3.79327059e−01 | −2.19954044e−01 | 2.88290650e−01 | −2.04822227e−01 |
| −6.11778758e−02 | 8.17402154e−02 | 7.94834569e−02 | 1.11996695e−01 |
| 1.38280734e−01 | 8.22787061e−02 | −1.31067038e−01 | 4.59648930e−01 |
| −1.36173740e−01 | 7.32402354e−02 | 6.39934897e−01 | 9.30819213e−02 |
| −2.10350230e−01 | 2.42074188e−02 | −7.28413582e−01 | 1.62515029e−01 |
| 4.52130616e−01 | 1.41108021e−01 | −2.28268102e−01 | −6.26341924e−02 |
| 1.75824061e−01 | −1.96676835e−01 | −2.69198149e−01 | −4.53872643e−02 |
| 2.84909964e−01 | −1.97680488e−01 | −2.43585348e−01 | 8.21140558e−02 |
| −1.14280313e−01 | 3.40322882e−01 | −6.08245842e−02 | −2.50305235e−01 |
| 5.25772683e−02 | −1.45772427e−01 | 1.03331774e−01 | 1.23176739e−01 |
| 6.38029575e−02 | 8.25031288e−03 | 1.43714070e−01 | 5.08887433e−02 |
| −1.13159508e−01 | 3.82241644e−02 | −2.93762475e−01 | 6.41184449e−02 |
| 7.30585074e−03 | −9.77999866e−02 | 2.31206223e−01 | 1.55154034e−01 |
| −3.72817740e−03 | 1.41170740e−01 | −1.82261355e−02 | 5.33481017e−02 |
| −2.73797214e−02 | 1.87018380e−01 | −1.78727373e−01 | 2.27191076e−01 |
| 7.53296120e−03 | 2.66993463e−01 | 1.07572421e−01 | 3.46948087e−01 |
| −1.30424708e−01 | 2.66183913e−01 | −5.80540225e−02 | 1.67254448e−01 |
| −1.80140045e−02 | 3.75553891e−02 | −1.43528536e−01 | −6.91717938e−02 |
| 1.86902449e−01 | −5.93433343e−02 | 2.77439892e−01 | −1.71131864e−02 |
| 2.63700429e−02 | −7.44317025e−02 | −9.96115357e−02 | −1.21713728e−01 |

TABLE $W_h^1$-continued

| | | | |
|---|---|---|---|
| 1.50203228e-01 | 1.27214631e-02 | 3.88354033e-01 | 3.09336931e-02 |
| 3.80415827e-01 | -1.52213931e-01 | -1.11737005e-01 | -1.60557777e-02 |
| 1.45811453e-01 | 5.88808537e-01 | 2.64211506e-01 | -2.08120397e-03 |
| 1.91052891e-02 | -2.83715576e-01 | 1.55225888e-01 | 1.33967668e-01 |
| -1.33945467e-02 | -2.64092326e-01 | -1.24400496e-01 | -8.39838535e-02 |
| -1.70983538e-01 | 2.47021690e-02 | -6.08100817e-02 | 1.15919270e-01 |
| 2.10389063e-01 | -1.33033484e-01 | 1.53743953e-01 | 3.13561484e-02 |
| 4.75389689e-01 | -2.33887196e-01 | -2.95728445e-02 | 9.72124934e-02 |
| 7.77223781e-02 | 3.24469894e-01 | 2.49491781e-01 | -1.17305845e-01 |
| 4.45266999e-02 | -8.43719393e-02 | 3.03601950e-01 | -1.52981609e-01 |
| 6.21282697e-01 | -3.26183140e-01 | 1.53195754e-01 | -1.63018733e-01 |
| -9.65150073e-02 | -4.97653708e-02 | 1.02682717e-01 | -1.47007734e-01 |
| -1.65507972e-01 | -1.31405056e-01 | 1.62230656e-01 | -5.20065352e-02 |
| 1.75894663e-01 | 8.64790976e-02 | 1.84947938e-01 | 5.50836213e-02 |
| 1.41004264e-01 | 2.35077009e-01 | -2.41594121e-01 | -4.42841262e-01 |
| -8.41889158e-02 | 2.48467326e-02 | 2.38601148e-01 | -4.37626727e-02 |
| 4.47432429e-02 | 5.96196592e-02 | 6.65036887e-02 | 1.41042620e-01 |
| -1.98930115e-01 | -1.78630874e-01 | 4.09655608e-02 | -2.73650475e-02 |
| 2.01870754e-01 | 2.15709433e-01 | 9.24468115e-02 | -2.23776758e-01 |
| -1.02186434e-01 | 2.17894062e-01 | -1.67478397e-01 | -9.21683758e-02 |
| 1.15461975e-01 | 4.47317690e-01 | -1.06409691e-01 | 1.77606568e-01 |
| 2.51360148e-01 | -4.72628802e-01 | 1.92805633e-01 | 2.10783526e-01 |
| 4.90868628e-01 | -1.68730225e-02 | 4.46009129e-01 | 1.55728430e-01 |
| 2.21229717e-01 | 9.49598327e-02 | 3.02533954e-01 | 1.42814010e-01 |
| -1.44847363e-01 | 4.12229210e-01 | 1.47741050e-01 | 1.49292961e-01 |
| -5.18938787e-02 | 4.41823304e-02 | -1.03992209e-01 | -7.77980089e-02 |
| 1.93988055e-01 | 4.41723652e-02 | -5.07666403e-03 | -1.11673392e-01 |
| -5.50548434e-02 | 3.34184080e-01 | 3.52758914e-01 | 2.53075749e-01 |
| 2.92891055e-02 | 2.09600404e-01 | -1.20163828e-01 | 1.56921551e-01 |
| 2.08932027e-01 | 2.75829494e-01 | -1.37512861e-02 | 1.65547565e-01 |
| -1.00797974e-02 | -2.19678078e-02 | 4.05652076e-02 | -9.44139734e-02 |
| 1.91991434e-01 | 1.79875642e-01 | 5.52205563e-01 | 5.46196215e-02 |
| 2.08387941e-01 | 8.42245575e-03 | -1.94487602e-01 | 2.00489402e-01 |
| 2.90038735e-02 | 1.35131136e-01 | -7.46377185e-02 | 1.53117895e-01 |
| 3.96454781e-01 | 2.75583237e-01 | -1.14742927e-01 | 1.41087756e-01 |
| 2.60880291e-01 | 1.54481828e-01 | 2.68912911e-01 | -3.88438880e-01 |
| -7.79092535e-02 | -3.30606967e-01 | -1.47768529e-02 | -2.54516780e-01 |
| -4.40131903e-01 | -5.46555482e-02 | -9.19599608e-02 | -1.86429471e-01 |
| 4.44808155e-02 | -2.97356039e-01 | 2.18515918e-01 | 3.33174527e-01 |
| 5.19460812e-02 | 9.34811980e-02 | 2.59295613e-01 | -2.56844044e-01 |
| 4.24812585e-01 | -6.51365204e-04 | 2.54757792e-01 | 2.47527540e-01 |
| 3.19491364e-02 | 1.57145619e-01 | -1.20148165e-01 | 4.99584228e-02 |
| 2.20877305e-02 | 1.42488748e-01 | 2.35867888e-01 | -9.22790263e-03] |
| [-2.67785132e-01 | 2.33454466e-01 | 4.89681870e-01 | 9.47713293e-03 |
| 1.14954881e-01 | 1.89956382e-01 | 5.08384347e-01 | 4.72763807e-01 |
| 6.36582673e-02 | -4.79630053e-01 | 2.50951737e-01 | -2.84159750e-01 |
| 1.22179631e-02 | 3.18766594e-01 | -5.86166620e-01 | -3.95247668e-01 |
| -3.16320628e-01 | 1.48700356e-01 | -7.97998533e-02 | 8.18167210e-01 |
| 5.48924565e-01 | 3.55520219e-01 | -5.94214424e-02 | 7.01409817e-01 |
| 3.07709277e-02 | 5.60435295e-01 | 3.56240094e-01 | 2.17806280e-01 |
| -3.26471664e-02 | 1.16840795e-01 | 3.97297114e-01 | 4.49733913e-01 |
| 3.45805347e-01 | -1.19880714e-01 | -5.94459055e-03 | -2.38540590e-01 |
| -6.26208037e-02 | 3.25932205e-01 | 5.00013173e-01 | 4.20736670e-01 |
| 4.31904137e-01 | 1.28411308e-01 | -5.07015958e-02 | -3.07046533e-01 |
| 7.77840972e-01 | 1.59561023e-01 | 2.97298819e-01 | 9.40259248e-02 |
| 1.60154581e-01 | 2.71952063e-01 | 5.21245480e-01 | 1.92667305e-01 |
| 3.88112336e-01 | 1.44045785e-01 | 3.01353365e-01 | 1.17085494e-01 |
| -1.27939180e-01 | 7.35639259e-02 | 6.66437685e-01 | -1.95701316e-01 |
| 3.19276392e-01 | 4.99167532e-01 | 5.40722132e-01 | 3.29119742e-01 |
| 6.71972483e-02 | 1.08742520e-01 | 2.25176007e-01 | 4.17492539e-01 |
| 1.14080487e-02 | 4.08485949e-01 | -7.46673644e-02 | 1.38932407e-01 |
| 4.76704001e-01 | 8.17424059e-03 | 2.36603752e-01 | 2.51253784e-01 |
| 5.96574485e-01 | 2.41833255e-01 | 5.54274678e-01 | 9.35990587e-02 |
| 2.49883741e-01 | 5.20497680e-01 | -1.06330449e-02 | 2.77842313e-01 |
| 1.71478674e-01 | 3.57804149e-01 | 5.55103302e-01 | 4.69556987e-01 |
| 3.85562986e-01 | 1.40993312e-01 | -1.23034425e-01 | -2.00383991e-01 |
| 3.55247706e-01 | 5.00189245e-01 | -6.88164458e-02 | 4.57400262e-01 |
| 5.40509336e-02 | 1.38715163e-01 | 1.94475472e-01 | 3.46148983e-02 |
| 5.30203998e-01 | 5.37373781e-01 | 3.92411486e-04 | 5.03085136e-01 |
| 2.33205736e-01 | 3.14995557e-01 | 5.37551701e-01 | -2.11343709e-02 |
| 3.40215921e-01 | 5.95226705e-01 | 8.49930644e-01 | 3.48246723e-01 |
| 7.16565728e-01 | 6.90723062e-02 | 2.81827766e-02 | -2.87310500e-02 |
| 1.78381339e-01 | 3.18742037e-01 | 5.18704832e-01 | 1.96447559e-02 |
| 1.15009271e-01 | 1.64295658e-01 | 3.66932988e-01 | -7.10558565e-03 |
| 2.04838682e-02 | 2.12470859e-01 | 1.89324349e-01 | 2.34015137e-01 |
| 7.52944350e-01 | -4.39957529e-02 | -3.56090553e-02 | 1.72472298e-01 |
| 1.82951003e-01 | 3.49971801e-02 | 3.72035116e-01 | -1.52187213e-01 |
| 9.66527779e-03 | -1.52411789e-01 | 5.70682943e-01 | 4.53754395e-01 |
| 2.12015897e-01 | 2.72509634e-01 | 1.32607535e-01 | 1.24136657e-02 |
| 3.88013542e-01 | -2.44354289e-02 | 4.43269193e-01 | 3.11526388e-01 |

TABLE $W_h^1$-continued

| | | | |
|---|---|---|---|
| 3.09719950e−01 | 2.61975348e−01 | 3.47358048e−01 | 2.26281837e−01 |
| 3.07721645e−01 | 2.55668133e−01 | −6.02862500e−02 | 1.59322619e−01 |
| 1.18574969e−01 | 2.92687654e−01 | 1.63684845e−01 | 5.58489680e−01 |
| 2.49437690e−01 | 1.95257694e−01 | 9.46059898e−02 | 4.80587393e−01 |
| −3.60536501e−02 | 2.59257972e−01 | 1.22045331e−01 | 1.06839359e−01 |
| 3.50558072e−01 | 4.57357138e−01 | 3.44509512e−01 | 2.38880187e−01 |
| 3.17355543e−01 | 1.58447996e−01 | 2.15528831e−01 | 5.38102239e−02 |
| 4.03447986e−01 | 6.14633441e−01 | −2.34353263e−02 | 2.61989653e−01 |
| 1.48733377e−01 | 3.52769613e−01 | 3.15879494e−01 | 3.02198052e−01 |
| 2.60686483e−02 | 3.72314632e−01 | 1.22801609e−01 | 8.86826515e−02 |
| 1.12420045e−01 | 3.80364746e−01 | 1.40314251e−01 | 3.33352089e−02 |
| 5.20163417e−01 | 6.74861014e−01 | 3.39486539e−01 | −1.06383793e−01 |
| −3.70034464e−02 | 1.51670501e−01 | 5.54696620e−01 | 1.23571977e−01 |
| 2.66311973e−01 | 1.08585291e−01 | 1.52658090e−01 | 8.97791326e−01 |
| 5.44260561e−01 | 8.01133692e−01 | 3.20793539e−01 | −2.06268564e−01 |
| 2.03851938e−01 | −1.69159129e−01 | 1.05812453e−01 | 2.55063862e−01 |
| 6.48809075e−02 | 4.34710890e−01 | 1.99961349e−01 | 4.07181308e−02 |
| 3.46515030e−01 | 8.06350112e−02 | 3.42984274e−02 | 1.54741570e−01 |
| 3.40450019e−01 | 2.23386243e−01 | 3.27396929e−01 | 1.55353040e−01 |
| −2.29791149e−01 | 6.44154251e−02 | 2.14604706e−01 | −1.12656970e−02 |
| 5.58189392e−01 | 3.75863224e−01 | 7.82460451e−01 | 3.34598213e−01 |
| 6.61221206e−01 | 2.93400347e−01 | 3.54750901e−01 | 2.34003916e−01 |
| 3.07807118e−01 | 1.02323771e−01 | 3.96129817e−01 | 3.40461940e−01 |
| 5.36537826e−01 | −4.18640435e−01 | −3.26346490e−03 | 8.21157396e−01 |
| −6.11819066e−02 | 2.22659763e−03 | 1.95746705e−01 | 1.54638797e−01 |
| 3.93379450e−01 | −5.67945480e−01 | 1.20951310e−01 | −4.31756154e−02 |
| 1.33474441e−02 | 4.49281067e−01 | 6.34504249e−03 | 2.34351471e−01] |
| [−1.10460028e−01 | −7.96078324e−01 | 4.26385075e−01 | 3.04121584e−01 |
| −2.48830944e−01 | 3.02960962e−01 | 8.04001242e−01 | 4.29449081e−01 |
| 8.50291178e−02 | 2.79779136e−01 | 2.73395270e−01 | 1.72452644e−01 |
| 9.90679935e−02 | 8.70062690e−03 | −1.02551535e−01 | −3.87094058e−02 |
| 4.09928322e−01 | 2.39644706e−01 | −2.81178445e−01 | 3.12016428e−01 |
| 3.74608070e−01 | −1.88866138e−01 | 1.94687814e−01 | 4.68507618e−01 |
| 1.55140668e−01 | 3.62297386e−01 | 1.41988266e−02 | 1.34263441e−01 |
| −9.16642025e−02 | 3.48353535e−01 | −2.57198632e−01 | 2.87369341e−01 |
| −2.23587573e−01 | 4.31362003e−01 | 2.51595914e−01 | 9.78360921e−02 |
| −3.92388813e−02 | −1.93262592e−01 | −1.27167860e−02 | 2.96025634e−01 |
| −1.23519629e−01 | 7.03015029e−02 | 6.13478087e−02 | 1.70193195e−01 |
| 5.79309881e−01 | 1.87844992e−01 | 1.90765947e−01 | 1.69506058e−01 |
| 3.03336710e−01 | 2.34690353e−01 | 4.66350131e−02 | 2.85199314e−01 |
| −3.14356349e−02 | 3.40647474e−02 | −1.52300552e−01 | 1.54579833e−01 |
| 1.47387400e−01 | 5.84768038e−03 | 3.29966187e−01 | 2.63154000e−01 |
| 1.02137908e−01 | 9.44274440e−02 | 2.26962686e−01 | 3.97762328e−01 |
| 3.75734478e−01 | −1.15767971e−01 | 3.10869459e−02 | 2.17111424e−01 |
| 2.95583785e−01 | 7.42505863e−02 | 3.91655117e−01 | 1.19868301e−01 |
| 5.10663807e−01 | 2.80713569e−01 | 3.93142700e−01 | 2.99298048e−01 |
| 1.59436971e−01 | 4.73205745e−01 | 5.48878685e−03 | 2.03609928e−01 |
| −2.48854816e−01 | 6.08179450e−01 | −3.76042902e−01 | 2.53512233e−01 |
| −1.00933038e−01 | 1.95594534e−01 | 3.20181608e−01 | −3.59440111e−02 |
| 2.94349551e−01 | 3.83671403e−01 | 6.22681156e−01 | 1.68913871e−01 |
| −1.67521641e−01 | −1.41342700e−01 | 4.21663284e−01 | 8.95960331e−02 |
| −2.78652519e−01 | 3.41944218e−01 | −1.43372333e−02 | −2.40361735e−01 |
| 3.52700710e−01 | 1.38911963e−01 | 8.34846973e−01 | 2.19717115e−01 |
| −1.06636174e−01 | 2.31896833e−01 | 1.87714010e−01 | −1.63909972e−01 |
| 3.47805656e−02 | 4.36457664e−01 | −8.33970457e−02 | −1.64926350e−01 |
| 4.67025191e−01 | 1.83917973e−02 | 3.32148783e−02 | 3.37613761e−01 |
| 3.83109450e−01 | 2.81676166e−02 | 2.08694518e−01 | 2.74700105e−01 |
| 5.02170086e−01 | −1.88057631e−01 | 3.44434142e−01 | 3.51838842e−02 |
| −1.21710271e−01 | 4.47792917e−01 | −9.40910354e−02 | 4.47946995e−01 |
| 2.83037424e−01 | 2.64528543e−01 | −3.18540968e−02 | 2.20800236e−01 |
| 4.91171837e−01 | 2.14880571e−01 | −1.17181182e−01 | −8.88672769e−02 |
| −2.06520081e−01 | −1.54455259e−01 | 2.03894228e−01 | −1.76453758e−02 |
| 1.95142806e−01 | 1.77917585e−01 | −6.39924034e−02 | 3.53287548e−01 |
| 4.07632440e−02 | 6.42417297e−02 | 3.81293856e−02 | 2.30925269e−02 |
| −5.49243748e−01 | −2.30245322e−01 | −1.74006492e−01 | 2.74242431e−01 |
| 8.31839070e−02 | 7.94359818e−02 | 2.56064028e−01 | 1.17070369e−01 |
| 1.96593285e−01 | 4.82175231e−01 | 2.95579508e−01 | 8.56364518e−02 |
| −1.97534502e−01 | −1.04775138e−01 | −4.53219801e−01 | 2.56190956e−01 |
| −1.40552253e−01 | −9.24670100e−02 | 9.51374620e−02 | 2.05241457e−01 |
| 2.79515058e−01 | 6.37439847e−01 | 8.19650367e−02 | 1.22706100e−01 |
| 2.99457371e−01 | −8.90779421e−02 | −1.43417224e−01 | −3.99713293e−02 |
| 2.44243443e−01 | 2.17870370e−01 | 2.56213367e−01 | −9.24523622e−02 |
| 1.22740678e−03 | 6.01122439e−01 | 3.94722193e−01 | 1.41815487e−02 |
| −2.61336304e−02 | −4.46898192e−02 | 5.62288761e−01 | −1.93651207e−02 |
| −1.38378426e−01 | 3.15441996e−01 | 2.91512966e−01 | 1.08885124e−01 |
| 1.97847605e−01 | 4.33170110e−01 | 4.38718021e−01 | 3.21317434e−01 |
| −4.31479573e−01 | 5.69838472e−02 | 1.07707158e−01 | 8.79833698e−02 |
| −1.98673770e−01 | 1.96456790e−01 | −1.01341836e−01 | 1.81780055e−01 |
| 4.48037475e−01 | 2.57368684e−01 | −1.54310182e−01 | 3.92996967e−01 |
| 2.77741045e−01 | 1.46377504e−01 | −1.32034391e−01 | 2.34762490e−01 |

TABLE $W_h^1$-continued

| | | | |
|---|---|---|---|
| 2.79871106e-01 | -7.53667578e-03 | -1.02987655e-01 | 5.96772194e-01 |
| 2.16687605e-01 | -9.21847969e-02 | 3.84842098e-01 | 1.11635901e-01 |
| -1.15609862e-01 | 3.18425447e-01 | 2.10280031e-01 | 1.17027536e-02 |
| 4.43117589e-01 | 2.48038501e-01 | 7.80378878e-02 | 2.18825400e-01 |
| 2.73174673e-01 | -5.90084754e-02 | 8.62712860e-02 | 6.59612238e-01 |
| 8.77546221e-02 | -1.30844846e-01 | 4.78416324e-01 | 9.67603773e-02 |
| 6.15544878e-02 | -2.50489498e-03 | -9.69958976e-02 | -6.35538921e-02 |
| 3.80629376e-01 | 1.30296379e-01 | 1.67028502e-01 | 2.06802655e-02 |
| 2.57710684e-02 | 4.32814695e-02 | -7.33108073e-02 | 2.61441737e-01 |
| 3.78060907e-01 | -1.16204143e-01 | 1.38333961e-01 | 3.27398628e-01 |
| -1.57922879e-02 | 1.54407606e-01 | 2.62191027e-01 | 1.18728727e-01] |
| [5.56716383e-01 | -4.14606631e-01 | 4.86041158e-01 | -4.48579669e-01 |
| 9.90021899e-01 | 5.93660653e-01 | 1.87791064e-01 | 4.83166486e-01 |
| 5.30474305e-01 | -4.25310612e-01 | 3.80103320e-01 | -1.03371948e-01 |
| -3.55191976e-01 | 5.26690960e-01 | -3.14444363e-01 | -2.10842974e-02 |
| -1.11366339e-01 | 2.66188711e-01 | 1.44606382e-02 | 4.60596323e-01 |
| 2.20306635e-01 | 3.17951471e-01 | -9.53148305e-02 | 6.72689930e-05 |
| -4.69770998e-01 | 4.87641037e-01 | 1.56634063e-01 | 4.11056161e-01 |
| -2.97627091e-01 | -1.62370801e-02 | 2.66854197e-01 | 4.01434809e-01 |
| 1.50099963e-01 | 4.70897615e-01 | -3.62286180e-01 | 1.37052229e-02 |
| -1.49099246e-01 | 1.27456978e-01 | 2.42506295e-01 | 4.55888987e-01 |
| 2.23369613e-01 | 3.78280222e-01 | 3.82005364e-01 | 1.79928355e-02 |
| 1.38918355e-01 | 3.84977758e-02 | -3.10568343e-04 | -1.42968222e-01 |
| -1.02532603e-01 | 2.34089032e-01 | 4.27022666e-01 | 1.66036561e-02 |
| 2.86832750e-01 | -6.19318243e-03 | 9.21449140e-02 | -4.94147874e-02 |
| -2.65863448e-01 | -7.27215037e-02 | 4.47893500e-01 | -4.72252183e-02 |
| -1.35105506e-01 | 3.68456751e-01 | 3.69046256e-02 | -1.17022842e-01 |
| 3.02779436e-01 | -1.06012926e-01 | 5.10189831e-01 | 4.16015267e-01 |
| 4.55610603e-02 | -4.96261604e-02 | 2.03435533e-02 | 2.00295448e-02 |
| 1.76662415e-01 | 7.97323883e-03 | 2.01069608e-01 | 4.81934175e-02 |
| 4.23884392e-01 | -1.39190257e-02 | 6.28240407e-01 | 3.52651507e-01 |
| -6.45339042e-02 | 5.89418709e-01 | 1.16726242e-01 | 2.70266563e-01 |
| -1.33076787e-01 | 5.25618732e-01 | 2.08857894e-01 | 1.39168262e-01 |
| 7.38472998e-01 | 2.63972402e-01 | -1.18132204e-01 | 1.15183361e-01 |
| 2.49223053e-01 | 1.49985924e-01 | -7.87224829e-01 | 1.94091156e-01 |
| 4.24081981e-01 | -1.21191815e-01 | 4.30538863e-01 | 4.30573344e-01 |
| 2.42169052e-01 | 1.52113333e-01 | -1.35048106e-01 | -7.64226019e-02 |
| 8.61897707e-01 | -6.11054860e-01 | 5.85647002e-02 | -1.17765561e-01 |
| 3.92033935e-01 | 1.94033399e-01 | 3.22092891e-01 | -1.63902283e-01 |
| -1.09944493e-01 | 5.95714569e-01 | 1.08605057e-01 | -2.90840805e-01 |
| 1.67201549e-01 | 2.42102847e-01 | 1.99229985e-01 | -2.06929475e-01 |
| 2.86158442e-01 | 5.85423410e-01 | -1.94772594e-02 | 2.74002224e-01 |
| -1.20410144e-01 | -8.06965530e-02 | 4.20815587e-01 | -4.30992126e-01 |
| 4.50292021e-01 | 8.79805908e-02 | 2.26166397e-01 | 4.19045150e-01 |
| 1.55167148e-01 | 4.70001340e-01 | -9.15868878e-02 | 6.94299042e-02 |
| 2.89639272e-01 | -2.42597103e-01 | -1.88721120e-02 | 7.00112820e-01 |
| 8.03121179e-02 | 4.45039332e-01 | -2.25107089e-01 | 1.68757066e-01 |
| 2.48070136e-01 | 1.18125811e-01 | 2.53617525e-01 | 2.07326293e-01 |
| -1.19475894e-01 | 3.88928115e-01 | 4.72297788e-01 | 9.76400375e-02 |
| -7.48526081e-02 | 3.21480215e-01 | -6.93526566e-02 | 2.08562434e-01 |
| 1.59505114e-01 | -8.43120068e-02 | 1.38844267e-01 | 3.15611988e-01 |
| 1.61414042e-01 | 6.73948348e-01 | 4.34065282e-01 | 1.74096122e-01 |
| 5.62501326e-02 | -1.07645795e-01 | 2.87721694e-01 | 8.02186280e-02 |
| -6.63757175e-02 | 5.48841059e-01 | 2.26896778e-01 | -1.03096761e-01 |
| 4.45195884e-01 | 7.23740458e-02 | 2.26003930e-01 | 3.23771894e-01 |
| 4.05133158e-01 | -3.07718609e-02 | -1.05962820e-01 | -1.26252785e-01 |
| 1.26277298e-01 | 2.75126785e-01 | 2.35370427e-01 | -1.01660555e-02 |
| 8.44182596e-02 | 3.39174978e-01 | 1.08434498e-01 | 2.07450613e-02 |
| -5.98361082e-02 | 2.50888258e-01 | 2.21208677e-01 | 4.29949343e-01 |
| 5.61161578e-01 | 3.83250684e-01 | 4.11113687e-02 | -4.07355931e-03 |
| 7.82004893e-01 | 1.86287820e-01 | 4.56813872e-01 | -3.54958177e-02 |
| 1.62350744e-01 | 1.68529391e-01 | 4.24561858e-01 | 1.28129661e-01 |
| -6.56865463e-02 | 2.54019380e-01 | 3.64767402e-01 | -1.20766185e-01 |
| -1.63660776e-02 | -7.21021518e-02 | 1.26184985e-01 | -1.65251419e-01 |
| 2.44728173e-03 | 6.96197674e-02 | 5.65568030e-01 | -2.85347947e-03 |
| 2.03965515e-01 | 2.59249747e-01 | -3.22257280e-02 | 4.74838018e-01 |
| 5.86766340e-01 | 3.46382886e-01 | 2.25545019e-01 | -1.23067945e-01 |
| 1.19863041e-01 | 4.82874155e-01 | 3.08382567e-02 | 2.13207528e-01 |
| 1.43684566e-01 | 1.18571550e-01 | -4.89367265e-03 | -2.57189929e-01 |
| -1.62545934e-01 | -4.41483170e-01 | 6.59299120e-02 | 4.68567848e-01 |
| 1.57361537e-01 | 1.11163370e-01 | 5.15052795e-01 | 3.57996583e-01 |
| 5.91571704e-02 | -2.69397795e-01 | -5.21213748e-02 | -1.33569971e-01 |
| 2.85346240e-01 | 2.69619823e-01 | 6.12816930e-01 | 2.24135354e-01 |
| 2.78636664e-01 | -1.67765349e-01 | -3.22688706e-02 | 2.22609773e-01 |
| -8.54680836e-02 | 4.55954283e-01 | 7.73629993e-01 | 3.50180000e-01] |
| [-4.02649306e-03 | 5.04082255e-03 | -2.20753491e-01 | -2.63098300e-01 |
| -9.03336331e-02 | 1.79758534e-01 | 3.21471766e-02 | 5.07290781e-01 |
| 3.42627436e-01 | 3.69176090e-01 | 1.90710828e-01 | 4.83684599e-01 |
| -1.52546704e-01 | 1.69112921e-01 | 2.72028953e-01 | 5.11393309e-01 |
| 6.53079569e-01 | 1.09366626e-01 | -3.93299349e-02 | 3.03769596e-02 |

TABLE $W_h^1$-continued

| | | | |
|---|---|---|---|
| 6.36247575e-01 | 1.06462598e-01 | 2.09874511e-01 | 1.69879254e-02 |
| 2.21095055e-01 | 3.38665217e-01 | -3.13030146e-02 | 1.89614862e-01 |
| 1.39436096e-01 | 5.37476778e-01 | -1.37345064e-02 | 1.08842224e-01 |
| 6.86741412e-01 | 3.55709754e-02 | 3.60470027e-01 | -1.14528917e-01 |
| -1.26416776e-02 | 2.61311740e-01 | 5.77425621e-02 | 4.90867972e-01 |
| 3.17949355e-01 | 1.02701880e-01 | 3.14286172e-01 | -3.07964347e-02 |
| 4.66877401e-01 | 2.08475977e-01 | 4.60387111e-01 | 4.55908984e-01 |
| -1.41969368e-01 | 3.15146297e-01 | 2.22323641e-01 | 1.20369621e-01 |
| 5.66885293e-01 | 3.33933979e-01 | 1.86061084e-01 | 5.60997188e-01 |
| 4.04081583e-01 | 9.00934041e-02 | 2.19542831e-01 | 1.26534179e-01 |
| -5.68373166e-02 | 3.20917338e-01 | 1.08137168e-02 | 2.35542968e-01 |
| 4.11681473e-01 | 1.87938288e-01 | -2.84724861e-01 | 1.12147816e-01 |
| 3.53158861e-01 | 4.72008735e-02 | -2.28672281e-01 | 1.11316005e-01 |
| 3.58162284e-01 | 2.08935916e-01 | 4.33473438e-02 | 3.06394190e-01 |
| -1.29839540e-01 | 3.83603066e-01 | 2.63193876e-01 | 1.84914172e-01 |
| -1.82093143e-01 | 9.47389603e-02 | 9.74568725e-02 | 3.82952511e-01 |
| 3.20073515e-01 | 7.30999261e-02 | 3.02484453e-01 | -1.44974381e-01 |
| 2.06610218e-01 | 2.86638945e-01 | 1.43392190e-01 | 3.36993217e-01 |
| -1.08840711e-01 | -1.07253350e-01 | -2.59163268e-02 | 5.74601851e-02 |
| 7.88018480e-02 | 4.97927099e-01 | 4.16514836e-02 | -2.91649938e-01 |
| -4.58013229e-01 | 3.40693712e-01 | 2.22701758e-01 | 2.87208408e-01 |
| -1.64932638e-01 | -1.11416593e-01 | -2.24883154e-01 | -1.77568700e-02 |
| 2.83803672e-01 | 1.57923311e-01 | 1.95779875e-01 | 1.47983611e-01 |
| 6.36485040e-01 | 3.28334659e-01 | 2.38735348e-01 | 4.48781997e-01 |
| 4.67118293e-01 | 2.16340963e-01 | 2.41907552e-01 | 7.73362070e-02 |
| 3.01767707e-01 | 3.03088337e-01 | 1.94106609e-01 | -1.15898266e-01 |
| -6.20231517e-02 | 6.04832649e-01 | 2.05528274e-01 | 1.48439541e-01 |
| 5.86963519e-02 | 3.58474031e-02 | 2.66775995e-01 | 3.02208245e-01 |
| 6.81098878e-02 | 2.39404187e-01 | 3.51534754e-01 | 3.54543775e-01 |
| 2.44805679e-01 | 3.03492337e-01 | 6.99158013e-03 | 2.22902089e-01 |
| 3.25010508e-01 | 2.58463532e-01 | 1.46233156e-01 | -9.66116786e-02 |
| 1.74435139e-01 | -2.03825861e-01 | -1.27329275e-01 | 5.07729426e-02 |
| -2.62038857e-01 | -1.22186638e-01 | 2.99370468e-01 | 4.35557932e-01 |
| 1.19973637e-01 | 1.30745277e-01 | 3.31390679e-01 | 3.23709995e-01 |
| 4.06280428e-01 | 4.46738839e-01 | 9.21037793e-02 | 5.13812244e-01 |
| 3.74043226e-01 | 3.58003169e-01 | -1.51479214e-01 | 7.91952014e-01 |
| 3.63394588e-01 | 1.05316818e-01 | 2.09131718e-01 | 1.27907932e-01 |
| 1.38576150e-01 | 4.84713256e-01 | -7.56955817e-02 | 1.45280451e-01 |
| -4.57099043e-02 | 3.41788113e-01 | -1.33129284e-01 | 2.29482189e-01 |
| 8.55398849e-02 | -2.59454995e-01 | -9.48437080e-02 | 3.19384515e-01 |
| 6.55073300e-02 | 2.77483284e-01 | -3.72489356e-02 | 1.74881443e-01 |
| 4.39421088e-02 | 1.82278212e-01 | 5.75777829e-01 | 2.65409857e-01 |
| -6.14997186e-02 | 1.41653627e-01 | 3.56624007e-01 | 1.61729634e-01 |
| -1.56989232e-01 | 2.51598895e-01 | 2.37322688e-01 | 1.88861132e-01 |
| -2.35996419e-03 | 8.01776201e-02 | -6.44261092e-02 | 7.83943459e-02 |
| 1.28819570e-01 | 2.19661027e-01 | -1.77817136e-01 | 2.56160349e-01 |
| 1.64373547e-01 | 1.43070847e-01 | 1.75039113e-01 | 1.65985703e-01 |
| 6.47738338e-01 | -3.70387822e-01 | 7.96513408e-02 | -1.68178707e-01 |
| 5.15898407e-01 | 1.59682721e-01 | -1.41909122e-02 | 2.09409952e-01 |
| -5.11025116e-02 | -8.74675512e-02 | 6.70079052e-01 | 4.44226354e-01 |
| 7.18309060e-02 | 2.60568440e-01 | 5.83127141e-01 | 7.14550838e-02 |
| 4.93356548e-02 | -4.21546288e-02 | 1.27682954e-01 | -6.34796768e-02 |
| -5.75943328e-02 | 5.34892917e-01 | 4.42093521e-01 | 3.35586190e-01 |
| 5.06639004e-02 | 2.40285899e-02 | 2.05664262e-01 | 4.34138924e-01 |
| 1.49525091e-01 | -3.19397032e-01 | -1.14275925e-01 | 2.26868019e-01 |
| 2.57221013e-01 | 4.66356546e-01 | 2.12121680e-01 | 4.05088425e-01 |
| 3.15753728e-01 | 2.88957030e-01 | 7.66895935e-02 | 1.55454174e-01 |
| 3.57047677e-01 | 1.95429012e-01 | 7.24941075e-02 | 3.25837016e-01 |
| 3.73849094e-01 | 2.21880674e-01 | 8.65171999e-02 | -2.20673367e-01] |
| [-2.14904919e-01 | 7.07376972e-02 | 4.53995019e-01 | 2.69821107e-01 |
| 2.10226804e-01 | 4.05802727e-01 | 3.32850873e-01 | 4.99497771e-01 |
| 4.92594421e-01 | 3.56234580e-01 | 3.52513999e-01 | 5.51255643e-01 |
| 2.33650208e-01 | 4.72443104e-01 | 3.41705412e-01 | -1.27256513e-01 |
| 7.43215740e-01 | 6.09532595e-01 | -3.27437446e-02 | 3.16606723e-02 |
| 6.80956244e-01 | 4.82766539e-01 | 5.54454327e-01 | 4.93322343e-01 |
| -5.82167767e-02 | 5.12899697e-01 | -1.57869738e-02 | 9.35861692e-02 |
| 1.48185402e-01 | 1.55663582e-01 | 2.32367173e-01 | 1.04709692e-01 |
| 4.76845741e-01 | 4.50073630e-01 | 7.57731318e-01 | 5.86944461e-01 |
| 1.21925645e-01 | 3.56309824e-02 | 4.50510204e-01 | 7.33495712e-01 |
| 2.39815146e-01 | 6.67873472e-02 | 4.23182957e-02 | 4.84813809e-01 |
| 2.53346920e-01 | 1.96751386e-01 | 2.27228403e-01 | 8.39592040e-01 |
| 6.26700893e-02 | 3.32843930e-01 | 8.78976762e-01 | 3.79700869e-01 |
| 2.25167796e-01 | 1.75410137e-01 | 2.72212118e-01 | 1.27076000e-01 |
| 4.57646906e-01 | 3.55264366e-01 | 5.49215198e-01 | 1.93857133e-01 |
| 7.46882141e-01 | 8.78871977e-01 | 8.54038835e-01 | 3.67596388e-01 |
| 2.98912264e-02 | -1.44749172e-02 | 2.25572154e-01 | 1.53577164e-01 |
| 2.07432508e-01 | 1.54773086e-01 | 2.70300567e-01 | 6.63698763e-02 |
| -3.29597890e-02 | 4.38838601e-01 | 1.83104604e-01 | 5.08661211e-01 |
| 6.01558685e-01 | 3.71044666e-01 | 4.77814436e-01 | -3.33810210e-01 |
| 2.23484740e-01 | 6.46782696e-01 | 2.90548950e-01 | 2.61296220e-02 |

TABLE $W_h^1$-continued

| | | | |
|---|---|---|---|
| 3.38497847e−01 | −2.51792759e−01 | 5.86635053e−01 | 1.37434110e−01 |
| 2.29591906e−01 | −3.70630734e−02 | 1.32453784e−01 | 4.86092001e−01 |
| 2.52983034e−01 | 5.19242994e−02 | 1.07488319e−01 | 4.31717247e−01 |
| 4.36217517e−01 | 2.70746499e−01 | 8.40786844e−02 | 1.63076431e−01 |
| 2.76715159e−01 | 6.82718217e−01 | 3.18451166e−01 | 4.46612686e−01 |
| −2.54025668e−01 | 5.23653686e−01 | 3.32963347e−01 | 1.26740962e−01 |
| 2.67731011e−01 | 6.35792077e−01 | 1.54060736e−01 | 1.31530300e−01 |
| 2.00116951e−02 | 1.20951012e−02 | 5.93699157e−01 | 3.81907821e−01 |
| 6.40204132e−01 | 1.85200363e−01 | −1.59009010e−01 | 3.33248824e−01 |
| 8.08321118e−01 | 4.40895289e−01 | 4.49281365e−01 | 3.40043455e−01 |
| 4.00405139e−01 | 3.31908673e−01 | 1.41100392e−01 | 5.28797328e−01 |
| 3.73593897e−01 | 7.28124261e−01 | 1.01162481e−00 | 4.06439304e−01 |
| 5.64755440e−01 | 3.08290005e−01 | 4.04408813e−01 | 2.69276410e−01 |
| 2.77324677e−01 | 7.17772320e−02 | 1.25352845e−01 | 1.93940371e−01 |
| 7.32172906e−01 | 4.46153671e−01 | 3.66339177e−01 | 1.91386372e−01 |
| 2.78017938e−01 | 1.92341805e−01 | 3.67506891e−01 | 6.25120461e−01 |
| −1.79411769e−01 | −2.55310088e−01 | −3.81781697e−01 | 5.12467504e−01 |
| 3.14220756e−01 | 4.83413666e−01 | 4.83713239e−01 | 3.14353377e−01 |
| 2.45899893e−02 | 3.46694916e−01 | 2.55671293e−01 | 1.19215287e−01 |
| 4.77441847e−01 | 5.25660574e−01 | 4.70461026e−02 | 3.36994231e−01 |
| 2.94353634e−01 | 2.27913141e−01 | 1.79102883e−01 | 2.28011847e−01 |
| 2.14125156e−01 | 2.79984027e−01 | 2.26930037e−01 | 2.48753801e−01 |
| 8.22741091e−01 | 4.21693295e−01 | −1.89546511e−01 | 3.48754495e−01 |
| 4.17444527e−01 | 4.68769252e−01 | 2.99836814e−01 | 3.32618147e−01 |
| 9.59151745e−01 | 2.97742635e−01 | 7.70295203e−01 | 3.99344414e−01 |
| 4.62182164e−02 | 1.42127946e−01 | 1.00422159e−01 | 1.73843637e−01 |
| 2.96274781e−01 | 4.71519142e−01 | 3.56327653e−01 | 2.41771385e−01 |
| −4.49832007e−02 | 5.17988503e−01 | 5.48044503e−01 | −2.64934227e−02 |
| 3.38787958e−02 | 2.17879191e−01 | 7.21522942e−02 | 5.12586355e−01 |
| 7.32015027e−03 | 3.59692246e−01 | −2.60628402e−01 | 2.57856041e−01 |
| 2.85371784e−02 | 3.14161211e−01 | 4.19391960e−01 | 3.19654852e−01 |
| 6.10599816e−01 | −2.63634682e−01 | 2.71983504e−01 | 2.80718803e−01 |
| 8.24502930e−02 | 3.76482040e−01 | −3.01990837e−01 | 1.82065517e−01 |
| 5.14755189e−01 | −3.14518720e−01 | 6.54996634e−01 | −3.34012747e−01 |
| 5.81656757e−04 | 1.88224912e−01 | 4.95826840e−01 | 2.95176893e−01 |
| 2.58344337e−02 | −2.00417101e−01 | 2.95033932e−01 | 1.96352541e−01 |
| 2.20582381e−01 | 4.06837046e−01 | 3.71361107e−01 | 6.29912615e−01 |
| 2.89618313e−01 | −2.57798970e−01 | 5.22378802e−01 | 5.64421952e−01 |
| 3.16458821e−01 | −2.63675377e−02 | 2.01307893e−01 | 3.97540033e−02 |
| 2.47841910e−01 | 2.43362665e−01 | 5.11073291e−01 | 2.60172427e−01 |
| 2.91928679e−01 | 3.96823943e−01 | 1.28540576e−01 | 3.25851500e−01 |
| 6.73326969e−01 | 5.57112277e−01 | 5.56025743e−01 | 2.42622063e−01 |
| 9.38206166e−03 | 3.30646992e−01 | 5.62783360e−01 | 3.33183631e−02] |
| [1.18057251e−01 | −1.12717502e−01 | 3.34848650e−02 | −2.78338790e−01 |
| 2.69940138e−01 | 1.66281667e−02 | 1.29698720e−02 | 1.76181510e−01 |
| 2.39846125e−01 | 6.69661444e−03 | 1.63704947e−01 | 1.08965307e−01 |
| 6.35742992e−02 | 2.63911784e−01 | −1.00907691e−01 | 1.52623370e−01 |
| 2.68826276e−01 | −1.77990153e−01 | 2.60580570e−01 | 3.04781497e−01 |
| 4.09656197e−01 | 4.43713227e−03 | 7.94740617e−02 | 7.14494586e−02 |
| 6.38173699e−02 | 4.09577303e−02 | 2.94862360e−01 | 2.08070233e−01 |
| 3.74015003e−01 | 4.45438921e−01 | 4.92315441e−01 | 4.93406914e−02 |
| 6.08042181e−01 | 1.32844165e−01 | 9.39444378e−02 | 2.12884005e−02 |
| 3.28986079e−01 | 3.45523864e−01 | 1.11910440e−01 | 2.91306794e−01 |
| 3.97936225e−01 | 1.59823358e−01 | 5.58804125e−02 | −1.20986747e−01 |
| −6.15816824e−02 | 1.32310867e−01 | 4.76717293e−01 | 3.38367373e−01 |
| 3.97060931e−01 | 5.41135013e−01 | −9.76524800e−02 | 2.80939698e−01 |
| 1.26125917e−01 | 5.28258860e−01 | 3.92550081e−01 | 1.51532874e−01 |
| 4.65391092e−02 | 4.72650707e−01 | 9.15159211e−02 | −7.47579783e−02 |
| 1.45643845e−01 | 2.25519180e−01 | 3.25849384e−01 | 1.30550146e−01 |
| 2.71823537e−03 | 4.32689309e−01 | 3.83622557e−01 | 6.07258379e−01 |
| 2.97244102e−01 | 2.78658390e−01 | 8.04690272e−02 | 2.25670431e−02 |
| 1.02897838e−01 | 2.79453158e−01 | 9.65979695e−02 | 2.16452971e−01 |
| 2.70458579e−01 | 6.71242476e−02 | 1.23707719e−01 | −9.04794484e−02 |
| 2.75264271e−02 | −2.57081203e−02 | 2.77951419e−01 | 1.24643497e−01 |
| −5.37808500e−02 | −1.34404004e−01 | 1.52309671e−01 | −5.25731891e−02 |
| 2.88482964e−01 | 1.24952540e−01 | −1.10127300e−01 | 2.22067922e−01 |
| 5.06767273e−01 | 2.05296353e−01 | −3.44650932e−02 | 2.30455905e−01 |
| −1.87183395e−01 | −7.89803118e−02 | 4.68035281e−01 | 3.80154997e−01 |
| 2.51230627e−01 | 1.71090424e−01 | −5.89574315e−02 | 2.76077420e−01 |
| 2.48436972e−01 | 3.63339424e−01 | −3.97164188e−02 | 7.21766129e−02 |
| 1.29996508e−01 | 1.07215650e−01 | 2.64673501e−01 | 1.63342297e−01 |
| 2.26425543e−01 | 2.32380062e−01 | 3.46755773e−01 | 2.77740151e−01 |
| 1.75761178e−01 | 8.07489529e−02 | −2.04818159e−01 | 3.14835399e−01 |
| 1.65883243e−01 | 1.74009934e−01 | 2.34670654e−01 | 4.13330317e−01 |
| 1.92910299e−01 | 6.07960932e−01 | 4.32555765e−01 | −2.01595142e−01 |
| 3.40449214e−01 | 2.26687998e−01 | 1.59974575e−01 | 2.03867210e−03 |
| 1.33253530e−01 | 5.70587039e−01 | 2.57285595e−01 | 1.72107071e−01 |
| 1.00691125e−01 | 2.12714314e−01 | −1.37821943e−01 | 2.74970621e−01 |
| 7.76870474e−02 | −7.13692605e−02 | 1.08992711e−01 | −1.83418840e−01 |
| 9.83563140e−02 | 2.36892194e−01 | 1.63251340e−01 | 3.11766922e−01 |

TABLE $W_h^1$-continued

| | | | |
|---|---|---|---|
| 1.66442156e-01 | 5.16134441e-01 | 7.03053713e-01 | 2.37781659e-01 |
| 7.55295008e-02 | 1.19710356e-01 | 3.02965604e-02 | 2.09152237e-01 |
| -2.12697908e-01 | 4.51890111e-01 | 2.62825608e-01 | 3.72736692e-01 |
| 2.08933845e-01 | 3.51937443e-01 | 2.78322458e-01 | -8.93292427e-02 |
| -7.23123923e-02 | 6.09324537e-02 | 2.00550884e-01 | -2.58814186e-01 |
| 3.46710831e-01 | -3.78445506e-01 | -7.29944929e-02 | 3.81342828e-01 |
| 9.77752730e-02 | 1.03884027e-03 | 3.07439655e-01 | 1.51467606e-01 |
| -2.95928400e-01 | 1.58953786e-01 | 1.52514681e-01 | 2.89851516e-01 |
| 2.68645078e-01 | 5.45993328e-01 | 3.95170569e-01 | 5.49074002e-02 |
| 1.00099921e-01 | 4.02251273e-01 | 8.83785114e-02 | 6.44609094e-01 |
| 3.06228131e-01 | 8.47533345e-02 | 1.50204167e-01 | 1.79457054e-01 |
| -1.83588967e-01 | 9.06786174e-02 | 5.86965308e-02 | 2.08896160e-01 |
| -5.31423539e-02 | 4.78310101e-02 | 4.10529822e-01 | 1.54847443e-01 |
| 1.69013083e-01 | -6.59961347e-03 | 1.20281711e-01 | -7.19767362e-02 |
| 6.98052272e-02 | 3.44435900e-01 | 3.36665250e-02 | -1.20293006e-01 |
| -4.90563363e-02 | 2.46601596e-01 | 2.58493990e-01 | -4.02094238e-02 |
| 2.01408297e-01 | 6.43480942e-02 | 4.75480020e-01 | 4.21245284e-02 |
| 3.14956844e-01 | 9.26256478e-02 | 2.00764641e-01 | 1.48426011e-01 |
| 1.41696990e-01 | 2.62895912e-01 | 4.12900120e-01 | -1.12043418e-01 |
| 2.58895289e-02 | 1.48605257e-01 | -1.32995024e-01 | 9.25094336e-02 |
| 1.69982523e-01 | 9.75040570e-02 | -2.63411347e-02 | 2.42614493e-01 |
| 3.66454244e-01 | -1.27919838e-01 | 3.67117226e-01 | -2.08471656e-01 |
| 1.12529375e-01 | -2.59151816e-01 | -2.04541355e-01 | -1.56920664e-02 |
| 4.69021872e-02 | -1.67173687e-02 | 1.11448273e-01 | 5.64675666e-02 |
| 1.96899995e-01 | 1.45124421e-01 | 4.14962918e-01 | 4.54384014e-02 |
| 1.04157865e-01 | -2.53229618e-01 | 3.71704847e-02 | 7.42032453e-02 |
| 6.52564839e-02 | 3.32961142e-01 | 1.25498071e-01 | 2.26516306e-01] |
| [1.34961486e-01 | 1.93218842e-01 | 3.26170288e-02 | 2.15465818e-02 |
| 2.75909483e-01 | 7.59108424e-01 | 3.44306380e-01 | -8.00542459e-02 |
| 1.38424024e-01 | 4.69263136e-01 | 4.18732822e-01 | 1.41144067e-01 |
| 1.10476784e-01 | 2.21084341e-01 | -3.65253866e-01 | -1.98338673e-01 |
| -7.20959604e-02 | 4.89086583e-02 | 2.63236791e-01 | 3.32975835e-01 |
| -3.79849877e-03 | 4.49507654e-01 | 5.02807021e-01 | 6.87195063e-01 |
| -1.06699407e-01 | 2.40011036e-01 | 4.46406066e-01 | 1.89102337e-01 |
| 1.17672525e-01 | 1.21159982e-02 | 2.23288178e-01 | 7.85262510e-02 |
| 2.42550075e-01 | -1.05624743e-01 | -3.30180526e-01 | 3.22226107e-01 |
| 5.44473708e-02 | 2.81355590e-01 | 6.44585565e-02 | -2.72664249e-01 |
| 6.33074120e-02 | 3.80290538e-01 | 1.17988609e-01 | 4.27764654e-02 |
| 2.88374066e-01 | 2.82993346e-01 | 1.02608383e-01 | 1.27756357e-01 |
| -3.17511410e-01 | 2.48259291e-01 | -2.73905415e-02 | 2.98804194e-01 |
| 1.72566816e-01 | -1.09597733e-02 | -3.09148461e-01 | 1.86240929e-03 |
| 1.57314748e-01 | 6.98606148e-02 | 1.75138950e-01 | 1.70348406e-01 |
| 2.48934910e-01 | 3.75876069e-01 | 1.35070264e-01 | 2.26541191e-01 |
| -9.95908305e-02 | -1.67535730e-02 | 9.53531731e-03 | -1.42471800e-02 |
| 2.57201523e-01 | 6.38160348e-01 | 4.85875338e-01 | 4.83031929e-01 |
| -4.53549027e-02 | 6.55283332e-02 | -5.41042769e-01 | 1.73305571e-01 |
| 5.57661772e-01 | 1.37955517e-01 | 3.11992466e-01 | -3.93463969e-02 |
| 1.37885630e-01 | 1.63249955e-01 | 8.98538679e-02 | -2.10953727e-02 |
| -1.86457515e-01 | 3.13381463e-01 | -6.58826903e-02 | 1.44987017e-01 |
| 1.53773129e-01 | 5.71903475e-02 | 6.70124264e-01 | 3.41635197e-01 |
| 9.85696074e-03 | 3.71126048e-02 | -5.53765893e-02 | 6.66427076e-01 |
| -3.84132594e-01 | 1.58090860e-01 | -9.66813602e-03 | 1.73088998e-01 |
| 5.06179988e-01 | 2.29046941e-01 | 8.79986733e-02 | 2.69213468e-02 |
| 9.47500095e-02 | 1.82458282e-01 | -5.80734760e-02 | -3.22184674e-02 |
| 6.85961246e-02 | 3.76577795e-01 | 2.49069631e-01 | -3.74116339e-02 |
| 4.93262261e-01 | 9.94217396e-03 | 3.12806189e-01 | -2.01992709e-02 |
| 3.36711287e-01 | -3.34010944e-02 | 5.16310036e-01 | -3.23122263e-01 |
| -3.28252226e-01 | -1.37237459e-01 | -1.25637844e-01 | 5.02492547e-01 |
| 5.03012300e-01 | -1.12475693e-01 | 2.35930383e-01 | -2.81779885e-01 |
| -1.06935389e-01 | 2.05100134e-01 | 3.59996468e-01 | 7.61710405e-01 |
| -1.08961470e-01 | -1.18317530e-01 | -3.07138652e-01 | -1.22225963e-01 |
| 2.60945499e-01 | 1.83045506e-01 | 1.09491348e-01 | 2.90079638e-02 |
| 1.10997014e-01 | 2.19792783e-01 | 3.59086871e-01 | 2.73422003e-01 |
| -2.20601127e-01 | -2.42557526e-01 | 2.92722553e-01 | -2.35672016e-03 |
| 2.67998010e-01 | -2.08890885e-01 | -2.40215734e-01 | 1.19940057e-01 |
| -7.20360270e-03 | 1.72069758e-01 | -1.41794890e-01 | 1.21472463e-01 |
| -5.94051659e-02 | -2.21526716e-01 | 3.25529367e-01 | 4.15682793e-01 |
| -3.05021346e-01 | 1.17754862e-01 | 2.49237478e-01 | 1.31570578e-01 |
| -1.20264739e-02 | -1.04257390e-01 | -1.13931589e-01 | 1.22461751e-01 |
| 4.15264845e-01 | -1.28978312e-01 | 3.74942988e-01 | 2.74971515e-01 |
| 4.54253018e-01 | -1.12677224e-01 | 5.25787771e-01 | 6.98145404e-02 |
| 2.18215268e-02 | -1.00348450e-01 | 7.11206421e-02 | 2.82748073e-01 |
| 1.93314418e-01 | -2.42131740e-01 | 1.87975079e-01 | 8.09437856e-02 |
| 1.30907565e-01 | 1.29976273e-01 | 1.72360420e-01 | -8.68556723e-02 |
| -5.01587331e-01 | 1.07220829e-01 | 2.24775180e-01 | 4.21225786e-01 |
| 2.80083537e-01 | 1.72262043e-02 | -2.78742760e-01 | 4.98419434e-01 |
| 5.09046540e-02 | 5.90308607e-01 | 3.11961547e-02 | 2.69651338e-02 |
| 2.90989578e-02 | -2.18690872e-01 | 2.39777505e-01 | -1.55681735e-02 |
| 2.07657203e-01 | -2.08230633e-02 | 1.88311398e-01 | 1.17169768e-01 |
| 1.18098326e-01 | 3.41675580e-01 | -2.54273742e-01 | 7.58079486e-03 |

TABLE $W_h^1$-continued

| | | | |
|---|---|---|---|
| 1.82424918e−01 | −2.56506115e−01 | −1.57366153e−02 | 4.80752766e−01 |
| 1.49869934e−01 | 3.00183356e−01 | 2.94644505e−01 | −2.04593226e−01 |
| −1.78361759e−01 | 9.83715653e−02 | −4.21024896e−02 | 1.38499856e−01 |
| 4.23502296e−01 | 1.35328606e−01 | 9.75665376e−02 | 4.99933958e−01 |
| 8.59530151e−01 | −1.32410526e−01 | 4.68109667e−01 | 8.68579298e−02 |
| 8.88530631e−03 | −2.79589295e−01 | 3.28449160e−01 | −2.24614128e−01 |
| 2.13874015e−03 | 5.95802546e−01 | −3.99911776e−02 | −4.95032184e−02 |
| 3.55304182e−01 | 4.89470586e−02 | 3.68597239e−01 | 2.52539814e−01 |
| 3.30610693e−01 | 4.03495222e−01 | 2.04627141e−01 | 2.45454326e−01 |
| −5.86054847e−02 | 4.28642988e−01 | −3.19729418e−01 | −5.33214025e−02 |
| −1.91980898e−01 | 2.65035897e−01 | 1.46848559e−01 | 3.38230699e−01] |
| [1.45683914e−01 | 2.37749577e−01 | 6.01679571e−02 | 3.09689820e−01 |
| 2.24971890e−01 | 2.14618966e−01 | 2.07039580e−01 | 1.17852904e−01 |
| 3.55432838e−01 | 2.60542214e−01 | 4.45248783e−01 | −6.13437630e−02 |
| 2.26123631e−01 | 1.87099338e−01 | 1.11345332e−02 | 1.45033360e−01 |
| −2.54440345e−02 | 1.35762155e−01 | 5.79518020e−01 | 1.87343478e−01 |
| 2.89460421e−01 | 6.32616431e−01 | 2.38709271e−01 | −8.48689973e−02 |
| 6.28710151e−01 | 2.09969908e−01 | 2.56659895e−01 | −6.46288618e−02 |
| 8.89856834e−03 | 4.33852114e−02 | 2.46512175e−01 | 1.19268656e−01 |
| 2.20120996e−01 | 1.18910626e−01 | 3.64661843e−01 | 7.79797062e−02 |
| −3.94943535e−02 | 6.64985701e−02 | 3.38716954e−01 | 2.55045176e−01 |
| 3.44175957e−02 | 1.77232772e−01 | 4.38319519e−02 | 1.61275804e−01 |
| 3.21062118e−01 | 2.61239171e−01 | 9.84145626e−02 | −4.91282009e−02 |
| 3.49794626e−01 | 3.36912364e−01 | 1.81262180e−01 | 6.22610413e−02 |
| 9.03142393e−02 | 5.23200274e−01 | −2.73044348e−01 | 2.90499479e−01 |
| 1.77167088e−01 | 2.50905484e−01 | 2.42798239e−01 | 3.63985986e−01 |
| 2.40855157e−01 | 2.66162008e−01 | 1.11338466e−01 | 1.23187289e−01 |
| 1.27911538e−01 | 1.95599616e−01 | −8.02107677e−02 | 2.79421955e−01 |
| 1.72970533e−01 | 1.72601357e−01 | 1.10180847e−01 | 1.24439029e−02 |
| 1.47961870e−01 | 2.76187122e−01 | −1.65527686e−01 | 2.01873243e−01 |
| 6.76120818e−01 | 2.26692677e−01 | 2.59885967e−01 | 1.10563107e−01 |
| 3.31295401e−01 | 4.80513781e−01 | 2.67835051e−01 | 1.38428956e−01 |
| 2.54548788e−01 | 1.28976349e−02 | −2.24972926e−02 | 1.57951906e−01 |
| −9.02875233e−03 | 1.45310640e−01 | 1.96354359e−01 | −2.35630050e−02 |
| 1.98430791e−01 | 2.57164448e−01 | 2.77914762e−01 | 1.13060817e−01 |
| 3.10548265e−02 | 4.16350402e−02 | 3.09972882e−01 | 2.14344069e−01 |
| 2.51491189e−01 | 1.39443785e−01 | 3.03921878e−01 | −3.22856784e−01 |
| 1.41346067e−01 | 4.46154743e−01 | 2.54227787e−01 | 1.70186713e−01 |
| 1.21359721e−01 | 4.21975017e−01 | 5.21875203e−01 | 2.87838072e−01 |
| 4.36275415e−02 | −3.31304669e−02 | 1.69380561e−01 | 4.00762618e−01 |
| 4.55249369e−01 | −2.29692534e−01 | 5.43417275e−01 | 3.00573796e−01 |
| 3.46318930e−01 | 1.73670068e−01 | 1.82525024e−01 | 4.01213676e−01 |
| 2.90513188e−01 | 1.35929227e−01 | 8.17565024e−01 | 2.40721315e−01 |
| 3.85403961e−01 | 1.79710343e−01 | −4.79772724e−02 | 4.88883674e−01 |
| 2.01812446e−01 | −2.87591647e−02 | 2.43299574e−01 | 1.58868939e−01 |
| −4.52114567e−02 | −3.29178721e−02 | 1.56223848e−01 | 2.77320147e−01 |
| 2.40550086e−01 | 4.64456640e−02 | 2.57297814e−01 | 9.78417695e−02 |
| 2.34123498e−01 | 5.32342255e−01 | −2.33068643e−03 | 2.09828347e−01 |
| −3.30442905e−01 | 4.09477264e−01 | 4.26105827e−01 | 9.99998376e−02 |
| 1.87330052e−01 | 3.86010506e−03 | 1.67419419e−01 | 9.28543583e−02 |
| −9.28807408e−02 | 1.63734540e−01 | 3.55076119e−02 | 2.12585434e−01 |
| 2.34435260e−01 | 1.75501227e−01 | 1.08913876e−01 | 1.14760511e−01 |
| −4.15390506e−02 | 3.76457542e−01 | 3.01781874e−02 | 1.25578105e−01 |
| 1.27296627e−01 | 1.26719788e−01 | 1.24961041e−01 | 2.25030780e−01 |
| −1.15794100e−01 | 1.46373942e−01 | 2.06212744e−01 | 5.06353557e−01 |
| 1.85126692e−01 | 6.69136792e−02 | 1.85946241e−01 | 2.94015735e−01 |
| 3.63260627e−01 | 1.76795781e−01 | 3.04843128e−01 | 3.30434829e−01 |
| 2.65250057e−01 | 1.12025939e−01 | 7.42826909e−02 | 2.26366460e−01 |
| 6.04175963e−02 | −8.67019687e−03 | 6.52931854e−02 | 2.65183330e−01 |
| 3.62614989e−02 | 2.88511068e−01 | 2.56540269e−01 | 1.32499024e−01 |
| −5.03668897e−02 | −2.91350454e−01 | 1.45324141e−01 | 1.65026218e−01 |
| 1.83143109e−01 | 3.02151054e−01 | −1.72952741e−01 | 2.18179688e−01 |
| 1.47986636e−01 | 3.68275613e−01 | 1.11437611e−01 | 1.35086343e−01 |
| 4.28579479e−01 | 5.36715031e−01 | 4.11073387e−01 | 3.25824916e−01 |
| 2.64432162e−01 | −1.44395366e−01 | −1.59993451e−02 | 3.01283270e−01 |
| 8.63005593e−02 | −2.78588951e−01 | 2.59250462e−01 | 2.26147294e−01 |
| 2.77934879e−01 | 2.56983429e−01 | 9.36512724e−02 | 1.46544546e−01 |
| 3.72419477e−01 | −7.41273025e−03 | 3.31066161e−01 | 3.04394364e−01 |
| 2.08164573e−01 | −5.42690605e−02 | 1.69800341e−01 | 2.98816681e−01 |
| 3.90729785e−01 | 3.13797891e−02 | 3.44782829e−01 | 1.22713231e−01 |
| 1.16113126e−01 | −3.08545589e−01 | −1.59081027e−01 | −3.78765464e−02 |
| 4.42377388e−01 | 1.42661631e−02 | 2.61596087e−02 | 2.54328791e−02 |
| 5.89499950e−01 | 1.39314532e−01 | 1.22728750e−01 | 1.36504462e−02 |
| 1.93817884e−01 | 1.00237370e−01 | 5.04871905e−01 | 2.10458022e−02 |
| 3.29471946e−01 | 1.97796151e−01 | 3.60964358e−01 | −1.86217483e−02] |
| [3.29236448e−01 | −3.42349447e−02 | 9.50968206e−01 | 4.12637979e−01 |
| 3.80298883e−01 | 3.68729308e−02 | 2.92355388e−01 | 5.99623740e−01 |
| 4.52158362e−01 | −1.69629931e−01 | −1.34455130e−01 | −4.59008425e−01 |
| 8.04976225e−02 | 6.46981359e−01 | −2.56477892e−01 | 6.59047887e−02 |
| −1.66374430e−01 | −2.64513679e−02 | 2.35450670e−01 | 5.01483440e−01 |

TABLE $W_h^1$-continued

| | | | |
|---|---|---|---|
| −8.78553316e−02 | −1.13873594e−01 | 3.55006605e−02 | 3.25691789e−01 |
| −3.31788868e−01 | 5.34742534e−01 | 4.40397322e−01 | 4.92316931e−01 |
| −3.95205051e−01 | 5.32601178e−01 | 4.99595493e−01 | 8.78906175e−02 |
| 5.10126948e−01 | 7.62423933e−01 | −4.14866716e−01 | −1.77300453e−01 |
| −1.39237056e−03 | 3.76843989e−01 | 2.57070512e−02 | 9.55785513e−01 |
| 9.13727403e−01 | 4.97393429e−01 | −3.69356990e−01 | −2.37108335e−01 |
| 2.27815375e−01 | 5.63254692e−02 | 5.18370748e−01 | −2.15403184e−01 |
| 4.42258447e−01 | 3.60418022e−01 | 2.27687612e−01 | −1.63507342e−01 |
| 8.97864550e−02 | 3.92930150e−01 | 2.05763027e−01 | 5.84751666e−01 |
| −3.08971226e−01 | −2.44972222e−02 | 5.43102622e−01 | −5.26757419e−01 |
| −2.39983411e−03 | 1.01694536e−00 | 1.37184039e−01 | 4.59651023e−01 |
| −7.72694498e−02 | 6.96208775e−01 | 5.99992692e−01 | 9.49732438e−02 |
| 1.02147453e−01 | −2.87713170e−01 | 4.34604704e−01 | −2.39140451e−01 |
| 3.19581121e−01 | −1.36556581e−01 | 4.70847845e−01 | 2.42041260e−01 |
| 3.91144454e−01 | −9.77333486e−02 | 3.99567723e−01 | −8.99172947e−02 |
| −2.15025261e−01 | 4.53966409e−01 | 2.12115750e−01 | −7.54847983e−03 |
| −4.73594546e−01 | −1.87955983e−02 | 2.91466326e−01 | 7.94463634e−01 |
| 5.38963139e−01 | 3.06248963e−01 | −1.44246012e−01 | −1.35363251e−01 |
| 2.32248202e−01 | 6.12128615e−01 | −3.68713170e−01 | 6.35344684e−01 |
| −2.64159262e−01 | −5.42552650e−01 | −3.75396729e−01 | 4.22252119e−01 |
| 1.00343466e−00 | 4.29751605e−01 | −4.35566790e−02 | 1.52471110e−01 |
| 1.84103847e−01 | 4.45180058e−01 | 6.59200996e−02 | 1.06474414e−01 |
| 9.04230118e−01 | 4.57052141e−01 | 6.21714175e−01 | 2.99659878e−01 |
| 1.70864999e−01 | 5.23656964e−01 | −2.58820266e−01 | −9.50189173e−01 |
| 4.13634449e−01 | 3.52799147e−01 | 2.76092082e−01 | −7.80184893e−03 |
| 5.70368826e−01 | 2.78954983e−01 | 5.04220426e−01 | 1.62780017e−01 |
| 7.25630894e−02 | 6.93839312e−01 | 2.87356347e−01 | 7.21251130e−01 |
| 7.21794367e−01 | 1.29504561e−01 | 7.56370604e−01 | 3.27527046e−01 |
| 2.54461646e−01 | 1.14063472e−01 | 1.97542399e−01 | −5.00531010e−02 |
| 5.34727335e−01 | −1.49872676e−01 | 2.02469483e−01 | 5.73246241e−01 |
| −1.00778952e−01 | 4.93783236e−01 | 3.90963972e−01 | −1.06351428e−01 |
| 3.94825816e−01 | 1.89739957e−01 | −9.32956301e−03 | 3.93419951e−01 |
| 3.51250708e−01 | 2.65360549e−02 | 1.15077741e−01 | 1.43417642e−01 |
| 1.54584557e−01 | 8.03999305e−01 | −3.22597176e−01 | 2.52934366e−01 |
| 5.97593248e−01 | −8.48129168e−02 | 3.13348882e−02 | 6.17039979e−01 |
| 4.84971255e−01 | 5.72377384e−01 | 8.98100078e−01 | 6.81809843e−01 |
| 2.34614819e−01 | 1.99005827e−01 | 5.16124010e−01 | 1.35702953e−01 |
| −1.89009860e−01 | 3.85484904e−01 | 4.18785453e−01 | −3.99316728e−01 |
| 5.97978413e−01 | 3.00748140e−01 | 4.20518696e−01 | −1.46558145e−02 |
| 6.57504916e−01 | −2.37957433e−01 | −5.18625736e−01 | 1.43729210e−01 |
| 6.91332400e−01 | 3.77959490e−01 | 7.81168282e−01 | 3.79560739e−01 |
| 5.51009953e−01 | 8.96096677e−02 | −8.02615192e−03 | 2.13420153e−01 |
| 4.20853108e−01 | 8.72651860e−02 | 1.61948383e−01 | 5.19649506e−01 |
| 9.38345671e−01 | 5.56580007e−01 | −1.18669257e−01 | −1.47513956e−01 |
| 3.44459116e−01 | 4.61586118e−01 | 1.30700782e−01 | −3.94341826e−01 |
| 1.58264473e−01 | 3.64699900e−01 | 4.40753073e−01 | 3.92971903e−01 |
| −1.98381692e−02 | 5.95861971e−01 | 5.43109238e−01 | −9.86960977e−02 |
| 3.79247934e−01 | −2.17810459e−02 | 4.76596802e−01 | 2.05797628e−01 |
| −1.65998697e−01 | 2.17632264e−01 | 6.68918490e−01 | −1.46666750e−01 |
| 3.83304566e−01 | 4.71680798e−03 | −1.18072562e−01 | 3.54260176e−01 |
| −2.15071719e−02 | 2.30252907e−01 | 1.44230664e−01 | −1.73920274e−01 |
| −2.08689701e−02 | −3.84642273e−01 | 2.77625293e−01 | 2.95929581e−01 |
| 5.28849959e−01 | −1.03176862e−01 | 9.97064888e−01 | 1.75516859e−01 |
| 2.62330413e−01 | 4.42821272e−01 | 5.82181334e−01 | 2.82623351e−01 |
| 1.33594172e−02 | 1.94465682e−01 | 2.58251995e−01 | 4.94742841e−01 |
| 7.44759338e−03 | −5.62110424e−01 | −1.55472085e−01 | 6.50893688e−01 |
| 5.58229387e−01 | −1.10153154e−01 | 1.73856020e−01 | 1.42168909e−01 |
| 5.51832139e−01 | −1.26947030e−01 | −3.80120635e−01 | 1.89229369e−01 |
| 1.75776090e−02 | 6.41599476e−01 | −1.50615633e−01 | −5.80951273e−01] |
| [3.20077151e−01 | 3.06105018e−01 | 2.48843227e−02 | −2.86740959e−01 |
| 2.63636351e−01 | −3.70805897e−02 | −7.94673339e−03 | 1.57974750e−01 |
| 2.76939183e−01 | 2.19339177e−01 | −5.24507575e−02 | 6.37902990e−02 |
| 4.32515323e−01 | 2.45499667e−02 | 3.57621551e−01 | 1.33184209e−01 |
| 2.39175394e−01 | 1.33032665e−01 | 7.28534907e−02 | 7.40308641e−03 |
| 3.77417266e−01 | −6.16024323e−02 | 1.12289764e−01 | 1.40355021e−01 |
| 3.47298712e−01 | 4.08458412e−02 | −4.19982046e−01 | 3.03226739e−01 |
| 1.07424989e−01 | −2.48204753e−01 | 1.28924340e−01 | −3.46803576e−01 |
| 1.88604221e−01 | 6.74920082e−02 | 1.93617418e−01 | 2.12692842e−01 |
| −2.63058633e−01 | 1.83839470e−01 | −5.30956946e−02 | 9.85629782e−02 |
| −2.45244995e−01 | 1.28505915e−01 | −2.37421423e−01 | 5.31391323e−01 |
| −6.69090599e−02 | 1.48801640e−01 | 4.21277583e−01 | 4.66782972e−01 |
| −9.96774659e−02 | 3.67441773e−02 | 1.43033281e−01 | 3.90446335e−01 |
| −7.43060708e−02 | −1.53806448e−01 | 4.78856951e−01 | 3.26724708e−01 |
| −6.13966882e−02 | −5.85760921e−02 | 2.23916858e−01 | 6.02066051e−04 |
| 4.88483980e−01 | 2.15834320e−01 | −1.18472539e−01 | −1.78000182e−01 |
| 1.26680449e−01 | 9.96879861e−02 | 1.61533311e−01 | 3.58751535e−01 |
| 3.28868866e−01 | 1.81554943e−01 | −9.57732648e−02 | −1.44096136e−01 |
| −2.05266271e−02 | 2.65401244e−01 | 1.05957687e−01 | −3.78657803e−02 |
| −8.08771178e−02 | 4.53053862e−01 | 3.92528921e−01 | 4.09975983e−02 |
| 1.08170584e−01 | 5.51338904e−02 | 2.87011921e−01 | 4.03411593e−03 |

TABLE $W_h^1$-continued

| | | | |
|---|---|---|---|
| 2.78864235e-01 | 1.35044515e-01 | 3.42193186e-01 | -2.56932788e-02 |
| 2.00284421e-01 | 2.69711167e-01 | 4.17837232e-01 | 3.65502536e-01 |
| 4.61535960e-01 | 2.58655608e-01 | 2.86156714e-01 | -5.01066521e-02 |
| 8.90795067e-02 | -7.88526312e-01 | 2.51991719e-01 | 3.58969182e-01 |
| -1.91803709e-01 | 3.26185338e-02 | -1.12348996e-01 | -1.60823278e-02 |
| 1.14203811e-01 | 2.90233403e-01 | -1.36162862e-01 | -4.37740795e-02 |
| 3.07032555e-01 | -2.06712093e-02 | 3.99043679e-01 | 1.27767697e-01 |
| -1.62240889e-04 | -6.22968674e-02 | 3.27857792e-01 | 1.04591511e-01 |
| 2.17778012e-02 | -5.04398309e-02 | 7.07212314e-02 | -4.70801175e-01 |
| 1.16837248e-01 | 1.22839138e-01 | -5.75992232e-03 | 1.58879831e-01 |
| -9.08102989e-02 | 1.71674386e-01 | -2.16738567e-01 | 2.74864864e-02 |
| -2.24614024e-01 | 1.70180380e-01 | -8.14037994e-02 | 1.44837424e-01 |
| -1.13405734e-01 | -1.84113495e-02 | -5.64200878e-02 | 1.84506327e-01 |
| 1.53405815e-01 | 1.23564743e-01 | -3.48089859e-02 | -1.71726450e-01 |
| 8.40042904e-02 | 1.41587839e-01 | 3.10654312e-01 | 1.14969194e-01 |
| 3.80787216e-02 | 2.23981485e-01 | -2.97013335e-02 | 4.03096557e-01 |
| 1.84952654e-01 | 4.95199770e-01 | 3.57582331e-01 | -3.55285168e-01 |
| 1.33119136e-01 | 2.63747126e-01 | 6.31609410e-02 | -3.52238715e-01 |
| 1.45126671e-01 | -6.33312464e-02 | 1.21122703e-01 | 5.87861799e-03 |
| 3.98254246e-01 | 1.58741325e-01 | 5.91606438e-01 | 4.42864560e-02 |
| 1.10179484e-01 | 1.63426489e-01 | 7.58680180e-02 | -2.11533442e-01 |
| 3.26231271e-01 | -1.40631586e-01 | 1.58624798e-01 | 3.65514874e-01 |
| 1.91455171e-01 | 1.49983734e-01 | 1.08053625e-01 | 1.27282903e-01 |
| -4.18101884e-02 | 8.55588093e-02 | 1.23473160e-01 | 9.92318317e-02 |
| 9.98318642e-01 | 3.59862417e-01 | 8.07005167e-02 | 4.96784113e-02 |
| 1.09085500e-01 | 2.86927521e-01 | 2.44833648e-01 | -4.77300882e-02 |
| 2.16702655e-01 | -2.54462939e-02 | -1.61699340e-01 | 4.53322798e-01 |
| 5.11524230e-02 | -1.17388871e-02 | 1.70427337e-02 | 3.31379145e-01 |
| 2.56808698e-01 | -4.20285277e-02 | 2.42268279e-01 | -4.61111255e-02 |
| 2.23817661e-01 | 4.56670135e-01 | 1.48851141e-01 | -3.16791981e-01 |
| 1.96213126e-01 | 3.61829400e-01 | 3.17898169e-02 | 1.53341264e-01 |
| 1.20217102e-02 | -1.81702614e-01 | 3.60657662e-01 | 1.53606698e-01 |
| -1.27457395e-01 | -1.16555475e-01 | -2.89384216e-01 | 2.82910883e-01 |
| 2.44821772e-01 | 1.24458633e-01 | -1.12349860e-01 | -3.03564161e-01 |
| 2.25626498e-01 | 2.12509066e-01 | 9.48596448e-02 | 5.00984304e-03 |
| 1.68971092e-01 | -1.86910369e-02 | 2.99237818e-01 | -1.56049222e-01 |
| -2.10041538e-01 | 2.74981350e-01 | 1.59158558e-01 | -1.68267608e-01 |
| -2.19656304e-01 | 1.57718897e-01 | 3.66991013e-02 | 1.53804749e-01 |
| 2.85025150e-01 | -1.02341818e-02 | 2.34728884e-02 | 2.18713898e-02 |
| 4.99145120e-01 | 5.49025238e-02 | 1.81609631e-01 | -2.33724967e-01 |
| -3.18921879e-02 | 9.16917697e-02 | 1.02383360e-01 | 2.31249869e-01 |
| 4.60084617e-01 | -7.71718845e-02 | -9.59806144e-02 | -1.46365345e-01 |
| 7.87397730e-05 | -5.95043134e-03 | 1.79649338e-01 | 1.59414694e-01] |
| [-3.37732621e-02 | 8.33202600e-02 | 5.10100927e-03 | 2.45865241e-01 |
| 7.61039257e-02 | 8.40209723e-02 | -1.16605580e-01 | -2.39297017e-01 |
| 5.58607727e-02 | -1.02213658e-02 | 3.17166716e-01 | 1.96166918e-01 |
| 1.76299125e-01 | 2.37725794e-01 | 2.07177605e-02 | 7.48187825e-02 |
| 1.13515466e-01 | 1.42567202e-01 | 3.80035080e-02 | -1.20148756e-01 |
| 2.10019156e-01 | 3.72779220e-01 | 5.56744218e-01 | 2.51071453e-01 |
| 3.62618834e-01 | 4.77950089e-02 | 3.07797879e-01 | 4.43523191e-01 |
| 1.66787788e-01 | 8.10401887e-02 | 2.37668872e-01 | -1.19466092e-02 |
| 2.78689265e-01 | -2.52430260e-01 | 3.06410313e-01 | 1.21213496e-01 |
| -1.87430698e-02 | 4.38195229e-01 | 4.23190087e-01 | -8.35166276e-02 |
| 3.30520183e-01 | -1.22973576e-01 | 2.32839972e-01 | 5.86430252e-01 |
| -2.64984518e-02 | 2.42343888e-01 | -8.30030814e-02 | 3.05284321e-01 |
| 2.25182503e-01 | 3.29282016e-01 | 2.64218688e-01 | -6.70706108e-02 |
| 1.30370811e-01 | -1.72493374e-03 | 2.97553483e-02 | -1.00814834e-01 |
| 1.97802395e-01 | 2.10696131e-01 | 7.81167150e-02 | 2.88430333e-01 |
| -1.53318301e-01 | 3.06531429e-01 | 4.59771007e-02 | 2.46274903e-01 |
| 4.37706679e-01 | 8.03887010e-01 | 8.01063478e-02 | -8.18237290e-03 |
| 1.75836712e-01 | 5.04580915e-01 | 1.11394748e-01 | 5.48352242e-01 |
| 7.16481134e-02 | 3.83684337e-01 | 4.54459786e-02 | 6.16986811e-01 |
| 3.60881299e-01 | 1.01955302e-01 | -7.95495138e-02 | 1.27289414e-01 |
| 5.26657254e-02 | 5.32642126e-01 | 1.93306338e-02 | -5.64889759e-02 |
| 1.71575218e-01 | 2.96601087e-01 | -7.73664191e-03 | 9.91480723e-02 |
| 1.98654279e-01 | 1.41373605e-01 | 6.01365827e-02 | 1.84236288e-01 |
| 2.02814117e-01 | 1.26063554e-02 | 1.46931991e-01 | 1.70965165e-01 |
| 2.91542083e-01 | 1.02941282e-01 | 2.05858558e-01 | 1.96077913e-01 |
| 5.15262336e-02 | 4.07194614e-01 | 2.42069900e-01 | 1.53925985e-01 |
| -2.05724195e-01 | 1.14100322e-01 | -6.35684351e-04 | 3.95168573e-01 |
| 2.23385125e-01 | 4.08559620e-01 | 1.67963758e-01 | 1.30453080e-01 |
| 1.65727362e-01 | 3.62841822e-02 | 3.44220459e-01 | 1.21751465e-01 |
| 8.52344185e-02 | 3.47427651e-02 | -1.30830780e-01 | 4.22594398e-01 |
| -1.52738407e-01 | 7.93048069e-02 | -6.95495903e-02 | -2.11571828e-02 |
| 3.51948947e-01 | -1.34731561e-01 | -2.60287225e-01 | 2.67943777e-01 |
| 7.59392902e-02 | -6.63006455e-02 | 2.12718204e-01 | 2.34032512e-01 |
| 5.59346452e-02 | 4.98500019e-01 | 2.72995643e-02 | 7.16166198e-02 |
| 2.39774376e-01 | 4.56353724e-02 | 6.94673419e-01 | 4.21949863e-01 |
| 3.87556791e-01 | -1.43829107e-01 | 1.79385617e-01 | 2.17802972e-01 |
| 4.71665757e-03 | 1.99336209e-03 | 1.87246084e-01 | -1.29369676e-01 |

TABLE $W_h^1$-continued

| | | | |
|---|---|---|---|
| −5.68431914e−02 | 2.20489874e−01 | −1.07365601e−01 | −1.71475634e−01 |
| 6.40201330e−01 | 1.70452625e−01 | 1.88475654e−01 | −1.68455392e−02 |
| 2.57717252e−01 | 2.13142782e−01 | 1.48681775e−01 | 2.00012565e−01 |
| 3.01291227e−01 | −3.76520935e−03 | −1.55827910e−01 | 2.44534358e−01 |
| 2.51332790e−01 | 6.33787215e−02 | 2.56757081e−01 | 1.30082116e−01 |
| 2.46339813e−01 | 3.26520503e−01 | 8.73745680e−02 | 2.72336304e−01 |
| 2.92737544e−01 | 2.09515244e−01 | 1.46515757e−01 | 7.64145404e−02 |
| 1.78536549e−01 | 3.04773629e−01 | 1.47357941e−01 | 7.38339722e−02 |
| 2.80521095e−01 | 4.53709699e−02 | 5.21944985e−02 | −1.42852038e−01 |
| 9.64110121e−02 | −6.32749498e−02 | 1.69450700e−01 | 4.64305192e−01 |
| −2.39312537e−02 | 3.36695582e−01 | 5.22835732e−01 | 2.42469415e−01 |
| 9.19275079e−03 | 2.10436493e−01 | −3.30065638e−02 | 1.67428762e−01 |
| 1.35990813e−01 | 3.04700166e−01 | 7.57199079e−02 | 1.33742183e−01 |
| −1.67988867e−01 | 2.22374067e−01 | 4.28378815e−03 | 1.30399480e−01 |
| 1.73493803e−01 | −7.05293333e−03 | 6.34563714e−02 | −4.14912961e−02 |
| 2.12110132e−01 | 1.45509034e−01 | −7.12391660e−02 | 1.03640690e−01 |
| 3.41032207e−01 | −8.13684165e−02 | −1.55941457e−01 | 3.86028774e−02 |
| −2.44359508e−01 | −1.34546712e−01 | −4.92942594e−02 | 4.01319385e−01 |
| 2.00411037e−01 | −1.26306862e−01 | 2.14743972e−01 | 3.53098422e−01 |
| 3.57600838e−01 | 8.66098851e−02 | −1.11238688e−01 | 3.21766764e−01 |
| 2.60232300e−01 | 2.73576796e−01 | −1.98835582e−02 | 1.45399973e−01 |
| 1.61739171e−01 | −7.58792534e−02 | −1.45418867e−01 | 2.88526148e−01 |
| −1.24229826e−01 | −3.27772528e−01 | −2.44758483e−02 | 2.13522315e−02 |
| 3.46716434e−01 | 7.29180053e−02 | 3.01090389e−01 | 2.85290271e−01 |
| 2.22473666e−01 | −1.19929358e−01 | −1.08319536e−01 | 1.83380008e−01 |
| 5.29548712e−03 | 2.02828541e−01 | −6.98194001e−03 | −1.05012670e−01 |
| −1.68983582e−02 | −1.78490117e−01 | −3.14402190e−04 | 1.05704457e−01] |
| [1.45897478e−01 | −3.16464961e−01 | −2.97116876e−01 | −3.62336159e−01 |
| −2.79258966e−02 | 4.87479344e−02 | 2.07423255e−01 | −9.97781754e−02 |
| 5.40690124e−02 | 1.87106699e−01 | 3.49593729e−01 | −1.60983697e−01 |
| −2.76462436e−02 | −3.07229698e−01 | −4.70698863e−01 | −2.86948029e−02 |
| 3.11988533e−01 | 5.06849527e−01 | −3.00166726e−01 | 1.45554736e−01 |
| 2.40608960e−01 | 4.19580698e−01 | 4.43176985e−01 | 1.65775314e−01 |
| 1.56540975e−01 | 6.58983171e−01 | 1.15379930e−01 | 1.97025537e−01 |
| −2.41072476e−01 | 3.03619385e−01 | 2.14258388e−01 | 2.12721109e−01 |
| −1.42085329e−01 | −1.07603648e−03 | 3.28380138e−01 | 3.09223622e−01 |
| 3.88116419e−01 | 1.74584314e−01 | 2.94770032e−01 | 1.68654412e−01 |
| 3.42264175e−01 | 1.31151497e−01 | −1.03053316e−01 | −3.53718340e−01 |
| 4.40992445e−01 | 2.66778618e−01 | 1.68104336e−01 | 6.29038036e−01 |
| 2.40518674e−01 | 2.81818122e−01 | 1.13705523e−01 | 3.90906066e−01 |
| 8.30461085e−02 | −8.75317678e−02 | −2.13664919e−01 | 2.57611603e−01 |
| 2.77785331e−01 | −4.85905297e−01 | 1.46086052e−01 | 2.19078466e−01 |
| 3.54233151e−03 | 3.55073929e−01 | 3.04838449e−01 | −5.43805882e−02 |
| 1.81834579e−01 | −6.57850951e−02 | 1.88384354e−01 | 2.74786770e−01 |
| 1.26947597e−01 | 3.25411223e−02 | −1.49236277e−01 | 2.88790911e−01 |
| 5.17592013e−01 | 9.59121138e−02 | −8.65533873e−02 | 2.45587260e−01 |
| 2.84594105e−04 | 2.17409983e−01 | 3.31760831e−02 | 1.95078671e−01 |
| −3.22783068e−02 | 4.29674000e−01 | 2.68064916e−01 | 1.51454844e−02 |
| 2.50324477e−02 | −2.76407003e−01 | 3.53179067e−01 | 2.53446233e−02 |
| 1.63403928e−01 | −2.15998471e−01 | 2.10550144e−01 | 1.79583669e−01 |
| −2.39840537e−01 | −1.96393818e−01 | 1.76805854e−02 | 3.46949339e−01 |
| −6.18192971e−01 | 3.18742126e−01 | 2.93677896e−01 | −3.47723544e−01 |
| 3.58593054e−02 | 3.03551733e−01 | 2.80821085e−01 | 3.86646509e−01 |
| −1.47651494e−01 | 4.49996203e−01 | 4.36762959e−01 | 1.84618473e−01 |
| −9.61088911e−02 | 2.26135492e−01 | −3.31895679e−01 | −1.50983240e−02 |
| 1.94167539e−01 | −1.10141762e−01 | 1.60226032e−01 | 2.94984519e−01 |
| 2.38512054e−01 | 1.51825592e−01 | 4.16089267e−01 | 3.57013881e−01 |
| 5.40879488e−02 | −1.95472762e−02 | 1.54756710e−01 | 1.32093534e−01 |
| 1.28334075e−01 | 4.07180578e−01 | 2.03684449e−01 | 2.73047626e−01 |
| 3.29971820e−01 | 4.46996391e−01 | −1.13213547e−01 | 3.72778356e−01 |
| 4.19921368e−01 | 2.05021769e−01 | 2.24610358e−01 | 5.64392470e−02 |
| −3.28358948e−01 | −1.53087884e−01 | 3.77811879e−01 | 4.15250689e−01 |
| 1.84443533e−01 | −5.14454171e−02 | −9.38500538e−02 | 6.10756040e−01 |
| 1.91071853e−01 | 1.65487751e−01 | 1.24955639e−01 | 6.75688609e−02 |
| −8.03574175e−02 | −2.89557308e−01 | 1.15067549e−01 | 3.30791354e−01 |
| 3.83226901e−01 | 1.90623209e−01 | 3.25453460e−01 | 8.18100125e−02 |
| −1.31708169e−01 | 3.04976165e−01 | 2.05904648e−01 | 1.12363964e−01 |
| −3.34536463e−01 | −3.34666446e−02 | −4.50896062e−02 | −2.08664164e−02 |
| −2.02596292e−01 | −8.50307271e−02 | 4.20972556e−02 | 1.73739120e−02 |
| 8.27946141e−02 | 3.31334323e−01 | 1.06379740e−01 | 5.10924399e−01 |
| 7.38843679e−02 | 1.38278112e−01 | −1.14103861e−01 | −2.06985518e−01 |
| 4.75797176e−01 | 1.80162698e−01 | 1.95170000e−01 | −1.05273850e−01 |
| 2.86064088e−01 | 5.06140180e−02 | 6.11799181e−01 | 2.26874739e−01 |
| 2.62485653e−01 | 1.11693434e−01 | 5.47374487e−01 | −6.51173964e−02 |
| 3.55719738e−01 | 1.35980397e−01 | 5.07230461e−01 | 4.70926315e−01 |
| 3.25752199e−01 | 3.27526420e−01 | 2.17545733e−01 | 2.33616561e−01 |
| −4.14567769e−01 | 7.66274929e−02 | −1.87290862e−01 | 2.58448690e−01 |
| 2.11609155e−02 | 2.33684853e−01 | 2.16150865e−01 | 2.40161702e−01 |
| 1.01520896e−01 | 6.47949055e−02 | −7.46648461e−02 | 1.37171760e−01 |
| 3.30600351e−01 | 4.91239399e−01 | 9.35021602e−03 | 5.34518063e−02 |

TABLE $W_h^1$-continued

| | | | |
|---|---|---|---|
| 7.17215091e−02 | 8.37040544e−02 | 1.59345329e−01 | 3.29198986e−01 |
| 2.94296533e−01 | −1.55342206e−01 | 4.35373902e−01 | 4.32311818e−02 |
| 1.22244768e−02 | 1.28269047e−01 | 2.33922765e−01 | −1.27247795e−01 |
| 4.18845236e−01 | 2.95780420e−01 | 6.30513951e−02 | 2.13473201e−01 |
| −6.70787469e−02 | 3.12167704e−01 | 3.61097753e−01 | 4.40147549e−01 |
| −1.16546988e−01 | 1.81748867e−01 | 2.33273983e−01 | 3.78257871e−01 |
| 3.24604213e−01 | 1.06612392e−01 | −8.43692198e−02 | −2.52955645e−01 |
| 4.57211912e−01 | −8.39671120e−02 | −1.99436359e−01 | 5.02338588e−01 |
| 1.67542160e−01 | 4.36289728e−01 | −1.54458182e−02 | −2.29938868e−02 |
| 4.20468241e−01 | 1.65432528e−01 | 2.50380397e−01 | 1.71802536e−01 |
| 1.11207291e−01 | 4.89964575e−01 | 2.07313612e−01 | 1.26304489e−03] |
| [4.77970332e−01 | 2.37495393e−01 | 7.90530086e−01 | 1.99360251e−01 |
| 1.48899615e−01 | 1.15043426e−00 | 6.55358195e−01 | 3.30618948e−01 |
| 8.49914610e−01 | 2.50997454e−01 | 5.54351628e−01 | 1.26508102e−01 |
| 3.48367542e−01 | 4.96953517e−01 | 1.65498301e−01 | −1.05256215e−01 |
| 5.20162821e−01 | 8.50408450e−02 | 3.81650805e−01 | −8.71724337e−02 |
| 9.36238945e−01 | 4.14839625e−01 | 6.12951040e−01 | 1.02447689e−01 |
| 6.27180219e−01 | 1.04346585e−00 | 7.46261775e−02 | 3.60245794e−01 |
| 2.11252868e−01 | 6.21841490e−01 | −3.64750087e−01 | 3.43975216e−01 |
| 3.97371203e−01 | 1.16552450e−01 | 7.25798547e−01 | 4.73103255e−01 |
| 5.78506529e−01 | 8.01202893e−01 | 3.79142106e−01 | 7.82032251e−01 |
| 2.34183341e−01 | 4.16254699e−01 | −4.48223263e−01 | 2.10307129e−02 |
| 1.16680443e−00 | 3.44739944e−01 | 1.00067151e−00 | 9.13079560e−01 |
| 3.08935136e−01 | 3.20859224e−01 | 5.06311357e−01 | 4.64237422e−01 |
| 4.52482879e−01 | 1.20046027e−01 | 2.16913153e−03 | 1.03588119e−01 |
| 6.24368072e−01 | 7.03036368e−01 | 1.07665694e−01 | 1.46413475e−01 |
| 1.99411973e−01 | 4.83374476e−01 | 8.56765582e−01 | 5.31742394e−01 |
| 3.67628276e−01 | 4.63753879e−01 | 5.20828247e−01 | 4.07491535e−01 |
| 2.84946412e−01 | 3.03410769e−01 | 4.18198466e−01 | −1.32008314e−01 |
| 8.60992432e−01 | 1.03855944e−00 | 4.00711834e−01 | 2.85856694e−01 |
| 6.50882185e−01 | 8.51061344e−01 | −2.27191344e−01 | 9.03894231e−02 |
| 1.02120601e−01 | 7.59506822e−01 | 5.97813666e−01 | 4.39958900e−01 |
| 1.96131185e−01 | 1.89423144e−01 | 4.34177130e−01 | 7.35627532e−01 |
| 1.10502291e−00 | −5.41207969e−01 | 6.21527582e−02 | 7.85679221e−02 |
| 7.11226046e−01 | 6.58190668e−01 | 6.05525613e−01 | 3.16868335e−01 |
| 1.50834590e−01 | 5.21360040e−01 | 1.52992547e−01 | 4.92425531e−01 |
| 3.59457374e−01 | 1.25110948e−00 | 4.26430970e−01 | 4.58404012e−02 |
| 4.00738567e−01 | 1.38258278e−01 | 3.32503438e−01 | 7.22873449e−01 |
| 4.82525416e−02 | 5.46387792e−01 | 2.16817185e−01 | 2.16693699e−01 |
| 7.29550898e−01 | 4.92569745e−01 | 4.46710080e−01 | −3.44825059e−01 |
| 4.01118875e−01 | 1.71977893e−01 | 1.51586771e−01 | 2.20931724e−01 |
| 8.89482617e−01 | 2.08459526e−01 | 6.23227715e−01 | 3.45513970e−01 |
| 7.82545686e−01 | 6.59053326e−01 | 3.41072500e−01 | 1.74931332e−01 |
| 1.01443005e−00 | 7.95326591e−01 | 4.71080057e−02 | 8.22785258e−01 |
| 5.83532035e−01 | 3.02438706e−01 | 1.23082153e−01 | −1.70398846e−01 |
| 4.12817001e−01 | 8.22674990e−01 | 9.38363433e−01 | 5.24853170e−01 |
| 4.24579978e−01 | 6.75077140e−01 | −9.81671512e−02 | 3.62950206e−01 |
| 2.98686594e−01 | 6.14516616e−01 | 5.02428412e−01 | 3.60877097e−01 |
| 5.40636241e−01 | 6.98076963e−01 | 2.87295491e−01 | 5.57483613e−01 |
| 6.64689660e−01 | 3.17802757e−01 | 5.80970466e−01 | 8.12752724e−01 |
| 1.83083788e−01 | 6.92657828e−01 | 8.03712904e−01 | 3.70888501e−01 |
| −1.39787599e−01 | 5.26454031e−01 | −7.01493174e−02 | 4.50238176e−02 |
| 5.75180769e−01 | 2.92620510e−01 | 7.36551583e−01 | 3.83987091e−02 |
| 5.65195501e−01 | 2.41722956e−01 | 5.38255811e−01 | 5.62155604e−01 |
| 6.59668922e−01 | 1.17585748e−01 | −3.24359983e−02 | 1.07439213e−01 |
| 5.99018455e−01 | 5.66616535e−01 | 4.17157859e−01 | 3.12760264e−01 |
| 4.09405202e−01 | 2.69755185e−01 | 8.93258035e−01 | 1.76975712e−01 |
| 4.77101296e−01 | 2.57996172e−01 | −5.59054136e−01 | 2.20965728e−01 |
| 3.68836708e−02 | 6.23656094e−01 | 8.19488287e−01 | 1.23506129e−00 |
| −7.40362480e−02 | 6.78068161e−01 | 5.68273626e−02 | 5.90887964e−01 |
| −8.36532414e−02 | 8.32740888e−02 | 4.24341351e−01 | 6.09395802e−01 |
| −2.76622027e−01 | −5.12697101e−01 | 4.47611421e−01 | −1.70689180e−01 |
| 1.45678863e−01 | 2.87759006e−01 | 4.49690104e−01 | 5.39499819e−01 |
| 9.87690687e−01 | 4.27777201e−01 | 8.24120164e−01 | 4.75925267e−01 |
| 6.63761735e−01 | 3.86274576e−01 | 5.37977397e−01 | 1.15306151e−00 |
| 4.19397801e−01 | 1.05613507e−01 | 5.68067133e−01 | 1.85313851e−01 |
| 1.67042315e−01 | 2.37880945e−01 | 5.47621369e−01 | 7.73792505e−01 |
| 2.18606099e−01 | 4.99278426e−01 | −5.89800119e−01 | 4.38152969e−01 |
| 7.40678608e−01 | 5.93087792e−01 | 9.75978255e−01 | 7.72054553e−01 |
| −5.93527704e−02 | 4.79003847e−01 | 7.59749353e−01 | 4.49659020e−01 |
| 4.57031876e−01 | 1.15494385e−01 | −4.70314085e−01 | 2.49279529e−01 |
| 1.59590408e−01 | 4.94043052e−01 | 5.52780449e−01 | 1.76676467e−01 |
| 5.91390431e−01 | 3.12006455e−02 | 4.13230419e−01 | −3.00636530e−01 |
| 7.53848195e−01 | −6.50604665e−02 | 2.80503690e−01 | 6.36824965e−01 |
| −7.84797430e−01 | 8.00759554e−01 | 5.24266779e−01 | 8.84208262e−01] |
| [−2.53689557e−01 | −3.80240500e−01 | 7.58757710e−01 | −3.51646304e−01 |
| 1.36152297e−01 | 7.42126107e−01 | 2.39295110e−01 | 5.57995662e−02 |
| 3.89022231e−01 | 1.95280120e−01 | 3.41136098e−01 | 3.95528823e−01 |
| 1.85841367e−01 | 3.96084219e−01 | −1.53595135e−01 | −3.14669348e−02 |
| 3.70947756e−02 | 4.29818034e−01 | −1.18947364e−01 | −3.72661948e−01 |

TABLE $W_h^1$-continued

| | | | |
|---|---|---|---|
| 3.59812468e-01 | 6.93910420e-01 | 2.45762542e-01 | 8.74149501e-01 |
| 2.52104104e-01 | 1.83067337e-01 | 1.06746830e-01 | 1.32464916e-01 |
| 5.14357649e-02 | 4.56412077e-01 | 2.08278328e-01 | -4.85831387e-02 |
| 3.39105397e-01 | 7.89075047e-02 | 1.00868717e-01 | -6.62106574e-02 |
| 6.22781396e-01 | 4.35905963e-01 | 3.54881108e-01 | 4.45678890e-01 |
| 8.86626914e-02 | 1.98944613e-01 | -1.06440345e-02 | 2.07089618e-01 |
| 1.06946123e-00 | 2.47824311e-01 | 1.07006764e-00 | 3.75882745e-01 |
| 2.00097755e-01 | 2.35691875e-01 | 3.21123451e-01 | -5.05681671e-02 |
| 4.23769861e-01 | 1.09578513e-01 | -1.51512533e-01 | 2.49579623e-01 |
| 3.35177034e-01 | 1.94556698e-01 | 5.38225055e-01 | 2.94844955e-01 |
| 7.08545268e-01 | 7.76876211e-01 | 1.40551582e-01 | -5.99332973e-02 |
| 1.52834728e-01 | 1.04681849e-01 | 1.04260914e-01 | 2.24777326e-01 |
| 3.30186516e-01 | 2.51472324e-01 | 4.21239227e-01 | -3.59405011e-01 |
| 7.99457610e-01 | 4.40644205e-01 | 2.98847318e-01 | 3.23642164e-01 |
| 4.52692568e-01 | 8.42200637e-01 | 3.31353217e-01 | 2.29525685e-01 |
| 1.26138136e-01 | 2.69802839e-01 | 7.58801354e-03 | 8.99020508e-02 |
| 5.32894731e-01 | 5.58763564e-01 | 2.90060431e-01 | -6.40056506e-02 |
| -1.62423462e-01 | -5.26194513e-01 | 1.00117937e-01 | 3.42092454e-01 |
| 4.97851998e-01 | 4.04259384e-01 | 1.78738326e-01 | 8.11766803e-01 |
| -2.53861547e-01 | 6.54816866e-01 | 2.09555060e-01 | -1.95467360e-02 |
| 4.47654217e-01 | 7.94899344e-01 | 6.50560081e-01 | 3.44010256e-02 |
| 7.39768371e-02 | 1.59280941e-01 | 2.61994779e-01 | 1.44390181e-01 |
| 4.50880051e-01 | 4.67617035e-01 | 9.82290655e-02 | -2.27810889e-01 |
| 5.47827661e-01 | -2.67412633e-01 | 1.48660183e-01 | 2.27640569e-01 |
| 2.26618767e-01 | 2.48409044e-02 | -1.12711936e-01 | -5.29833496e-01 |
| 3.66685897e-01 | 2.40602151e-01 | 1.95333928e-01 | 3.76283050e-01 |
| 4.73751724e-01 | 5.40217996e-01 | 5.23842037e-01 | 9.67246145e-02 |
| 4.91091192e-01 | 7.93794274e-01 | 3.57249290e-01 | 5.50657511e-01 |
| 5.23028374e-01 | 5.65922856e-02 | 2.46824309e-01 | 2.25715041e-02 |
| 2.49810547e-01 | 5.26861288e-02 | -2.34828219e-01 | 5.22211552e-01 |
| 2.73905545e-01 | 8.65728974e-01 | 2.22117424e-01 | -4.92808633e-02 |
| -2.09331363e-01 | 3.46138090e-01 | 4.85425055e-01 | 1.49352372e-01 |
| 1.64078966e-01 | 2.48937756e-01 | 7.91239145e-01 | 1.64065689e-01 |
| 6.60148561e-01 | 3.81039008e-02 | 6.49239123e-02 | 3.98432463e-01 |
| 2.56004184e-01 | 5.53121984e-01 | -1.22278191e-01 | 1.82829559e-01 |
| -3.13715972e-02 | 6.06683567e-02 | 1.16853282e-01 | 3.71223420e-01 |
| 4.35439408e-01 | 1.57522589e-01 | 2.02966735e-01 | 3.76765996e-01 |
| 3.92505080e-01 | 2.98450172e-01 | 4.53780353e-01 | 5.48985481e-01 |
| 1.01508152e-00 | 4.68995452e-01 | -2.92707719e-02 | 1.56539127e-01 |
| 2.66526908e-01 | 6.70763999e-02 | -1.42527610e-01 | -3.74570191e-02 |
| 3.53631258e-01 | 1.50180340e-01 | 1.80411443e-01 | 3.97509001e-02 |
| 3.06981534e-01 | 4.53807339e-02 | 2.16190651e-01 | 2.79724240e-01 |
| 9.94134992e-02 | 1.78170294e-01 | 4.73030627e-01 | 3.64441127e-01 |
| 3.70824754e-01 | 3.16675365e-01 | 3.42019856e-01 | 2.29986504e-01 |
| -2.54399002e-01 | 3.20346087e-01 | 3.72915298e-01 | 2.36580014e-01 |
| -2.23892033e-01 | 8.80318582e-02 | 1.55344173e-01 | 3.49961549e-01 |
| 1.45231476e-02 | 2.12032422e-01 | -8.22966732e-03 | 2.91685194e-01 |
| 7.51911640e-01 | 2.62201250e-01 | 6.76032364e-01 | -3.04349158e-02 |
| 6.25122041e-02 | 4.53508109e-01 | 4.92991030e-01 | 4.79941428e-01 |
| 4.72533889e-01 | -9.61935148e-02 | 5.83703637e-01 | 9.36824083e-02 |
| 3.27956453e-02 | 6.65130258e-01 | 3.10458720e-01 | -6.50457218e-02 |
| -2.33460069e-01 | 3.52640897e-01 | 3.87836069e-01 | 5.62840641e-01 |
| 8.61770749e-01 | 4.69878078e-01 | 6.68191075e-01 | 5.85753322e-01 |
| 1.82817671e-01 | 1.47652939e-01 | 2.14998722e-01 | 1.07989717e-00 |
| 6.10569566e-02 | -4.96455818e-01 | -2.75975233e-03 | 4.05398726e-01 |
| -1.22500658e-01 | 3.04252207e-01 | 2.14244708e-01 | 3.66299897e-01 |
| 1.89309865e-01 | -7.42201433e-02 | 1.02808632e-01 | -2.82221705e-01 |
| 7.64780700e-01 | 1.15663387e-01 | 3.13696623e-01 | 2.64874604e-02 |
| 5.89264572e-01 | 3.56851071e-01 | 2.58123398e-01 | 4.04403061e-01] |
| [7.47441500e-02 | 2.22668573e-02 | -9.03295167e-03 | 6.43511191e-02 |
| 1.03407964e-01 | -5.98307922e-02 | 8.13142806e-02 | -5.47128282e-02 |
| 6.83628814e-03 | 2.12250203e-02 | -7.22830072e-02 | -8.21880475e-02 |
| -9.78566427e-03 | 8.27565119e-02 | -7.56571144e-02 | 3.28694470e-02 |
| 8.05204958e-02 | -7.69108981e-02 | -1.01594098e-01 | -7.53785148e-02 |
| 7.86623731e-02 | -7.74074942e-02 | -5.90314344e-02 | 2.07059830e-02 |
| 3.98997515e-02 | 1.03059039e-01 | -8.38774666e-02 | -5.77034019e-02 |
| 7.94187710e-02 | -1.02198198e-01 | -1.10387206e-01 | -4.68056239e-02 |
| 3.65671217e-02 | -8.44246298e-02 | -7.12068453e-02 | -8.12791362e-02 |
| -5.25310710e-02 | 3.11567113e-02 | -8.46531242e-03 | -3.61839384e-02 |
| 2.42763176e-03 | -7.65928701e-02 | -6.34362400e-02 | 9.74584296e-02 |
| 3.60340029e-02 | -6.69405460e-02 | -1.03307091e-01 | -5.79589419e-02 |
| 9.88942459e-02 | -4.90406007e-02 | 9.72734243e-02 | 3.51075083e-02 |
| 1.60644054e-02 | -6.32388815e-02 | -8.24888796e-02 | 1.06114499e-01 |
| -2.98136957e-02 | 7.32057989e-02 | -1.08219385e-01 | 4.35160734e-02 |
| 2.15727035e-02 | 3.07583045e-02 | 9.28561687e-02 | 8.71193931e-02 |
| 4.52778004e-02 | -8.29369426e-02 | -3.58441174e-02 | 4.71585840e-02 |
| 1.83308180e-02 | -6.52194396e-02 | 4.16253321e-02 | 8.04149359e-02 |
| 2.36227587e-02 | -1.04217730e-01 | -6.04312234e-02 | -2.26345044e-02 |
| 1.02770396e-01 | -5.79055361e-02 | -6.60888925e-02 | 4.27823029e-02 |
| 4.03999910e-02 | 8.85566995e-02 | -5.26645482e-02 | 9.56601948e-02 |

TABLE $W_h^1$-continued

| | | | |
|---|---|---|---|
| 1.39213270e-02 | 8.08962062e-02 | 6.00020476e-02 | 1.00626118e-01 |
| 3.89052667e-02 | -9.57765132e-02 | 9.08265114e-02 | -1.08895734e-01 |
| 8.60859603e-02 | 9.35569108e-02 | -3.53744887e-02 | 8.63044243e-03 |
| 9.05619115e-02 | 5.56115620e-02 | 3.73770930e-02 | -9.38966125e-02 |
| -5.08958027e-02 | -9.49827880e-02 | 5.60022481e-02 | 2.60036010e-02 |
| 7.05352426e-02 | 2.35586949e-02 | -7.53082410e-02 | -2.64200848e-02 |
| -6.77755475e-02 | 4.98708375e-02 | -9.58772972e-02 | 9.25793424e-02 |
| -8.51693153e-02 | 1.05445080e-01 | 2.51102298e-02 | -4.38810922e-02 |
| -6.21924773e-02 | 8.73147547e-02 | -8.20203573e-02 | -1.05517283e-01 |
| -2.80806441e-02 | 8.20149258e-02 | 1.39201665e-02 | 2.75897756e-02 |
| 6.78316131e-02 | 4.11550552e-02 | -1.09959424e-01 | -9.49985012e-02 |
| -1.03688970e-01 | 1.01555639e-03 | 5.75400181e-02 | 9.76112613e-04 |
| 4.28245142e-02 | -8.42773095e-02 | -5.38456030e-02 | -8.69389251e-02 |
| 5.75671867e-02 | 5.35026900e-02 | -9.19403359e-02 | -2.39718854e-02 |
| 1.07899532e-01 | -5.57092838e-02 | -7.20672905e-02 | 3.58671956e-02 |
| 7.22363368e-02 | -3.83462906e-02 | 2.79473159e-02 | 8.12527165e-02 |
| 9.87792015e-02 | 3.35445292e-02 | 1.59811657e-02 | -1.13105709e-02 |
| -1.04708201e-03 | -9.32302624e-02 | -8.04563239e-03 | -9.39458981e-02 |
| 4.75576669e-02 | -1.05171651e-01 | -1.71817392e-02 | 8.59479159e-02 |
| -1.43011333e-02 | -3.77820097e-02 | 5.71079962e-02 | -8.38606730e-02 |
| 3.70355025e-02 | -2.34161578e-02 | -2.92439759e-02 | -5.26783131e-02 |
| 7.53065348e-02 | 5.11688069e-02 | -1.09600447e-01 | 1.03351004e-01 |
| 8.22598040e-02 | -2.49741971e-02 | -1.00063726e-01 | 8.23315755e-02 |
| 2.64877966e-03 | -7.18490928e-02 | 1.01742923e-01 | -1.53099224e-02 |
| -6.73899055e-02 | 1.05701394e-01 | -6.77957311e-02 | 1.04330637e-01 |
| -1.04860924e-01 | -1.63812600e-02 | 1.65525433e-02 | -3.06518003e-02 |
| -3.99254076e-03 | -4.39849542e-03 | -6.95786253e-02 | 1.06004030e-02 |
| 9.92952660e-02 | -5.65920137e-02 | -3.05922702e-02 | 3.32869329e-02 |
| 7.60940742e-02 | 6.49238676e-02 | -3.71865034e-02 | 1.58285461e-02 |
| 9.40654874e-02 | 1.05242163e-01 | 9.96096656e-02 | 3.18414532e-02 |
| -5.67922592e-02 | 5.93001656e-02 | -9.73820165e-02 | -2.69191377e-02 |
| -1.10588871e-01 | 5.43648824e-02 | -1.05838953e-02 | -9.73032340e-02 |
| 5.79520054e-02 | 6.68810168e-03 | -5.64674735e-02 | -9.47203264e-02 |
| 7.03480393e-02 | 6.20965362e-02 | 1.25158569e-02 | 9.28819273e-03 |
| 8.71065781e-02 | -5.67127727e-02 | -9.49279368e-02 | -2.92164367e-03 |
| -1.07074574e-01 | 7.69058540e-02 | -6.53005689e-02 | -8.28523710e-02 |
| -6.50083125e-02 | -1.00797340e-01 | 6.13663569e-02 | 7.50644458e-03 |
| 4.54502292e-02 | -8.47084522e-02 | 1.06978633e-01 | 5.83094126e-03 |
| 4.87902798e-02 | 7.55342618e-02 | 8.55485350e-02 | -7.17217550e-02 |
| -3.54755335e-02 | 2.53132312e-03 | -9.30243209e-02 | -4.67694625e-02 |
| 5.38713895e-02 | -8.54149833e-02 | 6.92126434e-03 | -8.60893056e-02 |
| 7.00258091e-02 | -2.43391637e-02 | 8.95592868e-02 | 5.47514036e-02 |
| 1.01859078e-01 | 7.19713941e-02 | -6.13933615e-02 | -9.52278003e-02] |
| [-1.65353879e-01 | 6.45481721e-02 | 2.25079712e-02 | 1.12510793e-01 |
| -1.17829837e-01 | 2.45473102e-01 | -3.05342153e-02 | 1.91787526e-01 |
| -4.23062705e-02 | 6.17938936e-02 | 1.80515945e-01 | 1.52871668e-01 |
| 2.11793333e-01 | 1.73124507e-01 | -4.38921750e-01 | 2.32569799e-01 |
| 1.61762521e-01 | -3.95493209e-02 | 2.85429191e-02 | 2.59059489e-01 |
| -8.57044980e-02 | 1.80179194e-01 | 2.27550313e-01 | -4.71607745e-02 |
| 5.05162358e-02 | -1.30627066e-01 | 1.49142325e-01 | 1.56688184e-01 |
| 2.21278928e-02 | -1.36025652e-01 | 5.57199903e-02 | -1.31997457e-02 |
| 2.74444273e-01 | -3.39362979e-01 | 3.67302448e-01 | 4.23496813e-02 |
| 1.26071095e-01 | 1.31965846e-01 | 9.11508352e-02 | 2.34699994e-01 |
| 1.93971723e-01 | 2.72008121e-01 | 2.26225883e-01 | 8.45813379e-02 |
| 3.24555725e-01 | 4.52985428e-02 | -1.18085258e-01 | 1.78529650e-01 |
| 2.05247894e-01 | 1.06667951e-02 | 1.60413131e-01 | 2.50924885e-01 |
| 2.87388504e-01 | -4.37961482e-02 | 2.40429595e-01 | -9.98027548e-02 |
| 4.12694812e-01 | 4.54166718e-02 | -2.06902679e-02 | 1.70056984e-01 |
| -1.47995487e-01 | 4.77528036e-01 | 1.15905695e-01 | -1.19441211e-01 |
| -1.42943352e-01 | -1.34403296e-02 | -4.01449353e-02 | 3.20823342e-01 |
| 3.66432786e-01 | 1.24366954e-01 | 1.65630445e-01 | 4.01481420e-01 |
| 6.04481138e-02 | -1.38606697e-01 | 1.33909568e-01 | 3.14363837e-02 |
| 2.58782059e-01 | -1.59656212e-01 | 2.97373921e-01 | -5.97052425e-02 |
| 3.46504629e-01 | 1.29019365e-01 | 1.82669908e-02 | 7.76813785e-03 |
| -8.87232572e-02 | -1.21479467e-01 | 4.20289822e-02 | -1.51817128e-01 |
| 7.64706358e-02 | 1.16813853e-01 | 9.24557522e-02 | 1.69151470e-01 |
| 5.53350449e-02 | 1.76092833e-01 | 3.87020975e-01 | 5.78461289e-02 |
| -3.08348060e-01 | 1.54484630e-01 | 2.94659406e-01 | 1.93000227e-01 |
| 9.41259116e-02 | 4.81076509e-01 | 3.20992544e-02 | -1.26920387e-01 |
| -9.77109522e-02 | -9.77392197e-02 | 2.71524489e-01 | 1.81697175e-01 |
| 6.00318313e-02 | 4.33140695e-02 | -4.81345728e-02 | 3.23102772e-01 |
| 2.35417247e-01 | -1.64518461e-01 | 5.93199618e-02 | 1.81740403e-01 |
| 8.49105418e-02 | -9.97128189e-02 | 1.81377500e-01 | -3.24726671e-01 |
| 8.01715627e-02 | 1.81880727e-01 | 1.61118180e-01 | 3.67282480e-01 |
| -1.01923980e-01 | 1.68132320e-01 | -4.83193360e-01 | 1.75904453e-01 |
| 4.82263029e-01 | 1.85820341e-01 | 1.58077896e-01 | -1.35136575e-01 |
| -6.49040341e-02 | 2.85770655e-01 | 2.39132553e-01 | 1.13315418e-01 |
| -3.77550632e-01 | -2.60341674e-01 | 3.69159073e-01 | 7.04907626e-02 |
| -1.47261806e-02 | 1.39539763e-02 | 3.09682697e-01 | 2.28841960e-01 |
| 3.06694895e-01 | 1.68852255e-01 | 6.13154657e-02 | 1.54200718e-01 |

TABLE $W_h^1$-continued

| | | | |
|---|---|---|---|
| 6.76910952e−02 | 3.64283592e−01 | 2.47217715e−01 | 6.82644472e−02 |
| 3.96869481e−01 | −4.60789129e−02 | 2.30606765e−01 | 1.60404995e−01 |
| −1.28542885e−01 | 1.94743231e−01 | 1.00189177e−02 | 1.42628998e−02 |
| −1.61474898e−01 | −3.33706260e−01 | 1.49441898e−01 | −5.09896576e−02 |
| 1.53676465e−01 | 1.35419488e−01 | 8.43989849e−02 | −7.25483149e−02 |
| 3.13988149e−01 | 6.69097826e−02 | 3.21694762e−01 | 2.11517081e−01 |
| −1.82075173e−01 | −1.76636785e−01 | 4.61874418e−02 | −1.80697322e−01 |
| 1.24278717e−01 | 3.43283504e−01 | 3.76015902e−01 | 1.81118891e−01 |
| 6.91888630e−02 | 5.87484725e−02 | 1.19959250e−01 | 4.97247837e−01 |
| 1.67674750e−01 | −6.48312038e−03 | 1.35699123e−01 | 5.89603893e−02 |
| 1.04235262e−01 | −1.35783896e−01 | −1.22187443e−01 | 3.76208961e−01 |
| −1.33356646e−01 | −4.49655987e−02 | 4.04821366e−01 | 1.36813894e−01 |
| 1.67912140e−01 | 2.25514501e−01 | 1.44462049e−01 | −6.34646267e−02 |
| 3.45957339e−01 | 1.71425536e−01 | 1.21083513e−01 | 3.30855340e−01 |
| 1.94088202e−02 | −1.74698681e−02 | −9.28359479e−02 | −6.80360124e−02 |
| 2.80460864e−01 | 2.80995220e−01 | 2.23299161e−01 | 1.54088050e−01 |
| 5.34077026e−01 | 2.68261135e−01 | −3.10452461e−01 | 3.66217911e−01 |
| −4.20101255e−01 | 3.38275641e−01 | 2.60612309e−01 | −4.78318781e−02 |
| 1.79094210e−01 | 1.86296478e−01 | 3.04526478e−01 | 5.50390668e−02 |
| 2.45707035e−02 | 7.29112104e−02 | 8.84532630e−02 | −6.99088201e−02 |
| 7.17713609e−02 | 6.80135936e−02 | 1.85262248e−01 | 2.44772416e−02 |
| 5.99729083e−02 | 1.26432315e−01 | 1.10960037e−01 | 1.12418637e−01 |
| −1.79602906e−01 | −9.33646224e−03 | 1.32137313e−01 | 1.02048278e−01 |
| 5.79375982e−01 | 2.60084808e−01 | 2.49801591e−01 | −2.02434480e−01 |
| 3.44649404e−01 | −1.58308260e−01 | 3.94522250e−01 | 3.75041328e−02 |
| −8.08727816e−02 | 7.86272287e−02 | 4.64671791e−01 | 1.57410473e−01 |
| 1.10776760e−01 | 2.40187161e−02 | 3.90606344e−01 | −3.79507840e−01] |
| [1.23262525e−01 | 4.73925143e−01 | 1.28045201e−00 | 3.63674849e−01 |
| 7.57826746e−01 | 3.54572386e−01 | 5.34761608e−01 | 8.27230453e−01 |
| 1.22897613e−00 | 9.15488005e−01 | 2.79225677e−01 | 1.53296208e−00 |
| 4.94157732e−01 | 7.60734260e−01 | 7.64388263e−01 | 5.13843954e−01 |
| 1.18757296e−00 | −2.70728230e−01 | 8.03013206e−01 | 8.95255357e−02 |
| 3.47441167e−01 | −2.95783252e−01 | 7.72979140e−01 | 1.36785412e−01 |
| 1.07080221e−00 | 1.11929500e−00 | −4.70602870e−01 | 6.23830736e−01 |
| −3.25846337e−02 | 9.07912970e−01 | 2.17970967e−01 | 1.18966810e−01 |
| 7.79293001e−01 | 2.38161281e−01 | 7.31915414e−01 | 2.13464335e−01 |
| 1.99967429e−01 | 1.14434791e−00 | 4.32719260e−01 | 6.18017554e−01 |
| 6.34655058e−01 | 5.84768891e−01 | 5.58537185e−01 | 6.65998459e−01 |
| 1.88281405e−00 | 4.39652085e−01 | 6.11771405e−01 | 1.18199146e−00 |
| 3.21873873e−01 | 3.01914036e−01 | −7.20234588e−02 | 6.09787643e−01 |
| 1.80942595e−01 | 7.73392320e−01 | 4.73968446e−01 | 6.91565454e−01 |
| 1.15894401e−01 | 3.79140787e−02 | 5.16357422e−01 | 2.94021100e−01 |
| 1.25235274e−01 | 1.42611969e−00 | 7.07593143e−01 | 8.77014160e−01 |
| −1.60621822e−01 | 5.80539405e−01 | 3.98986697e−01 | 3.46118778e−01 |
| 8.57997477e−01 | −2.25060642e−01 | 3.71581793e−01 | 6.62697181e−02 |
| 9.62801456e−01 | 2.44494677e−01 | 4.30084988e−02 | 3.22987139e−02 |
| 1.26007068e−00 | 8.65335584e−01 | 5.17750263e−01 | 8.40646744e−01 |
| 7.90567815e−01 | 8.29201341e−01 | 3.76549542e−01 | 6.03597224e−01 |
| −2.47130580e−02 | −2.94484705e−01 | 7.03095615e−01 | 8.31094027e−01 |
| 8.38708103e−01 | −2.99082607e−01 | 4.17004496e−01 | 3.56539428e−01 |
| 7.04685330e−01 | 8.73046041e−01 | 9.11398113e−01 | 1.01301515e−00 |
| 3.41162801e−01 | 6.73275173e−01 | −8.63493755e−02 | 9.12215173e−01 |
| 7.27931082e−01 | 8.31364274e−01 | 1.59957170e−01 | 1.22317679e−01 |
| 4.93160307e−01 | 4.47384566e−01 | 1.02096522e−00 | 7.03099728e−01 |
| 6.67858422e−01 | 8.21687877e−01 | 5.99158287e−01 | 5.64694822e−01 |
| 8.45266700e−01 | 3.77396315e−01 | 1.08655179e−00 | 7.00837195e−01 |
| 6.38951659e−01 | −1.62998363e−01 | 4.30566579e−01 | −1.99840754e−01 |
| 5.04325330e−01 | 8.58050287e−01 | 5.75601645e−02 | 3.03202063e−01 |
| 9.24665630e−01 | 7.66997755e−01 | 5.86839616e−01 | 1.06802201e−00 |
| 4.40922767e−01 | 6.99761689e−01 | 5.49869955e−01 | 7.53509939e−01 |
| −1.10684492e−01 | 4.36425060e−01 | 8.73553038e−01 | 3.56279969e−01 |
| 7.94113398e−01 | 7.65624166e−01 | 3.47449332e−01 | 8.99058759e−01 |
| 1.52658567e−01 | 5.05850494e−01 | 2.70333320e−01 | 9.66903985e−01 |
| 5.86088955e−01 | 7.53449380e−01 | 2.82430768e−01 | 6.96858406e−01 |
| 8.77824306e−01 | 9.03393626e−01 | 1.68990523e−01 | 6.31938457e−01 |
| 3.68072063e−01 | 6.89841747e−01 | 1.12664604e−00 | 2.20662028e−01 |
| 8.53742436e−02 | 8.54373157e−01 | 6.93282664e−01 | 9.82304454e−01 |
| 8.06264997e−01 | 1.16874015e−00 | 6.17541134e−01 | 3.46775472e−01 |
| 3.86133045e−01 | 7.87306607e−01 | 5.52590847e−01 | 1.05429426e−01 |
| 6.01438522e−01 | 2.35650718e−01 | 4.02494341e−01 | 8.63363922e−01 |
| 5.08580923e−01 | 1.14771879e−00 | 4.82941657e−01 | −2.81851918e−01 |
| 9.94847119e−01 | −3.61135811e−01 | 5.07690728e−01 | 4.37344491e−01 |
| 9.96324062e−01 | 8.12579632e−01 | 6.01652563e−01 | 3.96261036e−01 |
| 9.71075177e−01 | −1.08368017e−01 | 7.74661064e−01 | 4.58368093e−01 |
| 3.87360990e−01 | 3.87259573e−01 | 1.11085606e−00 | 1.41379273e−00 |
| 7.02868879e−01 | 1.79716837e−00 | 2.49784395e−01 | −1.56751290e−01 |
| 6.63071871e−01 | 9.09514189e−01 | 6.26050055e−01 | 3.71517390e−01 |
| 5.37373602e−01 | 5.88620067e−01 | 4.21289176e−01 | 4.02594469e−02 |
| 2.11882412e−01 | 5.18879533e−01 | 7.97824934e−02 | 9.44068372e−01 |
| 8.87397826e−01 | 7.46829331e−01 | 6.21863902e−01 | 1.11373401e−00 |

TABLE $W_h^1$-continued

| | | | |
|---|---|---|---|
| 8.32816482e−01 | 7.94738233e−01 | 2.53181398e−01 | 8.58911991e−01 |
| 3.02833557e−01 | 4.70455199e−01 | 5.76650739e−01 | −7.61854947e−01 |
| 4.95430499e−01 | 9.84131694e−01 | 2.79746920e−01 | 1.01698530e−00 |
| 9.94600892e−01 | 2.97059149e−01 | −1.42428830e−01 | 7.62440681e−01 |
| 1.23331237e−00 | 5.12509882e−01 | 9.54151869e−01 | 5.01742244e−01 |
| 6.82363570e−01 | −3.79934162e−01 | 1.32157719e−00 | 6.93932652e−01 |
| 6.01274312e−01 | 9.48237062e−01 | −1.75882414e−01 | 6.01039350e−01 |
| 4.54846770e−01 | 1.13075078e−00 | 8.21677148e−01 | 9.63431299e−01 |
| 6.63736641e−01 | 1.46658272e−01 | −1.12053446e−01 | 4.25395779e−02 |
| 9.72964704e−01 | 2.51840144e−01 | 5.08725464e−01 | 1.13609397e−00 |
| 3.23809773e−01 | 3.35201859e−01 | 5.91055810e−01 | 5.57111681e−01] |
| [4.41071600e−01 | 1.65494278e−01 | −1.03454292e−01 | 3.60803604e−01 |
| 5.07176816e−01 | 3.95590007e−01 | 6.13137603e−01 | −1.87691987e−01 |
| 5.73143899e−01 | 2.60286741e−02 | 2.81429142e−01 | 6.91121221e−01 |
| 4.51277435e−01 | 1.72462285e−01 | 5.57067059e−02 | 4.05011863e−01 |
| 4.82783437e−01 | 5.27333580e−02 | 9.82769877e−02 | −1.47981748e−01 |
| 3.17757994e−01 | −1.92672983e−01 | 9.29591238e−01 | 7.43215829e−02 |
| 6.88037276e−01 | 4.07119662e−01 | −2.27170289e−01 | 2.02889398e−01 |
| −3.80535014e−02 | −2.30562538e−01 | 1.95799902e−01 | −9.01159346e−02 |
| 1.88917935e−01 | −1.40923321e−01 | 4.11856204e−01 | 6.55358508e−02 |
| 6.82910308e−02 | 3.27805847e−01 | 9.36710462e−02 | 4.33626205e−01 |
| 2.78097510e−01 | −2.72127301e−01 | −3.52963954e−01 | 6.85157359e−01 |
| −1.76396564e−01 | 5.17940894e−02 | 2.15515807e−01 | 4.84140158e−01 |
| 1.25945866e−01 | 5.16317114e−02 | 9.78305191e−02 | 2.52916217e−02 |
| −4.45276350e−02 | 1.20351501e−01 | 6.09045804e−01 | −3.43484908e−01 |
| 2.40514457e−01 | −2.04535231e−01 | −5.96764609e−02 | 2.71153718e−01 |
| 3.33559930e−01 | 2.92890340e−01 | 5.41506350e−01 | −1.72133148e−02 |
| −6.12118989e−02 | 2.08910018e−01 | 8.62288773e−01 | 1.95417944e−02 |
| 2.25441352e−01 | 1.43043518e−01 | −9.52765271e−01 | −5.86928010e−01 |
| −1.61886334e−01 | −2.53858507e−01 | 4.19758260e−01 | 1.12541683e−01 |
| 5.44907391e−01 | 1.86585158e−01 | −4.86309826e−01 | 7.05289170e−02 |
| 4.96674091e−01 | 5.03488369e−02 | 2.06721321e−01 | 8.36625546e−02 |
| 1.00786552e−01 | 3.69640917e−01 | 1.25819314e−02 | 1.41487479e−01 |
| 1.47721976e−01 | −9.68232572e−01 | 5.52183211e−01 | −1.57467991e−01 |
| −4.44157720e−02 | −3.04340601e−01 | 1.21575803e−01 | −1.47945762e−01 |
| 2.69166797e−01 | 3.56369585e−01 | −1.09169193e−01 | 2.91928858e−01 |
| 2.55409181e−01 | 1.51546702e−01 | 2.79175878e−01 | 3.67145211e−01 |
| −1.53945923e−01 | 4.13382977e−01 | −8.29600915e−02 | 2.87602097e−01 |
| 7.28241578e−02 | 6.45134896e−02 | 1.02521040e−01 | 6.99886978e−01 |
| 5.95820606e−01 | 3.97176296e−01 | 4.29321051e−01 | 5.58464408e−01 |
| 6.55954242e−01 | −1.16322460e−02 | 4.28002954e−01 | 1.23808779e−01 |
| 8.57006535e−02 | 1.51143223e−01 | 5.43194771e−01 | 9.41734463e−02 |
| 6.82196975e−01 | 8.24814439e−02 | 6.18332401e−02 | 1.08623594e−01 |
| −1.29814908e−01 | 9.12427250e−03 | 3.14833760e−01 | 8.53878632e−02 |
| 2.40592256e−01 | 7.23970413e−01 | 1.65739089e−01 | 5.08292258e−01 |
| 3.08342546e−01 | 7.88311958e−01 | −2.48248219e−01 | −2.58339465e−01 |
| 6.99910820e−01 | 5.21037541e−02 | 2.19669059e−01 | 1.64622962e−01 |
| 3.56691301e−01 | 5.37907660e−01 | 1.51273031e−02 | 2.96009511e−01 |
| 2.77241349e−01 | 4.80581880e−01 | 4.36461270e−01 | −6.47603394e−03 |
| 9.28277429e−03 | 1.01243690e−01 | −2.98096150e−01 | 9.57408920e−01 |
| −2.86615025e−02 | 3.26554239e−01 | 4.65709805e−01 | 4.39375341e−01 |
| 3.29155773e−01 | 6.19904602e−02 | −4.27052304e−02 | 3.19969054e−01 |
| 3.98707479e−01 | 6.08903579e−02 | 2.54609466e−01 | 5.41145205e−02 |
| 1.06891237e−01 | 3.99100095e−01 | 1.43427119e−01 | −2.91616082e−01 |
| 3.81130248e−01 | 4.53814000e−01 | 5.24397552e−01 | 3.17104429e−01 |
| 2.81836420e−01 | −2.09247231e−01 | 5.50375044e−01 | 5.44500411e−01 |
| 1.00450702e−01 | 5.60119510e−01 | 7.22976089e−01 | 3.21428597e−01 |
| 6.79861307e−01 | 3.39537337e−02 | −2.69423872e−01 | 4.03410912e−01 |
| 1.74871430e−01 | 1.91461131e−01 | −1.49569185e−02 | 6.23196483e−01 |
| 2.33368263e−01 | 1.82946190e−01 | 2.04207554e−01 | 3.31951022e−01 |
| −1.76885694e−01 | −2.48182788e−01 | 2.68156946e−01 | −8.46337825e−02 |
| 1.79268286e−01 | 8.61888006e−02 | −1.37351766e−01 | 2.17573151e−01 |
| 3.93679380e−01 | 5.61456978e−01 | 8.97245482e−02 | 3.28040898e−01 |
| −2.04371154e−01 | −3.99761572e−02 | 3.83047074e−01 | −1.35496652e−00 |
| 2.90651053e−01 | 2.78324902e−01 | 3.95508945e−01 | 2.58522093e−01 |
| −5.93881495e−02 | 2.35968202e−01 | 1.52583435e−01 | 3.05140138e−01 |
| 3.77759516e−01 | 2.38795951e−01 | −3.79709691e−01 | 1.41457096e−01 |
| 1.64465263e−01 | 2.39923894e−01 | 1.36263207e−01 | 4.73274350e−01 |
| 5.94357662e−02 | 1.03274003e−01 | 4.73600999e−02 | −5.31959608e−02 |
| 3.13030362e−01 | −1.14653575e−00 | 3.67024750e−01 | −4.10510451e−02 |
| 2.70098150e−01 | 4.31251884e−01 | 2.98532844e−01 | 3.12415987e−01 |
| 2.33988613e−01 | 4.65747446e−01 | −1.37308210e−01 | 2.56379008e−01 |
| −2.85252959e−01 | 4.37982529e−01 | 2.38277093e−01 | 5.21108992e−02 |
| −1.50725707e−01 | 4.11187202e−01 | 4.04973239e−01 | 2.14830756e−01 |
| −5.03857508e−02 | 2.09960595e−01 | 3.12405527e−01 | 7.68985093e−01] |
| [−3.00892480e−02 | 3.09659272e−01 | 2.11633995e−01 | 1.60988063e−01 |
| 6.47512972e−01 | 4.29303616e−01 | −2.89685071e−01 | −8.60465298e−05 |
| 2.35291757e−02 | 1.33298144e−01 | 1.11691572e−01 | 4.62562948e−01 |
| 3.90633792e−01 | 8.02548230e−02 | −6.17007986e−02 | 4.40731078e−01 |
| 7.16003597e−01 | −5.83854079e−01 | 9.41547677e−02 | 1.40273705e−01 |

TABLE $W_h^1$-continued

| | | | |
|---|---|---|---|
| 1.39821187e-01 | 3.29956681e-01 | 4.98355329e-01 | -9.61670503e-02 |
| 2.13020951e-01 | -2.33788550e-01 | 6.88168928e-02 | 3.79755080e-01 |
| -3.09669841e-02 | 8.40040972e-04 | 2.59841204e-01 | 1.79183565e-03 |
| -3.18018317e-01 | 1.46352733e-02 | 4.04126681e-02 | -2.31726803e-02 |
| 1.23447331e-03 | 3.14516932e-01 | 1.89335585e-01 | 7.89963156e-02 |
| 1.23600513e-01 | 6.77520186e-02 | 2.57952780e-01 | 7.59039998e-01 |
| 4.80789617e-02 | -1.49157748e-01 | -3.13718766e-02 | -5.37728742e-02 |
| 3.82154703e-01 | 4.94836420e-01 | -4.50636111e-02 | 1.97359338e-01 |
| 1.56762049e-01 | 3.75283480e-01 | 2.68572688e-01 | 6.91407025e-01 |
| 1.74772128e-01 | 2.98365921e-01 | 1.27956718e-01 | 3.31844062e-01 |
| 4.24910523e-02 | 2.33574733e-01 | 8.68382826e-02 | 3.74084711e-01 |
| -1.35516539e-01 | 2.37907842e-01 | 6.70962632e-01 | 6.83627501e-02 |
| 3.31518471e-01 | 8.59381333e-02 | 1.52633071e-01 | 1.62482575e-01 |
| 2.44962588e-01 | 3.49410176e-02 | 4.72350091e-01 | -8.38872641e-02 |
| 4.47152734e-01 | 4.38179493e-01 | 1.64998069e-01 | -3.62058878e-01 |
| 3.16376001e-01 | -1.71554267e-01 | -1.51398376e-01 | 1.30975544e-02 |
| 2.91740835e-01 | 3.35111581e-01 | 1.81545094e-01 | 7.74329230e-02 |
| -7.69077837e-02 | -5.90587437e-01 | 3.05975884e-01 | 2.53350064e-02 |
| 1.16805874e-01 | 1.38498634e-01 | 3.34920317e-01 | 1.93634331e-01 |
| 8.28084290e-01 | 2.81431019e-01 | -2.75753796e-01 | 4.33535397e-01 |
| 2.32099161e-01 | -2.93594748e-01 | 8.74615684e-02 | 1.53826416e-01 |
| -3.14401230e-03 | 2.71915793e-01 | -4.78188545e-02 | 2.29882196e-01 |
| 2.06291258e-01 | 3.66183668e-02 | 2.36378819e-01 | 6.23127878e-01 |
| 2.49566644e-01 | 6.17230356e-01 | 3.92810404e-01 | 6.48388743e-01 |
| 1.16678789e-01 | -1.01624441e-00 | 4.37004566e-02 | 2.23235682e-01 |
| 4.51847464e-01 | 4.50206906e-01 | -3.08925728e-03 | 1.99360102e-01 |
| -2.33068526e-01 | 1.88230932e-01 | 2.79614270e-01 | 4.06956345e-01 |
| 1.10242896e-01 | 1.27475902e-01 | 1.62892208e-01 | 5.26884608e-02 |
| -5.20911552e-02 | 1.68777227e-01 | 1.85723156e-01 | 3.80950063e-01 |
| 4.84298915e-01 | 4.22559887e-01 | 5.41537479e-02 | 2.91554540e-01 |
| -1.24175787e-01 | 3.17740470e-01 | -5.87608479e-02 | -7.62900189e-02 |
| 4.87036258e-01 | 6.14661396e-01 | -5.07768914e-02 | 4.08931881e-01 |
| 5.61703742e-01 | 4.61339027e-01 | 4.83184040e-01 | 2.48945251e-01 |
| -1.39582947e-01 | 8.07006210e-02 | 2.51235038e-01 | 4.80899364e-01 |
| 1.21358141e-01 | -4.34775531e-01 | 3.41913015e-01 | 7.34173000e-01 |
| 9.92970467e-02 | 7.32161164e-01 | 2.52418488e-01 | 1.65306687e-01 |
| 3.23001534e-01 | 4.40349728e-01 | 4.45532538e-02 | 1.98097482e-01 |
| -3.77242804e-01 | -8.64167586e-02 | 3.42996508e-01 | 4.64456715e-02 |
| -8.97878930e-02 | 1.39027521e-01 | 1.52063191e-01 | 2.82216817e-01 |
| 2.90058106e-01 | 3.38256150e-01 | 1.45854428e-01 | 4.54573512e-01 |
| 1.73159391e-01 | 5.93168139e-02 | 7.08659649e-01 | 4.40978199e-01 |
| 4.88737971e-01 | -2.34364793e-01 | -1.43896401e-01 | 2.06966326e-01 |
| 2.35879317e-01 | 2.17915580e-01 | 5.11050969e-02 | 3.08518171e-01 |
| -2.77011186e-01 | 2.38690540e-01 | 1.29803479e-01 | 3.85505974e-01 |
| 1.73468590e-01 | -1.03921562e-01 | -3.33680920e-02 | 2.83479929e-01 |
| 3.75114173e-01 | -5.49609244e-01 | -4.55585234e-02 | 1.88188985e-01 |
| 3.57121915e-01 | 1.86002791e-01 | 2.03540325e-02 | 5.51181853e-01 |
| 8.73077512e-02 | -6.07599281e-02 | 3.78871635e-02 | -4.76528227e-01 |
| -6.74670190e-02 | 5.40701985e-01 | 3.36024076e-01 | 2.08192721e-01 |
| 2.15748981e-01 | 1.84384748e-01 | 2.83620089e-01 | 4.11243170e-01 |
| -7.31710419e-02 | 1.39038131e-01 | -2.43879296e-02 | 1.51700750e-01 |
| 5.17330766e-01 | -4.67633486e-01 | -2.93344855e-01 | 7.25960657e-02 |
| -8.23729485e-03 | 3.28497678e-01 | -5.57073532e-03 | -9.41349417e-02 |
| 1.43335998e-01 | -1.38377801e-01 | 1.97493449e-01 | -1.50794506e-01 |
| 4.11317527e-01 | 4.45825994e-01 | -1.78601399e-01 | 5.34981370e-01 |
| 2.08732903e-01 | 3.89438897e-01 | -3.85079622e-01 | 3.48017573e-01 |
| 2.04602540e-01 | 4.28340644e-01 | 3.15932095e-01 | 1.40593452e-02 |
| -1.45087957e-01 | 2.30369657e-01 | 8.15078896e-03 | 3.41707230e-01 |
| -9.40850303e-02 | 1.73724517e-01 | 1.93290055e-01 | 7.84694612e-01] |
| [2.56692469e-01 | 3.44760150e-01 | 4.60013241e-01 | -4.37137127e-01 |
| 3.17580886e-02 | 4.30911034e-01 | -1.77297592e-01 | 1.09732009e-01 |
| 2.74235845e-01 | -1.53370323e-02 | 1.36268228e-01 | 1.00965306e-01 |
| 4.08933282e-01 | -2.46776920e-01 | 7.17766136e-02 | -7.03977048e-02 |
| -2.01307818e-01 | 6.19613528e-01 | 3.32218498e-01 | 4.14503604e-01 |
| 8.54520220e-03 | 3.66795212e-01 | 3.83224219e-01 | 3.28313679e-01 |
| 2.81582236e-01 | 4.57801551e-01 | 5.11429846e-01 | 1.45057455e-01 |
| -1.56843156e-01 | 4.65710968e-01 | 6.73806518e-02 | -1.69086650e-01 |
| 7.40005374e-01 | 1.29346311e-01 | -1.43502355e-02 | 1.10704161e-01 |
| 2.80223638e-01 | 9.11842585e-02 | 1.49765149e-01 | -1.82899311e-02 |
| -1.25512689e-01 | 4.44194824e-01 | 3.99738342e-01 | 3.76671910e-01 |
| 1.78034216e-01 | 1.60508662e-01 | 5.16174138e-01 | 4.92844701e-01 |
| -7.34642372e-02 | 1.05797350e-01 | 7.22600996e-01 | 5.07130682e-01 |
| -2.09078565e-02 | -1.81031669e-03 | -5.94875950e-04 | -9.18402597e-02 |
| 4.61176276e-01 | 1.66486606e-01 | 3.47085446e-01 | 1.00444313e-02 |
| -2.34042499e-02 | 5.24280012e-01 | 1.14501983e-01 | -9.98506248e-02 |
| -2.64408290e-01 | -3.32840681e-02 | -1.46354571e-01 | 1.58705890e-01 |
| 2.18837216e-01 | 1.33530602e-01 | 1.92326114e-01 | -2.50407785e-01 |
| 3.61115545e-01 | 9.55288485e-02 | -2.86022611e-02 | 6.72827840e-01 |
| -9.57741439e-02 | 2.26290494e-01 | 6.48993194e-01 | 1.13606662e-01 |
| -8.06603059e-02 | 4.06967402e-01 | 1.56969443e-01 | 1.42971009e-01 |

TABLE $W_h^1$-continued

| | | | |
|---|---|---|---|
| 1.03082739e−01 | 4.59487826e−01 | 1.52918801e−01 | 7.41006434e−02 |
| 1.99952647e−01 | 2.01034799e−01 | 1.89815313e−01 | 3.87342423e−01 |
| 3.22896391e−01 | −3.04559227e−02 | 5.45919001e−01 | 3.33724290e−01 |
| −3.88956726e−01 | 4.05219406e−01 | 2.54598916e−01 | −4.98143107e−01 |
| −1.86508417e−01 | 8.23414207e−01 | 7.91796505e−01 | 2.81838506e−01 |
| 2.10860372e−01 | 3.52809697e−01 | 1.01944454e−01 | 2.50586629e−01 |
| 1.41778952e−02 | 1.91502854e−01 | 1.37049302e−01 | −9.75743029e−03 |
| 2.87180811e−01 | −9.29304212e−02 | 3.78084689e−01 | 6.36214390e−02 |
| 9.64585170e−02 | 4.40307260e−01 | 5.00549555e−01 | −1.09842815e−01 |
| 2.86377043e−01 | 2.40566030e−01 | 2.39460871e−01 | 1.08046450e−01 |
| 3.31772894e−01 | 4.74703699e−01 | 4.63415533e−01 | 1.90038845e−01 |
| 5.18613696e−01 | 5.73040247e−01 | −1.19491838e−01 | 4.97682482e−01 |
| 6.28580928e−01 | −2.14313537e−01 | 2.69684047e−01 | −4.95010875e−02 |
| 5.77397943e−02 | 6.64276108e−02 | 3.72837007e−01 | 5.51955700e−01 |
| 3.13182205e−01 | 2.33960122e−01 | 2.48968601e−02 | 2.38917843e−01 |
| −2.71632671e−01 | −1.96424410e−01 | 2.93151289e−01 | 4.07860056e−02 |
| 3.27095181e−01 | 6.64706454e−02 | 2.29902118e−01 | 3.06342900e−01 |
| 4.09970850e−01 | 2.03449711e−01 | 3.28488857e−01 | 5.03569186e−01 |
| 7.61021256e−01 | 7.27046371e−01 | 3.25333178e−01 | 1.25878513e−01 |
| 1.64616764e−01 | 4.43697050e−02 | −3.28099519e−01 | 3.92629087e−01 |
| 3.63895237e−01 | 1.31657958e−01 | 6.47291094e−02 | 2.81124592e−01 |
| 7.06671178e−01 | 7.00179458e−01 | 4.15815622e−01 | 3.61290276e−01 |
| 4.91427392e−01 | 1.49151072e−01 | −2.40145817e−01 | −2.91603148e−01 |
| 3.01689714e−01 | 2.64819175e−01 | 2.38815695e−01 | 8.37237462e−02 |
| 2.70553917e−01 | 8.87629986e−02 | 5.67545056e−01 | 3.41448039e−02 |
| 4.61098880e−01 | 2.43176848e−01 | −3.60689615e−03 | 4.65694696e−01 |
| −1.47932753e−01 | 4.36530471e−01 | 5.23277760e−01 | 3.26362818e−01 |
| 2.66622812e−01 | 4.95068759e−01 | 1.19534768e−01 | 2.52135210e−02 |
| −7.04923272e−03 | 5.70497438e−02 | 3.36857021e−01 | 1.29168808e−01 |
| 1.50590077e−01 | 7.53352493e−02 | 1.12556860e−01 | 2.30946109e−01 |
| 4.03630972e−01 | −4.95338999e−02 | 2.78389473e−02 | 1.09027408e−01 |
| 5.11743605e−01 | −1.14399018e−02 | 4.28669959e−01 | 4.17730838e−01 |
| 4.36978698e−01 | 4.23293650e−01 | 1.74442261e−01 | 4.24508452e−01 |
| 3.15038919e−01 | 5.29017270e−01 | 4.94194567e−01 | −1.28891781e−01 |
| −4.37504575e−02 | 5.45815349e−01 | −1.39552578e−01 | −4.86867689e−02 |
| −5.59023768e−02 | 2.66715854e−01 | 3.05998743e−01 | 1.37745431e−02 |
| 1.80862904e−01 | 4.00252283e−01 | 2.49715582e−01 | 5.87965906e−01 |
| −2.05169767e−01 | −3.09139583e−02 | 7.01706707e−02 | 8.32144797e−01 |
| 1.61022753e−01 | 3.34683657e−01 | 5.94067276e−01 | 1.30648717e−01 |
| 5.25352120e−01 | 1.59851626e−01 | 2.92310655e−01 | 3.84380668e−01 |
| 3.56588870e−01 | 1.36915773e−01 | −3.90115120e−02 | 4.82358001e−02 |
| 4.73154426e−01 | 3.52101982e−01 | 3.81467640e−01 | 3.96795303e−01 |
| 5.65488897e−02 | 2.07228288e−01 | 3.63771945e−01 | 6.67702556e−02] |
| [5.25391474e−02 | 2.79392064e−01 | 6.14964068e−02 | 1.19489945e−01 |
| −1.90394279e−02 | −3.48380774e−01 | −1.81968845e−02 | −4.07942802e−01 |
| −8.01453814e−02 | 5.28534688e−02 | 3.88556391e−01 | 1.91586956e−01 |
| 8.76861587e−02 | 2.58594472e−02 | −6.15587272e−03 | 1.42424852e−01 |
| 1.52482942e−01 | 5.04128337e−02 | 1.93895489e−01 | 1.30512014e−01 |
| −5.38525023e−02 | 3.38834614e−01 | −2.36156687e−01 | −8.25010315e−02 |
| −1.72036484e−01 | −1.86861143e−01 | −2.67560661e−01 | 2.12826952e−01 |
| −1.44934684e−01 | 8.57986603e−03 | 2.70885289e−01 | 1.70993924e−01 |
| 4.77141105e−02 | −1.40938595e−01 | 3.28552544e−01 | 1.16460465e−01 |
| 1.70519814e−01 | −1.27473595e−02 | 1.02059096e−01 | −2.74712026e−01 |
| 1.55528918e−01 | 3.20291787e−01 | −1.63969979e−01 | 4.01946157e−01 |
| −6.49999827e−02 | 2.08743796e−01 | −1.41826555e−01 | −1.86117858e−01 |
| 2.06620321e−02 | 3.75983626e−01 | 1.21695034e−01 | 2.15367481e−01 |
| 1.65065691e−01 | 6.10366315e−02 | 1.31329462e−01 | 1.53216422e−01 |
| −1.46292821e−01 | 4.59785610e−01 | 4.05753523e−01 | −2.06726734e−02 |
| −2.34739453e−01 | 3.18986893e−01 | 1.90411314e−01 | 1.04643509e−01 |
| 1.64571509e−01 | −3.27239871e−01 | −8.51088464e−02 | 5.56033552e−01 |
| 1.64844647e−01 | 2.44277358e−01 | −2.38925934e−01 | 3.21687430e−01 |
| −4.55938816e−01 | 6.46243542e−02 | 1.11278042e−01 | −2.30116129e−01 |
| −2.08830252e−01 | 5.57222310e−03 | 5.37041463e−02 | −4.75699723e−01 |
| 2.00991426e−02 | −6.94300458e−02 | 1.82349846e−01 | −8.45740922e−03 |
| 1.20428748e−01 | −1.13488518e−01 | −6.38426840e−02 | −3.01661491e−01 |
| 8.23498145e−02 | 3.34129989e−01 | 3.14092666e−01 | 2.03195512e−01 |
| 2.98065722e−01 | 2.72647347e−01 | −2.86932349e−01 | −4.63774316e−02 |
| −1.26273364e−01 | 1.00203604e−01 | −2.12291881e−01 | 4.51732039e−01 |
| −1.78554237e−01 | −8.52199569e−02 | −2.58523792e−01 | −2.26711288e−01 |
| 5.05112894e−02 | −1.50909409e−01 | −1.27285480e−01 | −3.54867727e−01 |
| −1.48610622e−01 | −1.91791698e−01 | 3.78107756e−01 | 2.42242143e−01 |
| 4.28659748e−03 | 3.68648291e−01 | −7.75648877e−02 | −5.59843816e−02 |
| 1.89990476e−01 | −1.82129204e−01 | 1.47766769e−01 | −1.95929520e−02 |
| −1.49361730e−01 | 2.66274452e−01 | 7.87820145e−02 | −2.88509965e−01 |
| −6.31975383e−02 | 1.91951901e−01 | 1.70801625e−01 | −6.37974888e−02 |
| −9.75601841e−03 | 5.86356111e−02 | −2.62836009e−01 | −1.51254341e−01 |
| −2.74506658e−01 | −2.61004902e−02 | −5.94010241e−02 | 1.12826072e−01 |
| 2.36027077e−01 | −2.33994499e−01 | −3.72549325e−01 | 1.95513278e−01 |
| −1.85819380e−02 | 3.32532413e−02 | 8.33740234e−02 | −7.44465217e−02 |
| −3.11432153e−01 | 2.59497285e−01 | −3.56280476e−01 | 3.67288440e−02 |

TABLE $W_h^1$-continued

| | | | |
|---|---|---|---|
| −1.03824459e−01 | 9.76578146e−02 | 1.33170500e−01 | 7.89432079e−02 |
| −2.45398447e−01 | −3.29343304e−02 | −3.48929882e−01 | −2.85559446e−01 |
| −2.05368027e−01 | 3.98337811e−01 | 6.71910793e−02 | 1.69386566e−01 |
| 9.54362825e−02 | 2.52871126e−01 | 3.82205367e−01 | 3.66548657e−01 |
| −9.14419368e−02 | −1.45953253e−01 | −8.07519555e−02 | −8.07507709e−02 |
| −2.17510387e−01 | −6.94713220e−02 | −1.20134644e−01 | 9.85407159e−02 |
| −1.66496649e−01 | −3.52502917e−04 | 4.23785150e−01 | 1.68686062e−01 |
| −4.87952307e−01 | 7.43421167e−02 | 1.26188815e−01 | 3.10208499e−01 |
| −1.89950198e−01 | 9.26318858e−03 | −1.45073012e−01 | 1.63301697e−03 |
| 3.69931757e−02 | 3.81319433e−01 | −9.32825133e−02 | −5.94542064e−02 |
| 5.79013526e−02 | −1.70293421e−01 | −1.10499896e−01 | 1.85012102e−01 |
| 2.58835524e−01 | −1.26020849e−01 | −9.18470845e−02 | 1.13914654e−01 |
| 1.29240587e−01 | −1.45851016e−01 | 4.59039778e−01 | −1.21367946e−01 |
| 2.65044391e−01 | 1.29410669e−01 | −1.77851319e−01 | 1.70282260e−01 |
| −7.41296038e−02 | 1.38088718e−01 | −5.22579290e−02 | 8.51875544e−02 |
| 1.42566219e−01 | 1.67515397e−01 | −1.10014573e−01 | −2.23680273e−01 |
| 1.32788317e−01 | 7.54050240e−02 | 3.80323946e−01 | −6.51568770e−02 |
| −1.66442737e−01 | −1.71032567e−02 | −5.36395190e−03 | −2.54746437e−01 |
| 1.89219728e−01 | −2.79923737e−01 | 1.95843503e−01 | 7.75943920e−02 |
| 4.06041332e−02 | −1.23157032e−01 | −2.00710207e−01 | 8.54196995e−02 |
| 3.70455354e−02 | 2.78584361e−01 | 2.22444143e−01 | −1.25808299e−01 |
| 2.84997046e−01 | 5.44295684e−02 | 2.54282981e−01 | −3.60926390e−01 |
| 2.93605298e−01 | −1.06727351e−02 | 2.90374431e−01 | −1.32598415e−01 |
| −3.01021457e−01 | 3.95511538e−02 | 2.35972956e−01 | −1.97427198e−01 |
| 1.37744755e−01 | 2.05073118e−01 | 2.51943052e−01 | −2.10604832e−01 |
| 5.91138043e−02 | 2.13530749e−01 | −3.55615705e−01 | 1.75474867e−01 |
| −5.93460202e−02 | −1.21567927e−01 | −5.34984544e−02 | 3.68459731e−01] |
| [−2.18530484e−02 | 3.27883065e−01 | 3.74946743e−01 | 6.58886582e−02 |
| 4.26481068e−02 | 7.91314483e−02 | 1.54380903e−01 | 8.86626363e−01 |
| 1.98934659e−01 | −1.95484936e−01 | 3.35323989e−01 | 1.67673733e−01 |
| −1.67674366e−02 | 2.98427224e−01 | 1.42088249e−01 | 2.37253524e−04 |
| 9.02552716e−03 | 9.51910019e−02 | 4.40174192e−01 | 6.43623650e−01 |
| −2.79422432e−01 | −1.28157765e−01 | 4.90623433e−01 | 2.05424711e−01 |
| 1.62712056e−02 | 2.59266347e−01 | 9.13079903e−02 | 2.73197800e−01 |
| 1.35877416e−01 | 3.04881036e−01 | 5.31871378e−01 | 3.07121664e−01 |
| 4.35366124e−01 | 2.19549015e−01 | 2.22241431e−01 | 2.66910344e−01 |
| 8.22898000e−02 | 3.61841202e−01 | −2.09052235e−01 | 4.20126319e−01 |
| 1.10496737e−01 | 3.86490971e−01 | 7.07609579e−02 | −2.39495918e−01 |
| 3.76620919e−01 | −4.20999825e−02 | −2.85127964e−02 | −9.89240780e−02 |
| 4.07837451e−01 | 5.98097146e−01 | 3.57272416e−01 | 1.37613475e−01 |
| 7.71913901e−02 | 4.13977712e−01 | 1.98416650e−01 | 3.54747213e−02 |
| 2.98469722e−01 | 5.80732152e−01 | 1.95838809e−01 | −2.87450224e−01 |
| −4.88881394e−02 | 5.33905447e−01 | 3.21580648e−01 | 2.73020089e−01 |
| −1.10635363e−01 | 4.20920879e−01 | 2.21333563e−01 | 4.10919309e−01 |
| 6.12908788e−02 | 1.28041863e−01 | 2.64151037e−01 | 2.87087053e−02 |
| 2.83407986e−01 | 1.68609053e−01 | 5.18851340e−01 | 7.62000233e−02 |
| 3.07242870e−01 | 1.00509025e−01 | 2.46703848e−01 | 1.08745657e−01 |
| 4.87725854e−01 | 2.80730695e−01 | 1.82181284e−01 | 1.11922130e−01 |
| −2.90812552e−01 | 2.82792717e−01 | 3.83325130e−01 | 2.44982600e−01 |
| 3.80319089e−01 | 3.08276206e−01 | 2.10485101e−01 | 1.56751260e−01 |
| 3.79113853e−01 | 6.79077208e−01 | −1.94403768e−01 | 4.89278764e−01 |
| 1.14464134e−01 | −1.62601694e−01 | 4.83992636e−01 | 2.00687870e−01 |
| 3.40896249e−01 | 4.56312865e−01 | 2.98276961e−01 | 4.09461349e−01 |
| 2.89214492e−01 | 1.40989214e−01 | −5.71663268e−02 | −5.47025502e−02 |
| 4.46959019e−01 | 3.71814072e−01 | 6.36936188e−01 | 2.27352530e−01 |
| 3.60715628e−01 | 4.35914069e−01 | −3.75054061e−01 | 2.07228467e−01 |
| −2.85631925e−01 | 2.27025319e−02 | 5.09588659e−01 | −1.46125942e−01 |
| 4.87939805e−01 | −3.52449827e−01 | 4.17501122e−01 | 1.07430317e−01 |
| 7.65421838e−02 | 1.25402674e−01 | 2.62012482e−01 | 2.64966220e−01 |
| 4.02559698e−01 | 1.34064779e−02 | 1.25435725e−01 | 7.50506222e−01 |
| 4.24612820e−01 | 4.98725921e−02 | 4.92782682e−01 | 4.34018001e−02 |
| 4.00903165e−01 | −2.88553350e−02 | 1.31943896e−01 | −9.13708135e−02 |
| 1.40594430e−01 | 2.02811778e−01 | 2.82171935e−01 | 5.57431206e−02 |
| −3.63541812e−01 | 2.04828992e−01 | 1.01394244e−02 | 5.21761477e−01 |
| 3.06492239e−01 | 2.12437510e−02 | −1.13991261e−01 | 8.84213299e−03 |
| −3.32059972e−02 | 3.48619908e−01 | −1.98466241e−01 | 5.32166660e−01 |
| −7.57775754e−02 | 3.22755933e−01 | 3.66951048e−01 | 1.39609441e−01 |
| 2.06641704e−01 | −4.83113825e−02 | 1.39599368e−01 | 1.46260977e−01 |
| 1.50884524e−01 | 2.24261820e−01 | −6.09203912e−02 | 2.91284528e−02 |
| 8.54260847e−02 | 4.43110794e−01 | 2.89743483e−01 | −4.36341688e−02 |
| 3.87186706e−01 | 2.74453729e−01 | 2.27759853e−01 | 2.00091526e−01 |
| 4.90012765e−01 | 2.88506627e−01 | −2.97526177e−02 | 2.79545367e−01 |
| 1.90084323e−01 | 3.70638222e−01 | 3.61897796e−01 | 4.82405603e−01 |
| 2.36094426e−02 | 1.67147592e−01 | −5.82515611e−04 | 1.67677194e−01 |
| 3.18133950e−01 | 1.26795277e−01 | 3.07771806e−01 | 1.45653844e−01 |
| 6.92947567e−01 | 2.77771801e−01 | 4.18984801e−01 | 2.65320778e−01 |
| 3.27864215e−02 | 1.72263116e−01 | 5.76531172e−01 | 2.42010176e−01 |
| −2.94553749e−02 | 2.03905761e−01 | 2.90014505e−01 | 1.83505669e−01 |
| −1.84896842e−01 | 2.65773296e−01 | 3.82924527e−01 | −8.02605972e−03 |
| −7.65545070e−02 | 5.10076642e−01 | 3.62015776e−02 | −2.79862452e−02 |

TABLE $W_h^1$-continued

| | | | |
|---|---|---|---|
| −6.70406893e−02 | 2.83688575e−01 | 2.84623116e−01 | 3.16355199e−01 |
| 5.51962793e−01 | 7.53192902e−02 | 3.52567106e−01 | −4.67174016e−02 |
| −1.45436406e−01 | 4.36305553e−01 | −4.14866805e−02 | 3.35079581e−01 |
| 2.79020250e−01 | 1.89514130e−01 | 4.59813595e−01 | 3.29899579e−01 |
| 5.24011850e−01 | −3.98138970e−01 | 6.41897172e−02 | 4.00380343e−01 |
| 2.78015107e−01 | 3.13391745e−01 | 4.04989749e−01 | 2.61321992e−01 |
| 3.62853974e−01 | 1.05831005e−01 | 3.93311858e−01 | 9.83719379e−02 |
| 1.08992353e−01 | −2.25015908e−01 | −1.22227892e−01 | 3.79472792e−01 |
| 2.63395011e−01 | −2.46166587e−02 | 2.30233908e−01 | −1.43600672e−01 |
| 2.28287980e−01 | 4.58828896e−01 | 1.48373753e−01 | 2.80949343e−02 |
| 1.99736774e−01 | 6.26692399e−02 | −5.15702786e−03 | 3.71719837e−01] |
| [3.11539352e−01 | 3.02422971e−01 | 8.74113739e−02 | 1.25871390e−01 |
| −2.32528746e−01 | 9.48021561e−03 | 1.60316959e−01 | 1.05481513e−01 |
| 4.90660101e−01 | 1.37747247e−02 | 8.78920108e−02 | −2.40639341e−03 |
| 3.05549037e−02 | −2.44323894e−01 | −1.34937719e−01 | −2.38562584e−01 |
| −9.14973766e−02 | 4.37391847e−01 | 1.91897035e−01 | −2.13717476e−01 |
| 3.27848762e−01 | 5.44824600e−01 | 3.48048180e−01 | 2.60414153e−01 |
| −3.66847068e−02 | 6.98195100e−01 | 1.46157503e−01 | −2.08645910e−01 |
| 3.85906398e−01 | 8.08148682e−02 | −4.12398010e−01 | 4.17743623e−01 |
| 8.75417218e−02 | 1.17674895e−01 | −8.18291083e−02 | −2.36893028e−01 |
| 1.68783277e−01 | −5.93421236e−02 | 2.95686647e−01 | 2.47062832e−01 |
| −1.00624792e−01 | −3.96633185e−02 | −8.14207196e−02 | 1.81108996e−01 |
| 3.00014436e−01 | 1.38319405e−02 | 1.49401128e−01 | 1.85658485e−01 |
| −2.23631591e−01 | 3.29879791e−01 | 1.22051723e−01 | −2.16692537e−01 |
| 2.53009230e−01 | −1.71198875e−01 | −3.70950401e−01 | −3.60888043e−05 |
| 2.59899586e−01 | 1.25530019e−01 | 1.89931959e−01 | 4.61012274e−01 |
| 3.57046761e−02 | −1.05910167e−01 | −7.53695741e−02 | 1.50439050e−02 |
| 3.20819914e−01 | −1.02460422e−01 | −3.11331600e−01 | −5.08438312e−02 |
| 1.67688772e−01 | 1.46023780e−01 | 3.26630622e−01 | −1.87971294e−01 |
| −1.40574053e−01 | 5.28097212e−01 | 3.00372243e−01 | 2.54246414e−01 |
| 3.89930725e−01 | 2.07465857e−01 | −5.25043942e−02 | −2.30013937e−01 |
| −1.89626053e−01 | 7.67540112e−02 | −1.45567447e−01 | 2.60541737e−01 |
| 3.04718405e−01 | 3.25159878e−01 | −7.93213472e−02 | 1.21343680e−01 |
| −1.73455924e−02 | 9.90427509e−02 | 3.02885268e−02 | 1.36317685e−01 |
| 4.42328185e−01 | 1.13769181e−01 | 1.72612026e−01 | −5.64514212e−02 |
| 2.56167084e−01 | 7.69982859e−02 | −1.31540552e−01 | −3.14318657e−01 |
| −2.24868596e−01 | 1.78678572e−01 | 1.18793696e−01 | 9.44827721e−02 |
| 1.78145424e−01 | 1.06727764e−01 | 4.50152189e−01 | 3.56708467e−01 |
| −3.02922010e−01 | 3.06233913e−01 | 1.92716403e−03 | −7.12449700e−02 |
| −8.11703280e−02 | −4.96412694e−01 | 2.95713633e−01 | 1.84707373e−01 |
| 7.04106092e−02 | 4.70885783e−01 | 2.20141828e−01 | 2.52845705e−01 |
| 4.76276241e−01 | −9.39778909e−02 | 1.35384455e−01 | 2.26271957e−01 |
| −3.49544175e−02 | 3.98596793e−01 | −1.22076496e−02 | −6.62615616e−03 |
| 1.22203901e−01 | 3.43900919e−01 | 2.04455048e−01 | 2.06765205e−01 |
| −1.02239244e−01 | 4.03870970e−01 | 1.37404174e−01 | 2.10335165e−01 |
| 2.82754544e−01 | 3.60440731e−01 | 9.23495218e−02 | 3.07182103e−01 |
| 1.32490456e−01 | 1.01239994e−01 | 2.41649643e−01 | 2.75822114e−02 |
| 6.42051250e−02 | −1.65230229e−01 | 1.46247283e−01 | −1.40742362e−01 |
| 1.70383155e−01 | −8.41942150e−03 | 2.12781176e−01 | −7.24893436e−02 |
| 4.15027559e−01 | 1.14252128e−01 | 6.07819557e−01 | 1.78021908e−01 |
| 5.75615168e−01 | 2.75519252e−01 | 4.34214398e−02 | −6.18967004e−02 |
| 2.13594824e−01 | 3.68843883e−01 | −6.73373401e−01 | −2.32761055e−02 |
| 1.10876106e−01 | 4.58340868e−02 | 5.33375978e−01 | 3.45528089e−02 |
| 4.74259585e−01 | 1.87515393e−01 | −8.06576610e−02 | 3.52000058e−01 |
| 1.77929774e−01 | −1.35507494e−01 | −1.40520200e−01 | 3.22219938e−01 |
| −1.90205276e−01 | −9.41544026e−02 | 2.13780403e−01 | 3.16475667e−02 |
| 4.81999129e−01 | 3.91363978e−01 | −4.79583666e−02 | 2.22108215e−01 |
| 2.44064778e−01 | −9.14446563e−02 | 1.96469828e−01 | 1.84634805e−01 |
| 1.97504357e−01 | 4.97938097e−01 | 4.02381331e−01 | 2.26970345e−01 |
| 1.45325601e−01 | −4.22213711e−02 | 1.23204947e−01 | 3.33195716e−01 |
| 2.38740161e−01 | −4.37553376e−02 | −3.99726301e−01 | −5.02530821e−02 |
| −1.12170316e−01 | 3.37108910e−01 | 6.39447793e−02 | −2.57806122e−01 |
| 2.62383401e−01 | 1.09853804e−01 | −6.25820830e−02 | 3.67192984e−01 |
| 3.36559832e−01 | 2.53229272e−02 | −2.72336099e−02 | 1.06770366e−01 |
| 5.25476038e−01 | −3.33952755e−02 | 1.87436435e−02 | 4.22925562e−01 |
| 3.25341135e−01 | 5.00250570e−02 | 2.48760656e−01 | 3.10732156e−01 |
| −1.76999509e−01 | 2.86675483e−01 | −9.91812050e−02 | 6.05113134e−02 |
| 3.94806445e−01 | 5.11978984e−01 | 2.04162467e−02 | 1.46591306e−01 |
| −3.74948829e−02 | 2.23660752e−01 | 3.99212778e−01 | 4.29348409e−01 |
| 3.72421712e−01 | 4.09895986e−01 | −1.25732705e−01 | 5.56321621e−01 |
| 1.19194105e−01 | 1.86608478e−01 | 1.74421296e−01 | 1.46489918e−01 |
| −3.03413272e−01 | 2.84776032e−01 | 5.44444751e−03 | 4.77268100e−01 |
| 3.63324583e−01 | 8.01049843e−02 | 1.63203001e−01 | −1.45071056e−02 |
| 3.16844769e−02 | 2.69716024e−01 | 3.53410363e−01 | 9.83746275e−02 |
| −1.03498541e−01 | 1.87959462e−01 | −1.50187518e−01 | −7.49785379e−02] |
| [3.70401144e−02 | −3.03855628e−01 | 1.44701734e−01 | −1.73190758e−01 |
| 7.37392485e−01 | 1.58379134e−02 | 1.49782598e−01 | 3.95463675e−01 |
| 3.13107550e−01 | −3.29386592e−01 | 3.61634851e−01 | −7.42199481e−04 |
| −3.09157699e−01 | 2.69545585e−01 | 1.85197443e−01 | 2.86702275e−01 |
| 5.06741941e−01 | −3.59295547e−01 | 3.53709042e−01 | 1.94683507e−01 |

TABLE $W_h^1$-continued

| | | | |
|---|---|---|---|
| 9.50129479e-02 | 5.27964458e-02 | -5.44665813e-01 | 1.32938623e-01 |
| -1.56710535e-01 | 3.23709190e-01 | 1.94061711e-01 | 5.36139786e-01 |
| 2.37919733e-01 | 3.53068292e-01 | 4.07548070e-01 | 1.89213455e-01 |
| -8.15119520e-02 | 2.22093999e-01 | -2.20607892e-01 | -1.69897497e-01 |
| 2.28617445e-01 | 1.42694721e-02 | 2.26336747e-01 | 2.47579947e-01 |
| -1.08953141e-01 | 5.60173929e-01 | 2.69438714e-01 | 1.39048491e-02 |
| 5.40573359e-01 | 1.87523127e-01 | -3.01702414e-02 | -1.20001726e-01 |
| 8.52754191e-02 | 1.42198086e-01 | 1.76520776e-02 | 1.55402035e-01 |
| 5.96040249e-01 | 1.22299179e-01 | 3.43616754e-01 | 3.74652565e-01 |
| 1.74114510e-01 | 8.49725306e-02 | 8.57375801e-01 | 1.26669765e-01 |
| -2.22412243e-01 | 2.15165392e-01 | 1.50408536e-01 | 2.45857388e-01 |
| 4.53619212e-01 | 1.75981566e-01 | 6.34748638e-01 | 4.07187134e-01 |
| 1.95055112e-01 | 3.43461841e-01 | -3.84780504e-02 | 1.63155138e-01 |
| 2.88339913e-01 | -3.62082273e-01 | -9.68872979e-02 | 3.35265286e-02 |
| -2.37251937e-01 | -2.19427034e-01 | 5.74296594e-01 | 4.10423011e-01 |
| -5.81825078e-01 | 4.74029481e-01 | 3.95591497e-01 | 3.42752099e-01 |
| 5.79455756e-02 | 4.42434490e-01 | 3.33633244e-01 | 8.65495384e-01 |
| 6.28631234e-01 | -4.85720672e-02 | -3.60137761e-01 | -1.29688727e-02 |
| -3.30977112e-01 | 3.02802533e-01 | -4.72488552e-01 | 3.11451197e-01 |
| 1.13716843e-02 | 1.45841122e-01 | 2.88365424e-01 | 3.20080101e-01 |
| 3.63492996e-01 | -1.87949434e-01 | 1.56310052e-01 | -7.89181441e-02 |
| 5.01204669e-01 | -8.83774459e-02 | 6.05865777e-01 | 5.65226935e-02 |
| 4.69967932e-01 | 2.42413655e-01 | 3.25914333e-03 | 4.26779352e-02 |
| 1.50026113e-01 | 2.00770065e-01 | -8.33351538e-02 | -1.82613552e-01 |
| 5.35889506e-02 | 3.67669851e-01 | 1.42846303e-01 | 1.80261642e-01 |
| 1.89088956e-01 | 3.65918696e-01 | 2.81949043e-02 | 2.03940012e-02 |
| -6.39314353e-02 | 5.33728488e-02 | -3.49014215e-02 | 6.39550984e-01 |
| 3.61725599e-01 | -2.60161106e-02 | 1.59279909e-02 | -1.28530338e-01 |
| 9.69535112e-02 | 5.50989985e-02 | 1.88044325e-01 | -1.76312998e-01 |
| 2.17945427e-01 | 6.15766421e-02 | -6.37260154e-02 | 4.01199609e-02 |
| 1.35982379e-01 | 2.33222637e-02 | 1.16174556e-02 | -2.04349592e-01 |
| 1.50644585e-01 | 1.58095941e-01 | 2.76376784e-01 | 8.28348473e-02 |
| 3.99359196e-01 | 5.73527515e-02 | 9.03036296e-02 | -9.31086913e-02 |
| 3.39211300e-02 | 6.53192341e-01 | -6.25716507e-01 | -2.58656770e-01 |
| 3.42241079e-01 | -4.49561000e-01 | 2.31872439e-01 | 1.91517808e-02 |
| 3.35684210e-01 | 3.59568983e-01 | 5.73417127e-01 | 1.14732616e-01 |
| -1.63259298e-01 | 2.12268814e-01 | 5.82759142e-01 | 3.46870124e-02 |
| -2.28730962e-01 | -1.54134035e-01 | -1.32187665e-01 | 1.45301623e-02 |
| -6.60198228e-03 | 5.59034765e-01 | 4.62205023e-01 | 3.74828637e-01 |
| 8.68378162e-01 | 2.40978092e-01 | -1.06772138e-02 | -1.01967670e-01 |
| -8.30187500e-02 | 8.67022797e-02 | 4.71169978e-01 | 5.41670881e-02 |
| -2.31324136e-01 | -2.44316697e-01 | 9.34110209e-03 | 4.71966058e-01 |
| -3.74079868e-02 | 4.21977311e-01 | 4.23088524e-04 | -1.37930140e-01 |
| 6.61890805e-01 | 2.42856994e-01 | 2.19532400e-01 | -1.27225250e-01 |
| 1.38584967e-03 | 5.76160669e-01 | 3.39115888e-01 | 2.01858789e-01 |
| 5.02254188e-01 | 4.80516404e-01 | 6.17364533e-01 | 5.40868223e-01 |
| 2.26451024e-01 | 9.30712074e-02 | 3.70113626e-02 | -5.79785705e-01 |
| 1.70034677e-01 | 2.93178052e-01 | 5.18815100e-01 | 3.78561288e-01 |
| -5.30271947e-01 | -3.74786556e-02 | 3.98830861e-01 | -1.78101182e-01 |
| 3.81302983e-01 | 3.91161971e-04 | 1.20988101e-01 | 1.39992550e-01 |
| 2.92415679e-01 | 5.92585132e-02 | 2.43565530e-01 | 3.18187177e-01 |
| -5.83261363e-02 | -5.28903715e-02 | -2.62414724e-01 | 9.68741719e-04 |
| 9.53214765e-02 | -9.48091000e-02 | 2.45706856e-01 | -2.16586381e-01 |
| 4.27466571e-01 | 2.66638607e-01 | 2.28155673e-01 | 3.36680561e-01 |
| -8.04049596e-02 | 4.81464058e-01 | 3.06946695e-01 | 2.47749865e-01 |
| 9.12103653e-02 | 2.32012898e-01 | -2.41312403e-02 | 4.14653063e-01 |
| 1.71288848e-01 | 2.59723067e-01 | 1.25922292e-01 | 1.86621025e-02 |
| 3.62061024e-01 | 4.80767518e-01 | -3.33400778e-02 | 2.49607235e-01 |
| 4.92782950e-01 | 5.91083229e-01 | 1.45311356e-01 | 8.37347582e-02] |
| [-1.29405528e-01 | 1.80025920e-01 | -2.68218182e-02 | 3.02618067e-03 |
| 3.19242716e-01 | 4.15864252e-02 | -1.00438371e-01 | -8.45773295e-02 |
| 3.12114418e-01 | 6.47189319e-02 | 2.77986258e-01 | 1.36186197e-01 |
| 2.45425925e-01 | 3.83262411e-02 | 4.03567329e-01 | 2.67202556e-01 |
| 2.46863216e-01 | 2.21456170e-01 | 1.46725595e-01 | -7.10667819e-02 |
| 2.67308891e-01 | 4.26193047e-03 | 2.91086704e-01 | -1.54378399e-01 |
| 4.79346573e-01 | 3.42782825e-01 | 2.06039026e-02 | -1.34824231e-01 |
| 7.07979081e-03 | 2.64843181e-01 | -2.28653446e-01 | -1.40931187e-01 |
| -2.44600385e-01 | -8.90308022e-02 | 4.03513402e-01 | 1.42040595e-01 |
| 1.30861834e-01 | -2.47279525e-01 | 2.18340576e-01 | 3.16154987e-01 |
| -2.60109514e-01 | 4.91185673e-02 | -9.17579755e-02 | 1.45590201e-01 |
| 3.50036770e-01 | 4.68919426e-01 | 3.24125350e-01 | 2.20608383e-01 |
| -4.54072393e-02 | -1.47381693e-01 | 2.18962282e-01 | 1.48028791e-01 |
| -8.20280984e-02 | 2.90574968e-01 | 1.25047982e-01 | 9.48954970e-02 |
| 1.12901524e-01 | 2.08398730e-01 | -4.68153059e-02 | 1.66258901e-01 |
| 4.21728432e-01 | 2.33534113e-01 | 3.13388050e-01 | 5.59454381e-01 |
| -3.04938257e-01 | -9.23747756e-03 | -2.13245764e-01 | -2.04061165e-01 |
| 1.13905236e-01 | 1.80667594e-01 | 9.21971202e-02 | 4.37073186e-02 |
| 4.33982879e-01 | 5.87432906e-02 | -6.89120471e-01 | 3.61721247e-01 |
| 1.22561753e-01 | -5.52113391e-02 | 8.95775948e-03 | 2.55264521e-01 |
| 6.27992824e-02 | 1.54304355e-01 | 1.79123998e-01 | -5.74144870e-02 |

TABLE $W_h^1$-continued

| | | | |
|---|---|---|---|
| 3.78716320e-01 | 3.02275509e-01 | 2.85419971e-01 | -5.23020104e-02 |
| 2.09397256e-01 | 1.15417324e-01 | 2.88622677e-01 | 2.63531923e-01 |
| 3.01270306e-01 | 1.48688093e-01 | 4.40442413e-02 | 3.78720765e-03 |
| 1.00436201e-02 | 2.79383570e-01 | 1.02614602e-01 | -1.73407912e-01 |
| 1.35983042e-02 | 8.94312412e-02 | 9.28166509e-02 | 2.35734731e-01 |
| 2.97084689e-01 | 9.75205097e-03 | -1.41987745e-02 | 1.51546851e-01 |
| -1.09638952e-01 | -5.88016249e-02 | -6.22349679e-02 | -5.67742109e-01 |
| 2.82949626e-01 | -8.20619240e-02 | 1.44403040e-01 | 2.73777843e-01 |
| 1.26646504e-01 | 7.93825760e-02 | 2.93027967e-01 | 3.70867044e-01 |
| 2.38123938e-01 | 3.17511380e-01 | 2.33866632e-01 | -4.05164734e-02 |
| 1.86987892e-01 | 5.26056349e-01 | 1.79067492e-01 | 2.12591812e-01 |
| 9.32751894e-02 | 3.91259581e-01 | 2.00493306e-01 | 1.80574223e-01 |
| 1.28847525e-01 | 1.41637027e-02 | 3.20439309e-01 | 1.56947583e-01 |
| -1.14034362e-01 | 3.25925767e-01 | 3.55412848e-02 | 2.94191152e-01 |
| 1.91618413e-01 | 2.97835886e-01 | 8.11092332e-02 | -1.01472968e-02 |
| 3.57843101e-01 | 9.18152481e-02 | -5.19732572e-02 | 5.05788684e-01 |
| -4.03137922e-01 | 6.07202435e-03 | 2.53450811e-01 | 6.36170730e-02 |
| 2.77304232e-01 | 1.71050668e-01 | 2.14008823e-01 | 7.79689774e-02 |
| 2.82638311e-01 | 4.36015397e-01 | 1.60103321e-01 | 1.72443852e-01 |
| 4.28030193e-01 | 1.70097619e-01 | 7.34722614e-02 | 1.39576614e-02 |
| 2.63649911e-01 | -1.91769786e-02 | 5.56683958e-01 | 8.93678591e-02 |
| 1.32532611e-01 | 2.45905608e-01 | -1.59014061e-01 | 6.18659616e-02 |
| -1.63335174e-01 | 1.57657377e-02 | -2.31571533e-02 | 1.01608336e-01 |
| 1.32009134e-01 | 1.92369804e-01 | -1.37193623e-04 | 4.04626727e-02 |
| 2.03749940e-01 | 3.90460551e-01 | 1.48377985e-01 | 7.81276375e-02 |
| 2.14167476e-01 | -2.02085525e-01 | 4.25519139e-01 | -1.39762908e-01 |
| 2.72726238e-01 | 1.37040555e-01 | 1.78936217e-02 | 1.96762636e-01 |
| 7.73792714e-02 | -5.68616092e-02 | 1.71891779e-01 | -1.88857540e-01 |
| 2.34876812e-01 | -3.19451421e-01 | 2.68989891e-01 | -1.89048587e-03 |
| 1.52473256e-01 | 6.82890564e-02 | 8.62090588e-02 | -2.17130676e-01 |
| 3.72595966e-01 | 8.04419696e-01 | -3.94910634e-01 | 3.77471924e-01 |
| 3.51876676e-01 | -1.75131664e-01 | 2.38582149e-01 | 7.42159365e-03 |
| 8.60070586e-02 | 5.30787110e-01 | 1.25921909e-02 | -2.19684932e-02 |
| 3.06942880e-01 | 1.36980444e-01 | 4.07324672e-01 | 3.75418276e-01 |
| 6.22700863e-02 | 3.11389804e-01 | -1.89084351e-01 | -4.04392689e-01 |
| 4.34507966e-01 | -3.05740595e-01 | -2.82494187e-01 | 1.32497653e-01 |
| 1.25588253e-01 | 2.33096167e-01 | 4.81667548e-01 | 1.76280141e-01 |
| 1.28553554e-01 | -3.70719843e-02 | -1.02704220e-01 | 3.59325618e-01 |
| 2.11481735e-01 | 6.32756129e-02 | 1.49793103e-02 | 5.34964621e-01 |
| 2.84209728e-01 | 2.27456838e-01 | 1.71633158e-02 | 1.82620510e-01 |
| 2.15914354e-01 | -2.13032022e-01 | 1.85160607e-01 | 2.66244859e-01 |
| 8.53392705e-02 | 2.46548742e-01 | -8.03538188e-02 | 6.20894656e-02 |
| -1.22897113e-02 | 3.34234387e-01 | 1.18554935e-01 | -4.78461564e-01] |
| [-1.75581962e-01 | -1.32395864e-01 | 2.97810704e-01 | -2.03023165e-01 |
| 1.70040414e-01 | 7.34667957e-01 | 3.52123469e-01 | 1.36803210e-01 |
| 3.17957699e-01 | 5.67773521e-01 | 4.70334232e-01 | -8.76526013e-02 |
| 2.98024774e-01 | 3.60032201e-01 | 2.71458834e-01 | -4.08670716e-02 |
| -2.61087734e-02 | 2.63579667e-01 | -1.87149361e-01 | 4.89544600e-01 |
| 9.24809337e-01 | 3.63023847e-01 | 5.55487514e-01 | 4.98050392e-01 |
| 5.88023067e-01 | 2.53641278e-01 | 3.40126902e-01 | -5.18633239e-02 |
| 3.37333620e-01 | -3.69793805e-03 | 3.01323123e-02 | 5.49322903e-01 |
| 2.77793705e-01 | 3.18057567e-01 | 2.24592298e-01 | 1.58084985e-02 |
| -6.20240066e-03 | -4.82477620e-02 | 1.33694321e-01 | 1.32818669e-01 |
| 3.77919823e-01 | 3.51334631e-01 | -6.53043270e-01 | 2.21123427e-01 |
| 4.57517058e-01 | 2.01003388e-01 | 1.77953079e-01 | 6.53006256e-01 |
| 5.76501042e-02 | 1.41691625e-01 | 2.93996543e-01 | 1.83238044e-01 |
| 3.90682101e-01 | 3.53505790e-01 | 1.93624824e-01 | 2.30498046e-01 |
| 4.21816081e-01 | 5.74097633e-01 | 2.70831417e-02 | 2.27375716e-01 |
| 2.24997476e-01 | 4.02879491e-02 | 8.41379702e-02 | 3.15985292e-01 |
| -3.80175672e-02 | -4.61802760e-04 | -2.48164639e-01 | 1.99017480e-01 |
| 3.42090309e-01 | 2.00324431e-01 | 1.96063876e-01 | 1.11787342e-01 |
| 4.11041617e-01 | 3.91342700e-01 | 4.26066518e-01 | 6.68878853e-02 |
| 3.37059319e-01 | 6.49203241e-01 | 1.26558959e-01 | 4.20319647e-01 |
| 1.99745193e-01 | 5.01021221e-02 | 5.15229762e-01 | 4.14877146e-01 |
| 1.00593440e-01 | 1.80264279e-01 | 4.18940514e-01 | 1.01567104e-01 |
| 2.18236580e-01 | 3.86533320e-01 | -1.40284941e-01 | 1.02988102e-01 |
| 2.06163630e-01 | -4.40458730e-02 | 7.51865327e-01 | 4.49174792e-01 |
| 2.59882629e-01 | 2.75688827e-01 | 1.83640659e-01 | 5.29083192e-01 |
| -2.58290291e-01 | 5.03298104e-01 | 5.23793995e-01 | 1.63930431e-01 |
| 3.89432102e-01 | 5.51337563e-02 | -1.31247818e-01 | 6.17603719e-01 |
| -2.30035707e-01 | 6.41301274e-01 | 5.55743128e-02 | -4.33352888e-02 |
| 3.71779948e-01 | 3.14141899e-01 | 5.70397377e-01 | 3.67983341e-01 |
| -3.79260257e-03 | 4.24387664e-01 | 4.84852046e-01 | 7.09953215e-01 |
| 5.84623873e-01 | 4.23596203e-02 | 4.56998169e-01 | 4.78547782e-01 |
| 4.16777223e-01 | 3.94466549e-01 | 3.84297752e-01 | 1.28694430e-01 |
| 4.55558062e-01 | 4.59734350e-02 | 1.82952061e-01 | 7.09719539e-01 |
| 3.43776435e-01 | -8.15835074e-02 | -7.00995252e-02 | 1.63032666e-01 |
| -1.46953061e-01 | 1.28283381e-01 | 5.49854636e-01 | 4.51837301e-01 |
| 5.91907322e-01 | 2.88163632e-01 | 3.84069979e-01 | 4.15882438e-01 |
| 2.82360405e-01 | -1.44139782e-01 | 5.06704450e-01 | 3.19535404e-01 |

TABLE $W_h^1$-continued

| | | | |
|---|---|---|---|
| 4.43165191e−02 | −3.98353003e−02 | 3.15701962e−01 | −9.32618752e−02 |
| 5.91459721e−02 | 3.23613226e−01 | 2.97692239e−01 | −1.83719203e−01 |
| 1.36278853e−01 | 3.89134735e−01 | 5.23001075e−01 | 2.44487803e−02 |
| 4.14958447e−01 | 4.32244658e−01 | 4.27494913e−01 | 3.97792995e−01 |
| 4.75047678e−01 | 9.02584791e−02 | 5.14975786e−01 | 2.50419140e−01 |
| −8.77831131e−02 | 1.91046759e−01 | 5.80115542e−02 | 3.27938288e−01 |
| 2.15728924e−01 | 4.70218986e−01 | −2.12742370e−02 | −3.32876325e−01 |
| 1.47058785e−01 | 2.75026727e−01 | −9.61245671e−02 | 1.33792773e−01 |
| 1.78789347e−01 | −1.01009635e−02 | 3.55002791e−01 | 5.14338076e−01 |
| 3.66789818e−01 | 1.43401235e−01 | 3.53177637e−01 | 4.14413840e−01 |
| −6.57131523e−02 | 2.69420117e−01 | 3.93942416e−01 | 3.09320450e−01 |
| 3.07384878e−01 | 5.94502687e−01 | 1.19529717e−01 | 1.66980088e−01 |
| 5.52608371e−01 | 1.23701677e−01 | 5.02647340e−01 | 4.60170418e−01 |
| 3.64593953e−01 | −1.96361870e−01 | 6.89485669e−01 | 1.96932182e−01 |
| 5.14067352e−01 | 2.53407747e−01 | 3.65231603e−01 | 2.69911170e−01 |
| 5.29499114e−01 | −7.11994842e−02 | 4.46333647e−01 | 3.39603633e−01 |
| 1.47841915e−01 | 5.19660115e−01 | −6.76278248e−02 | 6.28756046e−01 |
| 4.12940025e−01 | 3.95777673e−01 | 4.00246948e−01 | 1.52017415e−01 |
| 1.01794507e−02 | 5.72476387e−01 | 8.92523900e−02 | 2.58571684e−01 |
| 2.56272733e−01 | 5.18561840e−01 | −3.41288090e−01 | 3.39970082e−01 |
| 8.73686135e−01 | 6.35112584e−01 | 4.48218733e−01 | 2.91058630e−01 |
| 7.80870393e−02 | 8.25175494e−02 | 9.03197154e−02 | 5.56828201e−01 |
| −3.06719124e−01 | 1.33077621e−01 | 3.83769214e−01 | 1.90255165e−01 |
| −1.06672615e−01 | 9.34807658e−02 | 5.17915525e−02 | 2.17365816e−01 |
| −2.45835021e−01 | 1.55533746e−01 | 3.88264358e−01 | 1.18278235e−01 |
| 5.40472627e−01 | 3.27237070e−01 | 4.85043228e−02 | 1.66824862e−01 |
| −8.46601501e−02 | −2.60520369e−01 | 4.67307538e−01 | 3.95857722e−01] |
| [3.46035570e−01 | 1.46438897e−01 | 1.57936171e−01 | 5.12710452e−01 |
| 2.27278098e−01 | 4.76520509e−01 | 1.74495906e−01 | 1.84792385e−01 |
| 8.22038949e−02 | 8.09647590e−02 | 1.25294194e−01 | 1.74788877e−01 |
| −8.35801587e−02 | 7.48027489e−02 | 7.68688321e−02 | 9.98157188e−02 |
| 1.93163559e−01 | 1.30644575e−01 | 2.77829349e−01 | 1.46920875e−01 |
| 9.48960409e−02 | 2.38849923e−01 | 5.38951039e−01 | 1.53783813e−01 |
| 1.18457759e−03 | −5.19743040e−02 | 1.12717055e−01 | 3.16050172e−01 |
| 1.19216882e−01 | −2.26321459e−01 | 1.77968621e−01 | −1.42295569e−01 |
| 5.94457984e−02 | −2.21168250e−01 | 2.23791972e−01 | 6.15298390e−01 |
| 1.03991479e−01 | 2.83283055e−01 | 7.04505891e−02 | −4.31857966e−02 |
| 4.96310651e−01 | 8.84311348e−02 | 1.25833049e−01 | 4.22251821e−01 |
| 2.88078547e−01 | 2.03455552e−01 | 2.41770849e−01 | −2.37722605e−01 |
| 4.68086392e−01 | 2.72027426e−03 | −1.27891853e−01 | 1.79918564e−01 |
| 2.21965015e−01 | 4.92330119e−02 | 2.71114618e−01 | 1.84525829e−02 |
| −5.04153408e−02 | 1.84014142e−01 | 4.41131853e−02 | 1.75480507e−02 |
| 1.02996893e−01 | 5.28536379e−01 | 4.69805509e−01 | 4.58992451e−01 |
| −1.20565761e−02 | 5.76814860e−02 | 3.73925686e−01 | 3.18244308e−01 |
| 9.97553617e−02 | 4.55658704e−01 | −1.91032857e−01 | −6.30294532e−02 |
| −2.18250886e−01 | 3.18333842e−01 | −1.21684767e−01 | −5.26700616e−02 |
| 2.66524523e−01 | 5.44397198e−02 | 1.67819768e−01 | 3.21350843e−01 |
| 3.15191567e−01 | 2.56805062e−01 | 3.04415405e−01 | −1.21986993e−01 |
| 2.44216964e−01 | −1.35298103e−01 | 1.52311042e−01 | 4.30775464e−01 |
| 3.42407674e−01 | 7.72349536e−02 | 1.67053342e−01 | 1.91802755e−01 |
| 2.05378667e−01 | −9.42672119e−02 | 2.42837131e−01 | 1.50440693e−01 |
| −5.95633723e−02 | 2.26070762e−01 | −1.38694793e−01 | 4.09128554e−02 |
| 5.04998937e−02 | 1.98454514e−01 | 1.32597581e−01 | 3.20509642e−01 |
| 4.40340281e−01 | 2.40374610e−01 | −8.94782394e−02 | 3.90772760e−01 |
| 1.86358199e−01 | 1.17612295e−01 | 3.68002504e−01 | 2.41879657e−01 |
| −3.76362562e−01 | 1.55253708e−01 | 8.62126425e−02 | 2.79794574e−01 |
| 1.52199075e−01 | 2.73349583e−02 | 8.12999159e−02 | 1.25547901e−01 |
| 3.21211010e−01 | 3.19201738e−01 | 9.30583803e−04 | −2.25553334e−01 |
| 1.96462646e−01 | −2.74767160e−01 | 3.75396386e−01 | 3.33857387e−01 |
| 1.96308106e−01 | −2.53980339e−01 | 4.23897207e−01 | 2.10364237e−01 |
| −2.54127476e−02 | 1.71066314e−01 | 2.81214297e−01 | 1.21266544e−01 |
| 5.32724798e−01 | 6.24599382e−02 | −5.61165996e−02 | −6.22978546e−02 |
| 1.43151596e−01 | −2.67597705e−01 | 2.82481045e−01 | 2.00385898e−01 |
| −1.82601511e−01 | 4.15215820e−01 | 2.28612199e−02 | 4.37508494e−01 |
| 1.69971317e−01 | 2.18317658e−01 | 1.91726476e−01 | 1.92698672e−01 |
| 9.79652256e−02 | 4.73949909e−01 | −5.23849800e−02 | 1.34369954e−01 |
| 7.87479505e−02 | 6.38670623e−01 | 5.96233547e−01 | 8.01370889e−02 |
| 1.97417676e−01 | 3.38042200e−01 | 3.88885289e−01 | 3.15585583e−01 |
| 1.65712759e−01 | −1.23592779e−01 | 1.56787127e−01 | 4.17568028e−01 |
| −3.57886285e−01 | 4.79731634e−02 | 1.32871941e−01 | 7.08935410e−02 |
| 3.40572178e−01 | 3.42571944e−01 | 1.28971249e−01 | 3.72976452e−01 |
| 1.02297917e−01 | 1.53479755e−01 | −8.03133994e−02 | 3.04413855e−01 |
| 2.22922474e−01 | 1.99932232e−01 | −5.05643450e−02 | −1.87520891e−01 |
| −3.04183383e−02 | 1.41401634e−01 | 1.12157494e−01 | 1.89044550e−01 |
| 3.25122744e−01 | −7.10077211e−02 | 2.84887403e−01 | 4.96507764e−01 |
| 1.23972982e−01 | 4.88128364e−01 | 2.29824945e−01 | −1.45172765e−02 |
| 2.76318401e−01 | 1.91302225e−02 | −6.05936609e−02 | 2.88602084e−01 |
| −1.98052470e−02 | −5.95332310e−02 | 2.74778485e−01 | 4.37894881e−01 |
| −2.04301868e−02 | 2.75110036e−01 | −1.51459634e−01 | −2.21988857e−01 |
| 3.89644831e−01 | 4.00204845e−02 | −2.00787392e−02 | 1.96569234e−01 |

TABLE $W_h^1$-continued

| | | | |
|---|---|---|---|
| −2.02778071e−01 | −4.36697854e−03 | 2.89103031e−01 | 2.52927601e−01 |
| 4.99607399e−02 | −2.07415298e−02 | −2.44126245e−01 | 3.12364459e−01 |
| 1.13446325e−01 | 3.28591645e−01 | 4.69174385e−01 | 3.20016861e−01 |
| −6.71587810e−02 | −9.32275057e−02 | −2.24939018e−01 | 3.48557919e−01 |
| 3.08490545e−01 | 2.20361054e−01 | 3.88926752e−02 | 3.05733502e−01 |
| 6.34078443e−01 | 1.57214552e−01 | 3.95650417e−01 | −5.54840006e−02 |
| 5.76612830e−01 | 5.58918238e−01 | 2.30147392e−01 | 3.94318968e−01 |
| −3.83100398e−02 | 1.96065649e−01 | 2.46101543e−01 | −1.88950673e−02 |
| −1.50033668e−01 | 5.00056684e−01 | 1.51435465e−01 | 2.26197556e−01 |
| 2.39394113e−01 | 2.25574687e−01 | 2.24992663e−01 | 7.43824020e−02 |
| 2.16132298e−01 | 1.62156358e−01 | 3.46660882e−01 | 1.37542188e−01] |
| [−1.52556494e−01 | −8.23748931e−02 | 3.64992023e−01 | 5.45780063e−02 |
| 4.81156975e−01 | 2.12421939e−02 | 3.53336960e−01 | 2.01671198e−01 |
| 1.83305666e−01 | 1.73877716e−01 | 2.43902743e−01 | 3.76436681e−01 |
| 1.88416630e−01 | 2.82452404e−01 | −3.32664430e−01 | 1.88509524e−01 |
| −1.23521417e−01 | 2.05518991e−01 | 8.49915519e−02 | 1.20380782e−01 |
| −3.32068771e−01 | 1.05229206e−01 | −4.93538588e−01 | 3.76186937e−01 |
| 3.62105310e−01 | −3.68341282e−02 | 1.26331598e−01 | −1.27477333e−01 |
| 1.61260962e−01 | 4.19284463e−01 | 1.52726933e−01 | 1.88530833e−01 |
| −2.14902624e−01 | 6.33791625e−01 | 1.19636610e−01 | 1.10305063e−01 |
| −1.06068037e−01 | 1.08953476e−01 | 2.36341044e−01 | 1.23311907e−01 |
| 3.16676527e−01 | −2.06886753e−01 | −5.80193281e−01 | 3.67452174e−01 |
| −1.54371515e−01 | 1.57704666e−01 | 1.85006689e−02 | 1.62011817e−01 |
| −2.96535462e−01 | 2.77288049e−01 | −1.28229141e−01 | 4.40026969e−02 |
| −2.09806830e−01 | 5.13952076e−01 | 1.45647869e−01 | 1.68883815e−01 |
| 2.01294556e−01 | −5.58499359e−02 | −6.34998977e−02 | 2.77635515e−01 |
| −1.50141403e−01 | −4.98020537e−02 | −1.82768106e−01 | −2.10682768e−02 |
| 4.13755208e−01 | 3.66710454e−01 | 2.63962984e−01 | 6.53963827e−04 |
| −1.93380922e−01 | 1.87979043e−01 | 2.75517821e−01 | 2.22171620e−01 |
| 3.50152940e−01 | 4.57889624e−02 | 4.52177048e−01 | 1.20699823e−01 |
| 3.85607481e−01 | 1.58616796e−01 | 6.06484532e−01 | 1.42074153e−02 |
| −1.98464647e−01 | 2.57269621e−01 | −2.01423317e−02 | 2.64086127e−01 |
| −7.50281811e−02 | 8.88388231e−02 | 3.06269079e−01 | −4.58173752e−02 |
| 2.00094536e−01 | −4.55580577e−02 | −1.80527102e−02 | 7.96078071e−02 |
| −1.72482297e−01 | 5.90773880e−01 | 4.77738231e−02 | 1.07543595e−01 |
| −1.18850812e−01 | −5.27048111e−01 | −8.82450044e−02 | −1.80390626e−02 |
| 6.21788323e−01 | 4.92641717e−01 | −5.37867919e−02 | 2.26639077e−01 |
| 3.77474159e−01 | 3.29794914e−01 | −5.02690196e−01 | −1.13861315e−01 |
| −4.87058144e−03 | 5.71738124e−01 | −8.66888687e−02 | 2.14206442e−01 |
| 5.16938865e−01 | −9.76924133e−03 | 5.35120785e−01 | 2.12290376e−01 |
| 2.67875373e−01 | 1.84480369e−01 | 1.47067726e−01 | −1.86156392e−01 |
| 2.72183210e−01 | −2.40435377e−01 | 2.45796278e−01 | 1.51907787e−01 |
| 5.65750003e−01 | −1.96228087e−01 | −1.18892407e−02 | 2.30487764e−01 |
| −8.28734636e−02 | 1.60841286e−01 | −3.42999771e−02 | 1.55319259e−01 |
| −1.69988591e−02 | −2.66295820e−01 | −2.62619883e−01 | −1.40346467e−01 |
| 2.79758334e−01 | 3.17804635e−01 | 2.07106903e−01 | −1.59768194e−01 |
| 2.11783722e−02 | 6.78086758e−01 | −3.28868449e−01 | −2.02145383e−01 |
| 4.47639346e−01 | 2.38526240e−01 | −2.33692363e−01 | 4.18352000e−02 |
| 2.82036573e−01 | 5.25760531e−01 | 7.74098188e−02 | −2.58230492e−02 |
| −3.20933789e−01 | 4.35086200e−01 | −4.42910016e−01 | 2.35132635e−01 |
| −2.83460524e−02 | −3.64622205e−01 | 1.81288630e−01 | −1.61496252e−02 |
| −1.17807433e−01 | 2.58927912e−01 | −1.31800875e−01 | 1.27481639e−01 |
| 9.10112858e−02 | 3.75391496e−03 | 2.82106489e−01 | 3.76926005e−01 |
| 5.07190287e−01 | 2.09972769e−01 | 5.63132107e−01 | −6.22703917e−02 |
| 2.54209936e−01 | −2.01567054e−01 | 3.92255753e−01 | 3.04084003e−01 |
| −7.26446733e−02 | −1.37864515e−01 | 5.83081007e−01 | 2.80702472e−01 |
| −4.09973234e−01 | 6.43973291e−01 | −9.51052085e−02 | 3.20326477e−01 |
| −3.02367136e−01 | −4.06475574e−01 | −1.33665562e−01 | −2.43180931e−01 |
| 1.24272913e−01 | 2.14220695e−02 | 3.76743190e−02 | 2.77056783e−01 |
| −1.75413325e−01 | 1.86553776e−01 | 3.02489489e−01 | 5.99867940e−01 |
| 1.67302653e−01 | 3.91876936e−01 | 2.53998190e−01 | 3.88053626e−01 |
| 1.24608703e−01 | 2.32452258e−01 | −8.23064595e−02 | 1.62950754e−01 |
| 1.94220811e−01 | 3.16551626e−01 | 1.41121879e−01 | 3.88131142e−01 |
| −5.68189509e−02 | 2.69139916e−01 | 1.94868028e−01 | 1.72835618e−01 |
| 3.23797375e−01 | −4.49786410e−02 | 9.99044105e−02 | 6.17594644e−02 |
| 4.87132192e−01 | 3.20293784e−01 | −2.76109904e−01 | −5.47693312e−01 |
| 2.85331249e−01 | 1.23338297e−01 | −8.21797401e−02 | 2.76617080e−01 |
| −2.87844650e−02 | 3.02583188e−01 | 6.56218529e−01 | −1.63222656e−01 |
| 3.66786003e−01 | 1.18980976e−02 | 1.04706464e−02 | −1.92109689e−01 |
| −1.32073328e−01 | −7.79765725e−01 | 6.42360821e−02 | −5.15791118e−01 |
| 3.34759355e−01 | 3.34707528e−01 | 2.47929618e−01 | −7.70557970e−01 |
| 6.56754225e−02 | 3.93632859e−01 | 1.64882064e−01 | 4.38687384e−01 |
| 5.43201268e−01 | 1.68381289e−01 | 7.71020129e−02 | 1.15201786e−01 |
| −9.40505415e−02 | −1.02091759e−01 | −9.46355909e−02 | −1.07396236e−02 |
| −2.39471734e−01 | 1.93678692e−01 | 1.48757130e−01 | 3.61356765e−01] |
| [−1.17305949e−01 | 5.78194745e−02 | 5.54307103e−01 | 2.82328963e−01 |
| 3.15568268e−01 | −9.73313823e−02 | 3.58000875e−01 | 1.97826013e−01 |
| −3.63550857e−02 | 3.78830582e−02 | 2.45594382e−01 | −7.83961639e−02 |
| 7.13170394e−02 | 2.67732382e−01 | −1.08276218e−01 | 1.50191352e−01 |
| 3.43055248e−01 | −3.22267460e−03 | 7.31100589e−02 | −2.33506531e−01 |

TABLE $W_h^1$-continued

| | | | |
|---|---|---|---|
| 1.59054056e−01 | 1.03312984e−01 | −7.65727907e−02 | 2.48332843e−01 |
| 1.76480100e−01 | −1.37459621e−01 | 7.83653557e−03 | 5.10288894e−01 |
| 1.80829510e−01 | −6.75021037e−02 | 2.54193366e−01 | −1.20315425e−01 |
| 6.15995377e−02 | 7.96383247e−02 | 1.78055286e−01 | 4.17291641e−01 |
| 1.84200138e−01 | 5.60727835e−01 | 2.31222555e−01 | 1.61330432e−01 |
| 1.86089456e−01 | 9.66003835e−02 | 2.84164250e−01 | 3.31151754e−01 |
| 1.99954525e−01 | 8.39825571e−02 | 2.99005862e−02 | 8.27382877e−02 |
| 3.92307907e−01 | 8.02266300e−02 | −2.19187915e−01 | 2.46514976e−01 |
| −2.59199470e−01 | 2.08466858e−01 | −7.18812197e−02 | 4.83661294e−02 |
| 3.37579578e−01 | 2.50351012e−01 | 3.13408494e−01 | −9.57316980e−02 |
| −6.08350001e−02 | 1.25222012e−01 | 6.51956676e−03 | 2.35871658e−01 |
| 2.37563476e−01 | 2.52969474e−01 | 8.86930674e−02 | 1.23514302e−01 |
| 2.09010646e−01 | 1.56352639e−01 | 5.25548160e−01 | 5.48947453e−01 |
| 2.10257575e−01 | −2.07508832e−01 | −6.45890757e−02 | −3.57864387e−02 |
| 6.31776452e−01 | 4.66578901e−01 | 2.16676801e−01 | 9.66263041e−02 |
| 3.09960306e−01 | 8.75327177e−03 | 3.32879007e−01 | 7.65689760e−02 |
| −6.12308308e−02 | 2.13897958e−01 | 2.49406695e−01 | 6.40243441e−02 |
| 1.91759840e−01 | 8.20248127e−02 | 1.10697463e−01 | 1.59477249e−01 |
| −1.80199578e−01 | 9.03716683e−02 | 4.42146719e−01 | 4.28711325e−01 |
| −9.25335065e−02 | 1.58297554e−01 | 1.16074085e−01 | 1.18509606e−01 |
| 3.69447589e−01 | 3.06599140e−01 | 1.47297174e−01 | −5.51761985e−01 |
| 2.47454599e−01 | 3.73415947e−02 | 2.66337603e−01 | 1.92861259e−01 |
| 3.30995500e−01 | −3.31341252e−02 | 3.75953376e−01 | 1.33315071e−01 |
| 2.09711641e−01 | −3.15370858e−01 | 1.92872018e−01 | 4.54716861e−01 |
| 7.19034448e−02 | −3.44483584e−01 | 2.40454689e−01 | 3.68312359e−01 |
| 3.38103235e−01 | 4.49263752e−02 | 2.42320180e−01 | 6.19058535e−02 |
| 4.38216597e−01 | −1.02555715e−02 | 2.42551610e−01 | 2.57878274e−01 |
| 2.32558385e−01 | 2.54628092e−01 | 1.84965357e−01 | 4.03771013e−01 |
| 7.92685673e−02 | 9.51515585e−02 | 7.53662139e−02 | −9.70516577e−02 |
| 1.35216713e−01 | 2.92447418e−01 | 9.06758904e−02 | −1.31486089e−03 |
| 7.59788007e−02 | 3.63043211e−02 | 2.01992095e−01 | 4.68513519e−02 |
| 3.52628052e−01 | 2.50710428e−01 | 3.02033126e−02 | 9.33877155e−02 |
| 1.81522623e−01 | −1.04304358e−01 | −1.51714951e−01 | 1.98066279e−01 |
| 1.67030975e−01 | 2.49875918e−01 | 2.33264446e−01 | 2.16962293e−01 |
| 2.35333979e−01 | 6.81356490e−02 | 1.90810502e−01 | 3.58678818e−01 |
| 2.88252207e−03 | 4.00427788e−01 | 1.39365792e−01 | 3.35196167e−01 |
| 1.42419979e−01 | 2.55813390e−01 | 3.21266621e−01 | 1.65330693e−01 |
| 2.98655212e−01 | 1.93220794e−01 | 1.18187502e−01 | 1.38936505e−01 |
| 5.04112482e−01 | 2.25846961e−01 | 2.27472007e−01 | 4.87480372e−01 |
| −6.71390444e−02 | 6.35985658e−03 | −3.90350930e−02 | −1.57025978e−01 |
| 1.38304994e−01 | −6.77649304e−03 | 3.15580666e−01 | −1.09432481e−01 |
| 2.31798664e−01 | 2.28233770e−01 | 5.36470711e−02 | 1.04885034e−01 |
| −8.20071250e−02 | −9.01583731e−02 | 3.93261872e−02 | 1.85045004e−01 |
| 2.33027250e−01 | 4.08378631e−01 | 1.05829500e−01 | 1.23589031e−01 |
| 1.12231962e−01 | 2.92828619e−01 | 1.16245635e−01 | 1.75654620e−01 |
| 2.68860072e−01 | 9.88509357e−02 | 4.18296410e−01 | −9.42594185e−02 |
| 3.07299495e−01 | 2.55820692e−01 | −3.92573476e−02 | 3.37629527e−01 |
| −2.58135438e−01 | −9.39500891e−03 | 1.64880641e−02 | 2.58191526e−01 |
| −9.39805135e−02 | 2.27935806e−01 | 1.98235288e−01 | 3.93116325e−01 |
| −2.93346979e−02 | −4.08435799e−02 | 1.05037019e−01 | −3.07469387e−02 |
| 1.87491849e−01 | −1.54011637e−01 | −3.86109501e−02 | 3.67022425e−01 |
| 4.29972768e−01 | 1.87944472e−01 | 3.03172767e−01 | 1.55660912e−01 |
| 2.24080026e−01 | 2.95021117e−01 | 1.32734492e−01 | 2.47291133e−01 |
| 2.90321857e−01 | −6.99416637e−02 | 2.48533323e−01 | 6.33918168e−03 |
| 1.34376407e−01 | 5.03840208e−01 | 2.95987993e−01 | 2.84576882e−03 |
| 2.96819270e−01 | 2.37921193e−01 | 1.74105912e−01 | 4.05149966e−01 |
| 2.13173226e−01 | 2.03286260e−01 | 1.68337196e−01 | 3.51992458e−01 |
| 4.20046262e−01 | 3.02719977e−01 | 3.31098497e−01 | 3.47616345e−01 |
| 2.37215832e−01 | 9.30583403e−02 | 8.16732571e−02 | 2.11131856e−01] |
| [1.33326605e−01 | −1.15164980e−01 | 6.67351246e−01 | 1.40786637e−01 |
| 7.27406681e−01 | 1.66882664e−01 | 9.42207500e−02 | 6.73244476e−01 |
| 6.28862619e−01 | 1.48564830e−01 | 4.10390317e−01 | −3.67517143e−01 |
| 1.39694557e−01 | 3.50259431e−02 | −3.49009156e−01 | 3.45569253e−01 |
| 4.56072450e−01 | 1.91802122e−02 | 1.73719987e−01 | 8.05215061e−01 |
| −2.63225306e−02 | 1.88488439e−01 | 1.13353454e−01 | 9.40981414e−03 |
| −4.93608445e−01 | 5.72386026e−01 | 4.75378901e−01 | 6.39453709e−01 |
| −1.84210867e−01 | 5.08275986e−01 | 4.35894966e−01 | 2.53334254e−01 |
| 2.17918471e−01 | 4.60400730e−01 | −2.60349631e−01 | 6.90174460e−01 |
| 9.07976702e−02 | 4.92770195e−01 | 2.03759111e−02 | 2.13647515e−01 |
| 8.47320318e−01 | 3.70101362e−01 | 2.78064549e−01 | −1.97522461e−01 |
| 7.52616525e−01 | 4.70873594e−01 | −3.69764306e−02 | −3.64939272e−01 |
| 5.55065691e−01 | 3.79566312e−01 | −8.15697387e−02 | 2.03316420e−01 |
| 3.16149861e−01 | 4.93341118e−01 | 2.99302191e−01 | 5.33289790e−01 |
| −3.57596837e−02 | 2.21830517e−01 | 5.95655084e−01 | −1.06338523e−01 |
| 9.41960663e−02 | 8.79792809e−01 | 1.46964312e−01 | 4.84342486e−01 |
| 2.95921803e−01 | 9.38607872e−01 | 6.18239582e−01 | 4.16589417e−02 |
| 2.36181527e−01 | 1.09876476e−01 | −6.02159426e−02 | 2.69466579e−01 |
| 1.44060865e−01 | −4.14928228e−01 | 1.11993819e−01 | 2.53141940e−01 |
| −1.97547153e−02 | 2.09417120e−01 | 6.04894936e−01 | 6.82217717e−01 |
| −4.36753720e−01 | 6.51414514e−01 | 4.71933097e−01 | 1.83548331e−01 |

TABLE $W_h^1$-continued

| | | | |
|---|---|---|---|
| −3.02828252e−01 | 2.21892267e−01 | 5.42489946e−01 | 9.29693580e−01 |
| 5.49232841e−01 | 3.30692112e−01 | 5.62294871e−02 | 3.34954634e−02 |
| 4.07690823e−01 | 7.02944577e−01 | −4.83789623e−01 | 3.16053450e−01 |
| 1.19282119e−01 | −1.65028244e−01 | 1.01871729e−01 | 4.72960383e−01 |
| 4.62455392e−01 | 1.17987998e−01 | −3.68376598e−02 | 1.68776199e−01 |
| 2.25128636e−01 | 6.01576030e−01 | 2.56903291e−01 | 3.25981706e−01 |
| 1.04494047e−00 | −1.44234642e−01 | 3.28742027e−01 | −2.71609724e−01 |
| −8.87472779e−02 | 8.44779611e−01 | 2.21646369e−01 | −5.37779808e−01 |
| 2.72296995e−01 | −2.00095430e−01 | 1.79151788e−01 | 4.98404875e−02 |
| 3.78497541e−01 | 2.45432526e−01 | 5.11384070e−01 | −1.60509542e−01 |
| 1.24328874e−01 | 1.06642060e−01 | 4.37800080e−01 | 4.74045396e−01 |
| 8.10930192e−01 | −3.29163461e−03 | −2.46100277e−02 | 2.11380988e−01 |
| 2.49752216e−02 | 2.76562840e−01 | 2.98459589e−01 | −4.20245603e−02 |
| 3.52230668e−01 | 9.87252279e−05 | 3.26738149e−01 | 1.69205502e−01 |
| 4.06594455e−01 | 5.70292473e−01 | 1.11936241e−01 | 4.45505589e−01 |
| 4.11965638e−01 | −4.89414595e−02 | 4.63371098e−01 | 3.54045033e−01 |
| 7.24468231e−01 | 3.28758478e−01 | 2.16632873e−01 | 4.16019976e−01 |
| −1.19822532e−01 | 4.63488311e−01 | −3.25113237e−01 | 3.79431486e−01 |
| 8.38750973e−02 | −1.47096023e−01 | 1.45544676e−01 | 5.26850998e−01 |
| −3.94825488e−02 | 5.16519427e−01 | 5.82983971e−01 | 1.81181684e−01 |
| −2.88627446e−01 | 3.11696798e−01 | 1.15931720e−01 | −6.83113188e−03 |
| 1.93635345e−01 | −6.40228540e−02 | −8.09933394e−02 | −1.08818702e−01 |
| 1.87071398e−01 | 1.20611154e−01 | 3.69267732e−01 | 6.09862924e−01 |
| 6.46554172e−01 | 1.69542670e−01 | −1.56552140e−02 | −4.17969078e−01 |
| 2.32304335e−02 | 3.58685017e−01 | 2.60058939e−01 | 4.58074689e−01 |
| 5.49016446e−02 | 2.04958901e−01 | −3.54420066e−01 | −3.88460830e−02 |
| 4.03122872e−01 | 2.15524063e−01 | 1.73473284e−01 | −2.36653350e−02 |
| 3.67593676e−01 | −2.57795583e−03 | 2.72850692e−01 | −2.11584911e−01 |
| −1.97972044e−01 | 5.45806885e−01 | 5.25585413e−01 | 1.29842788e−01 |
| 2.49379992e−01 | 6.26788795e−01 | 4.03278053e−01 | 5.68771660e−01 |
| −4.43964042e−02 | 4.43860173e−01 | 3.17525893e−01 | −4.47488725e−01 |
| 3.24357152e−01 | 1.34946719e−01 | −1.15639687e−01 | 3.73133063e−01 |
| −3.90494257e−01 | −1.52939364e−01 | 6.25852942e−01 | 1.95299834e−01 |
| 2.31090397e−01 | 2.34468624e−01 | −3.15665662e−01 | 5.29346704e−01 |
| 3.39747280e−01 | −6.43587811e−03 | 4.84018981e−01 | −1.34686247e−01 |
| 9.23171043e−02 | −5.01325965e−01 | 3.95744532e−01 | −4.63611409e−02 |
| 2.58873343e−01 | 2.62952983e−01 | 2.93302268e−01 | 1.25861960e−02 |
| 5.50453067e−01 | 1.64495796e−01 | 5.62888645e−02 | 7.06641257e−01 |
| −7.46133029e−02 | 6.28122687e−01 | 2.10067719e−01 | 5.69104373e−01 |
| 4.29206967e−01 | −1.15145734e−02 | −3.60549130e−02 | 6.23925447e−01 |
| 2.83714950e−01 | −1.47517473e−01 | −5.52796479e−03 | 4.69854325e−02 |
| 6.28481030e−01 | −2.82875866e−01 | −3.81403029e−01 | 4.28886324e−01 |
| 2.17895508e−01 | 5.64828038e−01 | −4.80240695e−02 | −8.18776563e−02] |
| [8.09217840e−02 | 1.65075501e−01 | 9.70700458e−02 | −2.13072479e−01 |
| 1.64689183e−01 | 3.10460478e−01 | 1.33454129e−01 | 3.60576878e−03 |
| 3.14720839e−01 | −9.00204703e−02 | −8.21715817e−02 | 3.12154412e−01 |
| 4.07321274e−01 | 2.12823644e−01 | −5.58283567e−01 | 1.20675012e−01 |
| 1.22973062e−01 | −1.92040652e−01 | 6.07747249e−02 | 1.19611777e−01 |
| 7.76427612e−02 | 3.16793770e−01 | 3.49503487e−01 | 2.36814022e−01 |
| 2.98353255e−01 | 1.83785602e−01 | 2.26806551e−01 | 2.38515735e−01 |
| 2.40511507e−01 | 4.32057619e−01 | 2.08955944e−01 | 2.63463587e−01 |
| 2.95483857e−01 | −4.53487737e−03 | 3.73353750e−01 | 3.60554814e−01 |
| 3.50973904e−01 | 1.29840434e−01 | 4.78380658e−02 | 2.15569705e−01 |
| 5.49509585e−01 | 3.40217143e−01 | 1.21144615e−01 | 2.52657115e−01 |
| 2.33326003e−01 | 2.27506354e−01 | 1.15955994e−01 | 2.69642323e−01 |
| 1.10061042e−01 | 1.03931740e−01 | −5.25516212e−01 | −1.07947543e−01 |
| −1.64375827e−01 | −5.26378443e−03 | 4.41759944e−01 | 2.44244874e−01 |
| 3.98865640e−01 | −6.95869923e−02 | 1.90888479e−01 | 2.37367213e−01 |
| −8.15630034e−02 | 3.53047371e−01 | 1.56064615e−01 | −2.04834238e−01 |
| 2.89673150e−01 | 1.77596420e−01 | 3.52121502e−01 | 4.24432516e−01 |
| 2.60674834e−01 | 2.87127383e−02 | −3.01853120e−02 | −6.82116896e−02 |
| 3.23205739e−01 | 8.09942392e−02 | 2.87912697e−01 | −1.01951107e−01 |
| 3.62774402e−01 | 9.38531235e−02 | 1.95285767e−01 | 2.68416226e−01 |
| 2.33279109e−01 | 2.21696615e−01 | 2.41302624e−01 | −6.95961192e−02 |
| −1.85112447e−01 | 3.83582443e−01 | 1.22926712e−01 | 2.39845246e−01 |
| 2.36292645e−01 | 3.25614363e−01 | 3.42463732e−01 | 4.81679589e−02 |
| 3.62787545e−01 | 2.91962355e−01 | 4.44161564e−01 | 1.54749677e−01 |
| −6.76796436e−02 | −6.08629324e−02 | 4.47996885e−01 | 4.72105175e−01 |
| 2.13843212e−01 | −3.63494444e−04 | 1.22461669e−01 | −1.01540715e−01 |
| −5.98542765e−03 | −2.08152741e−01 | −3.59572768e−01 | −2.15957522e−01 |
| 1.72413349e−01 | −1.13770306e−01 | 2.22424716e−01 | 9.98966303e−03 |
| 1.40132634e−02 | 1.61206707e−01 | 2.93001980e−01 | 2.56668776e−01 |
| 2.53125101e−01 | 7.96838105e−02 | −7.90817756e−03 | −5.00186868e−02 |
| 9.35535040e−03 | 5.38938679e−02 | −4.79370691e−02 | 2.15783138e−02 |
| 4.55040246e−01 | −2.35002503e−01 | 3.72471809e−01 | 4.32405651e−01 |
| 1.60919845e−01 | 2.27762818e−01 | −2.32757986e−01 | 4.36924845e−01 |
| 4.90961283e−01 | 4.92576003e−01 | 2.85777152e−01 | 7.31996000e−02 |
| 6.07516348e−01 | 3.67854983e−02 | 2.93007523e−01 | 2.16394477e−03 |
| 5.59365332e−01 | −1.72064960e−01 | 2.26989895e−01 | 2.41120294e−01 |
| −1.09576337e−01 | 3.18106234e−01 | 1.59347668e−01 | −7.96459168e−02 |

TABLE $W_h^1$-continued

| | | | |
|---|---|---|---|
| 1.87540159e−01 | 1.21829838e−01 | 1.60608783e−01 | 1.68728411e−01 |
| 1.34812489e−01 | 3.70551676e−01 | 1.30128622e−01 | −3.02809727e−04 |
| −7.63102651e−01 | 4.41475332e−01 | 2.92654634e−01 | 3.65190580e−02 |
| 2.31375113e−01 | −2.12969333e−02 | 1.80064738e−01 | 3.29465687e−01 |
| 2.04499453e−01 | 3.01778316e−01 | −1.34435833e−01 | −7.99726509e−03 |
| −6.96363822e−02 | 1.04810692e−01 | 4.73632455e−01 | −2.26599723e−01 |
| −8.25821608e−02 | 8.90058503e−02 | 6.20702915e−02 | 2.95398086e−02 |
| −3.20565850e−02 | 2.95267045e−01 | 1.70517281e−01 | 3.04409474e−01 |
| 2.71117222e−02 | 2.78227925e−01 | −1.02906682e−01 | −1.84060317e−01 |
| 1.82613656e−02 | 6.26610965e−02 | 7.59422258e−02 | 3.27922851e−02 |
| 2.59863704e−01 | −3.77245128e−01 | 5.07533401e−02 | 5.48683107e−02 |
| −1.43515915e−01 | 2.88717389e−01 | 1.64747685e−01 | −1.19004190e−01 |
| 1.92026332e−01 | 1.37175158e−01 | −5.15898205e−02 | 2.45995089e−01 |
| 2.25124136e−01 | 2.51656532e−01 | 1.49679929e−01 | 1.09989665e−01 |
| −3.84919554e−01 | 1.56030566e−01 | 3.55595589e−01 | 4.88660485e−02 |
| −2.51498282e−01 | −2.64356941e−01 | 2.88057953e−01 | −2.46446654e−02 |
| 2.30982170e−01 | 8.91375989e−02 | 3.49154770e−01 | 1.16171382e−01 |
| 1.70644626e−01 | −1.77435219e−01 | 9.49649364e−02 | −1.40385434e−01 |
| 1.97682202e−01 | −1.18984148e−01 | 2.60652333e−01 | 7.17286244e−02 |
| 1.97961017e−01 | 1.99014857e−01 | 3.30469161e−02 | 1.43824235e−01 |
| 2.38944292e−01 | −6.59634471e−02 | 1.03065960e−01 | 3.08782607e−01 |
| 2.00611129e−01 | −1.23278819e−01 | 6.69533432e−01 | 6.50276542e−02 |
| 2.13057369e−01 | −8.00754875e−02 | 3.95400733e−01 | 1.74566016e−01 |
| −3.09342742e−02 | −1.52818143e−01 | 2.03488052e−01 | 1.62360162e−01 |
| 1.03393421e−01 | 3.56223404e−01 | 2.89763719e−01 | −1.96879692e−02 |
| −4.72802445e−02 | 1.51489809e−01 | 3.07562023e−01 | 1.03132188e−01 |
| 4.01730657e−01 | 9.67320651e−02 | 3.52084070e−01 | 7.79867589e−01] |
| [2.05395937e−01 | −5.06975055e−02 | 2.31780604e−01 | −2.63353527e−01 |
| 3.61576956e−01 | 1.80522725e−01 | −5.05925231e−02 | 2.68680662e−01 |
| 3.80946919e−02 | 4.06639338e−01 | 1.68027848e−01 | −9.29119587e−02 |
| 1.36260062e−01 | 3.14587168e−02 | −1.46363690e−01 | 9.89742428e−02 |
| 1.39105231e−01 | 9.04801637e−02 | 5.83964325e−02 | 3.39375943e−01 |
| −4.91356365e−02 | 4.28334653e−01 | −1.37223467e−01 | 8.74131694e−02 |
| 6.76744571e−03 | 3.12174827e−01 | −2.80223391e−03 | 1.76146805e−01 |
| −9.08377916e−02 | 3.22777867e−01 | 4.65742350e−01 | 3.95774484e−01 |
| 3.39261502e−01 | −9.30387601e−02 | 4.43955749e−01 | 1.26254514e−01 |
| 5.39598584e−01 | 3.65605563e−01 | 8.60155597e−02 | 1.62694290e−01 |
| −1.63666233e−01 | 1.96096539e−01 | −1.35985181e−01 | −1.57560214e−01 |
| 3.77230614e−01 | 1.38254136e−01 | 2.69073278e−01 | 1.66622013e−01 |
| −1.37237855e−03 | 1.91160157e−01 | 1.54494420e−01 | 2.38877028e−01 |
| 1.27198640e−03 | 1.98380738e−01 | 3.62206995e−02 | 1.85707048e−01 |
| 2.23013416e−01 | 2.25951761e−01 | 1.45832181e−01 | −2.07565665e−01 |
| 1.40999258e−01 | 3.37548137e−01 | 1.18411757e−01 | 1.24005564e−01 |
| 4.17371869e−01 | 2.61074752e−01 | 5.06311134e−02 | 2.89463043e−01 |
| 1.03920758e−01 | 3.06043066e−02 | 2.14308441e−01 | 3.09483051e−01 |
| 5.35326242e−01 | 5.07891225e−03 | −1.97299033e−01 | −6.32318184e−02 |
| 1.05385818e−01 | 1.50327280e−01 | 1.23576470e−01 | −2.59912103e−01 |
| 1.03324234e−01 | 1.79483458e−01 | 2.07781672e−01 | 6.11333270e−03 |
| 1.64494798e−01 | 1.49521083e−01 | −3.35741788e−02 | 3.00320268e−01 |
| −1.02307230e−01 | 1.77121222e−01 | 8.36502612e−02 | −9.30162072e−02 |
| 2.94346362e−01 | 7.42274448e−02 | 1.57177508e−01 | 3.06503922e−01 |
| −1.56377003e−01 | 2.35363722e−01 | 3.76194656e−01 | −4.18451056e−03 |
| 6.19015433e−02 | 3.31041485e−01 | 1.68094769e−01 | −1.89587045e−02 |
| 2.01186463e−01 | 4.20604229e−01 | 8.04597437e−02 | 7.33583719e−02 |
| 2.38772377e−01 | −5.85887060e−02 | −1.34522468e−01 | 4.93792772e−01 |
| 2.89917320e−01 | −1.47695109e−01 | 1.57454982e−01 | 3.05330008e−01 |
| 2.00197399e−01 | 1.93501249e−01 | −8.99210852e−03 | 1.54196978e−01 |
| 7.83885717e−02 | −5.63416146e−02 | 6.84906989e−02 | 1.74206913e−01 |
| 2.07227007e−01 | −3.42001207e−02 | 6.03401586e−02 | 9.54846814e−02 |
| 1.90772079e−02 | 3.38980794e−01 | 4.11390215e−02 | 4.34526443e−01 |
| 3.87758553e−01 | 1.53909996e−01 | −9.47726220e−02 | 1.00249872e−01 |
| 3.15611094e−01 | 2.14926571e−01 | 2.41013199e−01 | 3.68580908e−01 |
| 1.68833181e−01 | −3.97515185e−02 | 1.28540128e−01 | 3.14755917e−01 |
| 8.49492848e−02 | 2.72742864e−02 | −5.80757707e−02 | −1.88127637e−01 |
| −5.61158406e−03 | 1.13293424e−01 | 7.79410684e−03 | 1.60523862e−01 |
| 7.63811842e−02 | 3.45015138e−01 | 3.98454636e−01 | 3.29577960e−02 |
| 3.24121416e−02 | 2.22525939e−01 | −3.20197463e−01 | 1.08471453e−01 |
| 9.68393534e−02 | 1.73415303e−01 | 1.64723657e−02 | 2.79981103e−02 |
| 1.24529786e−01 | −7.21198693e−02 | 1.16271734e−01 | −1.52646393e−01 |
| −3.79379630e−01 | 1.54079214e−01 | −9.64688957e−02 | 2.26161703e−01 |
| 5.26007295e−01 | −2.56080870e−01 | 1.64098278e−01 | −8.62595662e−02 |
| 1.19197406e−01 | 1.99673519e−01 | 1.49002656e−01 | −2.21001580e−01 |
| −6.63681552e−02 | −1.05167128e−01 | 2.14668766e−01 | 3.16228807e−01 |
| 3.61242145e−01 | 1.44417867e−01 | 1.37677699e−01 | 3.75738889e−01 |
| 2.21632235e−01 | −1.87524378e−01 | 3.61820221e−01 | 3.43033791e−01 |
| 5.71982227e−02 | 7.27407187e−02 | −1.90810338e−01 | 1.87812611e−01 |
| 4.91104499e−02 | −9.04454216e−02 | 3.38417053e−01 | 9.81090888e−02 |
| 1.45418271e−01 | 1.61760241e−01 | 1.02927178e−01 | −1.29208772e−03 |
| 5.00551760e−01 | 3.59974176e−01 | 5.92887044e−01 | 8.19001570e−02 |
| −1.02050021e−01 | 2.52303600e−01 | −1.75063029e−01 | −1.93925872e−01 |

TABLE $W_h^1$-continued

| | | | |
|---|---|---|---|
| 2.16924027e−01 | 1.54751450e−01 | −2.73975223e−01 | 6.51689805e−03 |
| 1.85799792e−01 | 2.50336856e−01 | 2.72426933e−01 | 1.07963040e−01 |
| 1.79871932e−01 | 2.34436244e−01 | 7.64076561e−02 | −1.06251679e−01 |
| −2.98074573e−01 | 2.66335189e−01 | 7.96653405e−02 | 2.18043178e−01 |
| 1.42836556e−01 | −5.94265796e−02 | 2.81838119e−01 | 1.76738158e−01 |
| 8.09881091e−02 | −2.18232170e−01 | 2.51918614e−01 | 1.90839857e−01 |
| 2.42881775e−01 | 2.93067098e−01 | −3.70551497e−02 | 1.14607401e−02 |
| 6.91894367e−01 | 6.10525459e−02 | 3.67500693e−01 | −1.12826429e−01 |
| −2.42071897e−01 | 2.89795455e−01 | 2.74866939e−01 | 1.72807783e−01 |
| 3.26850712e−01 | 3.27473104e−01 | −1.78135872e−01 | −4.37159417e−03 |
| 4.71904501e−03 | 1.83773324e−01 | 1.84889868e−01 | −1.72075909e−02] |
| [2.34681547e−01 | 2.04049975e−01 | 1.56293467e−01 | 1.95974663e−01 |
| 2.51404773e−01 | 7.70615181e−03 | 3.31180125e−01 | −3.82762365e−02 |
| 8.55081826e−02 | 2.78066397e−01 | 7.45949708e−03 | 2.29493916e−01 |
| 1.07692115e−01 | 1.35740563e−01 | 6.94234073e−02 | −1.36732548e−01 |
| 6.21190015e−03 | −8.60674530e−02 | 2.31065363e−01 | 4.33082618e−02 |
| 3.34299117e−01 | 8.04419722e−03 | 1.37148723e−01 | 4.37019020e−01 |
| 2.57760100e−02 | 1.45749182e−01 | 2.43402913e−01 | 7.23482147e−02 |
| 3.57454240e−01 | 1.32194310e−01 | −1.13797359e−01 | 3.19353282e−01 |
| 1.62593082e−01 | −1.64569721e−01 | 1.16149127e−01 | 6.68954328e−02 |
| 9.87889767e−02 | 2.33471751e−01 | −4.36694957e−02 | 2.14274496e−01 |
| −2.59551220e−02 | 2.58201696e−02 | −1.32967317e−02 | 2.04912856e−01 |
| 2.38987319e−02 | 1.73843786e−01 | 5.83613336e−01 | 4.22389001e−01 |
| −9.58608836e−02 | 1.46820694e−01 | 3.35097641e−01 | −1.14266358e−01 |
| 8.93667564e−02 | 1.42594695e−01 | −1.72857642e−01 | −2.78804544e−01 |
| 4.58389521e−02 | −1.28157914e−01 | 4.25480574e−01 | 5.62647544e−02 |
| −1.47824764e−01 | 5.01291305e−02 | −1.89310253e−01 | 7.53846243e−02 |
| 1.41648531e−01 | 1.16775386e−01 | −1.83172762e−01 | 1.54269204e−01 |
| 4.20654863e−02 | 6.54288903e−02 | 4.04548109e−01 | −2.85681695e−01 |
| 3.28404546e−01 | 2.91660309e−01 | 4.36541699e−02 | 3.47017795e−01 |
| 4.46374267e−02 | 1.38919696e−01 | 7.47062117e−02 | 4.11834389e−01 |
| 1.28841221e−01 | 3.21587145e−01 | 1.03020608e−01 | −5.45670884e−03 |
| 3.98339555e−02 | −2.63248116e−01 | −1.29510090e−01 | −2.56296158e−01 |
| −9.94952992e−02 | 3.06843013e−01 | −1.50326818e−01 | 1.99578151e−01 |
| 2.60876745e−01 | 1.12697184e−02 | 4.57565576e−01 | 1.39101952e−01 |
| −1.08207755e−01 | 2.48023525e−01 | 1.19513616e−01 | −3.07477146e−01 |
| −1.37963016e−02 | 6.50301218e−01 | 3.50961059e−01 | 3.45725179e−01 |
| 5.32365926e−02 | 3.45792621e−01 | 1.52451396e−01 | 2.75504768e−01 |
| 2.33162135e−01 | 7.02228025e−02 | 8.49315822e−02 | −4.72314395e−02 |
| 3.60037275e−02 | −2.04648465e−01 | 2.82696635e−01 | 3.45870018e−01 |
| 8.34065527e−02 | 2.78682709e−01 | 1.83409810e−01 | 1.72756150e−01 |
| 3.59703839e−01 | −4.05458421e−01 | 1.88694671e−01 | 3.75541866e−01 |
| 4.07155454e−02 | 3.03243488e−01 | −1.06246628e−01 | 2.01635957e−01 |
| −2.20085710e−01 | 3.56332421e−01 | 3.25899541e−01 | 5.23490667e−01 |
| 5.20405829e−01 | 2.81779975e−01 | 1.81084543e−01 | 2.35862181e−01 |
| −2.21850634e−01 | 1.68214500e−01 | 4.65255499e−01 | 3.64456207e−01 |
| 2.72873938e−01 | 7.90852383e−02 | 2.55333662e−01 | 1.25729024e−01 |
| 8.19620192e−02 | 6.35353178e−02 | 2.75110528e−02 | −1.17242485e−02 |
| 1.22268483e−01 | −1.12303589e−02 | 2.08904892e−01 | −3.04853082e−01 |
| 4.17046458e−01 | 1.45735130e−01 | 4.06083345e−01 | −4.00134735e−03 |
| 1.27998263e−01 | 8.58558193e−02 | 4.79128249e−02 | 1.96257740e−01 |
| 2.14301169e−01 | 6.74867630e−02 | −2.39276335e−01 | −5.59416227e−02 |
| 3.97881925e−01 | 1.95903271e−01 | 3.77978861e−01 | 1.02542877e−01 |
| 4.50215846e−01 | 2.80464441e−01 | −2.77363956e−01 | 9.37236324e−02 |
| 3.34709853e−01 | 2.71251947e−02 | 1.44826442e−01 | 3.44938189e−01 |
| −5.16616963e−02 | −2.87242651e−01 | 1.30435999e−03 | −4.31819856e−02 |
| 1.74655288e−01 | 3.44007939e−01 | 1.09032415e−01 | 1.26189038e−01 |
| 5.94140291e−02 | 2.87357032e−01 | 1.29158571e−01 | 5.15560769e−02 |
| 1.53225020e−01 | 2.57815868e−01 | 3.47695917e−01 | 7.05247447e−02 |
| −2.10614651e−02 | 1.95744503e−02 | 1.89385131e−01 | 2.39732116e−01 |
| 3.74766767e−01 | 1.01804025e−01 | −4.59779575e−02 | −9.21445433e−03 |
| −1.72639415e−01 | 1.62394851e−01 | 2.22787969e−02 | 9.20917168e−02 |
| −1.27986565e−01 | 2.32614502e−01 | 3.89179915e−01 | 4.91359904e−01 |
| 1.08684681e−01 | −2.03717947e−01 | 3.22307020e−01 | 2.23625168e−01 |
| 2.23495319e−01 | 2.97333956e−01 | −2.43744150e−01 | 2.22695231e−01 |
| −2.55599797e−01 | −2.33384117e−01 | 3.88544708e−01 | 9.62889716e−02 |
| 7.44404644e−02 | 6.88737556e−02 | 3.07892263e−01 | 1.49695277e−01 |
| 2.31246333e−04 | 1.17069902e−02 | 1.58618674e−01 | 4.96577322e−01 |
| 7.32851028e−02 | 8.61359760e−02 | 4.53818649e−01 | 3.33981037e−01 |
| 1.87154174e−01 | −5.50639108e−02 | −1.43663391e−01 | 1.85138714e−02 |
| −2.47027818e−01 | −2.57722646e−01 | −4.84023750e−01 | −2.66321987e−01 |
| 1.62146136e−01 | 1.24325261e−01 | 1.62319645e−01 | 2.66720146e−01 |
| −1.22524485e−01 | 1.78322017e−01 | 2.99443100e−02 | 1.93153724e−01 |
| 1.44918449e−03 | 1.00700483e−01 | −2.87512299e−02 | −6.46652468e−03 |
| 1.83653221e−01 | 6.21909276e−02 | 2.10546032e−01 | −2.98673362e−01] |
| [−4.15309161e−01 | 2.78820664e−01 | 7.01252341e−01 | 7.66147301e−01 |
| 5.02795458e−01 | 5.82385600e−01 | 3.13761622e−01 | −7.06563070e−02 |
| 4.32769448e−01 | 5.25568604e−01 | 3.66338372e−01 | 3.13263237e−01 |
| 1.78850845e−01 | 2.76735514e−01 | 2.32517377e−01 | 2.16519606e−04 |
| 3.99614930e−01 | 6.11181080e−01 | 1.70875341e−01 | 8.12029541e−01 |

TABLE $W_h^1$-continued

| | | | |
|---|---|---|---|
| 2.61738002e−01 | 3.03270910e−02 | 7.09070802e−01 | 5.33727705e−01 |
| 5.52655756e−01 | 8.48870158e−01 | 3.08276862e−02 | 5.52478313e−01 |
| 1.33384287e−01 | −2.52455771e−02 | −2.25808710e−01 | 3.65414172e−01 |
| 6.10143803e−02 | 3.09271246e−01 | 6.75722539e−01 | 4.30708341e−01 |
| 2.71902084e−01 | 3.71440828e−01 | 7.37638831e−01 | 3.53674859e−01 |
| 6.71641350e−01 | 4.79471147e−01 | 4.35115039e−01 | 4.93135482e−01 |
| 5.93443036e−01 | 5.49845457e−01 | 8.81389454e−02 | 1.24970031e−00 |
| 2.29496837e−01 | 1.90637916e−01 | 5.78751326e−01 | 3.74168277e−01 |
| 9.48693752e−01 | 3.39715719e−01 | 2.53742456e−01 | 6.72060072e−01 |
| 1.02738333e−00 | 7.62148619e−01 | 2.77033269e−01 | 2.01924637e−01 |
| 3.31052542e−01 | 7.66427577e−01 | 5.03504753e−01 | 4.20771986e−01 |
| 4.85598743e−02 | 5.34611344e−01 | 7.79268444e−01 | 3.21395665e−01 |
| 1.68510944e−01 | −6.01634681e−02 | 3.87101173e−01 | 3.23254645e−01 |
| 3.99718970e−01 | 4.91620183e−01 | 8.61192822e−01 | 4.77215916e−01 |
| 1.60457388e−01 | 4.65063155e−01 | 1.02960534e−01 | 1.29192919e−01 |
| 3.05115461e−01 | 6.38771415e−01 | −9.96496901e−02 | 4.31938887e−01 |
| −6.03356957e−02 | −2.29120657e−01 | −4.23330933e−01 | 6.62421942e−01 |
| 6.81831658e−01 | −1.53404385e−01 | 2.27830157e−01 | −4.82831784e−02 |
| 5.15716434e−01 | 2.66053200e−01 | 7.12155700e−01 | 6.45757198e−01 |
| 5.00802040e−01 | 7.98030257e−01 | −4.34942096e−01 | 5.07823646e−01 |
| 7.11644590e−01 | 1.15243137e−00 | 2.79841661e−01 | −8.79366323e−02 |
| 9.51309875e−02 | 4.41694230e−01 | 7.25599766e−01 | 4.11557108e−01 |
| −2.07782374e−03 | 7.45693803e−01 | 3.67446184e−01 | 1.60981491e−01 |
| 9.81701910e−01 | 4.81528103e−01 | 7.86863863e−01 | 2.18355060e−01 |
| 4.25389916e−01 | 5.45221329e−01 | 8.44306231e−01 | 5.75510263e−02 |
| 4.89609361e−01 | 6.49606168e−01 | 3.03829372e−01 | 5.39018512e−01 |
| 1.80318385e−01 | 2.73269236e−01 | 9.43367183e−01 | 3.71723503e−01 |
| 6.48719013e−01 | 4.55695838e−01 | 7.21855581e−01 | 7.48414576e−01 |
| 4.77068335e−01 | 3.91616344e−01 | 6.80766165e−01 | 2.71460563e−02 |
| −1.18161626e−01 | 6.32265925e−01 | 5.02033830e−02 | 1.97869748e−01 |
| 1.40329704e−01 | 6.25351727e−01 | 2.78185103e−02 | 5.04391789e−01 |
| 3.65440220e−01 | 5.83471119e−01 | 5.35312854e−03 | 5.74448049e−01 |
| 4.20184642e−01 | 4.77117449e−01 | 9.22955498e−02 | 5.89119613e−01 |
| 3.20366770e−01 | 7.88809478e−01 | 2.99941689e−01 | 8.49436283e−01 |
| −9.05525014e−02 | 7.01834619e−01 | 5.62404454e−01 | 1.79896876e−01 |
| 2.56453335e−01 | 6.75300062e−01 | 5.31286120e−01 | 1.86062574e−01 |
| 6.47176728e−02 | 3.67094159e−01 | 4.55663234e−01 | −2.45483249e−01 |
| 6.54963791e−01 | 3.16000134e−01 | 6.71041191e−01 | 2.34658733e−01 |
| 6.77650750e−01 | 3.88035119e−01 | 2.27043509e−01 | 8.79308730e−02 |
| 3.98496062e−01 | 7.45019495e−01 | 4.71862286e−01 | 5.25375187e−01 |
| 3.09786379e−01 | 5.78291595e−01 | 6.50218904e−01 | 7.63548076e−01 |
| 1.25311148e−00 | 2.67760605e−01 | 2.49912441e−01 | 4.14563209e−01 |
| 1.85048878e−01 | 6.84458986e−02 | 6.49439335e−01 | 8.52855504e−01 |
| 1.95386782e−01 | 5.67095757e−01 | −1.53291156e−03 | 6.79646671e−01 |
| 5.85699141e−01 | 5.35423398e−01 | 5.80175877e−01 | 3.97190303e−01 |
| 6.55922443e−02 | −1.76856652e−01 | 4.70323086e−01 | 4.14497375e−01 |
| 3.17102402e−01 | 3.12959462e−01 | 3.19242746e−01 | 3.35707277e−01 |
| 8.43991935e−01 | 2.17044979e−01 | 4.64403510e−01 | 2.69153744e−01 |
| 2.07965583e−01 | 5.28473854e−01 | 4.00432825e−01 | 6.07632697e−01 |
| 2.63300717e−01 | 2.12633654e−01 | 9.06737149e−01 | −3.43201548e−01 |
| 1.45603254e−01 | 6.24576926e−01 | 3.30735929e−02 | −8.84021744e−02 |
| 3.26816291e−01 | 4.29070771e−01 | −2.68666688e−02 | 2.50259399e−01 |
| 9.64775681e−01 | 7.81956673e−01 | 7.34622061e−01 | 4.72469211e−01 |
| 1.00723051e−01 | −6.61950484e−02 | 8.99369657e−01 | 3.11551034e−01 |
| 3.28440934e−01 | 6.79204404e−01 | 1.65258944e−01 | 3.22950125e−01 |
| 8.08547363e−02 | 2.69184113e−01 | 7.41684258e−01 | 4.11136746e−01 |
| 2.85784960e−01 | 3.43004495e−01 | 1.32702470e−01 | 3.20558786e−01 |
| 2.69620925e−01 | 3.40254128e−01 | 3.16940784e−01 | 3.71336251e−01 |
| 1.36116117e−01 | 3.19438040e−01 | 6.43050849e−01 | 4.18683380e−01] |
| [1.44067928e−01 | 1.04239658e−01 | 4.40386295e−01 | 8.31651092e−02 |
| 3.45142156e−01 | 2.86493063e−01 | 2.75217324e−01 | 6.53815120e−02 |
| 1.52868927e−01 | 1.05089441e−01 | 4.70962137e−01 | 3.03463370e−01 |
| 6.55867681e−02 | 1.67063370e−01 | −1.34083228e−02 | 1.30449563e−01 |
| 3.33534986e−01 | 1.49171174e−01 | −3.55291486e−01 | 2.86181867e−02 |
| 6.85974240e−01 | 4.34871525e−01 | 3.44045550e−01 | 3.65312576e−01 |
| 2.10936591e−01 | 5.69630980e−01 | 1.82718709e−01 | 2.85011142e−01 |
| −2.93698013e−01 | 7.65351832e−01 | 2.62622625e−01 | 4.47662741e−01 |
| 6.06589079e−01 | −1.06253237e−01 | 2.84467101e−01 | −5.11402786e−02 |
| 6.64336681e−02 | 2.45187134e−01 | −1.87000725e−02 | 5.69061220e−01 |
| −1.29781097e−01 | 2.49845743e−01 | −2.47276992e−01 | 1.65131137e−01 |
| 2.09677979e−01 | 2.63485983e−02 | 2.17737574e−01 | 7.35102475e−01 |
| −2.93581009e−01 | 1.76860005e−01 | 2.58854866e−01 | 2.92974502e−01 |
| 3.90704125e−01 | 1.73894569e−01 | 1.60951346e−01 | 4.16430645e−02 |
| 5.90830803e−01 | 4.50027049e−01 | 4.71495867e−01 | 2.16077581e−01 |
| 3.93791735e−01 | 3.58722836e−01 | 1.22260854e−01 | 1.93738788e−01 |
| −7.39038140e−02 | 5.32177746e−01 | 2.95904517e−01 | 2.43259504e−01 |
| 3.07010651e−01 | 1.01644583e−02 | 3.98468412e−02 | −1.72853589e−01 |
| 2.16214970e−01 | 5.88350415e−01 | −2.47355234e−02 | 4.62274373e−01 |
| 1.56239301e−01 | 8.74366313e−02 | −3.11402082e−01 | −4.15970862e−01 |
| 2.57444859e−01 | 3.84328961e−01 | 2.77957827e−01 | 2.03574132e−02 |

TABLE $W_h^1$-continued

| | | | |
|---|---|---|---|
| −6.22623265e−02 | 4.00369167e−01 | −8.61544721e−03 | 4.62935537e−01 |
| 1.81389749e−01 | 1.69543192e−01 | 1.56793028e−01 | 3.52884740e−01 |
| 3.45435023e−01 | 9.07814354e−02 | 2.53252566e−01 | 1.75882310e−01 |
| 5.74738324e−01 | 4.08390611e−02 | 6.03543594e−02 | −5.09807244e−02 |
| 1.72256812e−01 | 8.86603892e−01 | 4.29965526e−01 | 6.27356321e−02 |
| 4.81752574e−01 | −1.68707520e−01 | 4.29030865e−01 | −1.46520987e−01 |
| 3.05968314e−01 | 5.37084818e−01 | 4.43065971e−01 | 5.45050167e−02 |
| 2.50209510e−01 | −3.42394769e−01 | 1.95576712e−01 | 7.15462506e−01 |
| −3.02357394e−02 | 4.11173075e−01 | 3.90234649e−01 | −7.77638108e−02 |
| 1.41184673e−01 | 6.52190447e−01 | 4.31884736e−01 | 3.14449728e−01 |
| −2.06556156e−01 | 2.58516043e−01 | 6.08588874e−01 | 4.31853414e−01 |
| 3.82519931e−01 | 3.97908419e−01 | 8.02550793e−01 | 4.88224030e−02 |
| 1.63330343e−02 | −1.26328871e−01 | 4.22648847e−01 | 3.31396878e−01 |
| 3.70554775e−01 | 4.17014986e−01 | 2.99501151e−01 | 2.77958423e−01 |
| −9.41214263e−02 | 2.00625271e−01 | 4.77533519e−01 | 5.36596067e−02 |
| 3.88212770e−01 | −1.18299827e−01 | 2.59291828e−01 | 5.32760918e−02 |
| 5.70020713e−02 | 1.94132179e−01 | 3.35481107e−01 | 2.14866742e−01 |
| 6.33364737e−01 | 1.82288602e−01 | 3.03753734e−01 | 4.74143624e−01 |
| 3.36902708e−01 | 3.73192877e−01 | 1.23922989e−01 | 4.52198833e−01 |
| 2.88882881e−01 | 1.75113574e−01 | 1.20793588e−01 | 1.89319089e−01 |
| 2.09567383e−01 | −7.86062479e−02 | 9.12358016e−02 | −3.47515911e−01 |
| −3.46743047e−01 | 4.20751572e−01 | 3.01678687e−01 | 1.16962142e−01 |
| 6.30749643e−01 | 5.10992587e−01 | 8.19258094e−02 | 5.55544853e−01 |
| 5.50572872e−01 | 2.54029065e−01 | 4.08046156e−01 | −1.16592623e−01 |
| 6.04108095e−01 | 1.90302700e−01 | 8.19035292e−01 | −1.48652121e−01 |
| 7.73932695e−01 | −2.61663318e−01 | 3.24608654e−01 | 2.25505736e−02 |
| 1.15855895e−01 | 4.86913055e−01 | 5.10162234e−01 | 2.08114579e−01 |
| 2.38556281e−01 | 4.79175001e−01 | 3.43131155e−01 | 8.02318677e−02 |
| 1.45463854e−01 | 4.18294311e−01 | 2.39943400e−01 | 2.93666571e−01 |
| 6.68358356e−02 | −1.61010966e−01 | 3.24024320e−01 | −3.36623564e−02 |
| 3.58886272e−01 | 1.50106266e−01 | 3.68265271e−01 | 2.23087922e−01 |
| 3.00786823e−01 | −1.05580941e−01 | 3.18687201e−01 | −3.02078445e−02 |
| 4.15596485e−01 | 1.88680232e−01 | 1.13558158e−01 | 9.25287008e−02 |
| 3.24316561e−01 | 1.67375654e−01 | 1.90519854e−01 | 6.83724042e−03 |
| 2.54105896e−01 | 3.96036386e−01 | 2.50211477e−01 | 1.01617612e−01 |
| 6.12226784e−01 | 2.79299378e−01 | −3.15632373e−01 | 2.66731858e−01 |
| 2.08924264e−01 | 7.10427523e−01 | 6.09941900e−01 | 5.36696255e−01 |
| 1.41759096e−02 | 3.68833750e−01 | 5.01691923e−02 | 7.35610783e−01 |
| 1.82475537e−01 | 2.63822339e−02 | 6.40484989e−01 | 3.96481276e−01 |
| 2.95558542e−01 | 3.31434697e−01 | 1.58168212e−01 | 3.19145352e−01 |
| 3.86780091e−02 | −6.34637922e−02 | 1.41448766e−01 | 5.17585456e−01 |
| 9.22162831e−01 | 1.84440683e−03 | 1.65815264e−01 | 4.96445261e−01 |
| −1.61445737e−01 | 4.70505595e−01 | 5.97530544e−01 | 1.11918762e−01] |
| [3.99629399e−02 | 2.24837571e−01 | 2.11139470e−01 | 3.34087312e−01 |
| 3.98982435e−01 | 1.79205686e−02 | −7.66050741e−02 | −5.04534617e−02 |
| 8.77521187e−02 | 9.46524590e−02 | 6.01401366e−02 | 3.68983179e−01 |
| 2.77245659e−02 | 9.03913155e−02 | 2.51654893e−01 | 2.98328042e−01 |
| −7.45216431e−03 | 3.87370676e−01 | 1.70228854e−01 | −5.61302491e−02 |
| −1.54126920e−02 | 2.65619494e−02 | 4.05273378e−01 | 2.17711642e−01 |
| 3.17001313e−01 | 2.29259759e−01 | 6.98340610e−02 | 2.14872912e−01 |
| 4.02287729e−02 | 3.41375291e−01 | 1.71630740e−01 | 2.59565830e−01 |
| 1.17417425e−01 | −4.14383486e−02 | −7.80523941e−02 | 9.76995006e−02 |
| 5.10056643e−03 | 9.28113312e−02 | −3.07114702e−02 | 1.07276872e−01 |
| 4.44465607e−02 | 4.23901409e−01 | 8.48158821e−02 | 3.56090039e−01 |
| −1.00689150e−01 | 6.25247210e−02 | 7.60184824e−02 | 7.74134994e−02 |
| 2.47913286e−01 | −7.54002258e−02 | 6.68364540e−02 | 2.54524350e−01 |
| 2.97383040e−01 | −2.77912691e−02 | 3.73507023e−01 | −5.53781688e−02 |
| 2.56703105e−01 | −7.62170702e−02 | 2.62056917e−01 | 6.24282584e−02 |
| 2.62708873e−01 | 4.73858044e−03 | 2.28600025e−01 | 2.10456252e−01 |
| 1.40824355e−02 | −1.37121999e−03 | 2.60255963e−01 | −5.96065409e−02 |
| −4.84111197e−02 | 7.49016926e−02 | 8.02292749e−02 | −1.23814605e−01 |
| 1.06871411e−01 | 1.01423718e−01 | 4.05990839e−01 | 2.05525786e−01 |
| 3.51179063e−01 | 1.20524742e−01 | −9.52218026e−02 | 1.75059214e−01 |
| 2.65720785e−01 | 7.35020339e−02 | 7.17215911e−02 | −1.09680109e−02 |
| 1.25801310e−01 | 3.02713096e−01 | 3.69937196e−02 | 3.90122712e−01 |
| 2.15626322e−02 | 2.25522265e−01 | 4.68672007e−01 | −2.86927689e−02 |
| −4.73922268e−02 | −8.58161449e−02 | 4.16695438e−02 | 2.77287900e−01 |
| 9.43059251e−02 | 2.35911652e−01 | 2.21475549e−02 | 3.16842228e−01 |
| 2.80006737e−01 | 2.34190613e−01 | 2.63744473e−01 | 9.86600816e−02 |
| 2.49395013e−01 | 2.24602163e−01 | 2.29223132e−01 | 3.49431992e−01 |
| −6.28201142e−01 | −1.00018568e−01 | 2.75656193e−01 | 1.06633812e−01 |
| 2.64324248e−01 | 2.46255860e−01 | 8.94120336e−02 | 4.54243235e−02 |
| 3.34254384e−01 | 2.66742498e−01 | 1.14067145e−01 | 8.32078680e−02 |
| 3.02300483e−01 | 3.63561511e−01 | 6.08833879e−02 | 3.89408261e−01 |
| −1.11112930e−01 | 9.08982456e−02 | −7.85014406e−02 | 3.68620977e−02 |
| −4.43732925e−02 | 2.11384818e−01 | 2.78100614e−02 | 3.09507042e−01 |
| 2.80801058e−01 | 3.59486714e−02 | 3.22412997e−01 | 1.39126107e−01 |
| 3.57827306e−01 | 2.51672059e−01 | 1.05750695e−01 | 2.70801961e−01 |
| 3.16208676e−02 | 1.00521155e−01 | 2.53361255e−01 | 2.09738374e−01 |
| 1.12873875e−01 | −7.11415932e−02 | 1.00021616e−01 | −9.07024443e−02 |

TABLE $W_h^1$-continued

| | | | |
|---|---|---|---|
| 1.40514106e−01 | −2.47342847e−02 | 6.50083050e−02 | 2.70308316e−01 |
| 1.01656370e−01 | 1.02605104e−01 | 1.69713013e−02 | 2.05149516e−01 |
| −1.02169558e−01 | 1.25577375e−01 | 2.06607863e−01 | −2.13106927e−02 |
| 4.41009589e−02 | 5.87506108e−02 | −1.08856045e−01 | 2.32688099e−01 |
| 2.06178427e−01 | −7.72250220e−02 | 3.40679467e−01 | −8.31609219e−02 |
| 6.17997982e−02 | 2.98215002e−01 | −1.79167837e−03 | −5.47080413e−02 |
| 3.76367420e−01 | 5.26475199e−02 | 2.43087560e−01 | −4.52251136e−02 |
| −5.58169521e−02 | 1.68717638e−01 | 1.26521677e−01 | −7.25559890e−02 |
| −3.30424570e−02 | 3.08798730e−01 | 3.19451421e−01 | 3.74453664e−01 |
| 1.13711029e−01 | 4.00320813e−02 | 2.61670083e−01 | 6.67931791e−03 |
| 3.11998904e−01 | 9.17176679e−02 | 3.99505675e−01 | 1.80029169e−01 |
| 2.01593250e−01 | 2.66174555e−01 | 1.03147022e−01 | 1.20646246e−01 |
| −5.01893908e−02 | 3.47985506e−01 | 1.34215504e−01 | 3.26774985e−01 |
| −1.40455458e−02 | 2.32177123e−01 | 3.04267883e−01 | 3.22262138e−01 |
| −3.20758186e−02 | 4.05062437e−01 | 3.18255693e−01 | 1.70727700e−01 |
| 3.76053482e−01 | 3.04624081e−01 | 2.39062339e−01 | 1.81378480e−02 |
| 5.08399960e−03 | 7.74118826e−02 | 2.41299599e−01 | 3.19737732e−01 |
| 7.24819228e−02 | 4.26683158e−01 | 2.21065149e−01 | 1.85910404e−01 |
| 4.05707732e−02 | 2.12342858e−01 | −9.41465199e−02 | 1.69953540e−01 |
| 2.78353900e−01 | 1.73802078e−02 | 1.79869652e−01 | 9.43774432e−02 |
| 9.34427697e−03 | 2.40271121e−01 | 3.99005190e−02 | 3.14253688e−01 |
| −9.08008069e−02 | 5.60924932e−02 | −9.90328789e−02 | 2.92522341e−01 |
| 4.19774413e−01 | 8.11529309e−02 | 3.00688028e−01 | 1.94922850e−01 |
| −9.18481033e−03 | 4.04533982e−01 | 2.71724015e−01 | −1.12497449e−01 |
| 1.03419773e−01 | 3.58945988e−01 | 2.27203265e−01 | −7.15591386e−02 |
| 4.56637561e−01 | −3.71818542e−02 | −7.46978745e−02 | 3.55940372e−01 |
| 9.14588720e−02 | 5.48203811e−02 | 8.67410079e−02 | 1.04111023e−01] |
| [−4.03791964e−02 | 4.19505015e−02 | 2.17006668e−01 | 5.37559211e−01 |
| 1.72011510e−01 | −3.25769596e−02 | −1.41664326e−01 | −5.38807437e−02 |
| 2.39438266e−02 | −1.47190168e−01 | 3.41717035e−01 | 1.24290474e−01 |
| 3.44520688e−01 | −4.08094823e−02 | 9.28227678e−02 | 2.72746950e−01 |
| 1.27634168e−01 | −2.85231527e−02 | 1.09792098e−01 | 1.50738955e−01 |
| 4.03693795e−01 | −2.50040174e−01 | 2.59632319e−01 | 8.87173861e−02 |
| −1.34251332e−02 | 2.27297485e−01 | 2.74011381e−02 | 1.70670539e−01 |
| 2.27881357e−01 | 1.71831593e−01 | 1.41359568e−01 | −1.11354878e−02 |
| 2.15611979e−01 | −1.83153316e−01 | 3.48011166e−01 | −4.55713212e−01 |
| 1.20150521e−01 | 4.50412668e−02 | 9.41606835e−02 | 2.56925076e−01 |
| 2.19699964e−01 | 1.11129045e−01 | −2.10879192e−01 | 5.32445788e−01 |
| 4.91363078e−01 | 2.04136282e−01 | 8.39998573e−02 | 1.71666846e−01 |
| −3.68975755e−03 | −1.09875537e−01 | 1.54259712e−01 | 1.67540014e−01 |
| 2.88382560e−01 | 3.06484491e−01 | 4.93844301e−02 | 1.84104294e−01 |
| 8.10690597e−02 | −9.33042839e−02 | 3.09587747e−01 | −1.92424193e−01 |
| 2.96281666e−01 | −8.12043101e−02 | 3.13087642e−01 | 3.23610276e−01 |
| 2.36936033e−01 | 3.07823896e−01 | −1.29720137e−01 | 1.48818463e−01 |
| 1.68515876e−01 | 1.48915895e−03 | 2.44156808e−01 | 8.99039209e−02 |
| 2.96271116e−01 | −8.13050792e−02 | −1.50778353e−01 | −1.28798783e−01 |
| 4.17073667e−01 | 3.97860259e−01 | 1.13099411e−01 | 2.07512841e−01 |
| 2.60600775e−01 | 3.77632946e−01 | 1.52667880e−01 | 2.73245890e−02 |
| 4.68696505e−01 | 3.50465387e−01 | 2.74565786e−01 | 3.41366947e−01 |
| 1.99449345e−01 | 2.54490599e−02 | −4.42672595e−02 | 1.99298993e−01 |
| 1.55676916e−01 | −4.42550741e−02 | 2.54682779e−01 | −1.37167707e−01 |
| 2.01665163e−01 | 2.95895517e−01 | 9.98284295e−02 | 3.90520245e−02 |
| 2.70211697e−01 | 5.63060760e−01 | −2.85654375e−03 | −4.60580438e−02 |
| −1.22082122e−01 | 2.02169254e−01 | 1.56335071e−01 | 7.44994357e−02 |
| 8.64928067e−02 | 5.74827492e−01 | 2.68398393e−02 | 2.72660136e−01 |
| 5.35066068e−01 | 6.96471706e−02 | −7.13909231e−03 | 2.86758840e−01 |
| 1.99974552e−01 | 3.41255426e−01 | 1.17528960e−01 | 9.59986970e−02 |
| −1.08341523e−01 | 3.85746032e−01 | 4.09832060e−01 | 9.61364433e−02 |
| 7.16200992e−02 | 8.72052237e−02 | 5.86474463e−02 | 4.22367565e−01 |
| 1.37065902e−01 | 1.75286233e−01 | 1.59231290e−01 | 3.39435413e−02 |
| −1.65243626e−01 | 3.62592548e−01 | 1.71288565e−01 | 2.28847966e−01 |
| 1.26209170e−01 | 2.19101623e−01 | 3.55590373e−01 | 1.21196911e−01 |
| 2.67393947e−01 | 2.22754166e−01 | 5.46683744e−02 | 1.14875078e−01 |
| 1.63102701e−01 | −1.14709297e−02 | 3.03480439e−02 | 4.29778218e−01 |
| 7.60725215e−02 | −2.23781429e−02 | 3.61116797e−01 | −1.27445310e−01 |
| 1.66215733e−01 | 2.75604308e−01 | 2.73093045e−01 | 2.93516964e−01 |
| −4.19121087e−02 | 5.52270375e−02 | −5.10537177e−02 | 2.04358227e−03 |
| −2.03677528e−02 | 4.05148387e−01 | 2.73707211e−01 | 8.52590874e−02 |
| 1.15167238e−01 | 1.40489161e−01 | 2.47892067e−01 | 1.03149138e−01 |
| 3.02361757e−01 | 9.72756594e−02 | 4.59030718e−02 | 3.99900563e−02 |
| 2.14798138e−01 | 2.72590965e−02 | 1.25292554e−01 | 2.74359081e−02 |
| 2.18924806e−02 | 3.81092638e−01 | 8.10088515e−02 | 1.40487134e−01 |
| 1.42405897e−01 | 5.40766895e−01 | −3.66838038e−01 | −2.14807801e−02 |
| 2.02662706e−01 | 5.90437977e−03 | 2.29244813e−01 | 1.21878283e−02 |
| 1.13702960e−01 | −6.72174990e−02 | 1.92920059e−01 | 1.00820467e−01 |
| −2.07503885e−01 | −2.30797008e−02 | 3.93214643e−01 | 2.85465330e−01 |
| 3.26384723e−01 | −5.43469079e−02 | 2.91540444e−01 | 2.07954869e−01 |
| 4.44658905e−01 | 6.25767633e−02 | −7.82801583e−02 | −2.63730437e−02 |
| 3.00695449e−01 | 2.06969202e−01 | −5.09828962e−02 | 1.35796601e−02 |
| 6.44155502e−01 | 1.93594933e−01 | 1.77569669e−02 | 1.48383200e−01 |

TABLE $W_h^1$-continued

| | | | |
|---|---|---|---|
| −2.15561002e−01 | 2.30859265e−01 | 9.67610478e−02 | −5.75936437e−02 |
| 9.06218365e−02 | 8.48183259e−02 | 4.52241927e−01 | 1.86686233e−01 |
| 1.84809253e−01 | −1.04559928e−01 | 2.74425089e−01 | 2.99249291e−01 |
| 6.36726944e−03 | 1.03949038e−02 | 3.42910200e−01 | −2.17377827e−01 |
| 3.41509759e−01 | 2.53582388e−01 | 9.01549757e−02 | 5.35043716e−01 |
| 2.03597739e−01 | 2.27965489e−02 | −9.80408937e−02 | −1.06085002e−01 |
| 3.02534133e−01 | 3.78476799e−01 | 9.90552753e−02 | 2.89188147e−01 |
| 2.27355674e−01 | 1.82822213e−01 | 3.64432573e−01 | −6.03160821e−02 |
| 3.96029741e−01 | 1.23260006e−01 | 2.34287634e−01 | −1.82370082e−01 |
| 9.04583260e−02 | −1.15131456e−02 | 1.86291426e−01 | 2.07121540e−02 |
| 2.42397830e−01 | 3.00190061e−01 | −1.01252094e−01 | −2.45834276e−01] |
| [5.61400533e−01 | 6.26390874e−01 | 1.00041413e−00 | 4.24067289e−01 |
| 7.49886155e−01 | 5.10162450e−02 | 8.56782675e−01 | 5.51717460e−01 |
| 9.17007148e−01 | 8.13753963e−01 | 3.10375154e−01 | 8.61861944e−01 |
| 5.92144072e−01 | 7.14401543e−01 | 6.50777459e−01 | 3.82390887e−01 |
| 9.63310838e−01 | −9.29061025e−02 | −5.15146911e−01 | 6.31464720e−01 |
| 3.72836351e−01 | 5.39615571e−01 | 5.47086716e−01 | 7.64133275e−01 |
| 7.45786667e−01 | 7.43768588e−02 | 1.65259048e−01 | 5.46841919e−01 |
| 2.65028536e−01 | 6.00848675e−01 | 7.69046172e−02 | 4.43513393e−01 |
| 9.85616803e−01 | 1.56106919e−01 | 8.53154063e−01 | 5.03038049e−01 |
| −1.74311802e−01 | 3.70288253e−01 | 5.31253934e−01 | 1.01020050e−00 |
| 6.54387236e−01 | 6.61325753e−01 | 2.20235571e−01 | 1.21948063e−00 |
| 8.55794668e−01 | −1.13408081e−01 | 1.17521930e−00 | 8.09933914e−01 |
| 2.09990740e−01 | 3.92065853e−01 | 3.32365245e−01 | 1.10624397e−00 |
| 4.57674593e−01 | 6.70595944e−01 | 4.15798426e−01 | 7.07179010e−02 |
| 1.23917103e−00 | −5.70508242e−02 | 1.01241745e−01 | −1.90784976e−01 |
| −1.40277296e−01 | 5.78477085e−01 | 5.67391217e−01 | 8.48342240e−01 |
| −6.97070826e−03 | 7.02099383e−01 | 9.78887320e−01 | 6.90218449e−01 |
| 4.58491504e−01 | −3.63290936e−01 | 7.62214243e−01 | −9.51508462e−01 |
| 6.68488145e−01 | 1.51146889e−01 | 2.45072693e−01 | −9.11104754e−02 |
| 1.48966539e−00 | 2.95198232e−01 | 5.71888089e−01 | 5.06981254e−01 |
| 5.40112257e−01 | 2.56963611e−01 | 5.42521119e−01 | 3.24049324e−01 |
| −6.02665544e−01 | −2.00124994e−01 | 1.15910125e−00 | 5.68115711e−01 |
| 1.07636523e−00 | −6.92162931e−01 | 9.77417886e−01 | 6.88876390e−01 |
| 8.24272275e−01 | 6.83376431e−01 | 6.73047543e−01 | −3.35164182e−02 |
| 1.17575896e−00 | 7.53901526e−02 | −9.04761404e−02 | 8.55300307e−01 |
| 1.33707356e−00 | 5.06966650e−01 | 4.74610299e−01 | 8.54653418e−02 |
| 6.99113429e−01 | 9.28654015e−01 | 8.43875885e−01 | 7.00830400e−01 |
| 4.96176898e−01 | 1.26382947e−00 | 4.50635344e−01 | 5.45498908e−01 |
| 6.99614286e−01 | 5.10388494e−01 | 1.26125014e−00 | 5.50417185e−01 |
| 1.31544912e−00 | 1.72574505e−01 | 1.25832307e−00 | 4.97084945e−01 |
| 7.37497628e−01 | 7.28233635e−01 | 4.02684629e−01 | 5.36414325e−01 |
| 5.96040010e−01 | 7.39272475e−01 | 3.37312251e−01 | 1.25506639e−00 |
| 1.10707366e−00 | 1.62285507e−01 | −2.12067842e−01 | 1.20559227e−00 |
| 3.27457160e−01 | 1.06806171e−00 | 5.74132740e−01 | 4.03122872e−01 |
| 4.31592077e−01 | 6.93927705e−01 | 9.23517406e−01 | 6.00081801e−01 |
| 7.05184102e−01 | 3.87569815e−01 | 2.72093713e−01 | 4.18333948e−01 |
| 6.28413439e−01 | 4.39971328e−01 | 6.13401711e−01 | 8.47956002e−01 |
| 7.20065236e−01 | 9.30696964e−01 | 1.90147340e−01 | 7.64913261e−01 |
| 2.46097539e−02 | 9.50109541e−01 | 7.56755531e−01 | 2.12906405e−01 |
| −1.27165154e−01 | 1.15741514e−01 | 3.00397873e−01 | 5.98751664e−01 |
| 7.72460639e−01 | 4.73827928e−01 | 6.78995788e−01 | 6.81513131e−01 |
| 9.95934829e−02 | 8.76140594e−01 | 1.05958533e−00 | 5.80406785e−01 |
| 6.81657016e−01 | 4.42373157e−01 | 2.17370257e−01 | 5.59753716e−01 |
| 7.12229609e−01 | 5.96695006e−01 | 7.99042106e−01 | 1.52710408e−01 |
| 7.88925290e−01 | 5.54373562e−01 | 3.20650369e−01 | 7.88451314e−01 |
| 8.09288323e−01 | 6.30265772e−01 | 1.01933770e−01 | 2.43467391e−01 |
| 6.12469673e−01 | 2.34991416e−01 | 3.72279584e−02 | 3.21466982e−01 |
| 5.80431461e−01 | 3.33263814e−01 | 8.32889438e−01 | 1.19096279e−00 |
| 4.07747537e−01 | 7.73816168e−01 | 3.82145673e−01 | −2.07664058e−01 |
| 1.06640184e−00 | 9.47441280e−01 | 5.22564590e−01 | 2.57542729e−01 |
| 7.65879095e−01 | 9.88673791e−02 | 4.93269980e−01 | 4.98586893e−01 |
| 4.53319639e−01 | 8.18211913e−01 | −1.49389818e−01 | 6.38238549e−01 |
| 7.23760843e−01 | −3.50777693e−02 | 9.23850417e−01 | 2.92355895e−01 |
| 9.03024256e−01 | 1.47431207e−00 | 1.34324670e−01 | 3.55711073e−01 |
| 3.20017666e−01 | 6.43691301e−01 | 1.01273477e−00 | −3.59142601e−01 |
| 8.88186455e−01 | 1.30961239e−00 | −4.49439675e−02 | 2.02782974e−01 |
| 1.05261452e−01 | 9.40898716e−01 | 2.52069443e−01 | 5.41298628e−01 |
| 8.27107906e−01 | 3.32729995e−01 | 4.45717067e−01 | 5.64569771e−01 |
| 2.26135418e−01 | 1.46982104e−01 | 5.48636734e−01 | 1.38085377e−00 |
| 8.99815798e−01 | 7.33700752e−01 | 5.59246361e−01 | 8.46104443e−01 |
| 6.97358906e−01 | 1.10837650e−00 | 6.79909945e−01 | 8.60057890e−01 |
| 1.03210378e−00 | 2.34434143e−01 | 4.59468096e−01 | 3.00012082e−01 |
| 5.95627606e−01 | 2.27686837e−01 | 4.46643203e−01 | 9.42953110e−01 |
| −9.73403919e−03 | 8.86892915e−01 | 5.01799166e−01 | 4.70865548e−01] |
| [1.95301063e−02 | 2.62675047e−01 | 6.91561103e−02 | 1.91653773e−01 |
| 8.73351932e−01 | 4.53194797e−01 | 2.33531848e−01 | 8.94286409e−02 |
| 5.32444656e−01 | 2.06501946e−01 | 3.54821943e−02 | 6.43368244e−01 |
| 4.09904718e−01 | −8.69284198e−02 | 1.12551585e−01 | 4.43717420e−01 |
| 5.90081394e−01 | 3.65292609e−01 | −1.03609934e−01 | 5.63850552e−02 |

TABLE $W_h^1$-continued

| | | | |
|---|---|---|---|
| 4.74530041e−01 | 4.97102082e−01 | 4.54011858e−01 | 6.58808708e−01 |
| 3.75667334e−01 | 5.61489880e−01 | 1.91983640e−01 | 4.36644822e−01 |
| −3.00669909e−01 | −6.02136970e−01 | 6.50406480e−01 | −3.60406633e−03 |
| 4.18478578e−01 | 2.62642622e−01 | 4.59560275e−01 | 5.52368104e−01 |
| −2.28170436e−02 | 5.58831334e−01 | 4.90641773e−01 | 1.75496712e−01 |
| 2.48763904e−01 | −1.69310234e−02 | 5.75255752e−02 | 6.58384204e−01 |
| −7.78028071e−02 | −4.04888624e−03 | 2.36181736e−01 | −8.33221674e−02 |
| 1.50502294e−01 | 2.13698015e−01 | −5.65268457e−01 | 5.26723918e−03 |
| 3.42360258e−01 | 3.01480204e−01 | 3.88577938e−01 | −6.24687858e−02 |
| 3.89518291e−01 | 2.97890663e−01 | 4.04078849e−02 | 8.26781541e−02 |
| 5.20637095e−01 | 6.35503888e−01 | 3.44166160e−01 | 3.70239109e−01 |
| 1.04219615e−01 | 7.06367254e−01 | 7.00432360e−01 | 3.06949735e−01 |
| 2.83818781e−01 | 2.95903414e−01 | 4.45576340e−01 | 5.08881092e−01 |
| 4.29264039e−01 | 4.39493358e−01 | −2.10684940e−01 | 5.27016699e−01 |
| 7.01845050e−01 | 1.93646178e−01 | −1.67836070e−01 | 3.86782214e−02 |
| 1.67274699e−01 | 1.36894092e−01 | 1.59365699e−01 | 8.95187929e−02 |
| 2.24960461e−01 | 7.12277412e−01 | 8.95588174e−02 | 2.59365678e−01 |
| −8.67357850e−02 | −1.77264556e−01 | 2.33014509e−01 | −2.91865438e−01 |
| 3.73300433e−01 | 3.87336254e−01 | 3.55983466e−01 | 5.11471212e−01 |
| 8.90756175e−02 | −8.88339430e−02 | 1.37367383e−01 | 6.29080474e−01 |
| 8.19765925e−01 | 5.20063341e−01 | 2.08597675e−01 | 5.16732782e−01 |
| 1.90288261e−01 | 4.32322502e−01 | −1.24752924e−01 | 4.83069837e−01 |
| 6.48806512e−01 | 3.96661639e−01 | 9.57441404e−02 | 6.96528494e−01 |
| 3.52432191e−01 | 3.81938308e−01 | 3.77640396e−01 | 4.28109139e−01 |
| 9.87816811e−01 | 1.02931350e−01 | 2.86987692e−01 | 1.41472280e−01 |
| 3.27957392e−01 | 3.67427945e−01 | 3.35148185e−01 | 6.54835582e−01 |
| 6.18537486e−01 | 1.27147764e−01 | 5.36677301e−01 | 4.88217920e−01 |
| −1.15517095e−01 | 2.60521561e−01 | 4.04781044e−01 | 3.24559152e−01 |
| 1.30632207e−01 | 3.07436436e−01 | 1.62427008e−01 | 3.86019439e−01 |
| 5.34749150e−01 | 2.76401967e−01 | 8.75553712e−02 | 1.43272817e−01 |
| 3.45606685e−01 | 1.25680253e−01 | 3.14303964e−01 | 2.02392220e−01 |
| 6.47017956e−01 | 5.45550287e−01 | −6.09239042e−02 | 6.67907536e−01 |
| 5.76728165e−01 | 7.42285013e−01 | 4.75704253e−01 | −5.84918745e−02 |
| 3.27256788e−03 | −7.73923397e−02 | 2.69199610e−01 | 1.54285859e−01 |
| −2.77265646e−02 | −1.06419772e−02 | 4.66028869e−01 | 6.55591637e−02 |
| −1.02201454e−01 | 3.43522549e−01 | 3.13470215e−02 | 2.57782429e−01 |
| 7.79292136e−02 | 6.69648886e−01 | 2.03705370e−01 | −3.44770551e−02 |
| 4.20692116e−01 | −1.00637302e−01 | 1.90532297e−01 | 2.34568357e−01 |
| 2.08974659e−01 | −1.67448595e−01 | 5.33766687e−01 | 2.35550087e−02 |
| 6.22599460e−02 | 3.46557319e−01 | 7.30230212e−02 | 4.56236243e−01 |
| 3.25632691e−01 | 4.53802854e−01 | 3.25045794e−01 | 1.10228345e−01 |
| 4.45538521e−01 | 3.55261594e−01 | −2.35927910e−01 | 2.07074270e−01 |
| 4.16505128e−01 | −2.59805680e−03 | 2.46828735e−01 | 4.99536276e−01 |
| 3.68810058e−01 | 2.20701396e−01 | 4.55652148e−01 | 3.88087422e−01 |
| 5.60933113e−01 | 3.01629156e−01 | 1.91731587e−01 | 5.24830341e−01 |
| −5.07278666e−02 | 4.09541339e−01 | −3.19319129e−01 | 1.08597532e−01 |
| 1.98450804e−01 | 7.48514295e−01 | 9.15415064e−02 | 2.55539179e−01 |
| −1.32039946e−03 | 5.92579007e−01 | 7.66850710e−01 | −1.29439414e−01 |
| 5.16157269e−01 | 5.06088197e−01 | 4.02312994e−01 | 2.54682750e−01 |
| 3.96116406e−01 | 5.12367427e−01 | 2.13095114e−01 | −2.13821620e−01 |
| 5.63395858e−01 | −2.46143378e−02 | 1.33565053e−01 | 3.80458504e−01 |
| 3.44228625e−01 | 4.53565836e−01 | 7.42772400e−01 | 5.96064851e−02 |
| 1.65487960e−01 | −3.33742023e−01 | −1.93756923e−01 | 3.99899185e−01 |
| 2.36298472e−01 | −6.50547445e−01 | 5.02129376e−01 | −1.60170734e−01 |
| −3.57093774e−02 | 2.33915187e−02 | 3.21957953e−02 | 1.30082309e−01 |
| 7.48133540e−01 | 6.55098498e−01 | −3.33648883e−02 | 2.35003635e−01 |
| 9.33084041e−02 | 3.87482733e−01 | 3.84274274e−01 | 3.82822365e−01 |
| −1.76402926e−01 | 4.10384238e−01 | 3.37155551e−01 | 3.09709966e−01 |
| 1.51737124e−01 | −8.84554163e−02 | 5.94395757e−01 | 3.30276370e−01] |
| [−2.43979350e−01 | 4.71708506e−01 | 5.58048010e−01 | −4.64792550e−02 |
| 2.57084310e−01 | 2.03594521e−01 | 6.52437985e−01 | 9.41134766e−02 |
| 2.84587741e−01 | 1.74934760e−01 | 3.24836284e−01 | 4.19551700e−01 |
| 4.72789764e−01 | 7.52383843e−02 | 4.83563244e−02 | 2.43338212e−01 |
| 6.52342319e−01 | 3.05148095e−01 | 2.64179915e−01 | −4.93023172e−02 |
| 4.66244519e−01 | −2.01012820e−01 | 2.51577675e−01 | 1.97740421e−01 |
| 5.57060063e−01 | 2.75310814e−01 | 3.41811836e−01 | 1.66335344e−01 |
| 6.58331113e−03 | −5.41882813e−01 | 3.22011948e−01 | 2.41547331e−01 |
| −1.87977523e−01 | 6.16233833e−02 | 2.68447697e−01 | −6.01372868e−03 |
| 3.36674958e−01 | 1.00879490e−01 | 2.39880055e−01 | 2.61206180e−01 |
| 1.83413431e−01 | −1.36110708e−01 | −1.83604527e−02 | 4.06229794e−01 |
| 1.44271269e−01 | 8.83532166e−02 | 1.96490318e−01 | −4.72506844e−02 |
| −1.60285771e−01 | 8.51575196e−01 | −1.19419694e−01 | −1.67290568e−01 |
| 1.26732379e−01 | 2.62934715e−01 | 6.51948035e−01 | 3.12340409e−01 |
| 2.37694215e−02 | 2.17474923e−01 | 3.53272468e−01 | 2.04937398e−01 |
| 1.52014032e−01 | −2.10530087e−01 | 2.57781297e−01 | 6.52362555e−01 |
| 1.93950400e−01 | 2.30675653e−01 | 2.93357730e−01 | 1.48189276e−01 |
| 1.49385154e−01 | 7.88696110e−02 | 3.00712347e−01 | 4.76790726e−01 |
| 4.17020679e−01 | 3.12704325e−01 | 9.80006382e−02 | 1.84674621e−01 |
| 5.50737500e−01 | −1.16683789e−01 | −1.40621185e−01 | 3.17440867e−01 |
| 3.71898144e−01 | 5.63584007e−02 | 2.34038681e−01 | −1.98151633e−01 |

TABLE $W_h^1$-continued

| | | | |
|---|---|---|---|
| −3.27256992e−02 | −4.51883152e−02 | 5.93856238e−02 | 1.93227157e−01 |
| −2.90754765e−01 | −3.69715184e−01 | −3.06587160e−01 | 7.37273600e−03 |
| −9.17442441e−02 | 4.88666855e−02 | 1.36712417e−01 | 5.67312121e−01 |
| 2.75051475e−01 | 4.48861904e−02 | 1.96207747e−01 | 3.35633159e−01 |
| 4.76955086e−01 | 1.34756893e−01 | 3.83991331e−01 | 3.68180238e−02 |
| 3.51559609e−01 | 3.11944455e−01 | 7.72049427e−02 | 2.79428393e−01 |
| 5.08313358e−01 | 4.34477806e−01 | 1.85500309e−01 | 6.43548012e−01 |
| 6.48740351e−01 | 2.51339465e−01 | 3.14117521e−01 | 4.88153279e−01 |
| 6.98234618e−01 | 3.79420310e−01 | 1.40507147e−01 | −1.72242165e−01 |
| 3.23880613e−01 | 1.76259950e−01 | 8.44633207e−02 | 1.14161074e−01 |
| 2.41466284e−01 | −4.12710220e−01 | −4.68957238e−03 | 7.20415175e−01 |
| 1.01198360e−01 | −2.83772568e−03 | 6.82432130e−02 | 2.74815500e−01 |
| 3.64917845e−01 | 1.76563099e−01 | 1.78136751e−01 | 4.94984090e−01 |
| 2.36567929e−01 | 5.47346175e−01 | 3.05282235e−01 | 2.67796993e−01 |
| −1.37880474e−01 | 3.52653056e−01 | 4.25270110e−01 | −4.88374308e−02 |
| 3.39463115e−01 | 4.70752984e−01 | 4.96886820e−02 | 2.23969653e−01 |
| 1.64685264e−01 | 4.08263326e−01 | 6.26991928e−01 | −1.20252341e−01 |
| 2.32422203e−01 | 3.26718353e−02 | 3.12447608e−01 | 2.03421593e−01 |
| −6.31073415e−02 | −7.62782916e−02 | 4.82721301e−03 | 1.45154655e−01 |
| 1.74996451e−01 | 2.59747267e−01 | −5.73000731e−03 | 9.12308991e−02 |
| 4.93655533e−01 | 2.76194632e−01 | 1.97376370e−01 | 1.25115201e−01 |
| 2.83653915e−01 | −2.00974047e−01 | 2.44337201e−01 | −1.66633967e−02 |
| 5.46698809e−01 | −1.30600527e−01 | 3.17529470e−01 | −1.38840511e−01 |
| 2.07263812e−01 | −1.99586973e−01 | 3.85549158e−01 | 4.65433031e−01 |
| 1.00862958e−01 | 4.53187585e−01 | 1.80989653e−01 | 9.71367359e−02 |
| 1.49288280e−02 | −3.88404285e−03 | −7.31270853e−03 | 2.71109879e−01 |
| 1.93935797e−01 | −1.22842655e−01 | 1.60113737e−01 | 2.85126328e−01 |
| 1.01148181e−01 | 5.39841831e−01 | −5.21513633e−02 | 1.32406995e−01 |
| 1.79054275e−01 | 2.43368044e−01 | −1.84711158e−01 | 3.45668137e−01 |
| 2.46314660e−01 | −1.07725255e−01 | 2.30740681e−01 | 1.79608032e−01 |
| 4.02691402e−02 | 5.22220731e−01 | 1.00457937e−01 | 4.31662530e−01 |
| −2.76585728e−01 | −6.61472753e−02 | 3.99880737e−01 | 1.65729731e−01 |
| 3.43676955e−01 | 2.01594144e−01 | −2.94132773e−02 | 2.64531761e−01 |
| 3.52183431e−01 | −1.13062009e−01 | 1.93994761e−01 | −1.07629932e−01 |
| 4.73674208e−01 | 8.25114027e−02 | 1.98605239e−01 | 8.84843096e−02 |
| −6.37634620e−02 | 3.90631437e−01 | 3.17311347e−01 | 5.03774822e−01 |
| 8.00624937e−02 | −1.06897257e−01 | 2.78907686e−01 | 8.53208825e−02 |
| 3.91390592e−01 | −3.98137718e−01 | 5.09684741e−01 | 3.36870179e−02 |
| 2.28093296e−01 | 2.95541108e−01 | 6.88296437e−01 | 2.17006847e−01 |
| 5.18812060e−01 | 3.01519096e−01 | −7.23673850e−02 | 6.43008173e−01 |
| 2.26278350e−01 | −8.98385197e−02 | 6.47816002e−01 | −7.18713775e−02 |
| −8.80193040e−02 | 2.59505026e−03 | 1.14955343e−01 | 6.64901268e−03 |
| 3.76959294e−01 | −1.83684558e−01 | 2.66142815e−01 | 6.76641107e−01] |
| [−6.39011115e−02 | −3.74716640e−01 | 2.16743097e−01 | 1.12312458e−01 |
| 1.40781067e−02 | 1.80620015e−01 | 2.15213671e−01 | 2.32269317e−01 |
| 7.35810459e−02 | 5.15308380e−01 | −2.24505469e−01 | 2.25938663e−01 |
| 2.20797360e−01 | 1.11103505e−01 | −2.53682630e−03 | 4.47685987e−01 |
| 1.15448376e−02 | 4.54732329e−01 | 2.19191432e−01 | 5.15398324e−01 |
| 1.72180563e−01 | 3.08756232e−01 | 4.43817109e−01 | 2.49523550e−01 |
| 6.58471957e−02 | 7.69150019e−01 | 1.22614413e−01 | 2.94193596e−01 |
| −9.78222955e−03 | 2.44122088e−01 | 4.10371162e−02 | 1.91664323e−01 |
| 3.71965557e−01 | −4.04209457e−02 | 5.47899127e−01 | −2.25507114e−02 |
| −1.61256567e−02 | 2.56866008e−01 | −3.30226049e−02 | 9.57673937e−02 |
| 1.19820304e−01 | −4.56079282e−02 | −8.08108151e−02 | 2.65635341e−01 |
| 2.14544803e−01 | −1.29191160e−01 | 1.94181815e−01 | 8.57971430e−01 |
| 6.22822605e−02 | 2.12510407e−01 | 3.02060068e−01 | 3.27423900e−01 |
| 2.76852041e−01 | −6.20638803e−02 | 1.86022162e−01 | 2.05048203e−01 |
| 6.72212005e−01 | 1.99113265e−01 | 5.47818601e−01 | 4.71915424e−01 |
| 3.05713177e−01 | 2.43514493e−01 | 9.99381915e−02 | 1.48715079e−01 |
| 8.77090022e−02 | −5.30295074e−02 | −1.69897661e−01 | 4.60612148e−01 |
| 4.20814395e−01 | 3.65469515e−01 | −6.95743226e−03 | −1.83865070e−01 |
| 4.90130484e−01 | 6.34667695e−01 | 7.38947392e−02 | 4.29525077e−01 |
| 5.39272845e−01 | 5.09163857e−01 | 2.19568759e−01 | −4.43612903e−01 |
| 3.97729427e−02 | 5.51052332e−01 | 3.02001059e−01 | 7.37677574e−01 |
| −2.59766012e−01 | 2.73716986e−01 | 2.01849654e−01 | 2.95594722e−01 |
| −2.82058418e−01 | 6.61565885e−02 | 1.75504103e−01 | 5.49339689e−02 |
| 1.94110632e−01 | −2.50245869e−01 | 4.02559996e−01 | 2.24101573e−01 |
| −3.66685539e−02 | 5.08381128e−01 | 3.74387652e−01 | −2.05267519e−01 |
| −1.49109997e−02 | 2.47700274e−01 | −3.15482654e−02 | 1.45421132e−01 |
| 4.75186348e−01 | 1.06648207e−01 | 6.43438280e−01 | 5.08099020e−01 |
| 1.81741551e−01 | 3.98228407e−01 | 1.60315156e−01 | −2.45857060e−01 |
| 2.49825940e−01 | −1.32933661e−01 | 5.18872201e−01 | 3.62196475e−01 |
| 3.03640336e−01 | 1.79824159e−01 | 4.97387409e−01 | 5.94581187e−01 |
| 3.65352780e−01 | 2.67066620e−02 | 2.63099998e−01 | 3.37535352e−01 |
| −3.98031324e−02 | 7.17503965e−01 | 1.79137394e−01 | 2.37888783e−01 |
| 8.86726081e−01 | −3.26091722e−02 | 2.93193460e−01 | 4.10047114e−01 |
| 3.97907883e−01 | 3.38856727e−01 | 8.01857114e−01 | 8.20437297e−02 |
| 3.10020298e−02 | 5.62897861e−01 | 7.54124582e−01 | 4.11943734e−01 |
| 2.05617547e−01 | −3.25559229e−02 | 3.61761823e−02 | −1.54903475e−02 |
| −5.11063114e−02 | 6.86365366e−01 | 3.45340699e−01 | 1.84454992e−01 |

TABLE $W_h^1$-continued

| | | | |
|---|---|---|---|
| 8.69206563e−02 | 7.75010735e−02 | 2.88257115e−02 | 1.39701411e−01 |
| 7.21935406e−02 | 4.65484023e−01 | 5.56783974e−01 | 6.48359120e−01 |
| 3.67310978e−02 | 7.98474789e−01 | −1.26617390e−03 | −5.43952025e−02 |
| −2.35409215e−01 | 2.97236294e−01 | −6.39862046e−02 | 1.21746995e−01 |
| 3.00256521e−01 | 8.97561833e−02 | 1.81378692e−01 | 1.16716392e−01 |
| 1.13725817e−00 | 1.31159322e−02 | 5.06507218e−01 | 3.11004937e−01 |
| 3.35083544e−01 | 3.77720267e−01 | 1.66568626e−02 | 7.59687424e−02 |
| 1.96279749e−01 | 4.52971309e−01 | −4.42569017e−01 | 4.70329851e−01 |
| 3.44343960e−01 | −7.23636597e−02 | 5.31647325e−01 | 3.17248046e−01 |
| 1.36514589e−01 | −2.22116411e−01 | 2.63895780e−01 | −2.22105384e−01 |
| −1.61325261e−01 | 6.53401136e−01 | 3.79785866e−01 | 1.57581434e−01 |
| 5.40911674e−01 | −3.79195847e−02 | 1.17662601e−01 | 5.80161512e−01 |
| −2.65961617e−01 | 5.08588135e−01 | −1.08129837e−01 | −2.63724290e−01 |
| 8.83489996e−02 | 5.48228085e−01 | −6.13622218e−02 | 4.61554497e−01 |
| 6.91491723e−01 | 4.64798361e−02 | 2.64895797e−01 | 3.21755260e−01 |
| 2.59007156e−01 | 2.42363259e−01 | 1.58783309e−02 | 5.58421537e−02 |
| 5.44790566e−01 | 6.96824640e−02 | −1.78508535e−01 | −1.33489847e−01 |
| 3.75772178e−01 | −1.81076780e−01 | 1.39266178e−01 | −1.94263965e−01 |
| −2.59464949e−01 | 9.56979543e−02 | 7.61166960e−02 | 9.80878621e−02 |
| 1.80567056e−01 | 1.94466427e−01 | −2.02335622e−02 | 9.54646915e−02 |
| 3.52298141e−01 | 1.32449262e−03 | 4.33446437e−01 | 4.65415120e−01 |
| 4.13955063e−01 | −2.96915442e−01 | 1.23891734e−01 | 5.79829037e−01 |
| 7.36651480e−01 | 5.93616426e−01 | 3.23967367e−01 | 5.44869423e−01 |
| −2.83288099e−02 | 3.58240604e−01 | 8.40243757e−01 | 2.61182755e−01 |
| 4.41772103e−01 | −2.71753711e−03 | 5.41966259e−01 | 5.40312827e−01 |
| 5.45212507e−01 | 1.05711795e−01 | 4.28324252e−01 | 1.90562695e−01 |
| −5.66850901e−01 | 4.45392817e−01 | 2.95319557e−01 | 5.88235021e−01] |
| [1.95125967e−01 | 3.16760004e−01 | −1.20090738e−01 | 1.59914736e−02 |
| 5.19792855e−01 | 5.67146778e−01 | 2.18209594e−01 | 1.97004095e−01 |
| 2.36399710e−01 | −3.47584695e−01 | 3.18738580e−01 | 2.56763309e−01 |
| 3.02056730e−01 | 4.50572401e−01 | 2.20610589e−01 | 3.57958496e−01 |
| 4.11902905e−01 | 8.16245601e−02 | −3.39067817e−01 | −4.53196466e−02 |
| 2.26487234e−01 | −5.48563719e−01 | 4.29010630e−01 | 3.25627327e−01 |
| 3.87807488e−01 | 3.91391695e−01 | 9.30253118e−02 | 5.70690989e−01 |
| 2.37719744e−01 | 5.54216564e−01 | −7.25763738e−02 | −1.17259495e−01 |
| 5.11263162e−02 | −1.29038289e−01 | 7.96800330e−02 | −7.91292414e−02 |
| 3.00564617e−01 | −3.31206918e−01 | 4.27082852e−02 | 4.65385616e−01 |
| 1.10767558e−01 | 9.34490323e−01 | −5.01435518e−01 | 7.89733887e−01 |
| −1.64631665e−01 | 2.22637668e−01 | −1.61865763e−02 | 3.87372404e−01 |
| −4.77930065e−03 | 1.00529842e−01 | 3.06305259e−01 | 1.95982680e−01 |
| 2.62131363e−01 | 3.92812788e−01 | 2.51476526e−01 | 1.91201597e−01 |
| −3.27179320e−01 | −9.42148194e−02 | −1.78209946e−01 | 1.99379742e−01 |
| −2.30681628e−01 | 7.28197515e−01 | 2.67904073e−01 | 1.19332053e−01 |
| 6.06087446e−01 | 4.86786038e−01 | −2.78161198e−01 | 4.75579470e−01 |
| −9.51528698e−02 | 1.84871063e−01 | 5.12079477e−01 | 1.29723847e−01 |
| −7.62210116e−02 | 3.64543378e−01 | 6.62624091e−02 | 3.04090083e−01 |
| 3.19968045e−01 | 1.39179483e−01 | 1.58701643e−01 | −5.76777831e−02 |
| 6.13700390e−01 | 2.47859061e−01 | 4.48203266e−01 | 1.19811092e−02 |
| 9.32264701e−02 | 2.49683484e−01 | 2.61002600e−01 | 7.10348964e−01 |
| 3.66631389e−01 | 5.96544594e−02 | 3.97585839e−01 | 2.02962622e−01 |
| 4.07917678e−01 | 6.86126947e−01 | 1.86770901e−01 | 3.87568831e−01 |
| 3.75131845e−01 | 9.30304155e−02 | 4.36155908e−02 | 8.15009654e−01 |
| 3.88626814e−01 | 4.03737724e−02 | 1.67523906e−01 | −1.72460392e−01 |
| 2.39808962e−01 | 1.44848168e−01 | −2.28427909e−02 | 2.58510530e−01 |
| 1.70085967e−01 | 2.13970333e−01 | 7.99977779e−02 | 5.51033556e−01 |
| 6.49151444e−01 | 2.96475619e−01 | 3.99588495e−02 | 3.63513917e−01 |
| 4.50866103e−01 | 1.49813741e−01 | 6.06494844e−01 | 5.87240696e−01 |
| 5.30142009e−01 | 3.67817044e−01 | 3.72573972e−01 | 1.50477216e−02 |
| 3.27123374e−01 | 1.79258198e−01 | 2.75019765e−01 | 1.48773283e−01 |
| −1.36647612e−01 | −3.41354936e−01 | 4.71801817e−01 | 1.18596770e−01 |
| 3.71555895e−01 | 3.49088579e−01 | 2.32939780e−01 | 6.35832906e−01 |
| 3.82396549e−01 | 1.04029931e−01 | 3.93184245e−01 | −9.27715525e−02 |
| 4.77867156e−01 | 2.62288481e−01 | 3.15327734e−01 | 1.50686353e−01 |
| 5.69497108e−01 | 2.00938180e−01 | 2.34530836e−01 | 4.43400115e−01 |
| 3.20209235e−01 | 3.70389372e−01 | 2.56973624e−01 | 4.02602047e−01 |
| 3.36088061e−01 | 3.14968169e−01 | 4.08688560e−02 | 4.97677833e−01 |
| 1.23668522e−01 | 3.25624853e−01 | −6.45133778e−02 | 6.36676908e−01 |
| −1.63895577e−01 | 4.53482032e−01 | 7.09789097e−01 | 4.24319617e−02 |
| −5.02644852e−02 | 2.34550014e−01 | 7.30198175e−02 | 2.27785334e−02 |
| 1.61777765e−01 | −1.11962751e−01 | 6.60580099e−01 | −1.17575387e−02 |
| 1.71129584e−01 | 2.69632667e−01 | 5.30069113e−01 | 4.48354214e−01 |
| 8.06784481e−02 | 3.86451036e−01 | −2.04630941e−01 | −6.68671131e−02 |
| −1.48401037e−01 | 5.87639064e−02 | 1.82216555e−01 | 2.90695339e−01 |
| 5.83203018e−01 | 1.22446381e−01 | −1.12960786e−02 | 9.02907550e−02 |
| 6.43778086e−01 | 2.07778409e−01 | 3.43152642e−01 | 7.81795289e−03 |
| −8.49987641e−02 | −3.24279845e−01 | 2.87284821e−01 | −1.49028748e−01 |
| 4.37084347e−01 | −2.02497512e−01 | 4.31289077e−01 | 2.73600489e−01 |
| 7.07909942e−01 | 1.24882273e−01 | −1.06727928e−01 | −1.76482997e−03 |
| 1.79166779e−01 | 8.62224877e−01 | 1.58409134e−01 | 1.60552010e−01 |
| 6.84170306e−01 | 1.57219768e−01 | 2.63093442e−01 | −4.48212206e−01 |

TABLE $W_h^1$-continued

| | | | |
|---|---|---|---|
| −2.60098755e−01 | −6.61012605e−02 | 6.14636719e−01 | −5.45048080e−02 |
| 4.08892542e−01 | 4.24219131e−01 | 5.40686131e−01 | 1.36491120e−01 |
| 5.69198191e−01 | −3.94109748e−02 | 7.18989968e−02 | 9.90073308e−02 |
| 1.33188367e−01 | −4.58798707e−02 | 5.53427748e−02 | 3.65163013e−02 |
| 7.65130818e−01 | 4.37860221e−01 | 1.81972653e−01 | 2.97508001e−01 |
| 4.80254889e−02 | −1.06120658e−00 | 2.96156794e−01 | −6.12712130e−02 |
| 4.57750529e−01 | −1.53353244e−01 | 1.41756788e−01 | 3.95056084e−02 |
| 2.80788273e−01 | 7.52149761e−01 | 3.65478992e−01 | 3.72995377e−01 |
| −2.65039466e−02 | 4.55362380e−01 | 3.89001407e−02 | 1.17170930e−01 |
| 3.01132500e−01 | 4.74450231e−01 | −5.85432164e−02 | 9.17108953e−02 |
| −3.02883774e−01 | 3.99094343e−01 | 1.25785545e−01 | 1.55276448e−01] |
| [−1.26449596e−02 | −3.02113533e−01 | 5.76090932e−01 | −1.33762151e−01 |
| −6.54955506e−02 | 6.01052344e−01 | 1.82236418e−01 | 4.96554047e−01 |
| 1.50867790e−01 | −1.72094330e−01 | 1.76788867e−01 | −2.13634036e−02 |
| −4.39773686e−02 | 4.86290038e−01 | −1.88760273e−02 | −1.80172771e−01 |
| −1.20825246e−01 | 4.64746393e−02 | 1.85441688e−01 | 2.33669683e−01 |
| 1.44844726e−01 | −7.29557201e−02 | −2.14988932e−01 | 1.07225981e−02 |
| 9.40033495e−02 | 1.74500570e−01 | 1.72013000e−01 | 2.49919742e−01 |
| 1.62169859e−01 | 3.05688202e−01 | 4.35351610e−01 | 2.57762522e−01 |
| 2.36057490e−01 | 3.97268161e−02 | 2.41422266e−01 | 2.70717412e−01 |
| −1.12891141e−01 | −1.18550949e−01 | 1.84001967e−01 | 2.73878574e−01 |
| 2.95147687e−01 | 8.39095563e−02 | 2.78289795e−01 | 1.68404445e−01 |
| 1.81828827e−01 | −1.46833584e−01 | 5.17092012e−02 | −3.94183725e−01 |
| −3.48755307e−02 | −4.04006213e−01 | 3.16436231e−01 | 1.14359833e−01 |
| 1.14062242e−01 | −9.89697278e−02 | 2.84375459e−01 | 3.62414084e−02 |
| 2.90329188e−01 | 3.60543817e−01 | 1.36213601e−01 | −8.75667259e−02 |
| −4.69106257e−01 | 1.99386761e−01 | −7.79132769e−02 | 2.49925643e−01 |
| 1.06069840e−01 | 5.41423261e−01 | 4.60882425e−01 | 2.66452730e−01 |
| −6.72633126e−02 | 2.65922219e−01 | 1.94906369e−01 | 3.03929061e−01 |
| 1.74697012e−01 | 1.65296532e−02 | 1.79255202e−01 | 1.69553578e−01 |
| 3.66858393e−01 | −1.19833313e−01 | −2.94400728e−03 | 4.13876399e−02 |
| −1.53689766e−02 | 1.02389741e−00 | 4.87022132e−01 | 8.79604667e−02 |
| 2.29271844e−01 | 1.08032562e−01 | −2.86154300e−01 | 4.16892529e−01 |
| 4.27574366e−01 | 3.24302614e−01 | −1.56874731e−02 | −3.27087529e−01 |
| −1.28642134e−02 | 4.50578094e−01 | −1.00372501e−01 | 8.98450166e−02 |
| 2.65339077e−01 | −1.26189470e−01 | 5.52161753e−01 | 6.83645383e−02 |
| 1.92642301e−01 | −9.01797712e−02 | 3.15779567e−01 | 6.73477799e−02 |
| −1.26612447e−01 | 3.15957606e−01 | −6.79831719e−03 | 1.00855798e−01 |
| 5.02443075e−01 | −4.06857841e−02 | −9.88642722e−02 | 3.21378380e−01 |
| 1.73775330e−01 | 2.42700368e−01 | 8.24970752e−02 | −1.22489773e−01 |
| 3.57479423e−01 | 2.36898917e−03 | 1.68375224e−02 | 3.40916783e−01 |
| 1.38141483e−01 | 1.33631873e−01 | 4.23479408e−01 | −5.43907285e−02 |
| 1.97102353e−01 | 2.24030986e−01 | 1.94328696e−01 | 3.39510798e−01 |
| 7.19360054e−01 | 2.84760177e−01 | 2.20416725e−01 | 1.79843809e−02 |
| 1.28291354e−01 | 1.44458652e−01 | 6.40377998e−01 | −2.57149875e−01 |
| 6.49012104e−02 | −4.87710126e−01 | 3.21754962e−01 | 2.24928364e−01 |
| 7.63211101e−02 | 4.58762825e−01 | 1.11875601e−01 | 3.70402068e−01 |
| 2.23074690e−01 | 1.10221840e−01 | −3.01497746e−02 | 1.78552672e−01 |
| 3.47929209e−01 | 1.41929045e−01 | 1.18045554e−01 | −1.30447939e−01 |
| 4.29675668e−01 | 9.40025225e−02 | 5.26047312e−02 | 2.65382797e−01 |
| 1.07506044e−01 | −1.53016493e−01 | −6.18605502e−02 | 1.33867875e−01 |
| 1.25010032e−03 | 2.25385368e−01 | 1.43393070e−01 | 4.82966214e−01 |
| 3.77652556e−01 | 2.54629433e−01 | 4.29163098e−01 | 1.95435554e−01 |
| 1.59738541e−01 | 2.21524090e−01 | −1.21900834e−01 | −3.72072875e−01 |
| 2.10902274e−01 | 1.73840925e−01 | 2.70588398e−01 | 2.18778431e−01 |
| 5.06374776e−01 | 1.85618833e−01 | 2.00745044e−03 | 2.97067612e−01 |
| 2.44802475e−01 | 2.98531294e−01 | 4.81384784e−01 | 3.30714852e−01 |
| 7.16551602e−02 | 4.08887714e−01 | 1.04551360e−01 | 2.30339728e−01 |
| −7.95075372e−02 | −1.13419220e−02 | 6.30421788e−02 | 2.04680756e−01 |
| 6.50124133e−01 | 2.91166425e−01 | 3.74031253e−02 | −2.15430856e−01 |
| 3.86520699e−02 | 2.55616069e−01 | 4.93219912e−01 | −1.34008124e−01 |
| 1.27475694e−01 | 3.07596564e−01 | 3.15706879e−01 | 1.76504761e−01 |
| 2.65789211e−01 | 6.87887788e−01 | 6.98578954e−01 | −1.29405245e−01 |
| 1.79523602e−01 | 7.09999800e−02 | 3.71251047e−01 | 1.99307874e−01 |
| 2.73997605e−01 | 1.90559506e−01 | 4.33969587e−01 | 3.53978351e−02 |
| 1.06303856e−01 | −3.66320014e−02 | −2.16422781e−01 | 1.57295883e−01 |
| 2.40651608e−01 | −1.51569089e−01 | 9.98592004e−01 | 9.93267745e−02 |
| 6.82306588e−02 | 5.13127968e−02 | 1.21226842e−02 | 1.20359883e−01 |
| 2.01433778e−01 | 6.47471026e−02 | 4.22244310e−01 | 6.08431548e−02 |
| 6.45371675e−01 | 2.73636401e−01 | 4.83669698e−01 | 2.45987847e−01 |
| 7.38701969e−01 | 3.75709236e−01 | 1.98361978e−01 | 1.15505919e−01 |
| 2.42579490e−01 | −2.94616282e−01 | 1.09756842e−01 | 3.18675578e−01 |
| 3.84774387e−01 | 1.00593425e−01 | 1.86535984e−01 | −9.59077254e−02 |
| 2.94555813e−01 | −2.75847346e−01 | 1.99192375e−01 | 2.92475522e−01 |
| −2.38928244e−01 | 3.46396655e−01 | 1.28179282e−01 | 1.45969570e−01] |
| [−2.12365970e−01 | 9.18115303e−02 | 6.21788315e−02 | −5.27215779e−01 |
| −1.96753070e−02 | 6.20945096e−01 | −4.54604998e−02 | −2.19314992e−02 |
| −1.48741275e−01 | −1.24018444e−02 | −8.77364501e−02 | 1.43361390e−01 |
| −2.30547652e−01 | −2.28021685e−02 | 3.68690714e−02 | 1.18741423e−01 |
| −3.61814946e−01 | 1.17818071e−02 | 2.60611206e−01 | 1.05781227e−01 |

TABLE $W_h^1$-continued

| | | | |
|---|---|---|---|
| −4.24908213e−02 | 2.79270262e−01 | 3.49881239e−02 | 2.53358155e−01 |
| 9.35045183e−02 | 1.67359084e−01 | −5.24653308e−02 | −1.37225270e−01 |
| 6.76971003e−02 | 2.35417902e−01 | −1.93439256e−02 | 6.19597375e−01 |
| −1.20378453e−02 | −1.56399220e−01 | −4.10588235e−01 | −4.44772989e−02 |
| 1.87912554e−01 | −1.87620074e−01 | −3.16139132e−01 | −2.58810878e−01 |
| −3.10660303e−01 | −7.21173137e−02 | 3.13942075e−01 | 2.30942667e−01 |
| 1.94605887e−01 | 3.51620764e−01 | 3.72828722e−01 | 1.53287649e−01 |
| −3.53682786e−02 | 1.74779728e−01 | −6.63826764e−01 | 6.29492849e−02 |
| 1.49529725e−01 | −1.64555475e−01 | 1.04012638e−01 | −6.94108084e−01 |
| 3.25994462e−01 | 1.84840903e−01 | 2.37078622e−01 | 1.78125143e−01 |
| 8.37287121e−03 | 3.68014425e−01 | 1.90848842e−01 | 1.00637320e−02 |
| 2.20761389e−01 | −1.02258295e−01 | 2.94719078e−02 | 2.49642938e−01 |
| 1.77115589e−01 | 2.50293851e−01 | −2.42296979e−01 | 3.14042717e−01 |
| 3.77171457e−01 | 3.78555954e−01 | −3.17423418e−02 | −8.67208689e−02 |
| 1.41168699e−01 | 1.59837931e−01 | 6.81348741e−01 | −1.08312860e−01 |
| 5.82423769e−02 | 1.49074271e−01 | −4.48519476e−02 | −5.57149388e−02 |
| 3.19156647e−01 | 1.25260174e−01 | −3.13997149e−01 | 1.88332826e−01 |
| 5.37127443e−03 | −1.77260429e−01 | 2.44185656e−01 | 1.85965002e−01 |
| 2.29917943e−01 | −2.74798483e−01 | 1.88791618e−01 | −8.45764130e−02 |
| −2.69658148e−01 | 5.30445218e−01 | 1.59763470e−01 | −8.25970992e−02 |
| 2.78114229e−02 | 6.10010624e−01 | 2.90530324e−01 | 4.55001473e−01 |
| 2.18137339e−01 | 1.48421526e−01 | 7.45475739e−02 | −2.71859895e−01 |
| 2.28015669e−02 | 3.45163018e−01 | 5.24758846e−02 | −3.36932302e−01 |
| 4.39795315e−01 | −1.76439464e−01 | 2.55559701e−02 | 1.92280099e−01 |
| −1.09761193e−01 | 2.83138901e−01 | 1.00542799e−01 | 3.93581629e−01 |
| 4.70959656e−02 | −2.20421597e−01 | −1.56558916e−01 | 1.19964331e−01 |
| −1.40133888e−01 | 1.54089078e−01 | 2.94821054e−01 | 8.56940523e−02 |
| 9.21524391e−02 | 7.10888743e−01 | 2.68568665e−01 | 1.80094525e−01 |
| 3.54931146e−01 | 1.21685885e−01 | −1.79548897e−02 | 2.71678597e−01 |
| 1.12993762e−01 | 6.12741470e−01 | 8.37410241e−02 | 6.14801466e−01 |
| 3.47088099e−01 | 2.68186718e−01 | −1.32480189e−01 | 4.00557309e−01 |
| −2.61691749e−01 | −1.61603242e−01 | 6.11470733e−03 | −8.45978633e−02 |
| 1.93538606e−01 | 7.78300986e−02 | 1.58334911e−01 | 2.96533793e−01 |
| 5.06741583e−01 | 2.50139177e−01 | 1.25571758e−01 | 2.78260231e−01 |
| 4.24387991e−01 | 2.14565098e−01 | 2.89854407e−01 | 1.46608144e−01 |
| 1.91491410e−01 | 2.84664519e−02 | 2.80894823e−02 | 2.27340922e−01 |
| 1.96114227e−01 | −1.04234815e−01 | 1.27287852e−02 | −9.05987322e−02 |
| −1.82229534e−01 | −1.84024066e−01 | −1.08985854e−01 | 3.02415609e−01 |
| 1.53661773e−01 | 8.71453732e−02 | 9.88402665e−02 | 1.77561402e−01 |
| 1.94799453e−02 | −3.64853889e−02 | 5.10851860e−01 | −8.81379619e−02 |
| −1.36218578e−01 | 6.02486506e−02 | 1.94844574e−01 | 8.93377513e−02 |
| −5.47651127e−02 | −1.72974974e−01 | 2.45889172e−01 | 2.00263143e−01 |
| −6.59633875e−02 | −1.22630194e−01 | −4.32813056e−02 | −1.91771984e−01 |
| 1.64292946e−01 | −3.67950872e−02 | 2.68475920e−01 | 4.94303703e−01 |
| 1.37155941e−02 | −1.81968465e−01 | −2.56289184e−01 | 8.31838995e−02 |
| −1.13491662e−01 | 8.42736140e−02 | −7.52343750e−03 | 1.30711049e−01 |
| 2.75588065e−01 | −1.65494271e−02 | −1.05862290e−01 | 4.69808206e−01 |
| −1.59113690e−01 | 2.07064047e−01 | 1.16465382e−01 | −2.68193007e−01 |
| 1.92722455e−02 | −8.57686028e−02 | 2.88971007e−01 | 4.00353134e−01 |
| 2.50514805e−01 | 2.21162453e−01 | 3.15532863e−01 | 1.74695253e−01 |
| −1.39784917e−01 | −6.31132200e−02 | −4.22543921e−02 | −2.53420949e−01 |
| 2.46844798e−01 | 3.92857909e−01 | 1.13344371e−01 | 2.28676260e−01 |
| 3.82683426e−02 | 2.36722127e−01 | 2.31677756e−01 | 3.09360415e−01 |
| 1.04440995e−01 | 3.07156801e−01 | 4.70582508e−02 | 3.20393741e−01 |
| 1.54589474e−01 | 8.58195499e−02 | 2.38122672e−01 | 4.56441045e−02 |
| 5.53429127e−01 | 5.27546883e−01 | 1.76564604e−01 | 5.01678050e−01 |
| −5.56524545e−02 | −1.96149051e−01 | 2.40043327e−02 | −3.05040479e−01 |
| 2.14235887e−01 | 3.87418047e−01 | −3.61733735e−01 | 2.92703867e−01 |
| 7.27143809e−02 | 1.58384845e−01 | −1.50777370e−01 | 3.92775834e−01] |
| [7.58186638e−01 | 4.90324020e−01 | 3.66391838e−01 | −8.71918127e−02 |
| 1.00626910e−00 | 2.28934214e−01 | 9.68359485e−02 | 2.67927706e−01 |
| 2.14419976e−01 | −8.84172097e−02 | 5.81895649e−01 | 1.20205291e−01 |
| −1.50176957e−01 | 5.11103988e−01 | 2.42470995e−01 | 3.53985399e−01 |
| 3.24572325e−01 | −3.42059612e−01 | 7.65597820e−02 | 5.42466700e−01 |
| 5.92674434e−01 | 3.16898078e−02 | 1.75549358e−01 | 3.71660829e−01 |
| −2.38859057e−01 | 6.97253525e−01 | 2.47836769e−01 | 2.72260636e−01 |
| 6.32172525e−01 | 6.79057717e−01 | 9.61661935e−02 | 4.17743698e−02 |
| 3.09829593e−01 | 3.99770766e−01 | 1.38046831e−01 | 3.11177671e−01 |
| 1.29106879e−01 | 4.29482073e−01 | −2.47342885e−03 | 4.91583169e−01 |
| 2.54047841e−01 | 3.99664491e−01 | 8.38214904e−02 | −2.09987074e−01 |
| 8.21674943e−01 | 3.66133183e−01 | 6.24523461e−01 | −2.07734212e−01 |
| 3.97202253e−01 | 6.22998876e−03 | 7.33507395e−01 | 4.33185577e−01 |
| 3.47013861e−01 | 8.00704062e−01 | −7.14460909e−02 | 3.75993073e−01 |
| −4.49953638e−02 | −2.48411104e−01 | 2.05903709e−01 | 1.52816549e−01 |
| 1.46291137e−01 | 6.68537259e−01 | 4.32288200e−01 | 3.69729310e−01 |
| −4.86025475e−02 | 6.42296791e−01 | 5.44533968e−01 | 1.98002905e−01 |
| 2.27920637e−01 | −1.84245989e−01 | 2.40170568e−01 | −2.76064426e−01 |
| 4.29559290e−01 | −1.90307647e−01 | 3.96282196e−01 | 3.48753184e−01 |
| 3.40610921e−01 | 4.39129211e−02 | 4.45451289e−01 | −3.84635329e−02 |
| −2.69429475e−01 | 3.63800406e−01 | 4.09555346e−01 | −3.60936970e−01 |

TABLE W$_h^1$-continued

| | | | |
|---|---|---|---|
| 7.01258183e−01 | 5.16244709e−01 | 2.76084721e−01 | 3.79377097e−01 |
| 7.27095544e−01 | 3.36175203e−01 | 8.36582363e−01 | 5.12920618e−01 |
| 4.97245759e−01 | 6.02910638e−01 | −1.69523865e−01 | 2.80449033e−01 |
| 6.95777535e−01 | −2.62822479e−01 | 2.71960258e−01 | 9.63916779e−02 |
| 6.63204968e−01 | 7.25627124e−01 | 4.67759639e−01 | −2.06608802e−01 |
| 2.54931867e−01 | 2.75137097e−01 | −4.16520923e−01 | 8.85362327e−02 |
| 4.77347314e−01 | 2.50059754e−01 | 2.24034265e−01 | 1.19821928e−01 |
| 3.21583673e−02 | 4.74560440e−01 | 1.44464001e−01 | −3.09093371e−02 |
| 3.61889333e−01 | 4.65978645e−02 | 5.47282219e−01 | −5.45521080e−02 |
| 3.77445847e−01 | 4.56129104e−01 | 1.42411739e−01 | −9.13704559e−02 |
| 2.23453298e−01 | 1.24061584e−01 | 9.52316463e−01 | −1.61703043e−02 |
| 1.77449048e−01 | −1.78074643e−01 | 8.01730715e−03 | 5.55662587e−02 |
| 1.58438042e−01 | −9.22158640e−03 | 3.56676787e−01 | −9.04704779e−02 |
| 5.02207279e−01 | 4.84909639e−02 | 1.87538490e−01 | 5.17027497e−01 |
| 3.25843841e−01 | 4.25424904e−01 | 8.28580651e−03 | 1.51590958e−01 |
| −5.38453721e−02 | 7.19994158e−02 | 2.55413502e−01 | 4.65524048e−01 |
| 4.14845854e−01 | 2.04396248e−01 | 6.33543849e−01 | 5.13226271e−01 |
| 2.49785930e−01 | 4.63589698e−01 | −4.84386474e−01 | 5.56335337e−02 |
| 3.49100590e−01 | 5.84640056e−02 | 4.79475334e−02 | −5.33197783e−02 |
| 6.55877531e−01 | 5.09771228e−01 | 5.30721366e−01 | 3.17778230e−01 |
| 4.41495895e−01 | 3.15216362e−01 | 4.89682883e−01 | 6.49728000e−01 |
| 3.72302741e−01 | 4.25246686e−01 | 4.28519160e−01 | −3.21290255e−01 |
| 4.69017655e−01 | 5.55424452e−01 | 3.43068659e−01 | 6.85554087e−01 |
| 5.46101213e−01 | −3.84832054e−01 | −4.34844606e−02 | 1.00423723e−01 |
| 5.75324357e−01 | 2.65208304e−01 | 1.05670285e−01 | 6.47439778e−01 |
| 3.17544758e−01 | 3.56371641e−01 | 7.97628053e−03 | 3.80715698e−01 |
| −5.85551411e−02 | 5.75247943e−01 | −5.53744920e−02 | 6.61393106e−01 |
| 5.50915539e−01 | 2.78533131e−01 | 3.89222503e−01 | 1.19776480e−01 |
| 2.76733160e−01 | 2.53556281e−01 | 5.49891770e−01 | 2.77262717e−01 |
| 5.94192743e−01 | 2.43038923e−01 | 1.98948593e−03 | 7.53844798e−01 |
| 3.69615048e−01 | 1.97868034e−01 | 9.15993452e−02 | −4.56514090e−01 |
| 1.98292986e−01 | 3.31050396e−01 | 4.63313311e−01 | 2.31016174e−01 |
| −4.87866104e−02 | 4.35674846e−01 | 4.40669417e−01 | −7.58405551e−02 |
| 3.28175873e−01 | 3.65245223e−01 | 5.95674999e−02 | 4.75618809e−01 |
| 4.48016226e−01 | −5.40008731e−02 | 1.41369164e−01 | −4.33344208e−02 |
| 1.53744176e−01 | −5.31445481e−02 | 1.47385731e−01 | 4.67225969e−01 |
| 1.23309426e−01 | 3.96564126e−01 | −7.91743845e−02 | −3.86086732e−01 |
| 9.17316973e−02 | 1.36058122e−01 | 6.31742597e−01 | 5.57498097e−01 |
| 3.84247482e−01 | 4.38477218e−01 | 1.46211594e−01 | 2.37506270e−01 |
| 1.23828370e−02 | −1.61334798e−01 | −7.65552325e−03 | 7.56634474e−01 |
| 3.72482687e−01 | 2.19267771e−01 | 3.27592850e−01 | −2.97792166e−01 |
| 3.32458884e−01 | 3.03428560e−01 | −6.98973760e−02 | 6.36397719e−01 |
| 1.14875481e−01 | 6.34199917e−01 | 2.00891554e−01 | 3.01319540e−01] |
| [−2.99706072e−01 | −1.43902019e−01 | 1.90567881e−01 | 1.15983613e−01 |
| 1.42215550e−01 | 3.54651362e−01 | 1.20529845e−01 | 1.17683217e−01 |
| 2.93924510e−01 | −1.86901644e−01 | 4.68629450e−01 | 2.72211492e−01 |
| 1.64992899e−01 | 4.49064344e−01 | −2.33821988e−01 | 3.27560514e−01 |
| 1.94563717e−01 | 5.61376750e−01 | 3.08018953e−01 | 3.69931370e−01 |
| 1.67183101e−01 | −8.69006440e−02 | 5.24342835e−01 | 4.29504067e−02 |
| 3.67684215e−01 | −2.45265633e−01 | 2.48700589e−01 | 5.22996008e−01 |
| −1.49449244e−01 | 4.41206582e−02 | −2.85372466e−01 | 2.22804144e−01 |
| 3.98145914e−01 | 7.84563795e−02 | 3.81969549e−02 | 4.43199575e−01 |
| −3.83598775e−01 | −1.54152498e−01 | 1.72209263e−01 | 9.00066122e−02 |
| 1.07491191e−03 | 2.14077935e−01 | 1.62971422e−01 | −5.63946515e−02 |
| 8.77302513e−02 | 9.65272933e−02 | −4.11325619e−02 | 7.52286911e−01 |
| 3.92586179e−02 | 1.89243540e−01 | 3.31650138e−01 | 3.41627717e−01 |
| −1.60090432e−01 | −1.50089741e−01 | 1.77294612e−01 | −9.48134437e−02 |
| 3.69341254e−01 | 1.89297885e−01 | 3.15487415e−01 | −5.12012616e−02 |
| −2.99889773e−01 | −6.32211342e−02 | 2.22770095e−01 | 1.06137298e−01 |
| 2.48131957e−02 | −1.85484886e−01 | −4.04391199e−01 | 2.00329363e−01 |
| 2.41511181e−01 | −3.97232920e−02 | −1.46408543e−01 | 2.57981300e−01 |
| 3.12996119e−01 | −1.68697298e−01 | 4.58827585e−01 | 2.78254393e−02 |
| −1.78292319e−01 | 2.99782395e−01 | 5.51343746e−02 | −6.80763647e−02 |
| −1.16435230e−01 | −1.33512244e−01 | −2.17484474e−01 | 5.84694035e−02 |
| −4.77270901e−01 | 2.05706149e−01 | 3.80272388e−01 | −2.75924206e−01 |
| 7.06616417e−02 | 5.15169322e−01 | 1.48246303e−01 | 2.88141817e−01 |
| 1.24303348e−01 | −1.62259646e−04 | −1.86574697e−01 | 3.90030324e−01 |
| −2.43811086e−01 | 5.59637666e−01 | −1.95614129e−01 | −2.84888864e−01 |
| −1.41961768e−01 | −1.81888640e−02 | 1.28289267e−01 | 2.34342828e−01 |
| 4.27863210e−01 | −5.74505150e−01 | 3.77679050e−01 | −2.87642032e−02 |
| 2.06241846e−01 | −1.28954470e−01 | −4.98456089e−03 | −8.48679319e−02 |
| −1.22226467e−02 | −2.44191200e−01 | 2.92548478e−01 | 2.19730631e−01 |
| 6.25782311e−02 | −2.71517843e−01 | −1.10543124e−01 | 1.87745437e−01 |
| 2.99010873e−01 | 1.69261217e−01 | 1.32894307e−01 | −4.31525856e−01 |
| −2.61682391e−01 | 1.77497521e−01 | −9.73941013e−02 | −2.82882124e−01 |
| −1.07246693e−02 | 1.46090865e−01 | 2.28925973e−01 | 2.13658184e−01 |
| 5.70111513e−01 | 5.16169548e−01 | 2.07646027e−01 | −1.88004166e−01 |
| −2.26669386e−02 | 1.66097343e−01 | 1.40657136e−02 | 2.52467155e−01 |
| −9.16124731e−02 | −3.22780162e−01 | 1.16177574e−01 | 1.20228171e−01 |
| 2.28438929e−01 | 3.11095178e−01 | −8.72315168e−02 | 3.50143433e−01 |

TABLE $W_h^1$-continued

| | | | |
|---|---|---|---|
| 8.40432793e−02 | 3.41160357e−01 | −1.50390074e−01 | 3.18805695e−01 |
| 1.82304293e−01 | 2.17411891e−01 | 7.09517837e−01 | 1.56504974e−01 |
| −9.53852683e−02 | 4.70719844e−01 | 7.05427349e−01 | 2.41379768e−01 |
| 1.76495835e−01 | 1.39815822e−01 | −1.57164752e−01 | 3.75413038e−02 |
| −2.50000805e−01 | 1.45836860e−01 | −3.04631919e−01 | −6.26405895e−01 |
| −4.45951009e−03 | −3.65818851e−02 | 6.00584671e−02 | 6.41838133e−01 |
| −2.13815093e−01 | 1.61830306e−01 | −7.57862255e−03 | 1.10550284e−01 |
| 7.52118379e−02 | 2.61111826e−01 | −1.14119530e−01 | −1.84390694e−01 |
| 1.08732462e−01 | −4.26828936e−02 | 1.09875619e−01 | −8.49724859e−02 |
| 1.25954673e−01 | 2.06764191e−01 | 1.51200265e−01 | 1.23548478e−01 |
| 1.30868703e−01 | 1.65113747e−01 | 6.49846066e−03 | 8.37399960e−02 |
| −1.32095546e−01 | −4.44269516e−02 | −3.85673881e−01 | 5.67382053e−02 |
| −2.35759646e−01 | −4.13257629e−01 | −1.01056978e−01 | −6.53052181e−02 |
| −8.34546313e−02 | 1.76215723e−01 | 9.76069737e−03 | −2.82243103e−01 |
| −4.85377237e−02 | −1.29022270e−01 | 1.57436833e−01 | 1.70956910e−01 |
| 2.62152344e−01 | −3.69197488e−01 | 4.21762094e−02 | 8.64922814e−03 |
| 3.47765684e−01 | 3.51297945e−01 | −8.73950496e−02 | 5.16530395e−01 |
| 5.60600907e−02 | 8.35943148e−02 | 3.33794773e−01 | 3.14362235e−02 |
| −1.29751861e−01 | −2.29851663e−01 | 3.51357728e−01 | −3.90364707e−01 |
| 7.62206987e−02 | −1.98637411e−01 | −3.13470542e−01 | 1.36012003e−01 |
| 4.46202792e−02 | 5.03750861e−01 | 2.26496235e−01 | 1.64313048e−01 |
| −2.40564317e−01 | −1.55274734e−01 | −3.36408228e−01 | 4.76634592e−01 |
| 3.94336842e−02 | −6.46218508e−02 | 1.13436006e−01 | 2.77944028e−01 |
| 2.45114952e−01 | 1.73022777e−01 | 3.18728127e−02 | −1.51446328e−01 |
| −2.14667067e−01 | 3.46237719e−02 | −1.94917381e−01 | 2.55970180e−01 |
| 2.06197158e−01 | 8.84465054e−02 | 1.18054464e−01 | 1.07222132e−01 |
| −2.09633827e−01 | −2.02682838e−01 | −1.66622028e−01 | 2.63082296e−01] |
| [−3.82265091e−01 | 3.68408889e−01 | 3.00688058e−01 | 5.98843694e−02 |
| 3.69242132e−01 | 5.46905100e−01 | 1.44025773e−01 | 3.39041390e−01 |
| 8.95606205e−02 | 2.25977451e−01 | 2.76262015e−01 | 3.46201062e−01 |
| −4.28503491e−02 | 4.70597863e−01 | −5.48842669e−01 | 1.94747206e−02 |
| 6.54143421e−03 | 1.89259544e−01 | 2.87996620e−01 | 4.34670120e−01 |
| 1.69140562e−01 | 2.91266620e−01 | 3.54310930e−01 | 1.33759737e−01 |
| 1.43552467e−01 | 4.99233305e−01 | 3.49179715e−01 | 1.75543457e−01 |
| −1.46792546e−01 | 1.30718902e−01 | −1.59762539e−02 | −3.42569128e−02 |
| −3.66785331e−03 | 3.34823251e−01 | −6.06044829e−02 | 3.80832136e−01 |
| −5.13779745e−02 | 7.87549376e−01 | 2.54350543e−01 | 4.60690796e−01 |
| −4.06748950e−01 | 3.13991934e−01 | 3.86483148e−01 | 1.39779508e−01 |
| −2.21929681e−02 | 5.27710915e−01 | 8.52510408e−02 | 4.99345750e−01 |
| −4.12209295e−02 | 7.36213550e−02 | 1.74540445e−01 | 3.50603551e−01 |
| −2.66140074e−01 | 4.54733282e−01 | 2.18591586e−01 | 2.59194255e−01 |
| 5.51454544e−01 | 2.90472865e−01 | 2.31627300e−01 | 1.48525380e−03 |
| 2.32559130e−01 | 5.27783215e−01 | 2.96455622e−01 | 5.34056835e−01 |
| 2.13915780e−01 | −1.90204814e−01 | −5.08376881e−02 | 2.91139036e−01 |
| 4.22772825e−01 | 1.66503608e−01 | 2.06687778e−01 | 1.14835955e−01 |
| −2.21887290e−01 | 1.81109741e−01 | 6.19989872e−01 | 2.24910423e−01 |
| 1.68391943e−01 | 2.64643312e−01 | 1.71176240e−01 | −4.09505516e−01 |
| 1.10100143e−01 | 2.84050703e−01 | 1.30310684e−01 | 4.81111914e−01 |
| −3.37017104e−02 | 4.66906931e−03 | 2.85715759e−01 | 2.59537339e−01 |
| 1.59966081e−01 | 2.03758907e−02 | 4.69930237e−04 | 1.30568162e−01 |
| 2.37894058e−01 | −3.89152877e−02 | 2.99337834e−01 | 2.65550435e−01 |
| −1.44024044e−01 | 3.48901451e−01 | −4.94161725e−01 | −3.54099758e−02 |
| 2.67328084e−01 | 3.85501832e−01 | 2.32624710e−01 | −1.45430118e−01 |
| 1.01685740e−01 | 6.89267874e−01 | 1.08488798e−01 | −1.41572103e−01 |
| 1.80593804e−01 | −2.51446635e−01 | 2.94270337e−01 | −1.46934688e−01 |
| 1.10866219e−01 | 1.81271583e−01 | 2.69472692e−02 | 3.37160558e−01 |
| −1.18119285e−01 | 1.08454987e−01 | 3.67435887e−02 | 8.38698149e−02 |
| 4.14822876e−01 | 2.26390749e−01 | 4.76946831e−01 | 8.72465074e−02 |
| 7.24620819e−01 | 1.49359912e−01 | 4.30241019e−01 | 3.07997286e−01 |
| 4.76215273e−01 | 5.87794542e−01 | 7.65085518e−02 | 1.92768633e−01 |
| 3.79778326e−01 | −1.22314528e−01 | 3.83692421e−02 | −9.23122317e−02 |
| −1.32462144e−01 | 1.40746370e−01 | 1.42581984e−02 | 2.81388685e−02 |
| 2.80940294e−01 | 5.00368357e−01 | −3.31848145e−01 | 4.14757758e−01 |
| 1.92841336e−01 | 2.80509681e−01 | −2.58919537e−01 | 4.23716128e−01 |
| 1.97712556e−01 | 1.47734001e−01 | 2.10611597e−02 | 4.70487088e−01 |
| 1.44525230e−01 | 5.27668059e−01 | 1.33906603e−01 | 3.88071954e−01 |
| 4.99586523e−01 | 1.79582790e−01 | 2.86195546e−01 | 2.74890214e−01 |
| −1.12177961e−01 | 5.18208146e−01 | 6.84330389e−02 | 3.87021959e−01 |
| −6.77829608e−02 | 7.19138980e−02 | 1.30826205e−01 | −8.04699212e−02 |
| 5.09920239e−01 | 4.19452637e−02 | 2.01795757e−01 | 3.36552680e−01 |
| 3.60720634e−01 | 1.11413635e−01 | 1.45510975e−02 | 6.21558189e−01 |
| 2.30717152e−01 | 3.49890649e−01 | −1.71109531e−02 | −1.31926283e−01 |
| −1.31796166e−01 | 3.09192359e−01 | 1.17056213e−01 | 2.84919709e−01 |
| 1.61137134e−01 | 4.44753110e−01 | 2.38437086e−01 | 1.92200541e−01 |
| 3.24791580e−01 | 1.54363766e−01 | 1.72713950e−01 | 6.61542416e−01 |
| 1.89558029e−01 | 3.43966454e−01 | 1.28222674e−01 | 3.11745971e−01 |
| −7.90997893e−02 | 4.34893847e−01 | 4.89367902e−01 | 5.61932385e−01 |
| 5.17537333e−02 | 2.14466751e−01 | 1.61831990e−01 | 4.88652796e−01 |
| −1.49877280e−01 | −8.75743851e−03 | −1.54902101e−01 | 2.71891773e−01 |
| 1.49822369e−01 | −4.80951108e−02 | 2.72635728e−01 | 1.88510060e−01 |

TABLE $W_h^1$-continued

| | | | |
|---|---|---|---|
| −1.11874558e−01 | 3.35452735e−01 | 4.22681943e−02 | 2.62756169e−01 |
| −1.10773884e−01 | −2.91937232e−01 | 1.94151625e−01 | 2.90964156e−01 |
| −7.46036768e−02 | 1.49095386e−01 | 2.17056021e−01 | 1.64163020e−02 |
| 3.38894308e−01 | 4.86215986e−02 | −2.26861648e−02 | −3.75619680e−02 |
| 3.16770256e−01 | 4.43194240e−01 | 2.97295421e−01 | 5.53017259e−01 |
| 9.42572281e−02 | 9.95305926e−02 | 2.38270402e−01 | 4.61062640e−01 |
| −8.41744617e−02 | 9.50855240e−02 | 4.00727719e−01 | 3.16736251e−01 |
| 1.36169523e−01 | −6.41918927e−02 | 1.36890188e−01 | 1.46486849e−01 |
| 8.79146457e−02 | 4.08142388e−01 | 1.15204543e−01 | 1.68357581e−01 |
| 9.17886794e−01 | −4.05591391e−02 | 1.76413059e−02 | −2.53625754e−02 |
| 8.45415369e−02 | −7.08850101e−02 | 1.32439360e−01 | 2.03112394e−01] |
| [2.70365357e−01 | 1.19295903e−01 | 1.13081723e−01 | 3.38527828e−01 |
| 4.49505627e−01 | 3.58036369e−01 | 1.21614046e−01 | 3.85885507e−01 |
| −7.44939968e−02 | 1.64057761e−01 | 3.19174290e−01 | 2.43437886e−02 |
| 1.90398358e−02 | 1.58624843e−01 | 1.76985770e−01 | −7.15982690e−02 |
| 3.06287348e−01 | −2.97877729e−01 | 1.34149462e−01 | 3.61522853e−01 |
| −2.38324255e−02 | 2.53739297e−01 | 7.55049065e−02 | 2.76401341e−01 |
| 2.43382707e−01 | −5.34165576e−02 | 1.22592844e−01 | −8.41096640e−02 |
| 1.34282023e−01 | 5.23850992e−02 | 5.10272801e−01 | −2.28464723e−01 |
| 3.84377867e−01 | 8.99686292e−02 | 1.38848603e−01 | 2.21968412e−01 |
| 6.98941201e−02 | 5.13166845e−01 | 3.42207491e−01 | 1.55135259e−01 |
| 4.73426515e−03 | 2.66461939e−01 | 1.48129731e−01 | 8.89916793e−02 |
| 9.63790640e−02 | 2.81882789e−02 | 1.66291714e−01 | 3.60436618e−01 |
| 3.67825508e−01 | 3.22233826e−01 | −2.52569705e−01 | −1.61721081e−01 |
| 1.34591326e−01 | 2.06251666e−01 | 1.40412869e−02 | 2.02572972e−01 |
| 9.12275463e−02 | 2.40120396e−01 | 3.00620705e−01 | −2.23928690e−01 |
| 2.49985978e−01 | 3.33009571e−01 | −1.49879277e−01 | −2.96781003e−03 |
| 1.32882878e−01 | 9.16845798e−02 | 2.11484805e−01 | 1.70313716e−01 |
| 1.75297067e−01 | 2.88725555e−01 | 1.83575943e−01 | −3.44786830e−02 |
| 3.21615934e−01 | 7.55195767e−02 | −9.92612615e−02 | −1.31768454e−02 |
| 2.45044157e−01 | 1.69277340e−01 | 3.03252161e−01 | 1.40177801e−01 |
| 3.27727020e−01 | −7.66013712e−02 | 7.32320368e−01 | −1.03753060e−01 |
| −2.16635335e−02 | 2.11228281e−01 | 1.23813421e−01 | 6.11248501e−02 |
| 4.21622634e−01 | 1.05144262e−01 | −1.68429375e−01 | 1.71174109e−01 |
| 2.15705991e−01 | 5.39619550e−02 | 2.36366034e−01 | 3.04987073e−01 |
| 4.03131336e−01 | −2.50432789e−01 | 3.64643484e−01 | 4.10508066e−01 |
| 1.20709382e−01 | 2.84406453e−01 | 4.88939553e−01 | 2.59515107e−01 |
| 2.52189487e−01 | 2.26570204e−01 | 2.86881864e−01 | 7.71164335e−03 |
| 1.28214344e−01 | 6.92764670e−02 | 5.73111415e−01 | 3.32920939e−01 |
| −1.48852216e−02 | −1.03795938e−02 | 2.38422602e−01 | 2.26683393e−01 |
| 1.41041905e−01 | 1.53410986e−01 | 1.00067802e−01 | −1.36921510e−01 |
| 1.66717514e−01 | 1.52757326e−01 | 4.06587422e−01 | −3.55945192e−02 |
| −1.47837445e−01 | 9.94117558e−02 | 4.78844613e−01 | 2.43826255e−01 |
| 5.46015203e−01 | −1.57532141e−01 | 1.47666633e−01 | 3.51640403e−01 |
| 1.86739936e−01 | 3.58925641e−01 | −3.15042436e−02 | 1.02107264e−01 |
| 9.94543657e−02 | 1.30866140e−01 | 2.56107479e−01 | 7.85791725e−02 |
| 1.95325673e−01 | 4.36094264e−03 | 1.26577631e−01 | 2.60379016e−01 |
| 6.36259541e−02 | 4.02575761e−01 | 2.13168219e−01 | −2.56068222e−02 |
| 2.47417361e−01 | 2.01281443e−01 | 2.88117319e−01 | 1.21489842e−03 |
| −3.87982242e−02 | 6.91453815e−02 | 6.14404082e−02 | 2.46808663e−01 |
| 2.60984749e−01 | 1.50805384e−01 | −4.95106019e−02 | 3.25502753e−01 |
| 2.10604995e−01 | 2.72284776e−01 | 1.14080377e−01 | 2.77231276e−01 |
| 1.36301368e−01 | 1.95612580e−01 | 4.88579899e−01 | −1.41289309e−01 |
| 2.57343739e−01 | 1.90831468e−01 | 4.27080065e−01 | 9.07846913e−03 |
| 3.55657935e−01 | −2.03081202e−02 | 3.32141727e−01 | 3.73407006e−01 |
| 3.07483256e−01 | 1.69292763e−01 | 9.96563360e−02 | 8.83935578e−03 |
| −9.69745293e−02 | −5.00200689e−02 | 3.22678328e−01 | 3.52722220e−02 |
| 1.25673637e−01 | −2.24688351e−01 | −1.60434946e−01 | −2.18181591e−02 |
| 1.03867888e−01 | 1.70790121e−01 | 2.94133455e−01 | 3.11756790e−01 |
| 4.69623283e−02 | 2.48041183e−01 | 2.68790156e−01 | 2.13354513e−01 |
| −1.54297292e−01 | 1.40310884e−01 | −4.06276025e−02 | 1.32022919e−02 |
| 2.86180556e−01 | 1.11260861e−01 | 3.48472327e−01 | 1.99982941e−01 |
| 3.16696167e−01 | 1.97693974e−01 | 1.42319798e−01 | 3.29764664e−01 |
| 2.04473972e−01 | 6.37695044e−02 | 4.44936931e−01 | 1.58079416e−01 |
| 2.74906516e−01 | 3.11819583e−01 | 4.88574952e−01 | −4.01268601e−02 |
| 3.60254794e−01 | 3.79992664e−01 | 8.12585875e−02 | 9.27593261e−02 |
| 5.91773912e−01 | 4.07111160e−01 | 2.48371109e−01 | 3.67055833e−01 |
| 2.12484896e−01 | 2.12338030e−01 | 5.02434000e−02 | 3.70282084e−01 |
| −3.50295603e−01 | 1.45264044e−01 | 4.77347881e−01 | −5.76044247e−03 |
| 2.75559574e−01 | 3.24302495e−01 | 1.20033465e−01 | 7.72865415e−02 |
| 3.48931283e−01 | 3.25156152e−01 | 1.38022587e−01 | 4.90695775e−01 |
| 2.00652137e−01 | 1.81622446e−01 | 1.99549034e−01 | 1.78232372e−01 |
| 3.20362253e−03 | 7.70482123e−02 | 2.50819236e−01 | 4.29747194e−01 |
| 3.08530927e−01 | 5.17349422e−01 | 1.46406770e−01 | 2.18869433e−01 |
| 3.05179715e−01 | 3.14840466e−01 | 2.71820635e−01 | 7.24700242e−02] |
| [4.38625902e−01 | −1.82400495e−01 | 2.83111095e−01 | 1.54177412e−01 |
| 1.17425852e−01 | 5.61717153e−01 | 4.33569819e−01 | −1.39388693e−02 |
| 6.72850609e−01 | 8.74023736e−02 | 3.15243661e−01 | 1.12439811e−01 |
| 3.54446143e−01 | 1.08008355e−01 | 1.46110579e−01 | 2.70234644e−01 |
| 7.02254996e−02 | −4.37793016e−01 | 6.24024689e−01 | 4.55562502e−01 |

TABLE $W_h^1$-continued

| | | | |
|---|---|---|---|
| 2.45539010e−01 | −1.86580852e−01 | −3.75772506e−01 | 7.64625847e−01 |
| 3.10115330e−02 | 2.85698473e−01 | 3.23987514e−01 | −2.63921976e−01 |
| −4.78147596e−01 | 6.41111135e−01 | 2.28114158e−01 | 6.39596939e−01 |
| 3.88910025e−01 | 3.16627592e−01 | 2.00476348e−02 | 1.88766286e−01 |
| 1.98588088e−01 | 2.32119501e−01 | 4.17428941e−01 | 2.32483655e−01 |
| 1.28963068e−02 | −9.82611403e−02 | 1.82553247e−01 | 2.74586439e−01 |
| 2.29300588e−01 | 4.22982633e−01 | 4.33156431e−01 | 1.95955653e−02 |
| 2.32307807e−01 | 2.44042099e−01 | 5.84279478e−01 | 1.01629913e−01 |
| 4.77070212e−01 | 2.86171675e−01 | −1.63791835e−01 | 2.07970366e−01 |
| 5.51317275e−01 | 4.09394771e−01 | 7.75974631e−01 | 4.54427302e−01 |
| 1.25439763e−01 | 4.03764933e−01 | 1.03324652e−01 | 2.28981465e−01 |
| 1.04327373e−01 | 4.94571686e−01 | 3.83201778e−01 | 2.40972444e−01 |
| 2.84549713e−01 | −1.19144857e−01 | 4.21386540e−01 | −5.48822712e−03 |
| 5.30824363e−01 | −1.29453959e−02 | 1.71843141e−01 | 1.82600185e−01 |
| 1.57495681e−02 | 3.50961506e−01 | 5.90895474e−01 | 1.80516213e−01 |
| −2.44895652e−01 | 1.31506816e−01 | 1.36143649e−02 | 6.37932479e−01 |
| 2.58468091e−01 | 1.82662368e−01 | 6.28151596e−02 | −2.27964759e−01 |
| 1.18471108e−01 | 1.87028915e−01 | 3.06161851e−01 | 9.72251780e−03 |
| 6.11415654e−02 | 1.95810840e−01 | 2.51145780e−01 | −3.63800466e−01 |
| −1.93750635e−01 | 1.39883056e−01 | 1.14544839e−01 | 3.41226272e−02 |
| 4.98522580e−01 | 3.12590361e−01 | 2.01759622e−01 | 2.23441169e−01 |
| 1.23159364e−01 | 3.90922159e−01 | 1.69678792e−01 | −1.13923118e−01 |
| −4.93297249e−01 | 5.66630602e−01 | 1.98880389e−01 | −8.92341807e−02 |
| 3.38689178e−01 | −1.81574047e−01 | −2.26893753e−04 | 1.62556142e−01 |
| 4.48608667e−01 | 4.95605052e−01 | 3.65253657e−01 | −5.57435989e−01 |
| 2.15806872e−01 | 1.48169249e−01 | 2.65430987e−01 | 2.30336696e−01 |
| 7.37990737e−02 | 2.73953378e−01 | 1.37931302e−01 | 3.61913353e−01 |
| 1.32303432e−01 | 8.16563189e−01 | −2.56192572e−02 | 3.74930114e−01 |
| −2.52295136e−01 | 1.52488604e−01 | 2.82754868e−01 | −1.72756642e−01 |
| 3.43802460e−02 | −4.14582700e−01 | 6.21366620e−01 | −5.54636754e−02 |
| −2.87517291e−02 | 3.21682692e−01 | −3.10782157e−02 | −3.40476036e−02 |
| 3.93022567e−01 | 2.22549766e−01 | 4.48328644e−01 | −6.56347647e−02 |
| −1.10525936e−01 | 1.42834693e−01 | −6.88269660e−02 | 4.11305904e−01 |
| 4.25541490e−01 | −2.12209642e−01 | 2.00347662e−01 | −2.36830506e−02 |
| 1.68618217e−01 | −1.67240277e−01 | 1.95874736e−01 | 2.25855768e−01 |
| 4.67409521e−01 | 4.18337733e−01 | −2.02312618e−01 | 6.08310342e−01 |
| 1.42722294e−01 | 1.87847957e−01 | 3.56775761e−01 | 4.04587001e−01 |
| 6.36789083e−01 | 1.92504246e−02 | 7.58149615e−03 | −6.49809912e−02 |
| 1.02176636e−01 | 1.57026455e−01 | 2.24713564e−01 | 1.83688462e−01 |
| 4.80102986e−01 | −2.33671591e−01 | 2.67339110e−01 | 1.85493976e−01 |
| −1.33983821e−01 | 7.45086223e−02 | 4.62481886e−01 | 4.97714281e−01 |
| 4.23061639e−01 | 7.76744112e−02 | −2.85263509e−01 | 2.96764731e−01 |
| 6.86724782e−02 | 8.61967579e−02 | 4.79568452e−01 | 6.49213076e−01 |
| 3.29823159e−02 | 8.48764479e−01 | 7.61252716e−02 | 3.24402303e−01 |
| 9.52079892e−02 | 2.33450621e−01 | 1.70558348e−01 | 5.44622600e−01 |
| 2.41264537e−01 | 3.00190568e−01 | 1.22818351e−01 | 4.60196614e−01 |
| 7.18859255e−01 | −2.39555631e−02 | 3.64234656e−01 | 3.27609509e−01 |
| 3.76841813e−01 | 3.60948741e−02 | 2.66105048e−02 | 4.94742215e−01 |
| 5.28769255e−01 | 1.89568207e−01 | 5.46912737e−02 | 3.52039397e−01 |
| 3.47261503e−01 | −1.73267331e−01 | 4.62273397e−02 | 4.19689864e−01 |
| 1.53801143e−02 | 5.04445791e−01 | −1.69276372e−01 | 6.09102957e−02 |
| 1.47361800e−01 | 3.93063903e−01 | 2.97158863e−02 | 3.22085708e−01 |
| 4.00749594e−01 | 1.97587773e−01 | 6.65689468e−01 | 4.46617842e−01 |
| 2.78618008e−01 | −8.21358323e−01 | 2.51917958e−01 | 4.59912986e−01 |
| −1.40349612e−01 | −4.24288988e−01 | −4.09740284e−02 | 1.23178378e−01 |
| −2.94005014e−02 | −6.87960237e−02 | 2.82246053e−01 | 4.00838315e−01 |
| 2.10020661e−01 | 1.76769629e−01 | 3.26371729e−01 | 1.62687734e−01 |
| 5.06803729e−02 | −3.80890876e−02 | 2.45783880e−01 | 4.24239606e−01 |
| 3.89919162e−01 | 2.51816243e−01 | 3.03727090e−01 | 1.65814701e−02] |
| [2.13851467e−01 | 1.48658201e−01 | 3.21409069e−02 | −1.93991706e−01 |
| 4.75735992e−01 | 1.28503084e−01 | 9.95899141e−02 | 1.48310915e−01 |
| 1.60851330e−01 | 1.62467897e−01 | 6.48243427e−02 | 1.99621931e−01 |
| 8.15936700e−02 | 1.64697304e−01 | −1.96894884e−01 | 1.95115269e−03 |
| 4.88410205e−01 | 2.95236140e−01 | 3.83733176e−02 | 1.11614496e−01 |
| 6.12944178e−02 | 1.93104476e−01 | 5.85977472e−02 | 1.10031106e−01 |
| 6.08215667e−02 | −1.06073804e−01 | 2.74915338e−01 | 1.56247199e−01 |
| −3.32339085e−03 | −4.96939495e−02 | 2.07337901e−01 | −9.18638930e−02 |
| −2.40559250e−01 | 1.84952512e−01 | 2.86229588e−02 | 5.80188036e−02 |
| 2.39622742e−01 | −5.38163446e−03 | 1.81160942e−01 | 2.12184414e−02 |
| 4.46740597e−01 | 1.53474361e−01 | 7.07846656e−02 | 1.48610935e−01 |
| −2.33242102e−03 | 2.03001842e−01 | 1.45440295e−01 | 3.20029594e−02 |
| 1.59504935e−01 | 3.16053927e−02 | 1.75258577e−01 | 1.21047296e−01 |
| −5.82007803e−02 | 1.17226295e−01 | 4.35585260e−01 | 4.21734452e−01 |
| −4.54604477e−01 | 2.59464771e−01 | 1.33838609e−01 | 2.96513010e−02 |
| −1.28301427e−01 | −2.94812713e−01 | 8.10803438e−04 | 1.45761266e−01 |
| −6.12681210e−02 | 4.12460327e−01 | 3.17922473e−01 | 3.48511368e−01 |
| 2.82755375e−01 | 2.86591858e−01 | 2.13426664e−01 | 1.22730829e−01 |
| 2.85949446e−02 | 1.20415844e−01 | −5.35640977e−02 | 6.63603991e−02 |
| 8.36899132e−02 | 1.92886114e−01 | −7.54507333e−02 | 2.81612039e−01 |
| −1.66789249e−01 | 2.09931195e−01 | −1.12201869e−01 | −2.04529524e−01 |

TABLE $W_h^1$-continued

| | | | |
|---|---|---|---|
| 2.75973920e-02 | 1.72608703e-01 | -2.09231172e-02 | 2.49952674e-01 |
| 2.77098566e-01 | -5.28872618e-03 | 8.22874010e-02 | 9.73287746e-02 |
| 2.61914134e-01 | 2.91357040e-01 | 1.39013529e-01 | 4.67456818e-01 |
| -2.42276624e-01 | 2.52277609e-02 | -2.35311359e-01 | 1.79632694e-01 |
| -1.04654297e-01 | 1.70321032e-01 | 4.86525208e-01 | 7.46737421e-02 |
| -2.11032107e-01 | 6.28300682e-02 | 2.55193561e-02 | 1.38022125e-01 |
| 2.70983040e-01 | 9.21133608e-02 | 1.01741113e-01 | 2.77716547e-01 |
| 1.95365205e-01 | 6.19561374e-02 | 4.15936977e-01 | 7.36763030e-02 |
| 2.00571120e-01 | 1.11882091e-01 | 1.75593391e-01 | -2.80406058e-01 |
| 1.47185743e-01 | 1.39331728e-01 | -1.04110047e-01 | 3.18222433e-01 |
| 1.37627572e-01 | 2.77713865e-01 | 3.10308814e-01 | 8.13060477e-02 |
| -5.40160351e-02 | -2.07039386e-01 | 5.71564622e-02 | 2.90253967e-01 |
| -2.32366815e-01 | 4.19827521e-01 | 1.02258101e-01 | -1.97797362e-02 |
| 1.66861519e-01 | 3.22277658e-02 | -2.10547652e-02 | -5.48779778e-02 |
| 1.59764588e-02 | 3.22755098e-01 | -2.07340382e-02 | 1.55506104e-01 |
| 9.10255462e-02 | 2.74989307e-01 | -1.12909772e-01 | 1.84175223e-01 |
| -6.19493378e-03 | 3.72841328e-01 | 2.93300271e-01 | 5.79878353e-02 |
| 2.31662735e-01 | 3.34211141e-01 | 8.48219171e-02 | 3.39728035e-02 |
| -5.44380359e-02 | -5.81981800e-02 | -2.13876963e-01 | 1.68113604e-01 |
| 9.92143974e-02 | 4.05774340e-02 | -4.72342223e-02 | -2.99921399e-03 |
| 2.43558027e-02 | 3.17118496e-01 | 9.63940322e-02 | -1.97621509e-01 |
| -1.99423328e-01 | 2.59071082e-01 | 2.09800974e-02 | 1.33942112e-01 |
| -1.16022043e-01 | 3.12553227e-01 | 2.31750563e-01 | 4.89818901e-02 |
| 8.13515857e-02 | 2.30096102e-01 | 9.93474796e-02 | 1.32661790e-01 |
| -3.19765776e-01 | 3.39297712e-01 | -1.76942348e-01 | -8.32530037e-02 |
| 3.19437176e-01 | -1.14986695e-01 | -4.31472575e-03 | -5.50840348e-02 |
| 2.00488418e-01 | 1.45562053e-01 | 5.24887562e-01 | 1.50127456e-01 |
| 1.72588661e-01 | 3.67289007e-01 | 4.88056511e-01 | 1.10639490e-01 |
| 1.91945821e-01 | 1.17292099e-01 | 1.18990228e-01 | -2.37346580e-03 |
| 2.01704293e-01 | 2.51592994e-01 | 5.97783998e-02 | 7.01423138e-02 |
| 7.92403589e-04 | 3.16105574e-01 | 8.12854171e-02 | 2.96693712e-01 |
| 1.47149727e-01 | 3.88508327e-02 | 4.88212645e-01 | 2.58103162e-01 |
| 1.55646086e-01 | 1.30192980e-01 | 2.33888626e-01 | 1.65351525e-01 |
| 9.44023579e-02 | 3.76697406e-02 | -1.93707675e-01 | -8.11344907e-02 |
| 5.86661249e-02 | 2.16872513e-01 | 1.03771865e-01 | -8.17958787e-02 |
| 1.04508661e-01 | -2.73900419e-01 | 2.38371775e-01 | 1.85255274e-01 |
| 1.74094886e-01 | 2.01659292e-01 | 1.04699574e-01 | 6.65219873e-02 |
| 1.59725472e-01 | -5.03702879e-02 | 1.88529193e-01 | -1.65054172e-01 |
| 2.97117569e-02 | 2.06554353e-01 | 2.82596827e-01 | -1.50073990e-01 |
| 1.58365164e-02 | 1.45102009e-01 | -7.29620904e-02 | -1.56886160e-01 |
| 1.81394666e-01 | 2.46012226e-01 | 1.17091663e-01 | 2.53309578e-01 |
| 1.49174584e-01 | 2.03759611e-01 | 2.01341391e-01 | 1.27134562e-01 |
| 4.79867719e-02 | 2.60466784e-01 | 4.68089551e-01 | 2.55570471e-01] |
| [3.13622117e-01 | 2.92055756e-01 | 9.17263627e-01 | 3.89644384e-01 |
| 5.41467428e-01 | 4.53818738e-01 | -3.51985358e-02 | 6.05896473e-01 |
| 3.30176532e-01 | -4.11459595e-01 | 1.16402902e-01 | 3.93766090e-02 |
| 2.36869410e-01 | 2.86213875e-01 | 1.17006630e-01 | 1.81235239e-01 |
| 3.24497610e-01 | 1.53617695e-01 | 1.38210908e-01 | 4.63272274e-01 |
| 3.98385584e-01 | -2.95218021e-01 | 3.19855511e-01 | 2.76600718e-01 |
| -2.12886974e-01 | 2.19453543e-01 | 3.93597037e-01 | 5.17448545e-01 |
| 1.27015337e-01 | 3.67507190e-01 | 4.39497054e-01 | -2.37028047e-01 |
| 1.57794312e-01 | 4.20591563e-01 | -9.28149298e-02 | 2.87634194e-01 |
| 4.40912880e-02 | 4.32197116e-02 | 1.86677739e-01 | 4.97009188e-01 |
| 6.29564583e-01 | 7.94982135e-01 | 3.27649325e-01 | -1.32655129e-01 |
| 4.35585082e-01 | 7.86341131e-01 | 2.67185181e-01 | -1.00600787e-01 |
| 5.31056225e-01 | 4.63017404e-01 | 4.31586504e-01 | 5.03427267e-01 |
| 1.38175502e-01 | 4.46927637e-01 | 3.77198905e-02 | 2.28664149e-02 |
| 2.41735786e-01 | 1.01891860e-01 | -2.48609692e-01 | 1.37177274e-01 |
| 5.53259579e-03 | 7.85024881e-01 | 3.69742066e-01 | 7.52804577e-01 |
| 1.92123696e-01 | 5.29658437e-01 | 5.61483085e-01 | 2.57799149e-01 |
| -1.11306310e-01 | -4.60578650e-01 | 3.80849302e-01 | -1.47373211e-02 |
| 2.41541833e-01 | -5.95124006e-01 | 4.07321543e-01 | 4.79312450e-01 |
| -5.36688557e-03 | -2.22366869e-01 | 4.24496084e-01 | 2.85575420e-01 |
| -3.59529614e-01 | 9.98699069e-02 | 2.33334184e-01 | 4.54250015e-02 |
| 4.19767573e-02 | 1.10659644e-01 | 5.78899741e-01 | 5.28276980e-01 |
| 6.79201245e-01 | 4.54606026e-01 | 6.19191229e-01 | 5.85778415e-01 |
| 2.27111503e-01 | 6.99811757e-01 | -1.43280581e-01 | 1.99512318e-01 |
| -2.40306947e-02 | 1.17284156e-01 | -1.34936422e-01 | 2.49926910e-01 |
| 4.25026298e-01 | 2.09230021e-01 | -2.02899799e-01 | 1.09372847e-01 |
| 1.48111030e-01 | 7.83207919e-03 | -5.49435258e-01 | 3.69387537e-01 |
| 5.08981109e-01 | 1.68524198e-02 | 2.54965693e-01 | -2.68216264e-02 |
| 1.90955207e-01 | 3.60617697e-01 | -4.25152667e-02 | -5.91623902e-02 |
| 3.13427120e-01 | -1.01258658e-01 | 7.60975406e-02 | -1.75927542e-02 |
| 2.24431902e-01 | 2.83611745e-01 | 1.25409856e-01 | -2.64713578e-02 |
| 5.12194395e-01 | -3.10039744e-02 | 2.21587017e-01 | 2.39730388e-01 |
| 5.14593363e-01 | 1.87458202e-01 | -1.34282663e-01 | -2.32962951e-01 |
| 3.36477518e-01 | 2.14079231e-01 | 5.34620047e-01 | -3.54638062e-02 |
| 1.75226390e-01 | -2.39777029e-01 | 1.10284656e-01 | 4.66028512e-01 |
| 9.81066525e-02 | 1.88273892e-01 | 2.39291847e-01 | 2.18118161e-01 |
| 2.69354701e-01 | -2.76558071e-01 | 5.43445110e-01 | 2.72521913e-01 |

TABLE $W_h^1$-continued

| | | | |
|---|---|---|---|
| 3.61719280e−01 | −1.39283389e−01 | −1.10116392e−01 | −2.43471146e−01 |
| 2.31686085e−01 | 5.00493228e−01 | −2.90053517e−01 | 3.17301929e−01 |
| −1.38551638e−01 | −2.13255972e−01 | −7.98409525e−03 | 6.89487159e−02 |
| 3.99744928e−01 | 8.22978735e−01 | 7.73508549e−01 | 3.87569726e−01 |
| −2.10669875e−01 | 1.83337480e−01 | 6.07090592e−01 | −3.34409215e−02 |
| 9.39581469e−02 | 7.07995176e−01 | 1.44430593e−01 | −6.58678357e−03 |
| 2.13339403e−01 | 4.19814110e−01 | 2.58601546e−01 | 1.62828758e−01 |
| 2.68929809e−01 | −5.93839847e−02 | −1.01765431e−01 | −4.64280620e−02 |
| 7.81272948e−02 | 3.85587364e−01 | 1.69940609e−02 | 1.00666024e−01 |
| 3.11999679e−01 | 3.67154956e−01 | 2.59106725e−01 | 2.77883172e−01 |
| 2.04085670e−02 | 2.24912226e−01 | −6.62955344e−02 | 7.02385843e−01 |
| 5.70706129e−01 | 2.15927407e−01 | −8.93411338e−02 | −5.73348403e−01 |
| 3.03393751e−01 | 4.89986002e−01 | 7.28211880e−01 | −1.53384566e−01 |
| 6.51255488e−01 | 6.91250637e−02 | 9.98015851e−02 | −1.87053353e−01 |
| 1.62642132e−02 | 4.72200125e−01 | −1.65542511e−01 | −5.36970556e−01 |
| 6.83315992e−02 | 1.02946624e−01 | 3.51194710e−01 | −2.25824445e−01 |
| −1.52894825e−01 | −2.51521885e−01 | 3.31196815e−01 | 3.51668186e−01 |
| −4.69425619e−02 | 1.40174513e−03 | −2.21394628e−01 | −2.04211608e−01 |
| 2.69285619e−01 | −6.76917657e−02 | 1.25031456e−01 | 6.84166849e−02 |
| 4.09918606e−01 | −2.84221917e−01 | 1.30158588e−01 | 3.00791226e−02 |
| 1.35586485e−01 | 3.59383941e−01 | 3.02310288e−01 | −6.33217156e−01 |
| 4.34714854e−01 | −2.17521444e−01 | 4.87063438e−01 | 2.23377541e−01 |
| 3.25022377e−02 | 4.15616482e−01 | −1.29403210e−01 | 4.64919090e−01 |
| 6.28766790e−02 | −1.38031840e−01 | 3.13696742e−01 | 5.49586296e−01 |
| 3.41452420e−01 | −8.98166895e−02 | −6.06315993e−02 | 2.68296450e−01 |
| 4.80190873e−01 | 1.56305835e−01 | 4.61004049e−01 | 5.43124795e−01 |
| −3.03321425e−02 | 2.70456851e−01 | 1.54534757e−01 | −2.09313825e−01] |
| [2.33636156e−01 | 4.08154517e−01 | 1.50690600e−01 | −1.98216870e−01 |
| 8.60476587e−03 | 6.41536042e−02 | 3.24775159e−01 | 1.65533703e−02 |
| 1.80995539e−01 | −7.08641782e−02 | 3.67559761e−01 | 9.44080278e−02 |
| 1.85186014e−01 | −1.38350707e−02 | −2.86182631e−02 | 2.86160320e−01 |
| 2.41172314e−01 | 1.43839568e−01 | 1.64030775e−01 | −2.61409312e−01 |
| 2.66182631e−01 | 2.10713491e−01 | 1.67365715e−01 | 8.48208666e−02 |
| 1.04984999e−01 | 2.04518586e−01 | 1.87944591e−01 | −1.98729653e−01 |
| 1.89290315e−01 | 1.00473434e−01 | 2.74377078e−01 | 6.16918691e−02 |
| 2.62462139e−01 | 5.06492257e−02 | 3.08662236e−01 | −9.27189067e−02 |
| 7.31387362e−02 | 1.04260162e−01 | 4.54026051e−02 | 7.83550665e−02 |
| −7.56961182e−02 | 4.59518194e−01 | −2.13651389e−01 | 3.87509167e−01 |
| −5.81851155e−02 | 1.93318725e−01 | 2.67019659e−01 | 3.71837504e−02 |
| 8.04611370e−02 | 1.93414509e−01 | −4.53686148e−01 | 4.47021335e−01 |
| −2.30592281e−01 | 2.35087529e−01 | 7.00227544e−02 | 9.38661322e−02 |
| 2.18110457e−01 | 1.10862497e−01 | −3.54323357e−01 | 1.73008531e−01 |
| −3.15115809e−01 | 1.63464546e−01 | 3.28432888e−01 | −2.42275260e−02 |
| 3.61275114e−02 | 1.49583826e−02 | 1.07142434e−01 | 1.46250188e−01 |
| −3.63419019e−02 | 1.41464353e−01 | −1.98066995e−01 | −1.76241860e−01 |
| −3.20149772e−02 | −2.11550631e−01 | 1.68016955e−01 | 2.78632611e−01 |
| 2.68874496e−01 | 6.58439919e−02 | 1.61003664e−01 | 1.09766044e−01 |
| 1.63744047e−01 | 5.54737747e−01 | 3.06163549e−01 | −5.17781153e−02 |
| 3.28323022e−02 | −3.17589998e−01 | −6.40327707e−02 | 3.57526720e−01 |
| 1.06996171e−01 | 7.46486709e−02 | −1.07043080e−01 | −9.15979780e−03 |
| 3.29525501e−01 | 5.33225596e−01 | 2.16163099e−01 | 3.71521235e−01 |
| −2.19331637e−01 | −7.68557787e−02 | −6.19245917e−02 | 2.72166818e−01 |
| 3.63654867e−02 | 3.16371292e−01 | 5.73741607e−02 | −6.82047829e−02 |
| −8.75505991e−03 | 1.01394184e−01 | −3.04980844e−01 | 1.64198264e−01 |
| −7.48539492e−02 | 3.01463991e−01 | 2.55291015e−01 | 2.93151081e−01 |
| 1.35933638e−01 | 2.04796776e−01 | 1.51289821e−01 | 4.59111668e−02 |
| 2.90282100e−01 | −1.29755601e−01 | 3.19631308e−01 | 1.61009192e−01 |
| 8.26886818e−01 | 2.93543458e−01 | 3.08885664e−01 | 1.24712884e−01 |
| −1.01138568e−02 | 1.15440227e−01 | 1.02785222e−01 | 1.40232276e−01 |
| −2.46591438e−02 | 8.18722099e−02 | −2.25320682e−01 | 4.98018339e−02 |
| −9.52972397e−02 | 2.10959673e−01 | −2.45862260e−01 | 3.83644789e−01 |
| 1.92373246e−01 | 3.74694727e−03 | 1.01648949e−01 | −5.45868427e−02 |
| 5.41142970e−01 | 5.44708222e−02 | −3.56950581e−01 | −3.74155879e−01 |
| 2.16134191e−01 | 1.75818071e−01 | 6.50570728e−03 | 4.35474403e−02 |
| 2.99622506e−01 | 1.02038337e−02 | 2.76011556e−01 | −4.68371958e−02 |
| 1.04283050e−01 | 1.30252503e−02 | −8.15809369e−02 | 3.53168756e−01 |
| −1.54800003e−03 | 2.80696481e−02 | 7.30563328e−02 | 2.19187468e−01 |
| 4.25429285e−01 | 1.03454582e−01 | 4.31915551e−01 | −6.75210059e−02 |
| 2.04031289e−01 | 1.16283089e−01 | 5.19091189e−02 | 7.49571845e−02 |
| −2.27639705e−01 | 4.41721231e−01 | −1.33877710e−01 | −1.03626385e−01 |
| 4.49354887e−01 | −1.31951660e−01 | 4.43346173e−01 | −1.42532229e−01 |
| 3.31282794e−01 | 1.16674513e−01 | 3.35627705e−01 | −6.39483519e−03 |
| −9.26467329e−02 | 3.49006176e−01 | −5.82649047e−03 | 3.39109659e−01 |
| 9.46846083e−02 | −9.84667838e−02 | 2.98647046e−01 | 9.51248705e−02 |
| 2.51779109e−01 | 3.37556571e−01 | 5.94527973e−03 | 8.63689557e−02 |
| −3.62149507e−01 | 7.95524046e−02 | 4.56293553e−01 | 4.21084203e−02 |
| 2.29582742e−01 | 1.22749396e−01 | 4.78918463e−01 | 3.08390170e−01 |
| 4.65984941e−01 | 3.17886323e−01 | 4.16288495e−01 | 2.14432687e−01 |
| −1.22121282e−01 | 1.87183291e−01 | −4.05085772e−01 | 3.04053634e−01 |
| 3.47718716e−01 | −1.58544168e−01 | 8.04910064e−02 | 6.94560111e−02 |

TABLE W$_h^1$-continued

| | | | |
|---|---|---|---|
| 1.97134316e−02 | 1.65537462e−01 | 3.87841702e−01 | −3.25574428e−01 |
| 3.97041887e−01 | 2.07783490e−01 | 2.69582689e−01 | 1.26662791e−01 |
| 3.88321221e−01 | 8.05303082e−02 | 7.69184381e−02 | 5.49911797e−01 |
| 1.05476245e−01 | 3.28569919e−02 | 1.67074665e−01 | 1.50273919e−01 |
| 2.40827613e−02 | 1.43553406e−01 | −2.31698453e−01 | 4.02416855e−01 |
| −6.32901501e−05 | −1.25902012e−01 | −2.54415665e−02 | 5.72313592e−02 |
| 2.58899987e−01 | 7.47278929e−02 | −3.06791607e−02 | 1.14341594e−01 |
| 2.81363130e−01 | 1.44456461e−01 | 1.06324136e−01 | 8.89270976e−02 |
| −2.54546523e−01 | 4.51576225e−02 | 1.88359126e−01 | −1.85538813e−01 |
| 1.10033758e−01 | 1.04083583e−01 | 4.91110906e−02 | 1.19288214e−01 |
| 1.77307025e−01 | 3.98362428e−01 | 1.53686646e−02 | −1.34760201e−01] |
| [1.42361438e−02 | 2.42919236e−01 | 1.77207351e−01 | −5.78449294e−02 |
| 1.10969134e−01 | 2.66821265e−01 | −2.23150626e−01 | 2.25842401e−01 |
| −4.36890721e−01 | −7.84625113e−02 | −2.46267579e−02 | −7.28915408e−02 |
| 2.90049434e−01 | −1.48866549e−01 | 5.95260598e−02 | −7.04027042e−02 |
| −1.39000118e−01 | 1.68834269e−01 | −1.37053326e−01 | −5.18135503e−02 |
| −2.80092973e−01 | 5.06016850e−01 | 1.14956954e−02 | 1.18092030e−01 |
| 1.05685838e−01 | 4.61206496e−01 | −6.33471878e−04 | 2.24718034e−01 |
| 1.64070457e−01 | 1.91907480e−01 | 1.00286059e−01 | 1.13297381e−01 |
| 2.03035861e−01 | 5.38882129e−02 | 1.22471407e−01 | −7.54187778e−02 |
| 1.77827790e−01 | 4.74210918e−01 | 1.22413091e−01 | −7.61448070e−02 |
| 3.10765624e−01 | 2.53181249e−01 | −1.23738714e−01 | 2.53076732e−01 |
| −3.53982225e−02 | 1.97948083e−01 | 4.08662669e−02 | −8.79035816e−02 |
| −4.30740900e−02 | −6.05856143e−02 | −2.43033201e−01 | −2.30125025e−01 |
| 1.92201331e−01 | −4.09965441e−01 | 2.06605002e−01 | −1.35681722e−01 |
| 1.27969030e−02 | 2.51108795e−01 | −2.97503531e−01 | 1.49568003e−02 |
| −3.89075428e−02 | 4.27995175e−01 | 2.25690097e−01 | 1.53670646e−02 |
| 1.99850991e−01 | 1.08853936e−01 | 4.90705408e−02 | 2.60558933e−01 |
| 1.88976049e−01 | 1.75453290e−01 | 5.74405007e−02 | 1.49646476e−01 |
| −1.47756031e−02 | −1.46888509e−01 | 1.65487513e−01 | −2.81578824e−02 |
| 1.12865523e−01 | 3.96594666e−02 | 2.66932070e−01 | 4.17772174e−01 |
| 1.65266693e−01 | 9.59294811e−02 | 1.28096953e−01 | −3.24388482e−02 |
| 1.71253398e−01 | 7.92087615e−02 | −5.31430729e−02 | 3.17280591e−01 |
| 1.83200743e−02 | −1.02011219e−01 | −1.49003997e−01 | 1.47663668e−01 |
| −3.18862386e−02 | 1.65011391e−01 | 3.75798762e−01 | −9.52807963e−02 |
| 1.68182015e−01 | −2.03583334e−02 | 4.28056084e−02 | 5.00763237e−01 |
| 2.33652055e−01 | 5.85017800e−02 | −1.28124997e−01 | 2.58704096e−01 |
| 6.25074133e−02 | 7.28283674e−02 | 2.35089406e−01 | 1.59757018e−01 |
| −2.86089092e−01 | −4.64816578e−02 | 4.41166967e−01 | −3.77928242e−02 |
| 1.04344398e−01 | 1.80312365e−01 | 4.36538368e−01 | 1.34025663e−01 |
| 6.45464361e−02 | −1.73517372e−02 | 1.96472198e−01 | 2.81418413e−01 |
| −4.23220657e−02 | 4.55049425e−02 | −6.06887974e−02 | 1.66123539e−01 |
| 3.87177318e−01 | −1.11920916e−01 | −5.52573912e−02 | 1.28013149e−01 |
| 3.99378352e−02 | 3.24098140e−01 | −6.93508657e−03 | 2.77358860e−01 |
| 1.64543644e−01 | 2.31856138e−01 | 5.79433106e−02 | 3.74111116e−01 |
| −8.55297223e−02 | 1.81678191e−01 | 9.84923542e−03 | 8.13857839e−02 |
| 1.32954240e−01 | 1.47587389e−01 | 2.26114899e−01 | 5.61376661e−03 |
| 2.91712433e−01 | −1.08104460e−02 | 1.12749971e−02 | 5.70776947e−02 |
| 2.66188681e−01 | 5.26127778e−02 | 3.36170226e−01 | −1.19693927e−01 |
| 1.44106209e−01 | 2.78009418e−02 | −3.81718995e−03 | −6.78995550e−02 |
| 1.00864999e−01 | −2.55682096e−02 | 1.27090245e−01 | −1.31822139e−01 |
| −2.98648745e−01 | −7.97566995e−02 | 1.46876082e−01 | 9.74398702e−02 |
| 1.28742591e−01 | 1.03321947e−01 | 1.50065660e−01 | 2.27560356e−01 |
| −3.19788307e−01 | −2.18051895e−01 | 3.76205444e−01 | 2.60083042e−01 |
| 5.21392286e−01 | 8.42440575e−02 | 1.90225512e−01 | 4.77994502e−01 |
| −1.60296395e−01 | −6.94842171e−03 | 1.34818908e−02 | 3.77603844e−02 |
| 1.45551227e−02 | −2.08018441e−02 | 5.70350476e−02 | 2.75086671e−01 |
| −3.09429795e−01 | 3.66419554e−01 | 2.27281466e−01 | −4.59706008e−01 |
| 3.29797566e−01 | 1.90442204e−01 | 1.79057360e−01 | 8.40155967e−03 |
| −1.36951923e−01 | −9.33428928e−02 | 1.70206819e−02 | 7.03796223e−02 |
| 5.94308600e−02 | −9.39255953e−02 | −1.00939879e−02 | 2.11217433e−01 |
| 2.52850920e−01 | 4.49698240e−01 | 5.74714988e−02 | 2.20621713e−02 |
| −3.18572335e−02 | −4.28235650e−01 | 1.56784624e−01 | −2.11639464e−01 |
| −3.04749668e−01 | −1.96161866e−01 | 7.12378835e−03 | 1.86679691e−01 |
| 3.74407880e−02 | 1.78791583e−01 | −1.25406459e−01 | 2.41606399e−01 |
| 5.64173888e−03 | −2.92648445e−03 | 4.99231135e−03 | −2.84805987e−02 |
| 3.36889736e−02 | 3.85497987e−01 | −1.79373920e−01 | 2.47347027e−01 |
| 1.03493832e−01 | 2.02804372e−01 | 7.99356252e−02 | −9.55882575e−03 |
| 6.70053139e−02 | 1.32600158e−01 | 2.71827932e−02 | −1.92532018e−01 |
| −6.86196536e−02 | −1.51199728e−01 | 2.22050592e−01 | −2.94118613e−01 |
| 1.82372957e−01 | 3.36478174e−01 | 2.19696090e−01 | 1.94201276e−01 |
| −2.99692482e−01 | −2.93717366e−02 | 5.60555458e−02 | 2.86052991e−02 |
| −9.67076495e−02 | −7.06094409e−02 | 1.52228057e−01 | −4.19978835e−02 |
| 9.07337219e−02 | −1.61493116e−03 | −2.13993728e−01 | −7.84504693e−03 |
| 1.90840200e−01 | 1.07077546e−01 | −4.11873832e−02 | 3.22659343e−01] |
| [4.93173338e−02 | −1.61958829e−01 | 2.09304437e−01 | 3.75182927e−01 |
| −3.26087922e−02 | −1.29215315e−01 | −4.74498458e−02 | −8.77760351e−03 |
| −1.74171925e−01 | 7.56341994e−01 | 7.33246387e−04 | −1.46274641e−01 |
| −1.82705969e−01 | −2.62740880e−01 | −3.45298648e−01 | −2.75992572e−01 |
| 5.37252128e−02 | 7.75720105e−02 | 3.01503152e−01 | −1.52958646e−01 |

TABLE $W_h^1$-continued

| | | | |
|---|---|---|---|
| 1.10495180e−01 | 5.89274704e−01 | 2.19117969e−01 | 3.96644890e−01 |
| 2.42080152e−01 | −1.85162559e−01 | 4.30415832e−02 | −7.34349713e−02 |
| 2.87580550e−01 | 1.49078920e−01 | −1.66339964e−01 | −2.48771414e−01 |
| −3.23528260e−01 | −3.78996044e−01 | 5.39379381e−02 | −7.43067488e−02 |
| 1.21565863e−01 | 2.10536495e−01 | 1.57560721e−01 | 2.60101203e−02 |
| 5.96000999e−03 | −4.96458597e−02 | −2.50692703e−02 | 3.08181524e−01 |
| 3.50354254e−01 | 4.15635146e−02 | 2.13952318e−01 | −2.77251508e−02 |
| −5.52455150e−02 | −1.62915900e−01 | 1.46930635e−01 | −2.11360782e−01 |
| 4.26213235e−01 | −1.38599128e−01 | 2.19283029e−01 | −5.16336374e−01 |
| 3.27034473e−01 | −8.70078132e−02 | −1.00067623e−01 | 2.83215102e−03 |
| 3.92872542e−01 | 3.96639913e−01 | −1.34915588e−02 | 6.58804178e−02 |
| 2.46889859e−01 | 7.24835992e−02 | 2.88439035e−01 | −7.44112134e−02 |
| 1.29979074e−01 | 2.86577880e−01 | 2.37671271e−01 | −8.87158215e−02 |
| 9.45446193e−02 | 1.20493799e−01 | −1.02853447e−01 | −2.31381822e−02 |
| −2.26683374e−02 | 4.48782355e−01 | 3.41482371e−01 | 5.21993265e−02 |
| 2.43172482e−01 | 2.28235036e−01 | −1.43989906e−01 | 8.34469274e−02 |
| 1.12004422e−01 | −3.05073671e−02 | −9.01852846e−02 | −3.75711948e−01 |
| 1.95510201e−02 | −2.66029269e−01 | 2.41443455e−01 | 3.45592499e−01 |
| 6.71438798e−02 | −2.78627127e−01 | 3.97416651e−01 | 4.60095555e−02 |
| 1.84697043e−02 | 4.75248724e−01 | 2.39705876e−01 | 5.53007275e−02 |
| −2.44347557e−01 | −1.51430249e−01 | 5.98851703e−02 | 3.87253553e−01 |
| 5.36869645e−01 | 1.82967320e−01 | 3.71118605e−01 | 3.88953805e−01 |
| 5.58166057e−02 | −1.35556653e−01 | 1.29147500e−01 | 7.24256178e−03 |
| 3.35476309e−01 | 1.38962016e−01 | 1.64322689e−01 | 1.68124229e−01 |
| 2.94478573e−01 | 2.27774471e−01 | 8.38570818e−02 | 1.25532836e−01 |
| 3.01129162e−01 | 1.71646401e−01 | 3.81891541e−02 | −1.12144262e−01 |
| 1.97596624e−01 | 2.84190387e−01 | 9.37609449e−02 | −1.50909811e−01 |
| −8.77929851e−02 | 1.73011258e−01 | 1.66035622e−01 | 1.98712230e−01 |
| 6.63519576e−02 | −2.45880768e−01 | 2.06742920e−01 | 2.18604982e−01 |
| 1.91306069e−01 | 5.32963276e−01 | −1.24888238e−03 | −1.68508351e−01 |
| 2.17542991e−01 | −1.56704143e−01 | 4.06270057e−01 | 3.98882836e−01 |
| −1.10128291e−01 | 1.13954186e−01 | −1.23212337e−01 | −2.02936530e−01 |
| −1.70171894e−02 | 7.24336281e−02 | −4.21946344e−04 | −8.89575407e−02 |
| −1.37043307e−02 | 1.94570333e−01 | 1.47838015e−01 | 1.64579645e−01 |
| 3.42163146e−01 | 3.36074114e−01 | 8.44205394e−02 | 1.32929251e−01 |
| 2.60379761e−01 | 1.75852075e−01 | −1.21717565e−01 | 1.75876141e−01 |
| 1.03115417e−01 | 9.80991870e−03 | 3.27415884e−01 | −4.37571071e−02 |
| 1.45118132e−01 | 1.71373054e−01 | −2.17480928e−01 | 2.88775027e−01 |
| 2.19585776e−01 | 4.13519800e−01 | 6.50975555e−02 | 1.22350298e−01 |
| −1.70444101e−02 | −1.82926834e−01 | 2.05583481e−01 | −3.40385968e−03 |
| −2.31419712e−01 | 8.45192559e−03 | −1.98426753e−01 | 8.55163261e−02 |
| −2.97308058e−01 | −3.82929482e−01 | 3.18332523e−01 | −1.26148209e−01 |
| −1.69558257e−01 | −2.36855954e−01 | −2.52572477e−01 | −2.51639485e−01 |
| 2.29929268e−01 | −1.59573987e−01 | 2.94374764e−01 | 3.55264068e−01 |
| 2.47830555e−01 | −5.70457727e−02 | −1.99312136e−01 | −2.64397949e−01 |
| 4.85958159e−02 | −2.19525233e−01 | 3.47408712e−01 | 6.89103231e−02 |
| −1.03625543e−01 | 1.63091749e−01 | 2.12510556e−01 | 3.93555649e−02 |
| −1.30731061e−01 | 2.13324711e−01 | 1.47435009e−01 | 5.51646724e−02 |
| 9.70708802e−02 | 2.53864437e−01 | −1.33098423e−01 | 3.22252750e−01 |
| 7.25400597e−02 | −1.70023218e−01 | 6.76028132e−02 | 2.41894990e−01 |
| −1.62139922e−01 | 4.45487201e−01 | 1.27345368e−01 | 1.90076604e−01 |
| 1.91879869e−01 | −1.59403831e−02 | 2.44991090e−02 | 2.65732348e−01 |
| 1.61380634e−01 | −3.43584061e−01 | 1.78782607e−03 | −2.80137777e−01 |
| 1.51903078e−01 | 6.02058530e−01 | 1.64090358e−02 | 6.51439875e−02 |
| 2.55913854e−01 | 1.92013875e−01 | 4.27125067e−01 | −2.56815225e−01 |
| 1.26649486e−02 | 7.79675692e−02 | −7.32053220e−02 | 2.76529282e−01 |
| 2.00951055e−01 | 4.98589009e−01 | −1.16799109e−01 | −4.05204356e−01 |
| 1.72050342e−01 | −1.86686054e−01 | −2.32295673e−01 | −1.50725320e−02 |
| −1.61044195e−01 | −1.73721671e−01 | 2.76405483e−01 | 3.39936435e−01] |
| [3.91232908e−01 | 2.37443879e−01 | 1.69907853e−01 | 1.45033151e−01 |
| −6.41163215e−02 | 4.84720826e−01 | 9.12867114e−02 | 4.30957288e−01 |
| 3.67889792e−01 | 6.44708276e−01 | 2.49593616e−01 | 5.86303413e−01 |
| −1.56955868e−01 | 5.73650122e−01 | −1.97851993e−01 | 4.61870581e−01 |
| 2.56607831e−01 | 4.72091764e−01 | 8.72532368e−01 | 3.86748046e−01 |
| 1.60568923e−01 | −1.83362756e−02 | 4.08210337e−01 | 6.12184703e−01 |
| 6.43868923e−01 | 4.21349347e−01 | 2.75292657e−02 | 5.33481598e−01 |
| −2.79118061e−01 | 2.56825596e−01 | 1.08336411e−01 | 3.40357274e−01 |
| 2.36705802e−02 | 2.46674508e−01 | 7.54947126e−01 | 3.14879388e−01 |
| 4.69929487e−01 | 1.31450444e−01 | 4.51110423e−01 | 5.83031356e−01 |
| 4.14229959e−01 | 5.67564070e−02 | 1.39030265e−02 | −4.88414280e−02 |
| 7.01169312e−01 | 2.53832731e−01 | 4.28937227e−01 | 8.09998214e−01 |
| 4.66775060e−01 | 6.40311956e−01 | 4.36074026e−02 | 6.24302745e−01 |
| −3.84348677e−04 | 2.43964106e−01 | −1.65202901e−01 | 3.20063263e−01 |
| 5.01952231e−01 | −8.67522731e−02 | 8.91265810e−01 | 3.56823474e−01 |
| 4.71468449e−01 | 4.51515466e−01 | 1.62689894e−01 | 6.37263298e−01 |
| 2.69659162e−02 | 3.31116915e−01 | 2.75458544e−01 | 5.04790902e−01 |
| 6.74345493e−01 | 6.11080766e−01 | 4.36765462e−01 | −8.67859423e−02 |
| 3.18852305e−01 | 6.71010971e−01 | 2.31607020e−01 | 5.79147816e−01 |
| 3.22567940e−01 | 8.96844685e−01 | −1.83990106e−01 | −5.14641702e−02 |
| 2.24752888e−01 | 2.53157318e−01 | 3.34375709e−01 | 3.25330824e−01 |

TABLE $W_h^1$-continued

| | | | |
|---|---|---|---|
| 2.95574605e−01 | 2.76665062e−01 | 1.81077525e−01 | 9.73522514e−02 |
| 2.09393680e−01 | 1.90982521e−01 | −1.50281135e−02 | 1.53872922e−01 |
| 4.65179682e−01 | −5.05910031e−02 | 2.83942312e−01 | 3.00214499e−01 |
| −8.90131816e−02 | 8.33899140e−01 | 3.38224284e−02 | −2.21693277e−01 |
| 1.75988123e−01 | 5.47768772e−01 | 2.75353312e−01 | 3.81193399e−01 |
| 2.29698434e−01 | 4.22639221e−01 | 3.00373912e−01 | 3.15178543e−01 |
| 2.94114292e−01 | 9.49949086e−01 | −7.97339752e−02 | −2.47809850e−02 |
| 7.06608295e−01 | 5.41912531e−03 | 3.27521265e−01 | 2.49272957e−01 |
| 3.31130207e−01 | 2.46428460e−01 | 4.00025338e−01 | 2.71635413e−01 |
| 3.65117282e−01 | 2.72755086e−01 | 4.32247132e−01 | 3.84681135e−01 |
| 5.04249036e−01 | 5.42813718e−01 | 1.65911794e−01 | 3.63590896e−01 |
| 8.52523625e−01 | 7.04450130e−01 | 1.21387281e−01 | 4.40546662e−01 |
| 5.99493444e−01 | 4.78343546e−01 | 7.73672462e−01 | −2.17609107e−01 |
| −4.63798977e−02 | 7.67345548e−01 | 5.42206585e−01 | 4.82236505e−01 |
| 1.22829787e−01 | 1.23540491e−01 | −8.21797922e−02 | 4.03843939e−01 |
| 9.57215354e−02 | 8.06921244e−01 | 2.09859267e−01 | 4.31116313e−01 |
| 9.10397023e−02 | 6.60405874e−01 | 1.99225351e−01 | 6.97713137e−01 |
| 5.90985477e−01 | 2.87365243e−02 | 7.16848671e−01 | 4.59779143e−01 |
| −1.76559821e−01 | 7.63874948e−01 | 2.89970338e−01 | 3.44517380e−01 |
| −3.07446439e−02 | 2.95900375e−01 | 2.19351441e−01 | −5.78000471e−02 |
| 1.71941258e−02 | −4.28916439e−02 | 2.34571978e−01 | 4.56157960e−02 |
| 9.38089490e−01 | 2.91376382e−01 | 3.73960584e−01 | 4.65586066e−01 |
| 6.68038130e−01 | 6.06848896e−02 | 2.12819241e−02 | 5.68381324e−02 |
| 3.87301087e−01 | 3.71479779e−01 | 2.73666382e−01 | 3.87744755e−01 |
| 2.08165348e−01 | 2.84671426e−01 | 2.98403323e−01 | 5.62925696e−01 |
| 4.95909184e−01 | 5.90902030e−01 | 6.23952225e−02 | 5.64029574e−01 |
| 2.65463620e−01 | 2.53292471e−01 | 8.94531906e−01 | 1.59082919e−01 |
| 2.42963210e−01 | 5.98855138e−01 | 3.18476319e−01 | 1.73738271e−01 |
| 3.56982023e−01 | 2.88925856e−01 | 4.49394435e−01 | 4.14789528e−01 |
| 4.83830571e−02 | 4.57088230e−03 | 2.83370942e−01 | 3.24669629e−01 |
| 1.03933923e−01 | 3.82717103e−01 | 1.57925293e−01 | 7.89873540e−01 |
| 5.43954194e−01 | 3.98575038e−01 | 4.60711807e−01 | 4.71231401e−01 |
| 6.91055119e−01 | 2.81591564e−01 | 2.37675264e−01 | 4.23890561e−01 |
| 2.25092068e−01 | 7.53185749e−02 | 4.59944516e−01 | −1.82998963e−02 |
| 1.59869507e−01 | −6.03751600e−01 | 5.10476589e−01 | 3.99291724e−01 |
| 5.33446074e−01 | 1.12583086e−01 | 2.49933124e−01 | 2.79413462e−01 |
| 3.88029665e−01 | 6.47474461e−01 | 5.80923378e−01 | 8.01981211e−01 |
| 5.39772511e−01 | 1.74669936e−01 | 4.12262231e−01 | 5.09700656e−01 |
| 4.84134436e−01 | 5.41733444e−01 | 3.55864286e−01 | 5.56436658e−01 |
| −3.88206868e−03 | 4.71890509e−01 | 4.31777179e−01 | 2.23596007e−01 |
| 8.83251607e−01 | 4.86236989e−01 | 2.32414082e−01 | 6.08431101e−01 |
| 7.09751308e−01 | 4.46757585e−01 | 1.43409118e−01 | 1.32916063e−01 |
| 1.90311357e−01 | −5.61657958e−02 | 7.26107359e−01 | 1.61656782e−01] |
| [−3.20745289e−01 | −4.14735883e−01 | 4.61889952e−02 | 1.86805084e−01 |
| −3.60842943e−01 | 7.33108595e−02 | −8.24332163e−02 | 1.03347875e−01 |
| 3.75077754e−01 | 2.44171858e−01 | 1.67757004e−01 | 3.04430187e−01 |
| 3.16801876e−01 | 3.46127242e−01 | −1.82673007e−01 | 4.38812636e−02 |
| 8.32848251e−02 | −3.29661220e−01 | −5.15579358e−02 | 2.15224177e−01 |
| 2.67878354e−01 | 1.52063310e−01 | 3.20649713e−01 | 1.24038167e−01 |
| 5.33527374e−01 | 5.32659352e−01 | 1.40892059e−01 | 4.61964190e−01 |
| −3.00690651e−01 | 3.68228883e−01 | 9.15033650e−03 | 4.92374897e−01 |
| 3.44397932e−01 | 2.76650339e−01 | 5.24615228e−01 | 1.34974029e−02 |
| 4.46534336e−01 | 2.19352335e−01 | 7.09577203e−02 | 4.35481310e−01 |
| −1.66745335e−01 | 1.12546772e−01 | −2.98128635e−01 | 9.07853991e−02 |
| 4.16430712e−01 | −2.11515844e−01 | 6.09853983e−01 | 7.03024447e−01 |
| 7.43844211e−02 | −2.09103316e−01 | 4.28973794e−01 | 1.56793952e−01 |
| 4.06491935e−01 | 2.59456336e−01 | 2.60273695e−01 | 1.78478152e−01 |
| 4.28762287e−01 | 2.44189590e−01 | 4.44808334e−01 | 8.30236003e−02 |
| −4.37502265e−02 | 5.65720141e−01 | 1.03098378e−01 | 1.75390720e−01 |
| 1.80245623e−01 | −2.51632221e−02 | 2.10345641e−01 | 4.16842014e−01 |
| 3.86338860e−01 | 2.23331898e−01 | 5.73176779e−02 | 1.38306737e−01 |
| 4.07419473e−01 | 2.98425138e−01 | 6.17602617e−02 | 2.73229450e−01 |
| 5.64762950e−02 | 3.77878457e−01 | 3.82207066e−01 | −7.85060897e−02 |
| 5.69468558e−01 | 1.23230584e−01 | 7.42237549e−03 | 7.77983844e−01 |
| 3.55335504e−01 | 2.72701859e−01 | 4.12251025e−01 | 1.65571287e−01 |
| −5.86234182e−02 | −2.73931324e−01 | 7.17989355e−02 | −9.56762508e−02 |
| 9.23134107e−03 | −1.45698354e−01 | 2.17086524e−01 | 7.15403557e−01 |
| 7.52032325e−02 | 1.38196900e−01 | 4.60422933e−01 | −1.90796077e−01 |
| 1.32738575e−01 | 2.37226173e−01 | 4.47689950e−01 | 3.51109840e−02 |
| 1.72504619e−01 | 4.33843046e−01 | −4.41123210e−02 | 3.62991691e−01 |
| 9.54282060e−01 | 5.59301257e−01 | −1.99103393e−02 | −2.67396063e−01 |
| 1.89894408e−01 | 1.15369402e−01 | −2.32481718e−01 | 4.01624858e−01 |
| 8.08396861e−02 | −3.74673307e−01 | 1.04040414e−01 | −1.34780183e−01 |
| 8.18424392e−03 | 1.91050023e−01 | −3.03952187e−01 | 1.69851944e−01 |
| 1.05353042e−01 | 6.76865518e−01 | 1.36940852e−01 | 6.32238448e−01 |
| 6.46966517e−01 | 5.19870162e−01 | 5.66167593e−01 | 7.03371048e−01 |
| 4.10280526e−01 | 2.10732281e−01 | 3.13508481e−01 | −3.44981328e−02 |
| −2.78994851e−02 | 1.83521748e−01 | 5.79926193e−01 | 5.17911494e−01 |
| 6.48482144e−03 | 1.68991327e−01 | 4.26258117e−01 | 8.22105035e−02 |
| 3.43504958e−02 | 1.38215765e−01 | 1.10755950e−01 | 3.53142262e−01 |

TABLE $W_h^1$-continued

| | | | |
|---|---|---|---|
| −8.00768510e−02 | −4.26621795e−01 | 3.57859522e−01 | 5.23781717e−01 |
| 1.04092158e−01 | 2.09445447e−01 | 3.37214231e−01 | 1.00200571e−01 |
| 1.32202432e−01 | 4.28554684e−01 | 2.12624788e−01 | 9.87983868e−02 |
| −1.41166419e−01 | 1.48390472e−01 | 7.16150627e−02 | 2.07071140e−01 |
| 5.55809289e−02 | 3.19093168e−01 | −1.08718351e−01 | 1.09028164e−02 |
| 3.04118335e−01 | −8.79859105e−02 | −9.36275646e−02 | 2.84878880e−01 |
| 4.39440787e−01 | 1.95262879e−01 | −3.54514807e−01 | 3.92401934e−01 |
| 8.17837059e−01 | 5.01942858e−01 | 2.84929872e−01 | 8.28534842e−01 |
| 4.88443732e−01 | 9.27512795e−02 | 1.11132964e−01 | 2.08326668e−01 |
| 1.20788112e−01 | 3.10590304e−02 | 3.04483563e−01 | −1.29008606e−01 |
| −1.65015996e−01 | 5.79099298e−01 | 6.22987926e−01 | 3.94627780e−01 |
| 4.45168376e−01 | 2.74040580e−01 | 7.57239461e−02 | −4.81471904e−02 |
| −3.50669086e−01 | 8.75148296e−01 | 4.02573235e−02 | 1.16409563e−01 |
| −1.47111982e−01 | 5.00369787e−01 | 6.62184581e−02 | 1.23533584e−01 |
| 3.03730726e−01 | 9.08301771e−02 | 7.20791578e−01 | 1.64246067e−01 |
| −9.62306485e−02 | −8.84451717e−02 | −2.74623454e−01 | 5.86336739e−02 |
| 6.91537678e−02 | 4.28024441e−01 | −1.11870445e−01 | −1.09186798e−01 |
| 3.32951248e−01 | −3.71062048e−02 | 2.75987327e−01 | −1.11235879e−01 |
| −4.30700444e−02 | −3.00489571e−02 | −1.85468927e−01 | −1.00595817e−01 |
| 3.43686640e−01 | 1.83229774e−01 | 3.69771063e−01 | 5.66821337e−01 |
| 2.02296615e−01 | −1.60136089e−01 | 5.05070388e−01 | 5.11230588e−01 |
| 2.48622552e−01 | 1.87281877e−01 | 2.37010032e−01 | 6.15306318e−01 |
| 3.06211293e−01 | 5.19821167e−01 | 1.09585850e−02 | 2.01778620e−01 |
| 3.67292225e−01 | −5.07306540e−03 | 4.86443460e−01 | 3.01976681e−01 |
| 1.03377676e−00 | 2.32322767e−01 | 4.94353920e−01 | 5.28506339e−01 |
| 4.92124557e−01 | −1.14884876e−01 | 2.01085746e−01 | 9.04934928e−02 |
| −4.15730238e−01 | 6.48290932e−01 | 2.93820381e−01 | 5.23647964e−01] |
| [−2.64104120e−02 | 9.17989910e−02 | 7.91805759e−02 | 8.08709264e−02 |
| 1.60290316e−01 | 5.01916856e−02 | 1.13295220e−01 | 1.15053907e−01 |
| 6.76292703e−02 | 6.66705668e−02 | 1.04460560e−01 | 2.79794019e−01 |
| 1.56848148e−01 | 1.51986375e−01 | 1.08991116e−01 | 5.27425669e−02 |
| 1.80737659e−01 | 1.78102538e−01 | 4.70142066e−02 | 1.22843966e−01 |
| 9.59981233e−02 | −9.37225670e−03 | 1.43286407e−01 | 9.56617072e−02 |
| 4.32515562e−01 | 7.24268138e−01 | 1.18223391e−01 | 1.40242413e−01 |
| 1.05948582e−01 | −1.69385038e−02 | −5.66911660e−02 | −1.30693624e−02 |
| 6.04471378e−02 | −3.47303934e−02 | 1.10245667e−01 | −1.59049798e−02 |
| −4.27276939e−02 | 9.24416557e−02 | 1.48463428e−01 | 9.07711163e−02 |
| 9.90559980e−02 | 1.97917581e−01 | 7.87093192e−02 | 1.10683724e−01 |
| −8.25914592e−02 | −7.31931906e−03 | 9.82302204e−02 | 1.92765649e−01 |
| 1.37106776e−01 | 9.44088548e−02 | −2.22908016e−02 | 9.42182392e−02 |
| 9.62989852e−02 | 1.18574075e−01 | 1.98635638e−01 | 2.83267349e−01 |
| 1.45576060e−01 | 9.01007950e−02 | 4.24938276e−01 | −1.47267312e−01 |
| 5.89209311e−02 | −5.47568593e−03 | 3.23294140e−02 | 1.80045724e−01 |
| 2.21311852e−01 | 1.76807657e−01 | 2.67769426e−01 | −6.26636297e−02 |
| 6.88686827e−03 | 7.91589245e−02 | −6.86422065e−02 | 1.58203363e−01 |
| 2.84803417e−01 | 5.74760586e−02 | 9.39771309e−02 | 8.35212879e−03 |
| −1.51242483e−02 | −6.67055547e−02 | 1.54205874e−01 | 1.09549157e−01 |
| −4.08806279e−02 | 6.82662614e−03 | 1.66317523e−02 | −4.17436920e−02 |
| −3.00262272e−02 | 2.77149640e−02 | 1.02471504e−02 | 3.17274407e−02 |
| −3.03859264e−02 | 8.83007329e−03 | 3.20822299e−01 | −6.46320134e−02 |
| 3.57736982e−02 | 1.78948194e−01 | 8.44809338e−02 | 1.03843518e−01 |
| −2.63425633e−02 | 9.88387242e−02 | 1.63627472e−02 | −6.45223632e−02 |
| −1.54965892e−02 | −4.28303890e−02 | −3.95127311e−02 | 3.84624787e−02 |
| −9.29529443e−02 | 1.79488033e−01 | 8.81851763e−02 | 1.99940056e−01 |
| −3.25326324e−02 | 7.12320209e−02 | 6.12807095e−01 | 1.20295219e−01 |
| 4.32937801e−01 | 2.23001212e−01 | 2.26315767e−01 | 9.33892559e−03 |
| 1.69686720e−01 | 1.17337428e−01 | 1.18554756e−01 | 6.25559539e−02 |
| 4.13604826e−02 | −1.50223495e−01 | −2.85889059e−02 | −5.80590628e−02 |
| 7.55129531e−02 | 1.39296055e−01 | 3.74822654e−02 | 8.17787945e−02 |
| 1.56161174e−01 | 9.35721576e−01 | 8.32910836e−02 | 1.60183027e−01 |
| 3.09443146e−01 | 3.04277726e−02 | 1.17836699e−01 | 2.28724971e−01 |
| −1.78203154e−02 | 9.38129306e−01 | 1.39723763e−01 | 4.12057824e−02 |
| 1.52807876e−01 | −1.17849801e−01 | 8.15398097e−02 | 2.42360793e−02 |
| 1.72651067e−01 | −2.33254675e−02 | −8.01569223e−02 | −3.02896369e−02 |
| −9.47625749e−03 | 1.44410953e−01 | 2.25651860e−01 | 1.85097694e−01 |
| 5.94097935e−02 | −4.66031320e−02 | 1.60249636e−01 | 7.32683614e−02 |
| 9.88918170e−02 | 7.37215430e−02 | 8.67973790e−02 | −2.60111789e−04 |
| 1.11070395e−01 | 1.53681114e−01 | 1.56660244e−01 | 3.41679342e−01 |
| 3.65062892e−01 | −3.87715874e−03 | 7.91830495e−02 | 1.34972423e−01 |
| −1.62255578e−02 | 8.60871017e−01 | 6.05838448e−02 | 7.47989938e−02 |
| 7.48050064e−02 | 1.71055719e−01 | 9.04099047e−02 | −1.14833368e−01 |
| 1.27873719e−01 | 7.48686790e−01 | 1.17873564e−01 | 6.21704981e−02 |
| 2.65089460e−02 | −3.37713100e−02 | 2.06325516e−01 | 6.31215051e−02 |
| 8.61594975e−02 | −3.84497223e−03 | 1.85971245e−01 | 9.66819897e−02 |
| 4.61432412e−01 | 6.02538027e−02 | 3.37996637e−03 | 9.79671478e−02 |
| 9.85798165e−02 | 5.74360937e−02 | 4.07710299e−01 | 4.73127276e−01 |
| 4.92586568e−02 | 5.31431148e−03 | 3.84516418e−02 | 8.31237197e−01 |
| 1.66549951e−01 | −2.63728108e−02 | 5.01787663e−01 | −1.22005194e−02 |
| 5.39949276e−02 | 7.70104071e−03 | 3.40550058e−02 | 7.93412864e−01 |
| −1.70639604e−02 | 2.04079166e−01 | 2.45275095e−01 | 1.58896431e−01 |

TABLE $W_h^1$-continued

| | | | |
|---|---|---|---|
| 1.59434125e-01 | 2.01055203e-02 | 1.16914824e-01 | 7.25114569e-02 |
| 1.08862847e-01 | 1.37166113e-01 | 7.77129084e-02 | -9.87550430e-03 |
| 1.10042416e-01 | 1.35787819e-02 | 1.30423317e-02 | 1.49666360e-02 |
| 2.13192001e-01 | 4.27767308e-03 | 8.77894536e-02 | 4.66175899e-02 |
| 6.24299981e-02 | 1.46572962e-01 | 5.12764156e-01 | 5.10493070e-02 |
| -4.30173948e-02 | 5.95432334e-02 | 1.43133461e-01 | 1.65155023e-01 |
| 1.06097984e-00 | 7.75779933e-02 | 8.03960040e-02 | 1.75603881e-01 |
| 1.54118165e-01 | 1.63667172e-01 | 1.36772186e-01 | -8.27058800e-04 |
| 4.83932160e-02 | 9.96975377e-02 | 9.57307100e-01 | 6.13127276e-02 |
| 5.74931353e-02 | -1.58047061e-02 | 7.93438852e-02 | 1.39133735e-02 |
| 1.10467777e-01 | 1.06399916e-01 | 1.07864728e-02 | 1.19732499e-01] |
| [4.53499705e-02 | 4.80512083e-02 | -5.87467151e-03 | -4.83388804e-02 |
| -2.67365336e-01 | 9.65851620e-02 | 2.36535609e-02 | -6.56730756e-02 |
| 9.65768024e-02 | -1.00020774e-01 | 2.50938535e-01 | 2.28612363e-01 |
| 1.58590943e-01 | 2.64946997e-01 | -5.27311683e-01 | 1.02542438e-01 |
| 4.92375344e-02 | -7.69074112e-02 | -1.15228519e-01 | -3.79475430e-02 |
| 1.59303844e-01 | -3.87132615e-01 | 1.58891723e-01 | -5.65537028e-02 |
| 7.57481158e-02 | -9.51066017e-02 | 8.58789682e-02 | 3.80912542e-01 |
| 3.16010237e-01 | -2.16196030e-02 | -6.16124682e-02 | 1.02231972e-01 |
| 1.00471906e-01 | -3.12676311e-01 | -2.50377953e-02 | 3.32173258e-01 |
| 2.98976809e-01 | -6.21741936e-02 | -5.68433106e-01 | 2.47092649e-01 |
| -1.75483361e-01 | 9.63827819e-02 | 2.30619699e-01 | 1.77187189e-01 |
| 8.17912519e-02 | 2.57227302e-01 | 5.61620593e-02 | 1.30498677e-01 |
| 2.94103585e-02 | 1.75335079e-01 | 9.33053438e-03 | 6.35377839e-02 |
| 2.46395364e-01 | 2.08314866e-01 | -4.51763757e-02 | 3.13870519e-01 |
| 2.17837647e-01 | -8.03966299e-02 | -1.76397666e-01 | -2.09431276e-01 |
| -2.00996995e-01 | -9.15238932e-02 | 2.18215346e-01 | -4.08058494e-01 |
| -2.35644504e-02 | 1.63187489e-01 | -1.44781992e-02 | 1.03910845e-02 |
| 2.89869905e-01 | -1.63140327e-01 | 9.30764303e-02 | 5.81201501e-02 |
| 1.23667553e-01 | 2.97612906e-01 | -1.56902745e-02 | 1.89568728e-01 |
| -1.79888770e-01 | 2.48135120e-01 | 1.61861569e-01 | 3.77490848e-01 |
| 1.29702061e-01 | 1.96027104e-02 | 7.98881277e-02 | 3.93529624e-01 |
| 4.08138365e-01 | -2.52395928e-01 | -2.15781048e-01 | 8.43122378e-02 |
| 8.18849653e-02 | -1.24617927e-01 | 2.76581086e-02 | -9.79641080e-02 |
| -8.79944190e-02 | -2.01311395e-01 | 6.12281542e-03 | 2.70903677e-01 |
| -3.55525762e-01 | 2.70229518e-01 | 6.95294365e-02 | 1.00774579e-01 |
| 1.87475890e-01 | 1.31761998e-01 | -1.56374142e-01 | -1.88694999e-01 |
| -1.23066485e-01 | -6.57197312e-02 | 7.73621723e-02 | -6.34454116e-02 |
| 4.18616503e-01 | 3.10112178e-01 | 6.60155267e-02 | 1.47678554e-01 |
| 4.42185104e-01 | 1.63165659e-01 | 8.98841545e-02 | 1.28110975e-01 |
| 1.61197513e-01 | 5.85543923e-02 | -1.50376618e-01 | 4.48376030e-01 |
| 1.64053768e-01 | 3.94661993e-01 | 2.59116322e-01 | 1.02148451e-01 |
| -1.50166288e-01 | 4.76218224e-01 | 2.42389888e-01 | -8.33417714e-01 |
| -5.78231327e-02 | -2.42343117e-02 | 3.72359380e-02 | 3.79515365e-02 |
| -3.19928378e-02 | 1.08475909e-01 | 2.04160735e-01 | 5.62679768e-01 |
| 5.41824222e-01 | 3.09798419e-01 | -2.65385807e-02 | 1.73491493e-01 |
| -1.80461720e-01 | 3.84321153e-01 | -1.24446027e-01 | 8.09258744e-02 |
| 2.30688021e-01 | 1.92842722e-01 | 2.30457470e-01 | -2.02850569e-02 |
| 1.60644680e-01 | 4.95833158e-01 | 2.20792115e-01 | -1.46537721e-01 |
| -3.49829383e-01 | 1.60460457e-01 | 3.56041014e-01 | 2.74034709e-01 |
| 1.43057823e-01 | 2.20266432e-01 | 2.05968484e-01 | 1.26835957e-01 |
| -1.14109017e-01 | -2.00068519e-01 | 3.17779571e-01 | 3.31381187e-02 |
| -3.83457728e-02 | -2.85022050e-01 | 1.43872425e-02 | -4.12719071e-01 |
| 7.77625963e-02 | 3.40778410e-01 | 1.13988593e-01 | 1.80411309e-01 |
| -4.57207933e-02 | -2.02821270e-01 | 2.30638459e-02 | 4.18765098e-02 |
| 3.14451195e-02 | 2.15280712e-01 | 1.66207224e-01 | -2.60913204e-02 |
| -1.54858744e-02 | 3.47171396e-01 | 3.80088836e-01 | -3.00130457e-01 |
| -2.06781909e-01 | -1.50678426e-01 | 2.72620082e-01 | -2.13530362e-01 |
| 2.19763041e-01 | 2.52057821e-01 | 3.46766710e-01 | -1.37992725e-01 |
| 1.57970339e-01 | 2.44544762e-01 | 7.72713423e-02 | -9.68114194e-03 |
| 3.24918628e-01 | 2.77350992e-01 | 9.88599733e-02 | 1.31124184e-01 |
| 8.31381753e-02 | -5.73251434e-02 | -1.04885800e-02 | -9.42501798e-02 |
| -1.99819393e-01 | 2.66821772e-01 | -2.60933220e-01 | 2.15159953e-01 |
| 1.93193138e-01 | -3.53642315e-01 | -5.52598424e-02 | -3.85654449e-01 |
| -1.02967089e-02 | 3.38131219e-01 | -2.13607624e-01 | -2.46093929e-01 |
| -1.34148747e-01 | 3.31295371e-01 | 1.34638876e-01 | 2.32361685e-02 |
| 2.64022440e-01 | -2.46619135e-01 | 9.89418924e-02 | -3.01854283e-01 |
| -5.70385978e-02 | -4.44413312e-02 | 1.53541956e-02 | -1.10417970e-01 |
| -2.30124459e-01 | 3.19114476e-01 | 1.61143422e-01 | 9.46107041e-03 |
| -1.29706383e-01 | -1.21311337e-01 | 2.94796348e-01 | 2.09944826e-02 |
| -1.86116040e-01 | 8.84032995e-02 | -7.07928240e-02 | 1.18707210e-01 |
| -1.99590936e-01 | 4.06149812e-02 | 2.25713551e-01 | 1.54420063e-01 |
| 1.71858534e-01 | -5.32927252e-02 | -1.50499403e-01 | -2.38028675e-01 |
| 8.82226080e-02 | -2.00786948e-01 | -2.08797663e-01 | -4.52984422e-02 |
| 2.10090131e-01 | -2.10553035e-01 | 3.99974659e-02 | 6.32275641e-02] |
| [1.15191668e-01 | 8.39709044e-01 | 6.06773794e-01 | 8.57235074e-01 |
| 4.84667659e-01 | 5.86446524e-01 | 6.27612412e-01 | 3.84159505e-01 |
| 6.87134027e-01 | 6.89039409e-01 | 2.73819685e-01 | 1.10073793e-00 |
| 7.75744796e-01 | 8.85305941e-01 | 5.16373754e-01 | 3.30960989e-01 |
| 1.01744080e-00 | -3.76490563e-01 | 1.01035513e-01 | 4.44777697e-01 |

TABLE $W_h^1$-continued

| | | | |
|---|---|---|---|
| 6.84718847e−01 | −6.48127258e−01 | 9.36225355e−01 | 9.85244513e−01 |
| 1.18271291e−00 | 1.22075999e−00 | −2.58349478e−01 | 6.43806696e−01 |
| 7.04440296e−01 | 1.11233282e−00 | −2.63971210e−01 | 2.75573105e−01 |
| 3.36356372e−01 | 4.07002330e−01 | 8.20902348e−01 | 3.67542773e−01 |
| −1.69035450e−01 | 5.75378895e−01 | 4.04672563e−01 | 6.29866064e−01 |
| 1.15403104e−00 | 3.33380342e−01 | 3.49243909e−01 | 1.30095673e−00 |
| 1.25022292e−00 | 4.53674763e−01 | 6.30471528e−01 | 1.01009011e−00 |
| 1.18803859e−00 | 5.50539374e−01 | 6.86347187e−01 | 1.01265168e−00 |
| 7.65304685e−01 | 4.93559539e−01 | 3.73408735e−01 | 6.06401622e−01 |
| 7.97679663e−01 | −1.52890283e−01 | 5.36470711e−01 | −6.90019038e−03 |
| 2.84076422e−01 | 8.52723539e−01 | 5.02874792e−01 | 7.42458165e−01 |
| 5.89234829e−01 | 5.16500771e−01 | 8.97852063e−01 | 5.47082841e−01 |
| 4.42500412e−01 | −3.71767819e−01 | 2.42371351e−01 | 2.11128686e−02 |
| 4.91773516e−01 | 6.41478240e−01 | 5.54208815e−01 | 4.68118072e−01 |
| 1.63630223e−00 | 5.01218140e−01 | 2.48362795e−01 | 1.62148044e−01 |
| 7.46109247e−01 | 3.55246484e−01 | 4.98505175e−01 | 5.65626502e−01 |
| 6.92734838e−01 | 4.37195003e−01 | −6.44732341e−02 | 4.73121136e−01 |
| 1.17396355e−00 | −4.77079690e−01 | 8.09432805e−01 | 4.90688443e−01 |
| 1.06291366e−00 | 9.65440750e−01 | 1.00046825e−00 | 2.79407531e−01 |
| 8.12580764e−01 | 3.10677141e−01 | 2.33772472e−02 | 8.18462849e−01 |
| 5.75811386e−01 | 9.20369387e−01 | 3.95564526e−01 | −5.26707135e−02 |
| 6.59361109e−02 | 8.17664087e−01 | 1.94685251e−01 | 6.46586418e−01 |
| 3.39981675e−01 | 9.80885625e−01 | 7.22809136e−02 | 7.44442701e−01 |
| 6.57903731e−01 | 7.91586101e−01 | 2.29951099e−01 | 5.37157953e−01 |
| 1.17316794e−00 | −1.86797213e−02 | 1.04078436e−00 | 3.48306060e−01 |
| 9.65610921e−01 | 1.09551780e−01 | 3.80525440e−01 | 4.19035256e−01 |
| 5.99586546e−01 | 8.21917415e−01 | 7.84709692e−01 | 1.33601737e−00 |
| 7.53368556e−01 | 6.04196250e−01 | 2.24631906e−01 | 7.26013541e−01 |
| 4.11711782e−01 | 8.67146134e−01 | 1.19322360e−00 | 3.83099049e−01 |
| 6.89632595e−01 | 9.69491482e−01 | 1.02840626e−00 | 5.21659672e−01 |
| 4.36636835e−01 | 2.27995932e−01 | 4.18820500e−01 | 3.49692613e−01 |
| 6.34804130e−01 | 4.45365638e−01 | 4.33988810e−01 | 9.15139079e−01 |
| 1.10141134e−00 | 9.05299187e−01 | 5.78996480e−01 | 1.13755345e−00 |
| 3.20778877e−01 | 2.25492284e−01 | 7.13105559e−01 | −3.42230964e−03 |
| −1.12165295e−01 | 7.20326781e−01 | 1.05008602e−00 | 1.38734415e−01 |
| 6.88792109e−01 | 6.42653286e−01 | 6.26747370e−01 | 4.28860009e−01 |
| 4.87249255e−01 | 7.28761196e−01 | 6.26154184e−01 | 1.03473735e−00 |
| 6.39821470e−01 | −1.50365293e−01 | 1.74638525e−01 | 6.30496621e−01 |
| 4.03564811e−01 | 9.00829852e−01 | 2.37734362e−01 | −1.77640200e−01 |
| 2.95619875e−01 | 5.25586903e−01 | 5.61697245e−01 | 5.01826406e−01 |
| 8.67757678e−01 | 1.00210512e−00 | 5.41080356e−01 | 5.07013798e−01 |
| 1.20141482e−00 | 3.11408099e−03 | 5.04143238e−01 | 6.07850552e−01 |
| 3.05261433e−01 | 1.40301153e−01 | 7.38199532e−01 | 4.66387182e−01 |
| 4.98456538e−01 | 7.42498755e−01 | 1.60626426e−01 | 3.58757734e−01 |
| 3.29831541e−01 | 7.23324716e−01 | 6.19965255e−01 | 2.79626012e−01 |
| 5.54711044e−01 | 7.42887318e−01 | 7.41417746e−01 | 4.72288549e−01 |
| −2.20361143e−01 | 6.85333133e−01 | 1.02295525e−01 | 9.58718240e−01 |
| 5.98061144e−01 | 4.20243621e−01 | 9.13136959e−01 | 8.21689308e−01 |
| 5.25189579e−01 | 1.00740731e−00 | 5.47422290e−01 | 7.13320673e−01 |
| 5.06728292e−01 | 5.52511334e−01 | 4.47420418e−01 | −2.01222494e−01 |
| 3.95213902e−01 | −2.97935344e−02 | 9.11409318e−01 | 6.53183222e−01 |
| 4.73601937e−01 | 1.70823544e−01 | 3.07257801e−01 | 1.42275465e−00 |
| 8.00477087e−01 | 6.39491856e−01 | 5.99175572e−01 | 9.63461757e−01 |
| 2.54186660e−01 | −3.22238654e−01 | 5.80639243e−01 | 1.11087191e−00 |
| 8.28884363e−01 | 1.00415492e−00 | −6.72851875e−02 | 8.84636223e−01 |
| 8.42073143e−01 | 9.84697521e−01 | 7.63514876e−01 | 8.24214220e−01 |
| 1.06498837e−00 | 1.82944775e−01 | 9.68485400e−02 | −3.25846761e−01 |
| 8.74310315e−01 | 3.48570436e−01 | 5.95955312e−01 | 1.35407782e−00 |
| −2.21699193e−01 | 6.51156545e−01 | 1.22596717e−00 | 9.25898790e−01] |
| [−2.35781044e−01 | 2.59552300e−01 | 7.02053666e−01 | 2.76624650e−01 |
| 2.22071186e−01 | 6.27955854e−01 | 4.34234649e−01 | 3.23779434e−01 |
| 2.39324033e−01 | 8.13820243e−01 | 7.26001740e−01 | 4.83016014e−01 |
| 3.57865453e−01 | 4.19194579e−01 | −3.09280694e−01 | 2.76074737e−01 |
| 6.41739070e−01 | −1.59876823e−01 | 2.77465016e−01 | 2.11845025e−01 |
| 6.15857780e−01 | 2.81205326e−01 | 6.59572780e−01 | 4.92070884e−01 |
| 1.65791810e−01 | 6.86686039e−02 | 1.47115678e−01 | 3.03992927e−01 |
| 2.96918124e−01 | 4.78662342e−01 | 4.86255735e−01 | 9.37169790e−01 |
| 5.53804636e−01 | 7.90400356e−02 | 5.77412903e−01 | −2.38719866e−01 |
| 3.83928239e−01 | 2.39466310e−01 | 7.72191063e−02 | 3.18524003e−01 |
| 2.18561992e−01 | 4.16563362e−01 | −6.04707748e−03 | 9.59405661e−01 |
| 3.77962708e−01 | 8.30625892e−01 | 3.93049270e−01 | −1.26123637e−01 |
| 6.84028864e−02 | 4.91669446e−01 | 4.76416498e−01 | 1.40643761e−01 |
| 3.28034312e−01 | 5.19894838e−01 | 4.47961956e−01 | 2.66261429e−01 |
| 1.39906645e−01 | −7.21339881e−02 | 7.88795531e−01 | −2.81525943e−02 |
| −3.92900109e−02 | 5.11598110e−01 | 2.30642855e−01 | 4.74065900e−01 |
| 3.65273893e−01 | 4.15087968e−01 | 6.06041193e−01 | 5.09831905e−01 |
| 2.56592751e−01 | 2.21128568e−01 | 1.96490824e−01 | 2.47512653e−01 |
| 4.54470590e−02 | 1.29461866e−02 | 4.63672161e−01 | 1.33121088e−01 |
| 4.00145590e−01 | 3.63689005e−01 | 3.15619469e−01 | −6.96746856e−02 |
| 4.41026628e−01 | 2.95444340e−01 | 3.08905303e−01 | 2.50849396e−01 |

TABLE $W_h^1$-continued

| | | | |
|---|---|---|---|
| 3.49936813e-01 | 6.12818301e-01 | 1.24594882e-01 | 1.94913581e-01 |
| 1.84045896e-01 | 2.44121566e-01 | 1.39895499e-01 | -4.71325964e-02 |
| 3.89598012e-02 | 7.25227535e-01 | 3.99031341e-01 | 3.23102266e-01 |
| -1.96541369e-01 | 1.44137979e-01 | 2.22137108e-01 | 6.45365298e-01 |
| 7.82213151e-01 | 5.51595092e-01 | 6.01988733e-01 | -9.33941826e-02 |
| 1.67719856e-01 | 9.50937927e-01 | 3.40713784e-02 | 3.00014257e-01 |
| 3.80741954e-01 | 4.18605119e-01 | 3.91154081e-01 | 5.24365366e-01 |
| 8.26982737e-01 | 4.55279052e-01 | 6.54234504e-03 | 2.35173404e-01 |
| 3.25652063e-01 | -1.21619944e-02 | 3.40599507e-01 | 4.55297023e-01 |
| 1.97676226e-01 | 5.72134197e-01 | 1.36663973e-01 | 2.24658754e-02 |
| 4.37600613e-01 | 4.56683993e-01 | 3.05920273e-01 | 4.18620914e-01 |
| 3.86567265e-01 | 4.04527426e-01 | 1.05407543e-01 | 4.77623910e-01 |
| 4.76556927e-01 | 1.15512826e-01 | 3.50368947e-01 | 3.94288629e-01 |
| 3.44800800e-01 | 5.18363953e-01 | 2.97357917e-01 | 5.72310627e-01 |
| 1.95582494e-01 | 2.14355543e-01 | 8.72297585e-02 | 4.30623084e-01 |
| 3.09145659e-01 | 5.87487996e-01 | -7.06042722e-02 | 3.72708514e-01 |
| 1.74220309e-01 | 5.23455203e-01 | 2.77962416e-01 | -2.30206206e-01 |
| 1.55424654e-01 | -4.67185630e-03 | -1.03333369e-01 | 3.08923632e-01 |
| 4.31907848e-02 | 2.79208094e-01 | 6.89088643e-01 | 2.78390825e-01 |
| 5.63053548e-01 | 3.65326166e-01 | 4.82144028e-01 | 3.81731004e-01 |
| 5.87096989e-01 | 1.16881073e-01 | 3.07875723e-01 | -2.84522027e-01 |
| 3.18884134e-01 | 2.19487503e-01 | 4.05293584e-01 | 2.23523024e-02 |
| 7.22141147e-01 | -1.14502594e-01 | 4.75675404e-01 | -8.79391730e-02 |
| 2.21354455e-01 | 4.24241513e-01 | 6.61740541e-01 | -4.57857065e-02 |
| 1.40330508e-01 | 5.15626490e-01 | 2.54101485e-01 | 2.91359544e-01 |
| 5.30951262e-01 | -3.65062170e-02 | 3.33348848e-02 | 1.33681372e-01 |
| 6.95039511e-01 | 4.34099168e-01 | 5.50985581e-01 | 6.12338066e-01 |
| 8.75073895e-02 | 4.03068244e-01 | 5.74012399e-01 | 5.08332431e-01 |
| 1.57883734e-01 | -1.10111229e-01 | 1.67440832e-01 | 5.18507719e-01 |
| 2.08340697e-02 | -2.31618032e-01 | -1.78604815e-02 | 5.57709217e-01 |
| 4.94248986e-01 | 8.47594202e-01 | 2.96461135e-01 | -1.00433687e-02 |
| 3.82598013e-01 | 5.58214247e-01 | 6.04979277e-01 | 3.03605467e-01 |
| 4.57047373e-01 | -1.54192030e-01 | 2.39273354e-01 | 3.49739134e-01 |
| 3.34343553e-01 | 1.52822718e-01 | 1.95793837e-01 | 1.37599394e-01 |
| 4.83354688e-01 | -1.55844554e-01 | -4.51170988e-02 | 2.13182271e-01 |
| 4.29243594e-01 | 2.66105831e-01 | 5.97543478e-01 | 1.77244499e-01 |
| 2.76458591e-01 | 5.50889373e-02 | 4.47824240e-01 | -1.21792495e-01 |
| 4.03672278e-01 | -1.07449420e-01 | 7.30053425e-01 | -1.04481671e-01 |
| 1.81928873e-01 | 4.48701471e-01 | 2.15311855e-01 | 5.92827424e-02 |
| 4.97345150e-01 | 6.97643399e-01 | 3.08372706e-01 | 6.75883651e-01 |
| 1.35634899e-01 | 8.57966363e-01 | 4.81829762e-01 | 3.88484478e-01 |
| 5.14352135e-02 | 4.26286429e-01 | 3.87498826e-01 | 4.46683913e-01 |
| -3.56685109e-02 | 4.43991780e-01 | 7.99668729e-02 | 4.24939275e-01] |
| [-3.54492739e-02 | 2.46364981e-01 | -2.29704008e-01 | 1.64918769e-01 |
| 4.46290784e-02 | 2.79131442e-01 | -7.65736401e-02 | 1.87994227e-01 |
| -9.31847468e-02 | 2.80979481e-01 | 3.86289470e-01 | -8.48264173e-02 |
| 4.06713456e-01 | 6.99516237e-02 | -9.82628167e-01 | 3.61365117e-02 |
| 5.73946536e-02 | 1.08142212e-01 | 1.93487510e-01 | -4.10447195e-02 |
| 3.12712491e-01 | 4.27813768e-01 | 2.49072060e-01 | 5.77216387e-01 |
| -3.61420512e-01 | -2.00033039e-01 | 5.40617146e-02 | 9.22601968e-02 |
| -2.07151063e-02 | 3.12141418e-01 | -8.03129897e-02 | 3.59127633e-02 |
| 8.65857080e-02 | -2.81222552e-01 | 1.51330680e-01 | 3.77620786e-01 |
| -1.99238975e-02 | -2.97242794e-02 | -1.21398456e-01 | 2.13530183e-01 |
| 1.52543202e-01 | -1.31497517e-01 | 2.25749593e-01 | 5.75415373e-01 |
| 7.72484094e-02 | -2.71889120e-01 | 2.01822504e-01 | -2.38549733e-03 |
| 2.62477070e-01 | 2.77544409e-01 | 2.78351218e-01 | 3.09845228e-02 |
| -1.76816583e-01 | 2.10709319e-01 | 3.78139764e-01 | 9.47014913e-02 |
| -5.79164512e-02 | -6.62658736e-02 | 6.33319438e-01 | -1.25952289e-01 |
| 2.81266481e-01 | 1.15404628e-01 | 1.36098102e-01 | -1.20566152e-01 |
| 1.54304907e-01 | 1.53097138e-01 | 1.21954277e-01 | 1.68117985e-01 |
| 3.45478594e-01 | -5.24737798e-02 | 2.48620838e-01 | 5.36913052e-02 |
| 2.32465684e-01 | 4.44129825e-01 | -1.06560379e-01 | -1.14538185e-01 |
| 6.61375821e-01 | 2.73117959e-01 | 9.37774181e-02 | -2.08668575e-01 |
| -2.61057854e-01 | 3.47104281e-01 | 2.57082015e-01 | 5.72832227e-02 |
| -1.58448517e-01 | -5.12723327e-02 | -2.72393357e-02 | -5.81782013e-02 |
| -2.69521534e-01 | -6.65516406e-02 | -7.62053207e-02 | -3.76635119e-02 |
| 2.50859767e-01 | 1.73279494e-01 | 2.05029547e-01 | 1.85474724e-01 |
| -1.41007438e-01 | -5.71944602e-02 | 6.54383302e-02 | 3.50211918e-01 |
| 4.84803841e-02 | 2.72522360e-01 | 1.32274076e-01 | 6.44420739e-03 |
| -1.02071613e-01 | 7.23480294e-03 | 8.44695568e-02 | -2.21693382e-01 |
| 1.21437587e-01 | 3.25735658e-01 | 4.02479321e-01 | 3.65921229e-01 |
| 5.40627360e-01 | 3.58043402e-01 | -2.87304759e-01 | 4.50332344e-01 |
| 4.71027136e-01 | -9.00030136e-02 | -1.79896832e-01 | -9.57451612e-02 |
| 1.24514177e-01 | 3.00249219e-01 | 1.20371707e-01 | -7.78812915e-02 |
| 2.19698057e-01 | 1.08874049e-01 | 3.34820569e-01 | 3.34283292e-01 |
| 1.58952743e-01 | 3.37864876e-01 | -1.57084893e-02 | 1.98073834e-01 |
| 2.27847159e-01 | 1.24604262e-01 | 2.39294469e-01 | 2.41009846e-01 |
| -1.49846748e-01 | 1.88290656e-01 | 8.07261765e-02 | 2.16342896e-01 |
| 4.31524888e-02 | 1.60153568e-01 | 1.99615657e-01 | -1.30436510e-01 |
| 3.94292921e-01 | 1.69316366e-01 | -4.82723117e-02 | -1.53198242e-01 |

TABLE $W_h^1$-continued

| | | | |
|---|---|---|---|
| 3.33822705e−02 | 3.09241414e−01 | 2.50350237e−01 | −3.32620323e−01 |
| −1.09367758e−01 | −6.60907477e−02 | 2.26128906e−01 | −1.47801533e−01 |
| −1.91125363e−01 | 1.09539768e−02 | 1.95917517e−01 | 2.20303684e−02 |
| 1.15284123e−01 | 3.55440885e−01 | 1.78588942e−01 | 3.71643126e−01 |
| 4.30120900e−02 | 1.29718006e−01 | 5.17733283e−02 | −5.13836324e−01 |
| 5.45526780e−02 | 2.49247566e−01 | 5.01308553e−02 | 1.88689053e−01 |
| 4.23754603e−02 | 2.54153490e−01 | 3.12781960e−01 | 2.56290615e−01 |
| −2.07926065e−02 | 1.78828582e−01 | 7.66333565e−02 | 1.94602311e−01 |
| −1.02452047e−01 | 2.95719802e−01 | 1.14417605e−01 | 3.64952147e−01 |
| −1.08761843e−02 | −3.80664110e−01 | 3.01965445e−01 | 9.09553915e−02 |
| 3.50523256e−02 | −7.76888579e−02 | 3.60690683e−01 | 6.08430505e−01 |
| −1.20045535e−01 | 2.92868555e−01 | −1.85385123e−01 | 1.44705459e−01 |
| 1.41846940e−01 | 7.86593184e−02 | −1.60145476e−01 | 2.39818707e−01 |
| −4.08018045e−02 | −1.44870669e−01 | 3.56243365e−02 | 2.26107687e−01 |
| 2.73901373e−01 | 1.46336243e−01 | 1.43691242e−01 | 2.37113893e−01 |
| −1.77367732e−01 | −1.98365659e−01 | 4.64688182e−01 | −4.73126657e−02 |
| 1.61833137e−01 | 1.54080346e−01 | 2.98614856e−01 | 2.08757594e−01 |
| 3.67907465e−01 | 4.60507214e−01 | 8.12907442e−02 | 1.20926641e−01 |
| 3.04246079e−02 | 1.51827618e−01 | −1.99804045e−02 | −7.99468383e−02 |
| −1.26540661e−01 | 2.15525508e−01 | 1.66284472e−01 | 1.23600915e−01 |
| 1.91304639e−01 | −2.42858157e−01 | 3.67142320e−01 | 1.93709906e−01 |
| 4.33076739e−01 | 1.12557255e−01 | 3.90837491e−01 | −1.08740084e−01 |
| 2.77995877e−02 | 3.26738954e−01 | 2.72654444e−01 | −1.27561197e−01 |
| 2.97957599e−01 | −1.76811621e−01 | 6.72086924e−02 | 2.64132023e−01 |
| 3.56050879e−01 | 3.05831730e−01 | 3.19460750e−01 | 6.93687275e−02 |
| −1.32316634e−01 | 2.04222843e−01 | 2.27335561e−02 | −3.43145393e−02 |
| −5.86298406e−02 | 4.42968547e−01 | −1.92712620e−01 | −1.49787635e−01] |
| [3.31443936e−01 | 6.33434430e−02 | 3.83762956e−01 | 3.89304072e−01 |
| 2.98328578e−01 | 7.02345729e−01 | 2.80540466e−01 | 4.79830146e−01 |
| −1.13973059e−02 | 5.49890876e−01 | 1.58786774e−01 | 8.92751142e−02 |
| 2.14165688e−01 | 1.09085895e−01 | 1.71854496e−01 | 3.84241551e−01 |
| 3.16205442e−01 | 3.51577461e−01 | 3.95097956e−02 | 3.76234174e−01 |
| 5.41473508e−01 | 2.73768395e−01 | 6.37793779e−01 | 5.10936797e−01 |
| 2.54070282e−01 | 9.06073749e−01 | 2.73492754e−01 | −5.38131781e−02 |
| 8.54712948e−02 | 5.98609269e−01 | 1.98173955e−01 | 5.29468775e−01 |
| 3.28267783e−01 | 2.47357219e−01 | 4.90337074e−01 | 4.12143618e−01 |
| −8.47300049e−03 | −7.19892606e−02 | 4.25853312e−01 | 2.53837645e−01 |
| 2.89503545e−01 | 2.73007601e−01 | 6.39903992e−01 | 2.81255841e−01 |
| 5.55449247e−01 | 4.08936173e−01 | 6.75049245e−01 | 4.33698714e−01 |
| 1.94278866e−01 | 1.85392931e−01 | −1.77937672e−01 | 2.00191185e−01 |
| 5.43771014e−02 | 1.45223349e−01 | −6.04599789e−02 | 1.22115411e−01 |
| 3.12262744e−01 | 1.67256892e−01 | 3.24730188e−01 | 4.17740226e−01 |
| 9.08364058e−02 | 3.72714520e−01 | 4.52832699e−01 | 3.91420573e−01 |
| 3.11222170e−02 | 6.18604422e−01 | 4.31898803e−01 | 4.26104695e−01 |
| 2.50100531e−02 | 2.39801019e−01 | 2.46307388e−01 | 1.72008753e−01 |
| 1.74317166e−01 | 2.52942592e−01 | 1.76485926e−02 | 8.78211632e−02 |
| 7.04230145e−02 | 2.34679252e−01 | 4.60648090e−01 | 5.29229492e−02 |
| 1.17464542e−01 | 3.89046341e−01 | 2.33599067e−01 | −5.75870425e−02 |
| 2.47309774e−01 | 3.73730123e−01 | 2.05658317e−01 | 2.15549722e−01 |
| 1.33668974e−01 | 2.48026848e−01 | 3.95111382e−01 | 4.24928427e−01 |
| 3.65513384e−01 | 1.43304676e−01 | 5.92170596e−01 | 2.66658008e−01 |
| 5.50422788e−01 | 4.38453168e−01 | 5.02894435e−02 | 7.06226081e−02 |
| 1.15560398e−01 | 2.71716595e−01 | 3.05498242e−01 | 2.29757473e−01 |
| 1.97120517e−01 | 1.26737356e−01 | −2.28078961e−01 | 2.01948836e−01 |
| −1.82825327e−01 | 1.67191729e−01 | −2.29592875e−01 | −1.23725787e−01 |
| 1.12423517e−01 | 5.33449017e−02 | 2.20861211e−01 | −7.37184882e−02 |
| 1.53019860e−01 | 3.01371098e−01 | 1.10267088e−01 | −1.01193219e−01 |
| 1.08512163e−01 | 1.83000892e−01 | 4.16683376e−01 | 4.29610640e−01 |
| 6.73822939e−01 | 3.06271434e−01 | 4.35909659e−01 | 1.89725801e−01 |
| 6.54770613e−01 | 4.01917309e−01 | 1.67703271e−01 | 1.02066211e−01 |
| 2.36040518e−01 | 3.48973811e−01 | 1.68123856e−01 | 2.84714103e−01 |
| 1.05165645e−01 | 2.43751943e−01 | 6.14756644e−01 | 5.76103449e−01 |
| 4.78964567e−01 | 3.06750178e−01 | 2.81209916e−01 | 2.49418661e−01 |
| 8.07146654e−02 | −1.26110107e−01 | −3.77064943e−01 | 6.16499424e−01 |
| 3.27994823e−01 | −2.30936021e−01 | 3.14173847e−01 | 2.37002790e−01 |
| 2.35489801e−01 | 6.66432679e−01 | 2.87346900e−01 | 4.23774987e−01 |
| 5.58710098e−01 | 5.04671752e−01 | 3.19297910e−01 | 2.76139289e−01 |
| 3.54730070e−01 | −9.65586752e−02 | −1.32124647e−01 | 5.19415438e−01 |
| 3.92117828e−01 | 2.44753554e−01 | 2.71739244e−01 | 5.70714831e−01 |
| 5.57637990e−01 | 4.28380638e−01 | 2.13345110e−01 | 1.91429019e−01 |
| 2.24841282e−01 | 3.31771642e−01 | 8.00673291e−02 | 1.20677851e−01 |
| 3.27064842e−01 | 2.21273780e−01 | −1.18907385e−01 | 2.00935423e−01 |
| 4.74238753e−01 | 5.08989811e−01 | 1.75827622e−01 | 3.02982390e−01 |
| 3.38243842e−01 | 3.57363433e−01 | 4.50794995e−01 | 2.90739328e−01 |
| 4.40555364e−01 | 1.46198675e−01 | 4.22348857e−01 | 5.39843500e−01 |
| 2.88648397e−01 | 4.36895907e−01 | −1.77426696e−01 | 3.36601406e−01 |
| 2.66250402e−01 | 2.39299610e−02 | 3.46779190e−02 | 3.65028560e−01 |
| 1.85283676e−01 | 1.27937660e−01 | 2.82175064e−01 | 3.01467776e−01 |
| 8.94218624e−01 | 2.19988123e−01 | −1.42709866e−01 | 3.47628780e−02 |
| 2.00457841e−01 | −4.86299455e−01 | −1.27960071e−01 | −1.09397257e−02 |

TABLE $W_h^1$-continued

| | | | |
|---|---|---|---|
| −1.19534850e−01 | 2.71754414e−01 | −2.46064827e−01 | 4.83230978e−01 |
| 1.85478643e−01 | 2.06814080e−01 | 4.16465670e−01 | −1.38220549e−01 |
| 3.79493356e−01 | 9.31128114e−02 | 1.35029450e−01 | 5.47766745e−01 |
| 3.88944060e−01 | 5.18900394e−01 | −2.48935707e−02 | 2.92434096e−01 |
| 3.35454762e−01 | 6.21663451e−01 | 5.85140228e−01 | 5.55732965e−01 |
| 1.34426385e−01 | 2.39914730e−01 | 1.99196994e−01 | 4.82311517e−01 |
| 5.51781714e−01 | 6.95839971e−02 | 1.51414007e−01 | 7.58023620e−01 |
| 4.04541939e−01 | 4.76806432e−01 | −8.78338888e−03 | −1.60363048e−01 |
| 1.84901699e−01 | 5.02723694e−01 | 2.74709404e−01 | 2.35507295e−01 |
| 1.82556361e−02 | −1.01368390e−01 | 4.70884234e−01 | 4.43996163e−03 |
| 1.95356295e−01 | 6.28007531e−01 | 6.00560188e−01 | 4.70352918e−01] |
| [2.54483819e−01 | 4.19070333e−01 | 3.35720003e−01 | 4.54711579e−02 |
| 8.85142758e−02 | 2.64029622e−01 | 2.14383796e−01 | 1.33354053e−01 |
| 2.14941978e−01 | 9.64810178e−02 | 2.41384968e−01 | 5.98903775e−01 |
| 4.44827452e−02 | 4.05410856e−01 | 3.69873881e−01 | −2.17841387e−01 |
| 5.04462123e−01 | 3.33200872e−01 | 3.27250004e−01 | 3.04760039e−01 |
| 1.83819905e−01 | 5.67618466e−04 | 3.80411655e−01 | 3.32881898e−01 |
| 2.20128015e−01 | 3.13868411e−02 | 3.17500085e−02 | 5.38579881e−01 |
| 2.23533109e−01 | 1.03106491e−01 | 2.38729641e−01 | 1.77733287e−01 |
| 1.42748594e−01 | 1.12559525e−02 | 3.79820108e−01 | −5.40142469e−02 |
| 2.76990771e−01 | 5.00533760e−01 | 6.08940385e−02 | −3.27249020e−02 |
| 4.99776483e−01 | 2.66058236e−01 | −3.53881329e−01 | 2.71774888e−01 |
| 8.08195844e−02 | 2.35387713e−01 | 3.06160957e−01 | 2.03119561e−01 |
| 1.83065027e−01 | 8.58641863e−02 | 2.03134716e−01 | 8.52959231e−02 |
| −9.46626440e−02 | −3.60569358e−01 | 1.08450852e−01 | 3.26782703e−01 |
| −1.62011951e−01 | −3.19996625e−01 | 2.99750902e−02 | 2.78879523e−01 |
| 6.58601075e−02 | 1.86453953e−01 | −1.28221065e−01 | 3.49671811e−01 |
| 3.01476628e−01 | 2.43848056e−01 | 4.88352090e−01 | 2.59110510e−01 |
| 5.41933440e−01 | 3.39888066e−01 | 3.43704186e−02 | 8.23071226e−02 |
| 2.29901165e−01 | −3.10317576e−01 | 5.33780344e−02 | 3.76189530e−01 |
| 1.38187900e−01 | 1.79002210e−01 | −2.21369460e−01 | 4.86271620e−01 |
| −3.16439420e−02 | 2.44469300e−01 | −1.06177770e−01 | 4.43173319e−01 |
| 2.67554730e−01 | 4.99974601e−01 | 2.21774533e−01 | 1.70490786e−01 |
| 3.09694111e−01 | 5.60931750e−02 | −3.06550469e−02 | 2.20642120e−01 |
| 2.96435177e−01 | 2.57141709e−01 | −4.55706334e−03 | 2.58415610e−01 |
| −5.04566990e−02 | 1.23724990e−01 | 1.21697105e−01 | −5.07834107e−02 |
| 3.37454945e−01 | 2.24639639e−01 | −4.28106599e−02 | 2.21290007e−01 |
| −5.46194464e−02 | 3.71670157e−01 | −1.26398832e−01 | 1.28258765e−01 |
| 4.51693945e−02 | −6.50090054e−02 | −3.09784442e−01 | 4.74778891e−01 |
| 3.66489381e−01 | 2.00643197e−01 | 3.60353962e−02 | 5.82257152e−01 |
| 3.60147536e−01 | 1.31382212e−01 | 6.94777519e−02 | 2.49637991e−01 |
| 8.41585547e−02 | 3.84236276e−01 | 1.66889220e−01 | 3.11947256e−01 |
| 4.37748767e−02 | 1.71103701e−02 | 1.27756998e−01 | 3.36112559e−01 |
| 2.33452410e−01 | 9.49068964e−02 | 2.01073438e−01 | 4.91420776e−02 |
| 2.37996921e−01 | 4.80715543e−01 | 1.20385438e−01 | 1.74422979e−01 |
| 4.16736215e−01 | 2.03191832e−01 | 4.18028161e−01 | −7.14976788e−02 |
| 8.80183652e−02 | 4.80645820e−02 | −3.82651836e−01 | −2.80371755e−01 |
| 6.44836575e−02 | 7.30229557e−01 | 1.81454167e−01 | 1.36923254e−01 |
| 3.74980628e−01 | 1.56465605e−01 | 2.90566415e−01 | 6.06438637e−01 |
| −2.36204356e−01 | 3.23148400e−01 | 1.54639468e−01 | 2.14351133e−01 |
| −3.60929728e−01 | 1.34142175e−01 | 3.15532655e−01 | −5.69687560e−02 |
| 1.85083315e−01 | 5.02983868e−01 | 3.98202948e−02 | 3.40677202e−02 |
| 6.43571913e−01 | 4.12556976e−01 | 2.30439499e−01 | 1.16330169e−01 |
| 3.80819529e−01 | 3.14213514e−01 | 1.15355961e−01 | 4.48816240e−01 |
| 7.60623887e−02 | 5.07302210e−02 | 1.42871886e−01 | −3.51261139e−01 |
| 1.60568461e−01 | 1.94068879e−01 | 2.67751127e−01 | 1.20187998e−01 |
| −3.14401269e−01 | 4.99558151e−01 | −1.63820893e−01 | 6.85114488e−02 |
| 2.89031923e−01 | 2.19460383e−01 | 2.27256957e−01 | 1.52278751e−01 |
| 1.38605595e−01 | −4.47110325e−01 | 4.49004322e−02 | 6.93531632e−01 |
| 1.21134833e−01 | 6.43707514e−02 | 1.75249457e−01 | 1.19418398e−01 |
| 2.03691378e−01 | 4.93862301e−01 | 1.07849739e−01 | −4.56980526e−01 |
| 1.19019859e−01 | 1.84582487e−01 | 5.30586168e−02 | 1.18141815e−01 |
| 2.96719849e−01 | 5.84907651e−01 | −9.79119763e−02 | 2.03611478e−01 |
| 4.53216583e−01 | 1.26237854e−01 | 1.45698622e−01 | −1.06054537e−01 |
| −1.32385164e−01 | 1.73310682e−01 | 3.30323577e−02 | 4.21442449e−01 |
| 5.34245670e−01 | −1.77799791e−01 | 5.16876161e−01 | 2.66539395e−01 |
| 3.73481303e−01 | −1.64596856e−01 | 1.34020731e−01 | 1.12502575e−01 |
| −3.43023419e−01 | −1.22136816e−01 | 3.51590887e−02 | −8.05257633e−02 |
| 3.62209439e−01 | −3.21129620e−01 | 2.12084770e−01 | 6.05055690e−02 |
| 1.23680912e−01 | 3.14761132e−01 | 3.45731258e−01 | −2.57721931e−01 |
| −4.32055108e−02 | 3.68250698e−01 | 3.34156342e−01 | 6.34882092e−01 |
| 2.42471755e−01 | 1.72401696e−01 | 9.42949858e−03 | 2.53474981e−01 |
| 5.02451733e−02 | 4.63454984e−04 | 3.03468168e−01 | 3.33398700e−01 |
| −1.75769404e−01 | 7.08264932e−02 | 1.96996555e−01 | 2.80330718e−01 |
| −1.51245058e−01 | 5.39016724e−01 | 4.70069110e−01 | 4.74797972e−02] |
| [1.50460243e−01 | 7.82826021e−02 | 1.39421344e−01 | 1.85607299e−01 |
| 2.77438700e−01 | 1.40046492e−01 | 1.58079714e−01 | 4.46751922e−01 |
| 2.50831038e−01 | 1.85098425e−01 | 3.20520788e−01 | −1.75792143e−01 |
| 4.82324883e−02 | 3.16742390e−01 | 1.42088975e−03 | 6.17787801e−02 |
| −3.87983508e−02 | −1.12256050e−01 | 2.09604532e−01 | 9.36265349e−01 |

TABLE W$_h^1$-continued

| | | | |
|---|---|---|---|
| 1.90222934e−01 | 2.21359923e−01 | −3.30104306e−02 | 1.28162205e−01 |
| −9.22903375e−02 | 6.05214238e−01 | −7.86233768e−02 | 2.52276540e−01 |
| 1.23170510e−01 | 3.56088817e−01 | 4.32035923e−01 | −1.41947806e−01 |
| 5.70435464e−01 | 6.42763436e−01 | 4.31456178e−01 | 4.15625215e−01 |
| 7.97074735e−02 | 3.54408860e−01 | 7.50711381e−01 | 3.57742846e−01 |
| 6.16953894e−02 | 1.10304803e−01 | −1.04162671e−01 | −2.43110359e−01 |
| 3.53417307e−01 | 1.15132742e−01 | 2.98965573e−01 | −3.28393787e−01 |
| −5.66863976e−02 | 3.50597113e−01 | 2.42744908e−01 | 2.21503496e−01 |
| 2.30625302e−01 | 3.51181626e−01 | −1.01671331e−01 | 9.41360146e−02 |
| −2.94889897e−01 | 2.03122035e−01 | 3.26033354e−01 | 3.15971404e−01 |
| 5.46913385e−01 | 6.48272693e−01 | 2.64217436e−01 | 3.69588494e−01 |
| 2.78298914e−01 | 4.99295741e−01 | 2.16662169e−01 | 5.70291758e−01 |
| −1.27855977e−02 | 4.51183587e−01 | 3.82302076e−01 | −3.49834412e−02 |
| 4.91671860e−01 | 9.16130915e−02 | 5.03035486e−01 | 2.87205458e−01 |
| 5.39720297e−01 | 3.13455284e−01 | 3.70743841e−01 | −4.25510630e−02 |
| 1.33489966e−01 | −5.50733730e−02 | 5.92114747e−01 | 1.40462324e−01 |
| 1.23010471e−01 | 3.80335480e−01 | 4.41942722e−01 | −5.23159467e−02 |
| 1.90720167e−02 | 3.10590625e−01 | 1.55217536e−02 | 9.37293321e−02 |
| 4.33336318e−01 | 5.91650486e−01 | 2.40161195e−01 | 4.39189911e−01 |
| 1.81898639e−01 | −1.17965788e−01 | 2.53856361e−01 | 4.96801250e−02 |
| 6.68563306e−01 | 1.97395340e−01 | 7.11829439e−02 | 2.58602351e−01 |
| 1.61936179e−01 | 4.90601480e−01 | 3.61828089e−01 | 4.31373507e−01 |
| 3.59658599e−01 | 4.24552649e−01 | 2.31649145e−01 | 3.22722077e−01 |
| 2.90027857e−01 | 5.18661559e−01 | 9.58508775e−02 | 1.78603917e−01 |
| 4.18353677e−01 | −3.49720001e−01 | 2.53002852e−01 | −1.12805806e−01 |
| 3.78539711e−01 | 3.02612364e−01 | −1.32341936e−01 | 2.46936753e−01 |
| 5.02425969e−01 | −2.33171418e−01 | 1.10399723e−01 | 3.84255588e−01 |
| 7.28268147e−01 | 7.85281360e−02 | −1.67757198e−01 | 7.47002661e−01 |
| 3.34632099e−01 | 2.93517917e−01 | 3.57710660e−01 | −2.39620015e−01 |
| 3.49222153e−01 | 1.41588822e−01 | −1.57699540e−01 | 3.87603164e−01 |
| 2.63370663e−01 | 1.76697150e−01 | −1.40800491e−01 | 2.32355893e−01 |
| 1.75867021e−01 | 3.66362818e−02 | 1.31866202e−01 | 1.55100077e−01 |
| −1.92988530e−01 | 2.80607015e−01 | 1.90659449e−01 | 2.58168161e−01 |
| 1.13630921e−01 | 3.68129462e−01 | −7.17622340e−02 | 1.66181043e−01 |
| 6.46085680e−01 | 6.90936923e−01 | 5.94839871e−01 | 2.02288523e−01 |
| 1.34146184e−01 | −7.28586316e−02 | 1.84788063e−01 | −5.91774620e−02 |
| 3.02240670e−01 | 1.62575483e−01 | 3.41272742e−01 | −3.66428569e−02 |
| 3.13336372e−01 | 3.85017693e−01 | 3.09488147e−01 | −1.83261216e−01 |
| 4.38938349e−01 | 4.12836105e−01 | 2.81888187e−01 | 2.29943156e−01 |
| 4.71099950e−02 | 3.81745517e−01 | 1.96571779e−02 | 8.41838270e−02 |
| 4.81615355e−03 | 7.66868442e−02 | 1.34005427e−01 | −1.52224183e−01 |
| 2.74938971e−01 | 4.79238689e−01 | 2.33818963e−01 | −3.26285418e−03 |
| −2.36457348e−01 | 4.92367625e−01 | 1.83208659e−01 | 2.33890042e−01 |
| 4.89845186e−01 | 3.48102629e−01 | 1.29734531e−01 | 4.06494975e−01 |
| 1.92268118e−01 | 1.00670017e−01 | 3.58048439e−01 | 2.16833144e−01 |
| 2.79412299e−01 | −6.52159797e−03 | 8.94079283e−02 | 2.49811649e−01 |
| −6.25656024e−02 | 1.19909091e−01 | 7.30704784e−01 | 1.48794428e−01 |
| 1.14649355e−01 | 1.36351615e−01 | −1.79398004e−02 | 2.06341133e−01 |
| 2.22026572e−01 | −1.81520477e−01 | 5.19978642e−01 | 5.95151372e−02 |
| 1.02705536e−01 | 1.06143586e−01 | −2.24666540e−01 | 4.67571586e−01 |
| −1.00814523e−02 | 5.85905075e−01 | 8.18350613e−01 | 8.30579475e−02 |
| −6.07593954e−02 | 4.04813468e−01 | −1.16178403e−02 | −2.98396230e−01 |
| 6.01091623e−01 | 1.50701836e−01 | 4.71791625e−01 | 2.54627377e−01 |
| 3.02250087e−01 | 5.75192571e−01 | 2.55568296e−01 | 4.45497334e−01 |
| 3.81978661e−01 | 4.57073033e−01 | 3.60965282e−02 | 2.97412843e−01 |
| 5.82500160e−01 | −4.72238138e−02 | 1.20371148e−01 | −4.38602686e−01 |
| 3.55467170e−01 | 8.51952434e−02 | 4.48722899e−01 | 4.99711126e−01 |
| 3.62461329e−01 | 3.96300048e−01 | 3.55562091e−01 | 8.82041641e−03 |
| −6.00064620e−02 | 5.17421961e−01 | 3.63562286e−01 | 1.56191424e−01] |
| [−1.55587539e−01 | −5.11287246e−04 | 9.10742432e−02 | 2.20398724e−01 |
| 2.95477062e−01 | 2.23288059e−01 | −1.79253191e−01 | 6.77231997e−02 |
| 3.09460938e−01 | 5.22282124e−01 | −1.05227731e−01 | 2.52432466e−01 |
| 5.38572192e−01 | −1.60561755e−01 | 5.79032339e−01 | 5.29959500e−01 |
| 3.71274203e−01 | −2.73581475e−01 | −3.02798301e−01 | −2.52200644e−02 |
| 3.57819110e−01 | 5.75150073e−01 | 6.52099967e−01 | 4.26109910e−01 |
| 3.99302602e−01 | 4.85386729e−01 | 6.52190447e−02 | −2.66821198e−02 |
| 1.01941824e−01 | −1.90016121e−01 | −3.52222502e−01 | −1.16064675e−01 |
| 4.71611887e−01 | 1.69652984e−01 | −6.10820076e−04 | 3.61859888e−01 |
| 1.58593431e−01 | 1.92742541e−01 | −9.07200053e−02 | 5.31629384e−01 |
| 1.96324632e−01 | 4.95631993e−01 | 4.14855033e−01 | 3.56423438e−01 |
| 1.02484152e−01 | −7.03993067e−02 | 5.50374985e−01 | 4.42159176e−01 |
| −2.97691375e−01 | 1.98700428e−01 | 3.14809591e−01 | 5.68402484e−02 |
| 4.50065821e−01 | 1.41775340e−01 | 1.64448500e−01 | −2.08871067e−01 |
| 2.33014539e−01 | 7.42899239e−01 | 1.27103463e−01 | 2.00333893e−01 |
| −4.62877419e−04 | 2.46142685e−01 | 1.16218694e−01 | −9.49559063e−02 |
| 1.12138592e−01 | 3.01272511e−01 | −3.74494120e−02 | 2.88314283e−01 |
| −8.04948360e−02 | −1.19632430e−01 | 4.89521623e−01 | 1.83612555e−01 |
| 1.22134186e−01 | −1.15045428e−01 | 1.45987496e−01 | 2.04102900e−02 |
| 3.41389388e−01 | 2.44109184e−01 | 3.24571490e−01 | 4.11085397e−01 |
| 2.10860476e−01 | 2.66981155e−01 | 7.29713961e−02 | 4.58233744e−01 |

TABLE $W_h^1$-continued

| | | | |
|---|---|---|---|
| 3.89422639e−03 | 1.02371588e−01 | 1.60457417e−01 | −5.49899936e−02 |
| −2.05910280e−02 | 6.97871149e−02 | 6.85118794e−01 | 1.08897455e−01 |
| −3.73781621e−02 | −3.98164913e−02 | 4.42078471e−01 | 3.39391470e−01 |
| 1.73452660e−01 | 5.64314783e−01 | 3.08138371e−01 | 2.72000581e−01 |
| 3.92513186e−01 | 7.96619952e−01 | 2.81453654e−02 | 1.94196016e−01 |
| 1.97188128e−02 | 1.21886060e−01 | 2.98657268e−01 | 1.84946328e−01 |
| 5.68277426e−02 | 3.91570091e−01 | 1.28904209e−01 | 2.36026749e−01 |
| 1.35514811e−01 | 7.61057809e−02 | 4.61068720e−01 | 1.93807125e−01 |
| −7.65278116e−02 | 1.30058423e−01 | 3.91903371e−01 | −6.18561134e−02 |
| 5.87513670e−02 | 1.39125562e−01 | 2.14578331e−01 | 2.85871714e−01 |
| 1.62213132e−01 | −1.68534126e−02 | 1.71803251e−01 | 1.96395859e−01 |
| 6.76879957e−02 | 5.52863121e−01 | 2.36735016e−01 | 4.87997204e−01 |
| 2.18715265e−01 | 3.65126312e−01 | 1.82921275e−01 | 6.36865795e−01 |
| 4.20320511e−01 | 5.29086471e−01 | −6.43285811e−02 | 2.64122903e−01 |
| 2.40733758e−01 | −1.49448523e−02 | 1.79890335e−01 | 2.23444421e−02 |
| −2.31730178e−01 | 2.82653302e−01 | −1.65444463e−01 | 6.85462773e−01 |
| 5.01624607e−02 | 4.94050141e−03 | 3.17407072e−01 | 6.70831203e−01 |
| 5.23639977e−01 | 2.47479856e−01 | 3.94020826e−01 | 1.58673421e−01 |
| 3.18369895e−01 | 2.86157399e−01 | 5.30476160e−02 | 2.48231784e−01 |
| 3.27339232e−01 | 3.62793982e−01 | 2.08710074e−01 | 6.60179198e−01 |
| 2.38775074e−01 | 9.24060196e−02 | 4.53254670e−01 | 4.47809339e−01 |
| 2.00291440e−01 | 5.41265905e−01 | −1.32032722e−01 | 5.46171844e−01 |
| 3.54929745e−01 | −3.17016602e−01 | 3.06442440e−01 | 1.45163044e−01 |
| 6.06103092e−02 | 3.17007095e−01 | 3.99664044e−01 | 7.67918468e−01 |
| 1.68003172e−01 | 6.99122017e−03 | 2.05021560e−01 | 2.18263865e−01 |
| −1.48658082e−01 | −7.73970932e−02 | 2.59824723e−01 | 5.62754273e−02 |
| 3.04893732e−01 | 1.01068772e−01 | 6.45725906e−01 | 5.39642394e−01 |
| 5.21960914e−01 | 1.03651032e−01 | 4.05521780e−01 | 3.31042260e−01 |
| 6.18051253e−02 | 2.47643575e−01 | −3.97345386e−02 | −9.82039869e−02 |
| 5.97220659e−01 | −1.25842676e−01 | 1.33983493e−01 | 5.72769701e−01 |
| −7.89783150e−02 | 2.95667380e−01 | 3.72286320e−01 | 2.05807462e−01 |
| 4.59593572e−02 | −1.45133555e−01 | 6.50750101e−01 | −2.60030419e−01 |
| 1.01201303e−01 | 3.19625139e−01 | 5.68488205e−04 | 4.22808416e−02 |
| 2.96549559e−01 | 1.34705501e−02 | 4.58653197e−01 | −8.37187171e−02 |
| −1.38285667e−01 | 4.80949849e−01 | 1.96492877e−02 | −4.01159793e−01 |
| 2.84761786e−01 | 7.97234178e−01 | −2.05270872e−01 | 7.34872818e−01 |
| 1.41422376e−01 | 3.40696186e−01 | 1.97139516e−01 | 2.05391154e−01 |
| −2.27694288e−01 | 5.10912947e−02 | 2.16169864e−01 | −5.34649845e−03 |
| 2.14290217e−01 | 1.60926849e−01 | −8.23444128e−03 | 3.54265392e−01 |
| 6.40056431e−01 | 4.23777938e−01 | 1.30192965e−01 | 1.41996980e−01 |
| 2.63166547e−01 | 1.31111741e−01 | 4.20935787e−02 | −8.92698485e−03 |
| 8.75176787e−01 | 5.00093475e−02 | −1.39243394e−01 | 9.31668282e−01 |
| 4.45045710e−01 | 4.02249023e−03 | 3.01300526e−01 | 5.38642526e−01] |
| [2.07107484e−01 | −3.57992575e−03 | 4.28457618e−01 | −1.98963180e−01 |
| 4.44810599e−01 | 3.16419959e−01 | 3.35316628e−01 | 4.36734915e−01 |
| 2.86746264e−01 | 2.65274961e−02 | −1.09853894e−01 | −4.37748462e−01 |
| −3.26122344e−01 | 1.45933524e−01 | −2.50978470e−01 | −7.82052800e−02 |
| −7.33153662e−03 | 1.83094963e−01 | −2.00780239e−02 | 6.08890772e−01 |
| 4.39763933e−01 | 2.31033310e−01 | −2.01388016e−01 | 4.29678798e−01 |
| −1.96559623e−01 | 2.39124060e−01 | 2.57887483e−01 | 2.57921636e−01 |
| 7.40302354e−02 | 1.16565675e−01 | 2.08322197e−01 | 3.07262003e−01 |
| 3.57872427e−01 | 5.78228474e−01 | 5.62359765e−02 | 1.08023301e−01 |
| −2.95873284e−01 | 5.34669280e−01 | 8.44261765e−01 | 2.81539798e−01 |
| −3.17623243e−02 | 2.27719560e−01 | 9.99587029e−03 | 7.25133494e−01 |
| 6.45157173e−02 | 6.73028454e−02 | 4.70026791e−01 | 9.62990969e−02 |
| 2.92960167e−01 | −2.11489603e−01 | 2.14466363e−01 | 1.17474943e−01 |
| 4.48905438e−01 | −8.23928490e−02 | 1.03321105e−01 | 2.22031265e−01 |
| 2.00213701e−01 | 1.21436633e−01 | 2.74540156e−01 | 2.89323092e−01 |
| 2.02247977e−01 | 4.46036369e−01 | −4.10590917e−02 | 2.19299540e−01 |
| 2.63661325e−01 | 3.99153858e−01 | 3.09220433e−01 | 5.14516532e−01 |
| −1.17062286e−01 | 3.13832223e−01 | −3.47377062e−02 | 3.10773462e−01 |
| 5.47599971e−01 | −2.08701044e−01 | −2.01508805e−01 | −1.93964727e−02 |
| 2.83362329e−01 | −3.36005129e−01 | 5.36521494e−01 | 1.40864238e−01 |
| 2.93958575e−01 | 4.95141506e−01 | 4.49982546e−02 | 8.35078657e−02 |
| 2.36362576e−01 | 1.71855971e−01 | 5.56468606e−01 | 4.23968673e−01 |
| 4.08565670e−01 | 3.83744955e−01 | 5.03830835e−02 | 4.19427156e−01 |
| 3.18354219e−01 | 3.11128467e−01 | −9.23227146e−02 | 1.66662440e−01 |
| 2.98215181e−01 | −4.17561922e−03 | 2.10347921e−01 | 1.78693101e−01 |
| 5.01175165e−01 | 2.80919820e−01 | 1.54905975e−01 | 4.91862297e−01 |
| 3.16608131e−01 | 2.31115729e−01 | 3.33971716e−02 | 1.30055889e−02 |
| 1.48727074e−01 | −5.49495853e−02 | 2.11359426e−01 | −1.35052511e−02 |
| 1.89771131e−02 | 1.26058921e−01 | 2.69148231e−01 | −1.98885123e−03 |
| 4.22587574e−01 | 1.60635203e−01 | −4.07143116e−01 | −5.39920449e−01 |
| 1.86105311e−01 | −3.35529707e−02 | 5.41471057e−02 | 3.12415779e−01 |
| −1.18477410e−02 | −1.67867854e−01 | 2.58782744e−01 | 4.76995036e−01 |
| 9.23619330e−01 | −2.52124161e−01 | 2.51121759e−01 | 2.52711862e−01 |
| 1.36421667e−03 | 1.54591026e−02 | −1.28445670e−01 | −3.06651473e−01 |
| 1.03695333e−01 | −8.11328217e−02 | 1.97882399e−01 | −9.56673548e−03 |
| 1.23012885e−01 | 3.76480162e−01 | −2.06594095e−01 | 2.15690553e−01 |
| 9.08249468e−02 | −9.95176211e−02 | 1.73657805e−01 | 2.85449535e−01 |

TABLE W$_h^1$-continued

| | | | |
|---|---|---|---|
| −6.95301406e−03 | 9.73460972e−02 | 1.79809421e−01 | 7.04701198e−03 |
| 5.81194222e−01 | 2.11375788e−01 | −1.76222473e−01 | −2.40321338e−01 |
| 2.96173513e−01 | −8.14616680e−02 | 4.34996001e−02 | 5.22280335e−01 |
| −1.54944956e−01 | 3.50725442e−01 | 1.07162535e−01 | 1.40596345e−01 |
| 7.18689114e−02 | 3.95449936e−01 | 2.40698546e−01 | 2.69155890e−01 |
| −1.31628171e−01 | −6.10473938e−02 | 3.95879090e−01 | −8.59847069e−02 |
| −2.48660874e−02 | 3.74237716e−01 | 3.36329430e−01 | 3.40036541e−01 |
| 2.66110897e−01 | 3.52780819e−01 | −2.36466616e−01 | 2.99127430e−01 |
| 2.17204630e−01 | −1.17215440e−01 | 4.71939743e−01 | 4.15751226e−02 |
| 2.57546395e−01 | 4.19879526e−01 | −6.30167872e−02 | 5.01912892e−01 |
| 2.00185657e−01 | 3.54516536e−01 | −3.74716818e−01 | −1.24414988e−01 |
| 6.42172039e−01 | 1.62168384e−01 | 1.04734302e−01 | −9.32921320e−02 |
| 1.64617747e−01 | 1.76072240e−01 | 2.22516149e−01 | −1.37944996e−01 |
| 1.41540214e−01 | 7.94779435e−02 | 3.80533546e−01 | 2.60600388e−01 |
| 1.49647623e−01 | 1.65895417e−01 | 4.27227408e−01 | −2.11992651e−01 |
| −4.69669746e−03 | −2.43149064e−02 | 2.61231005e−01 | 7.30470046e−02 |
| −5.26495986e−02 | −7.29869027e−03 | 6.38281584e−01 | 3.32314968e−01 |
| −9.97729413e−03 | 6.72807917e−02 | −3.30144279e−02 | −1.53609246e−01 |
| −1.46057859e−01 | 2.58618593e−01 | 5.20676672e−01 | −1.68223888e−01 |
| 3.36376667e−01 | −2.33781546e−01 | −1.45828411e−01 | 2.79469043e−01 |
| 1.89585075e−01 | 8.73440653e−02 | 3.14727843e−01 | −1.16708390e−01 |
| −2.48441130e−01 | 2.54542530e−01 | 1.79059252e−01 | 4.58772406e−02 |
| 2.18673736e−01 | 2.80825436e−01 | 2.72777438e−01 | 1.40652671e−01 |
| 8.88149291e−02 | −1.21360503e−01 | 3.66565511e−02 | 2.71161832e−02 |
| 1.53008878e−01 | 3.57913166e−01 | −7.52048790e−02 | 1.30553946e−01 |
| 6.35327160e−01 | 4.19188023e−01 | 4.53067273e−01 | 2.36192510e−01 |
| 1.44548506e−01 | 3.76858413e−01 | 2.08540469e−01 | 4.35429037e−01] |
| [−6.86296821e−02 | −9.14360732e−02 | 1.70629844e−01 | 2.09480315e−01 |
| −6.14338815e−02 | 5.58105297e−02 | 1.18251778e−01 | 8.92716497e−02 |
| 2.81394243e−01 | 3.10369805e−02 | 5.68336733e−02 | 6.28000021e−01 |
| 4.66756560e−02 | −2.51454026e−01 | −2.18962163e−01 | 6.87708914e−01 |
| 3.75060365e−02 | 2.11652189e−01 | 3.67330134e−01 | 2.23699376e−01 |
| 3.45968306e−02 | 2.13549018e−01 | 3.97881538e−01 | 1.68709740e−01 |
| 2.14786783e−01 | 3.93455893e−01 | −1.89189702e−01 | 7.97681361e−02 |
| −2.87640303e−01 | 5.25256157e−01 | 4.30929847e−02 | −1.29819185e−01 |
| −6.43370301e−02 | 6.97454885e−02 | 1.98841631e−01 | 1.00670367e−01 |
| 1.99337289e−01 | 3.16733658e−01 | 7.78761357e−02 | 3.13576162e−02 |
| 8.32923576e−02 | 3.80520880e−01 | 1.48692233e−01 | 1.29129305e−01 |
| 1.80167735e−01 | 1.12152379e−02 | 9.88104418e−02 | 3.01956117e−01 |
| −3.35709870e−01 | 2.43110638e−02 | 2.69405004e−02 | 1.76618733e−02 |
| −7.78393969e−02 | 1.60287932e−01 | −5.77325448e−02 | −4.14211266e−02 |
| −2.91872561e−02 | 4.54782426e−01 | 1.08626820e−01 | 3.59556705e−01 |
| 1.35769233e−01 | 8.36929753e−02 | 3.71864557e−01 | 2.65877247e−01 |
| −1.53246537e−01 | −5.89678101e−02 | 2.14856505e−01 | 4.86665517e−01 |
| 7.70822242e−02 | 1.64155051e−01 | −1.19887620e−01 | 4.61221129e−01 |
| −1.26647249e−01 | 2.56048858e−01 | 4.52334480e−03 | 2.09555760e−01 |
| −2.79089153e−01 | 8.83772150e−02 | 1.45771503e−01 | −2.16325164e−01 |
| 2.92233098e−02 | −5.88864833e−02 | 3.75907645e−02 | −3.24947760e−02 |
| −1.95826486e−01 | 4.75185245e−01 | 1.82565480e−01 | −2.96671450e−01 |
| −1.71433493e−01 | 2.00933769e−01 | 3.30756783e−01 | 1.35189757e−01 |
| 3.32801372e−01 | 1.04085557e−01 | 7.78297987e−03 | 8.05921033e−02 |
| 3.63644511e−01 | 2.65296161e−01 | 2.17533380e−01 | 1.07852973e−01 |
| 1.34578608e−02 | 4.14916538e−02 | 3.44657421e−01 | −3.44296917e−02 |
| 2.98835039e−01 | 4.08554412e−02 | −2.61058398e−01 | 1.73130810e−01 |
| −1.47288308e−01 | 1.22853629e−01 | −2.94173986e−01 | 2.12545946e−01 |
| 1.53489009e−01 | −2.68980384e−01 | 5.58794200e−01 | 2.35342413e−01 |
| 2.46239424e−01 | 2.30914891e−01 | −8.04341957e−02 | −1.04771838e−01 |
| 7.57964998e−02 | −2.09657192e−01 | 3.43703061e−01 | 9.92836356e−02 |
| 1.38225988e−01 | 3.91650200e−01 | −3.13291341e−01 | 1.75715581e−01 |
| 9.96649414e−02 | −1.59754291e−01 | 1.50259435e−01 | 3.58203389e−02 |
| 7.47226104e−02 | 2.88925707e−01 | 1.90622546e−02 | 3.27934176e−02 |
| 9.75140929e−03 | −4.95320670e−02 | −1.58556942e−02 | −1.37827367e−01 |
| 1.55864969e−01 | −2.30076283e−01 | −1.19636767e−01 | 3.35843533e−01 |
| −3.63034248e−01 | −2.12220456e−02 | −2.35278919e−01 | 4.99774814e−01 |
| 1.05369724e−01 | −1.18790865e−01 | 1.35766551e−01 | 4.54046756e−01 |
| 4.06924814e−01 | 3.59786987e−01 | 2.06913546e−01 | −9.60627664e−03 |
| −2.92637739e−01 | 4.53761011e−01 | −1.81445926e−01 | 5.40905036e−02 |
| 2.91579455e−01 | −1.87616982e−02 | −2.50343770e−01 | 1.30540356e−01 |
| −2.39730015e−01 | 2.51350254e−01 | 1.92251503e−01 | 4.47240502e−01 |
| 2.58047223e−01 | 1.90554917e−01 | −3.17005366e−01 | 2.23908782e−01 |
| 1.45027921e−01 | 2.53888041e−01 | −3.42415683e−02 | 1.90458298e−01 |
| 3.36283118e−01 | −2.79093564e−01 | −1.51192144e−01 | 1.12120822e−01 |
| −7.75860026e−02 | 1.87587634e−01 | 1.22587010e−01 | −8.43249038e−02 |
| 4.93495882e−01 | 3.78894024e−02 | 3.26891422e−01 | −1.29676849e−01 |
| 1.90176621e−01 | −9.44378898e−02 | −1.84696496e−01 | 1.47335958e−02 |
| −1.77398175e−01 | 2.68902719e−01 | 4.41196263e−01 | 1.39189929e−01 |
| 1.78878933e−01 | 1.03397794e−01 | 3.89613211e−01 | 2.70819979e−01 |
| 3.20861697e−01 | 3.06261986e−01 | 9.43627954e−02 | 1.56242214e−03 |
| 1.73523739e−01 | −2.45635256e−01 | 1.38979987e−03 | 3.73133302e−01 |
| 4.11395073e−01 | 7.38964230e−02 | 8.93227309e−02 | −2.42092788e−01 |

TABLE $W_h^1$-continued

| | | | |
|---|---|---|---|
| 1.79469734e−01 | 2.22018883e−02 | 2.64659435e−01 | 3.48270312e−02 |
| −3.44432332e−02 | 1.18722163e−01 | 1.49457514e−01 | 6.08826242e−02 |
| −3.06009911e−02 | 1.70751423e−01 | −3.79899532e−01 | 1.85900807e−01 |
| 3.08603942e−01 | 1.85158014e−01 | 1.78713292e−01 | 4.48160842e−02 |
| 3.74911666e−01 | 3.05558085e−01 | 3.97066027e−02 | 3.49575371e−01 |
| 2.94536293e−01 | −1.43522650e−01 | −9.85701680e−02 | 1.24734230e−01 |
| 7.95047939e−01 | 3.87826651e−01 | 3.68768305e−01 | 4.34679270e−01 |
| 8.20116624e−02 | 4.09070581e−01 | 2.09075257e−01 | 8.26870725e−02 |
| 2.26178378e−01 | 2.88088650e−01 | 7.55189732e−02 | −4.25261348e−01 |
| 2.12754115e−01 | 1.91896453e−01 | 1.24364436e−01 | 2.59216666e−01 |
| 9.75800864e−03 | −1.54060647e−02 | 1.76731366e−04 | 2.59448476e−02] |
| [2.87925184e−01 | −5.20922765e−02 | 4.33467478e−01 | 1.52635798e−01 |
| 4.22064096e−01 | 2.64116764e−01 | 4.84205574e−01 | 5.97269200e−02 |
| 4.01715040e−01 | 1.69547707e−01 | 1.09151530e−00 | 1.96065068e−01 |
| 4.64585513e−01 | 1.30539671e−01 | 3.77237290e−01 | −9.93976891e−02 |
| 1.21156842e−01 | 3.48954350e−01 | 3.00635308e−01 | −6.32998571e−02 |
| −1.41533669e−02 | 2.18618765e−01 | 1.02969810e−01 | 6.91542804e−01 |
| −5.38856648e−02 | 5.10119319e−01 | 2.82330867e−02 | 1.87640563e−02 |
| 1.66076601e−01 | 7.00246692e−01 | 3.26730251e−01 | 1.87271029e−01 |
| 8.94348860e−01 | −1.20776609e−01 | −2.39382852e−02 | 1.78963289e−01 |
| 4.52565759e−01 | −2.94829775e−01 | 3.98819894e−01 | 8.27521920e−01 |
| 2.32718468e−01 | 4.03294444e−01 | 2.62764603e−01 | 4.19542473e−03 |
| 7.12391853e−01 | 2.48992696e−01 | 5.44373691e−01 | 3.94698769e−01 |
| 2.13470891e−01 | 2.00790972e−01 | 3.54701169e−02 | 3.07660103e−01 |
| 2.04111964e−01 | 2.13475123e−01 | 3.77751231e−01 | 5.60502529e−01 |
| 2.94582367e−01 | 1.07643202e−01 | 9.88184288e−02 | 4.84593287e−02 |
| 6.66260347e−02 | 3.44126612e−01 | 2.88455814e−01 | 3.48773807e−01 |
| 3.93541157e−01 | 1.80304661e−01 | 1.88599303e−01 | 2.11807176e−01 |
| 2.52801627e−01 | 6.85566843e−01 | 6.35683477e−01 | 4.33247834e−01 |
| 5.91182649e−01 | 4.06648278e−01 | 5.20659804e−01 | 3.53284091e−01 |
| 2.35695198e−01 | 1.76781371e−01 | 7.15043604e−01 | 3.57889719e−02 |
| 3.35408062e−01 | 3.22427332e−01 | 3.08809966e−01 | 1.99262217e−01 |
| 4.43693221e−01 | 1.90196753e−01 | 4.83845770e−01 | −1.03842176e−01 |
| 2.53043771e−01 | 2.02179551e−01 | 5.15578985e−01 | 3.53991300e−01 |
| 2.42012292e−02 | 2.86001444e−01 | 4.82653975e−01 | 6.13024533e−01 |
| 7.44831041e−02 | 1.61050811e−01 | 3.00864398e−01 | 1.96234465e−01 |
| 5.24611294e−01 | 2.76553661e−01 | 1.00599639e−01 | 3.59871238e−01 |
| 3.84696305e−01 | 5.05728304e−01 | 6.02252424e−01 | 1.19564407e−01 |
| 5.08903749e−02 | 3.86469513e−01 | 2.03016713e−01 | 1.97612360e−01 |
| 4.41263884e−01 | −1.49661213e−01 | 2.91934758e−01 | −3.35036069e−02 |
| 4.70664620e−01 | −3.17551680e−02 | 2.27494940e−01 | −1.22687273e−01 |
| 7.88471103e−02 | 3.13957155e−01 | 4.82630074e−01 | 4.44247842e−01 |
| 3.53799701e−01 | 4.74319667e−01 | 7.80520618e−01 | 5.58994770e−01 |
| 6.83481336e−01 | 3.22423965e−01 | 5.94928861e−01 | 3.41358781e−01 |
| −1.83859468e−02 | −4.99982340e−03 | 3.36343020e−01 | 2.01305687e−01 |
| 1.07911989e−01 | −1.77775472e−01 | 1.59570992e−01 | 2.31401592e−01 |
| 6.17344916e−01 | −2.13684328e−02 | 1.21380888e−01 | 4.49428022e−01 |
| 1.50770470e−01 | 8.37836415e−02 | 4.46998745e−01 | 4.85141486e−01 |
| 2.64587164e−01 | 9.81520191e−02 | 1.01143733e−01 | 3.19718957e−01 |
| −3.70165817e−01 | 2.69132286e−01 | 1.31061941e−01 | 2.63806909e−01 |
| 1.93988100e−01 | 4.77644473e−01 | 3.29472929e−01 | 6.40803456e−01 |
| 3.63550454e−01 | 2.37174824e−01 | 1.56156287e−01 | 4.01336998e−01 |
| −1.38544897e−02 | 2.48555839e−01 | 5.79229653e−01 | 2.96033099e−02 |
| 1.33926952e−01 | 3.66947442e−01 | 3.75930488e−01 | 4.83200759e−01 |
| 7.76974678e−01 | 1.05361827e−01 | 8.64130780e−02 | −5.56124263e−02 |
| −1.38697058e−01 | 2.46067688e−01 | 4.91650164e−01 | 1.03047334e−01 |
| 6.23781204e−01 | 1.43600509e−01 | 6.21480905e−02 | 1.60103068e−02 |
| 2.56043017e−01 | −4.90218261e−03 | 6.21789515e−01 | −2.01763734e−02 |
| −1.99465320e−01 | 4.97212499e−01 | 5.51662445e−01 | 4.66526031e−01 |
| 2.40845308e−01 | 6.90203428e−01 | 3.53529751e−01 | 2.76877224e−01 |
| 2.68566966e−01 | −3.59150916e−01 | 1.07240468e−01 | 1.59538358e−01 |
| 4.57673013e−01 | 3.65843236e−01 | 8.62631500e−02 | 3.14352125e−01 |
| 7.89055109e−01 | 3.90691847e−01 | 8.12698901e−01 | 9.34509486e−01 |
| 1.29537433e−01 | 5.78152359e−01 | 6.65319383e−01 | 3.38744462e−01 |
| 3.86602104e−01 | 2.90380954e−03 | 3.72254521e−01 | 4.47981358e−01 |
| 3.56062740e−01 | 9.70904306e−02 | 3.34126055e−01 | −2.42758498e−01 |
| 1.60586372e−01 | 3.48459631e−01 | 4.12714124e−01 | −6.83524907e−01 |
| 2.04489946e−01 | 1.58827439e−01 | −3.38428527e−01 | −1.02260098e−01 |
| 4.03312773e−01 | 7.26395190e−01 | 3.82951409e−01 | 1.15518443e−01 |
| 2.89161116e−01 | −2.59731233e−01 | 4.26990896e−01 | 3.78770977e−01 |
| 3.60307008e−01 | 4.36408907e−01 | 7.01259822e−02 | 9.32186246e−01 |
| 4.20077592e−01 | 1.81800053e−01 | 3.48494560e−01 | 2.61641871e−02 |
| 3.46188605e−01 | 1.14315800e−01 | 6.74222589e−01 | 5.43738678e−02 |
| 1.11919791e−01 | 6.28609896e−01 | 4.73289430e−01 | 6.17169797e−01 |
| 5.54380119e−01 | 4.37528878e−01 | 3.43917042e−01 | 2.52160996e−01] |
| [−2.74885409e−02 | −1.27982020e−01 | 1.47522077e−01 | −5.02582908e−01 |
| 5.13119996e−01 | −3.03939208e−02 | 1.54366150e−01 | 2.16453731e−01 |
| −2.18930364e−01 | 6.38387322e−01 | 4.16737825e−01 | 2.25082517e−01 |
| −1.78542025e−02 | −1.01787351e−01 | 4.32046682e−01 | 4.73756492e−02 |
| 1.92585543e−01 | 4.20593530e−01 | 1.61299735e−01 | −2.75851315e−04 |

TABLE $W_h^1$-continued

| | | | |
|---|---|---|---|
| 2.36127526e−02 | 2.41746962e−01 | −6.75483095e−03 | 2.00391486e−02 |
| 2.86281779e−02 | 2.77373254e−01 | 1.84445649e−01 | −2.23043328e−03 |
| 2.98038721e−01 | 8.72092545e−02 | 3.22608083e−01 | −3.74172777e−01 |
| 4.86600429e−01 | 2.93062866e−01 | 2.89545774e−01 | 1.85526088e−01 |
| 1.48619004e−02 | 4.34611887e−01 | 3.67236376e−01 | −1.21231964e−02 |
| 3.74742329e−01 | 2.02701896e−01 | −3.02285105e−01 | 2.56254137e−01 |
| 1.06504031e−01 | 5.26884019e−01 | 1.60828039e−01 | 3.73711914e−01 |
| 4.34314013e−01 | 2.42683887e−01 | 3.42576951e−01 | 1.00341082e−01 |
| 4.64513302e−01 | 9.43596885e−02 | 1.79293305e−01 | 1.35962814e−01 |
| 5.42551577e−01 | 1.26454964e−01 | 9.11867499e−01 | 3.66532743e−01 |
| 2.85280850e−02 | 4.36453223e−01 | 3.27302396e−01 | 4.64062721e−01 |
| 5.60149364e−02 | −4.49138805e−02 | 1.07728697e−01 | 4.13344592e−01 |
| 5.53822666e−02 | 1.55190632e−01 | 2.09340796e−01 | −1.00341611e−01 |
| 4.44476098e−01 | −6.01667613e−02 | 1.96621776e−01 | 1.14447176e−01 |
| 6.17102027e−01 | 2.12991059e−01 | 1.93057477e−01 | 3.00530732e−01 |
| 1.07105456e−01 | 2.14034766e−01 | 2.26937816e−01 | 2.43365951e−02 |
| −8.48507509e−02 | 5.31760931e−01 | −1.10992238e−01 | 2.74608254e−01 |
| 2.08718568e−01 | −3.77867967e−02 | 3.66119593e−02 | 3.75438809e−01 |
| −5.73410233e−03 | −3.92844900e−02 | −2.19191238e−01 | −6.43431619e−02 |
| 4.56675351e−01 | −3.34305018e−02 | 6.83086663e−02 | 2.76103795e−01 |
| 1.78585291e−01 | 5.57138473e−02 | 3.72975558e−01 | 3.17143738e−01 |
| 4.63098347e−01 | 3.21011096e−01 | 5.47284663e−01 | 1.83392674e−01 |
| −2.83292569e−02 | 2.39124656e−01 | 4.40115571e−01 | 8.22520554e−02 |
| 1.94811940e−01 | 5.85052408e−02 | 6.16572857e−01 | −2.59408355e−02 |
| 4.72680360e−01 | 5.93821883e−02 | 4.49429564e−02 | 4.27684009e−01 |
| 1.58861697e−01 | −1.02253653e−01 | 4.88155246e−01 | 4.58844453e−01 |
| 3.27176034e−01 | −9.97682512e−02 | 4.31217393e−03 | 6.40639186e−01 |
| 2.31593549e−01 | 4.19722378e−01 | 1.32006556e−01 | 6.08170033e−01 |
| 9.16944817e−02 | 4.61963192e−03 | 2.57675350e−01 | 1.18147925e−01 |
| 1.84511557e−01 | 2.37769753e−01 | 9.77272242e−02 | −1.28198341e−01 |
| 2.86373019e−01 | 1.33688480e−01 | −4.36611623e−01 | 3.19926769e−01 |
| −1.01313941e−01 | 5.31916022e−01 | 3.85421701e−02 | 1.10113978e−01 |
| 3.06167454e−01 | 1.46184146e−01 | 5.03536999e−01 | −8.14318731e−02 |
| 2.76986122e−01 | 3.34137470e−01 | 1.13984659e−01 | 1.86537236e−01 |
| 2.43374303e−01 | −1.11882627e−01 | −2.94160008e−01 | 6.21662140e−01 |
| 2.70394892e−01 | 1.56674609e−01 | 1.88307211e−01 | 7.02422336e−02 |
| 1.37872979e−01 | −3.43112610e−02 | 2.77935892e−01 | 2.47681484e−01 |
| 1.84679285e−01 | 3.78370345e−01 | 5.69873810e−01 | −7.62086809e−02 |
| 1.00283310e−01 | 8.95226747e−02 | −1.47400782e−01 | 2.06391096e−01 |
| 5.41202188e−01 | −2.11035028e−01 | −4.06599976e−02 | 2.83669829e−01 |
| 1.58160627e−02 | 1.83853269e−01 | 3.63771319e−01 | 1.59871176e−01 |
| 6.90738559e−01 | 1.94576550e−01 | −4.64495003e−01 | −2.96228170e−01 |
| 9.39072445e−02 | −3.60227674e−02 | 2.69053459e−01 | 1.42317891e−01 |
| −8.06800053e−02 | 4.00884777e−01 | −1.64363712e−01 | 5.09871244e−01 |
| −2.42382318e−01 | 1.67617410e−01 | 1.51105905e−02 | 2.06371188e−01 |
| 5.66351414e−02 | 2.65383095e−01 | 1.58637762e−01 | 4.08060431e−01 |
| 7.40962522e−03 | 5.96933365e−01 | 3.76819789e−01 | 2.71341711e−01 |
| −3.35131198e−01 | 2.78287113e−01 | 1.13312621e−02 | 9.72626172e−03 |
| 3.03844690e−01 | −8.77607986e−02 | 7.62317032e−02 | 2.76414216e−01 |
| 5.33933103e−01 | −4.02969010e−02 | 1.38506621e−01 | 3.07073474e−01 |
| 2.83504516e−01 | 1.35734119e−02 | 8.39280635e−02 | 2.29977250e−01 |
| −4.62738901e−01 | 5.09012461e−01 | 1.12886555e−01 | 1.55763343e−01 |
| −1.04747012e−01 | −1.48414046e−01 | 3.21434110e−01 | 2.10944369e−01 |
| 3.47412199e−01 | 2.94001698e−01 | 1.00175790e−01 | −9.17444602e−02 |
| 3.57874393e−01 | 4.31285501e−01 | −7.01381937e−02 | 4.00489628e−01 |
| 1.21209346e−01 | 9.21874493e−02 | 1.64069980e−01 | 1.29767612e−01 |
| 7.70224109e−02 | 1.61341518e−01 | 5.77682853e−01 | 3.72503668e−01 |
| 3.46467733e−01 | 1.74016178e−01 | 2.36716524e−01 | 1.01274632e−01 |
| −5.02641723e−02 | 3.69258553e−01 | 4.75494415e−01 | 2.72931457e−01] |
| [2.66052693e−01 | −1.09312885e−01 | 3.26922745e−01 | 4.25384879e−01 |
| 9.88484383e−01 | 5.89975655e−01 | 1.00335039e−01 | −2.72320211e−02 |
| −1.33896753e−01 | 3.52768362e−01 | 1.05427332e−01 | 1.99131832e−01 |
| 4.83300805e−01 | 6.32493436e−01 | 2.92055637e−01 | 5.28050661e−01 |
| −2.13288009e−01 | −7.19781101e−01 | −4.33007509e−01 | 1.31086081e−01 |
| 1.29187614e−01 | 4.94205505e−01 | 1.04974955e−01 | 1.86477363e−01 |
| −7.60222003e−02 | 6.42105460e−01 | 2.66325563e−01 | 5.91600478e−01 |
| 9.82359722e−02 | 5.32247484e−01 | −4.47523564e−01 | 7.94221461e−02 |
| 4.82866406e−01 | −5.17952144e−01 | 1.42038986e−01 | −1.57301456e−01 |
| −9.16335657e−02 | −3.68504201e−02 | −3.13577741e−01 | 1.62757069e−01 |
| 1.86292484e−01 | 8.77499402e−01 | −3.19709390e−01 | −3.99633087e−02 |
| 5.99564314e−01 | 6.32583201e−01 | 3.15240234e−01 | −1.91070050e−01 |
| −2.84456849e−01 | 1.38345003e−01 | −1.22274496e−01 | −1.95029527e−01 |
| 1.76681895e−02 | 6.27453864e−01 | −7.96883702e−02 | 8.59498754e−02 |
| 3.12342167e−01 | −1.44803002e−01 | 1.04839481e−01 | 1.24245197e−01 |
| −2.30217442e−01 | 2.08423749e−01 | 1.23805538e−01 | 4.69964981e−01 |
| 1.14381686e−01 | 3.93883735e−01 | 3.83157134e−01 | −1.78468496e−01 |
| 7.39957094e−02 | 4.84277338e−01 | 3.01422566e−01 | 4.74913776e−01 |
| 5.48574567e−01 | −4.86993510e−03 | 2.29870364e−01 | 4.60723311e−01 |
| −1.55187324e−01 | 1.49186254e−01 | 1.09960461e−00 | −1.73988238e−01 |
| 2.95093030e−01 | 6.63388312e−01 | −1.49660870e−01 | 3.63657027e−01 |

TABLE $W_h^1$-continued

| | | | |
|---|---|---|---|
| −9.11900103e−02 | −7.28088260e−01 | 8.04607421e−02 | 4.87415165e−01 |
| 3.16093475e−01 | 1.48980096e−01 | 5.87813139e−01 | 3.77695531e−01 |
| 7.79834330e−01 | 5.23702085e−01 | −2.39674494e−01 | 3.46053764e−03 |
| 2.51497984e−01 | 4.49844599e−01 | 1.29350618e−01 | 1.58294842e−01 |
| 4.62488174e−01 | 3.52014214e−01 | 2.43095815e−01 | −1.16201304e−01 |
| 1.74972117e−01 | 2.17908904e−01 | 1.90708023e−02 | −4.04247254e−01 |
| −4.31802213e−01 | −8.19892213e−02 | 6.62848294e−01 | −1.60451323e−01 |
| 1.90574124e−01 | 5.19428372e−01 | 4.95462537e−01 | 1.52526513e−01 |
| −3.86612028e−01 | −2.18758538e−01 | 3.99835169e−01 | 2.67585162e−02 |
| 2.91142315e−01 | 4.60788727e−01 | 4.34913933e−01 | −1.38770025e−02 |
| 5.66507697e−01 | 8.28779221e−01 | 2.24932387e−01 | 5.59872270e−01 |
| −4.05458808e−02 | 1.95657443e−02 | −5.49737692e−01 | 8.05511549e−02 |
| 4.03203875e−01 | 3.90146017e−01 | 9.78775501e−02 | −3.48773785e−02 |
| 1.11449277e−02 | 1.14449191e−00 | −4.49678712e−02 | 2.72637218e−01 |
| 4.21124756e−01 | 3.21380883e−01 | −4.39040303e−01 | 4.43415940e−01 |
| −2.64147043e−01 | 5.25471807e−01 | 1.24774665e−01 | 1.60875559e−01 |
| 7.24393129e−01 | 3.08687806e−01 | 3.21362615e−01 | 2.08031401e−01 |
| 1.50959700e−01 | 4.33056027e−01 | 2.93147266e−01 | 1.27370819e−01 |
| −5.16043156e−02 | 1.03994858e−00 | 3.73838127e−01 | 4.03673977e−01 |
| 4.48782831e−01 | 1.62464470e−01 | 2.68120497e−01 | 5.55745721e−01 |
| 1.51030749e−01 | 2.14134946e−01 | 6.16632402e−01 | −1.72988012e−01 |
| 3.13803524e−01 | 7.80650318e−01 | 1.10628895e−01 | 3.55909795e−01 |
| 1.70273975e−01 | 3.31330359e−01 | 1.43128306e−01 | −4.39620793e−01 |
| 7.10411131e−01 | 3.09987098e−01 | 1.95796844e−02 | 1.92522004e−01 |
| 4.16166604e−01 | 4.23962861e−01 | 5.08211136e−01 | −1.21125374e−02 |
| 3.97531599e−01 | 1.71812490e−01 | 2.49935895e−01 | 2.20309302e−01 |
| 5.27393460e−01 | 1.06040329e−01 | −9.32935346e−03 | 4.75139439e−01 |
| 2.18508393e−01 | 2.85954122e−02 | 9.89768922e−01 | 3.38287175e−01 |
| 3.60244364e−01 | 2.32515186e−01 | −4.05964330e−02 | 1.62358452e−02 |
| 1.11514008e−00 | 2.30956867e−01 | 2.92152137e−01 | 3.25403363e−01 |
| 6.16132557e−01 | −1.96906954e−01 | −2.84595102e−01 | 1.62093133e−01 |
| 3.45519036e−01 | 2.75721967e−01 | −1.78687587e−01 | −1.69214904e−01 |
| 2.21033812e−01 | 5.20916939e−01 | −1.98152289e−01 | −1.54934898e−01 |
| 2.43015781e−01 | 2.53439635e−01 | 3.39049220e−01 | −4.59370643e−01 |
| 3.12983215e−01 | −3.75153929e−01 | 3.16480212e−02 | −1.22919530e−01 |
| 1.28761604e−01 | 1.94906220e−02 | 1.94468588e−01 | 1.52341887e−01 |
| 3.69913608e−01 | 7.51181543e−01 | 4.34656292e−01 | 6.60593033e−01 |
| 4.43574458e−01 | −8.93749833e−01 | 2.03964174e−01 | 1.89056650e−01 |
| 3.58463466e−01 | 2.50721246e−01 | −1.36089116e−01 | 1.55370966e−01 |
| −7.44440546e−03 | 7.96904564e−01 | 9.42902982e−01 | −3.81391346e−01 |
| −2.97525555e−01 | 5.85841648e−02 | −2.83345550e−01 | 2.08908543e−01 |
| 3.68302912e−01 | 6.63931668e−02 | −2.52036929e−01 | 7.96552673e−02 |
| −5.53771615e−01 | 2.51338005e−01 | 7.07988262e−01 | 4.19978887e−01] |
| [1.30050644e−01 | 2.20481351e−01 | 4.28487480e−01 | −8.79194811e−02 |
| 4.92311627e−01 | 2.37149164e−01 | 1.26509950e−01 | −1.22001082e−01 |
| 1.55146956e−01 | 1.37559637e−01 | 2.53028423e−01 | −5.87908691e−03 |
| −9.18942988e−02 | 1.37693331e−01 | 1.08109908e−02 | −1.18141323e−01 |
| −9.57197137e−03 | 3.17531914e−01 | 2.65821546e−01 | 4.29188982e−02 |
| 2.69829005e−01 | 2.79156238e−01 | −1.35149583e−01 | 1.12851977e−01 |
| 1.78368643e−01 | 1.23589613e−01 | 1.08444713e−01 | 1.37645617e−01 |
| 2.25168496e−01 | −2.67250068e−03 | 4.08344448e−01 | 1.67786419e−01 |
| 1.17233582e−01 | −1.97707452e−02 | 9.92493406e−02 | 1.25765011e−01 |
| −1.83416471e−01 | −3.62605825e−02 | 2.10590705e−01 | 4.56165709e−02 |
| 3.31401527e−01 | −1.04465634e−01 | 2.04618856e−01 | 2.49273498e−01 |
| 1.27787054e−01 | 1.65316492e−01 | 2.97180563e−01 | −5.99412667e−03 |
| 2.46428102e−01 | −2.00735644e−01 | 1.05860345e−01 | 3.01998764e−01 |
| 1.77870214e−01 | 3.47610340e−02 | 3.86425942e−01 | 1.01343378e−01 |
| −6.15942851e−02 | 1.41439587e−01 | 3.52167189e−02 | −1.31867565e−02 |
| 1.47006050e−01 | −6.53030500e−02 | 1.38414443e−01 | 4.28303108e−02 |
| 7.47738034e−02 | 1.27094999e−01 | 1.11987188e−01 | 1.94351092e−01 |
| 3.14085066e−01 | 1.61887899e−01 | −2.33215228e−01 | 2.63226151e−01 |
| 2.00427771e−01 | −2.89418083e−02 | −1.35740312e−02 | 2.69002408e−01 |
| 1.29725993e−01 | −1.45924002e−01 | 5.11868484e−02 | −1.30121946e−01 |
| −7.03098774e−02 | 5.58138229e−02 | 1.67427525e−01 | −4.63071540e−02 |
| 2.34124102e−02 | 3.45913589e−01 | 1.85640514e−01 | 2.22598061e−01 |
| 1.46563724e−01 | −5.11287868e−01 | −1.67198405e−01 | 2.22459346e−01 |
| 1.69820696e−01 | 2.94500023e−01 | 1.36504024e−01 | 3.09806108e−01 |
| −8.99820477e−02 | 3.11905652e−01 | 2.51714624e−02 | 1.08745709e−01 |
| 1.07310250e−01 | −1.92958653e−01 | −8.73473063e−02 | 2.87268341e−01 |
| 3.79928082e−01 | 4.04346175e−02 | 1.98280841e−01 | 1.33236185e−01 |
| 3.73447776e−01 | 7.24474043e−02 | 3.68815064e−01 | −1.95531528e−02 |
| 2.49819338e−01 | −1.42915145e−01 | 1.27191886e−01 | 3.02745104e−01 |
| 1.76114932e−01 | 5.54505944e−01 | 1.59648523e−01 | 3.54002953e−01 |
| −5.13706431e−02 | 8.72767866e−02 | −1.81623429e−01 | 2.65494168e−01 |
| 1.00561470e−01 | 8.30464661e−02 | 4.01950739e−01 | 9.02598575e−01 |
| 7.66331032e−02 | −8.68076272e−03 | −5.11360951e−02 | 1.43168211e−01 |
| 3.93342316e−01 | 1.09393448e−01 | 1.16671540e−01 | −1.49159610e−01 |
| −3.13358486e−01 | 1.00735798e−02 | 1.13305345e−01 | 1.02222435e−01 |
| 3.09835702e−01 | 2.04401731e−01 | −2.32546523e−01 | −1.05278634e−01 |
| −3.10725477e−02 | 2.91212708e−01 | 1.15226150e−01 | 1.73085839e−01 |

TABLE $W_h^1$-continued

| | | | |
|---|---|---|---|
| 2.90285259e−01 | 2.54225850e−01 | 1.64841160e−01 | −6.35907985e−03 |
| −1.18504398e−01 | 1.11533165e−01 | −1.24888763e−01 | 3.99742246e−01 |
| 6.68952763e−02 | 1.73306555e−01 | 1.05027832e−01 | 1.76784948e−01 |
| −1.25148878e−01 | 1.92048162e−01 | 7.47291073e−02 | −1.24023162e−01 |
| −6.01335503e−02 | 1.68321788e−01 | 1.60012469e−01 | 4.10269722e−02 |
| 2.83451080e−01 | −3.92820239e−02 | 2.96653777e−01 | 2.27293540e−02 |
| 9.69765931e−02 | 2.90210962e−01 | 6.43994212e−02 | 2.86702722e−01 |
| 1.97282489e−01 | −1.12766260e−01 | 4.01521504e−01 | −1.72709133e−02 |
| −3.42831463e−02 | 6.07409589e−02 | 1.54889956e−01 | −1.54343829e−01 |
| −2.44310498e−03 | −1.07975295e−02 | −4.09099460e−02 | 1.15893438e−01 |
| −4.55703102e−02 | 2.16890648e−01 | −1.58876956e−01 | −9.93356183e−02 |
| −7.30251819e−02 | 6.92402199e−02 | 3.14627379e−01 | 2.17386380e−01 |
| 6.91092946e−03 | −1.65003841e−03 | 1.17672674e−01 | 1.48618728e−01 |
| 1.66484043e−02 | 3.25410753e−01 | 7.87368342e−02 | 1.59048572e−01 |
| 1.14431120e−01 | 3.01662594e−01 | 3.61884087e−01 | 1.66312695e−01 |
| 2.26374120e−01 | 1.20185390e−01 | 2.19615817e−01 | 4.01726328e−02 |
| 1.95961416e−01 | 4.46930945e−01 | 4.89774533e−02 | 2.67577618e−01 |
| 1.21214770e−01 | −2.92249620e−01 | 4.32504341e−02 | −1.07399084e−01 |
| −8.18360820e−02 | 3.30299646e−01 | 3.84728402e−01 | 3.58179808e−01 |
| 6.89527318e−02 | −1.21660665e−01 | 2.15633050e−01 | −7.45783150e−02 |
| 4.37592238e−01 | −1.07789757e−02 | 6.84921443e−02 | 1.06725134e−01 |
| 2.69104660e−01 | 2.28209663e−02 | −2.22016111e−01 | 2.18555294e−02 |
| 6.98229894e−02 | 7.06189871e−02 | 2.92067081e−01 | 8.82338136e−02 |
| 1.03353254e−01 | 1.03845015e−01 | 4.84052449e−02 | 1.61239341e−01 |
| 2.28788912e−01 | 9.19847004e−03 | 1.71751574e−01 | 5.11283353e−02 |
| 6.23590127e−02 | 2.78378397e−01 | −1.22400582e−01 | 1.16821369e−02 |
| 2.72150338e−01 | 3.03074121e−01 | −1.23465210e−02 | 3.58681887e−01] |
| [2.88019598e−01 | −1.07016325e−01 | 5.48631132e−01 | −3.48360762e−02 |
| 3.91965955e−01 | 1.36439696e−01 | 4.78890926e−01 | 6.27318025e−01 |
| 3.44555765e−01 | −3.78970429e−02 | 9.38858613e−02 | 1.54127628e−01 |
| 8.83979723e−02 | 3.27610667e−03 | −1.55331060e−01 | 1.95791855e−01 |
| 2.63746470e−01 | −1.14860222e−01 | −4.32223715e−02 | 3.38242888e−01 |
| 4.21196073e−01 | 4.01465595e−01 | −4.58846956e−02 | 3.95027697e−01 |
| −1.66728169e−01 | 6.64165676e−01 | 8.00659120e−01 | 4.48198318e−01 |
| −2.03009039e−01 | 7.53180757e−02 | 5.30532837e−01 | 2.94233114e−01 |
| 4.25634623e−01 | 3.64384085e−01 | 1.19838201e−01 | 6.85460865e−02 |
| −1.19190559e−01 | 1.85684368e−01 | 4.07093287e−01 | 2.91196138e−01 |
| 2.93629140e−01 | 1.33841619e−01 | −3.01258147e−01 | −1.25319093e−01 |
| −1.37979746e−01 | 2.41693556e−01 | 4.44694132e−01 | −1.37018353e−01 |
| 4.62084934e−02 | −1.22941602e−02 | 1.02572426e−01 | 4.75457251e−01 |
| 1.40176073e−01 | 5.82174718e−01 | 3.22981179e−01 | 2.70119041e−01 |
| −1.12760127e−01 | 1.92953989e−01 | 4.43415880e−01 | 3.25400084e−01 |
| 1.06252559e−01 | 5.65892696e−01 | 1.75358653e−01 | 5.31896651e−01 |
| 1.98997781e−02 | 4.49652821e−01 | 4.91218895e−01 | 4.08994794e−01 |
| −2.69193113e−01 | −5.79972528e−02 | 1.21620685e−01 | 1.84555084e−01 |
| 3.98986012e−01 | −9.84088928e−02 | 4.49536353e−01 | −6.66165277e−02 |
| 1.71935603e−01 | 4.69983257e−02 | 4.52238768e−01 | 7.33393848e−01 |
| −1.42222852e−01 | 4.68346924e−01 | 2.78775126e−01 | −4.32199910e−02 |
| −4.49422449e−02 | 3.51801962e−01 | 5.98798096e−01 | 5.94128907e−01 |
| 5.92272580e−01 | 5.05020618e−01 | 3.45271677e−01 | 7.21049774e−03 |
| 2.68338680e−01 | 5.56317031e−01 | 9.90482979e−03 | 2.00326756e−01 |
| −1.23324044e−01 | 3.57125849e−01 | 1.11450963e−01 | 4.40285563e−01 |
| 3.38126183e−01 | 3.42576176e−01 | 2.36536622e−01 | 1.67701364e−01 |
| 3.15035582e−01 | 3.80449109e−02 | 2.81325758e−01 | 6.62490353e−03 |
| 5.63747466e−01 | 2.35728353e−01 | −1.16470054e−01 | 3.77014577e−01 |
| 2.49176417e−02 | 3.02126706e−01 | 2.28798434e−01 | 1.92066103e−01 |
| 4.53979939e−01 | 1.54760048e−01 | 4.08864439e−01 | 5.88920433e−03 |
| 1.04456522e−01 | 4.90366342e−03 | 2.44964913e−01 | 4.82548773e−02 |
| 4.12538767e−01 | −9.82986242e−02 | 2.44231746e−01 | 4.43616182e−01 |
| 3.92326474e−01 | 6.55513955e−04 | 4.17587698e−01 | 1.28582940e−01 |
| 2.86889970e−01 | 4.14989829e−01 | 3.63963604e−01 | −4.63062674e−01 |
| 3.38582426e−01 | −1.03079773e−01 | 2.37230211e−01 | −8.66823196e−02 |
| 3.20520818e−01 | 4.85851884e−01 | 1.78746417e−01 | 6.16743788e−02 |
| 3.04857641e−01 | 1.17007263e−01 | 2.89086193e−01 | 5.35596430e−01 |
| 3.89313638e−01 | 1.40909076e−01 | 1.69627711e−01 | 3.38251069e−02 |
| 6.45524204e−01 | 6.11838162e−01 | −3.59542042e−01 | 7.19315782e−02 |
| 3.46161753e−01 | −3.88850681e−02 | −1.57313541e−01 | 4.59036916e−01 |
| −5.99946305e−02 | 2.02555299e−01 | 5.75201452e−01 | 4.42304015e−01 |
| −1.41359910e−01 | 2.81368405e−01 | 3.70596617e−01 | 1.76453948e−01 |
| 3.45394313e−01 | 5.72694242e−02 | 8.73898044e−02 | 1.46605998e−01 |
| 2.06153512e−01 | 1.49826244e−01 | 4.30553466e−01 | 3.70524406e−01 |
| 9.38256681e−02 | 4.75834720e−02 | 1.32518291e−01 | 5.88533357e−02 |
| 1.54765457e−01 | 6.47447305e−03 | 2.46047348e−01 | −1.42796421e−02 |
| −9.08342563e−03 | 9.01592493e−01 | 8.05875519e−04 | 7.26664215e−02 |
| 2.31514484e−01 | 3.76776606e−01 | −3.10474355e−02 | 2.06946686e−01 |
| 4.71752495e−01 | 1.23989150e−01 | 1.64551675e−01 | 2.03919858e−01 |
| −4.00864109e−02 | 1.31585002e−01 | 4.05949950e−01 | 1.51733324e−01 |
| 2.30178878e−01 | 4.95310932e−01 | 5.46461418e−02 | 3.85392420e−02 |
| 1.97816059e−01 | 1.31741107e−01 | 5.36410570e−01 | 7.25300312e−02 |
| 2.46179208e−01 | 7.24128485e−02 | 3.92145991e−01 | 4.98118222e−01 |

TABLE $W_h^1$-continued

| | | | |
|---|---|---|---|
| −1.35900646e−01 | 1.50499150e−01 | 5.33976495e−01 | 3.95539105e−01 |
| 1.48656219e−01 | 1.91121101e−01 | −1.94635510e−01 | 2.88443685e−01 |
| 1.77260205e−01 | 2.50111490e−01 | 2.49388248e−01 | −7.84495175e−02 |
| 8.50357562e−02 | −2.52450079e−01 | −8.16103593e−02 | 2.76272446e−01 |
| 3.21872622e−01 | −3.55405845e−02 | 6.38146460e−01 | 1.90835938e−01 |
| 2.82632709e−01 | −8.75111520e−02 | 2.81999350e−01 | 3.10802963e−02 |
| 1.14842050e−01 | 8.44797343e−02 | 2.65838765e−02 | 5.24179161e−01 |
| 3.92295122e−01 | 5.80541492e−02 | 1.59332514e−01 | −2.91858241e−02 |
| 3.04047257e−01 | 2.95596123e−01 | 1.00438602e−01 | 1.08884558e−01 |
| 6.05896473e−01 | 1.46094278e−01 | 3.12605381e−01 | 2.22794428e−01 |
| 2.82880753e−01 | 4.67847973e−01 | 2.41743743e−01 | 1.21576421e−01] |
| [2.66554598e−02 | 2.88669288e−01 | −8.56460482e−02 | −5.40075064e−01 |
| −2.14745700e−01 | −1.41519643e−01 | 1.53002903e−01 | −6.10119626e−02 |
| 1.65261582e−01 | −2.28635341e−01 | 1.65279031e−01 | −7.26920832e−03 |
| 3.71661425e−01 | 2.05352873e−01 | 9.10978615e−02 | 4.81508039e−02 |
| 2.75702238e−01 | −1.96898028e−01 | −1.06963445e−03 | 1.23393029e−01 |
| 7.39579275e−02 | −3.04746866e−01 | 5.47141172e−02 | 1.07723184e−01 |
| 4.97998558e−02 | 1.27808407e−01 | −1.83811128e−01 | 1.40470013e−01 |
| −6.72448799e−02 | −2.55461037e−01 | 2.80212402e−01 | 1.98507935e−01 |
| 1.97333813e−01 | −9.16313380e−02 | 1.65758371e−01 | 1.00955106e−01 |
| −1.39327735e−01 | −1.23536766e−01 | −9.91885886e−02 | −5.56200705e−02 |
| −7.34810606e−02 | 1.27741814e−01 | 1.85054511e−01 | −1.49519751e−02 |
| 4.47452843e−01 | −1.20551638e−01 | −3.65588069e−02 | 2.80160531e−02 |
| −1.68112352e−01 | 3.11400414e−01 | −2.02098668e−01 | −4.30391319e−02 |
| 1.45755634e−01 | −3.78212512e−01 | −2.05384761e−01 | −6.64499253e−02 |
| 4.29674119e−01 | −3.15469056e−01 | 6.36678264e−02 | −2.10388571e−01 |
| −3.20526809e−01 | 1.42377391e−01 | 6.18749224e−02 | 2.73403954e−02 |
| 4.38531220e−01 | 3.14481109e−01 | −3.83547805e−02 | −2.04420835e−01 |
| 3.93450946e−01 | −1.40958369e−01 | 2.04980493e−01 | −6.23092912e−02 |
| 1.16050258e−01 | 6.51488826e−02 | 1.67101458e−01 | 8.28883573e−02 |
| 2.54481435e−01 | −2.39050835e−02 | −3.27710845e−02 | −2.88836539e−01 |
| −7.15660304e−02 | −6.05459400e−02 | 3.45115811e−01 | 3.06921959e−01 |
| 8.83154944e−02 | −3.99532206e−02 | 1.18047141e−01 | −1.41562790e−01 |
| 1.10566281e−01 | −3.96482758e−02 | −2.83735283e−02 | −3.30608189e−01 |
| 7.02700540e−02 | 1.89070985e−01 | −1.01920843e−01 | −3.52346674e−02 |
| −4.18178618e−01 | 1.76267046e−02 | 3.17998342e−02 | −4.94727530e−02 |
| −1.63052544e−01 | −1.68271586e−01 | 8.80442634e−02 | −3.23139727e−01 |
| 1.56824049e−02 | 2.69336905e−01 | 8.60732719e−02 | 3.76043946e−01 |
| 2.49807760e−02 | 1.40936583e−01 | 2.92928725e−01 | 1.25746027e−01 |
| 7.50667080e−02 | −2.60375351e−01 | −7.86828473e−02 | 6.67348085e−03 |
| 1.13448456e−01 | 1.86740942e−02 | 1.38004094e−01 | −3.85322988e−01 |
| 7.15608746e−02 | 1.80581391e−01 | −2.94893950e−01 | −1.75539572e−02 |
| −2.53054909e−02 | 1.57646239e−01 | −2.09500626e−01 | −1.44888043e−01 |
| 1.05249308e−01 | 1.85824677e−01 | 4.12847459e−01 | −4.88763154e−02 |
| 9.79153216e−02 | 8.92293379e−02 | 6.30623400e−02 | 1.45089431e−02 |
| 1.07442848e−01 | 1.90934062e−01 | 6.45535290e−02 | 1.79745331e−01 |
| −2.22863052e−02 | −1.02546297e−01 | −1.40340418e−01 | −1.54659748e−01 |
| 4.93475765e−01 | 2.55441993e−01 | −2.49028534e−01 | −2.07604498e−01 |
| 1.93860352e−01 | 3.23059380e−01 | 2.55939454e−01 | −2.35482469e−01 |
| 1.08667836e−01 | −1.73564672e−01 | 2.00379163e−01 | 4.81274247e−01 |
| −2.44721789e−02 | −6.78615943e−02 | 8.49198177e−02 | 2.29180995e−02 |
| −3.61411795e−02 | 7.73509741e−02 | 1.65981516e−01 | −3.54725420e−02 |
| 1.95265695e−01 | −2.64982402e−01 | 1.40268113e−02 | −3.60219926e−01 |
| 5.22302315e−02 | −1.47977039e−01 | 1.02783017e−01 | 2.27425210e−02 |
| 2.34316364e−01 | 1.16658859e−01 | −1.56221958e−02 | 1.61981881e−01 |
| 2.15763777e−01 | 1.00274943e−01 | 3.23540926e−01 | −1.42793125e−02 |
| 6.87034875e−02 | −6.42343685e−02 | 1.06056839e−01 | −2.97973827e−02 |
| −6.82685524e−02 | −3.02682310e−01 | 1.17248707e−01 | 1.36582538e−01 |
| 8.49864855e−02 | 3.16731155e−01 | 5.58754653e−02 | −2.07757741e−01 |
| 1.79357976e−02 | 9.20302942e−02 | −2.07384601e−01 | −3.31772506e−01 |
| 1.25240892e−01 | 8.95250663e−02 | 1.81570783e−01 | −8.36258531e−02 |
| 1.25053734e−01 | 9.48148668e−02 | 1.75509125e−01 | 2.36045763e−01 |
| 1.02787048e−01 | −1.69042666e−02 | −1.13476187e−01 | 1.55384019e−01 |
| 4.65611815e−02 | −1.08126737e−01 | 2.31263619e−02 | 2.73999363e−01 |
| −7.14748949e−02 | 5.55393696e−02 | −2.62799859e−01 | −1.30709425e−01 |
| −4.44698118e−04 | −2.63757318e−01 | −2.03564763e−02 | 2.96662748e−01 |
| 1.14187032e−01 | 6.23883009e−02 | 4.10287455e−02 | 2.75594294e−01 |
| −1.18446842e−01 | 1.61846802e−01 | 3.64267342e−02 | 2.29403019e−01 |
| −4.06835414e−03 | 3.26973796e−02 | −3.88274223e−01 | 2.72323102e−01 |
| 1.00356869e−01 | −4.52106863e−01 | 1.82689548e−01 | 5.15861750e−01 |
| −8.60550851e−02 | 5.67303300e−02 | 1.03793718e−01 | 7.59117305e−02 |
| −2.03360453e−01 | 3.20730843e−02 | 6.33173510e−02 | 4.70428795e−01 |
| 3.52009237e−02 | 1.09696425e−01 | −7.46008754e−02 | 1.94411713e−03 |
| −2.08691597e−01 | 2.35115625e−02 | −9.52472910e−02 | 5.80557734e−02 |
| −5.60044311e−02 | 1.94738388e−01 | −2.96858847e−01 | 1.15294077e−01] |
| [−1.67056441e−01 | −9.89683568e−02 | −1.30625904e−01 | 2.19850600e−01 |
| 2.01185256e−01 | −1.95418477e−01 | −2.95081791e−02 | −1.46047594e−02 |
| 3.56528163e−01 | −3.11539233e−01 | 2.32130066e−01 | −2.01890841e−01 |
| 2.00609833e−01 | 1.74349882e−02 | −1.77423760e−01 | 2.03183182e−02 |
| 2.00700581e−01 | −4.50284481e−02 | 1.23794287e−01 | −1.58357292e−01 |

TABLE $W_h^1$-continued

| | | | |
|---|---|---|---|
| 7.37873539e−02 | 2.45953556e−02 | −7.09280744e−02 | 8.79411399e−02 |
| 1.17357627e−01 | −3.63077193e−01 | 5.82258068e−02 | 3.03176939e−02 |
| 1.62089884e−01 | 6.38427883e−02 | 9.35330838e−02 | −2.67763287e−01 |
| 7.79279247e−02 | −1.67366743e−01 | 2.52056867e−02 | −1.98479053e−02 |
| −1.00351617e−01 | 1.89338297e−01 | 3.57552692e−02 | 1.82180539e−01 |
| −1.24370977e−01 | −8.16899016e−02 | 9.87133682e−02 | 3.34343821e−01 |
| −1.11409336e−01 | 3.98215264e−01 | −7.36244991e−02 | 1.12201147e−01 |
| −8.07527378e−02 | 1.12852668e−02 | 1.02578744e−01 | 5.25973774e−02 |
| 1.19960137e−01 | −1.50153741e−01 | 1.56287745e−01 | 1.69354320e−01 |
| −1.21816486e−01 | 1.42463192e−01 | −3.44545484e−01 | 1.01992838e−01 |
| 5.79712652e−02 | 3.21494460e−01 | 2.06072390e−01 | 4.54138219e−03 |
| 4.41216193e−02 | 7.02626631e−02 | 1.07519254e−01 | −1.08131029e−01 |
| 2.92725056e−02 | 2.54280090e−01 | 2.46058121e−01 | 7.03338010e−04 |
| −5.12677841e−02 | 1.38999417e−01 | 5.79359941e−02 | 1.95712253e−01 |
| −3.13503057e−01 | 1.91272929e−01 | 3.98347713e−03 | 3.52505594e−02 |
| 1.95536837e−01 | −6.17442001e−03 | 1.13992142e−02 | −7.82741532e−02 |
| −5.95827848e−02 | 3.83582152e−02 | 1.19309373e−01 | 3.38119775e−01 |
| 3.38437110e−01 | 4.22975980e−02 | −4.02276069e−02 | 1.34488776e−01 |
| 1.65918112e−01 | −1.45933986e−01 | 4.54619735e−01 | 9.13867205e−02 |
| −6.07358932e−01 | −1.00137711e−01 | 1.60886183e−01 | 3.22137475e−02 |
| −1.01758204e−01 | −1.03357978e−01 | 1.45867124e−01 | −3.57380867e−01 |
| 5.45326881e−02 | −2.22793198e−03 | −2.95873620e−02 | 4.24254596e−01 |
| 1.19611874e−01 | 1.12140715e−01 | 4.77416873e−01 | −2.49813020e−01 |
| −3.18619013e−01 | −2.26880223e−01 | 8.83581117e−02 | −3.99802886e−02 |
| 8.70112181e−02 | 2.18290120e−01 | 1.38321087e−01 | 8.16743225e−02 |
| 3.24069649e−01 | 1.69170722e−02 | −1.82639621e−02 | −2.11509615e−02 |
| −2.38640662e−02 | 1.22629739e−01 | −1.71370029e−01 | −5.27214818e−02 |
| 4.72445553e−03 | 3.00378412e−01 | 9.26852152e−02 | 3.06669742e−01 |
| 1.86946779e−01 | −1.45945311e−01 | 2.23103985e−01 | 1.93181008e−01 |
| 2.72300303e−01 | 1.45458847e−01 | −3.40847634e−02 | 2.02741280e−01 |
| −3.16283852e−02 | −4.49171476e−02 | 3.38783771e−01 | −6.31582644e−03 |
| 8.57113823e−02 | −3.20828222e−02 | 1.22007042e−01 | 3.49405669e−02 |
| −3.80833372e−02 | −1.80544928e−02 | 6.10797433e−04 | −4.25802432e−02 |
| 3.00136488e−02 | −1.10313736e−01 | −1.22482583e−01 | −1.74895599e−02 |
| −2.92639315e−01 | −5.65517209e−02 | −1.38750240e−01 | −5.57480790e−02 |
| −1.41991973e−01 | 9.26781222e−02 | −1.49971649e−01 | 2.12011173e−01 |
| 8.47494975e−02 | 2.26432353e−01 | −7.59585202e−02 | −1.31212488e−01 |
| 2.80553162e−01 | −1.22706793e−01 | −6.63251057e−02 | −1.14671253e−01 |
| 4.03419703e−01 | 9.09717977e−02 | 2.71461289e−02 | 1.73161387e−01 |
| 1.22930497e−01 | 3.54659557e−02 | 3.43996286e−01 | 3.15644175e−01 |
| 9.18266997e−02 | 3.40304011e−03 | 3.63443822e−01 | 4.92256023e−02 |
| −6.54310361e−02 | −2.91316777e−01 | 9.96005163e−02 | 6.23764209e−02 |
| −1.46537777e−02 | 9.68311280e−02 | −1.59784600e−01 | 3.45792808e−02 |
| −5.45173883e−02 | −1.81066737e−01 | −8.91168937e−02 | 3.18141878e−01 |
| 2.39484265e−01 | 2.43266389e−01 | −6.26244470e−02 | 1.07117176e−01 |
| 6.08246364e−01 | 7.51197059e−03 | −8.99603590e−02 | −6.44253865e−02 |
| 7.16013685e−02 | 3.36030304e−01 | −3.70375395e−01 | 8.34967345e−02 |
| 1.50362387e−01 | 4.11435574e−01 | 2.42683128e−01 | 2.18833193e−01 |
| 1.89901650e−01 | 3.85081828e−01 | −4.66094986e−02 | 3.93788479e−02 |
| 5.22302054e−02 | 2.55889222e−01 | −5.78250624e−02 | 3.18126440e−01 |
| −2.26802841e−01 | 2.52465993e−01 | 2.14656979e−01 | 2.79869348e−01 |
| −1.17183547e−03 | 1.09557822e−01 | 5.51837496e−02 | 5.58388591e−01 |
| −1.68854564e−01 | 1.42708376e−01 | −1.38126031e−01 | −8.41089189e−02 |
| 2.02996284e−01 | −2.26355910e−01 | 4.19249833e−01 | 3.82500403e−02 |
| −3.82795095e−01 | −4.13094819e−01 | 1.00641102e−01 | 3.97869386e−03 |
| 2.71401912e−01 | −9.70128700e−02 | 1.62666976e−01 | 9.95421968e−03 |
| −8.68180096e−02 | −2.16380879e−01 | −1.93561807e−01 | −8.14195350e−02 |
| 5.75219356e−02 | 7.13337436e−02 | 2.68698037e−01 | 1.30936980e−01 |
| −8.05642903e−02 | 1.40784726e−01 | −4.82029952e−02 | 4.86180298e−02] |
| [1.05988950e−01 | 3.91871691e−01 | 1.33143617e−02 | 1.16999552e−01 |
| −2.20491111e−01 | 1.87178478e−01 | 1.00693353e−01 | 9.64359418e−02 |
| 6.21404909e−02 | −3.28625619e−01 | 9.92545485e−02 | 1.54290516e−02 |
| 1.31351098e−01 | 7.50410231e−03 | −4.76141600e−03 | 1.27890959e−01 |
| 1.07585080e−01 | 1.99212745e−01 | 1.79731566e−01 | −3.45442504e−01 |
| 8.06077719e−02 | 2.73303390e−01 | 2.53915161e−01 | 2.31589660e−01 |
| 7.26428866e−01 | 2.60862142e−01 | −7.17250779e−02 | −5.92684112e−02 |
| 6.59637712e−03 | 4.60545540e−01 | −7.11322203e−02 | 2.83698440e−01 |
| −1.52269855e−01 | −2.23831266e−01 | −1.29658461e−01 | 1.87781513e−01 |
| 4.04485613e−01 | −3.91770154e−01 | −4.75404441e−01 | 4.46073920e−01 |
| −5.75916946e−01 | 4.04342115e−01 | 1.40362322e−01 | 3.23524848e−02 |
| 1.27446622e−01 | 6.59105256e−02 | 1.09836973e−01 | 2.29094159e−02 |
| −4.52050656e−01 | 1.50186926e−01 | −3.02876651e−01 | −1.42073289e−01 |
| 3.22653770e−01 | 6.97812140e−02 | 2.48031259e−01 | 1.56523839e−01 |
| 1.26013551e−02 | 3.77725899e−01 | 3.16588968e−01 | 5.09777851e−03 |
| 1.73206240e−01 | 6.97763562e−02 | 1.40062213e−01 | −3.00544560e−01 |
| −1.29094914e−01 | −8.00460204e−02 | 1.76515326e−01 | 1.24467023e−01 |
| 4.72984696e−03 | 7.95822684e−03 | 2.33235791e−01 | 9.91977975e−02 |
| 2.82233685e−01 | −2.05925494e−01 | 5.23940511e−02 | 1.55369593e−02 |
| −1.05678597e−02 | 2.20485836e−01 | 2.77490497e−01 | −1.49626225e−01 |
| 2.12854177e−01 | 3.40169489e−01 | 1.02462798e−01 | −3.49930488e−02 |

TABLE $W_h^1$-continued

| | | | |
|---|---|---|---|
| −1.30600080e−01 | −2.00339124e−01 | 7.79511705e−02 | 2.47204676e−01 |
| 8.17024037e−02 | 7.16318265e−02 | 3.47230136e−01 | 1.47532344e−01 |
| −5.23565039e−02 | −5.33715725e−01 | 3.51119816e−01 | 3.48654389e−01 |
| 1.10447533e−01 | 2.42399022e−01 | 3.02889735e−01 | 7.72964433e−02 |
| 1.91702202e−01 | 2.98252702e−01 | −5.09971846e−03 | 9.77592822e−03 |
| 6.31542280e−02 | 2.41919383e−01 | 4.63882126e−02 | 1.25645371e−02 |
| 1.04496680e−01 | 2.79922903e−01 | −1.79419443e−02 | 8.87945220e−02 |
| 3.39060187e−01 | −2.36592099e−01 | 2.00135693e−01 | −7.31855333e−02 |
| 2.48199910e−01 | −2.05557942e−01 | 2.99940169e−01 | 7.79399052e−02 |
| 1.07900731e−01 | 1.21128447e−01 | 3.29298973e−02 | 2.35929966e−01 |
| 8.05698186e−02 | 1.25506952e−01 | 2.02353150e−01 | −2.63387293e−01 |
| −1.52385369e−01 | −1.08023040e−01 | 6.56421995e−03 | 1.06423132e−01 |
| 3.32370460e−01 | −5.52513264e−02 | 1.22748382e−01 | 5.24085343e−01 |
| 1.00017779e−01 | 1.54115051e−01 | 4.58569437e−01 | 4.52537715e−01 |
| 3.43796425e−02 | 6.50821179e−02 | 5.82397461e−01 | −2.88114343e−02 |
| −7.88522288e−02 | −1.29936859e−01 | −1.64290950e−01 | 1.03462242e−01 |
| −5.62192015e−02 | 2.34187827e−01 | −6.27223924e−02 | 1.86695203e−01 |
| 1.88678831e−01 | 3.29935759e−01 | 1.38166413e−01 | 1.70556441e−01 |
| 1.43217966e−01 | −1.09740734e−01 | 4.26282525e−01 | 3.63314077e−02 |
| 9.62963179e−02 | 2.75293380e−01 | −2.38264306e−03 | 4.44443338e−02 |
| 3.24011706e−02 | −2.07739070e−01 | −1.28963098e−01 | −2.06162393e−01 |
| 2.64546182e−03 | −1.03743009e−01 | −1.36051342e−01 | 2.58256316e−01 |
| 1.88956648e−01 | 1.01056233e−01 | 1.63495570e−01 | 2.31092632e−01 |
| 3.19229402e−02 | 4.10866737e−02 | 1.24788433e−02 | 1.25214662e−02 |
| −2.25437343e−01 | 2.39148382e−02 | 8.17240402e−02 | 6.47361651e−02 |
| −5.37039280e−01 | −2.05969766e−01 | 3.95891070e−01 | −6.60952851e−02 |
| 1.37970120e−01 | 1.19751953e−02 | 1.08892106e−01 | 8.06516856e−02 |
| −2.35452477e−04 | −4.84646820e−02 | −2.06973091e−01 | 1.53252095e−01 |
| −1.21441685e−01 | −6.26536533e−02 | −1.02501906e−01 | 1.36967391e−01 |
| 4.00828183e−01 | 4.53747958e−02 | −7.85090402e−02 | 1.98094055e−01 |
| −3.31227392e−01 | −1.32525086e−01 | −1.86012641e−01 | −1.43847004e−01 |
| 3.42233330e−01 | 5.58466476e−04 | 1.12431459e−01 | 3.53982419e−01 |
| 3.67746562e−01 | 3.05394650e−01 | −6.50143400e−02 | −3.93351614e−02 |
| 5.54664098e−02 | 2.25276470e−01 | 1.93075016e−01 | −1.29247323e−01 |
| −3.36423814e−01 | 1.57017574e−01 | −2.92397551e−02 | 5.31355925e−02 |
| 4.93563801e−01 | 3.66289407e−01 | −1.47127539e−01 | 3.94276083e−01 |
| 1.99117243e−01 | −1.77769318e−01 | −6.11778535e−02 | 1.48413181e−01 |
| −8.36939812e−02 | −5.15331507e−01 | 2.67650217e−01 | 4.68527317e−01 |
| 1.25037894e−01 | 1.94472969e−01 | 3.99235278e−01 | 5.58570074e−03 |
| −4.40002799e−01 | −1.99899763e−01 | 2.01405048e−01 | 1.66098133e−01 |
| −1.05561437e−02 | −9.23412442e−02 | 1.52381107e−01 | −3.55766825e−02 |
| 7.20037594e−02 | 7.34354034e−02 | −4.04123873e−01 | 4.53882337e−01 |
| 3.64304148e−02 | −6.57568872e−02 | 1.29110709e−01 | 9.19609219e−02] |
| [−4.52846110e−01 | 8.08272481e−01 | 4.73025858e−01 | 1.35646105e−01 |
| 6.23245716e−01 | 8.98072064e−01 | 3.94262999e−01 | 1.09858596e−00 |
| 7.58422256e−01 | 3.10209453e−01 | 4.41703945e−01 | 9.88677621e−01 |
| 1.02645285e−01 | 6.00939810e−01 | 5.86240292e−01 | 7.41101444e−01 |
| 1.33404624e−00 | 1.01454556e−01 | 1.88108593e−01 | 3.19466710e−01 |
| 4.81995732e−01 | −2.57070333e−01 | 7.40516901e−01 | 6.86659455e−01 |
| 4.64766532e−01 | 2.55349427e−01 | 3.26939195e−01 | 6.14976764e−01 |
| 2.35386297e−01 | 3.30377996e−01 | 2.97007769e−01 | 1.28378451e−01 |
| 3.73773158e−01 | 2.90462434e−01 | 1.06188560e−00 | 2.38145459e−02 |
| 4.71622825e−01 | 2.81756938e−01 | 5.77368021e−01 | 5.56940019e−01 |
| 7.66787708e−01 | 3.54317933e−01 | 4.59597617e−01 | 6.24893121e−02 |
| 6.34111822e−01 | 4.72207755e−01 | 8.01789105e−01 | 6.62975192e−01 |
| 3.22057724e−01 | 6.60785794e−01 | 2.80146807e−01 | 6.90665960e−01 |
| 8.25903565e−02 | 4.87684667e−01 | 7.34394372e−01 | 4.53984082e−01 |
| 1.00072610e−00 | 6.15887828e−02 | 2.99054563e−01 | 6.85173944e−02 |
| 3.70790035e−01 | 4.25444990e−01 | 7.73340166e−01 | 5.40083289e−01 |
| −4.47078049e−02 | −2.29854658e−01 | 5.23519456e−01 | 4.88786042e−01 |
| 1.29680634e−01 | 2.47031748e−01 | 3.06623667e−01 | −5.38644373e−01 |
| 4.10792947e−01 | −9.21719074e−02 | 6.15931690e−01 | 3.39945704e−01 |
| 8.51464212e−01 | 6.14341259e−01 | 7.39325166e−01 | 1.06298298e−01 |
| 5.15343308e−01 | 3.48666430e−01 | 5.76172113e−01 | 1.92661539e−01 |
| 5.03133237e−02 | 4.59480554e−01 | 5.67049980e−01 | 2.16557071e−01 |
| 3.83782715e−01 | −6.15645230e−01 | 4.78101522e−01 | 9.60873961e−02 |
| 4.73703623e−01 | 6.43280029e−01 | 6.67446971e−01 | 5.82255602e−01 |
| 5.98711193e−01 | 2.47672692e−01 | −9.49212492e−01 | 1.08883941e−00 |
| 2.60566622e−01 | 7.82441437e−01 | 3.22668433e−01 | 1.88902393e−01 |
| 9.19150859e−02 | 6.71779692e−01 | 1.62591651e−01 | 7.33875513e−01 |
| 5.20406961e−01 | 6.18197978e−01 | −2.82958802e−02 | 1.03957042e−01 |
| 4.41764295e−01 | 3.97532791e−01 | 9.88526940e−01 | 9.99209136e−02 |
| 5.50695956e−01 | 4.41615731e−01 | 7.17701316e−01 | 9.70688015e−02 |
| 3.73939484e−01 | 3.94959211e−01 | 5.24254978e−01 | 6.68603837e−01 |
| 5.05472541e−01 | 8.13490629e−01 | 3.91673237e−01 | 1.14857447e−00 |
| 6.18465185e−01 | 2.64400005e−01 | 1.57593414e−01 | 2.54245132e−01 |
| 3.27929437e−01 | 7.03831196e−01 | 9.03499305e−01 | 8.68556574e−02 |
| 6.53322458e−01 | 9.90256250e−01 | 5.59458673e−01 | 2.46028766e−01 |
| 3.26693088e−01 | 3.53985220e−01 | 4.87226039e−01 | 7.09247768e−01 |
| 3.05651069e−01 | 8.13185573e−01 | 6.36387318e−02 | 5.59675157e−01 |

TABLE $W_h^1$-continued

| | | | |
|---|---|---|---|
| 5.35267293e-01 | 2.37508476e-01 | 7.09407032e-01 | 4.75553691e-01 |
| 1.61900178e-01 | 6.26408994e-01 | 6.87919796e-01 | 4.45502937e-01 |
| -7.40613118e-02 | -1.64461792e-01 | 2.34210968e-01 | 4.41337496e-01 |
| 7.70075142e-01 | 7.54515171e-01 | 7.16982543e-01 | 4.11500186e-01 |
| 4.05870676e-01 | 1.80496618e-01 | 6.02250934e-01 | 1.28732175e-01 |
| 1.78549483e-01 | 4.80196565e-01 | 3.06331336e-01 | 5.95298111e-01 |
| 1.45276621e-01 | 4.29527998e-01 | 5.89623570e-01 | 2.86572993e-01 |
| 5.17164588e-01 | -1.96934611e-01 | 9.91688609e-01 | 4.81467128e-01 |
| 5.73530138e-01 | 9.10271645e-01 | 4.02408153e-01 | 4.51710492e-01 |
| 9.36871827e-01 | 3.44789654e-01 | 1.41022682e-01 | 7.40431190e-01 |
| 4.15573537e-01 | 2.52020746e-01 | 7.37981081e-01 | 8.34030330e-01 |
| 2.87275851e-01 | 4.21270013e-01 | 2.00204805e-01 | 2.69607991e-01 |
| 5.80391884e-01 | 5.10522068e-01 | 5.10992825e-01 | -4.95456718e-03 |
| 3.85977149e-01 | 2.87300080e-01 | 4.73862857e-01 | 9.31774005e-02 |
| 3.18823427e-01 | 1.01547372e-00 | 1.58862948e-01 | 9.92537737e-01 |
| 6.02916241e-01 | 6.18170537e-02 | 4.01830345e-01 | 2.74656832e-01 |
| 4.66185540e-01 | 7.41486132e-01 | 3.30986798e-01 | 6.20730817e-01 |
| 1.62464276e-01 | 1.38755431e-02 | 7.05139399e-01 | 4.41137403e-01 |
| 1.19670498e-00 | 4.66521949e-01 | -1.89430341e-01 | 1.28703162e-01 |
| 9.53619599e-01 | 2.00072199e-01 | 2.77055711e-01 | 5.00949621e-01 |
| 9.80078459e-01 | 6.64834619e-01 | 6.34986520e-01 | 7.68214047e-01 |
| 5.73793471e-01 | 2.53381342e-01 | 2.08525792e-01 | 3.88708860e-01 |
| 7.12943435e-01 | 6.49266005e-01 | 3.04902822e-01 | 9.99527395e-01 |
| 7.28790760e-01 | 9.03100193e-01 | 4.76595521e-01 | 7.26700187e-01 |
| 6.22315407e-01 | 9.71617579e-01 | 2.90328234e-01 | 3.25426683e-02 |
| 7.41848230e-01 | 1.54036045e-01 | 4.21533436e-01 | 7.70395875e-01 |
| -4.35170755e-02 | 5.99981904e-01 | 6.24189138e-01 | 5.82045734e-01] |
| [3.05407971e-01 | 3.17882359e-01 | 1.19160399e-01 | -2.39738509e-01 |
| 4.91848469e-01 | 6.75960839e-01 | 1.28746569e-01 | 3.46612275e-01 |
| 4.74305928e-01 | 1.69571117e-01 | -1.25270098e-01 | 1.69411734e-01 |
| 4.75928411e-02 | -2.18075767e-01 | -1.33200362e-01 | 9.40492973e-02 |
| 1.11970112e-01 | 4.53075051e-01 | 1.77025720e-01 | -6.85132146e-02 |
| -5.82298590e-03 | 1.46858484e-01 | 5.23146272e-01 | 2.11804911e-01 |
| -4.82479990e-01 | 5.18733263e-01 | 4.32294935e-01 | -8.29801559e-02 |
| 2.21617043e-01 | -1.53718144e-01 | 5.88389523e-02 | -3.35376076e-02 |
| -2.63027042e-01 | -1.01133443e-01 | 4.04247075e-01 | -7.19359815e-02 |
| 7.26661503e-01 | -1.32861480e-01 | 3.67013097e-01 | -4.22684625e-02 |
| -1.32524595e-01 | 1.54651731e-01 | 2.58454084e-01 | 5.49303889e-01 |
| 1.15300886e-01 | -1.82558566e-01 | 1.89835459e-01 | 4.03045326e-01 |
| 2.39117637e-01 | 1.72830209e-01 | -4.23822217e-02 | 5.06137431e-01 |
| -1.32389471e-01 | 3.37604374e-01 | 9.80670154e-02 | 1.17911689e-01 |
| 2.12515369e-01 | -2.77493577e-02 | 5.97275019e-01 | 2.91214317e-01 |
| 2.63768554e-01 | 3.50150615e-01 | 4.74015214e-02 | 2.02719525e-01 |
| -7.01618195e-02 | 2.18520239e-01 | -4.43534292e-02 | 1.43653780e-01 |
| 2.84674317e-01 | 2.19238251e-01 | 5.84562063e-01 | 1.57137379e-01 |
| -1.68333307e-01 | 1.30615503e-01 | 4.34705615e-01 | 1.12749353e-01 |
| 5.38513243e-01 | 2.44830236e-01 | 7.43234903e-02 | -5.12941834e-03 |
| 2.41791323e-01 | 3.01611841e-01 | -2.95811053e-02 | 2.53735840e-01 |
| 5.29518306e-01 | 2.69665807e-01 | 1.55408103e-02 | 5.40880114e-02 |
| -1.90534052e-02 | -5.45232184e-02 | 2.43605629e-01 | 3.58571529e-01 |
| -1.50716037e-01 | 3.53137434e-01 | 4.00013417e-01 | -3.98989506e-02 |
| -6.50115758e-02 | 3.55143517e-01 | -1.77413493e-01 | 3.78303900e-02 |
| -6.17660657e-02 | 1.33958627e-02 | 3.38682085e-01 | 5.85502923e-01 |
| 2.28585705e-01 | 8.10963586e-02 | 6.49472550e-01 | 1.07706003e-01 |
| -4.74872023e-01 | 2.78535515e-01 | -1.59616739e-01 | 9.15480033e-02 |
| -3.20345581e-01 | 3.80021334e-01 | 1.59761846e-01 | 3.79316896e-01 |
| 2.15302289e-01 | 1.59626886e-01 | 1.82735443e-01 | -2.68178321e-02 |
| 1.53489962e-01 | -1.97977662e-01 | 2.67378956e-01 | 4.85651672e-01 |
| 5.96766412e-01 | -7.87377432e-02 | -1.73051119e-01 | 1.92117959e-01 |
| -4.95808981e-02 | -7.36545846e-02 | 2.39587039e-01 | 9.55278352e-02 |
| 1.23550110e-01 | -7.71208927e-02 | 1.04375251e-01 | 8.30250308e-02 |
| -2.39541698e-02 | 4.89329934e-01 | 3.90873581e-01 | 2.99066007e-01 |
| 5.79835892e-01 | 1.80490538e-01 | -1.64267510e-01 | 4.57785428e-01 |
| -4.16756481e-01 | 1.83839485e-01 | -2.18606479e-02 | 7.90365577e-01 |
| 1.10203385e-01 | -1.93180218e-01 | -3.38783026e-01 | 2.43862540e-01 |
| 1.52991876e-01 | 1.39402270e-01 | 2.49293461e-01 | 2.02941924e-01 |
| 3.94608647e-01 | 3.59294951e-01 | 2.57850617e-01 | 1.55801117e-01 |
| 1.44923091e-01 | 2.49520447e-02 | -7.02798963e-02 | -1.43418582e-02 |
| 3.11172009e-01 | 1.20374665e-01 | 5.09099722e-01 | 3.75673681e-01 |
| 2.63638169e-01 | -1.69235282e-02 | 2.67608047e-01 | 1.32838920e-01 |
| 2.15424210e-01 | 2.97625661e-01 | 3.18605155e-01 | 5.10732114e-01 |
| 3.84995073e-01 | -1.10960804e-01 | -3.97257477e-01 | 3.61296862e-01 |
| 4.72163595e-02 | -1.71593323e-01 | 2.86684960e-01 | 1.52460650e-01 |
| 8.46643448e-01 | 1.91099003e-01 | 4.87652123e-02 | -7.71916732e-02 |
| 2.04616323e-01 | 6.57243058e-02 | 3.16646457e-01 | 6.90495610e-01 |
| 2.49587283e-01 | 5.05755365e-01 | 3.35491359e-01 | 1.30667180e-01 |
| 5.05917221e-02 | -2.73866922e-01 | 3.71221811e-01 | 2.63209105e-01 |
| -2.39950582e-01 | 3.18628281e-01 | 2.84651872e-02 | 3.01943272e-01 |
| 1.47126466e-01 | 4.39013600e-01 | 1.82965741e-01 | 2.49430001e-01 |
| 2.33546495e-01 | 3.62396939e-03 | -5.25700487e-02 | -3.16363424e-01 |

TABLE $W_h^1$-continued

| | | | |
|---|---|---|---|
| 7.31503725e−01 | 4.05326247e−01 | 5.11979103e−01 | 4.39769119e−01 |
| −2.61027098e−01 | −9.89773870e−03 | 5.10574758e−01 | 1.24485493e−01 |
| 6.48403317e−02 | 2.74929017e−01 | −3.23925972e−01 | −1.69375211e−01 |
| 2.48489633e−02 | 2.46354967e−01 | −9.23408195e−02 | 1.43216282e−01 |
| 1.87969193e−01 | 4.76925494e−03 | 6.55246377e−01 | 2.67834276e−01 |
| −2.66142730e−02 | 2.47030526e−01 | 1.66249096e−01 | 3.18732589e−01 |
| 1.07120025e−00 | 5.81405640e−01 | 9.66872349e−02 | 1.73118412e−01 |
| 3.14456522e−01 | 4.27808352e−02 | −3.86246771e−01 | −7.70887583e−02 |
| 2.87006795e−01 | −2.95879319e−02 | 2.82737523e−01 | 2.86348850e−01 |
| 4.80065316e−01 | −2.36441553e−01 | 2.58982092e−01 | −4.71184636e−03 |
| −5.56879267e−02 | 2.51068294e−01 | 3.28481048e−01 | −7.65875801e−02] |
| [3.46913517e−01 | 1.60936013e−01 | 4.98369664e−01 | 5.24625659e−01 |
| 9.65849578e−01 | 2.90228307e−01 | 3.51728588e−01 | 3.47816974e−01 |
| 5.32473564e−01 | 7.57923722e−01 | −6.18111575e−04 | 1.06363988e−00 |
| 1.03649759e−00 | 3.31881702e−01 | 7.08139837e−01 | 9.47168291e−01 |
| 1.03254306e−00 | 2.71798491e−01 | 1.07357074e−02 | 1.74502388e−01 |
| 2.69496441e−01 | −2.78740339e−02 | 7.76133776e−01 | 1.70179442e−01 |
| 1.43137228e−00 | 3.76099169e−01 | 3.33661973e−01 | 6.70833349e−01 |
| 7.23665118e−01 | 4.73679185e−01 | 4.12399322e−01 | 3.95653605e−01 |
| 2.37970248e−01 | 5.55219948e−02 | 3.92904907e−01 | −1.66524619e−01 |
| 9.65346545e−02 | 1.19839825e−01 | 6.03168428e−01 | 2.57331461e−01 |
| 8.01023424e−01 | 8.03567827e−01 | 4.10479754e−01 | 8.04465532e−01 |
| 2.55777866e−01 | 8.50063562e−01 | 7.08881021e−02 | 1.94914952e−01 |
| 3.65111828e−01 | 6.03172243e−01 | 1.57713771e−01 | 4.28376913e−01 |
| 1.57101735e−01 | 4.45619941e−01 | 7.05644369e−01 | 4.75236556e−01 |
| 2.32064396e−01 | 4.70371991e−02 | 1.65232599e−01 | −4.65939283e−01 |
| 4.87631619e−01 | 1.72681004e−01 | 6.99767292e−01 | 4.40456480e−01 |
| 4.61606711e−01 | 4.65882748e−01 | 6.41139328e−01 | 3.40750962e−01 |
| 3.80411148e−01 | −8.01185519e−02 | 1.65407345e−01 | 4.50809509e−01 |
| 5.66268086e−01 | 6.68453053e−02 | 6.77137613e−01 | 3.86567742e−01 |
| 4.87764150e−01 | 1.54226482e−01 | 5.64042985e−01 | −4.26381417e−02 |
| 7.30185330e−01 | 2.01902241e−02 | 1.31424427e−01 | 4.69148159e−01 |
| 3.60756636e−01 | 1.94579691e−01 | 3.48820761e−02 | 9.56078470e−02 |
| 4.88805741e−01 | 1.11432977e−01 | 1.25054765e−00 | 2.99560189e−01 |
| 4.30645466e−01 | 6.67766929e−01 | 4.70926344e−01 | 3.07836294e−01 |
| 4.89915788e−01 | 3.94899458e−01 | 7.56971240e−02 | 5.47797620e−01 |
| 3.26812506e−01 | 1.29780561e−01 | 1.26311153e−01 | 5.54407053e−02 |
| 1.20823726e−01 | 4.65631157e−01 | 7.32292831e−01 | 1.03110385e−00 |
| 6.49844468e−01 | 2.76576459e−01 | 8.76890600e−01 | 7.01132655e−01 |
| 1.05830193e−00 | 8.56616795e−01 | 1.50544214e−00 | 5.14634073e−01 |
| 7.45501518e−01 | 2.05114275e−01 | 3.26344132e−01 | −2.13673972e−02 |
| 2.01529451e−02 | 5.27873218e−01 | 1.18111730e−01 | 8.51070136e−02 |
| 3.08027565e−01 | 6.01249993e−01 | 1.20893180e−01 | 6.30711615e−01 |
| 5.13560534e−01 | 3.98473382e−01 | 2.09289581e−01 | 5.80461442e−01 |
| 9.23933089e−01 | 7.50546753e−01 | 1.09206331e−00 | 9.79614317e−01 |
| 4.68840241e−01 | 1.03345478e−00 | 3.29525381e−01 | 3.34733546e−01 |
| 4.16426867e−01 | 2.35834464e−01 | 8.70786384e−02 | 4.25519884e−01 |
| 7.87340701e−01 | 3.84582490e−01 | 8.70738253e−02 | 4.74859625e−01 |
| 5.01966596e−01 | 5.88150978e−01 | 5.85143328e−01 | 3.45310748e−01 |
| 3.65562677e−01 | 2.13853642e−01 | 7.34145045e−01 | 3.21614742e−01 |
| 8.33854005e−02 | 2.05609992e−01 | 2.30189338e−01 | 4.01039988e−01 |
| 8.26291978e−01 | 5.91911674e−01 | 6.49864435e−01 | 4.93483424e−01 |
| 1.41179323e−00 | 2.93371111e−01 | 7.73345888e−01 | 3.89387339e−01 |
| 3.57736796e−01 | 1.18660617e−00 | −2.91312169e−02 | 3.75475019e−01 |
| 2.09834814e−01 | 9.33070302e−01 | 8.43026698e−01 | 1.17424451e−01 |
| 5.21497130e−01 | 6.95397079e−01 | 2.02352092e−01 | 4.54912424e−01 |
| 2.05878511e−01 | 5.29309213e−01 | 6.94851339e−01 | 3.10713440e−01 |
| 2.73558110e−01 | 2.77211368e−01 | 2.18590274e−01 | 5.26113749e−01 |
| 1.02158904e−00 | 2.85479099e−01 | 1.68023631e−01 | 2.27696449e−01 |
| 1.20676979e−01 | 2.08188593e−01 | 5.00771046e−01 | 1.08531892e−00 |
| 5.32834530e−01 | 5.11996448e−01 | 5.23135602e−01 | 3.90661120e−01 |
| 7.81313717e−01 | 5.40342212e−01 | 1.27954209e−00 | 1.70039237e−01 |
| 7.29049146e−02 | 4.46167231e−01 | 3.69470417e−01 | 9.83715713e−01 |
| 6.59339309e−01 | 7.69417346e−01 | 8.05398464e−01 | 3.19853604e−01 |
| 5.18478572e−01 | 1.45381887e−03 | 2.82825112e−01 | 4.88398939e−01 |
| −5.64339161e−02 | 5.53951502e−01 | 8.03305507e−01 | 3.35639775e−01 |
| 4.73036528e−01 | 2.77490560e−02 | 9.02971402e−01 | 3.80113542e−01 |
| 9.11502659e−01 | 1.57356501e−01 | 5.14920615e−02 | 7.97776103e−01 |
| 6.32160380e−02 | 6.93214953e−01 | 9.32705283e−01 | 5.61657369e−01 |
| 3.29256952e−01 | 2.80569315e−01 | 3.04944366e−01 | 5.53544521e−01 |
| 1.33687460e−01 | 5.89707434e−01 | 3.20862234e−01 | 5.32915294e−01 |
| 5.07610381e−01 | 9.86459017e−01 | 4.97781277e−01 | 1.00836001e−01 |
| 5.66920698e−01 | 5.45221329e−01 | 1.50392520e−00 | 2.06922650e−01 |
| 7.62543082e−01 | 8.04699063e−02 | 6.83426023e−01 | 7.48839021e−01 |
| 1.87641025e−01 | 2.75384396e−01 | 4.69077468e−01 | 4.11026210e−01] |
| [9.84037668e−03 | 5.00263236e−02 | 3.52111071e−01 | 4.61996160e−01 |
| −2.57301778e−01 | 5.25364399e−01 | 2.93407530e−01 | −8.82359445e−02 |
| 5.10353029e−01 | 1.09999284e−01 | 4.98243451e−01 | −2.57585756e−02 |
| 8.32967639e−01 | 5.33679605e−01 | −1.28598854e−01 | −2.56411761e−01 |
| −6.47884235e−03 | 1.47566721e−01 | 3.10852043e−02 | 2.62766212e−01 |

TABLE $W_h^1$-continued

| | | | |
|---|---|---|---|
| 4.93523255e−02 | 4.01302010e−01 | 2.33631119e−01 | 3.78893048e−01 |
| 8.35972667e−01 | 1.90362558e−01 | 3.36715207e−02 | 1.49978638e−01 |
| −1.71313047e−01 | 1.22315846e−01 | 3.32350135e−01 | 3.95994782e−01 |
| 1.18621871e−01 | −7.78136551e−02 | −1.53198931e−02 | 1.92440942e−01 |
| 1.39062792e−01 | −1.19590610e−01 | 2.84703434e−01 | −8.65209252e−02 |
| 1.99314132e−01 | 2.33040098e−02 | 6.53187156e−01 | 1.10239528e−01 |
| 5.94197392e−01 | 2.36277699e−01 | −7.55475089e−02 | −3.10320467e−01 |
| 4.56351638e−01 | 1.19083724e−03 | −1.35850847e−01 | 1.35112032e−01 |
| 2.91186988e−01 | −2.39730269e−01 | −3.58512551e−02 | −1.89484492e−01 |
| −2.88822725e−02 | 2.16688603e−01 | 3.35612446e−01 | 9.74179804e−02 |
| 1.84343144e−01 | 2.75962055e−01 | −3.12407225e−01 | 4.42439824e−01 |
| 3.08070093e−01 | 3.38204414e−01 | −5.14161885e−02 | 1.74674034e−01 |
| 3.06213409e−01 | 1.34792984e−01 | 4.14211333e−01 | −2.22573638e−01 |
| 7.08556175e−02 | −1.28259808e−01 | 3.55548263e−01 | −6.81416690e−01 |
| 1.70732349e−01 | 1.36019230e−01 | 6.06043100e−01 | 9.18567032e−02 |
| 1.50847286e−01 | 3.57943505e−01 | 2.43232414e−01 | 7.98458457e−01 |
| 4.50841308e−01 | 7.18721747e−01 | 1.59089699e−01 | 3.54370512e−02 |
| 3.76796573e−01 | 3.98040652e−01 | 4.15721506e−01 | −4.02882993e−01 |
| −1.31446332e−01 | −3.80746901e−01 | −9.31628123e−02 | 4.80699241e−01 |
| 2.35386550e−01 | −1.00175269e−01 | 3.49870861e−01 | 5.87683082e−01 |
| 1.62480086e−01 | 3.73638242e−01 | 3.85455966e−01 | −4.12630774e−02 |
| 3.24099183e−01 | −1.33447042e−02 | 3.27090561e−01 | −4.81468327e−02 |
| −1.06888168e−01 | 4.88797456e−01 | −3.11933551e−02 | −2.54239053e−01 |
| 1.27635849e−00 | 6.59737214e−02 | 3.57164145e−02 | 4.15909052e−01 |
| 1.07179427e−00 | 8.03465426e−01 | 1.63259119e−01 | 5.58462918e−01 |
| 1.96285725e−01 | 4.40534391e−02 | 4.42998707e−01 | −1.23652443e−01 |
| 6.42321825e−01 | 7.14258790e−01 | 2.52148211e−01 | 1.05071403e−01 |
| 1.74177706e−01 | 9.74686593e−02 | 1.06002808e−01 | 3.45103443e−02 |
| −1.25549063e−01 | 3.44348311e−01 | −1.14514947e−01 | 6.18051924e−02 |
| −1.86974019e−01 | 1.01241434e−00 | 7.69834101e−01 | 2.04086691e−01 |
| 3.17321390e−01 | 4.96315747e−01 | 1.09876670e−01 | 4.31182683e−02 |
| 3.47340763e−01 | 2.78970189e−02 | 3.11428368e−01 | −2.91070025e−02 |
| 5.82743809e−03 | 5.24384975e−02 | 2.53844380e−01 | −5.00494540e−01 |
| 1.80468768e−01 | −1.53020350e−02 | 7.63678789e−01 | 1.84469879e−01 |
| −2.15194210e−01 | 2.55016774e−01 | 6.70200288e−02 | 4.94789392e−01 |
| 3.91544521e−01 | −3.64652872e−01 | 8.69567096e−02 | −1.83949322e−01 |
| −5.52155524e−02 | 4.50256646e−01 | 3.73049170e−01 | −7.12505281e−02 |
| 2.78118253e−01 | 1.68545414e−02 | −3.55933040e−01 | 5.52622452e−02 |
| 3.05203944e−01 | 9.94263217e−02 | 1.59345508e−01 | −1.75570231e−02 |
| 9.10735056e−02 | −1.45771012e−01 | 1.89710319e−01 | 6.46091819e−01 |
| 3.67943913e−01 | 2.69063771e−01 | 6.52321815e−01 | 9.29793492e−02 |
| 3.34316865e−01 | 9.82024893e−02 | −2.45136037e−01 | 2.06263453e−01 |
| −3.50082964e−02 | 1.62346020e−01 | 2.26714119e−01 | 8.07924047e−02 |
| 5.91155350e−01 | 7.17899859e−01 | 8.49015452e−03 | −1.08929768e−01 |
| 4.47549015e−01 | 3.98870856e−01 | −1.58968359e−01 | 4.92873251e−01 |
| 4.31194067e−01 | 2.16105908e−01 | −1.16701555e−01 | 6.10733390e−01 |
| 4.95289266e−01 | 9.84862804e−01 | 6.68002218e−02 | 8.17210823e−02 |
| −2.52257794e−01 | 7.18303919e−01 | 4.01664019e−01 | 6.75599754e−01 |
| −1.55119136e−01 | 3.09338391e−01 | −2.17884511e−01 | −4.80751432e−02 |
| −1.12148695e−01 | 1.62312180e−01 | −7.77074471e−02 | −3.98848444e−01 |
| −6.62151426e−02 | 1.08125992e−01 | 2.61904746e−01 | −1.54027671e−01 |
| −8.25139061e−02 | −3.12656499e−02 | −9.21563506e−02 | 7.12237895e−01 |
| 7.65729845e−01 | 7.25760385e−02 | 5.26685238e−01 | 5.60972691e−01 |
| 8.00595999e−01 | 4.38287497e−01 | 5.75642467e−01 | 4.07240130e−02 |
| 3.56144875e−01 | 4.19150054e−01 | 1.40054718e−01 | −2.70246923e−01 |
| 1.47511572e−01 | −6.78842589e−02 | −1.85358822e−01 | 5.24281442e−01 |
| 9.03566301e−01 | −5.75564951e−02 | −8.89258757e−02 | 5.94518900e−01 |
| 3.38350356e−01 | 2.37876564e−01 | 1.60481051e−01 | 5.02479494e−01 |
| 7.31030703e−02 | 1.12034172e−01 | 6.34172559e−01 | 3.07642132e−01] |
| [2.72306174e−01 | 5.54374635e−01 | 4.70453799e−01 | 5.16941965e−01 |
| 8.41391265e−01 | 3.43657404e−01 | 3.29060048e−01 | 5.74437976e−01 |
| 1.09804809e−00 | 1.02307081e−00 | 1.54299185e−01 | 8.12580526e−01 |
| 1.03068733e−00 | 9.61725116e−01 | 6.10924721e−01 | 6.85701966e−01 |
| 7.99794018e−01 | 3.08293283e−01 | −2.98433919e−02 | 3.18340153e−01 |
| 6.12140894e−01 | 3.55373889e−01 | 6.67112410e−01 | 5.34692585e−01 |
| 9.26195264e−01 | 7.65997469e−01 | 8.05299997e−01 | 5.20324647e−01 |
| 3.64656180e−01 | 3.21604371e−01 | 8.08263481e−01 | 1.73623562e−01 |
| 1.62914559e−01 | 4.69521731e−01 | 8.54611099e−01 | −4.44125608e−02 |
| −4.20545787e−02 | 1.29499125e−00 | 5.29652059e−01 | 8.25642586e−01 |
| 7.85510838e−01 | 5.42451859e−01 | 3.59096490e−02 | 1.21440077e−00 |
| 3.48246783e−01 | 7.31289923e−01 | 3.19278806e−01 | 4.01136279e−01 |
| 1.64237082e−01 | 7.71718085e−01 | 1.54235363e−01 | 5.83245695e−01 |
| 1.05899595e−01 | 7.71921635e−01 | 4.65022504e−01 | 3.65597814e−01 |
| 6.90099895e−01 | 6.27416432e−01 | 6.28498673e−01 | 3.80011797e−01 |
| 4.91653740e−01 | 7.86122143e−01 | 5.24435818e−01 | 4.86826271e−01 |
| 8.29075336e−01 | 5.59721708e−01 | 7.93352485e−01 | 3.61235946e−01 |
| 6.79399312e−01 | −6.27373978e−02 | 2.75259852e−01 | 6.82061732e−01 |
| 7.22517669e−01 | 6.00573778e−01 | 5.46641111e−01 | 1.49869204e−01 |
| 5.94279826e−01 | 2.13319391e−01 | 7.76777267e−01 | 4.00265194e−02 |
| 4.37913805e−01 | 5.61243415e−01 | 4.65990484e−01 | 4.90012854e−01 |

TABLE $W_h^1$-continued

| | | | |
|---|---|---|---|
| 3.25127453e−01 | 1.77648678e−01 | 1.52542979e−01 | 3.31756711e−01 |
| 5.58674514e−01 | −8.98746103e−02 | 5.24130166e−01 | 5.49343646e−01 |
| 7.22983658e−01 | 4.86415178e−01 | 1.11078548e−00 | 6.23735428e−01 |
| 6.79736793e−01 | 2.37500459e−01 | 7.05364287e−01 | 9.72436845e−01 |
| 2.30843559e−01 | 6.95703506e−01 | 1.81106076e−01 | 4.56250966e−01 |
| 1.19998761e−01 | 8.75746310e−01 | 4.77272600e−01 | 8.04615080e−01 |
| 6.51799619e−01 | 1.02569616e−00 | 2.39758953e−01 | 7.15956450e−01 |
| 1.40618765e−00 | 8.50828469e−01 | 7.78327942e−01 | 8.53875995e−01 |
| 8.44430387e−01 | −1.07364856e−01 | 3.42988729e−01 | 7.08562732e−01 |
| 5.63213408e−01 | 5.00569284e−01 | 5.88141441e−01 | 6.94744349e−01 |
| 1.19568813e−00 | 3.42738897e−01 | 5.88060558e−01 | 8.94059896e−01 |
| 4.69699800e−01 | 3.61082107e−01 | 2.41389751e−01 | 6.25737011e−01 |
| 5.41392088e−01 | 7.90552914e−01 | 8.09004188e−01 | 7.40834296e−01 |
| 9.95966852e−01 | 9.22877133e−01 | 5.00000715e−01 | 7.38881648e−01 |
| 7.50356495e−01 | 2.93711901e−01 | 8.43913436e−01 | 5.37995517e−01 |
| 6.52808845e−01 | 6.51434600e−01 | 8.56546998e−01 | 5.09358227e−01 |
| 4.32171553e−01 | 8.72829616e−01 | 8.01421583e−01 | 2.85794526e−01 |
| 7.11246371e−01 | 5.32084823e−01 | 1.00441027e−00 | 4.03766036e−01 |
| 6.62241057e−02 | 3.59802008e−01 | 2.81988740e−01 | 9.18448091e−01 |
| 5.60404718e−01 | 4.53241974e−01 | 5.91467083e−01 | 9.20297384e−01 |
| 5.79890788e−01 | 7.58925557e−01 | 1.06210613e−00 | 1.37257373e−00 |
| 8.99342716e−01 | 9.20500994e−01 | 1.58455104e−01 | 3.47907543e−02 |
| 5.74888349e−01 | 9.03069377e−01 | 1.11469388e−00 | 5.16182542e−01 |
| 5.26889682e−01 | 8.90910864e−01 | 4.62330908e−01 | 5.00806689e−01 |
| 1.19232452e−00 | 8.75132799e−01 | 6.19111657e−01 | 3.21322441e−01 |
| 6.31615341e−01 | 1.19998977e−01 | 1.02358818e−00 | 4.61178392e−01 |
| 6.02718532e−01 | 4.53415781e−01 | 4.75676447e−01 | 8.17280650e−01 |
| 4.86604422e−01 | 2.03608036e−01 | 4.38783407e−01 | 5.14748096e−03 |
| 8.09481025e−01 | 1.00556648e−00 | 8.04708600e−01 | 4.51477850e−03 |
| 4.93291825e−01 | 6.67943299e−01 | 8.15087616e−01 | 4.30833787e−01 |
| 2.50128090e−01 | 7.79183507e−01 | 5.62353075e−01 | 2.70592153e−01 |
| 6.33859456e−01 | 8.85498643e−01 | 8.71625185e−01 | 4.44229543e−01 |
| 9.74918723e−01 | 4.27265704e−01 | 4.81451571e−01 | 6.87184930e−01 |
| 1.58225492e−01 | 6.05323851e−01 | 4.09850925e−01 | 1.35624498e−01 |
| 9.10661161e−01 | 6.85260057e−01 | 9.89449561e−01 | 1.40841770e−00 |
| 1.01816690e−00 | 5.44509768e−01 | 8.65563631e−01 | 9.34854209e−01 |
| 7.52608836e−01 | 6.94687843e−01 | 4.80211318e−01 | 6.93531394e−01 |
| 8.09604526e−01 | 3.29511642e−01 | 6.54859662e−01 | 5.63563406e−01 |
| 9.74984884e−01 | 7.52353191e−01 | 2.64500678e−01 | 5.51322401e−01 |
| 7.56648839e−01 | 7.85031617e−01 | 1.07410502e−00 | 2.79735088e−01 |
| 8.04026246e−01 | 6.73237741e−01 | 3.72109771e−01 | 1.51963902e−00 |
| 9.94865596e−01 | 2.15835989e−01 | 6.15763783e−01 | 1.06093395e−00 |
| 1.24026708e−01 | 5.73259354e−01 | 8.93152595e−01 | 5.69917202e−01] |
| [1.56694853e−00 | 4.23160255e−01 | 6.81256831e−01 | 7.29017913e−01 |
| 9.80834484e−01 | 6.85298562e−01 | 9.04174566e−01 | 7.45628774e−01 |
| 6.10199273e−01 | 5.64836502e−01 | 3.14222932e−01 | 1.46307433e−00 |
| 9.64148283e−01 | 4.53152329e−01 | 8.48666608e−01 | 1.35145772e−00 |
| 1.16732311e−00 | 7.10869193e−01 | −1.41758576e−01 | 3.49739194e−01 |
| 3.73939663e−01 | 1.08724087e−01 | 1.46259117e−00 | 5.74182212e−01 |
| 1.15296054e−00 | 8.57019797e−02 | 3.48630697e−01 | 1.01018667e−00 |
| 7.94364095e−01 | 4.14997965e−01 | 3.22716057e−01 | 2.03122273e−01 |
| 9.94244874e−01 | 6.82327747e−02 | 1.30725300e−00 | −2.00466327e−02 |
| −3.45535606e−01 | 4.54052836e−01 | 7.64390528e−01 | 4.58949864e−01 |
| 6.82719409e−01 | 6.33114040e−01 | 9.33566570e−01 | 1.34898150e−00 |
| 4.58496332e−01 | 3.96175206e−01 | 9.19883922e−02 | 9.35868621e−01 |
| 6.66149557e−01 | 4.82515812e−01 | 3.99452031e−01 | 4.20844287e−01 |
| 5.20078599e−01 | 5.91963172e−01 | 1.19109344e−00 | 4.44932312e−01 |
| 1.29078913e−00 | 4.49826904e−02 | 4.32387769e−01 | −6.32396460e−01 |
| 1.43110514e−00 | 7.16114104e−01 | 3.23865056e−01 | 4.16000932e−01 |
| 1.03018783e−01 | 5.35473108e−01 | 9.49597239e−01 | 5.82626760e−01 |
| 5.58527887e−01 | −4.38478827e−01 | 3.33339036e−01 | 1.08678031e−00 |
| 6.04500949e−01 | 8.66121709e−01 | 4.52279955e−01 | 7.16424584e−01 |
| 6.20168388e−01 | 4.45875555e−01 | 7.34453082e−01 | 7.22659156e−02 |
| 5.30254602e−01 | 4.05047715e−01 | 5.23191452e−01 | 4.86448914e−01 |
| 8.55506003e−01 | 3.19223374e−01 | 4.27940607e−01 | 5.08026659e−01 |
| 4.95093644e−01 | −3.66155267e−01 | 6.21443331e−01 | 1.13247454e−00 |
| 9.48784590e−01 | 7.56377220e−01 | 7.31846154e−01 | 3.50417644e−01 |
| 7.25522101e−01 | 1.41625896e−01 | 6.80918217e−01 | 8.73632431e−01 |
| 4.27387178e−01 | 4.09291297e−01 | 2.90443540e−01 | −2.95301434e−02 |
| 3.78409401e−02 | 3.69439721e−01 | 4.75466192e−01 | 1.38195801e−00 |
| 7.77009726e−01 | 7.48173714e−01 | 2.88967758e−01 | 7.77212679e−01 |
| 8.79262209e−01 | 9.11412418e−01 | 1.46086490e−00 | 9.61679041e−01 |
| 1.15337980e−00 | 6.12213723e−02 | 5.64024389e−01 | 4.07873154e−01 |
| 2.85014004e−01 | 8.72010708e−01 | 3.43267992e−02 | 5.72806597e−01 |
| 5.91251910e−01 | 6.99012458e−01 | 6.60985649e−01 | 7.62051940e−01 |
| 8.26756001e−01 | 4.18102711e−01 | 3.42582077e−01 | 3.49937230e−01 |
| 7.32195199e−01 | 7.63881683e−01 | 9.02189136e−01 | 8.64051998e−01 |
| 5.81346929e−01 | 9.25483167e−01 | 7.73929358e−01 | 1.52920485e−00 |
| 4.67996418e−01 | −2.01624930e−01 | 3.20524186e−01 | 6.32443428e−01 |
| 8.11549067e−01 | 6.52675271e−01 | 2.51432925e−01 | 8.99852216e−01 |

TABLE $W_h^1$-continued

| | | | |
|---|---|---|---|
| 6.98527217e−01 | 5.19326448e−01 | 6.16020679e−01 | 9.36024249e−01 |
| 4.63684946e−02 | 4.12644625e−01 | 7.71194816e−01 | 1.58965990e−01 |
| −3.13504525e−02 | 4.32839990e−01 | 4.88014936e−01 | 6.30297601e−01 |
| 7.66567588e−01 | 7.92656720e−01 | 8.44666839e−01 | 5.10969400e−01 |
| 6.39585495e−01 | 1.04173827e−00 | 1.10963321e−00 | 7.69897699e−01 |
| 4.18875575e−01 | 5.84727228e−01 | 1.68833360e−01 | 1.06625926e−00 |
| 3.46123040e−01 | 1.04199708e−00 | 7.69249439e−01 | 1.42939031e−01 |
| 5.23074865e−01 | 9.62783635e−01 | 4.88172889e−01 | 2.82217115e−01 |
| 6.59901500e−01 | 8.62882078e−01 | 3.29194337e−01 | 4.94641066e−01 |
| 8.56419265e−01 | 2.00057819e−01 | 2.10009456e−00 | 4.27446991e−01 |
| 5.09163141e−01 | 2.71880031e−01 | 5.38961649e−01 | 3.65884036e−01 |
| 4.80908424e−01 | 5.04924774e−01 | 8.55090559e−01 | 1.20525312e−00 |
| 5.72558999e−01 | 1.44212949e−00 | 8.31515431e−01 | 5.23606479e−01 |
| 7.24761367e−01 | 9.95061696e−01 | 5.35852075e−01 | 5.08369327e−01 |
| 1.05333731e−01 | 9.44266379e−01 | 1.79379061e−01 | 1.19734502e−00 |
| 2.05676734e−01 | 9.10420954e−01 | 9.98486400e−01 | 6.16443753e−01 |
| 1.25461340e−00 | 5.86646199e−01 | 4.79601115e−01 | 8.96386027e−01 |
| 6.90842941e−02 | 4.57698345e−01 | 1.21735454e−00 | 2.67011642e−01 |
| 9.36125398e−01 | 1.23215842e−00 | 7.36344337e−01 | 4.81587440e−01 |
| 7.39642322e−01 | 2.19707713e−01 | 1.78513646e−01 | 5.03028333e−01 |
| 2.22569883e−01 | 3.34538490e−01 | 5.14221489e−01 | 6.18135512e−01 |
| 3.07332814e−01 | −9.66902301e−02 | 8.26936126e−01 | 6.38431907e−01 |
| 1.10384774e−00 | 1.05378294e−00 | 3.87144268e−01 | 2.86176622e−01 |
| 3.39738786e−01 | 1.15758026e−00 | 1.10471773e−00 | 5.28180301e−01 |
| 9.95626926e−01 | 7.94158638e−01 | 4.21087086e−01 | 6.57983422e−01 |
| 5.61475515e−01 | 4.24218982e−01 | 7.86644816e−01 | 9.80228007e−01 |
| 9.80575025e−01 | 2.16369659e−01 | 1.00098300e−00 | 4.50708777e−01] |
| [6.47383153e−01 | 4.92913902e−01 | 1.01179218e−00 | 4.60644901e−01 |
| 1.18578267e−00 | 6.13166913e−02 | 8.09642911e−01 | 1.41271770e−00 |
| 8.13773215e−01 | 6.08103514e−01 | 1.00154601e−01 | 1.19874895e−00 |
| 5.67131460e−01 | 8.29668641e−01 | 7.29225874e−01 | 1.33095109e−00 |
| 5.35900533e−01 | 5.07799566e−01 | 4.48423550e−02 | 8.43715787e−01 |
| 7.50292480e−01 | −7.30430484e−02 | 1.41436434e−00 | 3.19500148e−01 |
| 7.15772152e−01 | 5.85526764e−01 | 1.48489431e−01 | 1.09588563e−00 |
| 7.83775508e−01 | 9.65438008e−01 | 2.73520678e−01 | 3.04739147e−01 |
| 2.07669228e−01 | 4.85263944e−01 | 8.78713191e−01 | −8.01553279e−02 |
| −3.48733872e−01 | 1.40416574e−00 | 1.08421314e−00 | 4.64480460e−01 |
| 5.66670120e−01 | 7.56489992e−01 | 5.34108043e−01 | 1.62505877e−00 |
| 5.97636759e−01 | 6.88946605e−01 | 1.46210760e−01 | 1.13214135e−00 |
| 3.28375906e−01 | 6.92952693e−01 | 5.79597354e−01 | 6.07289195e−01 |
| 4.04325247e−01 | 3.35585535e−01 | 1.07905638e−00 | 1.04314637e−00 |
| 2.62955993e−01 | −2.79938936e−01 | 6.92199707e−01 | −1.22733451e−01 |
| 2.52774954e−01 | 5.98499477e−01 | 4.33874667e−01 | 4.00378853e−01 |
| 6.31580353e−01 | 9.94830966e−01 | 5.52946389e−01 | 2.25668028e−01 |
| 8.07199717e−01 | 2.63833344e−01 | −1.03833191e−01 | 1.01287651e−00 |
| 6.28260136e−01 | 1.74712789e−01 | 4.90447193e−01 | 9.66500640e−01 |
| 2.19208145e−00 | 1.57681316e−01 | 8.34136903e−01 | 8.64596307e−01 |
| 3.73164713e−01 | 2.90495813e−01 | 3.85804772e−01 | 4.11071658e−01 |
| 1.24858953e−01 | 2.48214841e−01 | 9.19962764e−01 | 6.56796455e−01 |
| 6.16647363e−01 | −7.77214706e−01 | 3.32658499e−01 | 7.78226554e−01 |
| 9.31565106e−01 | 1.64314544e−00 | 6.07408524e−01 | 8.83981705e−01 |
| 3.63827646e−01 | 7.15412796e−01 | 8.08490992e−01 | 1.27061665e−00 |
| 7.25360036e−01 | 1.82680875e−01 | −9.95520968e−03 | −1.17997251e−01 |
| 2.17136711e−01 | 7.22317815e−01 | 5.90649486e−01 | 1.31844759e−00 |
| 8.57214749e−01 | 4.68290210e−01 | 1.06894588e−00 | 3.46967369e−01 |
| 7.92579114e−01 | 6.80402815e−01 | 9.38205779e−01 | 6.75951183e−01 |
| 1.20972002e−00 | 2.42250666e−01 | 9.18035507e−01 | 3.43184739e−01 |
| 6.02025151e−01 | 6.26910031e−01 | 1.31529167e−01 | 7.68136203e−01 |
| 8.55250061e−01 | 5.92200875e−01 | 9.06300724e−01 | 7.57093668e−01 |
| 2.86206901e−01 | 3.70964147e−02 | 1.57738507e−01 | 1.57894897e−00 |
| 4.76355493e−01 | 1.70429420e−00 | 7.27792144e−01 | 1.27511322e−01 |
| 7.62841284e−01 | 6.37250841e−01 | 7.80899644e−01 | 4.17533636e−01 |
| 2.38874525e−01 | 7.34625906e−02 | 5.86741418e−03 | 7.18059063e−01 |
| 7.99951851e−01 | 6.40272379e−01 | 2.05825377e−00 | 5.10781229e−01 |
| 4.98156458e−01 | 9.09045398e−01 | 6.29495561e−01 | 2.57933378e−01 |
| 3.35530907e−01 | 3.87442440e−01 | 4.92502719e−01 | −8.19446295e−02 |
| 4.36672866e−02 | 5.36972642e−01 | 3.62465471e−01 | 4.49589998e−01 |
| 5.87605894e−01 | 6.27360642e−01 | 5.82913935e−01 | 6.36376917e−01 |
| −1.23836212e−02 | 8.61499310e−01 | 8.26308310e−01 | 7.52529323e−01 |
| 2.81794280e−01 | 6.58773959e−01 | 2.54285008e−01 | 5.88313758e−01 |
| 6.45955145e−01 | 5.34433126e−01 | 9.92403209e−01 | 7.80223534e−02 |
| 6.37330651e−01 | 5.20607866e−02 | 1.82641402e−01 | 4.67652172e−01 |
| 1.09589946e−00 | 1.06740546e−00 | 1.00722229e−00 | 1.39913842e−01 |
| 6.47926450e−01 | 2.37599194e−01 | 6.23694658e−01 | 1.50141656e−00 |
| 8.10920835e−01 | 1.06625152e−00 | 7.44383514e−01 | 5.66037118e−01 |
| 9.91746843e−01 | 1.14496875e−00 | 3.91318709e−01 | −2.28401810e−01 |
| 1.01335049e−00 | 8.33144605e−01 | 8.12097132e−01 | 3.22872788e−01 |
| 7.26077497e−01 | 2.12471038e−01 | 8.62987161e−01 | 1.88987225e−01 |
| 1.23745108e−00 | 8.57842207e−01 | 5.50074935e−01 | 3.75590771e−01 |
| 6.55477226e−01 | 9.11346495e−01 | 8.37860882e−01 | 1.79903996e−00 |

TABLE $W_h^1$-continued

| | | | |
|---|---|---|---|
| 1.45670652e-00 | 9.68642294e-01 | 4.33010608e-01 | 7.16977894e-01 |
| 2.02563275e-02 | 5.04495054e-02 | 1.05197215e-00 | 2.32494876e-01 |
| 1.36816740e-00 | 1.49560702e-00 | 9.36473429e-01 | 8.27870011e-01 |
| 6.51321828e-01 | 1.11091483e-00 | 3.88456941e-01 | 5.97497404e-01 |
| 6.03589952e-01 | 2.95225352e-01 | 8.75331759e-01 | 5.91197729e-01 |
| 1.42109334e-01 | 8.12613428e-01 | 4.96125184e-02 | 1.06508756e-00 |
| 9.74235773e-01 | 1.06946313e-00 | 8.66707340e-02 | 7.15477467e-02 |
| 6.34631634e-01 | 1.09400260e-00 | 9.70691442e-01 | 1.46729922e-00 |
| 5.48619926e-01 | 8.22730601e-01 | 7.82239676e-01 | 3.54846120e-02 |
| 3.34865212e-01 | 5.61231315e-01 | 6.32142127e-02 | 5.52365601e-01 |
| 7.54920781e-01 | 9.82614756e-01 | 3.50612521e-01 | 5.64515591e-01] |
| [8.64847526e-02 | −5.61808087e-02 | −1.32135987e-01 | −7.55270347e-02 |
| −2.35656559e-01 | −4.82676208e-01 | −4.09799010e-01 | 8.35188851e-02 |
| −1.28463283e-01 | −1.87746435e-01 | −1.45200476e-01 | −2.07436904e-01 |
| −1.94444656e-01 | −2.07587302e-01 | −1.73547357e-01 | −2.72773951e-01 |
| 8.33230793e-01 | 1.20120004e-01 | −1.00263402e-01 | 1.72346458e-01 |
| −2.37466469e-01 | −1.93082076e-02 | −4.99544352e-01 | −1.64329872e-01 |
| −2.40463763e-01 | −1.70154005e-01 | −1.42086282e-01 | −6.80577815e-01 |
| −2.75272697e-01 | −4.42587882e-01 | −1.38126045e-01 | 1.42107159e-01 |
| 4.77212906e-01 | −1.45565063e-01 | −4.27674502e-01 | −7.50436038e-02 |
| 2.14722067e-01 | −3.45969290e-01 | −3.98510396e-01 | −2.27909756e-01 |
| 4.44711708e-02 | 8.94329771e-02 | −2.97786176e-01 | −2.18294844e-01 |
| −2.48576835e-01 | −8.27389061e-02 | −3.04102659e-01 | 1.00871816e-01 |
| −1.30768493e-01 | −3.38308252e-02 | −1.22968694e-02 | −3.56067196e-02 |
| −1.92024365e-01 | −1.25892416e-01 | −1.87198967e-01 | 7.94940114e-01 |
| −4.44266200e-01 | −1.82368383e-01 | −1.75258666e-01 | 2.68167481e-02 |
| −3.21881980e-01 | −4.25427482e-02 | −4.06413317e-01 | −2.93463856e-01 |
| 8.46866369e-02 | −2.99992085e-01 | 2.89176613e-01 | −4.16324943e-01 |
| −1.99015349e-01 | −4.41618413e-01 | −5.56842126e-02 | 4.02033836e-01 |
| −3.32956731e-01 | 3.62972349e-01 | −8.79678652e-02 | 1.10861588e-00 |
| −5.03424525e-01 | −4.85442758e-01 | 1.71327330e-02 | −1.97377298e-02 |
| −1.90898865e-01 | −4.38627332e-01 | 2.43500769e-01 | −2.11925700e-01 |
| −1.96479678e-01 | −8.43187422e-03 | 3.02865654e-01 | −3.07225913e-01 |
| −2.76466072e-01 | −5.59266470e-02 | −3.63033354e-01 | 2.94137727e-02 |
| −8.31781089e-01 | −4.28884804e-01 | −4.44959775e-02 | −5.94070613e-01 |
| −5.87804057e-02 | −2.04006940e-01 | 3.36902231e-01 | −7.30611503e-01 |
| −2.73740828e-01 | −4.48385775e-01 | −4.71775264e-01 | −1.20862938e-01 |
| −1.27504557e-01 | −7.46407270e-01 | −3.58090788e-01 | 2.76840955e-01 |
| −2.86571383e-01 | −6.93551242e-01 | −5.12427032e-01 | −2.23617852e-01 |
| −8.94786358e-01 | −2.52341390e-01 | −3.23900938e-01 | −3.03874880e-01 |
| −6.10903442e-01 | −1.78708881e-01 | −2.32630610e-01 | −2.15396229e-02 |
| −8.03390145e-02 | −4.69977230e-01 | 2.81966746e-01 | −1.69719100e-01 |
| −3.52948606e-01 | −2.25830008e-05 | −1.11815177e-01 | −7.03383330e-03 |
| −5.30373514e-01 | −9.63682160e-02 | −1.72370866e-01 | −3.57310861e-01 |
| −4.64569569e-01 | −4.71696228e-01 | 8.06387141e-02 | 5.28890342e-02 |
| −4.67588454e-01 | −3.76277894e-01 | −4.10288543e-01 | −5.89826167e-01 |
| −3.92325997e-01 | −4.95813161e-01 | −2.15202481e-01 | 2.25148834e-02 |
| −3.88991684e-01 | 3.50213191e-03 | −3.36839944e-01 | −2.02473953e-01 |
| 7.64732733e-02 | −6.37255251e-01 | −5.01148403e-01 | −3.10954582e-02 |
| −4.20078486e-01 | 1.20884418e-01 | −2.53639132e-01 | −1.32786706e-01 |
| −2.71213084e-01 | 5.93163595e-02 | −9.44187567e-02 | −5.47823310e-01 |
| 1.94157427e-03 | 1.60189852e-01 | 5.61469831e-02 | −3.61961156e-01 |
| −8.09618533e-02 | −6.01822615e-01 | −3.17685694e-01 | 2.87041694e-01 |
| −1.59782961e-01 | −1.67845443e-01 | −4.05749887e-01 | 4.79421288e-01 |
| −2.21406147e-01 | −1.51363552e-01 | −5.82659841e-01 | 3.90985571e-02 |
| −4.82469529e-01 | −2.37317057e-03 | 3.18784058e-01 | 4.03374583e-02 |
| −2.71914780e-01 | −1.74432099e-01 | −4.55804735e-01 | −1.20700654e-02 |
| −5.70022613e-02 | −2.23803326e-01 | −1.99868694e-01 | −4.03242648e-01 |
| 1.99152917e-02 | −2.30904102e-01 | −2.48394653e-01 | 3.17332558e-01 |
| −2.12583840e-02 | −5.31111300e-01 | −6.64166927e-01 | 2.40845710e-01 |
| −2.34752893e-01 | 9.99643058e-02 | −1.78156346e-01 | −3.16689163e-01 |
| −4.96727854e-01 | −1.75162822e-01 | −1.14076845e-01 | −2.24845007e-01 |
| 1.76675335e-01 | −2.00601101e-01 | −2.02533185e-01 | −6.02806062e-01 |
| 1.76832065e-01 | −1.61115572e-01 | −5.37074685e-01 | −4.39412296e-01 |
| 1.17140912e-01 | 1.12421788e-01 | 1.10766277e-01 | −3.10222387e-01 |
| 8.44769031e-02 | −4.62733358e-01 | −7.66822100e-01 | 1.13544464e-01 |
| −2.91044593e-01 | 2.59316027e-01 | −2.99021956e-01 | 3.99000496e-01 |
| −5.40770352e-01 | −1.80593506e-01 | 3.63258049e-02 | −7.72393942e-01 |
| −5.41100323e-01 | −2.58535117e-01 | −9.74164084e-02 | −4.91323084e-01 |
| −4.22307700e-01 | −3.63270752e-02 | −3.34041595e-01 | −1.78966582e-01 |
| −2.53863245e-01 | −5.75810552e-01 | −2.15813801e-01 | −2.60670722e-01 |
| −1.25963271e-01 | −1.83150023e-01 | −1.93980724e-01 | −2.58812815e-01 |
| −8.07095349e-01 | −2.33395219e-01 | −4.01490957e-01 | −2.57067978e-01 |
| −2.72515088e-01 | −4.01182920e-01 | 1.03871278e-01 | −1.81210503e-01 |
| 5.17006323e-04 | −4.57385361e-01 | −6.73119724e-01 | −1.48574919e-01] |
| [1.12508185e-01 | −6.17528334e-02 | 7.16784477e-01 | 6.30885541e-01 |
| 1.07692838e-00 | 2.93708090e-02 | 4.10651654e-01 | 6.44305468e-01 |
| 1.09982455e-00 | 3.95051181e-01 | 2.82190382e-01 | 1.39953446e-00 |
| 1.11256146e-00 | 5.33525527e-01 | 5.27612269e-01 | 9.84500110e-01 |
| 1.15474141e-00 | 7.63647497e-01 | −2.51200229e-01 | 3.68549109e-01 |

TABLE $W_h^1$-continued

| | | | |
|---|---|---|---|
| 4.00070965e−01 | 1.22681439e−01 | 5.99534214e−01 | 1.19880176e−00 |
| 5.84733665e−01 | 9.05660808e−01 | −7.95950517e−02 | 1.27972269e−00 |
| 6.41700208e−01 | 1.54592365e−01 | 6.82283521e−01 | 6.13395721e−02 |
| 4.17240292e−01 | −3.90850790e−02 | 6.26826882e−01 | 4.44548251e−03 |
| −1.67653970e−02 | 6.82839870e−01 | 7.45110691e−01 | 3.76264483e−01 |
| 6.93288386e−01 | 1.05160689e−00 | 3.03478897e−01 | 7.08968937e−01 |
| 1.11276686e−00 | 8.42774808e−01 | 1.34387299e−01 | 5.64012110e−01 |
| 6.24487996e−01 | 2.38070801e−01 | 1.94321766e−01 | 6.31489515e−01 |
| 8.40134084e−01 | 5.47011018e−01 | 1.32532823e−00 | 3.33839983e−01 |
| 7.10401952e−01 | −1.69076368e−01 | 3.64643186e−01 | −5.86227000e−01 |
| 6.44137561e−02 | 7.13957012e−01 | 5.30205667e−01 | 8.14284265e−01 |
| 5.96138716e−01 | 9.25821722e−01 | 6.30584180e−01 | 6.47943676e−01 |
| 1.21155694e−01 | 2.60381043e−01 | 2.62731940e−01 | 4.13144007e−03 |
| 5.28814554e−01 | 6.43217087e−01 | 1.70343444e−01 | 1.81760058e−01 |
| 2.61563957e−01 | 1.87144607e−01 | 9.00782287e−01 | −2.11226404e−01 |
| 1.21634138e−00 | 2.08590046e−01 | 3.00764710e−01 | 6.09613299e−01 |
| −3.12792659e−01 | 5.78979552e−02 | 8.79479289e−01 | 6.90343857e−01 |
| 3.49460453e−01 | 6.28821075e−01 | 8.74284029e−01 | 6.32637978e−01 |
| 8.21908832e−01 | 1.06078410e−00 | 1.06979394e−00 | 3.58205110e−01 |
| 5.54124951e−01 | 1.27980411e−00 | −4.72465008e−01 | 7.32268691e−01 |
| 2.94776767e−01 | 1.63283730e−00 | 1.55071557e−01 | −1.49057964e−02 |
| 3.66604328e−01 | 6.61933839e−01 | 6.35077000e−01 | 1.30279005e−00 |
| 5.91781259e−01 | 4.60460544e−01 | 7.03476191e−01 | 8.19735527e−01 |
| 7.44224966e−01 | 7.10839570e−01 | 1.02003026e−00 | 1.01144540e−00 |
| 1.31893909e−01 | 2.84102589e−01 | 1.86915889e−01 | 4.73018885e−01 |
| 5.60002148e−01 | 9.76416588e−01 | 3.10603589e−01 | 7.57221729e−02 |
| 5.50100207e−01 | 3.61822039e−01 | 7.77046263e−01 | 8.45219731e−01 |
| 7.85825312e−01 | 1.59540281e−01 | 1.41777754e−00 | 3.84314567e−01 |
| 4.93596584e−01 | 6.35006785e−01 | 1.12384474e−00 | 6.51558459e−01 |
| 9.11019087e−01 | 7.28672326e−01 | 5.85497022e−01 | 5.29023111e−01 |
| 3.28709096e−01 | 7.45341241e−01 | 5.17279029e−01 | 7.82187641e−01 |
| 5.46510696e−01 | 4.45751190e−01 | −1.91779435e−01 | 9.68655586e−01 |
| 9.21277344e−01 | 6.10820234e−01 | 4.06677157e−01 | 7.70660400e−01 |
| 4.54581618e−01 | 5.80596209e−01 | 5.96408904e−01 | −7.10860267e−02 |
| −2.60272659e−02 | 9.87855196e−01 | 3.54697444e−02 | 4.63264257e−01 |
| 7.94984221e−01 | 2.33043253e−01 | 6.70613647e−01 | 1.13204277e−00 |
| 1.36687005e−00 | 5.31714082e−01 | 1.52677214e−00 | 3.09411168e−01 |
| 1.76592931e−01 | 3.36280912e−01 | −2.56654561e−01 | −6.29500002e−02 |
| 3.32905024e−01 | 1.24083292e−00 | 6.58028960e−01 | 4.34445471e−01 |
| 1.03803873e−00 | 1.07133961e−00 | 1.48709774e−01 | 4.01473522e−01 |
| 8.50664139e−01 | 5.27074993e−01 | 4.96764243e−01 | 3.04973632e−01 |
| 8.67025375e−01 | 3.81175965e−01 | 1.02664828e−00 | 7.25094736e−01 |
| 6.76849902e−01 | 6.64734423e−01 | 1.99507043e−01 | 7.82775700e−01 |
| 7.61614799e−01 | 6.31231248e−01 | 1.38394341e−01 | 3.58178109e−01 |
| 7.79757082e−01 | 7.17825174e−01 | 1.14801490e−00 | 2.36327693e−01 |
| 1.06616485e−01 | 5.57983816e−01 | 7.47451842e−01 | 5.17348647e−01 |
| 2.49582231e−02 | 6.09549463e−01 | 1.41758591e−01 | 6.43816054e−01 |
| 1.09469526e−01 | 1.05637872e−00 | 8.47519457e−01 | 8.12502444e−01 |
| 1.08700919e−00 | 1.70535505e−01 | 2.20487922e−01 | 6.74247086e−01 |
| 1.46806389e−01 | −6.49107387e−03 | 9.29762363e−01 | 8.76411915e−01 |
| 5.08765996e−01 | 7.85152316e−01 | 4.51215297e−01 | 6.86702728e−01 |
| 6.23330235e−01 | 4.10038918e−01 | 4.77250695e−01 | 2.60838121e−01 |
| 1.78127825e−01 | 7.08353460e−01 | 2.02067518e−00 | 6.10967517e−01 |
| 3.47994030e−01 | 1.09774840e−00 | 8.75915170e−01 | 2.93076217e−01 |
| 1.16735911e−00 | 9.38036442e−01 | 2.09024236e−01 | 7.17179894e−01 |
| 1.31078973e−01 | 8.46260071e−01 | 4.78693813e−01 | 8.86857092e−01 |
| 1.00361538e−00 | 9.43848252e−01 | 4.46053684e−01 | 5.33864081e−01 |
| 5.36838233e−01 | 1.38807863e−01 | 8.93069923e−01 | 3.94719183e−01 |
| 7.07429945e−01 | 1.65933043e−01 | 7.98798323e−01 | 5.56730807e−01] |
| [5.66361725e−01 | 5.71615636e−01 | 5.50368488e−01 | 3.24237198e−01 |
| 9.95531678e−02 | 1.42966676e−00 | 9.52799499e−01 | 3.38480063e−02 |
| 6.82994485e−01 | 3.34138185e−01 | 1.35541332e−00 | 5.56515604e−02 |
| −2.78348010e−02 | 4.16945428e−01 | 4.18649524e−01 | −3.45003784e−01 |
| −2.25724176e−01 | 9.24584270e−01 | 2.24344730e−01 | 4.01969552e−01 |
| 7.22822472e−02 | 5.34931362e−01 | 7.03324974e−01 | 8.85724127e−01 |
| 3.57558787e−01 | 2.60173976e−01 | 4.07317162e−01 | 7.99105704e−01 |
| 1.15068388e−00 | 9.05364752e−01 | 6.47337019e−01 | 4.70327616e−01 |
| 1.02858520e−00 | 3.26457947e−01 | 1.57907099e−01 | 8.47654119e−02 |
| 9.27751541e−01 | 5.01949966e−01 | 1.23066463e−01 | 3.25357080e−01 |
| 5.75341523e−01 | 5.73194981e−01 | 1.54457465e−01 | 7.00324118e−01 |
| 4.35862750e−01 | 1.75195813e−01 | 4.94785845e−01 | 8.33155870e−01 |
| 5.78511178e−01 | 1.86865523e−01 | 6.32995069e−01 | 1.05132568e−00 |
| 5.88076115e−01 | 2.27778688e−01 | 2.28535935e−01 | 1.37550458e−01 |
| 4.09824759e−01 | −1.74642265e−01 | 9.45193708e−01 | 1.14207640e−01 |
| 2.87813693e−01 | 8.23660851e−01 | 6.31812274e−01 | 1.55552343e−01 |
| 1.46502659e−01 | 2.02827424e−01 | 4.08796698e−01 | 2.40375981e−01 |
| −2.12809458e−01 | 3.09071094e−02 | 7.01626003e−01 | 4.84116701e−03 |
| 8.55560303e−01 | 3.21824580e−01 | −2.92148471e−01 | 3.54708999e−01 |
| 8.49462211e−01 | 9.17348981e−01 | 9.05083179e−01 | 7.17536211e−01 |
| 3.92760754e−01 | 1.45386890e−01 | 3.70978445e−01 | −9.64758694e−02 |

TABLE $W_h^1$-continued

| | | | |
|---|---|---|---|
| 1.20863698e−01 | −2.01975286e−01 | 4.59434450e−01 | 5.41907609e−01 |
| 2.45161712e−01 | 3.69097680e−01 | −2.74795681e−01 | 7.95127928e−01 |
| 7.11623311e−01 | 7.84349263e−01 | 5.75155377e−01 | 2.71438152e−01 |
| 1.34095564e−01 | 2.61651039e−01 | 1.46062762e−01 | 7.96339571e−01 |
| 2.25217521e−01 | 6.04393423e−01 | 3.81927252e−01 | 5.84303737e−01 |
| −1.67669490e−01 | 7.25336730e−01 | 4.42965180e−01 | −1.25417933e−01 |
| −1.24449037e−01 | 4.12149191e−01 | −2.65909396e−02 | 4.65775616e−02 |
| 6.00049496e−01 | 6.26488566e−01 | 7.29498982e−01 | 4.03084934e−01 |
| 8.33551943e−01 | 5.43787897e−01 | 8.27526212e−01 | −2.37467945e−01 |
| 2.36613169e−01 | 2.82159328e−01 | 3.45180064e−01 | 4.77078438e−01 |
| 3.42221648e−01 | 1.39889628e−01 | 5.15770316e−01 | 1.23065519e−00 |
| 3.37055773e−01 | 9.69236717e−02 | 3.30425054e−01 | 1.40473878e−00 |
| 7.02586591e−01 | 2.53418863e−01 | 4.65723015e−02 | 1.49143279e−01 |
| 3.74928653e−01 | 2.43779510e−01 | 3.37477416e−01 | 8.04686904e−01 |
| 3.66734296e−01 | 7.66281664e−01 | 6.01716042e−01 | 1.36868298e−01 |
| −2.18969092e−01 | −1.39558569e−01 | 8.60404015e−01 | 1.92521751e−01 |
| 5.25573492e−01 | 5.72453253e−02 | 2.96654403e−01 | −1.99169070e−01 |
| −5.83140887e−02 | 1.87014431e−01 | 2.22686782e−01 | 5.79118073e−01 |
| 5.92519045e−01 | 7.96198368e−01 | 1.99524850e−01 | 3.45534146e−01 |
| 2.15151042e−01 | 3.35884504e−02 | 1.69778481e−01 | 4.22148913e−01 |
| 6.68431997e−01 | −1.91139411e−02 | 9.10683274e−01 | 4.42742020e−01 |
| 5.87952137e−01 | 2.54230469e−01 | 5.70401669e−01 | −4.13646638e−01 |
| 1.01980567e−00 | 5.02464890e−01 | 3.42156470e−01 | 2.00424433e−01 |
| 5.30207098e−01 | 1.97942302e−01 | 2.52633899e−01 | 6.85481280e−02 |
| 1.36997473e−00 | 2.56535262e−01 | 1.20713735e−00 | 1.20974231e−00 |
| 3.08767617e−01 | 3.04447301e−02 | 4.26362604e−01 | 1.87005937e−01 |
| −2.86277026e−01 | 4.46883798e−01 | 5.82296848e−01 | 6.90937579e−01 |
| −1.59420133e−01 | 1.19070983e−00 | 7.31291622e−02 | 8.81958604e−02 |
| 1.60272226e−01 | 4.77706611e−01 | 6.32192016e−01 | 3.75894964e−01 |
| 3.53173792e−01 | 3.94570321e−01 | 7.91335642e−01 | 5.38419068e−01 |
| 4.79577243e−01 | −5.32858819e−02 | −4.69530523e−02 | 3.84961128e−01 |
| 7.39611149e−01 | 5.20259023e−01 | −1.13364197e−01 | 4.83479410e−01 |
| 2.51404583e−01 | 6.01604581e−01 | 6.95628896e−02 | 2.53558129e−01 |
| 2.27844402e−01 | 5.55597723e−01 | 5.51412165e−01 | 7.17007667e−02 |
| 4.20217574e−01 | 7.11484194e−01 | 2.55163342e−01 | 5.19731164e−01 |
| 2.79138871e−02 | 7.70000696e−01 | 5.40794432e−01 | 5.76471567e−01 |
| 4.42215025e−01 | 9.58303273e−01 | 1.18130279e−00 | 2.89995223e−01 |
| 1.05529174e−01 | 1.89791262e−01 | 6.46353126e−01 | 1.78155616e−01 |
| 4.70676512e−01 | 2.71386772e−01 | −8.66337046e−02 | −1.33483186e−01 |
| 1.24544048e−00 | −3.31181288e−01 | 5.34503579e−01 | 3.62357348e−01 |
| 2.32819781e−01 | 2.40085684e−02 | 6.68153167e−01 | 1.14707299e−01 |
| 2.31856763e−01 | −2.72693653e−02 | −2.03314368e−02 | −2.65315294e−01 |
| 2.14944720e−01 | 9.75817382e−01 | 3.65555763e−01 | −3.29980180e−02] |
| [4.30050641e−01 | −1.43869355e−01 | −4.95236255e−02 | 4.75731641e−02 |
| 4.78265025e−02 | 4.32662636e−01 | 3.82700831e−01 | −2.85968870e−01 |
| −1.72035053e−01 | 2.54158285e−01 | 3.73555422e−01 | −4.84421104e−01 |
| 2.66818941e−01 | −2.48289421e−01 | −1.95498429e−02 | −2.63553113e−01 |
| −3.99027348e−01 | −1.40402779e−01 | 1.97456673e−01 | −4.19695210e−03 |
| 1.15952127e−01 | 2.07257077e−01 | −2.81363696e−01 | 4.22931582e−01 |
| 1.13363750e−01 | 2.60323703e−01 | 2.42512710e−01 | −4.01222676e−01 |
| −4.72393930e−01 | 6.33428991e−01 | −6.09469898e−02 | 1.63562909e−01 |
| −1.74652673e−02 | 4.98489350e−01 | 3.47040117e−01 | 1.32903039e−01 |
| 2.08128870e−01 | 4.14650738e−01 | 7.30565667e−01 | −2.19866410e−01 |
| 1.39662743e−01 | 1.39263896e−01 | −1.39878646e−01 | 2.44791210e−02 |
| 3.61153662e−01 | 3.61372441e−01 | −1.52559280e−01 | −1.72519162e−02 |
| 2.06712157e−01 | −3.61699581e−01 | −2.71752596e−01 | −3.22481632e−01 |
| 4.03271139e−01 | −2.44144037e−01 | −1.86957344e−01 | −2.74335802e−01 |
| 1.77092016e−01 | 3.70600410e−02 | 2.26535574e−01 | 4.06978488e−01 |
| 2.60756940e−01 | 2.77549982e−01 | 7.04446554e−01 | 8.25606734e−02 |
| 4.96466123e−02 | −1.54943794e−01 | −3.20657372e−01 | 1.52957380e−01 |
| −2.51283683e−02 | 4.04738247e−01 | 2.73255408e−01 | 1.50041685e−01 |
| 4.99578685e−01 | −3.00004128e−02 | 2.71219909e−01 | −3.42906341e−02 |
| 1.20791765e−02 | 5.38238138e−02 | −2.83410728e−01 | −9.88875926e−02 |
| 9.63662937e−02 | 1.12011008e−01 | −9.38241091e−03 | −4.41040963e−01 |
| 2.52994150e−01 | 1.42257437e−02 | −2.71817476e−01 | −8.86048824e−02 |
| −8.81976187e−02 | −1.67629749e−01 | −6.45226985e−02 | −1.75308853e−01 |
| −2.69941092e−01 | −1.80345312e−01 | 3.22596431e−01 | 3.40515561e−01 |
| 2.35255927e−01 | 7.19987750e−02 | −3.43061276e−02 | −1.00888081e−01 |
| −2.42889449e−01 | 2.16286838e−01 | 2.99611777e−01 | −4.58804853e−02 |
| 1.85162663e−01 | 2.39458665e−01 | −4.76691306e−01 | 2.61290520e−01 |
| −1.30668864e−01 | 1.19740605e−01 | 6.47309482e−01 | 1.78893388e−03 |
| 1.05165638e−01 | 1.56635135e−01 | 2.46750675e−02 | −7.62096047e−01 |
| −8.62704590e−02 | −2.60557801e−01 | −1.83125630e−01 | −1.33665027e−02 |
| −6.48449287e−02 | 1.39796764e−01 | 2.12845027e−01 | 2.05315053e−01 |
| 1.55458763e−01 | 1.29426375e−01 | −4.25857753e−01 | 4.05488223e−01 |
| 1.19860554e−02 | −1.67110085e−01 | 1.34166226e−01 | 5.21328390e−01 |
| 2.89448649e−01 | −1.21901773e−01 | −2.92423934e−01 | 9.33527946e−02 |
| 5.56645027e−05 | −2.95867473e−01 | 1.78856432e−01 | 4.41591263e−01 |
| 2.78659433e−01 | 1.18407026e−01 | 4.28025782e−01 | 3.08849663e−01 |
| 2.58344173e−01 | 1.01014394e−02 | 2.36890674e−01 | 3.61110777e−01 |

TABLE $W_h^1$-continued

| | | | |
|---|---|---|---|
| −1.33734927e−01 | −2.02702239e−01 | 5.90490960e−02 | 1.83067657e−02 |
| −4.55829531e−01 | −2.08345391e−02 | −5.68340063e−01 | −1.79658290e−02 |
| 2.52542138e−01 | 8.48321393e−02 | −9.98299569e−02 | 1.79940641e−01 |
| −3.25590521e−02 | −6.76715747e−02 | −3.17973457e−02 | −1.17348395e−02 |
| −1.51134908e−01 | 4.67326462e−01 | −7.16972128e−02 | 4.50486094e−01 |
| −7.50919208e−02 | 3.54137331e−01 | 4.06156749e−01 | 5.44470660e−02 |
| 1.33285210e−01 | −7.70725533e−02 | −1.25533074e−01 | 1.79180473e−01 |
| 1.22626618e−01 | 3.43844295e−01 | −4.53220069e−01 | −1.14292711e−01 |
| 3.70169789e−01 | 1.21532874e−02 | 7.56107867e−02 | 4.62799132e−01 |
| −6.01082087e−01 | 5.05993813e−02 | −9.13131088e−02 | 9.53738391e−02 |
| −4.05598432e−01 | −6.41541779e−02 | 5.21004647e−02 | 4.54142988e−01 |
| −2.05497265e−01 | 6.60106689e−02 | −4.25737113e−01 | 5.56318998e−01 |
| 2.04375491e−01 | −4.32685733e−02 | −1.63859040e−01 | −9.36141461e−02 |
| 3.63462687e−01 | 1.35133103e−01 | −1.54736072e−01 | 2.95441628e−01 |
| 1.17259607e−01 | −1.00360624e−01 | 5.88712394e−02 | 1.18797487e−02 |
| 2.54817218e−01 | 5.75274646e−01 | −3.60389739e−01 | 5.53163886e−01 |
| 6.30578578e−01 | −3.68120000e−02 | 2.97010541e−01 | 5.69456398e−01 |
| 2.07577601e−01 | −1.29624456e−01 | −1.27475604e−01 | 3.14028263e−01 |
| 4.20767903e−01 | 6.05773807e−01 | −1.37664247e−02 | 1.53538764e−01 |
| 1.71755871e−03 | −5.50624169e−02 | 2.39299804e−01 | −4.98978853e−01 |
| 2.63817787e−01 | 2.25566804e−01 | 4.85395968e−01 | −1.32816881e−01 |
| −1.56914026e−01 | 4.98405918e−02 | 2.49110773e−01 | −2.87658930e−01 |
| −2.14456797e−01 | −4.02269602e−01 | 3.13664407e−01 | −2.08563983e−01 |
| 2.84839630e−01 | −1.48522958e−01 | −5.80256760e−01 | −3.16439953e−04 |
| −3.48073505e−02 | 3.85132372e−01 | −2.01323837e−01 | −4.17972095e−02 |
| −2.04660953e−03 | 1.21971391e−01 | 5.46466649e−01 | 6.16917908e−01 |
| 7.35609680e−02 | −2.53744016e−04 | 1.91541672e−01 | 2.07905874e−01] |
| [−5.32705069e−01 | −4.16743904e−01 | −1.83570728e−01 | 5.21424234e−01 |
| −1.81386724e−01 | −1.85643472e−01 | −1.00572161e−01 | −1.16719849e−01 |
| 1.08147837e−01 | 7.21920788e−01 | −6.80406988e−01 | −2.35869601e−01 |
| −9.94921923e−02 | −2.54041016e−01 | 7.05573738e−01 | 3.13084573e−01 |
| −8.44366550e−02 | 2.18294084e−01 | −1.04534841e−00 | 1.43405106e−02 |
| −3.69861662e−01 | −4.34555441e−01 | −4.95183766e−01 | −1.24526575e−01 |
| −4.41442430e−01 | −2.92265683e−01 | −2.02836469e−01 | 5.27426302e−01 |
| −9.82866585e−02 | −3.65409881e−01 | −3.32490206e−01 | −3.37551177e−01 |
| −3.81445229e−01 | −3.14413041e−01 | 2.03736022e−01 | −5.23708642e−01 |
| −5.23738682e−01 | −1.50733888e−01 | −3.94634873e−01 | −9.74743143e−02 |
| −3.83406401e−01 | −4.08065766e−02 | −2.50095636e−01 | 5.98710477e−01 |
| −5.26265875e−02 | 6.13115549e−01 | −2.28967622e−01 | 7.92907655e−01 |
| −2.16067001e−01 | −3.62833321e−01 | 2.02768996e−01 | 3.81731033e−01 |
| −5.01762331e−01 | −2.78346479e−01 | −1.06542697e−02 | −5.58729410e−01 |
| −5.62749505e−01 | −7.54562140e−01 | −7.63732716e−02 | −2.22949654e−01 |
| −3.54403585e−01 | −5.35104752e−01 | 7.29622781e−01 | −8.87277961e−01 |
| −4.63207304e−01 | −4.19306904e−01 | −2.73905188e−01 | −5.75535834e−01 |
| −8.73384714e−01 | −1.23647416e−00 | −3.16601127e−01 | 1.40183762e−01 |
| −2.06073880e−01 | −1.10347986e−01 | −2.08412901e−01 | −1.08795047e−00 |
| −1.95184067e−01 | −1.29453272e−01 | 4.82271105e−01 | −9.30478126e−02 |
| −8.83345827e−02 | −5.90745695e−02 | −4.19948488e−01 | −2.12950110e−01 |
| −6.41901076e−01 | −5.70495784e−01 | 3.58361512e−01 | 5.93456551e−02 |
| −1.62037998e−01 | 8.50067195e−03 | −5.04699070e−04 | 4.21491623e−01 |
| 9.22626317e−01 | 7.94702590e−01 | −1.57627478e−01 | −3.50130975e−01 |
| 6.78675294e−01 | 7.73553848e−01 | −4.54331130e−01 | −3.16389143e−01 |
| −1.90247148e−01 | −2.90177047e−01 | −3.81016582e−01 | −1.93882376e−01 |
| −5.70841670e−01 | −9.52969044e−02 | 1.01703608e−00 | −7.54050910e−01 |
| −3.97258371e−01 | −1.88388959e−01 | 4.23550196e−02 | 2.46223181e−01 |
| −1.40433297e−01 | −4.43080127e−01 | 1.40196383e−00 | −2.74059623e−02 |
| −7.61429667e−02 | −4.30564910e−01 | −2.76933074e−01 | 6.39919043e−02 |
| −3.24336499e−01 | −4.82437283e−01 | 8.76065865e−02 | −4.63509738e−01 |
| −3.42907369e−01 | −5.59765339e−01 | −1.32966518e−01 | 6.59076571e−01 |
| −1.58883750e−01 | −5.40993288e−02 | 1.48875311e−01 | −4.00780797e−01 |
| −1.21085420e−01 | 1.07044853e−01 | −1.49533570e−01 | −4.38936889e−01 |
| −2.17899323e−01 | 1.11398244e−00 | 7.93241560e−01 | −3.27745885e−01 |
| −4.80729043e−01 | −1.65461108e−01 | −4.85335708e−01 | −3.49304110e−01 |
| −1.13214694e−01 | −4.57316220e−01 | −4.17743057e−01 | −4.72664058e−01 |
| −2.72674024e−01 | 2.28715107e−01 | −4.19343352e−01 | −4.81178761e−01 |
| −2.85734087e−01 | 1.30841792e−01 | 2.25424785e−02 | −5.17848969e−01 |
| 3.71881783e−01 | −1.86832607e−01 | −3.50409865e−01 | −4.90779668e−01 |
| −2.25537151e−01 | 2.26055495e−02 | −2.05296680e−01 | −4.47753584e−03 |
| −3.57472867e−01 | −7.46768042e−02 | 7.95356512e−01 | −4.61144507e−01 |
| 7.20493734e−01 | −2.69624591e−01 | 3.25836033e−01 | −4.65714753e−01 |
| −6.22396767e−01 | 1.00539267e−01 | −1.04418851e−01 | −2.31645674e−01 |
| 1.34421214e−02 | −7.19153434e−02 | −3.64970684e−01 | −5.97256482e−01 |
| −4.29940999e−01 | −2.14226037e−01 | −1.48497045e−01 | −3.86236399e−01 |
| 3.01703215e−01 | −2.59557813e−01 | 3.04003149e−01 | −1.82678446e−01 |
| 1.73497051e−01 | −3.71249944e−01 | 3.96924108e−01 | −2.02357560e−01 |
| −4.39381078e−02 | −4.56450373e−01 | 1.46977320e−01 | −7.03118682e−01 |
| 5.98937511e−01 | −4.56145078e−01 | 3.44051868e−01 | −9.78122205e−02 |
| 7.88618803e−01 | 4.31781225e−02 | 2.14994505e−01 | −2.37904713e−01 |
| −4.13525105e−01 | 1.68326423e−01 | −6.79278746e−02 | −2.17464611e−01 |
| −5.58698952e−01 | −8.26860726e−01 | −1.96772650e−01 | −2.16725081e−01 |

TABLE $W_h^1$-continued

| | | | |
|---|---|---|---|
| −6.96071267e−01 | −5.44240117e−01 | −6.41770214e−02 | −2.14691103e−01 |
| −2.57831872e−01 | 7.67363831e−02 | 1.14803576e−00 | 1.73924789e−02 |
| −1.00019306e−01 | 5.62985707e−03 | 1.22093402e−01 | −4.89350289e−01 |
| −2.13974729e−01 | −1.80338435e−02 | −2.92717159e−01 | −3.98250222e−01 |
| −2.68732458e−01 | 3.48420441e−01 | −4.00912970e−01 | −2.27886200e−01 |
| 1.23264287e−02 | 5.13202310e−01 | −5.83644927e−01 | 5.25904894e−01 |
| 9.31957483e−01 | −1.95044264e−01 | 2.59529382e−01 | −3.10896546e−01 |
| 3.08470875e−02 | 5.59118748e−01 | 7.97402978e−01 | −3.51017594e−01 |
| −3.94241750e−01 | −6.94796622e−01 | 7.14615583e−01 | 1.72155157e−01 |
| 3.26908350e−01 | −1.80809021e−01 | −1.20538928e−01 | −4.26329076e−01 |
| −2.21214965e−02 | 2.47128502e−01 | 3.76576453e−01 | −1.64086252e−01] |
| [9.59465057e−02 | −2.71454126e−01 | −2.49255687e−01 | −8.23307335e−02 |
| −3.59104842e−01 | −3.45883816e−01 | −4.18454230e−01 | −3.28434408e−01 |
| −3.01757276e−01 | −3.34777892e−01 | −3.23990226e−01 | −1.57807156e−01 |
| −7.60080889e−02 | −8.86581913e−02 | −8.25364441e−02 | −2.01972090e−02 |
| −3.57423335e−01 | −5.11420786e−01 | 9.05200988e−02 | −2.22352937e−01 |
| −1.97458878e−01 | 3.48995835e−01 | −2.41033047e−01 | −2.79673278e−01 |
| 5.30843548e−02 | −1.44548461e−01 | −1.69392049e−01 | −4.92512047e−01 |
| −6.57539546e−01 | −3.16887081e−01 | −5.00803947e−01 | −4.23325926e−01 |
| 2.14933995e−02 | 5.47433682e−02 | −1.08304955e−01 | −2.42716204e−02 |
| −1.03716776e−01 | −7.84134790e−02 | −1.59775436e−01 | −1.97549775e−01 |
| −2.46612698e−01 | −1.73732594e−01 | −8.71135071e−02 | −5.35358727e−01 |
| −3.35577816e−01 | 5.16896974e−03 | −4.74264413e−01 | −7.43672311e−01 |
| −7.61551976e−01 | −2.91670948e−01 | −8.09556395e−02 | −7.61163354e−01 |
| 1.91945329e−01 | −3.72084767e−01 | −4.55380142e−01 | 3.96058291e−01 |
| −3.33201110e−01 | 2.59051800e−01 | −4.23627555e−01 | 1.91184148e−01 |
| 3.64466719e−02 | −4.15842049e−03 | −1.61442831e−01 | 2.75266945e−01 |
| −1.11777652e−02 | 1.51163399e−01 | −9.64548767e−01 | −1.33690611e−01 |
| 1.75393686e−01 | 2.27918342e−01 | −2.13426664e−01 | −3.02607715e−01 |
| −3.24297041e−01 | 1.56477660e−01 | −4.40425962e−01 | 3.55567008e−01 |
| −3.12505841e−01 | −3.80529135e−01 | −7.14305162e−01 | 1.09315842e−01 |
| −4.68999773e−01 | −1.07128114e−01 | 1.42558426e−01 | −3.75725716e−01 |
| −2.13263363e−01 | −1.54383332e−01 | 3.74748707e−02 | 1.73745528e−01 |
| −4.00782451e−02 | −2.42733240e−01 | −3.27159375e−01 | −3.16254616e−01 |
| −2.68683702e−01 | −5.38946949e−02 | −3.86927366e−01 | −5.15763462e−01 |
| 2.98939571e−02 | 2.39504248e−01 | 3.23676080e−01 | −2.91631222e−01 |
| −5.86515009e−01 | −4.09869581e−01 | −5.35024069e−02 | −3.66156846e−02 |
| 6.28962457e−01 | −2.91968137e−01 | −2.44682163e−01 | −2.38159522e−01 |
| −1.68224305e−01 | −3.58068526e−01 | 5.52168667e−01 | 2.27190614e−01 |
| −5.11813819e−01 | −6.21516109e−01 | −2.21423060e−01 | −1.81591630e−01 |
| −1.96519598e−01 | −3.40467215e−01 | −2.20854893e−01 | −2.77702808e−01 |
| 8.17352459e−02 | 1.37433141e−01 | −2.30744988e−01 | −2.33190700e−01 |
| −9.73549262e−02 | −3.13276529e−01 | −1.28117129e−01 | −7.55157530e−01 |
| −3.09505224e−01 | −5.85243404e−01 | −5.65511346e−01 | 4.77703921e−02 |
| 3.16228308e−02 | −3.77149917e−02 | −4.95567054e−01 | 4.23390120e−01 |
| 2.80516714e−01 | −5.04487693e−01 | −5.80823839e−01 | 5.48440278e−01 |
| 7.51816183e−02 | −1.97303191e−01 | −1.38164729e−01 | −2.34169170e−01 |
| −1.70892447e−01 | −4.17015016e−01 | −1.07633211e−01 | −3.55562747e−01 |
| −3.22118163e−01 | −1.30112067e−01 | 7.55524486e−02 | 2.67966576e−02 |
| 7.92125016e−02 | −5.43226264e−01 | −1.05398007e−01 | −1.27788827e−01 |
| −8.34239125e−02 | −2.22300515e−01 | −2.69367516e−01 | 9.05402098e−03 |
| −3.47126603e−01 | 2.33651891e−01 | 1.25566617e−01 | −1.53697878e−01 |
| −3.61966729e−01 | −8.45651329e−02 | −4.96894598e−01 | −2.62736619e−01 |
| 9.67778563e−02 | −1.36167005e−01 | −3.53857160e−01 | 1.74634859e−01 |
| −2.59562105e−01 | −6.06119692e−01 | 5.70040829e−02 | −9.34031159e−02 |
| −2.68679023e−01 | −2.10275322e−01 | 1.52310923e−01 | 6.40941262e−01 |
| −1.71706945e−01 | −7.08872676e−01 | −3.82747561e−01 | −3.54735792e−01 |
| −4.50587034e−01 | −3.20738077e−01 | 4.01748508e−01 | −1.36360362e−01 |
| −7.12471530e−02 | −1.23191454e−01 | −4.33825195e−01 | −4.05261248e−01 |
| −2.93784946e−01 | −4.06306326e−01 | −2.02600345e−01 | 2.28259310e−01 |
| −3.62893879e−01 | −3.31516713e−01 | −4.01037067e−01 | −4.46903221e−02 |
| −1.90402612e−01 | −2.45914131e−01 | −3.44140291e−01 | −3.48755151e−01 |
| −1.88481793e−01 | −5.68141997e−01 | −2.68447936e−01 | −2.27140129e−01 |
| −2.01336697e−01 | 4.73323837e−02 | −1.09213853e−00 | −6.21283054e−01 |
| 1.24164768e−01 | −2.74293423e−01 | −5.54447055e−01 | 1.74620733e−01 |
| −7.34806180e−01 | −2.92615920e−01 | −3.01197082e−01 | 2.20319808e−01 |
| 2.02879131e−01 | −8.29187110e−02 | −4.18572843e−01 | −3.26358639e−02 |
| 1.31873593e−01 | 2.43984148e−01 | 3.10887903e−01 | 1.67386606e−01 |
| 1.94276512e−01 | −1.36830628e−01 | −2.54477322e−01 | −5.70883691e−01 |
| −1.97558686e−01 | −4.06436831e−01 | −9.46839392e−01 | −3.17435741e−01 |
| −3.80161196e−01 | −3.84560108e−01 | −1.87677115e−01 | −1.12472497e−01 |
| −1.04147114e−01 | −7.73880854e−02 | 1.51029840e−01 | −3.17833751e−01 |
| −1.34623930e−01 | 3.59409302e−01 | −2.08263800e−01 | −3.17654759e−01 |
| −7.05037117e−01 | −6.85942592e−03 | −3.24940026e−01 | 2.64916033e−01 |
| −4.46849763e−01 | −2.56095737e−01 | −3.73831809e−01 | −3.80462646e−01] |
| [2.93457538e−01 | −1.67368017e−02 | 1.08021513e−01 | 8.92743189e−03 |
| −2.20719740e−01 | 4.14966732e−01 | 2.86514640e−01 | 1.99643761e−01 |
| 5.60065992e−02 | −3.05887043e−01 | 1.13561265e−01 | −2.89261729e−01 |
| −4.13527608e−01 | 2.88961112e−01 | −5.61319292e−01 | −6.00663900e−01 |
| 1.87846601e−01 | −1.93551347e−01 | 1.52177513e−01 | 3.64161253e−01 |

TABLE $W_h^1$-continued

| | | | |
|---|---|---|---|
| 1.75551414e−01 | −3.93051118e−01 | −4.42605734e−01 | 1.49642944e−01 |
| −3.56641382e−01 | 1.06401086e−01 | −1.85304850e−01 | −1.80322528e−01 |
| −2.22956035e−02 | 2.91591018e−01 | −3.24865341e−01 | 1.20563827e−01 |
| 4.26810235e−01 | 2.03915432e−01 | −3.43744569e−02 | 6.66134238e−01 |
| 1.18734464e−01 | −1.43476352e−01 | 2.03380764e−01 | −9.43702087e−02 |
| −4.59112152e−02 | 8.19903463e−02 | −4.93210346e−01 | 5.45090484e−03 |
| 4.32567537e−01 | −2.45320573e−01 | 1.98008865e−01 | −4.22754258e−01 |
| −1.82132483e−01 | −2.70608328e−02 | 2.55917639e−01 | −2.48686552e−01 |
| 2.69380301e−01 | −1.58496320e−01 | −6.54962882e−02 | −1.54316336e−01 |
| −4.43129754e−03 | 1.54120326e−01 | 2.11376533e−01 | 3.28111589e−01 |
| −2.19916686e−01 | 3.22487727e−02 | −3.77880901e−01 | 4.52148944e−01 |
| 1.00550339e−01 | 1.43373221e−01 | −2.18856543e−01 | −2.85593241e−01 |
| 2.96482891e−01 | 1.88010812e−01 | −1.33290470e−01 | −1.80975899e−01 |
| −2.04204023e−02 | 1.88310102e−01 | −4.12024796e−01 | 5.04874051e−01 |
| −3.13412040e−01 | 1.26822237e−02 | −1.73511460e−01 | −1.86226204e−01 |
| 6.62786424e−01 | −2.14938730e−01 | 1.55699447e−01 | 2.19172671e−01 |
| −1.24862239e−01 | 4.32240903e−01 | 3.94568652e−01 | 6.46799728e−02 |
| −1.80379391e−01 | 1.16446584e−01 | −5.22102937e−02 | 4.12608534e−02 |
| −6.76414967e−02 | −2.45515071e−02 | −2.19353482e−01 | −2.00518847e−01 |
| 2.21938029e−01 | −6.52093589e−02 | −2.58741409e−01 | −4.12837081e−02 |
| 2.60296434e−01 | −1.12568952e−01 | 4.78773206e−01 | 2.92464554e−01 |
| 1.47357643e−01 | 3.51974398e−01 | −4.19621654e−02 | −5.10610417e−02 |
| −1.55153587e−01 | −3.54040474e−01 | 1.27323329e−01 | 5.51148057e−02 |
| −4.36405480e−01 | −2.04630077e−01 | −4.96599495e−01 | 1.62669923e−02 |
| 1.56159341e−01 | 3.90671613e−03 | 1.05656505e−01 | 2.02998906e−01 |
| −3.94462526e−01 | 3.87087576e−02 | 2.70687193e−01 | 4.48691428e−01 |
| −6.38559312e−02 | −2.13694215e−01 | −1.52235240e−01 | 3.91638875e−01 |
| −1.45355120e−01 | −3.07711095e−01 | 3.68355989e−01 | −2.04948820e−02 |
| 2.47168634e−01 | −3.41198981e−01 | −1.06792741e−01 | 7.98902571e−01 |
| 1.27448915e−02 | −7.00503707e−01 | −2.19021905e−02 | −4.30070087e−02 |
| 1.12726405e−01 | 7.04436600e−02 | 4.40794714e−02 | 1.50461182e−01 |
| −6.59310967e−02 | −4.00670052e−01 | 3.92648637e−01 | −4.55150485e−01 |
| −2.14124084e−01 | −3.10093760e−01 | −5.18082500e−01 | 2.18741879e−01 |
| 2.47992352e−01 | −1.18866704e−01 | −3.83750618e−01 | −6.11220114e−02 |
| 1.60806790e−01 | 6.73054010e−02 | −2.00304851e−01 | 2.20567454e−02 |
| −2.67792791e−02 | −2.30635926e−01 | 9.60839912e−02 | 1.06304720e−01 |
| 1.40887409e−01 | −1.79645136e−01 | −4.01541084e−01 | 2.31200576e−01 |
| 3.29612345e−02 | −3.50110270e−02 | −3.32892835e−01 | 3.44297349e−01 |
| 2.08324101e−02 | −3.43413323e−01 | 1.99547946e−01 | −9.58015919e−02 |
| −4.64957021e−02 | −7.11833909e−02 | 7.27163911e−01 | −2.35904474e−03 |
| 4.00873601e−01 | 7.30238631e−02 | 3.08266766e−02 | 1.39180839e−01 |
| −1.25424966e−01 | 2.82030821e−01 | 2.81673759e−01 | −9.73570868e−02 |
| 2.79170632e−01 | −5.21162935e−02 | −4.40229215e−02 | 8.20624456e−02 |
| −2.63566583e−01 | −2.58540381e−02 | −1.15529165e−01 | −1.73060909e−01 |
| −3.55318010e−01 | −9.98184532e−02 | −4.90067825e−02 | 1.04671672e−01 |
| −4.64443058e−01 | 1.94361210e−01 | −3.04925859e−01 | −2.85748094e−01 |
| 4.65243906e−01 | −2.73515165e−01 | −4.40913215e−02 | 1.71427608e−01 |
| −2.78002679e−01 | 9.21520367e−02 | −6.24834895e−01 | −2.04757214e−01 |
| −2.27310464e−01 | 1.72053158e−01 | −2.27873042e−01 | 2.73932219e−01 |
| 4.00531650e−01 | −3.09124142e−01 | −4.03505504e−01 | 1.59837037e−01 |
| 5.33391088e−02 | 3.20459396e−01 | −3.05781215e−01 | 3.28572482e−01 |
| −1.00035056e−01 | 2.77779073e−01 | 2.03452587e−01 | 8.84419978e−02 |
| 2.45457321e−01 | −8.86391476e−02 | 8.15308392e−02 | −9.15667191e−02 |
| −5.34015037e−02 | 1.72076195e−01 | −2.78906226e−01 | −2.74203122e−01 |
| −2.66252756e−01 | 3.65853816e−01 | −9.34699625e−02 | −9.66446176e−02 |
| 2.63547719e−01 | −1.60368130e−01 | 5.25313139e−01 | −1.57813374e−02 |
| −5.07971563e−04 | 6.42906278e−02 | −1.68460995e−01 | 2.53574938e−01 |
| −4.69535232e−01 | 1.98439166e−01 | −6.04916476e−02 | −1.30771220e−01 |
| 2.81568855e−01 | 3.24793279e−01 | −2.30204910e−01 | 2.89938331e−01] |
| [5.06414354e−01 | 4.36809689e−01 | 4.07379597e−01 | 5.68675160e−01 |
| 6.85173512e−01 | 2.46492416e−01 | 4.35844779e−01 | 1.07001138e−00 |
| 8.39531004e−01 | 4.97894555e−01 | 1.10191357e−00 | 8.95850539e−01 |
| 6.76201999e−01 | 6.46259665e−01 | 7.93077111e−01 | 4.22619820e−01 |
| 7.10857332e−01 | 6.08155131e−01 | −4.49323267e−01 | 3.45106512e−01 |
| 2.89708436e−01 | −1.70526445e−01 | 8.51221621e−01 | 8.59554350e−01 |
| 1.40700257e−00 | 8.66323352e−01 | 2.72679806e−01 | 7.26366162e−01 |
| 1.02176785e−00 | 5.58749795e−01 | 5.10873258e−01 | 3.54469299e−01 |
| 1.90635073e−00 | 6.37263477e−01 | 8.74254942e−01 | 1.38380572e−01 |
| −1.22076064e−01 | 8.03075314e−01 | 4.83585417e−01 | 9.51176703e−01 |
| 9.89400864e−01 | 6.61741972e−01 | 3.54071140e−01 | 7.68850923e−01 |
| 8.12555850e−01 | 2.72126049e−01 | 6.58270478e−01 | 7.40414977e−01 |
| 2.62996882e−01 | 6.03344977e−01 | 1.16710532e−00 | 1.08955312e−00 |
| 2.03672066e−01 | 3.04462135e−01 | 5.59348762e−01 | 3.75209868e−01 |
| 4.88787353e−01 | 5.04890919e−01 | 3.28174114e−01 | 1.50594831e−01 |
| 2.57141262e−01 | 8.63117874e−01 | 4.48678762e−01 | 4.37646151e−01 |
| 8.29303682e−01 | 5.69371104e−01 | 3.96234781e−01 | 3.48170787e−01 |
| 1.61362529e−01 | −8.15200135e−02 | 1.50800914e−01 | 7.31190741e−01 |
| 9.49707627e−01 | 6.53082430e−01 | 4.27631319e−01 | 6.67203367e−01 |
| 1.25193238e−00 | 3.61610889e−01 | 6.15071237e−01 | 8.56412828e−01 |
| 4.78686124e−01 | 8.36233616e−01 | 4.50866044e−01 | 5.24519444e−01 |

TABLE $W_h^1$-continued

| | | | |
|---|---|---|---|
| 2.55348951e−01 | 4.44940388e−01 | 6.15489841e−01 | 4.53241855e−01 |
| 7.75870979e−01 | −3.04537974e−02 | 2.82270819e−01 | 3.03111404e−01 |
| 8.71288776e−01 | 7.24250853e−01 | 7.60354698e−01 | 1.88732475e−01 |
| 3.96247834e−01 | 3.63005936e−01 | 8.72383490e−02 | 7.69965827e−01 |
| 1.01890719e−00 | 1.30837500e−00 | 1.77298874e−01 | −4.83907480e−03 |
| 6.33677363e−01 | 1.41161525e−00 | 9.53564286e−01 | 6.13308311e−01 |
| 1.08223116e−00 | 3.15868676e−01 | 1.51926744e−00 | 5.16023517e−01 |
| 7.51571417e−01 | 9.85354185e−01 | 9.63424921e−01 | 7.51347303e−01 |
| 6.15451515e−01 | 1.68729097e−01 | 3.78252596e−01 | 2.36930743e−01 |
| −7.10871071e−02 | 1.22770894e−00 | 5.65557301e−01 | 7.01128900e−01 |
| 4.34039503e−01 | 8.91119838e−01 | 4.34049457e−01 | 1.53765893e−00 |
| 1.93416274e−00 | 4.18347865e−01 | 6.47759795e−01 | 7.46037126e−01 |
| 7.64653325e−01 | 3.50814879e−01 | 6.54580116e−01 | 3.45609099e−01 |
| 2.57675439e−01 | 8.95102203e−01 | 1.18687725e−00 | 7.00066328e−01 |
| 3.35210472e−01 | 5.51640749e−01 | 2.03447133e−01 | 5.63223183e−01 |
| 9.01452661e−01 | 7.06372976e−01 | 4.01798576e−01 | 6.90285802e−01 |
| 8.44401658e−01 | 7.32753813e−01 | 6.57097816e−01 | 1.58094212e−01 |
| 4.69529390e−01 | 1.17007434e−01 | 7.41517901e−01 | 3.64436895e−01 |
| −1.12598181e−01 | 4.51865137e−01 | 2.15289921e−01 | 4.66434568e−01 |
| 6.26293600e−01 | 4.72281903e−01 | 5.51423192e−01 | 7.75869608e−01 |
| 2.65182015e−02 | 9.38624203e−01 | 1.49561584e−00 | 8.24368596e−01 |
| 5.41043043e−01 | 1.50909498e−01 | 4.38364804e−01 | 4.28066850e−01 |
| 5.35031855e−01 | 7.85882711e−01 | 3.70645374e−01 | 4.32006389e−01 |
| 1.07293618e−00 | 4.78407264e−01 | 6.27811626e−02 | 3.23813379e−01 |
| 8.44949424e−01 | 3.71994287e−01 | 6.98733985e−01 | 1.32224098e−01 |
| 8.77437472e−01 | 2.49153614e−01 | 1.61813438e−00 | 1.00292647e−00 |
| 7.69054711e−01 | 9.66001809e−01 | 4.27639246e−01 | 7.81429529e−01 |
| 5.09863257e−01 | 8.37041974e−01 | 3.67029548e−01 | 5.23426831e−01 |
| 1.16774452e−01 | 8.40453506e−01 | 9.57415462e−01 | 4.94707584e−01 |
| 8.92409027e−01 | 5.80594063e−01 | 8.10073674e−01 | 6.25583053e−01 |
| 6.66985333e−01 | 6.79932356e−01 | 3.88182580e−01 | 5.41796386e−01 |
| 1.30980706e−00 | 1.07020342e−00 | 2.88306534e−01 | 1.20209849e−00 |
| 5.48474133e−01 | 9.84856308e−01 | 7.78965712e−01 | 9.94363546e−01 |
| 3.28386992e−01 | 4.81055707e−01 | 7.20495164e−01 | 4.43072710e−03 |
| 2.21194878e−01 | 7.87374914e−01 | 7.79354513e−01 | 9.25315380e−01 |
| 3.87351215e−01 | 3.43948036e−01 | 3.47430378e−01 | 1.28373075e−00 |
| 4.55005586e−01 | 9.45667207e−01 | 5.28090239e−01 | 6.47333264e−01 |
| 5.95282137e−01 | 1.42291236e−00 | 7.37692952e−01 | 7.23930538e−01 |
| 6.16095781e−01 | 9.39755619e−01 | 5.68843633e−02 | 3.94172668e−01 |
| 3.65843862e−01 | 6.93466246e−01 | 3.62447858e−01 | 6.83927596e−01 |
| 1.05753613e−00 | 7.34542489e−01 | 1.43260550e−00 | 1.52455044e−00 |
| 8.12094510e−01 | 4.27632660e−01 | 7.88489699e−01 | 6.28327489e−01 |
| 1.03407264e−00 | 7.94588447e−01 | 8.34860742e−01 | 7.92656541e−01] |
| [1.00743122e−01 | 3.34190965e−01 | 5.28860629e−01 | 5.16521931e−01 |
| 2.06673667e−01 | 5.82808435e−01 | 3.67522001e−01 | 5.63924134e−01 |
| 6.29981935e−01 | 5.34000695e−01 | 1.11326706e−00 | 3.60114239e−02 |
| 8.04851592e−01 | 2.87893355e−01 | 2.24306956e−02 | 1.86530322e−01 |
| 6.36972189e−02 | 8.07199061e−01 | −9.43451703e−01 | 5.56699693e−01 |
| 1.61433950e−01 | −4.52133305e−02 | 7.02538788e−01 | 6.91799223e−01 |
| 1.15569437e−00 | 2.81874657e−01 | 6.59354150e−01 | 6.47379100e−01 |
| −3.71528745e−01 | 4.29385751e−01 | 4.56020117e−01 | −1.92811377e−02 |
| 9.91898775e−01 | 4.09639597e−01 | 2.61314064e−01 | 1.76537409e−01 |
| −1.58976689e−01 | 1.82177335e−01 | 2.70296782e−01 | 8.22379589e−01 |
| 2.07496271e−01 | 5.58253586e−01 | 7.37519026e−01 | 1.17929912e−00 |
| 1.31777334e−00 | 1.02934152e−01 | 3.24864358e−01 | 2.16452986e−01 |
| 6.13218434e−02 | 3.32013220e−01 | 2.62410104e−01 | 7.28942633e−01 |
| 7.25680411e−01 | 8.38801041e−02 | 3.12919199e−01 | −4.51746672e−01 |
| 1.40205038e−00 | 6.24434471e−01 | 7.76364326e−01 | −2.11371854e−01 |
| 9.53638554e−02 | 9.86984909e−01 | 1.06640100e−00 | 7.13683441e−02 |
| 2.21536532e−01 | 7.79628992e−01 | 4.19238567e−01 | 6.70521200e−01 |
| 3.42437744e−01 | 8.43519032e−01 | 8.55475426e−01 | 7.81689286e−01 |
| 6.43047392e−01 | 3.35861951e−01 | 3.66344333e−01 | −3.27028394e−01 |
| 1.03671741e−00 | 3.00788552e−01 | 2.89912015e−01 | 7.92059243e−01 |
| 9.85842347e−01 | 7.58784950e−01 | 7.39715695e−01 | 7.52753854e−01 |
| 7.12927103e−01 | 9.34282005e−01 | 3.05363029e−01 | −2.26179492e−02 |
| 6.06877953e−02 | 6.45228505e−01 | 9.96421099e−01 | 1.28267616e−00 |
| 4.64278609e−01 | −3.83964747e−01 | 8.60774457e−01 | 4.52683359e−01 |
| 8.44472647e−01 | 5.16075380e−02 | 1.71474263e−01 | 9.11732256e−01 |
| 3.71416122e−01 | 1.19099903e−00 | 5.79304278e−01 | −5.83469331e−01 |
| 2.58529007e−01 | 1.06736207e−00 | 5.75489521e−01 | 4.76500660e−01 |
| 8.31935108e−01 | 1.22395718e−00 | 1.46171719e−01 | −3.69413979e−02 |
| 2.48177245e−01 | 6.84173644e−01 | 1.66732818e−01 | 5.02213895e−01 |
| 7.75235891e−01 | 2.07033008e−01 | 1.08826375e−00 | 3.32401395e−01 |
| 4.23542857e−01 | 2.54476398e−01 | 6.54421449e−01 | 1.07146072e−00 |
| 1.10441589e−00 | 9.73625422e−01 | 3.26315671e−01 | 3.78910840e−01 |
| 5.73296130e−01 | 6.12131298e−01 | 9.67218757e−01 | 6.94045663e−01 |
| 6.63216233e−01 | 7.01722383e−01 | 6.85507178e−01 | 4.36118066e−01 |
| 4.44521308e−01 | 7.42450118e−01 | 9.10536706e−01 | 5.27297378e−01 |
| 5.51087499e−01 | 4.72184211e−01 | 2.27156967e−01 | 5.00945866e−01 |
| 4.72408623e−01 | 7.07092106e−01 | 4.16022614e−02 | 1.06330049e−00 |

TABLE $W_h^1$-continued

| | | | |
|---|---|---|---|
| 9.19093072e−01 | 3.32729965e−01 | 6.98215783e−01 | 6.60582602e−01 |
| 6.21191263e−01 | 3.70005846e−01 | 6.76440060e−01 | 8.89670193e−01 |
| 3.14217389e−01 | 5.99120677e−01 | 6.12052619e−01 | 1.18602514e−00 |
| 8.32830489e−01 | −1.08367419e−02 | 2.21614793e−01 | 7.42950559e−01 |
| 1.22209167e−00 | 3.57511759e−01 | 9.87446427e−01 | 4.20572132e−01 |
| 3.20123315e−01 | 2.55527824e−01 | 5.43277204e−01 | 8.65146935e−01 |
| 9.67607319e−01 | 6.45215631e−01 | 4.92469311e−01 | 1.78171974e−02 |
| 2.71103591e−01 | 1.20025706e−00 | −2.49900185e−02 | 4.77798611e−01 |
| 9.26125407e−01 | 7.14272738e−01 | 7.49753952e−01 | 6.40811622e−01 |
| 2.72427589e−01 | 4.93057907e−01 | 2.57657677e−01 | 5.24289571e−02 |
| 3.15607578e−01 | 3.08632940e−01 | 9.76447523e−01 | 7.31016397e−01 |
| 3.19889277e−01 | 6.38465345e−01 | −9.04464126e−02 | 3.37696612e−01 |
| 6.45451903e−01 | 7.04971611e−01 | 1.45943418e−01 | −1.97825715e−01 |
| 1.55264556e−00 | 3.60407531e−01 | 8.09598923e−01 | 8.49351823e−01 |
| 8.51494521e−02 | 5.12014329e−01 | 8.67566824e−01 | 5.51693082e−01 |
| 4.79989350e−02 | 6.64894521e−01 | 4.94901150e−01 | −1.62794024e−01 |
| 3.69408786e−01 | 1.95646852e−01 | 3.09909821e−01 | 5.61499894e−01 |
| 4.89084184e−01 | 3.77214760e−01 | 2.78294593e−01 | −6.79045841e−02 |
| 1.92996025e−01 | 6.20159924e−01 | 8.82110059e−01 | 4.17164236e−01 |
| 3.30071628e−01 | 4.47508663e−01 | 3.14725906e−01 | 7.16602385e−01 |
| 8.29046667e−01 | 1.46973431e−01 | 9.24374878e−01 | 9.50160205e−01 |
| 7.36448288e−01 | 3.46483231e−01 | 4.89089221e−01 | 5.58321893e−01 |
| 4.34918106e−02 | 1.15932429e−00 | −3.61040533e−02 | −9.58329514e−02 |
| 3.13489735e−01 | 7.11619183e−02 | 3.16382766e−01 | 3.56154382e−01 |
| 7.35506237e−01 | 5.64240813e−02 | 2.50670075e−01 | 1.48194224e−01 |
| 8.14542532e−01 | −1.95972383e−01 | 4.58601922e−01 | 1.17699742e−00 |
| 1.03038156e−00 | 3.68759513e−01 | 4.44617838e−01 | 5.97836375e−01] |
| [6.02651119e−01 | 3.16573352e−01 | 5.61285853e−01 | 5.43713272e−01 |
| 1.87289238e−00 | 5.93714356e−01 | 5.71033418e−01 | 8.39331806e−01 |
| 1.38597071e−00 | 2.05676854e−01 | 4.10041928e−01 | 9.54252839e−01 |
| 2.51995474e−01 | 9.30623949e−01 | 9.14939344e−01 | 7.88228214e−01 |
| 4.38491195e−01 | 2.09933653e−01 | −2.02951565e−01 | 7.30615973e−01 |
| 8.66233766e−01 | 5.61473891e−01 | 4.89314854e−01 | 3.60926628e−01 |
| 4.95900095e−01 | 6.37382269e−01 | −7.12284027e−03 | 6.87689662e−01 |
| 3.93489450e−01 | 3.64159793e−01 | 6.10742092e−01 | −2.70710848e−02 |
| 7.42925763e−01 | 1.33184564e−00 | 6.69549763e−01 | −3.49046201e−01 |
| −9.88421664e−02 | 3.42479736e−01 | 5.87400317e−01 | 7.43815541e−01 |
| 9.39885080e−01 | 5.83079398e−01 | 3.30827773e−01 | 1.17880285e−00 |
| 1.64341962e−00 | 1.05069900e−00 | 2.31926858e−01 | 5.14401615e−01 |
| 1.15841222e−00 | 8.46705794e−01 | 1.12861085e−00 | 6.31764412e−01 |
| 7.81136334e−01 | 6.14531815e−01 | 5.12555659e−01 | 1.33434668e−01 |
| 7.82685339e−01 | −3.10754851e−02 | 2.85736740e−01 | 1.56964183e−01 |
| 4.67003614e−01 | 9.90405828e−02 | 7.38948464e−01 | 1.20625627e−00 |
| −1.46139175e−01 | 1.09125221e−00 | 3.60421360e−01 | 8.12500298e−01 |
| 4.43376482e−01 | −5.73379034e−03 | 1.26653731e−00 | 8.13141525e−01 |
| 1.71238828e−00 | 1.82453644e−00 | 8.72350186e−02 | 5.93811810e−01 |
| 8.07740867e−01 | 5.69877446e−01 | 7.62065828e−01 | 3.60042542e−01 |
| 9.70313668e−01 | 6.17155433e−01 | 1.08577885e−01 | 3.48777443e−01 |
| 3.60197037e−01 | 9.26367939e−02 | 7.74057508e−01 | 4.20393825e−01 |
| 6.16896152e−01 | 6.34099483e−01 | 9.65928495e−01 | 8.36059570e−01 |
| 9.32463467e−01 | 1.52884424e−00 | 9.48219895e−01 | 2.92734742e−01 |
| 3.60176384e−01 | 3.15369457e−01 | 2.63547122e−01 | 1.04457021e−00 |
| 7.79362857e−01 | 1.44182432e−00 | 2.28815392e−01 | 2.34322354e−01 |
| 4.34181869e−01 | 6.15222096e−01 | 5.49173295e−01 | 1.05951095e−00 |
| 8.03003609e−01 | 4.05223876e−01 | 3.42768073e−01 | 3.98331106e−01 |
| 9.22148883e−01 | 7.14437589e−02 | 8.64253998e−01 | 1.06531286e−00 |
| 1.00712073e−00 | 1.68198988e−01 | 6.64088428e−01 | 3.46318692e−01 |
| 4.02345031e−01 | 9.61840808e−01 | 2.87463516e−01 | 4.67002094e−01 |
| 9.89703774e−01 | 1.13951457e−00 | 4.60332662e−01 | 7.71499395e−01 |
| 1.29084659e−00 | 2.44875833e−01 | 9.32051599e−01 | 1.92173064e−00 |
| 8.60392690e−01 | 6.03677690e−01 | 7.72148788e−01 | 5.31673610e−01 |
| 6.21696293e−01 | 3.61474514e−01 | 8.60820234e−01 | 9.09539461e−01 |
| 5.41831076e−01 | 7.14092374e−01 | 1.83901161e−01 | 1.05128896e−00 |
| 7.69401431e−01 | 8.76288056e−01 | 7.11144030e−01 | 1.12837029e−00 |
| 8.15956414e−01 | 8.53561342e−01 | 7.75745273e−01 | 2.63042897e−01 |
| 1.36541271e−00 | 2.35978231e−01 | 1.50465757e−01 | 8.45085323e−01 |
| 7.16892704e−02 | 4.10057843e−01 | 1.18446803e−00 | 1.70101300e−01 |
| 6.22076452e−01 | 5.63985705e−01 | 3.18940282e−01 | 7.45907187e−01 |
| 1.17910874e−00 | 6.31399333e−01 | 7.92422533e−01 | 2.64904708e−01 |
| 7.14196801e−01 | 1.29571342e−00 | 2.99699754e−01 | 8.88632238e−01 |
| 3.03258270e−01 | 5.21574199e−01 | 9.92787123e−01 | −4.09797542e−02 |
| 7.53911257e−01 | 4.25417662e−01 | 1.77849919e−01 | 1.60101339e−00 |
| 7.95593083e−01 | 7.78700888e−01 | 9.41899717e−01 | 9.59153652e−01 |
| 8.06398869e−01 | 7.26263002e−02 | 6.57117307e−01 | 9.04530406e−01 |
| 5.60925543e−01 | 6.79641187e−01 | 1.95576847e−01 | 1.29495645e−00 |
| 9.52595711e−01 | 5.87176621e−01 | 1.16637409e−00 | 4.72831249e−01 |
| 6.09432340e−01 | 8.13737333e−01 | 8.59920859e−01 | 1.24483123e−01 |
| 1.32045567e−00 | 5.45613468e−01 | 4.51465756e−01 | 4.23304141e−01 |
| 8.75964910e−02 | 6.44804120e−01 | 2.00060561e−01 | 5.04755914e−01 |
| 5.83660662e−01 | 1.00060594e−00 | 8.34363818e−01 | 6.94558680e−01 |

TABLE $W_h^1$-continued

| | | | |
|---|---|---|---|
| 3.91584635e−01 | 1.18254375e−00 | 1.04592109e−00 | 8.67423356e−01 |
| 7.73320615e−01 | 1.79571837e−01 | 1.20158470e−00 | 5.79063952e−01 |
| 8.93828094e−01 | 5.44330895e−01 | 4.23945606e−01 | 1.14576364e−00 |
| 6.85273409e−02 | 8.63821387e−01 | 5.03764153e−01 | 4.41537917e−01 |
| 5.45489192e−01 | 5.77045083e−01 | 3.36273581e−01 | 6.56569183e−01 |
| 3.80438894e−01 | 8.69347513e−01 | 9.02685523e−01 | 7.46223688e−01 |
| 7.50321150e−01 | 5.91222048e−01 | −6.72789738e−02 | 2.96739548e−01 |
| 1.94610551e−01 | 7.06397414e−01 | 1.22966862e−00 | 3.46812457e−01 |
| 4.79987919e−01 | 6.07249439e−01 | 1.13682353e−00 | 1.02195096e−00 |
| 5.94091117e−01 | 3.07499707e−01 | 6.00264847e−01 | 6.21258020e−01 |
| 4.14095074e−01 | 9.90199447e−01 | 8.05334091e−01 | 2.82626390e−01] |
| [4.55448367e−02 | −2.62603581e−01 | −2.81981915e−01 | −3.65556628e−01 |
| 2.90457815e−01 | 2.26432621e−01 | −3.97090405e−01 | 3.92534100e−02 |
| −9.06920955e−02 | −3.28071415e−02 | −3.85903180e−01 | 5.66296518e−01 |
| −4.92371432e−02 | −2.06046104e−01 | 6.51898265e−01 | 2.77758420e−01 |
| 4.61576551e−01 | 1.10848439e−00 | −8.68876159e−01 | −3.24981958e−01 |
| −3.22416335e−01 | −3.26255292e−01 | −5.01286834e−02 | 8.47431831e−03 |
| 1.10265082e−02 | 1.64989352e−01 | −4.91598099e−01 | 9.02527988e−01 |
| 7.25215793e−01 | −4.54602271e−01 | −1.46824300e−01 | −4.67924654e−01 |
| −1.94721967e−01 | −4.38896745e−01 | −2.49838933e−01 | 2.02566683e−01 |
| −1.49195030e−01 | −4.65495855e−01 | 5.25752977e−02 | 2.39597961e−01 |
| 2.36336797e−01 | 2.94396669e−01 | 1.94247246e−01 | 8.18542778e−01 |
| 1.20039113e−01 | 6.08911335e−01 | −7.67917335e−01 | 2.54097283e−01 |
| 5.80107808e−01 | 1.43690169e−01 | −2.12669894e−01 | −2.55758196e−01 |
| −9.12251472e−02 | 5.07339358e−01 | 2.86635727e−01 | −4.02138263e−01 |
| 7.35110164e−01 | −5.83260097e−02 | −2.17567131e−01 | −1.69061739e−02 |
| −3.82982284e−01 | −7.23171115e−01 | −9.22080874e−02 | −4.94995892e−01 |
| −7.04761624e−01 | 2.13189796e−01 | 2.52683729e−01 | 3.57228875e−01 |
| −7.05841959e−01 | −5.55040002e−01 | −4.57519025e−01 | −2.45324194e−01 |
| 7.50419796e−02 | 2.69430220e−01 | 3.14489782e−01 | −8.07669163e−01 |
| 3.40407372e−01 | −1.60725772e−01 | 3.04639637e−01 | 9.08707738e−01 |
| 2.17872970e−02 | −2.69512057e−01 | −5.39286911e−01 | −3.29794586e−01 |
| −7.89666355e−01 | −3.03445995e−01 | −1.31572485e−01 | 2.03629449e−01 |
| 9.27862704e−01 | 4.97382246e−02 | 6.74633682e−02 | 8.60905290e−01 |
| 4.84703094e−01 | 5.42607844e−01 | 1.01527996e−01 | −2.32190788e−01 |
| 2.96996951e−01 | −1.13542534e−01 | −5.20757437e−01 | −1.93771929e−01 |
| 4.95592095e−02 | −4.62138414e−01 | −3.35042953e−01 | 6.32268071e−01 |
| −1.11050165e−00 | −1.40702054e−01 | 5.10386646e−01 | −1.00529268e−01 |
| −2.83390045e−01 | 1.30906805e−01 | 1.18971050e−01 | 6.63048029e−01 |
| −2.45438516e−01 | −5.63165009e−01 | 1.46478963e−00 | 3.10419559e−01 |
| 2.08920702e−01 | −6.02944195e−01 | −2.42695019e−01 | −2.39096433e−01 |
| 7.72846937e−02 | −5.21533825e−02 | 1.59909621e−01 | −1.73493013e−01 |
| 8.87260139e−02 | −9.90129188e−02 | 5.33715151e−02 | 1.10381007e−00 |
| 2.90529560e−02 | −4.80885565e−01 | 1.73477292e−01 | −3.91158730e−01 |
| 4.01167363e−01 | 2.76360884e−02 | 8.89017344e−01 | 5.22561491e−01 |
| 2.47321472e−01 | 1.50480127e−01 | 2.56479308e−01 | −2.15756759e−01 |
| −1.87635515e−02 | −5.29548228e−01 | 1.81505725e−01 | −4.79612142e−01 |
| 2.63963550e−01 | −9.31239277e−02 | −2.75262445e−01 | −5.95843613e−01 |
| −5.95774204e−02 | −2.14525864e−01 | 4.50775512e−02 | −1.22119598e−01 |
| −2.13207409e−01 | −1.99897766e−01 | −2.69244790e−01 | −2.41334751e−01 |
| 9.26009178e−01 | −6.74016654e−01 | −3.36523354e−01 | −5.04122913e−01 |
| 9.88593027e−02 | −6.73249736e−03 | −3.02560449e−01 | −1.34367034e−01 |
| −5.30801564e−02 | 2.33038634e−01 | 5.05522609e−01 | 3.77911657e−01 |
| −3.47067535e−01 | −4.93448563e−01 | −5.68688691e−01 | −5.56191206e−01 |
| −2.97054648e−01 | 5.77548631e−02 | 1.60547107e−01 | −2.26896673e−01 |
| −1.03496738e−01 | 2.68848985e−01 | 7.12183043e−02 | −9.79722440e−02 |
| 4.32421872e−03 | −4.19443160e−01 | −6.50973618e−02 | −6.07187301e−02 |
| −4.68341969e−02 | −1.94850817e−01 | −4.88051713e−01 | 9.73344296e−02 |
| −3.86168420e−01 | −5.40424943e−01 | −3.03719863e−02 | 2.53776908e−01 |
| −4.26279545e−01 | −8.58891904e−02 | 9.10001457e−01 | −7.69755185e−01 |
| −4.94758636e−01 | −4.74215686e−01 | 3.68534595e−01 | −2.72098392e−01 |
| −3.18866223e−02 | 3.95416200e−01 | 8.73353541e−01 | −1.50582030e−01 |
| 4.75412831e−01 | 3.05656910e−01 | 1.85253888e−01 | −6.55597746e−01 |
| −5.00311442e−02 | −4.24358010e−01 | 4.29531246e−01 | −4.46545511e−01 |
| −1.22869059e−01 | −1.50700599e−01 | 5.99367023e−01 | −8.41605842e−01 |
| −5.10197163e−01 | 1.34462893e−01 | 9.09315109e−01 | −2.78126359e−01 |
| 4.27302957e−01 | −4.88965482e−01 | 3.91743422e−01 | −4.53957051e−01 |
| −4.44797784e−01 | −4.09451388e−02 | −4.29943681e−01 | 3.93679917e−01 |
| −6.03955805e−01 | 7.86035135e−02 | −2.06671551e−01 | −2.47181401e−01 |
| 6.83280170e−01 | 1.37931335e−00 | −2.22150102e−01 | 5.53562880e−01 |
| −2.20462885e−01 | 2.49508202e−01 | 8.98346379e−02 | 2.70937771e−01 |
| −1.18760921e−01 | 5.53346694e−01 | 9.37117040e−01 | 2.94650882e−01 |
| −1.11885993e−02 | 6.97038397e−02 | 1.24368262e−00 | 4.38219070e−01 |
| 5.62269986e−01 | −2.70066857e−01 | 2.36031398e−01 | −3.28922272e−02 |
| −9.98091474e−02 | 5.04415929e−01 | −5.09294607e−02 | −7.98251666e−03] |
| [1.04374826e−00 | 6.43200278e−01 | 4.62970763e−01 | 6.23955309e−01 |
| 9.34482217e−01 | 2.70219177e−01 | 8.54096591e−01 | 9.55822229e−01 |
| 8.90551984e−01 | 5.41927934e−01 | 8.12395334e−01 | 9.43434775e−01 |
| 9.48548257e−01 | 3.11785340e−01 | 2.68845797e−01 | 6.44132912e−01 |
| 6.46497965e−01 | 8.84910822e−01 | 3.78564388e−01 | 4.39982206e−01 |

TABLE $W_h^1$-continued

| | | | |
|---|---|---|---|
| 5.47863781e−01 | 2.16565952e−01 | 1.30411327e−00 | 3.61053884e−01 |
| 1.98253334e−00 | 2.51975417e−01 | 9.82379690e−02 | 1.07718349e−00 |
| 8.18295538e−01 | 4.74483371e−01 | 8.63805711e−01 | 4.16924506e−01 |
| 9.37594831e−01 | 3.45693767e−01 | 3.87620211e−01 | −3.72595377e−02 |
| 2.32610665e−02 | 1.42473793e−00 | 1.07968307e−00 | 6.26790822e−01 |
| 6.37781143e−01 | 6.50426507e−01 | 4.41730380e−01 | 1.18324995e−00 |
| 3.05537879e−01 | 7.67205000e−01 | 2.04248399e−01 | 9.48722422e−01 |
| 7.10265994e−01 | 6.12174809e−01 | 6.99052274e−01 | 8.45856428e−01 |
| 5.18553197e−01 | 7.22193599e−01 | 4.98869836e−01 | 4.06207383e−01 |
| 4.89500374e−01 | 5.30927122e−01 | 7.25241661e−01 | −1.24718390e−01 |
| 1.09082960e−01 | 4.26346481e−01 | 5.81240892e−01 | 4.50135827e−01 |
| −1.08796775e−01 | 5.52347064e−01 | 8.67005944e−01 | 5.49757242e−01 |
| 1.85544148e−01 | 5.03267348e−01 | 3.82877022e−01 | 2.80486614e−01 |
| 1.09600997e−00 | 9.85665500e−01 | 5.23878634e−01 | 5.26052952e−01 |
| 6.62980556e−01 | 2.92884976e−01 | 3.97144407e−01 | 1.02301753e−00 |
| 9.07118738e−01 | 3.80880058e−01 | 2.66507626e−01 | 6.33867264e−01 |
| 4.37038094e−01 | 4.01733279e−01 | 7.84186482e−01 | 4.20126557e−01 |
| 5.36110699e−01 | −2.83625662e−01 | 6.64132297e−01 | 4.41907793e−01 |
| 1.22966671e−00 | 8.24497938e−01 | 8.93472075e−01 | 3.80490810e−01 |
| 5.19998908e−01 | 1.38545692e−01 | 1.37470037e−01 | 1.03077018e−00 |
| 9.17924941e−01 | 1.85057068e−00 | 3.19031477e−01 | 1.59135088e−01 |
| 3.85943115e−01 | 6.44575119e−01 | 7.77469575e−01 | 1.01959896e−00 |
| 9.50062513e−01 | 7.31944203e−01 | 3.39606792e−01 | 3.61021012e−01 |
| 1.25147986e−00 | 3.77534360e−01 | 1.01022899e−00 | 1.06675994e−00 |
| 7.37045109e−01 | 2.52823293e−01 | 5.73181927e−01 | 7.62245774e−01 |
| 3.41251671e−01 | 9.83846307e−01 | 9.07328725e−01 | 1.42277181e−00 |
| 6.60464227e−01 | 7.88565278e−01 | 1.01034403e−00 | 6.33387804e−01 |
| 1.50269544e−00 | 5.33824980e−01 | 9.13747430e−01 | 8.59572947e−01 |
| 8.60779822e−01 | 8.22187543e−01 | 6.25612438e−01 | 3.58630389e−01 |
| 5.57735801e−01 | 8.26808333e−01 | 1.04432404e−00 | 7.43490934e−01 |
| 7.89655820e−02 | 8.96736607e−02 | 5.06680071e−01 | 5.95235407e−01 |
| 6.08785987e−01 | 6.34338260e−01 | −1.89149126e−01 | 1.14816761e−00 |
| 8.61217737e−01 | 7.98875868e−01 | 7.61683702e−01 | 3.85012865e−01 |
| 4.62767065e−01 | 7.79769719e−01 | 9.38955188e−01 | 3.68289441e−01 |
| −9.61002186e−02 | 3.76196414e−01 | 5.20765007e−01 | 7.33587801e−01 |
| 8.11880350e−01 | 5.34525275e−01 | 1.91616565e−01 | 3.53923768e−01 |
| 1.06811404e−00 | 1.12776577e−00 | 1.00897706e−00 | 8.83839607e−01 |
| 9.67459202e−01 | 8.19007695e−01 | 3.27556938e−01 | 5.75319767e−01 |
| 4.92279053e−01 | 5.96704245e−01 | 4.13989842e−01 | 1.87558189e−01 |
| 4.25842196e−01 | 6.57492042e−01 | 2.24358618e−01 | 5.01975000e−01 |
| 8.96879792e−01 | 4.37953621e−01 | 8.77858877e−01 | 5.61217725e−01 |
| 6.52586281e−01 | 3.32515270e−01 | 1.08045614e−00 | 3.77315909e−01 |
| 5.14093697e−01 | 5.12925565e−01 | 8.01544249e−01 | 4.22065467e−01 |
| 5.37885666e−01 | 3.28909338e−01 | 6.80860221e−01 | 2.94906765e−01 |
| 3.39082986e−01 | 7.22562015e−01 | 7.94023812e−01 | 3.44597638e−01 |
| 1.07970154e−00 | 4.31628674e−01 | 6.79434717e−01 | 8.41217697e−01 |
| 2.08750919e−01 | 9.99906301e−01 | 3.08211356e−01 | 9.02969658e−01 |
| 6.39114499e−01 | 8.97931576e−01 | 9.60301995e−01 | 6.95662498e−01 |
| 9.84963834e−01 | 2.12813780e−01 | 7.67894089e−01 | 1.40299428e−00 |
| 2.11989298e−01 | 7.02978969e−01 | 9.09354687e−01 | −2.46404499e−01 |
| 8.19658458e−01 | 1.58042789e−00 | 1.24865091e−00 | 8.35914671e−01 |
| 7.61195242e−01 | 5.80407202e−01 | 5.94463381e−01 | 8.08916986e−01 |
| 8.81448388e−01 | 5.43637276e−01 | 6.80029392e−01 | 6.91027045e−01 |
| 5.76744437e−01 | 1.53996795e−02 | 7.96078265e−01 | 1.15506661e−00 |
| 7.61099398e−01 | 1.02110732e−00 | 8.33053231e−01 | 1.06216244e−00 |
| 1.98621154e−01 | 7.23001003e−01 | 5.16176581e−01 | 6.36674166e−01 |
| 1.26855230e−00 | 1.28315961e−00 | 6.13367617e−01 | 1.17460871e−00 |
| 6.62132204e−01 | 3.91665727e−01 | 6.30217254e−01 | 6.47268772e−01 |
| 5.66539541e−02 | 6.54398382e−01 | 3.22634846e−01 | 9.13223505e−01] |
| [3.79472315e−01 | 1.95573449e−01 | 5.73675215e−01 | 3.15224528e−01 |
| 1.01153207e−00 | 4.20435637e−01 | 6.42925858e−01 | 2.33361661e−01 |
| 2.50689805e−01 | 2.35615775e−01 | 5.00049591e−01 | −5.24017699e−02 |
| 5.58602631e−01 | 5.39633453e−01 | 6.01556292e−03 | 5.97182848e−02 |
| 2.99309552e−01 | 6.05278730e−01 | 4.16132450e−01 | 1.19924575e−00 |
| 6.05149031e−01 | 2.28736326e−01 | 5.89237630e−01 | 5.66351295e−01 |
| 8.06233466e−01 | 4.76843566e−01 | 7.06845582e−01 | 4.53133076e−01 |
| 2.42934749e−01 | 7.10706890e−01 | 1.30203038e−01 | 1.24414414e−01 |
| 7.76807547e−01 | 1.56926345e−02 | 3.27066362e−01 | 2.37186760e−01 |
| 3.11338723e−01 | 3.15752804e−01 | 9.77780998e−01 | 2.68878251e−01 |
| 3.68963003e−01 | 5.06868243e−01 | 3.09521765e−01 | 9.86949325e−01 |
| 5.34983158e−01 | 6.01331711e−01 | 6.42679095e−01 | −9.59844980e−03 |
| −2.04169318e−01 | −3.05663571e−02 | 4.92558926e−01 | 1.70335546e−01 |
| 4.91985768e−01 | 3.22340190e−01 | 5.74069858e−01 | 3.34238946e−01 |
| 4.22334582e−01 | −1.26866207e−01 | 8.38921428e−01 | 1.06530420e−01 |
| −1.56692550e−01 | 1.15608752e−00 | 1.79826856e−01 | 4.18308854e−01 |
| 2.83704370e−01 | 6.25136852e−01 | 4.42309290e−01 | 2.18593597e−01 |
| 4.30454314e−01 | 3.79595548e−01 | 2.77720302e−01 | 5.38209558e−01 |
| 4.00307536e−01 | 2.95618057e−01 | 5.16523361e−01 | 9.92763638e−02 |
| 6.85690999e−01 | 1.47227570e−01 | 3.12936246e−01 | 4.79857832e−01 |
| 8.15154314e−01 | 4.23546970e−01 | 4.28758413e−01 | 5.85397124e−01 |

TABLE $W_h^1$-continued

| | | | |
|---|---|---|---|
| 1.76806018e−01 | 5.65659463e−01 | 4.91082430e−01 | 4.40403670e−01 |
| 4.05063421e−01 | 4.44303095e−01 | 4.42980289e−01 | 8.02404657e−02 |
| 4.87277329e−01 | 3.53592694e−01 | −1.81509219e−02 | 8.48184526e−01 |
| 4.84737009e−01 | −4.12548892e−02 | 4.02740866e−01 | 5.32866538e−01 |
| 4.58990842e−01 | 2.31088325e−01 | 5.37153363e−01 | 3.43171090e−01 |
| 5.25236666e−01 | 1.00456583e−00 | 6.98150575e−01 | 7.46085942e−01 |
| 3.13436180e−01 | 7.64542878e−01 | 1.17614590e−01 | 5.13675034e−01 |
| 1.04191244e−00 | 5.14694333e−01 | −9.04199630e−02 | 3.91897649e−01 |
| 8.73927355e−01 | 5.05713582e−01 | 5.69576919e−01 | 1.37714639e−01 |
| 2.06879318e−01 | 3.80424112e−01 | 5.35967052e−01 | 5.28069019e−01 |
| 6.59832895e−01 | 2.73515463e−01 | 1.46736205e−01 | 7.49401331e−01 |
| 4.36474919e−01 | 5.00372887e−01 | 3.20679128e−01 | 8.63740802e−01 |
| 2.19859198e−01 | 2.88738072e−01 | 4.32163514e−02 | 6.12603605e−01 |
| 4.34767425e−01 | 4.81894851e−01 | 6.91290081e−01 | 1.51544854e−01 |
| 4.79158759e−01 | −2.65714014e−03 | −5.31634279e−02 | 2.84918725e−01 |
| 1.06416893e−00 | 7.39830256e−01 | −3.78983608e−03 | 4.75414127e−01 |
| 5.12654662e−01 | 6.04216516e−01 | 3.92099947e−01 | 1.21264182e−01 |
| 7.37866163e−01 | 3.58457297e−01 | 3.44339460e−01 | 1.92933634e−01 |
| 2.60105997e−01 | 3.52530748e−01 | 4.49361920e−01 | 8.27109516e−01 |
| 2.67246366e−01 | 6.29137516e−01 | 3.74992996e−01 | 9.64971840e−01 |
| 3.68299693e−01 | 6.06611431e−01 | 6.16550148e−01 | 6.13045335e−01 |
| 8.26489687e−01 | 5.71290255e−01 | 3.39097977e−01 | −3.83708179e−02 |
| 2.77771086e−01 | 2.09168121e−01 | 6.45066738e−01 | 6.06610477e−01 |
| 6.42768860e−01 | 2.64864534e−01 | −7.99416825e−02 | 3.41718286e−01 |
| 9.07471895e−01 | −1.66324005e−01 | 5.44551492e−01 | 3.09552282e−01 |
| 5.28720975e−01 | 3.23236436e−01 | 5.02052128e−01 | 4.64835167e−01 |
| 3.33126783e−01 | 3.39638591e−01 | 5.32725751e−01 | 1.12725222e−00 |
| 2.54134864e−01 | 4.23559994e−01 | 3.07205617e−01 | 2.76207685e−01 |
| −3.32385488e−02 | 3.56902689e−01 | −1.46858990e−02 | 2.77544498e−01 |
| 8.09425712e−01 | 9.56293106e−01 | 2.67546833e−01 | 6.18625522e−01 |
| 7.06385434e−01 | 5.46083391e−01 | 7.26086140e−01 | 1.95043266e−01 |
| 1.86979949e−01 | 9.13372219e−01 | 6.78627849e−01 | 4.59591329e−01 |
| 5.91851890e−01 | 2.90641129e−01 | 2.36858070e−01 | 1.20527315e−00 |
| 5.49273491e−01 | 3.33835542e−01 | 1.85976475e−01 | −2.37947464e−01 |
| 4.16552246e−01 | 1.09010410e−00 | 6.72184750e−02 | 7.47702360e−01 |
| 7.16910422e−01 | 5.78841627e−01 | 1.67372137e−01 | 6.97736800e−01 |
| 1.25447130e−00 | 2.00013667e−01 | 7.50062406e−01 | 4.56460714e−01 |
| 2.94173807e−01 | 7.73603678e−01 | 4.26556915e−01 | 3.21457624e−01 |
| 4.48344797e−01 | 8.61104131e−01 | −1.13537898e−02 | −7.09690899e−02 |
| −2.74095625e−01 | 4.01097208e−01 | 2.61770338e−02 | 2.87199676e−01 |
| 1.01637352e−00 | 1.29705250e−00 | 4.57699805e−01 | 1.60851145e−00 |
| 7.44372368e−01 | −9.25499722e−02 | 5.74011207e−01 | 7.06073642e−01 |
| 4.76640344e−01 | 1.32054853e−00 | 2.73825288e−01 | 3.11153773e−02] |
| [1.44776255e−01 | −6.31611124e−02 | −4.98282373e−01 | 1.43614903e−01 |
| 2.49214739e−01 | 9.84064415e−02 | 2.47514635e−01 | −4.27500345e−02 |
| −2.82179043e−01 | 2.62577422e−01 | −3.75963986e−01 | −1.76974386e−01 |
| 8.40971395e−02 | −2.45462731e−03 | −1.18178628e−01 | −3.08133028e−02 |
| −5.84394753e−01 | −6.81283832e−01 | −2.52262890e−01 | −1.55828327e−01 |
| 1.98847830e−01 | 1.87037155e−01 | −1.09318770e−01 | 1.43264860e−01 |
| 1.84347443e−01 | 2.48212188e−01 | −5.71022853e−02 | −1.86969802e−01 |
| −3.23166668e−01 | 8.77863839e−02 | −4.67004534e−03 | −1.67805836e−01 |
| 7.72395283e−02 | −2.39854604e−01 | 1.46269836e−02 | 4.08526182e−01 |
| 3.49810928e−01 | 2.26888999e−01 | 7.63968289e−01 | −2.08513945e−01 |
| −8.23541172e−03 | −7.99319074e−01 | −1.20140374e−01 | −7.26906210e−01 |
| −1.43008187e−01 | 1.60849988e−01 | 1.68299768e−02 | −3.86780351e−01 |
| −2.58194059e−01 | −8.45054835e−02 | −2.73039043e−01 | −1.41818365e−02 |
| 3.53145182e−01 | −2.15362206e−01 | −9.54636186e−02 | −4.32532758e−01 |
| 1.37455761e−01 | 1.93431884e−01 | 2.86204368e−01 | 3.12820166e−01 |
| 4.89527494e−01 | 5.12997448e−01 | 2.52302759e−03 | −8.77658650e−02 |
| 9.71866772e−02 | 2.55996495e−01 | 8.64104331e−02 | 2.58404523e−01 |
| 6.60500348e−01 | 3.92643124e−01 | 3.38051319e−01 | 4.43691760e−02 |
| 9.09548774e−02 | −3.85446995e−01 | −5.84859923e−02 | −2.12229922e−01 |
| 1.72976345e−01 | 3.45213935e−02 | −5.25135338e−01 | −4.52833891e−01 |
| −9.16974172e−02 | 1.33432075e−01 | −1.48806900e−01 | −1.76098868e−02 |
| 1.99359193e−01 | 4.23595011e−01 | −1.61566645e−01 | 5.07946789e−01 |
| −7.70381391e−02 | −8.11843872e−02 | 5.57164708e−03 | −5.88447034e−01 |
| −5.00861168e−01 | −3.58050287e−01 | 1.54533461e−01 | −6.10375516e−01 |
| 1.63858399e−01 | 1.96904093e−02 | −2.85152555e−01 | 2.29130223e−01 |
| 5.48688889e−01 | −1.46987289e−01 | 2.42125407e−01 | −5.12656212e−01 |
| −1.12725161e−01 | 5.91969378e−02 | 2.63202965e−01 | −3.78891945e−01 |
| −5.37199378e−01 | 2.44058937e−01 | 8.52009654e−03 | −2.69132257e−01 |
| 2.27539584e−01 | 1.15229867e−01 | −4.63838696e−01 | −1.68349862e−01 |
| 5.86584397e−02 | 4.59090412e−01 | −1.09728247e−01 | 1.19728327e−01 |
| −3.28744888e−01 | 1.73673183e−02 | 1.40743479e−01 | −1.06437176e−01 |
| 9.58806574e−01 | −3.63696069e−02 | −2.47003406e−01 | 1.41420057e−02 |
| 1.48904055e−01 | −2.13805974e−01 | −2.59193242e−01 | 5.36985159e−01 |
| 6.15554273e−01 | 3.18730682e−01 | −5.05626440e−01 | 2.90138364e−01 |
| −1.28125995e−01 | −2.59363323e−01 | 6.22605756e−02 | 2.06601709e−01 |
| 1.22103728e−01 | 5.24079382e−01 | 1.60401046e−01 | 3.98671329e−01 |
| 5.49884200e−01 | −6.41909242e−02 | 3.70673805e−01 | −2.70143241e−01 |

TABLE $W_h^1$-continued

| | | | |
|---|---|---|---|
| −2.94084609e−01 | −1.17383368e−01 | −3.43885601e−01 | −3.73301893e−01 |
| −3.30809802e−02 | 6.31417334e−02 | 2.20767092e−02 | −3.93333249e−02 |
| −4.55448180e−02 | 6.73110422e−04 | −3.28196645e−01 | 2.26634577e−01 |
| 7.67407566e−02 | −1.52771071e−01 | 1.00540318e−01 | −6.69092417e−01 |
| 6.09889142e−02 | 5.87430596e−01 | 6.97370529e−01 | 9.98998731e−02 |
| −1.90855879e−02 | 4.16637927e−01 | 4.75589275e−01 | −1.44667491e−01 |
| 1.40524909e−01 | −3.73220593e−01 | 1.72246546e−01 | 3.06961179e−01 |
| 7.56013468e−02 | 4.75109033e−02 | −5.62315762e−01 | −2.03628223e−02 |
| −1.85228437e−01 | 1.45788252e−01 | 2.10581589e−02 | −6.30486012e−02 |
| −4.37892914e−01 | 2.48597369e−01 | 1.59413785e−01 | 4.59038377e−01 |
| −2.29608715e−01 | 1.54114500e−01 | 1.58435494e−01 | 1.95869654e−01 |
| −2.55278498e−01 | 1.62533477e−01 | 1.02138016e−02 | 1.53321385e−01 |
| 6.66425228e−01 | 4.48606387e−02 | −3.31234932e−01 | 3.15710634e−01 |
| −1.94552213e−01 | −1.08632408e−01 | 1.71137080e−01 | 3.32293697e−02 |
| 9.65663716e−02 | −4.17350888e−01 | 4.52024430e−01 | 3.48736703e−01 |
| 1.87305883e−01 | 3.77895057e−01 | 6.17791526e−02 | 3.66366088e−01 |
| 5.95150590e−01 | 3.64717185e−01 | 2.02446625e−01 | 6.54781997e−01 |
| −9.78517011e−02 | −1.67758793e−01 | 9.43180695e−02 | 3.29744071e−01 |
| −1.70996606e−01 | −1.52159752e−02 | −8.77253413e−02 | −4.81061161e−01 |
| 8.26481059e−02 | 4.04335797e−01 | −2.50296265e−01 | 2.22040638e−01 |
| 3.94374356e−02 | −3.26500237e−02 | 2.90974438e−01 | 3.56115520e−01 |
| −3.02270472e−01 | 1.76268280e−01 | 7.98194706e−02 | −9.15865228e−02 |
| −2.97858212e−02 | −4.97190505e−02 | −2.20608413e−01 | −1.82924241e−01 |
| 1.84858054e−01 | −2.05369711e−01 | −4.86939609e−01 | −2.14709148e−01 |
| −3.67917866e−02 | 5.92749476e−01 | −2.60726362e−01 | −4.40229475e−02 |
| 2.88285434e−01 | −3.10546130e−01 | −3.34097385e−01 | 1.90501094e−01 |
| −2.57649422e−02 | 3.19924980e−01 | 9.03424099e−02 | 2.68537074e−01] |
| [−1.47072509e−01 | 1.65048409e−02 | 5.27181812e−02 | −2.66468793e−01 |
| −2.05007732e−01 | −5.79790287e−02 | 3.68868619e−01 | 5.31487390e−02 |
| 5.54304659e−01 | −2.32002392e−01 | 1.05804875e−02 | −1.34353578e−01 |
| 9.08121914e−02 | −4.26522732e−01 | 1.00861180e−00 | 2.56171674e−01 |
| 1.65119934e−00 | 4.33031052e−01 | 1.49231076e−01 | −3.24855447e−01 |
| −5.58045506e−02 | −3.19388390e−01 | 2.50306457e−01 | −8.24594423e−02 |
| −4.59598541e−01 | −5.81450403e−01 | 4.18308407e−01 | −2.85349786e−01 |
| −3.86732310e−01 | 1.53525531e−01 | 1.02288938e−00 | −2.84764647e−01 |
| −1.48113862e−01 | 3.84260744e−01 | −1.22421481e−01 | 2.71574650e−02 |
| −6.41858876e−02 | 1.43062189e−01 | −4.92110215e−02 | −3.13427329e−01 |
| 9.72207665e−02 | −4.17200834e−01 | −3.30240399e−01 | −4.08745408e−01 |
| −9.64057669e−02 | −9.47903097e−03 | −5.41771837e−02 | 6.36376321e−01 |
| −2.25796893e−01 | 5.17789185e−01 | 4.40784127e−01 | 1.42265379e−01 |
| −4.66573447e−01 | 1.30161718e−01 | −1.93095475e−01 | 5.33379376e−01 |
| 4.09549296e−01 | −2.11040199e−01 | −4.13176835e−01 | 2.10986793e−01 |
| −3.57841879e−01 | −7.59676024e−02 | −1.95616245e−01 | 1.11260444e−01 |
| −3.42842460e−01 | −2.07279548e−01 | 7.54563153e−01 | −2.60742486e−01 |
| 2.78155804e−01 | 1.85296327e−01 | 1.24489434e−01 | 1.26103580e−01 |
| −4.75730926e−01 | −1.92730919e−01 | 3.58763188e−01 | 7.73789227e−01 |
| −6.20344341e−01 | −1.81440398e−01 | −8.47552836e−01 | −2.65582740e−01 |
| −8.98218095e−01 | −2.20956683e−01 | 3.15321863e−01 | −3.80492598e−01 |
| −6.10109530e−02 | −5.59511222e−02 | 5.54306321e−02 | −4.38654512e−01 |
| −3.92566562e−01 | −1.08107448e−01 | −8.94785523e−02 | 5.69981873e−01 |
| 2.46845782e−01 | 3.75628740e−01 | 3.28091085e−01 | −4.02356386e−01 |
| 1.70162871e−01 | 1.21942267e−01 | 3.47872376e−01 | −8.54198396e−01 |
| −3.15536052e−01 | −1.13952413e−01 | −3.60464007e−01 | −1.71964526e−01 |
| −3.39013815e−01 | −8.94569606e−02 | −5.93669057e−01 | 1.57010567e−00 |
| 5.41743696e−01 | −3.57865691e−01 | 2.11868599e−01 | −4.69961435e−01 |
| −3.46328288e−01 | 5.66139877e−01 | −6.54736698e−01 | −2.24248096e−01 |
| −4.28192466e−01 | −7.14431226e−01 | −4.15072709e−01 | 7.99581707e−02 |
| −2.99013764e−01 | −3.59412342e−01 | −6.84128925e−02 | 3.00553083e−01 |
| −4.39778000e−01 | −1.17724404e−01 | −2.55636662e−01 | −3.00198287e−01 |
| 4.21878964e−01 | −1.50164053e−01 | 1.16959202e−00 | −3.42399567e−01 |
| −4.15572613e−01 | −5.41280746e−01 | −8.55598822e−02 | −4.85270917e−01 |
| −1.52099416e−01 | −6.09680712e−02 | −1.86039373e−01 | −3.56098205e−01 |
| −1.11935688e−02 | −2.96763182e−01 | 4.32375103e−01 | −1.70775786e−01 |
| −4.87468541e−01 | −1.79011598e−01 | −8.31285492e−02 | 1.09047341e−00 |
| 2.01194007e−02 | 1.94811970e−01 | 6.79276645e−01 | 1.36599422e−01 |
| 3.40516776e−01 | 5.86618304e−01 | −5.09784102e−01 | −7.21642002e−02 |
| 2.49119997e−01 | −1.17851160e−01 | −1.78228393e−01 | −3.13495666e−01 |
| 8.17712486e−02 | −4.46683764e−01 | −1.54499695e−01 | −1.92356899e−01 |
| −7.10099399e−01 | 9.92895365e−02 | −4.46133427e−02 | −7.04983762e−03 |
| −3.76965314e−01 | −1.33506516e−02 | 7.23235831e−02 | 6.50938526e−02 |
| −4.83744234e−01 | 8.94036070e−02 | −2.61086702e−01 | 1.54074103e−01 |
| 1.66170552e−01 | −4.81297374e−01 | −3.47491115e−01 | 4.83610928e−01 |
| 1.72668427e−01 | 7.06596792e−01 | 1.74607098e−01 | 1.45894364e−01 |
| 4.18565534e−02 | 5.20652413e−01 | 1.05158454e−02 | −3.11256886e−01 |
| 3.36686999e−01 | −2.11404040e−01 | −1.37478307e−01 | −2.03800917e−01 |
| −3.79247405e−02 | −3.51983190e−01 | −4.64751899e−01 | 1.98965948e−02 |
| −1.92319170e−01 | 9.60853338e−01 | −2.83198595e−01 | −4.32411432e−01 |
| 1.32379055e−01 | −1.77180350e−01 | −6.03223324e−01 | 4.79639143e−01 |
| 2.85668701e−01 | 1.97241813e−01 | −3.48204792e−01 | 3.72853205e−02 |
| 5.54670215e−01 | 2.93784231e−01 | −7.86408484e−02 | 1.23593785e−01 |

TABLE $W_h^1$-continued

| | | | |
|---|---|---|---|
| −2.89515674e−01 | 2.01348960e−01 | 6.59063220e−01 | −6.12405360e−01 |
| −3.57238948e−01 | −2.29116350e−01 | −6.45997822e−01 | 7.08911061e−01 |
| −4.73382473e−01 | 1.93720579e−01 | 1.44406438e−01 | 2.66907334e−01 |
| −1.14166819e−01 | −5.05371869e−01 | −2.29595900e−01 | −4.96522218e−01 |
| −6.45911396e−02 | −4.25124876e−02 | −1.10103697e−01 | −3.52278352e−01 |
| −4.73873802e−02 | 1.49312124e−01 | 1.77601233e−01 | −9.47823673e−02 |
| −1.81392640e−01 | −2.46581599e−01 | −4.23326343e−02 | 9.95696127e−01 |
| −3.04515243e−01 | −4.66511041e−01 | −4.64380026e−01 | −3.41068774e−01 |
| −1.35528743e−01 | −6.32492065e−01 | −1.44986391e−01 | −1.10184819e−01 |
| −2.06503987e−01 | 8.45047906e−02 | 6.14144206e−01 | 1.82048500e−01 |
| 1.11900830e−00 | −2.98434824e−01 | −3.65667313e−01 | 6.21193200e−02] |
| [−2.72873729e−01 | 1.60932139e−01 | −2.36037731e−01 | −6.74710155e−01 |
| −4.41351086e−01 | −3.57098967e−01 | −1.88432470e−01 | 5.50428212e−01 |
| −1.09641835e−01 | −7.05199897e−01 | −7.44031370e−01 | 4.40373451e−01 |
| −4.19677824e−01 | −1.40678719e−01 | −8.23707759e−01 | −2.72847116e−01 |
| 1.65222764e−01 | 5.17064095e−01 | −1.88604787e−01 | 1.75268143e−01 |
| −5.67282319e−01 | −2.02590078e−01 | −3.41380328e−01 | −4.71340597e−01 |
| −6.78573668e−01 | −3.08421135e−01 | 2.67055035e−01 | 6.47145391e−01 |
| 7.45711386e−01 | 1.27355069e−01 | 3.47880334e−01 | −3.33354980e−01 |
| −1.11434117e−01 | −3.53679568e−01 | −2.76123315e−01 | −1.78411797e−01 |
| −2.19011664e−01 | −5.59405565e−01 | −4.29794434e−01 | −6.31113470e−01 |
| −7.96359420e−01 | −4.12339866e−01 | −5.96683562e−01 | −1.67958558e−01 |
| −5.81173003e−01 | −5.84471762e−01 | −1.80628628e−01 | 9.30597186e−02 |
| −1.41507357e−01 | −5.58433652e−01 | −3.41128767e−01 | 2.82517940e−01 |
| 3.03414594e−02 | −2.69436389e−01 | 2.38110304e−01 | 3.25266927e−01 |
| −3.54154050e−01 | −6.44343674e−01 | −1.07432373e−01 | −3.45976681e−01 |
| −6.29536688e−01 | −4.98660773e−01 | −9.80920434e−01 | −7.44755864e−01 |
| −4.54038829e−01 | −1.09082520e−00 | 2.44961381e−01 | −7.12791085e−01 |
| 1.22315750e−01 | 1.33653834e−01 | −6.78144515e−01 | 6.75987005e−01 |
| −5.95721900e−01 | 1.19304329e−01 | 1.12111922e−02 | 2.09954739e−01 |
| −5.34436703e−01 | −2.56465971e−01 | −1.05723515e−01 | −1.42520413e−01 |
| −1.92408726e−01 | −7.35014439e−01 | −4.13943417e−02 | −4.69635101e−03 |
| −5.31029180e−02 | −2.08856910e−01 | −1.11850239e−01 | −5.90370774e−01 |
| −4.54216659e−01 | 6.00256324e−01 | −3.49652410e−01 | 7.19168842e−01 |
| −4.38481569e−01 | −4.61372942e−01 | −1.52047366e−01 | −8.64568949e−01 |
| −1.45017147e−01 | −3.67090791e−01 | −2.00830951e−01 | −4.78841931e−01 |
| −3.86037290e−01 | −5.76516628e−01 | −2.07954332e−01 | −3.00990373e−01 |
| −2.76627570e−01 | −4.63433653e−01 | −8.42171133e−01 | 9.90521312e−02 |
| 5.68643630e−01 | −5.11399031e−01 | −1.28277469e−00 | −6.09913468e−01 |
| −6.69682920e−01 | 2.97434442e−02 | −3.35079283e−01 | 6.79311872e−01 |
| −9.86979783e−01 | −4.58831191e−01 | −2.34660804e−01 | −1.17784314e−01 |
| −3.18238616e−01 | −6.47882998e−01 | −7.41675720e−02 | −4.01657879e−01 |
| −8.75880122e−01 | −6.77599311e−01 | −6.64566994e−01 | −2.20211551e−01 |
| −1.07269369e−01 | −2.66219288e−01 | 4.95872170e−01 | −1.11922491e−00 |
| −8.79901350e−01 | −7.87379444e−01 | −7.50009120e−02 | −4.79501158e−01 |
| −3.71242225e−01 | −3.89610976e−01 | −2.07547680e−01 | −8.78286064e−01 |
| −5.49769759e−01 | −4.43993479e−01 | −6.67285860e−01 | −3.95562202e−01 |
| −9.17620003e−01 | 8.38131905e−02 | −3.51681620e−01 | 8.98410454e−02 |
| −1.29972905e−01 | −3.22076708e−01 | −2.90924102e−01 | −4.69567567e−01 |
| −6.39926791e−01 | −2.00300664e−01 | −6.82399988e−01 | −2.91042417e−01 |
| −6.46054566e−01 | 2.88643271e−01 | 3.86391819e−01 | −3.73829007e−01 |
| −3.88799012e−01 | −1.05902985e−01 | −2.13909388e−01 | −5.26127517e−01 |
| 2.23491013e−01 | −9.06338513e−01 | −8.58371973e−01 | 7.67518654e−02 |
| −2.98812717e−01 | −3.85325551e−01 | −4.33399707e−01 | −2.00836197e−01 |
| −5.22775888e−01 | −3.57567012e−01 | −5.38193524e−01 | −1.62872940e−01 |
| −1.99623674e−01 | 3.05810034e−01 | −4.92242813e−01 | −5.31283319e−01 |
| −2.35053137e−01 | −2.86091894e−01 | −2.10467368e−01 | −5.76741636e−01 |
| −2.15058759e−01 | −1.31135985e−01 | −5.83207250e−01 | −2.85845786e−01 |
| 3.34509343e−01 | −2.60766238e−01 | −6.85692251e−01 | −8.44856679e−01 |
| −1.46990627e−01 | −4.04660683e−03 | −2.11841643e−01 | −2.17404794e−02 |
| −7.35497236e−01 | −1.31477728e−01 | 7.29482919e−02 | −5.35207212e−01 |
| −5.47139347e−01 | 4.19220358e−01 | −7.31182635e−01 | 1.73505500e−01 |
| −2.07118541e−01 | −3.93062085e−01 | −2.11910069e−01 | 1.10177003e−01 |
| −5.42229116e−01 | −1.04142964e−00 | −3.61109942e−01 | −4.19669837e−01 |
| −3.90628785e−01 | −3.08886945e−01 | −1.28360361e−01 | −1.09089077e−00 |
| 2.21795261e−01 | −2.20141888e−01 | −7.70756900e−02 | −6.65412843e−01 |
| −5.30555844e−01 | −4.61172491e−01 | 2.36461371e−01 | 3.01450640e−01 |
| −1.74993113e−01 | −2.09172979e−01 | 2.62790203e−01 | −4.97138500e−01 |
| −6.73022807e−01 | −3.33608955e−01 | −5.97260416e−01 | −2.48159334e−01 |
| −8.54661405e−01 | −5.83020091e−01 | −6.94956779e−01 | −1.24218300e−01 |
| −1.97329566e−01 | −5.27161062e−01 | −2.65654504e−01 | 1.08260833e−01 |
| −4.32366610e−01 | −4.44594949e−01 | −1.37374684e−01 | −6.57103211e−02 |
| −6.36347353e−01 | −7.60183394e−01 | −4.07504886e−01 | 4.13207710e−01 |
| −3.49251211e−01 | −2.50917107e−01 | −7.41898343e−02 | −4.41208929e−01 |
| 4.77228194e−01 | −3.76564234e−01 | −2.80835181e−01 | −2.65350074e−01]] |

The invention claimed is:

1. A method for identifying one or more antigens from one or more tumor cells of a subject that are likely to be presented on surface of the tumor cells, comprising the steps of:

obtaining at least one of exome, transcriptome, or whole genome nucleotide sequencing data from the tumor cells and normal cells of the subject, wherein the nucleotide sequencing data is used to obtain data representing peptide sequences of each of a set of antigens identified by comparing the nucleotide sequencing data from the tumor cells and the nucleotide sequencing data from the normal cells, wherein the peptide sequence of each antigen comprises at least one alteration that makes it distinct from the corresponding wild-type peptide sequence identified from the normal cells of the subject, and wherein the peptide sequences comprise a plurality of peptide sequences having lengths other than 9 amino acids;

encoding the peptide sequences of each of the antigens into a corresponding numerical vector, each numerical vector including information regarding a plurality of amino acids that make up the peptide sequence and a set of positions of the amino acids in the peptide sequence;

determining, using a neural network model stored in a non-transitory computer readable medium of one or more computing devices, a set of presentation likelihoods for the set of antigens, each presentation likelihood in the set representing the likelihood that a corresponding antigen is presented by one or more class I MHC alleles on the surface of the tumor cells of the subject, the neural network model comprising:

two or more layers comprising a first layer and a second layer, each layer comprising one or more nodes, wherein said nodes comprise a memory location for one or more input values;

a plurality of connections between nodes of said first layer and one or more nodes of said second layer, optimized parameters stored in memory locations, wherein the optimized parameters transform input values of nodes of the first layer into input values for nodes of the second layer connected to the nodes of the first layer, wherein the optimized parameters are generated using a training data set comprising:

training peptide sequences encoded as numerical vectors including information regarding a plurality of amino acids that make up the peptide sequence and a set of positions of the amino acids in the peptide sequence; and at least one class I MHC allele associated with the training peptide sequences; and for each of the training peptide sequences, a label indicating whether the training peptide sequence was presented by the at least one class I MHC allele;

wherein said determining comprises:
forward feeding the numerical vectors, using a computer processor, through nodes of the first layer and the second layer of the neural network model, said forward feeding comprising transforming values of the numerical vectors as they are fed from nodes of the first layer to nodes of the second layer using the optimized parameters;
generating, using a computer processor, a set of presentation likelihoods for the set of antigens from the transformed numerical vectors, each presentation likelihood in the set representing the likelihood that a corresponding antigen is presented by one or more class I MHC alleles on the surface of the tumor cells of the subject;
selecting a subset of the set of antigens based on the set of presentation likelihoods to generate a set of selected antigens; and
returning the set of selected antigens.

2. The method of claim 1, wherein the training peptide sequences comprise peptide sequences having lengths other than 9 amino acids.

3. The method of claim 1, wherein the peptide sequences comprise peptide sequences having lengths of 8 or 10-15 amino acids.

4. The method of claim 1, wherein encoding the peptide sequence comprises encoding the peptide sequence using a one-hot encoding scheme.

5. The method of claim 1, wherein generating the set of presentation likelihoods for the set of antigens comprises:
generating a dependency score for each of the one or more class I MHC alleles, the dependency scores indicating whether the class I MHC alleles will present the antigen based on the particular amino acids at the particular positions of the peptide sequence.

6. The method of claim 5, wherein generating the set of presentation likelihoods for the set of antigens further comprises:
transforming the dependency scores to generate a corresponding per-allele likelihood for each class I MHC allele indicating a likelihood that the corresponding class I MHC allele will present the corresponding antigen; and
combining the per-allele likelihoods to generate the presentation likelihood of the antigen.

7. The method of claim 6, wherein the transforming the dependency scores models the presentation of the antigen as mutually exclusive across the one or more class I MHC alleles.

8. The method of claim 5, generating the set of presentation likelihoods for the set of antigens further comprises:
transforming a combination of the dependency scores to generate the presentation likelihood, wherein transforming the combination of the dependency scores models the presentation of the antigen as interfering between the one or more class I MHC alleles.

9. The method of claim 5, wherein the set of presentation likelihoods are further identified by at least one or more allele noninteracting features, and further comprising:
applying the neural network model to the allele noninteracting features to generate a dependency score for the allele noninteracting features indicating whether the peptide sequence of the corresponding antigen will be presented based on the allele noninteracting features.

10. The method of claim 9, further comprising:
combining the dependency score for each class I MHC allele in the one or more class I MHC alleles with the dependency score for the allele noninteracting feature; and
transforming the combined dependency scores for each class I MHC allele to generate a per-allele likelihood for each class I MHC allele indicating a likelihood that the corresponding class I MHC allele will present the corresponding antigen; and
combining the per-allele likelihoods to generate the presentation likelihood.

11. The method of claim 10, further comprising:
transforming a combination of the dependency scores for each of the class I MHC alleles and the dependency score for the allele noninteracting features to generate the presentation likelihood.

12. The method of claim 1, wherein the one or more class I MHC alleles include two or more class I MHC alleles.

13. The method of claim 1, wherein the at least one class I MHC allele includes two or more different types of class I MHC alleles.

14. The method of claim 1, wherein the plurality of samples comprise at least one of:
(a) one or more cell lines engineered to express a single MHC class I allele;
(b) one or more cell lines engineered to express a plurality of MHC class I alleles;
(c) one or more human cell lines obtained or derived from a plurality of patients;
(d) fresh or frozen tumor samples obtained from a plurality of patients; and
(e) fresh or frozen tissue samples obtained from a plurality of patients.

15. The method of claim 1, wherein the set of presentation likelihoods are further identified by at least expression levels of the one or more class I MHC alleles in the subject, as measured by RNA-seq or mass spectrometry.

16. The method of claim 1, wherein the set of numerical likelihoods are further identified by features comprising at least one of:
(a) the C-terminal sequences flanking the antigen encoded peptide sequence within its source protein sequence; and
(b) the N-terminal sequences flanking the antigen encoded peptide sequence within its source protein sequence.

17. The method of claim 1, wherein selecting the set of selected antigens comprises selecting antigens that have an increased likelihood of being presented on the tumor cell surface relative to unselected antigens.

18. The method of claim 1, further comprising generating an output for constructing a personalized cancer vaccine from the set of selected antigens.

19. The method of claim 18, wherein the output for the personalized cancer vaccine comprises at least one peptide sequence or at least one nucleotide sequence encoding the set of selected antigens.

20. The method of claim 1, further comprising identifying one or more T-cells that are antigen-specific for at least one of the antigens in the subset or identifying one or more T-cell receptors that are antigen-specific for at least one of the antigens in the sub set.

21. A system comprising:
a processor configured to execute computer-executable instructions for performain a method comprising:
obtaining at least one of exome, transcriptome, or whole genome nucleotide sequencing data from the tumor cells and normal cells of the subject, wherein the nucleotide sequencing data is used to obtain data representing peptide sequences of each of a set of antigens identified by comparing the nucleotide sequencing data from the tumor cells and the nucleotide sequencing data from the normal cells, wherein the peptide sequence of each antigen comprises at least one alteration that makes it distinct from the corresponding wild-type peptide sequence identified from the normal cells of the subject, and wherein the peptide sequences comprise a plurality of peptide sequences having lengths other than 9 amino acids;

encoding the peptide sequences of each of the antigens into a corresponding numerical vector, each numerical vector including information regarding a plurality of amino acids that make up the peptide sequence and a set of positions of the amino acids in the peptide sequence;

determining, using a neural network model stored in a non-transitory computer readable medium of one or more computing devices, a set of presentation likelihoods for the set of antigens, each presentation likelihood in the set representing the likelihood that a corresponding antigen is presented by one or more class I MHC alleles on the surface of the tumor cells of the subject, the neural network model comprising:
two or more layers comprising a first layer and a second layer, each layer comprising one or more nodes, wherein said nodes comprise a memory location for one or more input values;
a plurality of connections between nodes of said first layer and one or more nodes of said second layer,
optimized parameters stored in memory locations, wherein the optimized parameters transform input values of nodes of the first layer into input values for nodes of the second layer connected to the nodes of the first layer,
wherein the optimized parameters are generated using a training data set comprising:
training peptide sequences encoded as numerical vectors including information regarding a plurality of amino acids that make up the peptide sequence and a set of positions of the amino acids in the peptide sequence; and
at least one class I MHC allele associated with the training peptide sequences; and
for each of the training peptide sequences, a label indicating whether the training peptide sequence was presented by the at least one class I MHC allele;

selecting a subset of the set of antigens based on the set of presentation likelihoods to generate a set of selected antigens; and
returning the set of selected antigens.

22. The system of claim 21, wherein the training peptide sequences comprise peptide sequences having lengths other than 9 amino acids.

23. The method of claim 21, wherein the peptide sequences comprise peptide sequences having lengths of 8 or 10-15 amino acids.

24. The system of claim 21, wherein generating the set of presentation likelihoods for the set of antigens comprises:
generating a dependency score for each of the one or more class I MHC alleles, the dependency scores indicating whether the class I MHC alleles will present the antigen based on the particular amino acids at the particular positions of the peptide sequence.

25. The system of claim 24, wherein generating the set of presentation likelihoods for the set of antigens further comprises:
transforming the dependency scores to generate a corresponding per-allele likelihood for each class I MHC allele indicating a likelihood that the corresponding class I MHC allele will present the corresponding antigen; and
combining the per-allele likelihoods to generate the presentation likelihood of the antigen.

26. The system of claim 25, wherein the set of presentation likelihoods are further identified by at least one or more allele noninteracting features, and further comprising:
applying the neural network model to the allele noninteracting features to generate a dependency score for the allele noninteracting features indicating whether the peptide sequence of the corresponding antigen will be presented based on the allele noninteracting features.

27. The system of claim 21, wherein the set of presentation likelihoods are further identified by at least expression levels of the one or more class I WIC alleles in the subject, as measured by RNA-seq or mass spectrometry.

28. The method of claim 1, wherein the labels in the training data set are derived from mass spectrometry data.

29. The method of claim 1, wherein the antigens are neoantigens.

30. The method of claim 1, wherein two or more optimized parameters transform an input value for a node of the first layer into an input value of a node in the second layer.

31. The method of claim 1, wherein the neural network model exhibits a positive predictive value (PPV) that achieves 0.114 at 10% recall rate.

* * * * *

UNITED STATES PATENT AND TRADEMARK OFFICE
CERTIFICATE OF CORRECTION

PATENT NO. : 10,847,252 B2
APPLICATION NO. : 16/001569
DATED : November 24, 2020
INVENTOR(S) : Roman Yelensky et al.

Page 1 of 1

It is certified that error appears in the above-identified patent and that said Letters Patent is hereby corrected as shown below:

In the Claims

In Column 456, Claim 20, Line 62, replace "sub set" with --subset--;

In Column 456, Claim 21, Line 65, replace "performain" with --performing--;

In Column 458, Claim 23, Line 8, replace "method" with --system--; and

In Column 458, Claim 27, Line 37, replace "I WIC" with -- -I MHC--.

Signed and Sealed this
Twenty-ninth Day of November, 2022

*Katherine Kelly Vidal*

Katherine Kelly Vidal
*Director of the United States Patent and Trademark Office*

SEQUENCE LISTING

<160> NUMBER OF SEQ ID NOS: 20

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Val Tyr Val Ala Asp Val Ala Ala Lys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Glu Met Phe Asn Asp Lys Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Glu Met Phe Asn Asp Lys Ser Phe
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pyrrolysine
<220> FEATURE:
<221> NAME/KEY: MOD_RES
<222> LOCATION: (11)..(11)
<223> OTHER INFORMATION: Ile or Leu

<400> SEQUENCE: 4

His Arg Xaa Glu Ile Phe Ser His Asp Phe Xaa
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Leu
<220> FEATURE:

```
<221> NAME/KEY: MOD_RES
<222> LOCATION: (5)..(5)
<223> OTHER INFORMATION: Ile or Leu
<220> FEATURE:
<221> NAME/KEY: MOD_RES
<222> LOCATION: (7)..(7)
<223> OTHER INFORMATION: Pyrrolysine

<400> SEQUENCE: 5

Phe Xaa Ile Glu Xaa Phe Xaa Glu Ser Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pyrrolysine

<400> SEQUENCE: 6

Asn Glu Ile Xaa Arg Glu Ile Arg Glu Ile
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Leu
<220> FEATURE:
<221> NAME/KEY: MOD_RES
<222> LOCATION: (11)..(11)
<223> OTHER INFORMATION: Ile or Leu
<220> FEATURE:
<221> NAME/KEY: MOD_RES
<222> LOCATION: (15)..(15)
<223> OTHER INFORMATION: Selenocysteine

<400> SEQUENCE: 7

Xaa Phe Lys Ser Ile Phe Glu Met Met Ser Xaa Asp Ser Ser Xaa
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Pyrrolysine

<400> SEQUENCE: 8

Lys Asn Phe Leu Glu Asn Phe Ile Glu Ser Xaa Phe Ile
1               5                   10

<210> SEQ ID NO 9
<211> LENGTH: 15
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pyrrolysine
<220> FEATURE:
<221> NAME/KEY: MOD_RES
<222> LOCATION: (14)..(14)
<223> OTHER INFORMATION: Ile or Leu

<400> SEQUENCE: 9

Phe Xaa Glu Ile Phe Asn Asp Lys Ser Leu Asp Lys Phe Xaa Ile
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Pyrrolysine

<400> SEQUENCE: 10

Gln Cys Glu Ile Xaa Trp Ala Arg Glu
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Selenocysteine

<400> SEQUENCE: 11

Phe Ile Glu Xaa His Phe Trp Ile
1               5

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ile or Leu
<220> FEATURE:
<221> NAME/KEY: MOD_RES
<222> LOCATION: (10)..(10)
<223> OTHER INFORMATION: Selenocysteine
<220> FEATURE:
<221> NAME/KEY: MOD_RES
<222> LOCATION: (11)..(11)
<223> OTHER INFORMATION: Ile or Leu

<400> SEQUENCE: 12

Phe Glu Trp Arg His Arg Xaa Thr Arg Xaa Xaa Arg
1               5                   10
```

```
<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ile or Leu
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (8)..(8)
<223> OTHER INFORMATION: Ile or Leu

<400> SEQUENCE: 13

Gln Ile Glu Xaa Xaa Glu Ile Xaa Glu
1               5

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (9)..(9)
<223> OTHER INFORMATION: Pyrrolysine
<220> FEATURE:
<221> NAME/KEY: MOD_RES
<222> LOCATION: (11)..(11)
<223> OTHER INFORMATION: Ile or Leu

<400> SEQUENCE: 14

Phe Xaa Glu Leu Phe Ile Ser Asx Xaa Ser Xaa Phe Ile Glu
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (9)..(9)
<223> OTHER INFORMATION: Ile or Leu

<400> SEQUENCE: 15

Ile Glu Phe Arg Xaa Glu Ile Phe Xaa Glu Phe
1               5                   10

<210> SEQ ID NO 16
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (9)..(9)
<223> OTHER INFORMATION: Ile or Leu

<400> SEQUENCE: 16

Ile Glu Phe Arg Xaa Glu Ile Phe Xaa
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pyrrolysine
<220> FEATURE:
<221> NAME/KEY: MOD_RES
<222> LOCATION: (8)..(8)
<223> OTHER INFORMATION: Ile or Leu

<400> SEQUENCE: 17

Glu Phe Arg Xaa Glu Ile Phe Xaa Glu
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pyrrolysine
<220> FEATURE:
<221> NAME/KEY: MOD_RES
<222> LOCATION: (7)..(7)
<223> OTHER INFORMATION: Ile or Leu

<400> SEQUENCE: 18

Phe Arg Xaa Glu Ile Phe Xaa Glu Phe
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Selenocysteine
<220> FEATURE:
<221> NAME/KEY: MOD_RES
<222> LOCATION: (7)..(8)
<223> OTHER INFORMATION: Pyrrolysine
```

```
<400> SEQUENCE: 19

Phe Glu Gly Arg Lys Xaa Xaa Xaa Ile
1               5

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (7)..(7)
<223> OTHER INFORMATION: Ile or Leu
<220> FEATURE:
<221> NAME/KEY: MOD_RES
<222> LOCATION: (8)..(8)
<223> OTHER INFORMATION: Pyrrolysine
<220> FEATURE:
<221> NAME/KEY: MOD_RES
<222> LOCATION: (10)..(10)
<223> OTHER INFORMATION: Ile or Leu
<220> FEATURE:
<221> NAME/KEY: MOD_RES
<222> LOCATION: (14)..(14)
<223> OTHER INFORMATION: Pyrrolysine

<400> SEQUENCE: 20

Pro Xaa Phe Ile Xaa Glu Xaa Xaa Ile Xaa Gly Glu Ile Xaa
1               5                   10
```